United States Patent
Kim et al.

(10) Patent No.: US 9,815,821 B2
(45) Date of Patent: *Nov. 14, 2017

(54) CONDENSED-CYCLIC COMPOUND AND ORGANIC LIGHT EMITTING DIODE INCLUDING THE SAME

(71) Applicants: SAMSUNG DISPLAY CO., LTD., Yongin-si, Gyeonggi-do (KR); SFC CO., LTD., Cheongwon-gun, Chungbuk (KR)

(72) Inventors: Myeong-Suk Kim, Yongin-si (KR); Tae-Kyung Kim, Yongin-si (KR); Jeoung-In Yi, Yongin-si (KR); Jeong-Soo Kim, Cheongwon-gun (KR); Su-Jin Lee, Cheongwon-gun (KR); Hyun-Jung Kwon, Cheongwon-gun (KR); Sang-Won Ko, Cheongwon-gun (KR)

(73) Assignees: Samsung Display Co., Ltd., Yongin-si (KR); SFC Co., Ltd, Cheongwon-gun (KR)

(*) Notice: Subject to any disclaimer, the term of this patent is extended or adjusted under 35 U.S.C. 154(b) by 836 days.

This patent is subject to a terminal disclaimer.

(21) Appl. No.: 13/681,208

(22) Filed: Nov. 19, 2012

(65) Prior Publication Data
US 2013/0175509 A1    Jul. 11, 2013

(30) Foreign Application Priority Data
Dec. 27, 2011 (KR) .................. 10-2011-0143911

(51) Int. Cl.
*H01L 51/50* (2006.01)
*C07D 403/14* (2006.01)
(Continued)

(52) U.S. Cl.
CPC ......... *C07D 403/14* (2013.01); *C07D 209/86* (2013.01); *C07D 307/91* (2013.01);
(Continued)

(58) Field of Classification Search
None
See application file for complete search history.

(56) References Cited

U.S. PATENT DOCUMENTS 6,720,573 B2   4/2004   Son et al.
2002/0102772 A1   8/2002   Takata et al.
(Continued)

FOREIGN PATENT DOCUMENTS

CN    101562234 A    10/2009
EP    0 963 981 A1    12/1999
(Continued)

OTHER PUBLICATIONS

Korean Patent Application Publication No. 10-2006-0053119A, corresponding to KR 10-0718765, 2 pages.
(Continued)

*Primary Examiner* — Gregory Clark
(74) *Attorney, Agent, or Firm* — Lewis Roca Rothgerber Christie LLP

(57) ABSTRACT

Embodiments of the present invention are directed to a condensed-cyclic compound and an OLED including the same.

19 Claims, 9 Drawing Sheets

(51) Int. Cl.
*C07D 209/86* (2006.01)
*C07D 403/10* (2006.01)
*C07D 307/91* (2006.01)
*C07D 333/76* (2006.01)
*H01L 51/00* (2006.01)

(52) U.S. Cl.
CPC .......... *C07D 333/76* (2013.01); *C07D 403/10* (2013.01); *H01L 51/006* (2013.01); *H01L 51/5092* (2013.01); *H01L 51/0054* (2013.01); *H01L 51/0081* (2013.01); *H01L 51/5012* (2013.01); *H01L 2251/308* (2013.01)

(56) References Cited

U.S. PATENT DOCUMENTS

| | | | |
|---|---|---|---|
| 2007/0190355 A1 | 8/2007 | Ikeda et al. | |
| 2008/0111473 A1 | 5/2008 | Kawamura et al. | |
| 2008/0131731 A1 | 6/2008 | Igawa et al. | |
| 2009/0091240 A1 | 4/2009 | Ikeda et al. | |
| 2009/0096356 A1 | 4/2009 | Murase et al. | |
| 2009/0288707 A1 | 11/2009 | Lee et al. | |
| 2012/0181520 A1* | 7/2012 | Kim ................. | C07B 59/001 257/40 |

FOREIGN PATENT DOCUMENTS

| | | | | |
|---|---|---|---|---|
| JP | 2003-342258 | 12/2003 | | |
| JP | 2005-008600 | 1/2005 | | |
| JP | 2006-131519 | 5/2006 | | |
| JP | 2007-131722 | 5/2007 | | |
| JP | 2008-137978 | 6/2008 | | |
| JP | 2010-229053 | * 10/2010 | ............ | C09K 11/06 |
| JP | 2011-046627 | * 3/2011 | ............ | H01L 51/50 |
| KR | 10-2007-0030759 | 3/2007 | | |
| KR | 10-0718765 | 5/2007 | | |
| KR | 10-2007-0088728 | 8/2007 | | |
| KR | 10-2008-0055891 | 6/2008 | | |
| KR | 10-2009-0093897 A | 9/2009 | | |
| KR | 10-2009-0110014 | 10/2009 | | |
| KR | 10-2011-0115887 | 10/2011 | | |
| KR | 10-2011-0120076 | 11/2011 | | |

OTHER PUBLICATIONS

KIPO Office action dated Mar. 11, 2014, for Korean priority Patent application 10-2011-0143911, (2 pages).

Korean Office Action dated Jun. 20, 2013 of the corresponding Korean Patent Application No. 10-2011-0143911.

SIPO Office action dated Sep. 11, 2015, for corresponding Chinese Patent application 201210579950.5. (9 pages).

SIPO Office action dated Apr. 14, 2016, with English translation, for corresponding Chinese Patent application 201210579950.5, (18 pages).

English Abstract and partial English machine translation of relevant parts of Korean Publication 10-2011-0115887 dated Oct. 24, 2011, (4 pages).

* cited by examiner

CONDENSED-CYCLIC COMPOUND AND ORGANIC LIGHT EMITTING DIODE INCLUDING THE SAME

CROSS-REFERENCE TO RELATED PATENT APPLICATION

This application claims priority to and the benefit of Korean Patent Application No. 10-2011-0143911, filed on Dec. 27, 2011 in the Korean Intellectual Property Office, the entire content of which is incorporated herein by reference.

BACKGROUND

1. Technical Field

The present invention relates to a condensed-cyclic compound and an organic light-emitting diode including the same.

2. Description of the Related Art

Organic light-emitting diodes (OLEDs) are self-emitting devices having advantages such as wide viewing angles, good contrast, quick response times, high brightness, and good driving voltage. OLEDs can provide multicolored images. A typical OLED has a structure including a substrate, and an anode, a hole transport layer (HTL), an emission layer (EML), an electron transport layer (ETL), and a cathode sequentially stacked on the substrate. In this regard, the HTL, the EML, and the ETL are organic layers formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

According to an aspect of the present invention, there is provided a condensed-cyclic compound represented by Formula 1 below:

Formula 1

In Formula 1, $Ar_1$ may be a substituted or unsubstituted $C_5$-$C_{60}$ aromatic ring or a substituted or unsubstituted $C_2$-$C_{60}$ heteroaromatic ring.

q may be an integer of 1 to 6, and when q is 2 or greater, the 2 or more of the $Ar_2$ groups may be identical to or different from each other.

In some embodiments, $Ar_2$ may be represented by Formula 2 below:

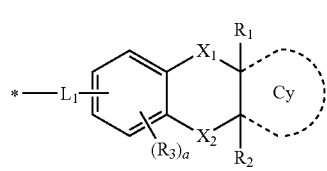

Formula 2

In Formula 2, Cy may be a substituted or unsubstituted $C_3$ to $C_8$ cycloalkane.

$X_1$ may be $N(R_{11})$, $B(R_{11})$, $Si(R_{11})(R_{12})$, O, or S.

$X_2$ may be a single bond or —$[C(R_{15})(R_{16})]_n$—, where n is an integer of 1 to 3, but when n is 2 or greater, the 2 or more $R_{15}$ and $R_{16}$ groups may be identical to or different from each other.

$L_1$ may be a single bond, a substituted or unsubstituted $C_1$-$C_{60}$ alkylene group, a substituted or unsubstituted $C_2$-$C_{60}$ alkenylene group, a substituted or unsubstituted $C_2$-$C_{60}$ alkynylene group, a substituted or unsubstituted $C_3$-$C_{60}$ cycloalkylene group, a substituted or unsubstituted $C_2$-$C_{60}$ heterocycloalkylene group, a substituted or unsubstituted $C_5$-$C_{60}$ arylene group, or a substituted or unsubstituted $C_2$-$C_{60}$ heteroarylene.

$R_1$ through $R_3$, $R_{11}$, $R_{12}$, $R_{15}$, and $R_{16}$ may each independently be hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_{10}$-$C_{60}$ alkylthio group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a (substituted or unsubstituted $C_1$-$C_{60}$ alkyl)amino group, a di(substituted or unsubstituted $C_1$-$C_{60}$ alkyl)amino group, or a (substituted or unsubstituted $C_5$-$C_{60}$ aryl)amino group, or a di(substituted or unsubstituted $C_5$-$C_{60}$ aryl) amino group.

a may be an integer of 1 to 3, and when a is 2 or greater, the 2 or more $R_3$ groups may be identical to or different from each other.

* may be a binding site to $Ar_1$ of Formula 1.

According to another aspect of the present invention, there is provided an organic light-emitting diode including a first electrode; a second electrode facing the first electrode; and an organic layer between the first electrode and the second electrode, wherein the organic layer may include at least one of the condensed-cyclic compounds.

BRIEF DESCRIPTION OF THE DRAWINGS

The above and other features and advantages of the present invention will become more apparent by reference to the following detailed description when considered in conjunction with the attached drawings in which.

DETAILED DESCRIPTION

Figure 1:
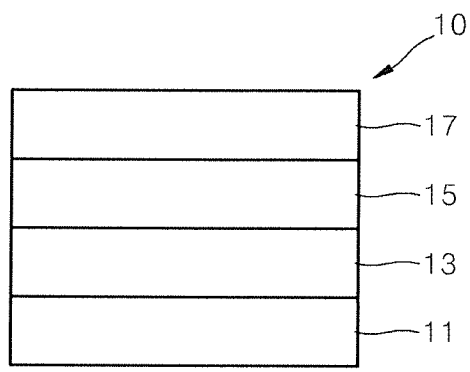
FIG. 1 is a schematic diagram illustrating an organic light-emitting diode (OLED) according to an embodiment of the present invention.
Figure 2:
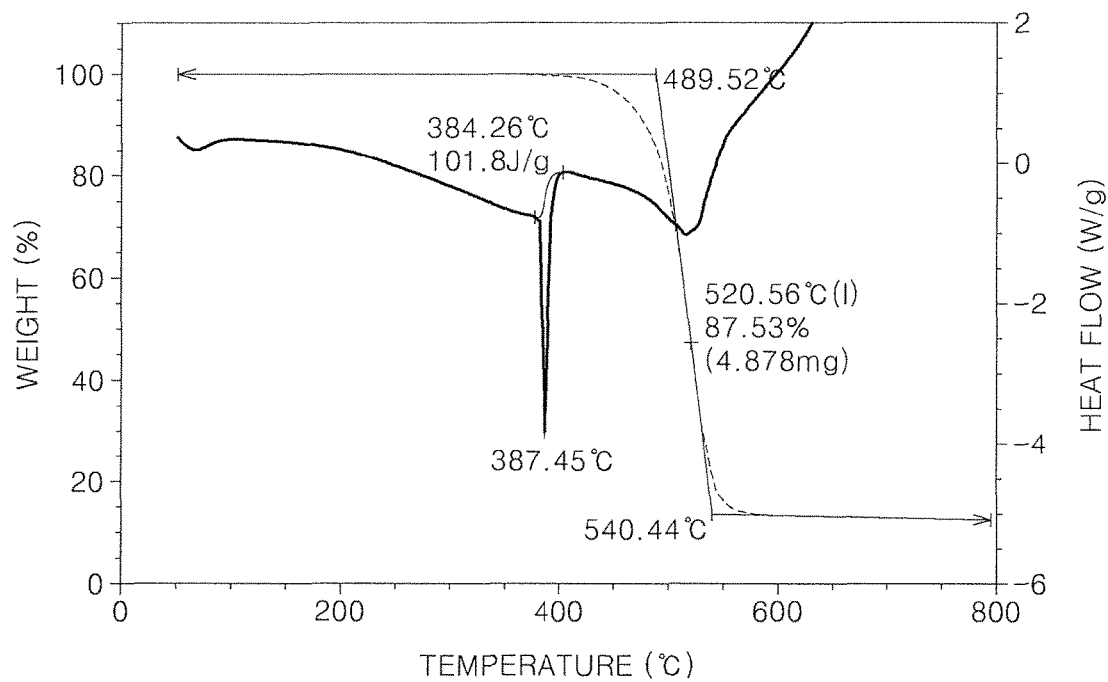
FIG. 2 is a thermogravimetric analysis (TGA) graph of Compound 38.
Figure 3:
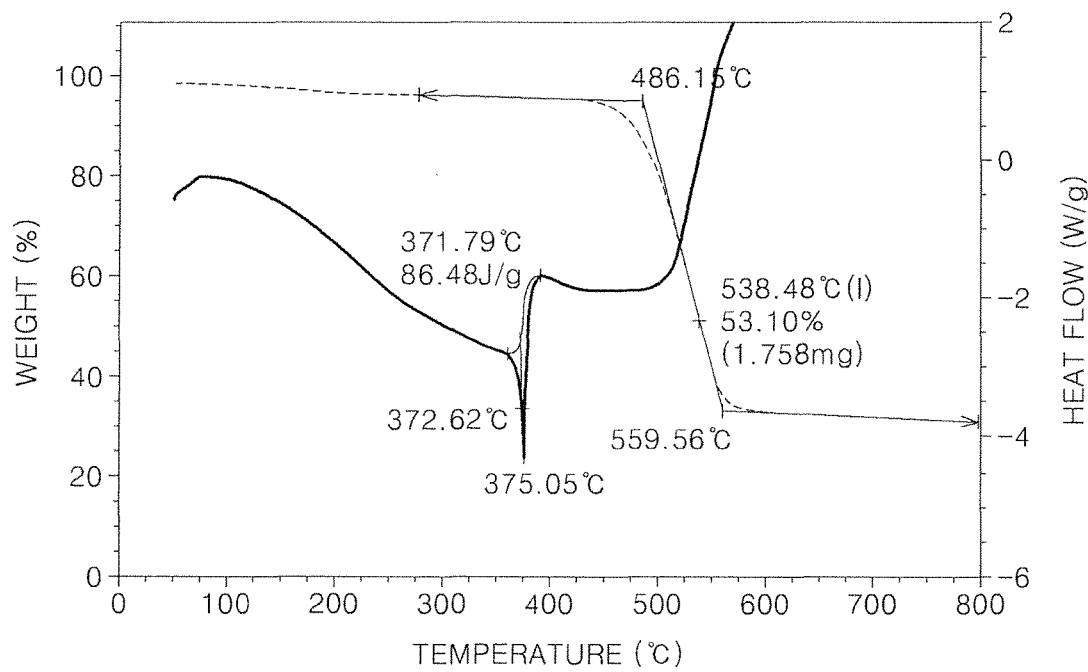
FIG. 3 is a TGA graph of Compound 262.
Figure 4:
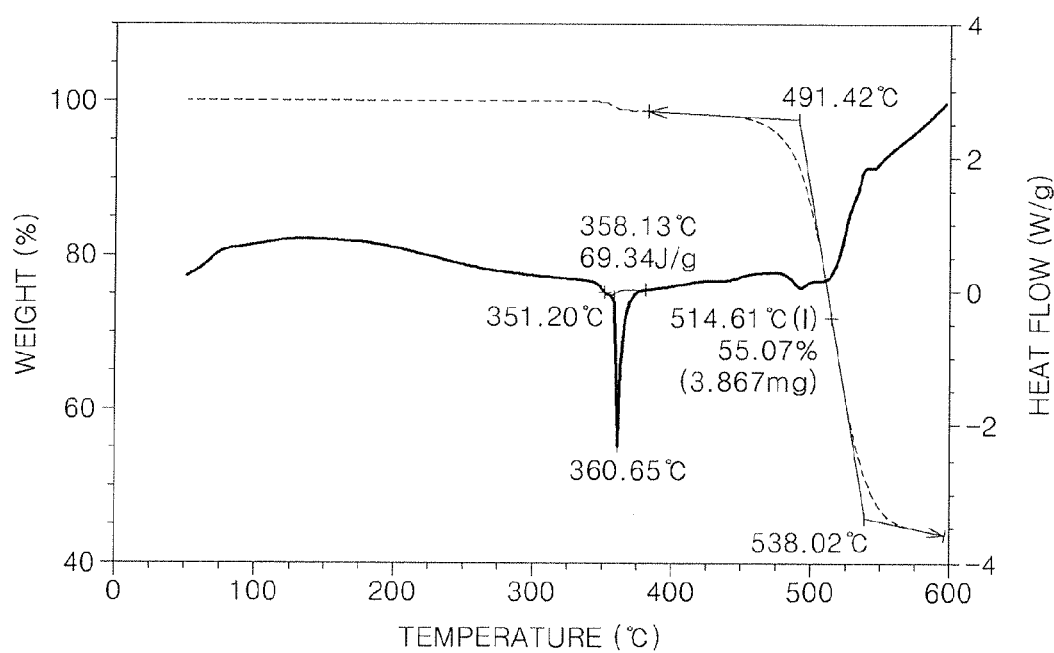
FIG. 4 is a TGA graph of Compound 586.
Figure 5:
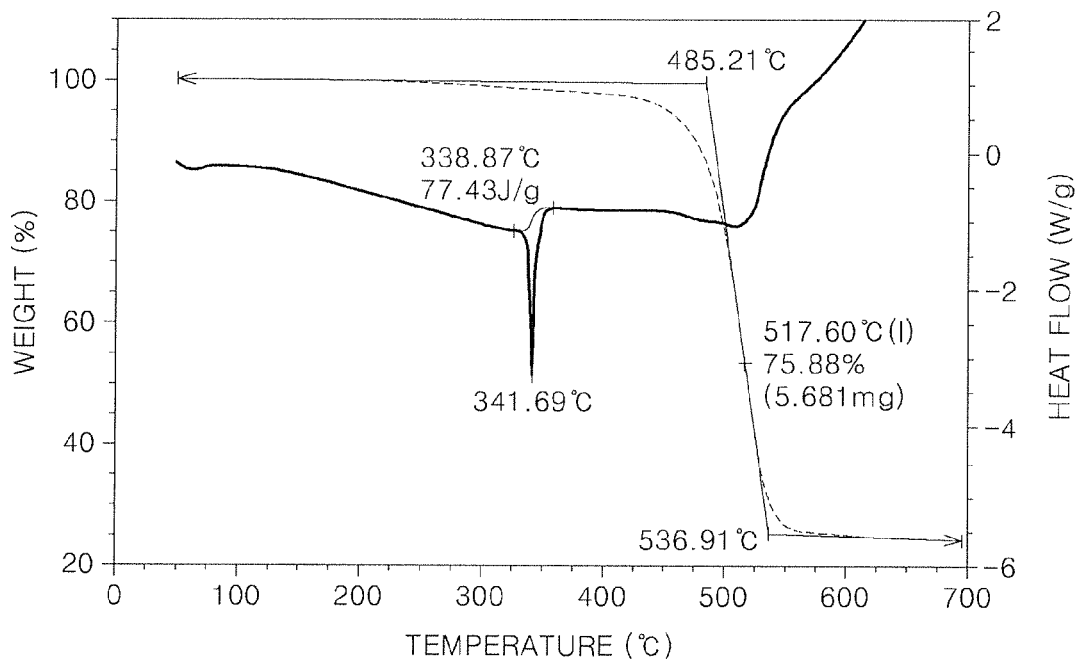
FIG. 5 is a TGA graph of Compound 726.
Figure 6:
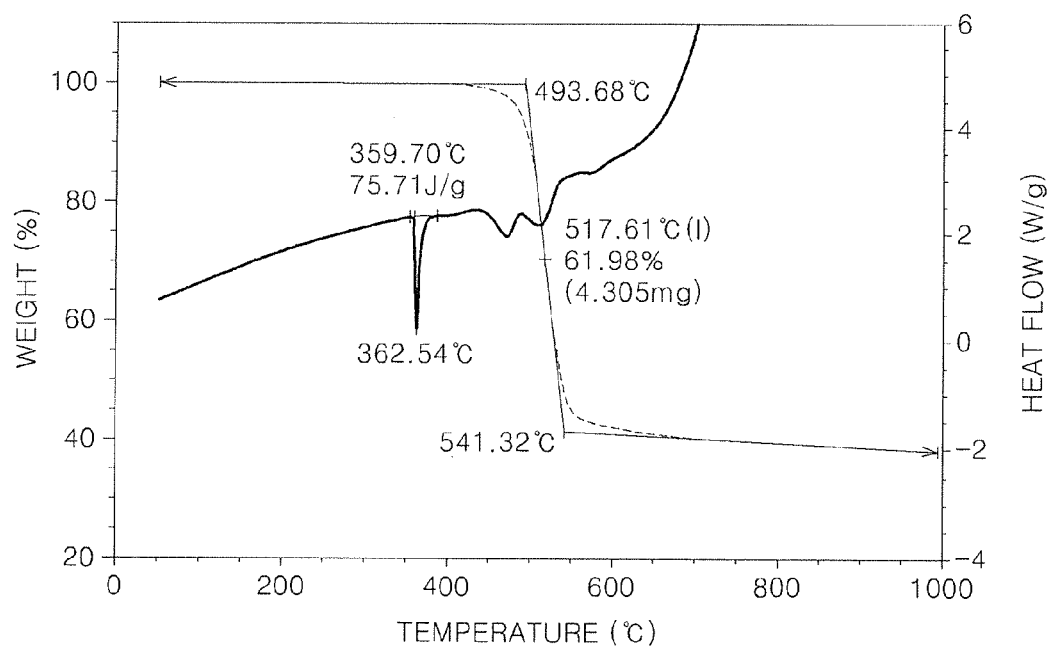
FIG. 6 is a TGA graph of Compound 929.

Hereinafter, the present embodiments will be described more fully with reference to the accompanying drawings, in which exemplary embodiments are shown. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a condensed-cyclic compound represented by Formula 1 below:

Formula 1

In Formula 1, $Ar_1$ may be a substituted or unsubstituted $C_5$ to $C_{60}$ aromatic ring or a substituted or unsubstituted $C_2$ to $C_{60}$ heteroaromatic ring, and q is an integer of 1 to 6. When q is 2 or greater, the 2 or more $Ar_2$ groups may be identical to or different from each other. $Ar_2$ is represented by Formula 2 below:

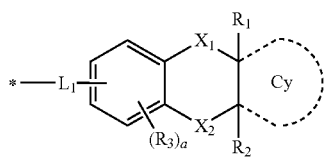
Formula 2

For example, $Ar_1$ of Formula 1 may be represented by any one of Formulae 3A through 3G below:

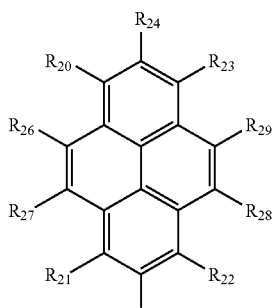
Formula 3A

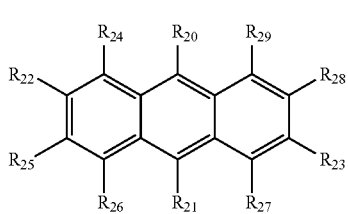
Formula 3B

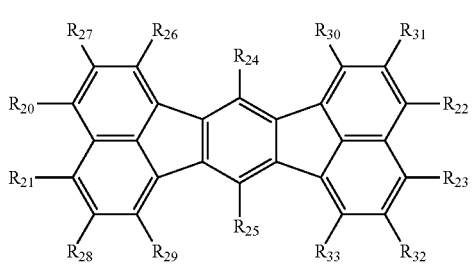
Formula 3C

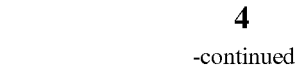
Formula 3D

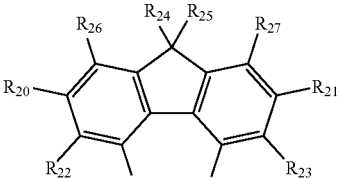
Formula 3E

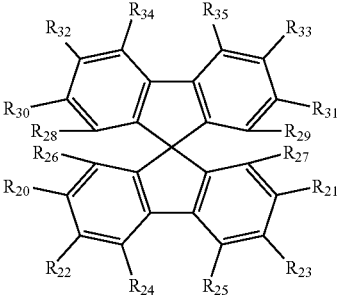
Formula 3F

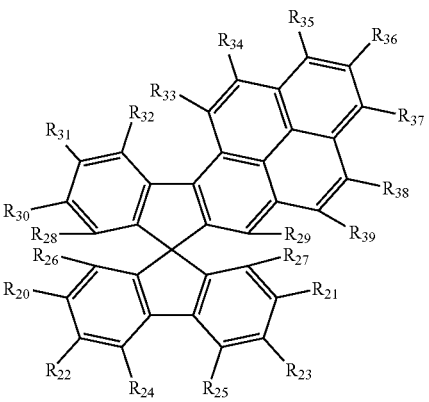
Formula 3G

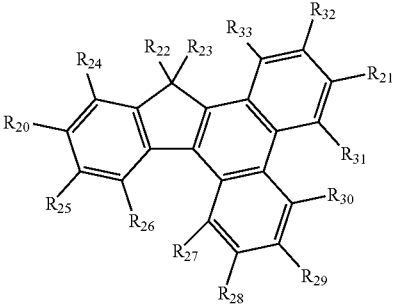

In Formulae 3A through 3G, $R_{20}$ through $R_{39}$ are each independently a binding site to $Ar_2$ (represented by Formula 2), hydrogen, deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_1$-$C_{60}$ alkylthio group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a (substituted or unsubstituted $C_1$-$C_{60}$ alkyl)amino group, a di(substituted or unsubstituted $C_1$-$C_{60}$ alkyl) amino group, or a (substituted or unsubstituted $C_5$-$C_{60}$ aryl)amino group or a di(substituted or unsubstituted $C_5$-$C_{60}$ aryl)amino group. One, two, three, four, five, or six groups selected from $R_{20}$ through $R_{39}$ may be the binding site to $Ar_2$ (represented by Formula 2). For example, one, two, three, or four groups selected from $R_{20}$ through $R_{39}$ above may be the binding site to $Ar_2$ (represented by Formula 2).

For example, $R_{20}$ through $R_{39}$ may each independently be a binding site to $Ar_2$ (represented by Formula 2); hydrogen, deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted alkoxy group, a substituted or unsubstituted $C_1$-$C_{20}$ alkylthio group, a substituted or unsubstituted $C_3$-$C_{20}$ cycloalkyl group, a substituted or unsubstituted $C_5$-$C_{20}$ aryl group, a substituted or unsubstituted $C_5$-$C_{20}$ aryloxy group, a substituted or unsubstituted $C_5$-$C_{20}$ arylthio group, a substituted or unsubstituted $C_2$-$C_{20}$ heteroaryl group, a (substituted or unsubstituted $C_1$-$C_{20}$ alkyl)amino group, a di(substituted or unsubstituted $C_1$-$C_{20}$ alkyl) amino group, or a (substituted or unsubstituted $C_5$-$C_{20}$ aryl)amino group or a di(substituted or unsubstituted $C_5$-$C_{20}$ aryl)amino group. One, two, three, four, five, or six groups selected from $R_{20}$ through $R_{39}$ may be the binding site to $Ar_2$ (represented by Formula 2).

For example, $R_{20}$ through $R_{39}$ may each independently be one of a binding site to $Ar_2$ (represented by Formula 2), hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl)amino group; or a di($C_6$-$C_{20}$ aryl)amino group, where the $C_6$-$C_{20}$ aryl group is a phenyl group, a naphthyl group, a fluorenyl group, a phenanthrenyl group, an anthryl group, a pyrenyl group, or a chrysenyl group. One, two, three, four, five, or six groups selected from $R_{20}$ through $R_{39}$ may be the binding site to $Ar_2$ (represented by Formula 2).

For example, $Ar_1$ may be represented by any one of Formula 3A-1 through Formula 3G-1, but is not limited thereto.

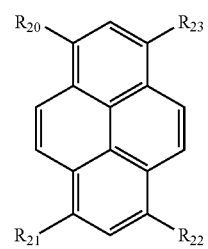

Formula 3A-1

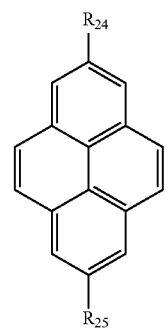

Formula 3A-2

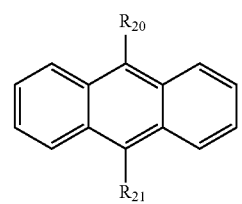

Formula 3B-1

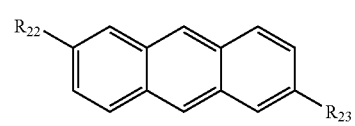

Formula 3B-2

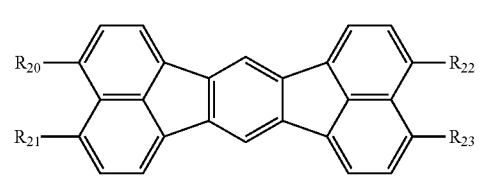

Formula 3C-1

Formula 3D-1
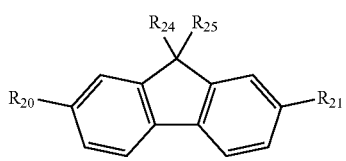

Formula 3D-2
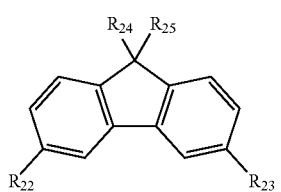

Formula 3E-1
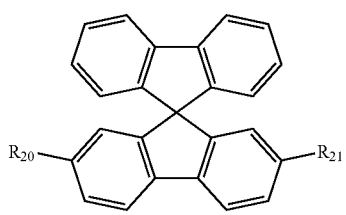

Formula 3E-2
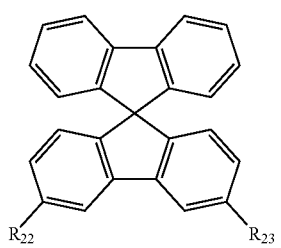

Formula 3F-1
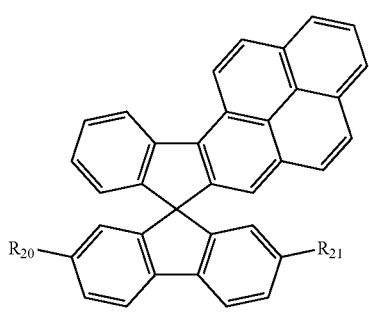

Formula 3F-2
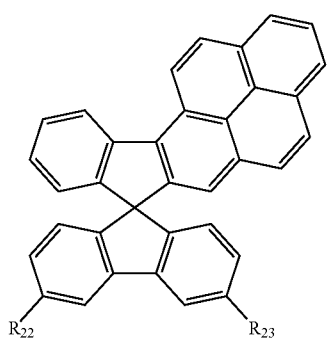

Formula 3G-1
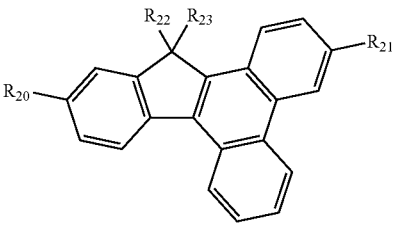

In the above Formula 3A-1 through 3G-1, $R_{20}$ through $R_{25}$ may each independently be a binding site to $Ar_2$ (represented by Formula 2); hydrogen, deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolylgroup; an imidazolyl group; an imidazolinyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl) amino group; and a di($C_6$-$C_{20}$ aryl)amino group, where the $C_6$-$C_{20}$ aryl group is a phenyl group, a naphthyl group, a fluorenyl group, a phenanthrenyl group, an anthryl group, a pyrenyl group, or a chrysenyl group. Also, i) at least one of $R_{20}$ through $R_{23}$ in Formulae 3A-1 and 3C-1 may be a binding site to $Ar_2$ (represented by Formula 2), ii) at least one of $R_{24}$ through $R_{25}$ in Formula 3A-2 may be a binding site to $Ar_2$ (represented by Formula 2), iii) at least one of $R_{20}$ through $R_{21}$ in Formulae 3B-1, 3D-1, 3E-1, 3F-1, and 3G-1 may be a binding site to $Ar_2$ (represented by Formula 2), and iv) at least one of $R_{22}$ through $R_{23}$ in Formulae 3B-2, 3D-2, 3E-2, and 3F-2 may be a binding site to $Ar_2$ (represented by Formula 2).

According to an embodiment, $Ar_1$ may be represented by Formula 3A-1 or 3B-1, but is not limited thereto.

$X_1$ in Formula 2 may be $N(R_{11})$, $B(R_{11})$, or $Si(R_{11})(R_{12})$, wherein $R_{11}$ and $R_{12}$ may each independently be hydrogen, deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzopuranyl group, a substituted or unsubstituted triazinyl group, or a substituted or unsubstituted oxadiazolyl group.

For example, $X_1$ in Formula 2 may be $N(R_{11})$, $B(R_{11})$, or $Si(R_{11})(R_{12})$, and $R_{11}$ and $R_{12}$ may each independently be represented by any one of Formulae 4A through 4H.

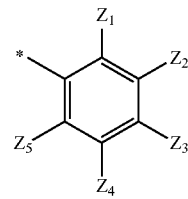

Formula 4A

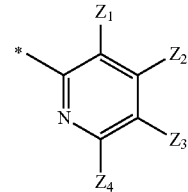

Formula 4B

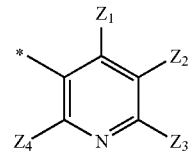

Formula 4C

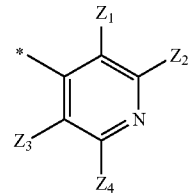

Formula 4D

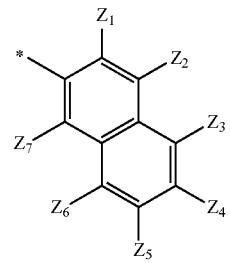

Formula 4E

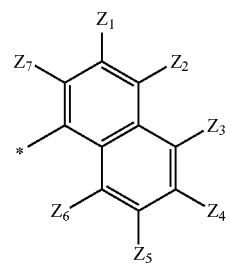

Formula 4F

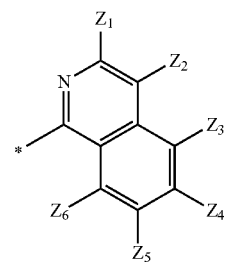

Formula 4G

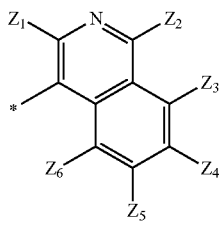

Formula 4H

In Formulae 4A through 4F, $Z_1$ through $Z_7$ may each independently be hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl)amino group; and a di($C_6$-$C_{20}$ aryl)amino group, the $C_6$-$C_{20}$ aryl group may be a phenyl group, a naphthyl group, a fluorenyl group, a phenanthrenyl group, an anthryl group, a pyrenyl group, or a chrysenyl group.

In Formula 2, $X_1$ may be O or S. $X_2$ in Formula 2 may be a single bond or —[C($R_{15}$)($R_{16}$)]$_n$—, where n is 1 or 2. For a detailed description of $R_{15}$ and $R_{16}$, refer to the description of $R_{11}$. For example, $R_{15}$ and $R_{16}$ may be hydrogen.

According to an embodiment, $X_2$ in Formula 2 may be a single bond.

In Formula 2, $L_1$ may be a single bond, a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted pycenylene group, a substituted or unsubstituted perylenylene group, a substituted or unsubstituted pentacenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinyl group, a substituted or unsubstituted quinolinyl group, a substituted or unsubstituted phthalazinyl group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, or a substituted or unsubstituted oxadiazolylene group.

For example, $L_1$ may be a single bond, a substituted or unsubstituted phenylene group, a substituted or unsubstituted naphthylene group, a substituted or unsubstituted anthrylene group, a substituted or unsubstituted pyridinylene group, or a substituted or unsubstituted quinolinylene group, but is not limited thereto.

For example, $L_1$ in Formula 2 may be a single bond or any one from Formulae 5A through 5K below:

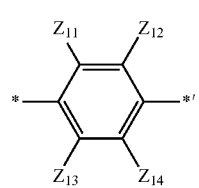

Formula 5A

-continued

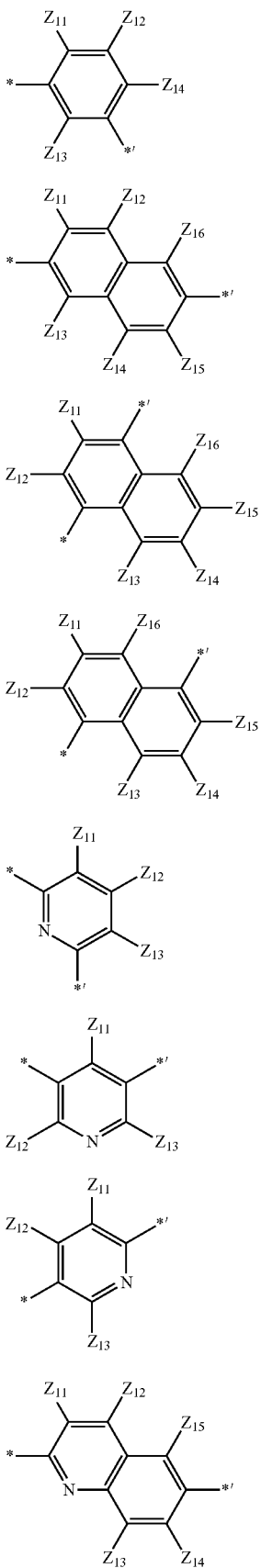

Formula 5B

Formula 5C

Formula 5D

Formula 5E

Formula 5F

Formula 5G

Formula 5H

Formula 5I

Formula 5J

Formula 5K

In Formulae 5A through 5K, $Z_{11}$ through $Z_{16}$ may each independently be one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolyl group; an imidazolyl group; an imidazolynyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl) amino group; and a di($C_6$-$C_{20}$ aryl)amino group, where the $C_6$-$C_{20}$ aryl group may be a phenyl group, a naphthyl group, a fluorenyl group, a phenanthrenyl group, an anthryl group, a pyrenyl group, or a chrysenyl group.

For example, $Ar_2$ may be represented by any one of Formulae 2A through 2K below:

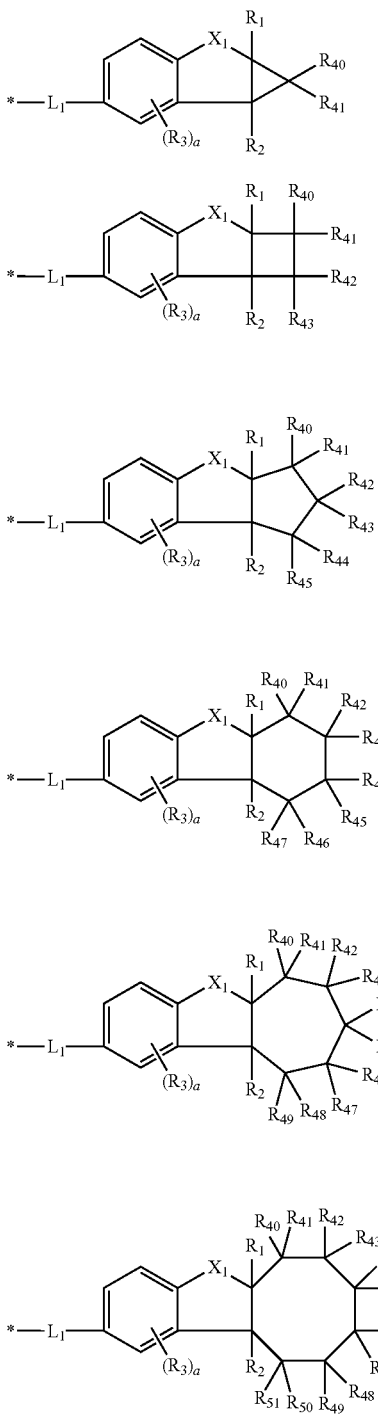

Formula 2A
Formula 2B
Formula 2C
Formula 2D
Formula 2E
Formula 2F

In Formulae 2A through 2F, $X_1$, $L_1$, $R_1$ through $R_3$, a, and * are as described above. $R_{40}$ through $R_{51}$ may each independently be one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl) amino group; and a di($C_6$-$C_{20}$ aryl)amino group, where the $C_6$-$C_{20}$ aryl group may be a phenyl group, a naphthyl group, a fluorenyl group, a phenanthrenyl group, an anthryl group, a pyrenyl group, or a chrysenyl group.

For example, $R_{40}$ through $R_{51}$ may each independently be one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl; a $C_1$-$C_{10}$ alkoxy group; a $C_1$-$C_{10}$ alkylthio group; and a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof, but is not limited thereto.

In Formula 2, $R_1$ through $R_3$ may each independently be one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; and a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof.

According to an embodiment, $Ar_2$ may be represented by Formula 2-1 below, but is not limited thereto:

Formula 2-1

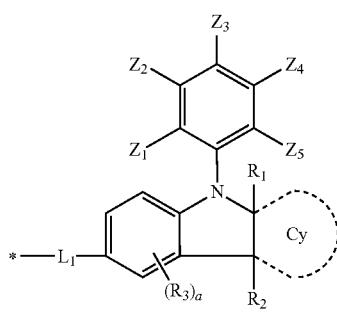

In Formula 2-1, $L_1$, $R_1$ through $R_3$, a, Cy and $Z_1$ through $Z_5$ are as described above.

In some embodiments of the condensed-cyclic compound, $Ar_1$ in Formula 1 may be one of Formulae 3A through 3G; q in Formula 1 may be one of 1 through 4; and $Ar_2$ may be a compound represented by one of Formulae 2A through 2K.

In some embodiments of the condensed-cyclic compound, $Ar_1$ in Formula 1 may be one of Formulae 3A-1 through 3G-1; q in Formula 1 may be one of 1 through 4; $X_1$ in Formula 2 may be $N(R_{11})$, $B(R_{11})$, or $Si(R_{11})(R_{12})$, and $R_{11}$ and $R_{12}$ may each independently be represented by one of Formulae 4A through 4H; $X_2$ in Formula 2 may be a single bond; Cy in Formula 2 may be a substituted or unsubstituted $C_6$ cycloalkane (here, the substituted cycloalkane is as described above with respect to $R_{40}$); and $L_1$ in Formula 2 may be a compound represented by Formulae 5A through 5K.

Also, in some embodiments of the condensed-cyclic compound, $Ar_1$ in Formula 1 may be Formula 3A-1 or 3B-1; q in Formula 1 may be one of 1 through 4; and $Ar_2$ may be Formula 2-1.

In some embodiments, the condensed-cyclic compound may be any one of Compounds 8 through 2000 represented by Formulae 8 through 2000, but is not limited thereto:

Formula 8

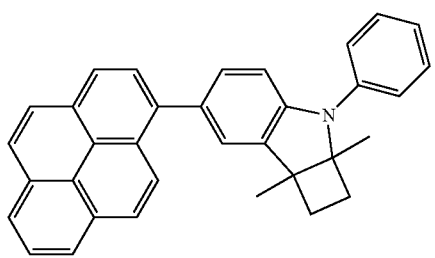

Formula 9

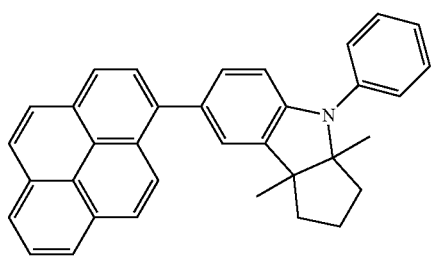

Formula 10

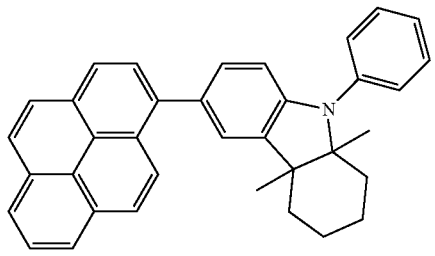

Formula 11

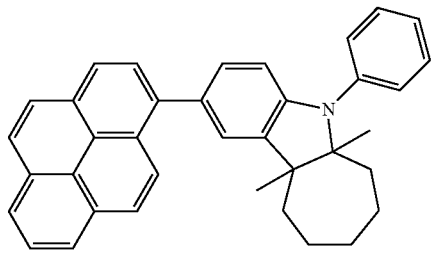

Formula 12

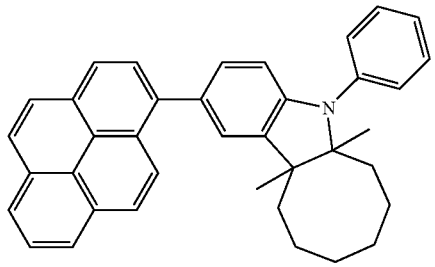

Formula 13

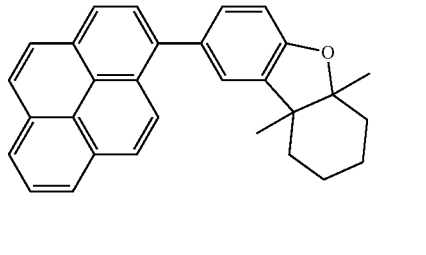

Formula 14

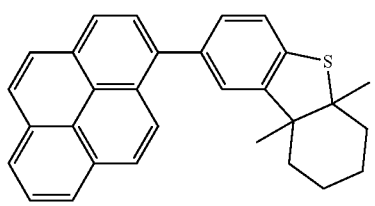

Formula 15

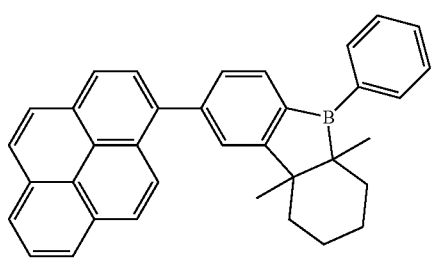

Formula 16
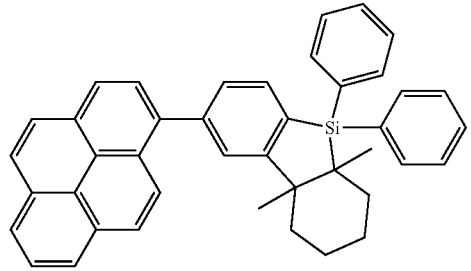
Formula 17
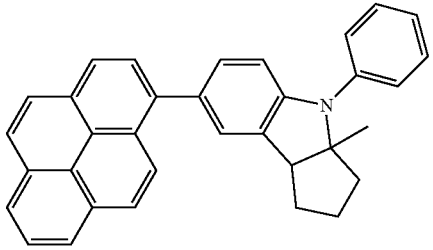
Formula 18
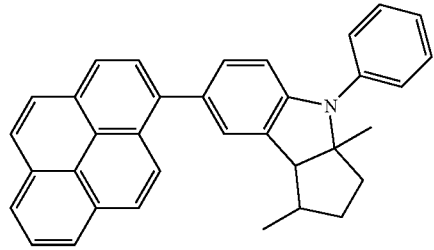
Formula 19
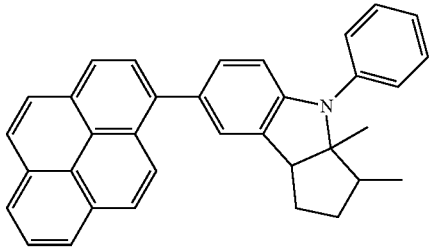
Formula 20
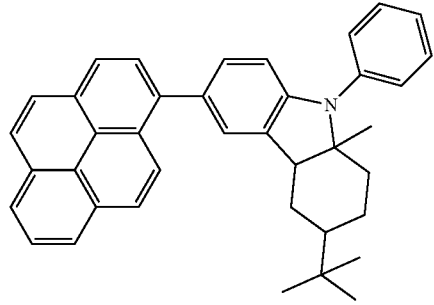
Formula 21
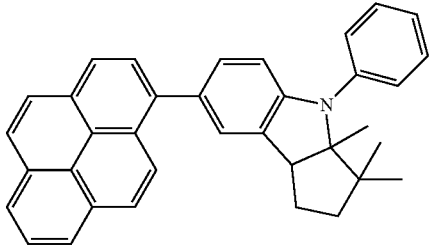
Formula 22
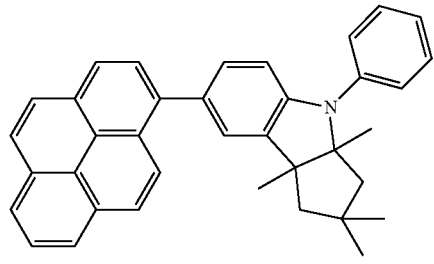
Formula 23
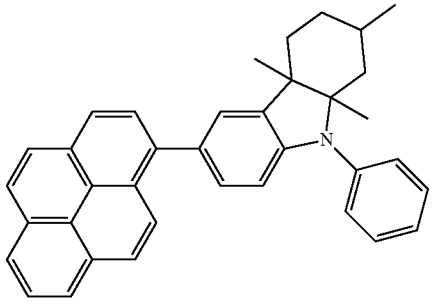
Formula 24
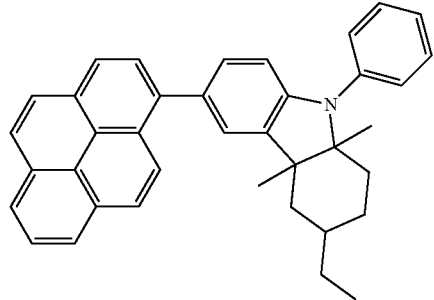
Formula 25
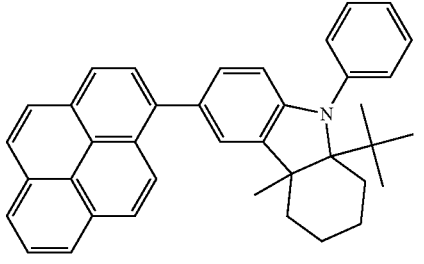

-continued
Formula 26
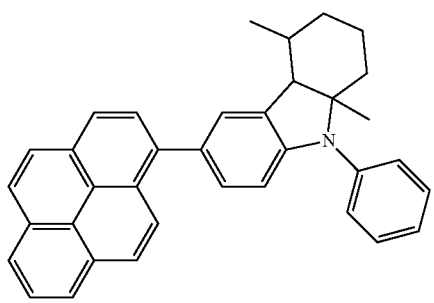
Formula 27
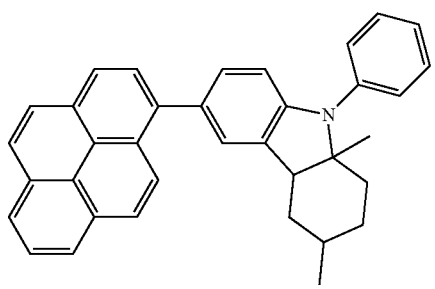
Formula 28
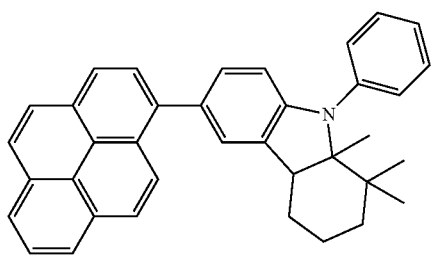
Formula 29
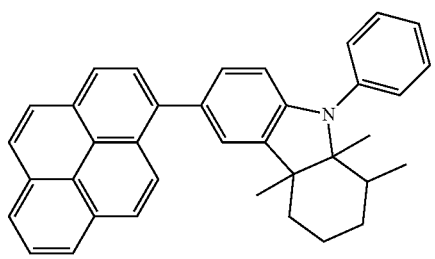
Formula 30
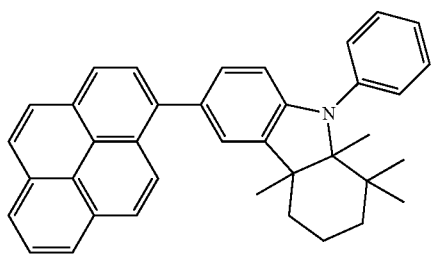
Formula 31
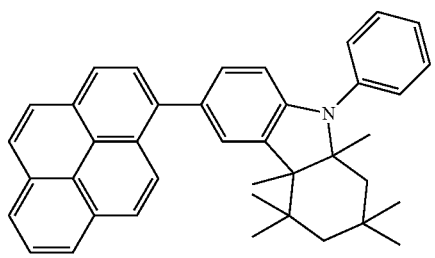
Formula 32
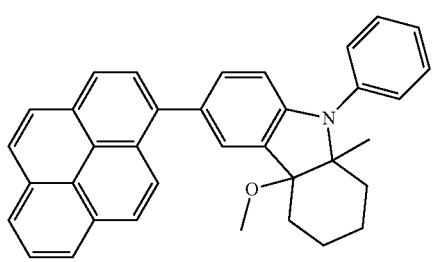
Formula 33
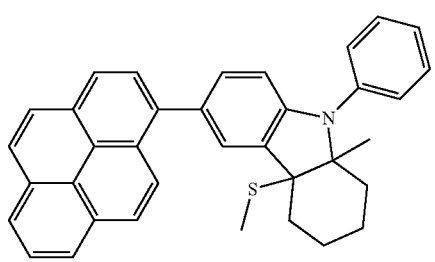
Formula 34
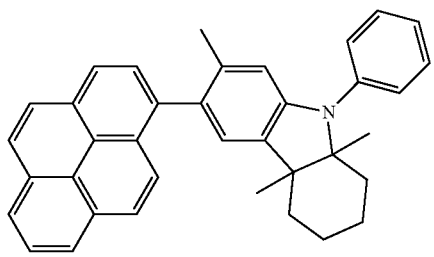
Formula 35
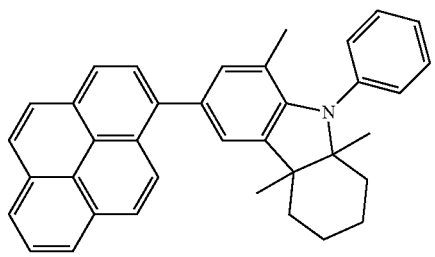
Formula 36
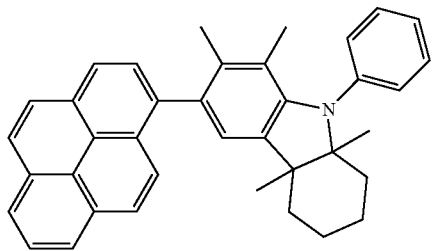
Formula 37
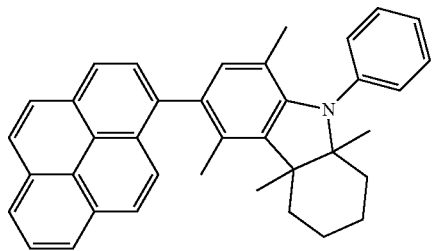

-continued
Formula 38
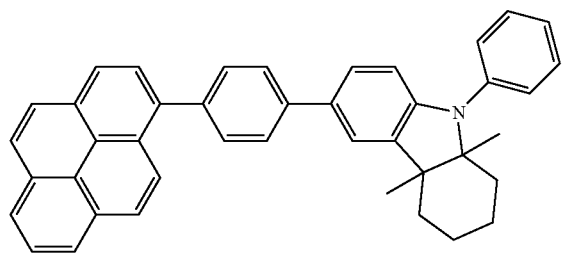
Formula 39
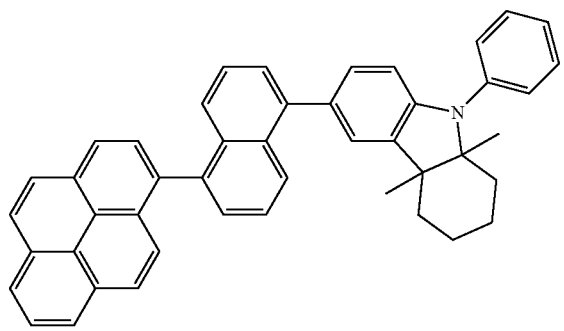
Formula 40
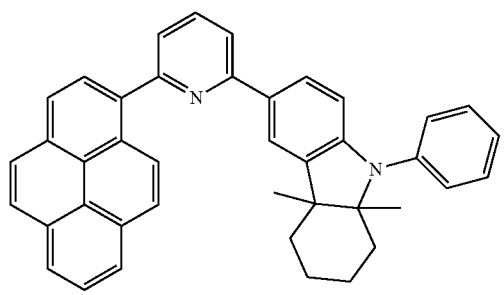
Formula 41
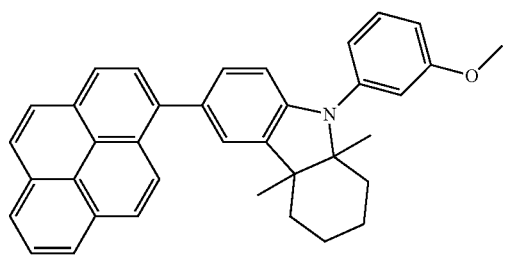
Formula 42
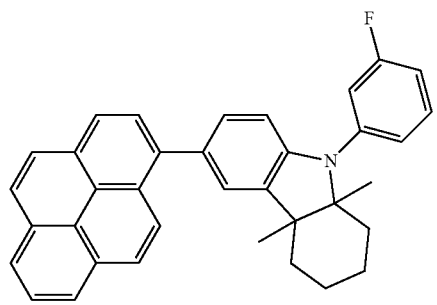
Formula 43
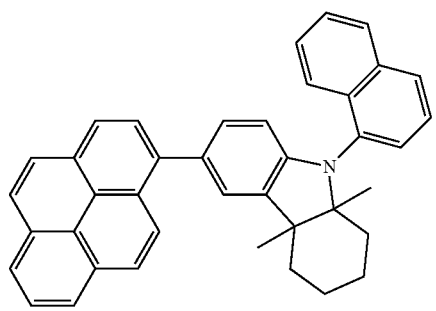
Formula 44
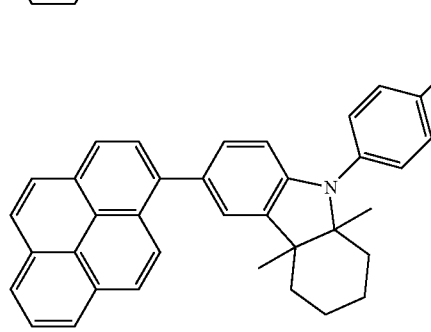
Formula 45
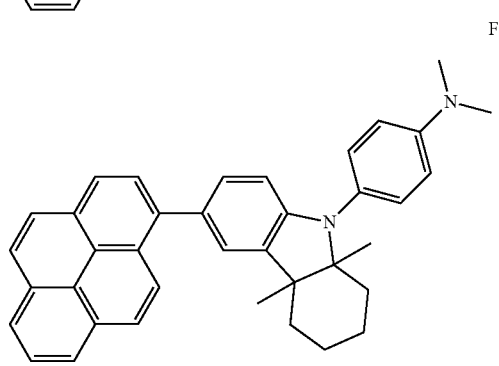
Formula 46
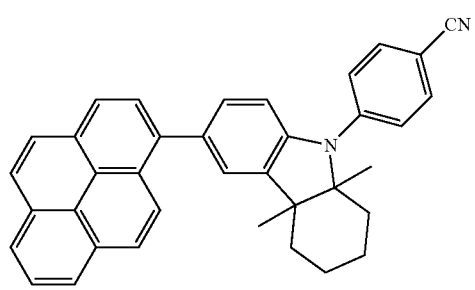
Formula 47
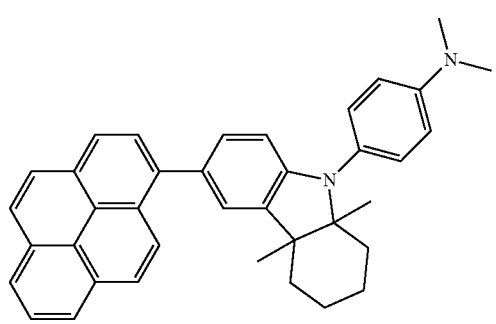
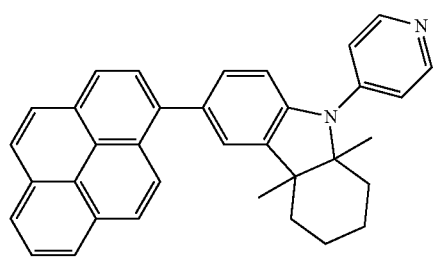
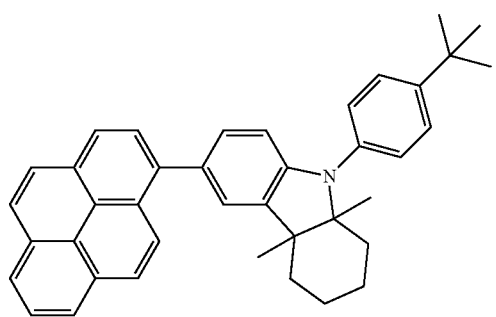

-continued
Formula 48
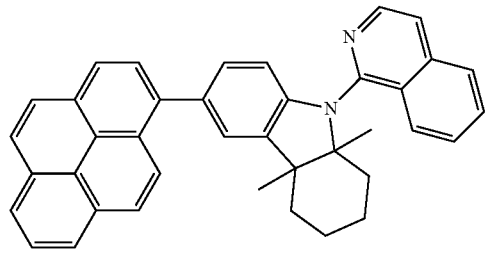
Formula 49
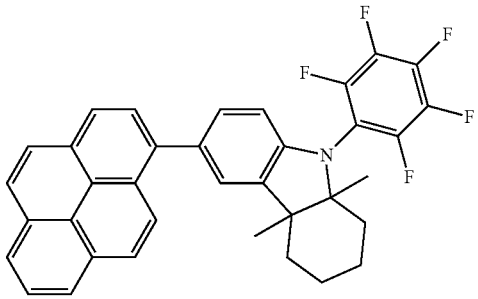
Formula 50
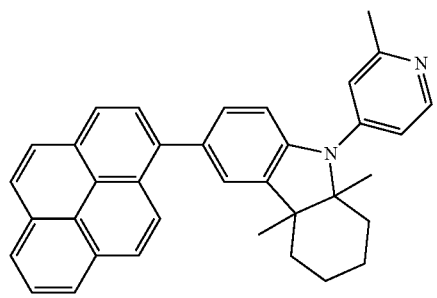
Formula 51
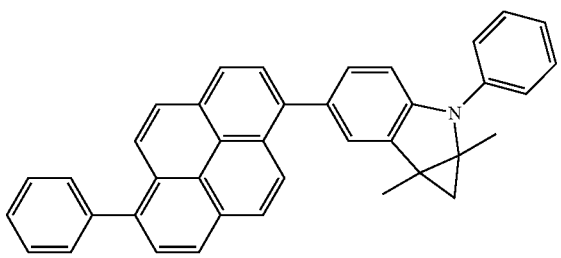
Formula 52
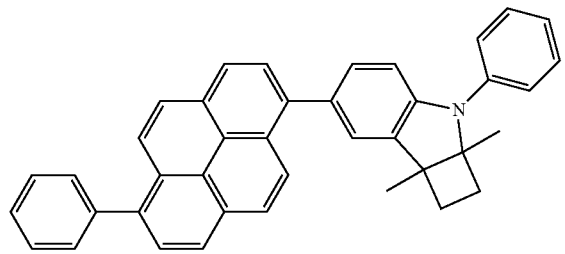
Formula 53
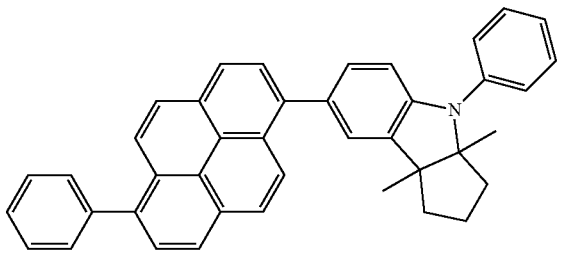
Formula 54
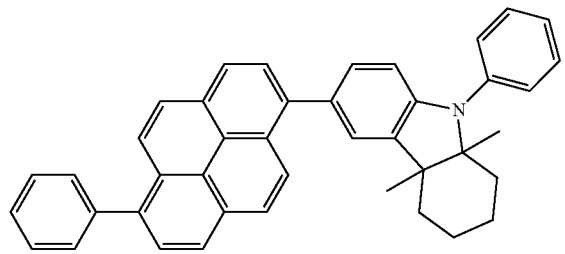
Formula 55
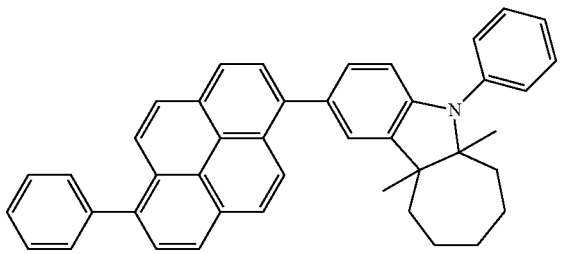
Formula 56
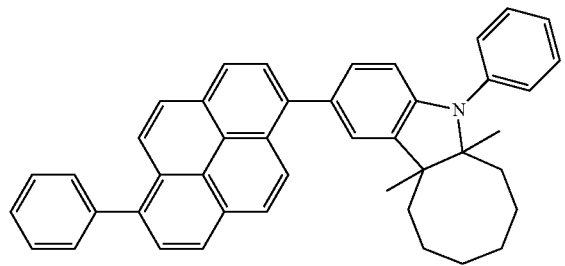
Formula 57

-continued
Formula 58
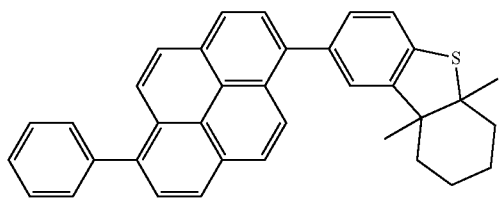
Formula 59
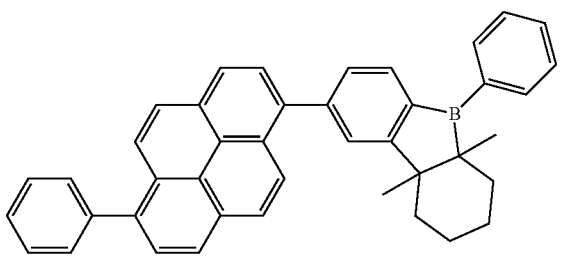
Formula 60
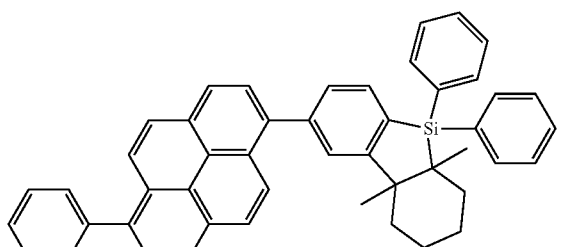
Formula 61
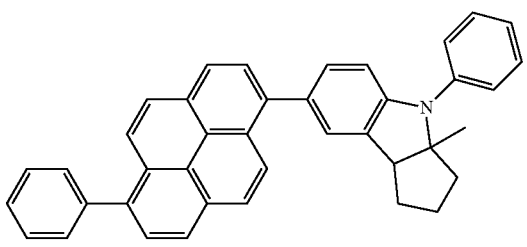
Formula 62
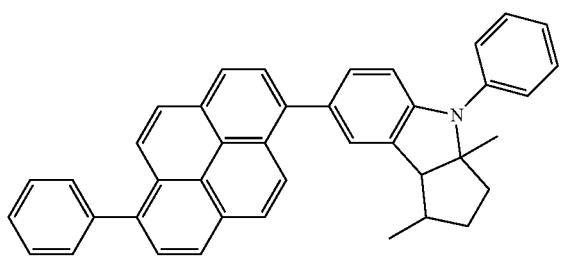
Formula 63
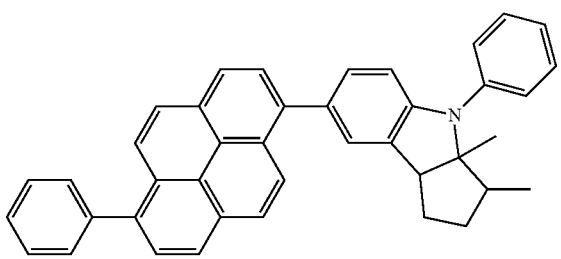
Formula 64
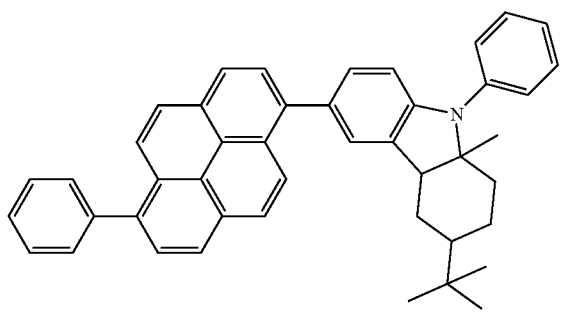
Formula 65
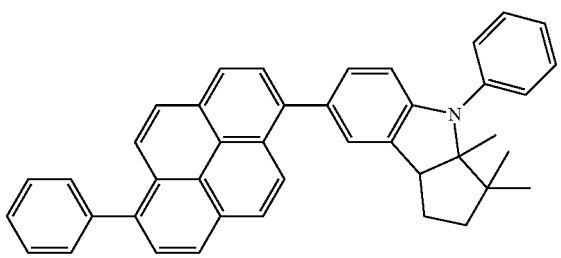
Formula 66
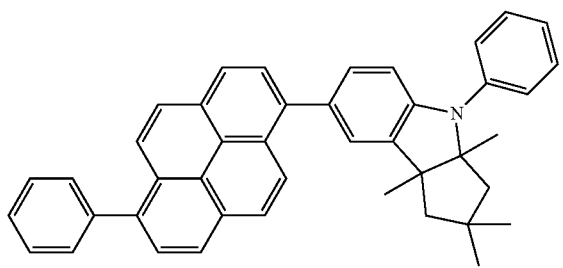
Formula 67
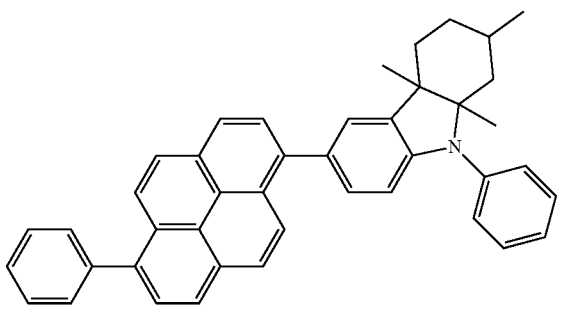

-continued
Formula 68
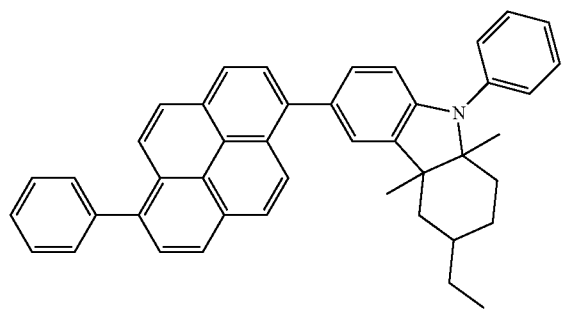
Formula 69
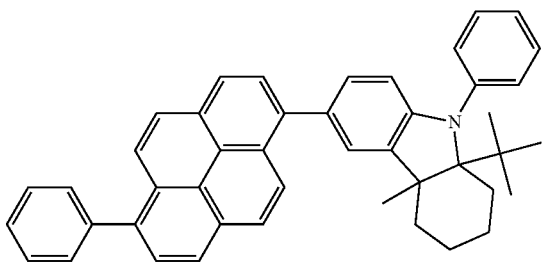
Formula 70
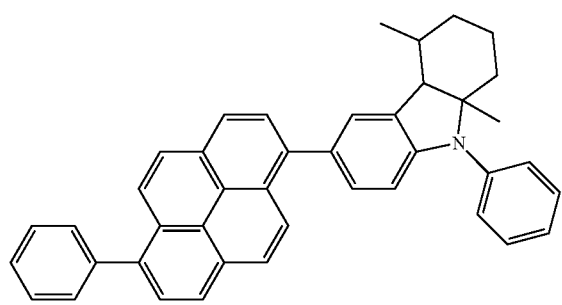
Formula 71
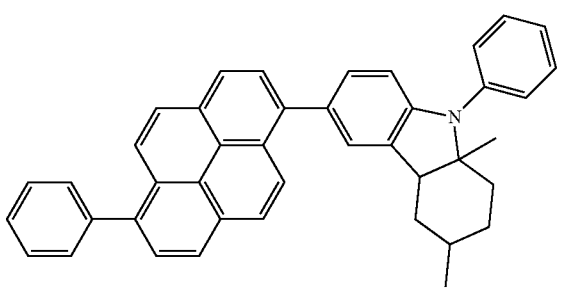
Formula 72
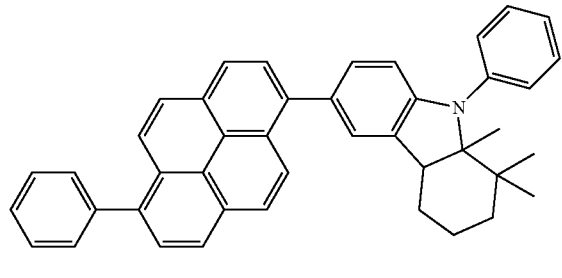
Formula 73
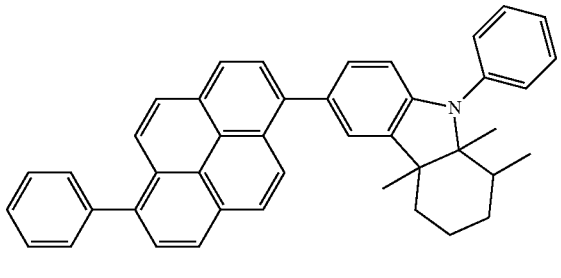
Formula 74
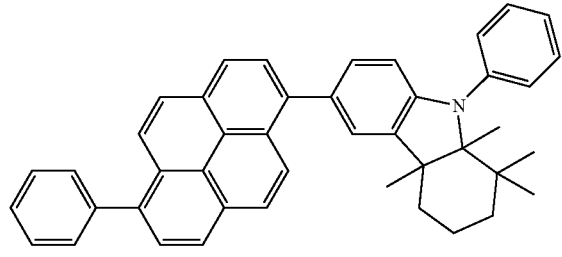
Formula 75
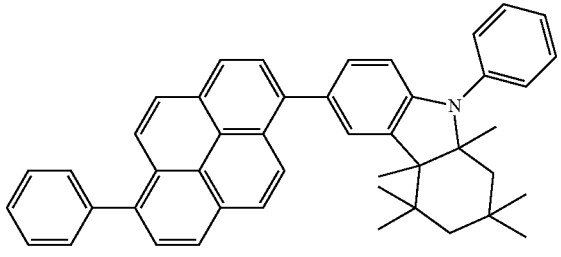
Formula 76
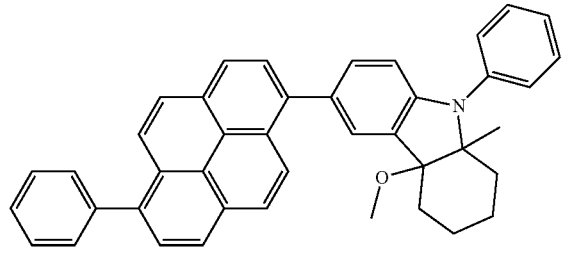
Formula 77
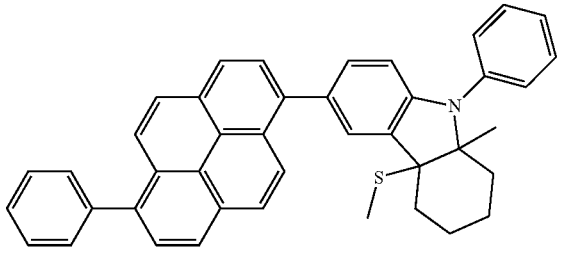

-continued
Formula 78
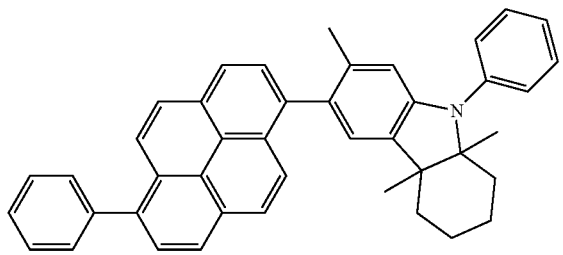
Formula 79
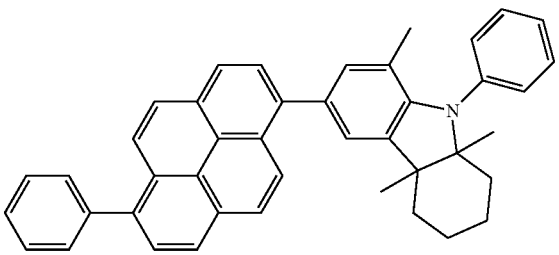
Formula 80
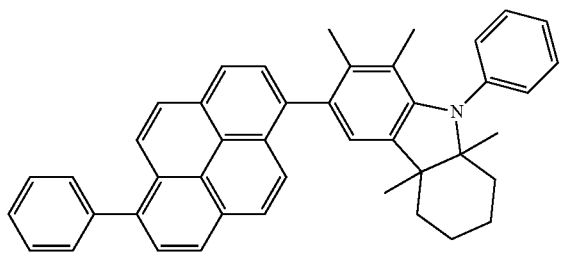
Formula 81
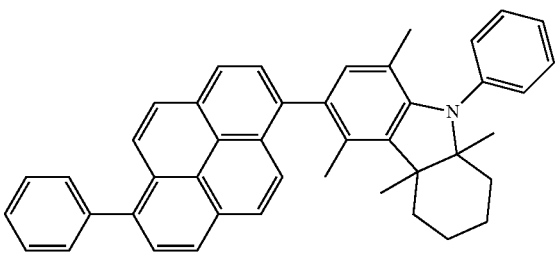
Formula 82
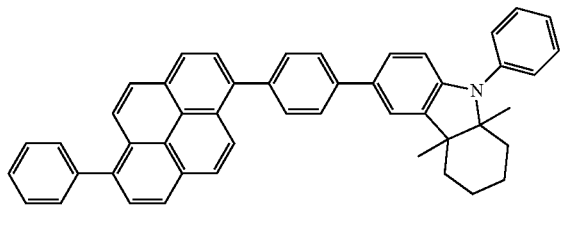
Formula 83
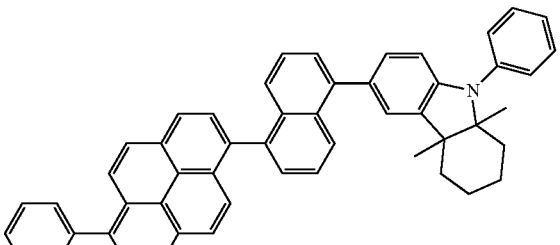
Formula 84
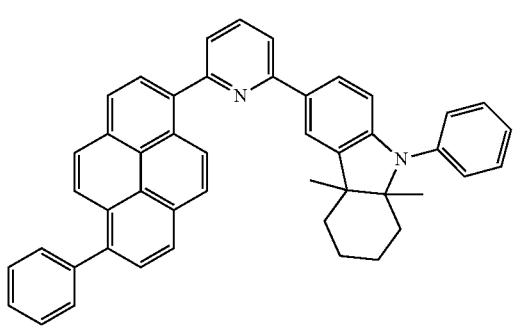
Formula 85
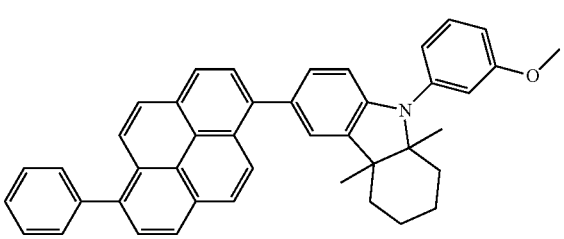
Formula 86
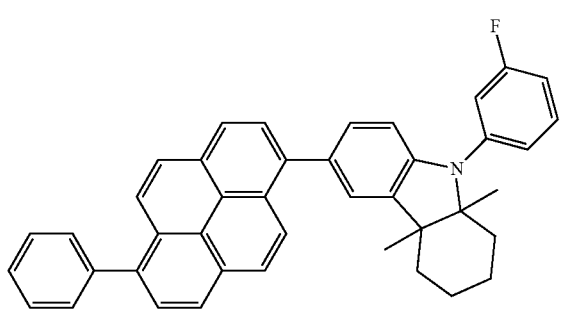
Formula 87
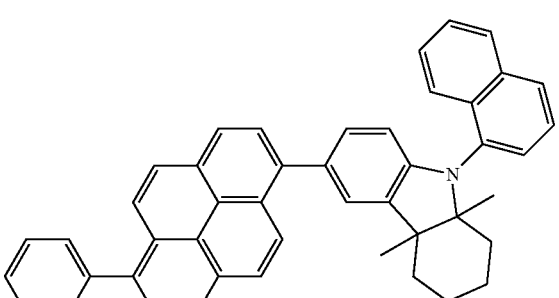

-continued
Formula 88
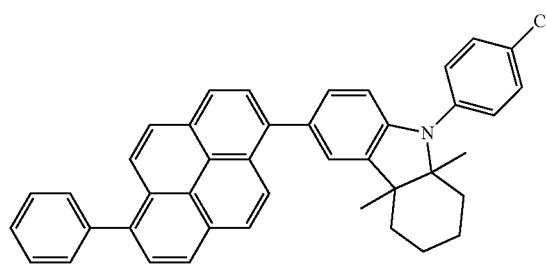
Formula 89
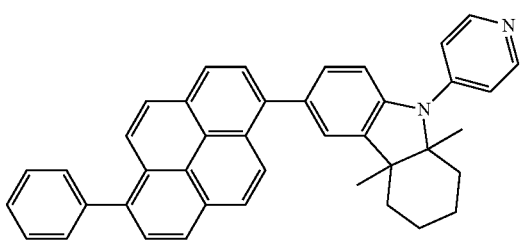
Formula 90
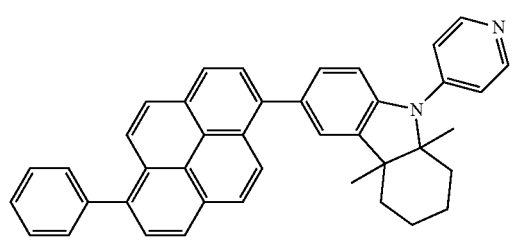
Formula 91
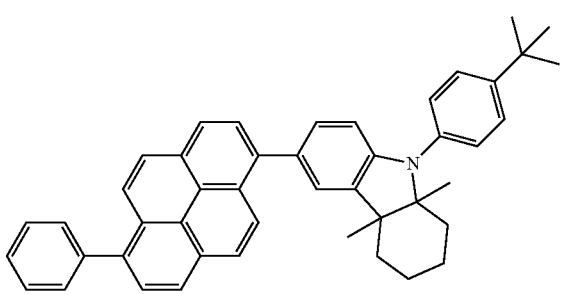
Formula 92
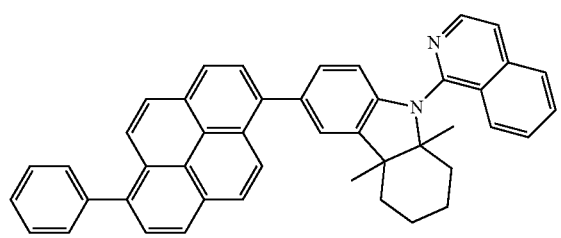
Formula 93
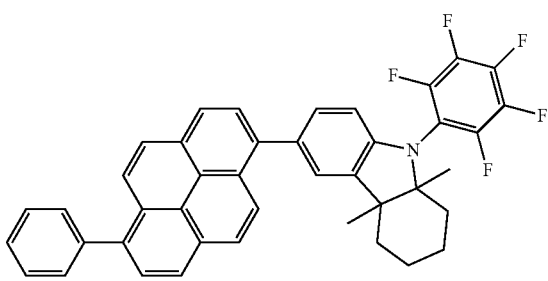
Formula 94
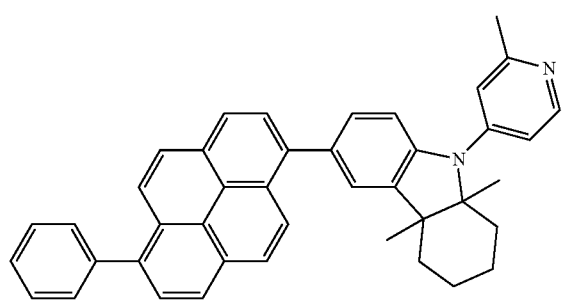
Formula 95
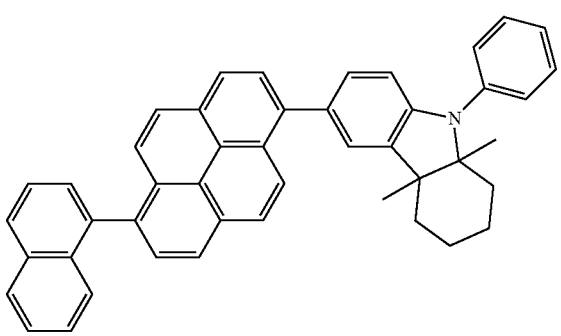
Formula 96
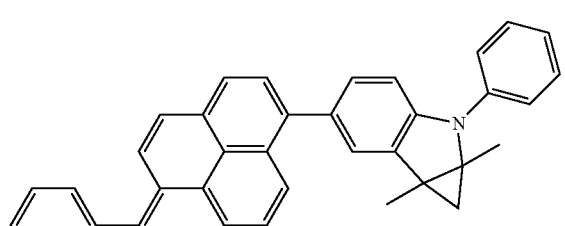
Formula 97
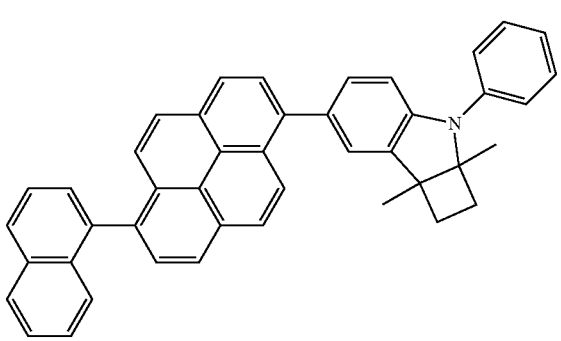

-continued
Formula 98
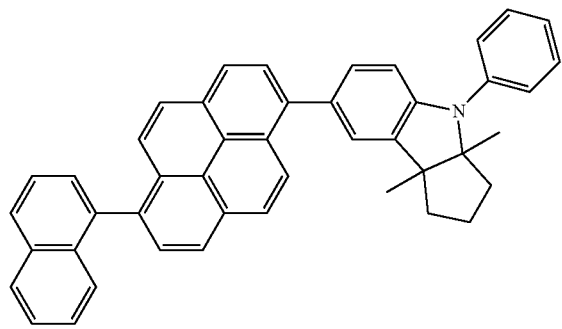
Formula 99
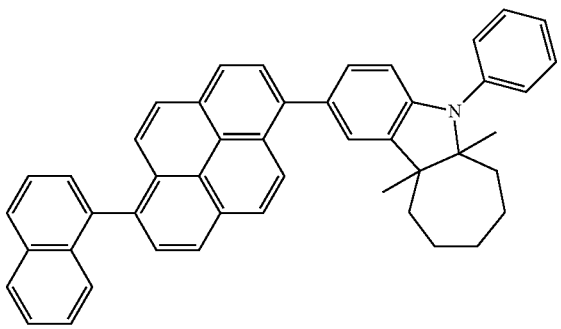
Formula 100
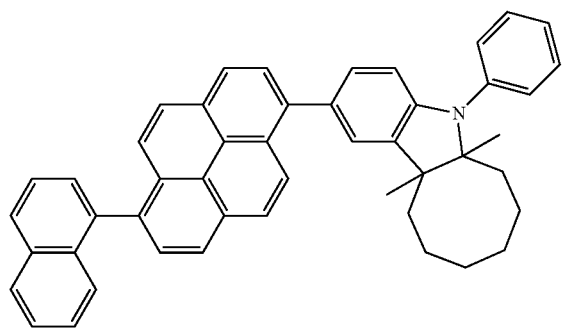
Formula 101
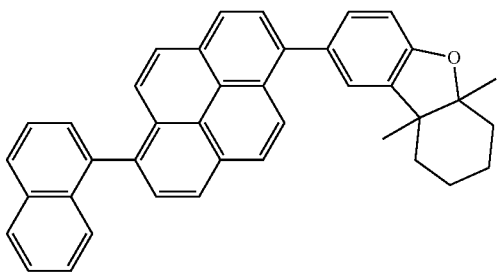
Formula 102
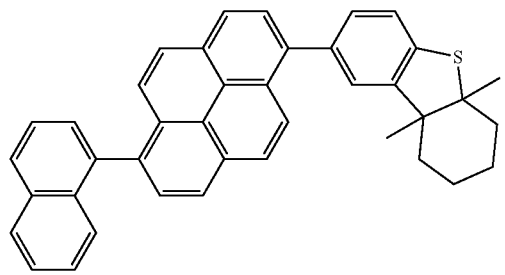
Formula 103
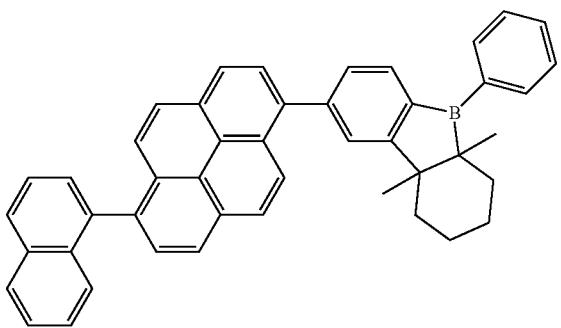
Formula 104
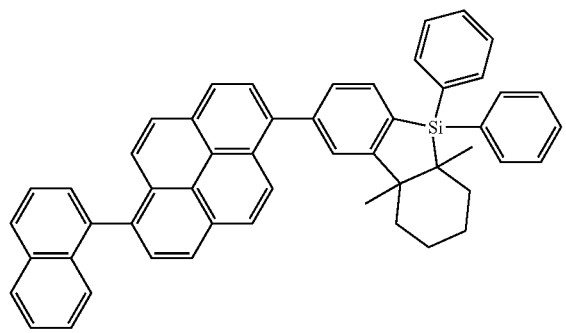
Formula 105
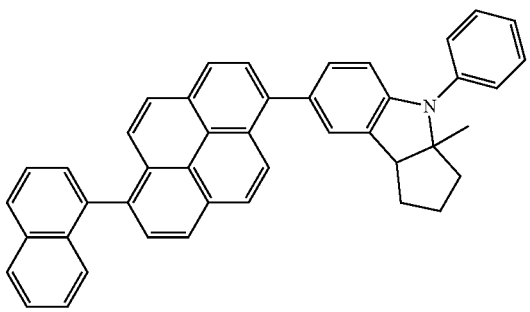

-continued
Formula 106
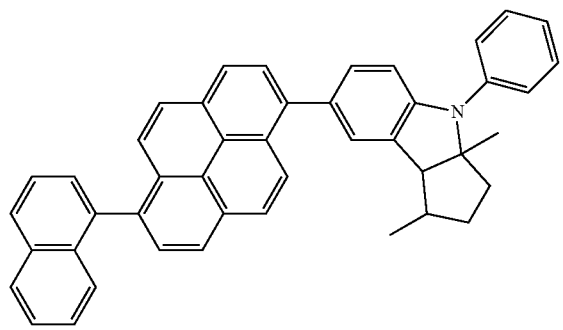
Formula 107
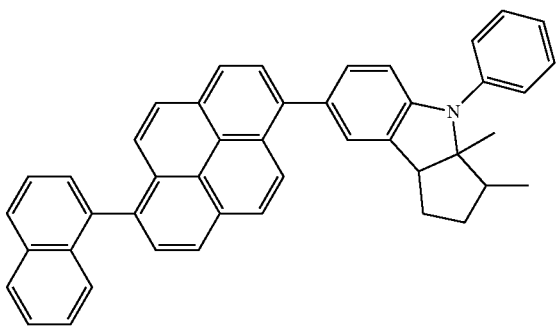
Formula 108
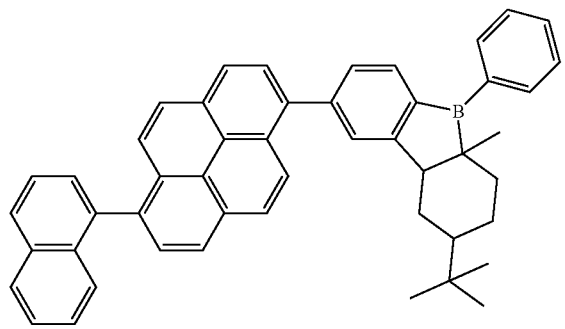
Formula 109
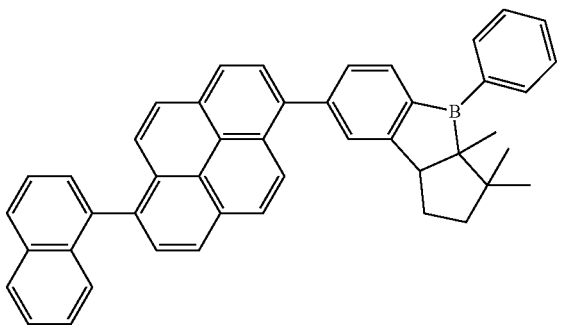
Formula 110
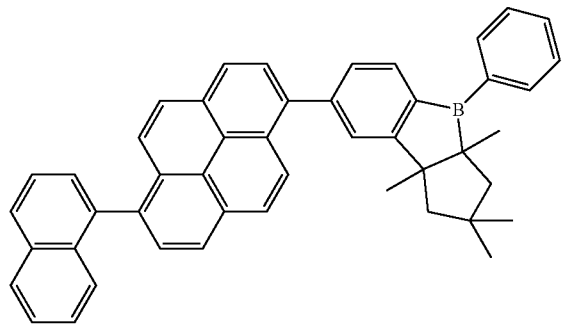
Formula 111
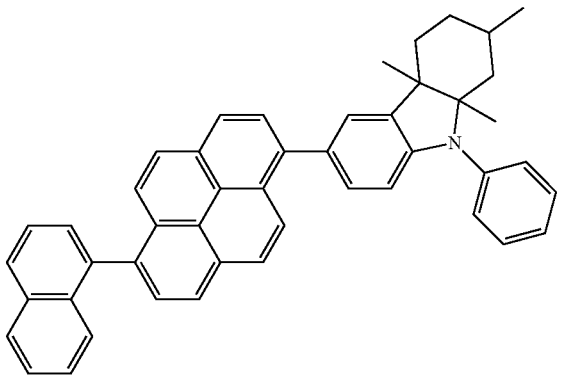
Formula 112
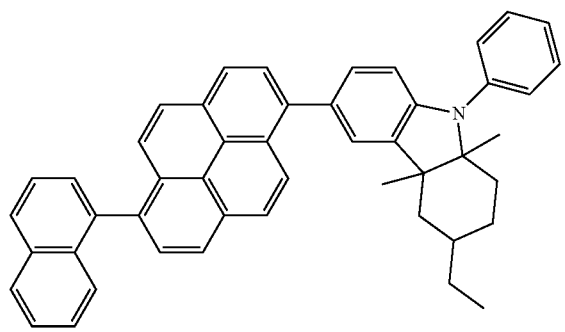
Formula 113
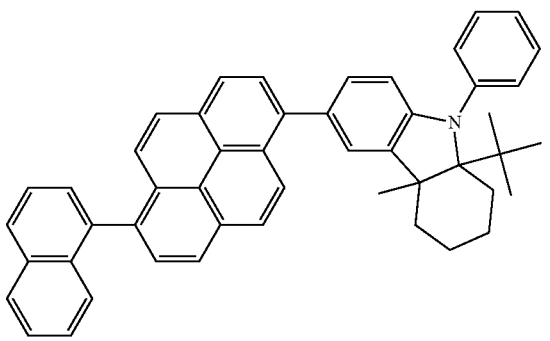

-continued
Formula 114
Formula 115
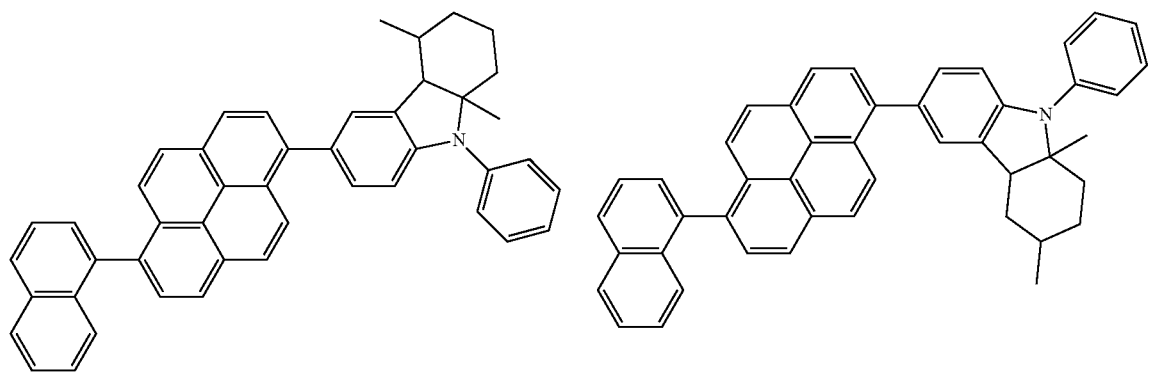
Formula 116
Formula 117
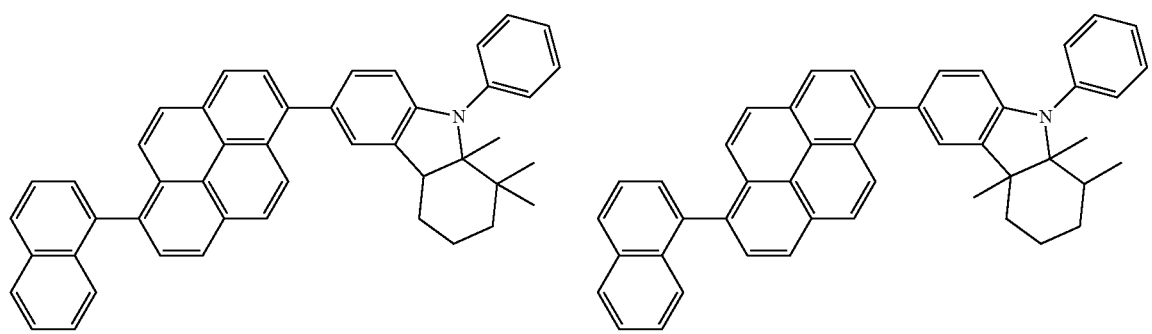
Formula 118
Formula 119
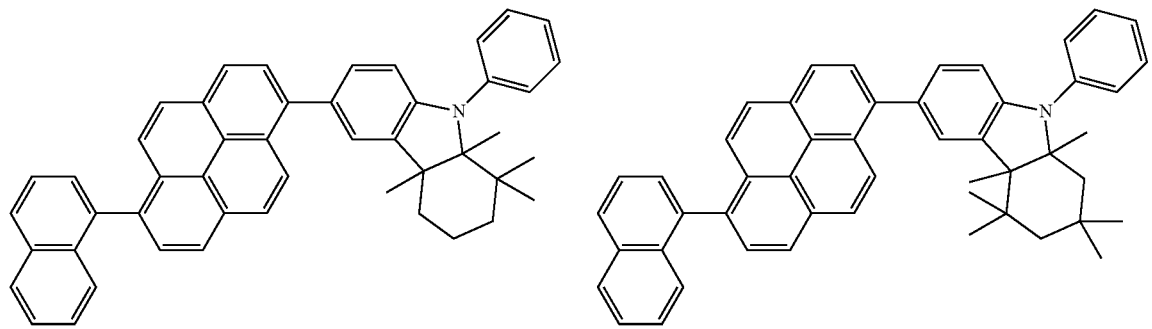
Formula 120
Formula 121
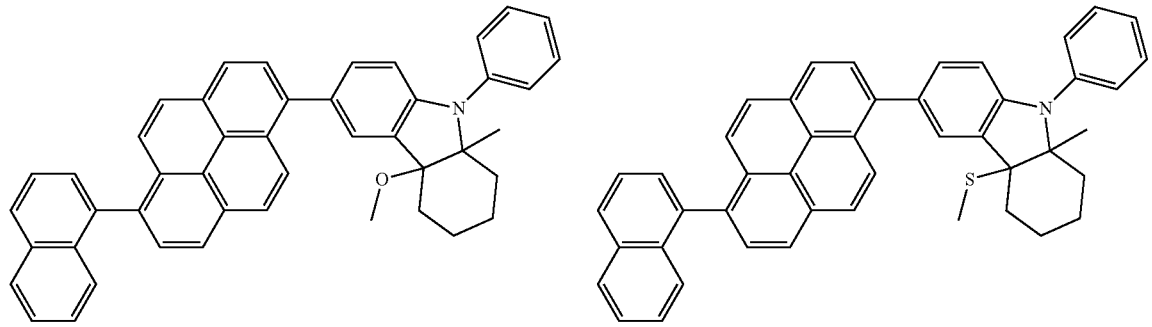

-continued
Formula 122
Formula 123
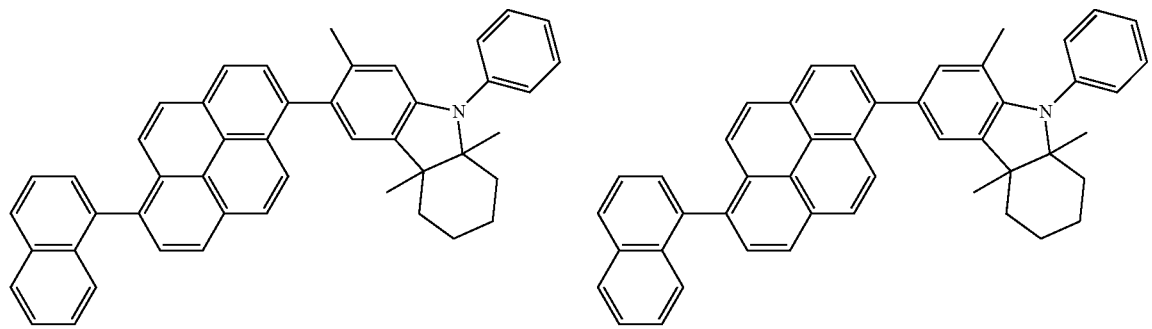
Formula 124
Formula 125
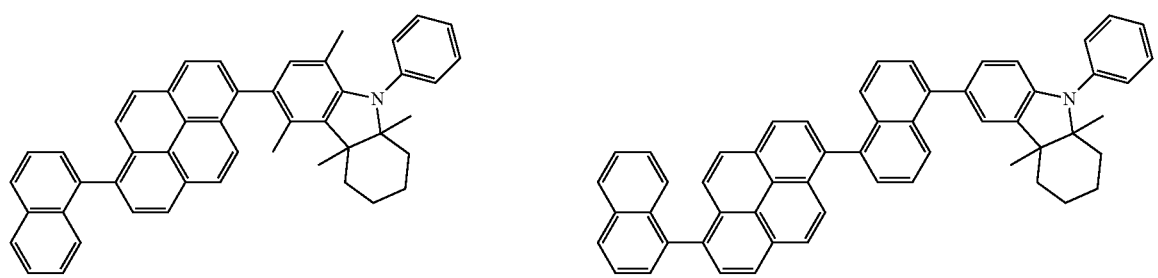
Formula 126
Formula 127
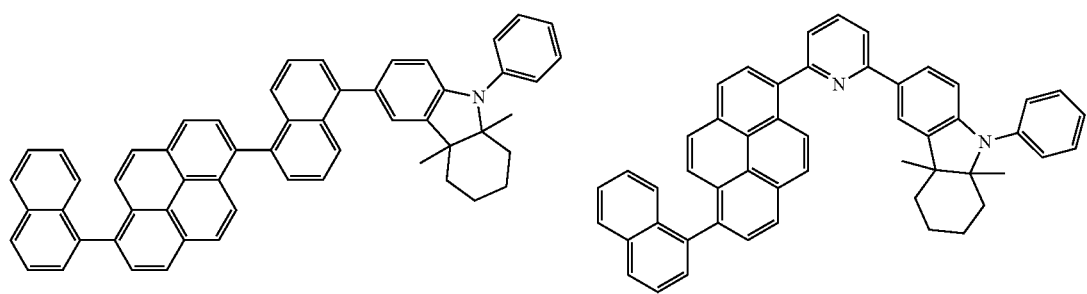
Formula 128
Formula 129
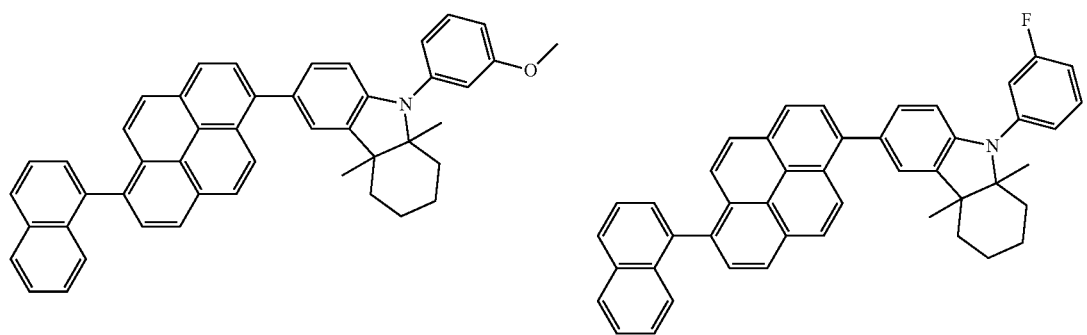

Formula 130
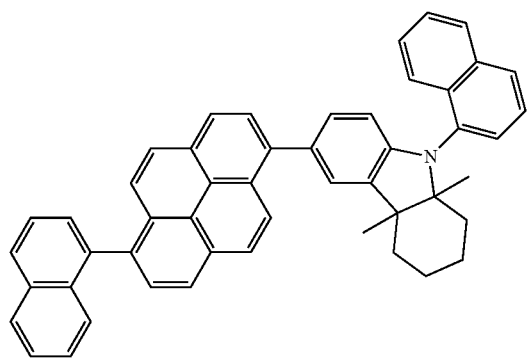
Formula 131
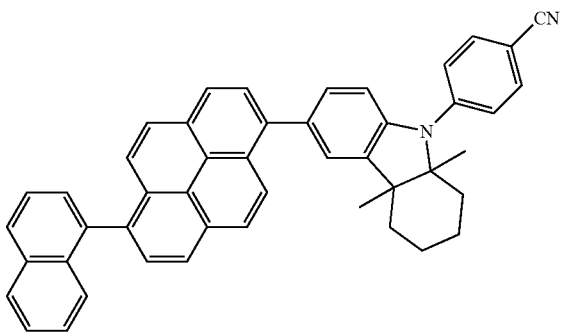
Formula 132
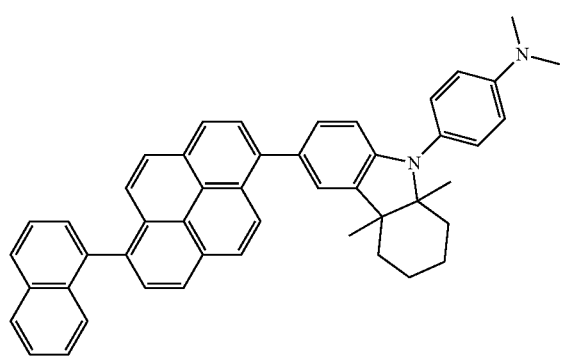
Formula 133
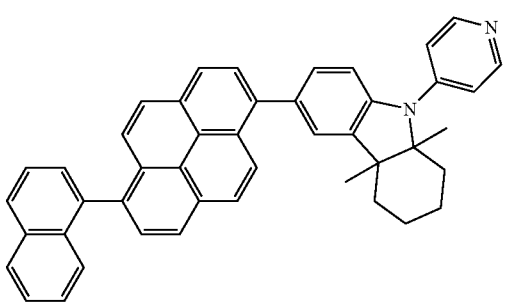
Formula 134
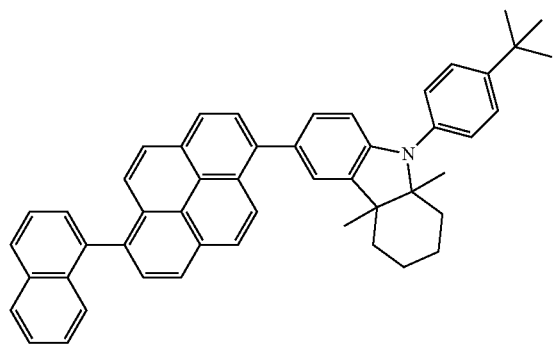
Formula 135
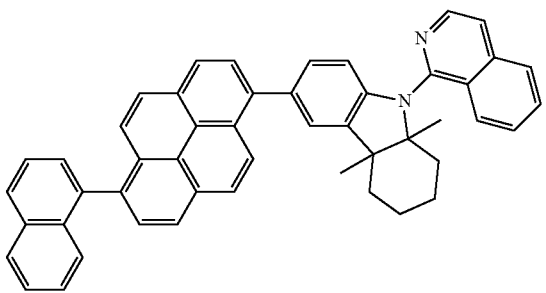
Formula 136
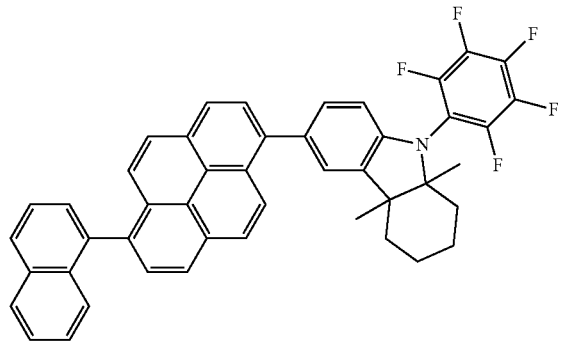
Formula 137
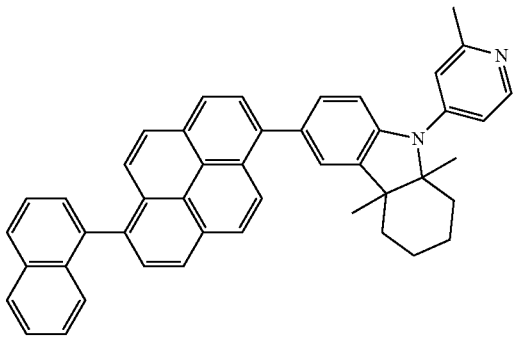

-continued
Formula 138
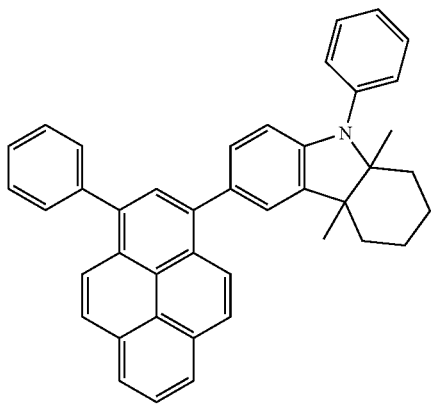
Formula 139
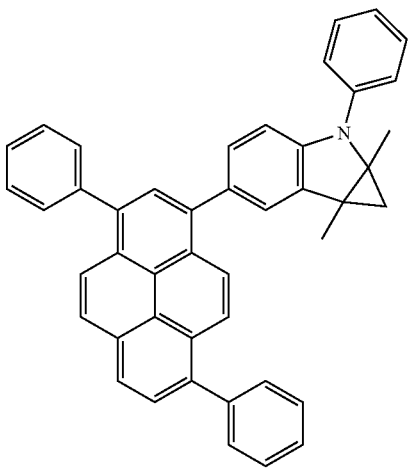
Formula 140
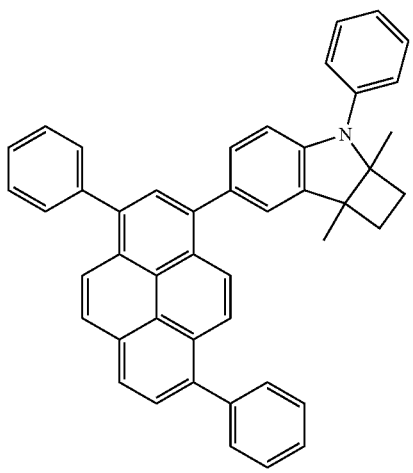
Formula 141
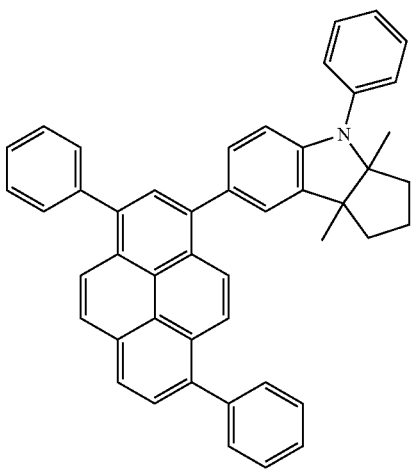
Formula 142
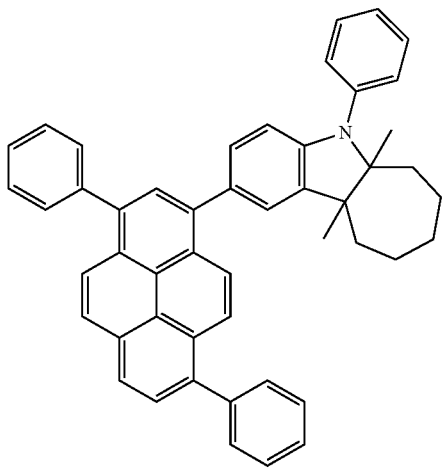
Formula 143
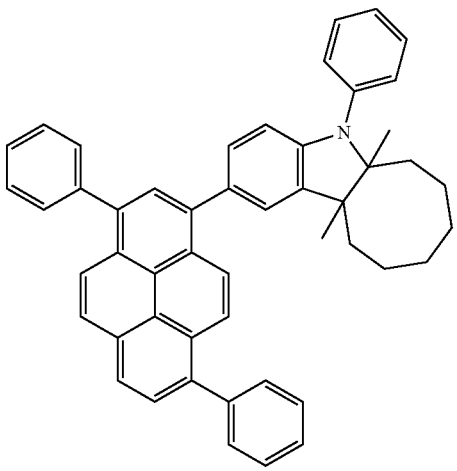

-continued
Formula 144
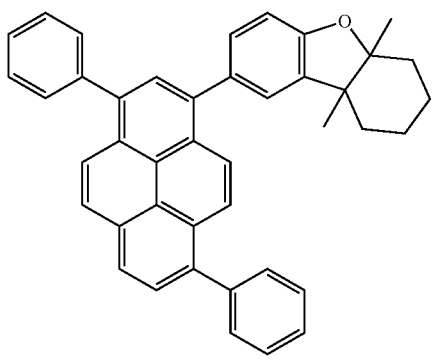
Formula 145
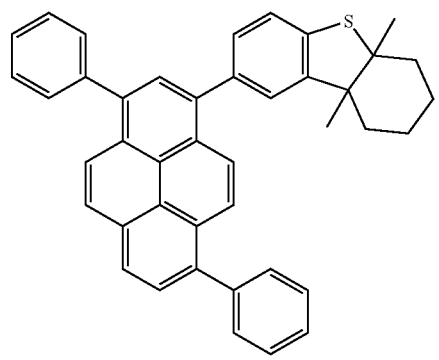
Formula 146
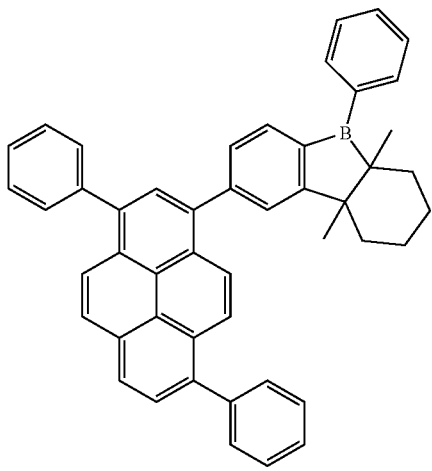
Formula 147
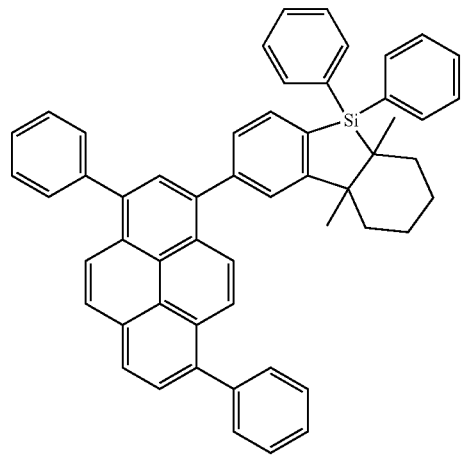
Formula 148
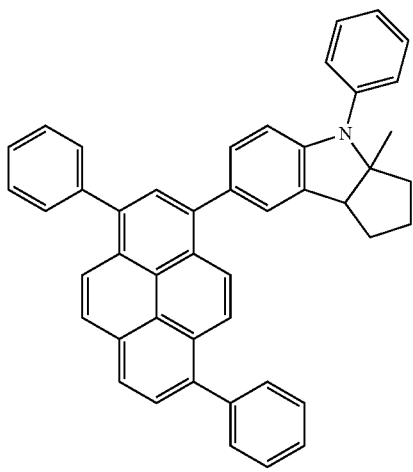
Formula 149
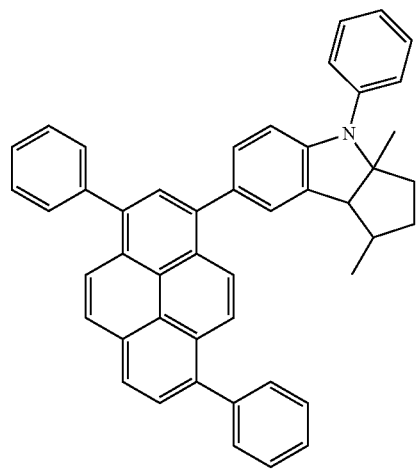

-continued
Formula 150
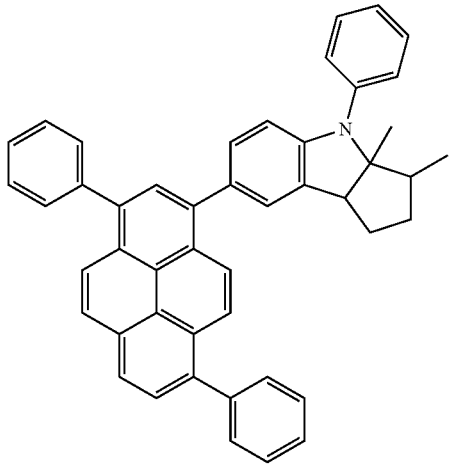
Formula 151
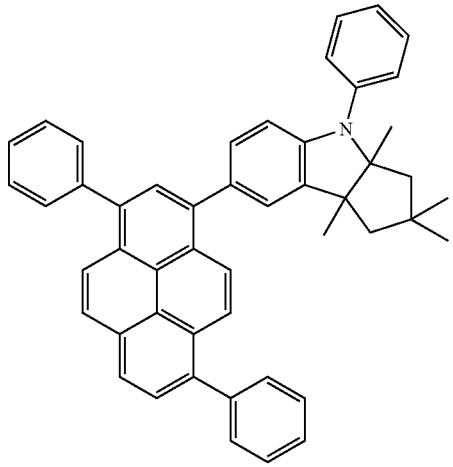
Formula 152
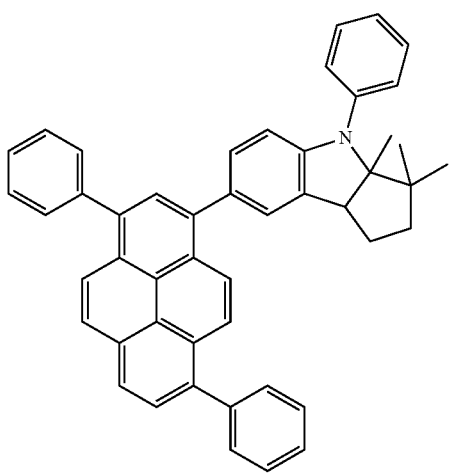
Formula 153
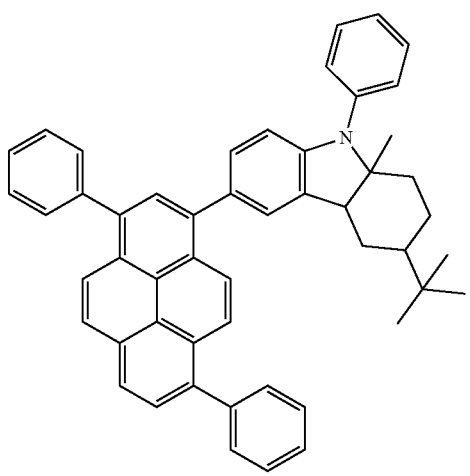
Formula 154
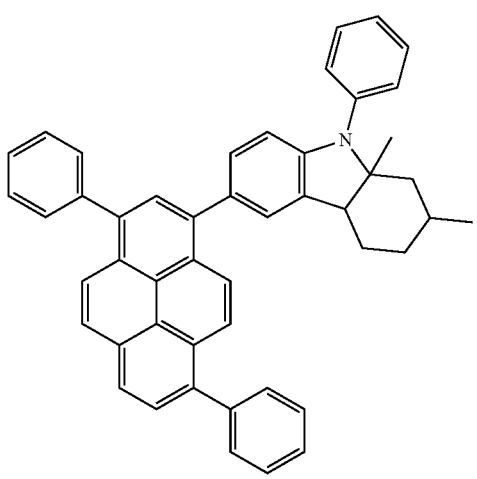
Formula 155
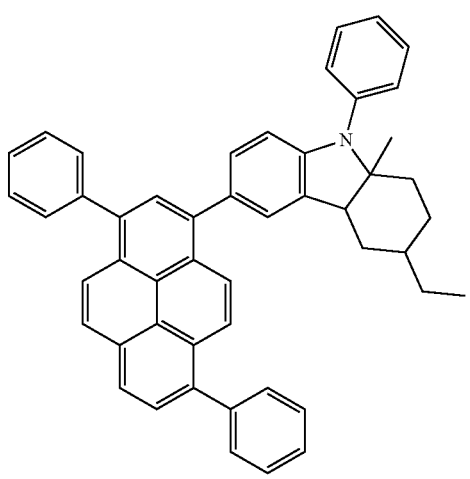

-continued
Formula 156
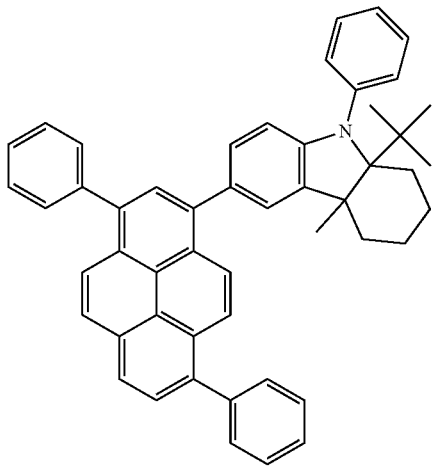
Formula 157
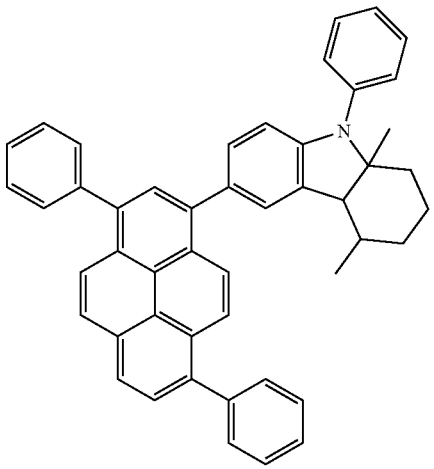
Formula 158
Formula 159
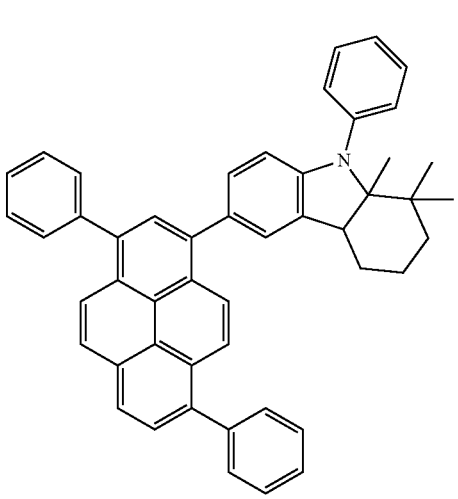
Formula 160
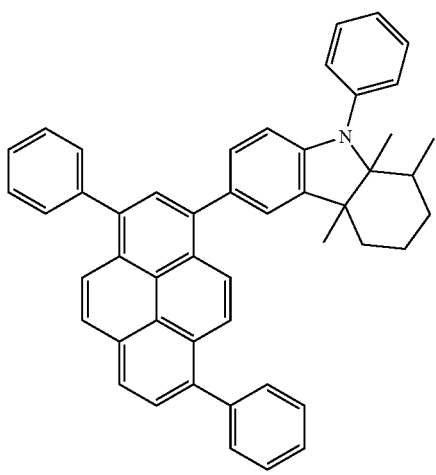
Formula 161
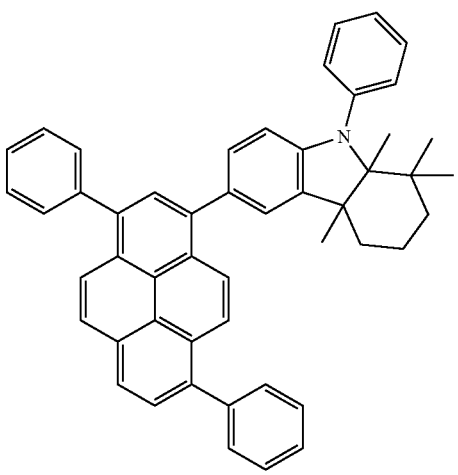

-continued
Formula 162
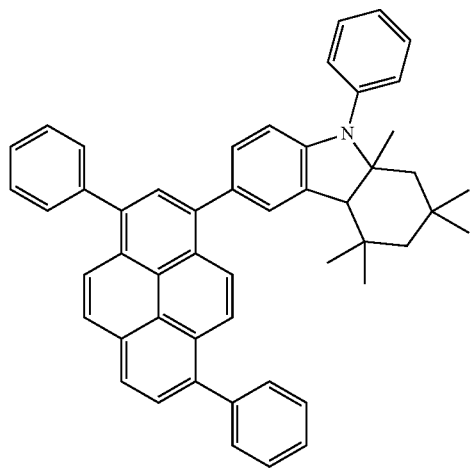
Formula 163
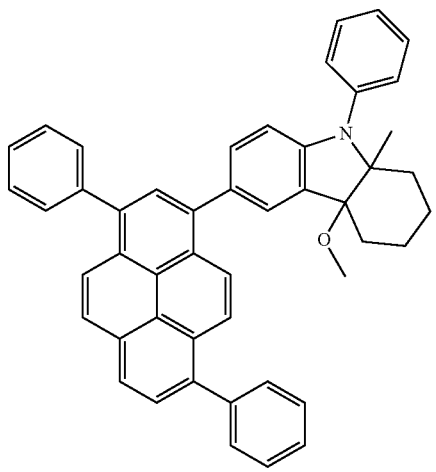
Formula 164
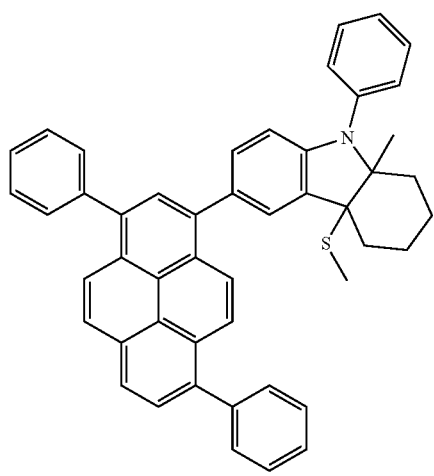
Formula 165
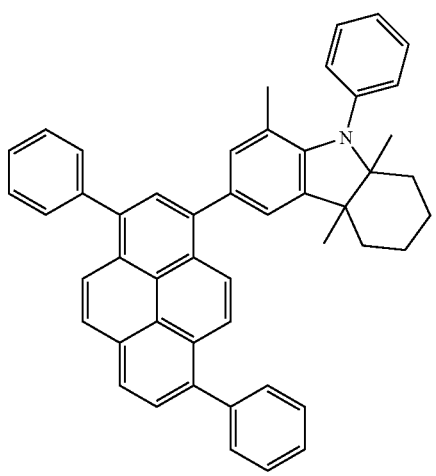
Formula 166
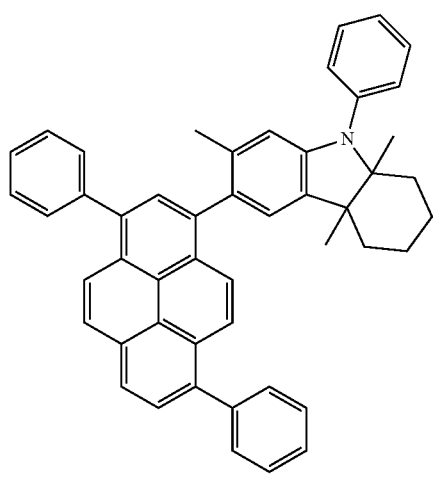
Formula 167
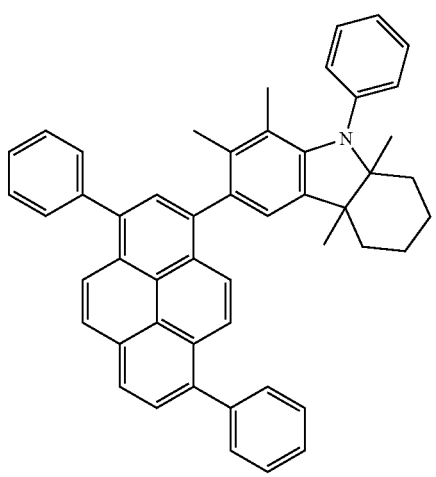

-continued
Formula 168
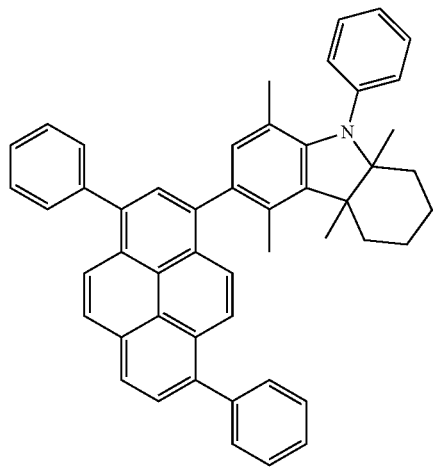
Formula 169
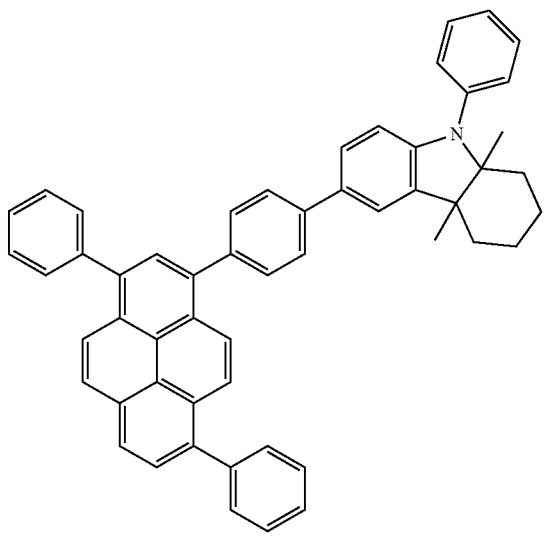
Formula 170
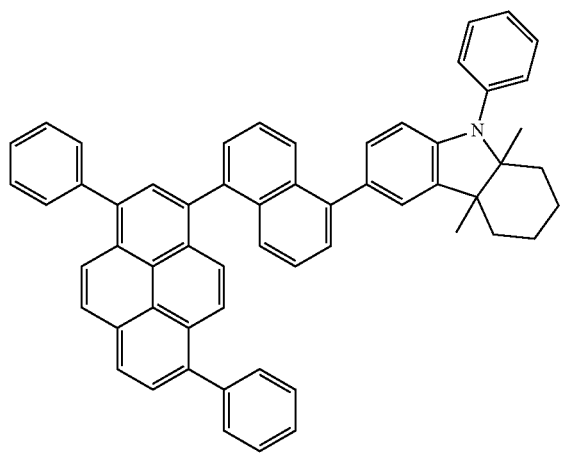
Formula 171
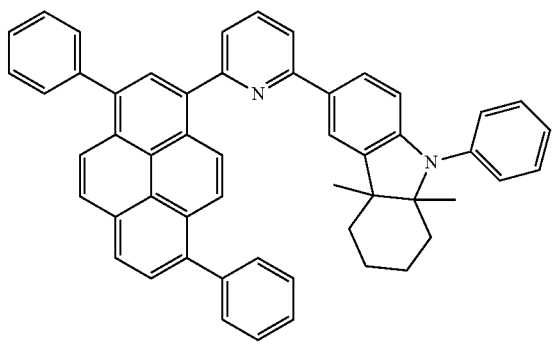
Formula 172
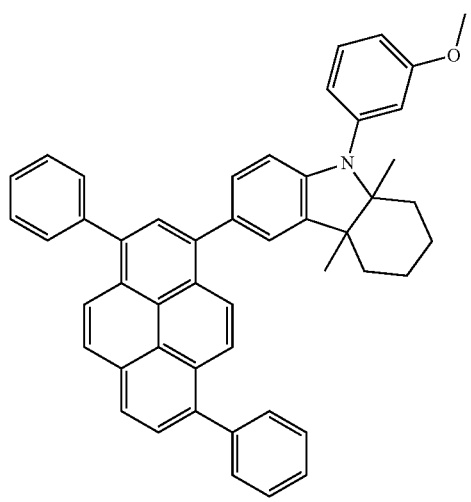
Formula 173
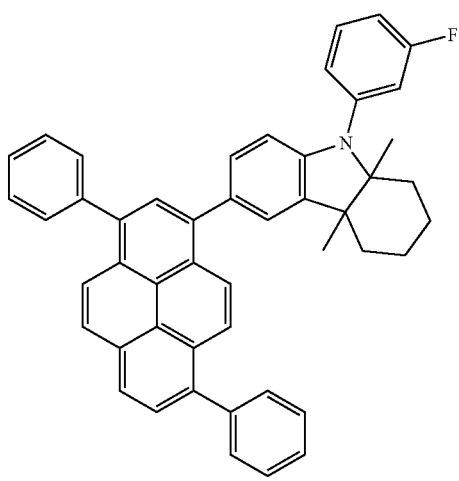

-continued
Formula 174
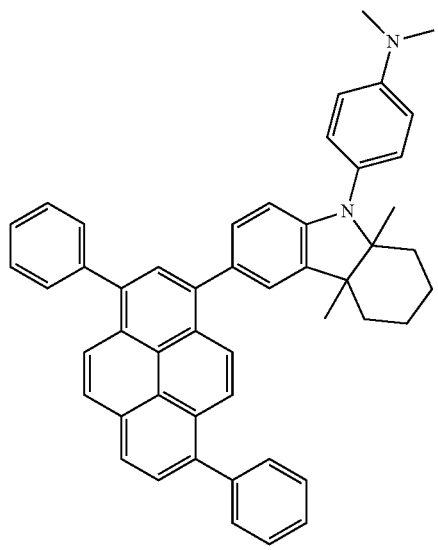
Formula 175
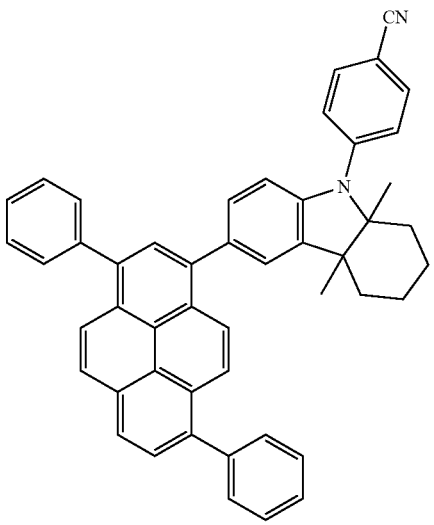
Formula 176
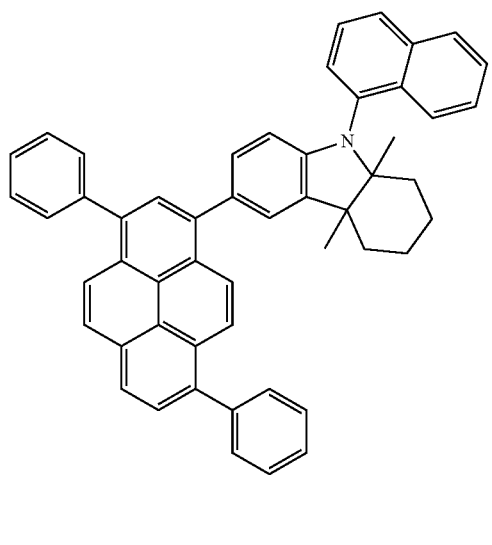
Formula 177
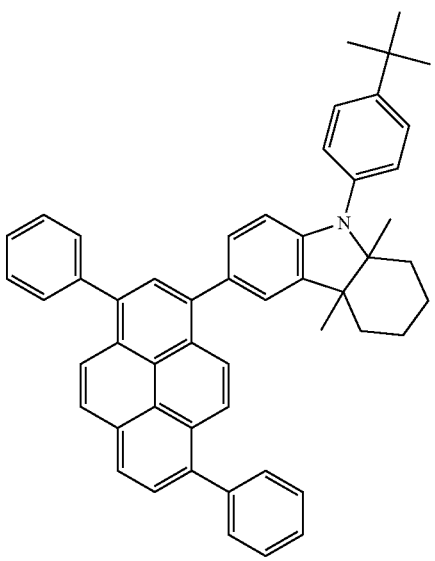
Formula 178
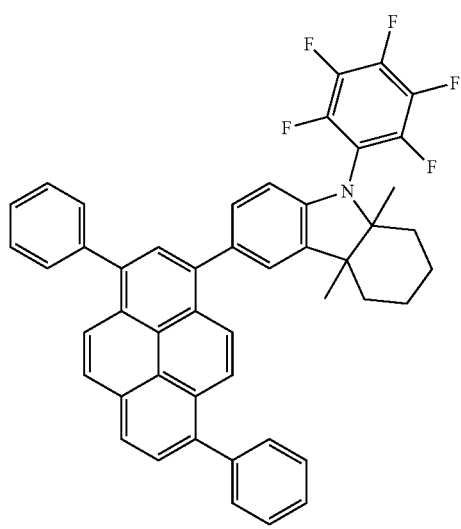
Formula 179
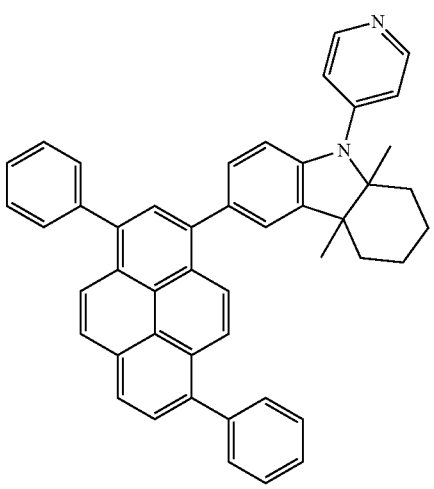

-continued
Formula 180
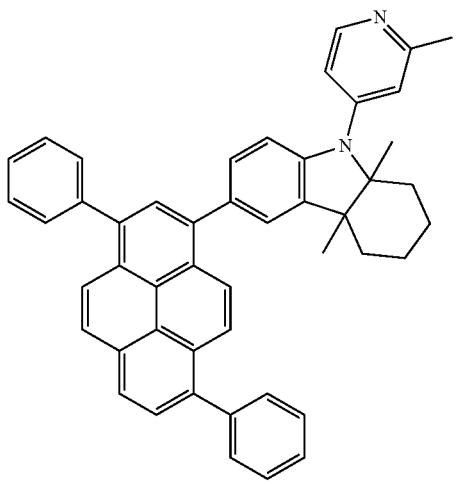
Formula 181
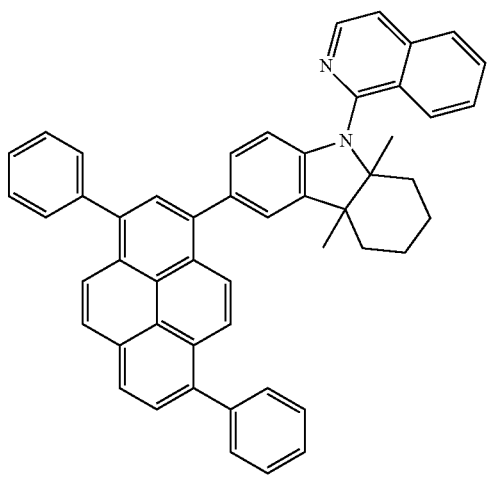
Formula 182
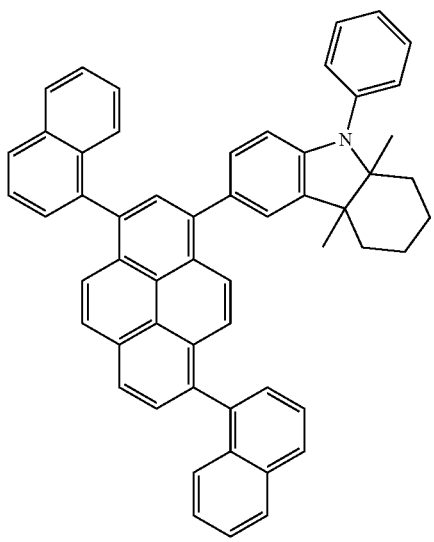
Formula 183
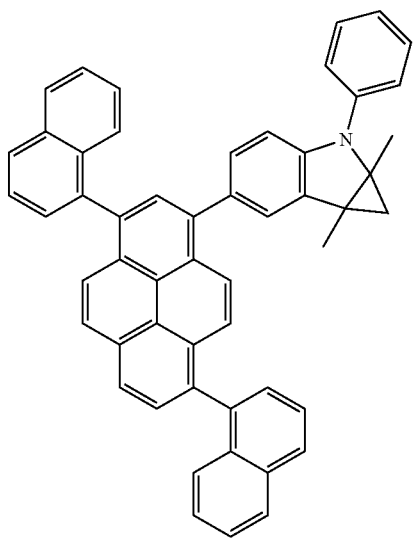
Formula 184
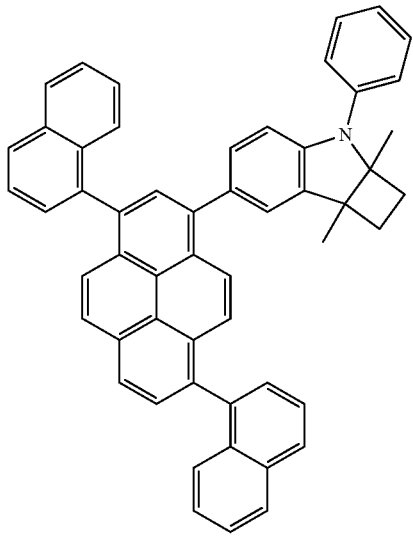
Formula 185
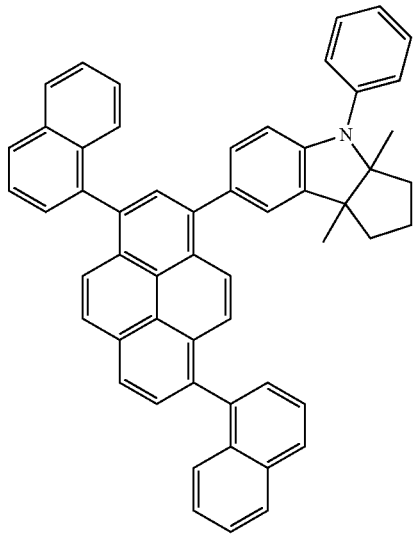

-continued
Formula 187
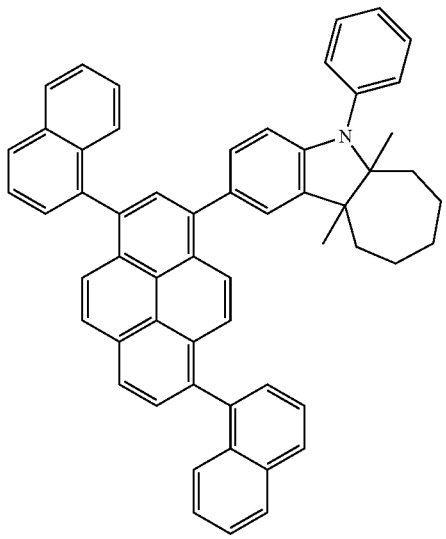
Formula 188
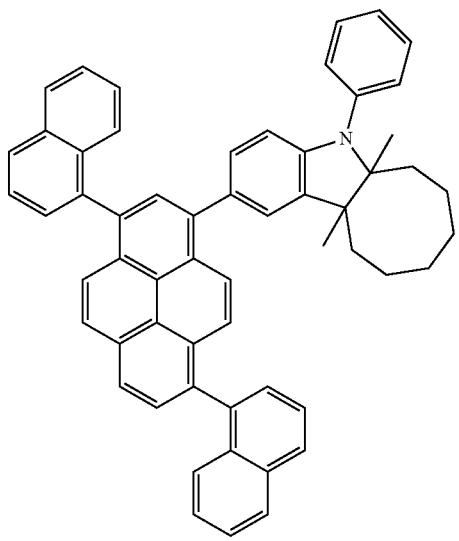
Formula 189
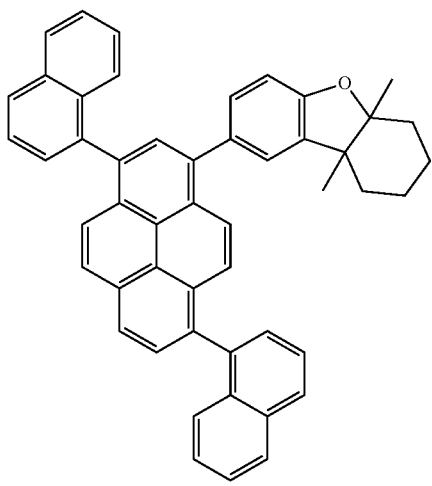
Formula 190
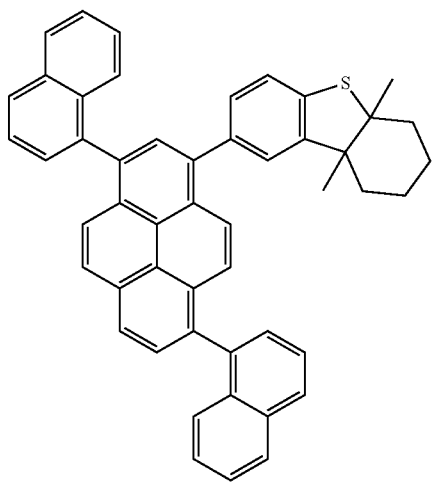
Formula 191
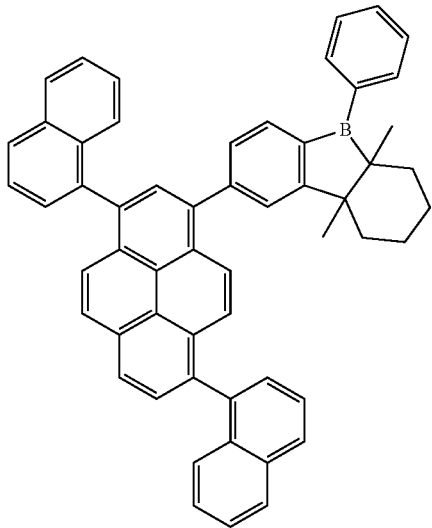
Formula 192
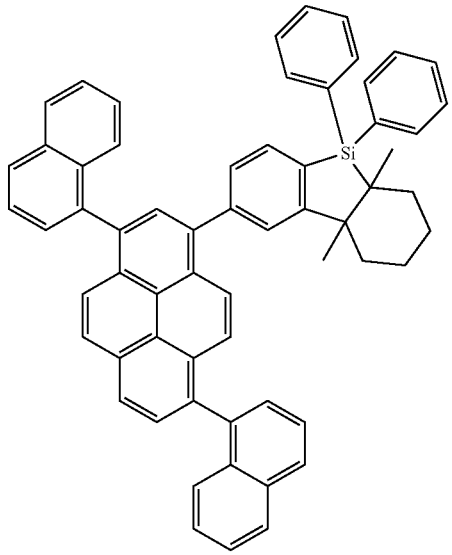

-continued
Formula 193
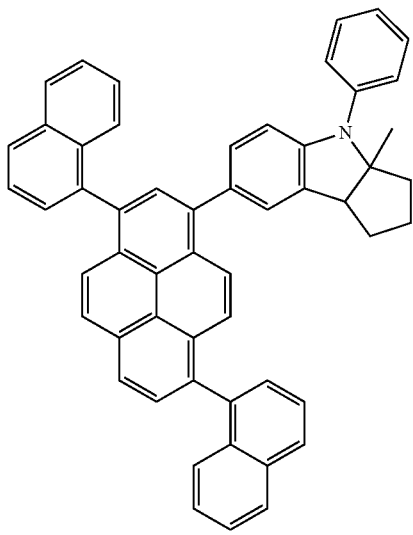
Formula 194
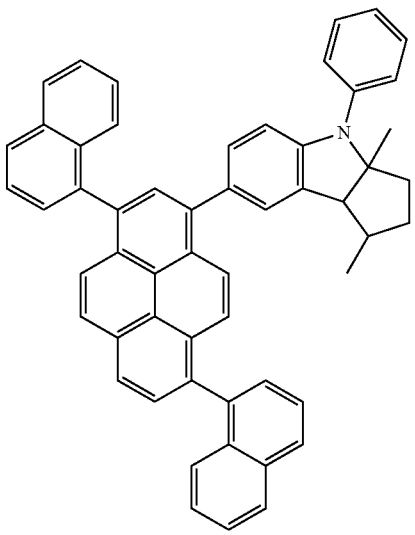
Formula 195
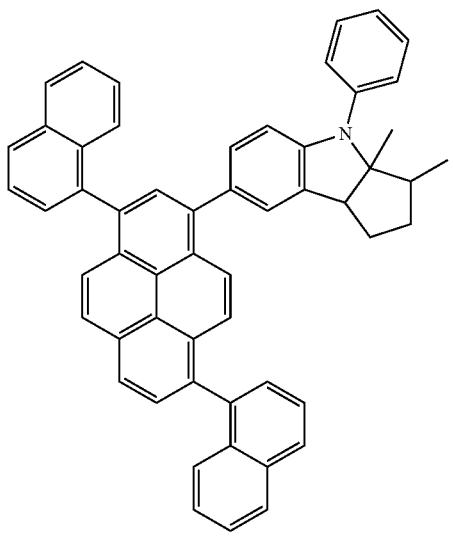
Formula 196
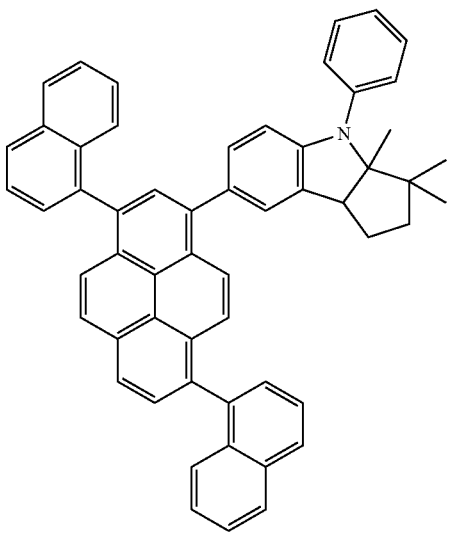
Formula 197
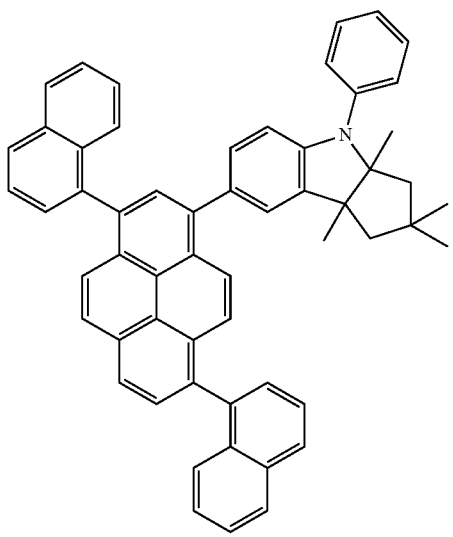
Formula 198
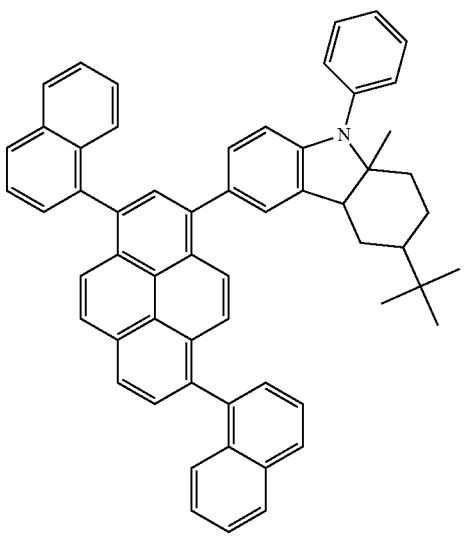

-continued
Formula 199
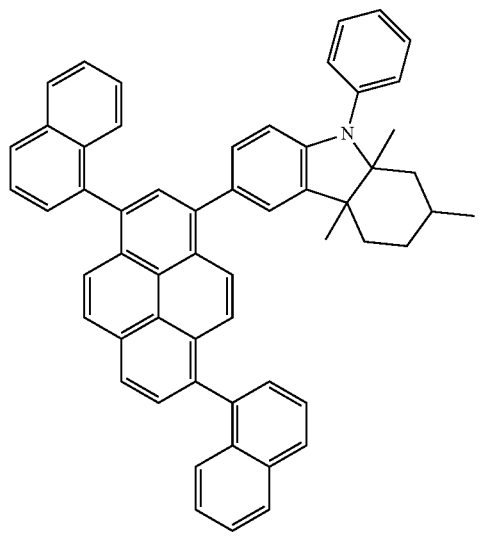
Formula 200
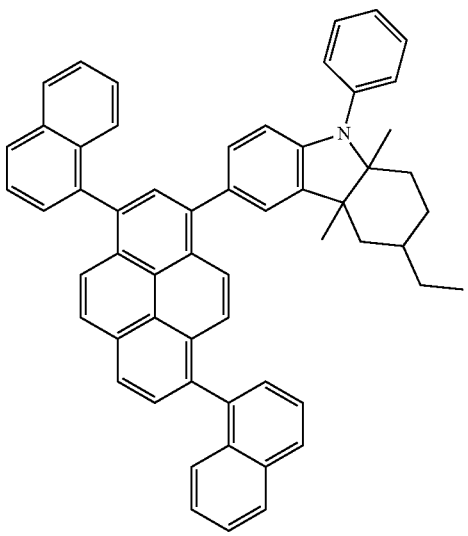
Formula 201
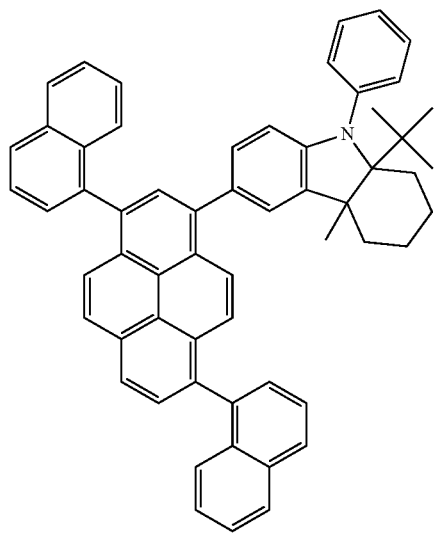
Formula 202
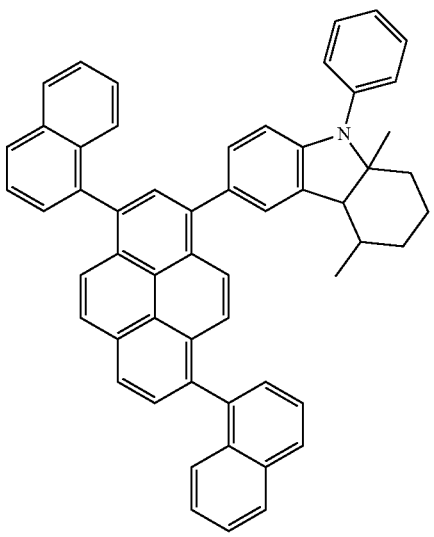
Formula 203
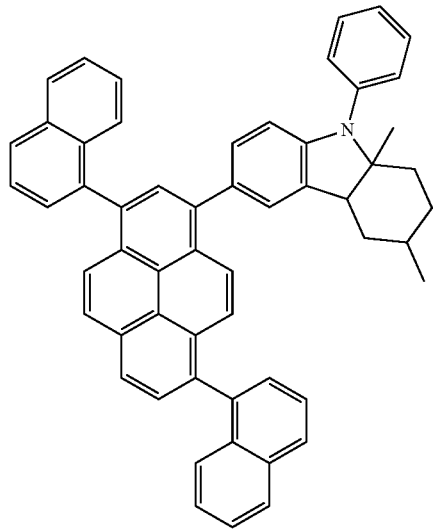
Formula 204
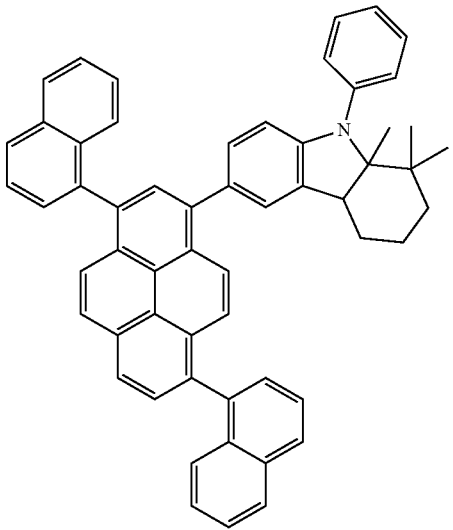

-continued
Formula 205
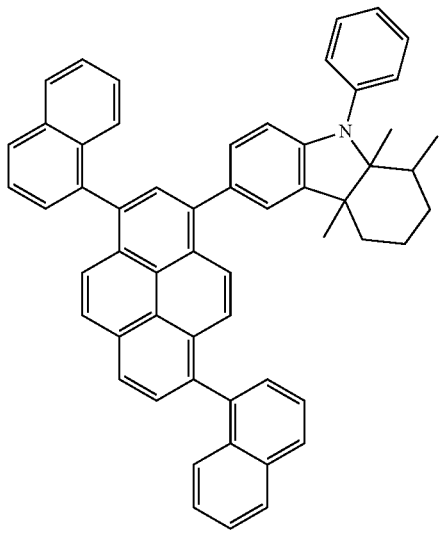
Formula 206
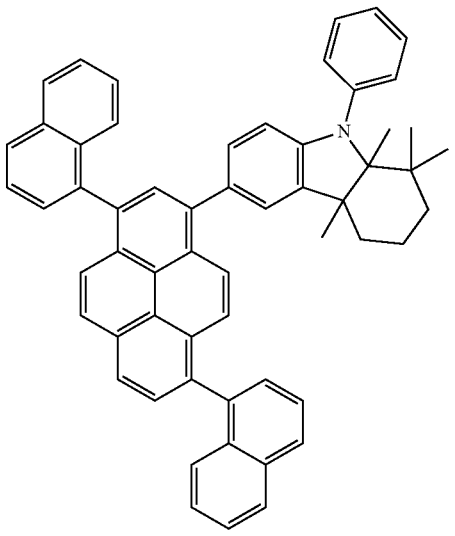
Formula 207
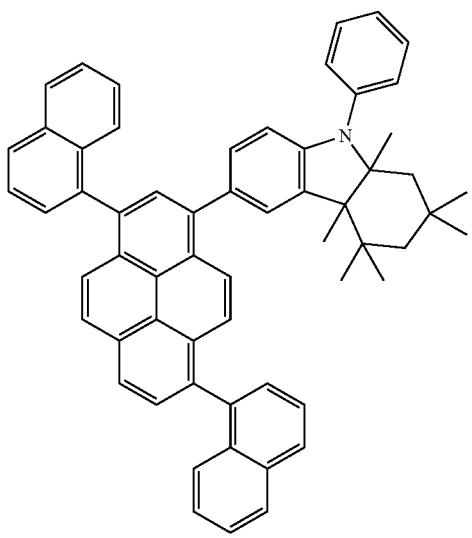
Formula 208
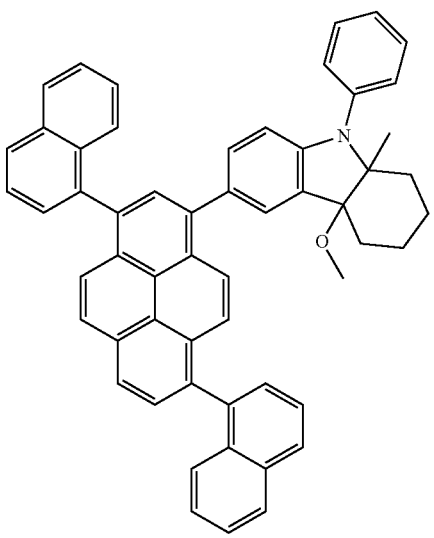
Formula 209
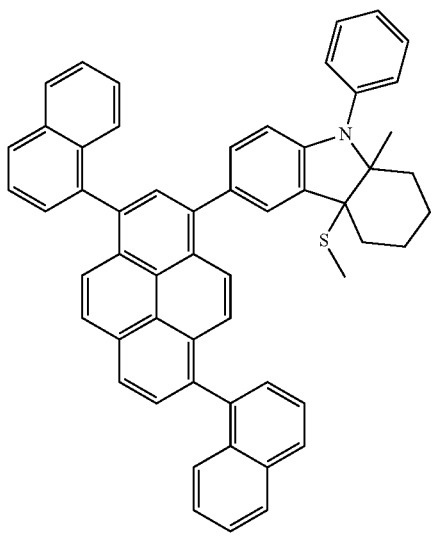
Formula 210
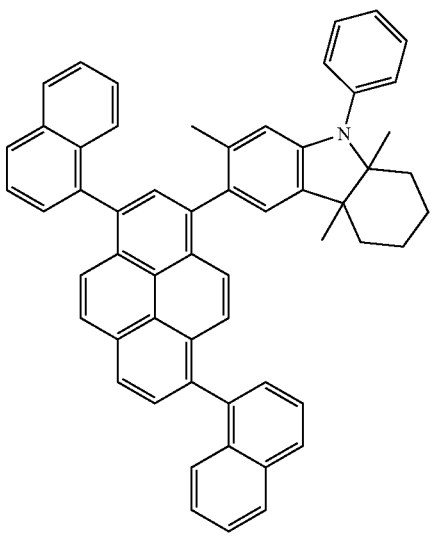

-continued
Formula 211
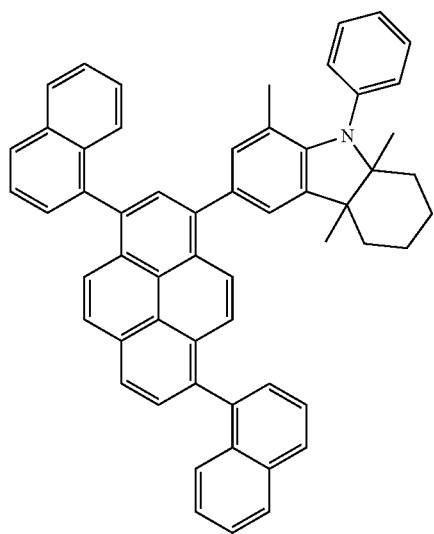
Formula 212
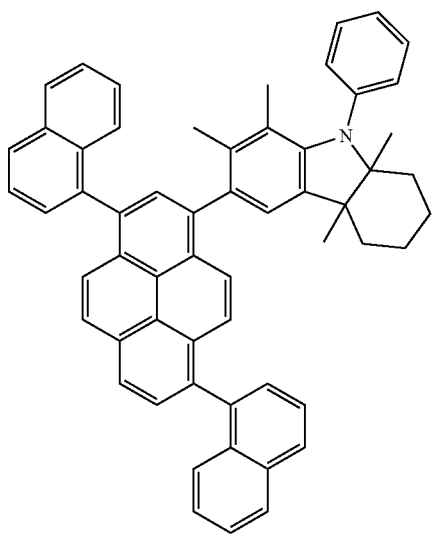
Formula 213
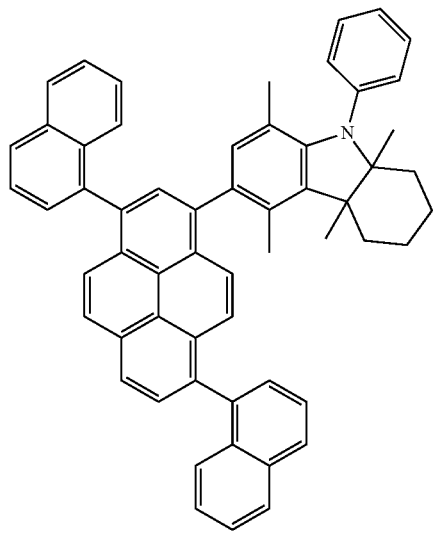
Formula 214
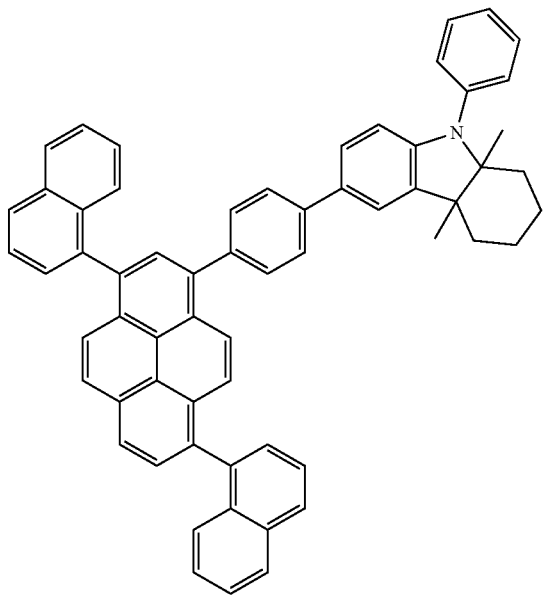

-continued
Formula 215
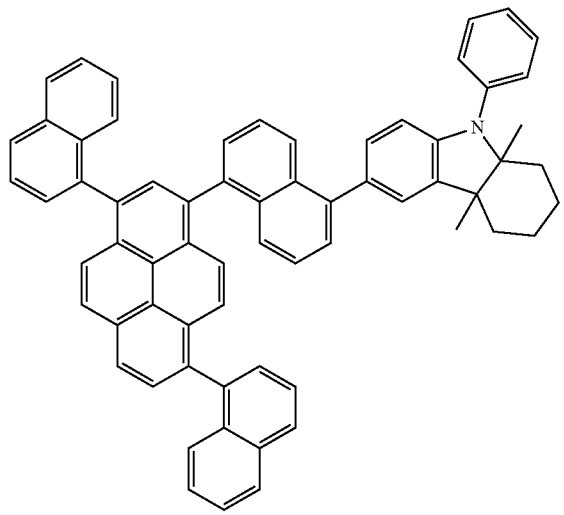
Formula 216
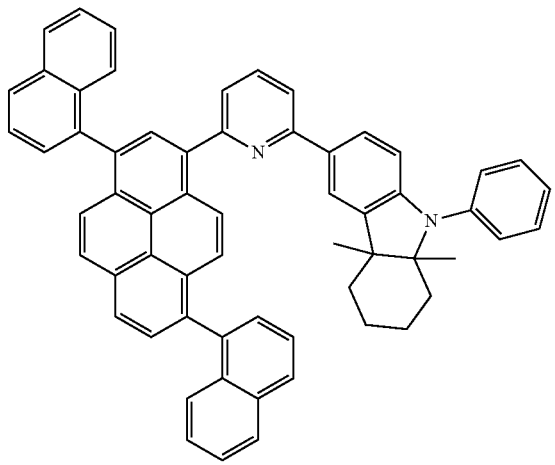
Formula 217
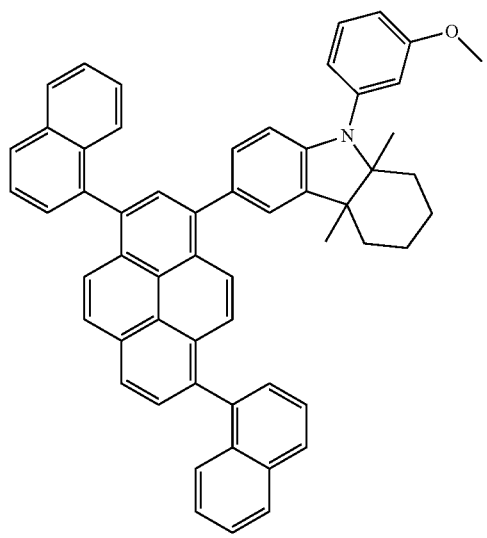
Formula 218
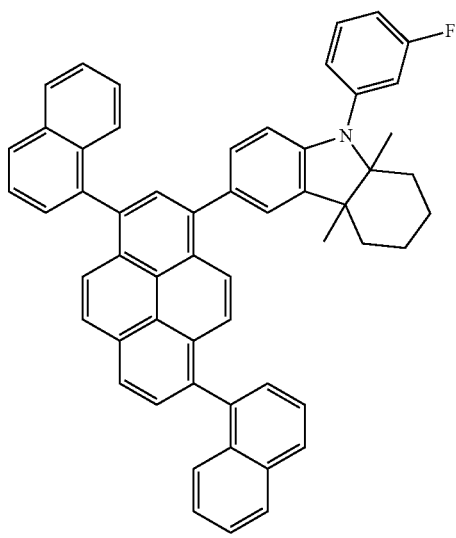
Formula 219
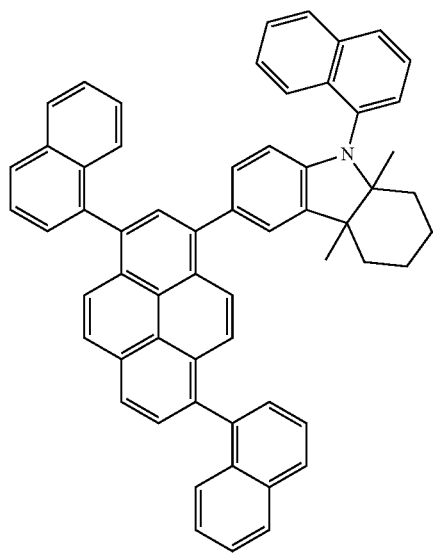
Formula 220
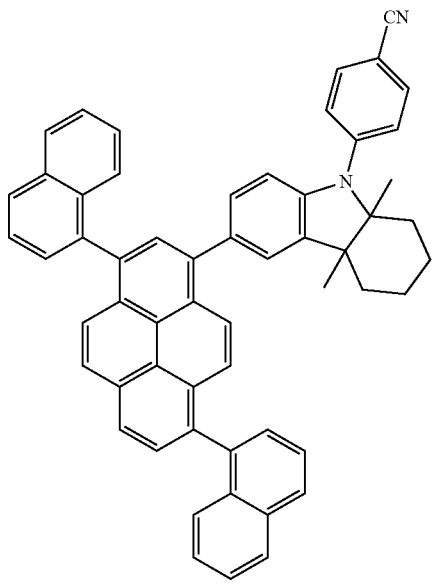

-continued
Formula 221
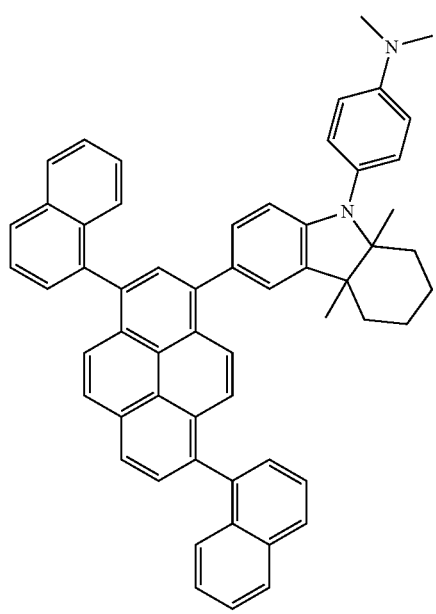
Formula 222
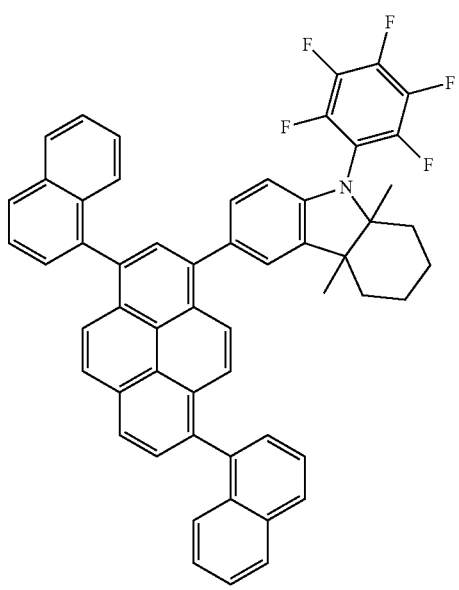
Formula 223
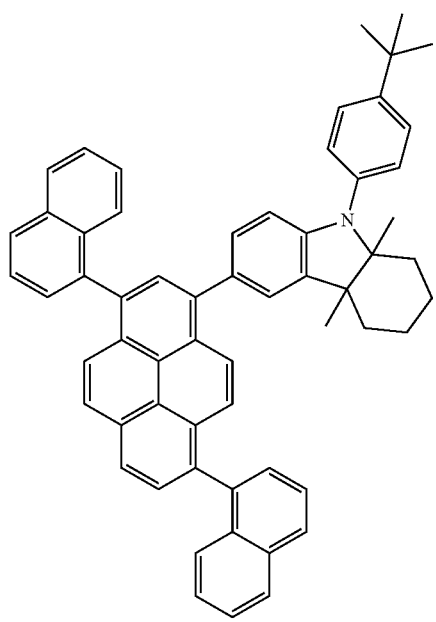
Formula 224
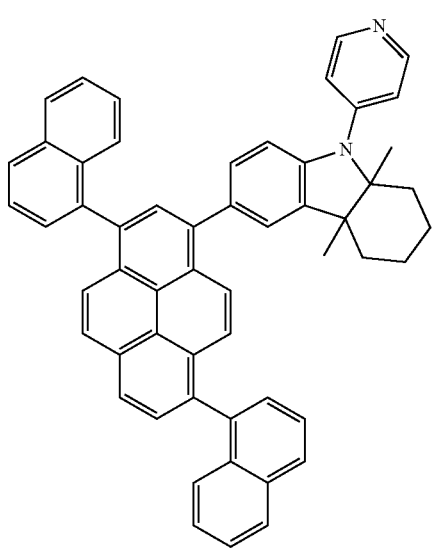

-continued
Formula 225
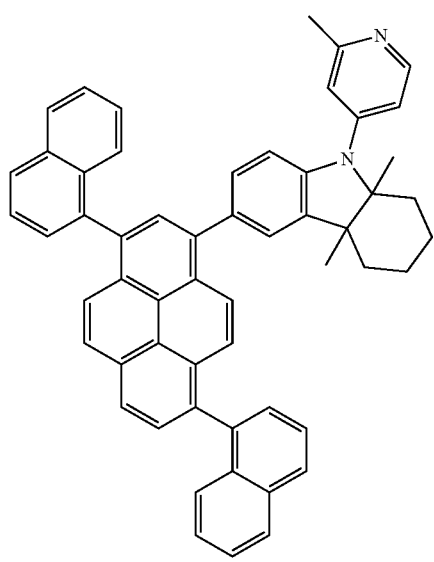
Formula 226
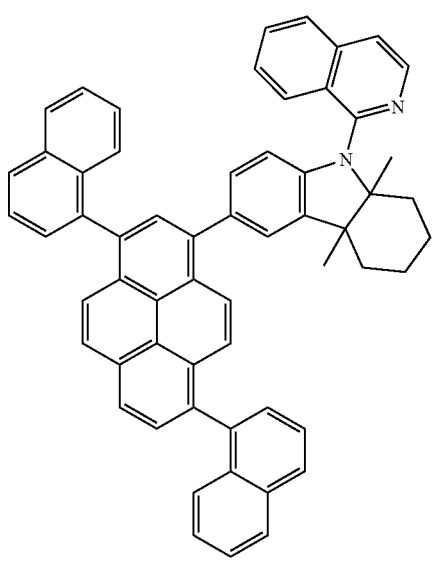
Formula 227
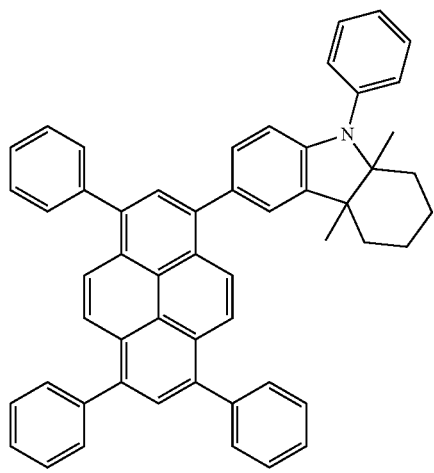
Formula 228
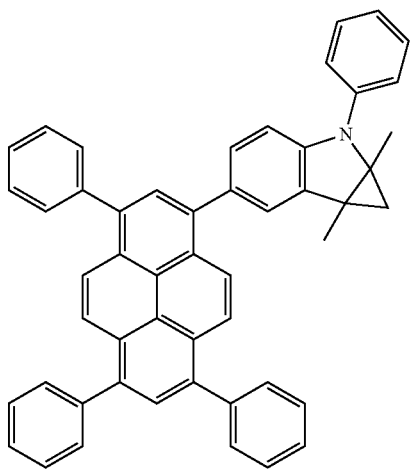
Formula 229
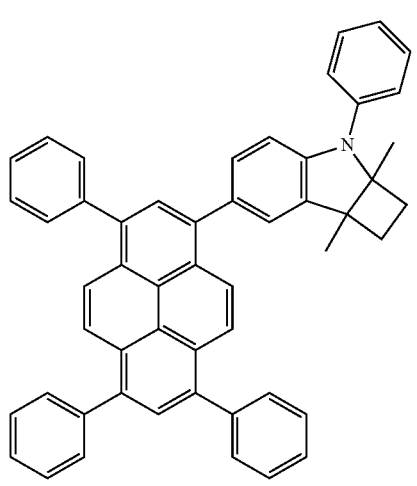
Formula 230
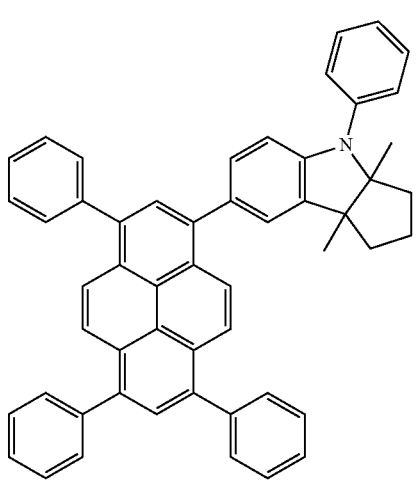

Formula 231
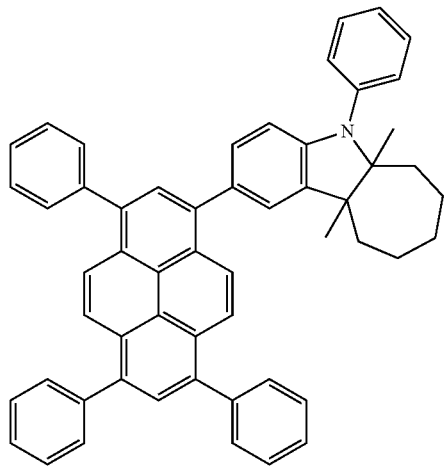
Formula 232
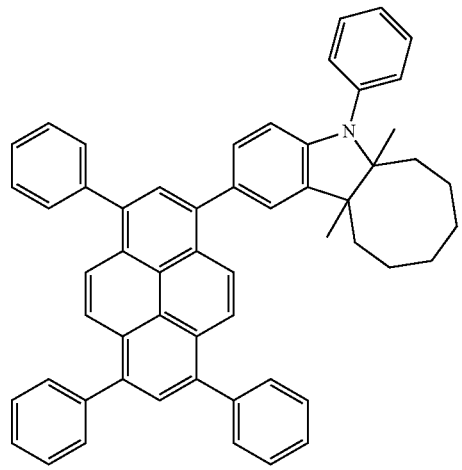
Formula 233
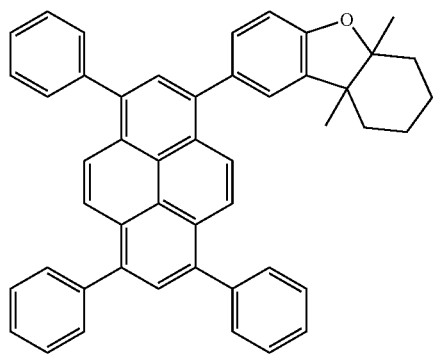
Formula 234
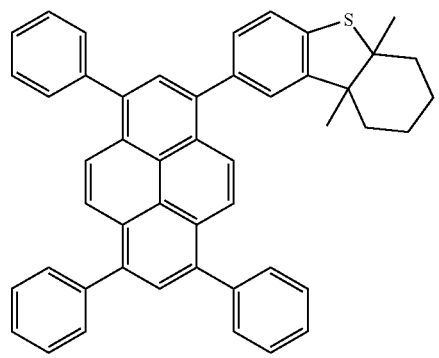
Formula 235
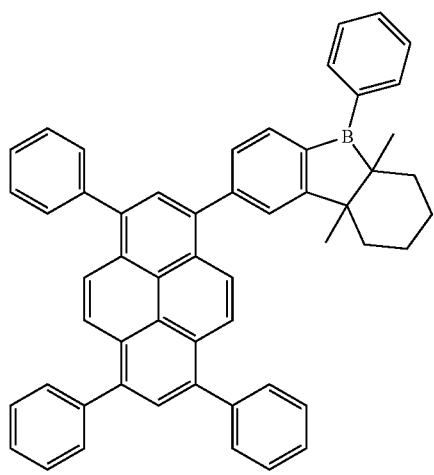
Formula 236
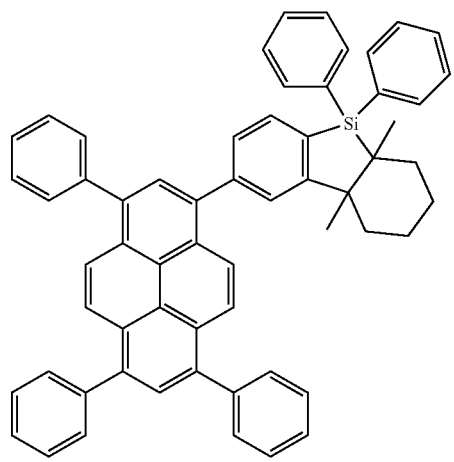

Formula 237
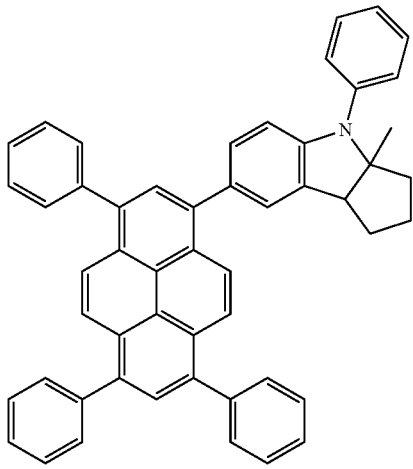
Formula 238
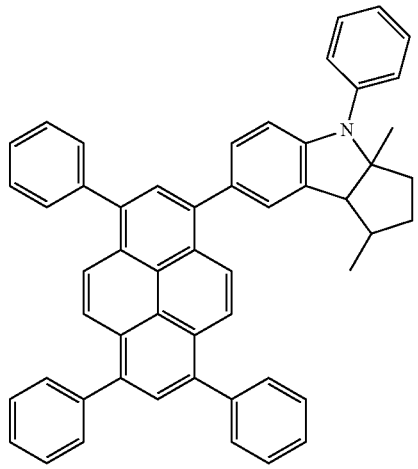
Formula 239
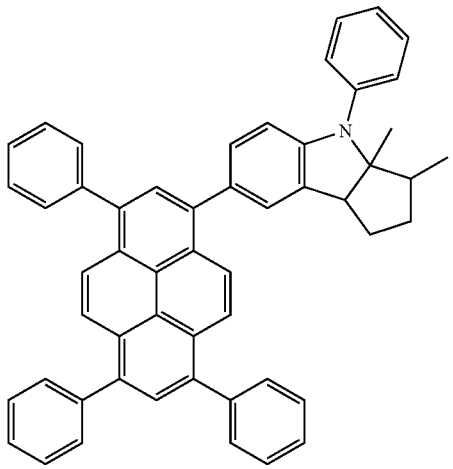
Formula 240
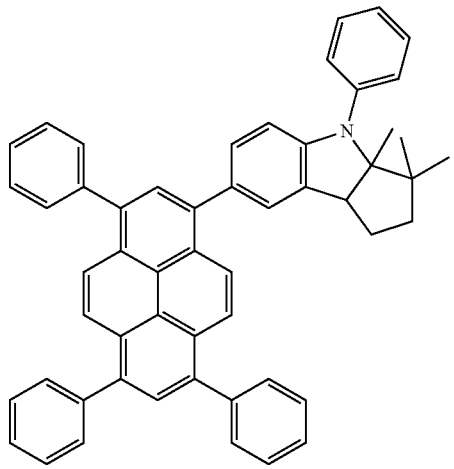
Formula 241
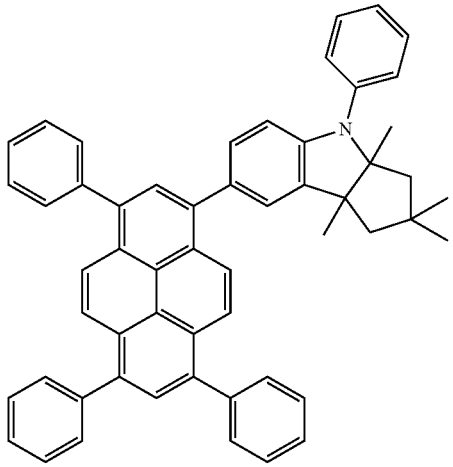
Formula 242
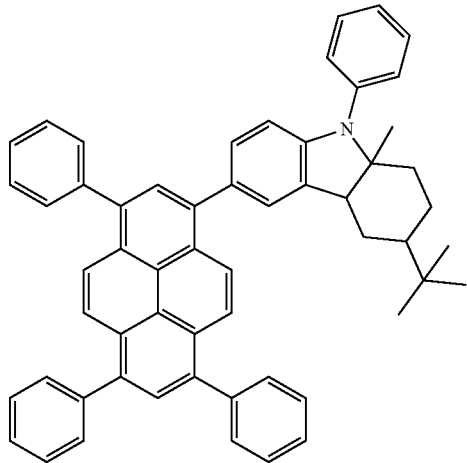

-continued
Formula 243
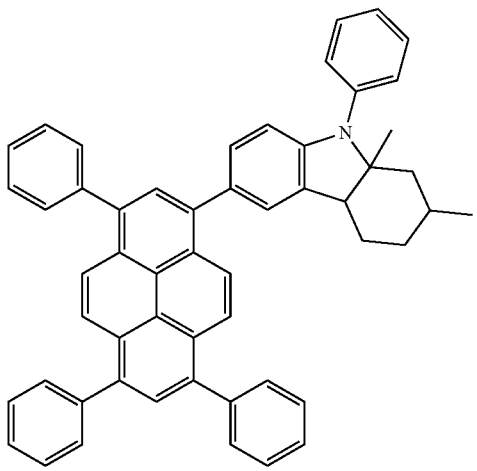
Formula 244
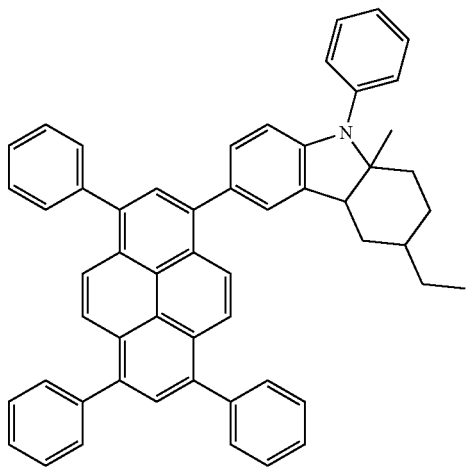
Formula 245
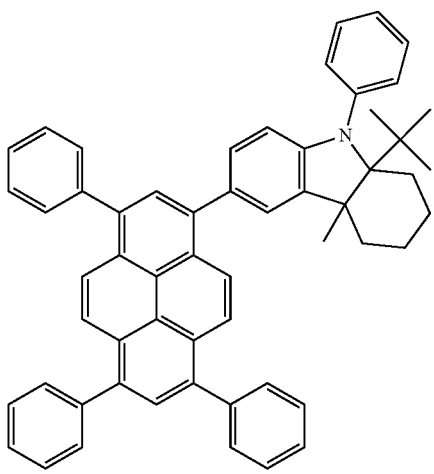
Formula 246
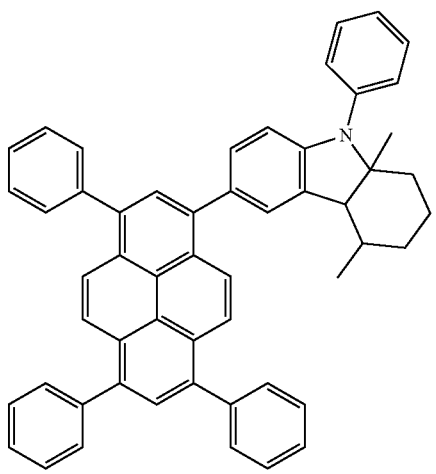
Formula 247
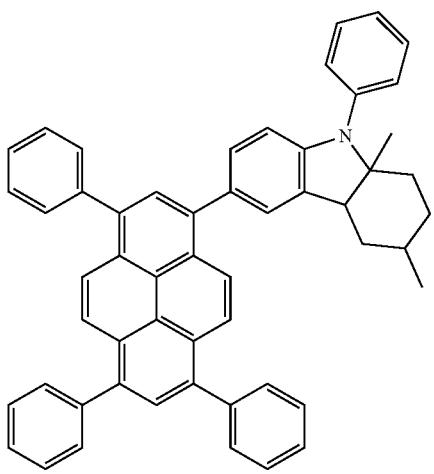
Formula 248
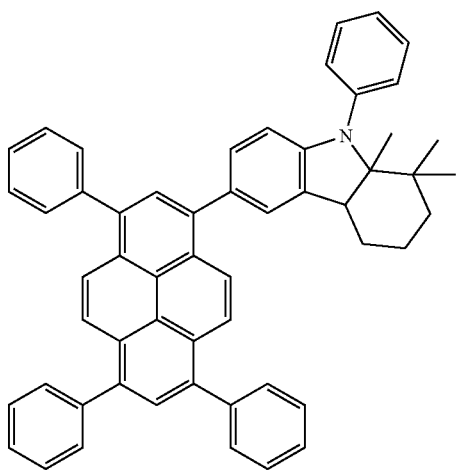

-continued
Formula 249
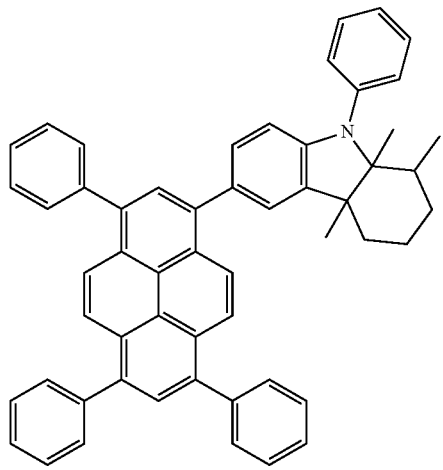
Formula 250
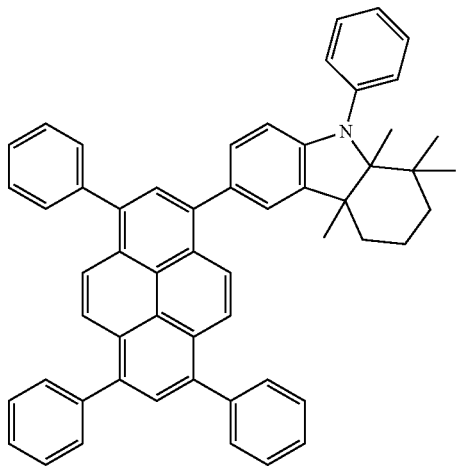
Formula 251
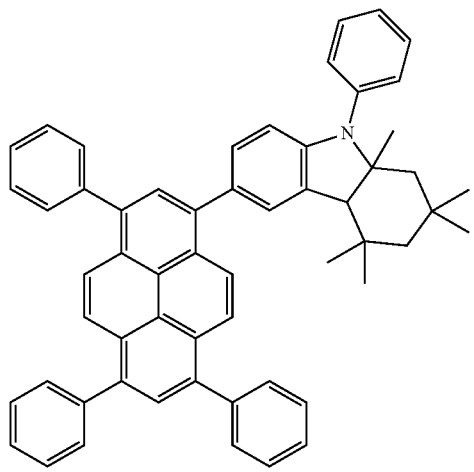
Formula 252
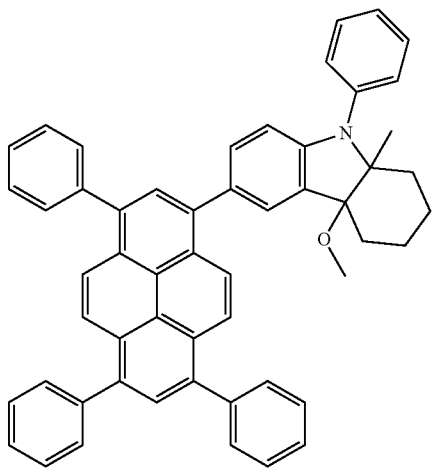
Formula 253
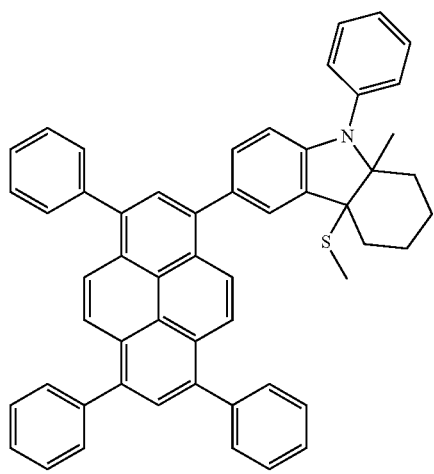
Formula 254
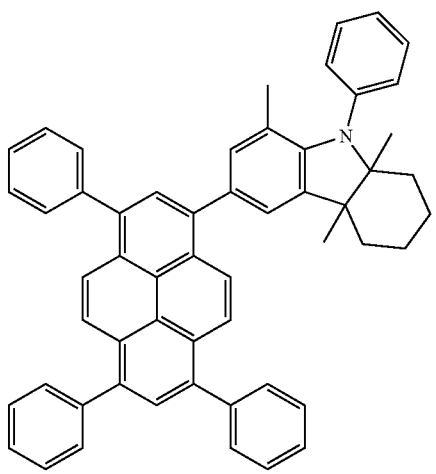

Formula 255
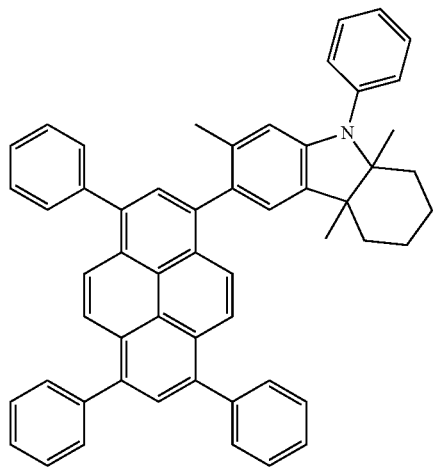
Formula 256
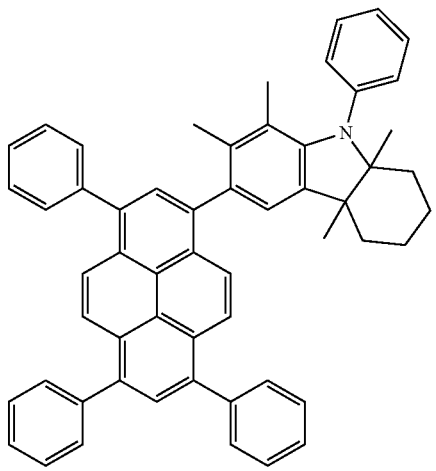
Formula 257
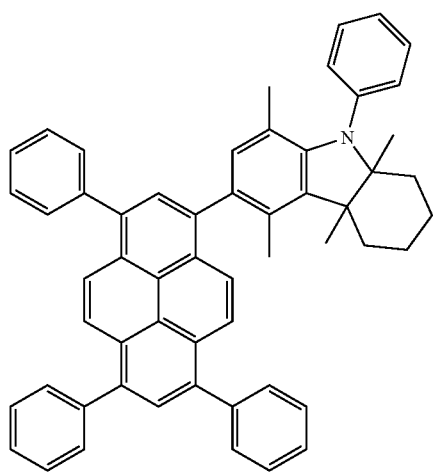
Formula 258
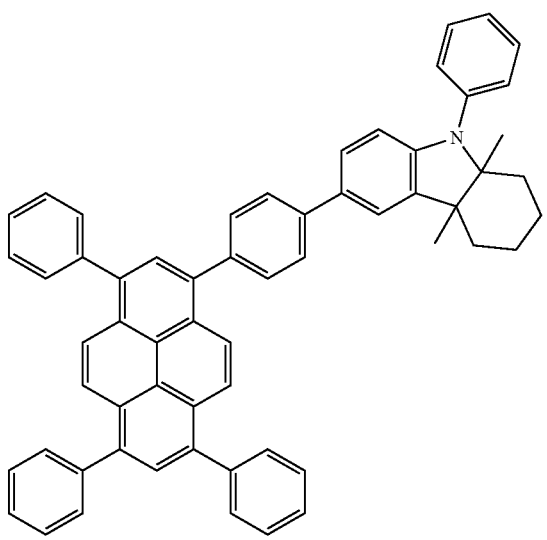
Formula 259
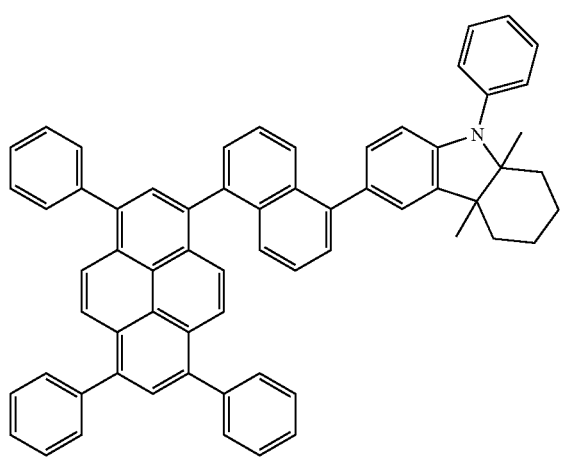
Formula 260
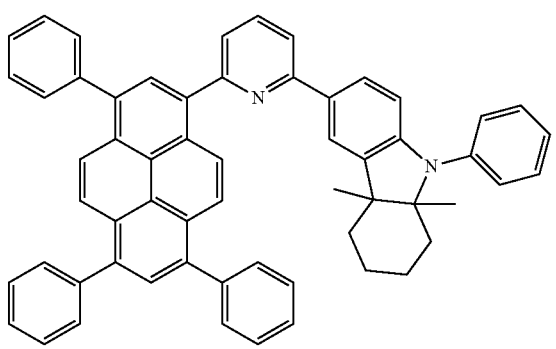

Formula 261
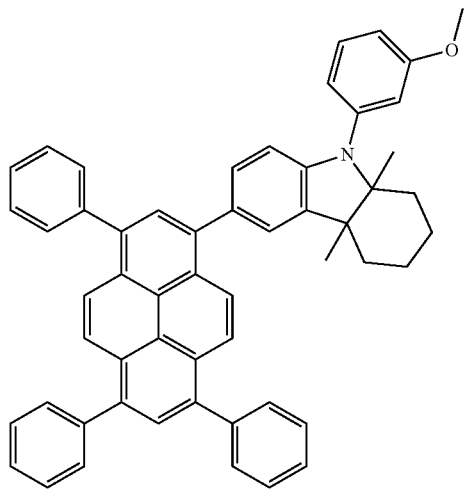
Formula 262
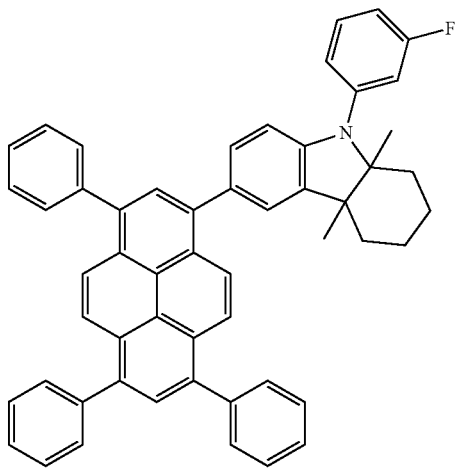
Formula 263
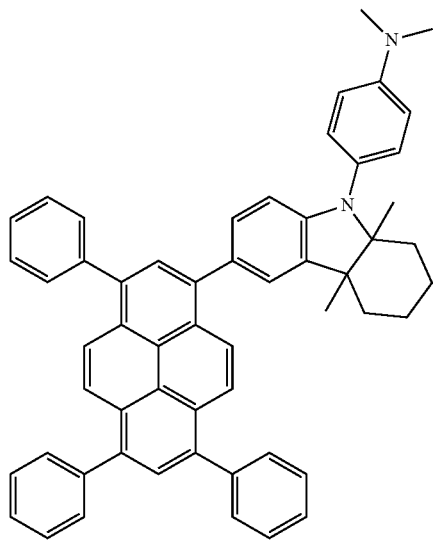
Formula 264
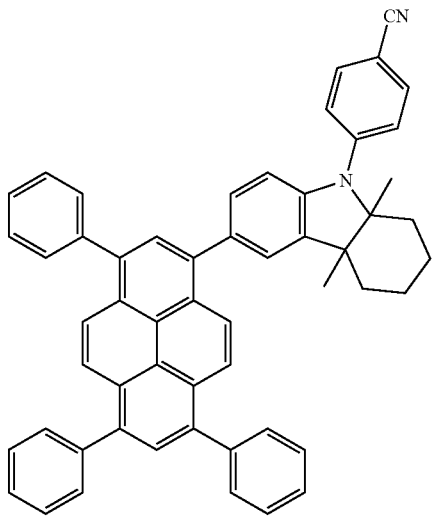
Formula 265
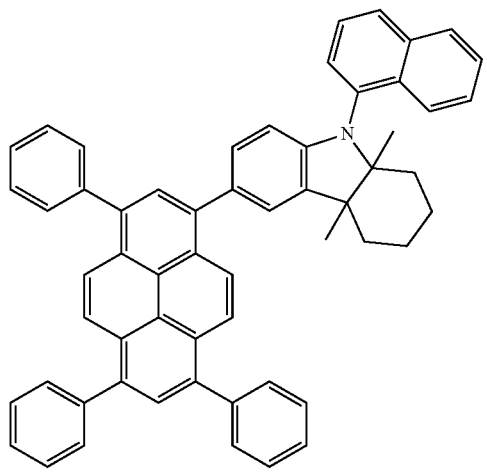
Formula 266
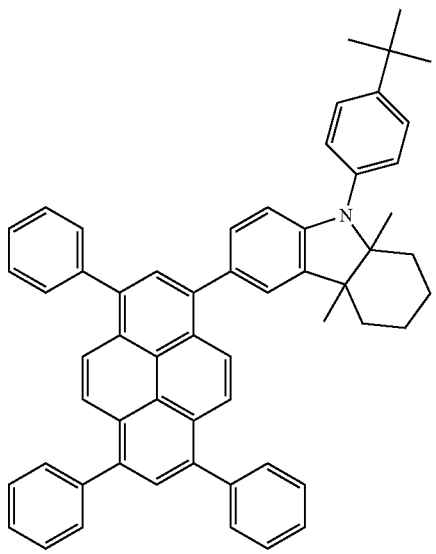

-continued
Formula 267
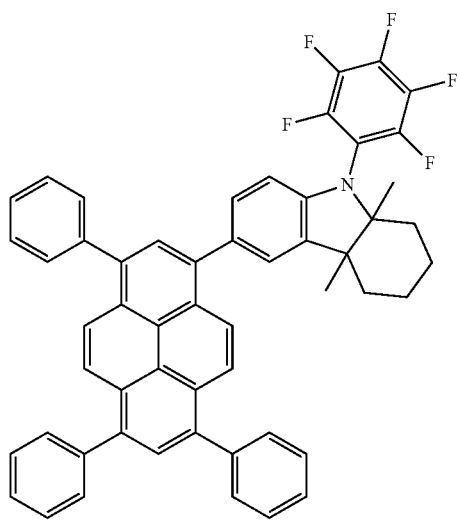
Formula 268
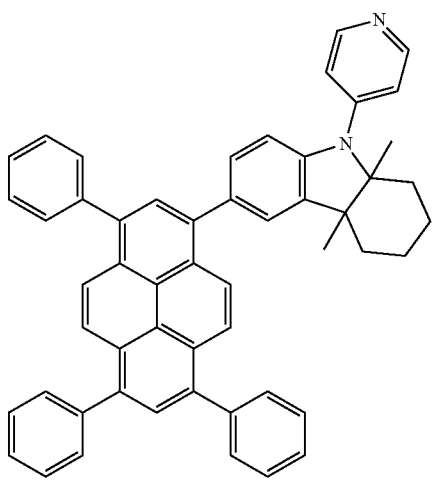
Formula 269
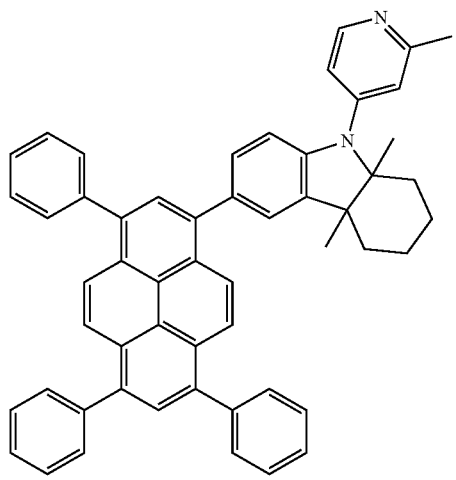
Formula 270
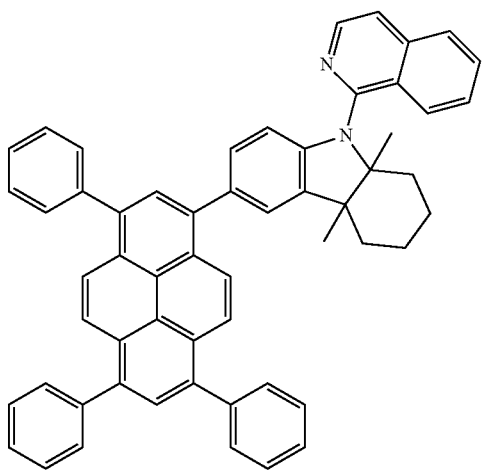
Formula 271
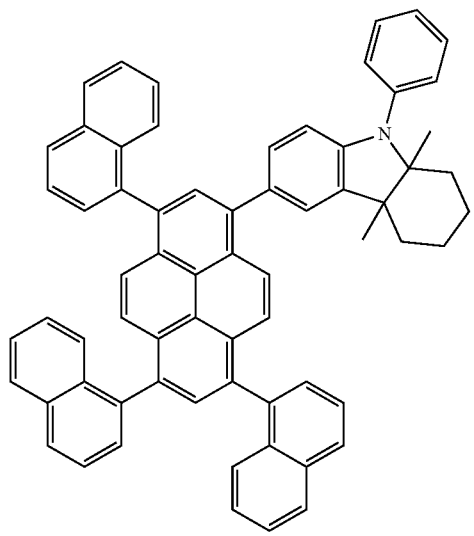
Formula 272
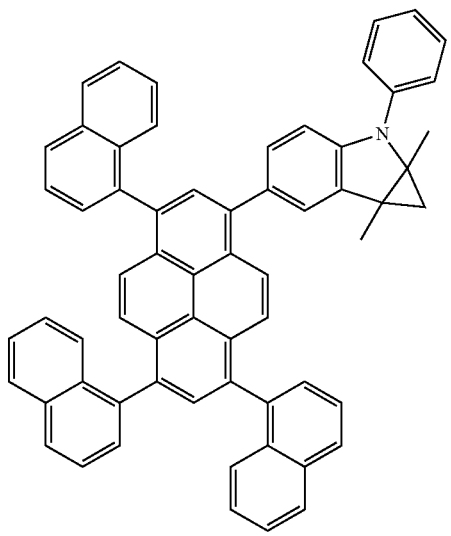

-continued
Formula 273
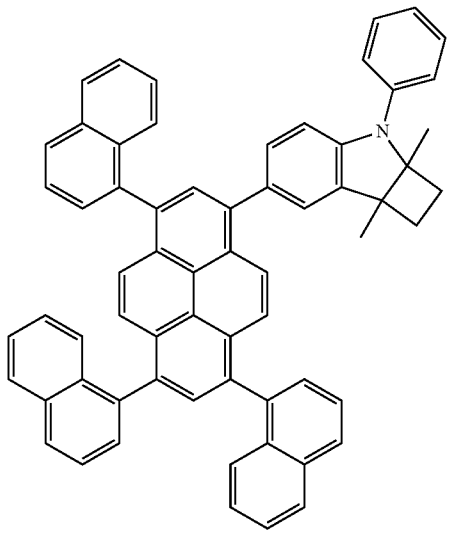
Formula 274
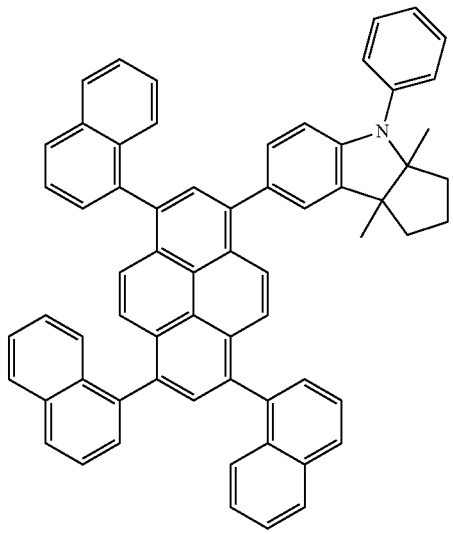
Formula 275
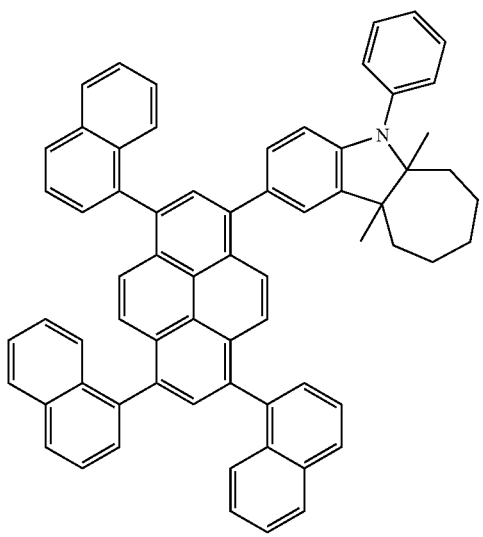
Formula 276
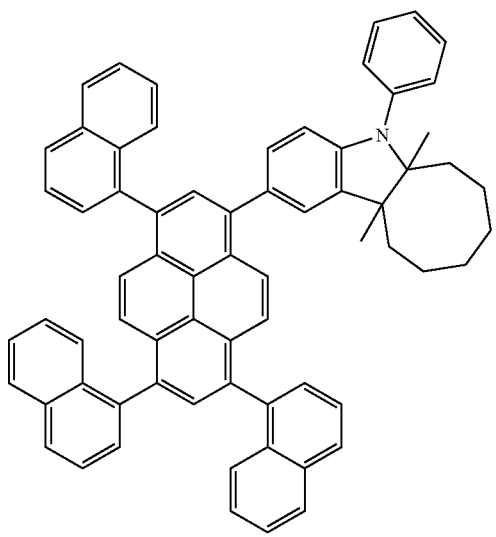
Formula 277
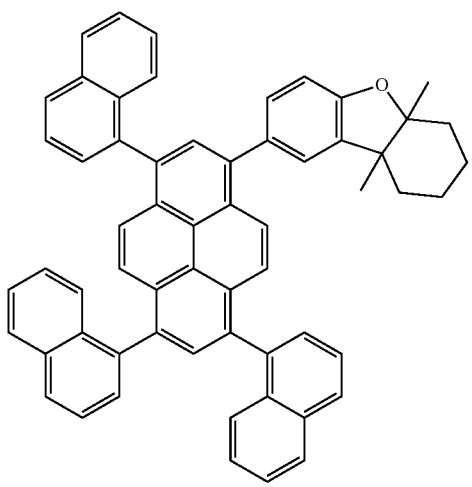
Formula 278
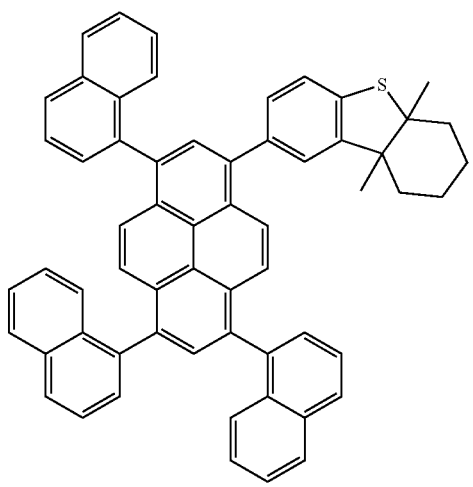

-continued
Formula 279
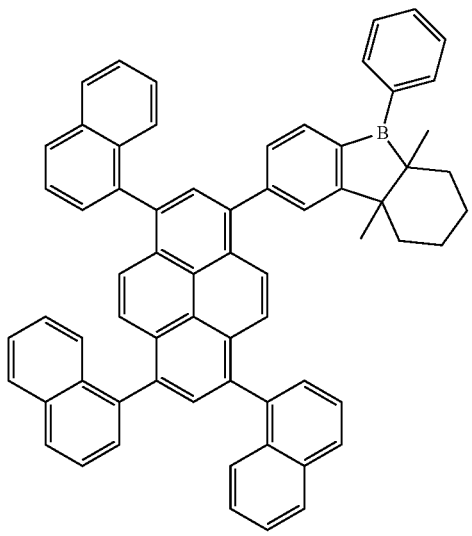
Formula 280
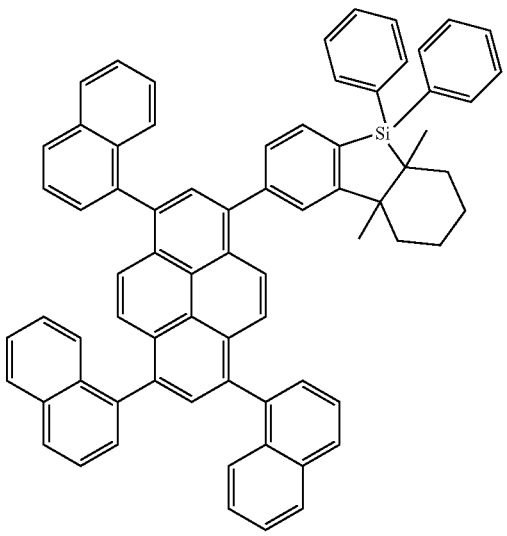
Formula 281
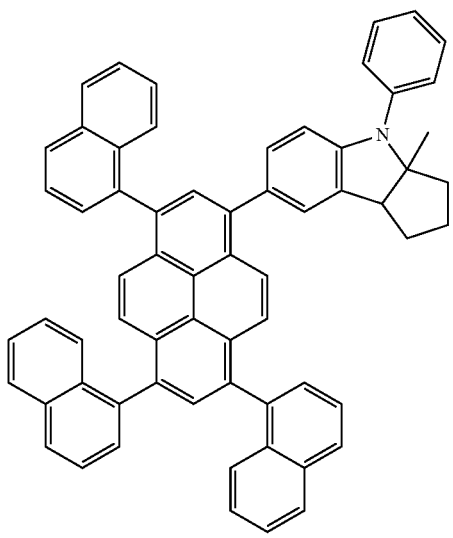
Formula 282
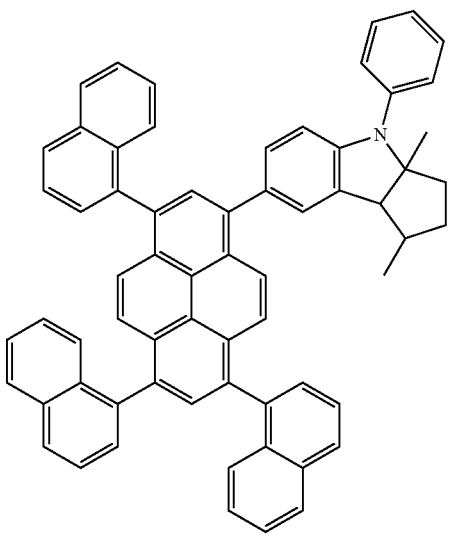
Formula 283
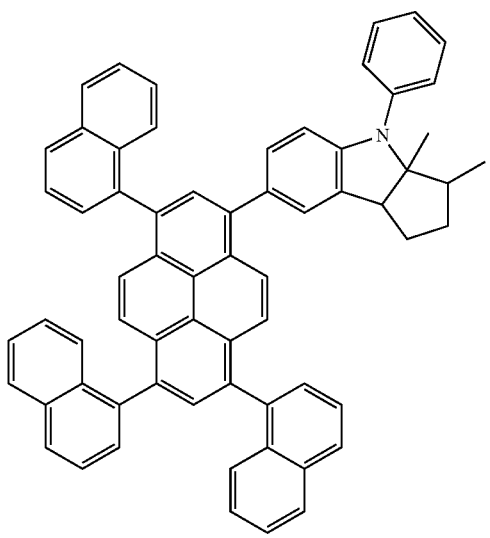
Formula 284
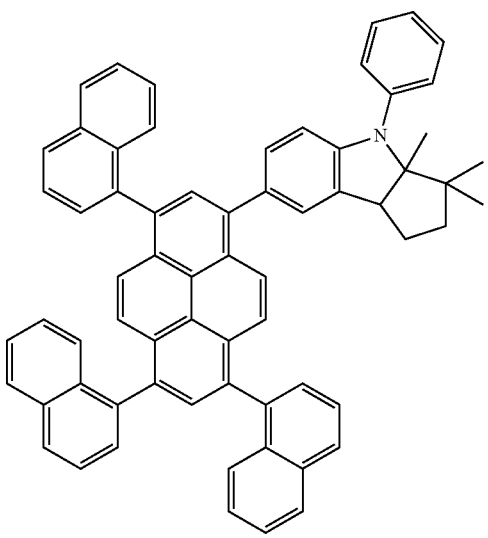

-continued
Formula 285
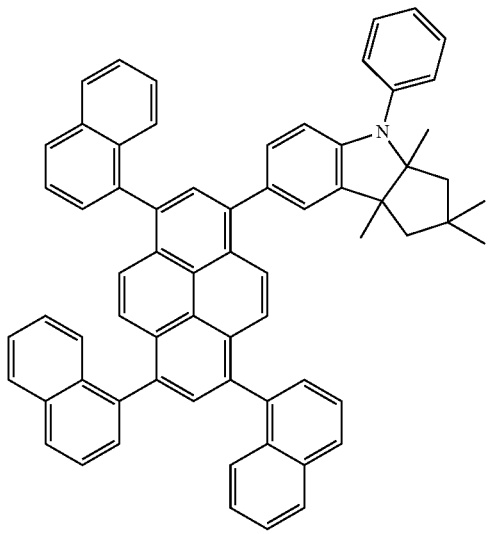
Formula 286
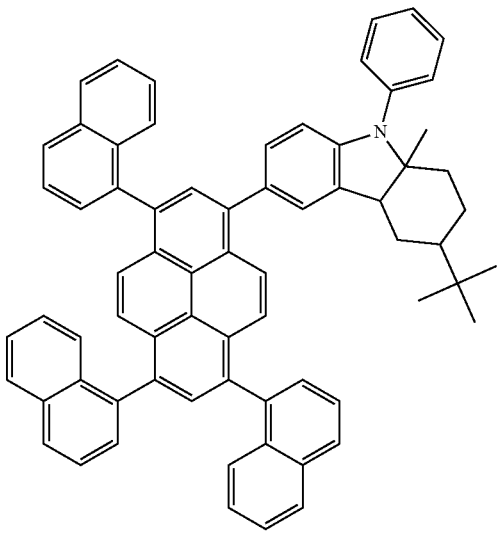
Formula 287
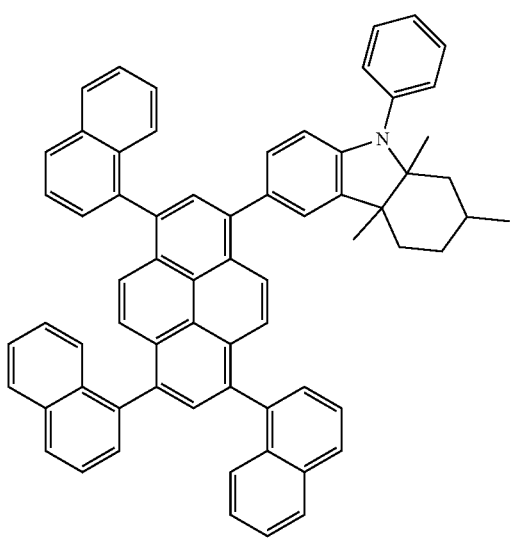
Formula 288
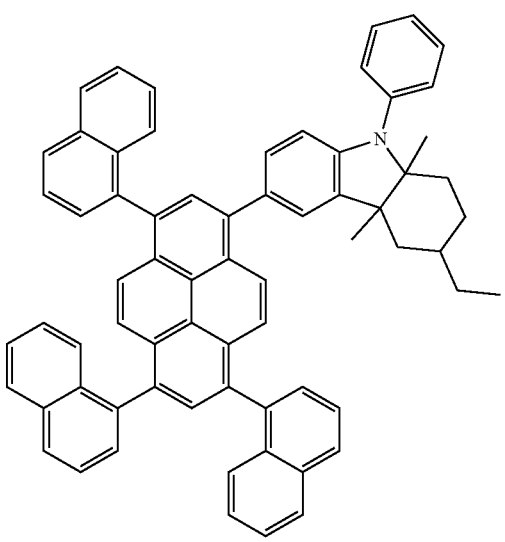
Formula 289
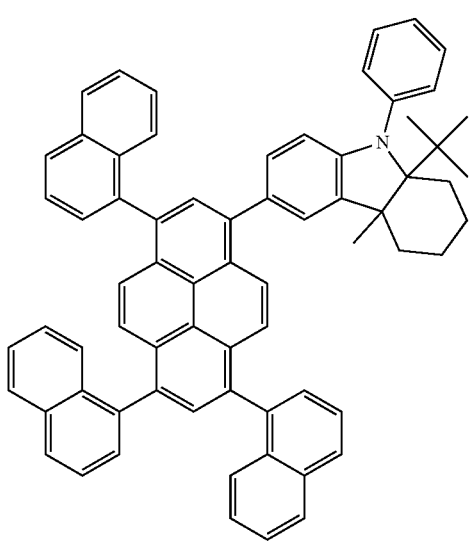
Formula 290
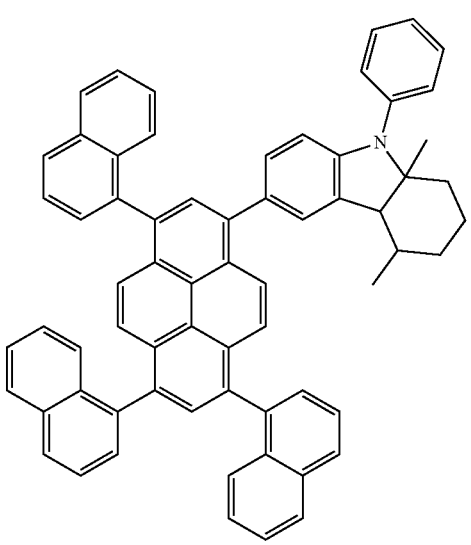

-continued
Formula 291
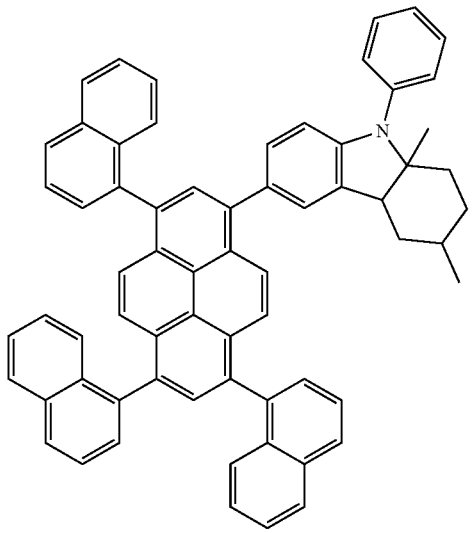
Formula 292
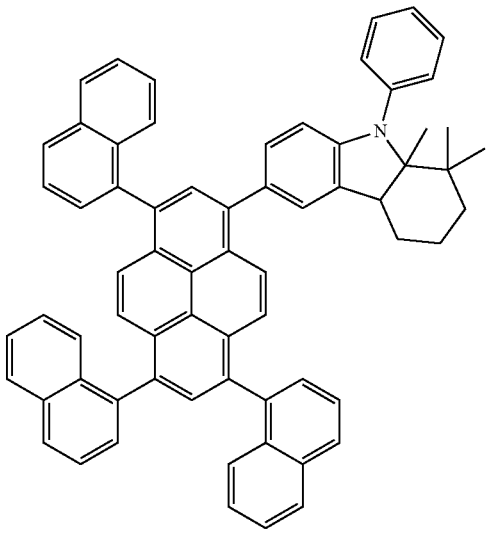
Formula 293
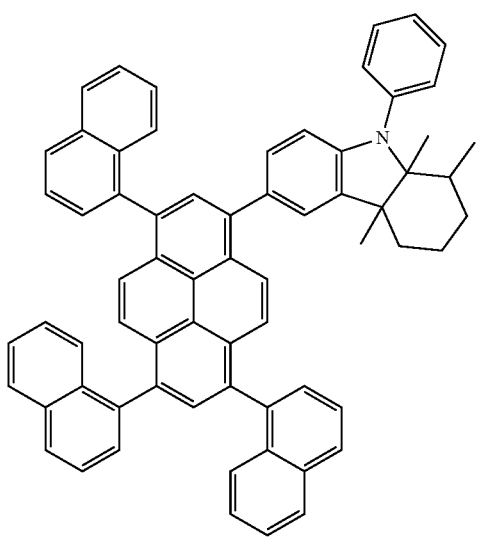
Formula 294
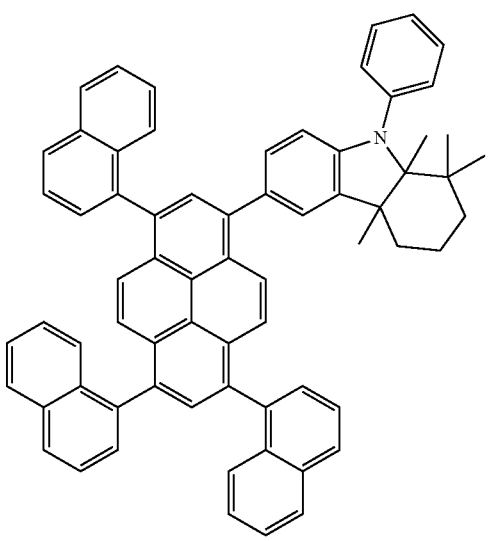
Formula 295
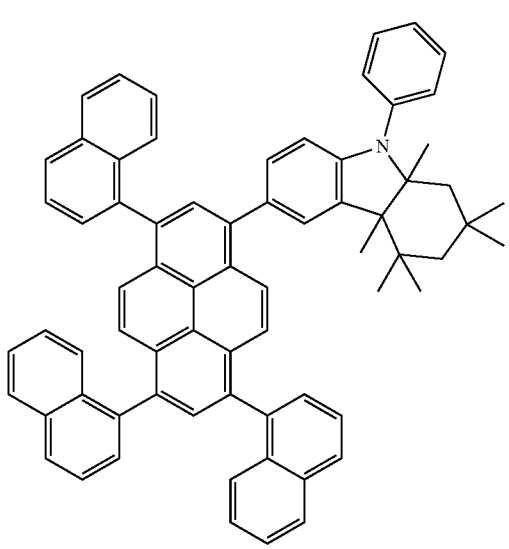
Formula 296
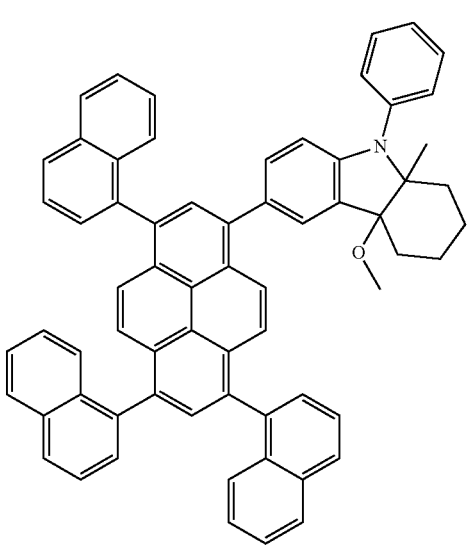

-continued
Formula 297
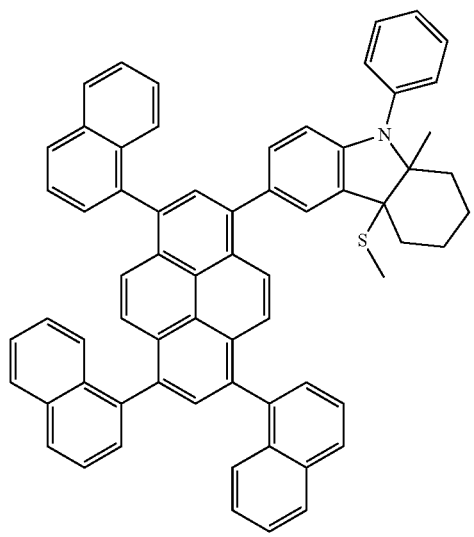
Formula 298
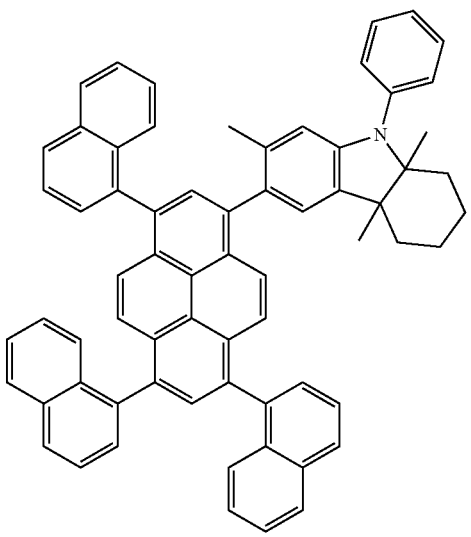
Formula 299
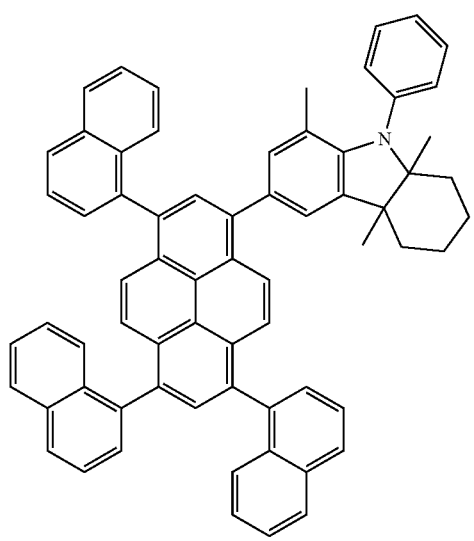
Formula 300
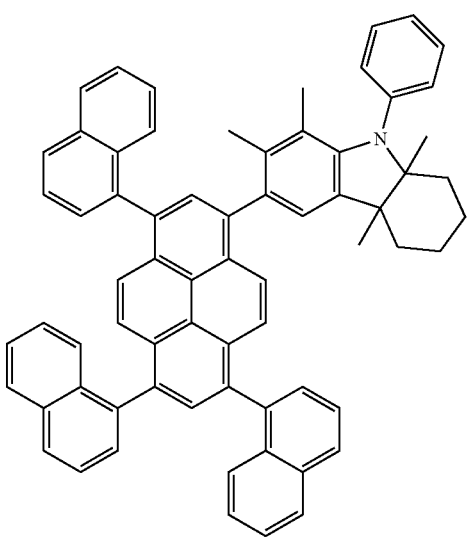

-continued
Formula 301
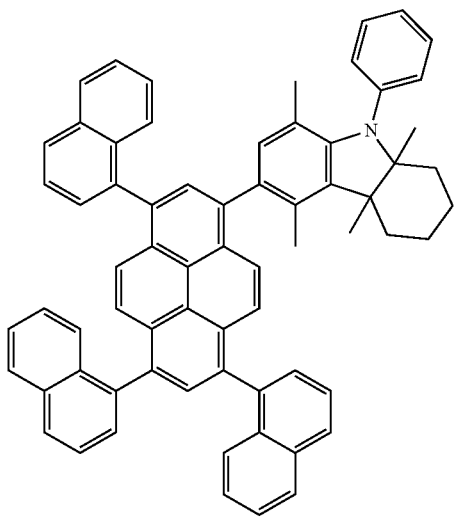
Formula 302
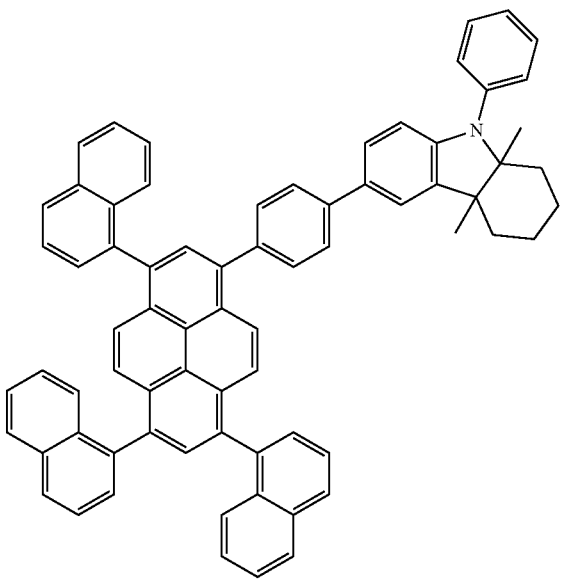
Formula 303
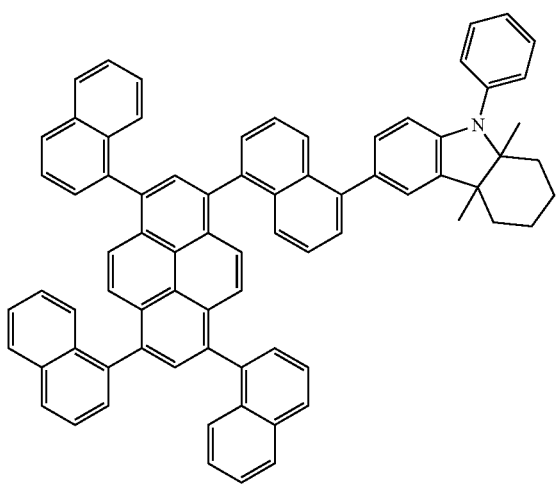
Formula 304
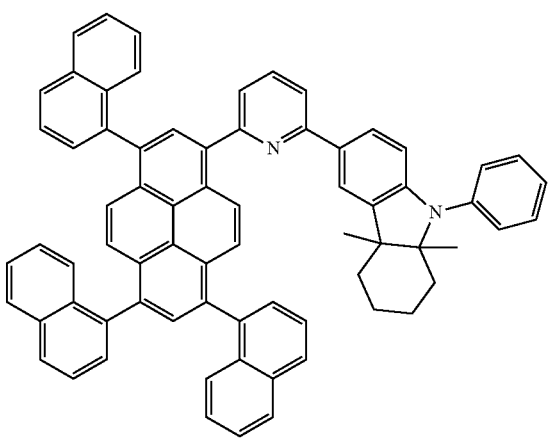
Formula 305
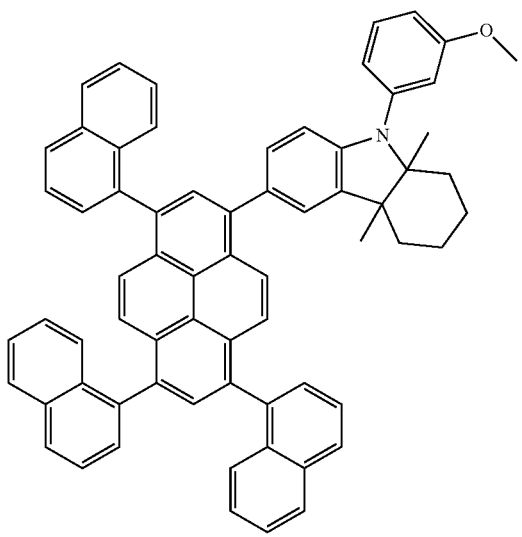
Formula 306
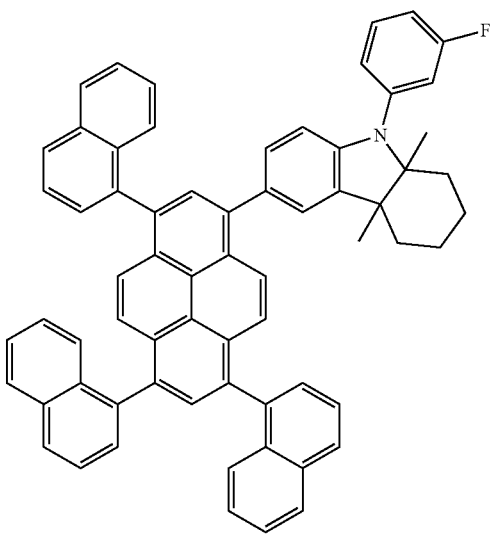

-continued
Formula 307
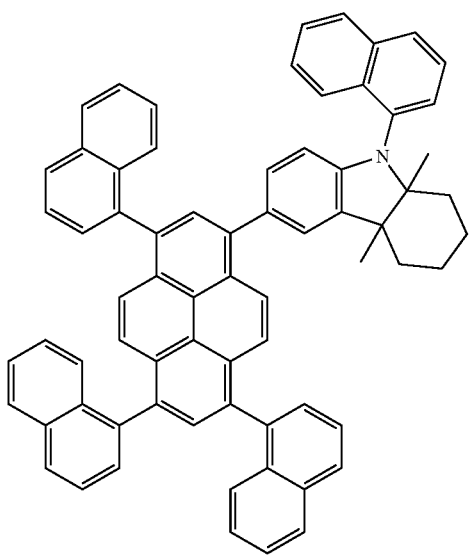
Formula 308
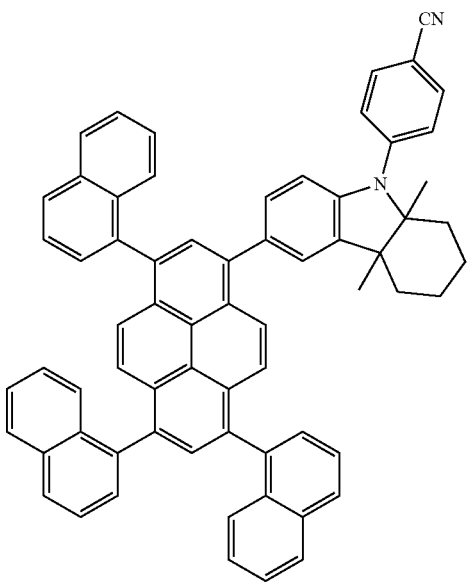
Formula 309
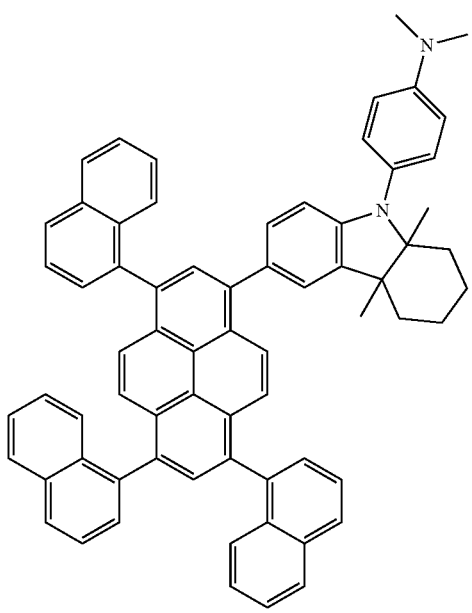
Formula 310
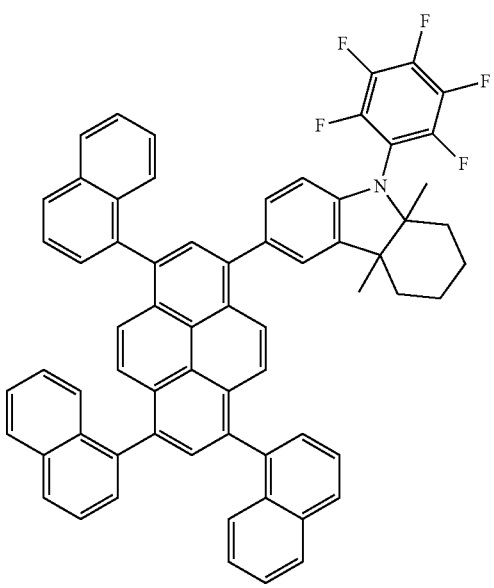

-continued
Formula 311
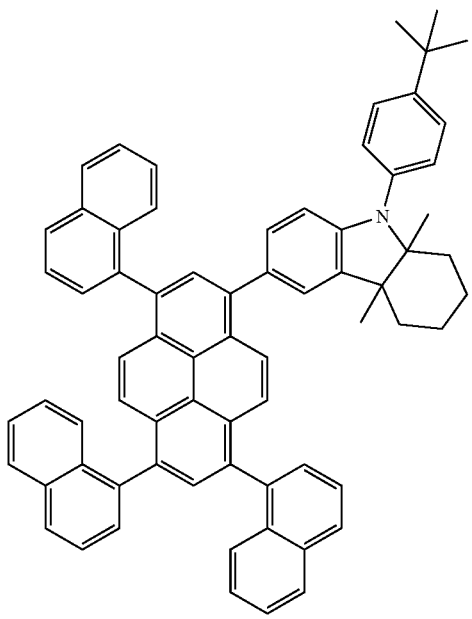
Formula 312
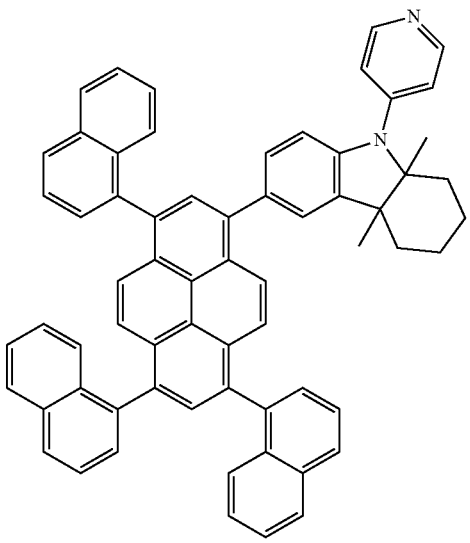
Formula 313
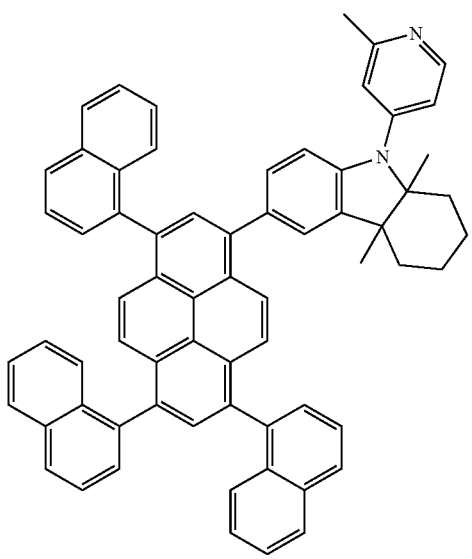
Formula 314
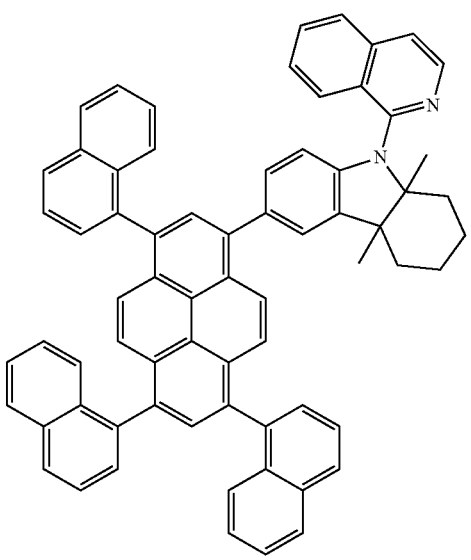

Formula 315
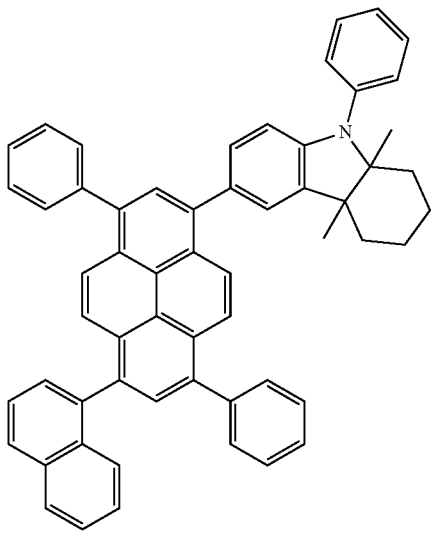
Formula 316
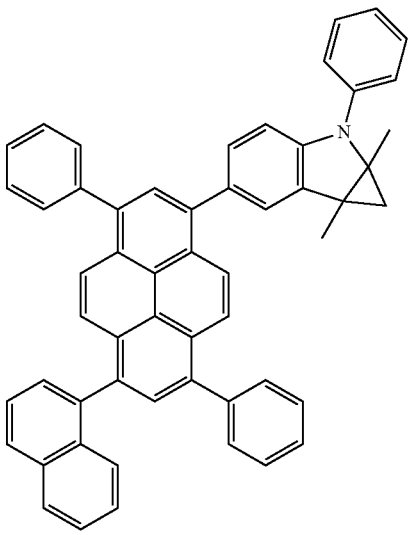
Formula 317
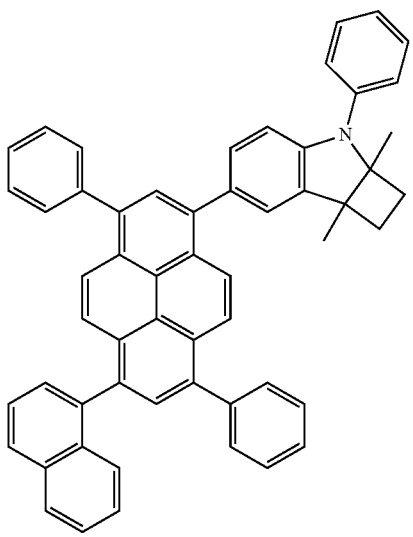
Formula 318
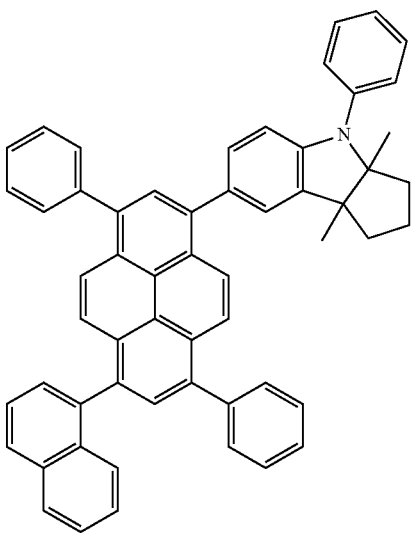
Formula 319
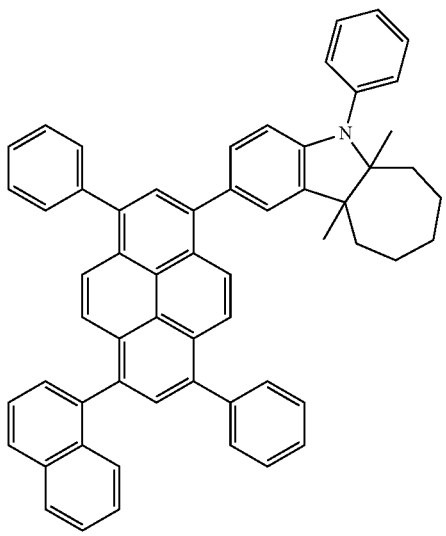
Formula 320
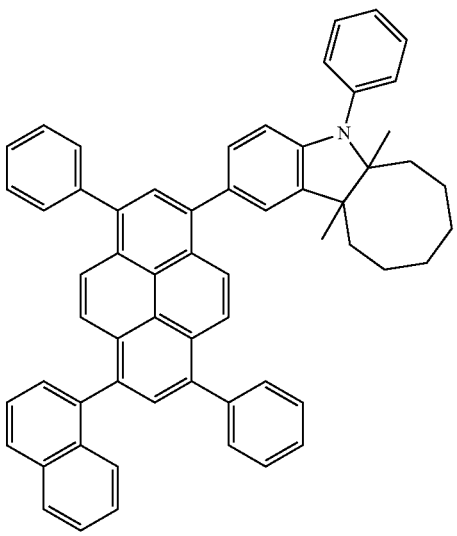

-continued
Formula 321
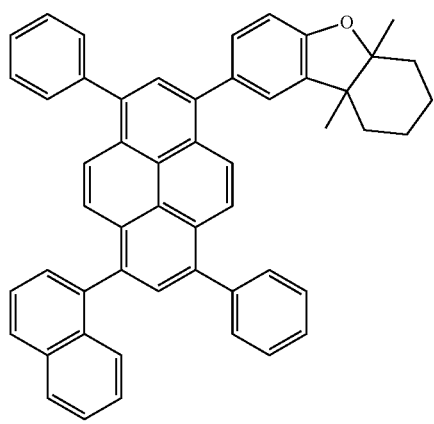
Formula 322
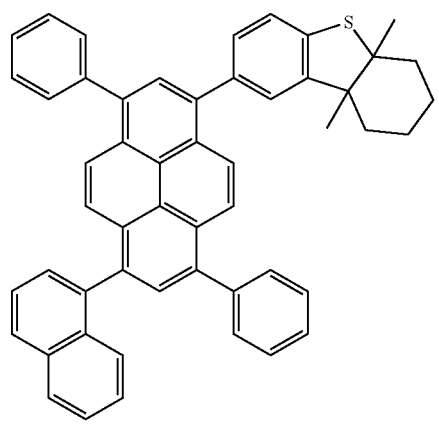
Formula 323
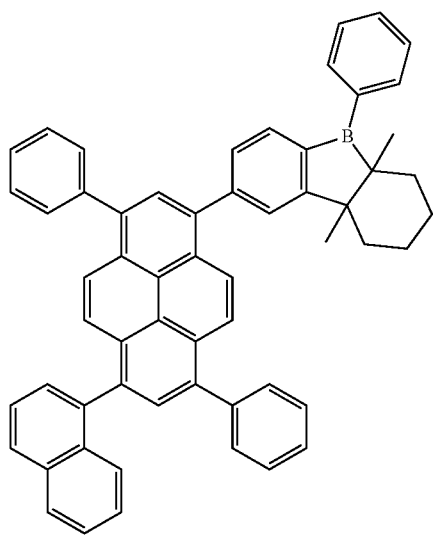
Formula 324
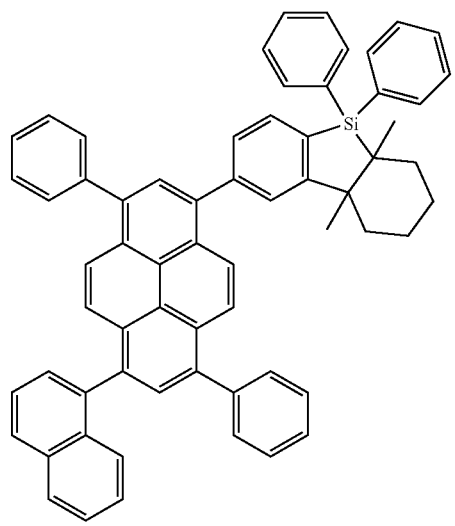
Formula 325
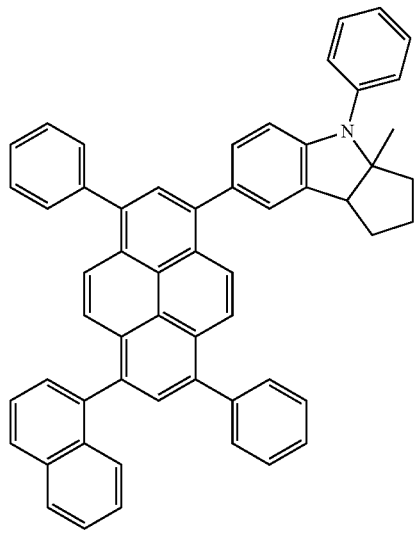
Formula 326
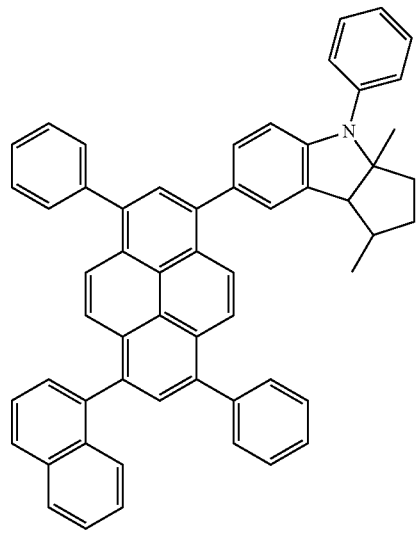

-continued
Formula 327
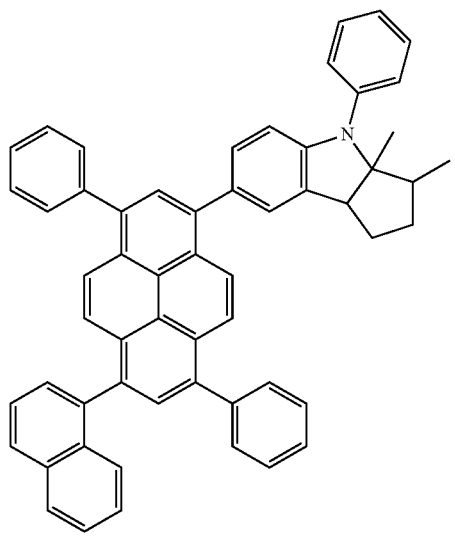
Formula 328
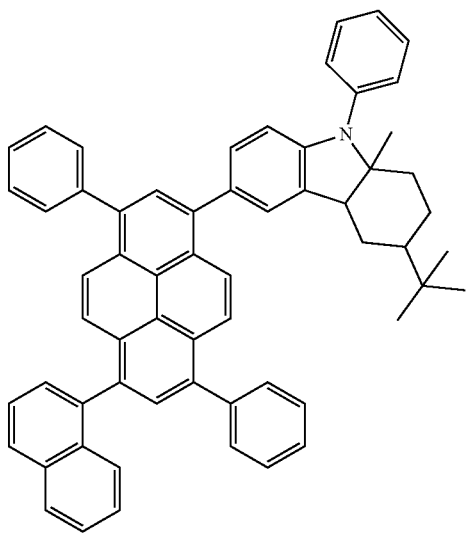
Formula 329
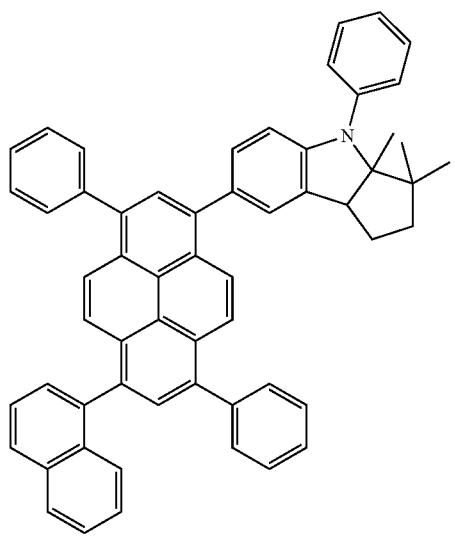
Formula 330
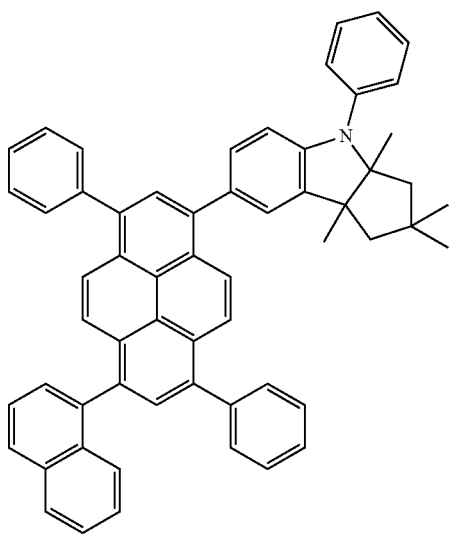
Formula 331
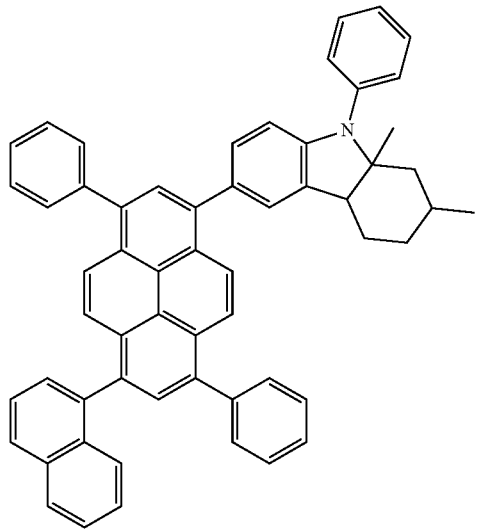
Formula 332
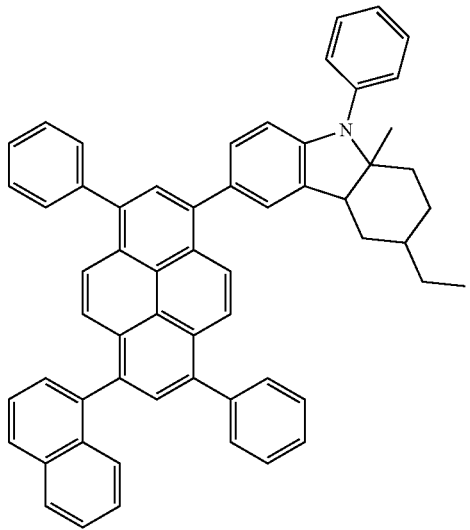

-continued
Formula 333
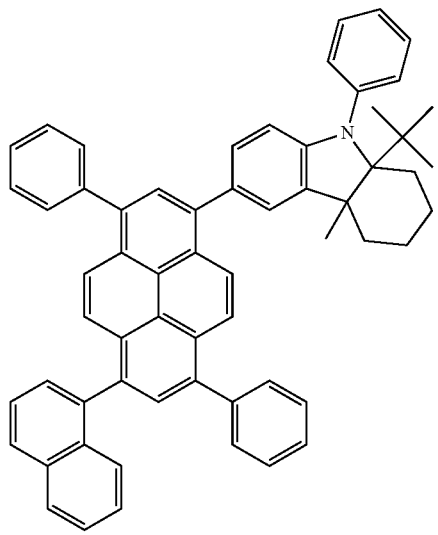
Formula 334
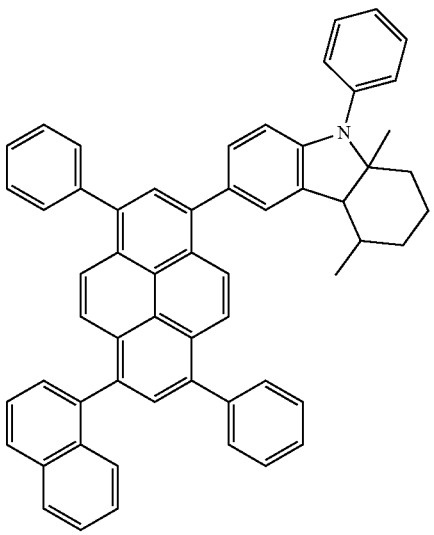
Formula 335
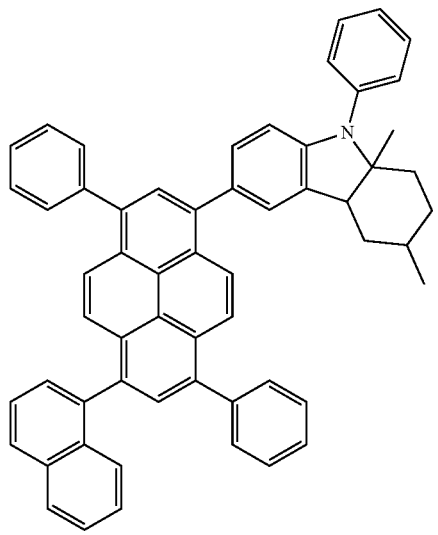
Formula 336
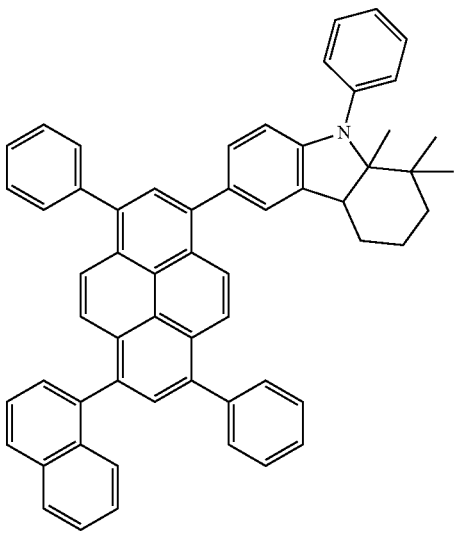
Formula 337
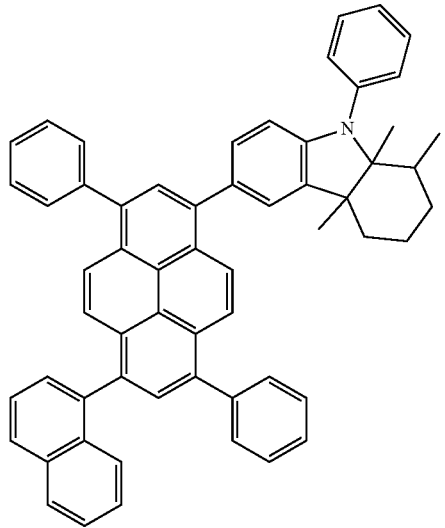
Formula 338
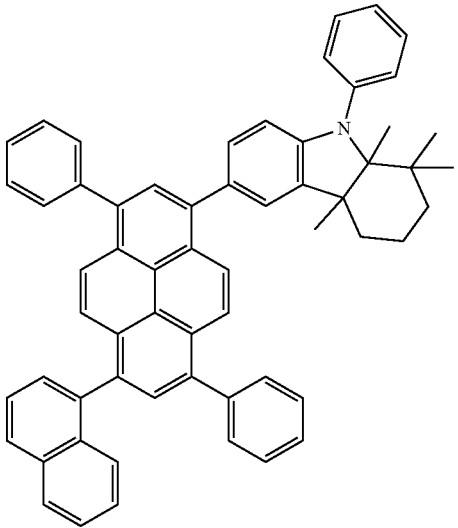

-continued
Formula 339
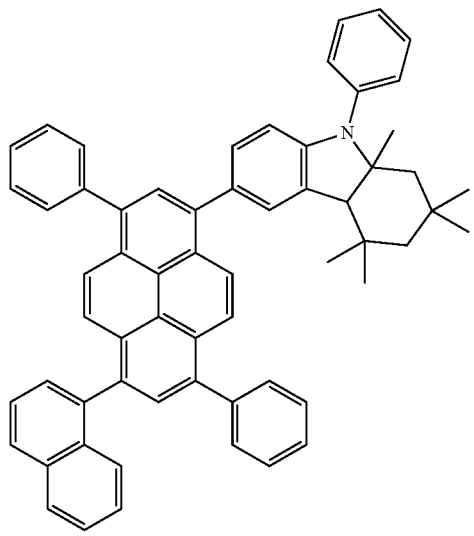
Formula 340
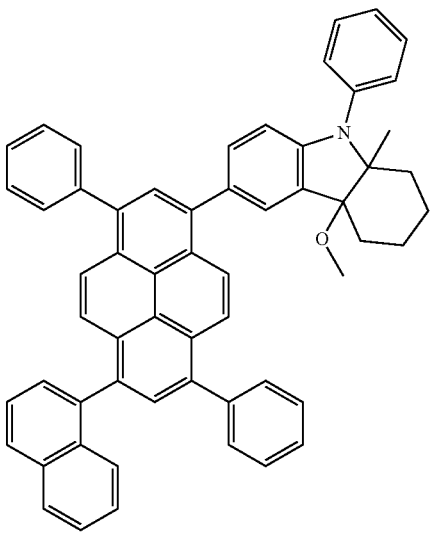
Formula 341
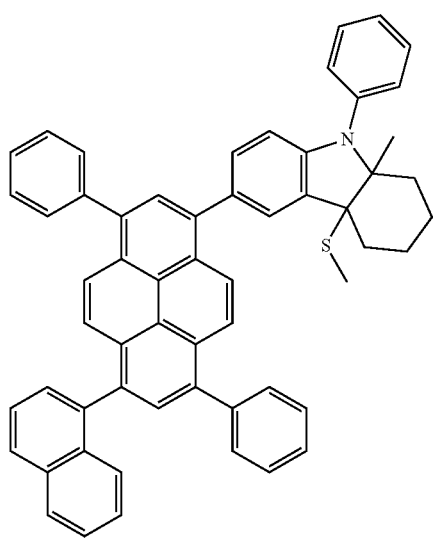
Formula 342
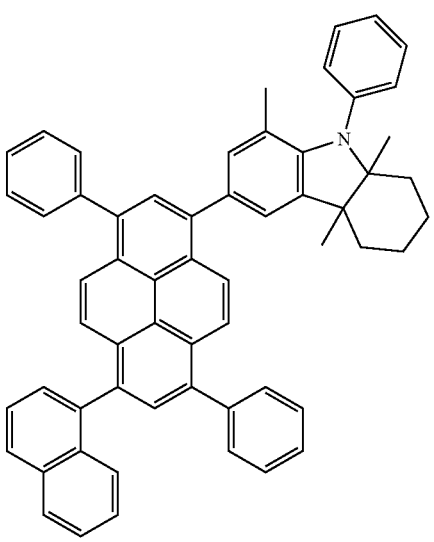
Formula 343
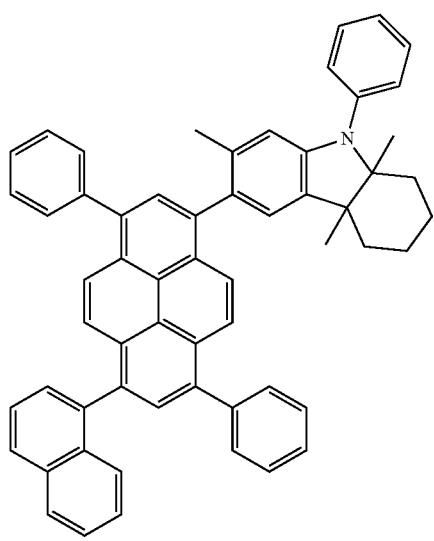
Formula 344
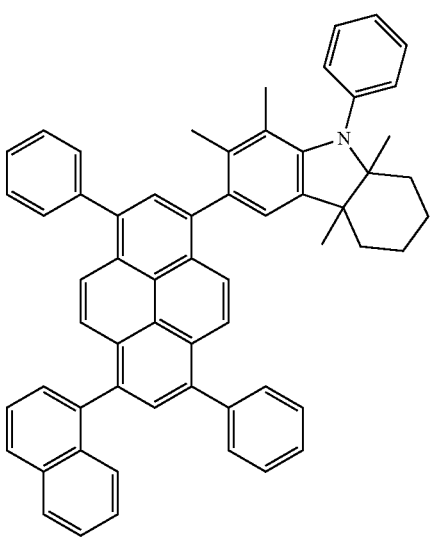

-continued
Formula 345
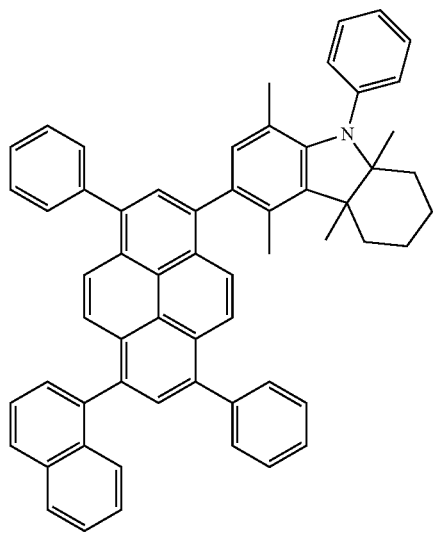
Formula 346
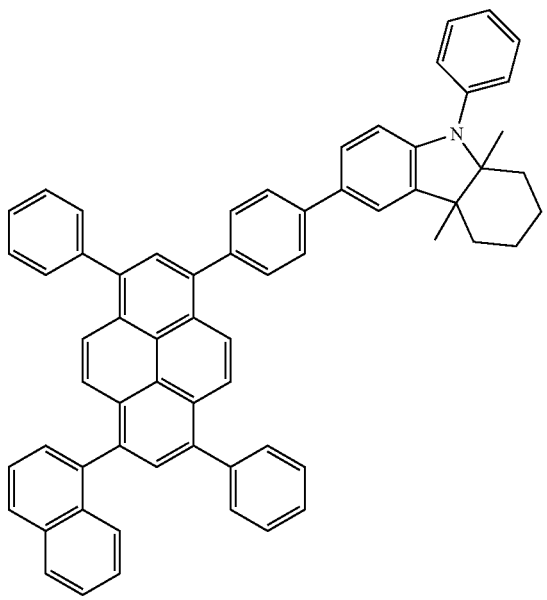
Formula 347
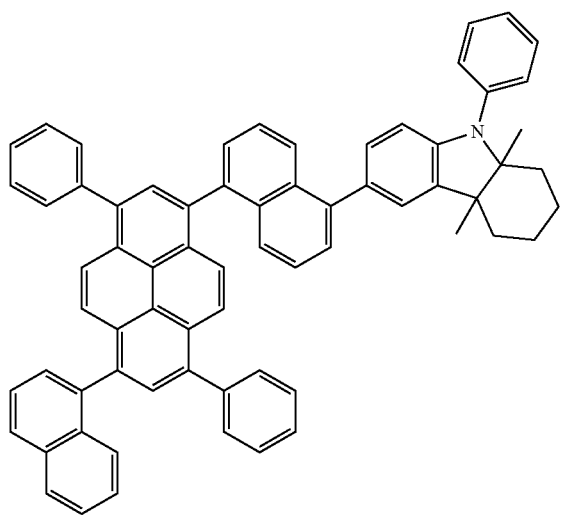
Formula 348
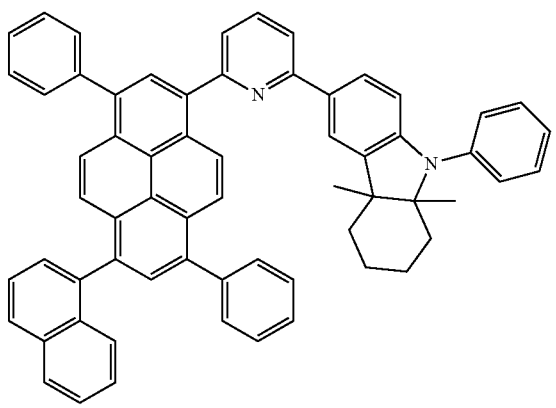

-continued
Formula 349
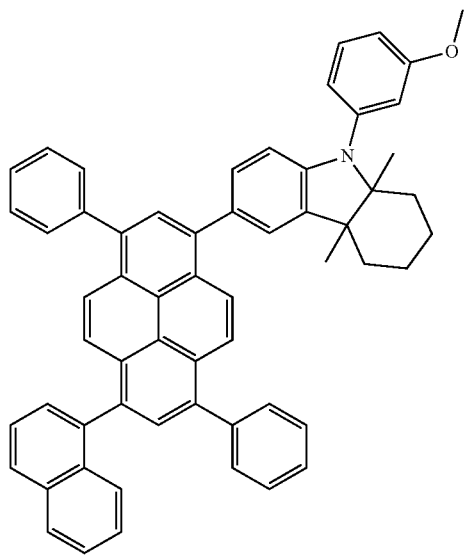
Formula 350
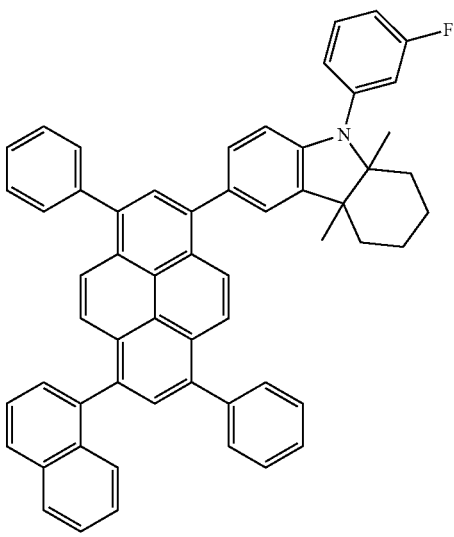
Formula 351
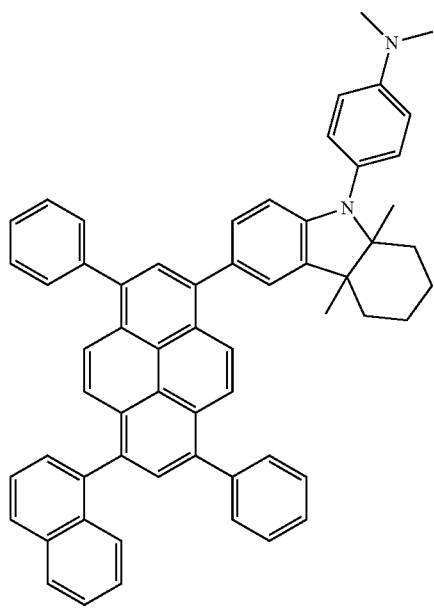
Formula 352
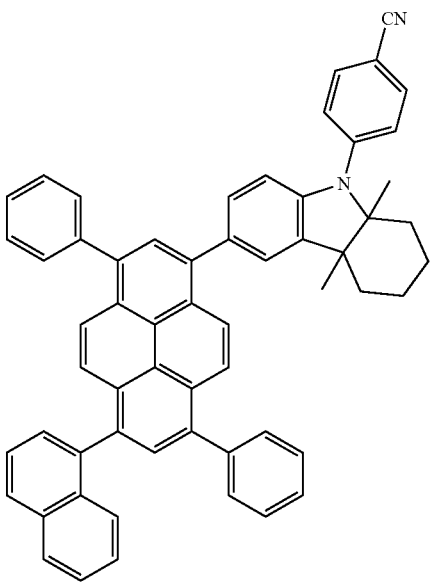

-continued
Formula 353
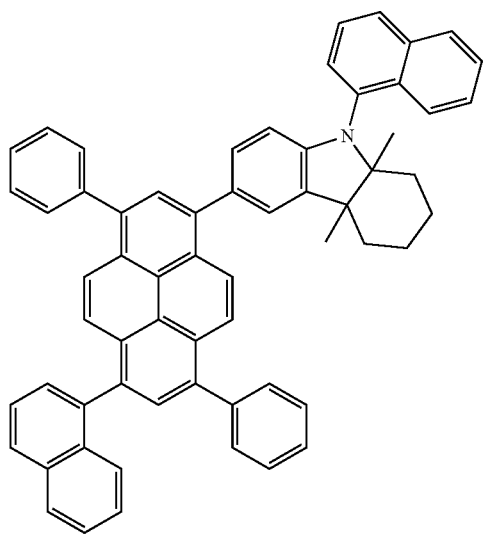
Formula 354
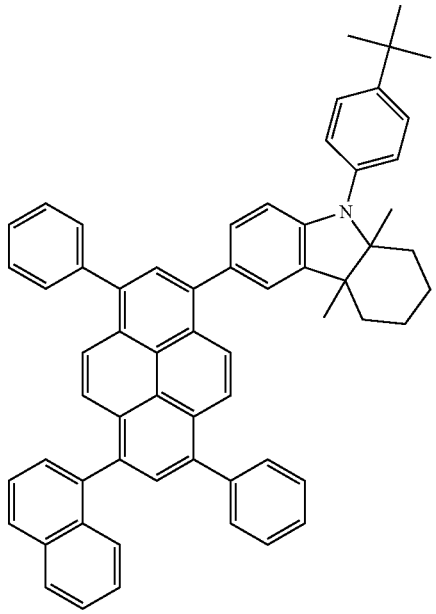
Formula 355
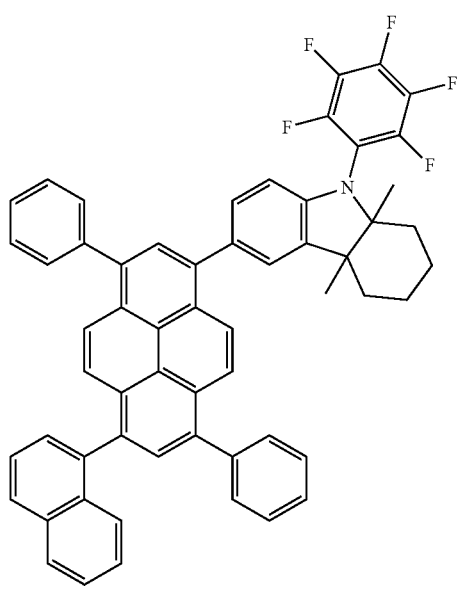
Formula 356
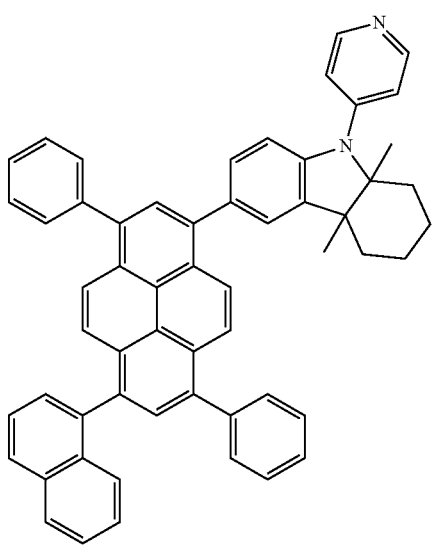

-continued
Formula 357
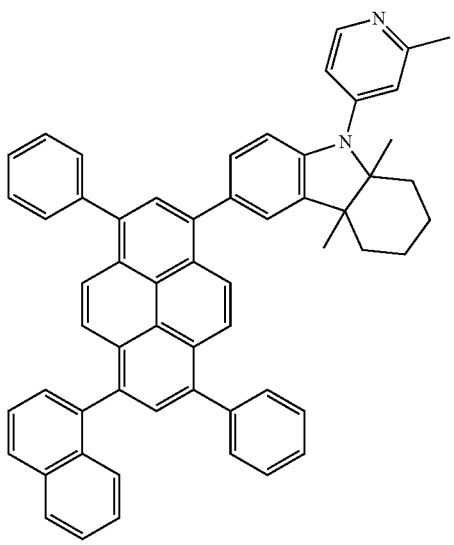
Formula 358
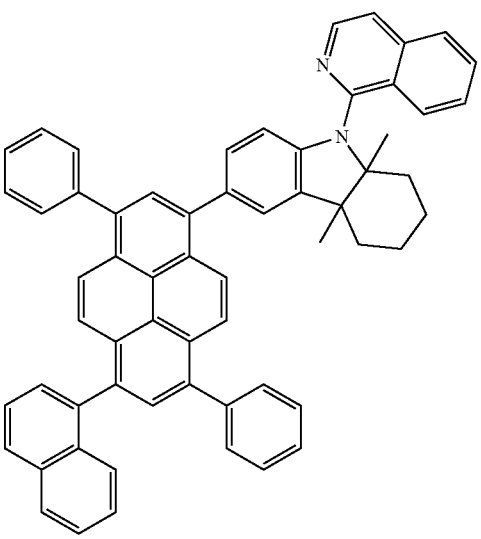
Formula 359
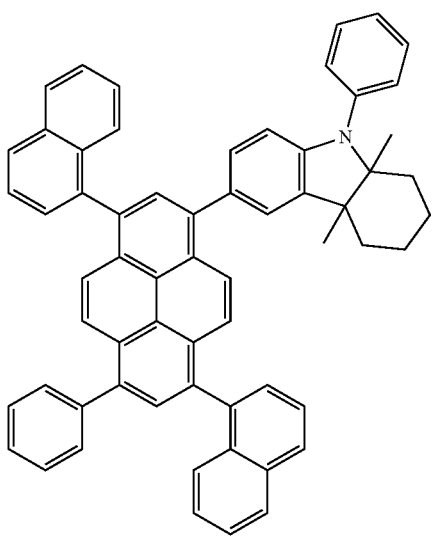
Formula 360
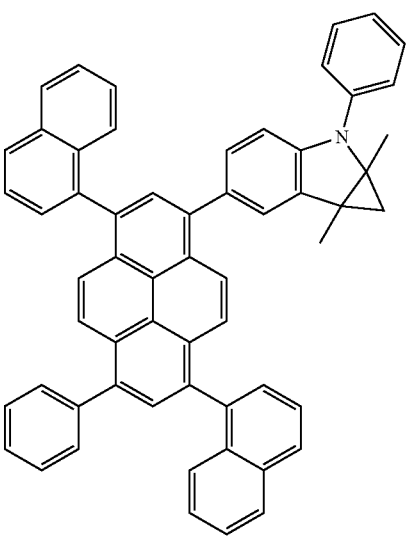
Formula 361
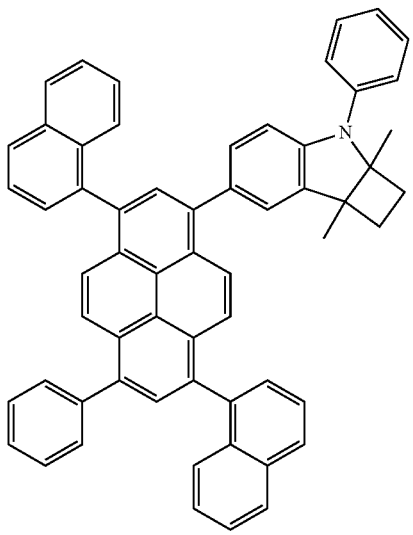
Formula 362
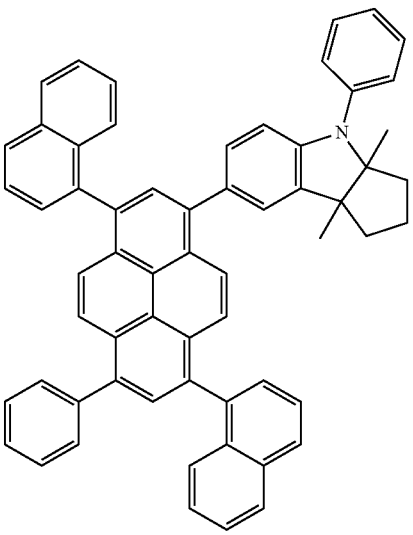

Formula 363
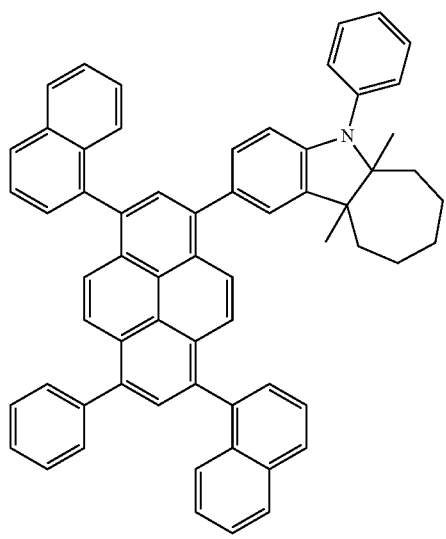
Formula 364
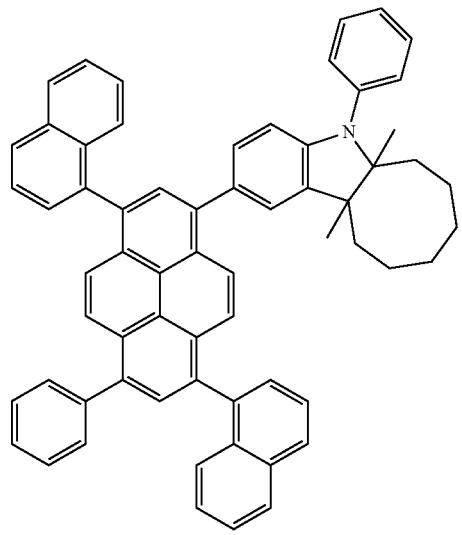
Formula 365
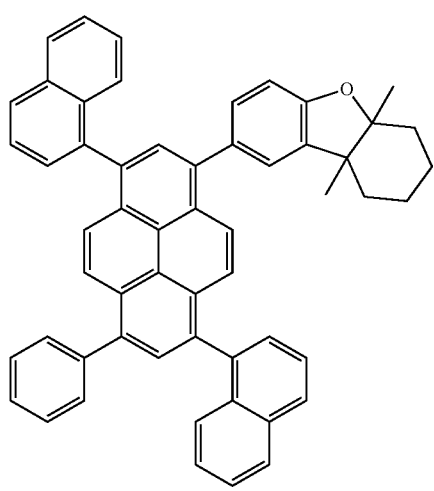
Formula 366
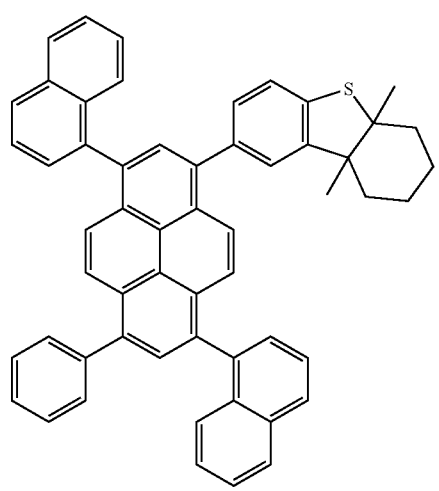
Formula 367
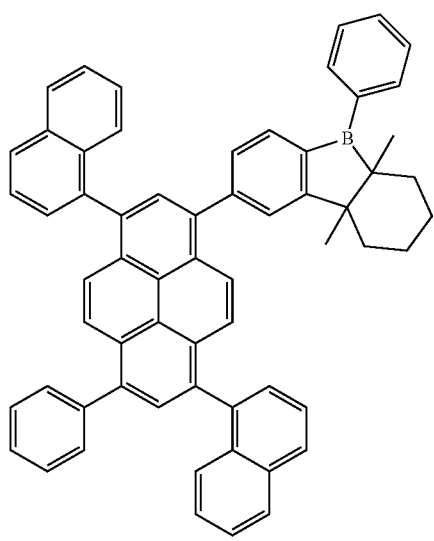
Formula 368
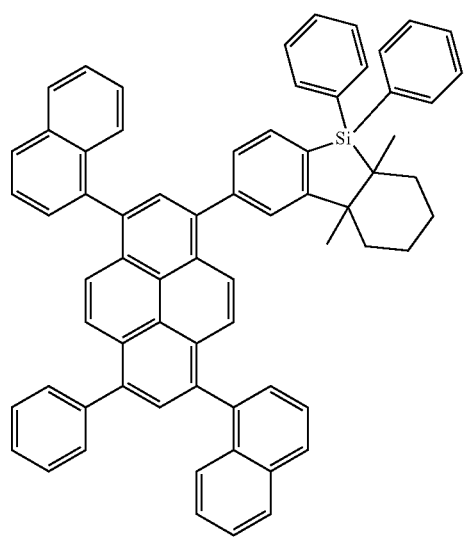

-continued
Formula 369
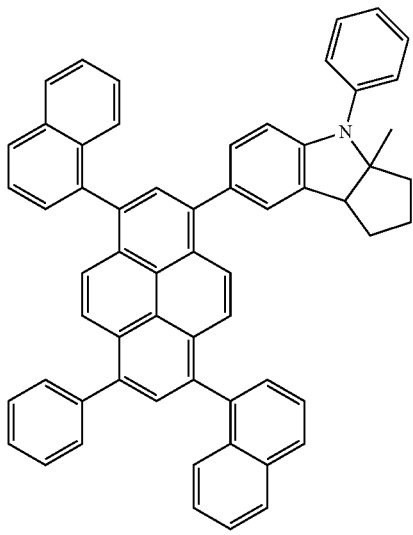
Formula 370
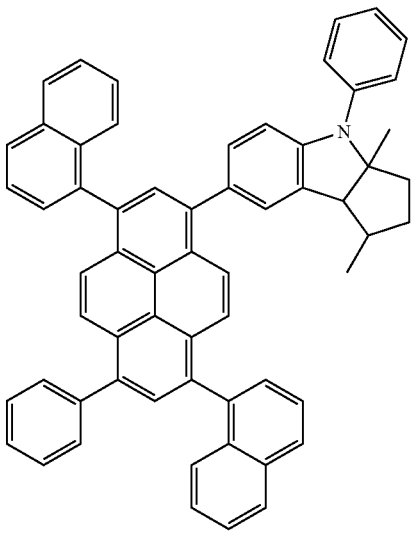
Formula 371
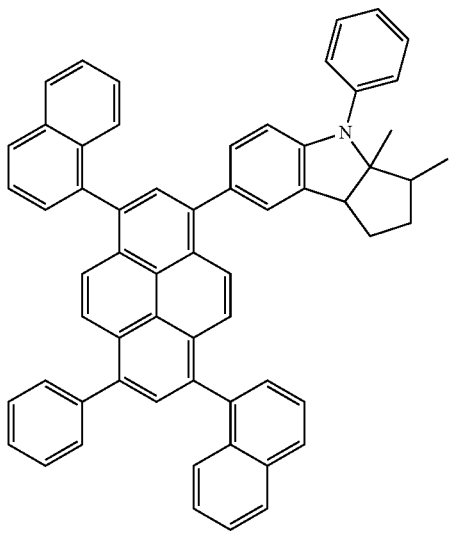
Formula 372
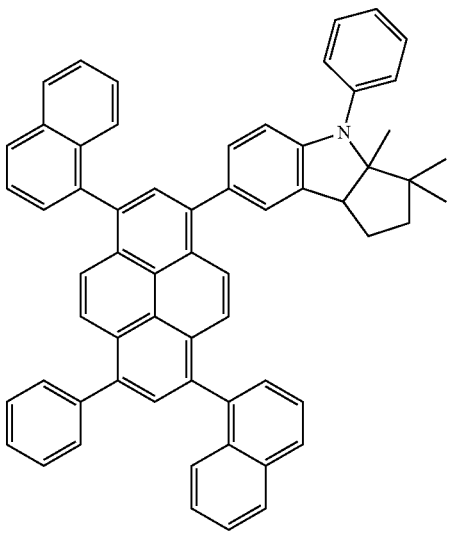
Formula 373
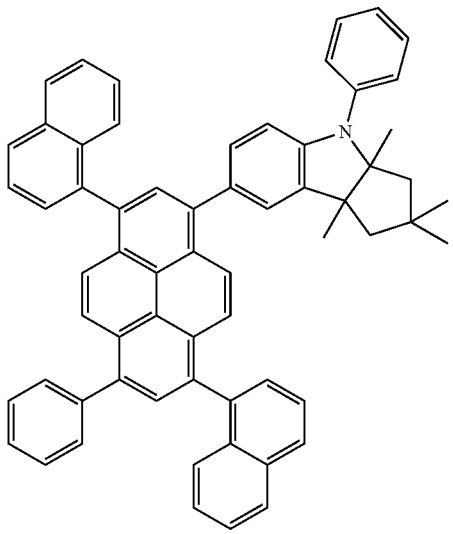
Formula 374
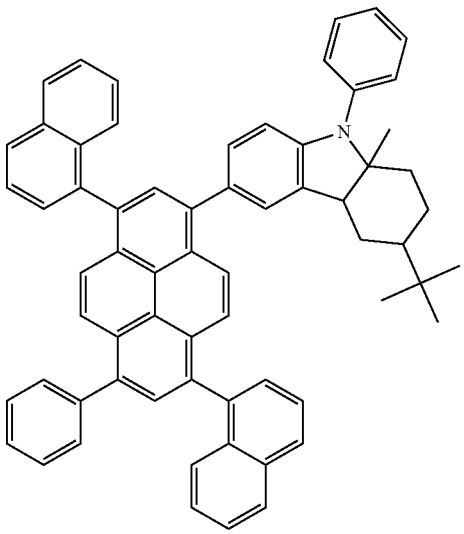

-continued
Formula 375
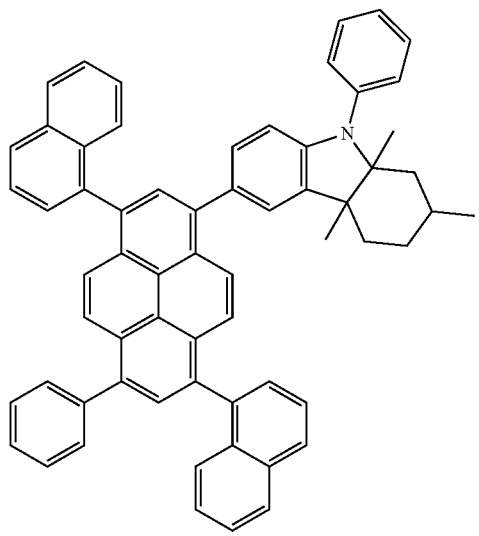
Formula 376
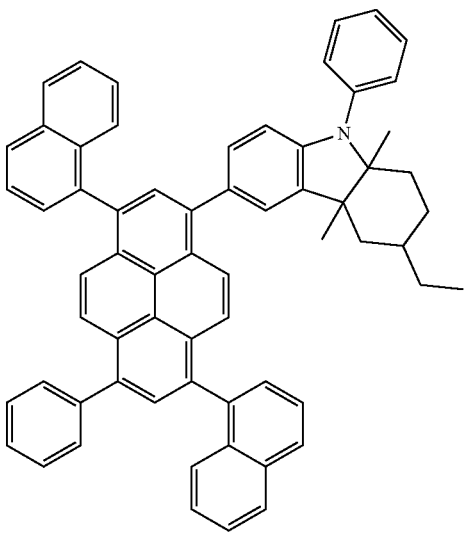
Formula 377
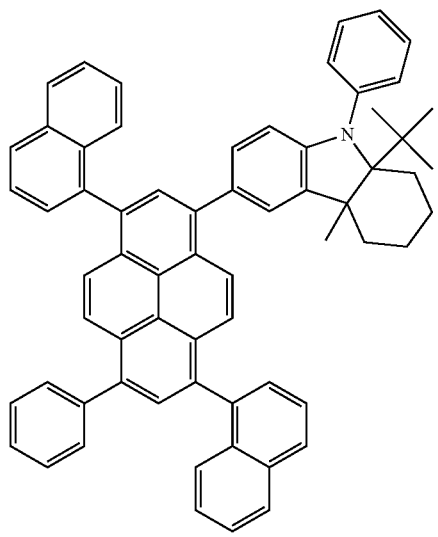
Formula 378
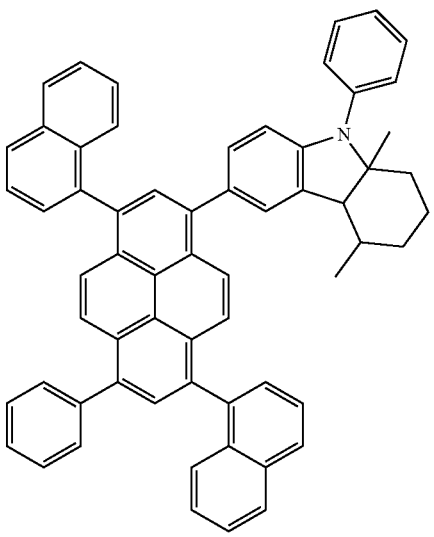
Formula 379
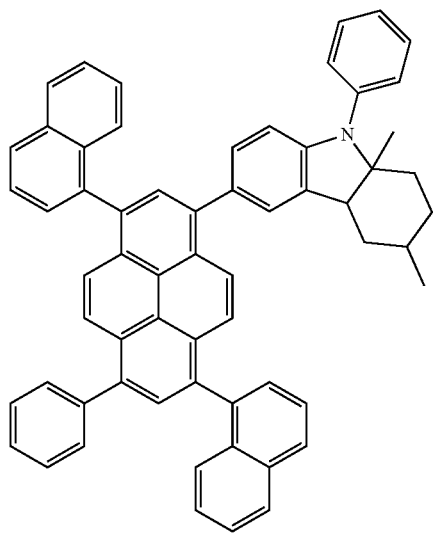
Formula 380
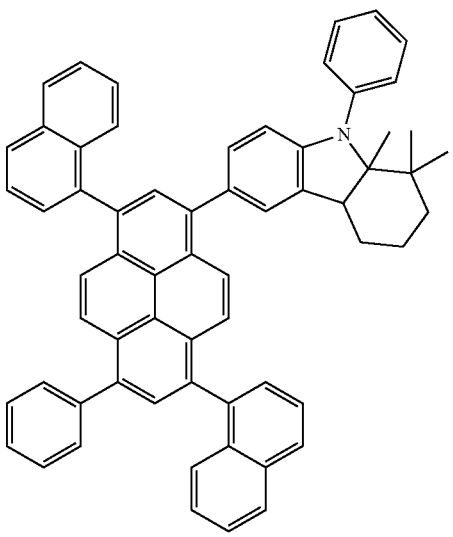

Formula 381
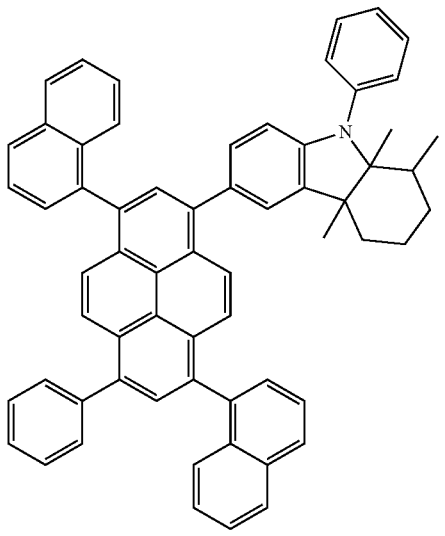
Formula 382
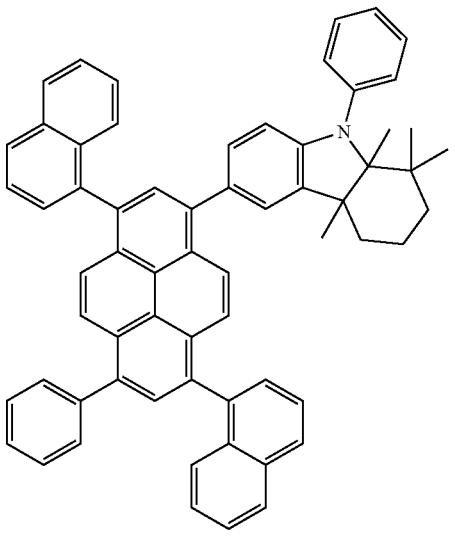
Formula 383
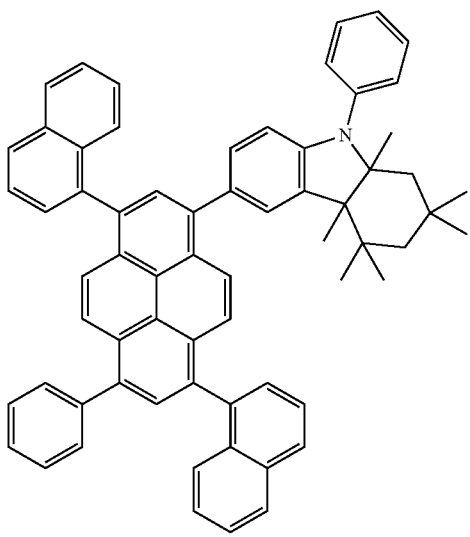
Formula 384
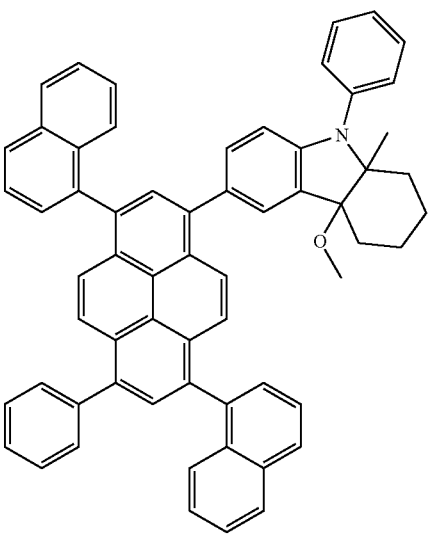
Formula 385
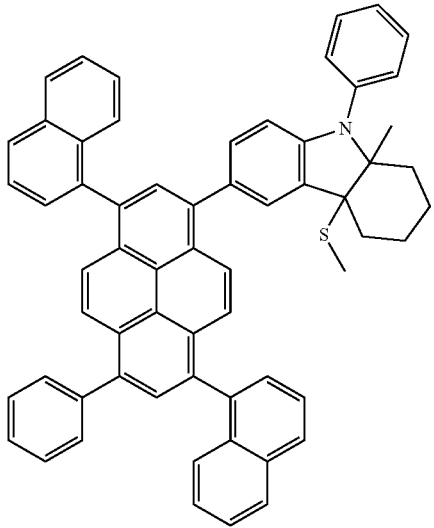
Formula 386
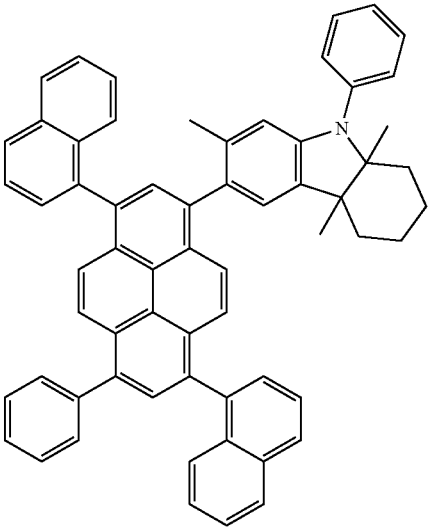

-continued
Formula 387
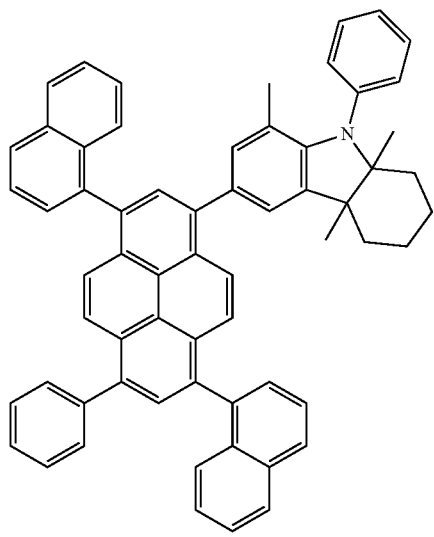
Formula 388
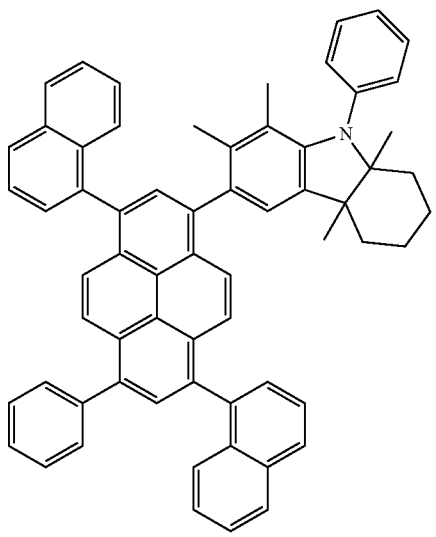
Formula 389
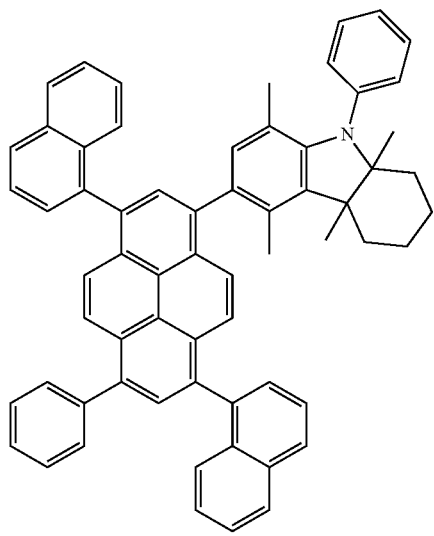
Formula 390
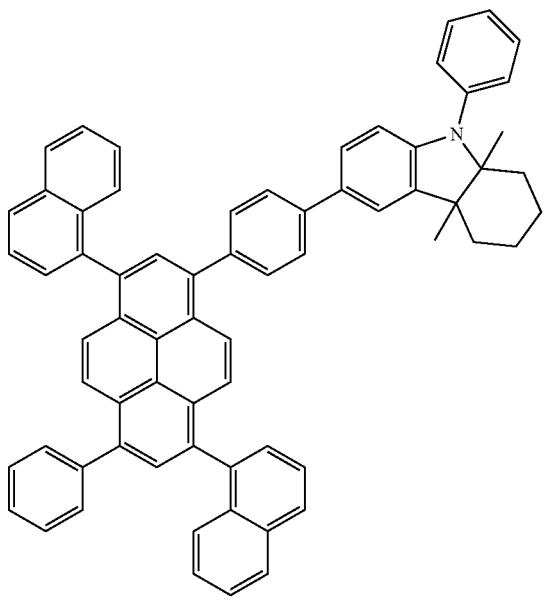

-continued
Formula 391
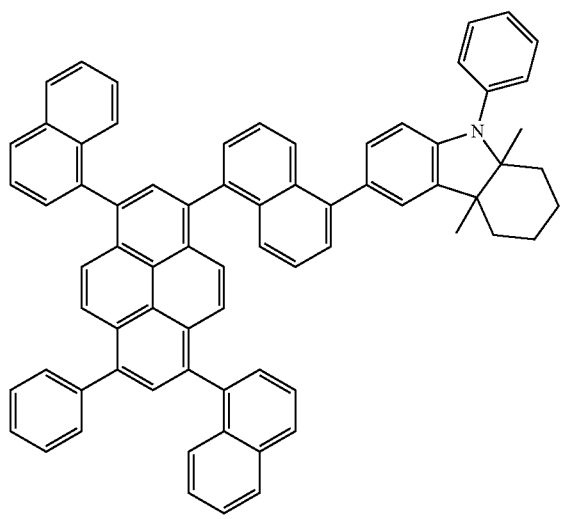
Formula 392
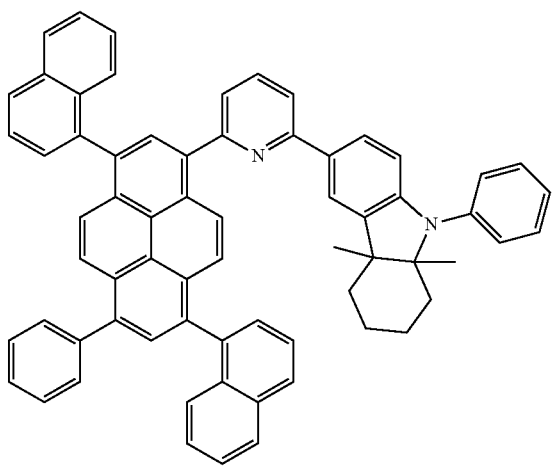
Formula 393
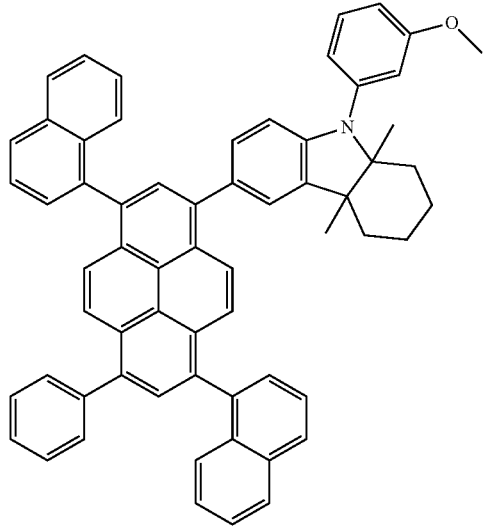
Formula 394
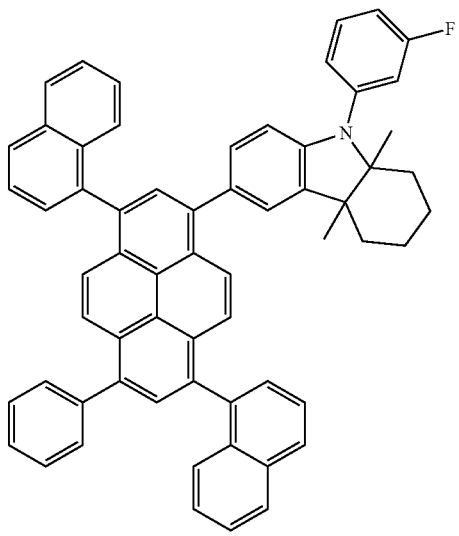
Formula 395
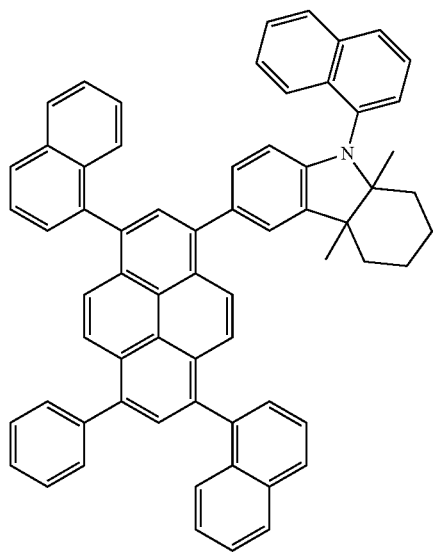
Formula 396
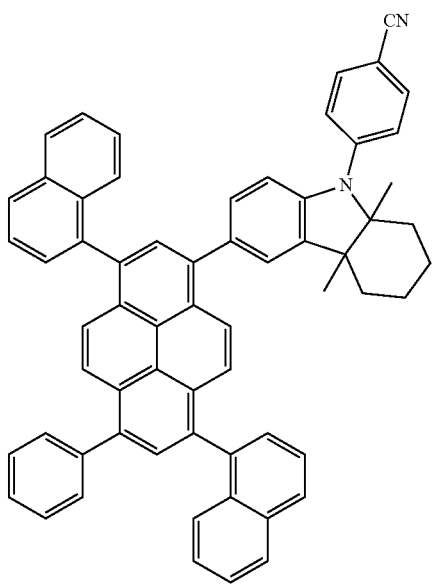

-continued
Formula 397
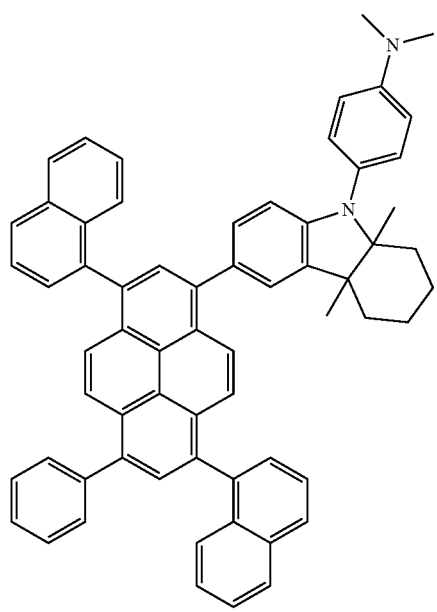
Formula 398
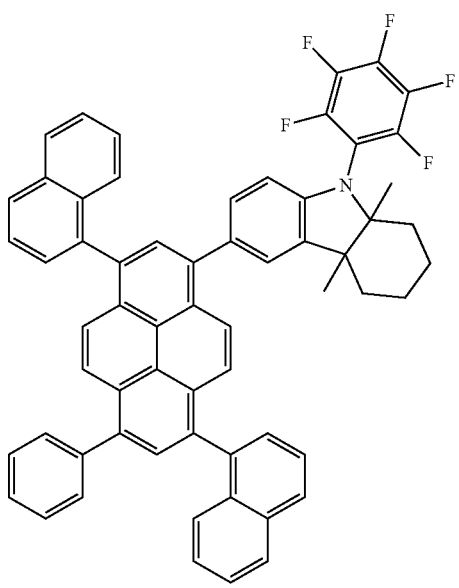
Formula 399
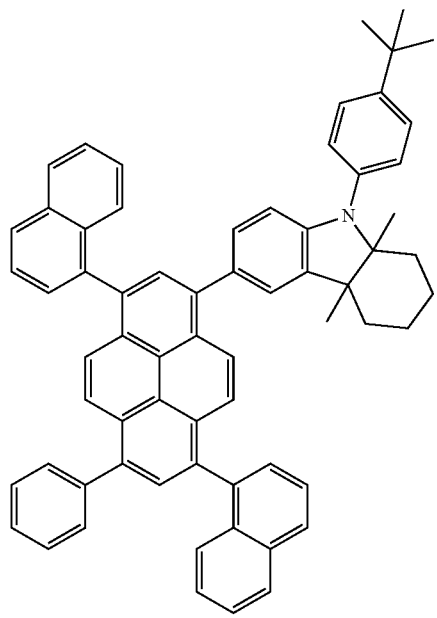
Formula 400
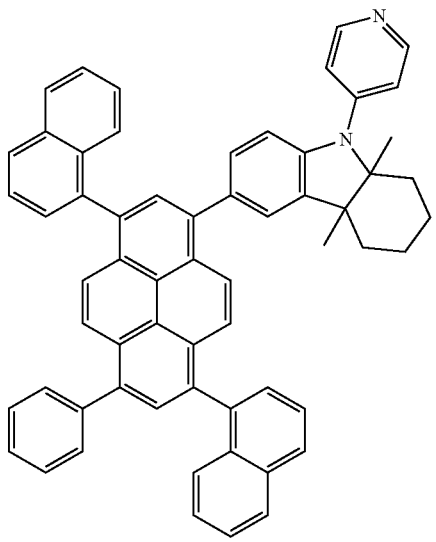

-continued
Formula 401
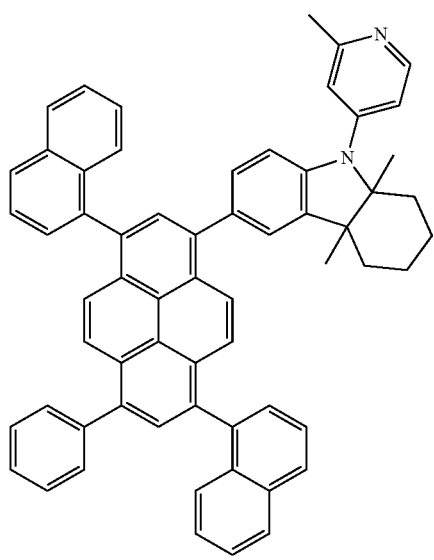
Formula 402
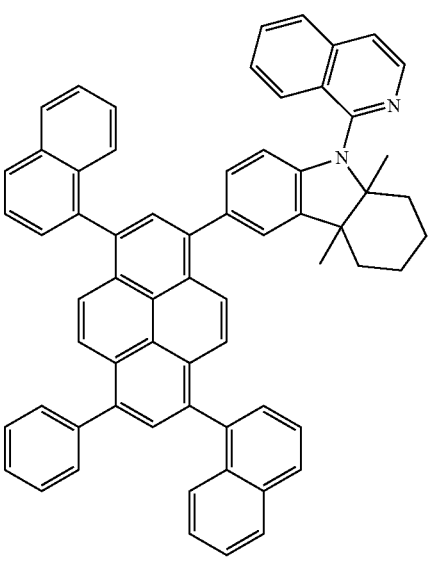
Formula 403
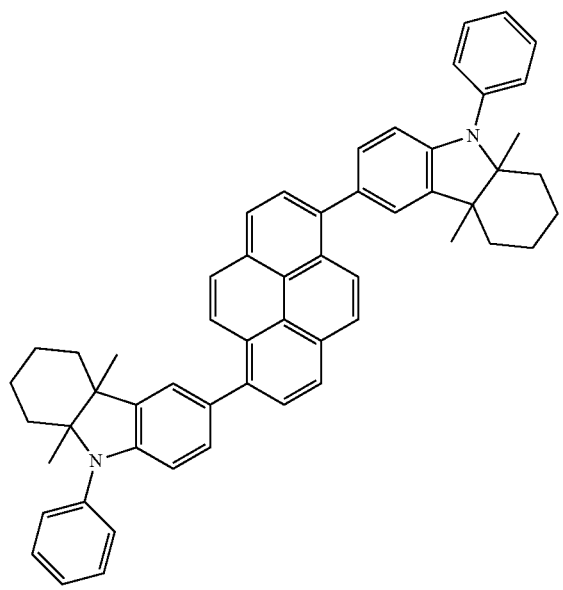
Formula 404
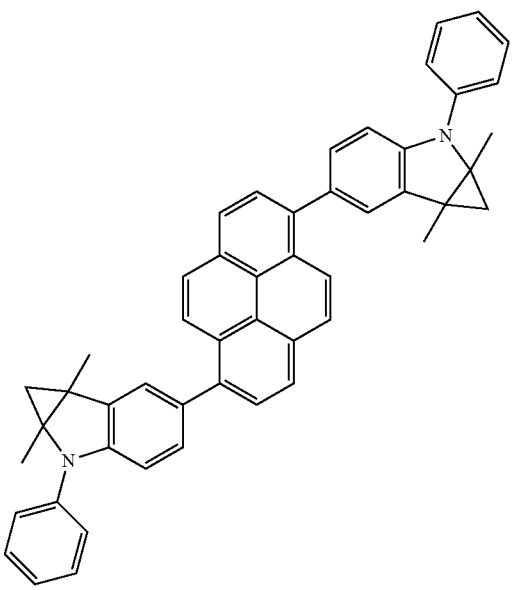

Formula 405
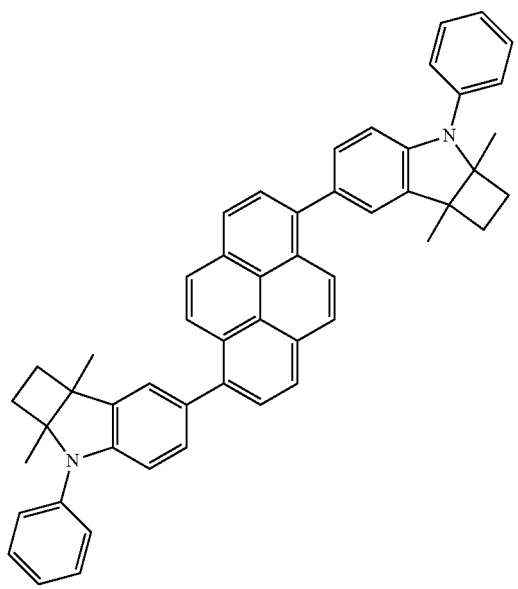
Formula 406
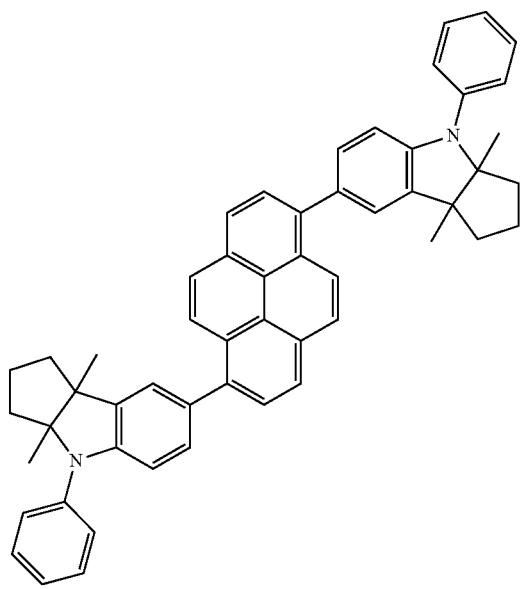
Formula 407
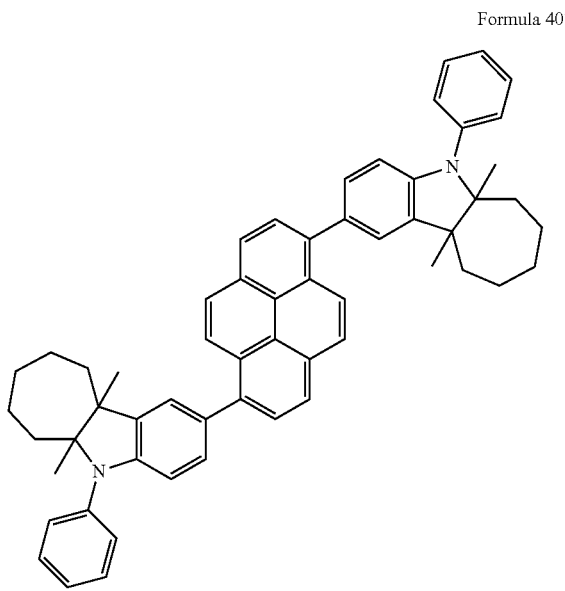
Formula 408
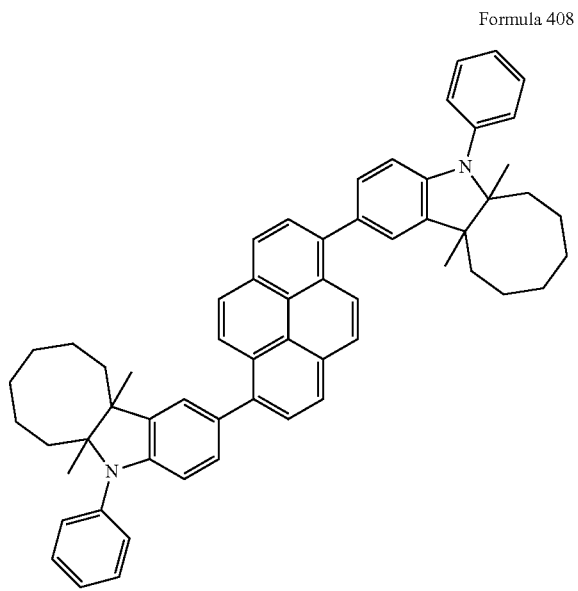
Formula 409
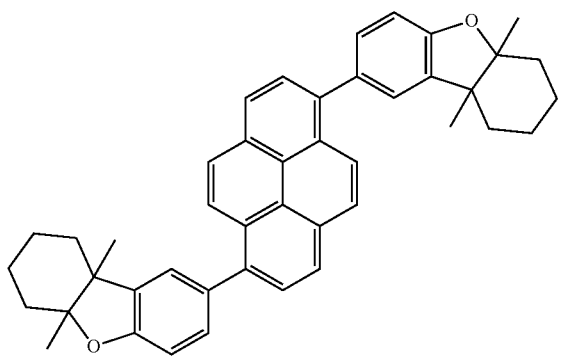
Formula 410
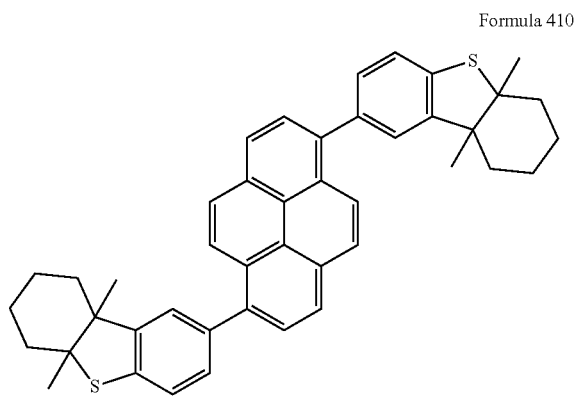

-continued
Formula 411
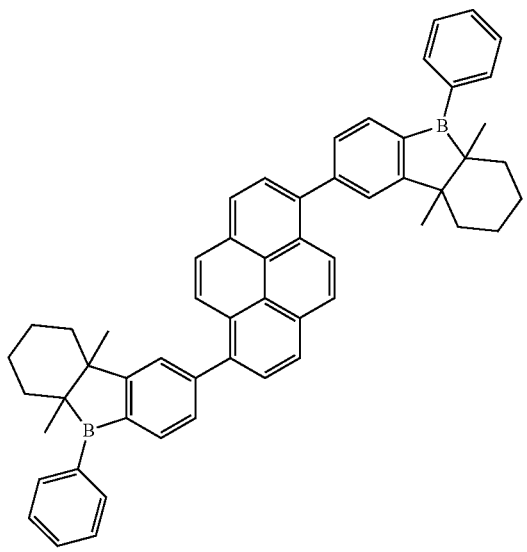
Formula 412
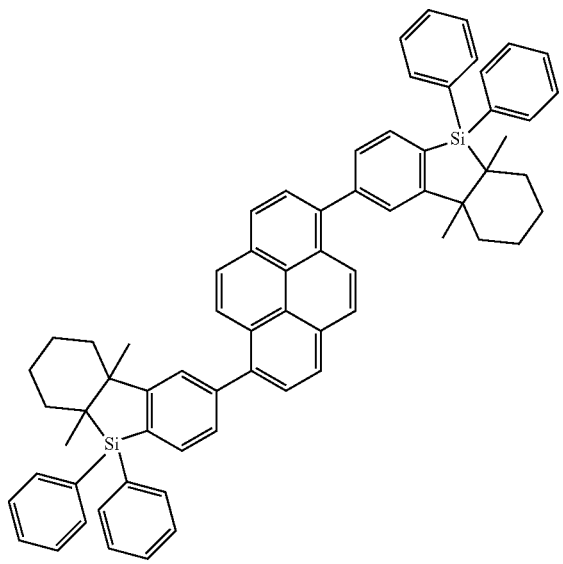
Formula 413
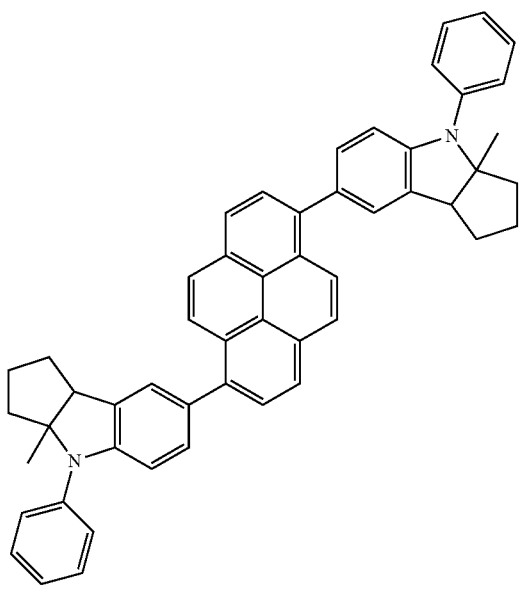
Formula 414
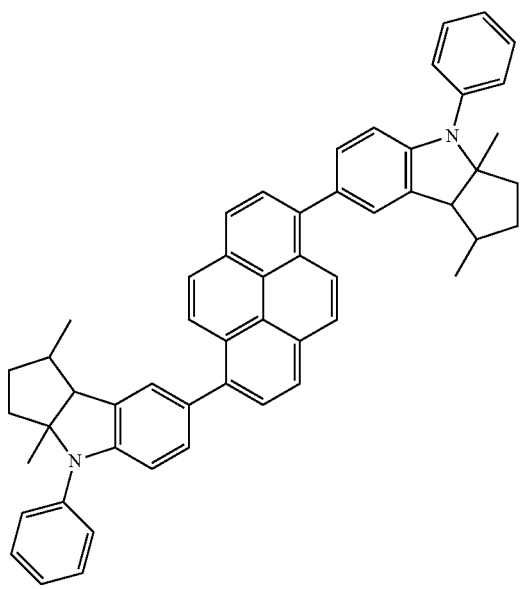

-continued
Formula 415
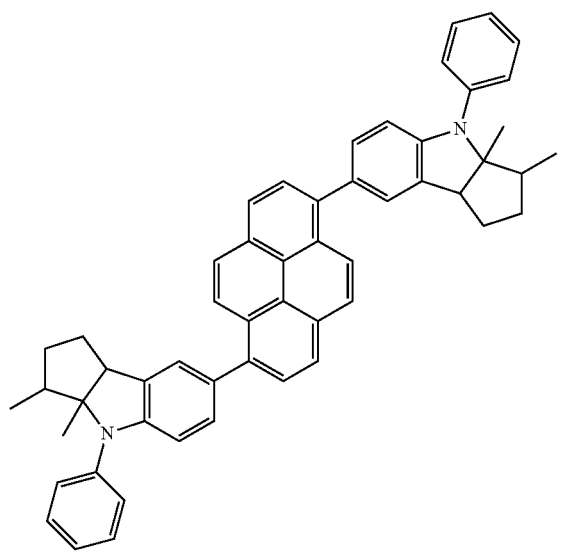
Formula 416
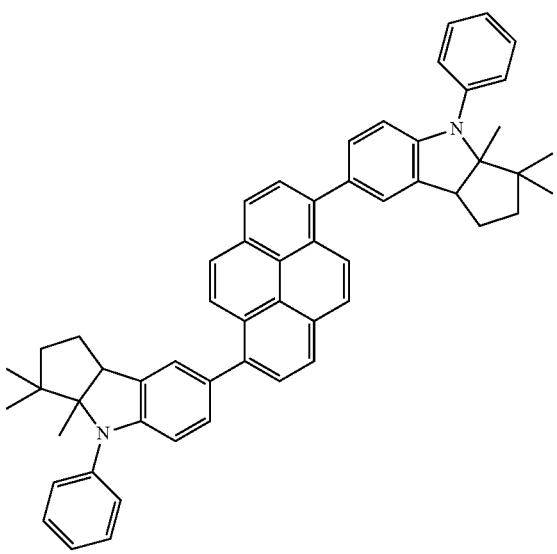
Formula 417
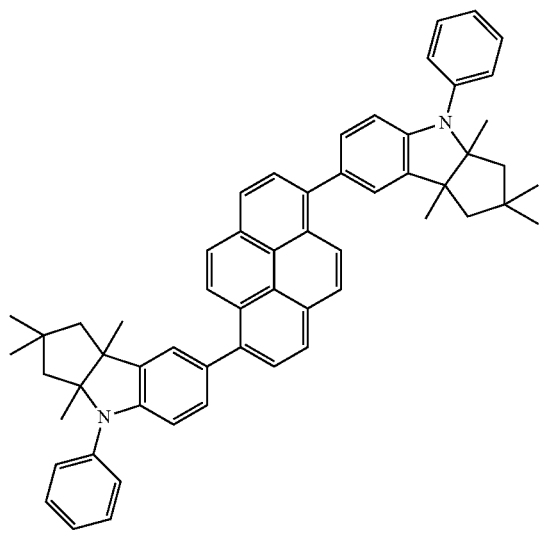
Formula 418
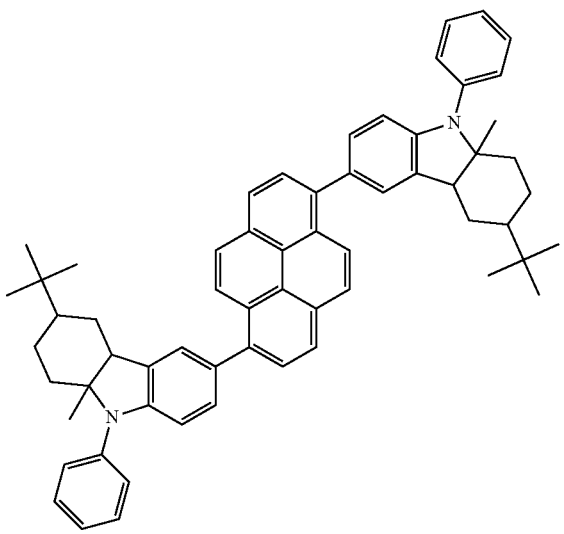
Formula 419
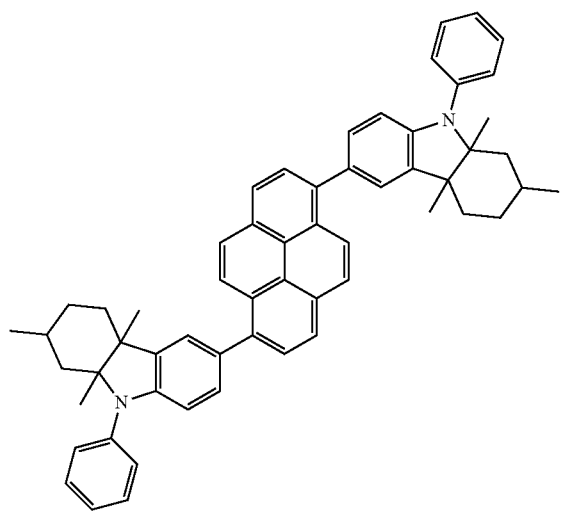
Formula 420
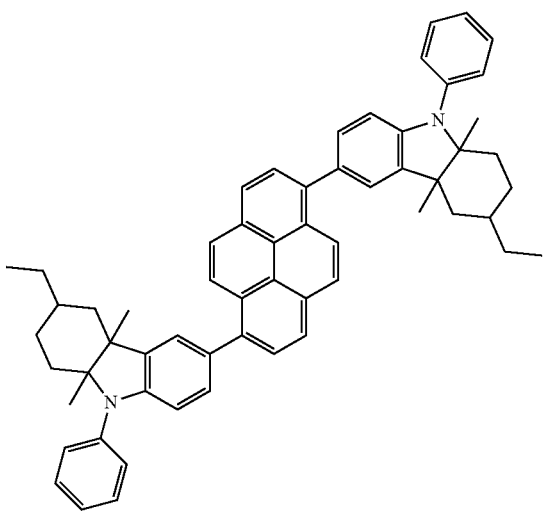

-continued
Formula 421
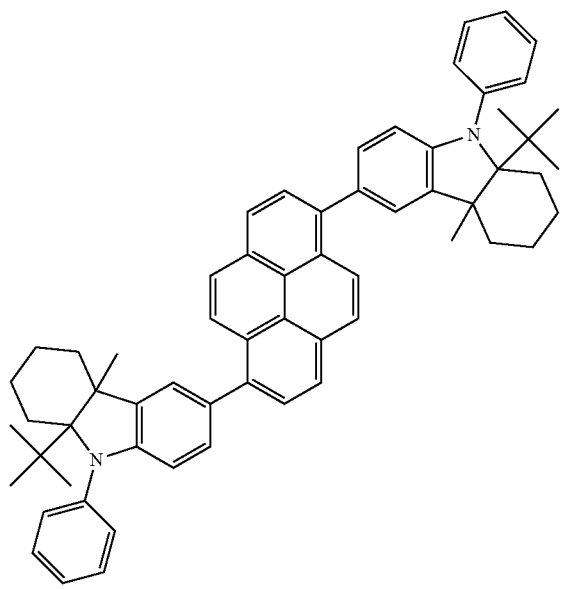
Formula 422
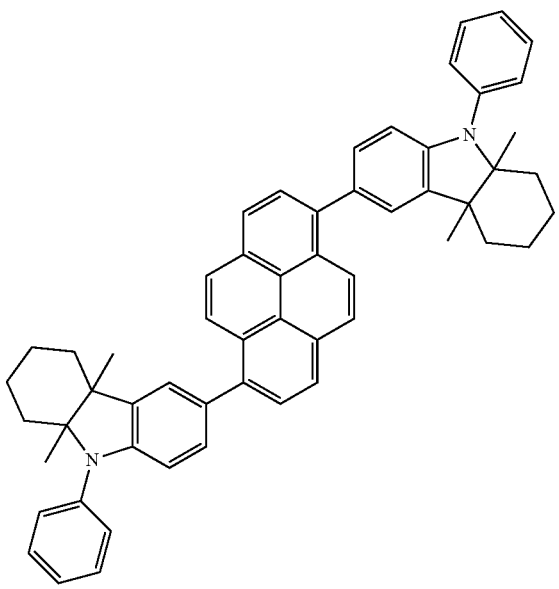
Formula 423
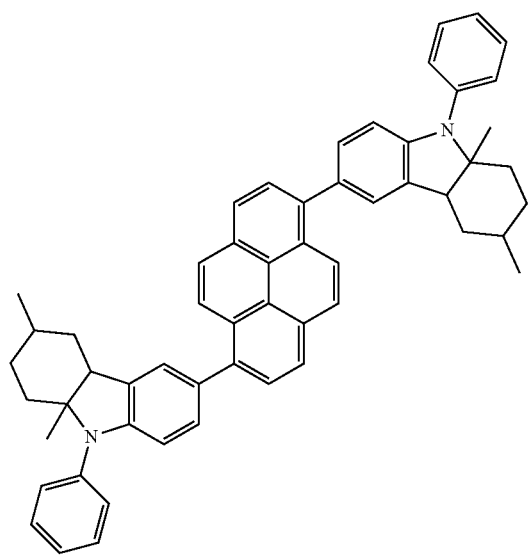
Formula 424
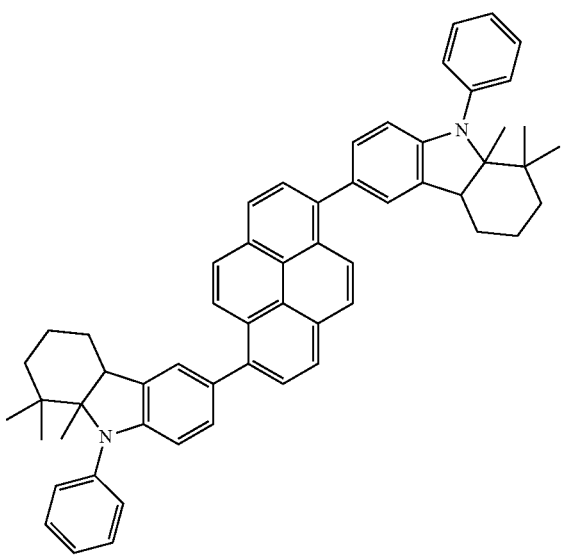

-continued
Formula 425
Formula 426
Formula 427
Formula 428
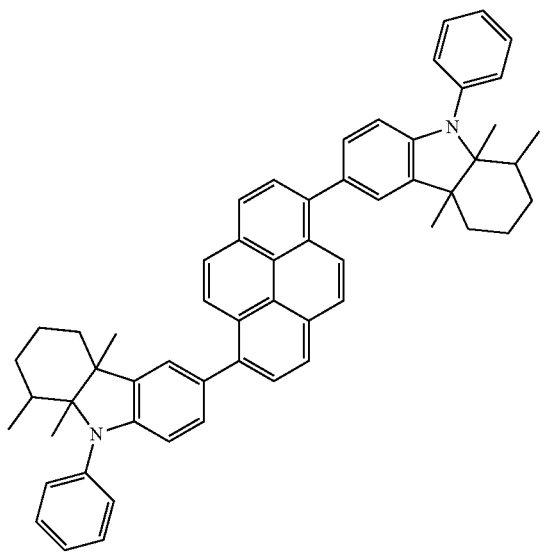

-continued
Formula 429
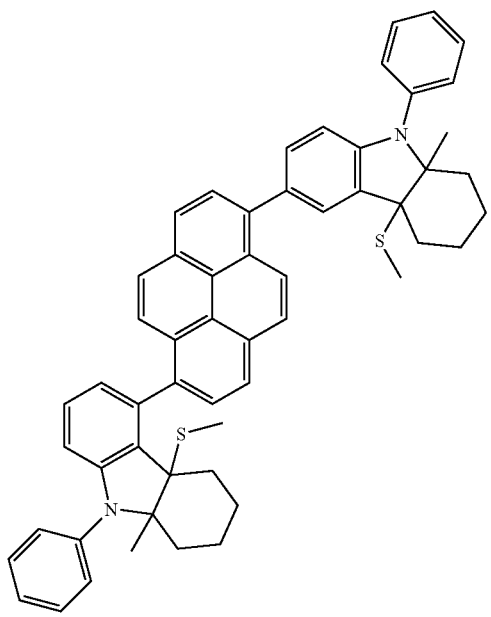
Formula 430
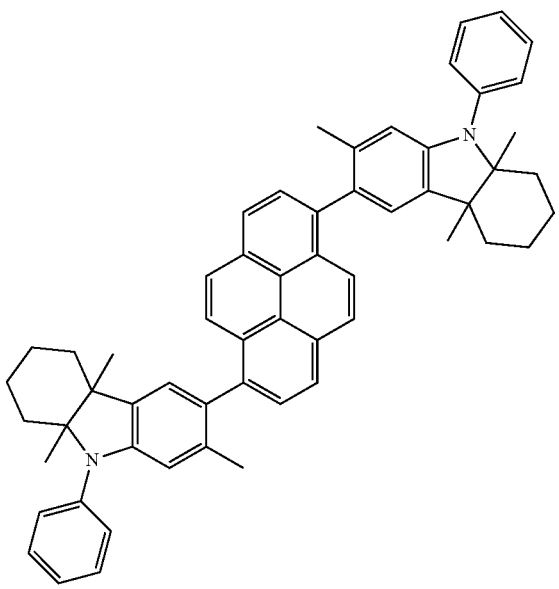
Formula 431
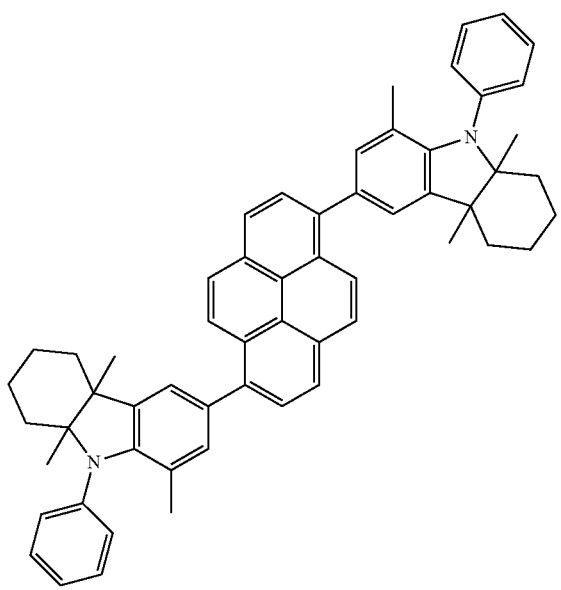
Formula 432
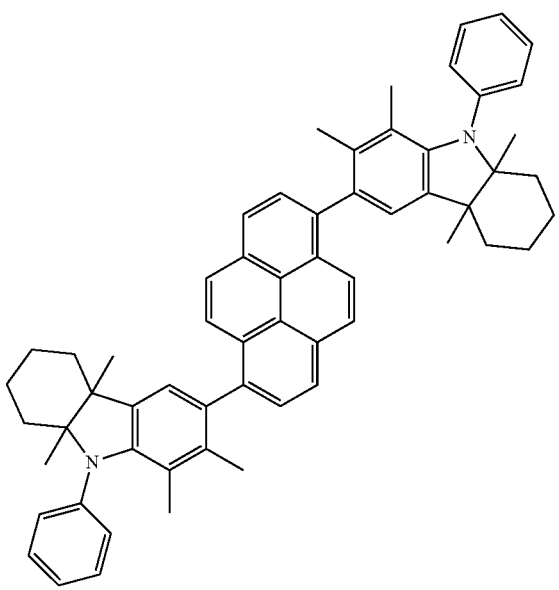

Formula 433
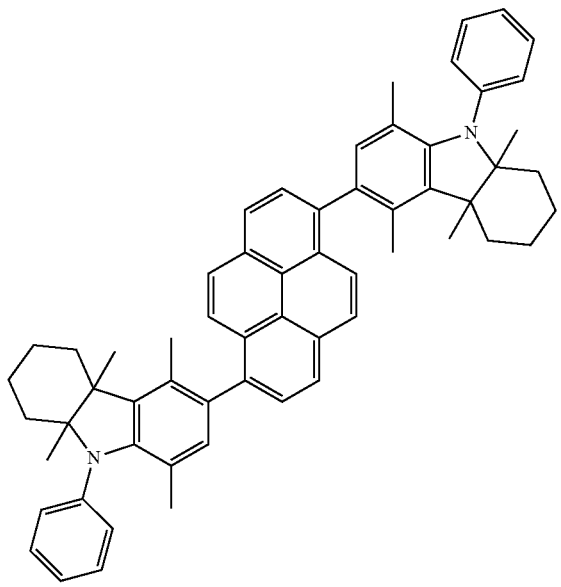
Formula 434
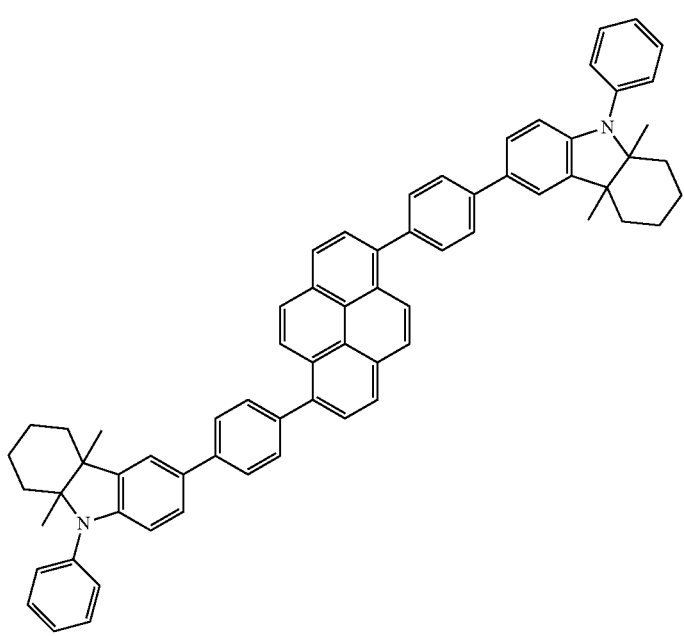

Formula 435
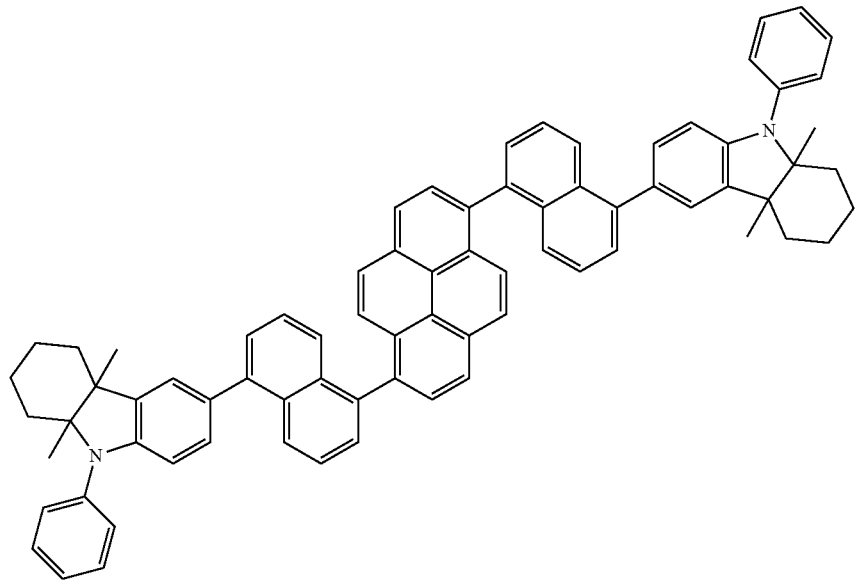
Formula 436
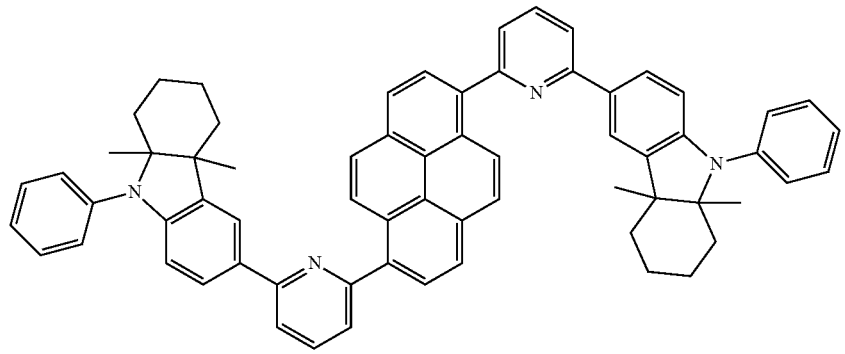
Formula 437
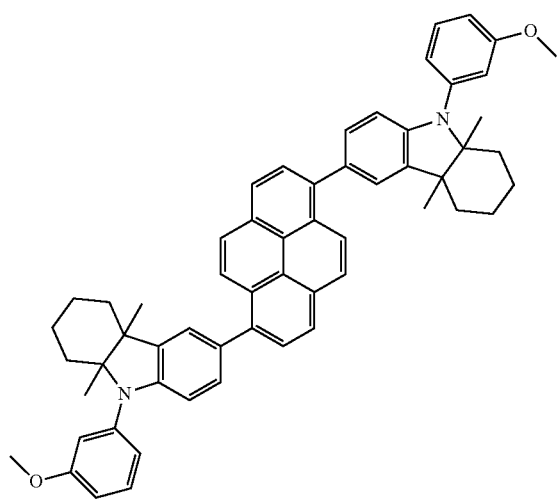
Formula 438
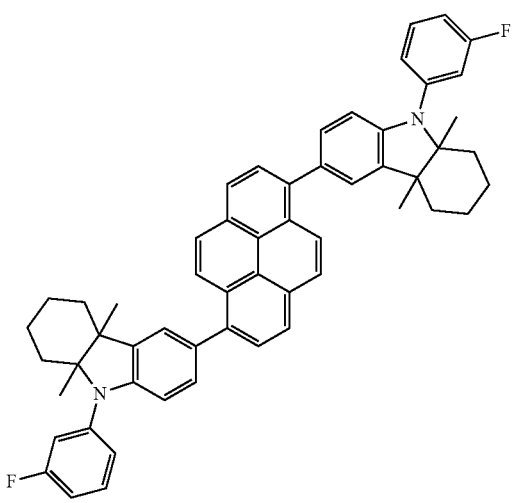

-continued
Formula 439
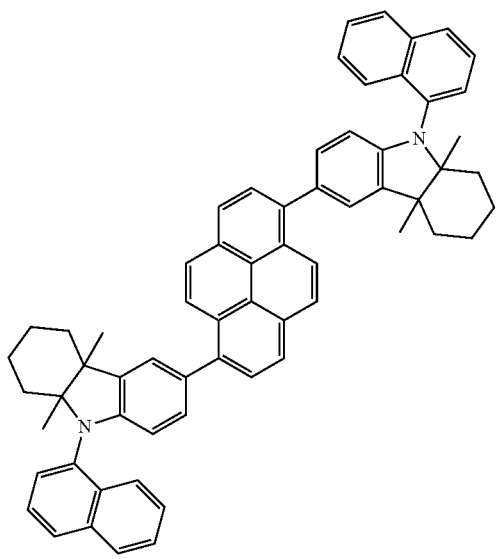
Formula 440
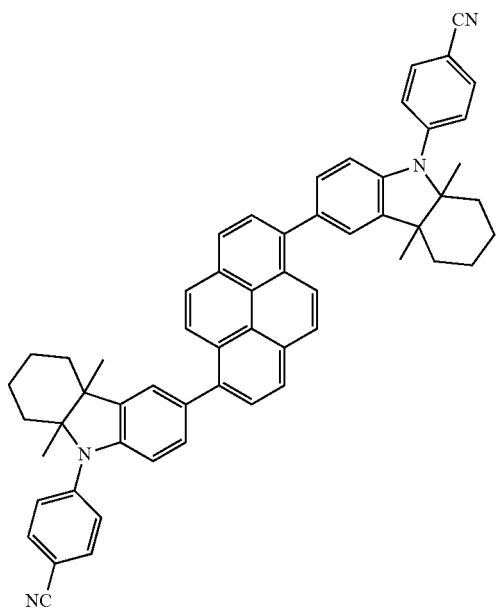
Formula 441
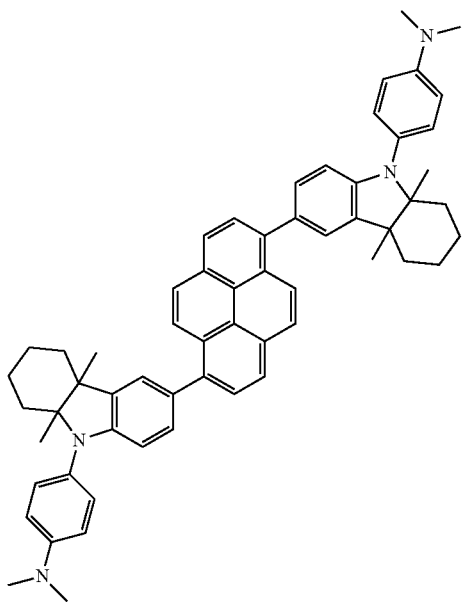
Formula 442
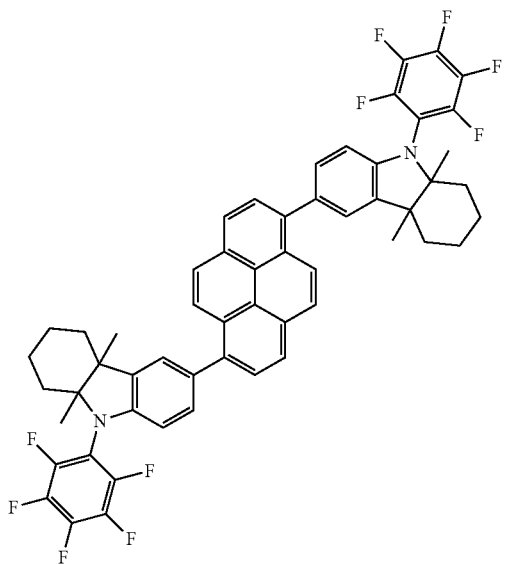

-continued
Formual 443
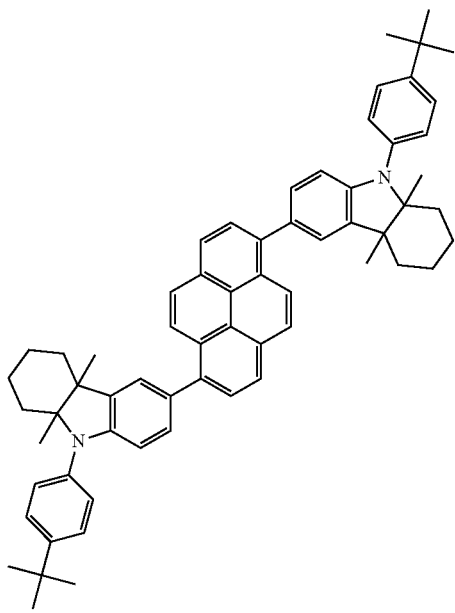
Formula 444
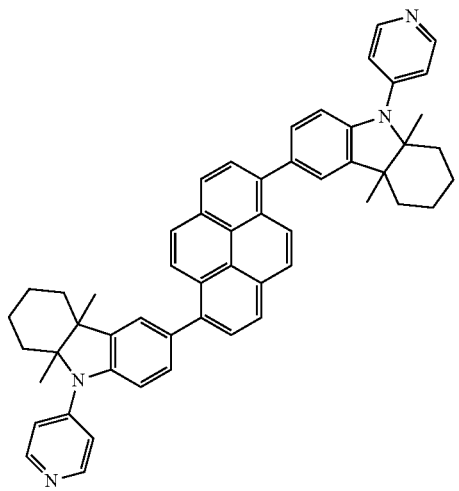
Formula 445
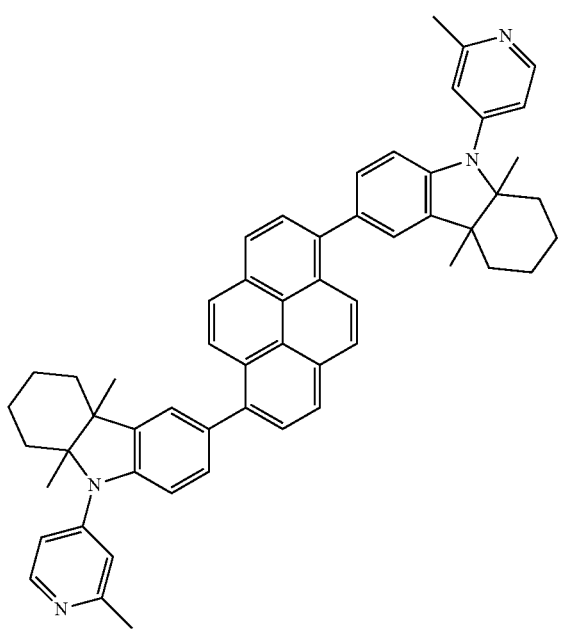
Formula 446
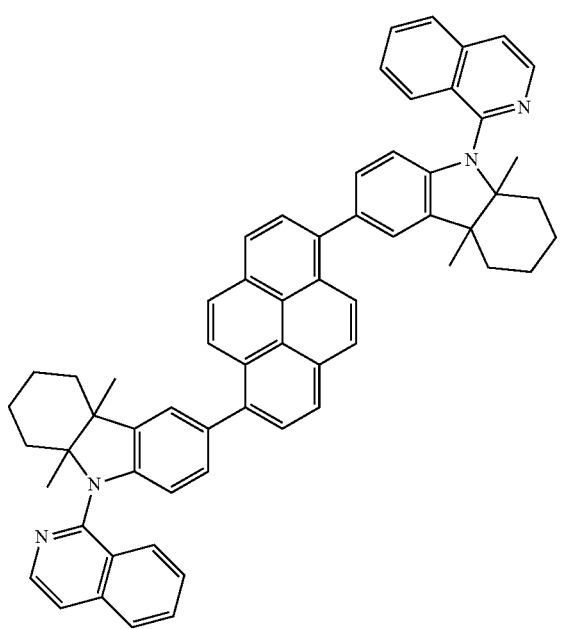

-continued
Formula 447
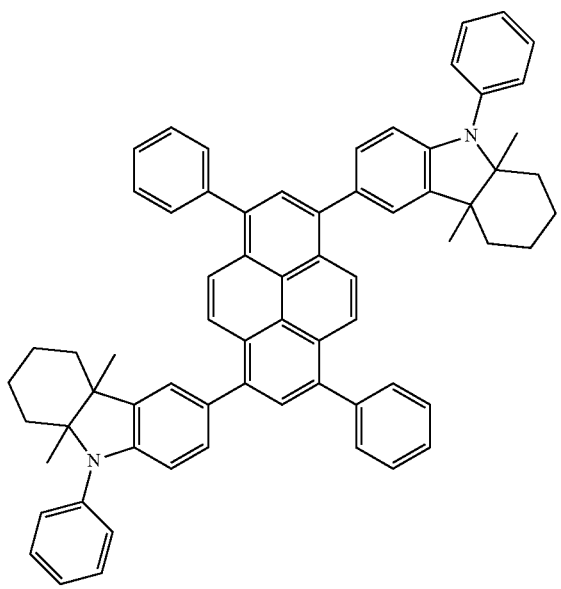
Formula 448
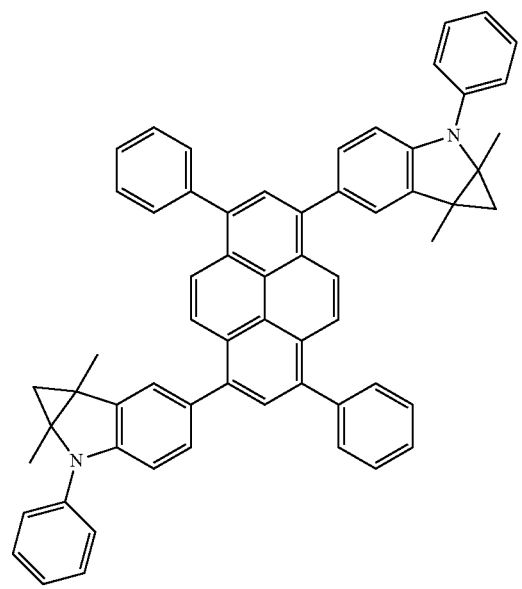
Formula 449
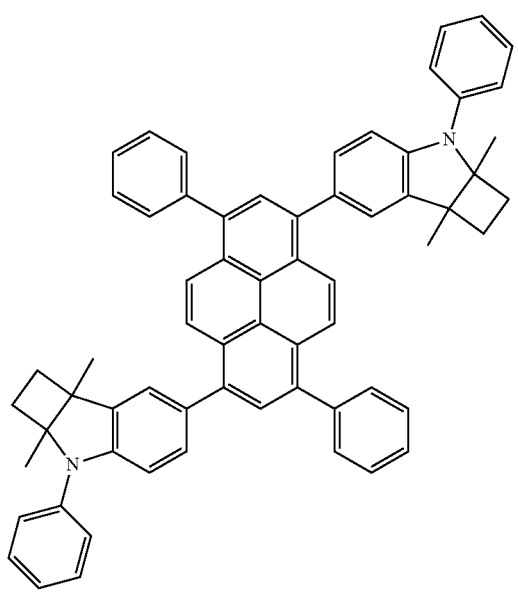
Formula 450
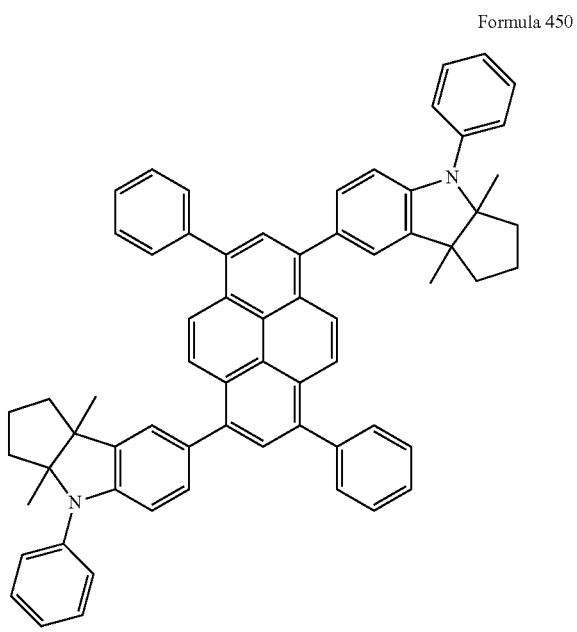

-continued
Formula 451
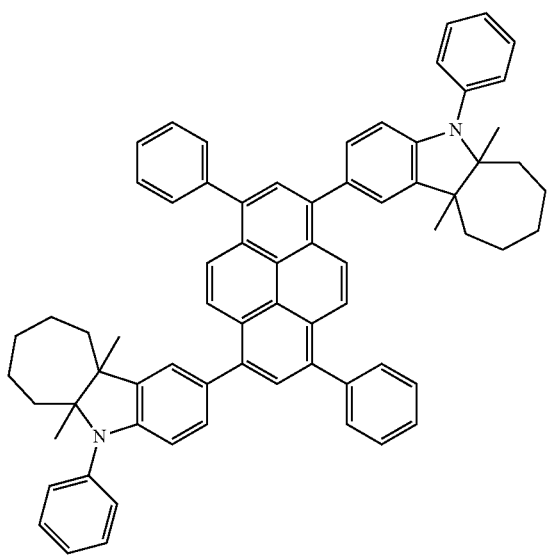
Formula 452
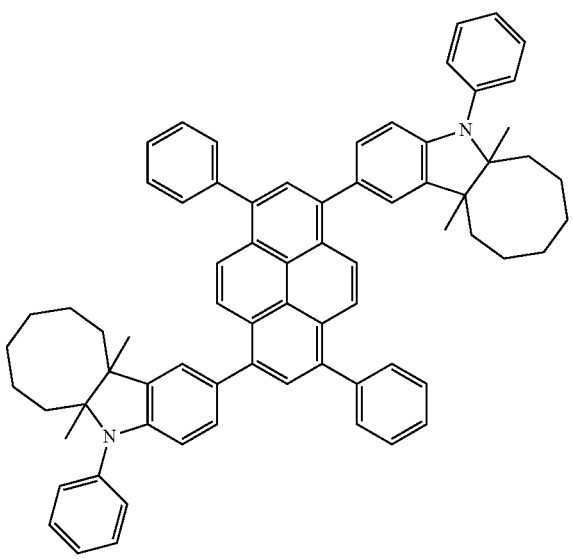
Formula 453
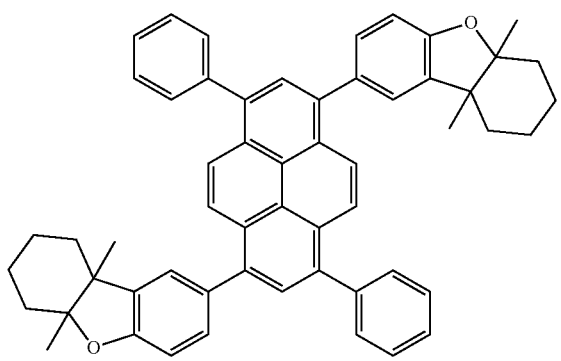
Formula 454
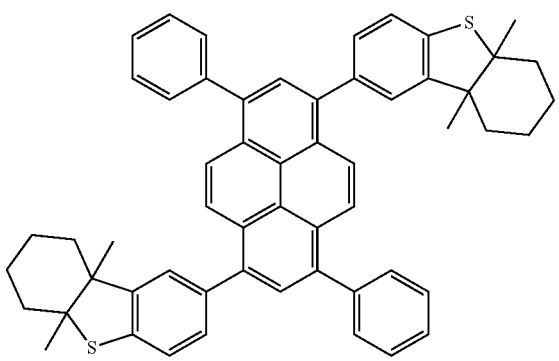
Formula 455
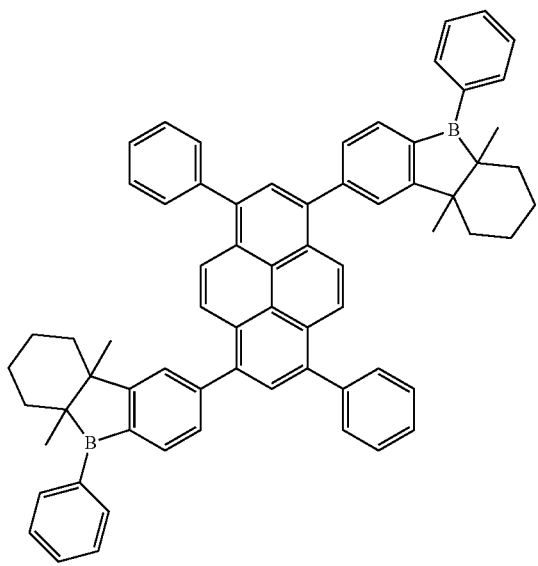
Formula 456
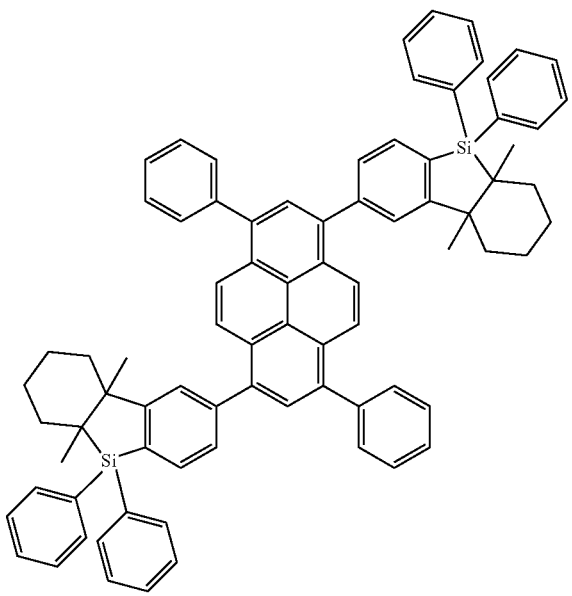

Formula 457
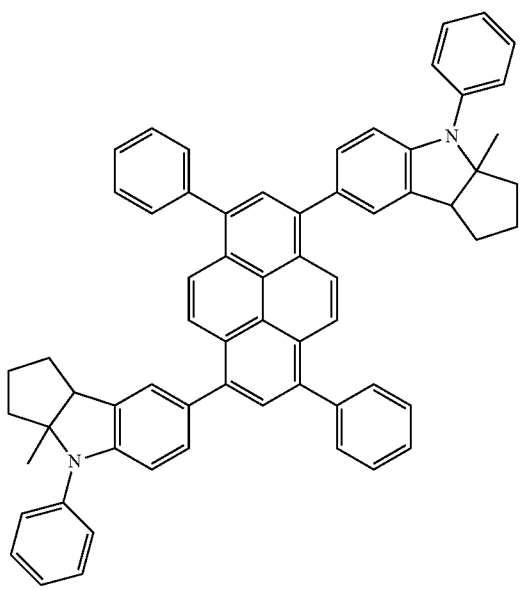
Formula 458
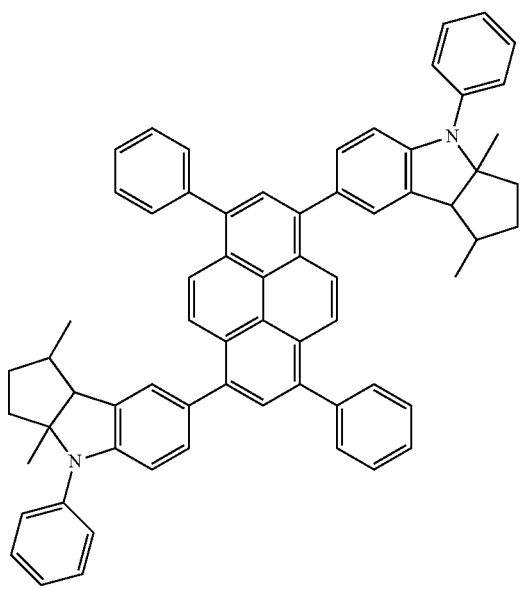
Formula 459
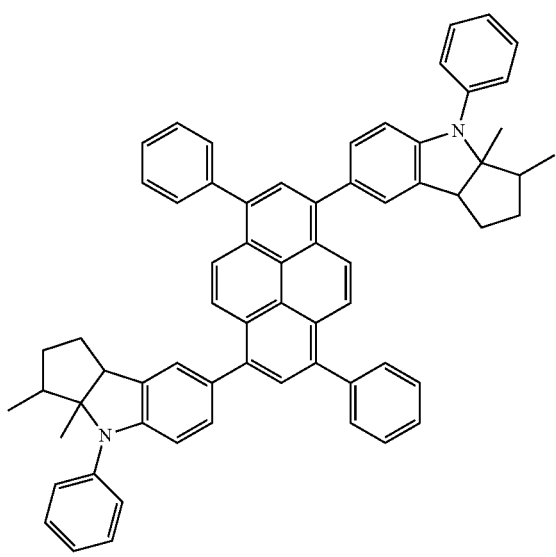
Formula 460
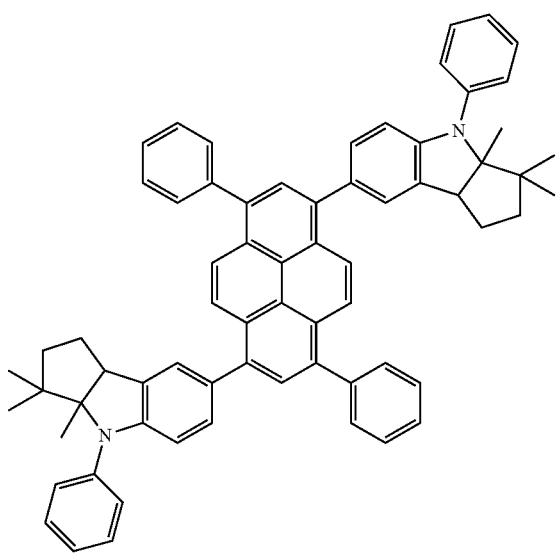

-continued
Formula 461
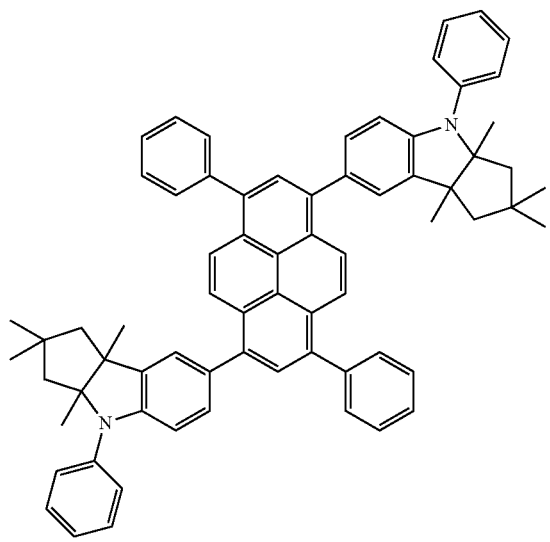
Formula 462
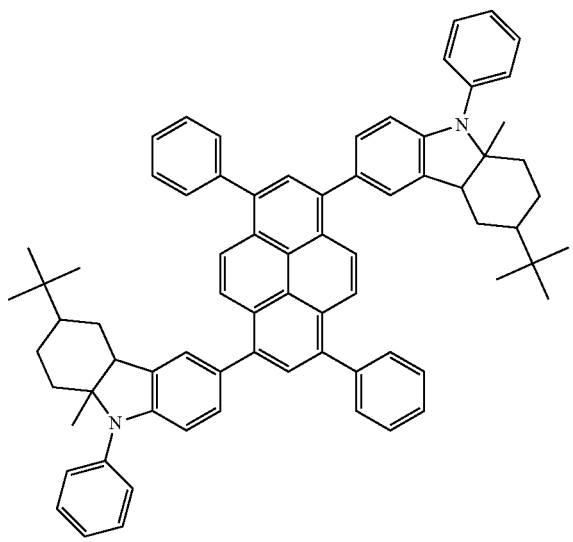
Formula 463
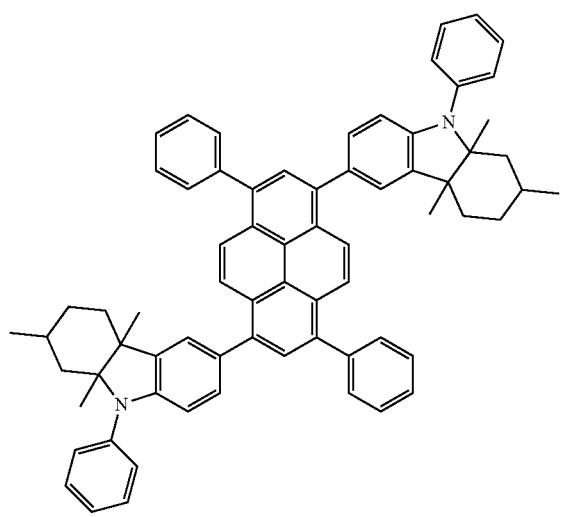
Formula 464
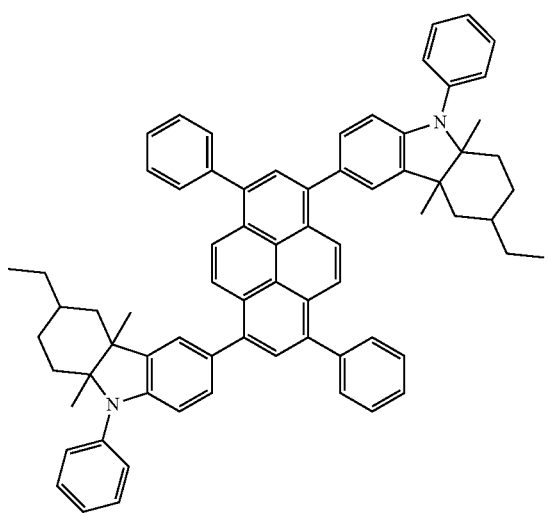
Formula 465
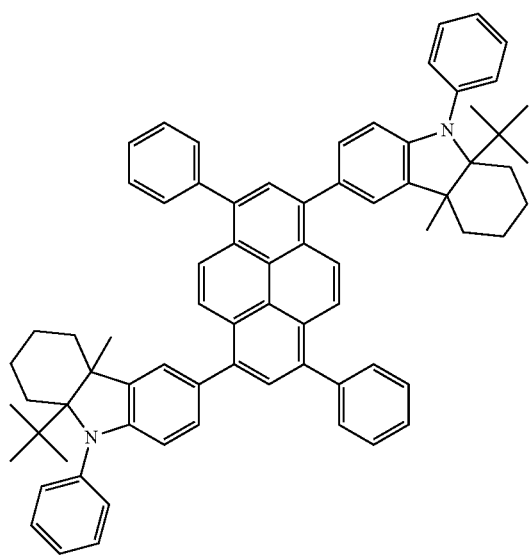
Formula 466
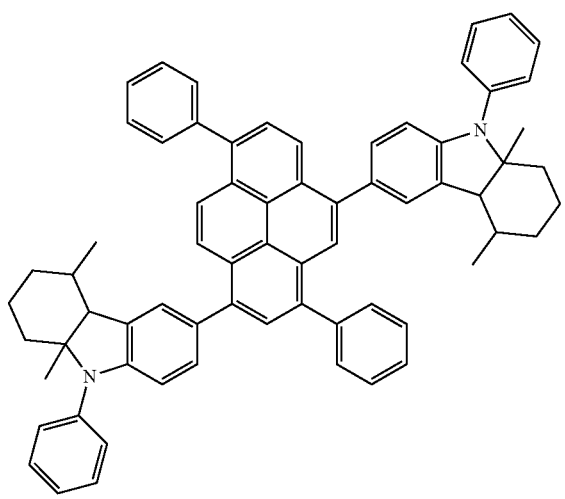

-continued
Formula 467
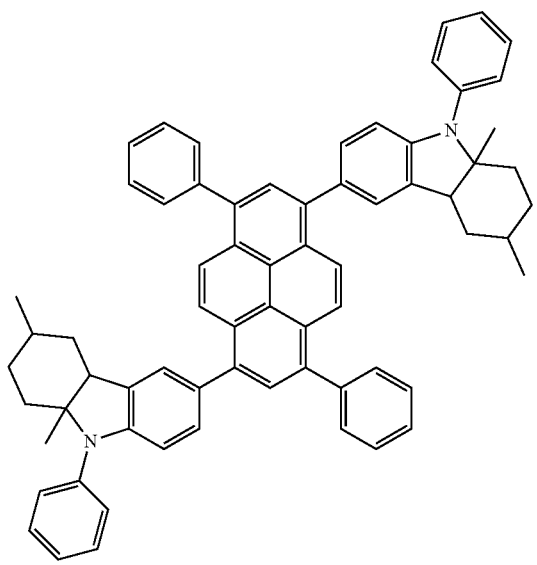
Formula 468
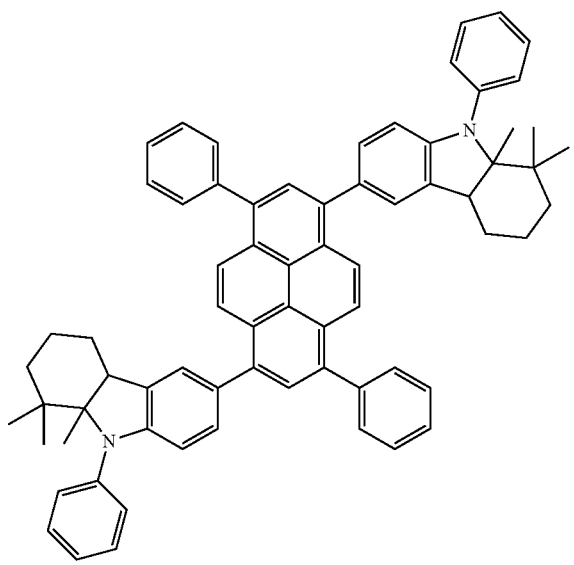
Formula 469
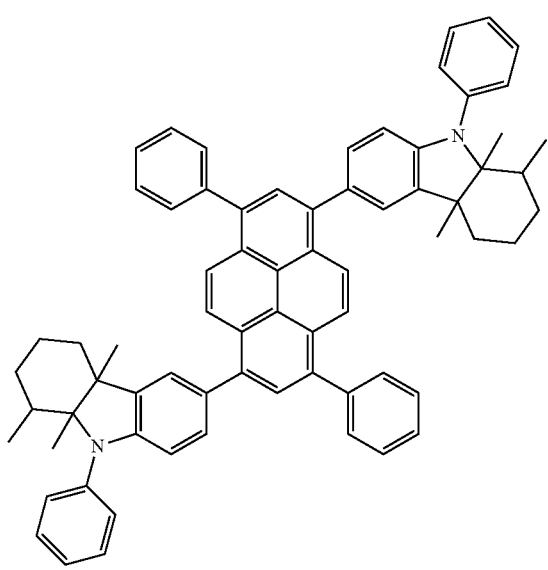
Formula 470
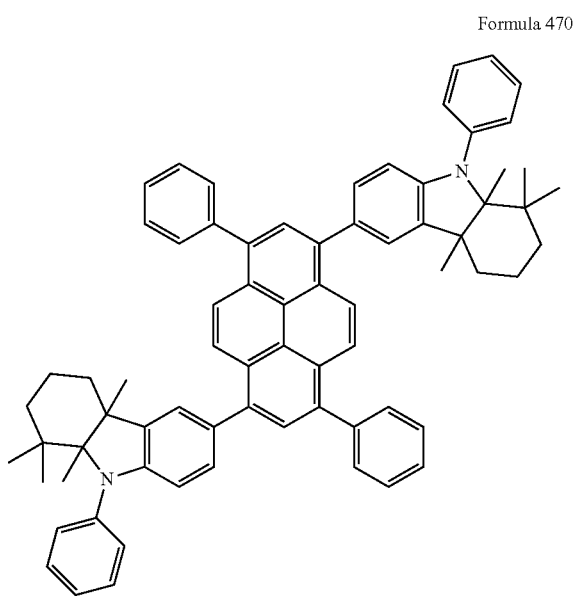

-continued
Formula 471
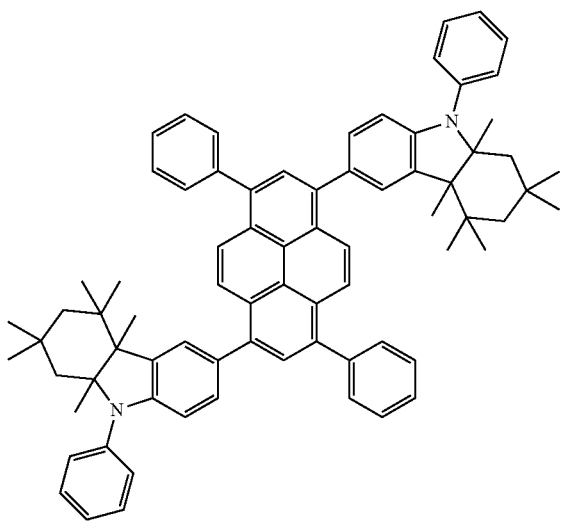
Formula 472
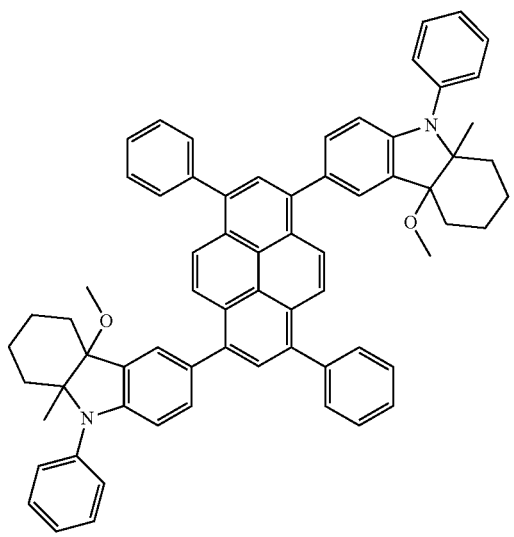
Formula 473
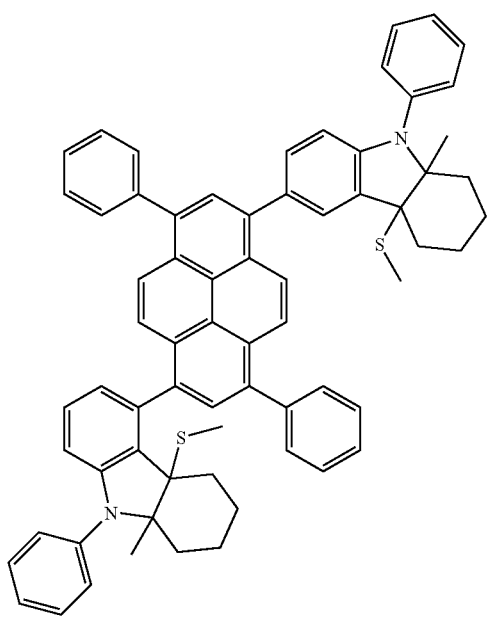
Formula 474
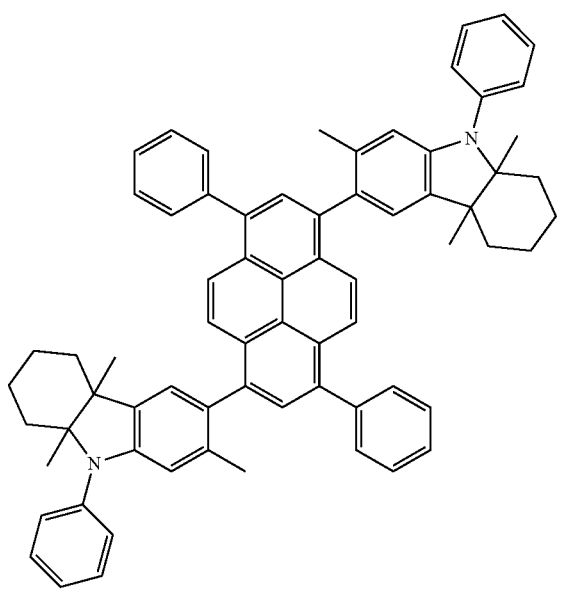

Formula 475
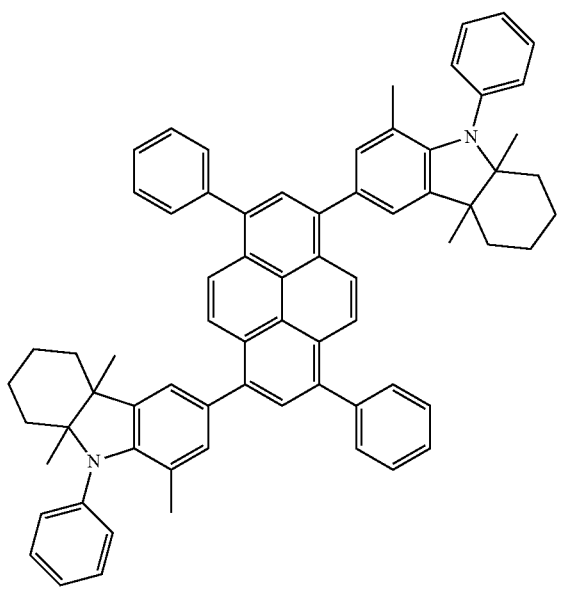
Formula 476
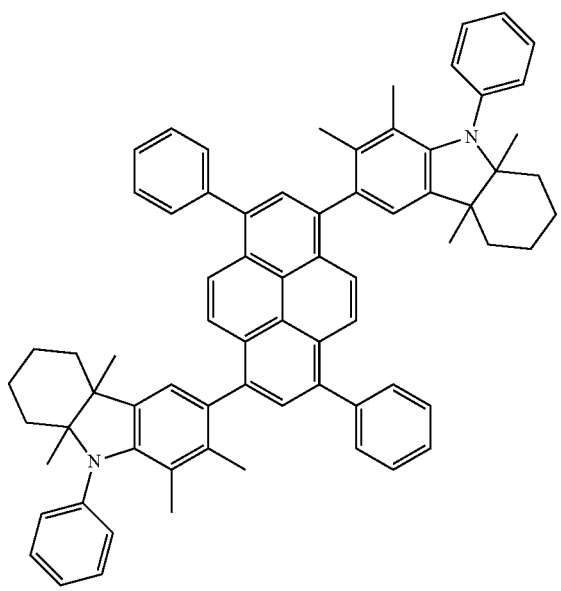
Formula 477
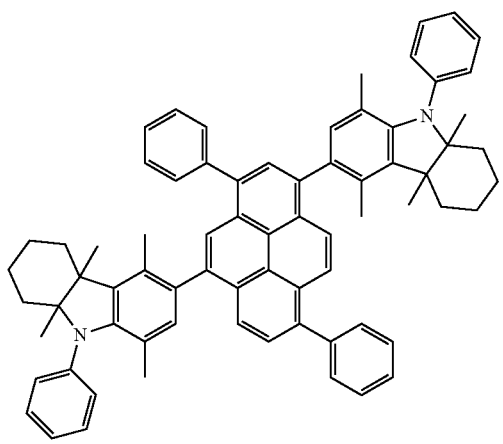
Formula 478
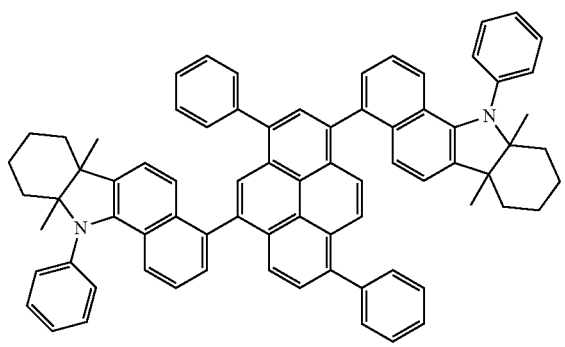
Formula 479
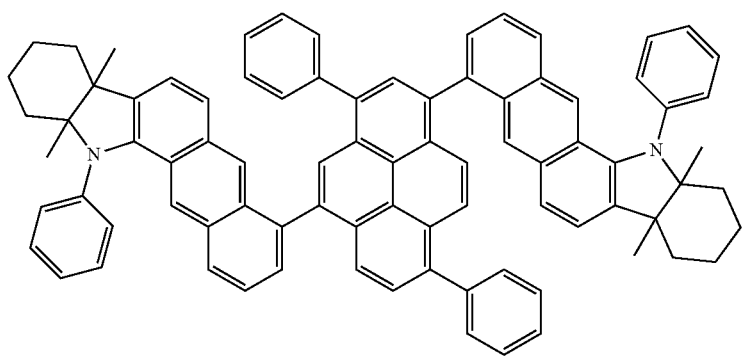

Formula 480
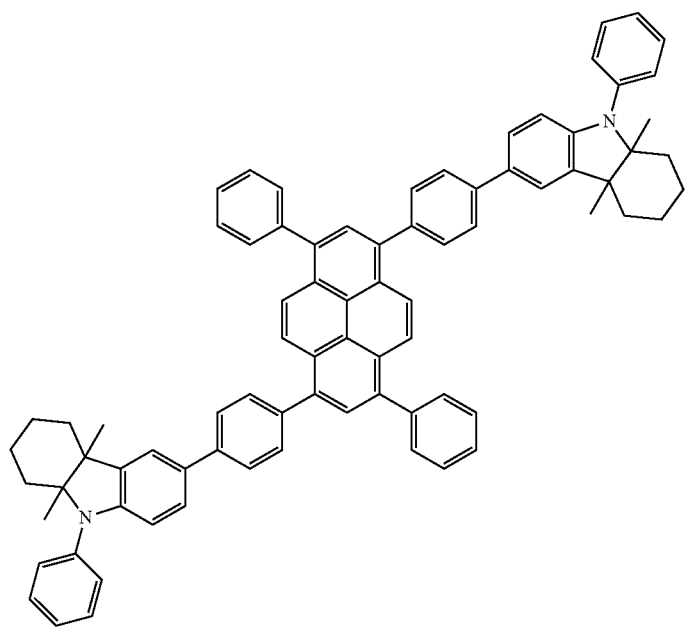
Formula 481
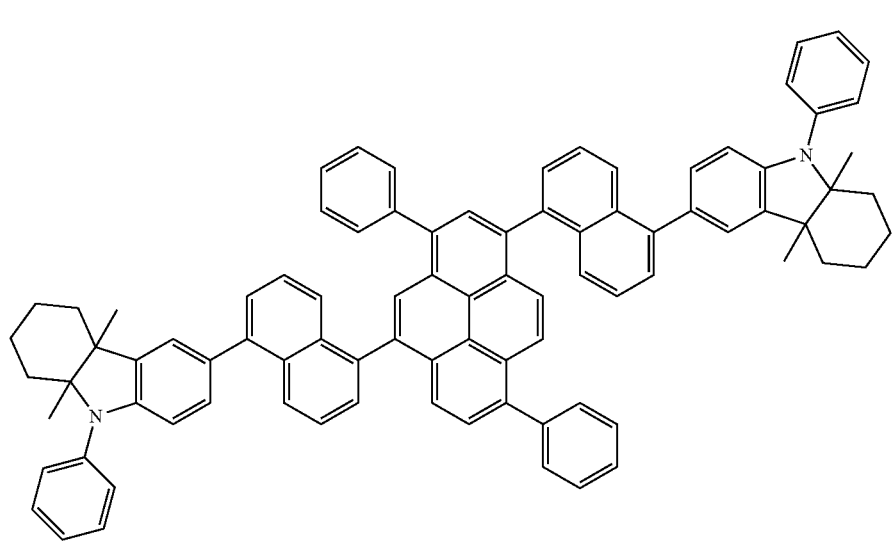
Formula 482
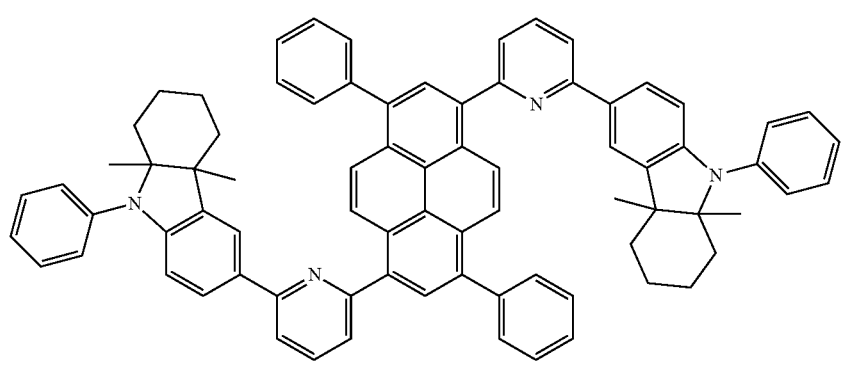

-continued
Formula 483
Formula 484
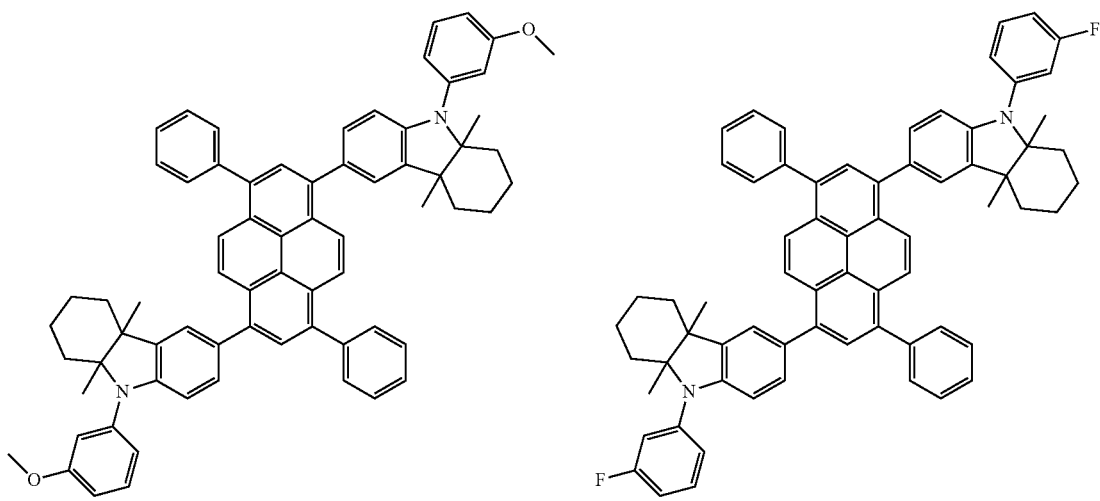
Formula 485
Formula 486
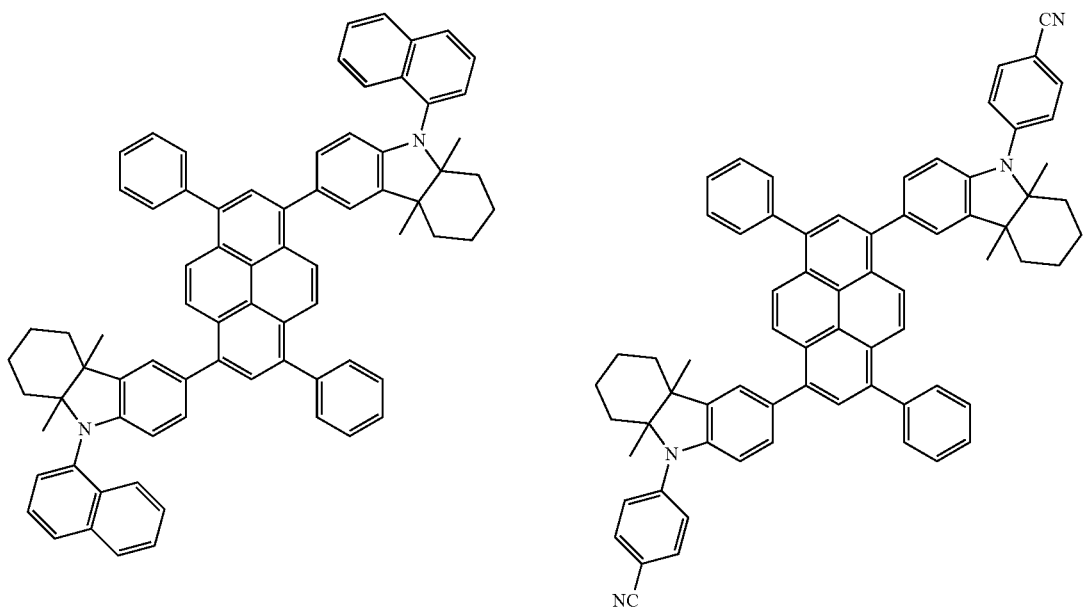

-continued
Formula 487
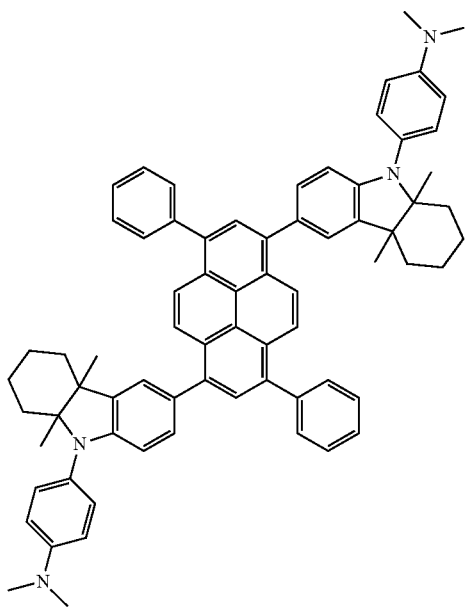
Formula 488
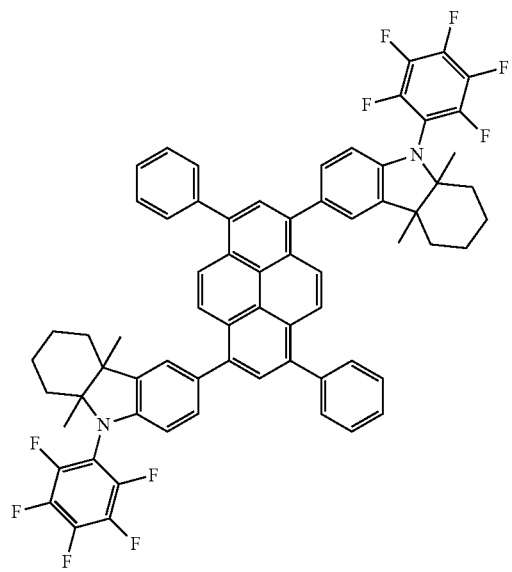
Formula 489
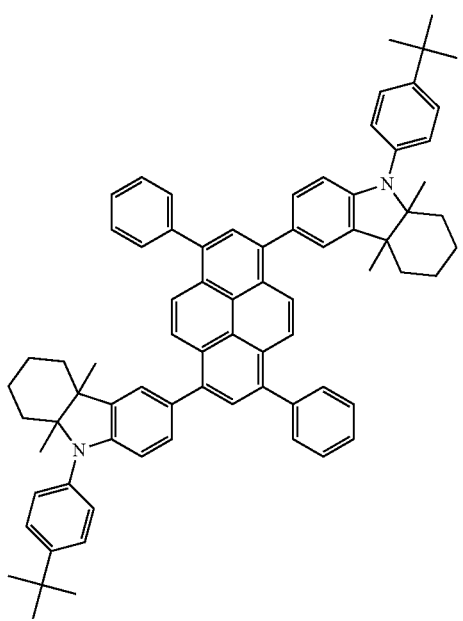
Formula 490
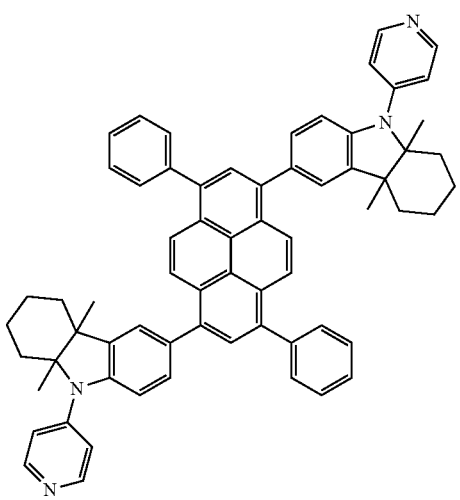

-continued
Formula 491
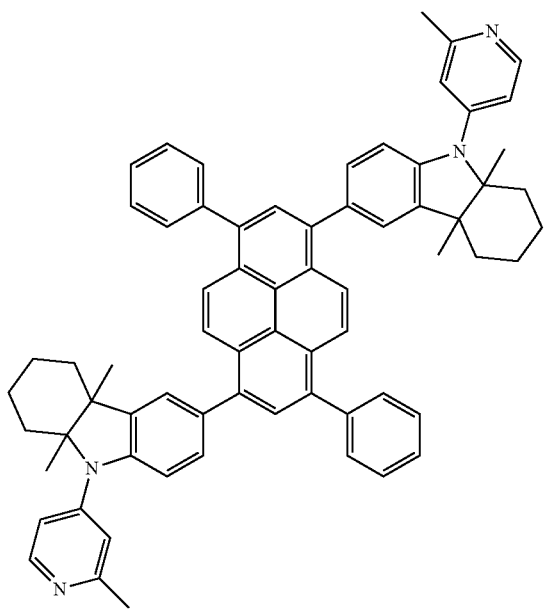
Formula 492
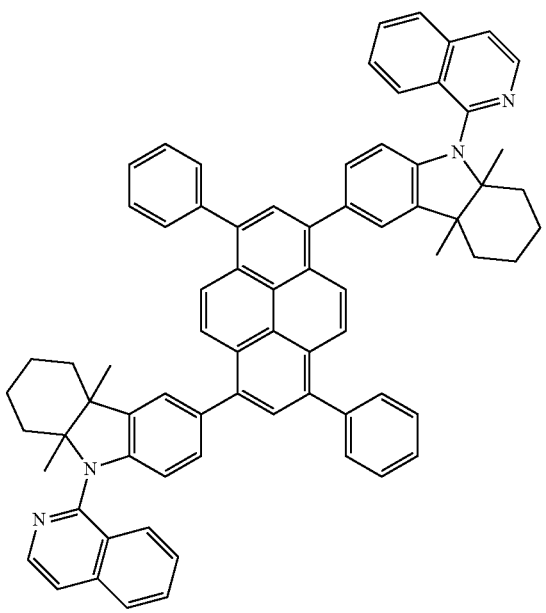
Formula 493
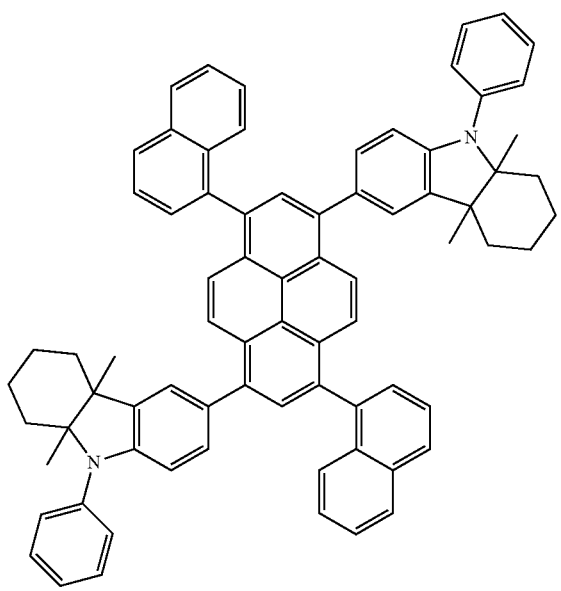
Formula 494
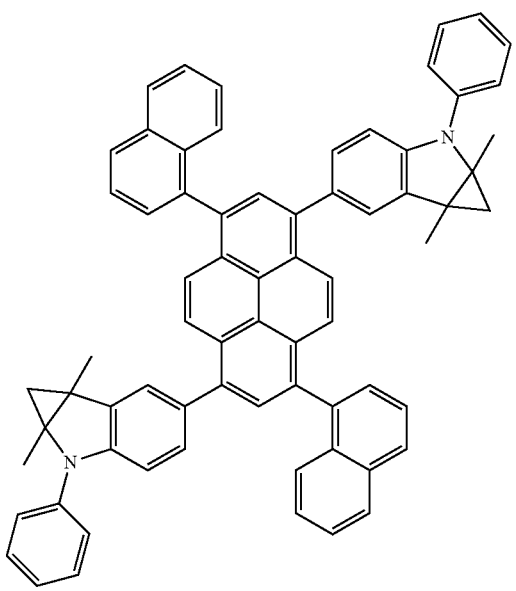

-continued
Formula 495
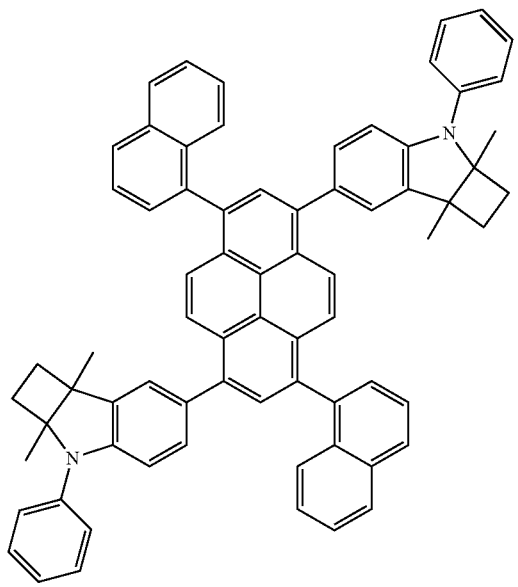
Formula 496
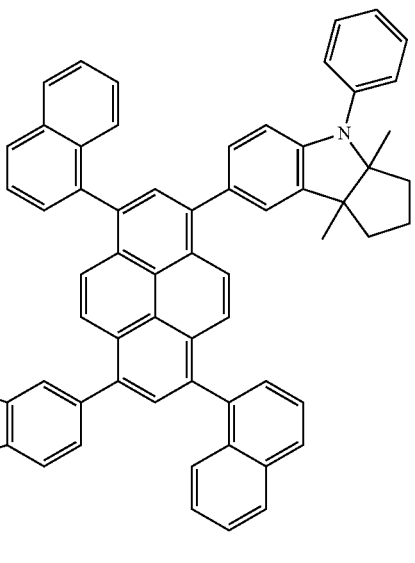
Formula 497
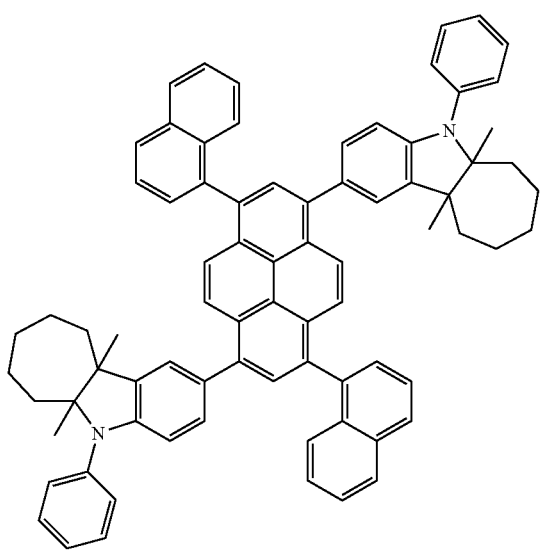
Formula 498
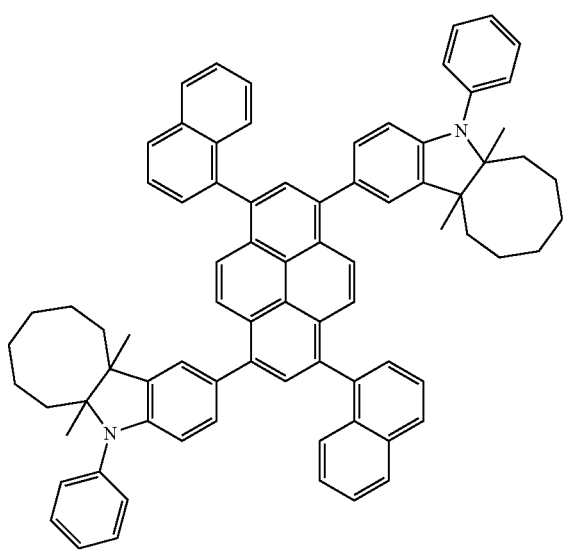
Formula 499
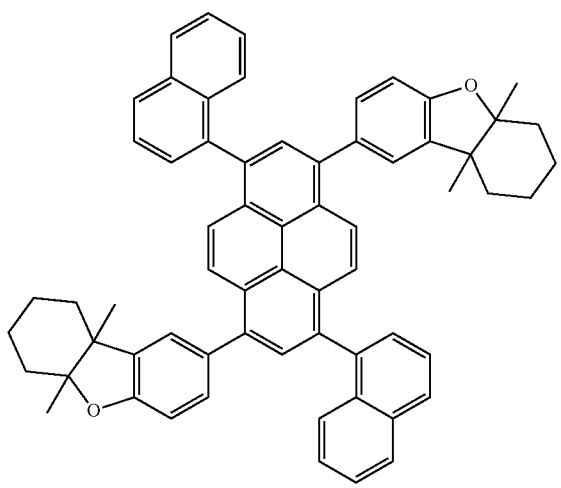
Formula 500
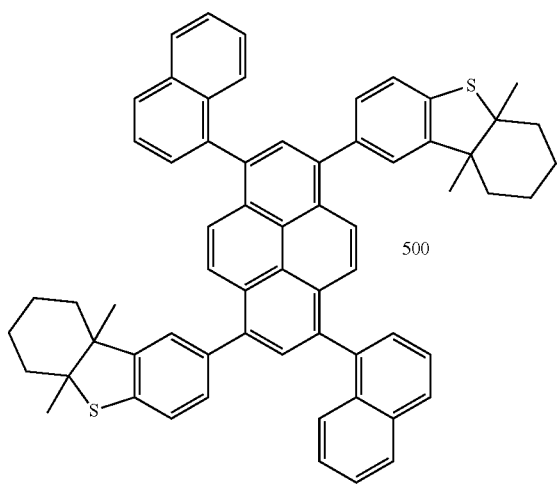

-continued
Formula 501
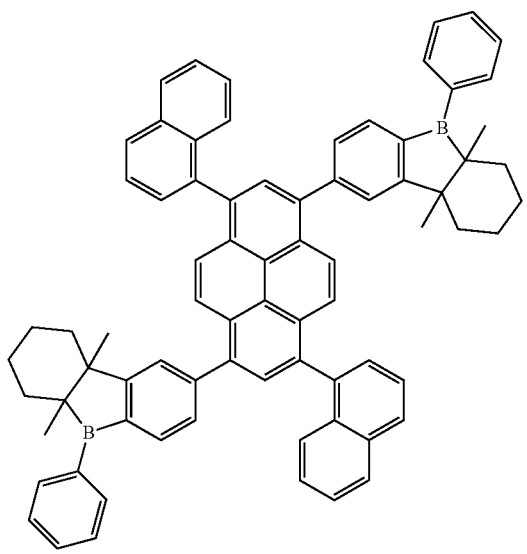
Formula 502
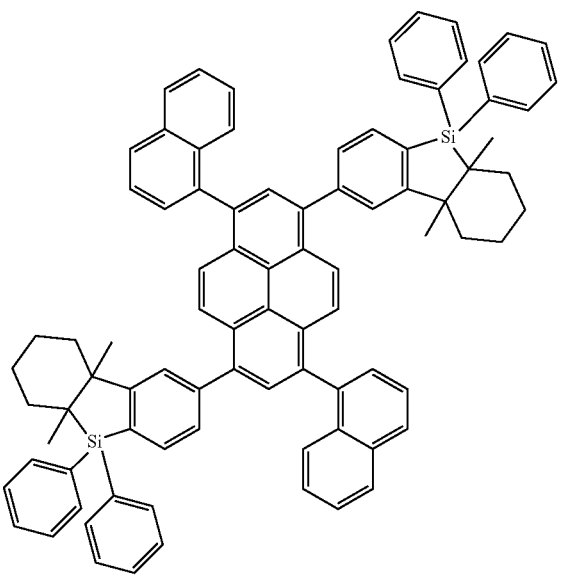
Formula 503
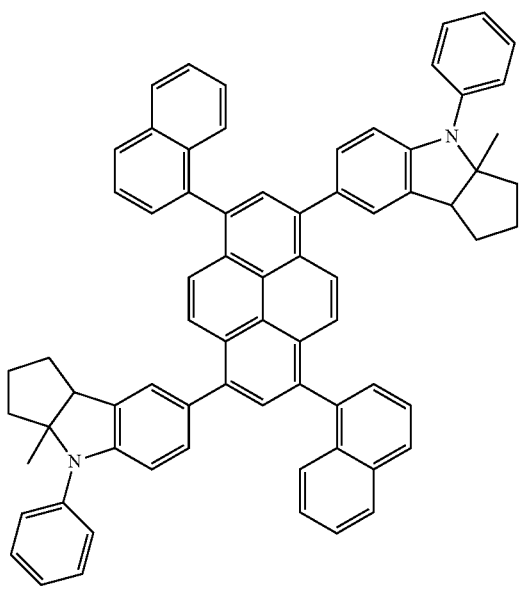
Formula 504
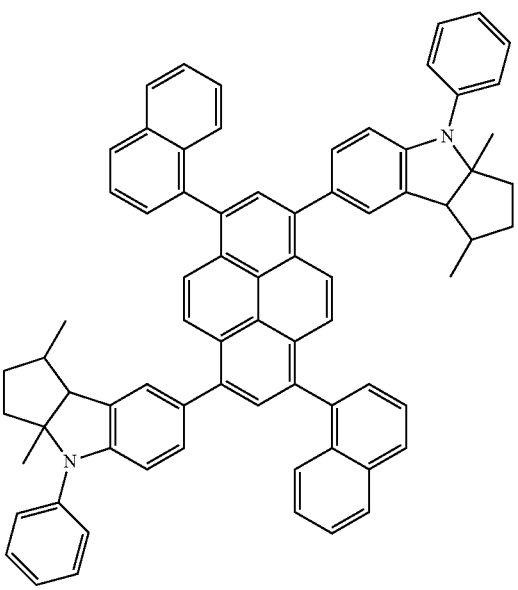

-continued
Formula 505
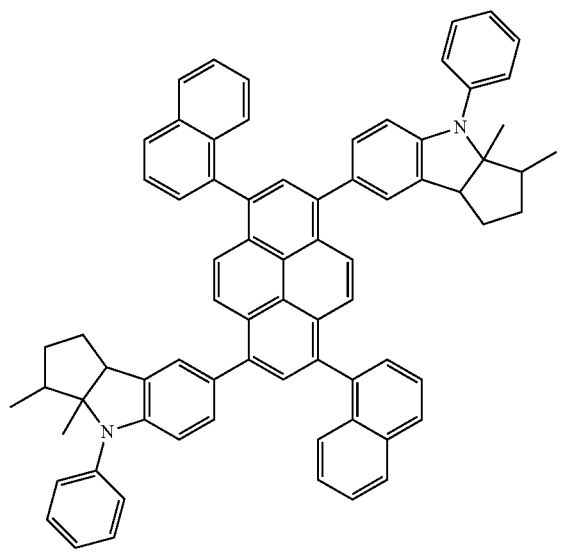
Formula 506
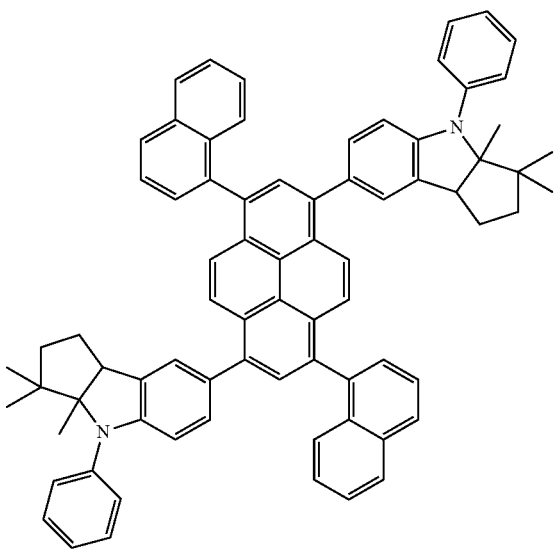
Formula 507
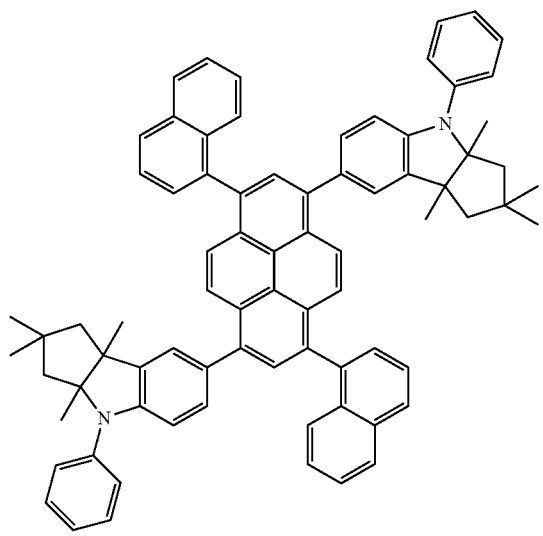
Formula 508
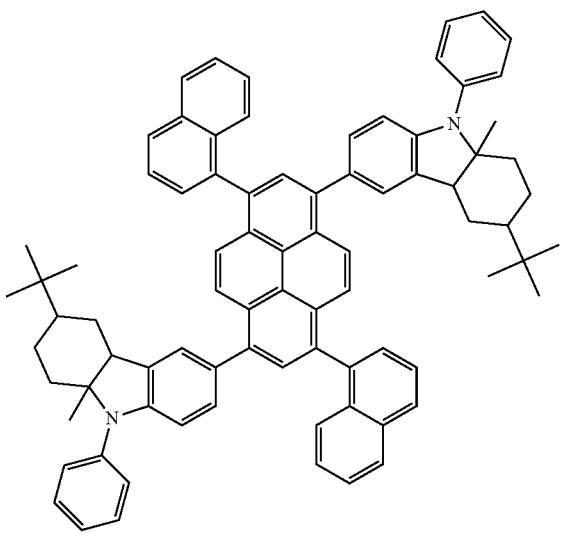
Formula 509
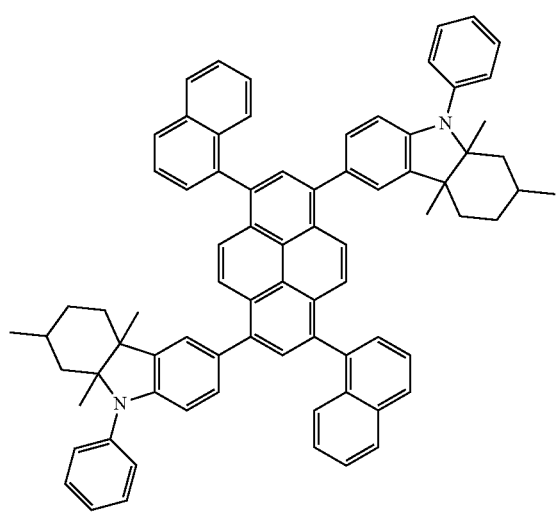
Formula 510
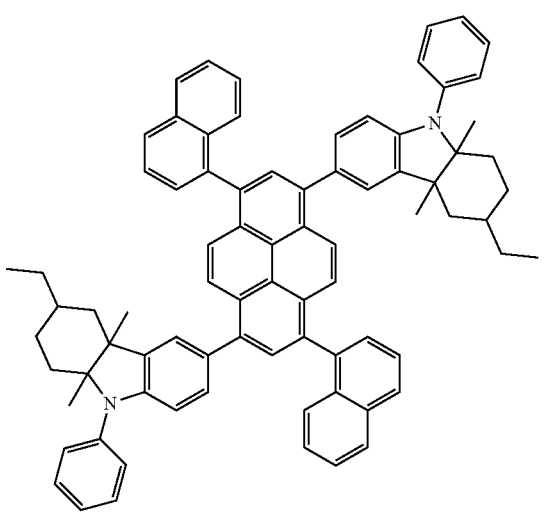

-continued
Formula 511
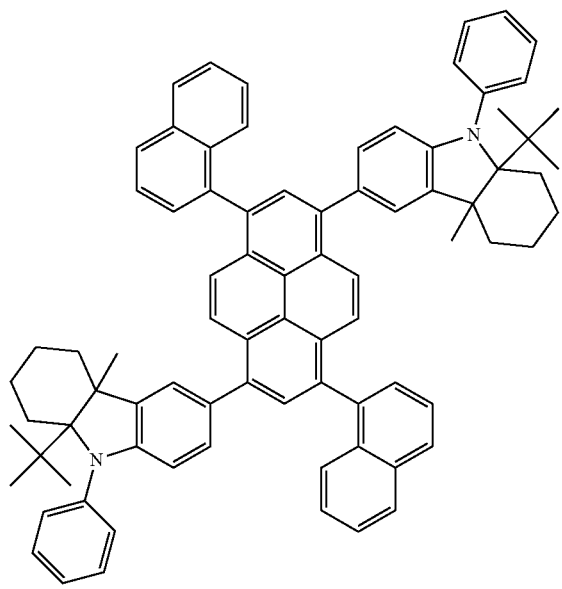
Formula 512
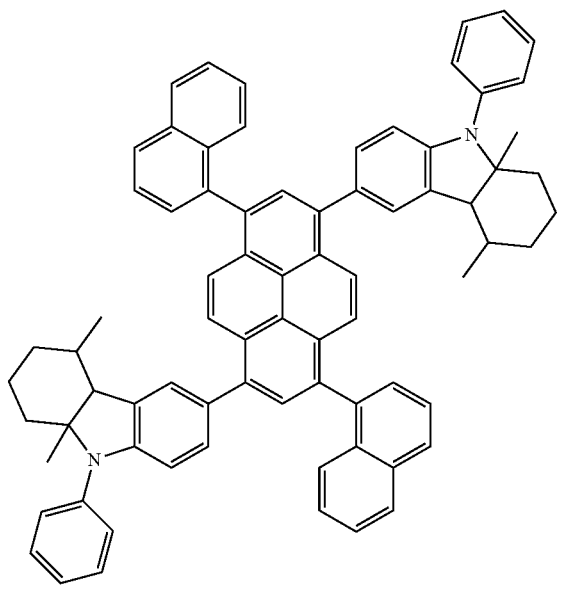
Formula 513
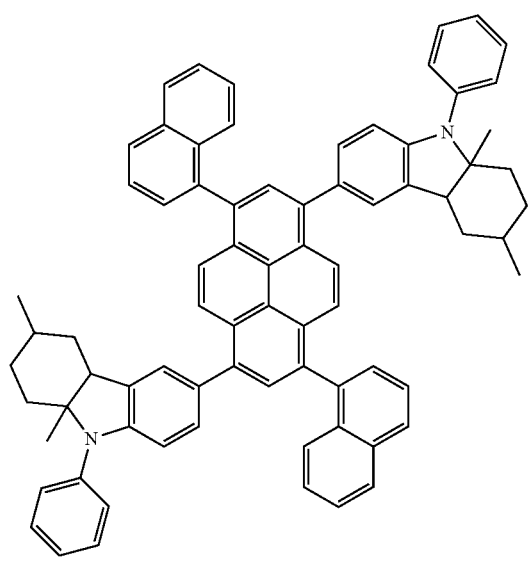
Formula 514
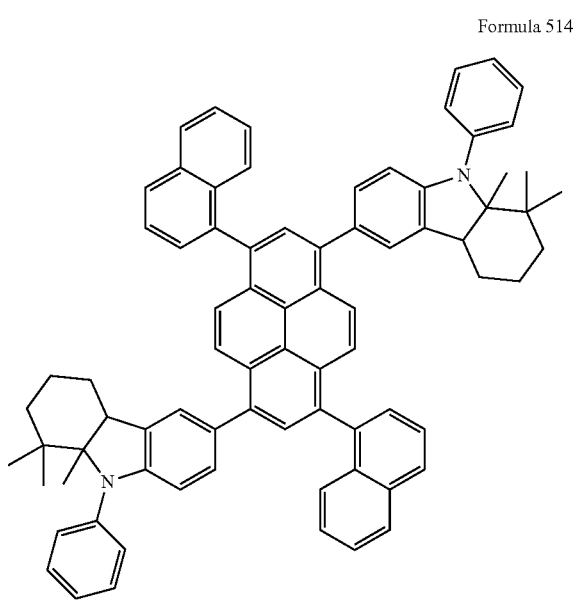

-continued
Formula 515
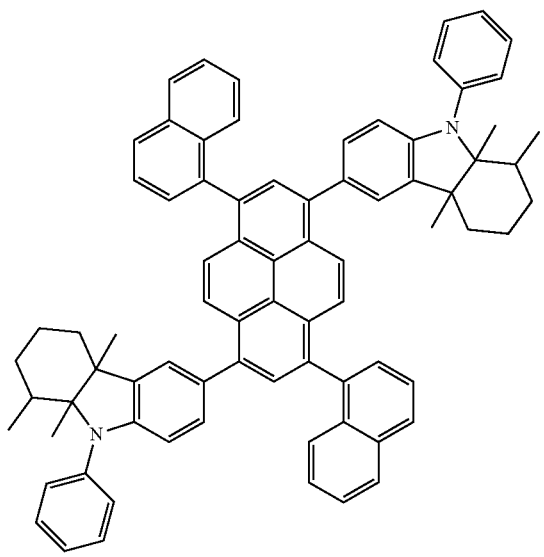
Formula 516
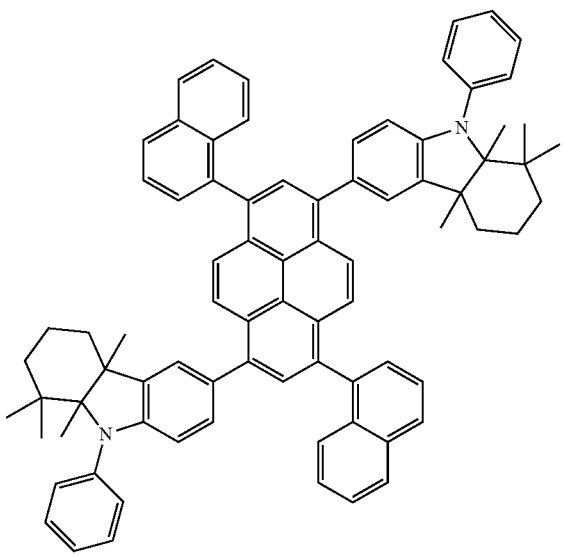
Formula 517
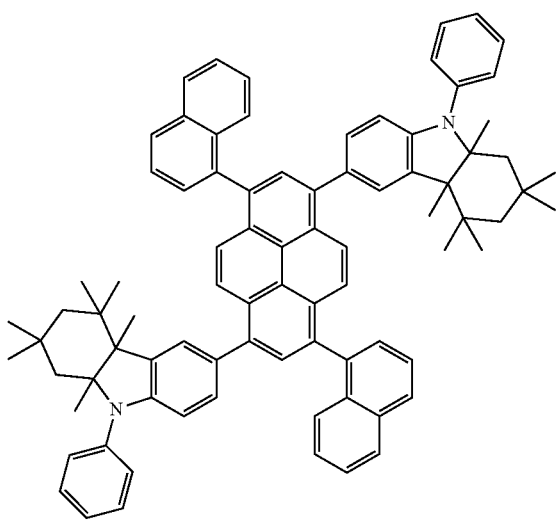
Formula 518
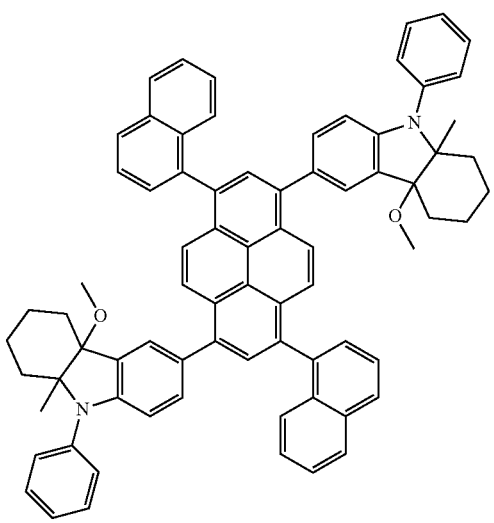

-continued
Formula 519
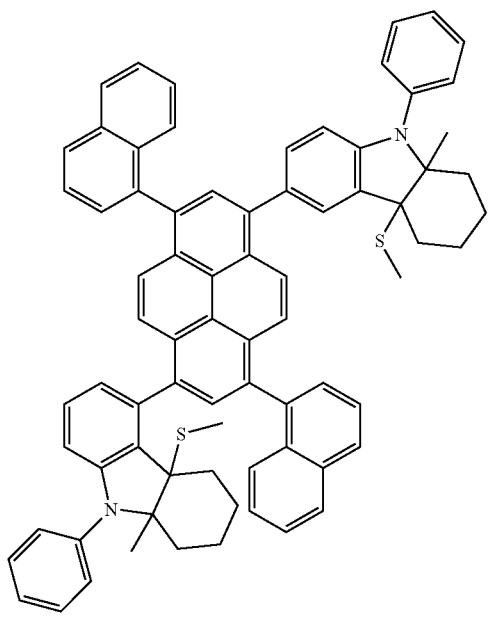
Formula 520
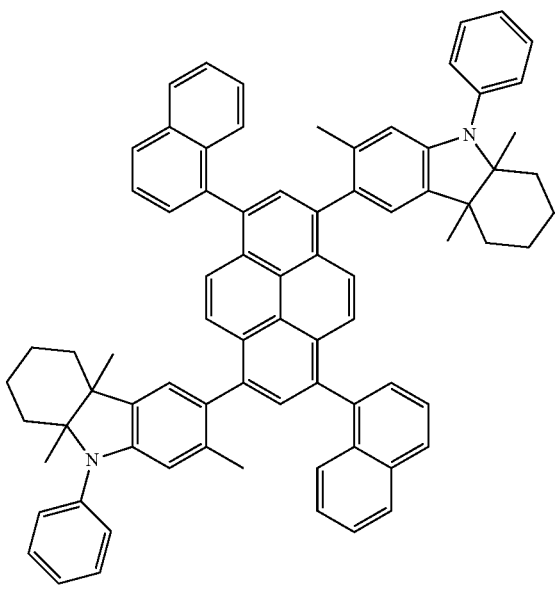
Formula 521
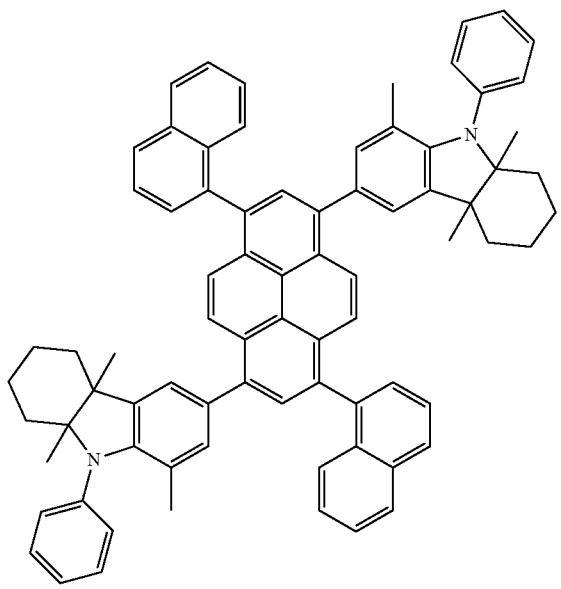
Formula 522
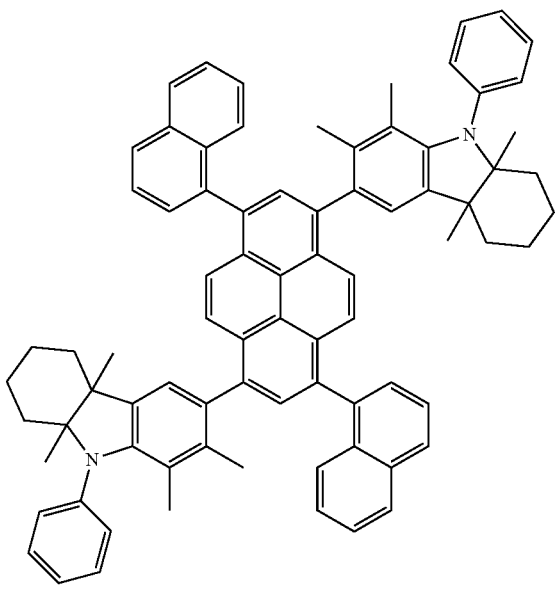

-continued
Formula 523
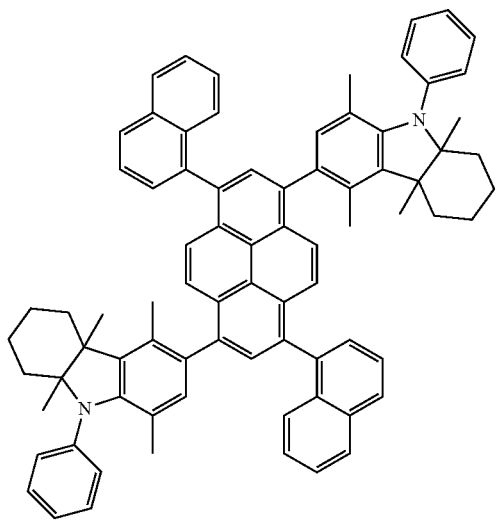
Formula 524
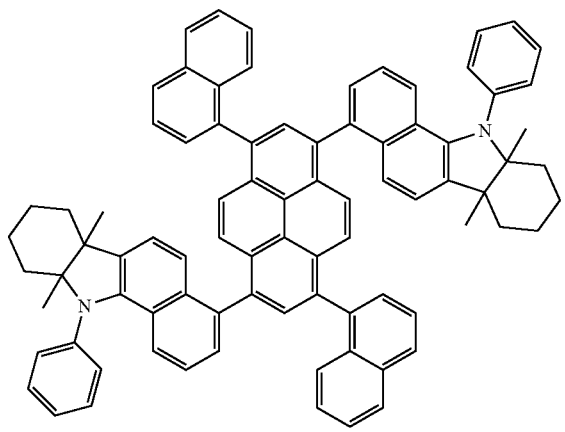
Formula 525
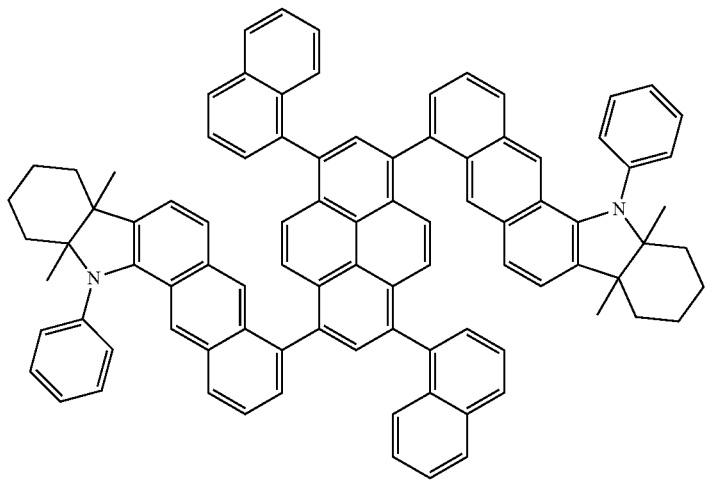
Formula 526
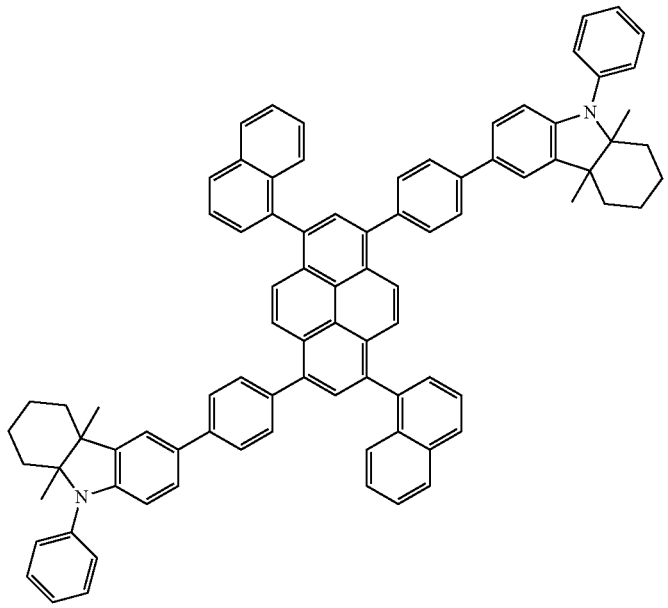

-continued
Formula 527
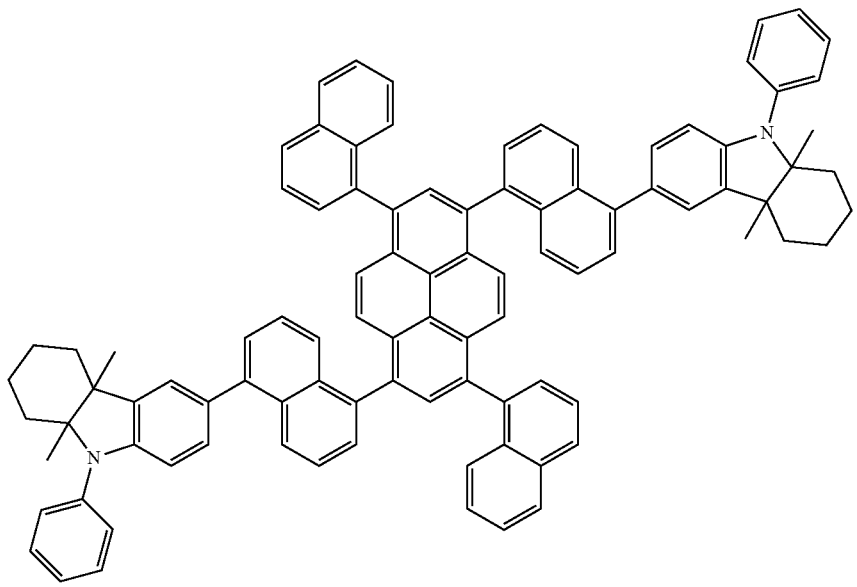
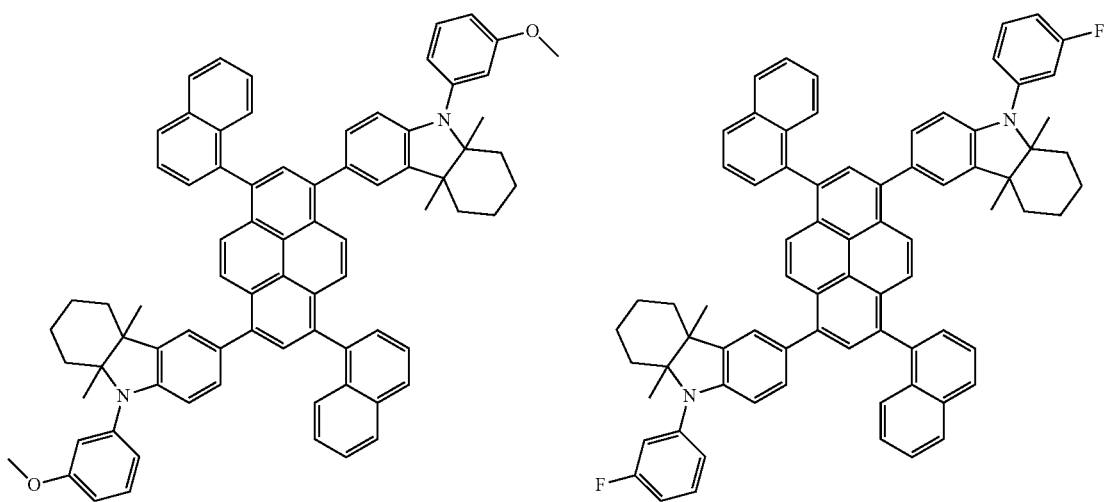
Formula 528
Formula 529

-continued
Formula 530
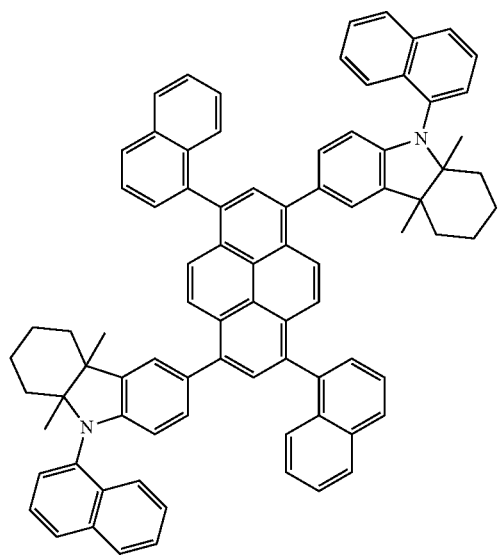
Formula 531
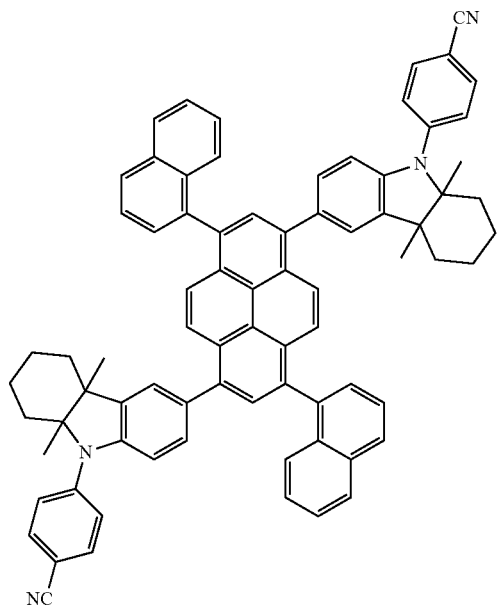
Formula 532
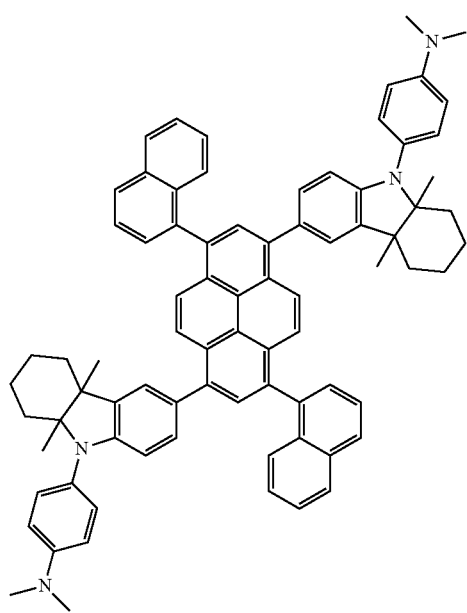
Formula 533
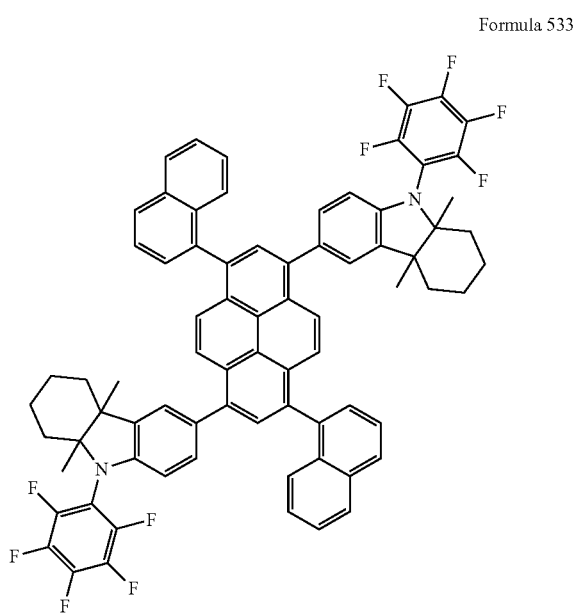

-continued
Formula 534
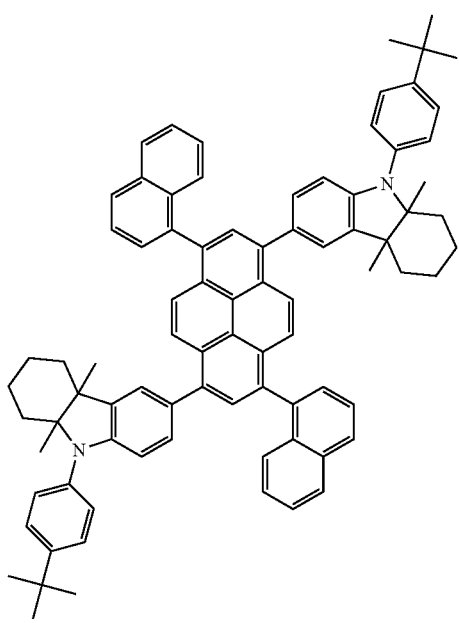
Formula 535
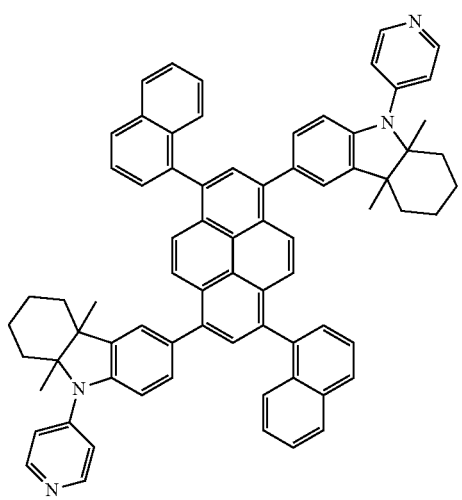
Formula 536
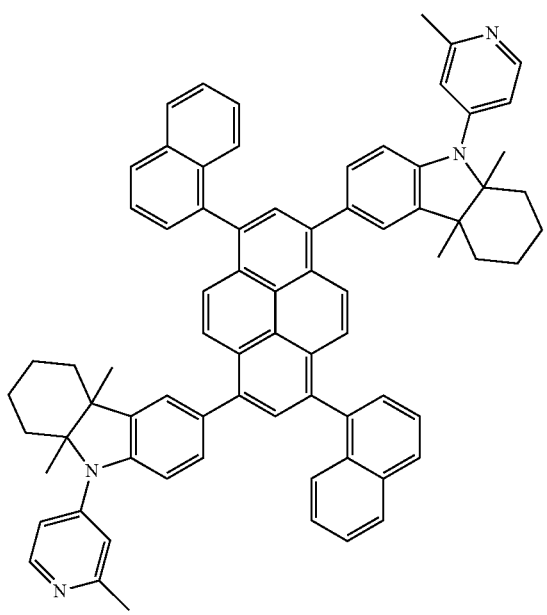
Formula 537
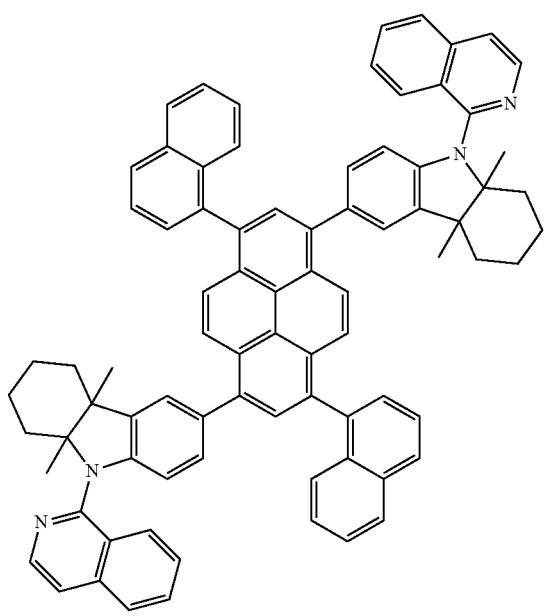
Formula 538
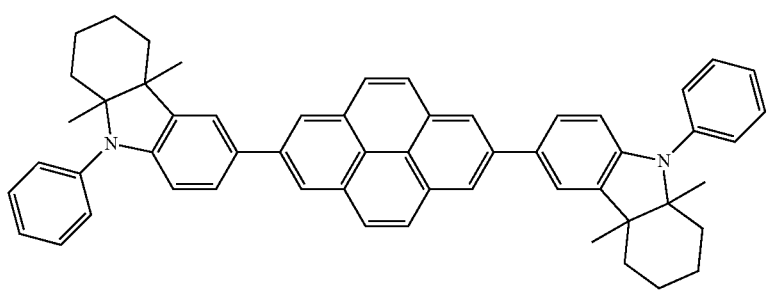

Formula 539
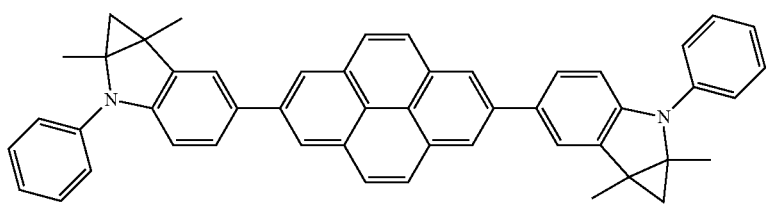
Formula 540
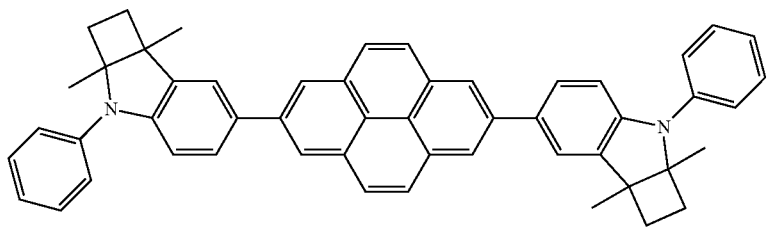
Formula 541
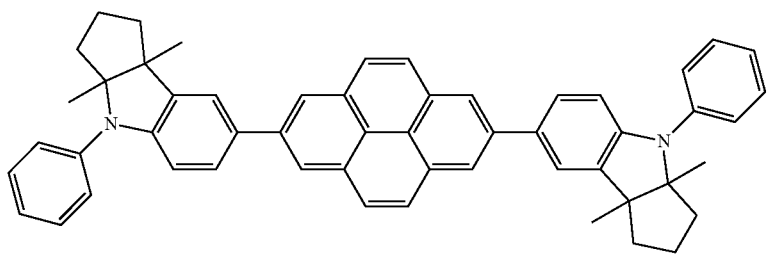
Formula 542
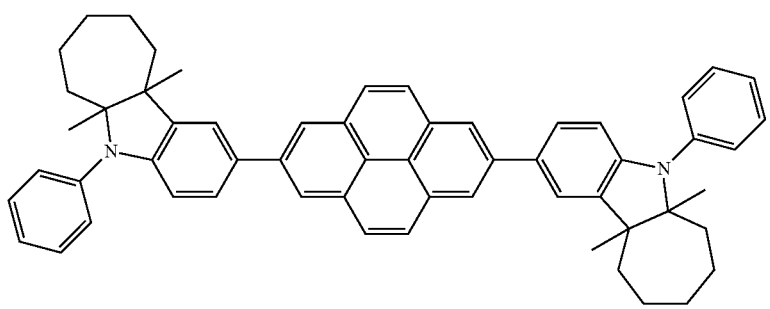
Formula 543
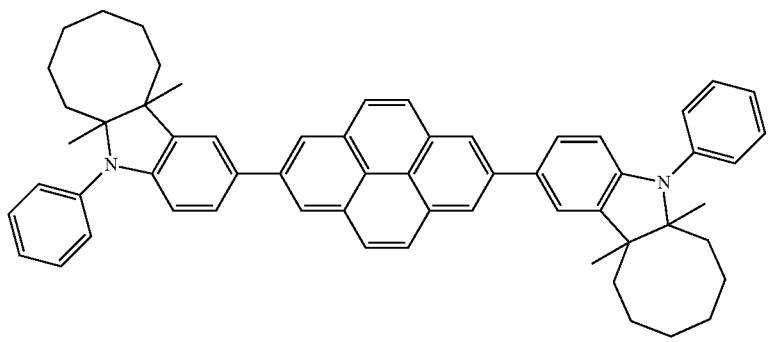
Formula 544
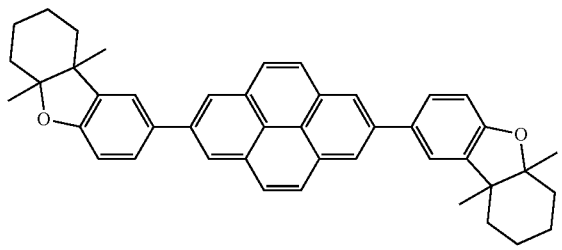
Formula 545
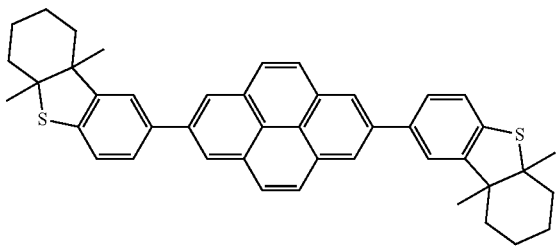

-continued
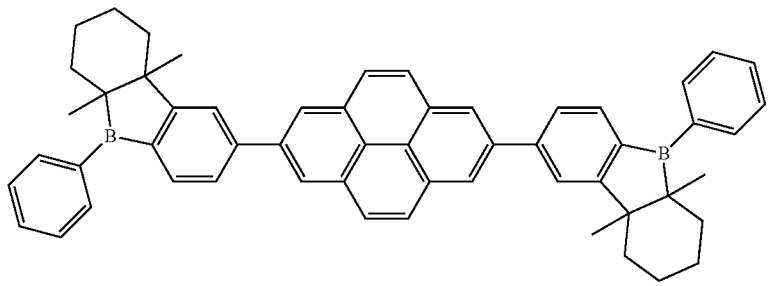
Formula 546
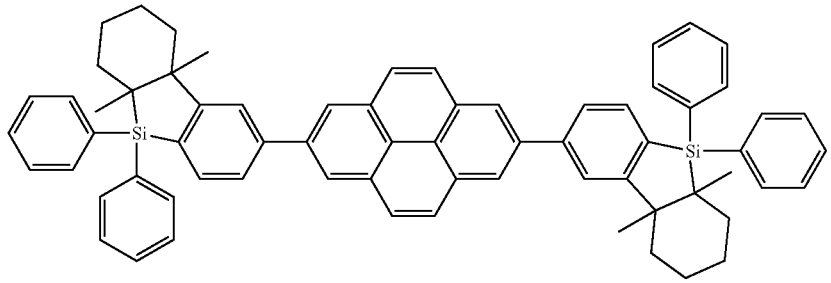
Formula 547
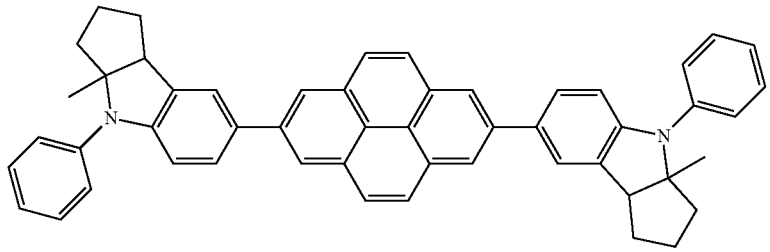
Formula 548
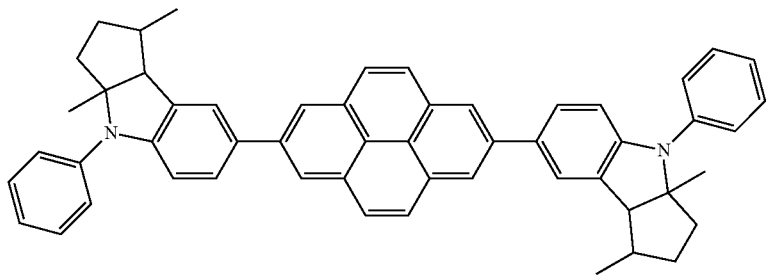
Formula 549
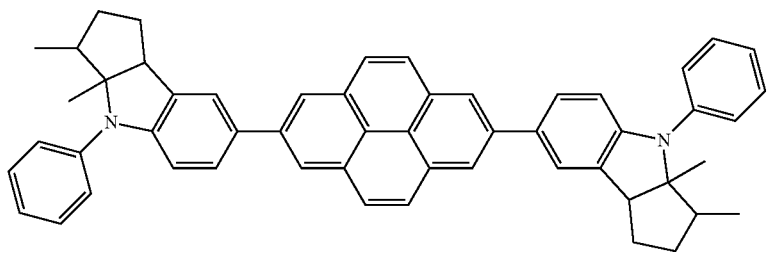
Formula 550
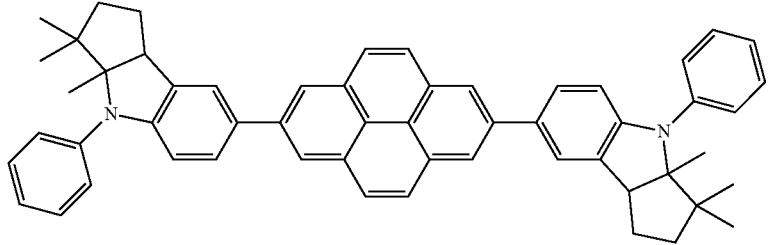
Formula 551

-continued
Formula 552
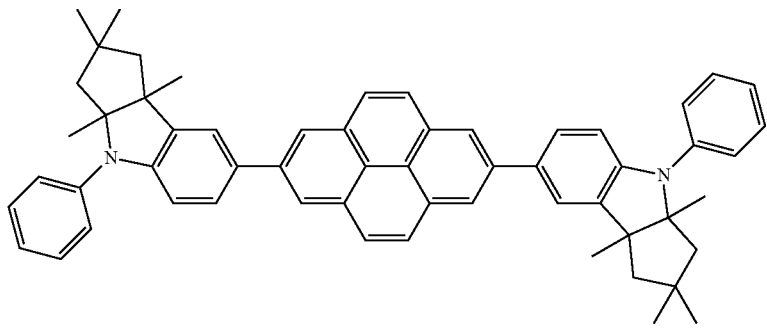
Formula 553
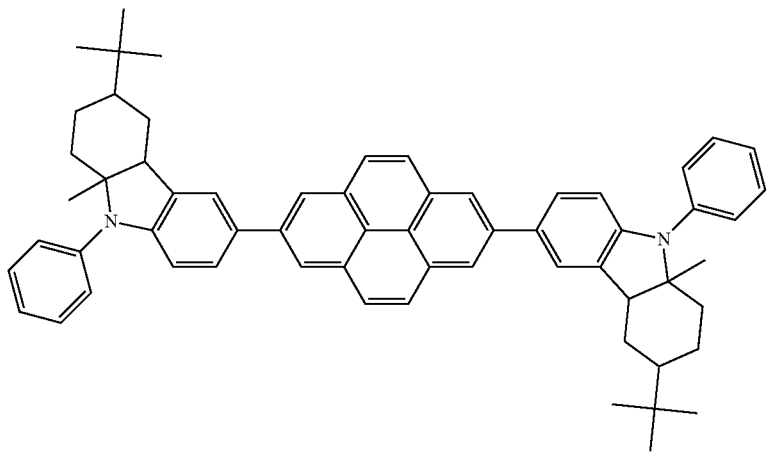
Formula 554
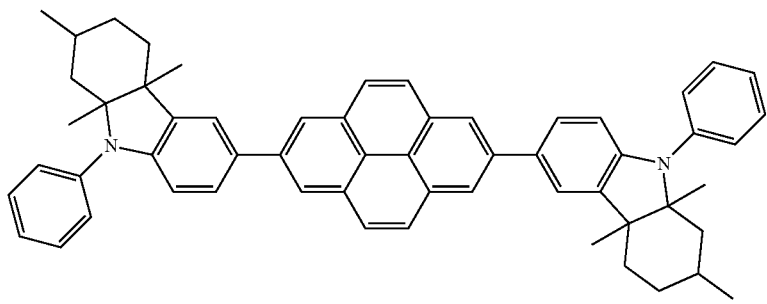
Formula 555
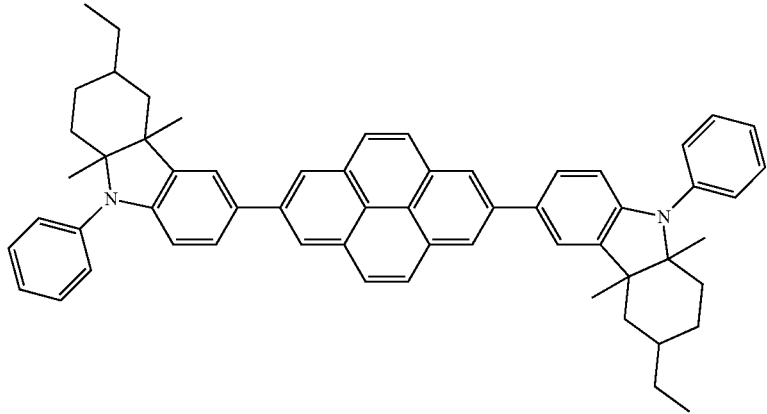

-continued
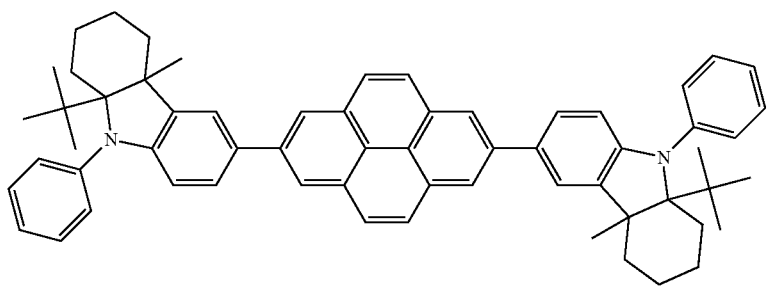
Formula 556
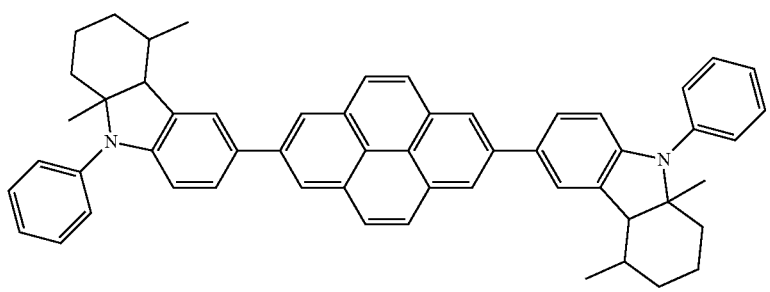
Formula 557
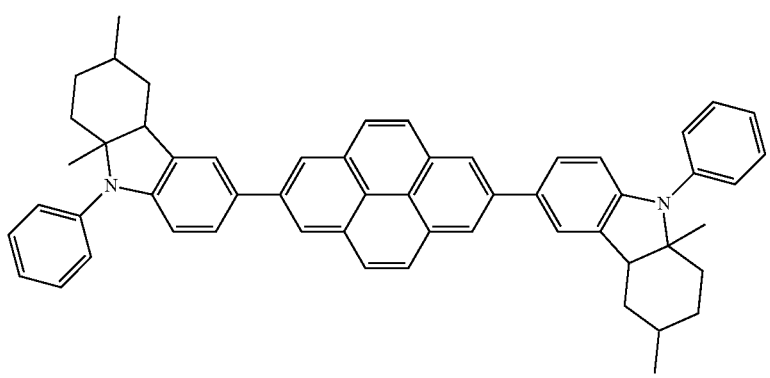
Formula 558
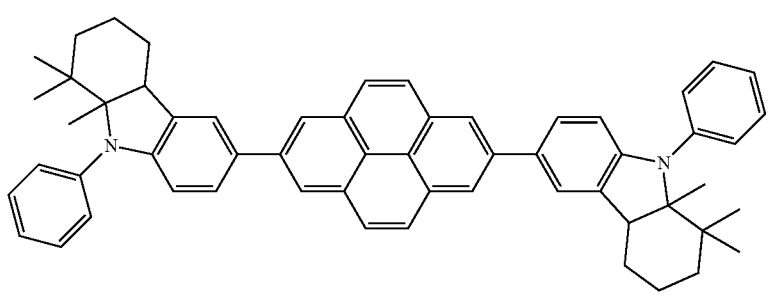
Formula 559
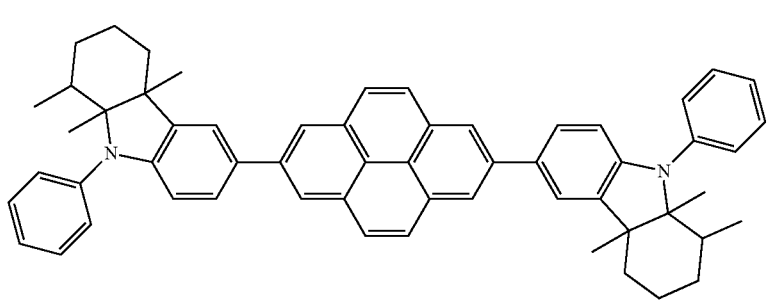
Formula 560

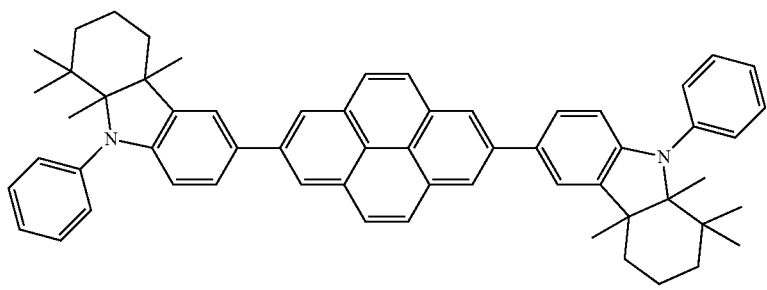
Formula 561
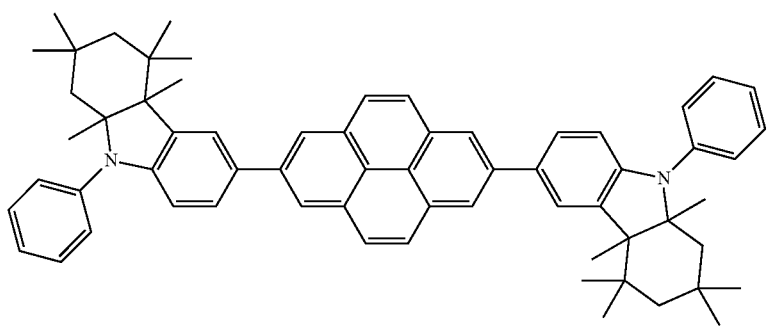
Formula 562
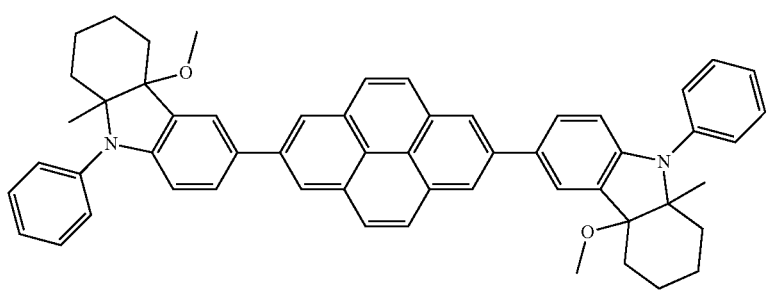
Formula 563
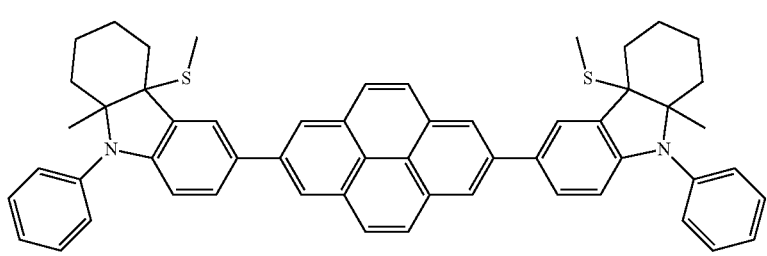
Formula 564
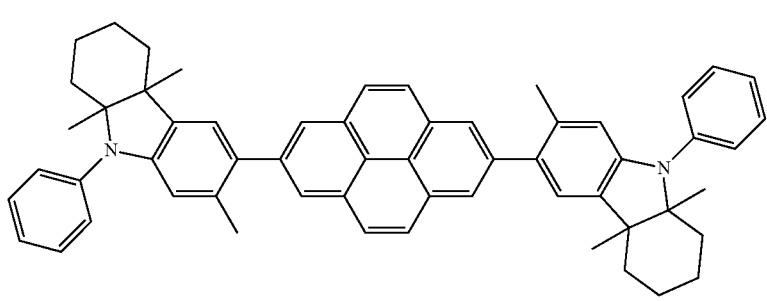
Formula 565

Formula 566
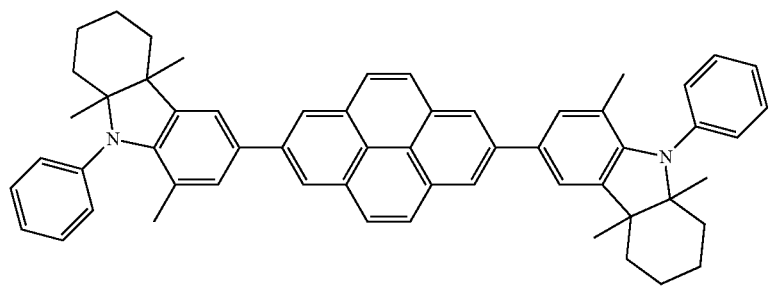
Formula 567
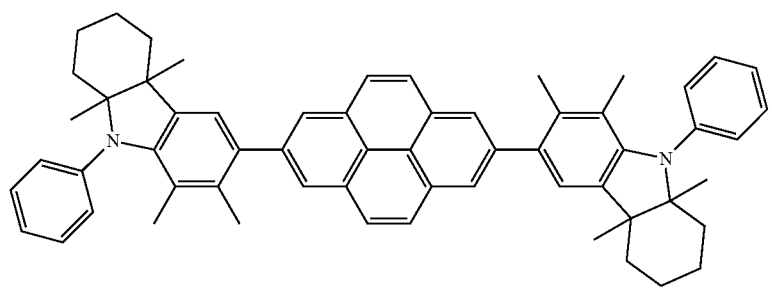
Formula 568
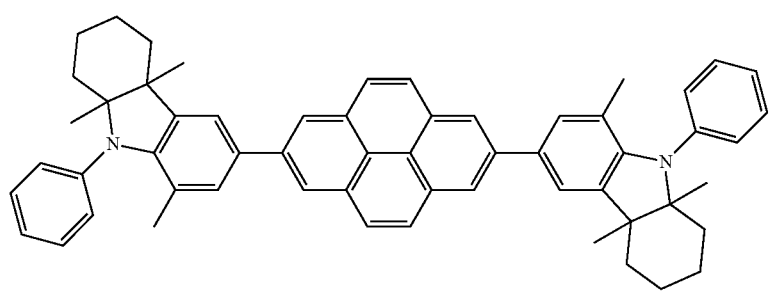
Formula 569
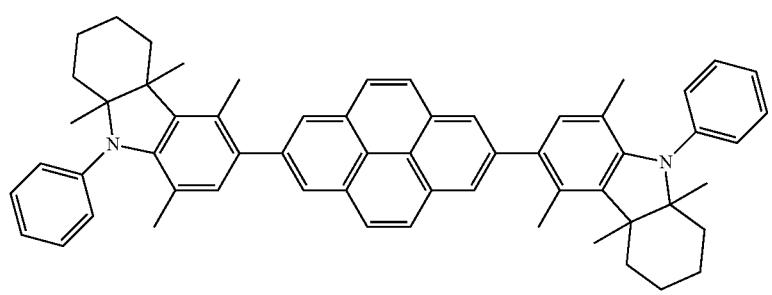
Formula 570
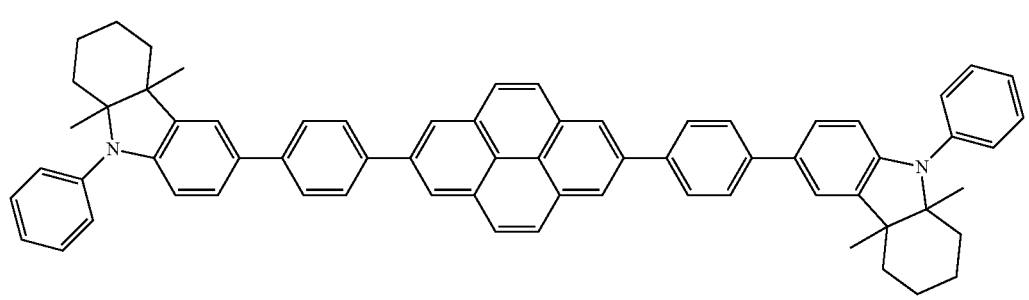

Formula 571
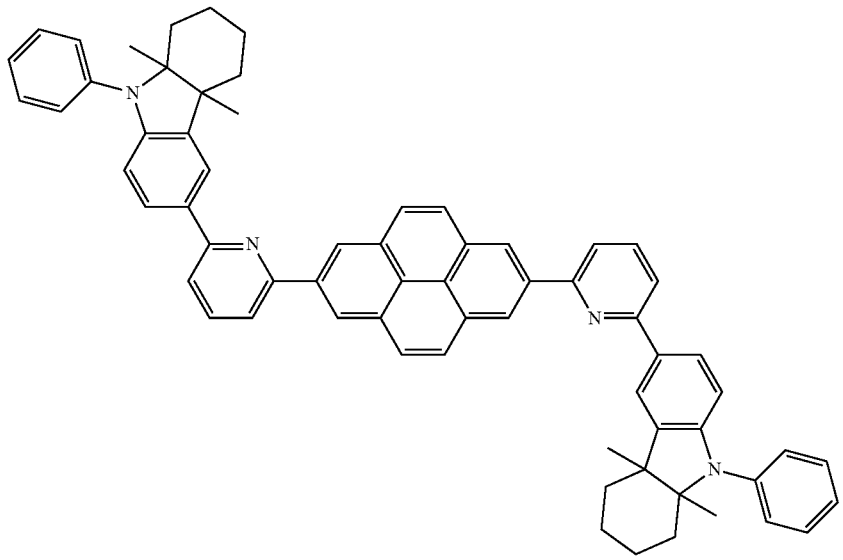
Formula 572
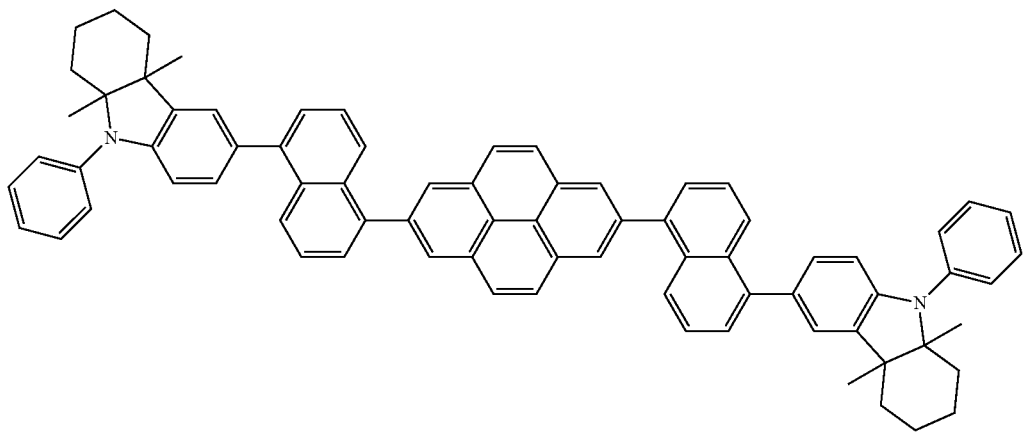
Formula 573
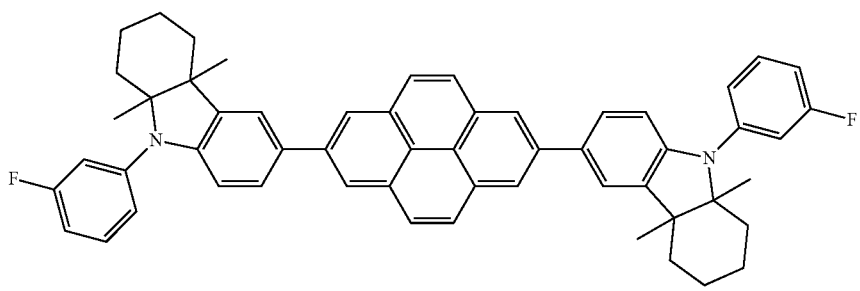
Formula 574
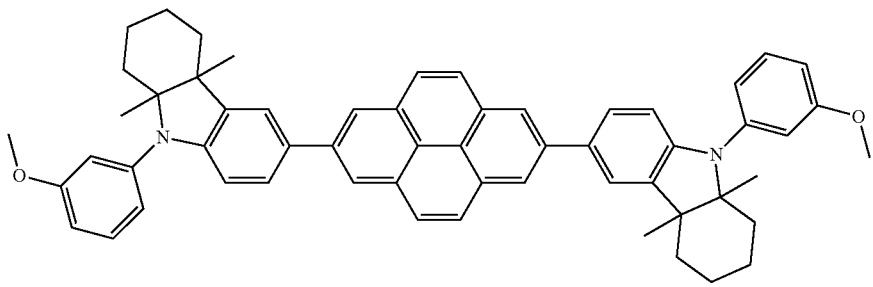

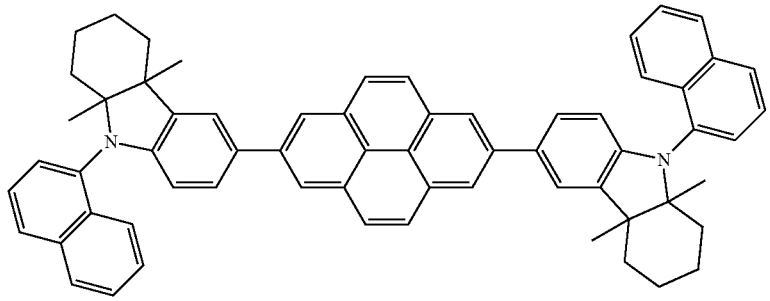
Formula 575
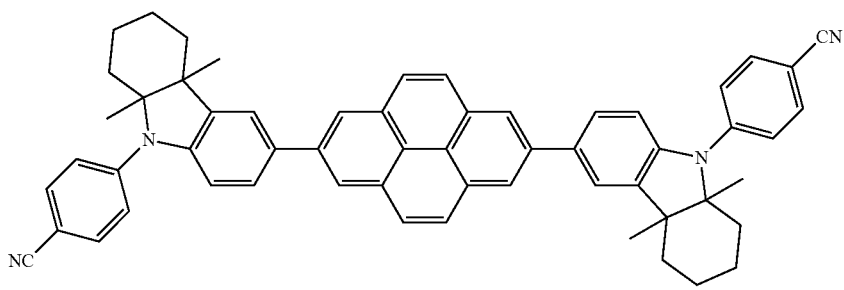
Formula 576
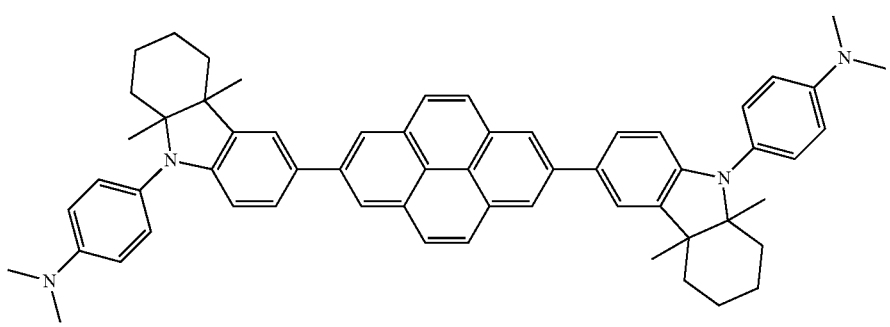
Formula 577
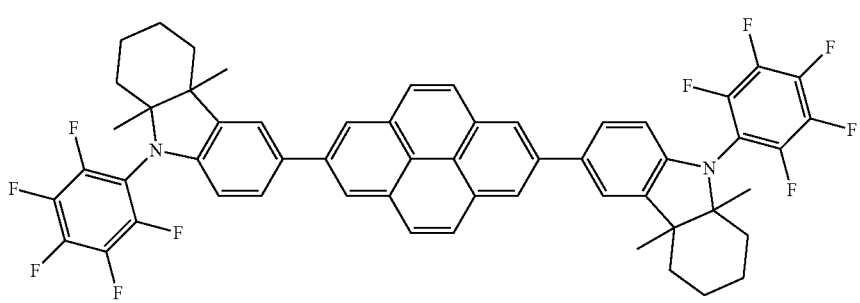
Formula 578
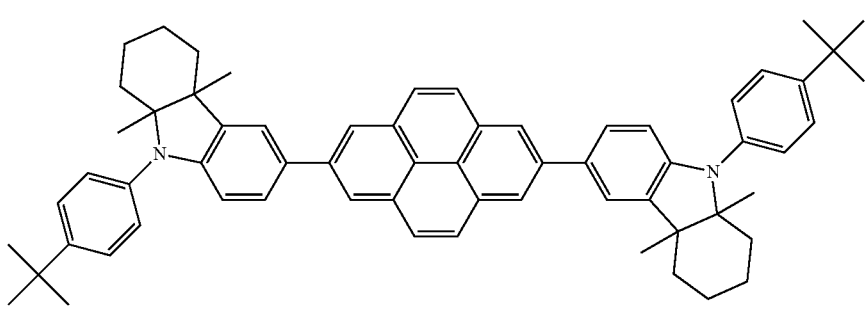
Formula 579

-continued
Formula 580
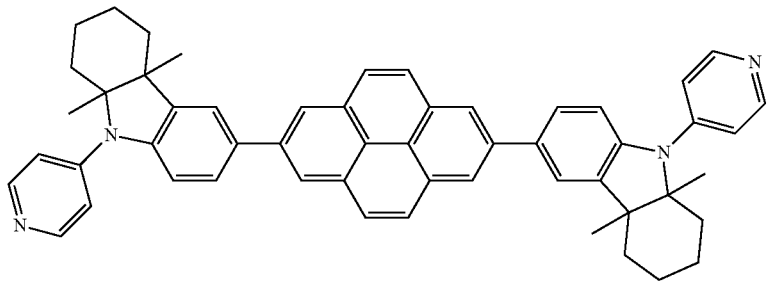
Formula 581
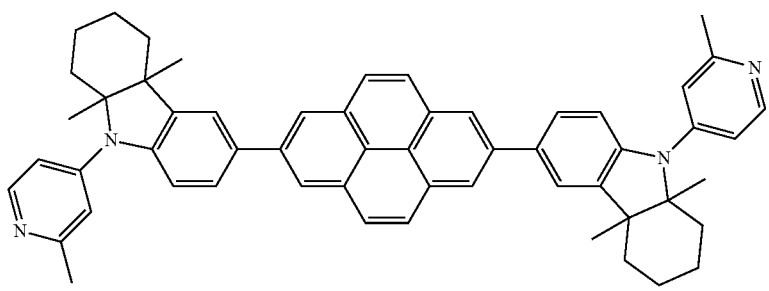
Formula 582
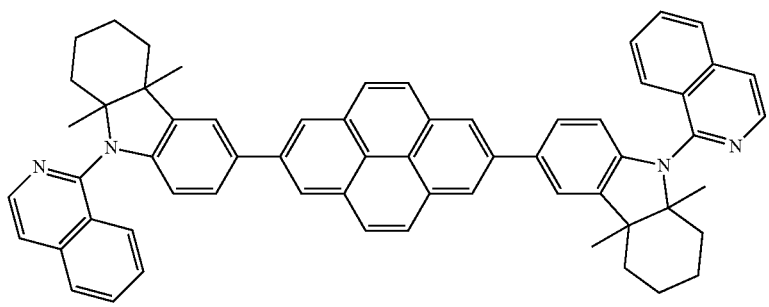
Formula 583
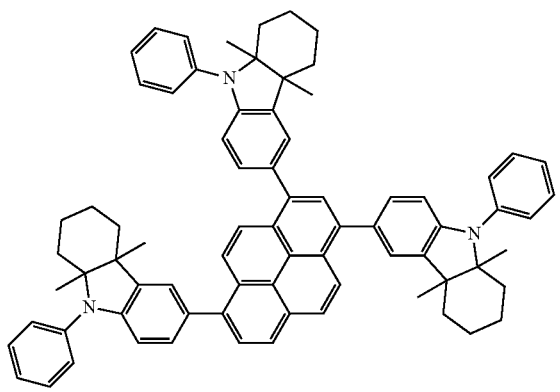
Formula 584
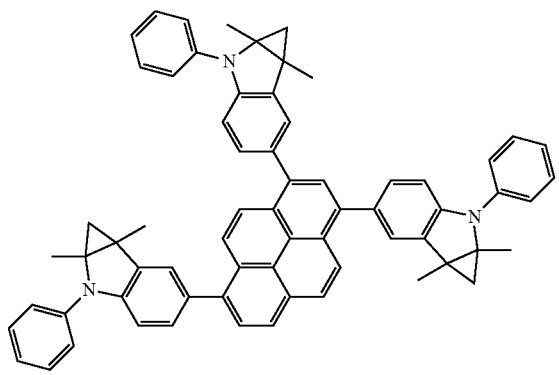

-continued
Formula 585
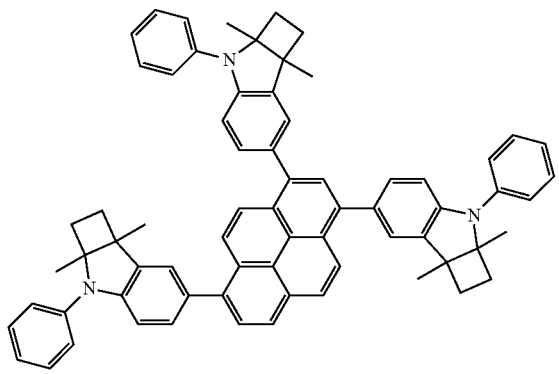
Formula 586
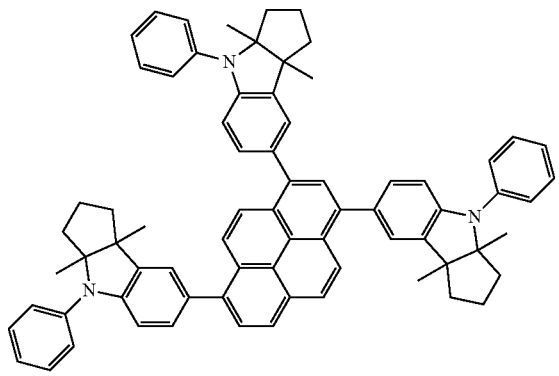
Formula 587
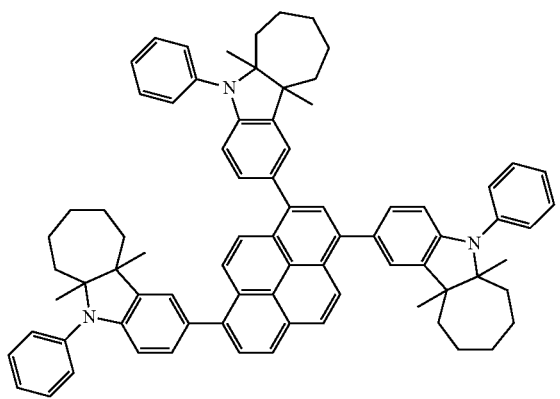
Formula 588
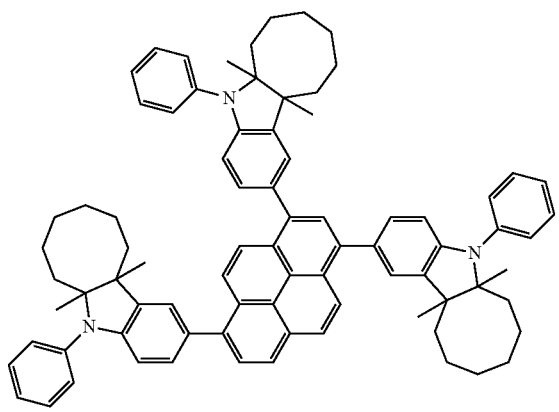
Formula 589
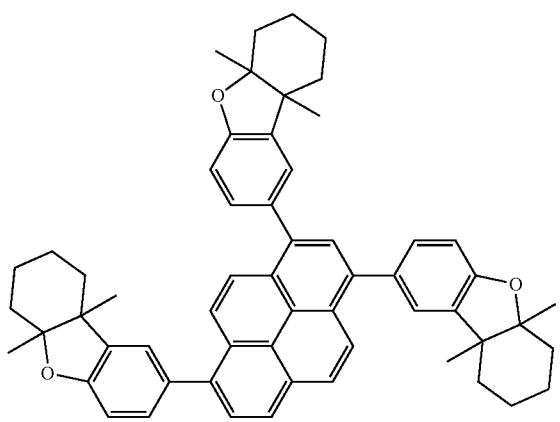
Formula 590
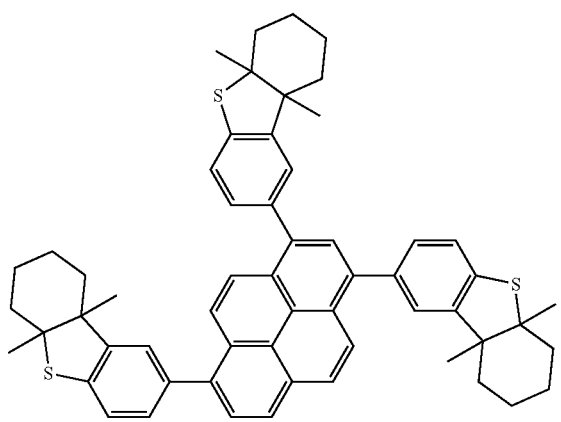

-continued
Formula 591
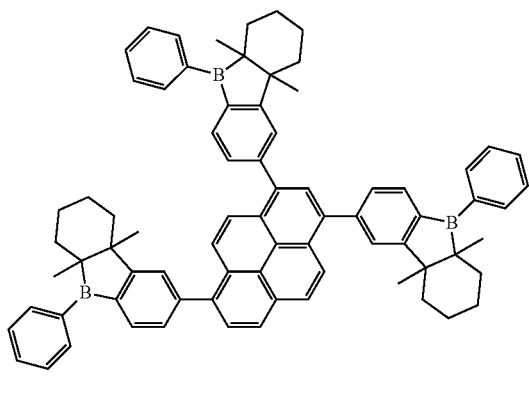
Formula 592
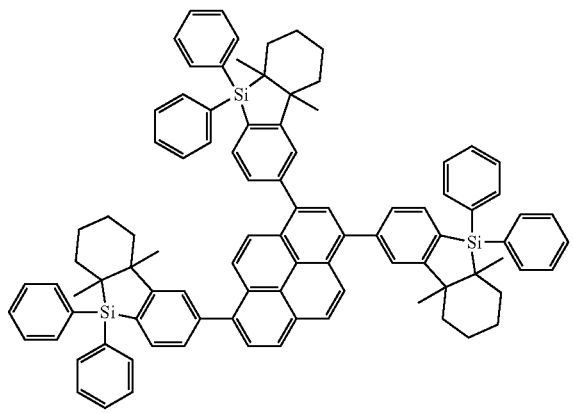
Formula 593
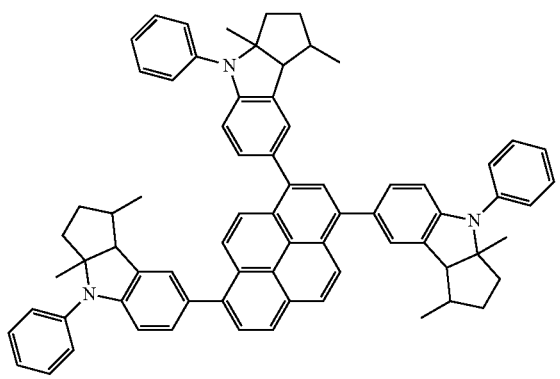
Formula 594
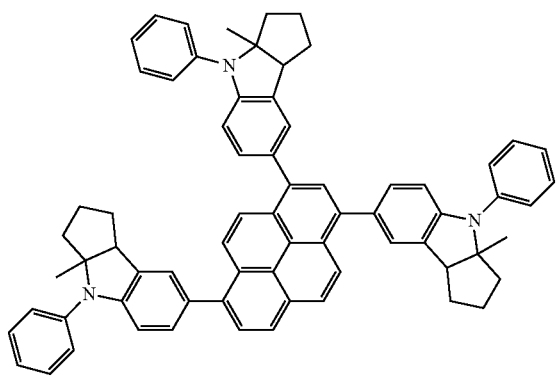
Formula 595
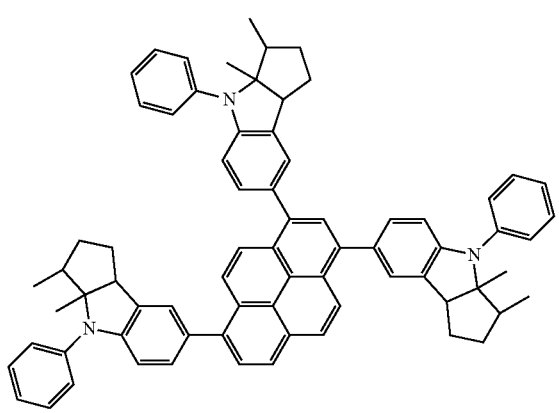
Formula 596
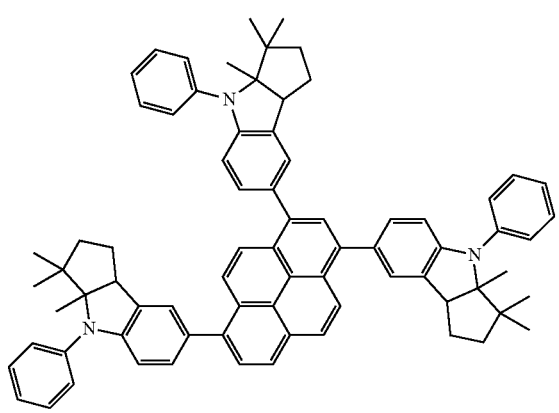

-continued
Formula 597
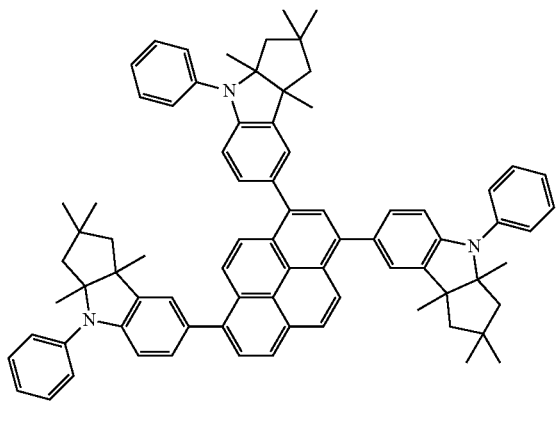
Formula 598
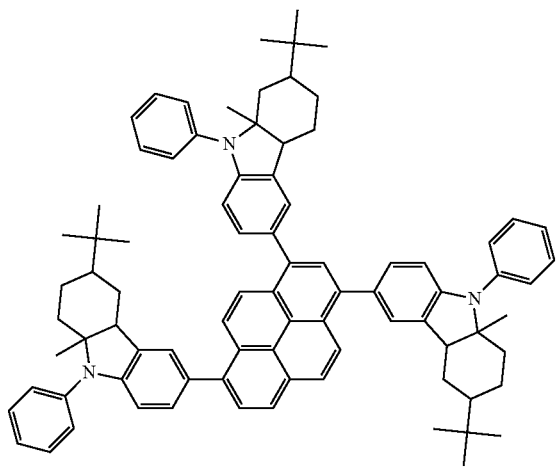
Formula 599
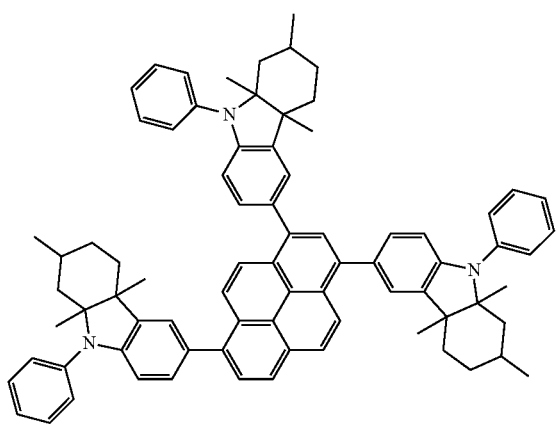
Formula 600
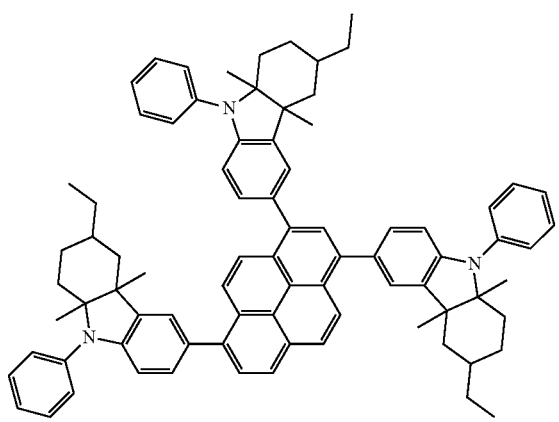
Formula 601
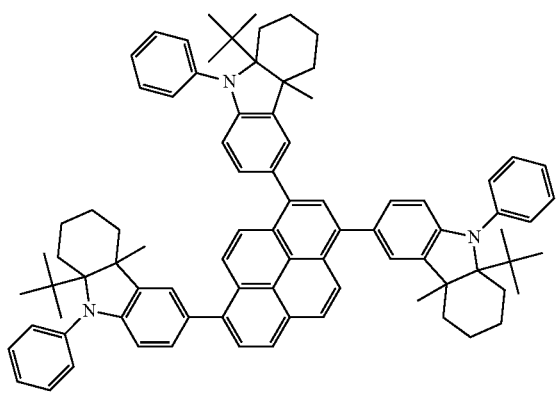
Formula 602
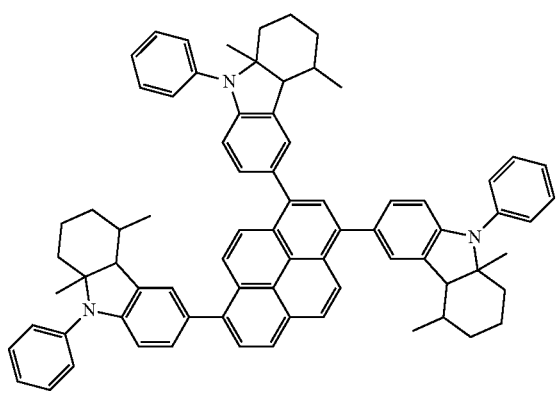

-continued
Formula 603
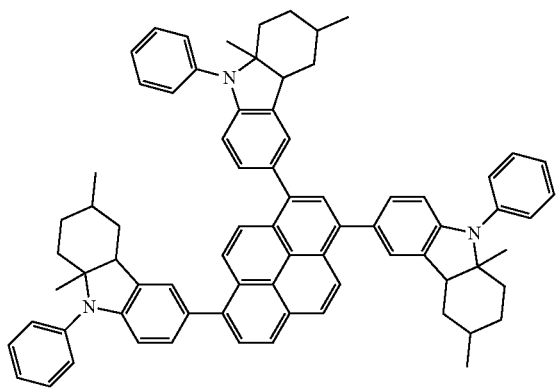
Formula 604
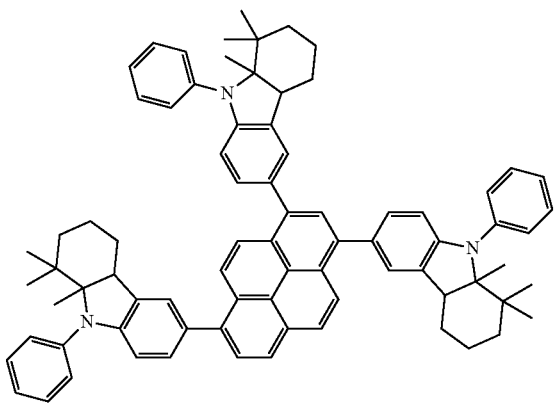
Formula 605
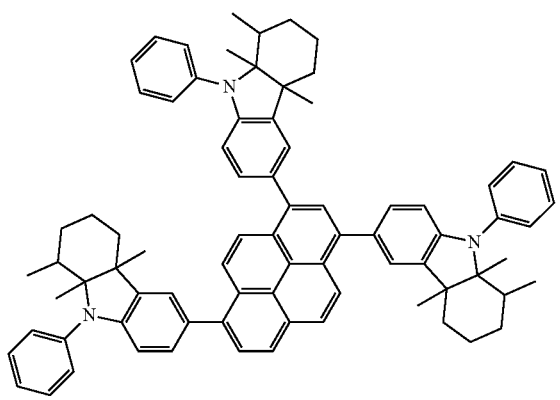
Formula 606
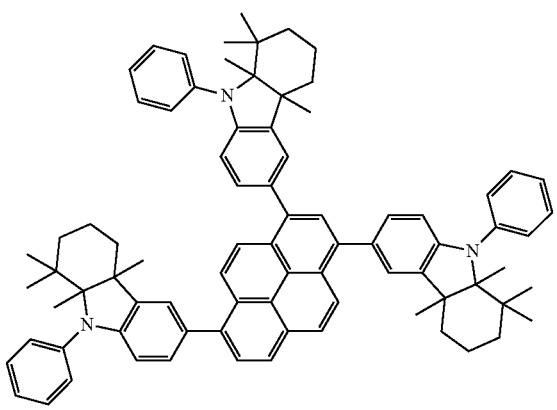
Formula 607
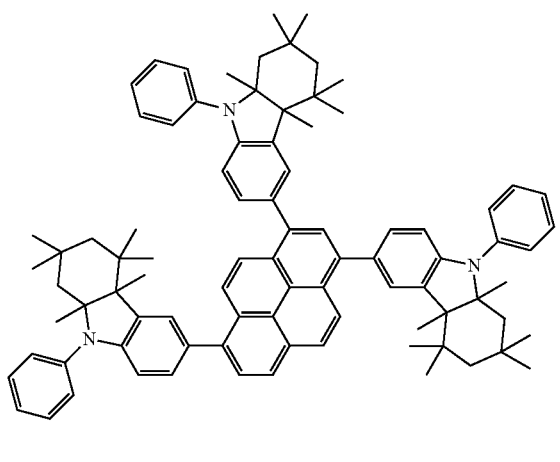
Formula 608
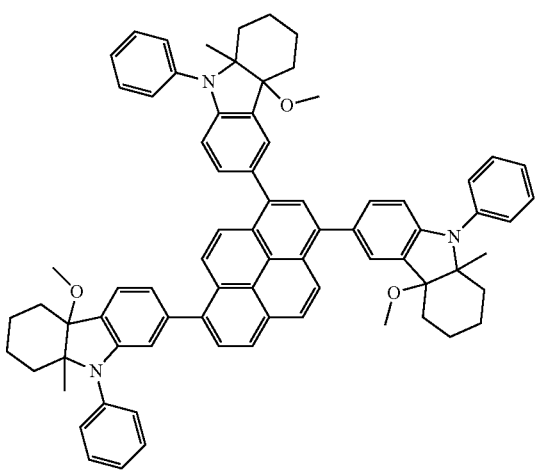

-continued
Formula 609
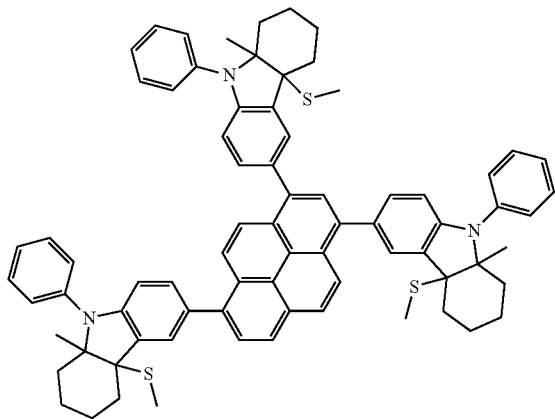
Formula 610
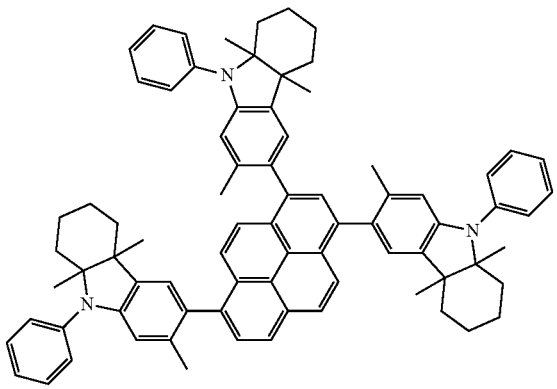
Formula 611
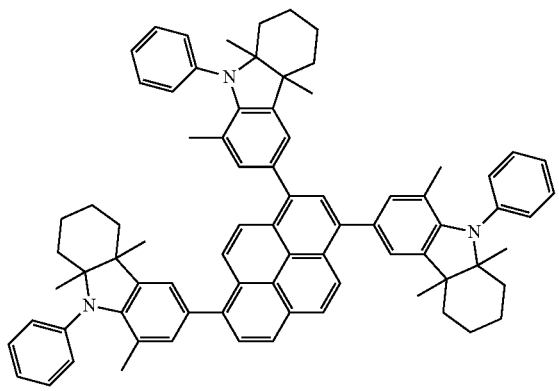
Formula 612
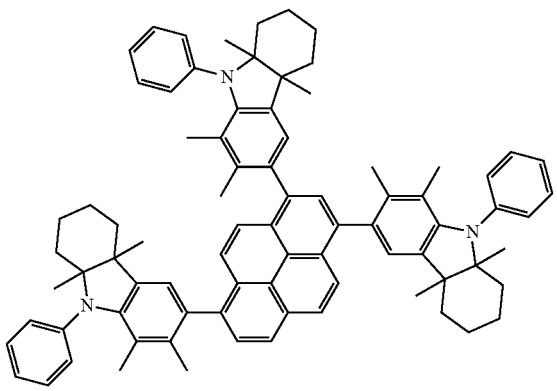
Formula 613
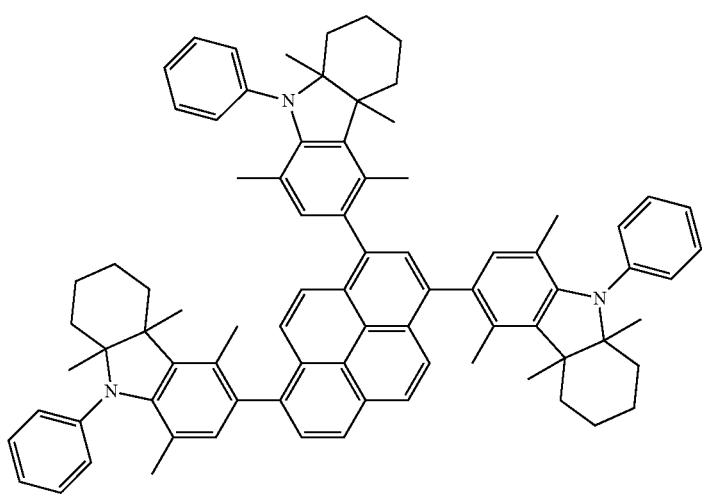

-continued
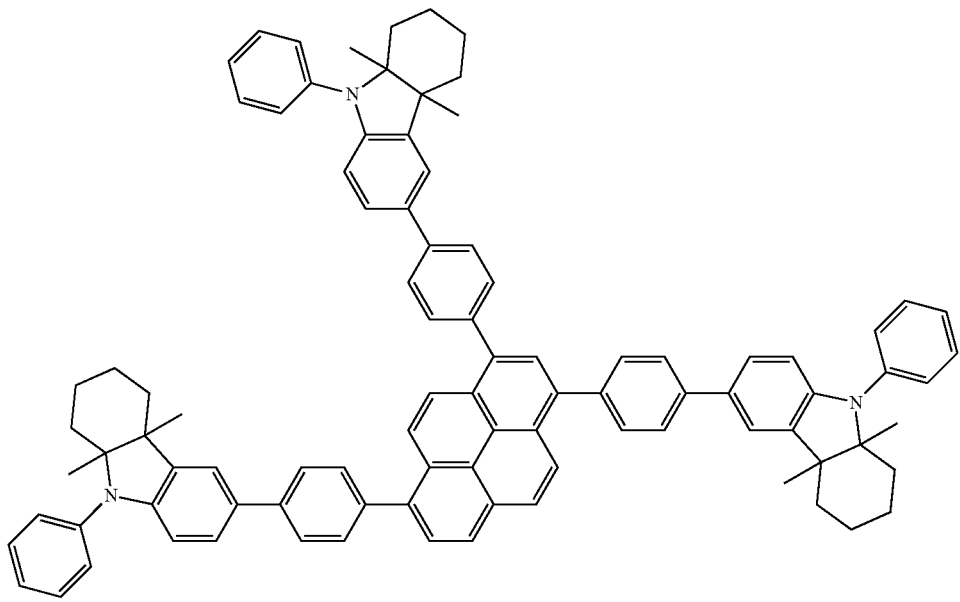
Formula 614
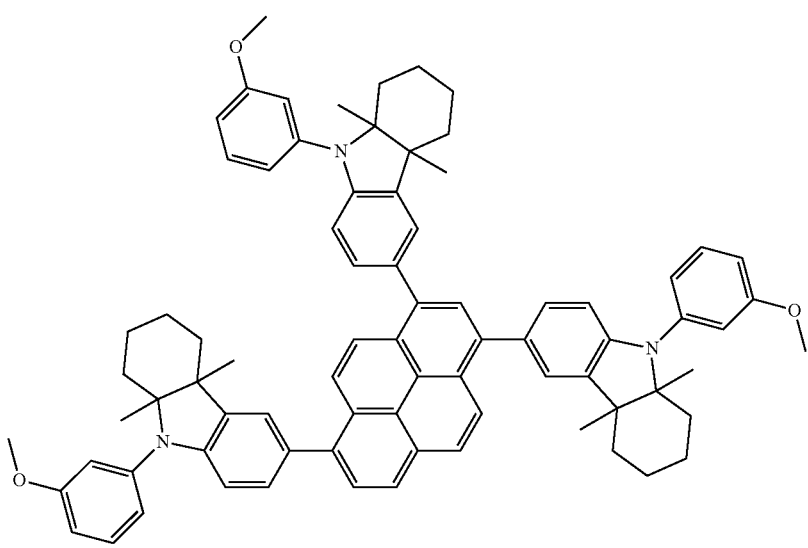
Formula 615

-continued
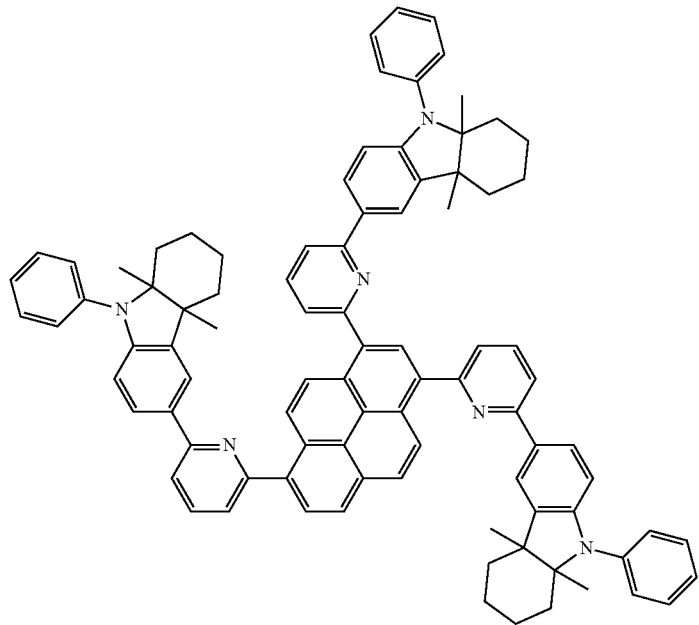
Formula 616
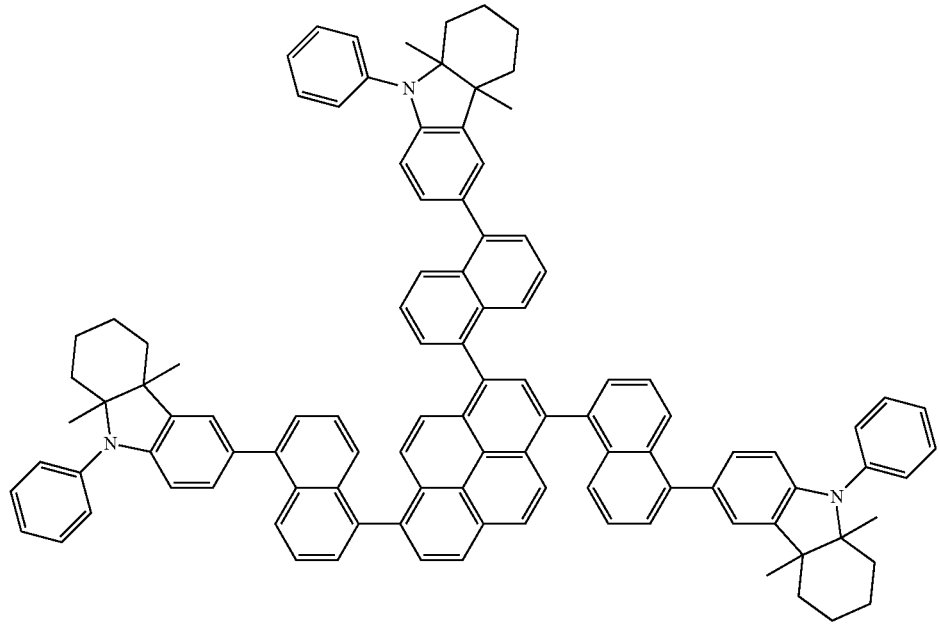
Formula 617

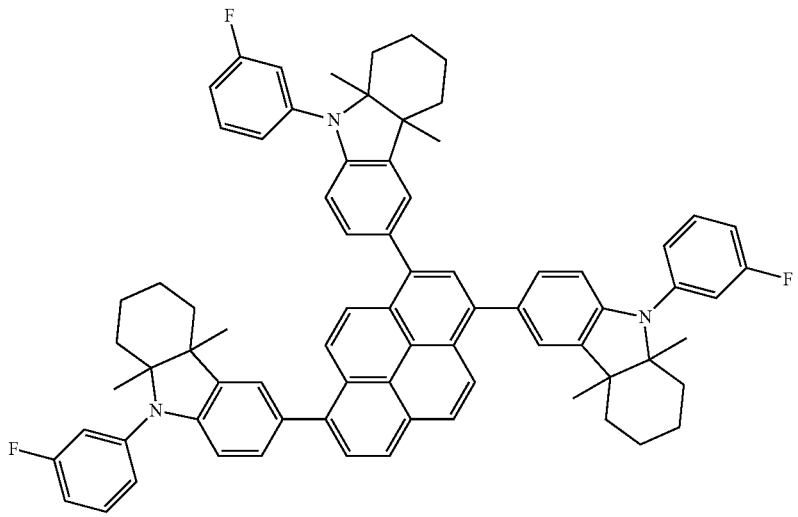
Formula 618
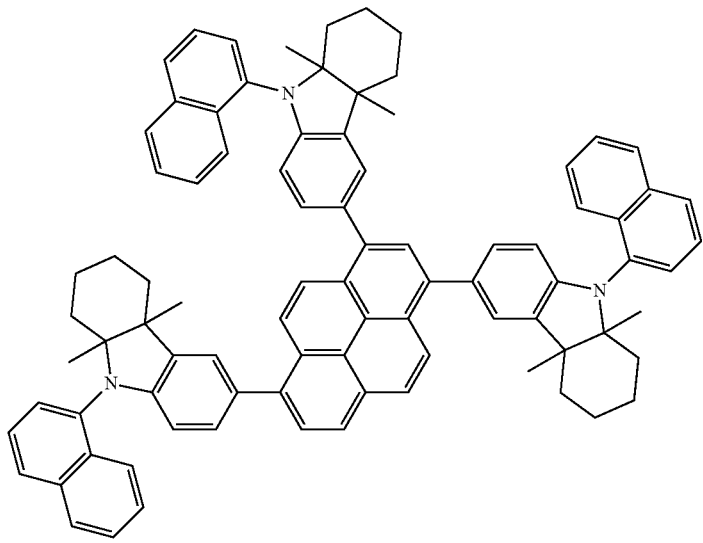
Formula 619
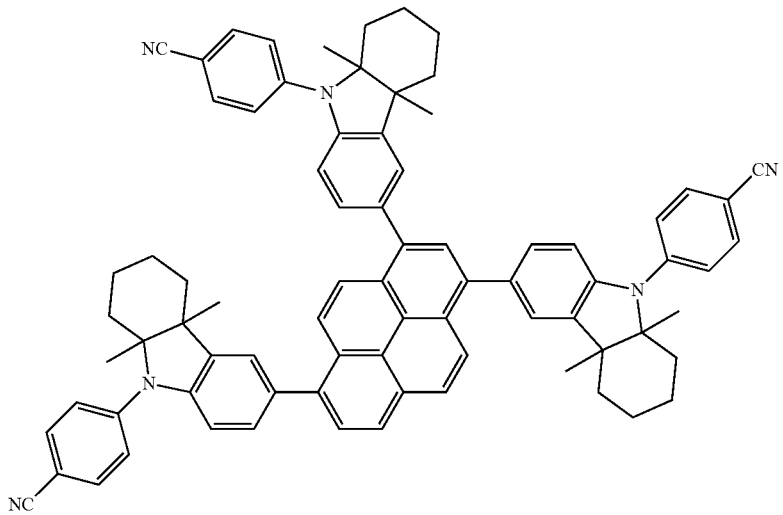
Formula 620

Formula 621
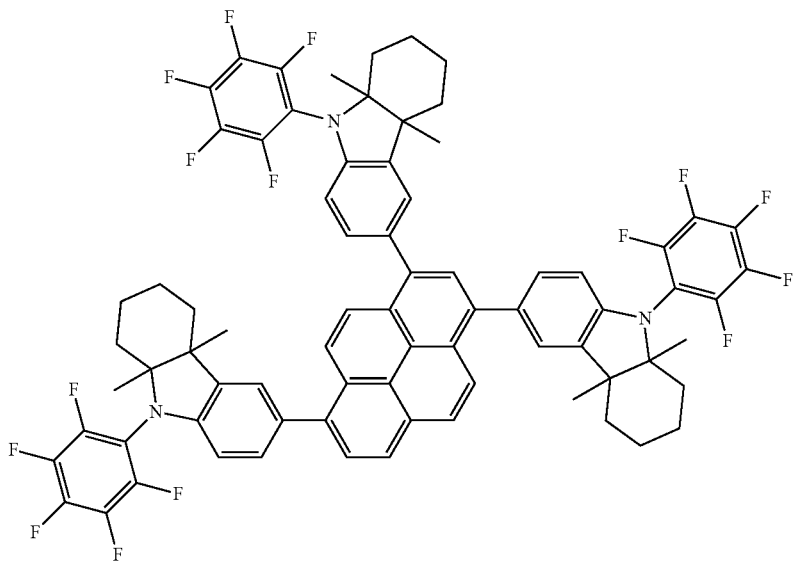
Formula 622
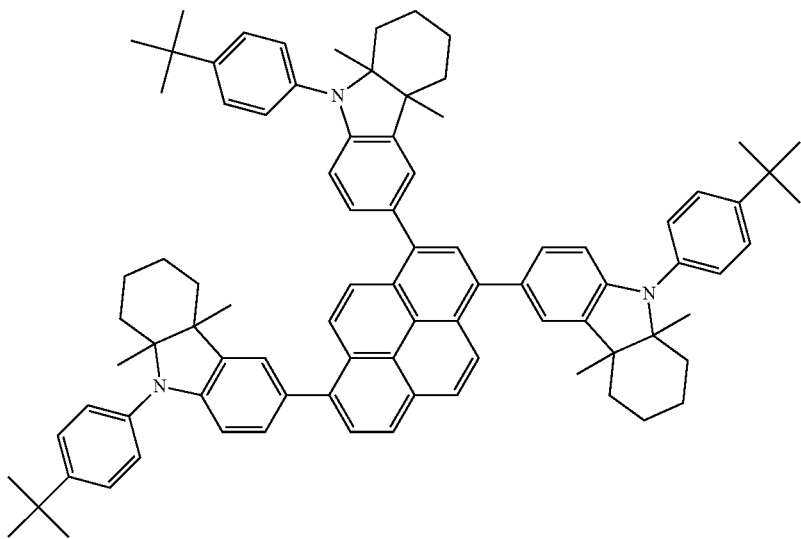
Formula 623
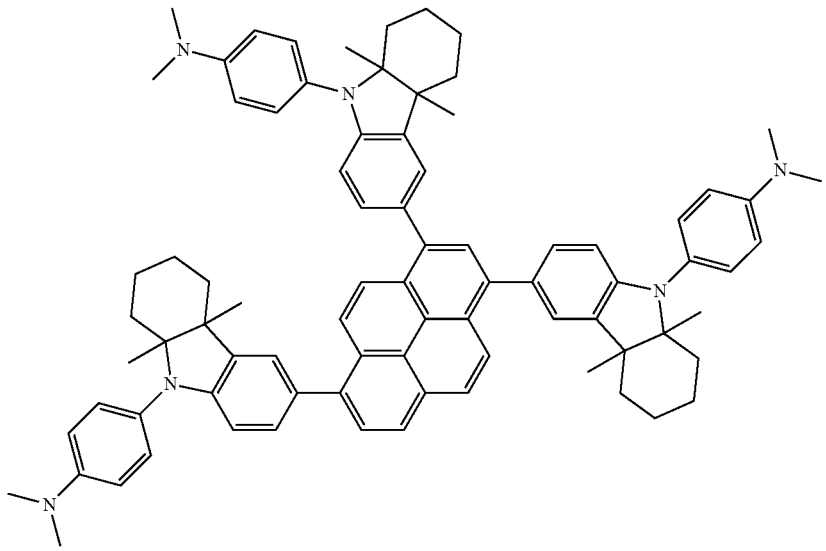

-continued
Formula 624
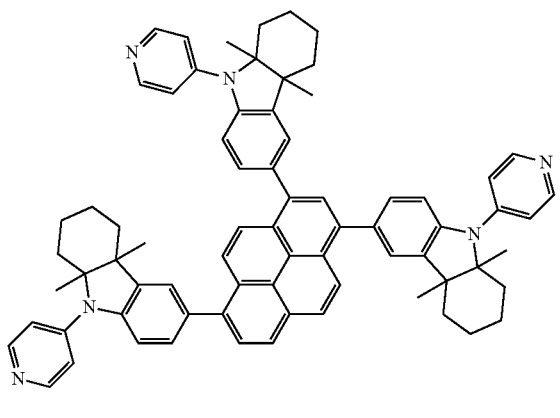
Formula 625
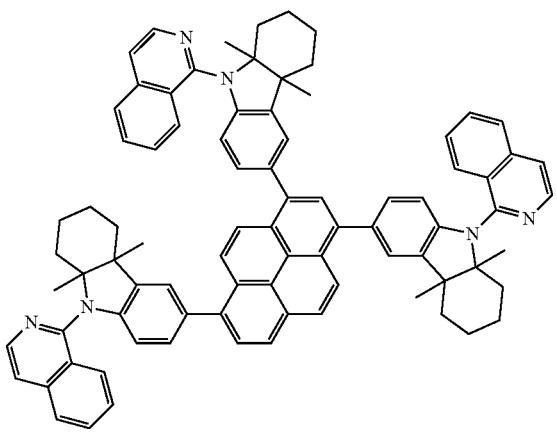
Formula 626
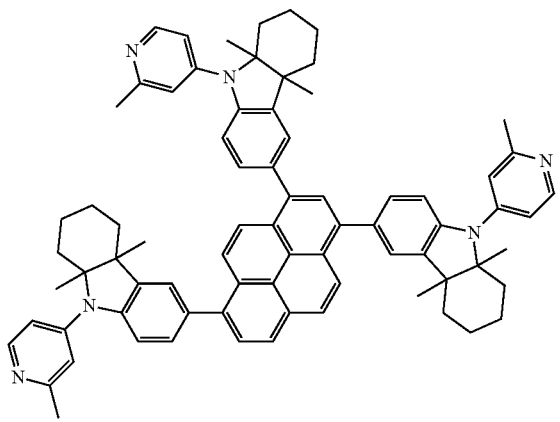
Formula 627
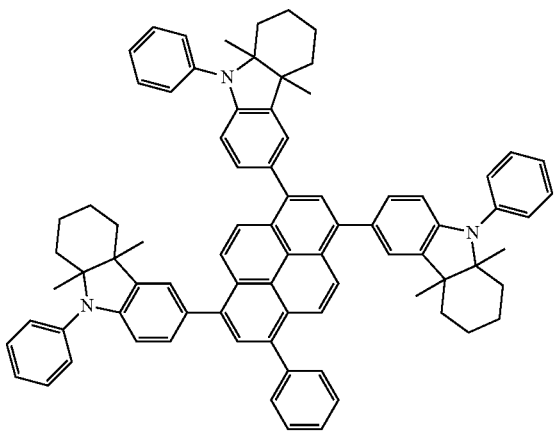
Formula 628
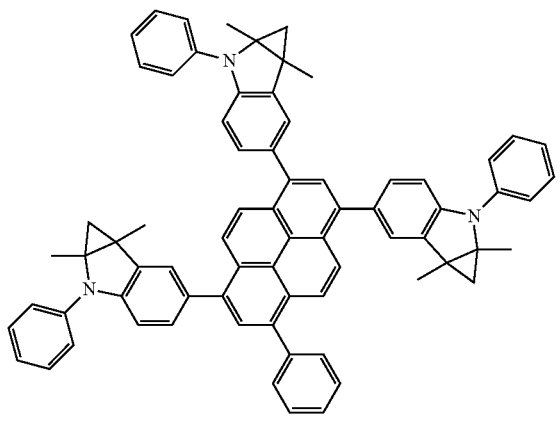
Formula 629
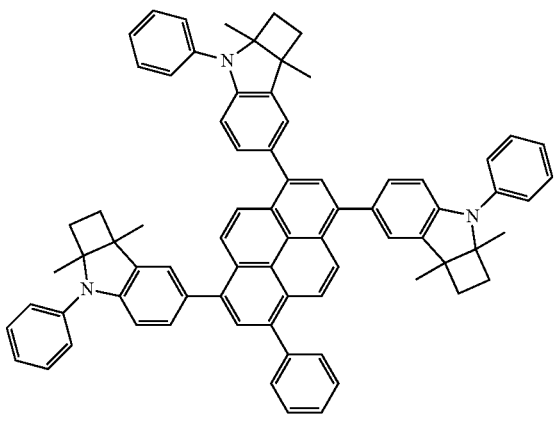

-continued
Formula 630
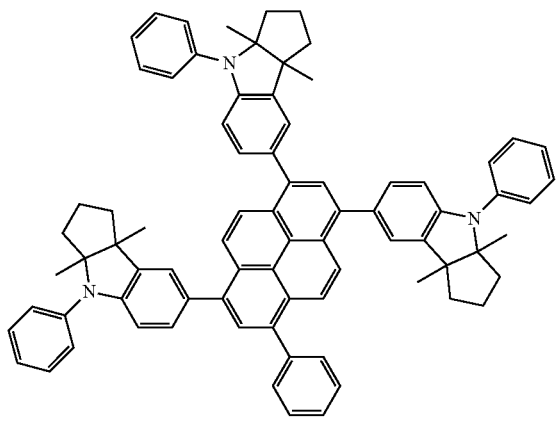
Formula 631
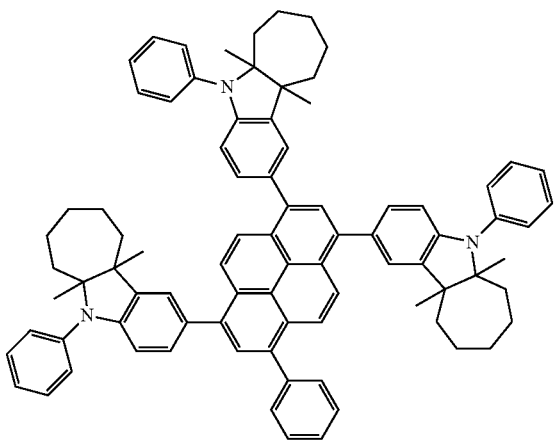
Formula 632
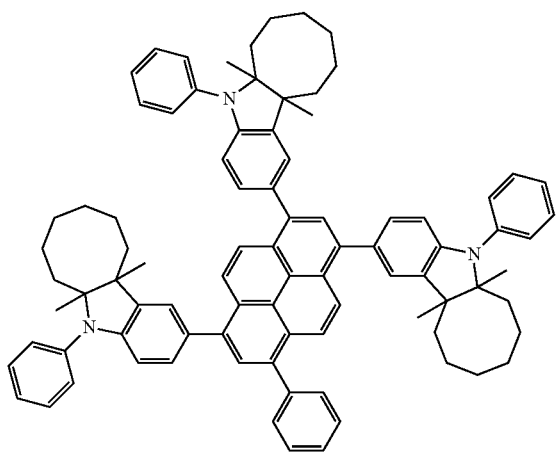
Formula 633
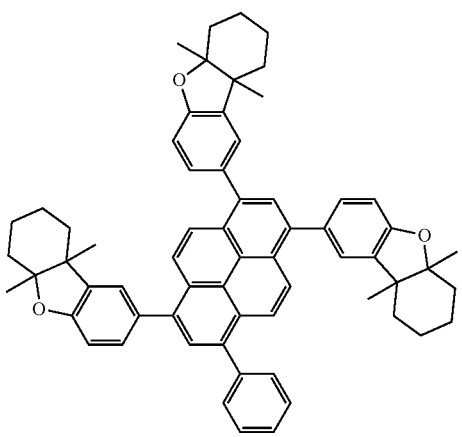
Formula 634
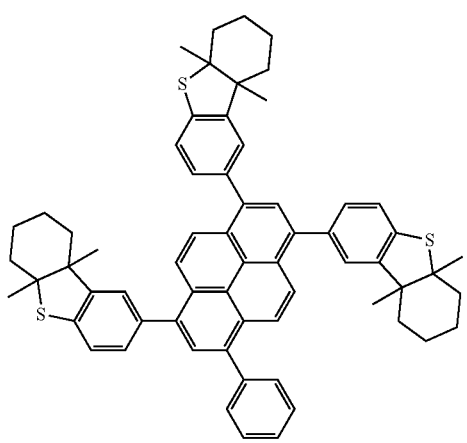
Formula 635
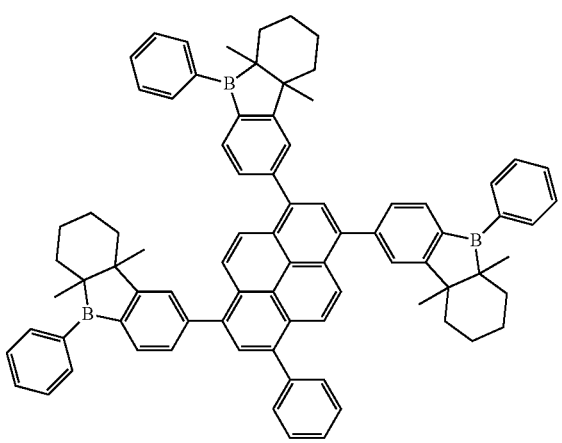

Formula 636
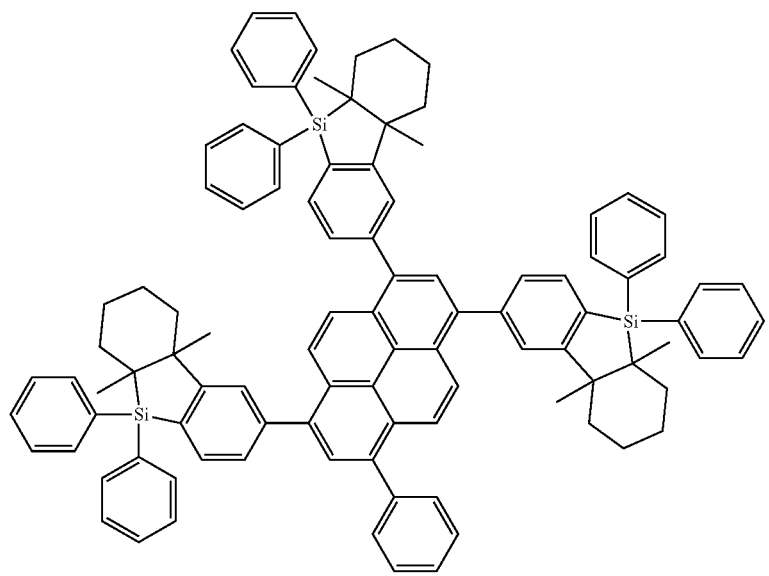
Formula 637
Formula 638
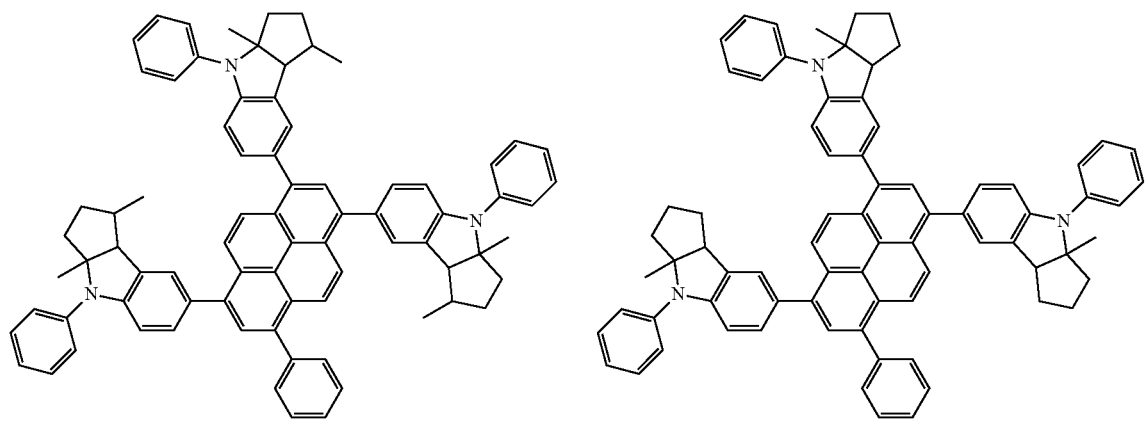
Formula 640
Formula 641
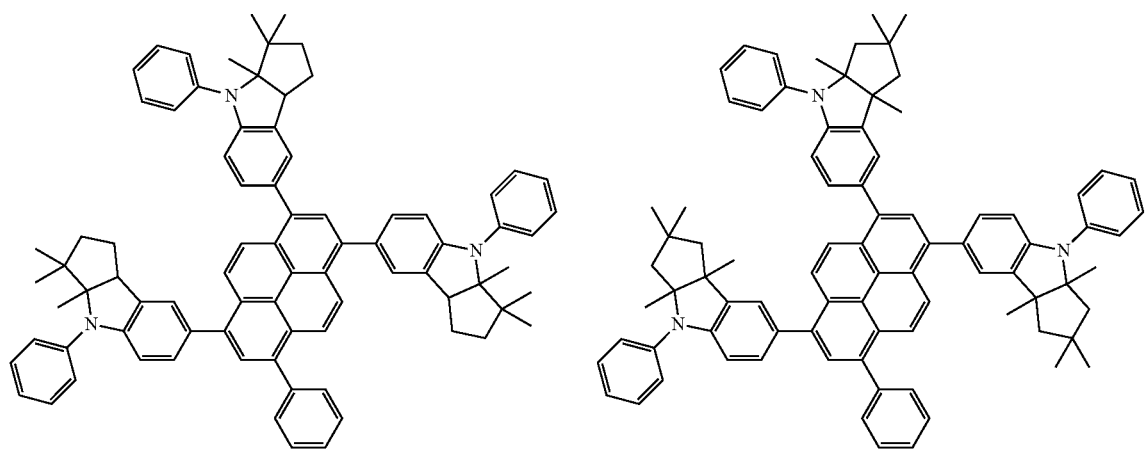

-continued
Formula 642
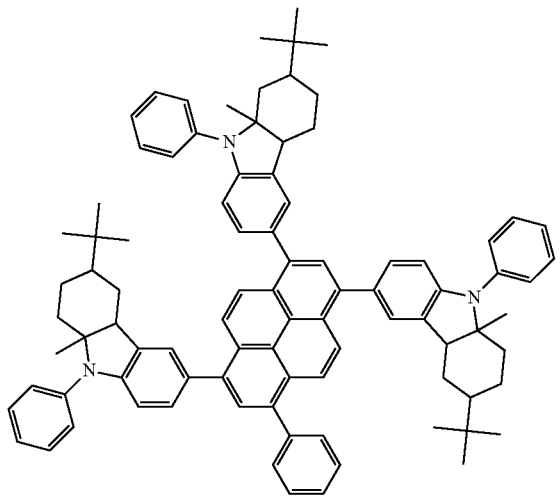
Formula 643
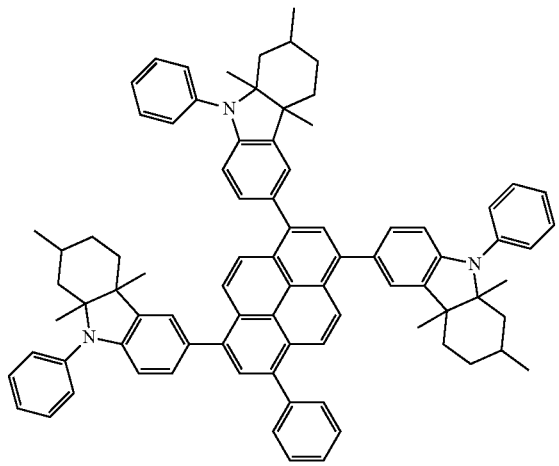
Formula 644
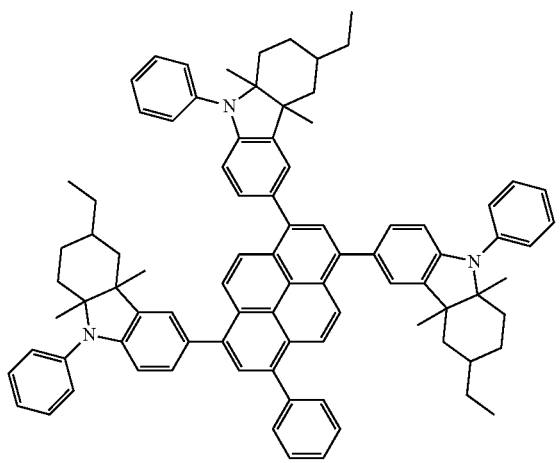
Formula 645
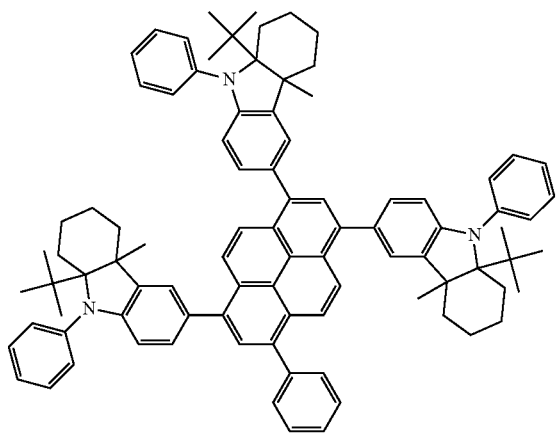
Formula 646
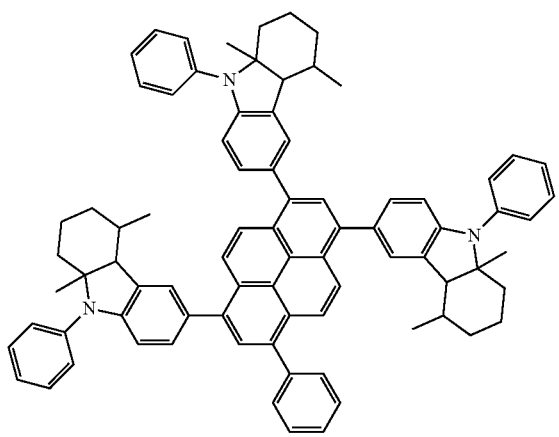
Formula 647
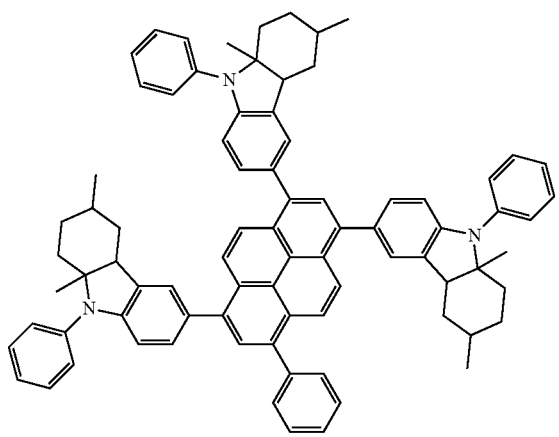

-continued
Formula 648
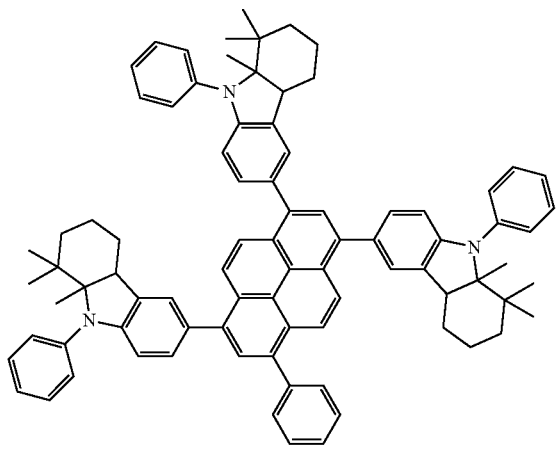
Formula 649
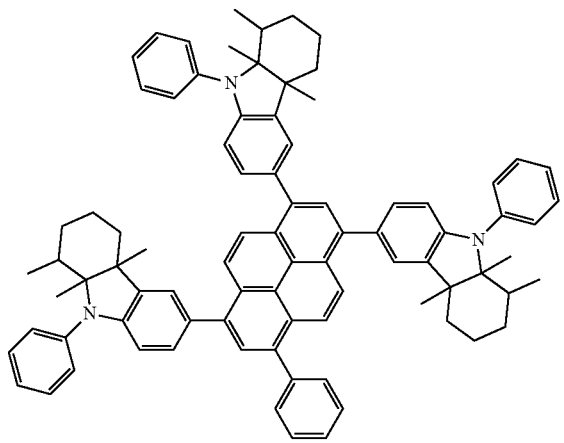
Formula 650
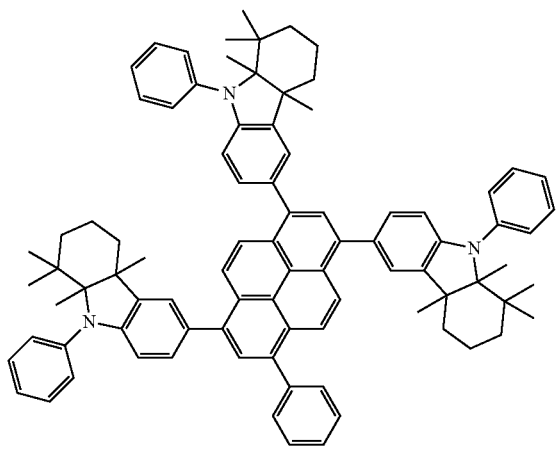
Formula 651
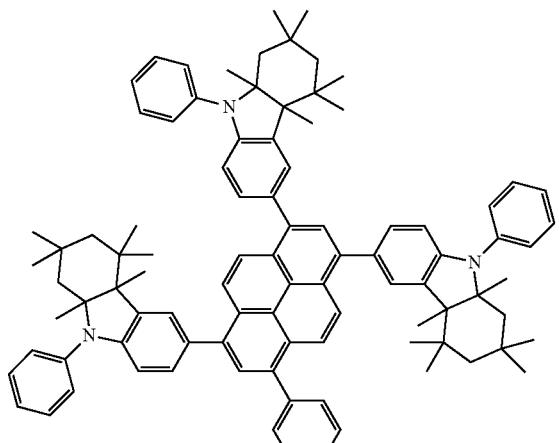
Formula 652
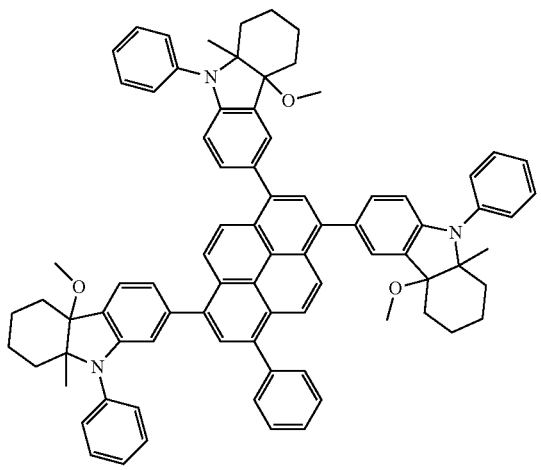
Formula 653
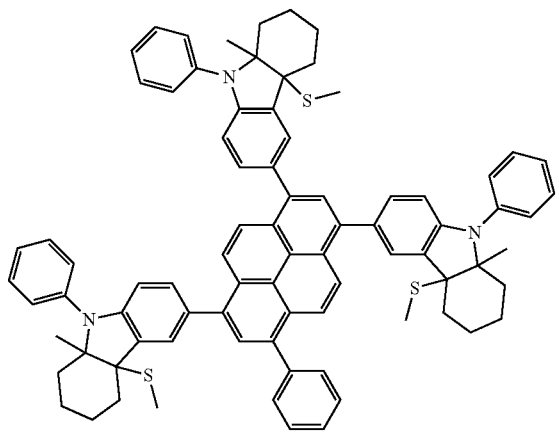

-continued
Formula 654
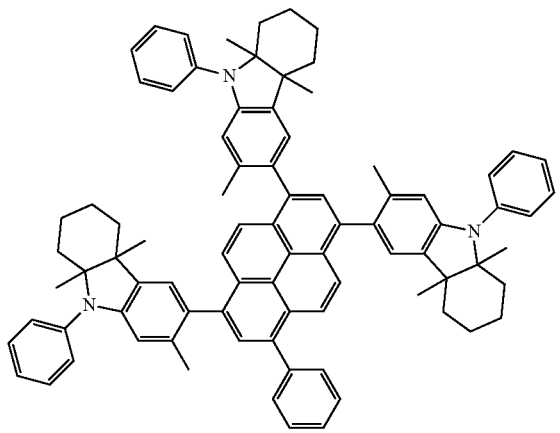
Formula 655
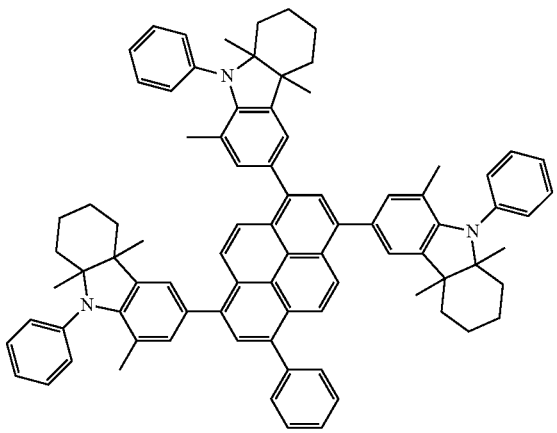
Formula 656
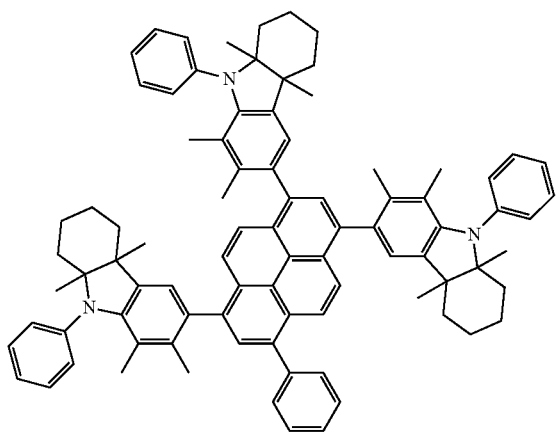
Formula 657
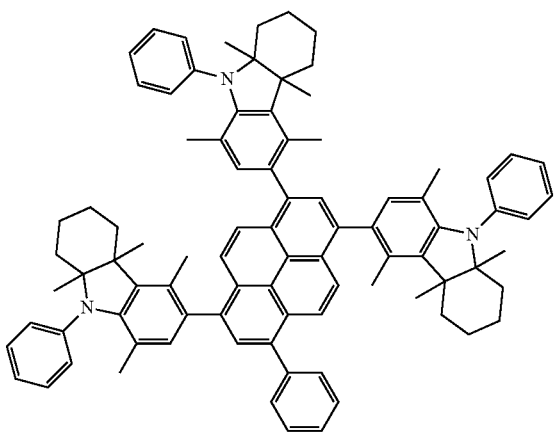
Formula 658
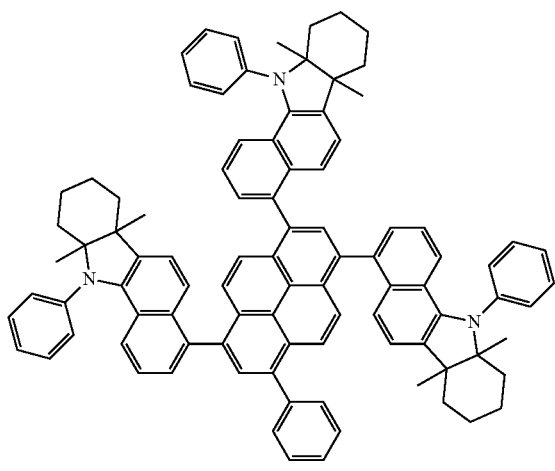
Formula 659
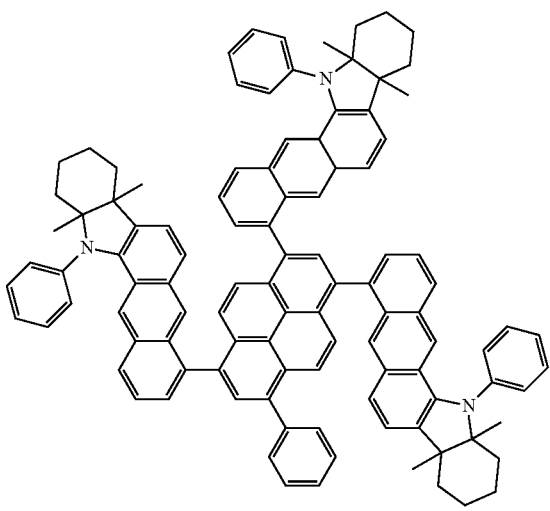

-continued
Formula 660
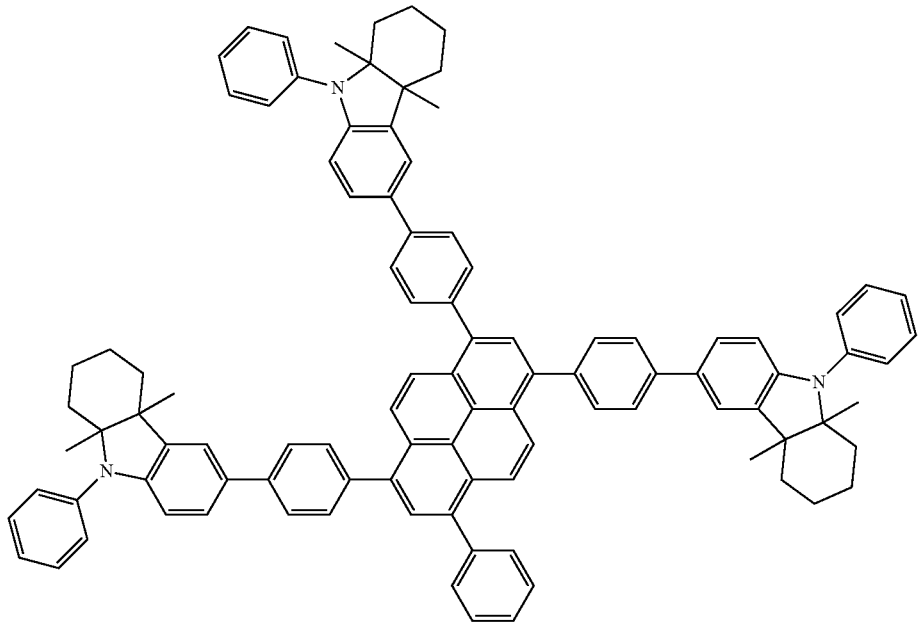
Formula 661
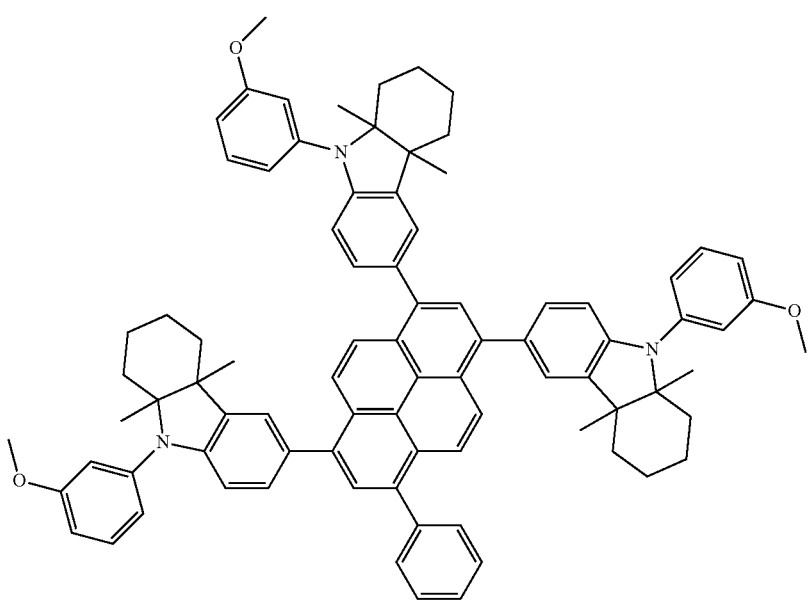

-continued
Formula 662
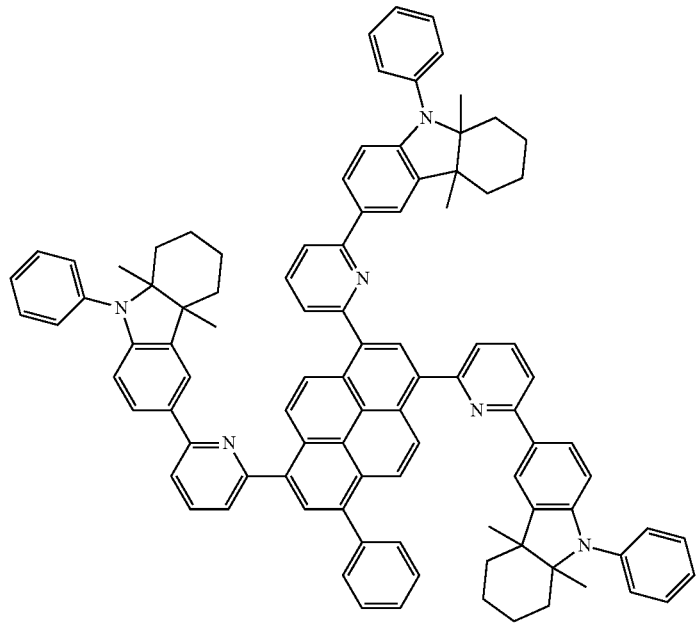
Formula 663
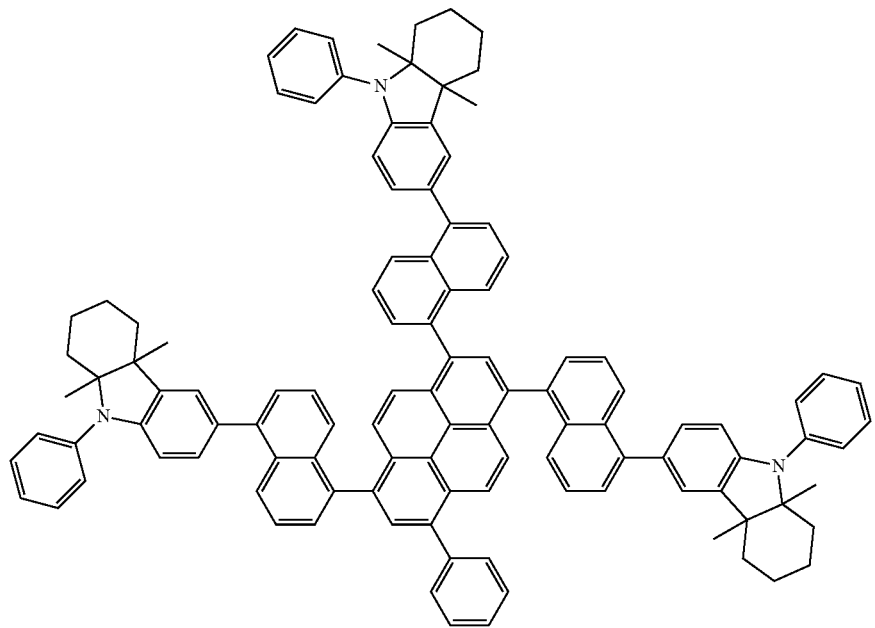

Formula 664
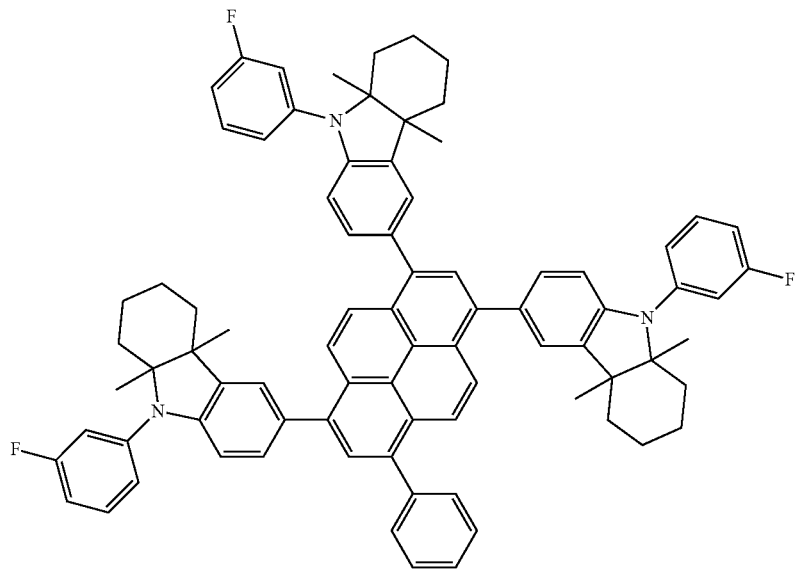
Formula 665
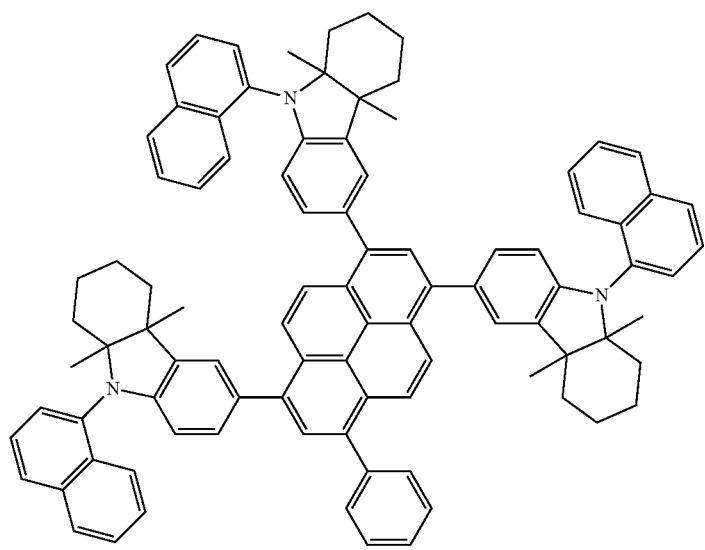
Formula 666
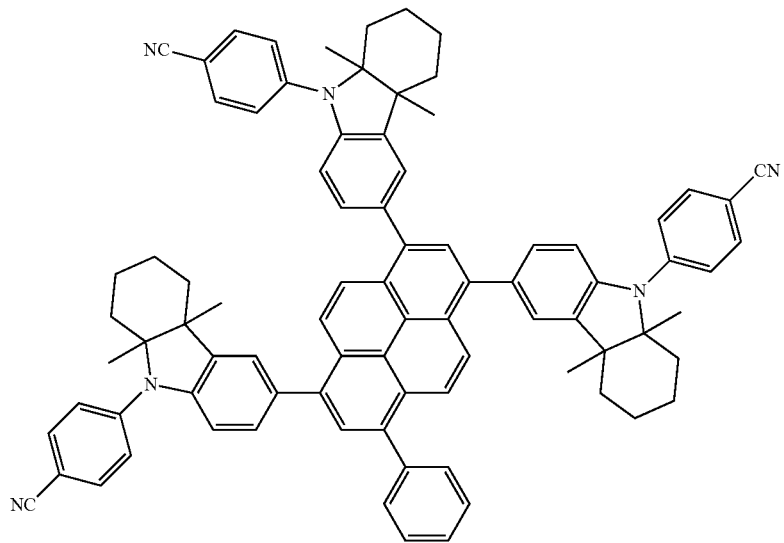

-continued
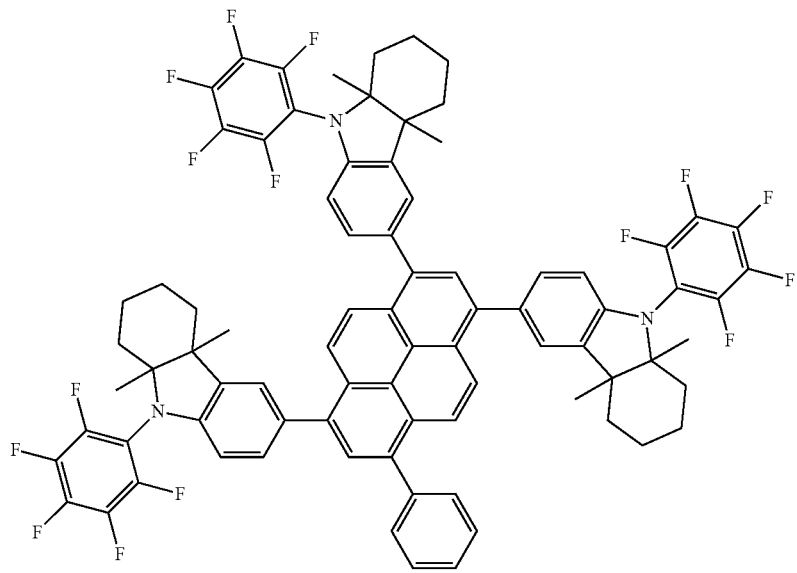
Formula 667
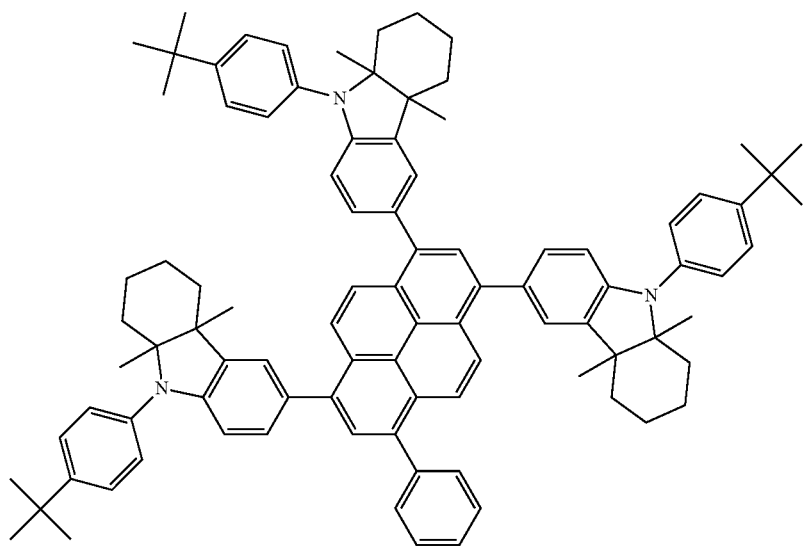
Formula 668
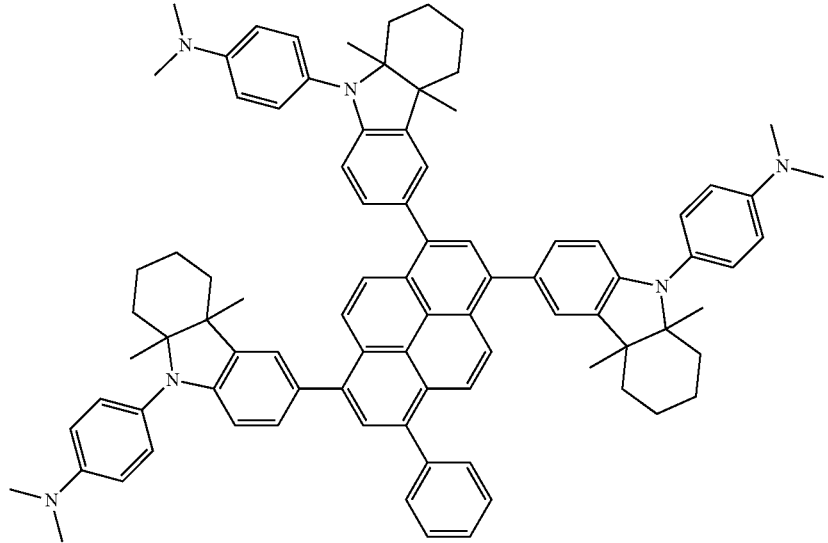
Formula 669

-continued
Formula 670
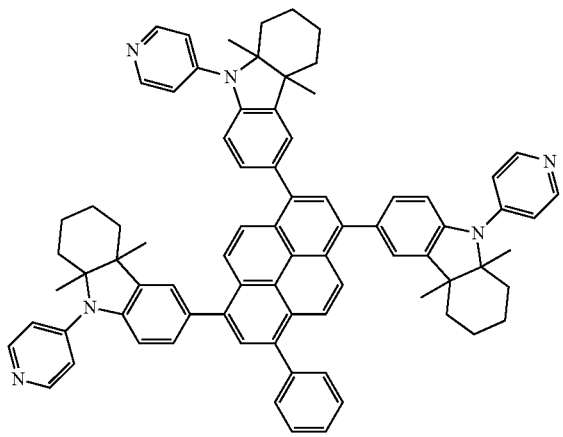
Formula 671
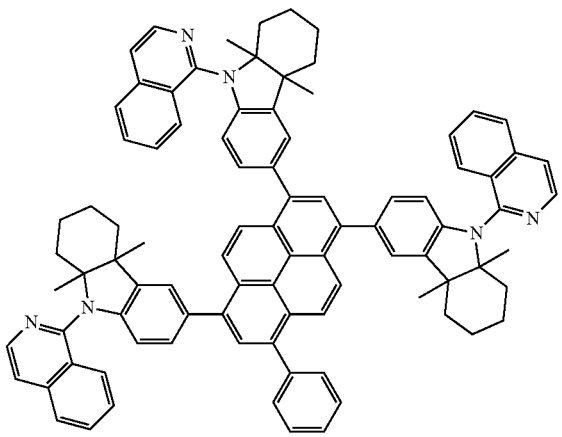
Formula 672
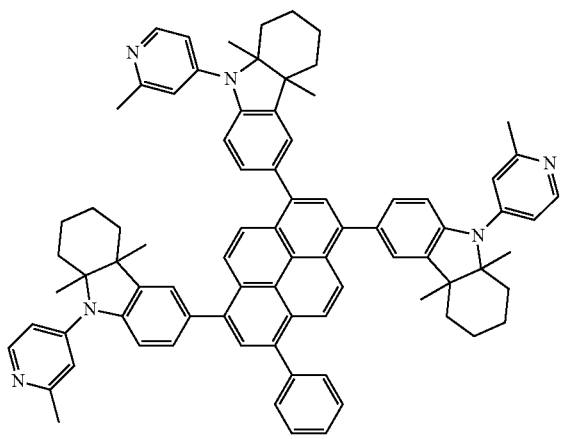
Formula 673
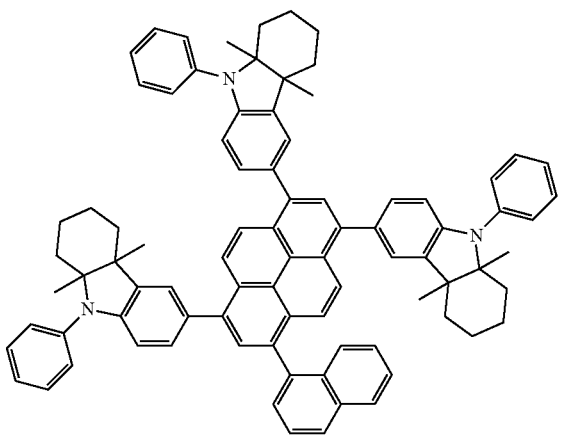
Formula 674
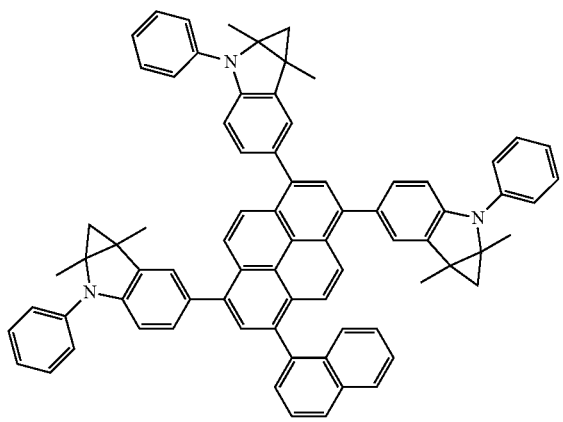
Formula 675
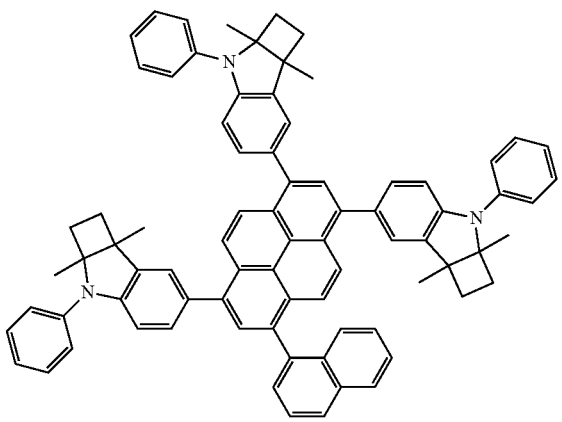

-continued
Formula 676
Formula 677
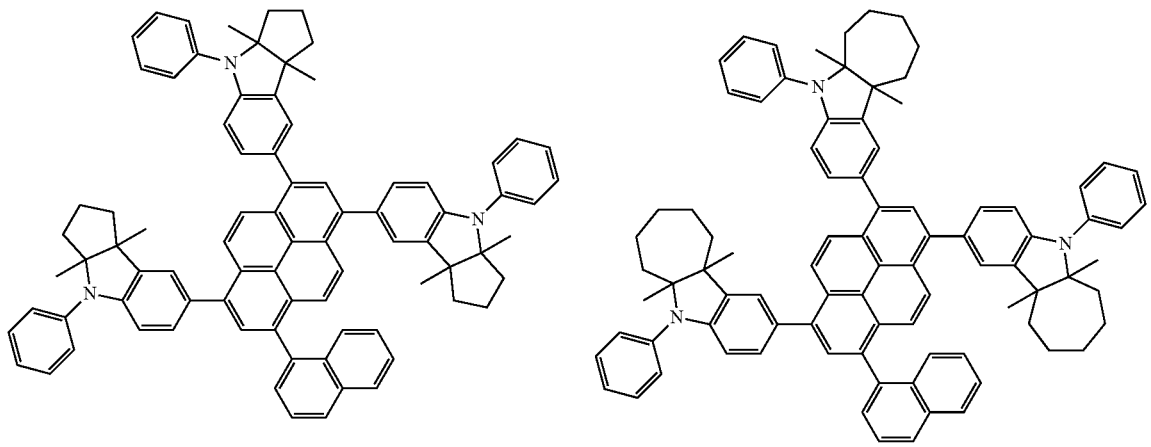
Formula 678
Formula 679
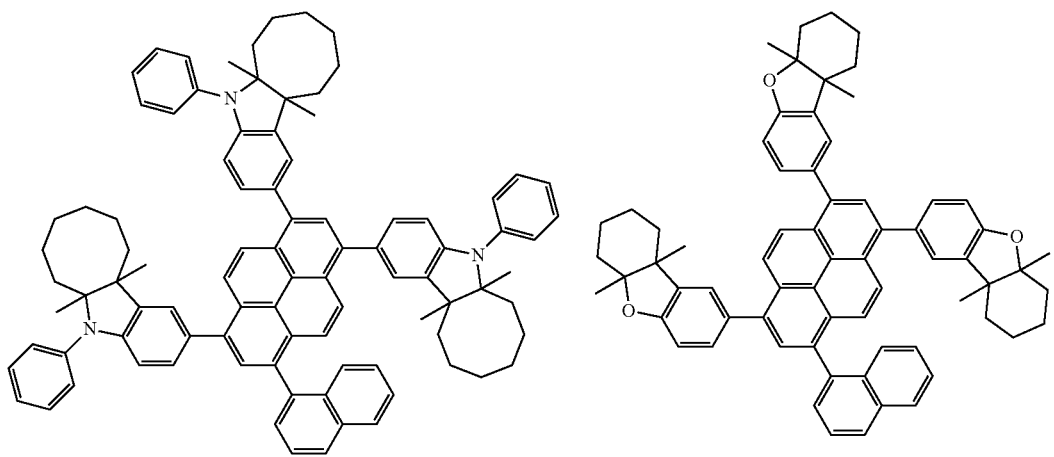
Formula 680
Formula 681
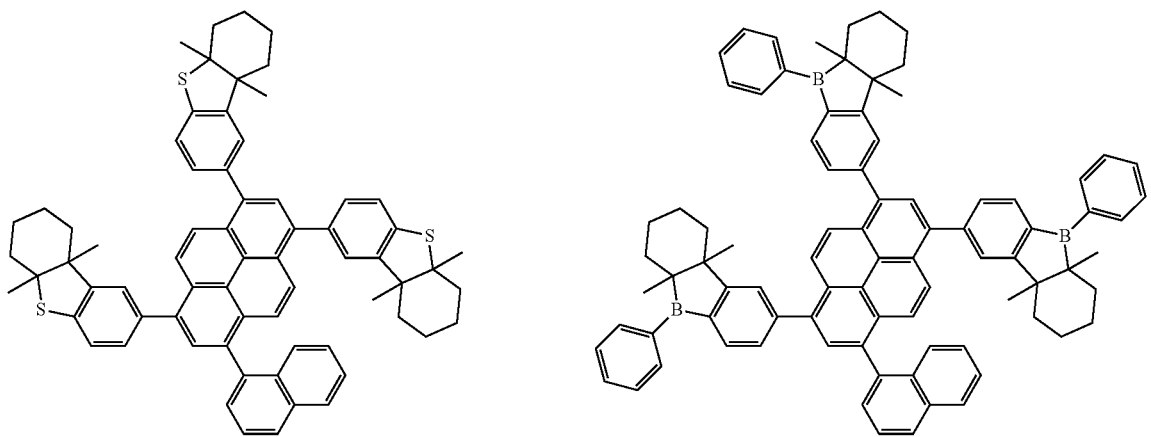

Formula 682
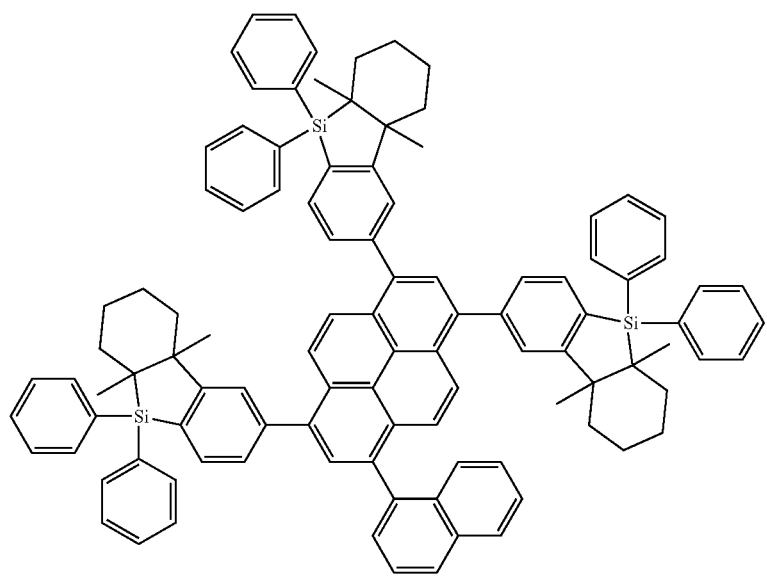
Formula 683
Formula 684
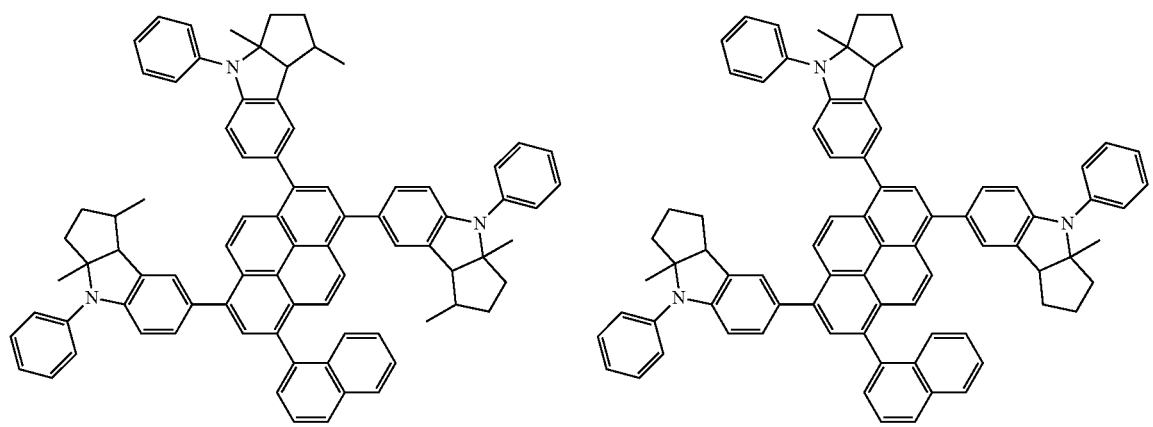
Formula 685
Formula 686
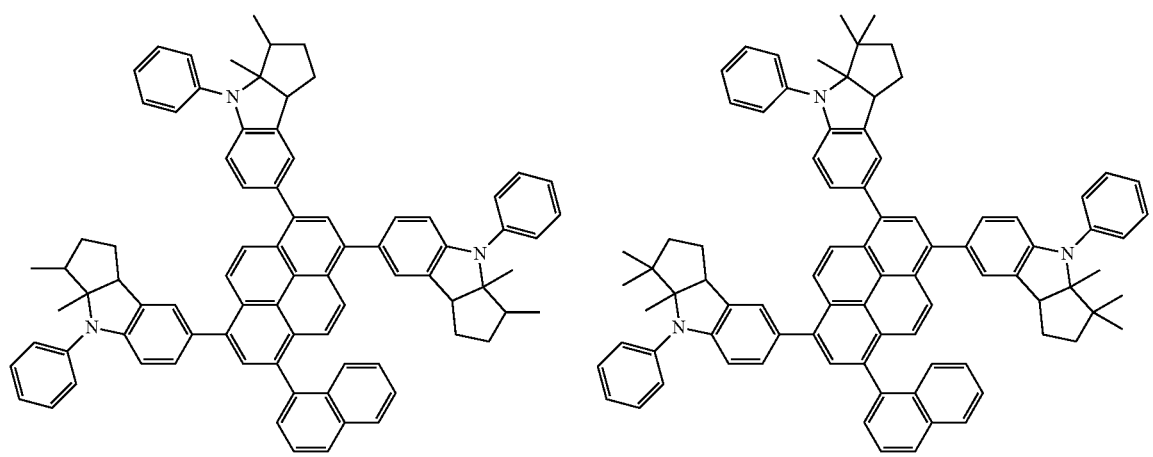

-continued
Formula 687
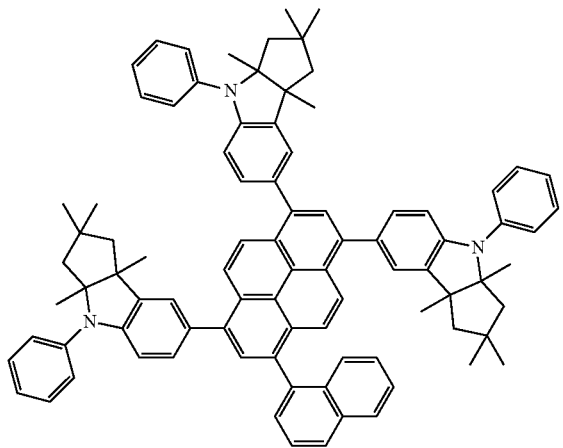
Formula 688
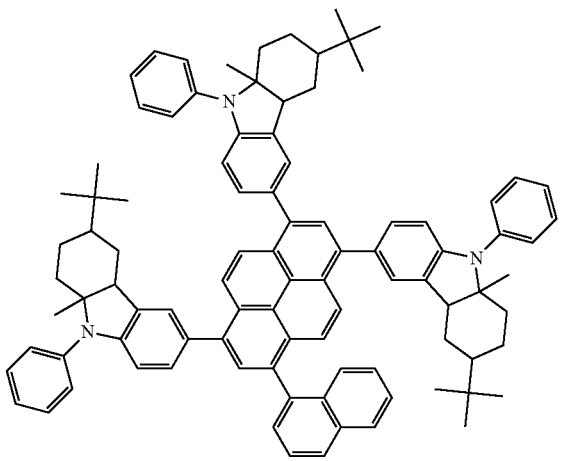
Formula 689
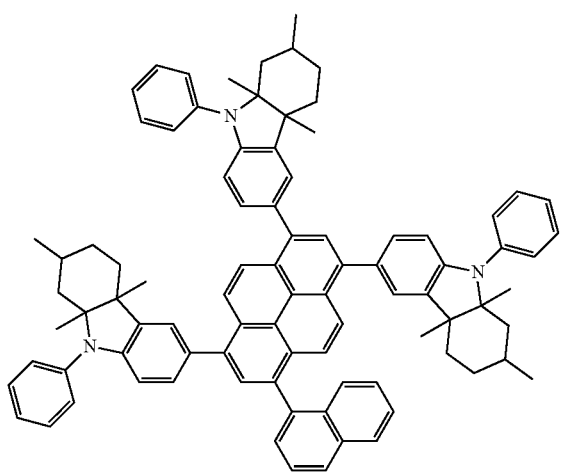
Formula 690
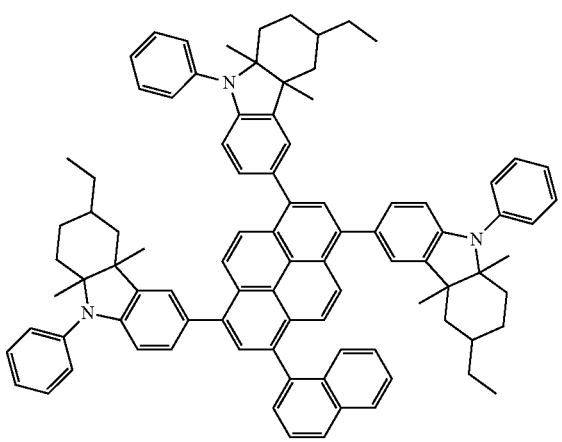
Formula 691
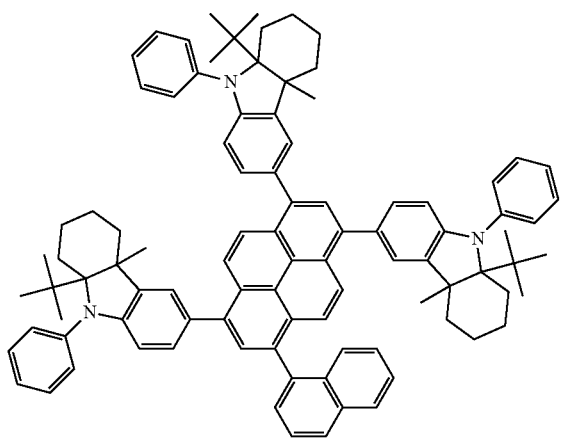
Formula 692
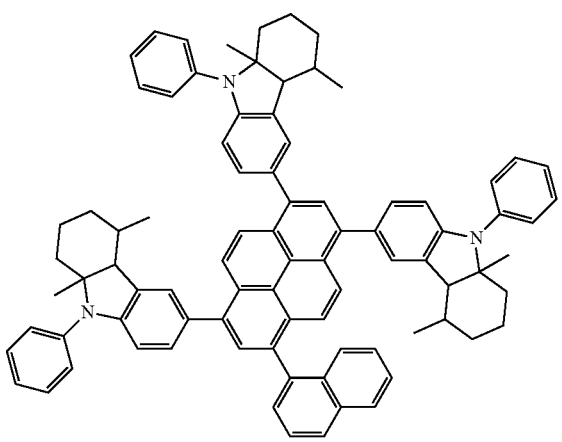

-continued
Formula 693
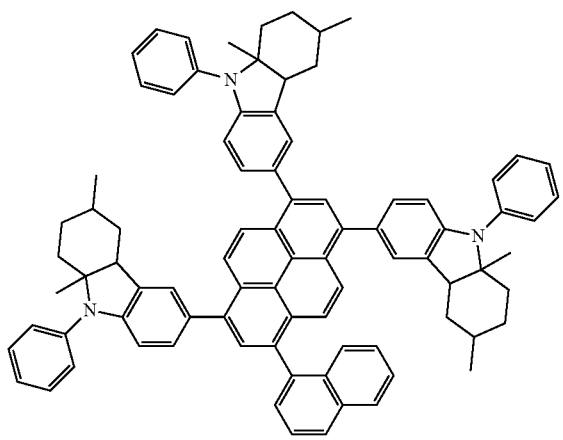
Formula 694
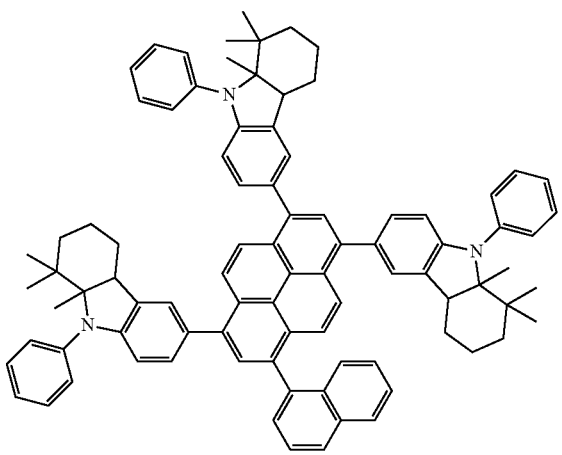
Formula 695
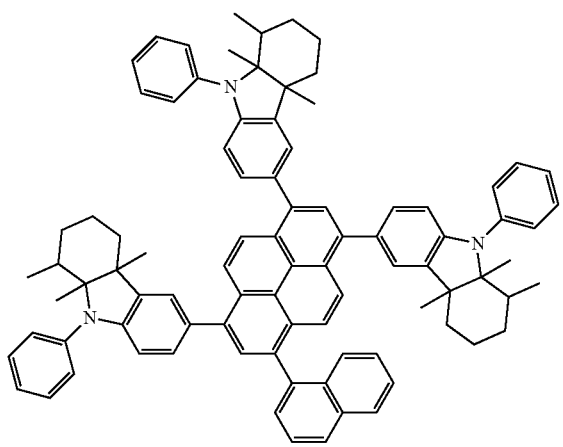
Formula 696
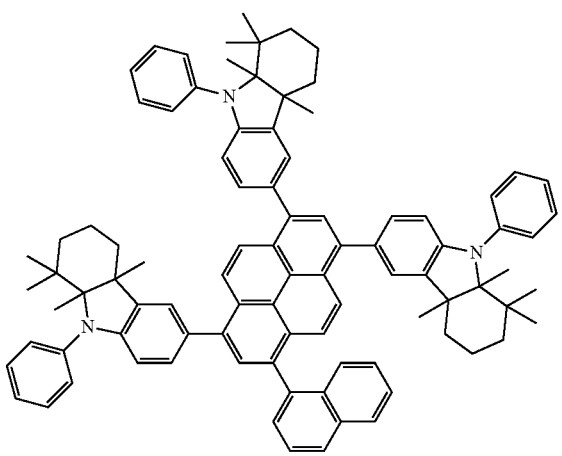
Formula 697
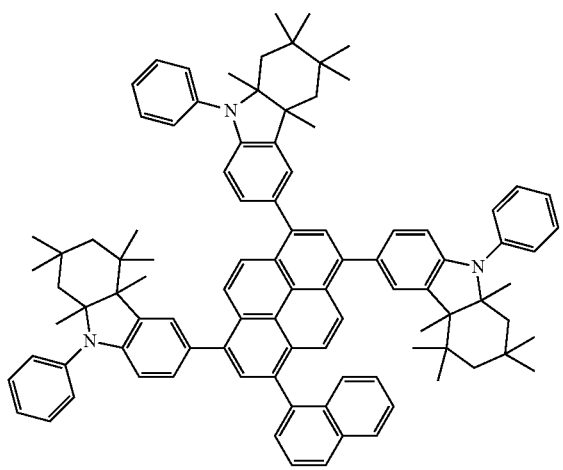
Formula 698
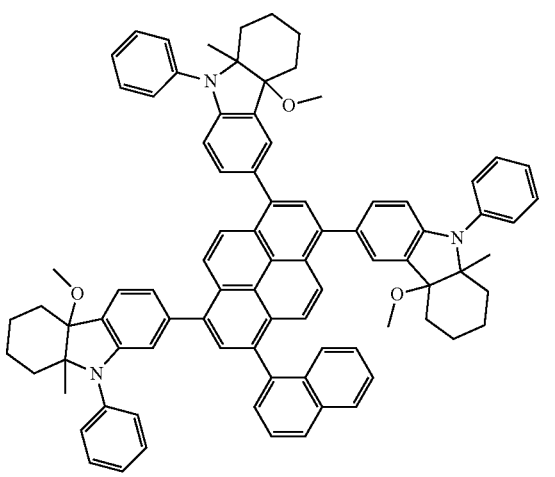

-continued
Formula 699
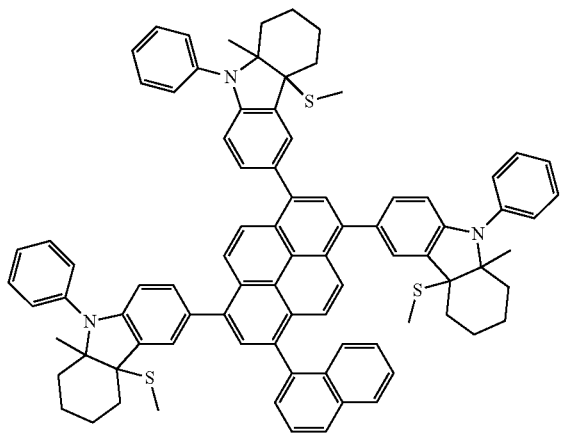
Formula 700
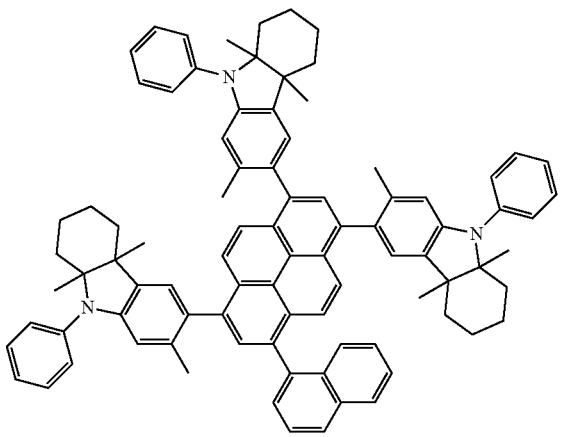
Formula 701
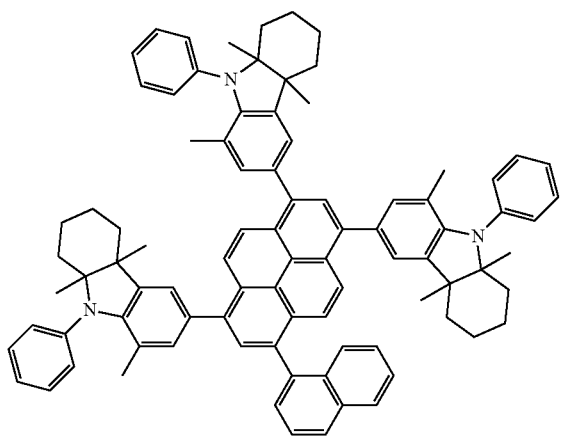
Formula 702
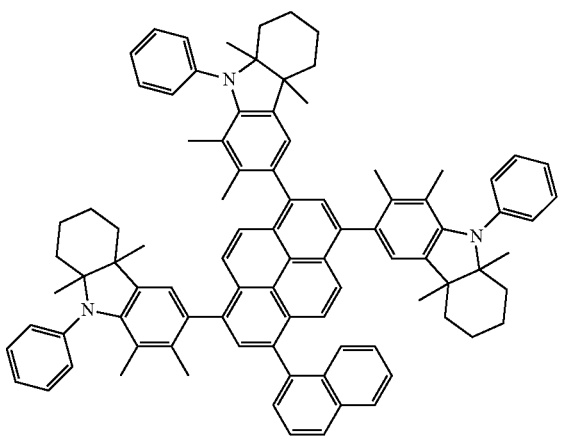
Formula 703
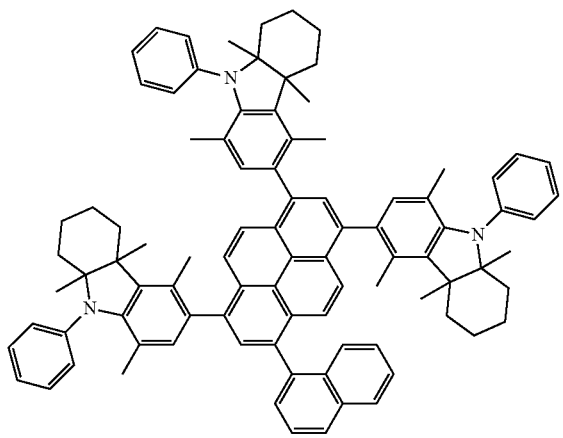
Formula 704
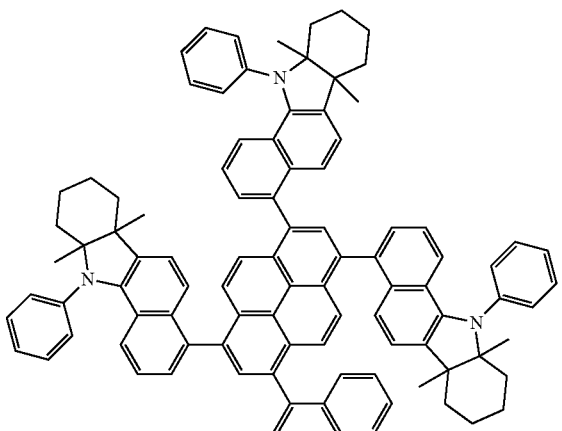

-continued
Formula 705
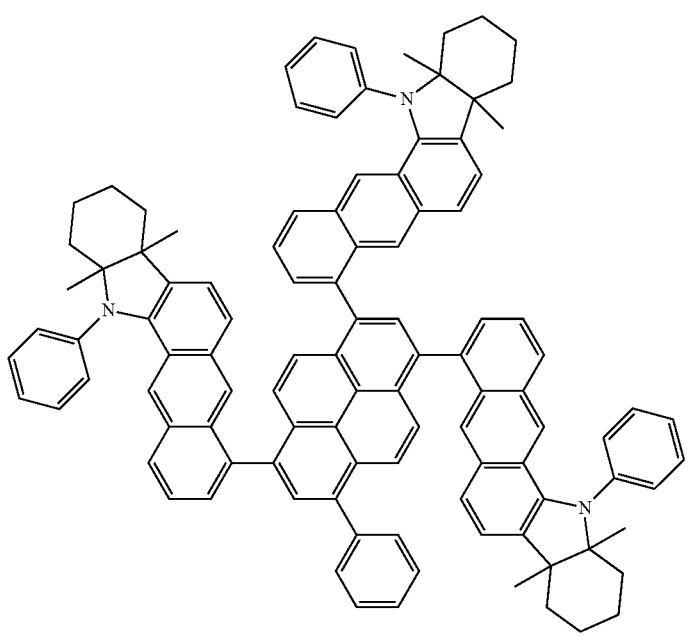
Formula 706
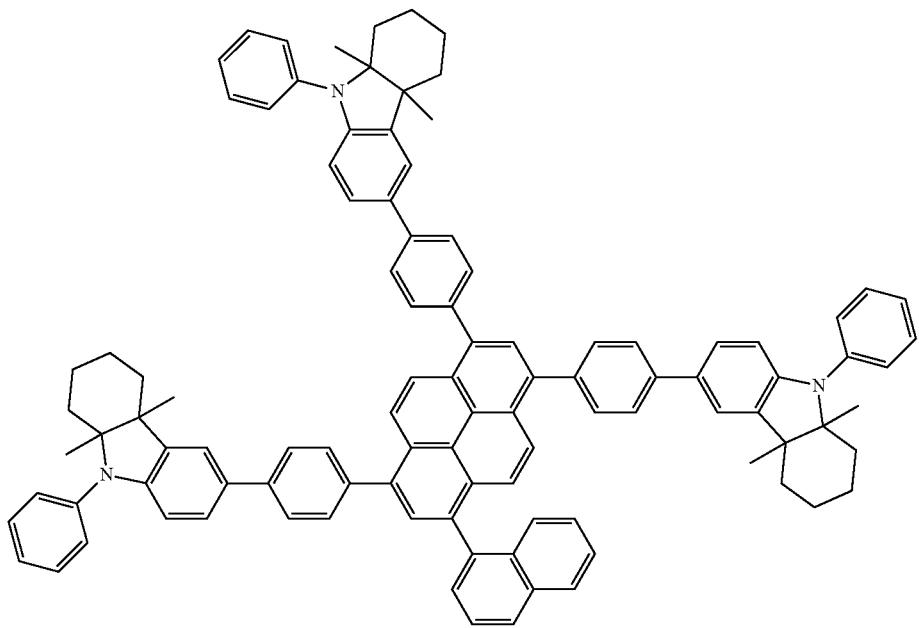

Formula 707
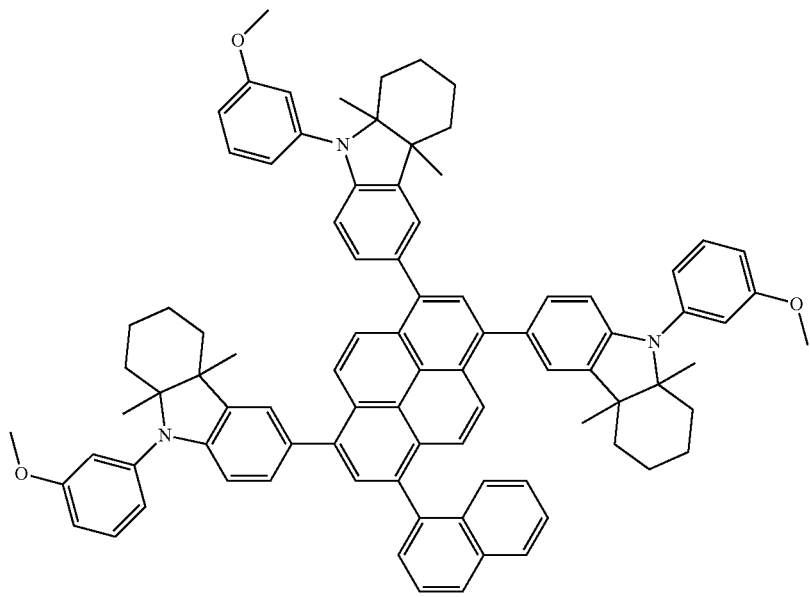
Formula 708
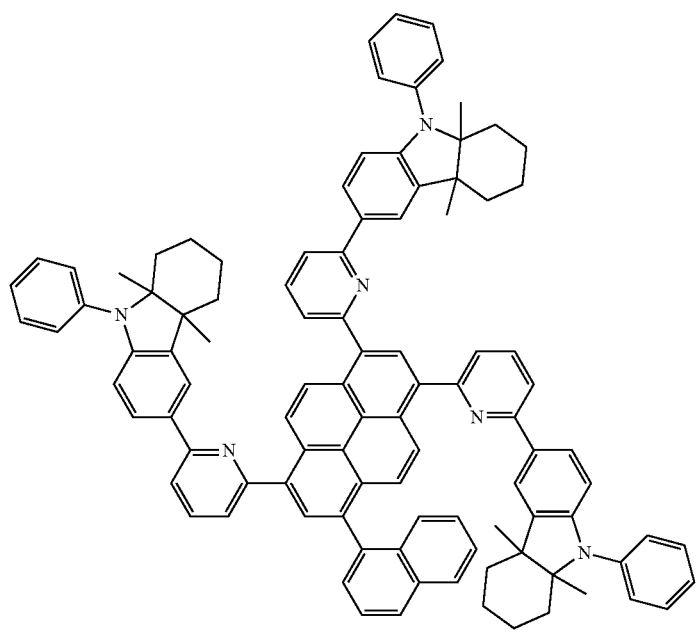

-continued
Formula 709
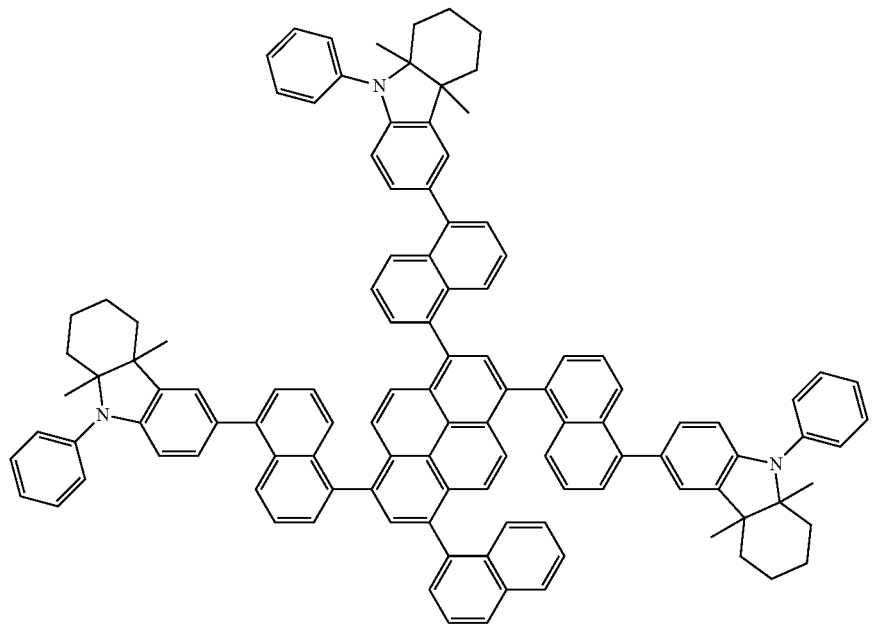
Formula 710
Formula 711
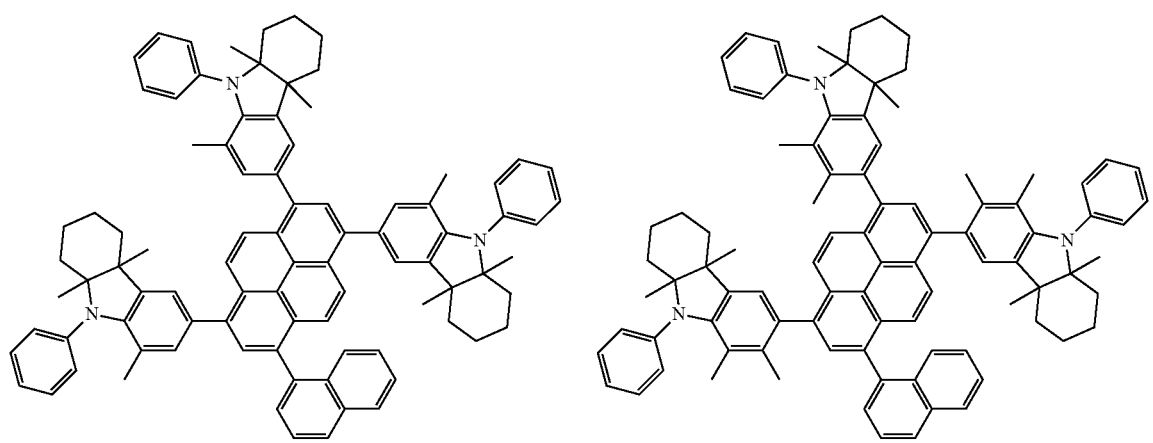
Formula 712
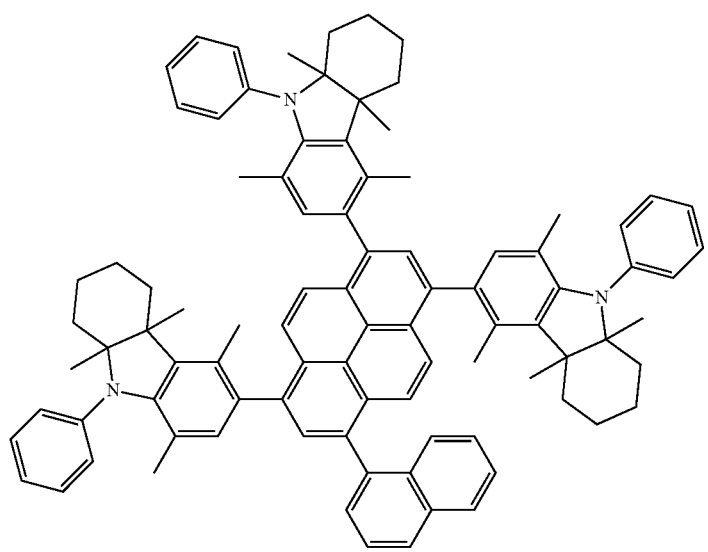

-continued
Formula 713
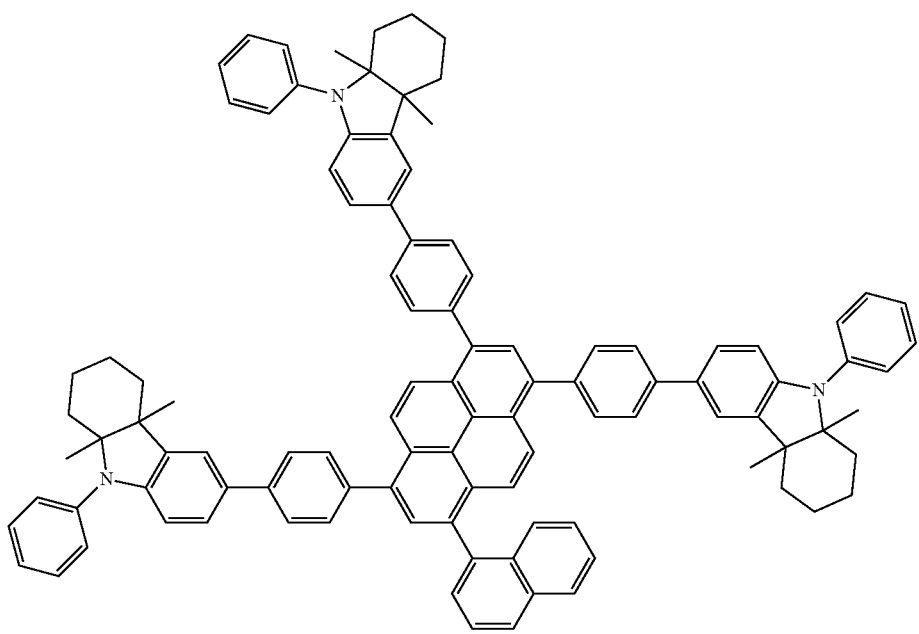
Formula 714
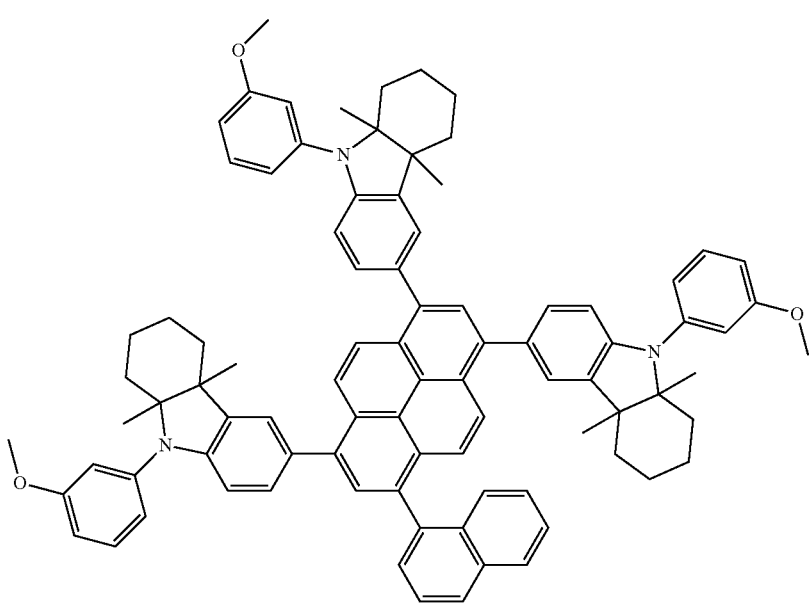

-continued
Formula 715
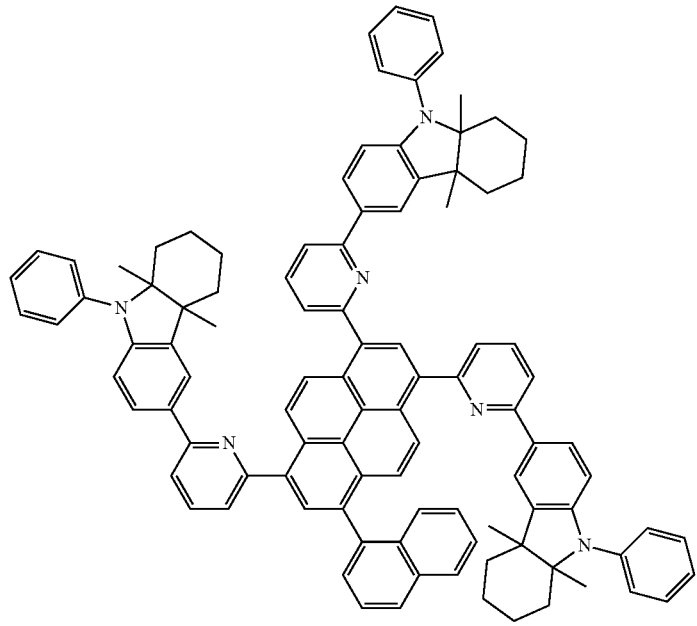
Formula 716
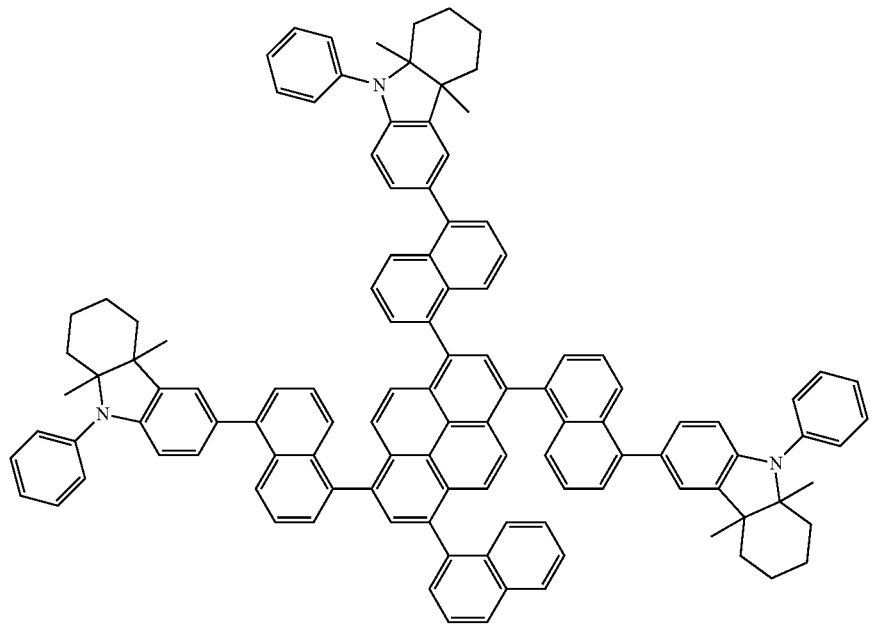

Formula 717
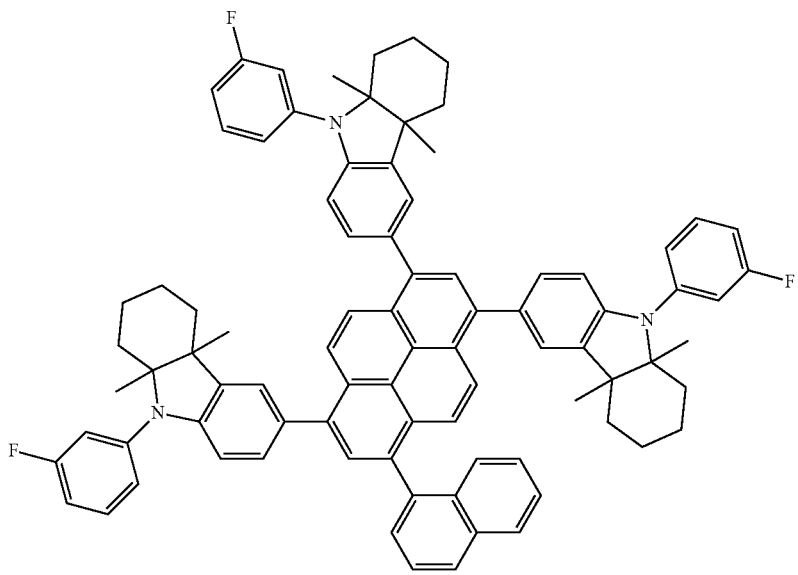
Formula 718
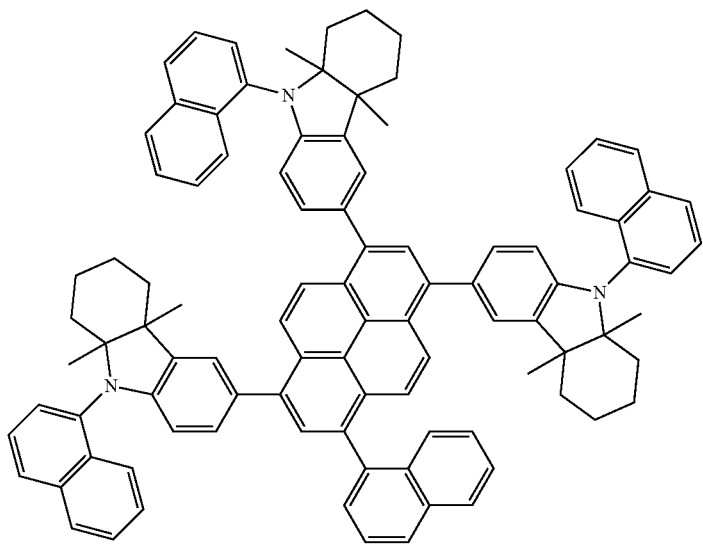
Formula 719
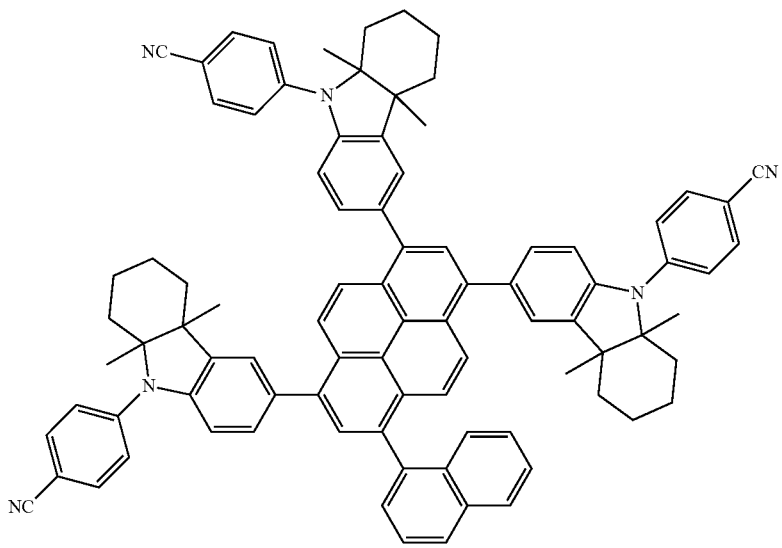

-continued
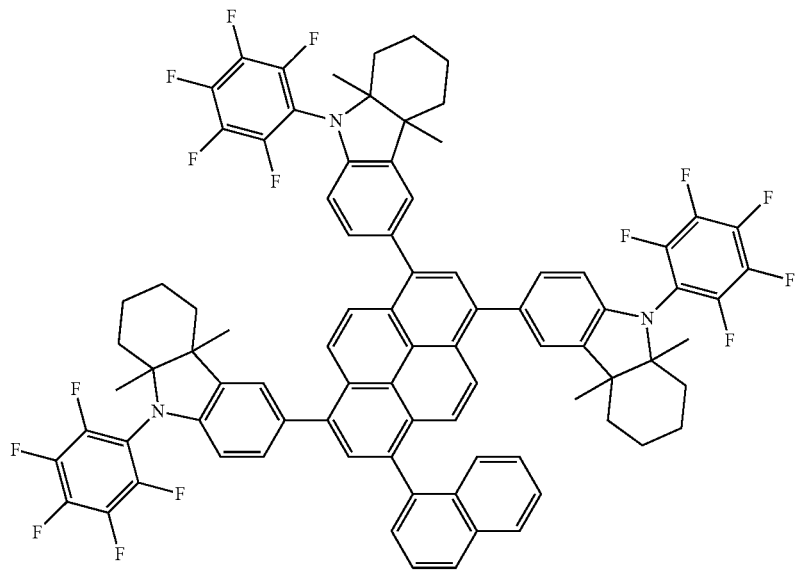
Formula 720
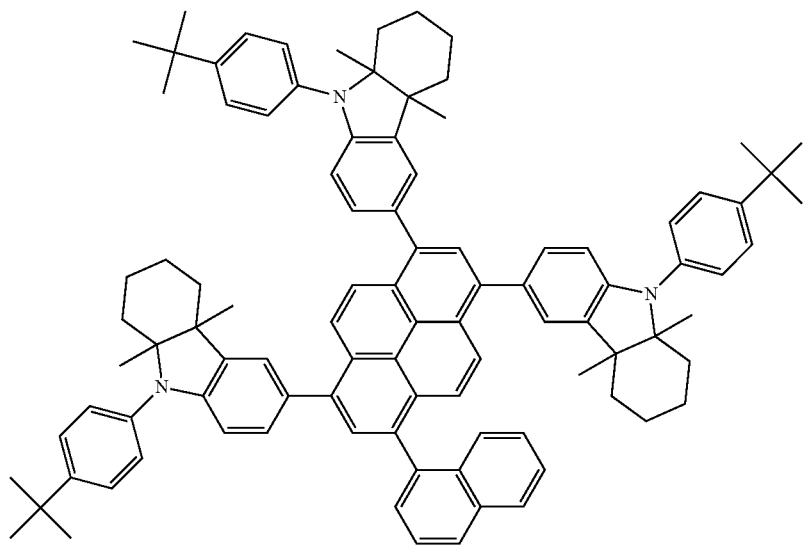
Formula 721
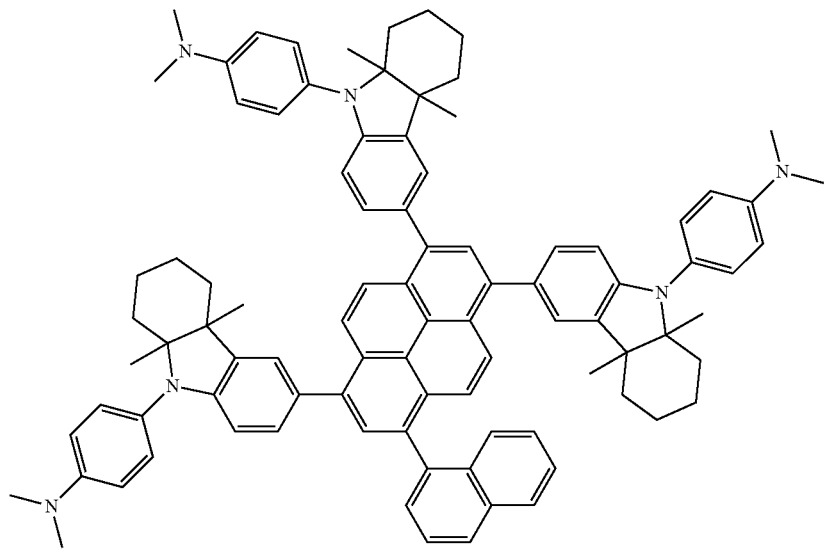
Formula 722

-continued
Formula 723
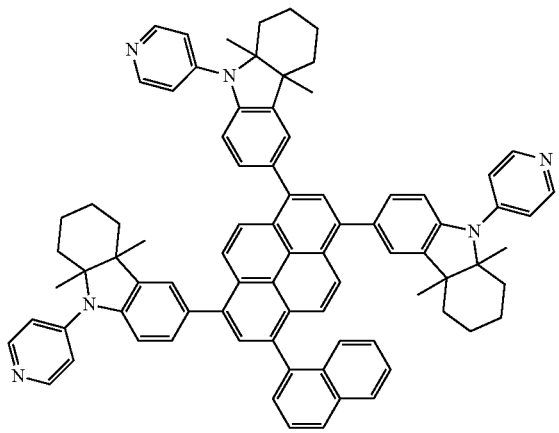
Formula 724
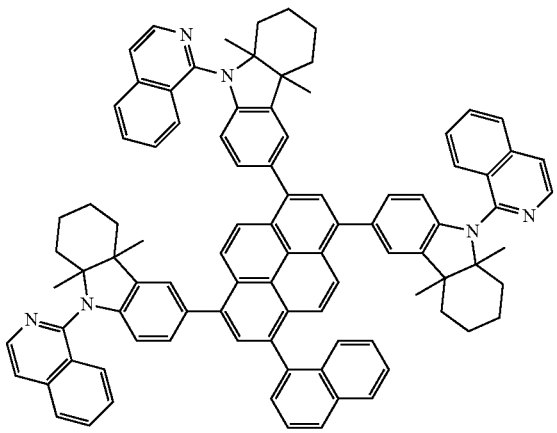
Formula 725
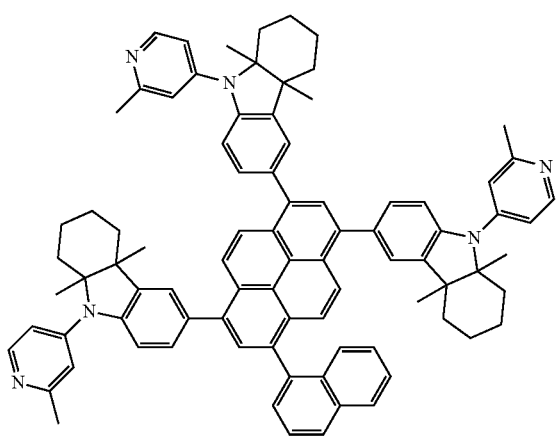
Formula 726
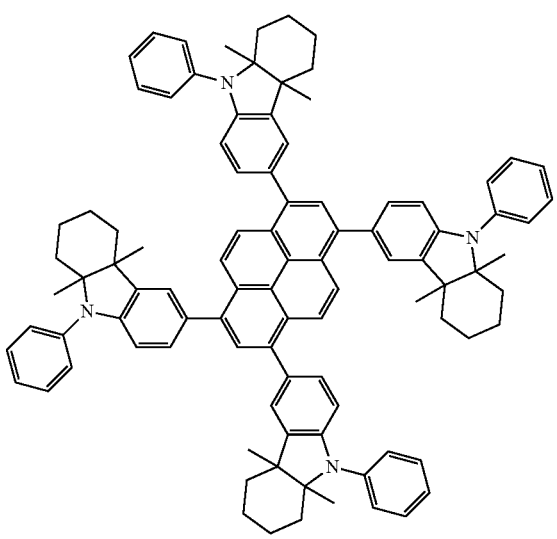
Formula 727
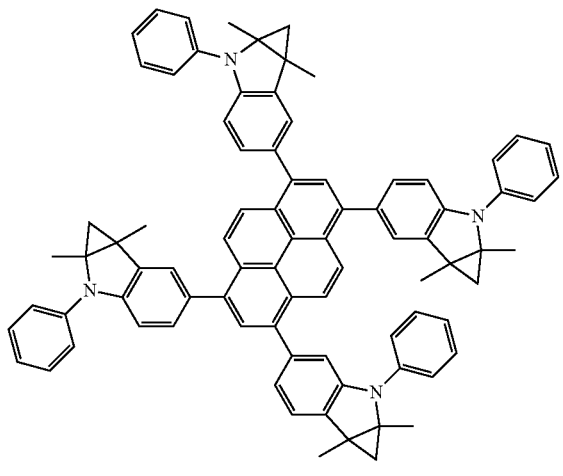
Formula 728
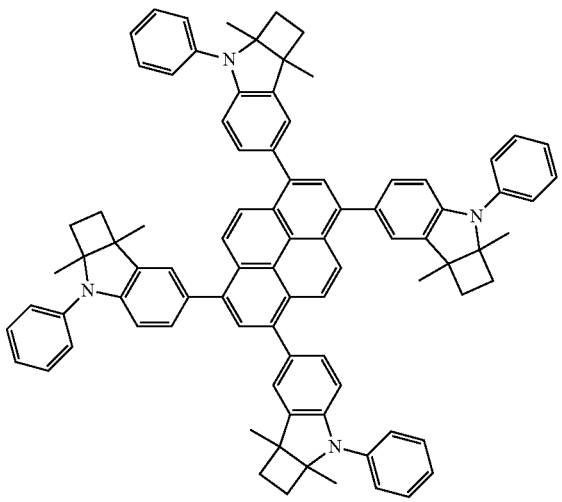

-continued
Formula 729
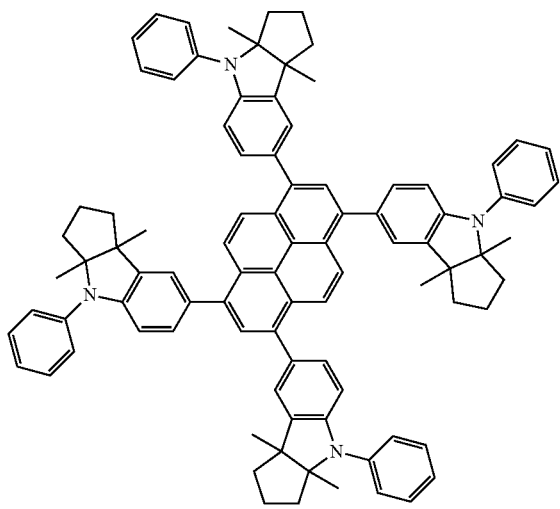
Formula 730
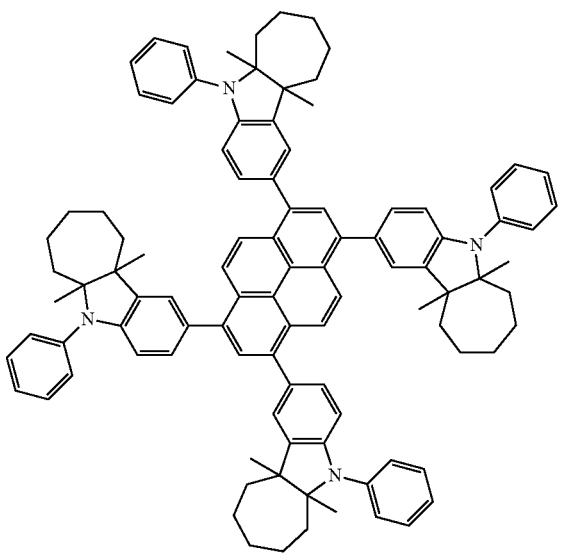
Formula 731
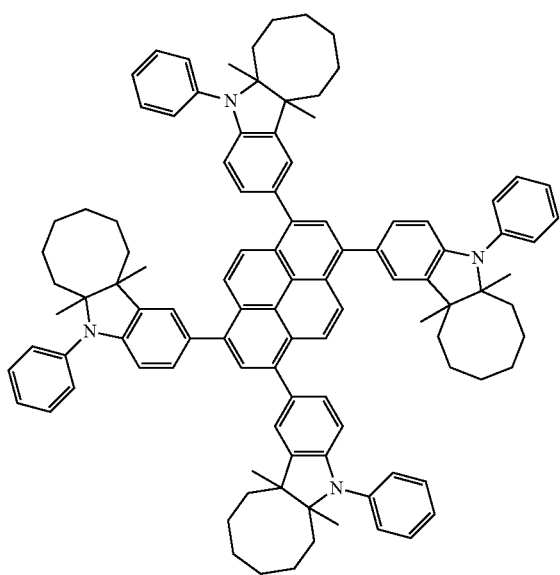
Formula 732
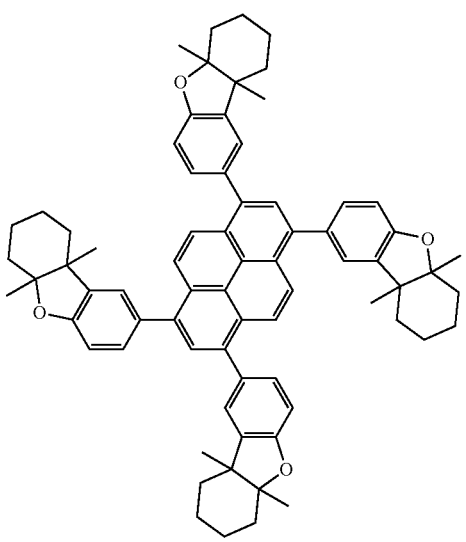

-continued
Formula 733
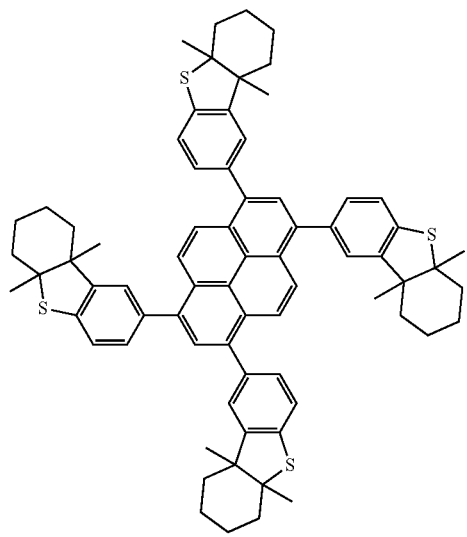
Formula 734
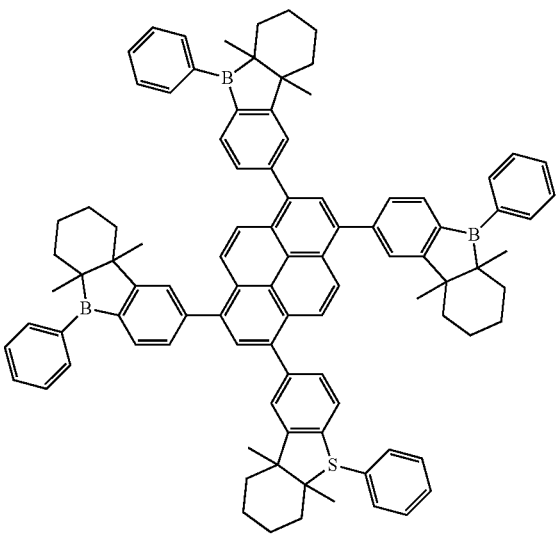
Formula 735
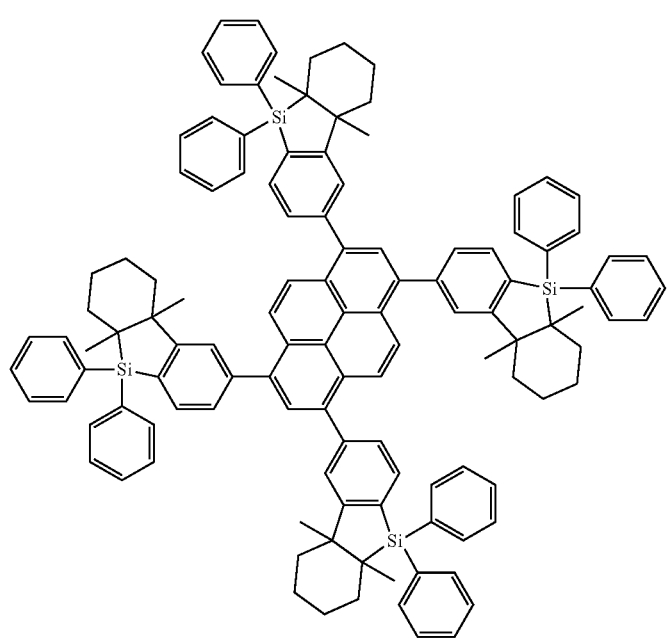

-continued
Formula 736
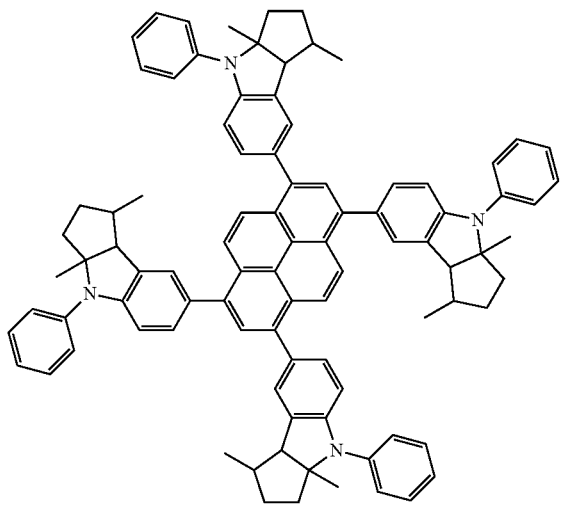
Formula 737
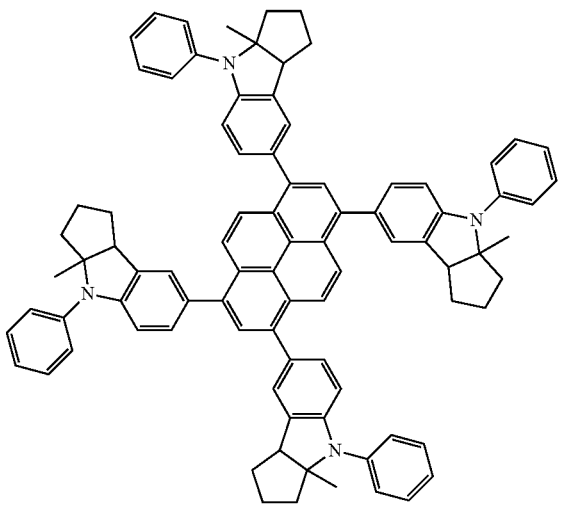
Formula 738
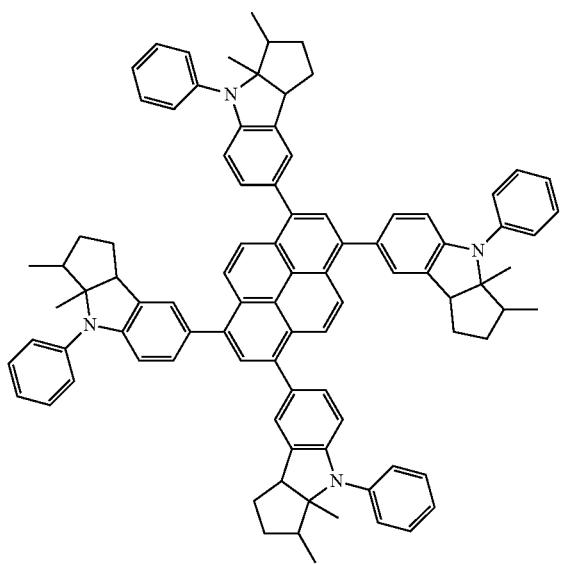
Formula 739
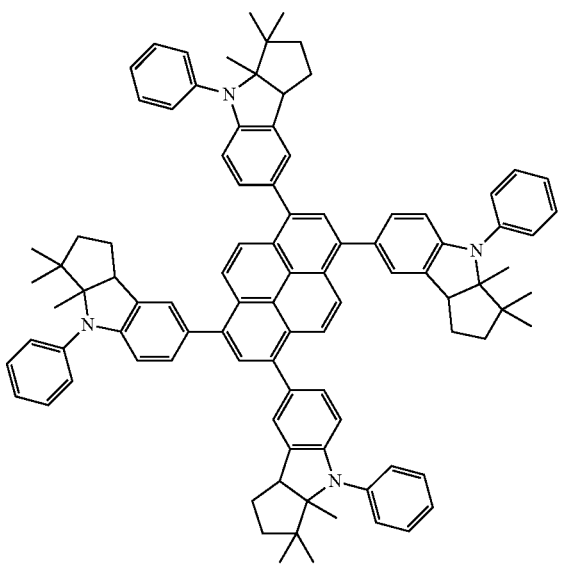

-continued
Formula 740
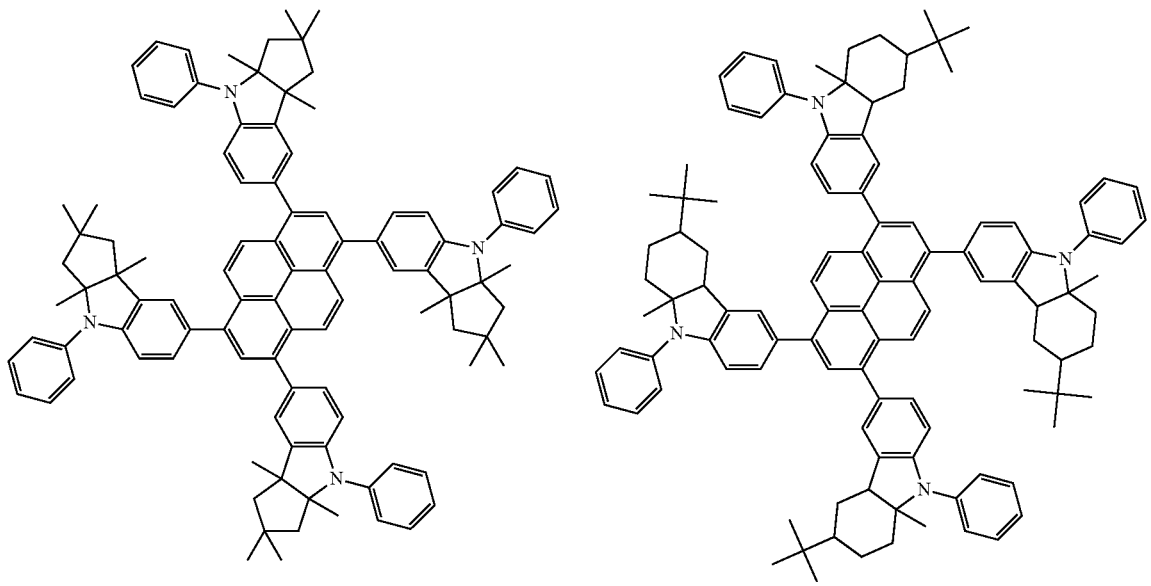
Formula 741
Formula 742
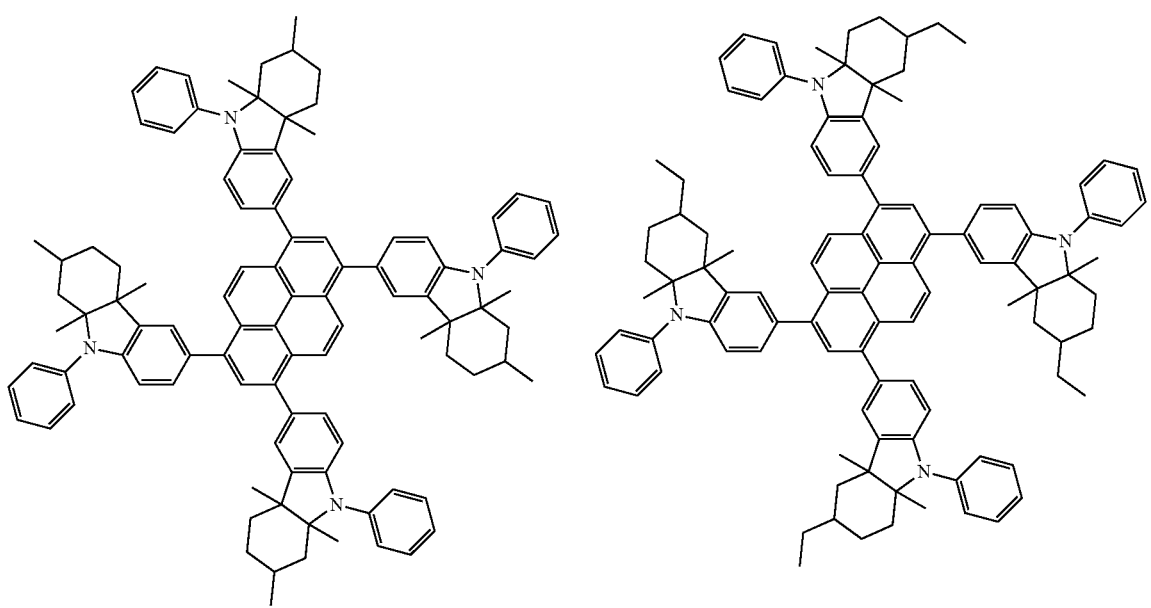
Formula 743

-continued
Formula 744
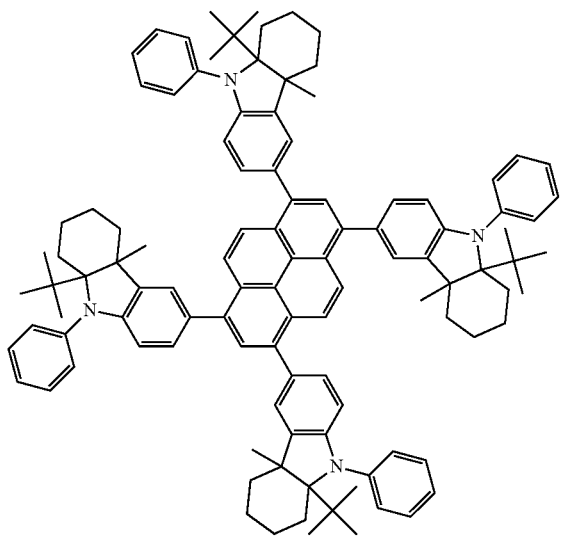
Formula 745
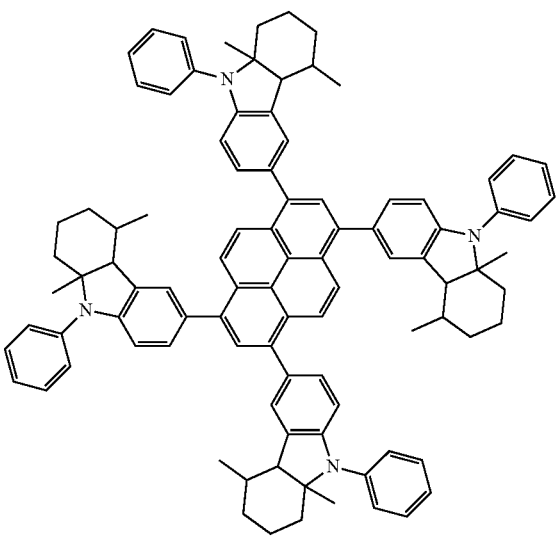
Formula 746
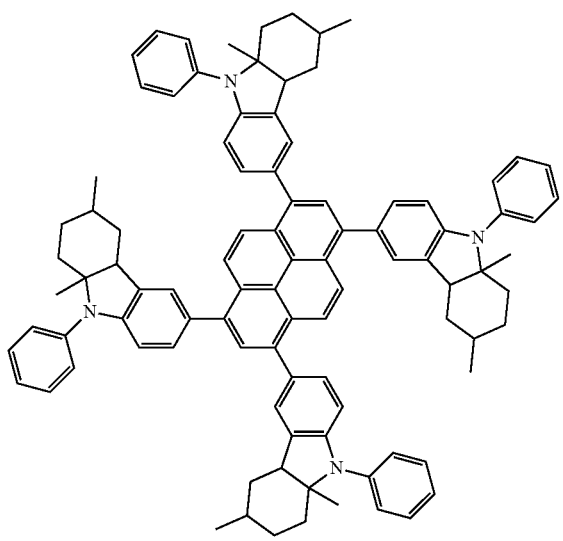
Formula 747
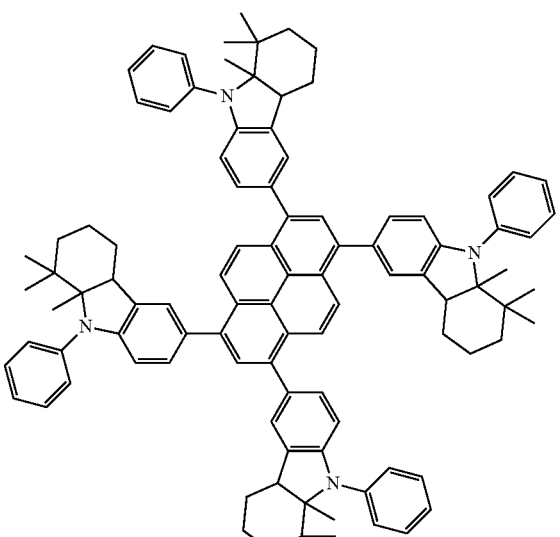

-continued
Formula 748
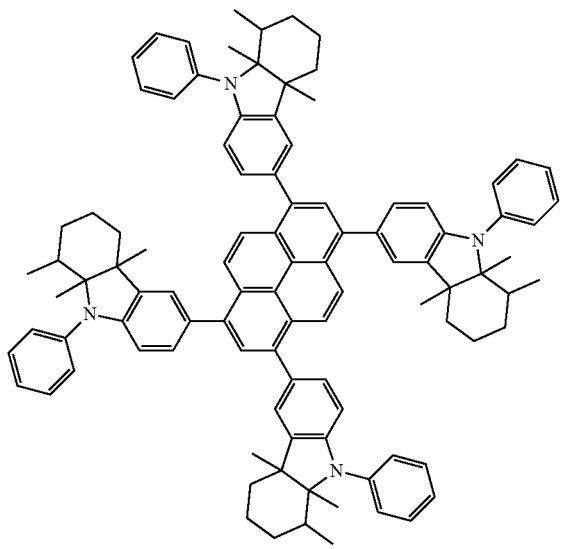
Formula 749
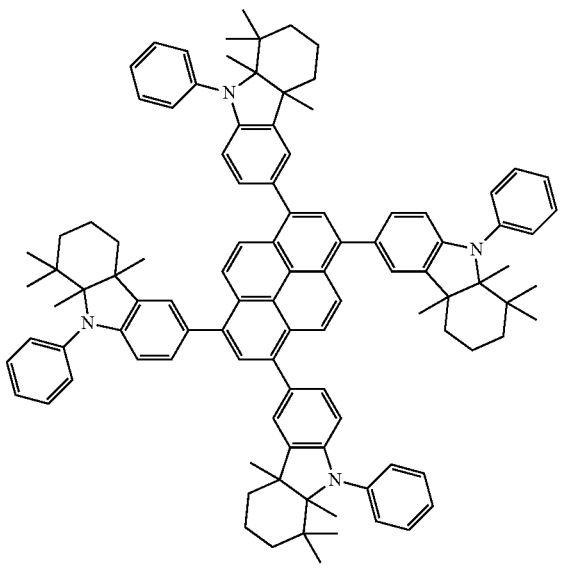
Formula 750
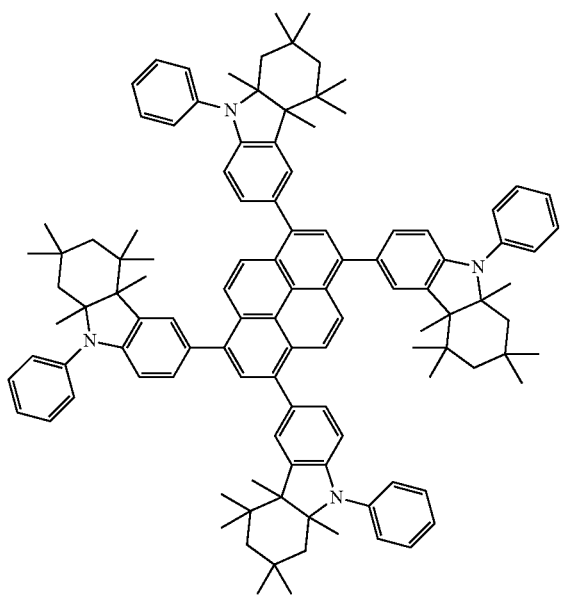
Formula 751
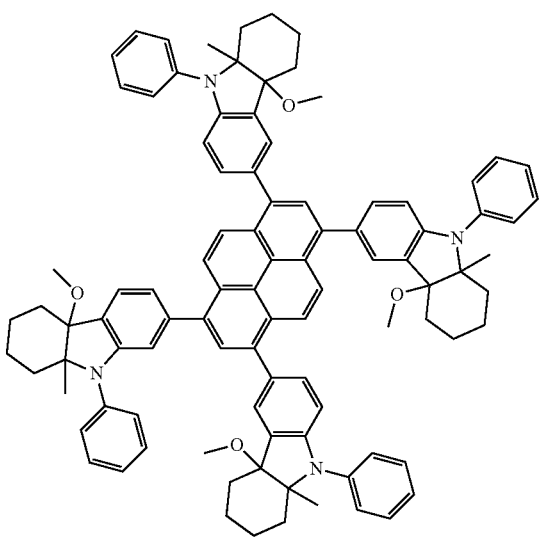

-continued
Formula 752
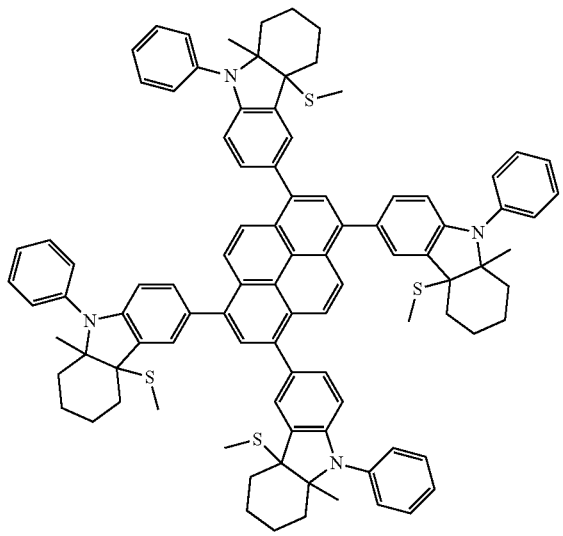
Formula 753
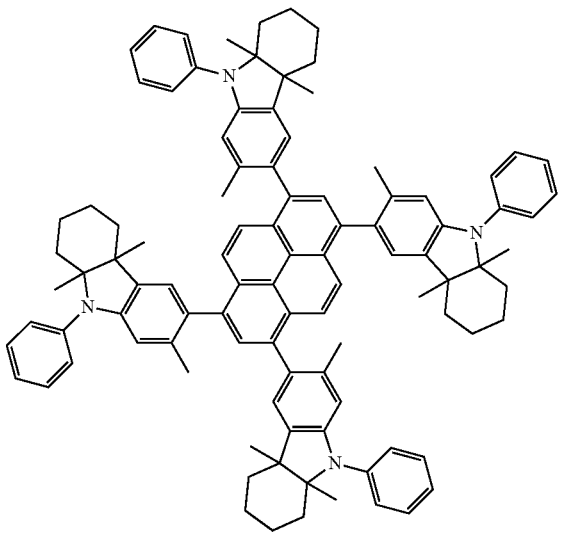
Formula 754
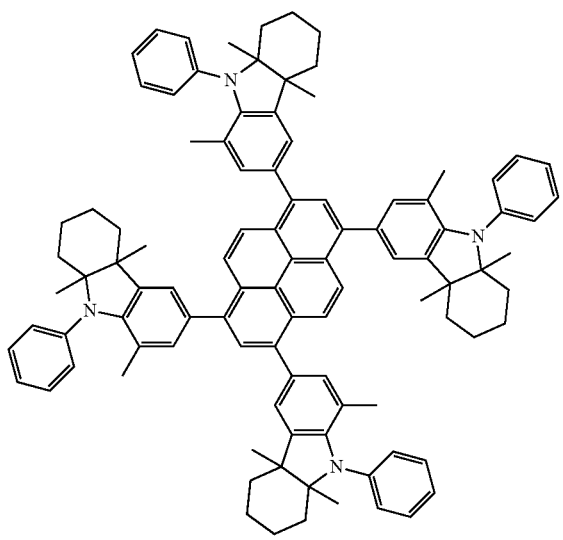
Formula 755
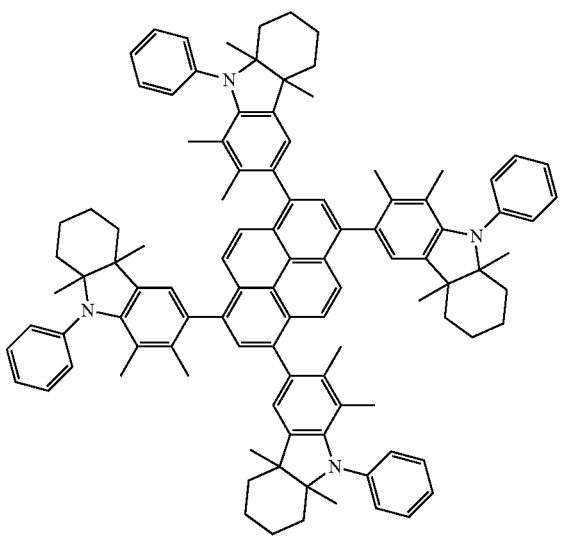

-continued
Formula 756
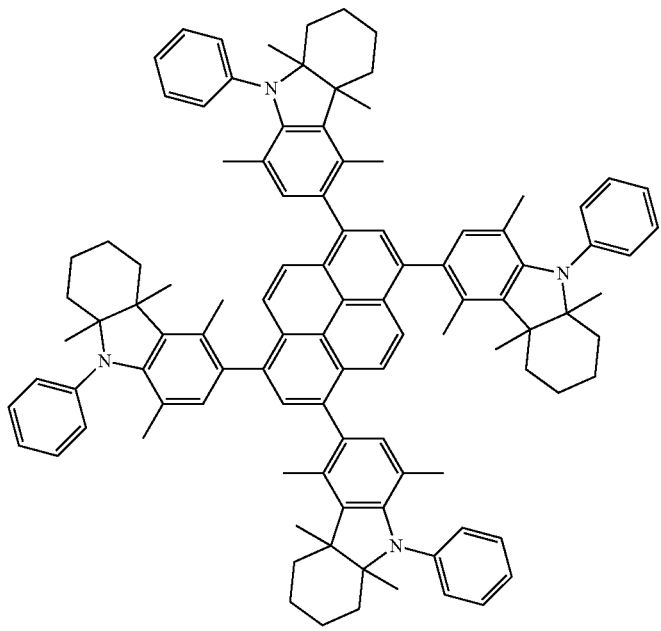
Formula 757
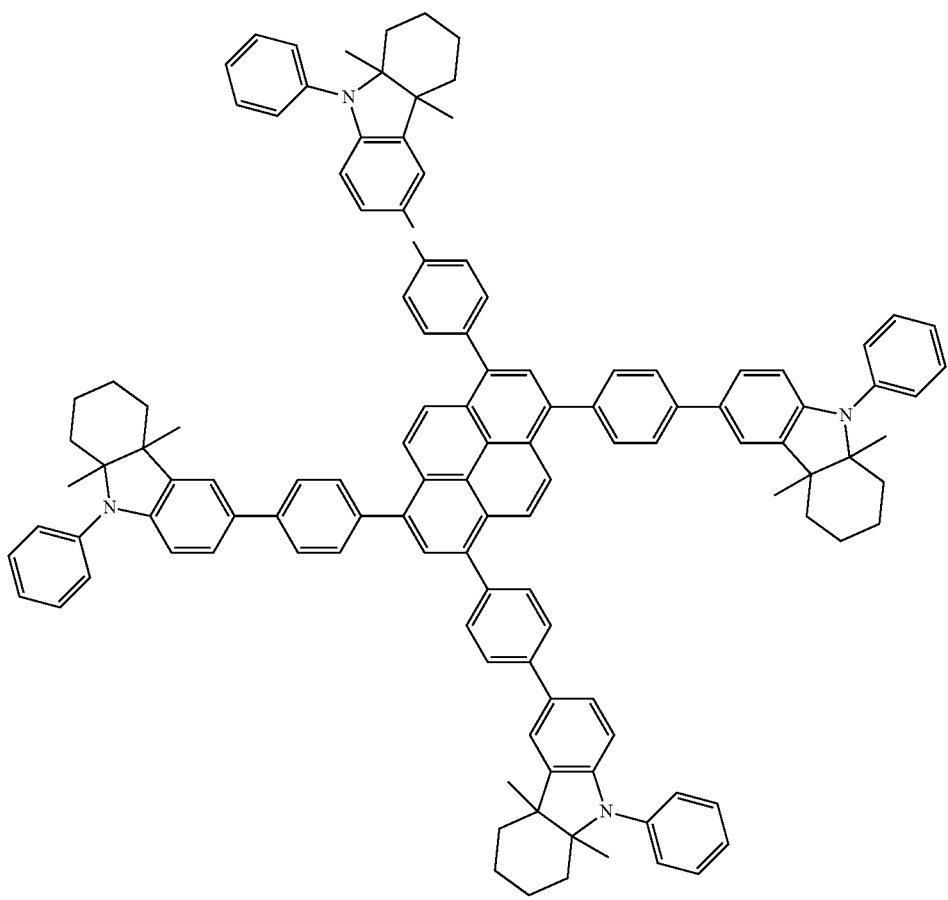

Formula 758
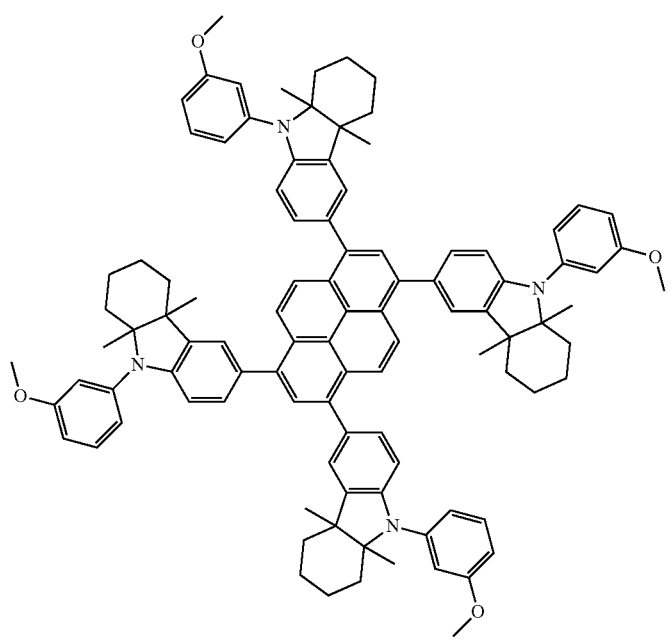
Formula 759
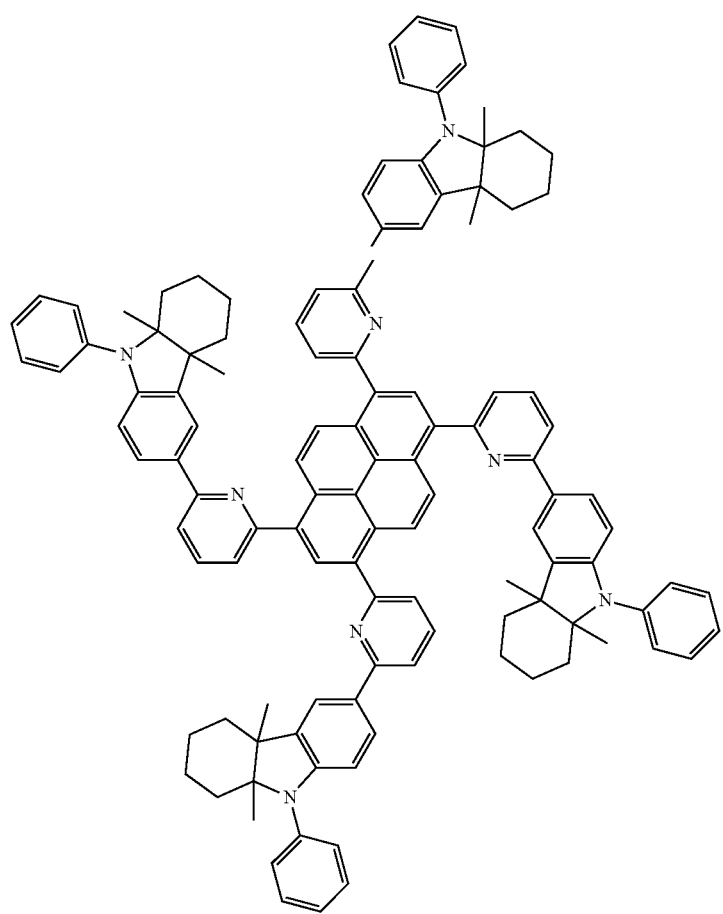

-continued
Formula 760
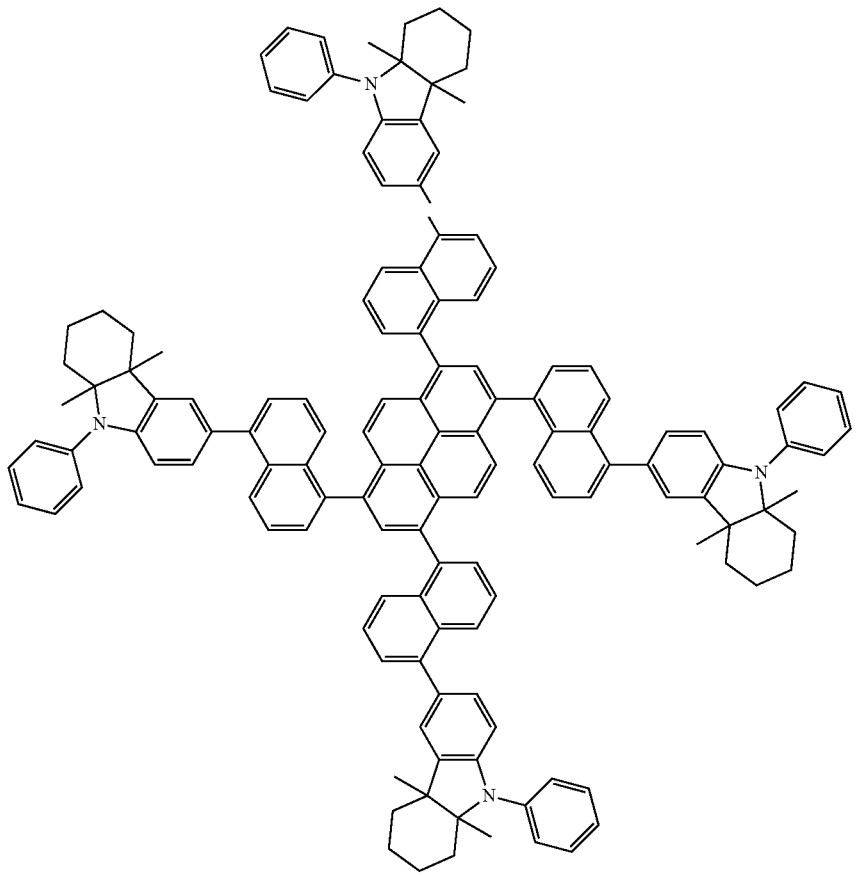
Formula 761
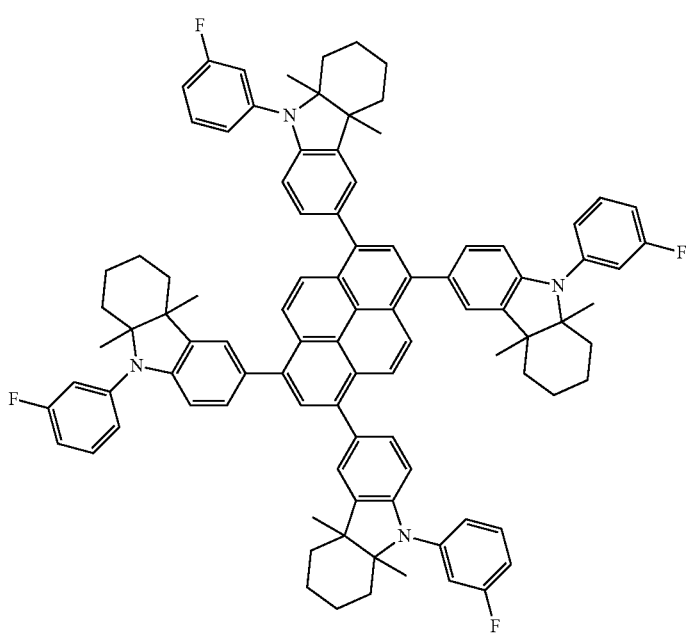

-continued
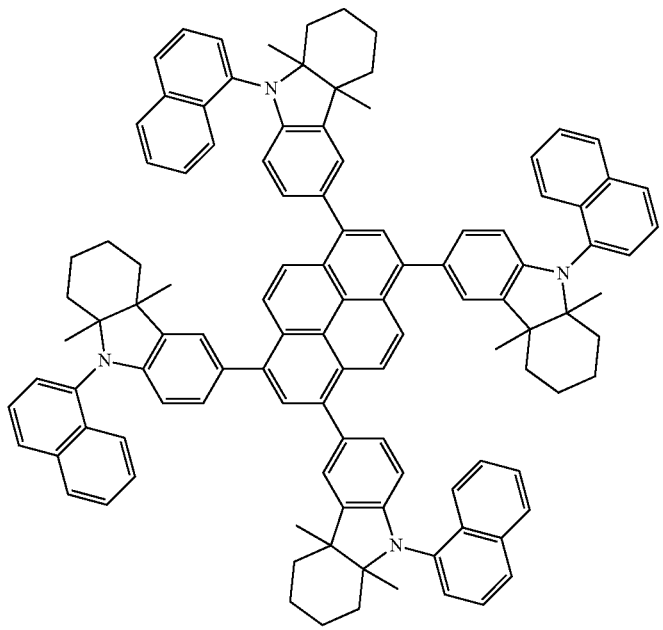
Formula 762
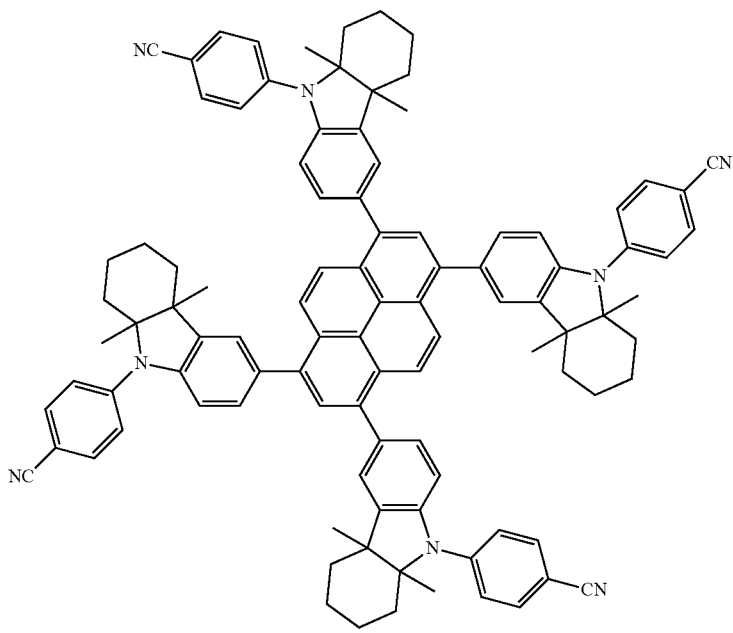
Formula 763

-continued
Formula 764
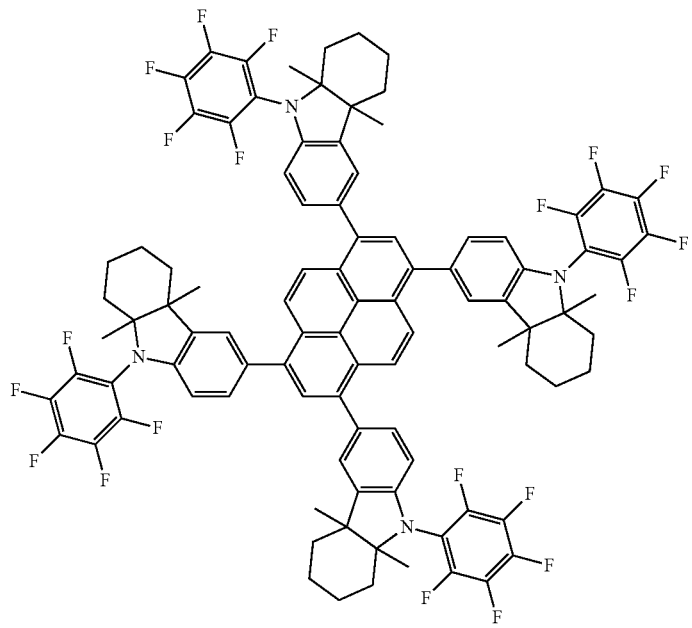
Formula 765
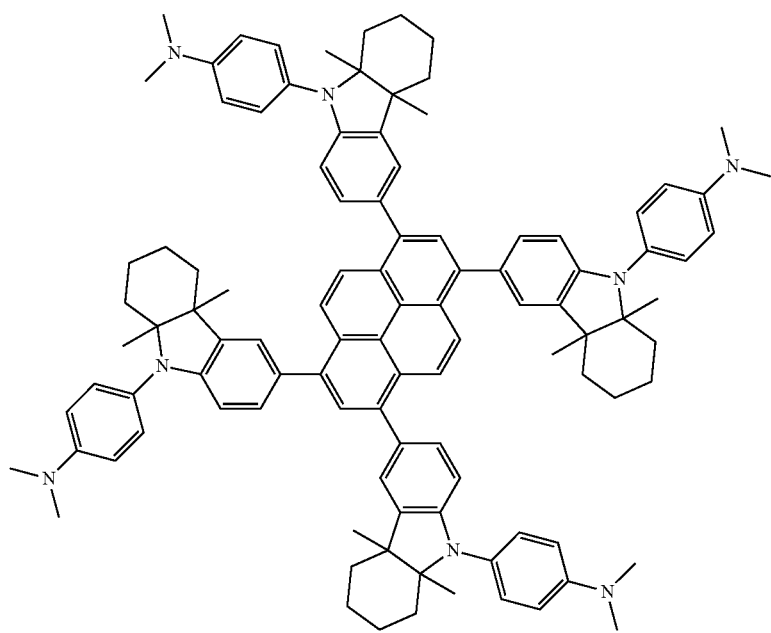

Formula 766
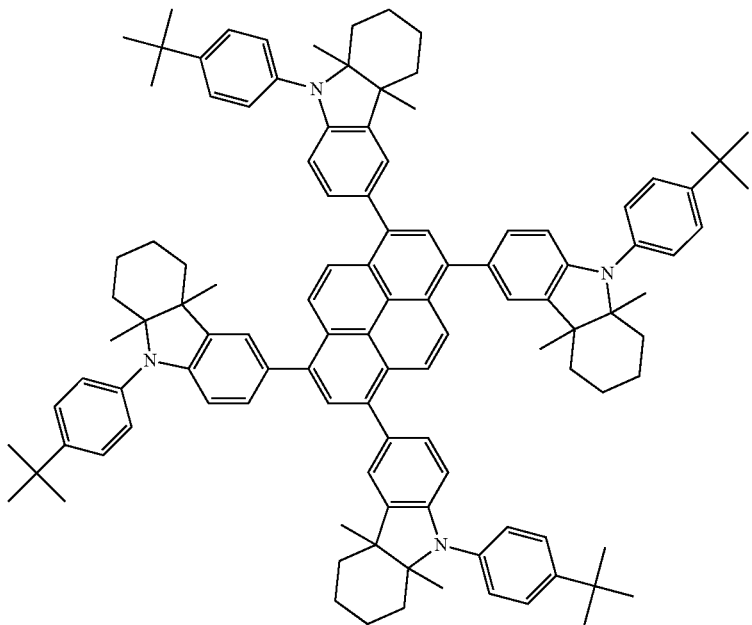
Formula 767
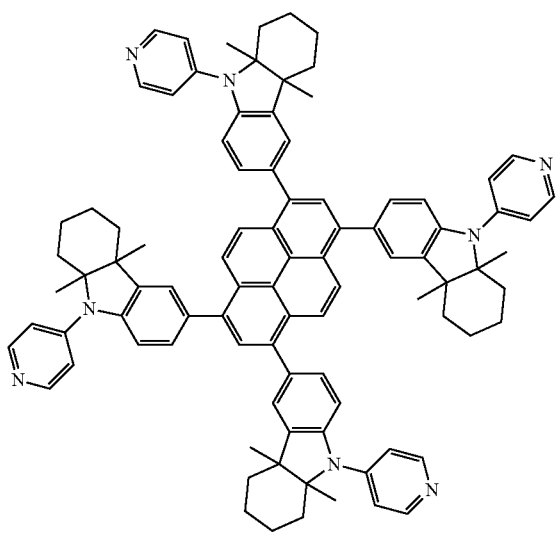
Formula 768
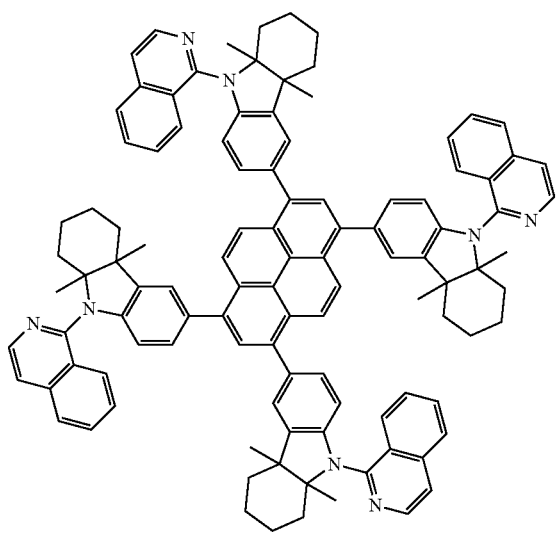

-continued
Formula 769
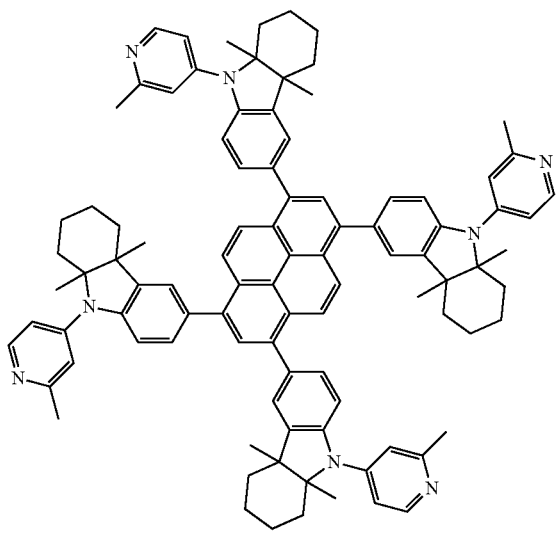
Formula 770
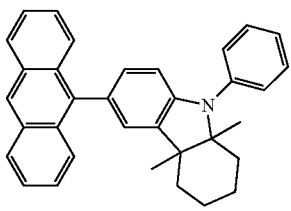
Formula 771
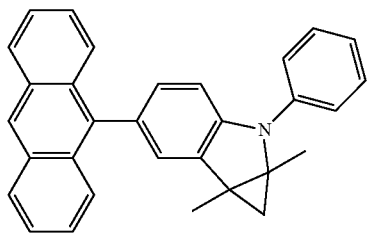
Formula 772
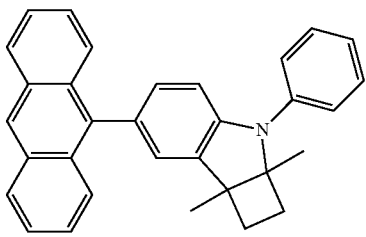
Formula 773
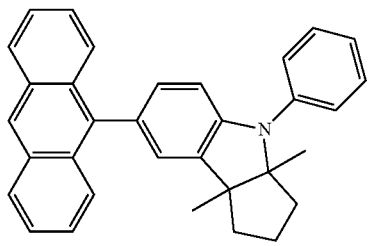
Formula 774
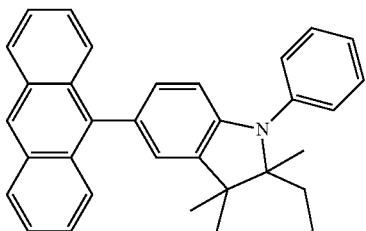
Formula 775
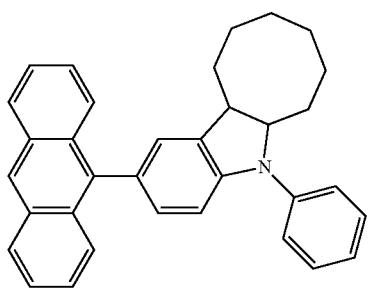
Formula 776
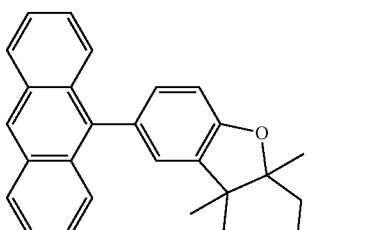
Formula 777
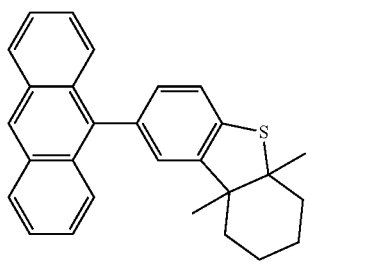
Formula 778
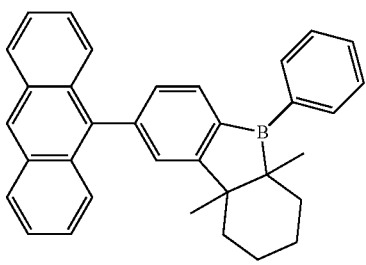

-continued
| Formula 779 | Formula 780 |
|---|---|
| 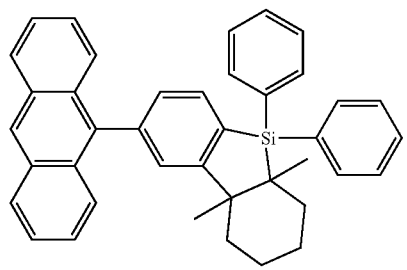 | 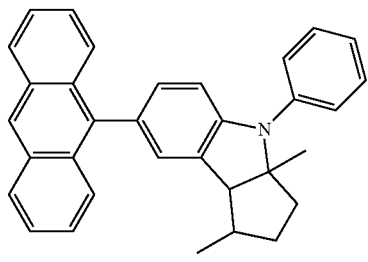 |
| Formula 781 | Formula 782 |
| 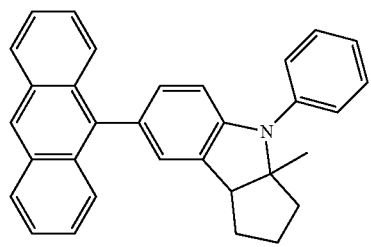 | 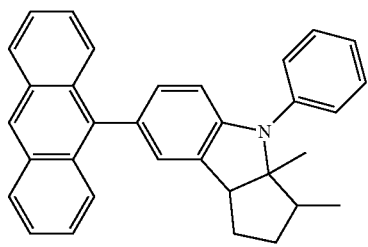 |
| Formula 783 | Formula 784 |
| 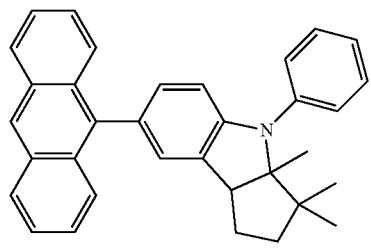 | 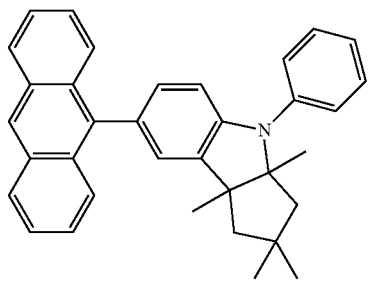 |
| Formula 785 | Formula 786 |
| 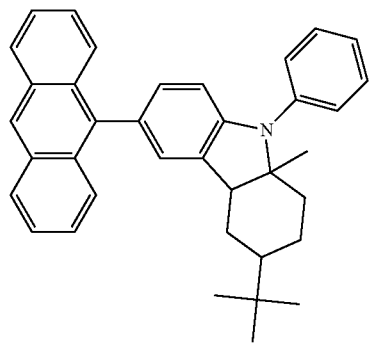 | 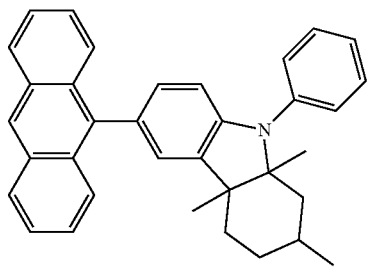 |
| Formula 787 | Formula 788 |
| 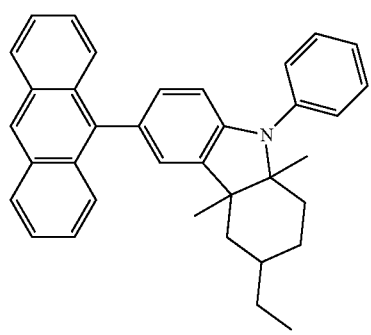 | 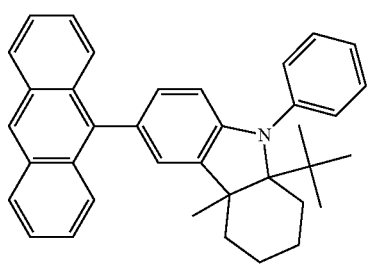 |

-continued
Formula 789
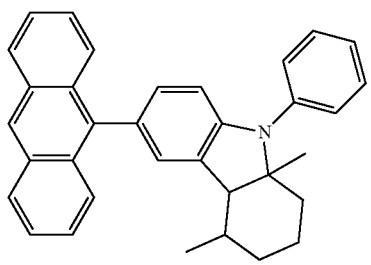
Formula 790
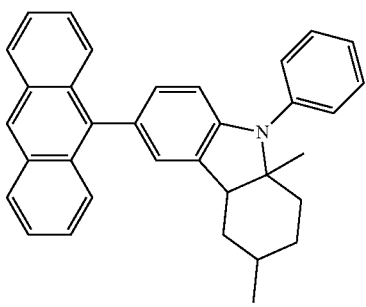
Formula 791
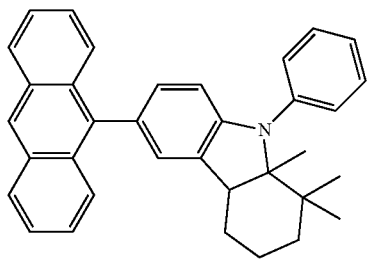
Formula 792
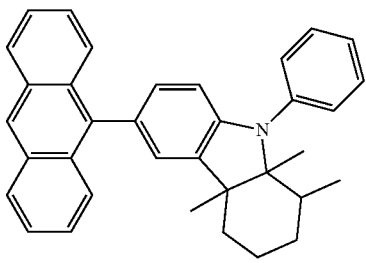
Formula 793
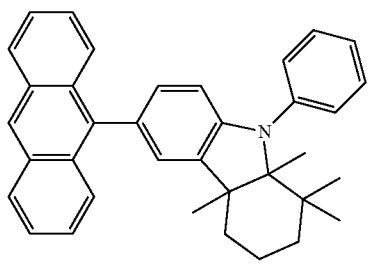
Formula 794
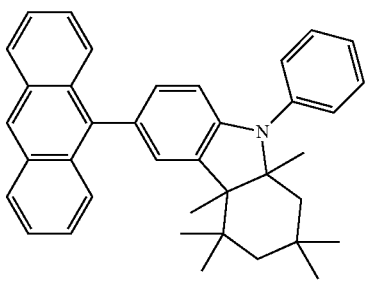
Formula 795
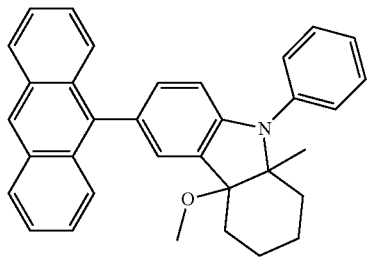
Formula 796
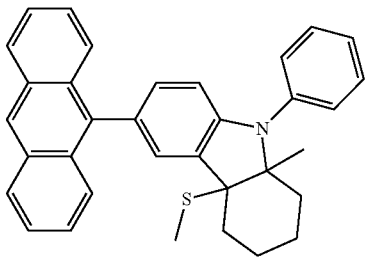
Formula 797
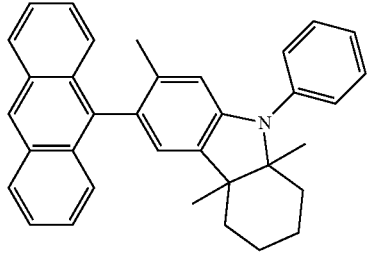
Formula 798
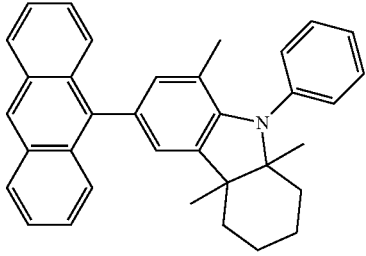
Formula 799
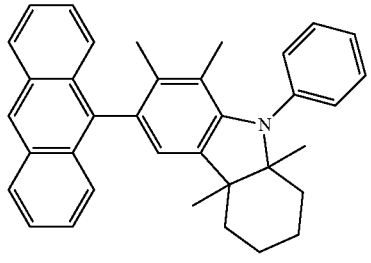
Formula 800
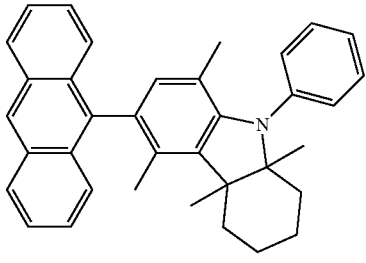

-continued
Formula 801
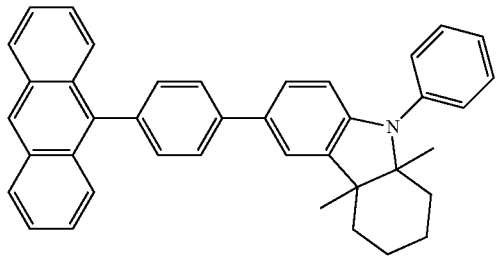
Formula 802
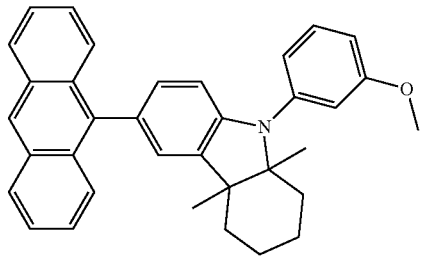
Formula 803
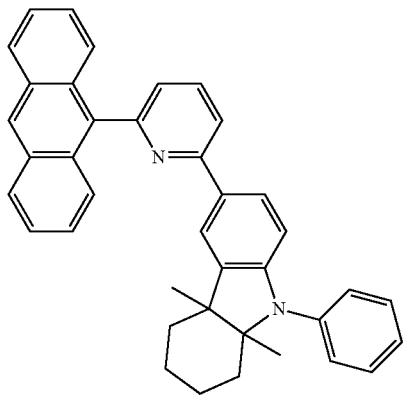
Formula 804
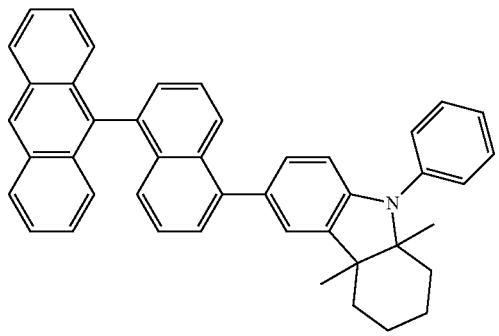
Formula 805
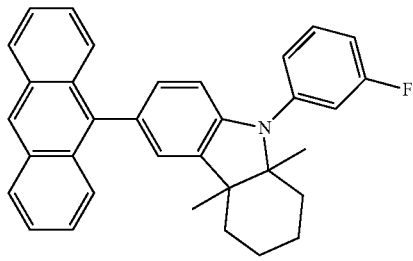
Formula 806
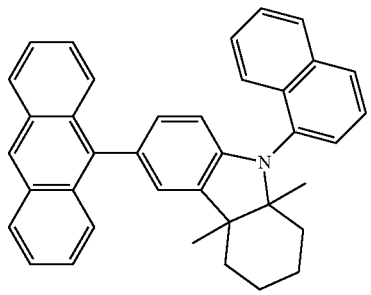
Formula 807
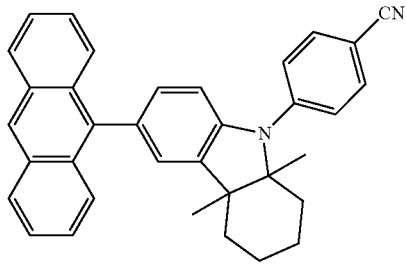
Formula 808
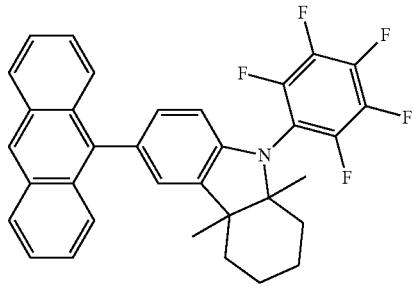
Formula 809
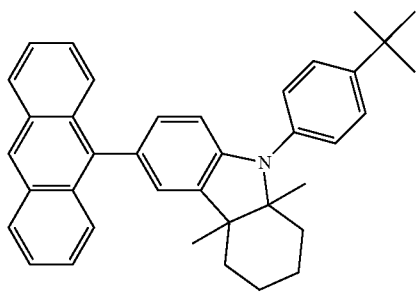
Formula 810
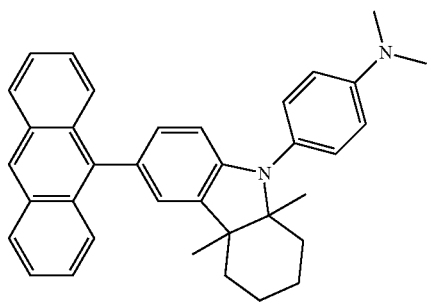

-continued
Formula 811
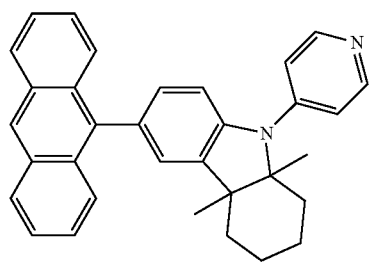
Formula 812
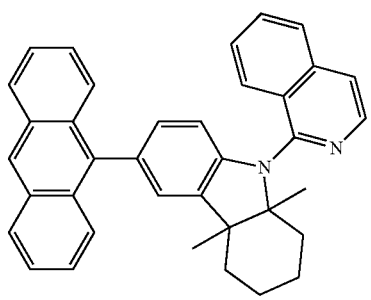
Formula 813
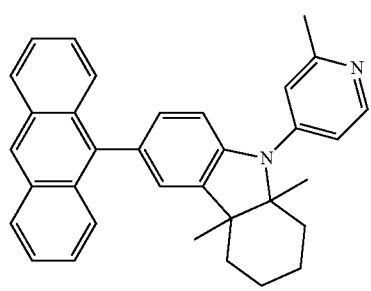
Formula 814
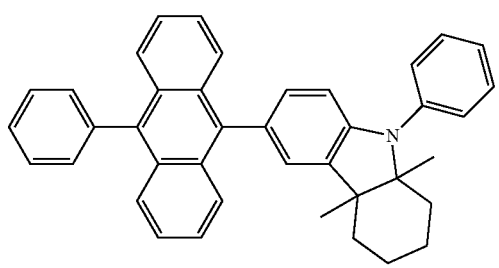
Formula 815
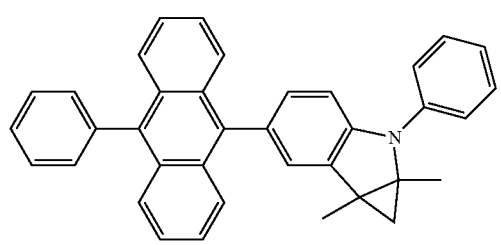
Formula 816
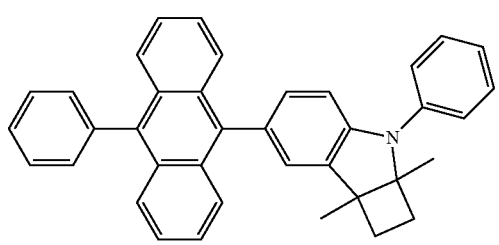
Formula 817
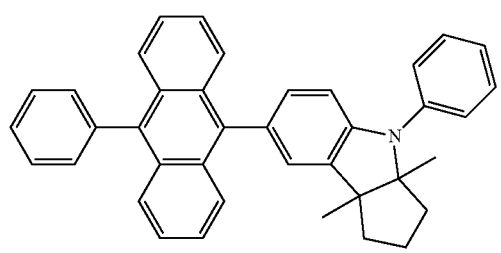
Formula 818
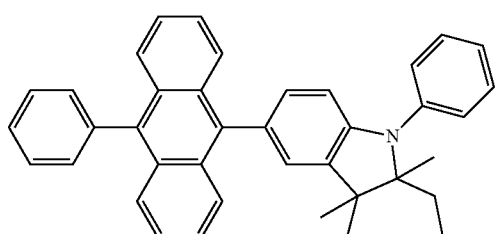
Formula 819]
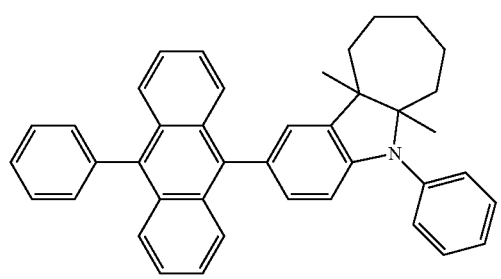
Formula 820
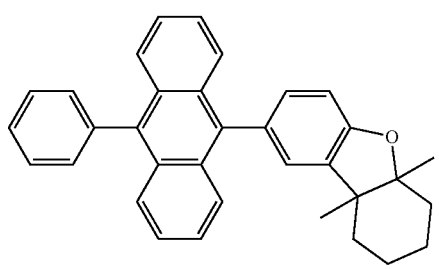

-continued
Formula 821
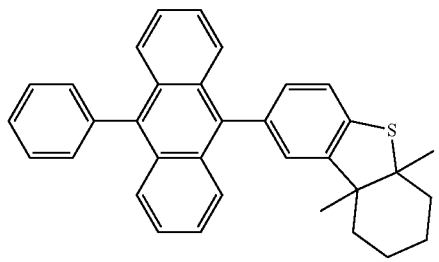
Formula 822
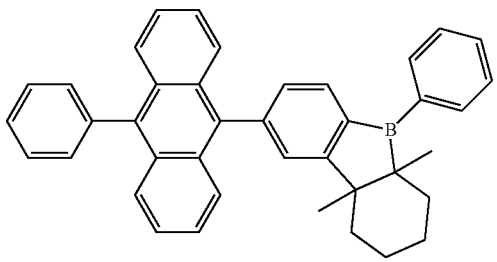
Formula 823
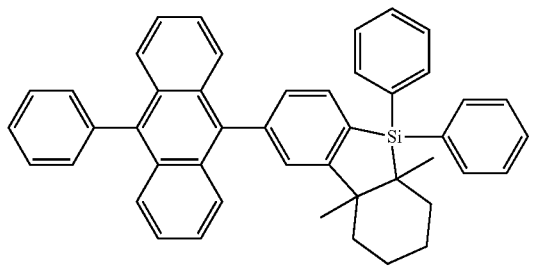
Formula 824
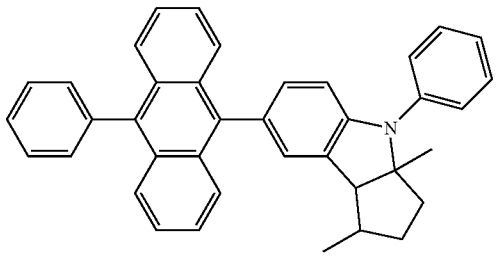
Formula 825
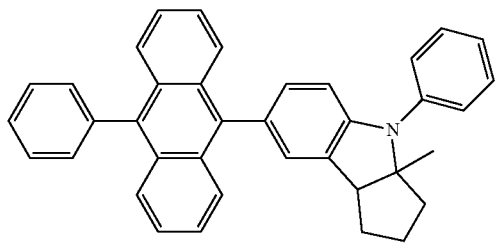
Formula 826
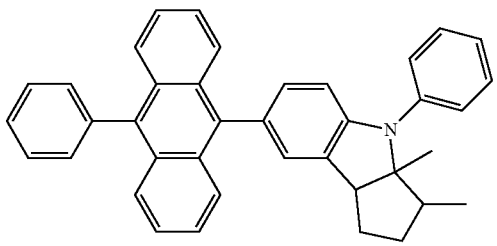
Formula 827
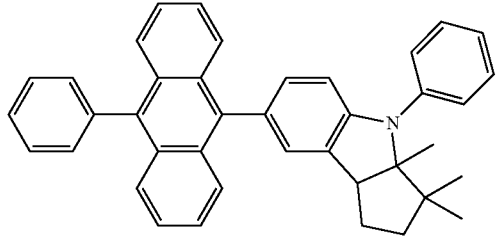
Formula 828
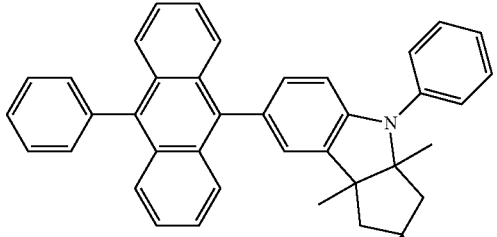
Formula 829
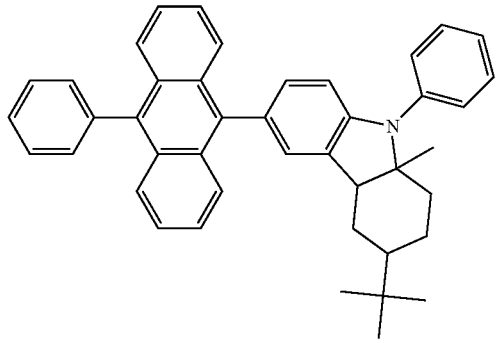
Formula 830

-continued
Formula 831
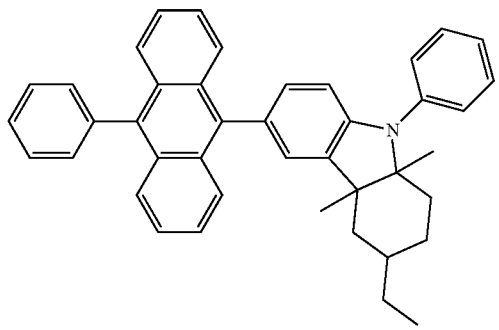
Formula 832
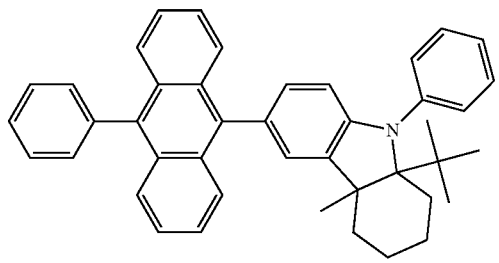
Formula 833
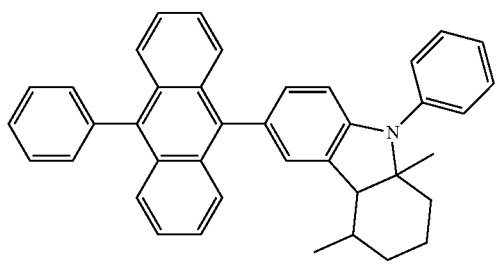
Formula 834
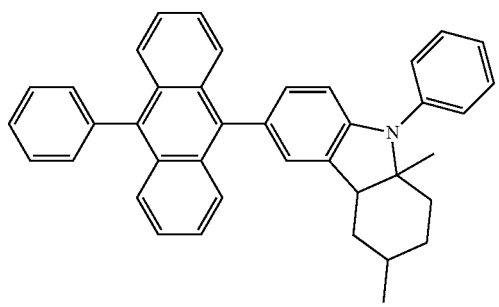
Formula 835
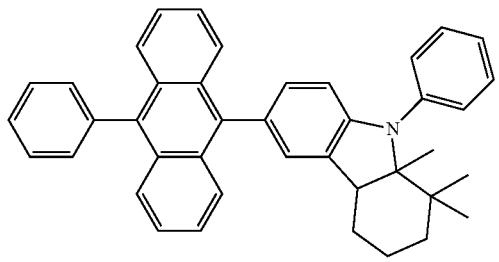
Formula 836
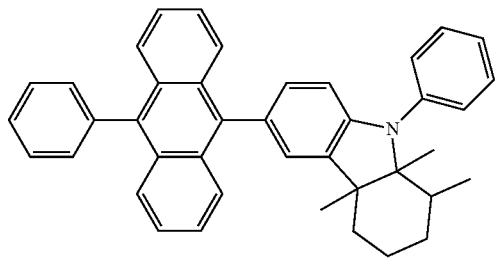
Formula 837
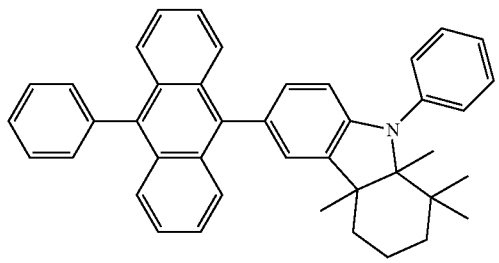
Formula 838
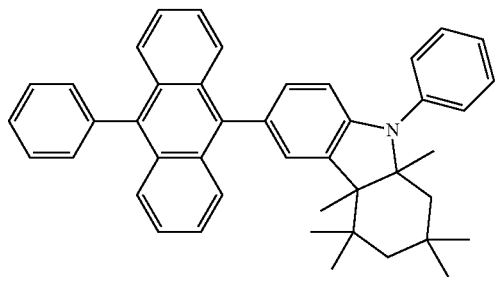
Formula 839
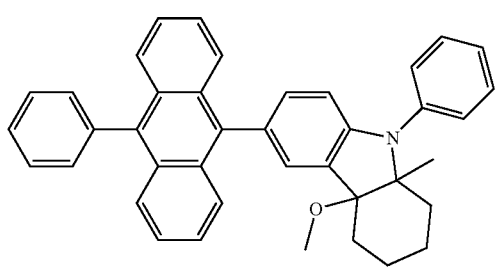
Formula 840
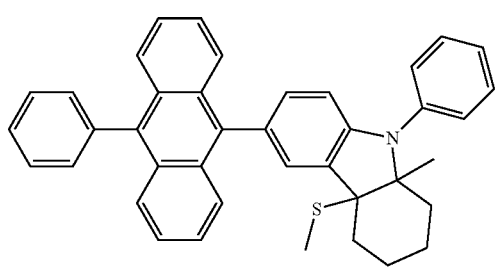

-continued
Formula 841
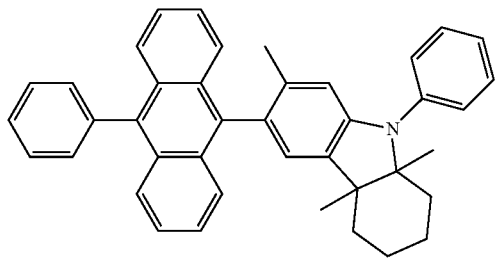
Formula 842
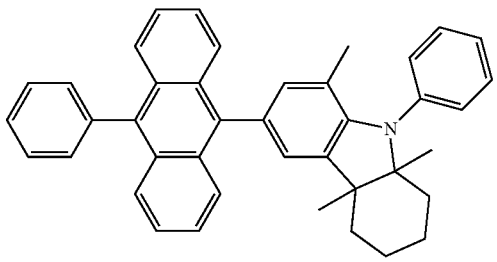
Formula 843
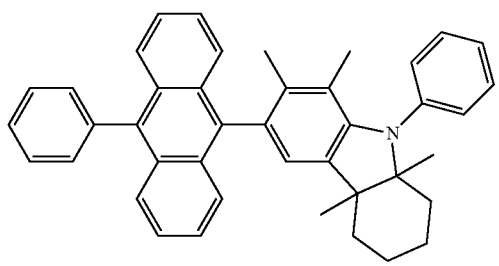
Formula 844
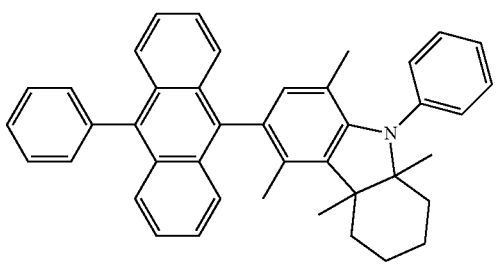
Formula 845
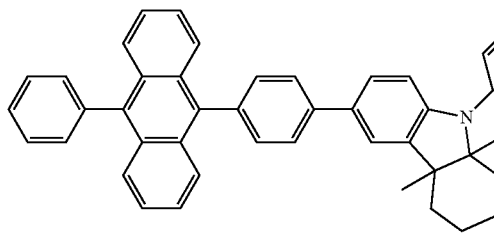
Formula 846
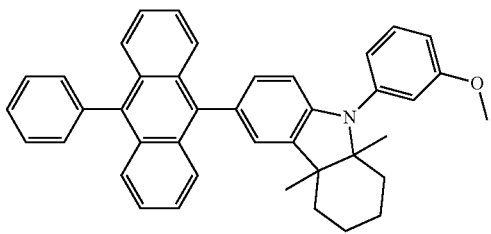
Formula 847
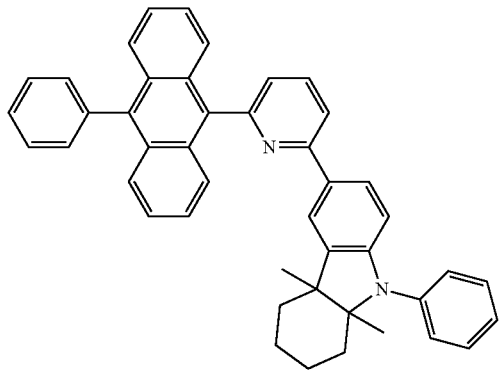
Formula 848
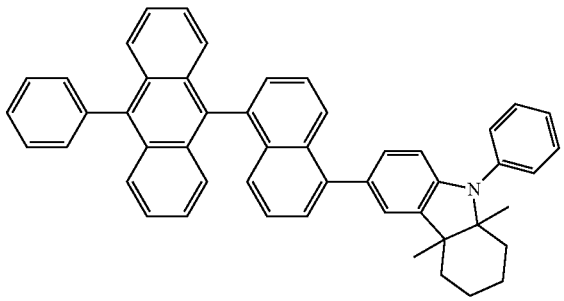
Formula 849
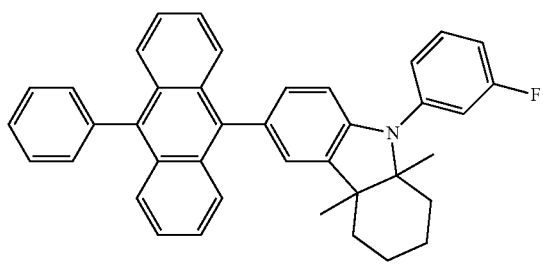
Formula 850
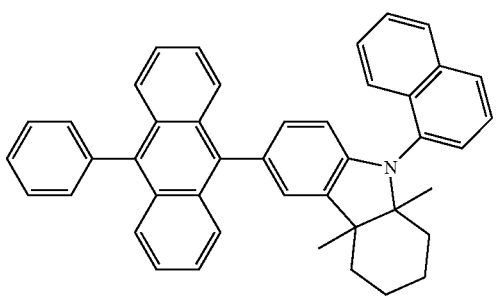

-continued
Formula 851
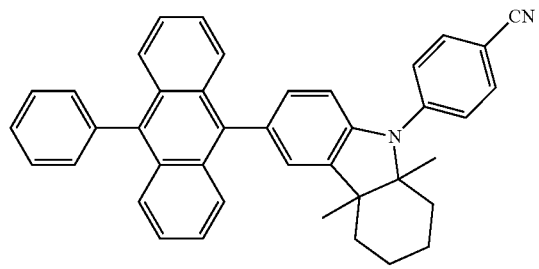
Formula 852
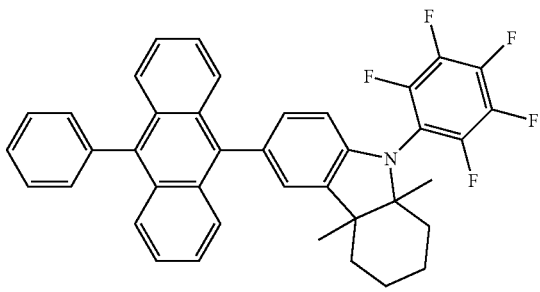
Formula 853
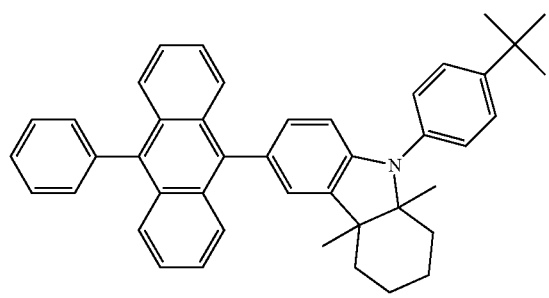
Formula 854
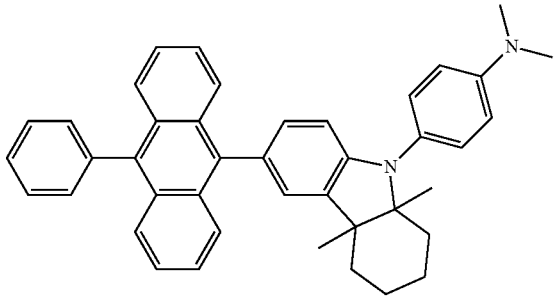
Formula 855
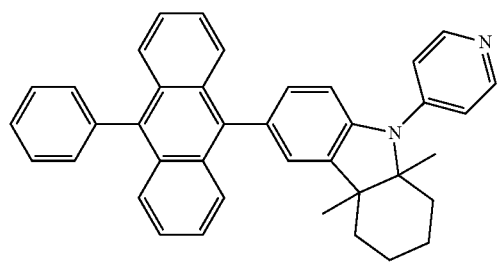
Formula 856
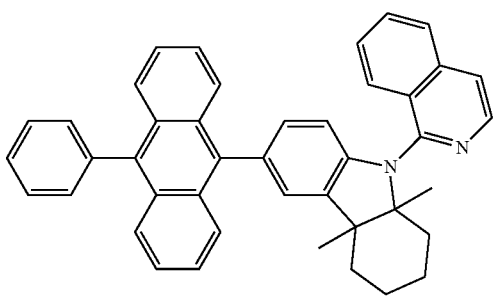
Formula 857
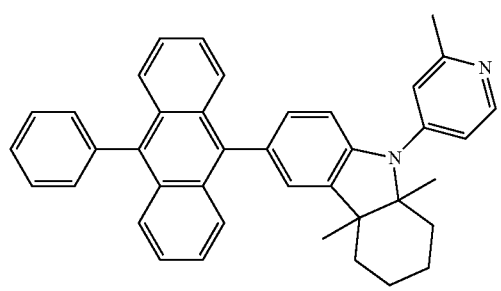
Formula 858
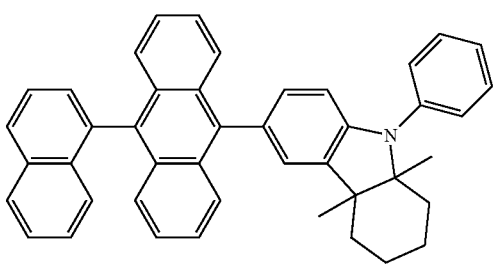
Formula 859
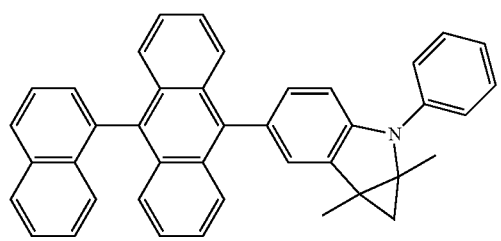
Formula 860
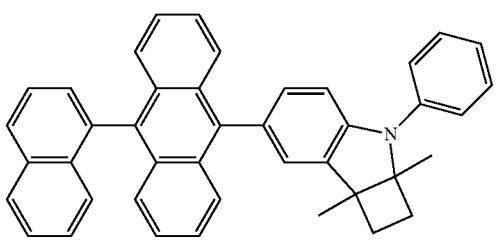

-continued
Formula 861
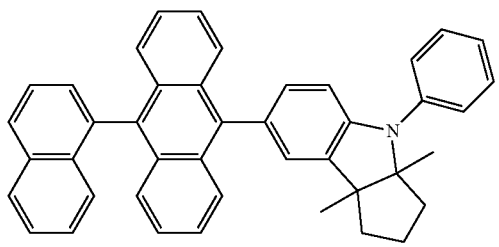
Formula 862
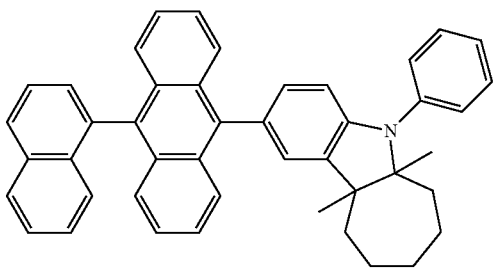
Formula 863
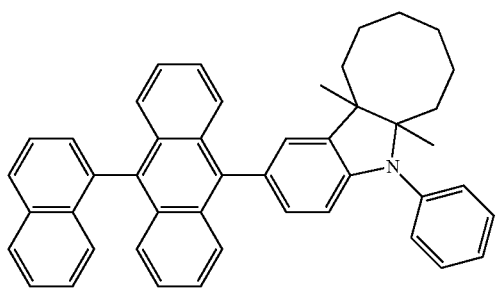
Formula 864
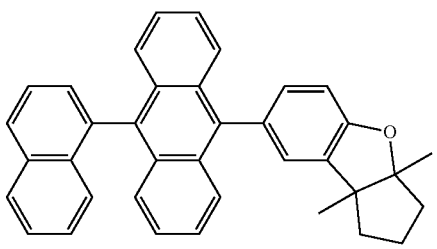
Formula 865
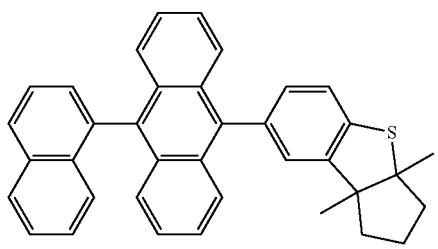
Formula 866
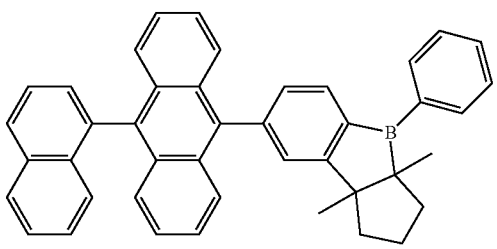
Formula 867
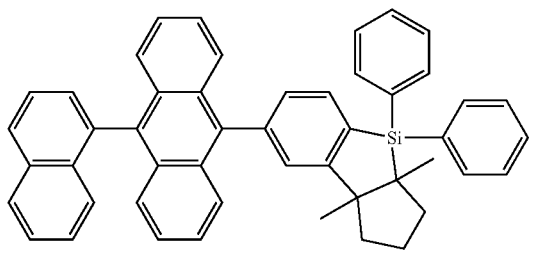
Formula 868
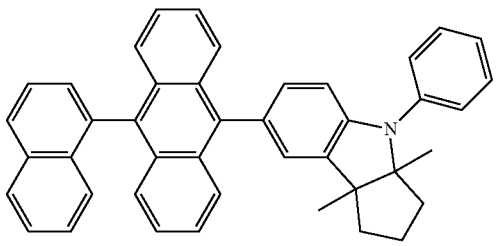
Formula 869
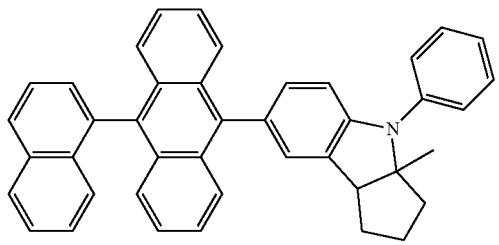
Formula 870
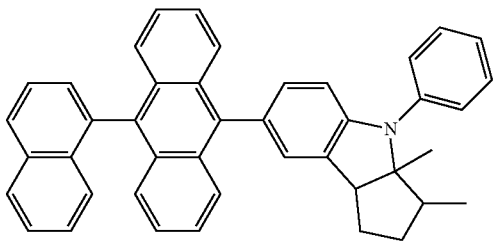

-continued
Formula 871
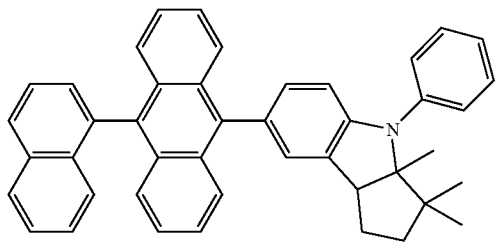
Formula 872
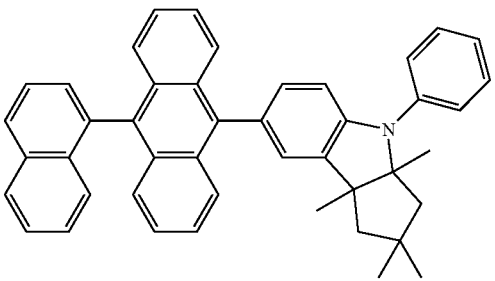
Formula 873
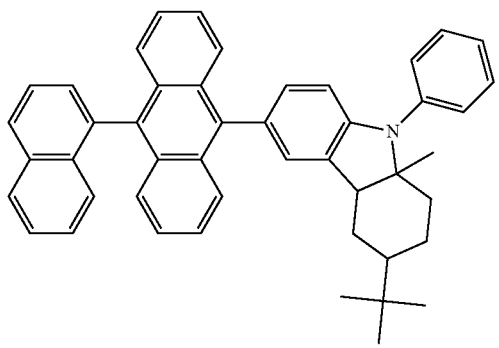
Formula 874
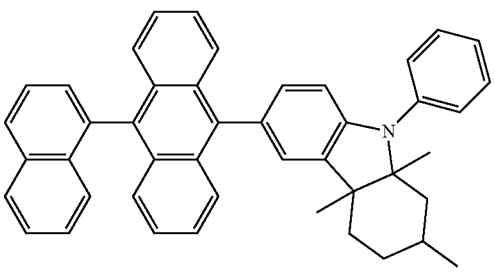
Formula 875
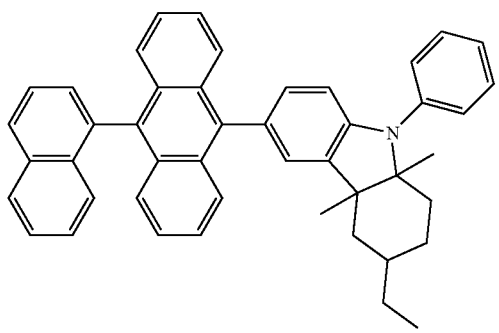
Formula 876
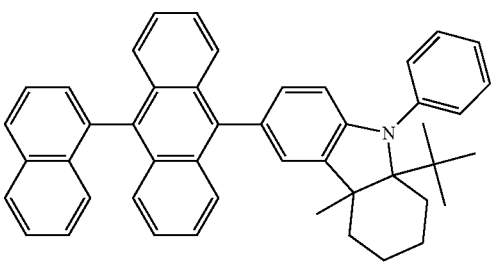
Formula 877
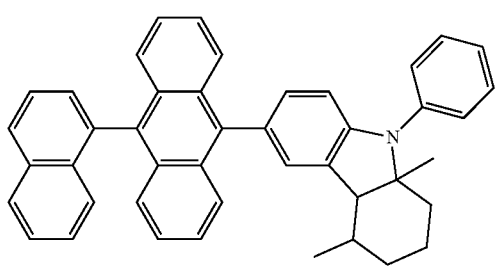
Formula 878
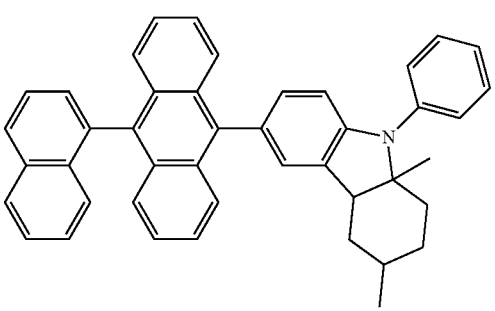
Formula 879
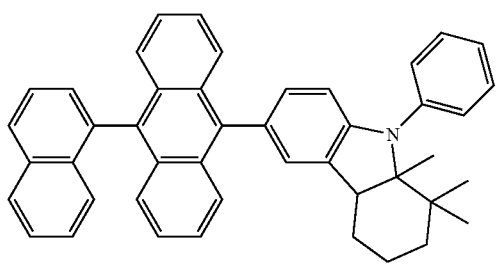
Formula 880
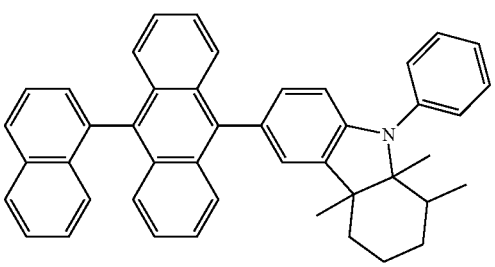

-continued
Formula 881
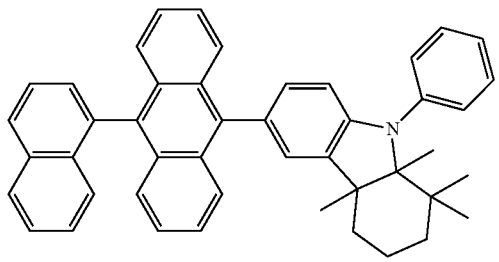
Formula 882
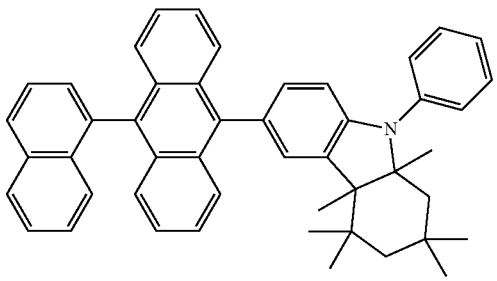
Formula 883
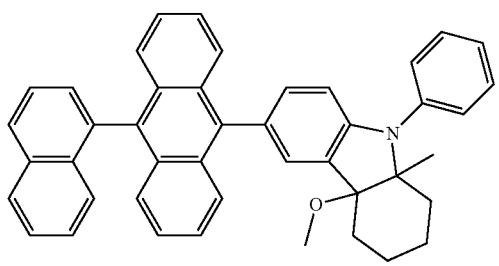
Formula 884
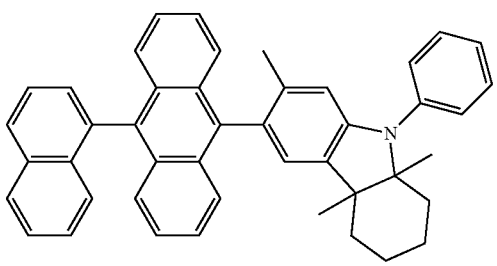
Formula 885
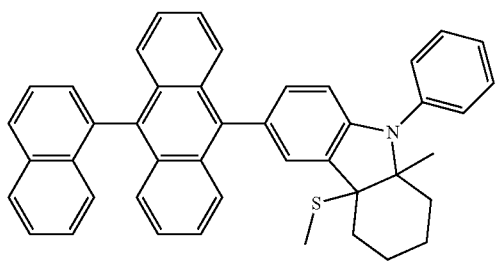
Formula 886
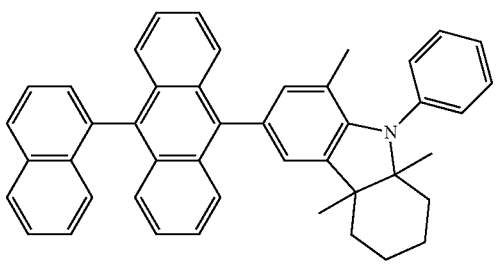
Formula 887
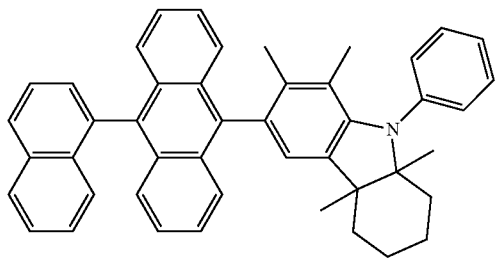
Formula 888
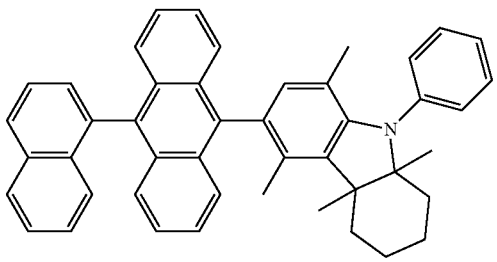
Formula 889
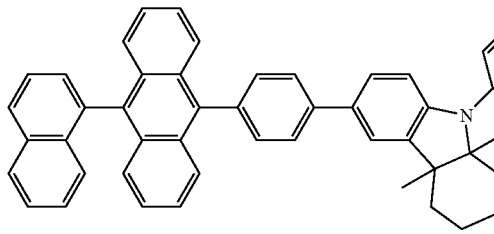
Formula 890
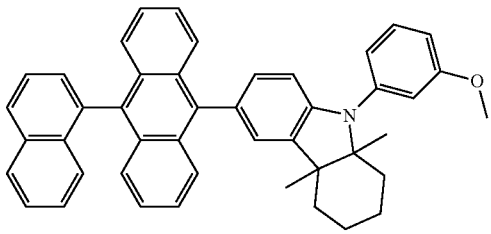

-continued
Formula 891
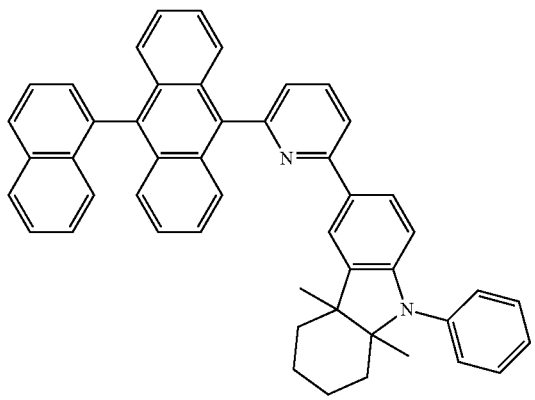
Formula 892
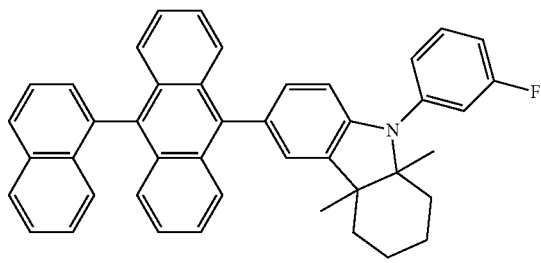
Formula 893
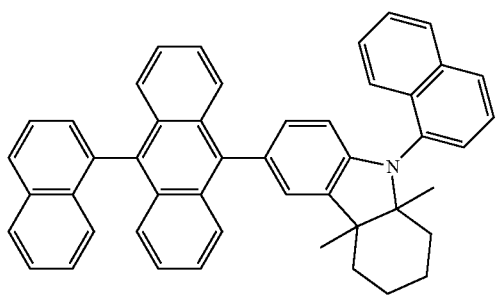
Formula 894
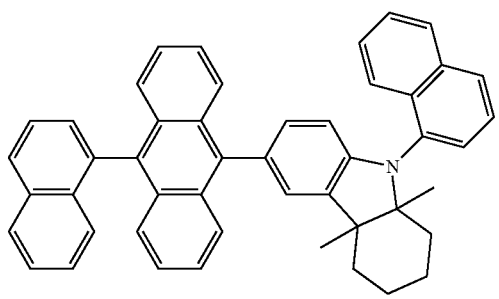
Formula 895
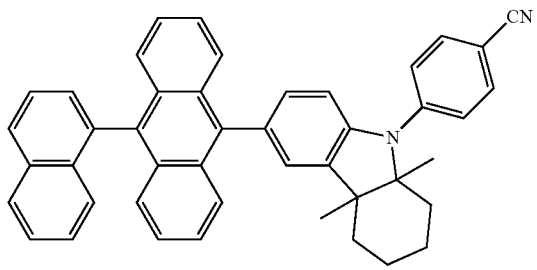
Formula 896
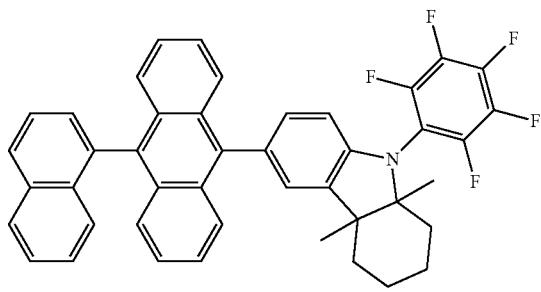
Formula 897
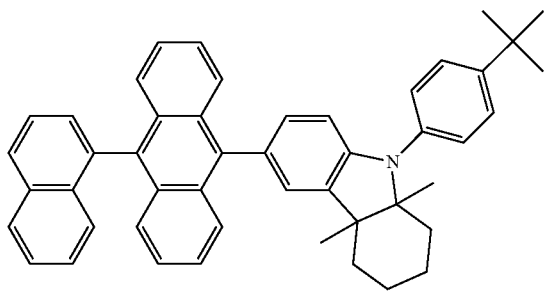
Formula 898
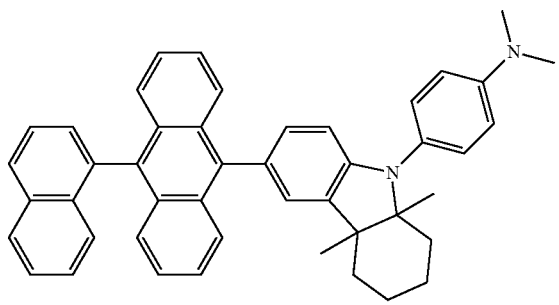

-continued
Formula 899
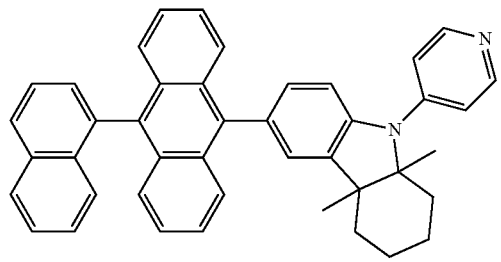
Formula 900
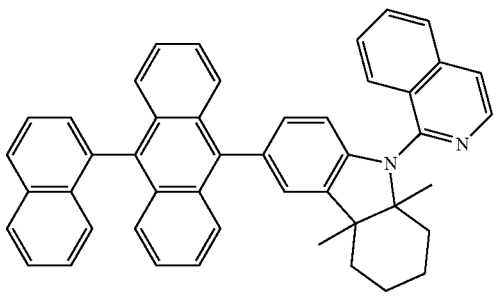
Formula 901
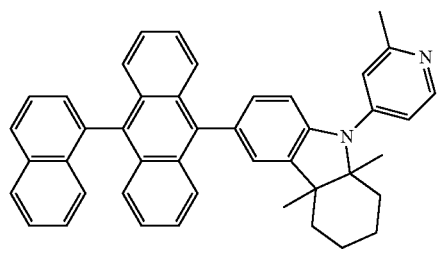
Formula 902
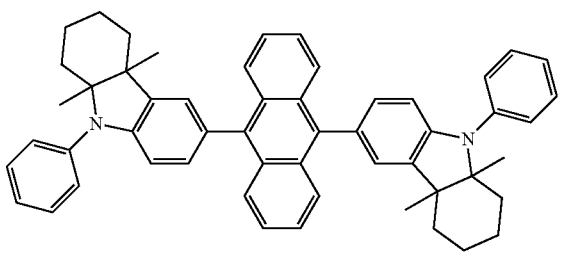
Formula 903
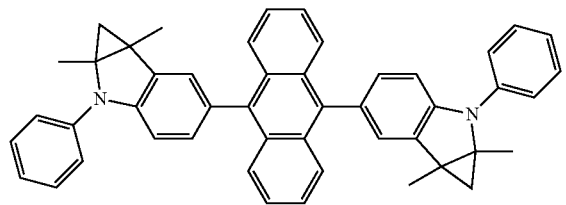
Formula 904
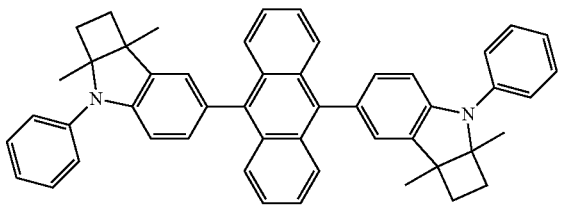
Formula 905
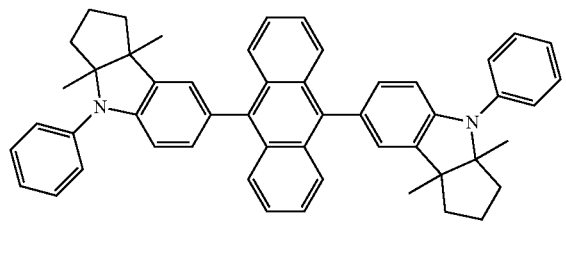
Formula 906
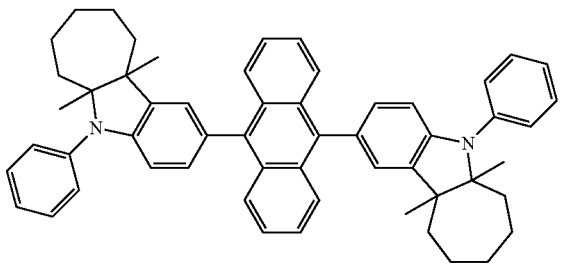
Formula 907
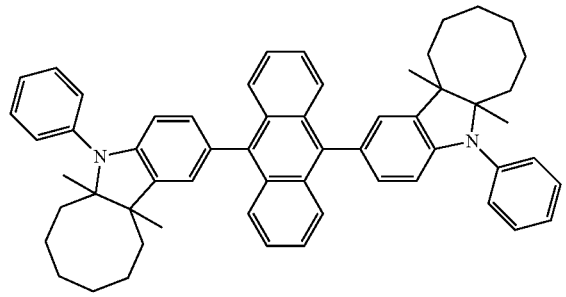
Formula 908
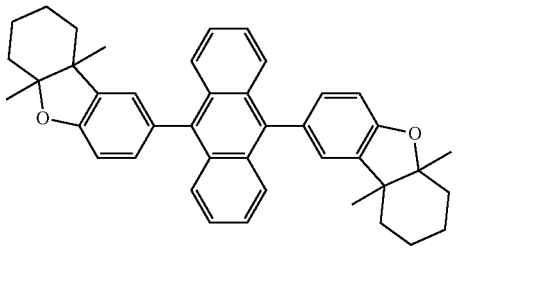

-continued
Formula 909
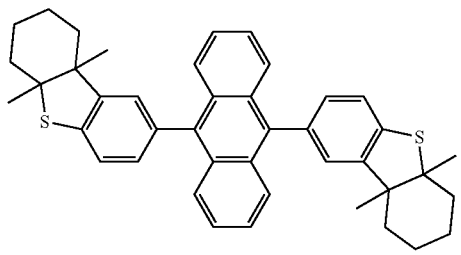
Formula 910
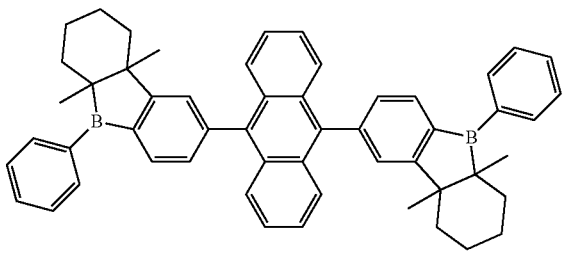
Formula 911
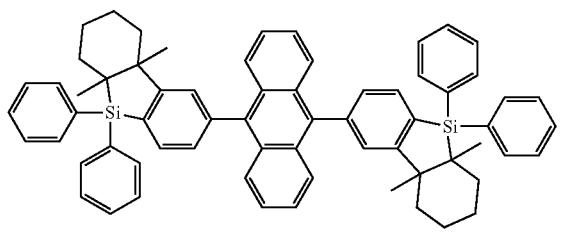
Formula 912
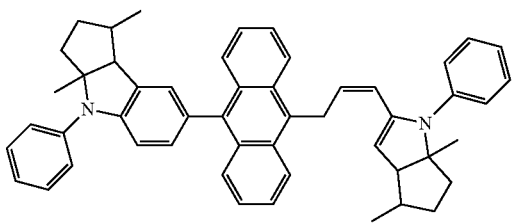
Formula 913
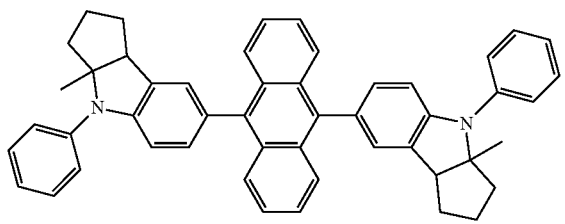
Formula 914
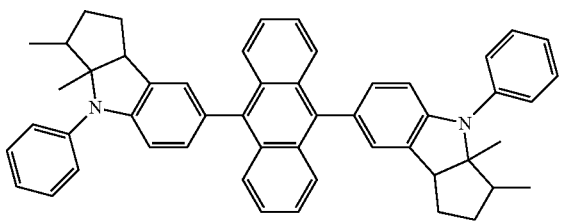
Formula 915
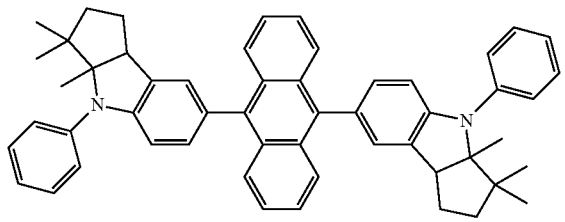
Formula 916
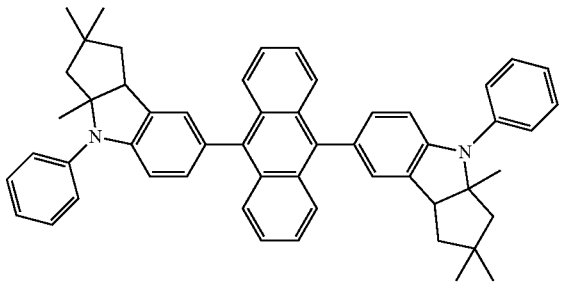
Formula 917
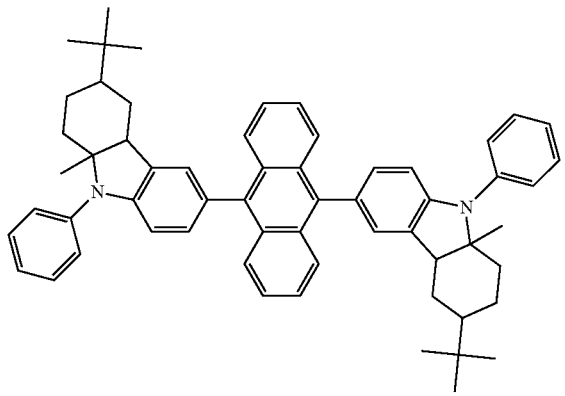
Formula 918

-continued
Formula 919
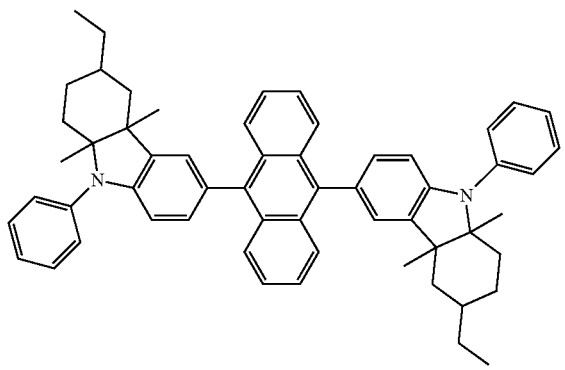
Formula 920
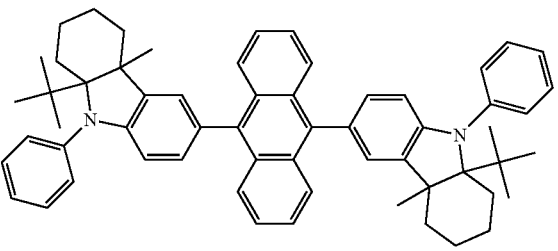
Formula 921
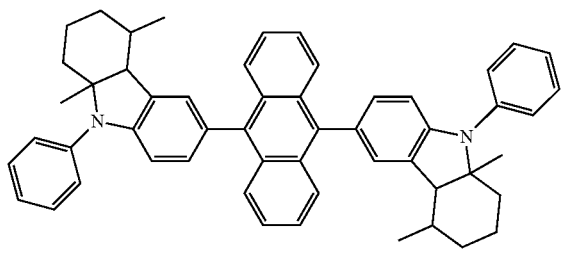
Formula 922
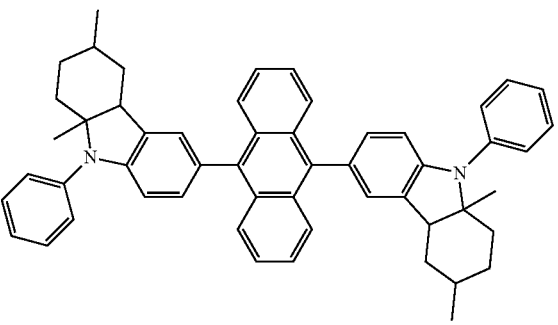
Formula 923
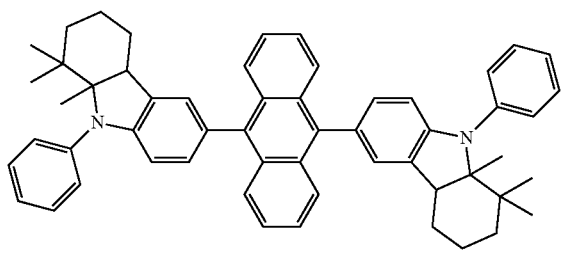
Formula 924
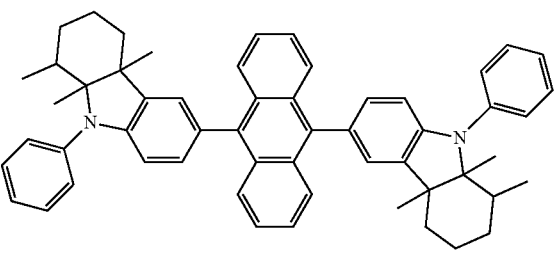
Formula 925
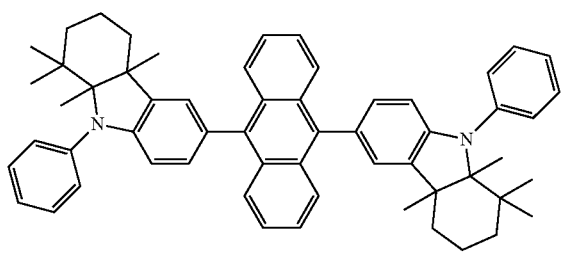
Formula 926
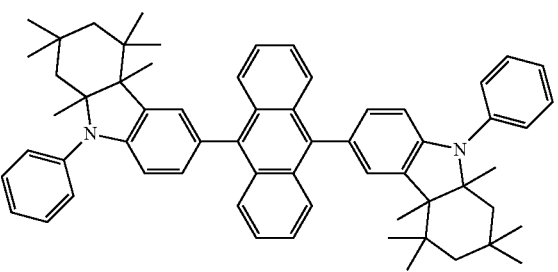
Formula 927
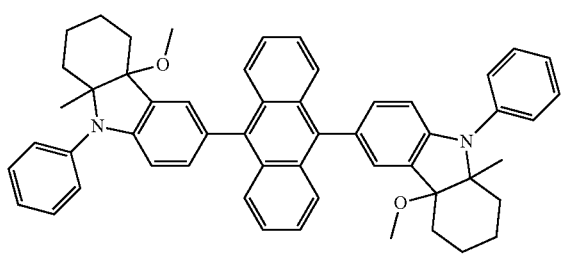
Formula 928
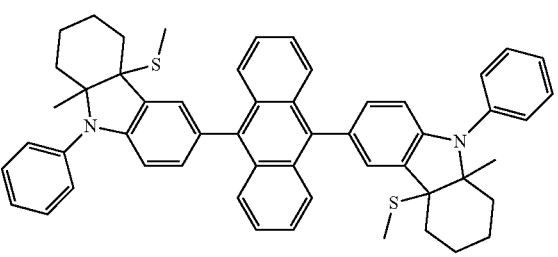

-continued
Formula 929
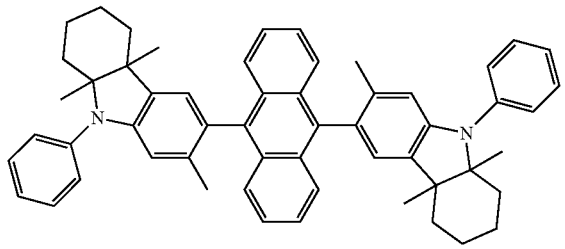
Formula 930
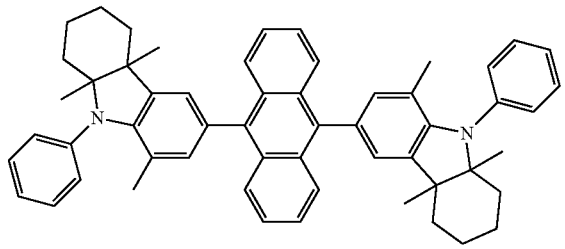
Formula 931
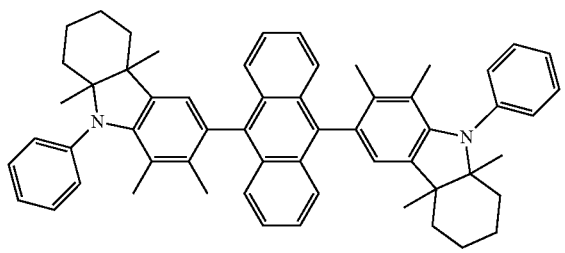
Formula 932
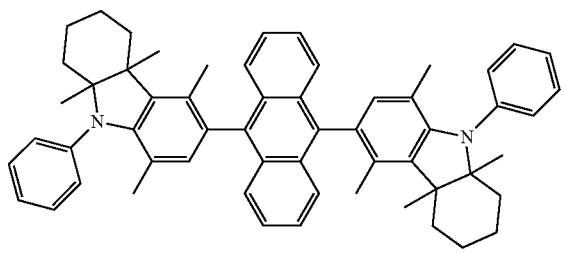
Formula 933
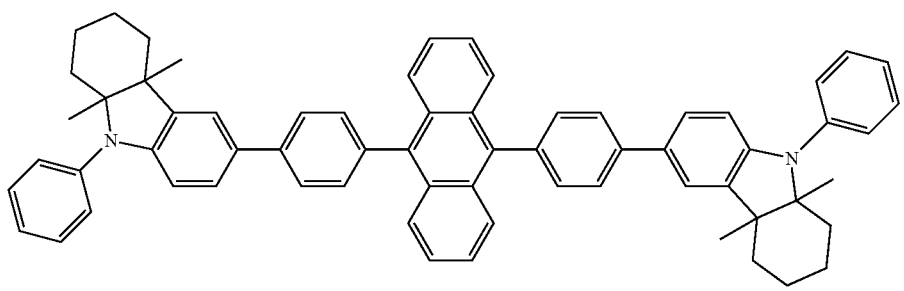
Formula 934
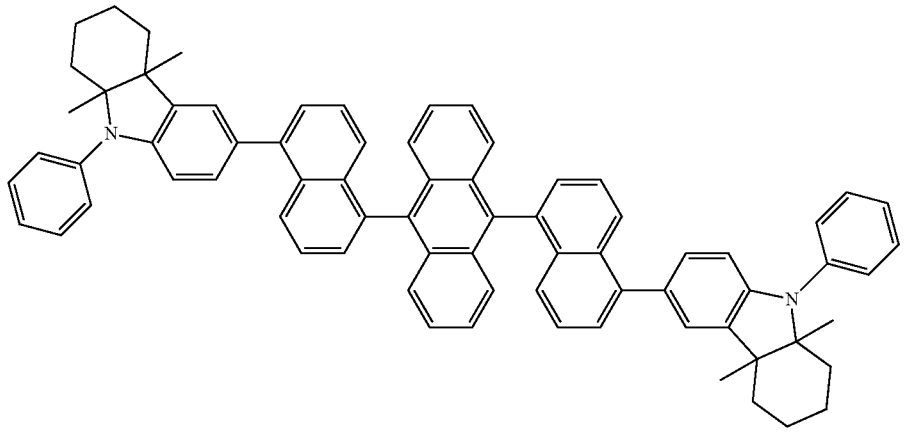
Formula 935
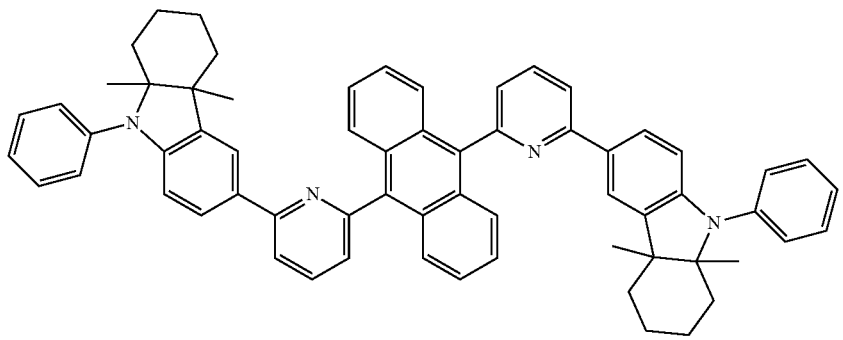

-continued
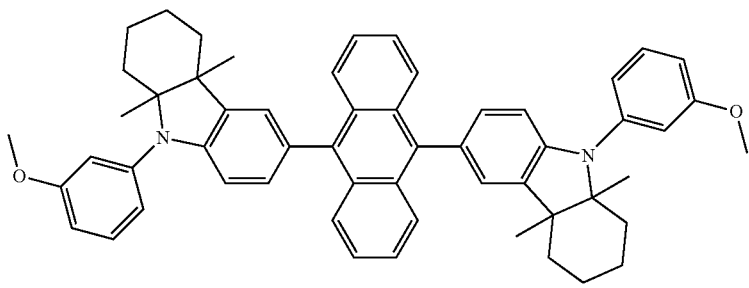
Formula 936
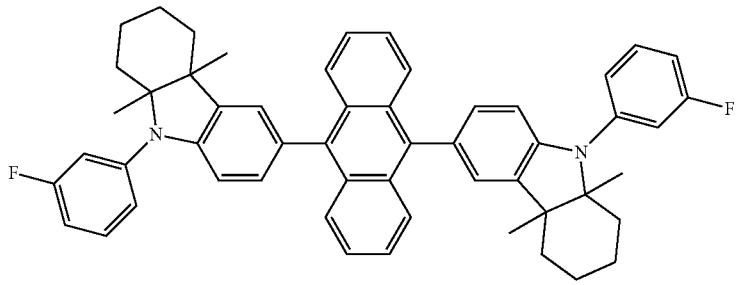
Formula 937
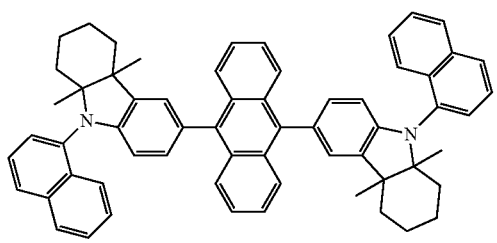
Formula 938
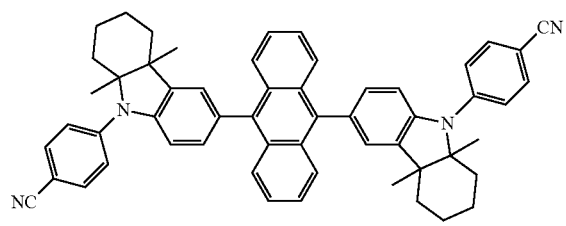
Formula 939
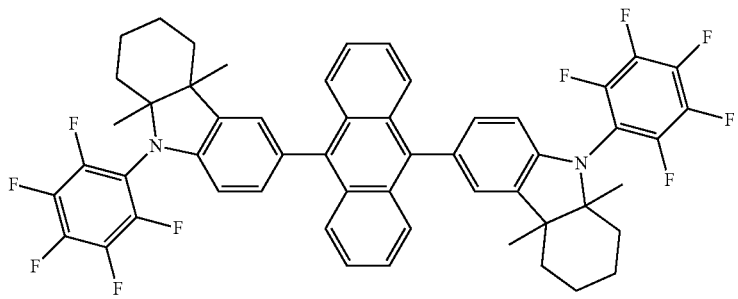
Formula 940
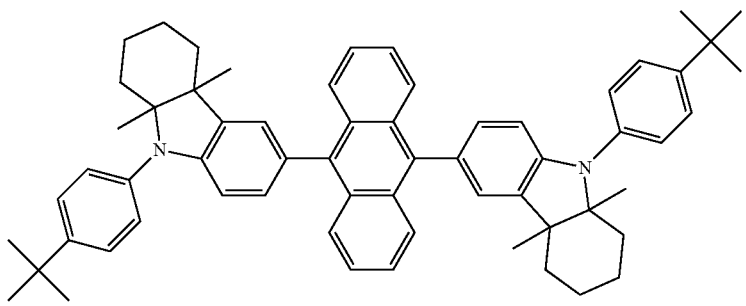
Formula 941

Formula 942
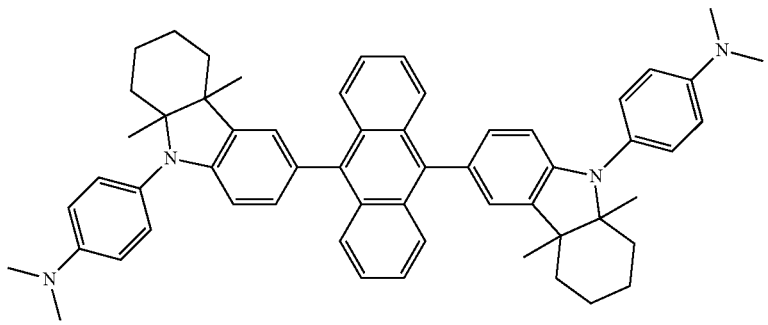
Formula 943
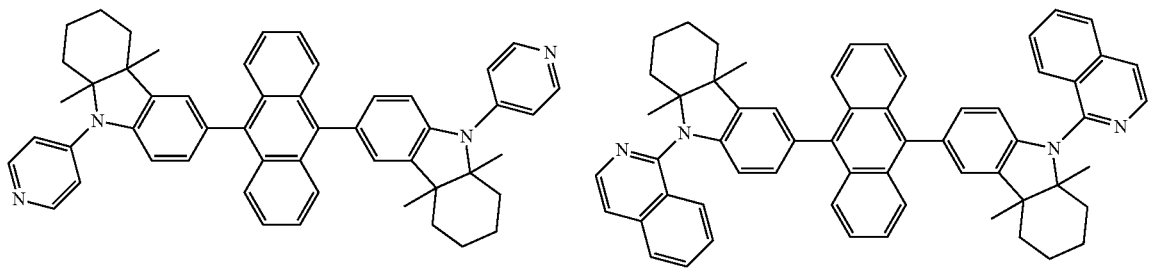
Formula 944
Formula 945
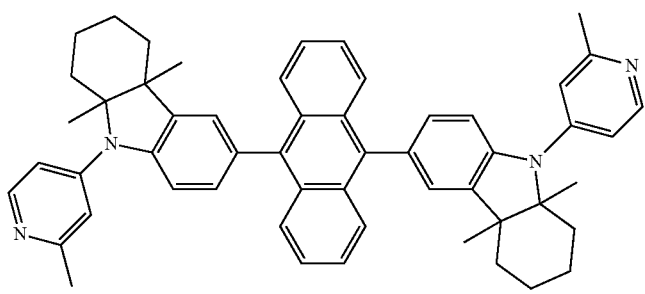
Formula 946
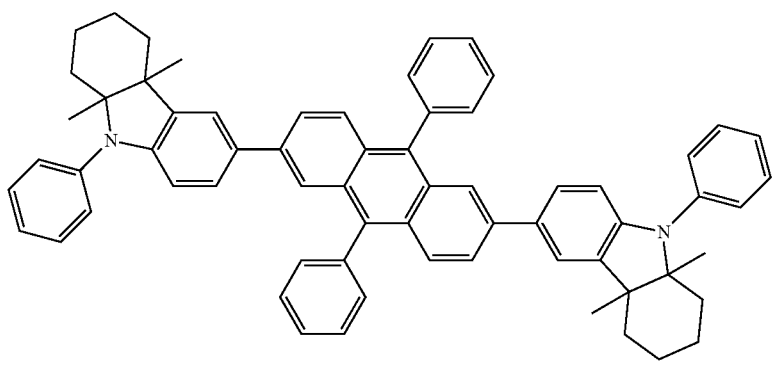
Formula 947
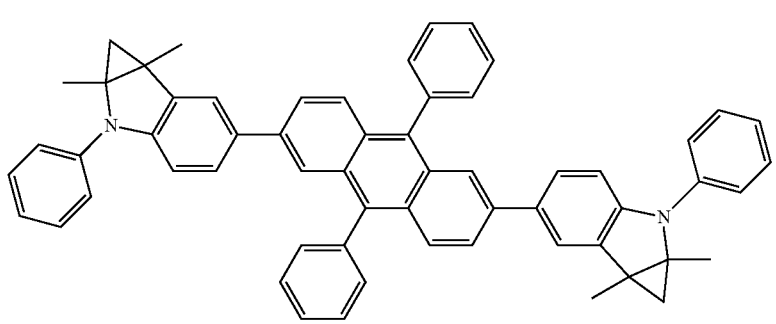

-continued
Formula 948
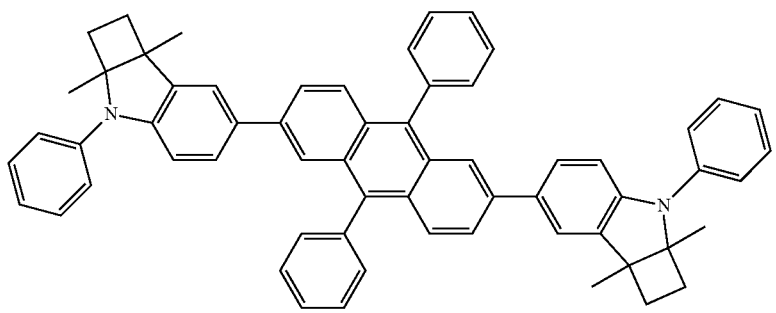
Formula 949
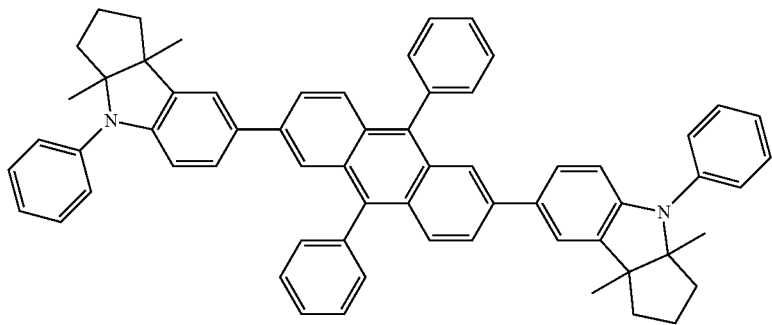
Formula 950
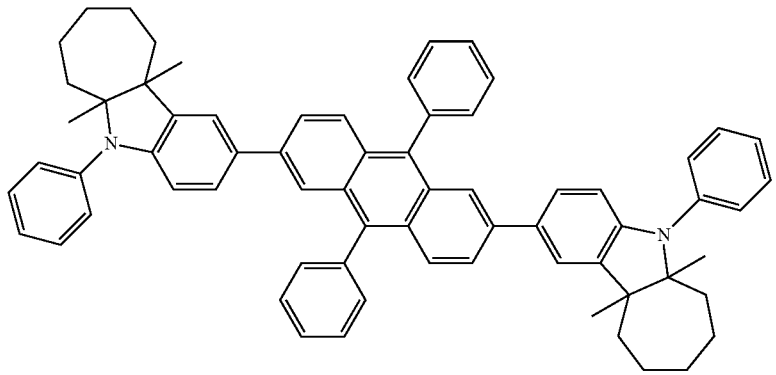
Formula 951
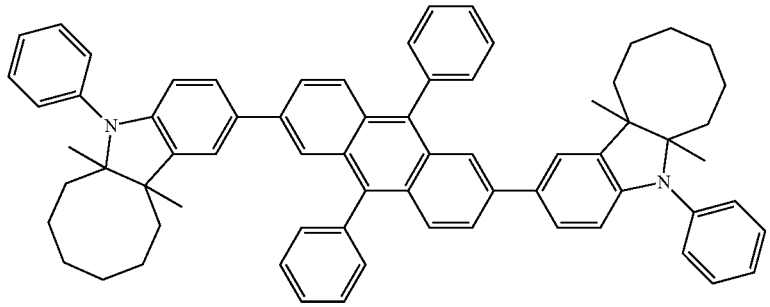
Formula 952
Formula 953
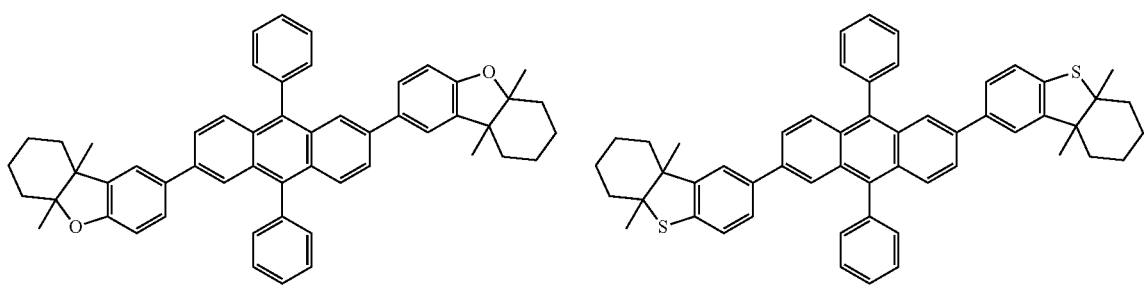

Formula 954
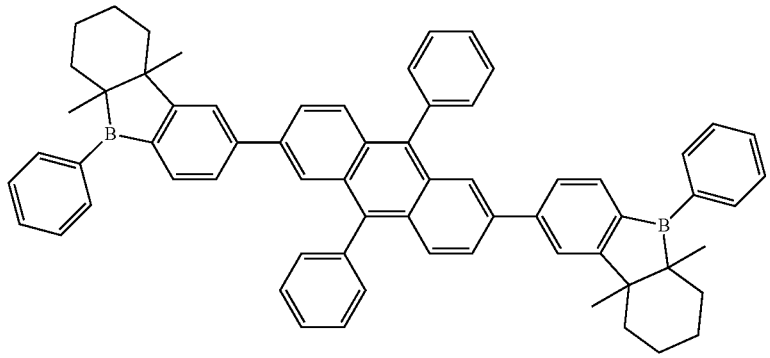
Formula 955
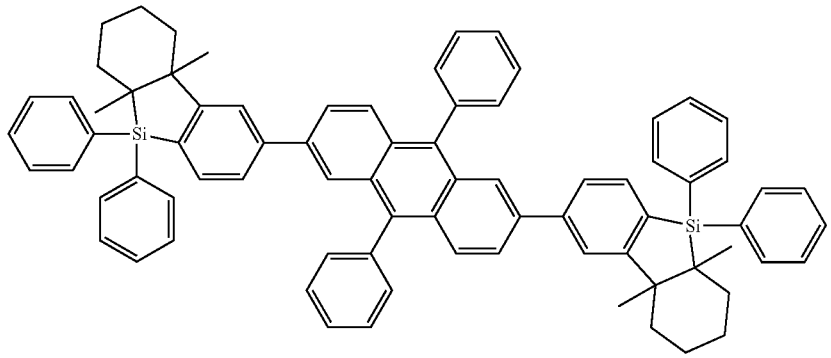
Formula 956
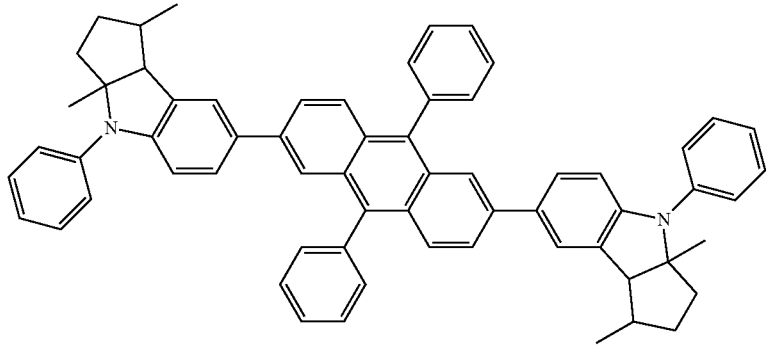
Formula 957
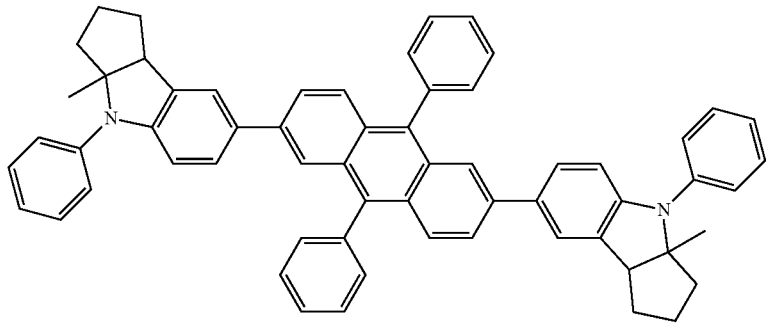

-continued
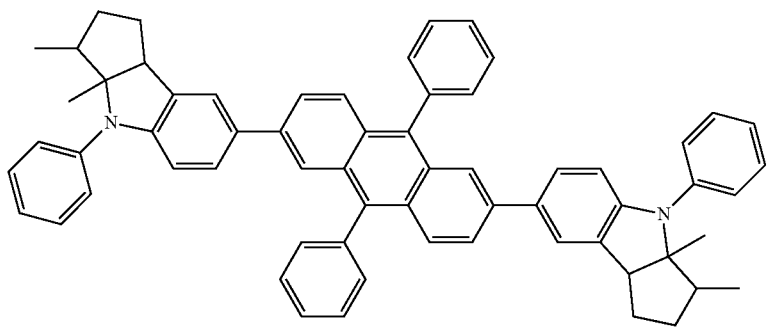
Formula 958
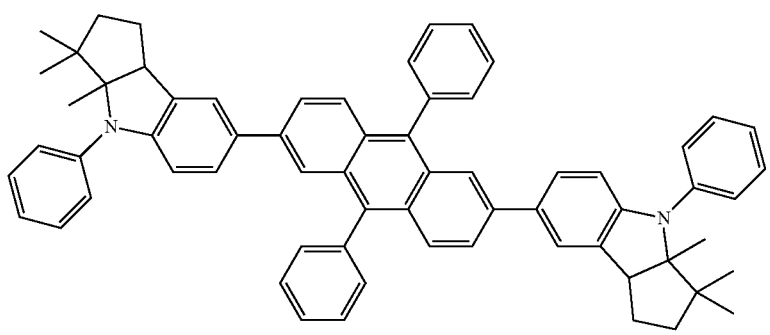
Formula 959
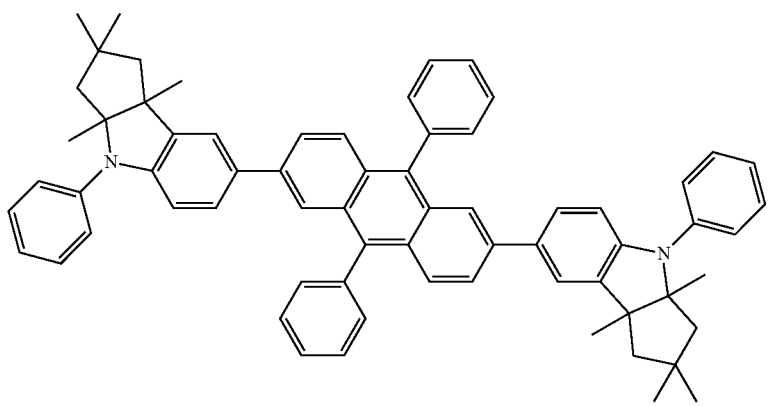
Formula 960
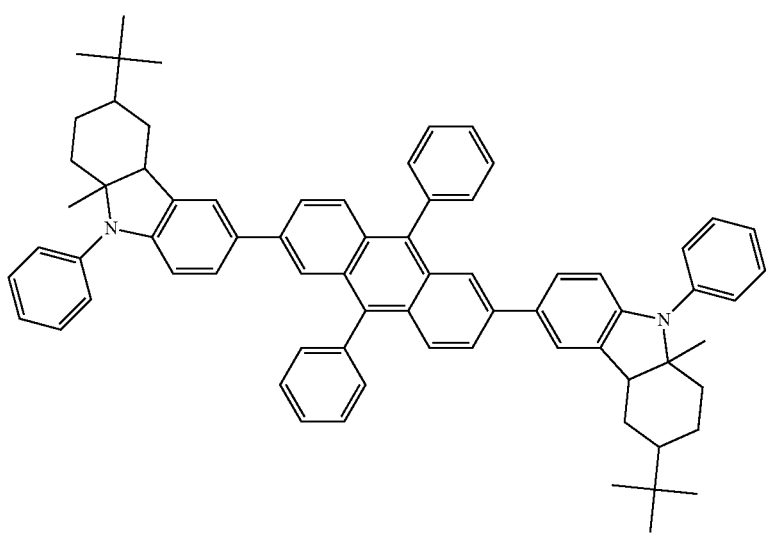
Formula 961

Formula 962
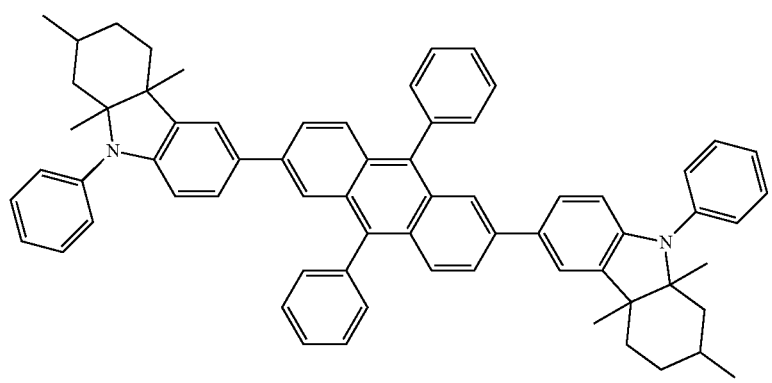
Formula 963
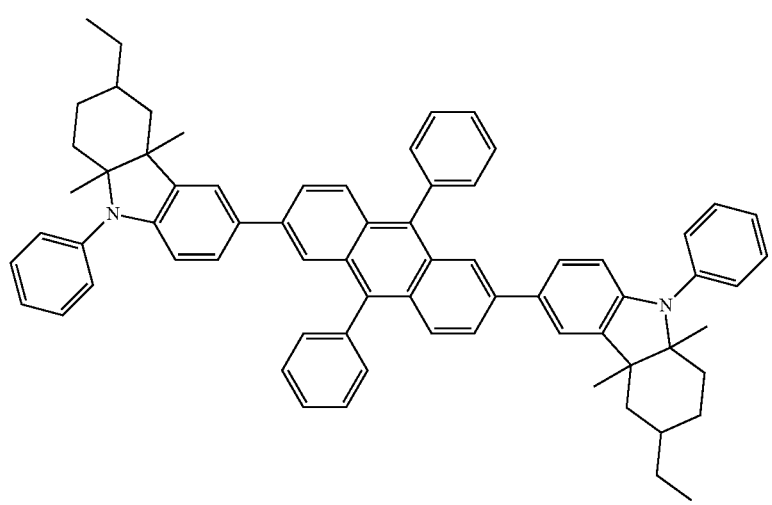
Formula 964
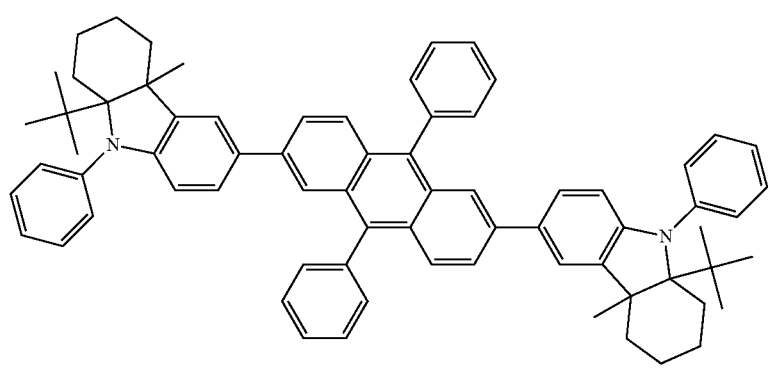
Formula 965
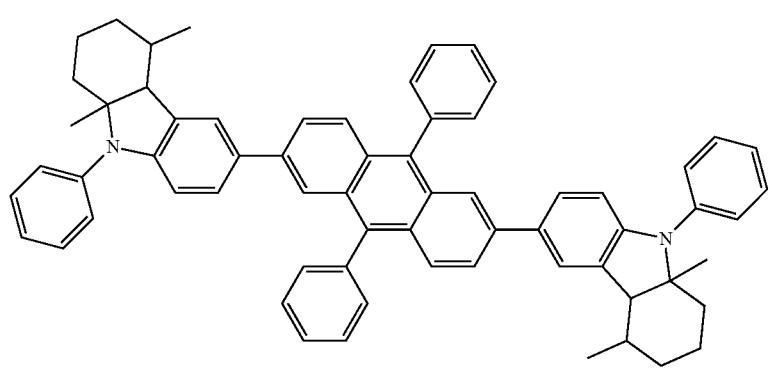

-continued
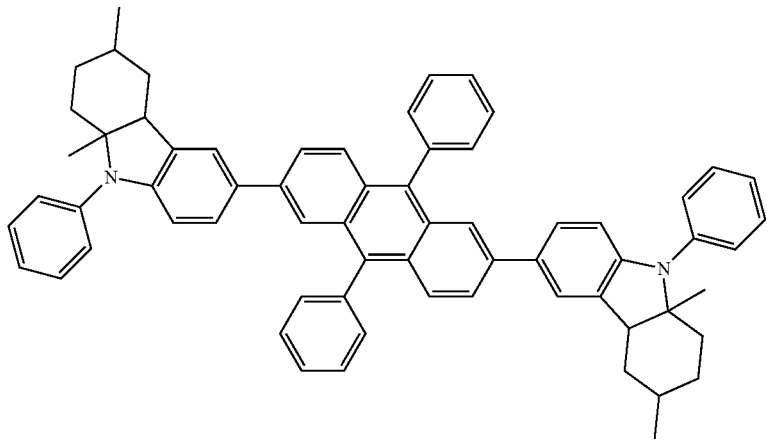
Formula 966
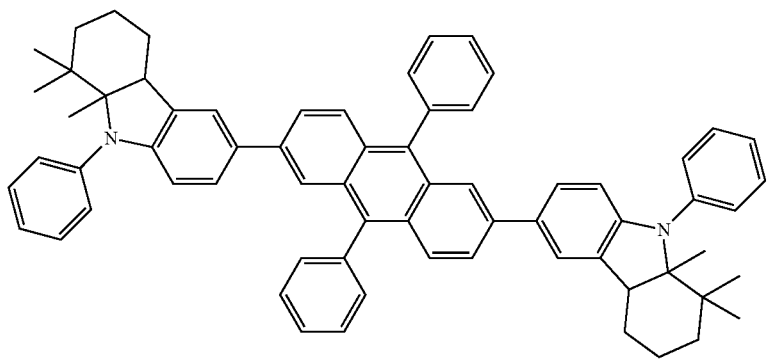
Formula 967
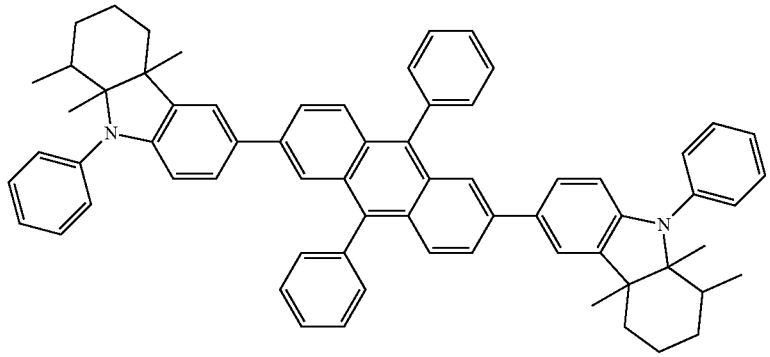
Formula 968
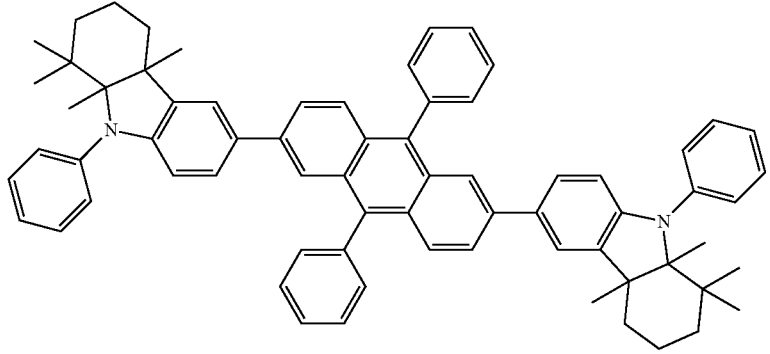
Formula 969

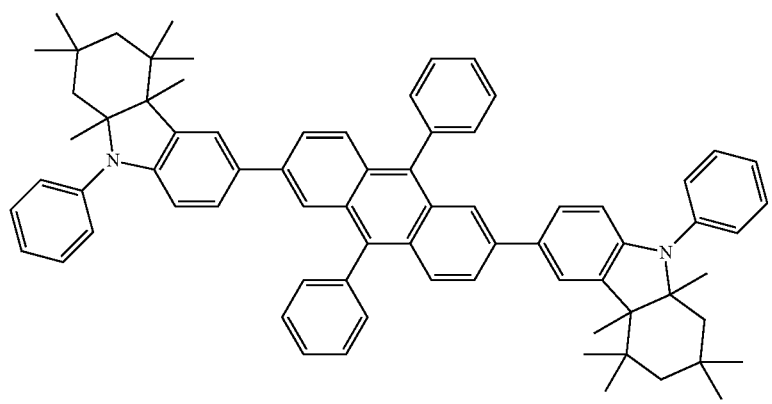
Formula 970
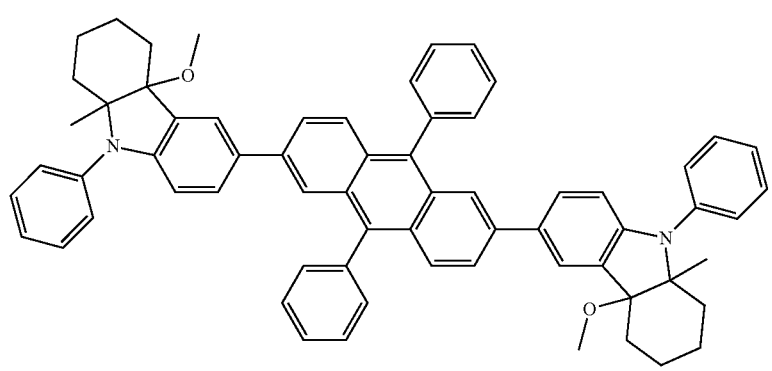
Formula 971
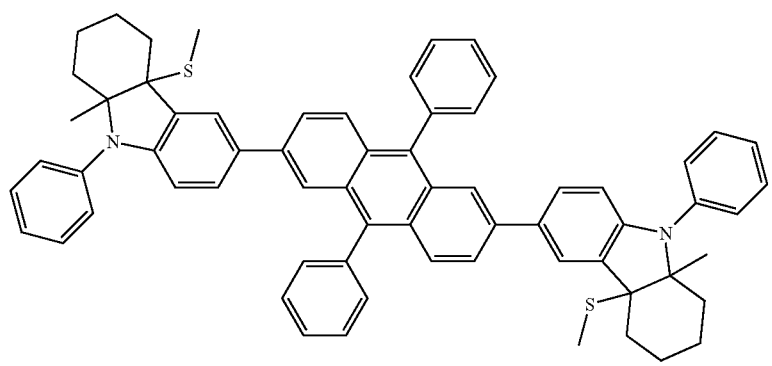
Formula 972
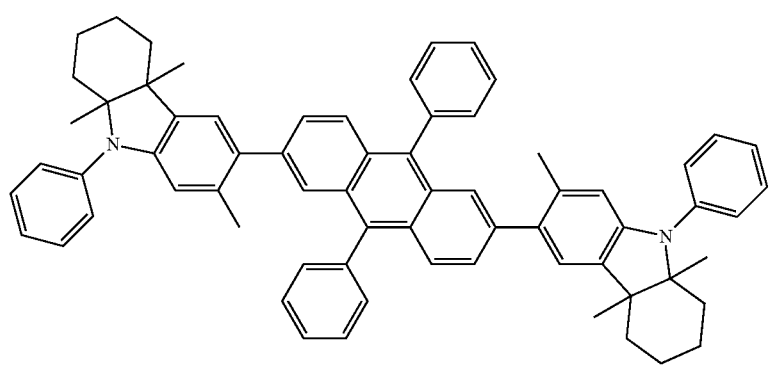
Formula 973

-continued
Formula 974
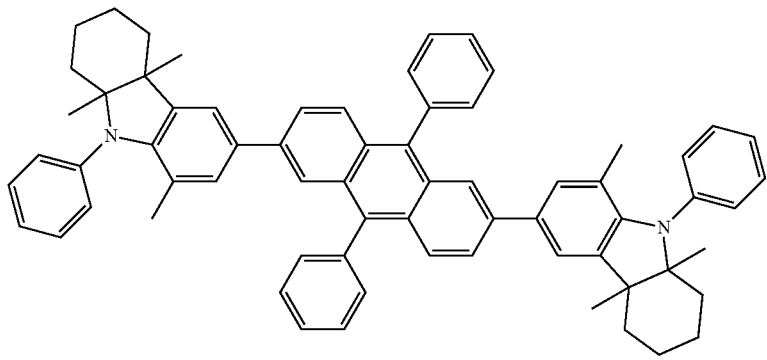
Formula 975
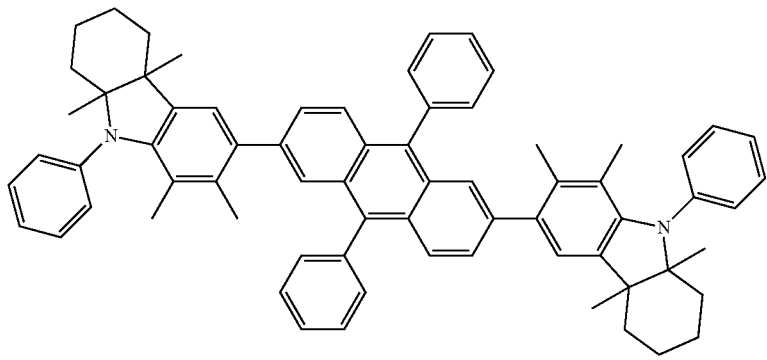
Formula 976
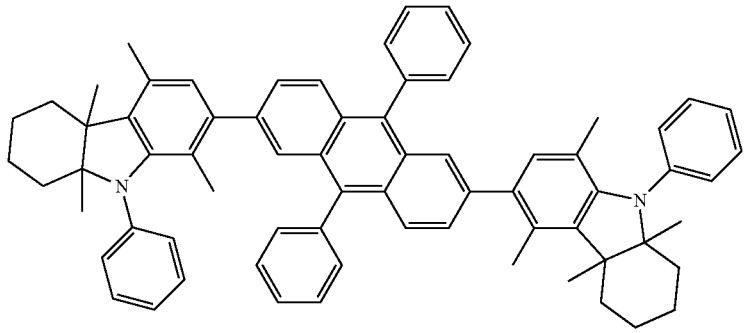
Formula 977
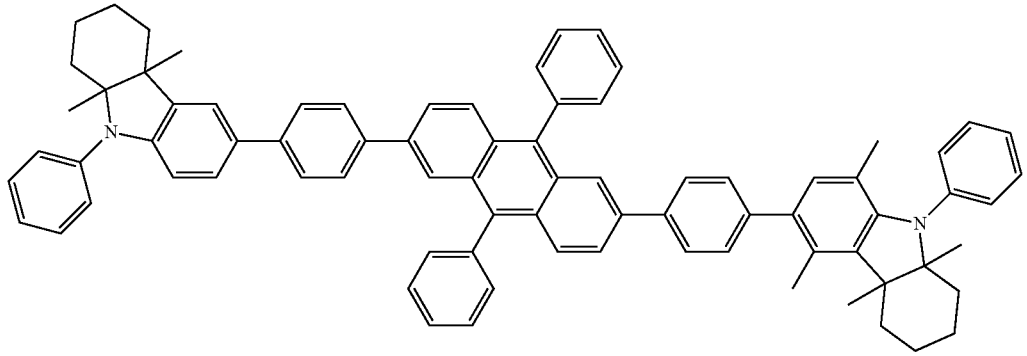

Formula 978
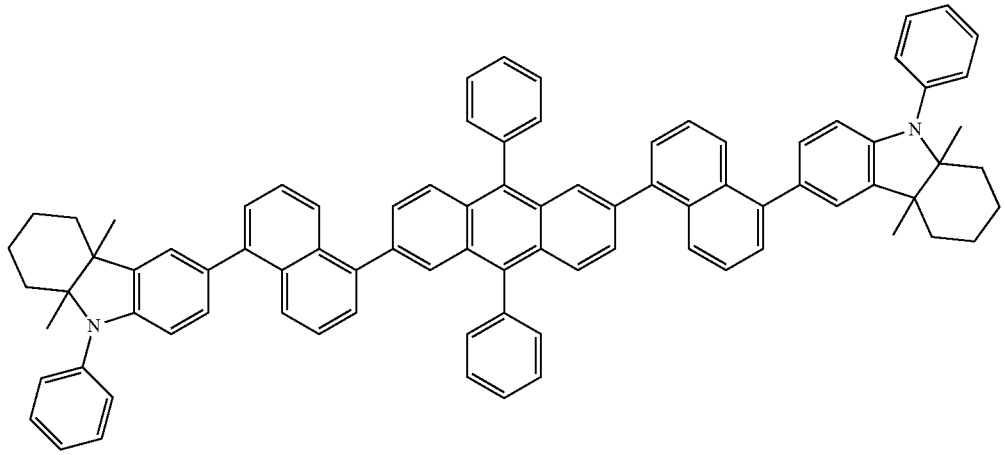
Formula 979
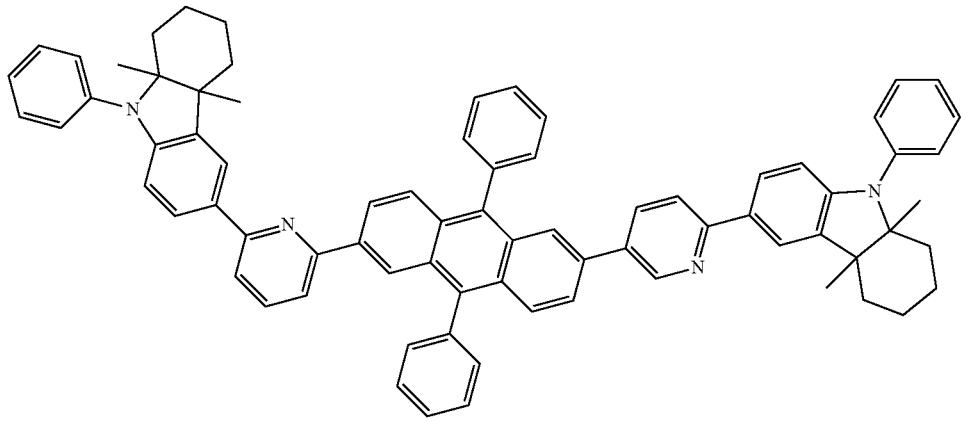
Formula 980
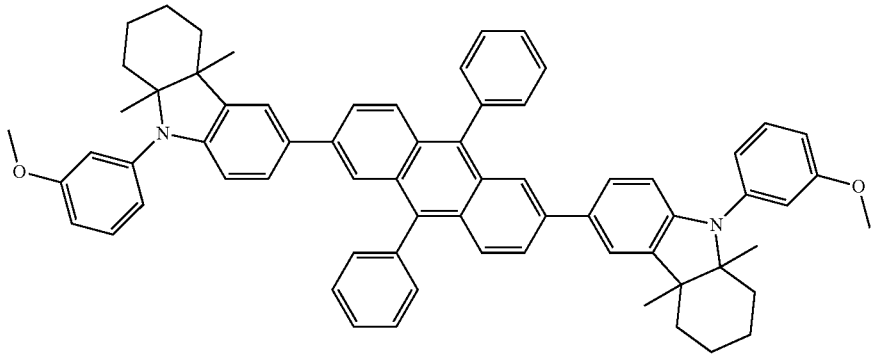
Formula 981
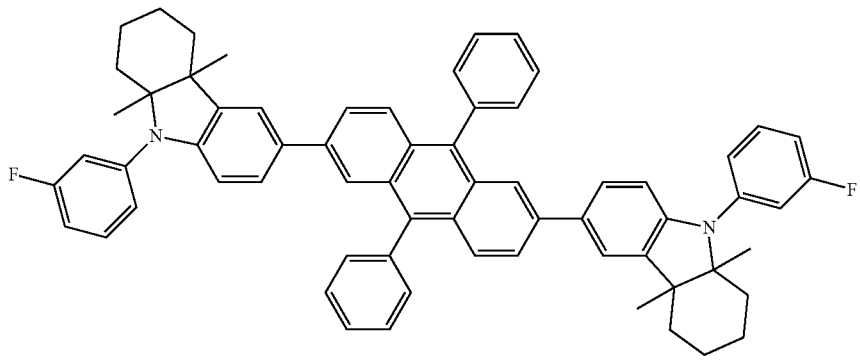

-continued
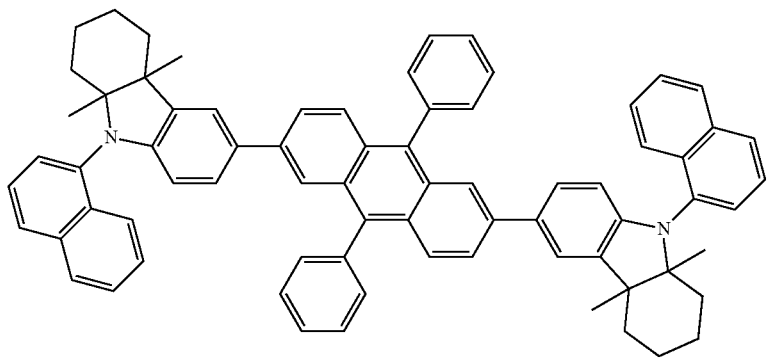
Formula 982
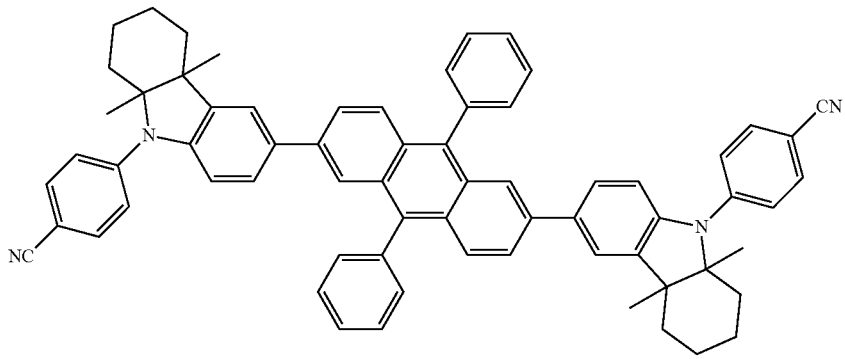
Formula 983
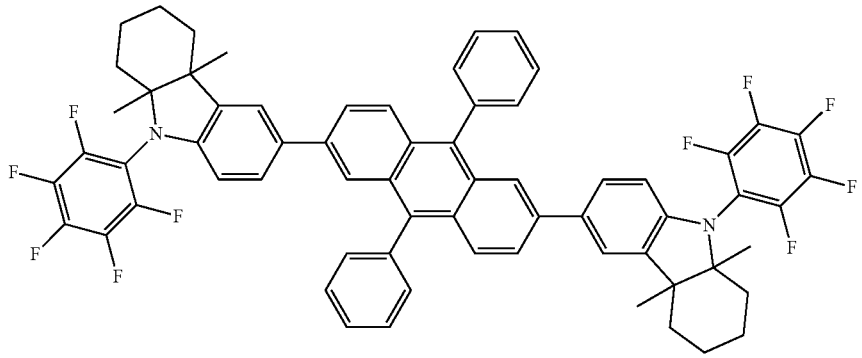
Formula 984
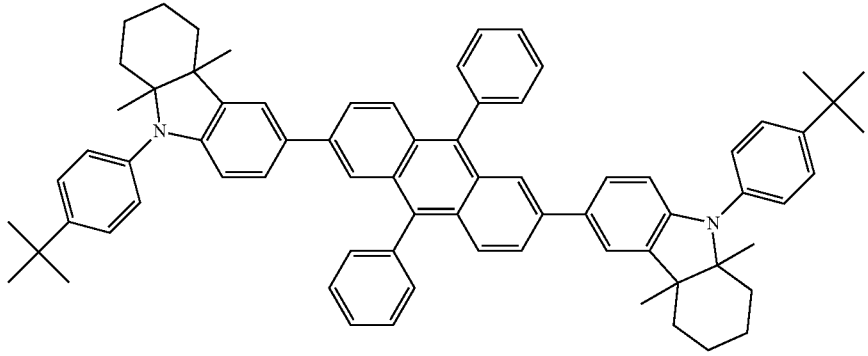
Formula 985

Formula 986
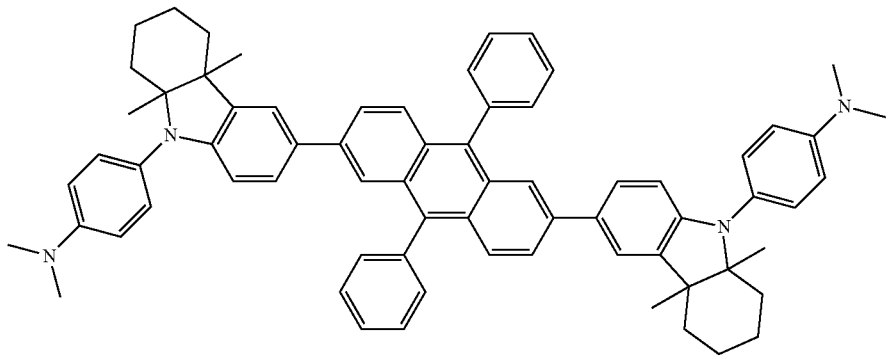
Formula 987
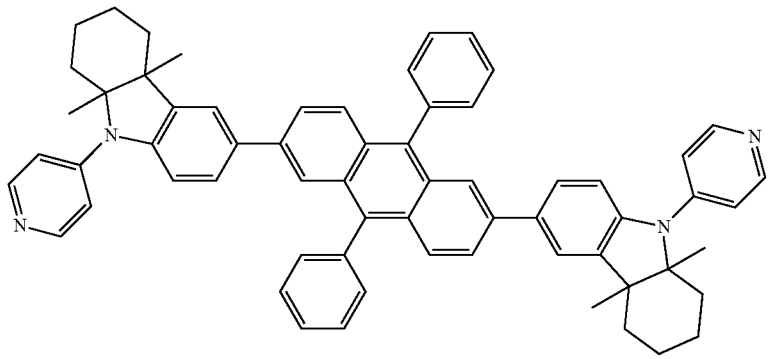
Formula 988
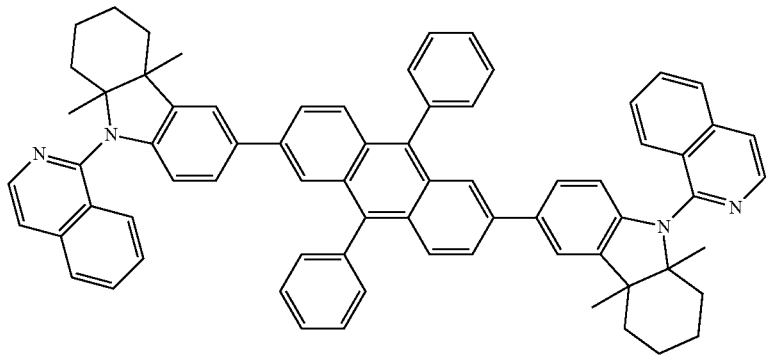
Formula 989
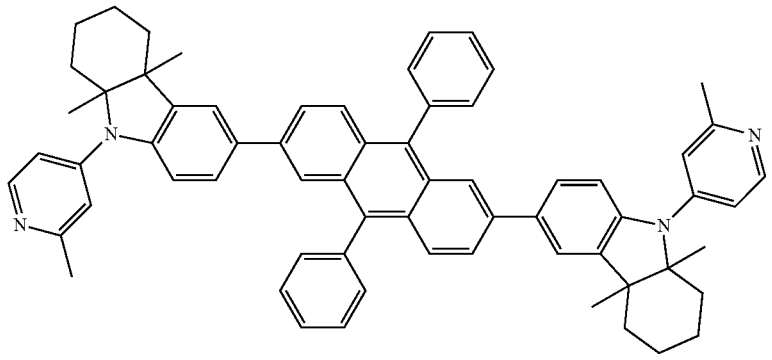

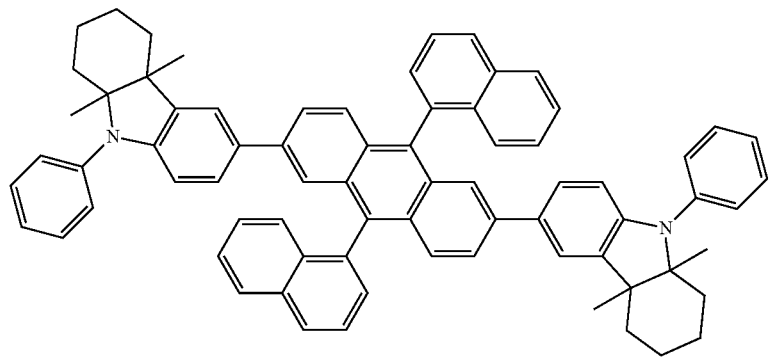
Formula 990
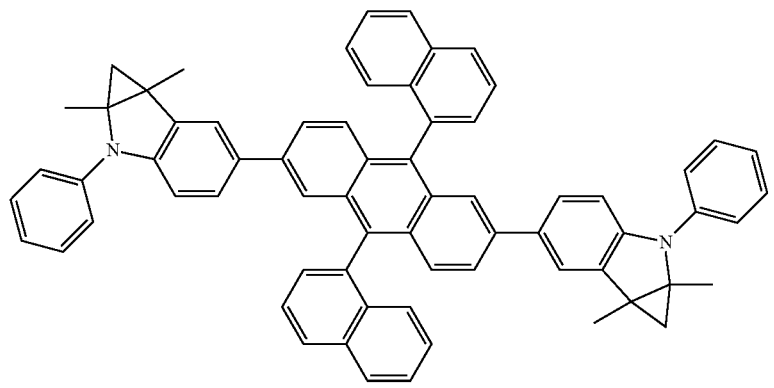
Formula 991

Formula 992

Formula 993

Formula 994
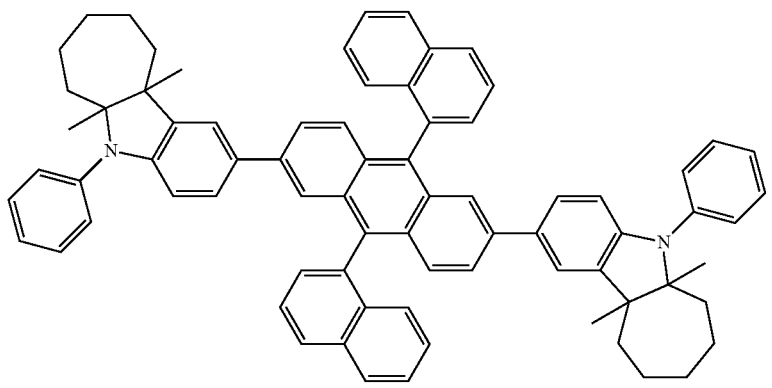
Formula 995
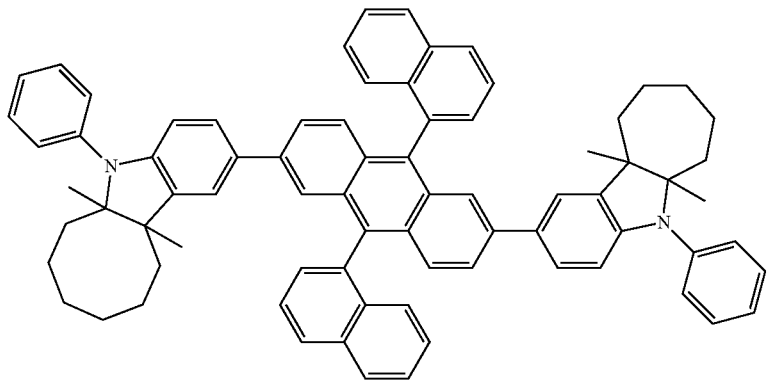
Formula 996
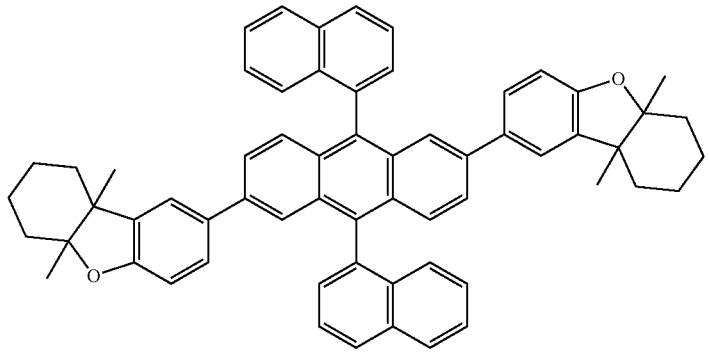
Formula 997
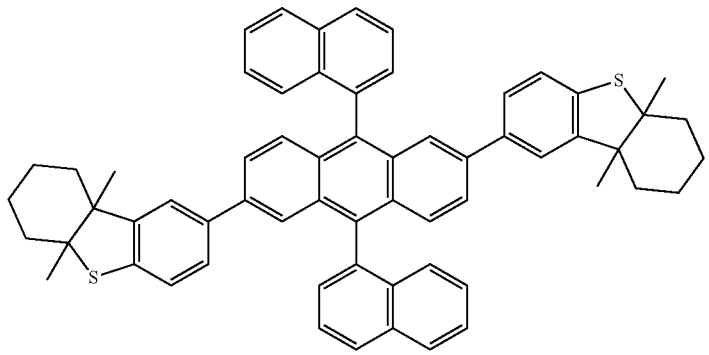

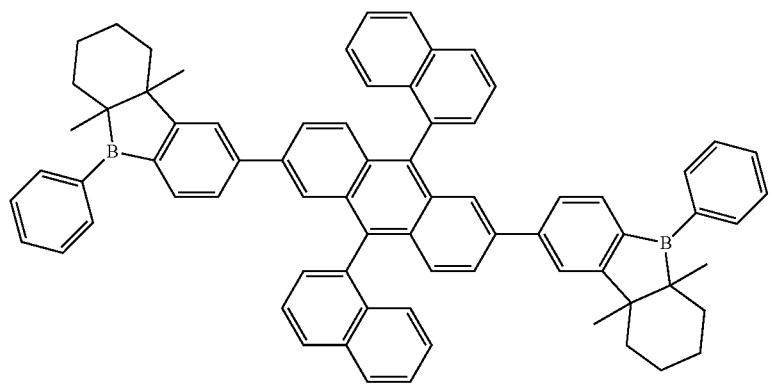
Formula 998
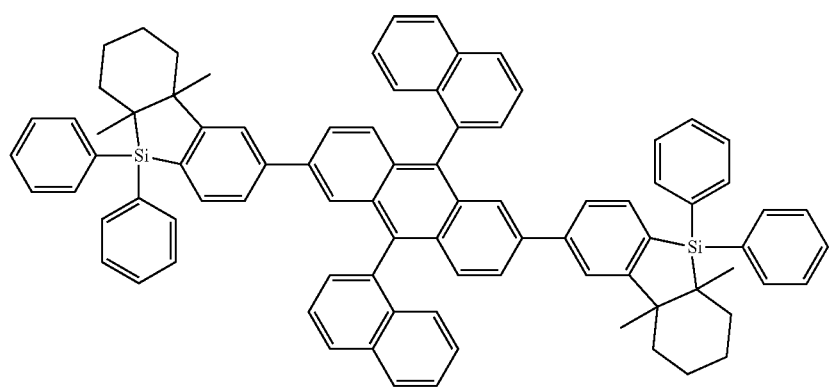
Formula 999
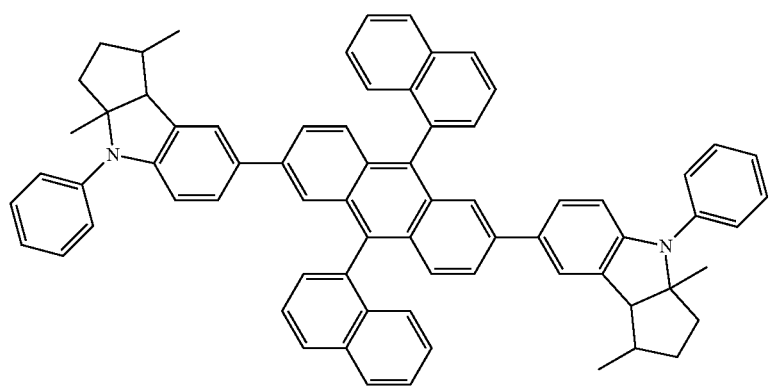
Formula 1000

Formula 1001

Formula 1002
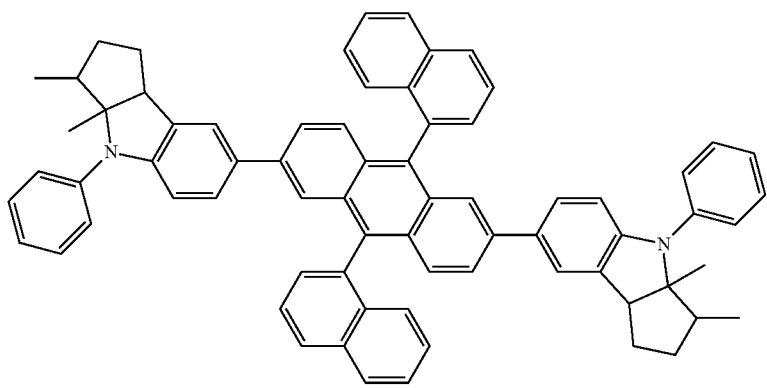
Formula 1003
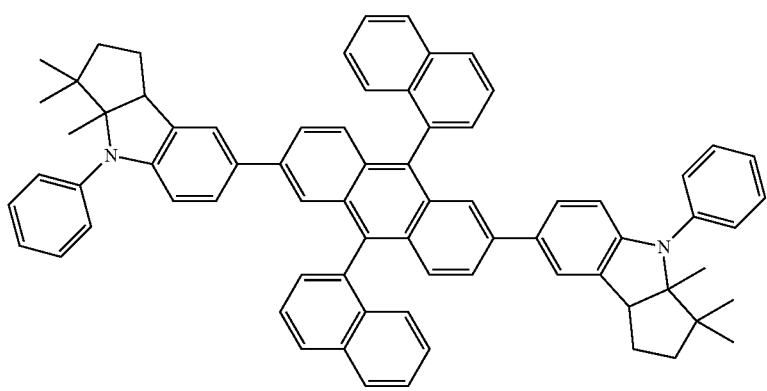
Formula 1004
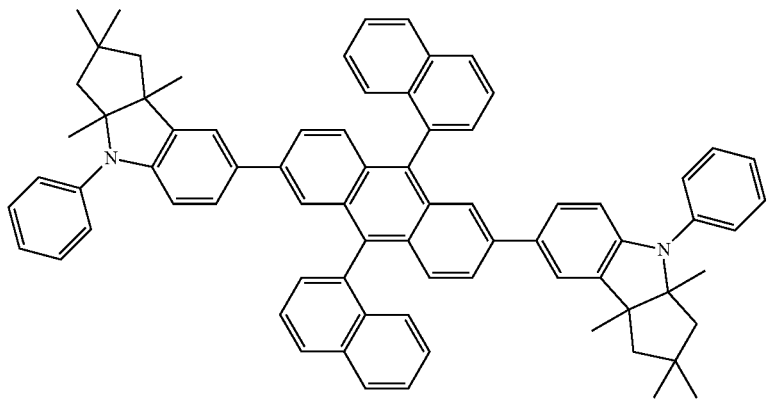

-continued
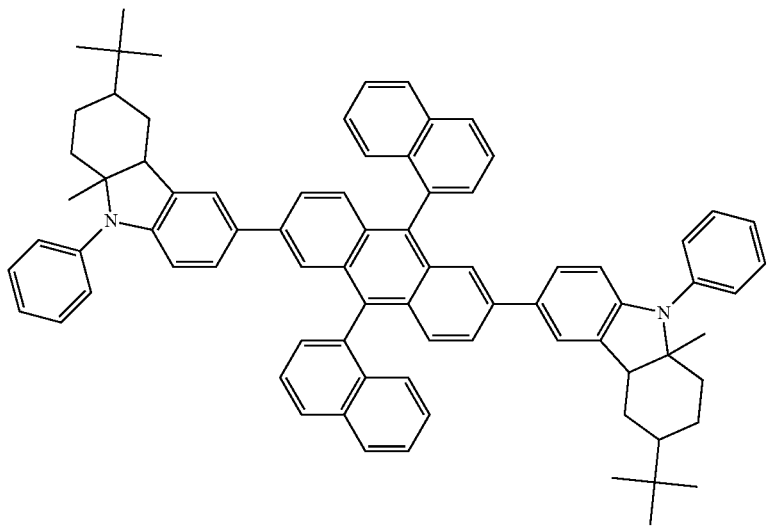
Formula 1005
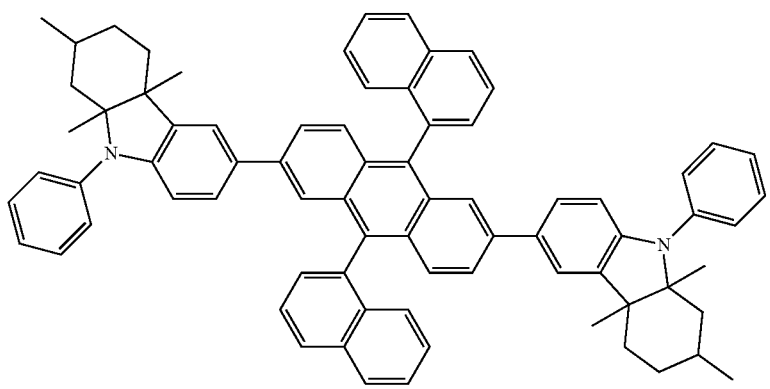
Formula 1006
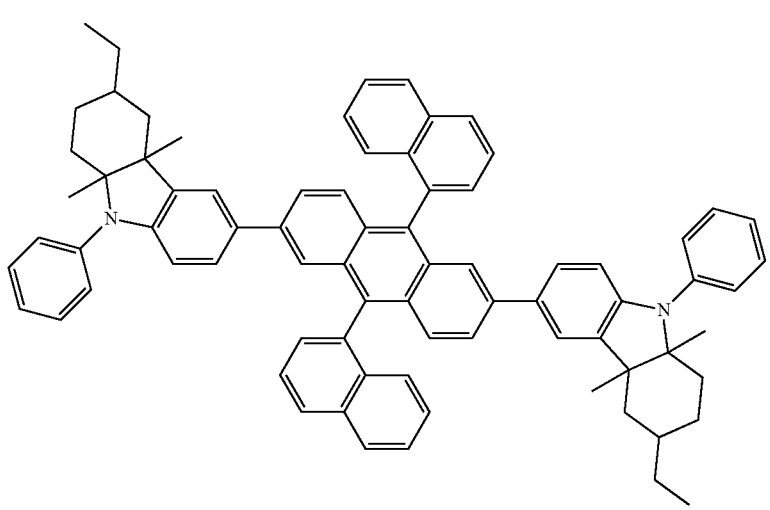
Formula 1007

-continued
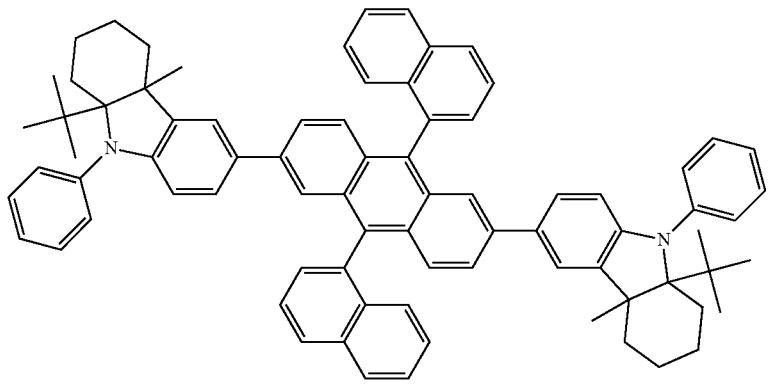
Formula 1008

Formula 1009
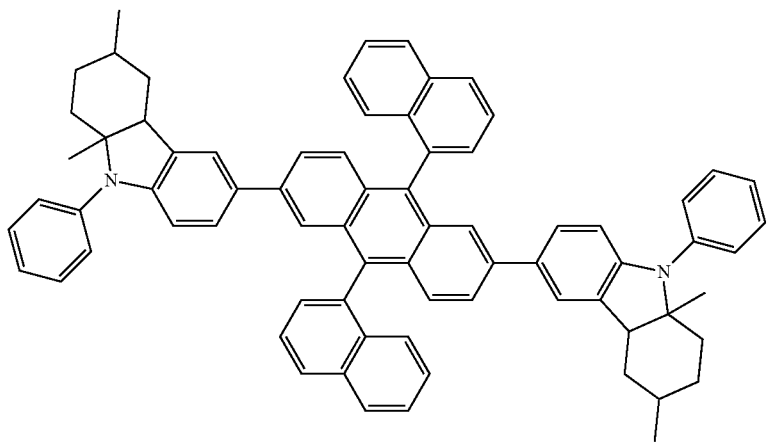
Formula 1010
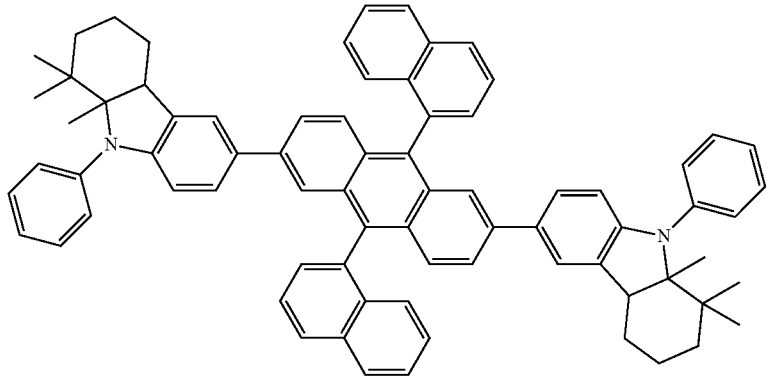
Formula 1011

Formula 1012
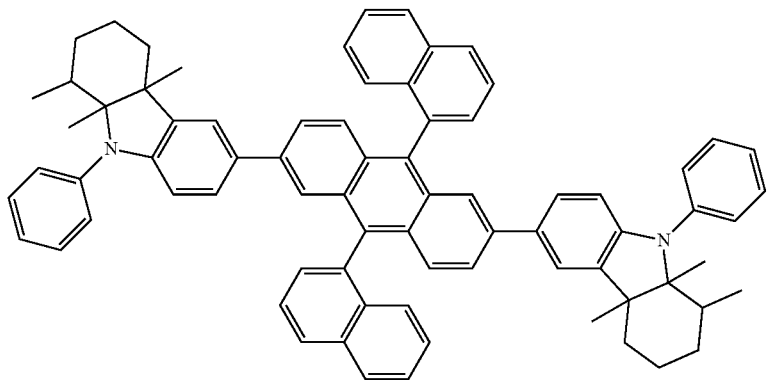
Formula 1013
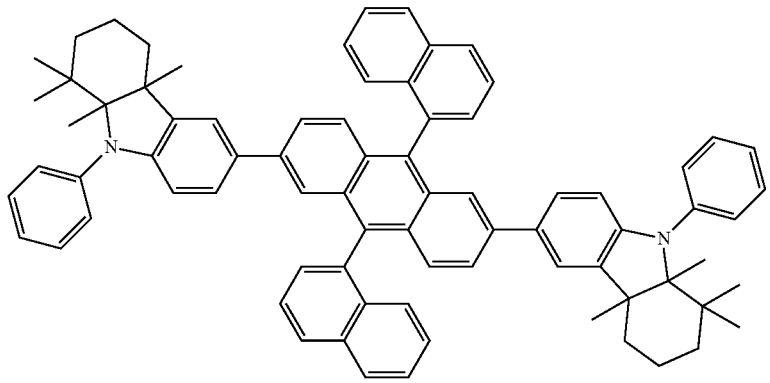
Formula 1014
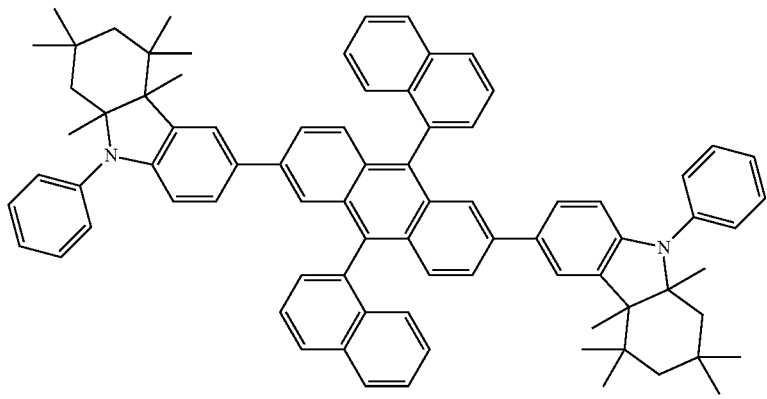
Formula 1015
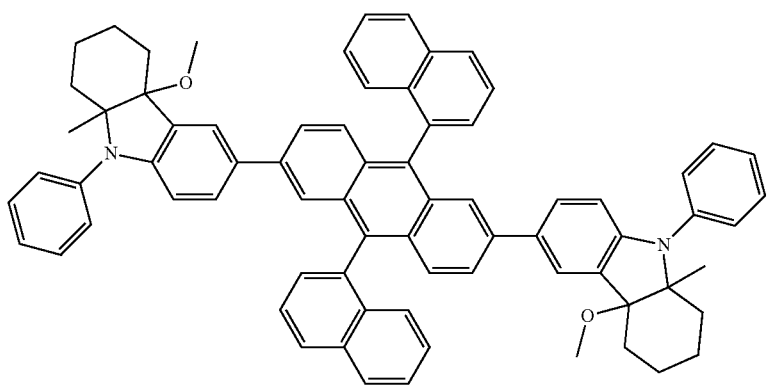

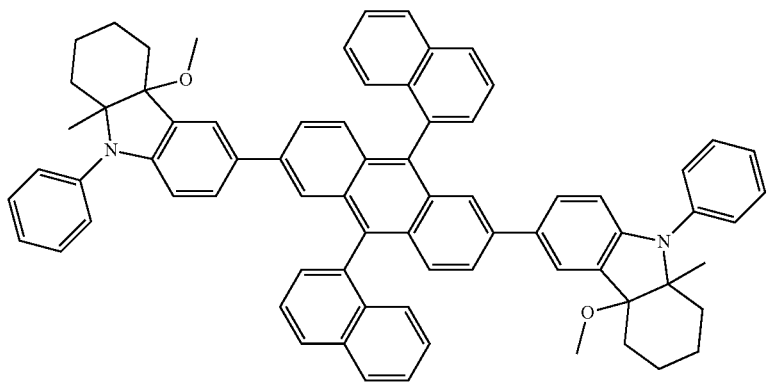
Formula 1015
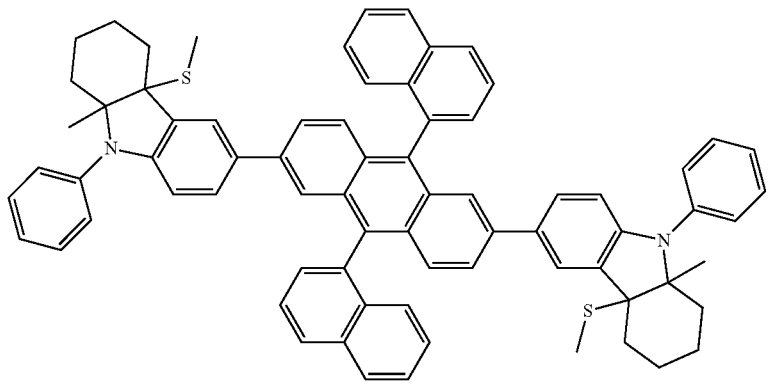
Formula 1016
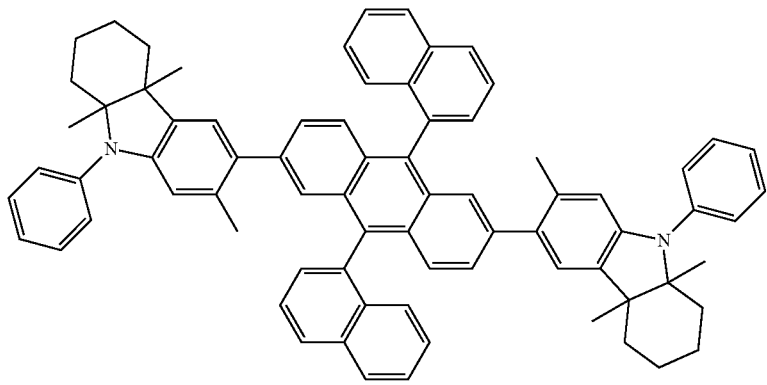
Formula 1017
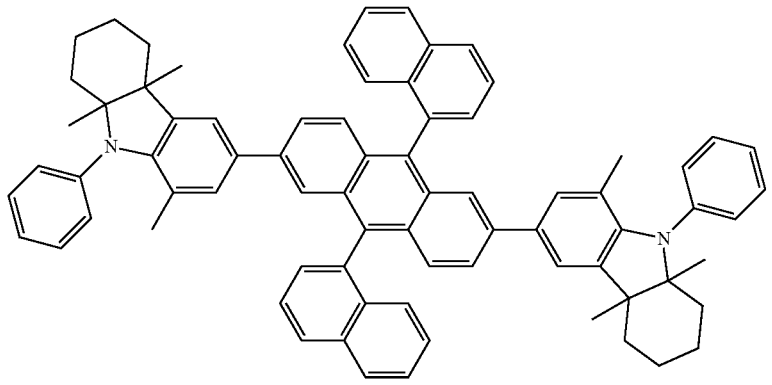
Formula 1018

-continued
Formula 1019
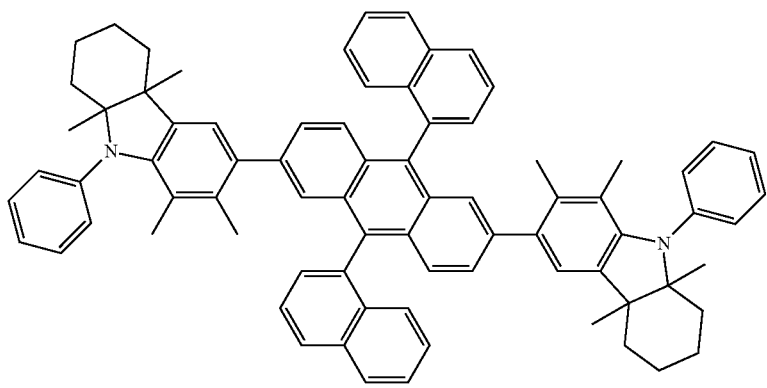
Formula 1020
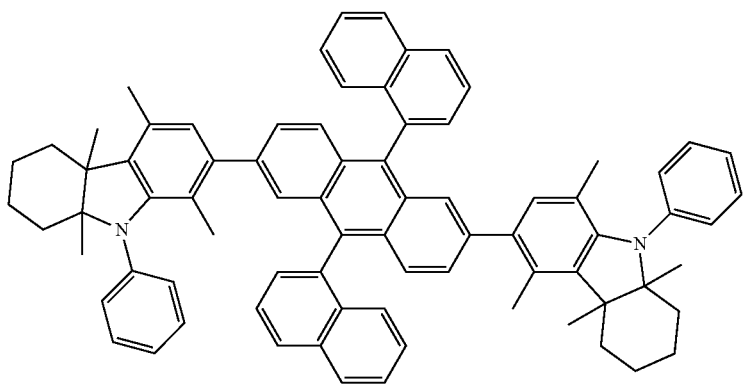
Formula 1021
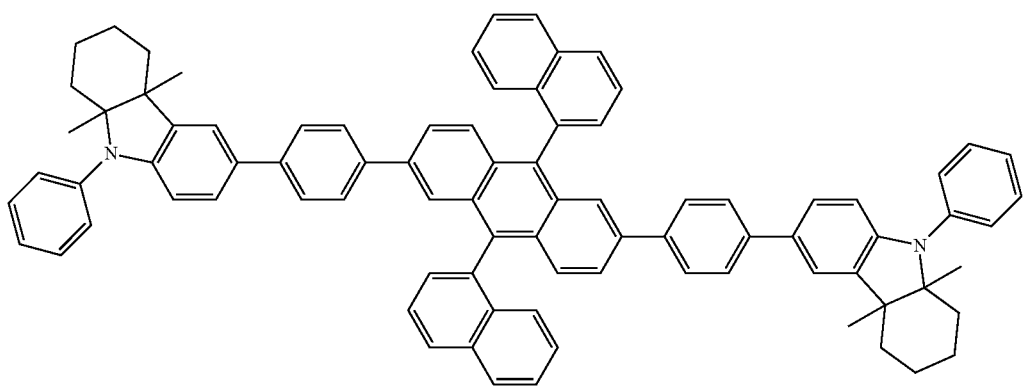
Formula 1022
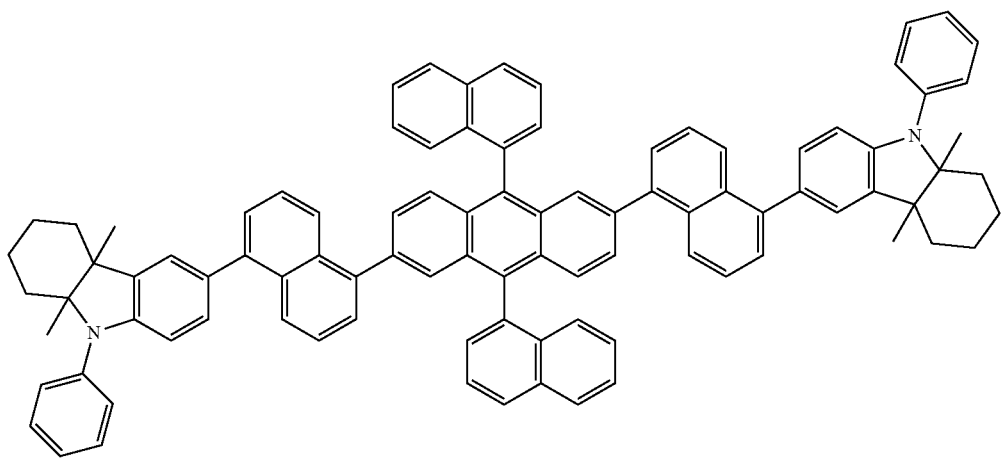

-continued
Formula 1023
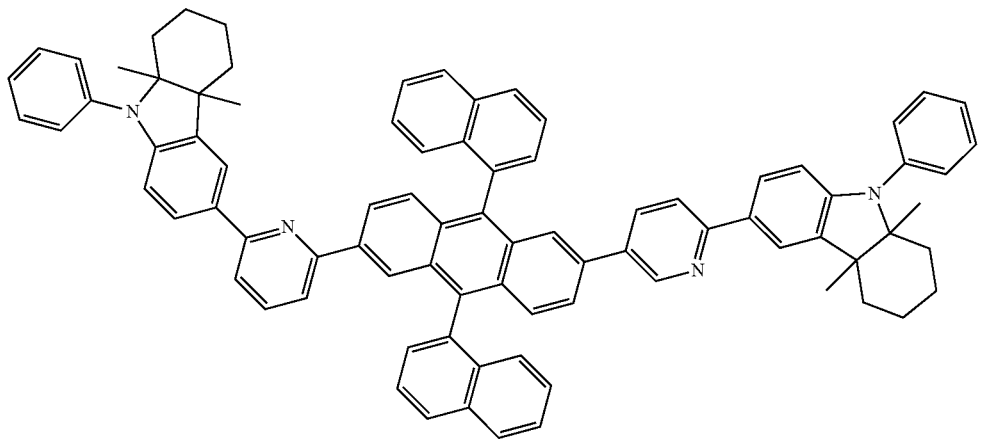
Formula 1024
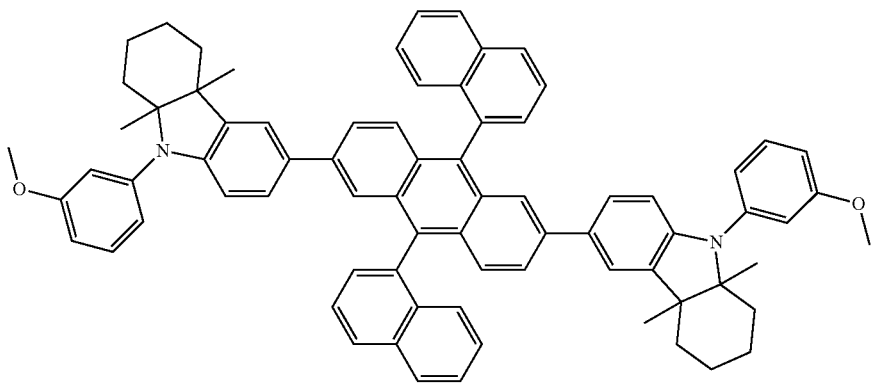
Formula 1025
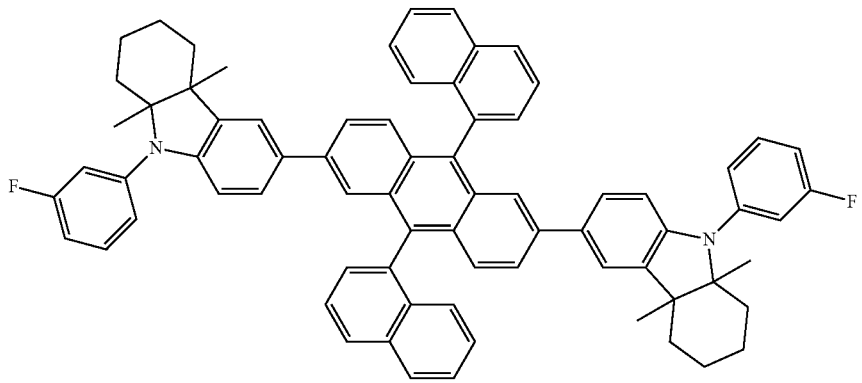
Formula 1026
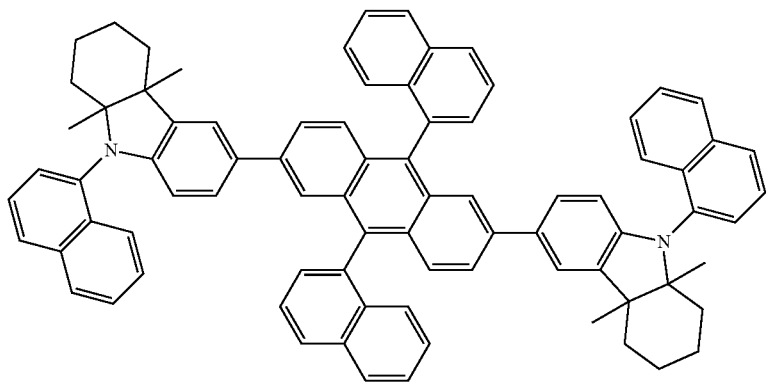

-continued
Formula 1027
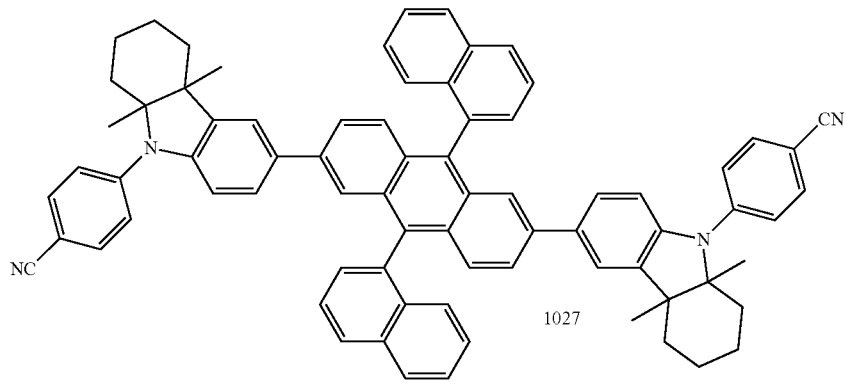
Formula 1028
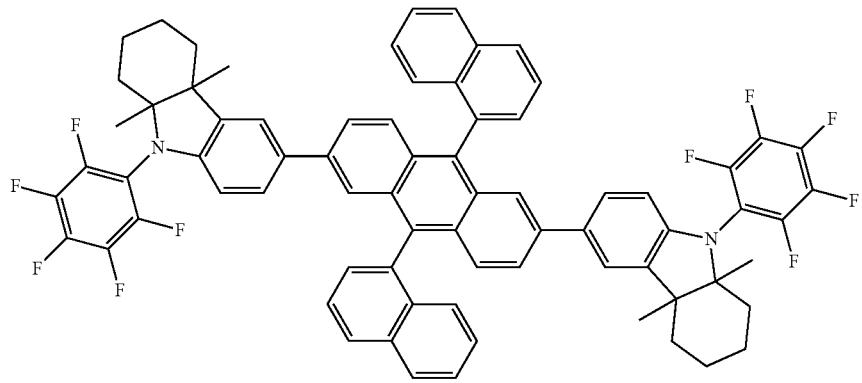
Formula 1029
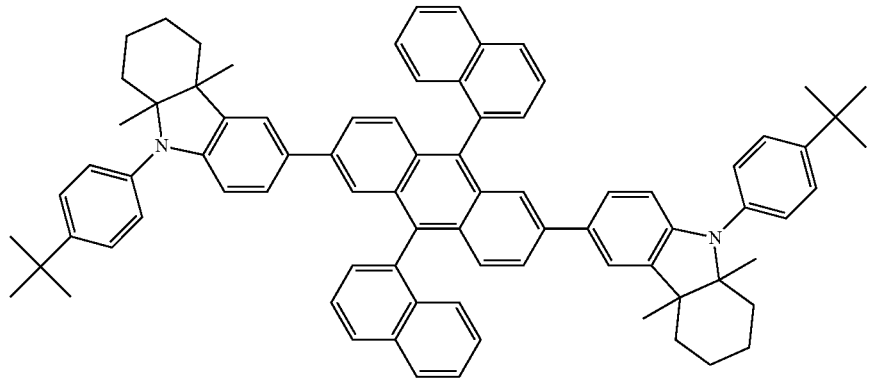
Formula 1030
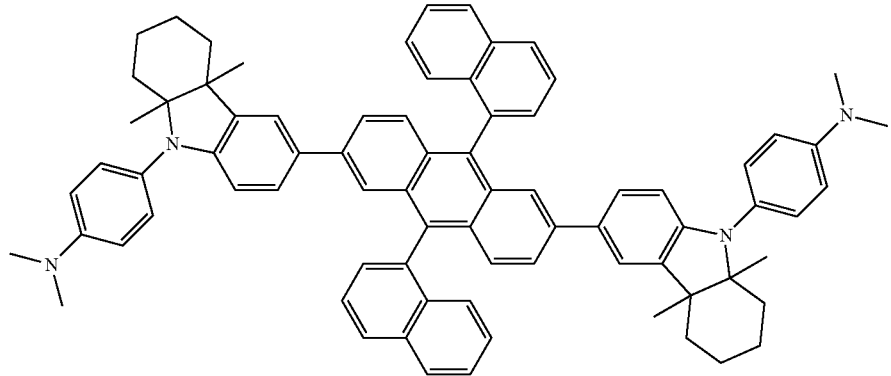

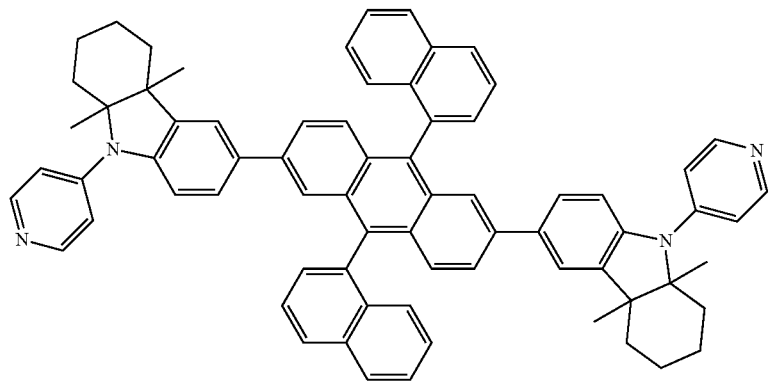
Formula 1031
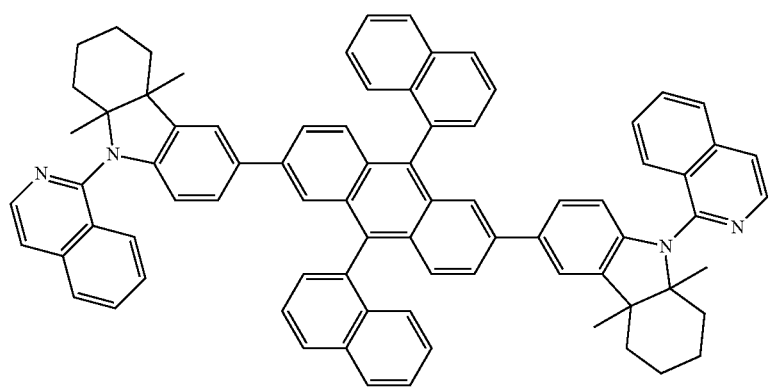
Formula 1032
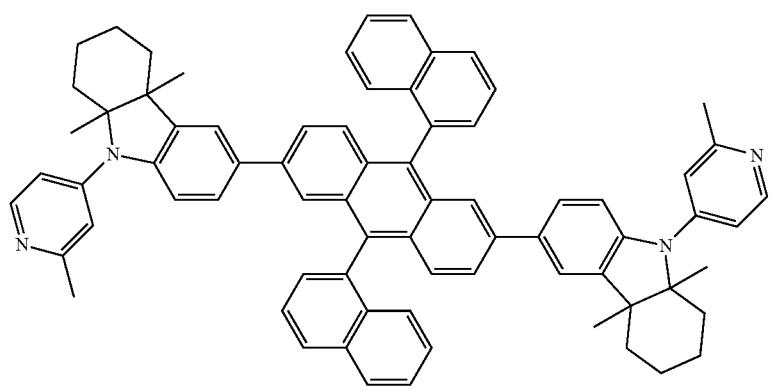
Formula 1033

Formula 1034
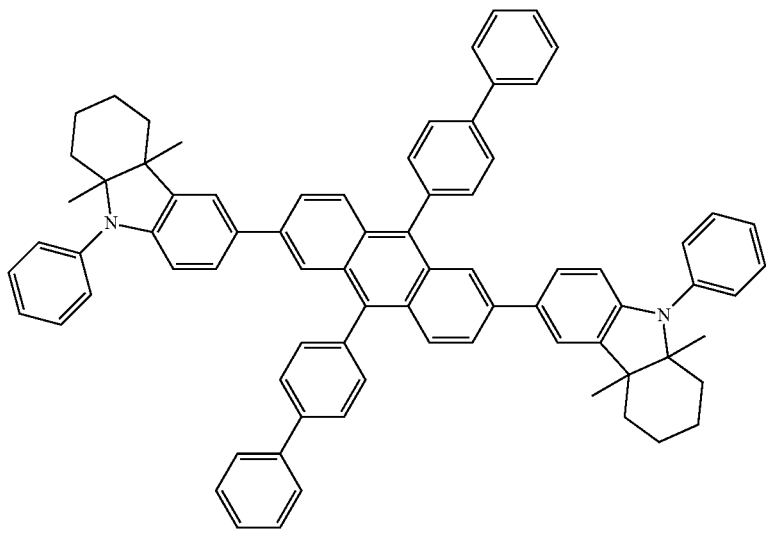
Formula 1035
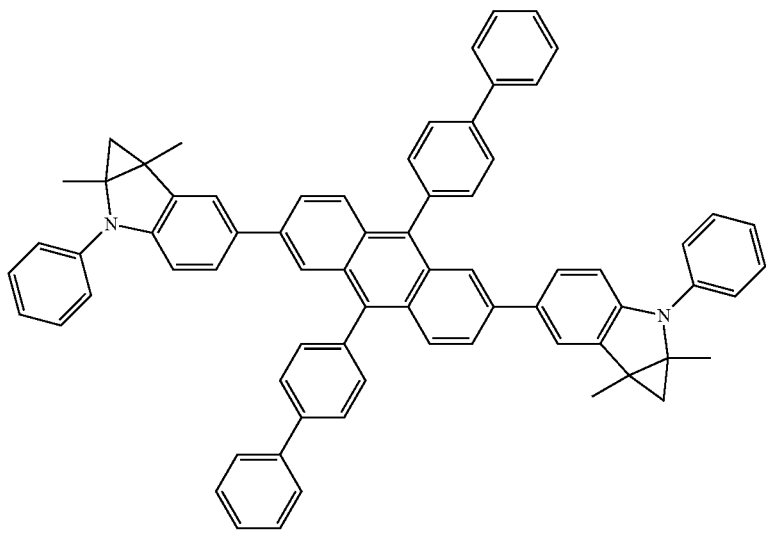
Formula 1036
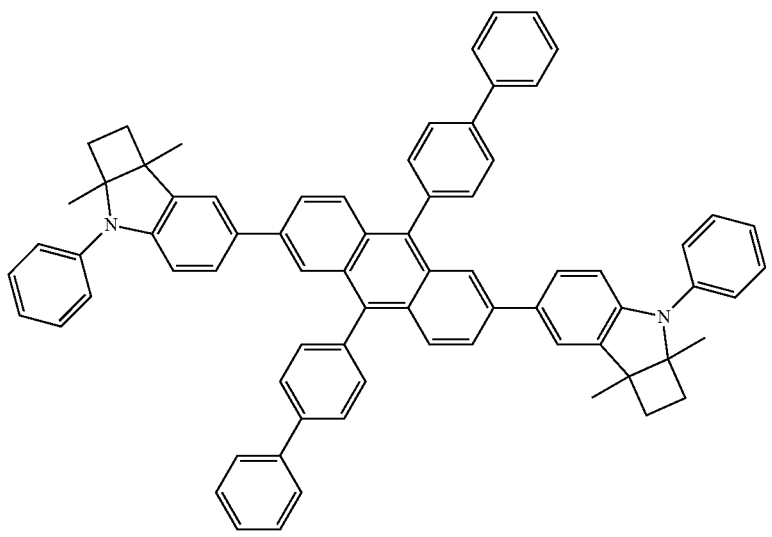

Formula 1037
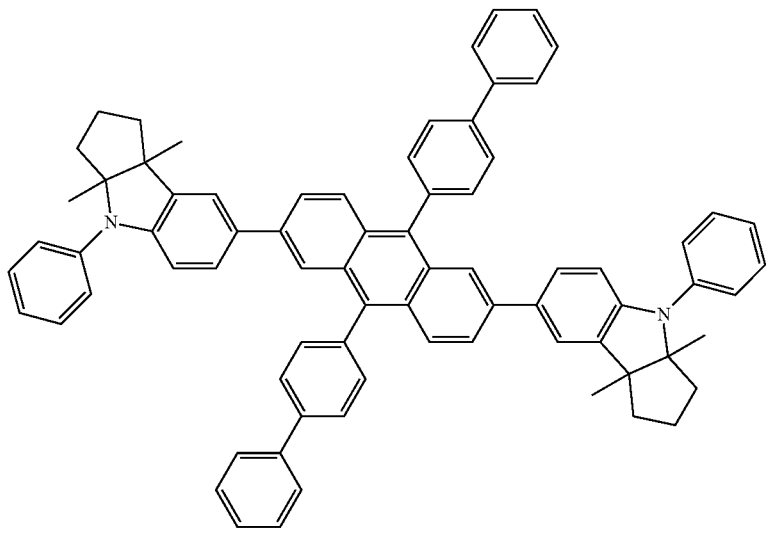
Formula 1038
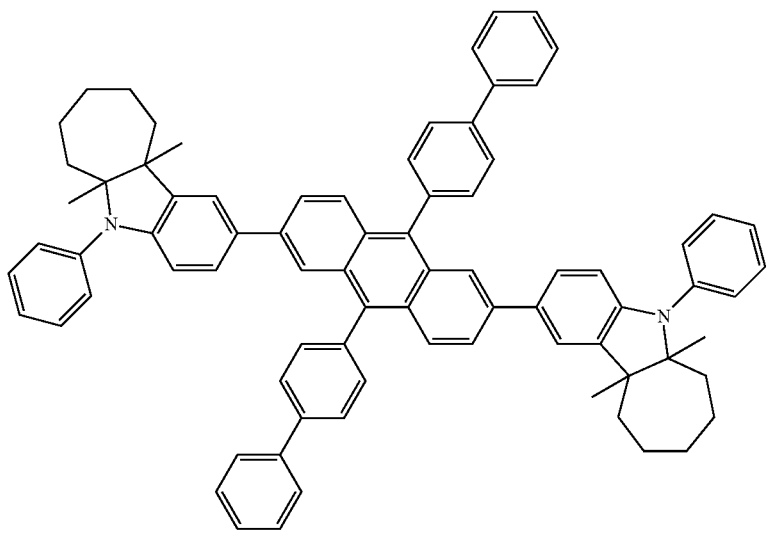
Formula 1039
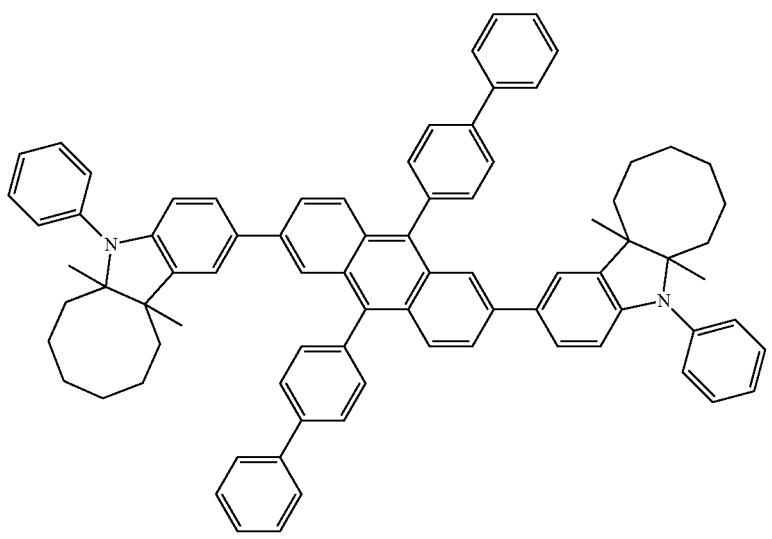

-continued
Formula 1040
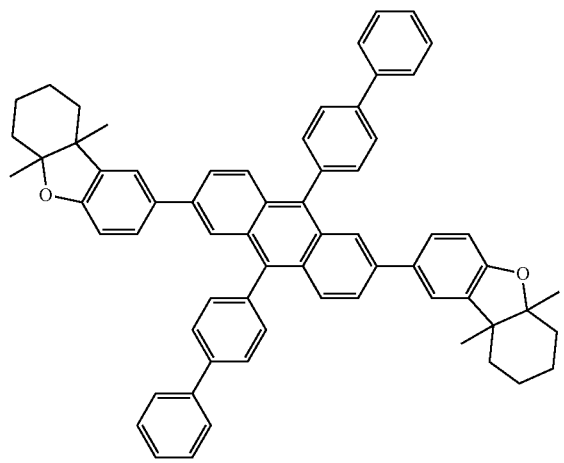
Formula 1041
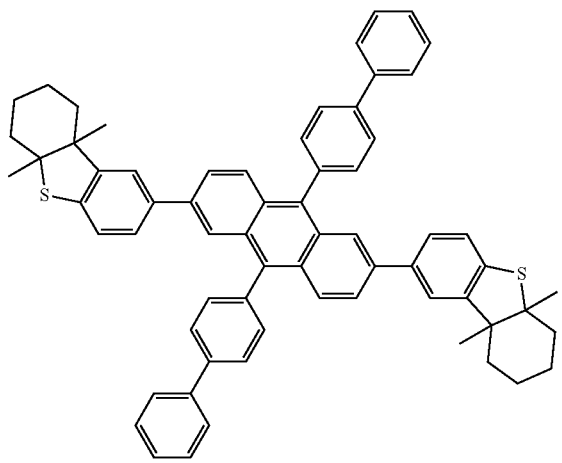
Formula 1042
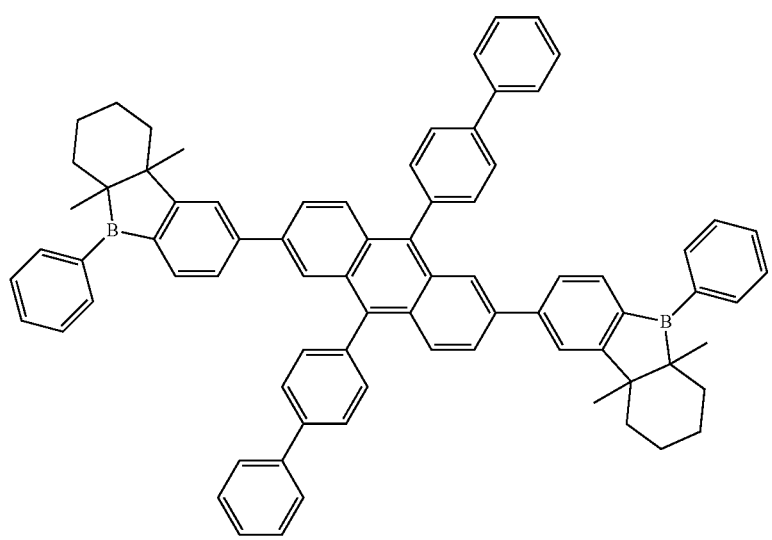
Formula 1043
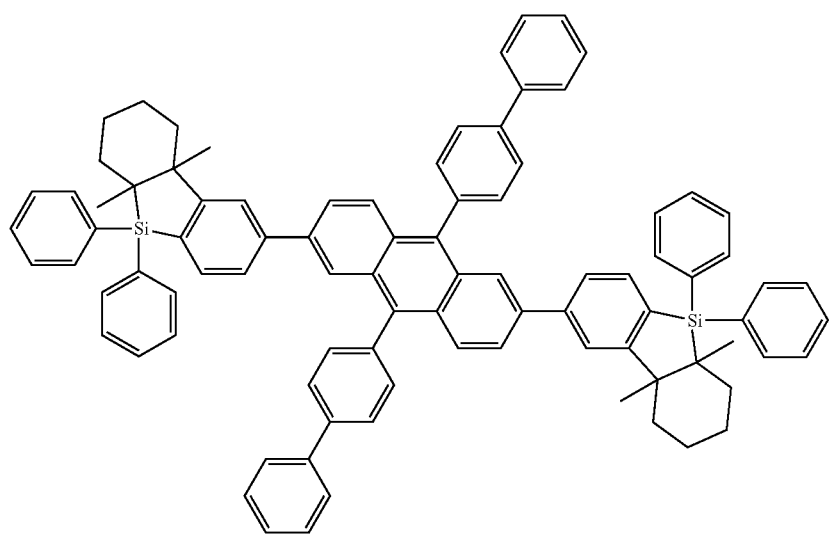

Formula 1044
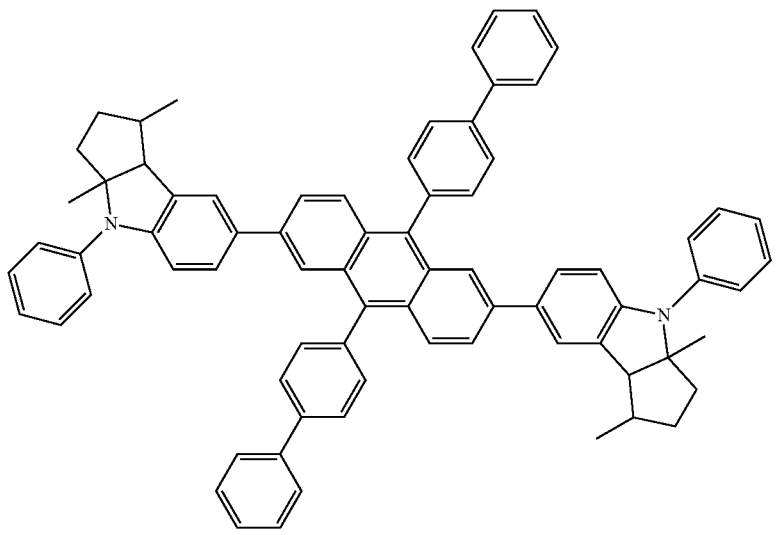
Formula 1045
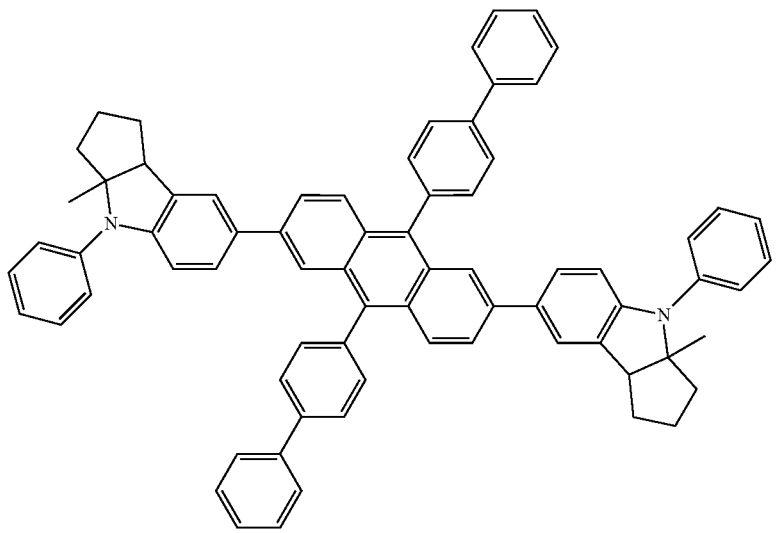
Formula 1046
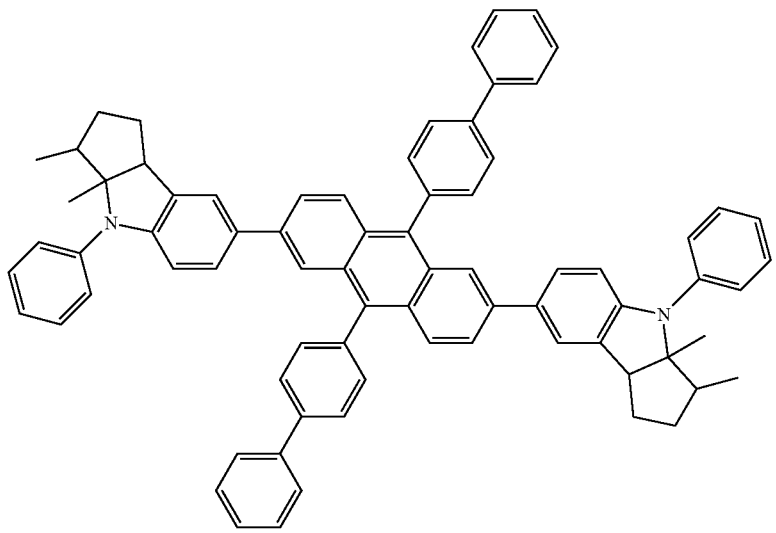

-continued
Formula 1047
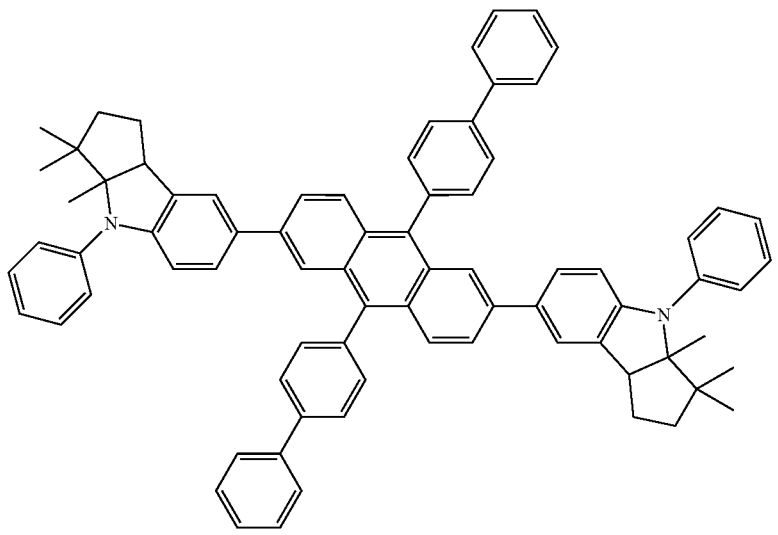
Formula 1048
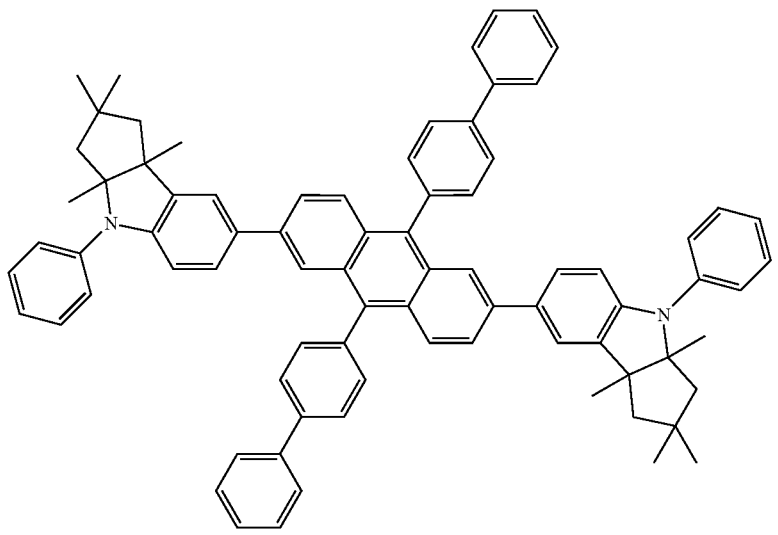
Formula 1049
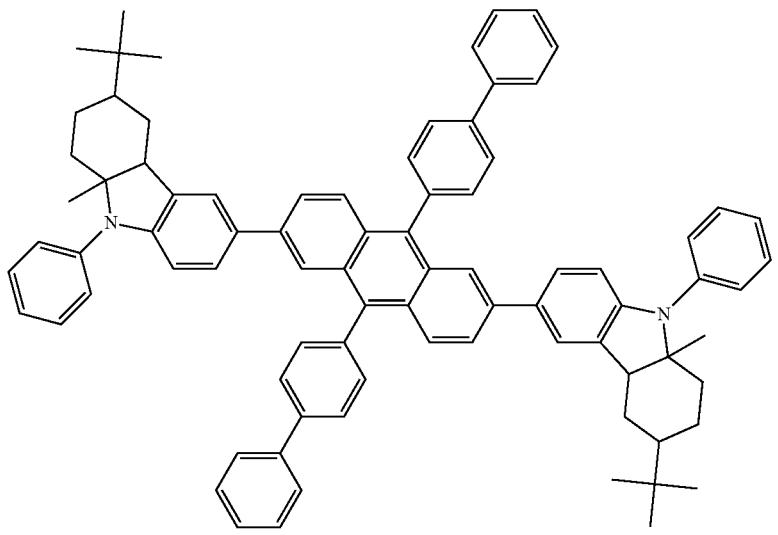

Formula 1050
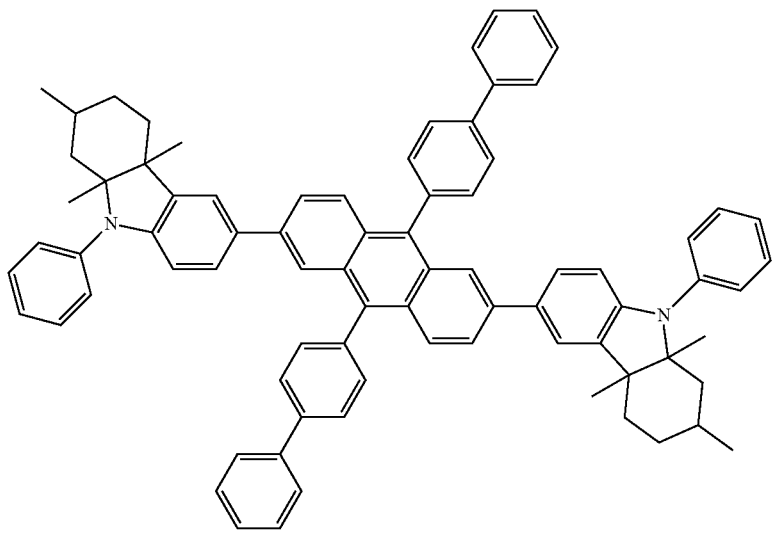
Formula 1051
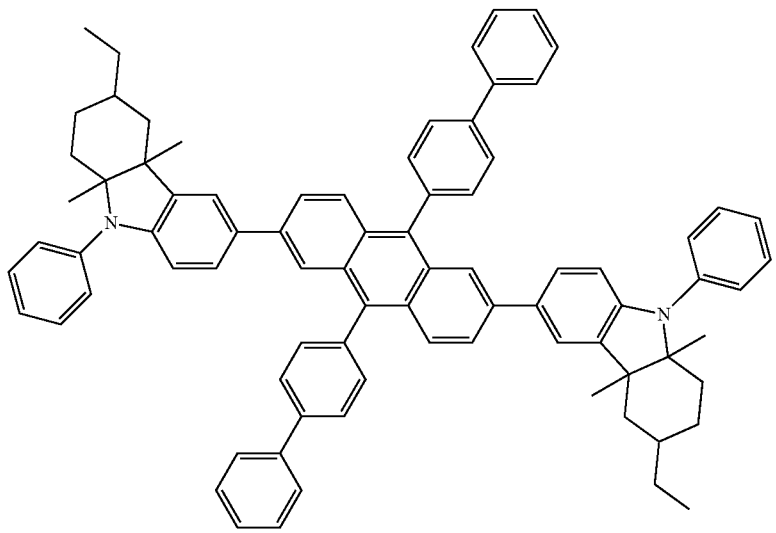
Formula 1052
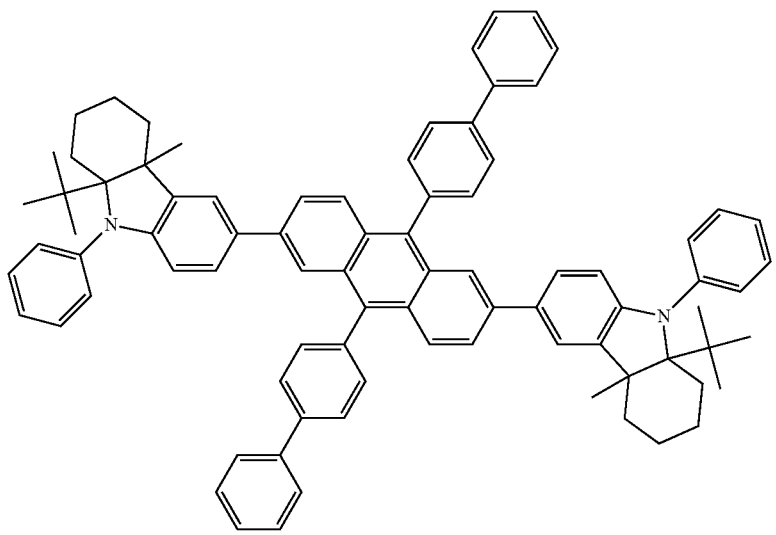

-continued
Formula 1053
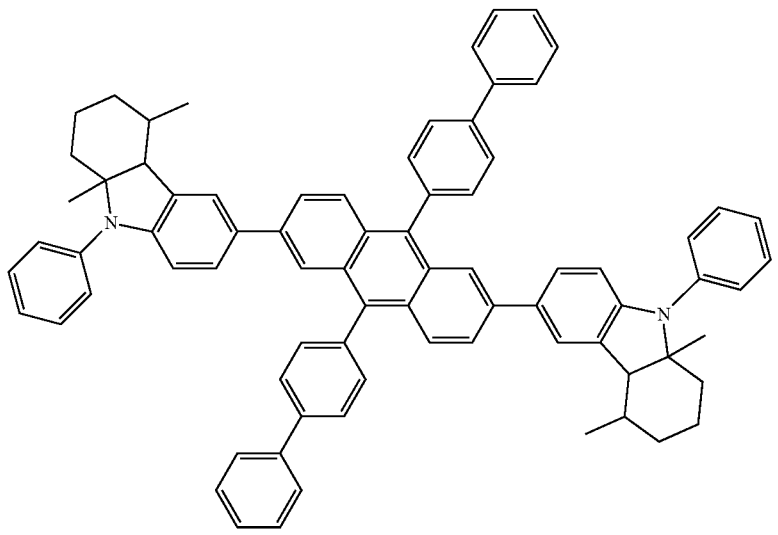
Formula 1054
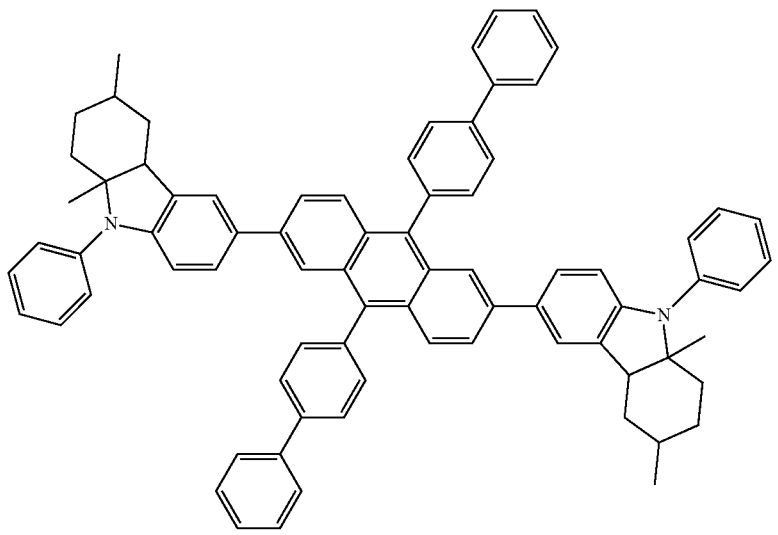
Formula 1055
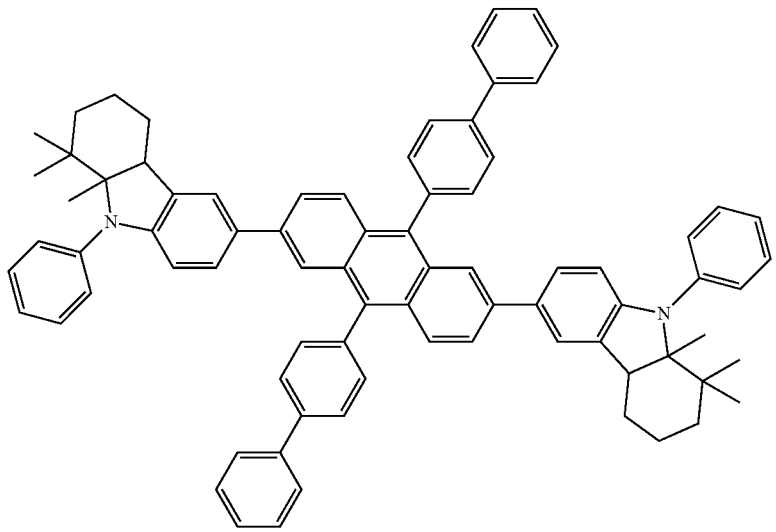

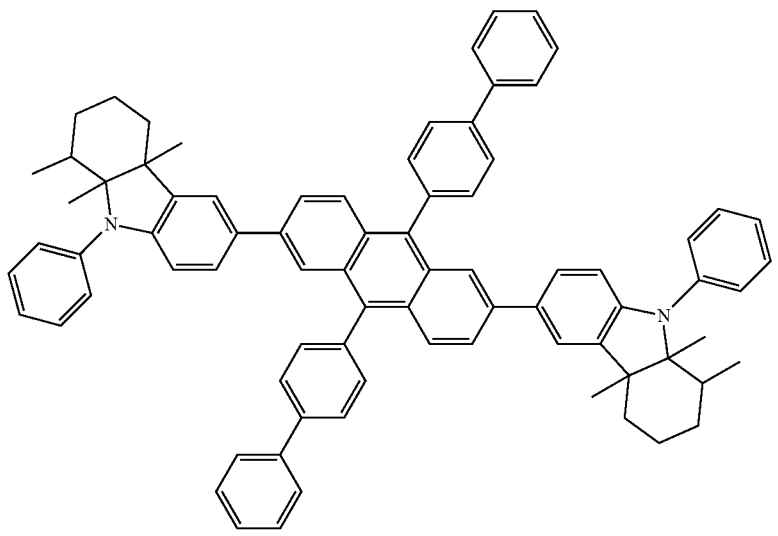
Formula 1056

Formula 1057

Formula 1058

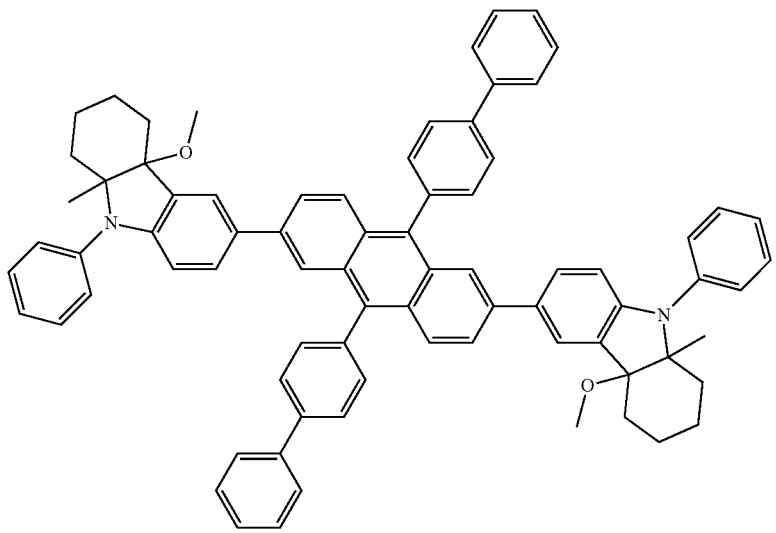
Formula 1059
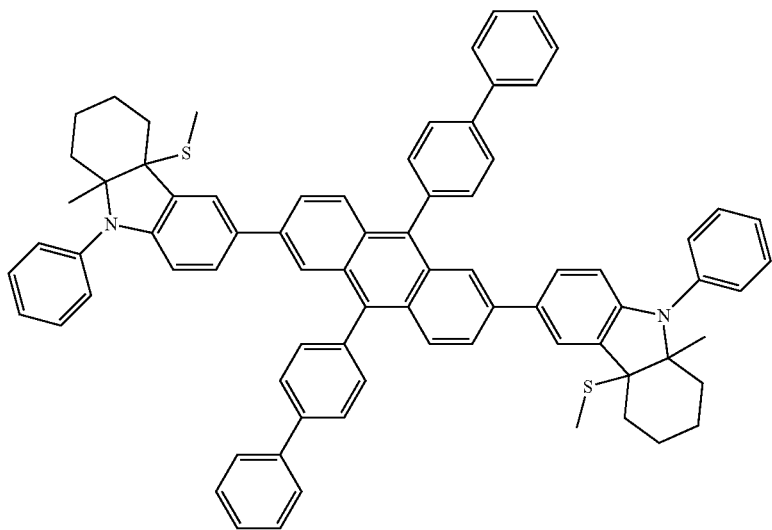
Formula 1060
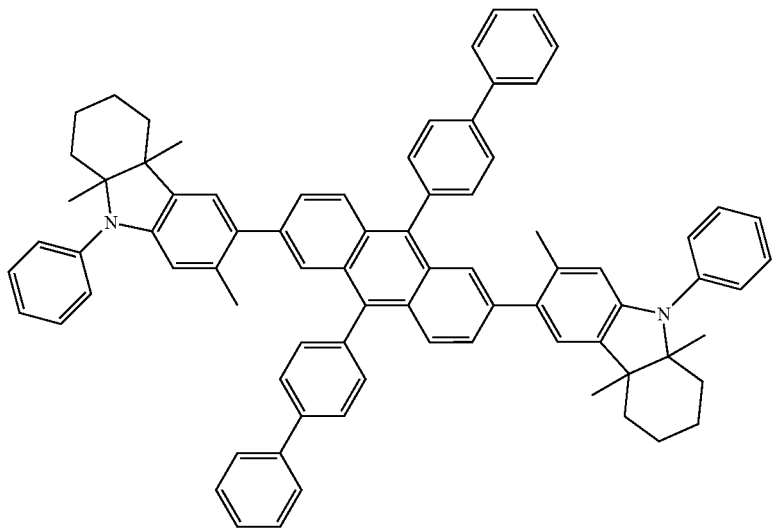
Formula 1061

-continued
Formula 1062
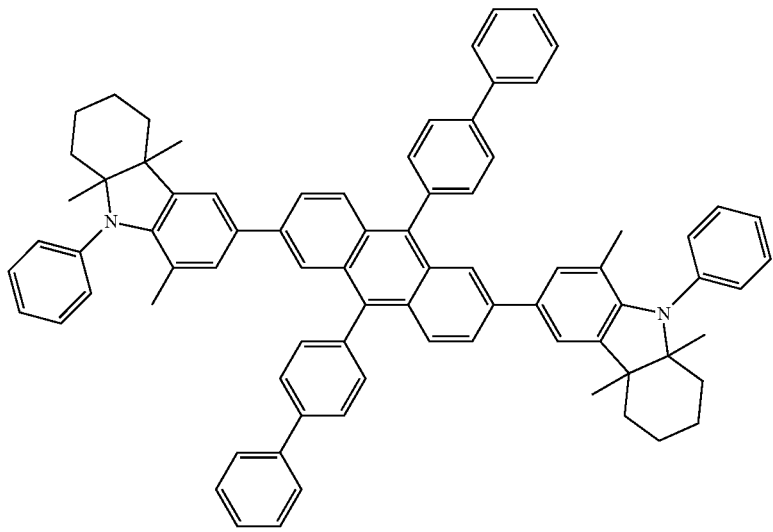
Formula 1063
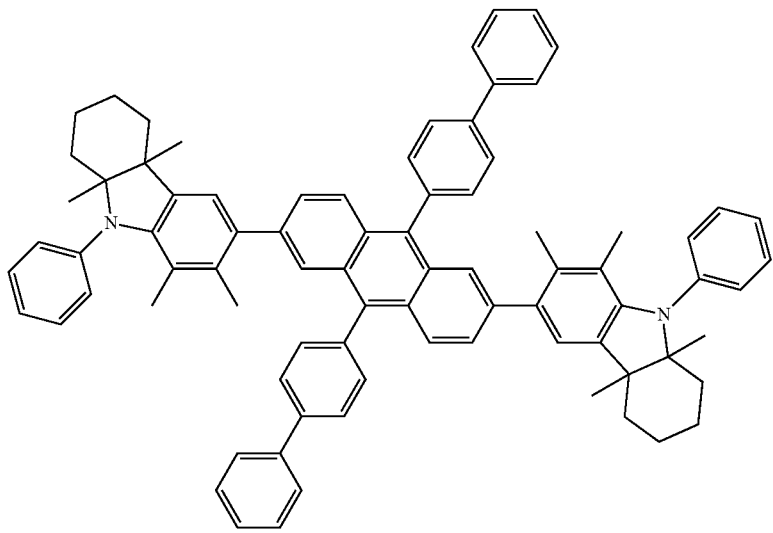
Formula 1064
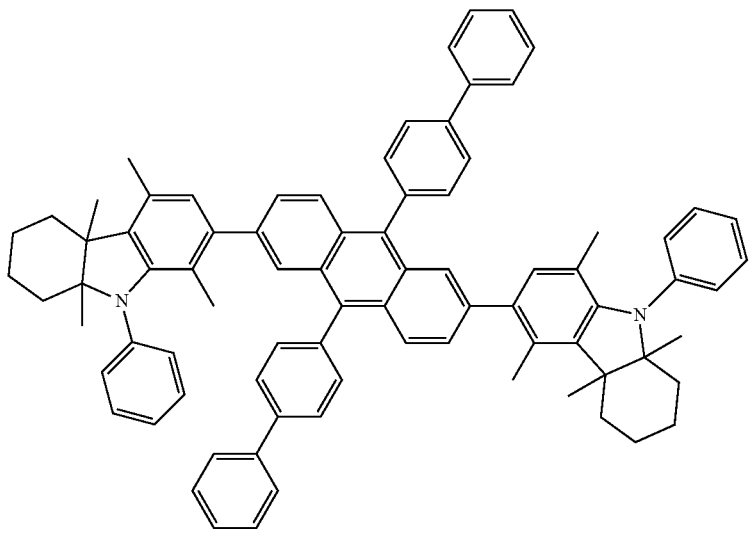

Formula 1065
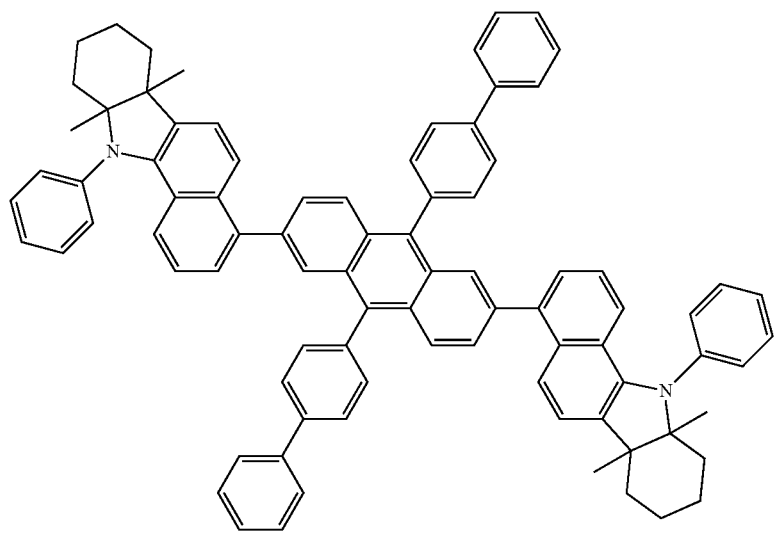
Formula 1066
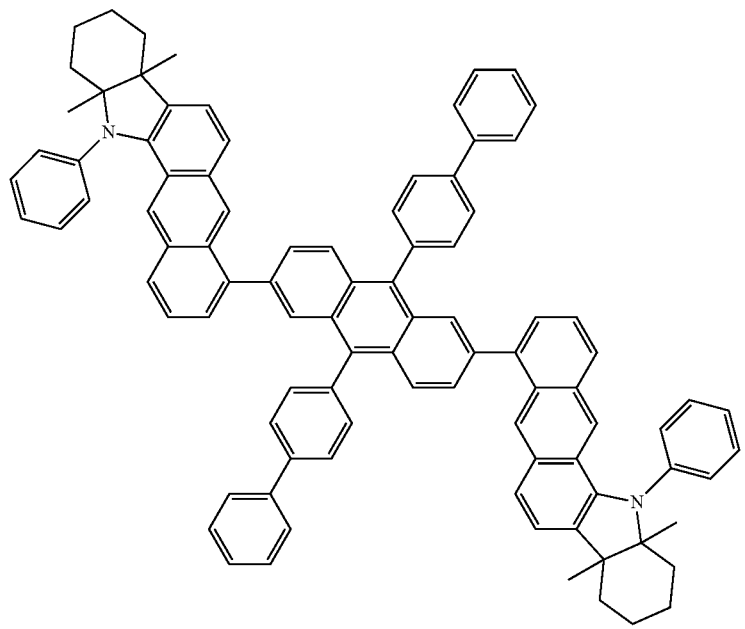

-continued
Formula 1067
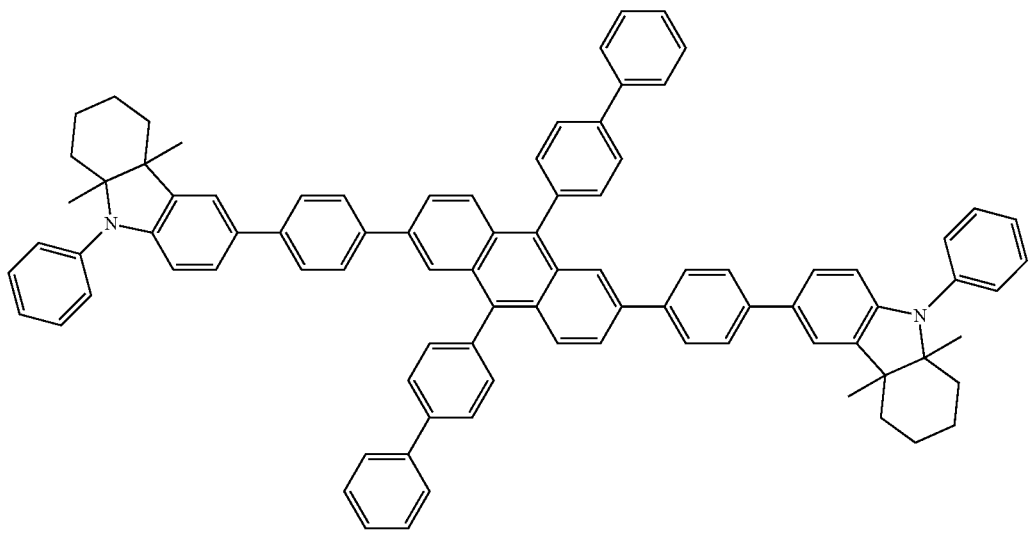
Formula 1068
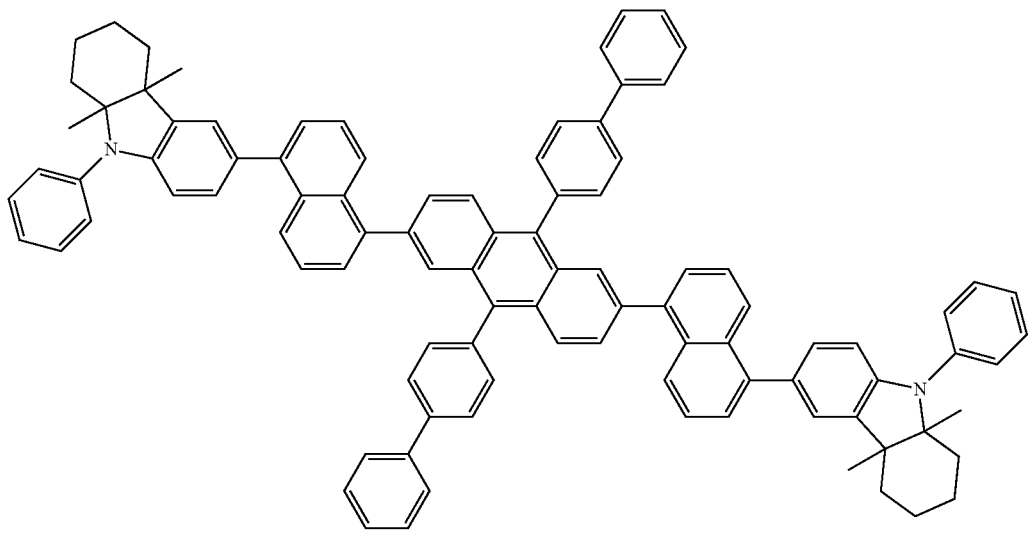
Formula 1069
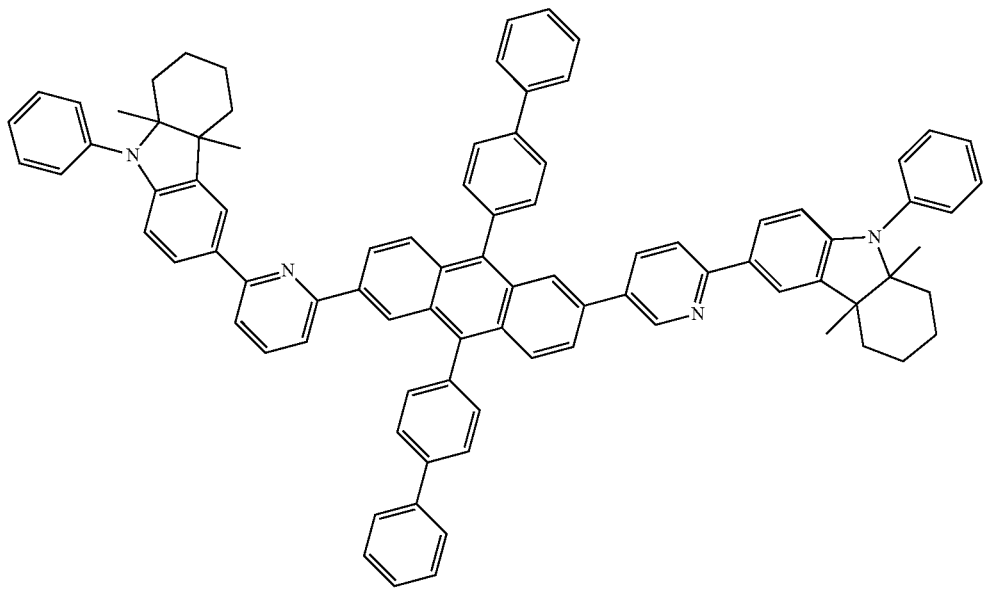

-continued
Formula 1070
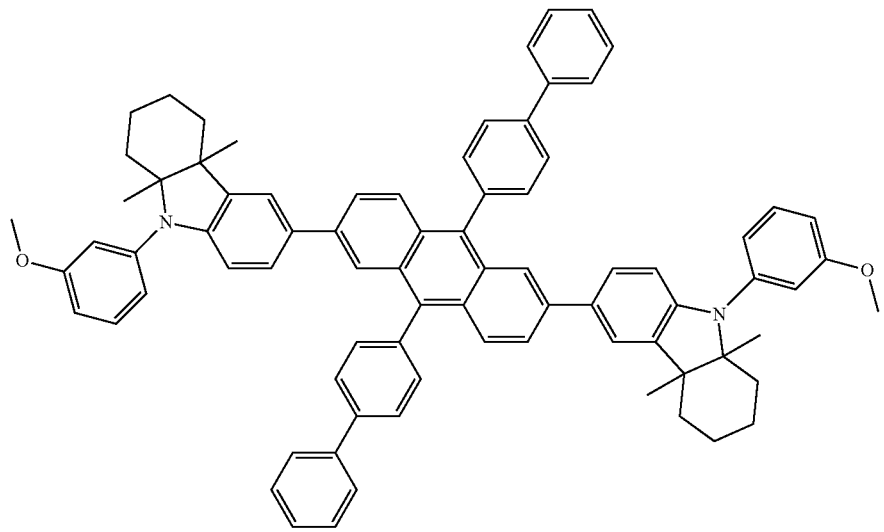
Formula 1071
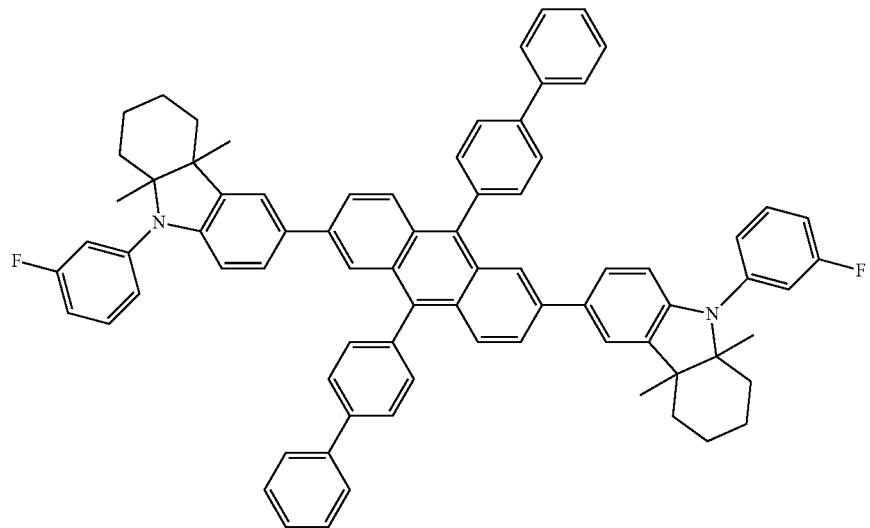
Formula 1072
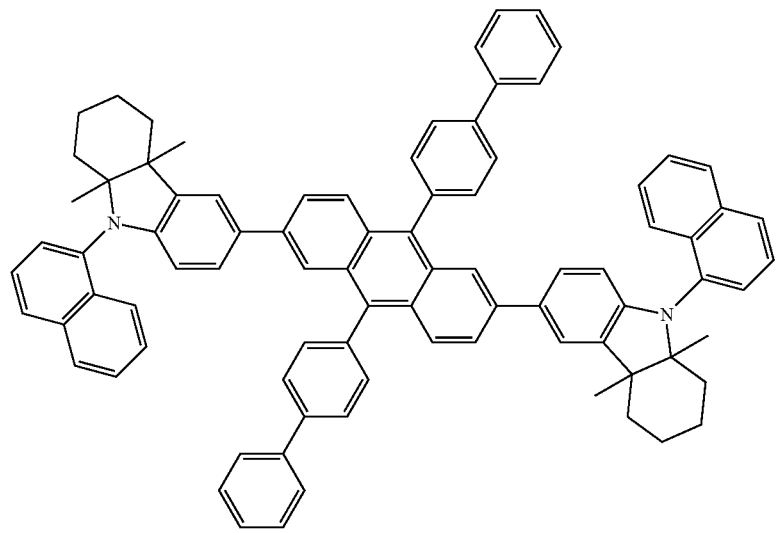

Formula 1073
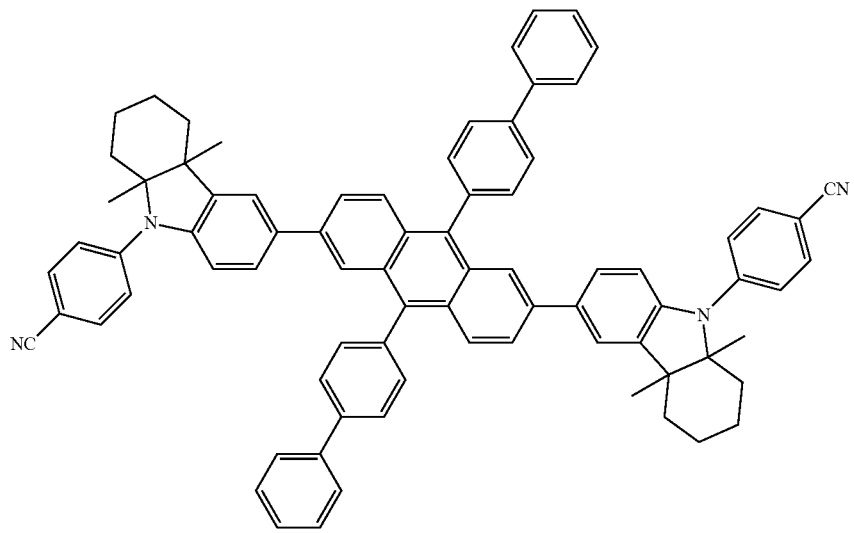
Formula 1074
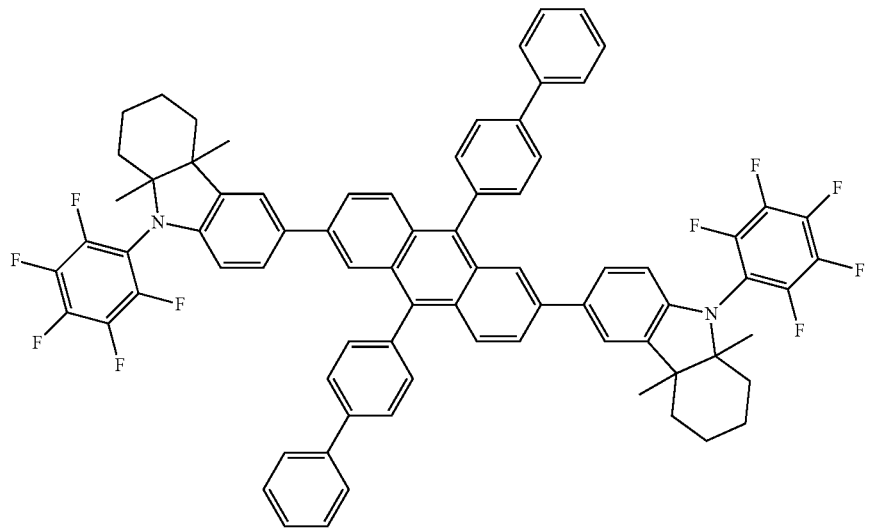
Formula 1075
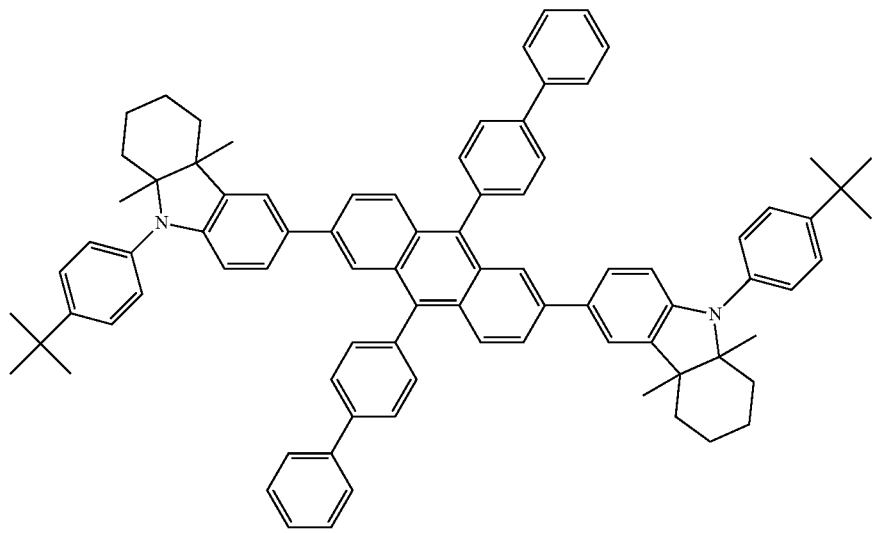

-continued
Formula 1076
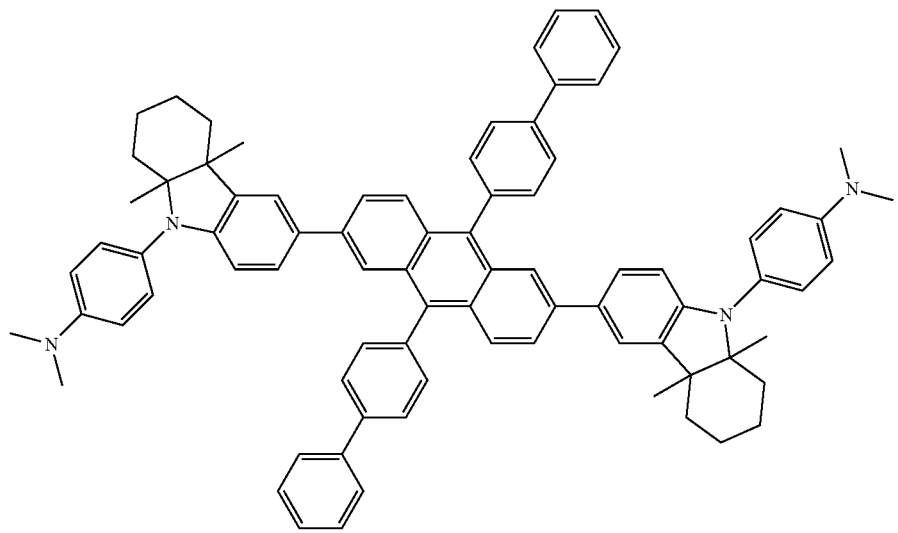
Formula 1077
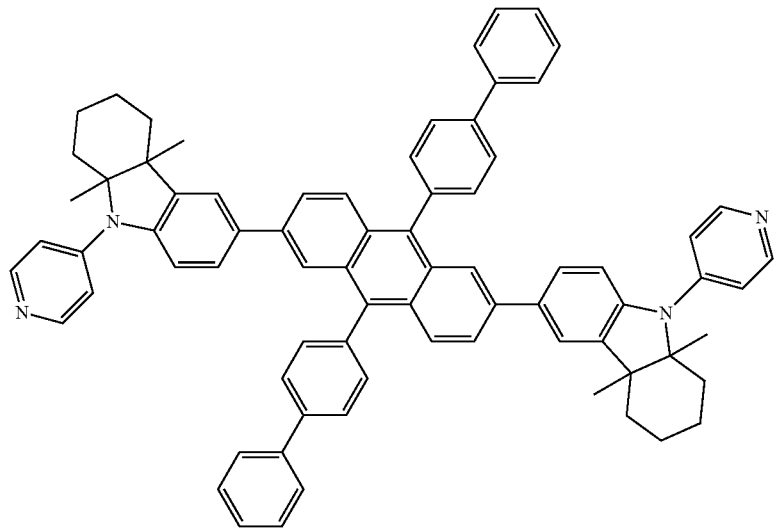
Formula 1078
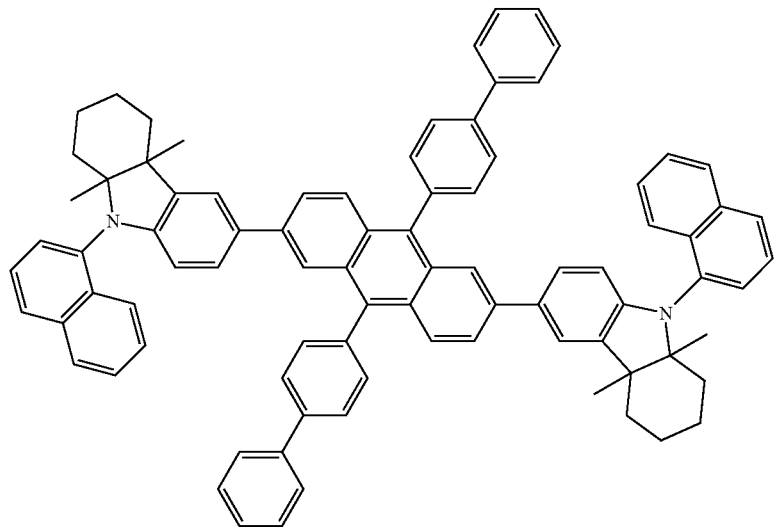

-continued
Formula 1079
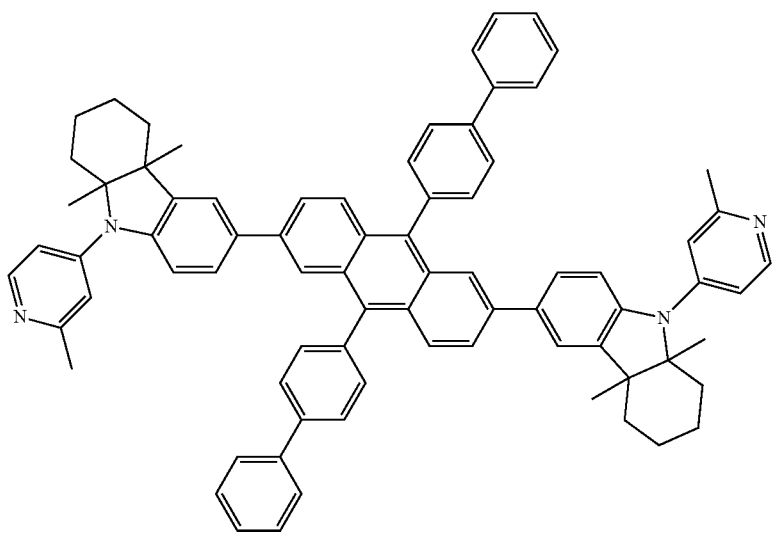
Formula 1080
Formula 1081
Formula 1082
Formula 1083
Formula 1084
Formula 1085
Formula 1086
Formula 1087
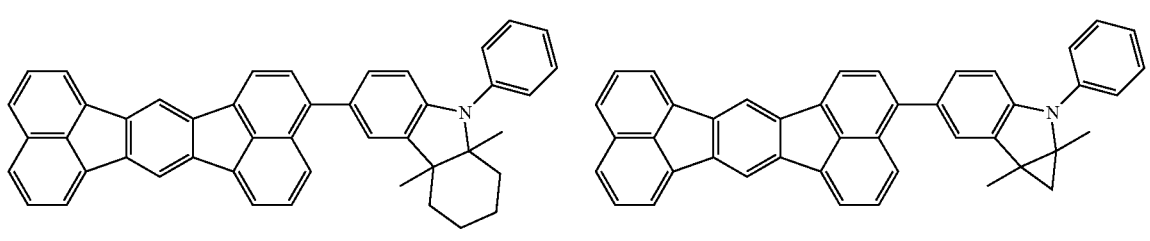
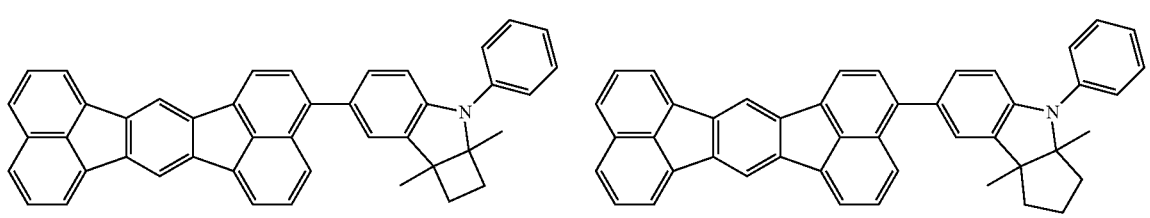
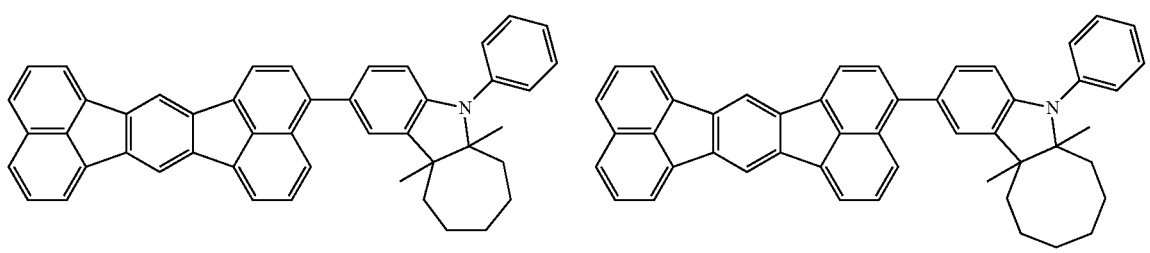

-continued
Formula 1088
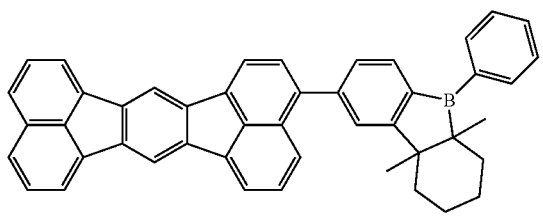
Formula 1089
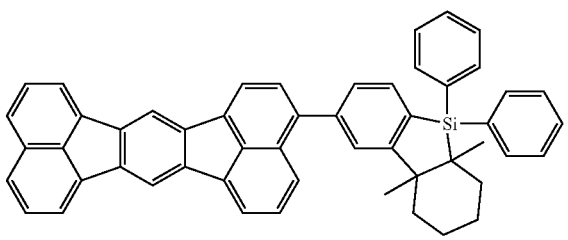
Formula 1090
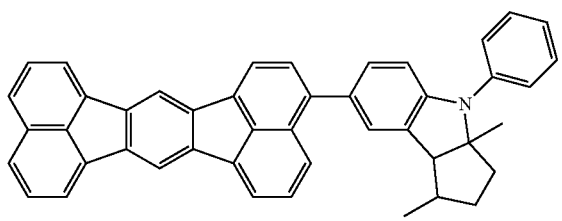
Formula 1091
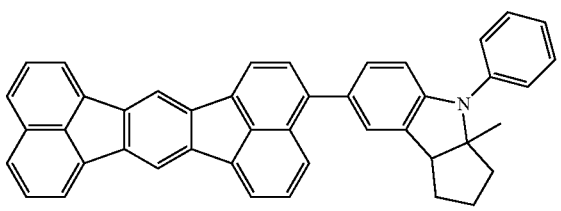
Formula 1092
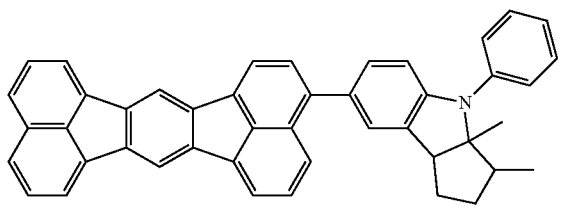
Formula 1093
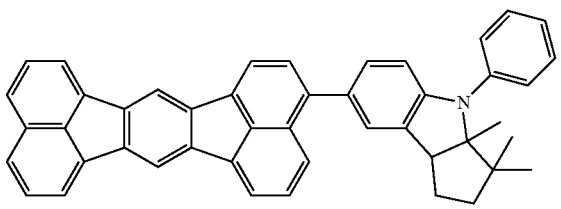
Formula 1094
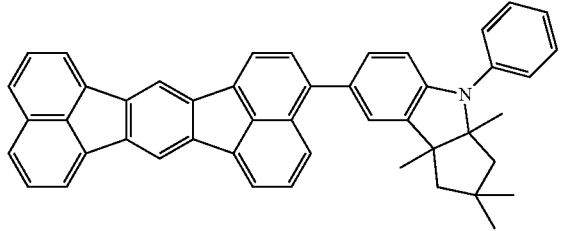
Formula 1095
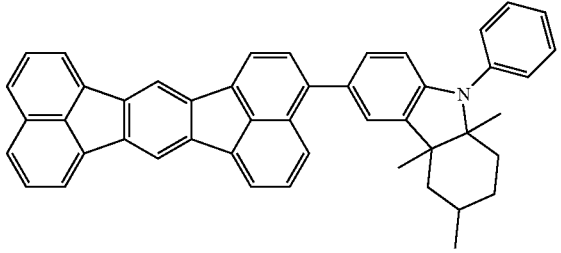
Formula 1096
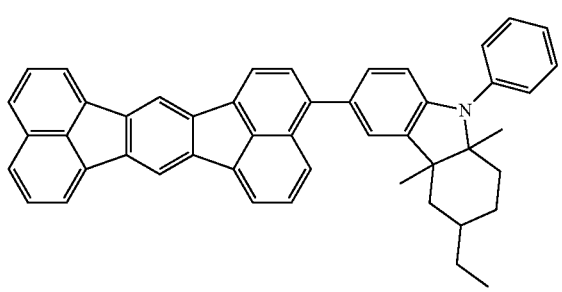
Formula 1097
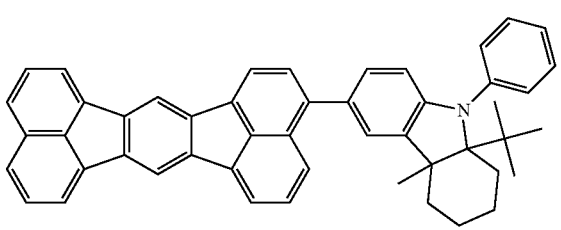
Formula 1098
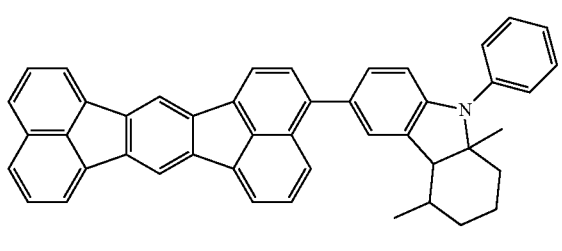
Formula 1099
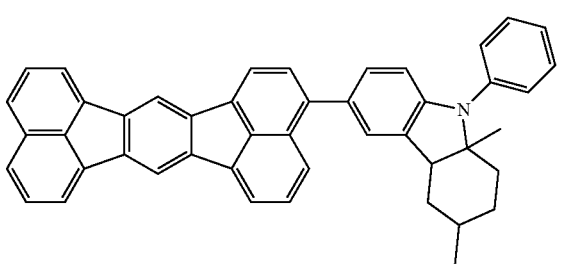

-continued
Formula 1100
Formula 1101
Formula 1102
Formula 1103
Formula 1104
Formula 1105
Formula 1106
Formula 1107
Formula 1108
Formula 1109
Formula 1110
Formula 1111
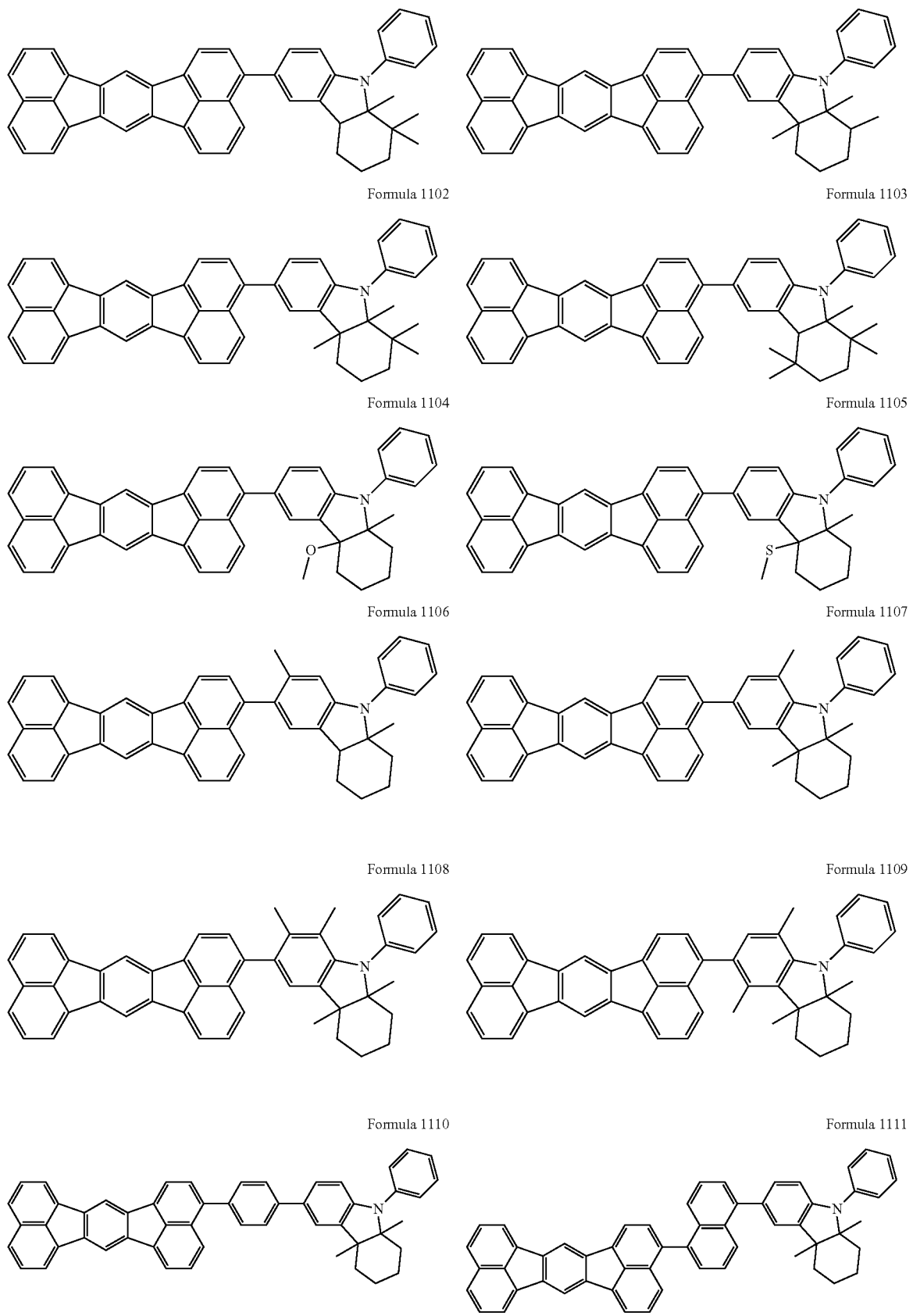

-continued
Formula 1112
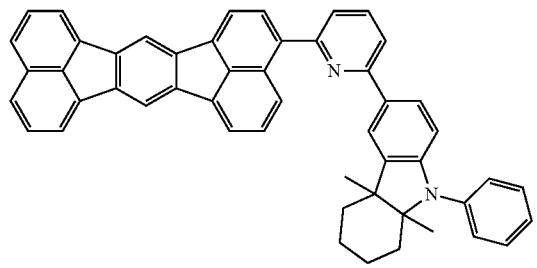
Formula 113
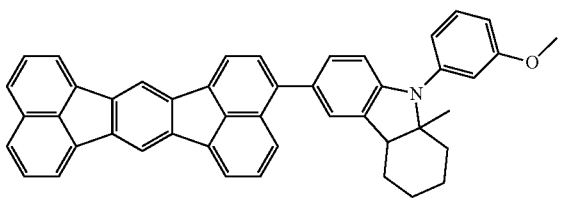
Formula 114
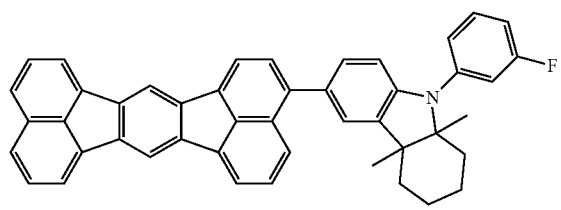
Formula 115
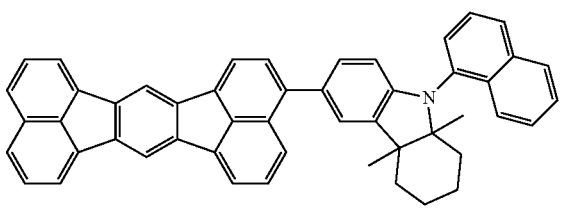
Formula 116
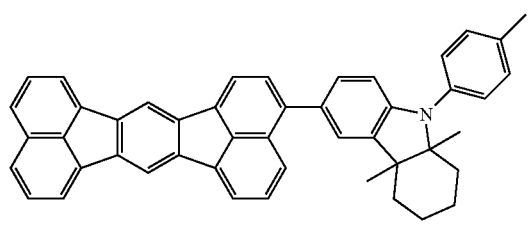
Formula 117
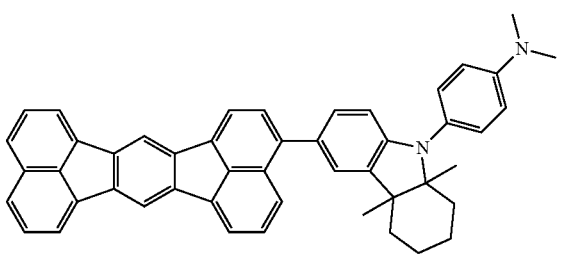
Formula 1118
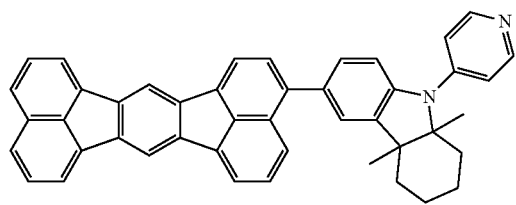
Formula 1119
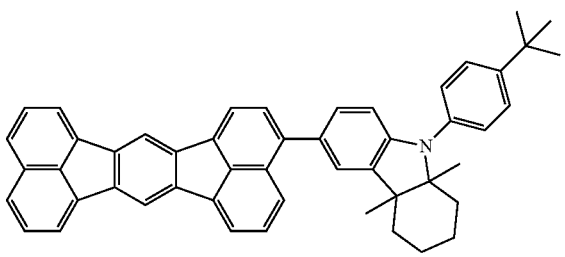
Formula 1120
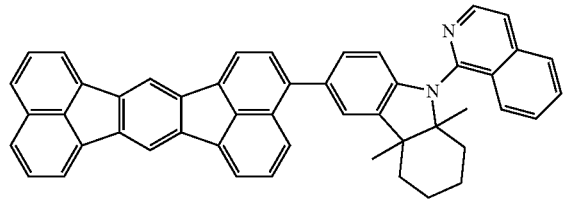
Formula 1121
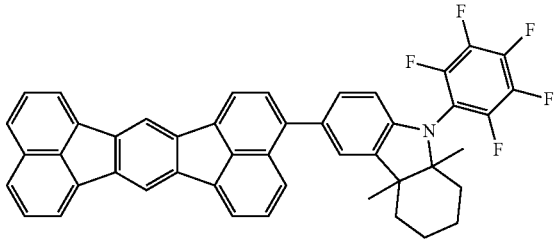

-continued
Formula 1122
Formula 1123
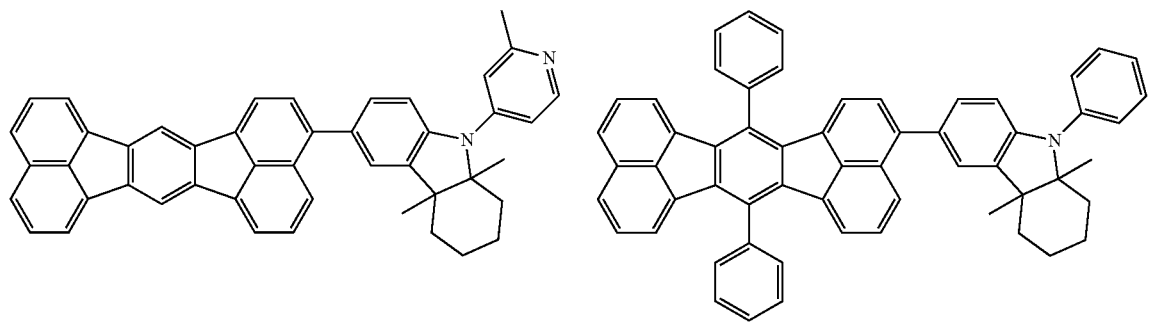
Formula 1124
Formula 1125
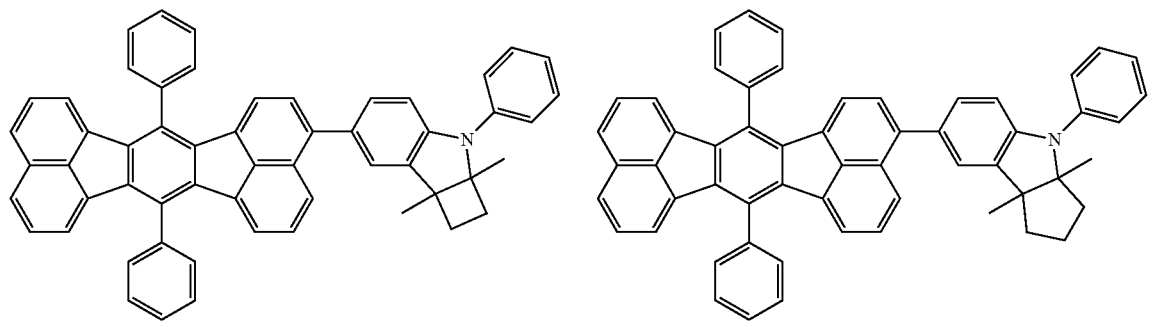
Formula 1126
Formula 1127
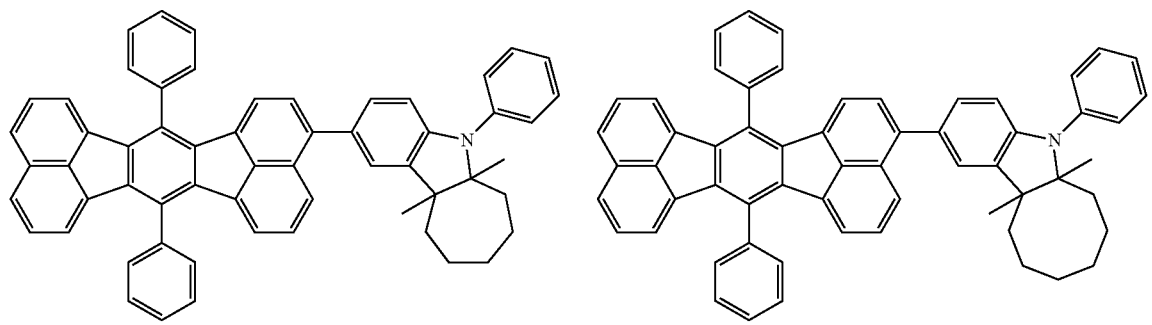
Formula 1128
Formula 1129
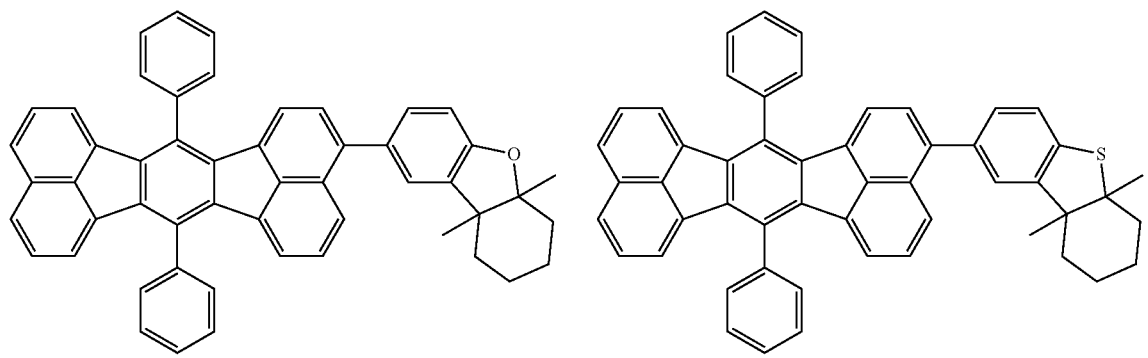

Formula 1130
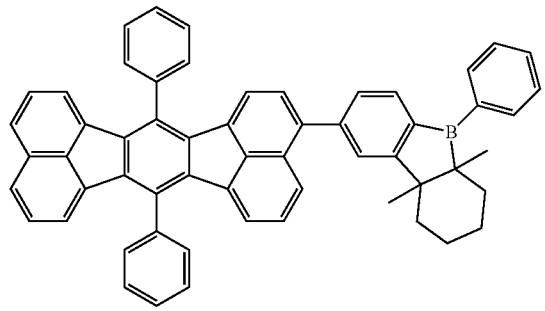
Formula 1131
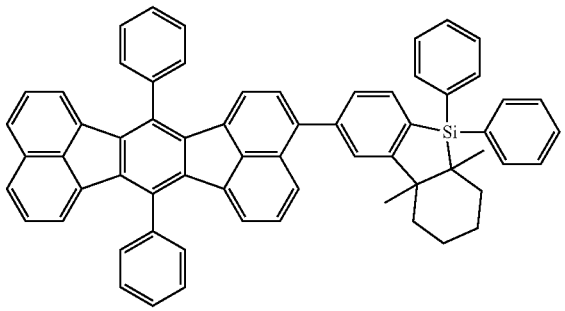
Formula 1132
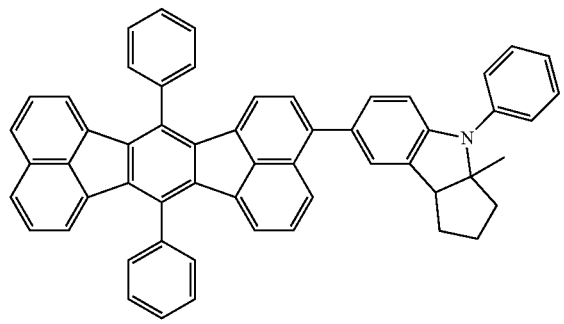
Formula 1133
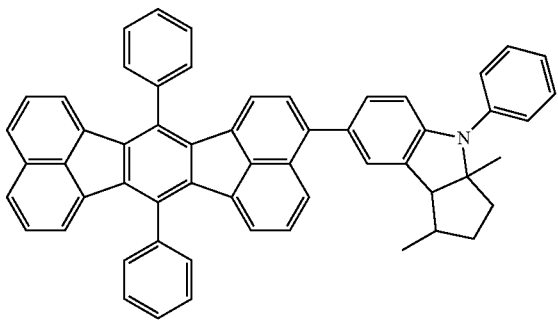
Formula 1134
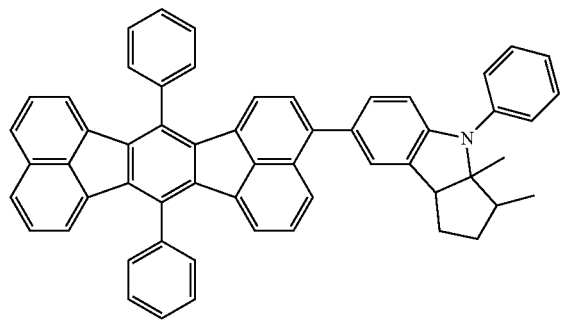
Formula 1135
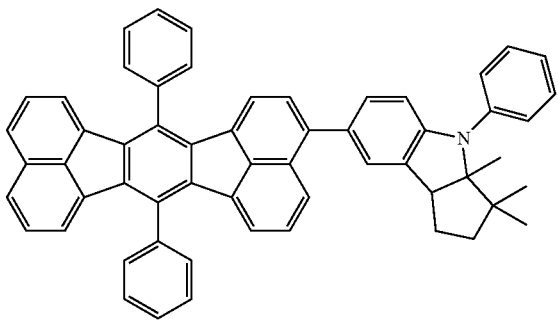
Formula 1136
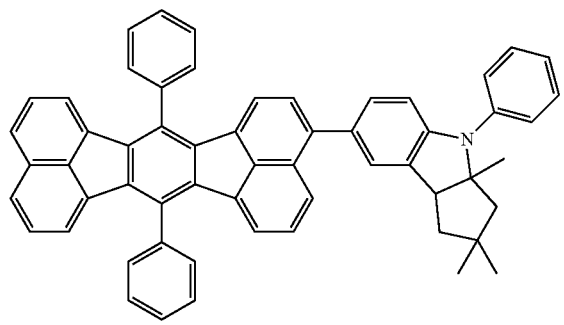
Formula 1137
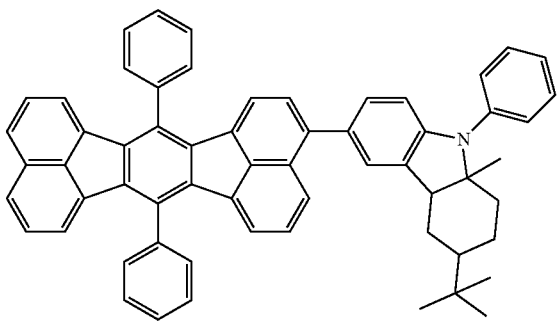

-continued
Formula 1138
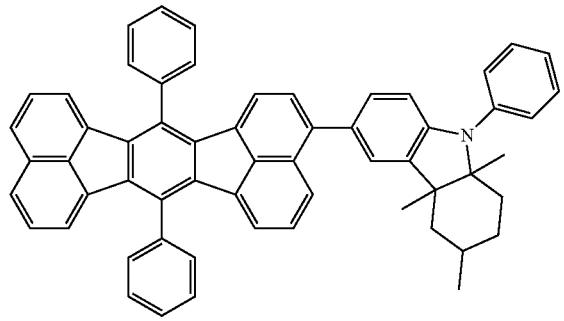
Formula 1139
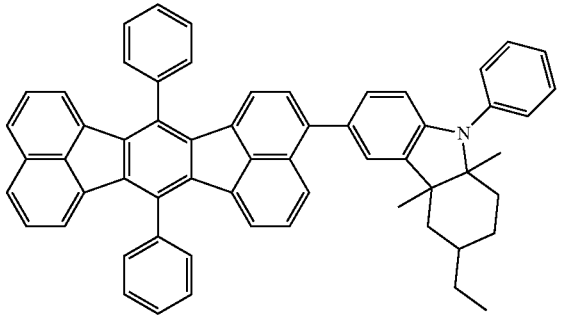
Formula 1140
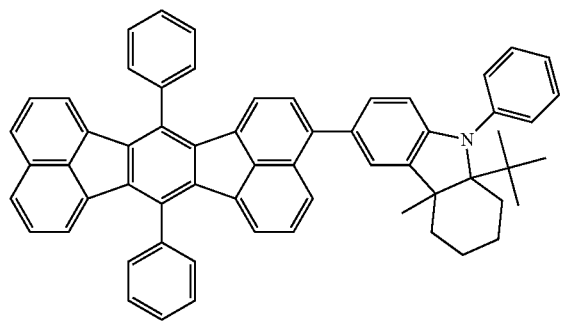
Formula 1141
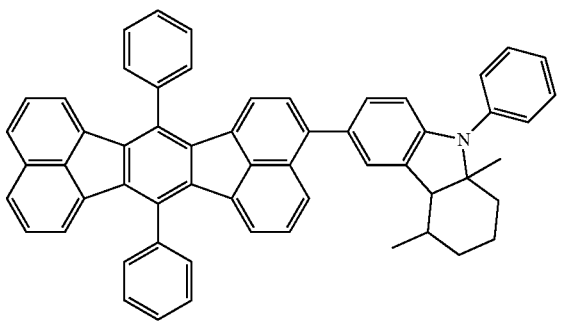
Formula 1142
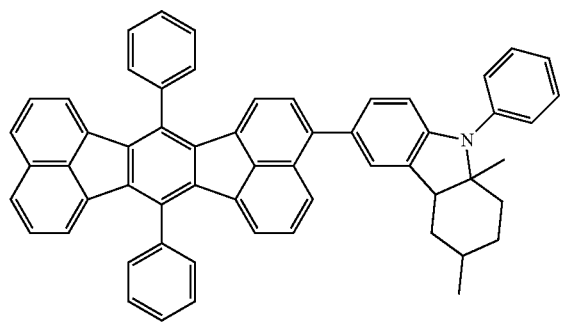
Formula 1143
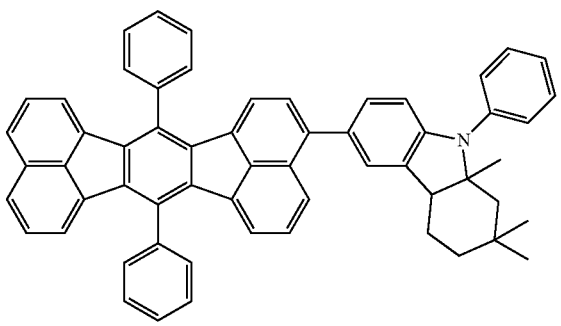
Formula 1144
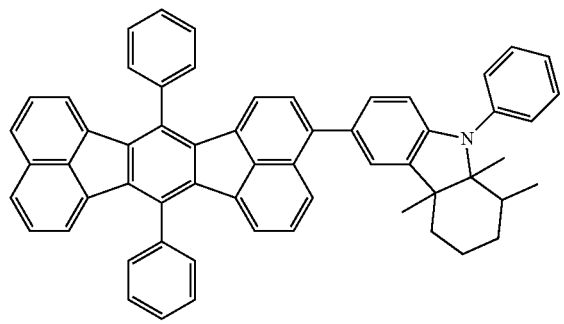
Formula 1145
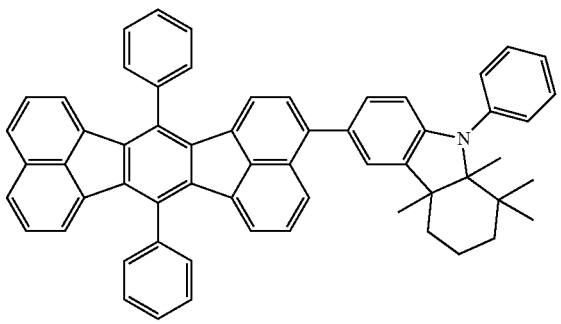

-continued
Formula 1146
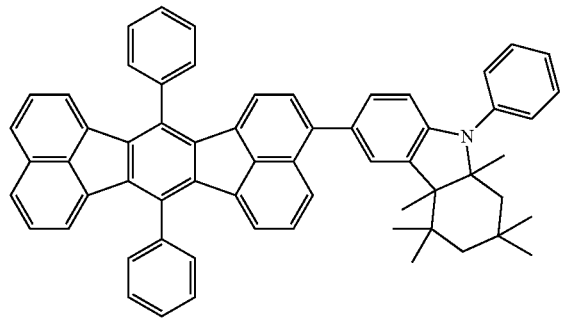
Formula 1147
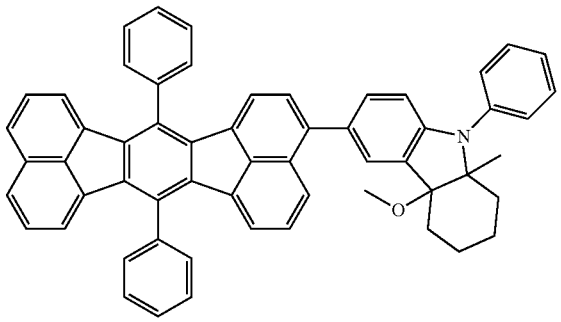
Formula 1148
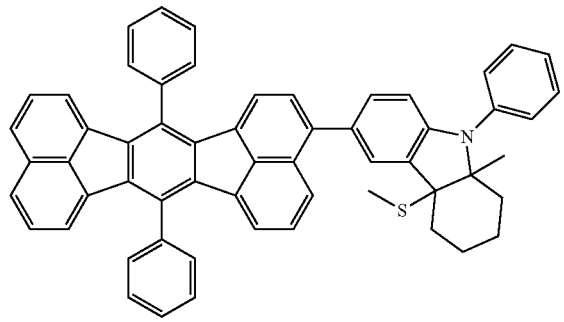
Formula 1149
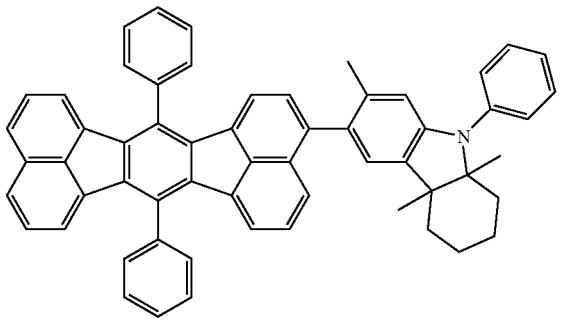
Formula 1150
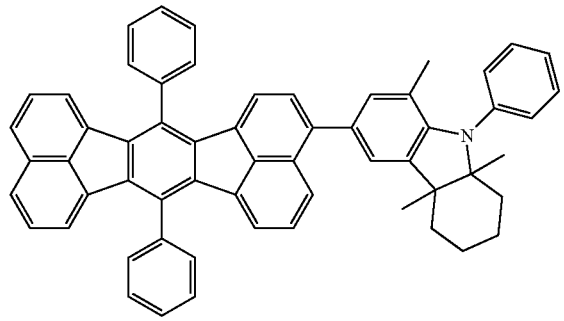
Formula 1151
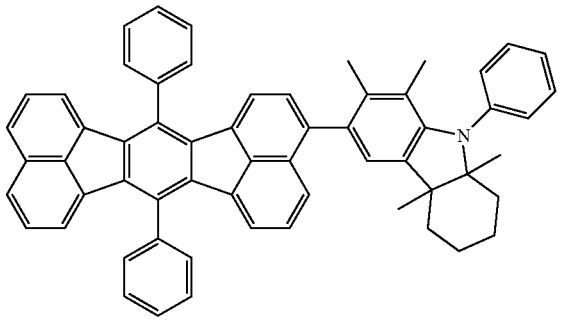
Formula 1152
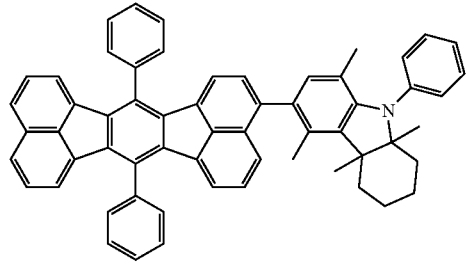
Formula 1153
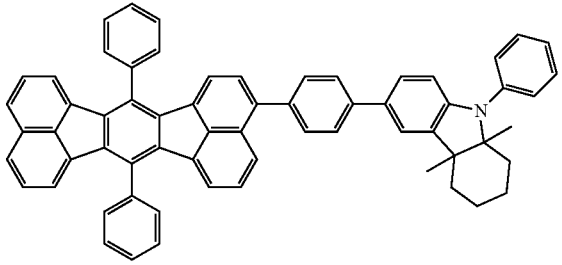

-continued
Formula 1154
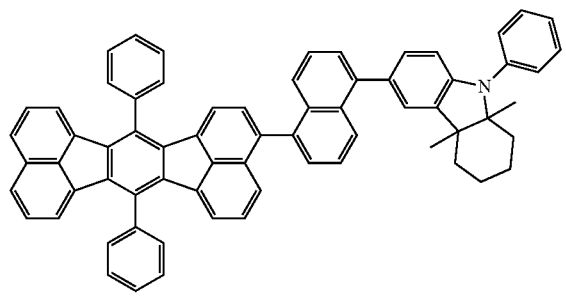
Formula 1155
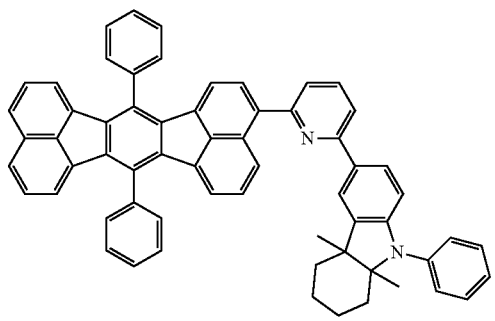
Formula 1156
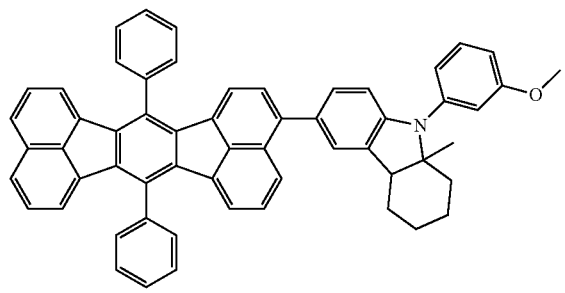
Formula 1157
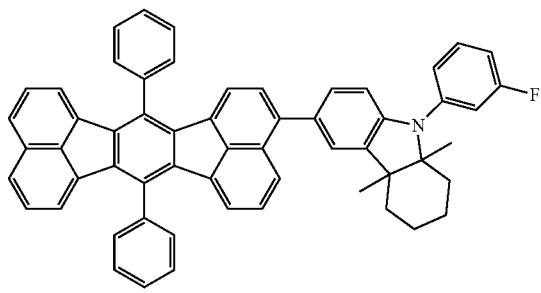
Formula 1158
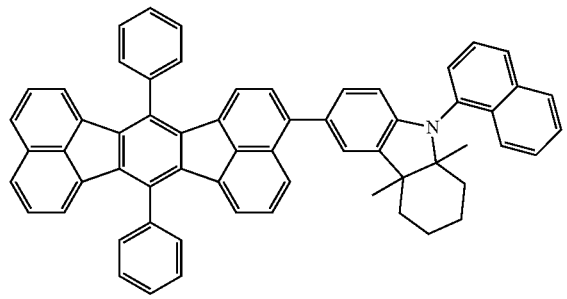
Formula 1159
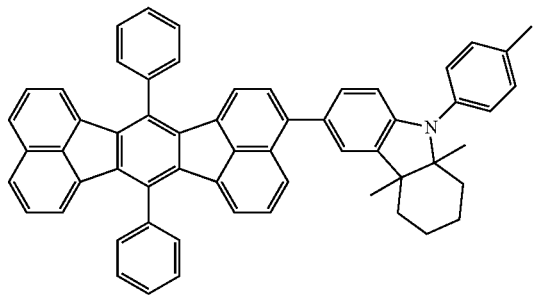
Formula 1160
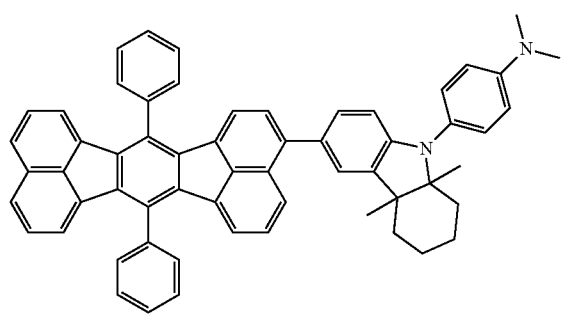
Formula 1161
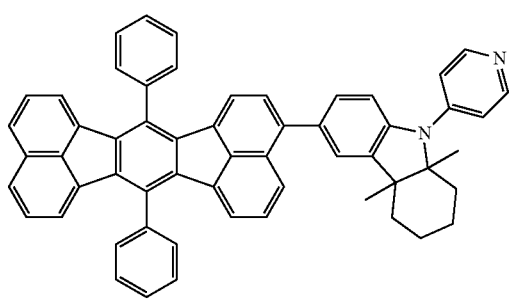
Formula 1162
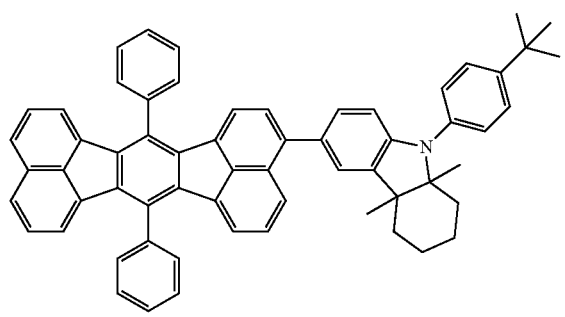
Formula 1163
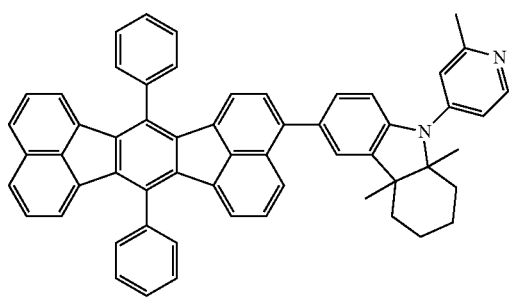

-continued
Formula 1164
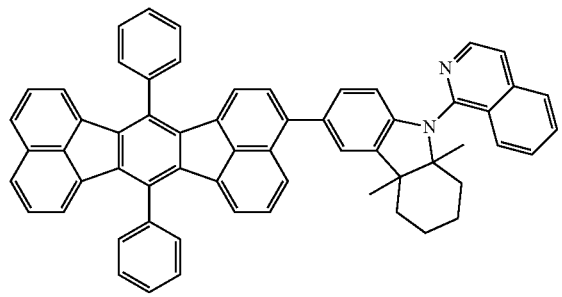
Formula 1165
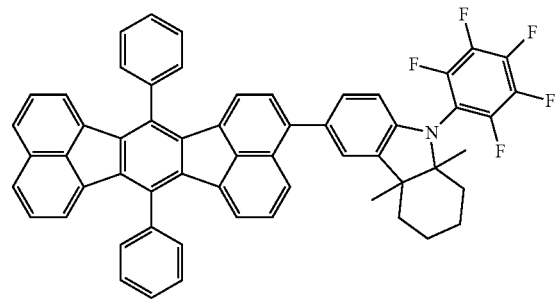
Formula 1166
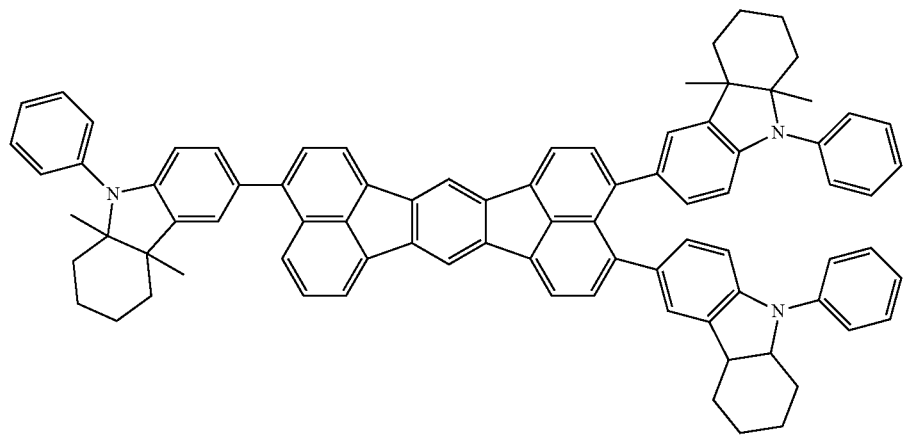
Formula 1167
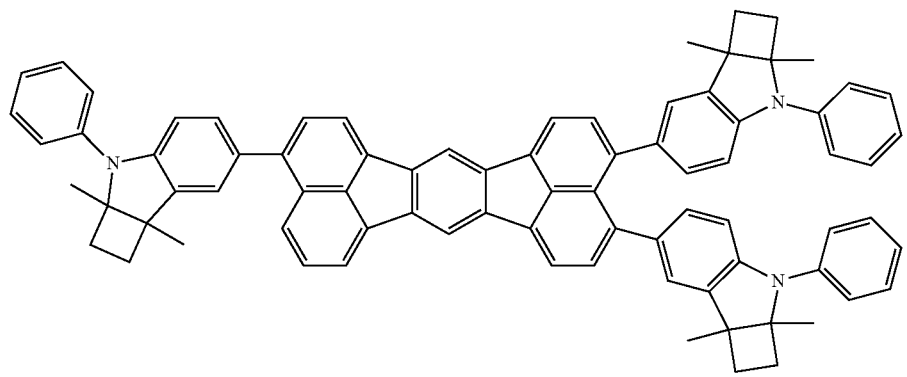
Formula 1168
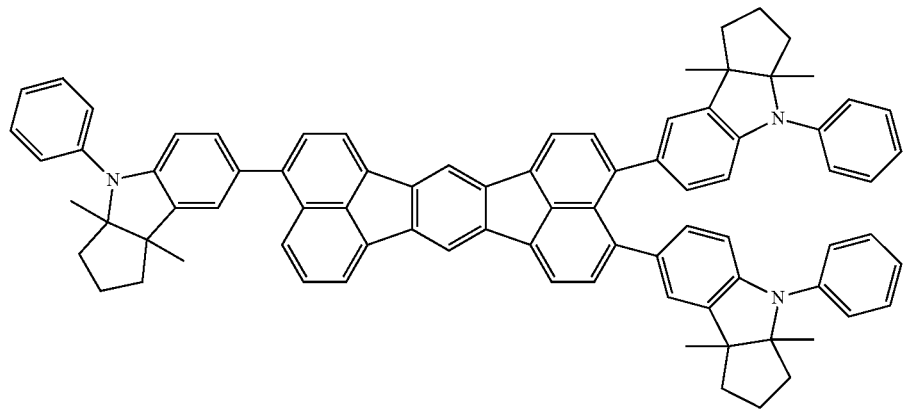

-continued
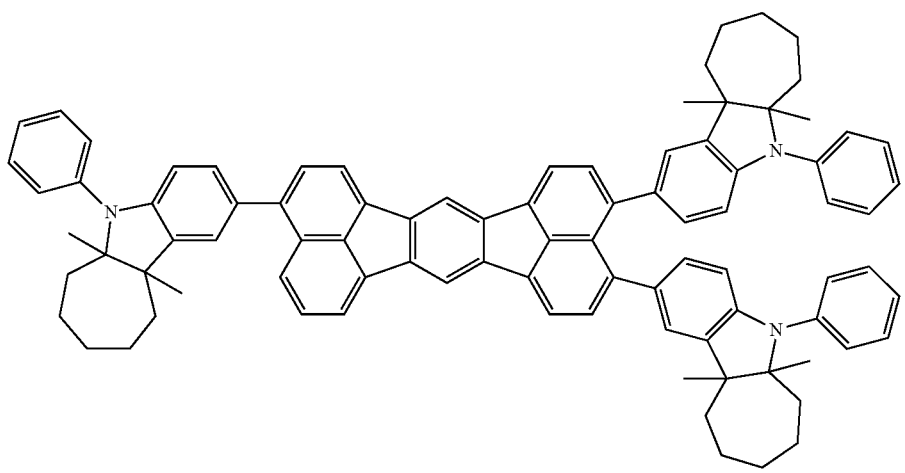
Formula 1169
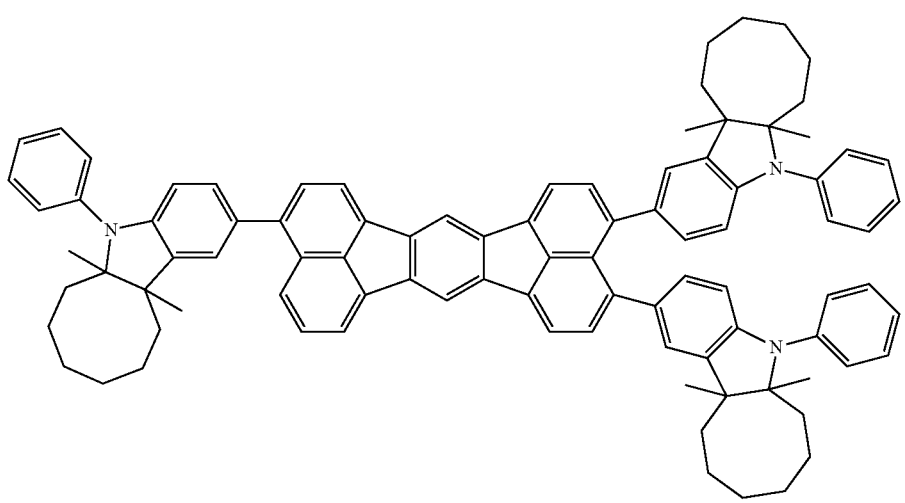
Formula 1170
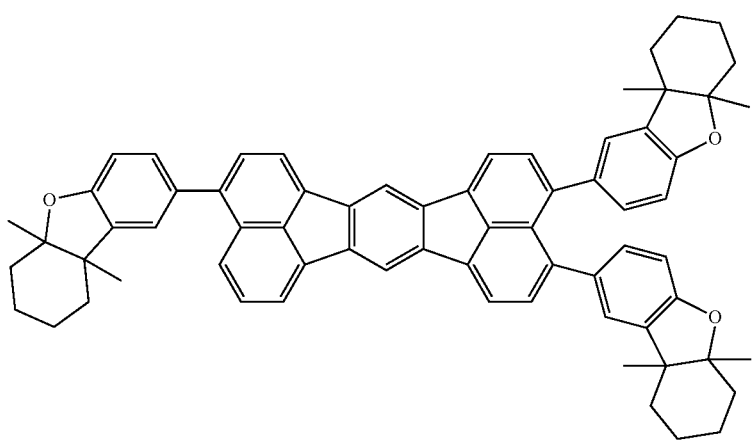
Formula 1171

-continued
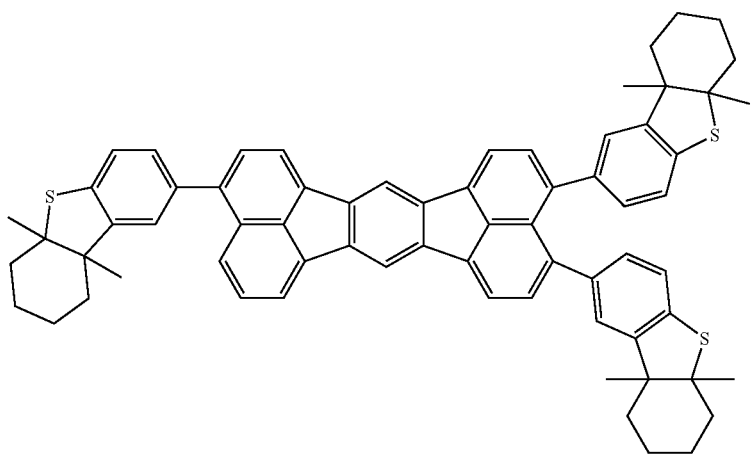
Formula 1172
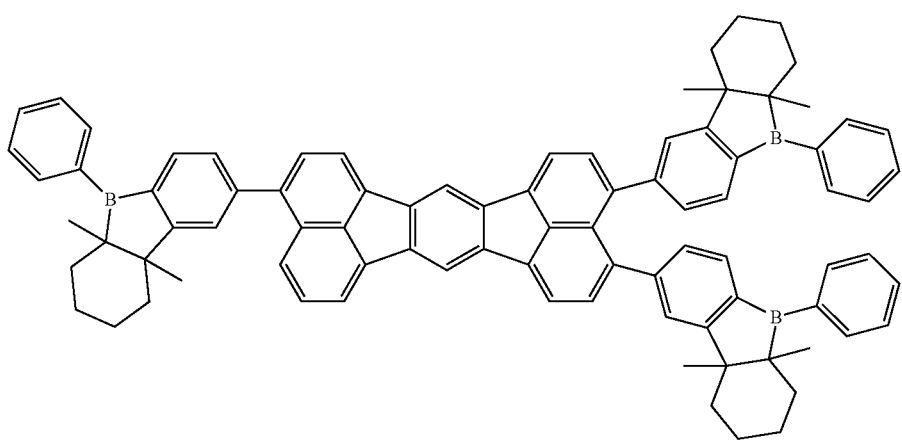
Formula 1173
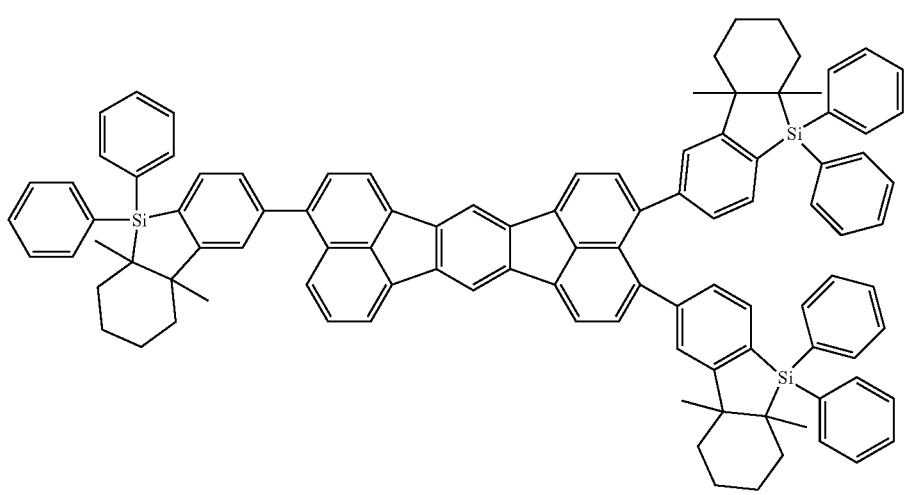
Formula 1174

-continued
Formula 1175
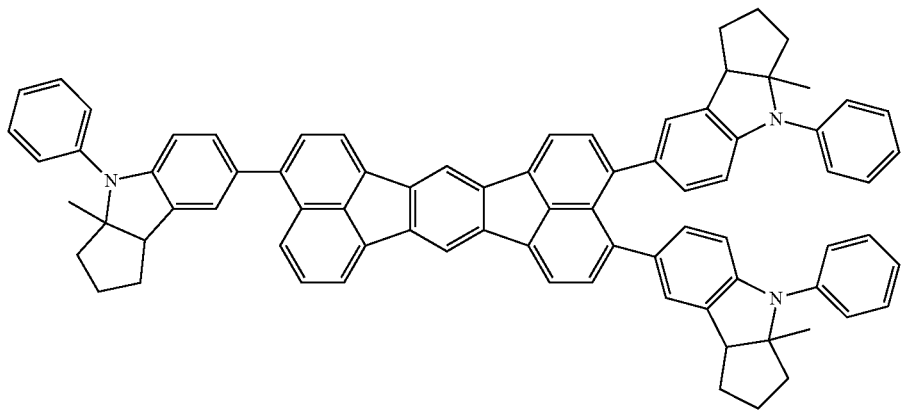
Formula 1176
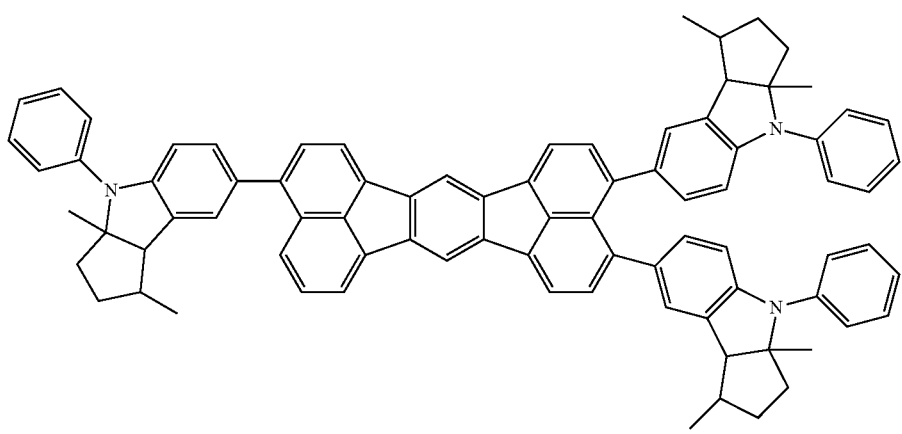
Formula 1177
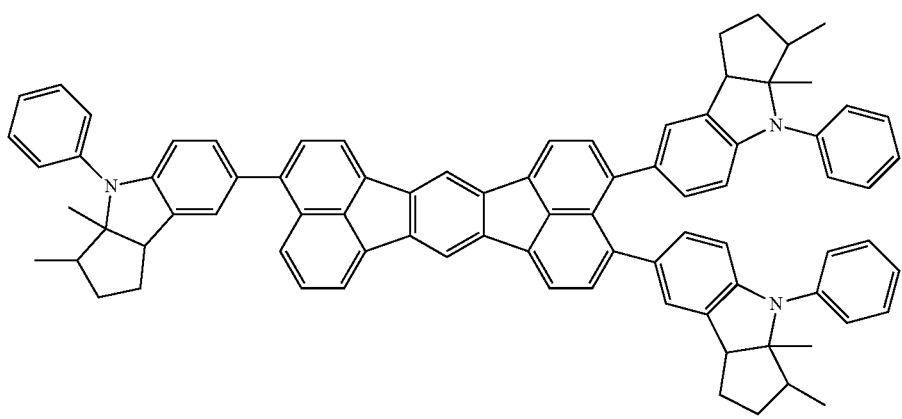

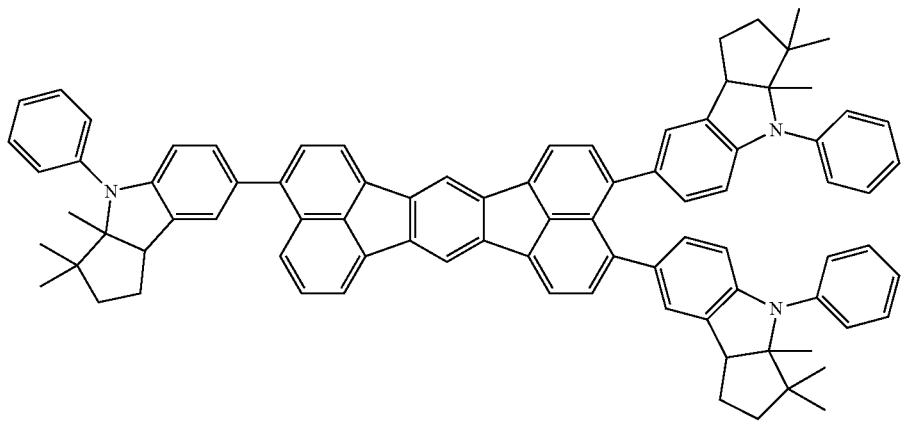
Formula 1178
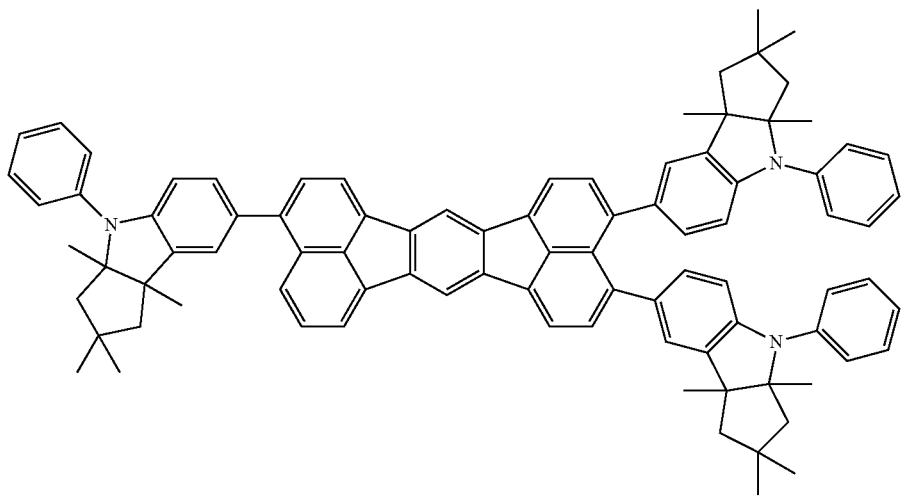
Formula 1179
Formula 1180

Formula 1181
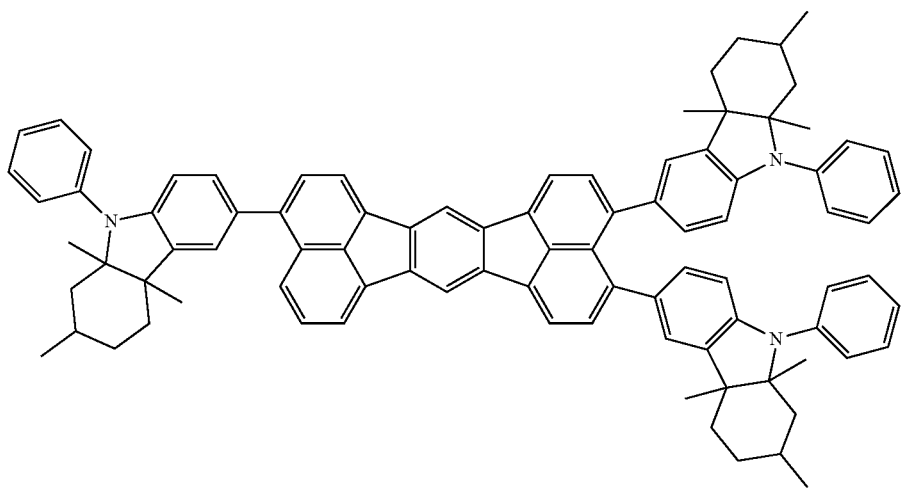
Formula 1182
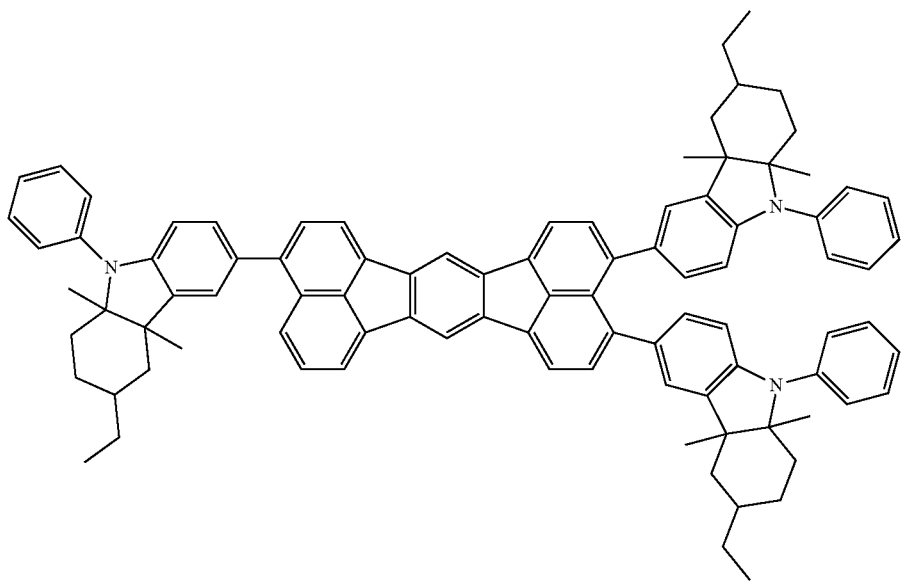
Formula 1183
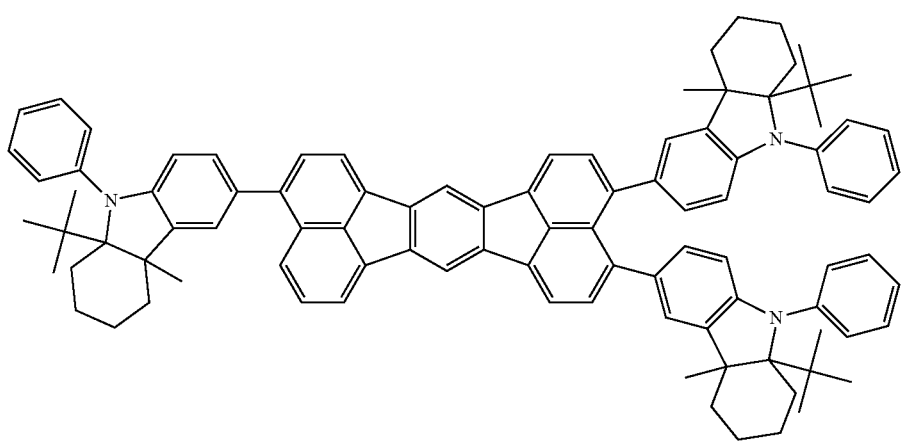

Formula 1184
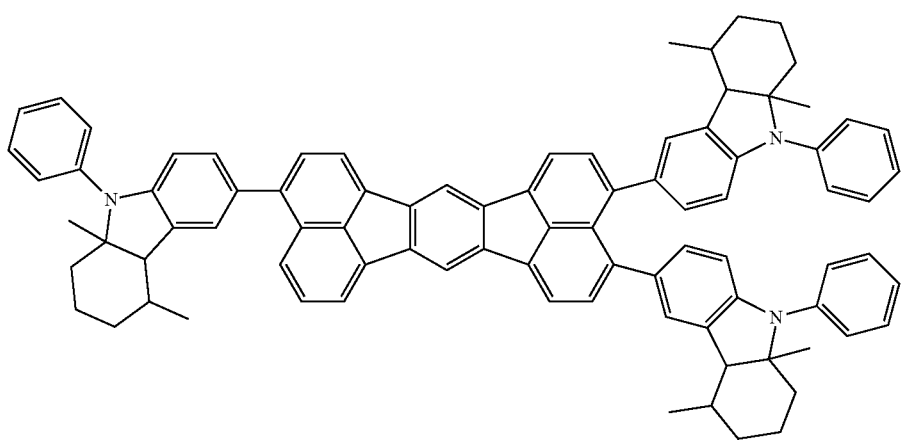
Formula 1185
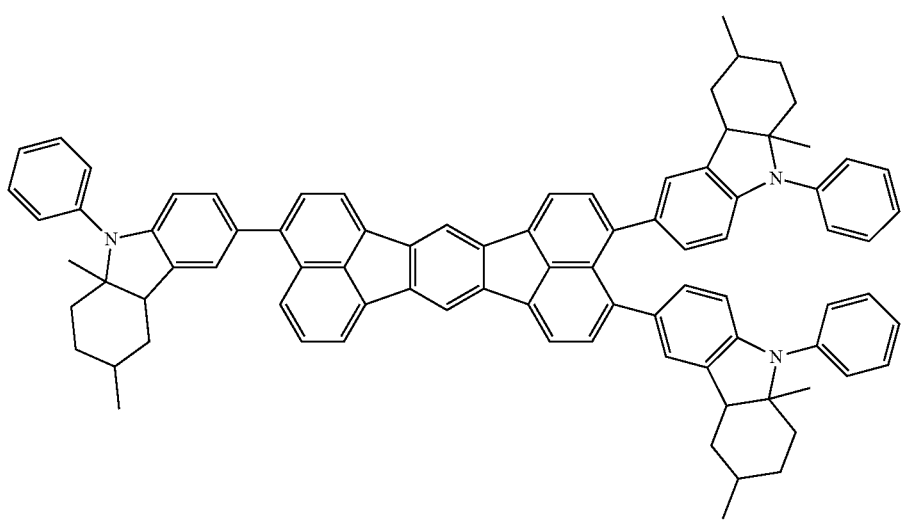
Formula 1186
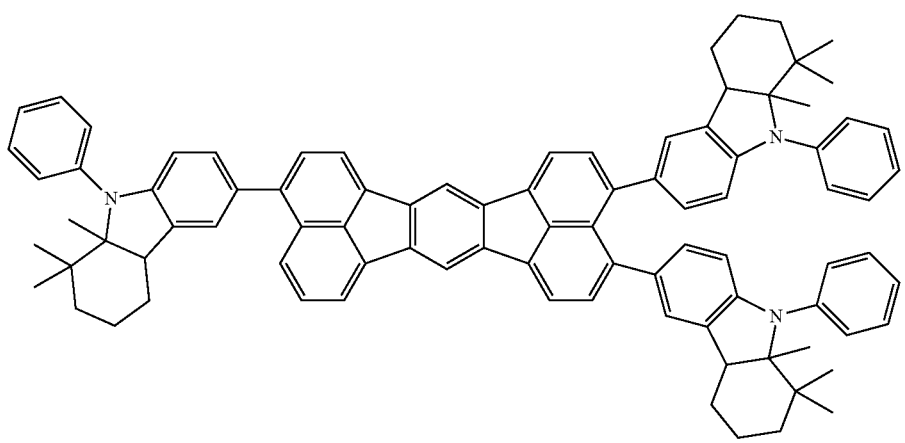

-continued
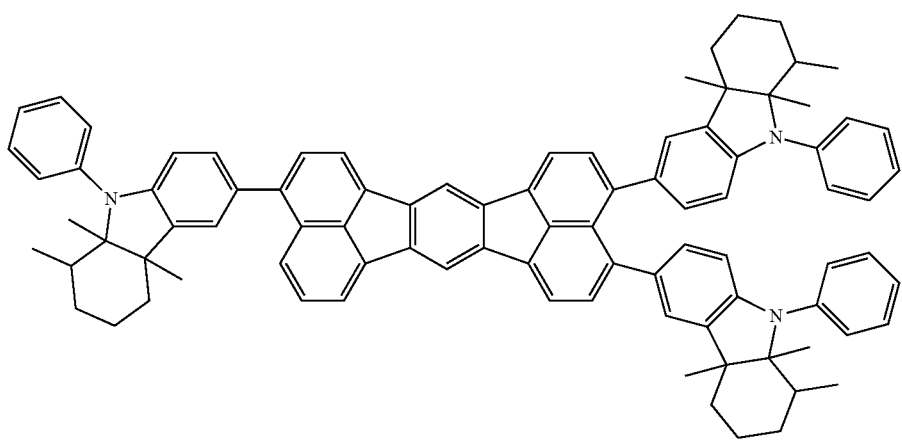
Formula 1187
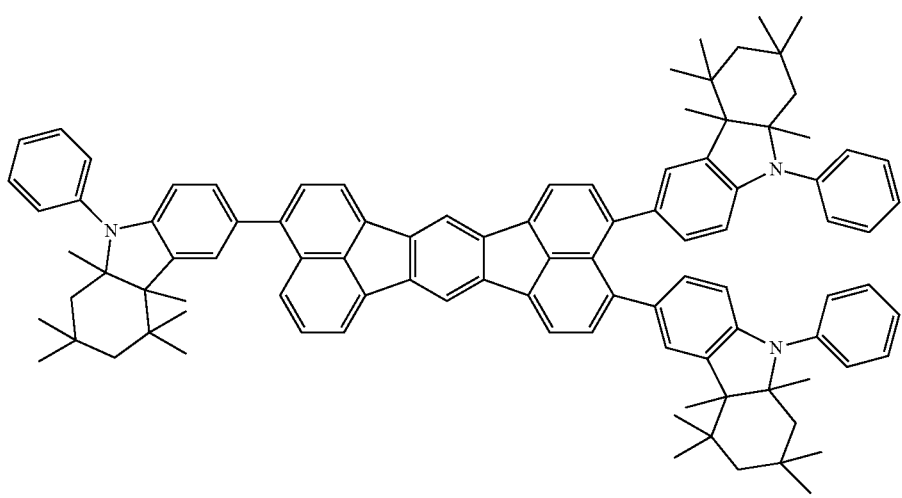
Formula 1188
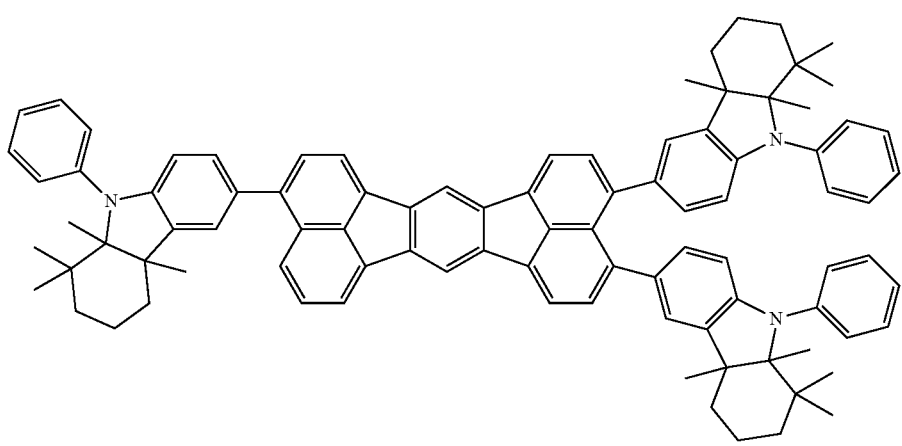
Formula 1189

Formula 1190
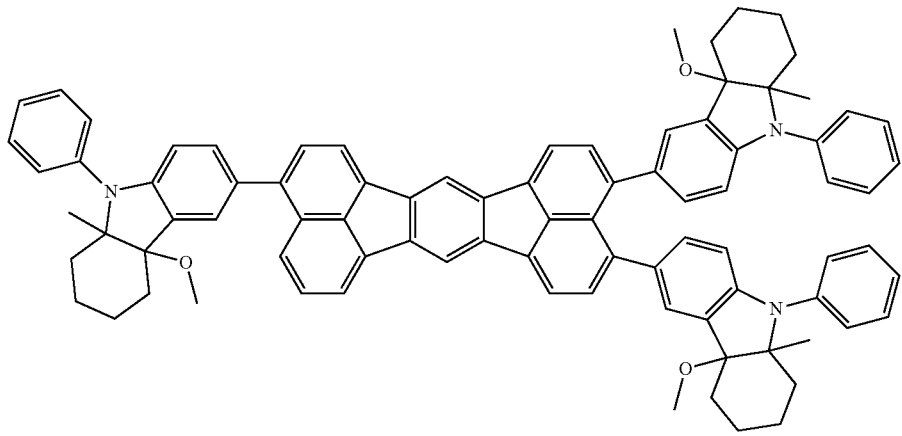
Formula 1191
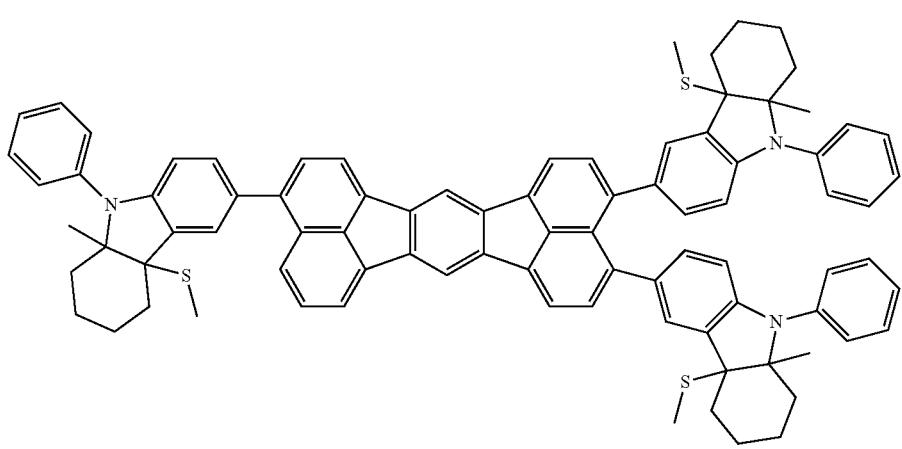
Formula 1192
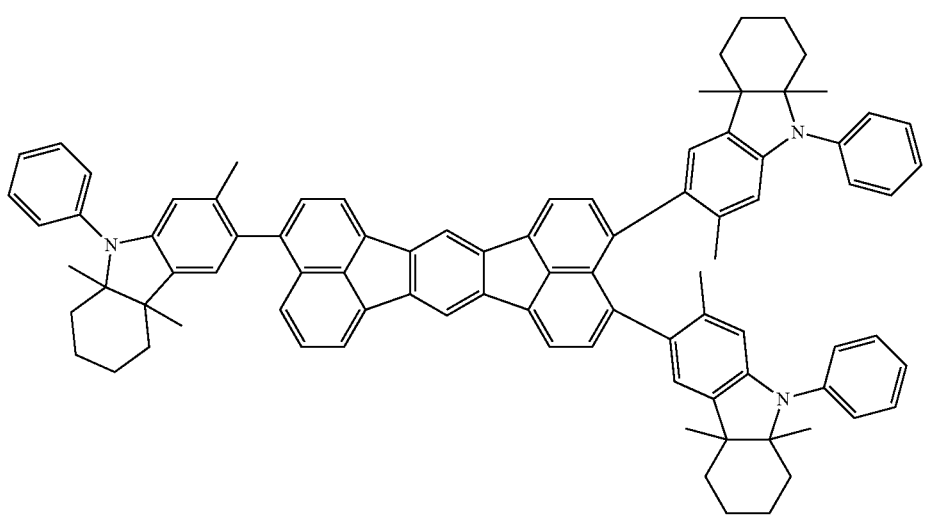

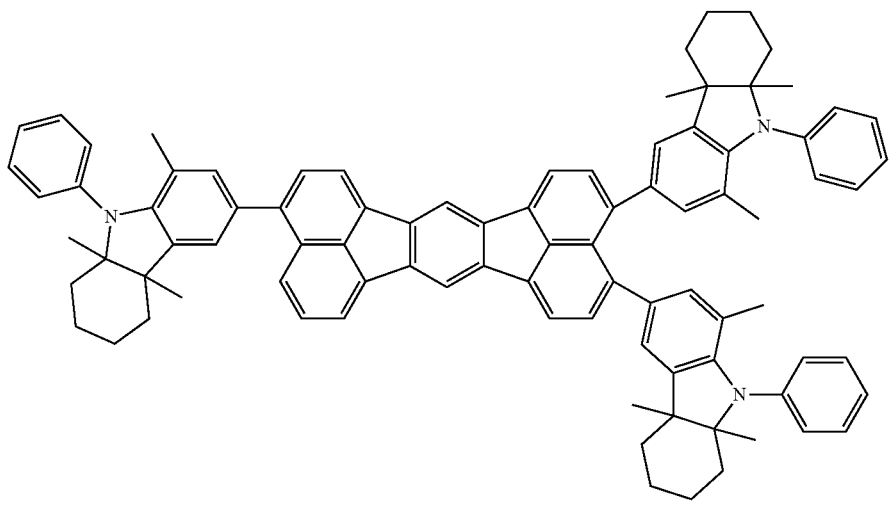
Formula 1193
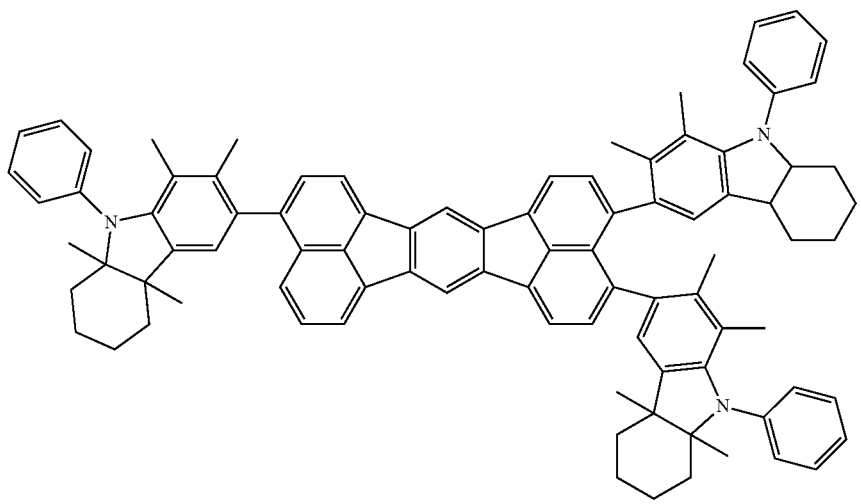
Formula 1194
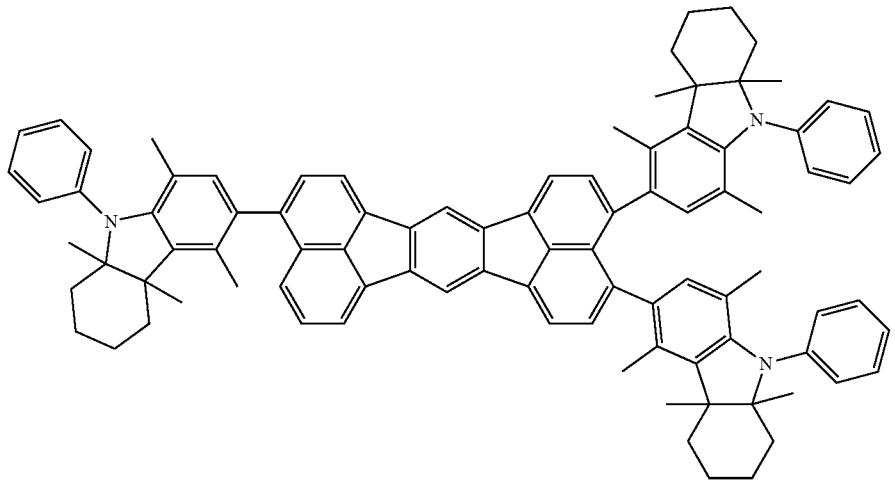
Formula 1195

-continued
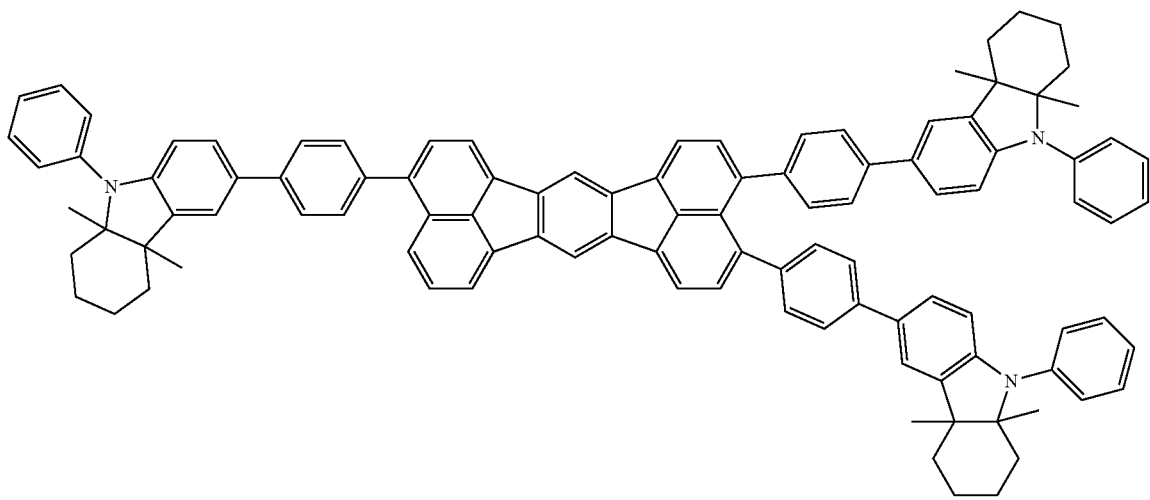
Formula 1196
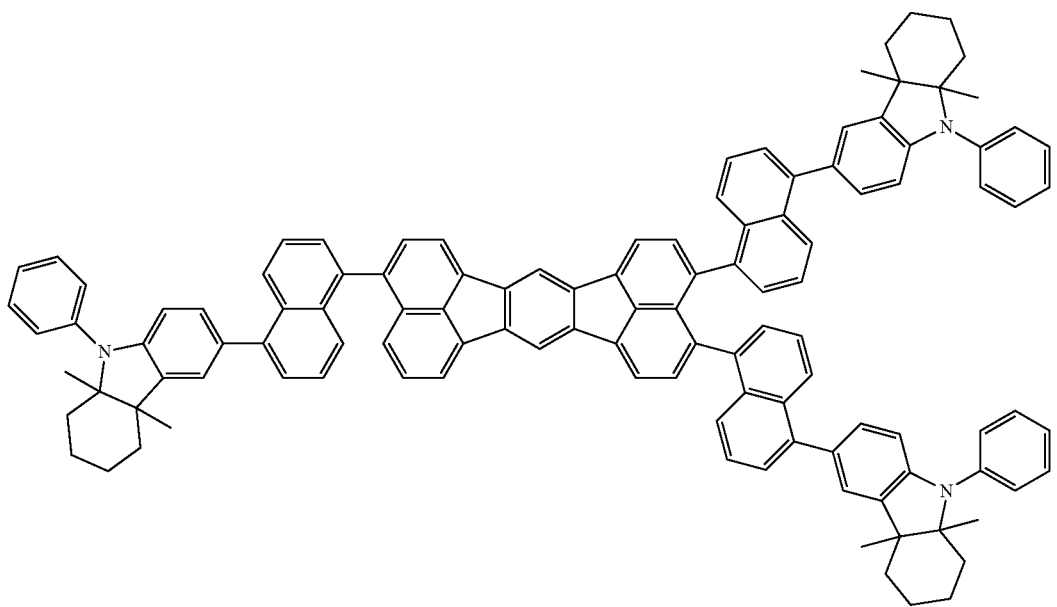
Formula 1197

-continued
Formula 1198
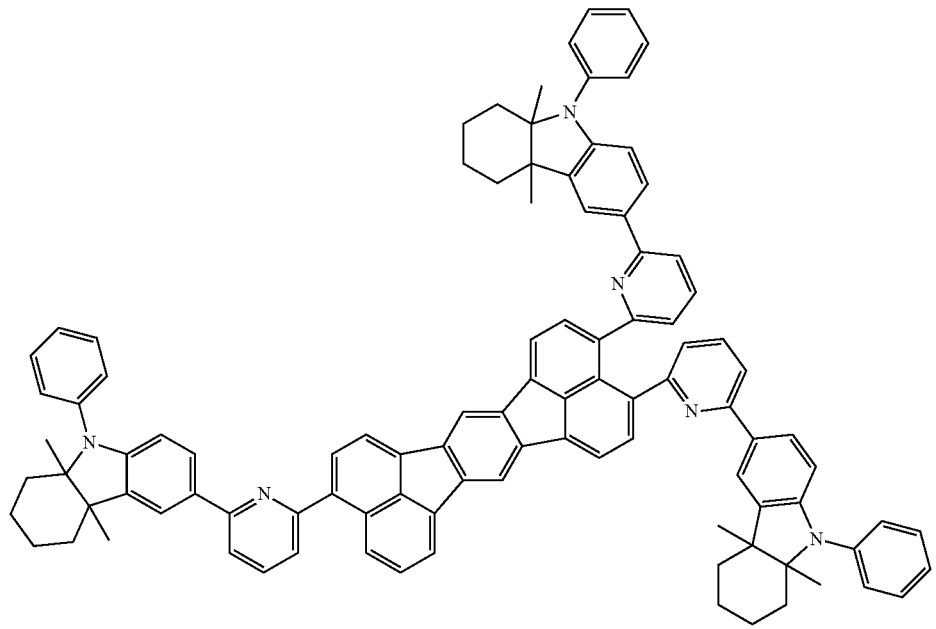
Formula 1199
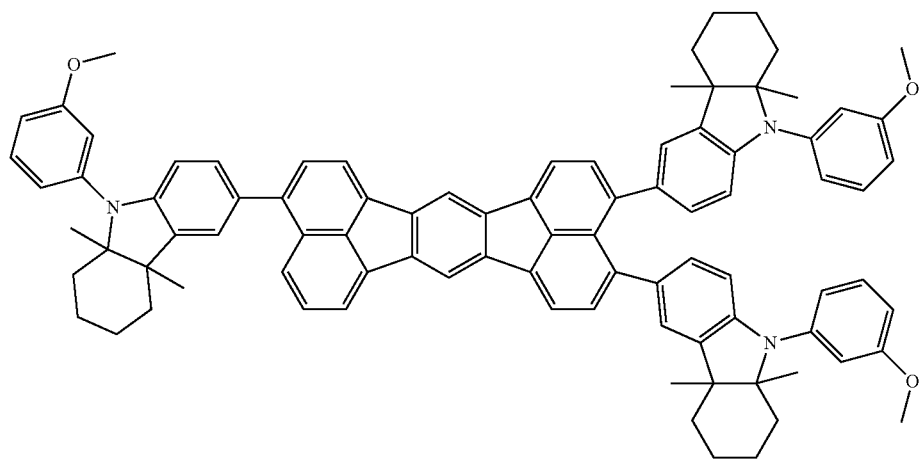
Formula 1200
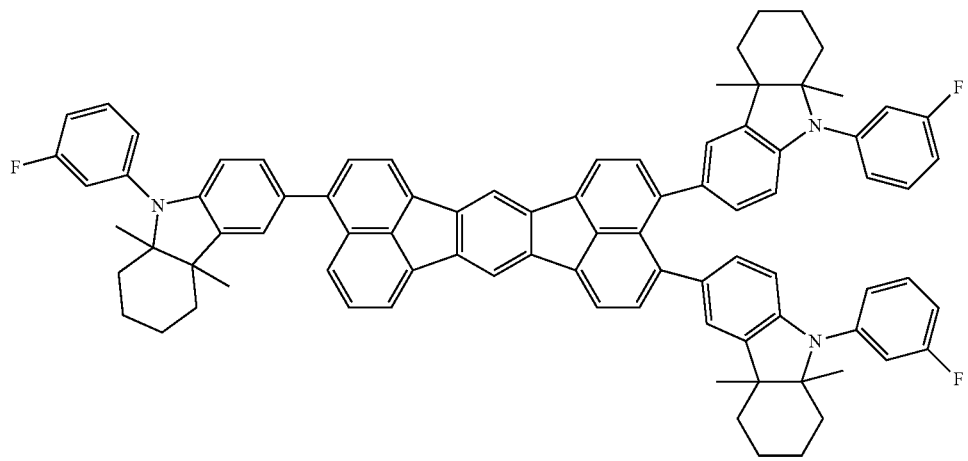

-continued
Formula 1201
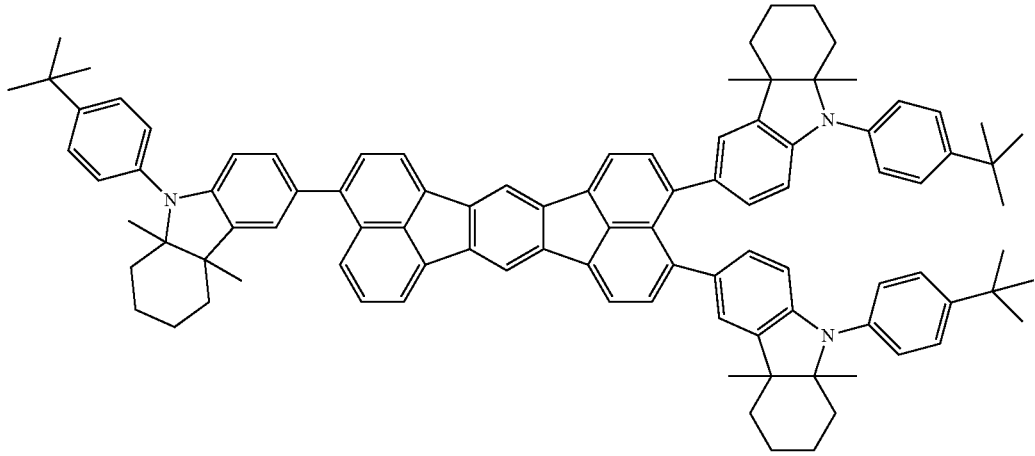
Formula 1202
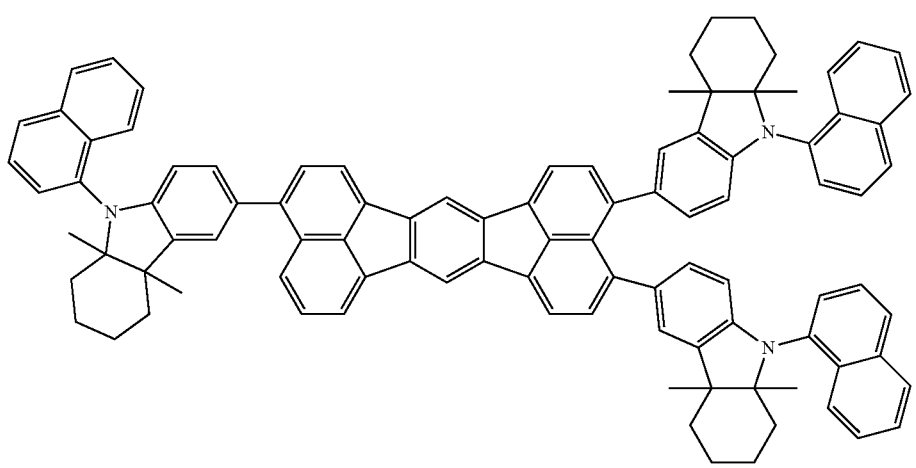
Formula 1203
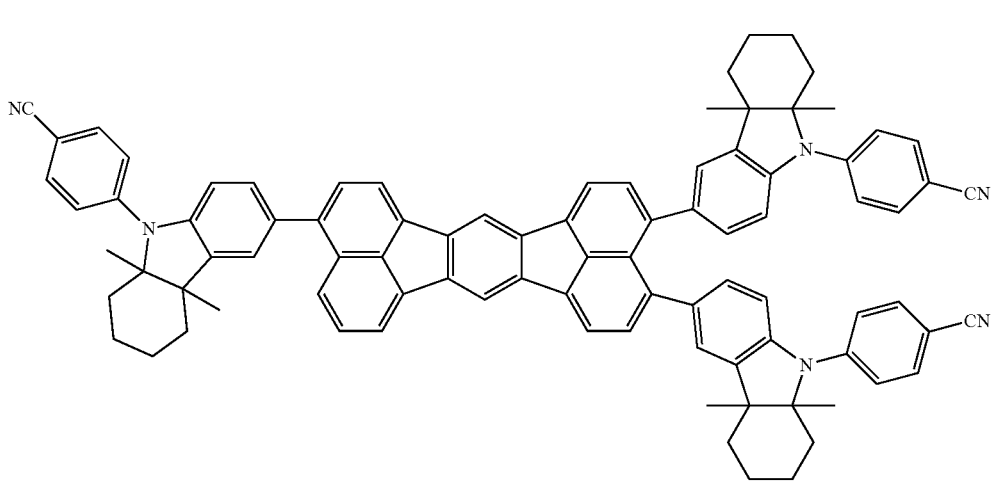

Formula 1204
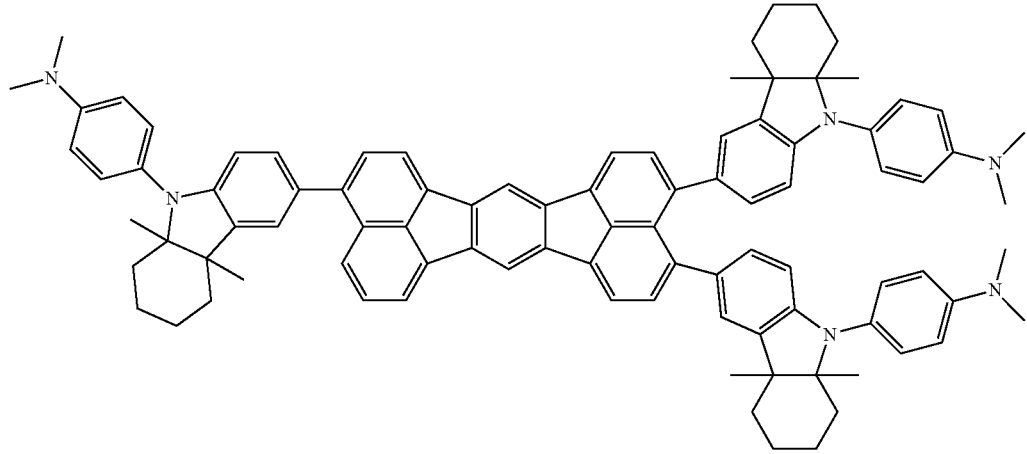
Formula 1205
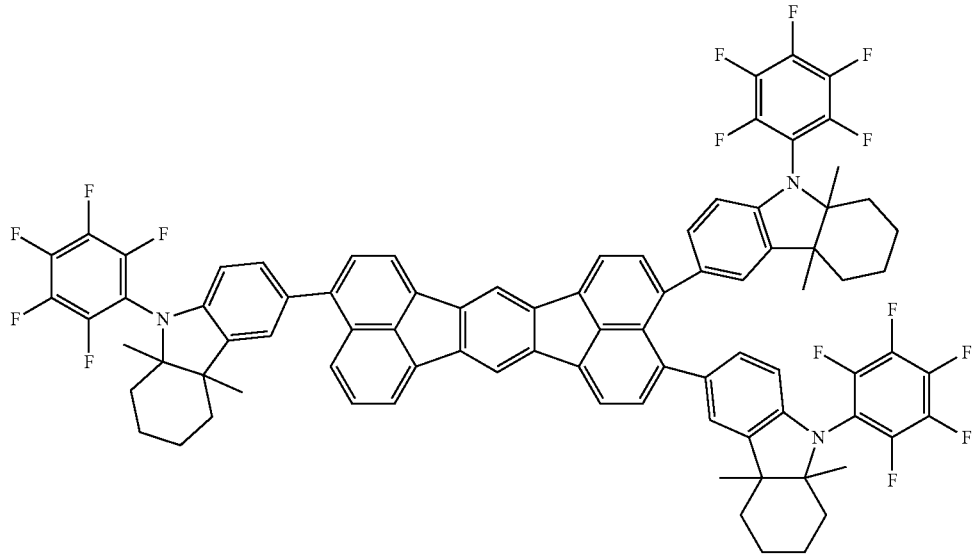
Formula 1206
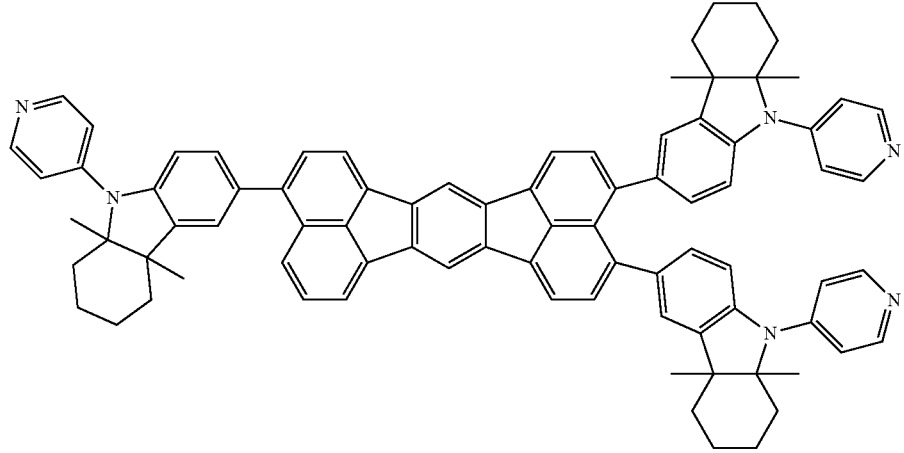

Formula 1207
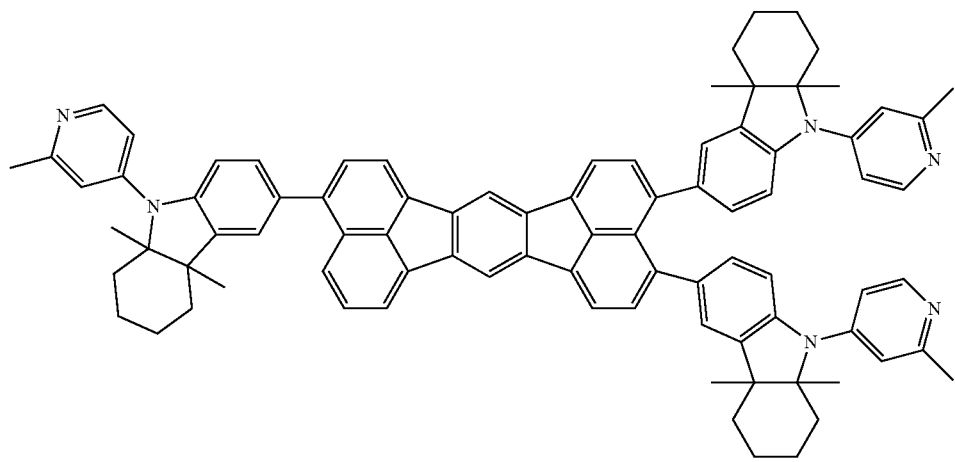
Formula 1208
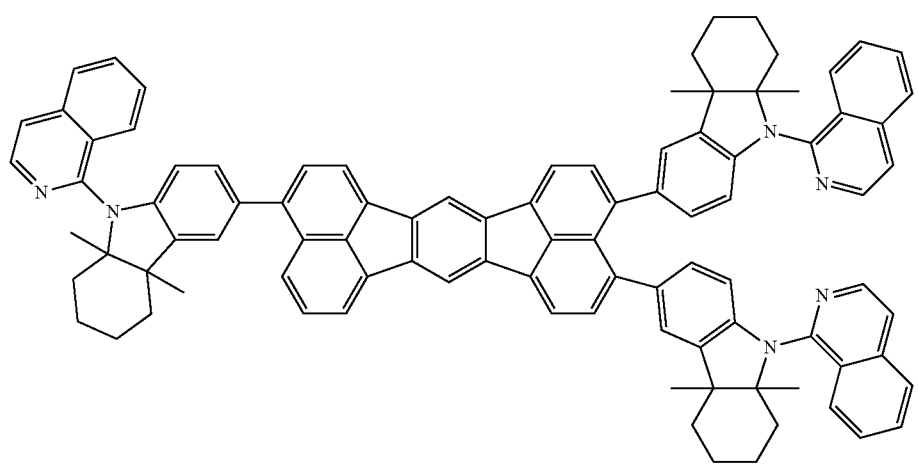
Formula 1209
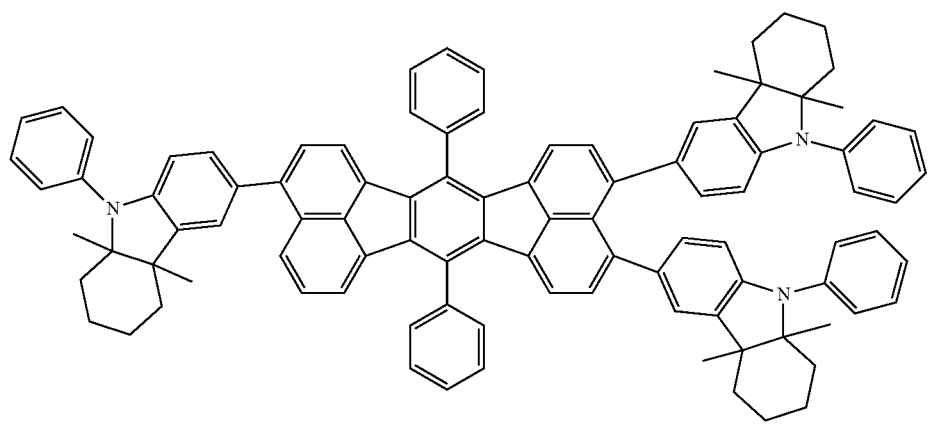

-continued
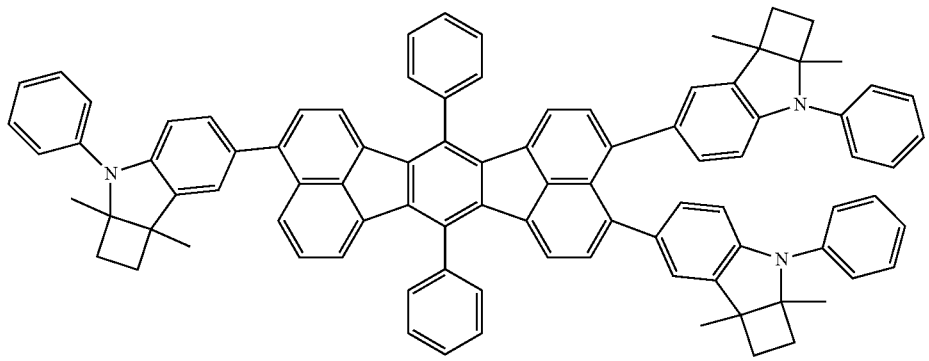
Formula 1210
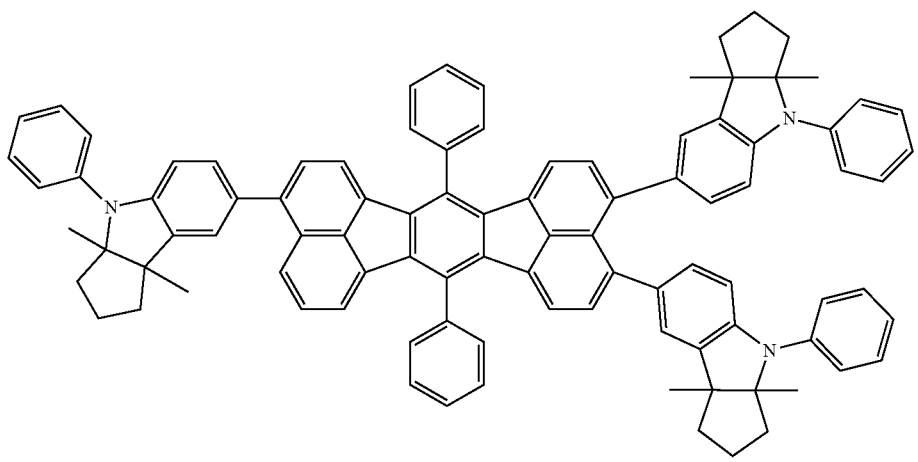
Formula 1211
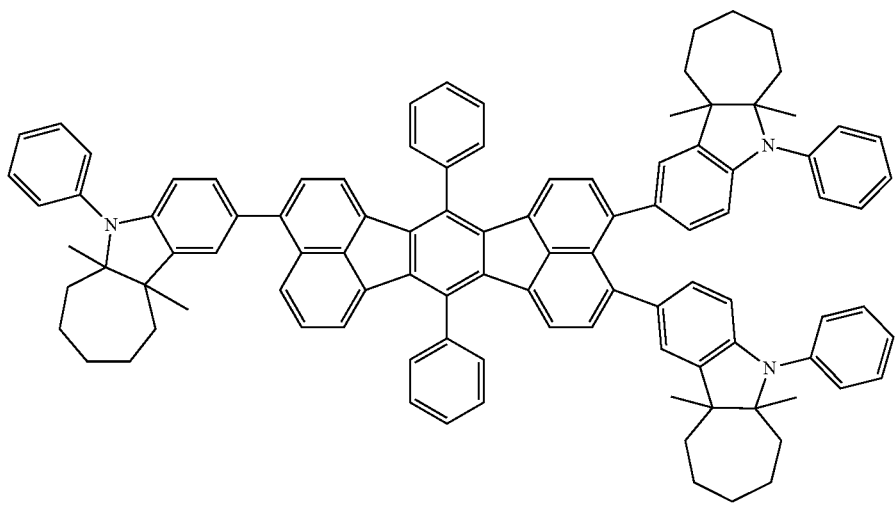
Formula 1212

Formula 1213
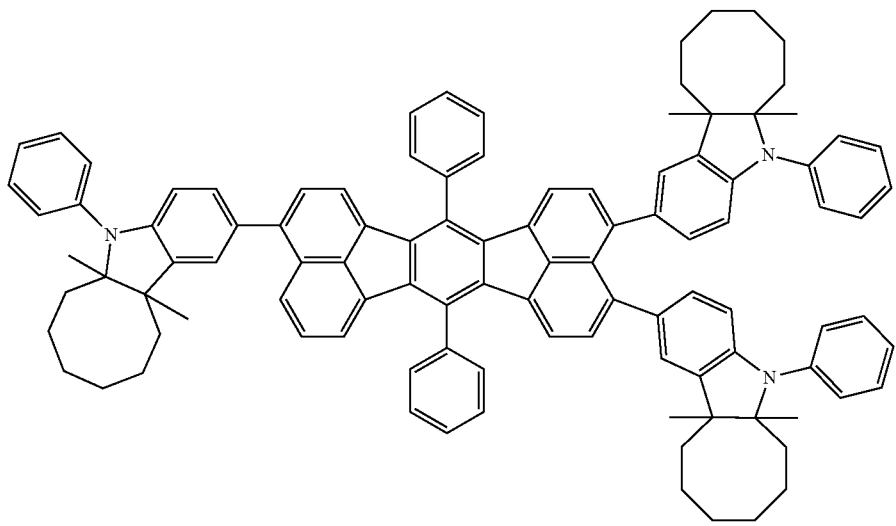
Formula 1214
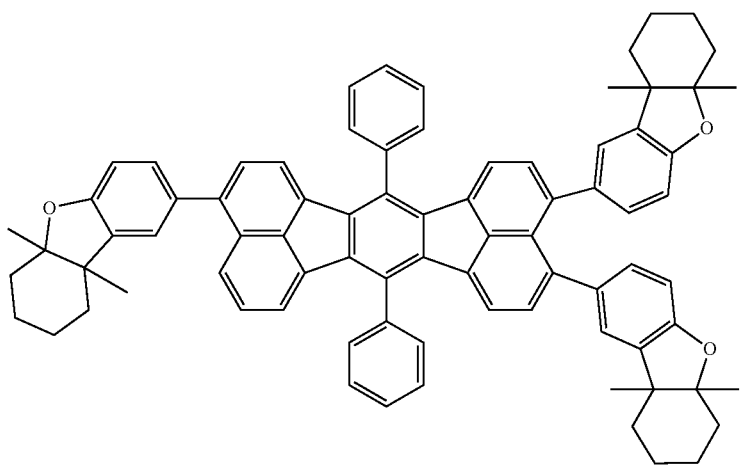
Formula 1215
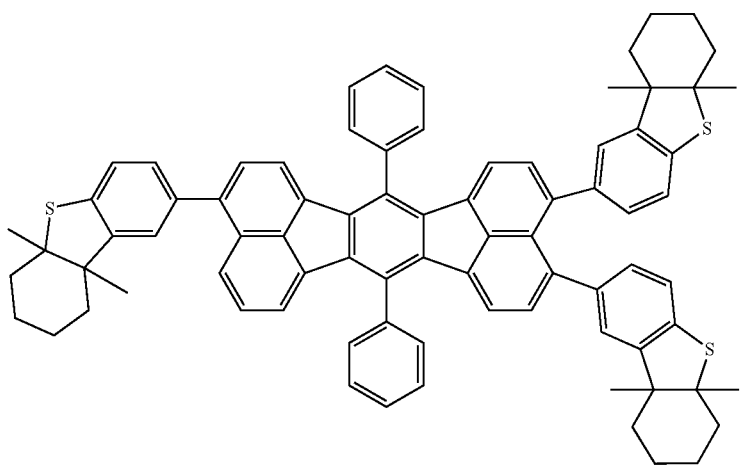

-continued
Formula 1216
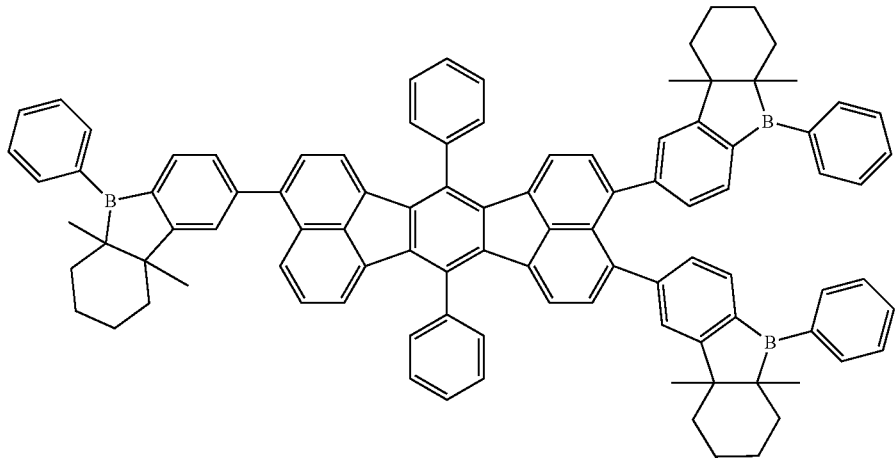
Formula 1217
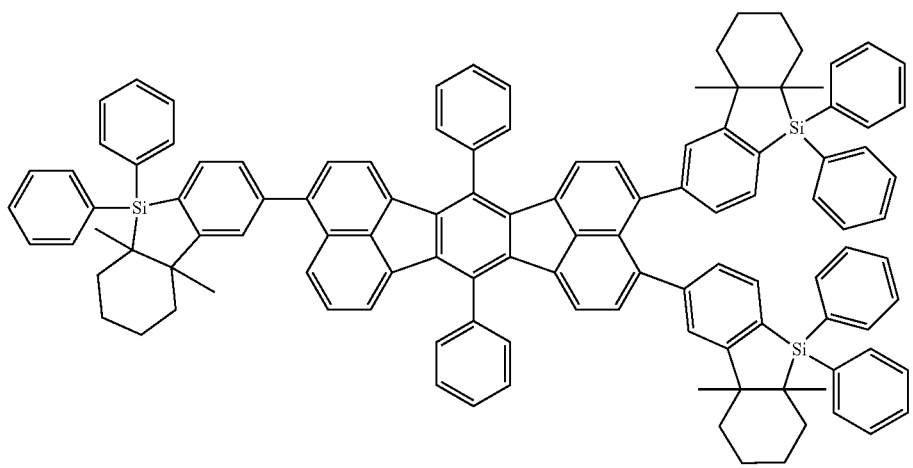
Formula 1218
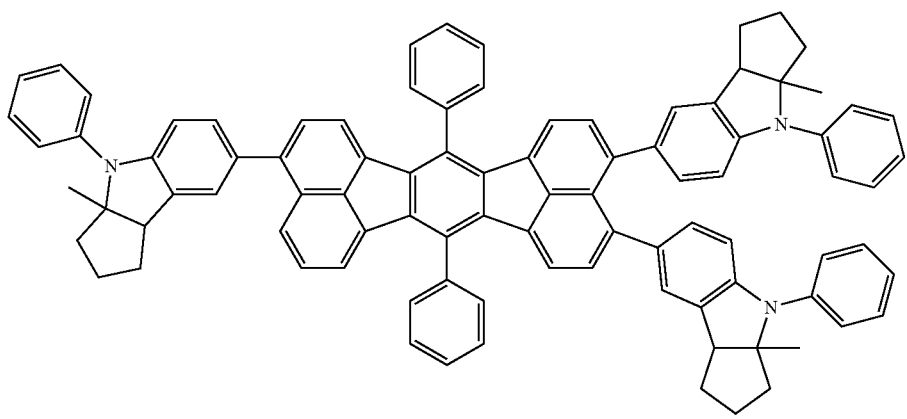

-continued
Formula 1219
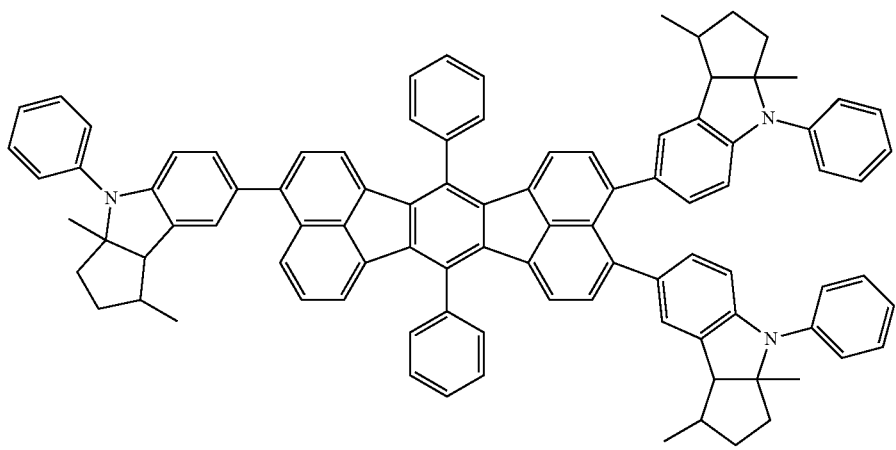
Formula 1220
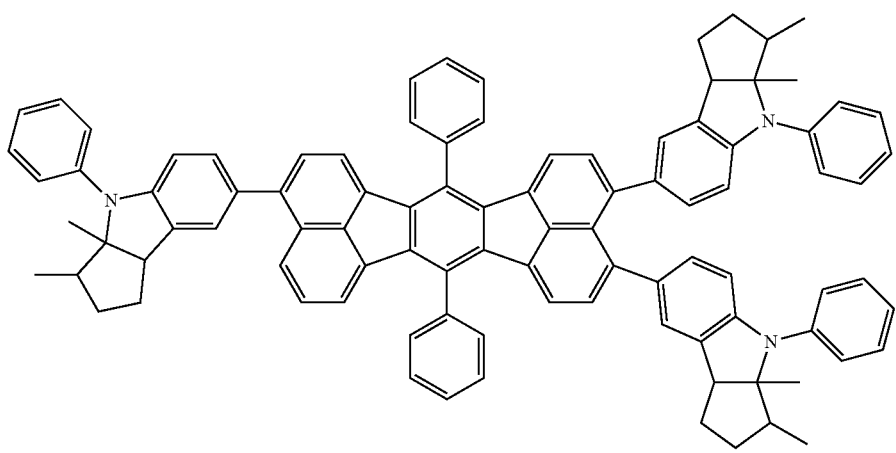
Formula 1221
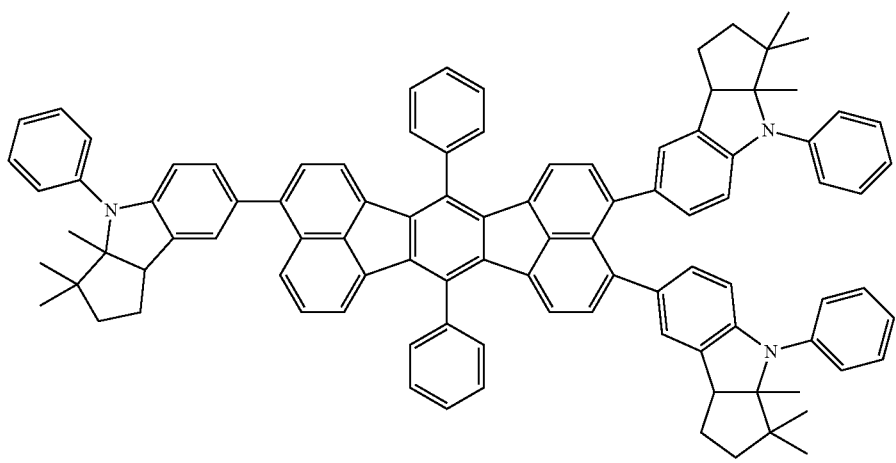

Formula 1222
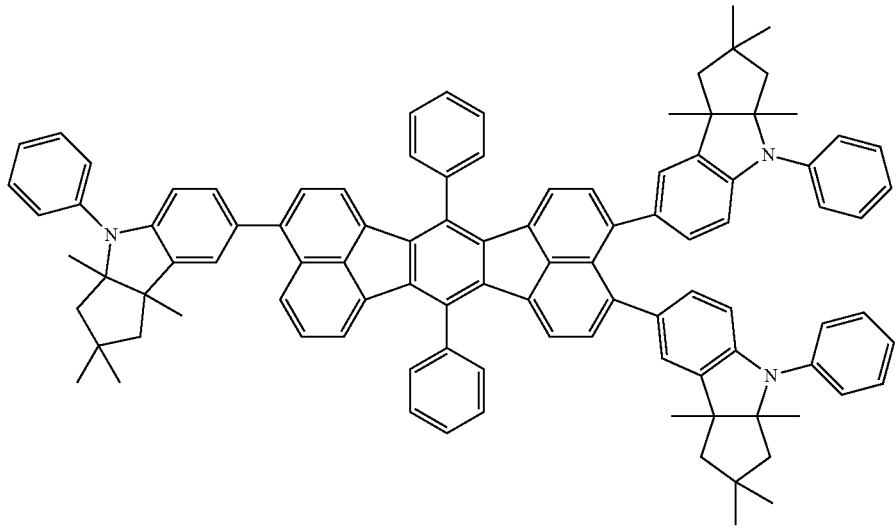
Formula 1223
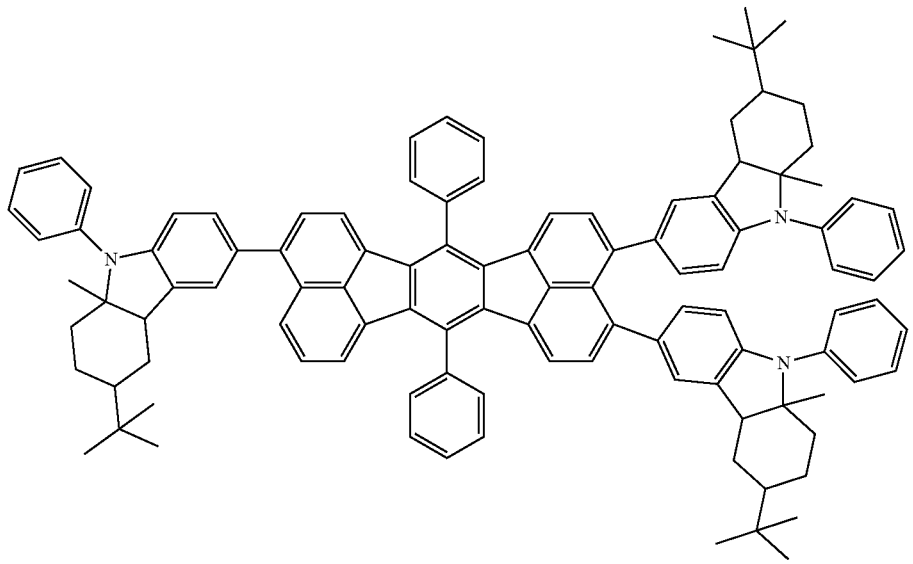
Formula 1224
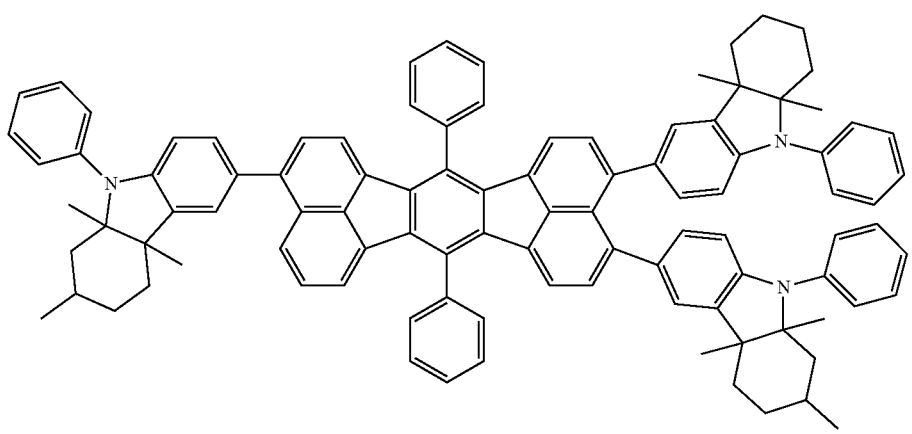

Formula 1225
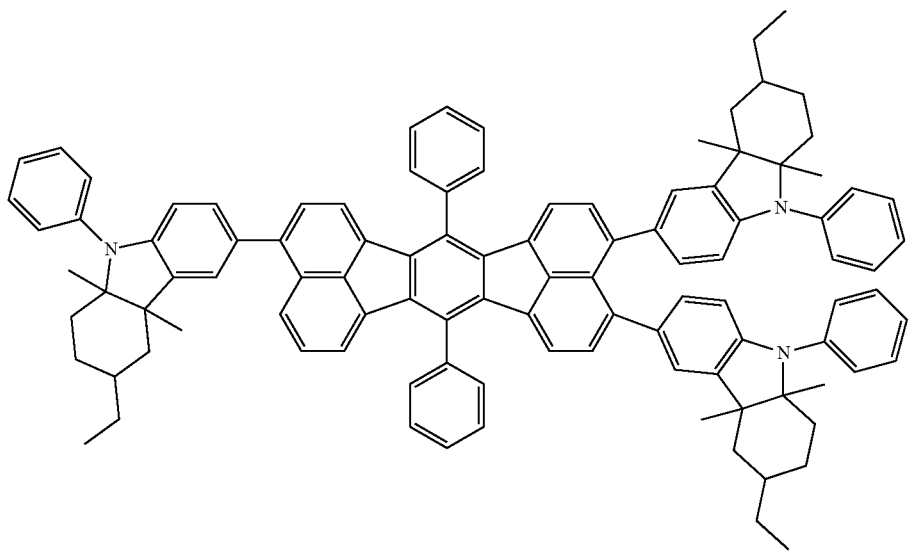
Formula 1226
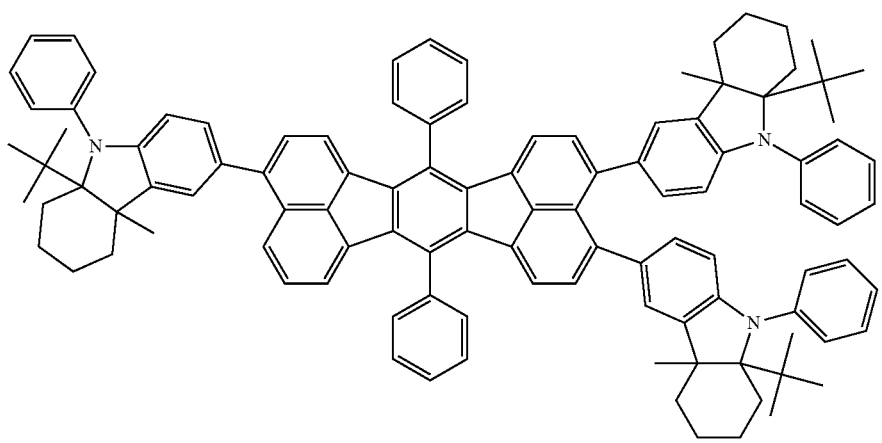
Formula 1227
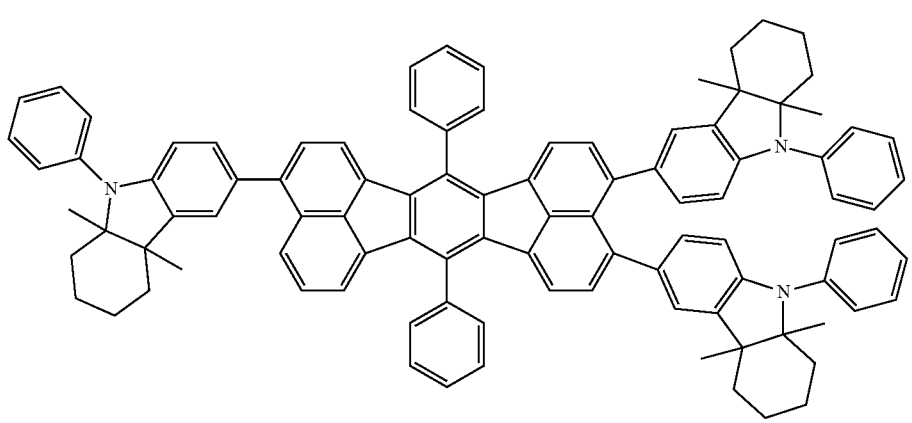

-continued
Formula 1228
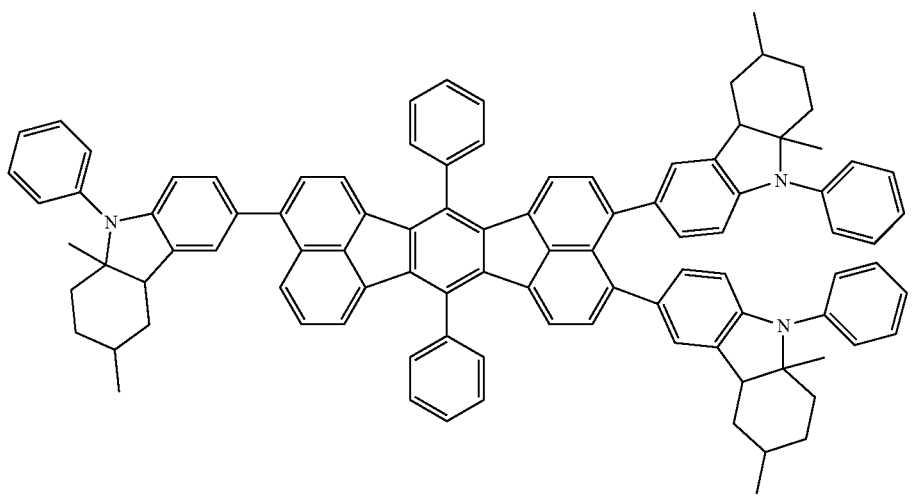
Formula 1229
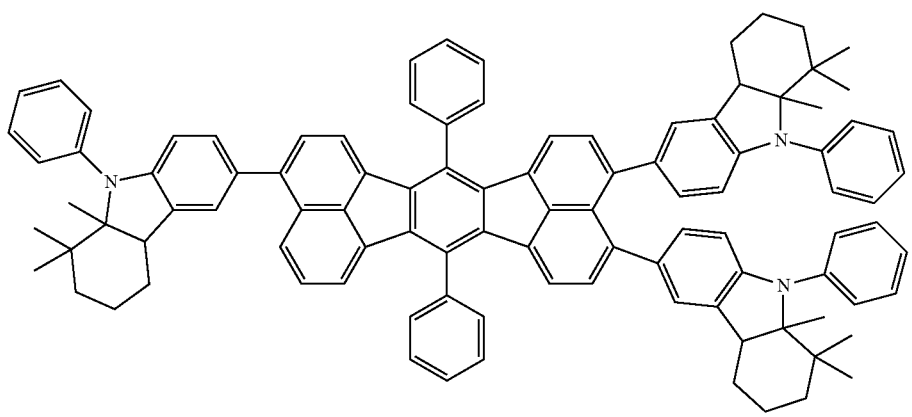
Formula 1230
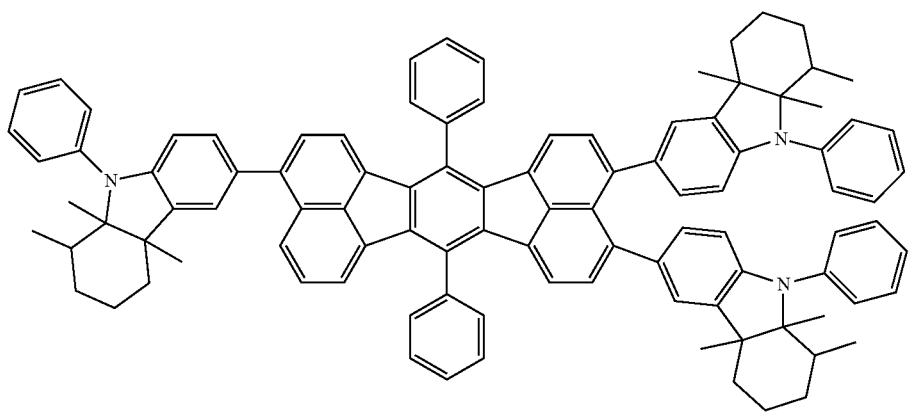

Formula 1231
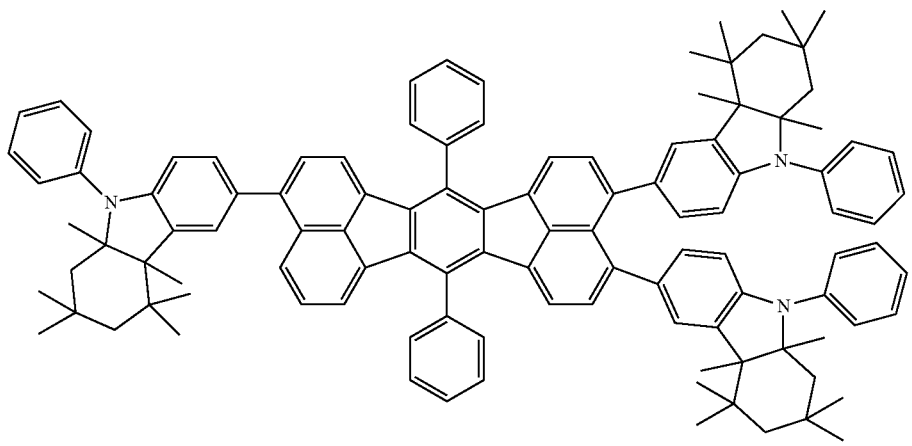
Formula 1232
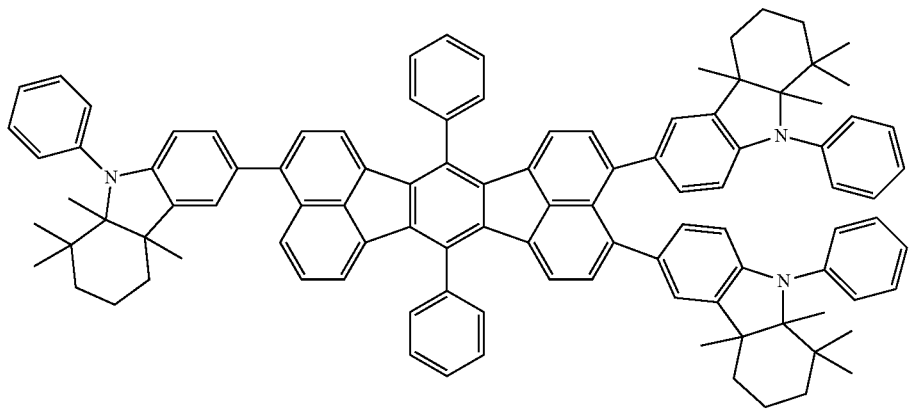
Formula 1233
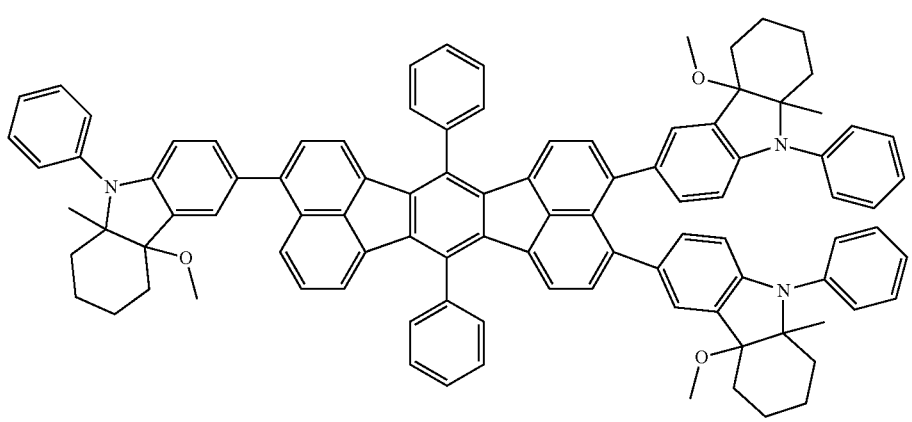

Formula 1234
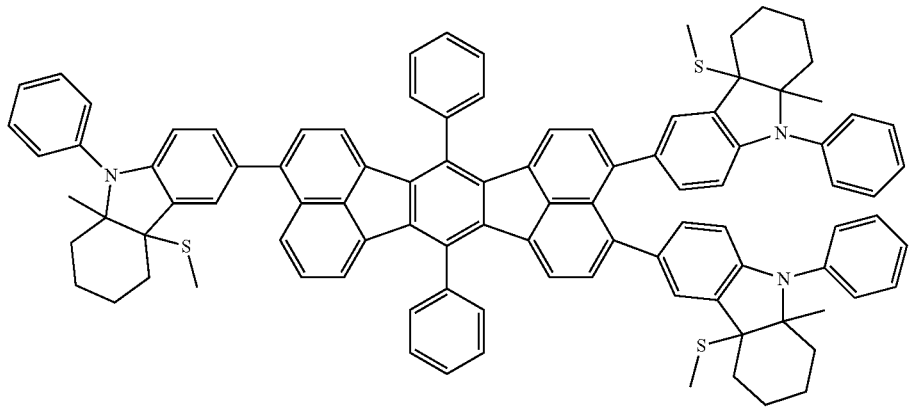
Formula 1235
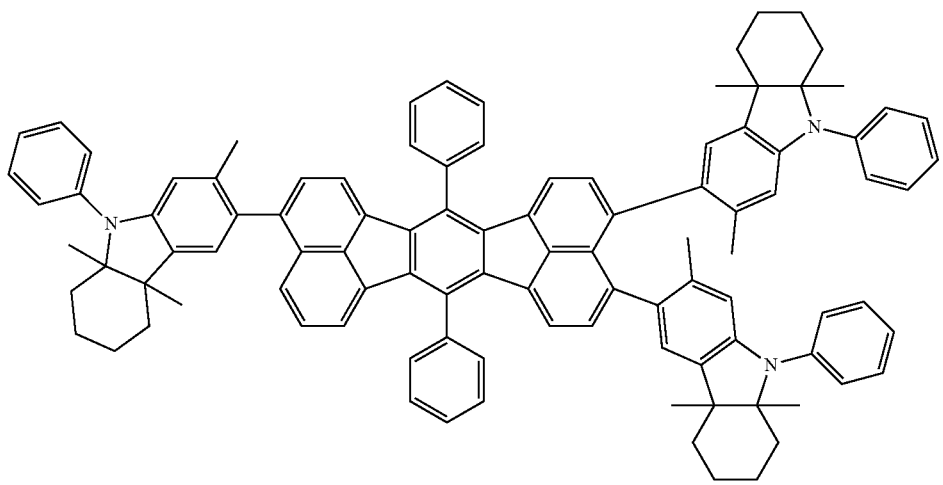
Formula 1236
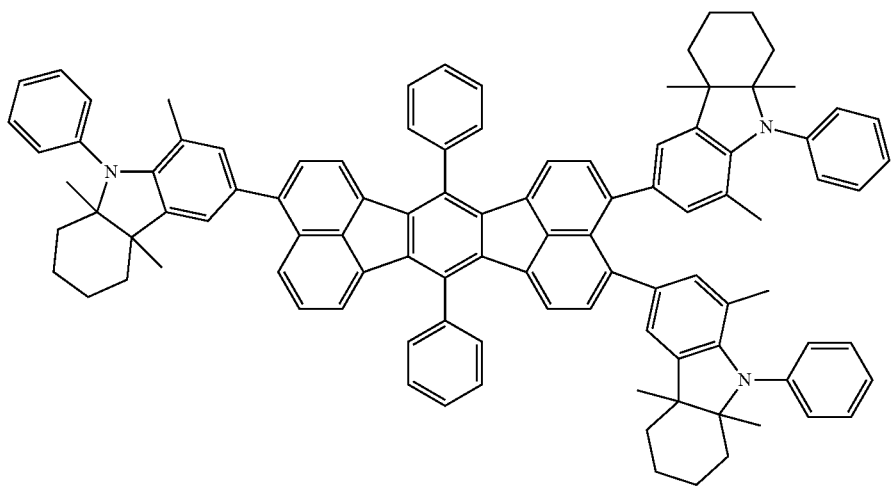

Formula 1237
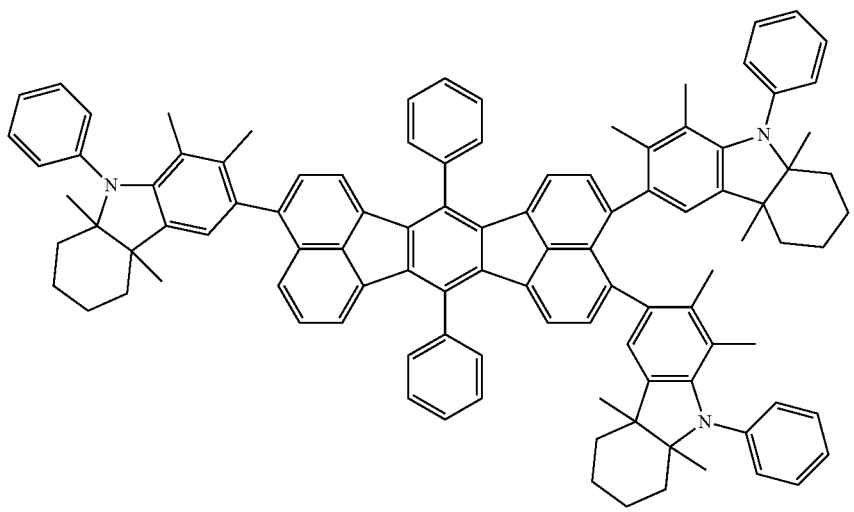
Formula 1238
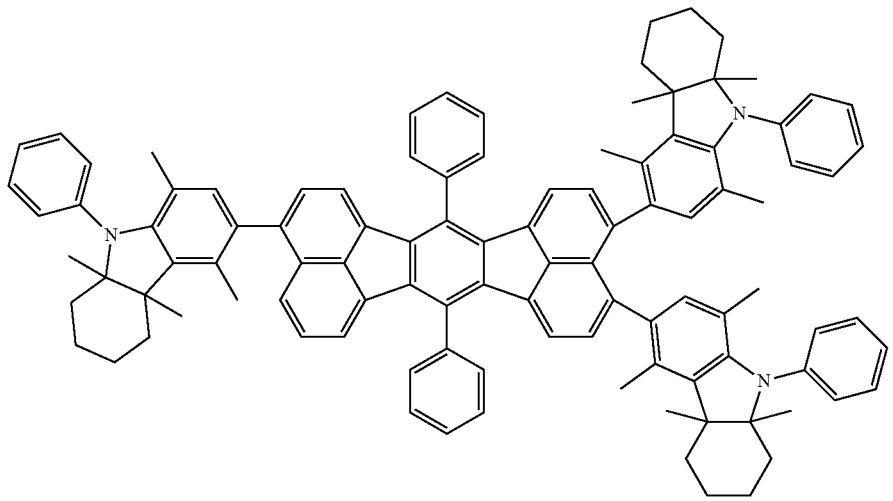
Formula 1239
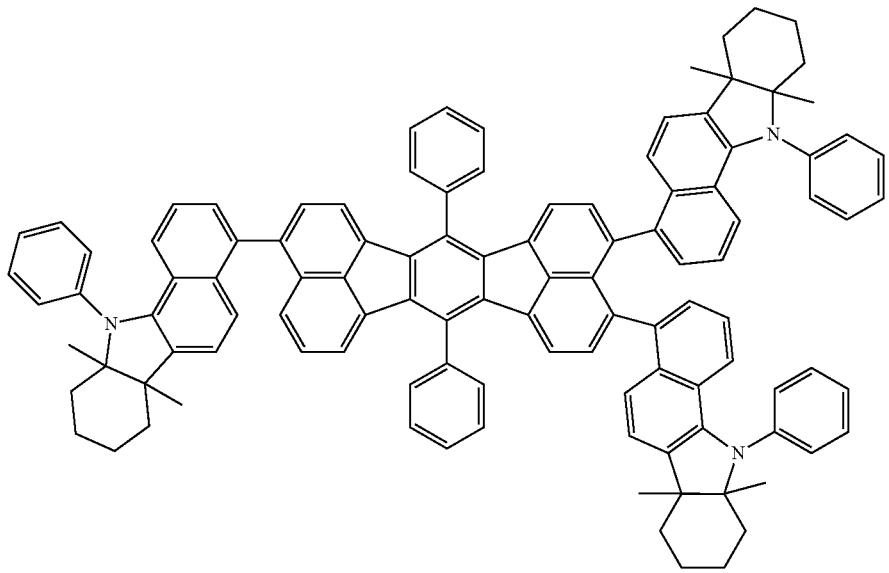

-continued
Formula 1240
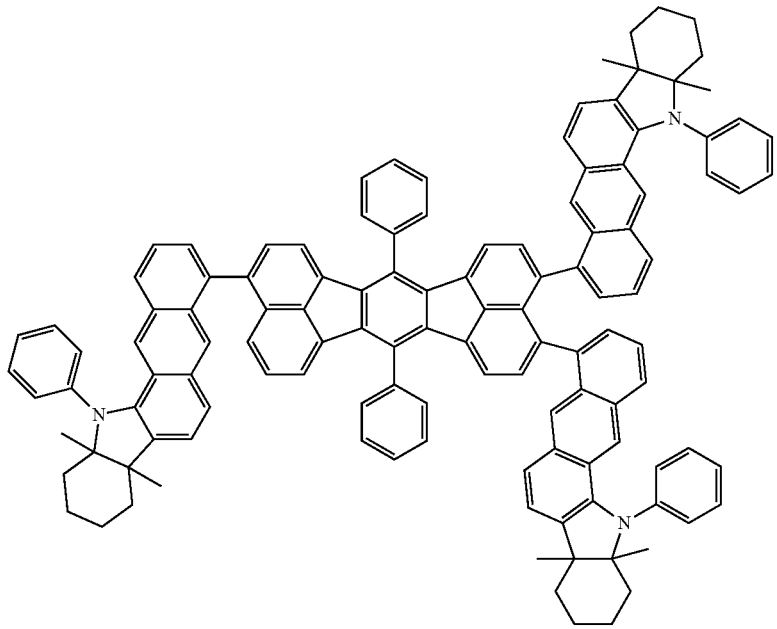
Formula 1241
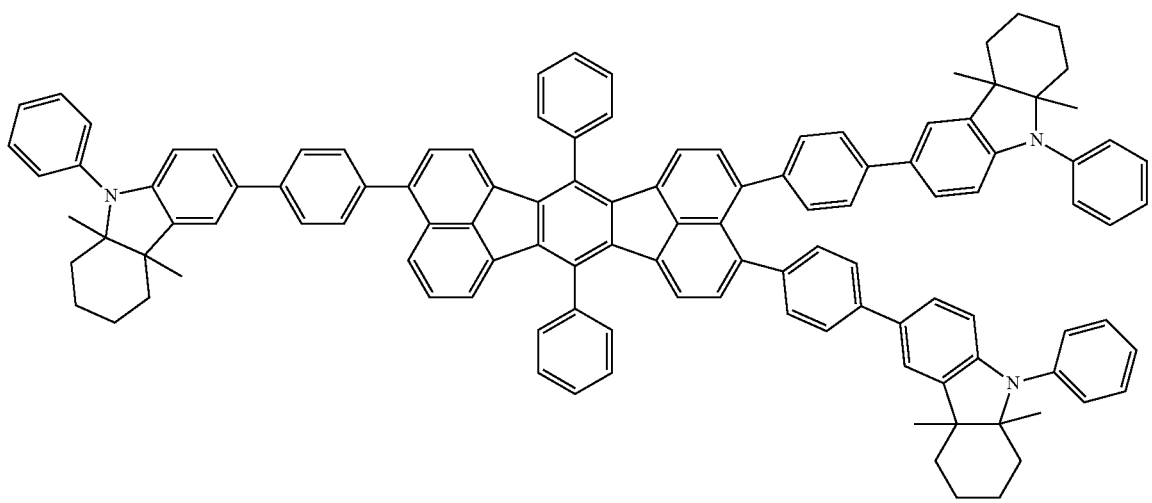

-continued
Formula 1242
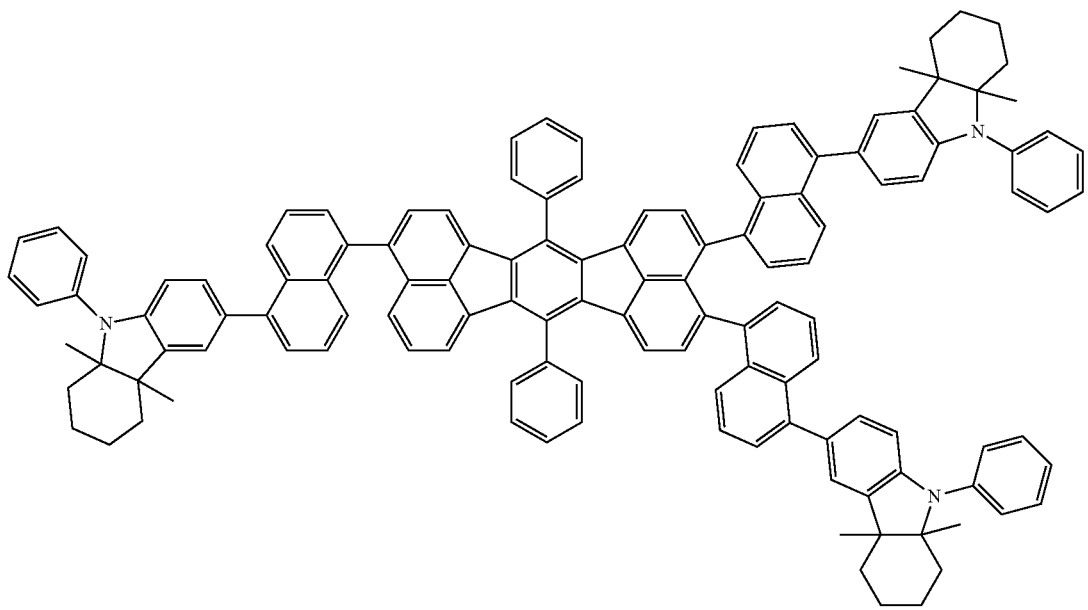
Formula 1243
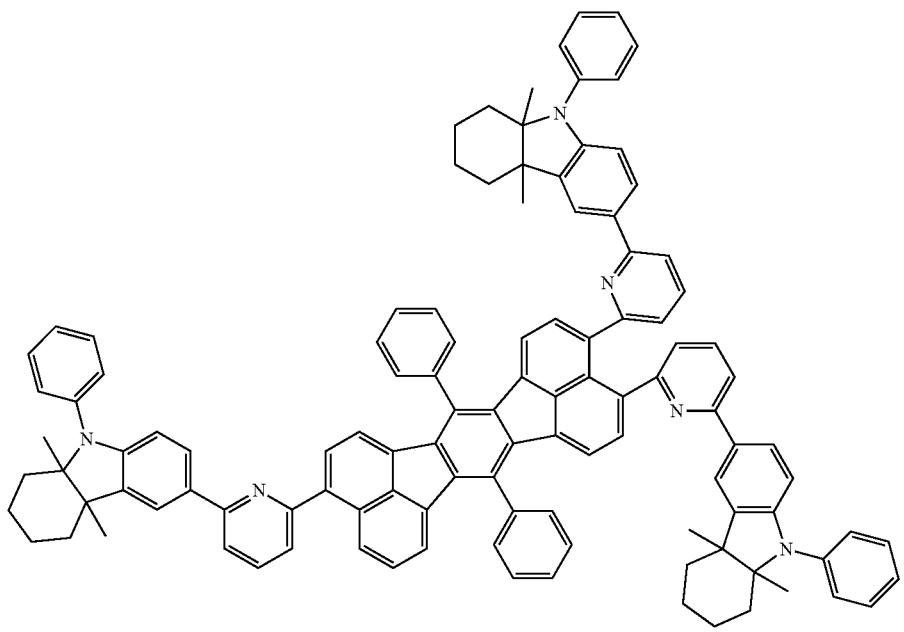

Formula 1244
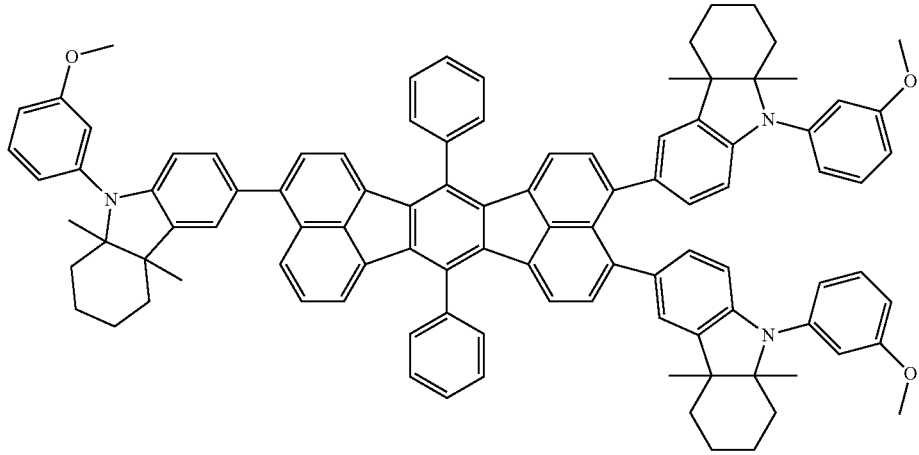
Formula 1245
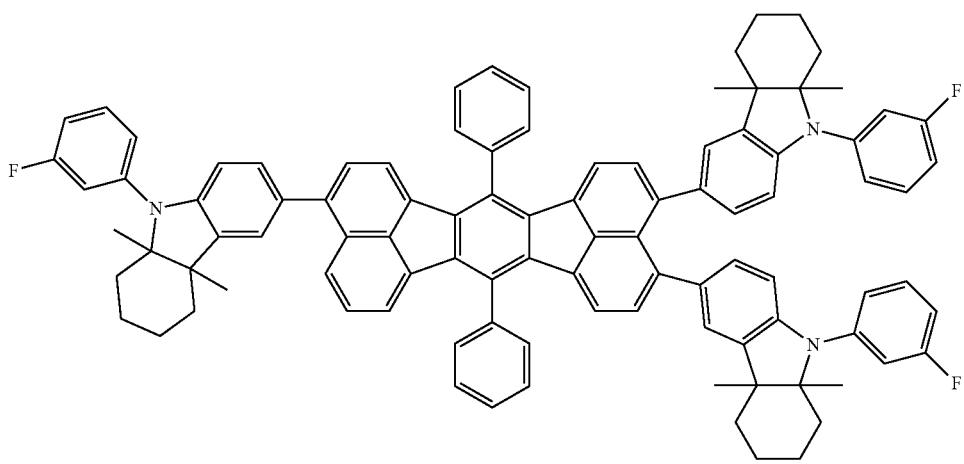
Formula 1246
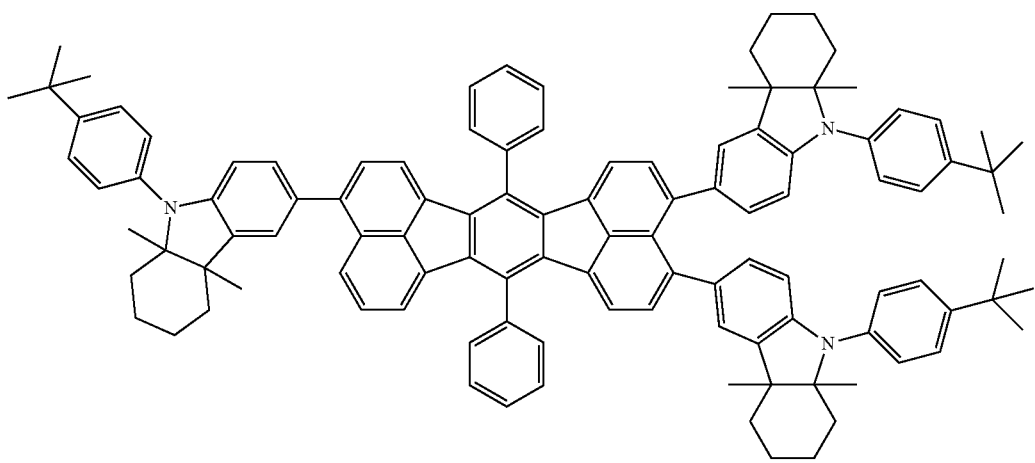

Formula 1247
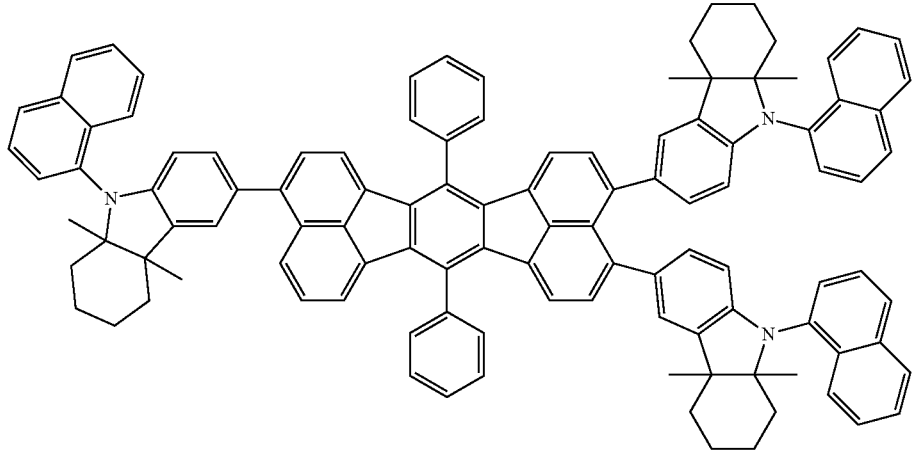
Formula 1248
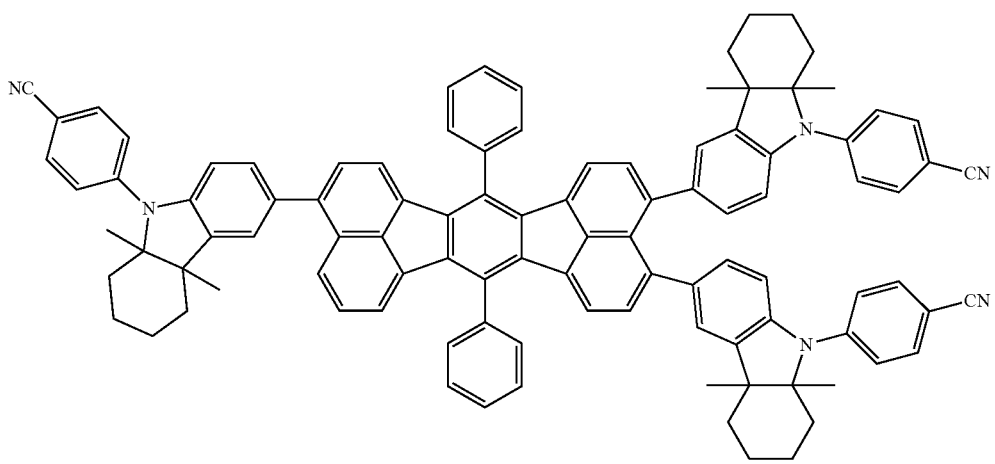
Formula 1249
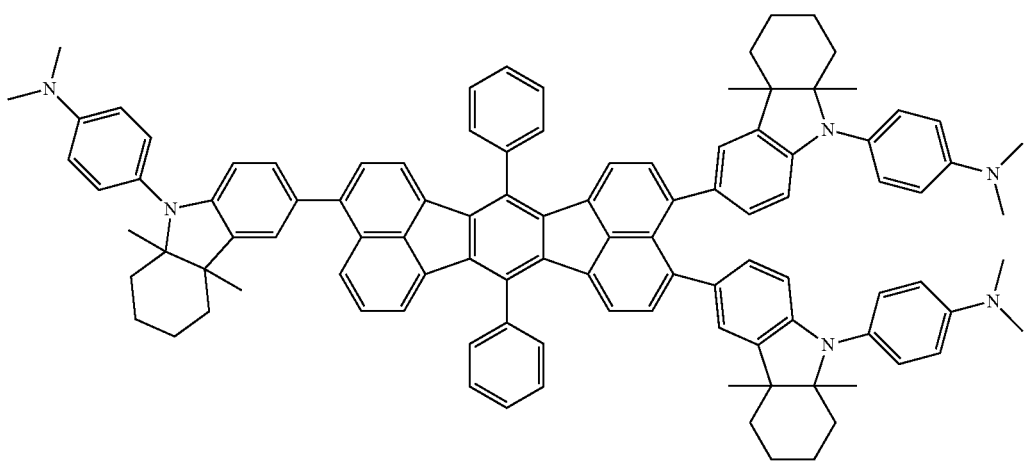

Formula 1250
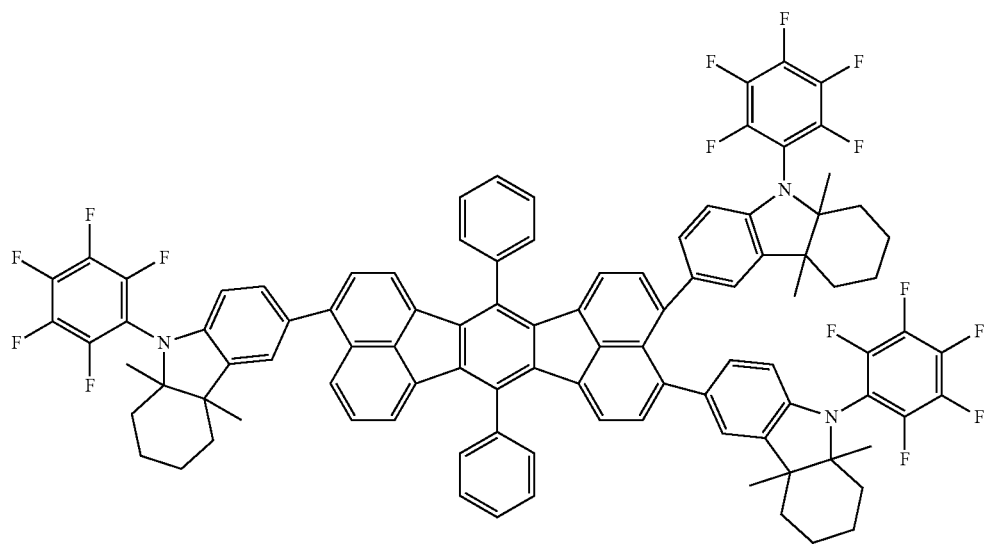
Formula 1251
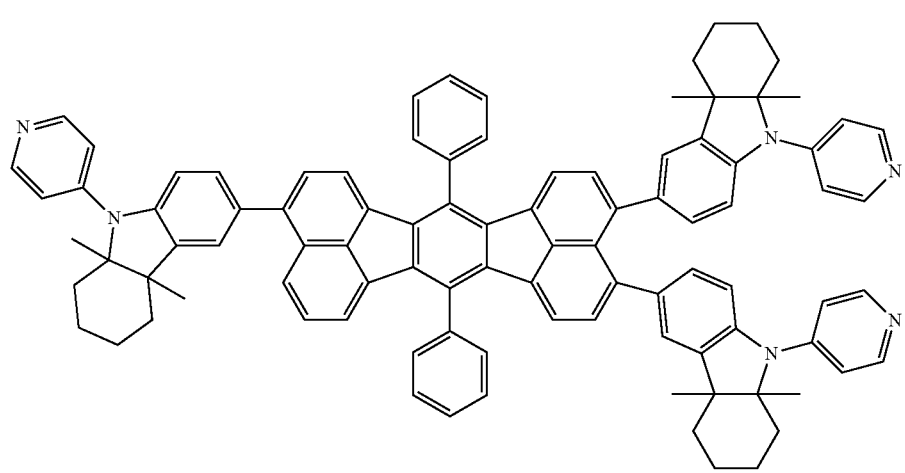
Formula 1252
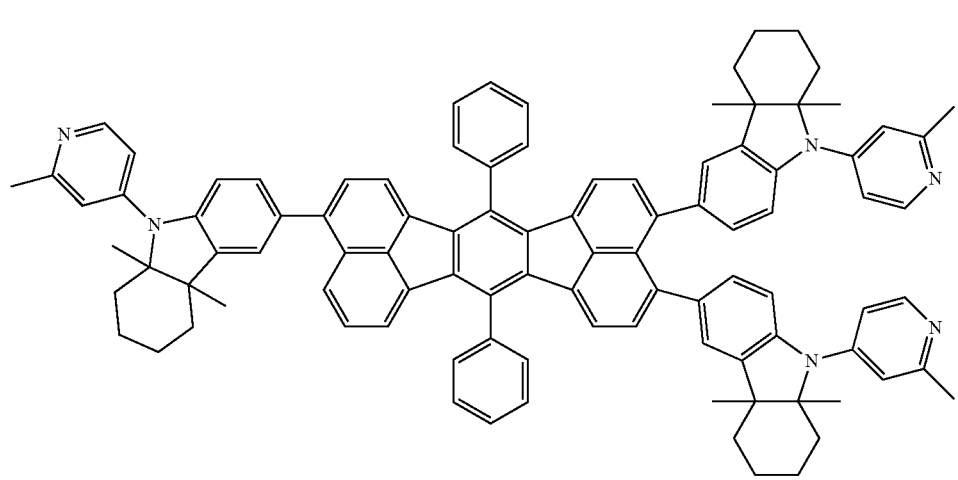

Formula 1253
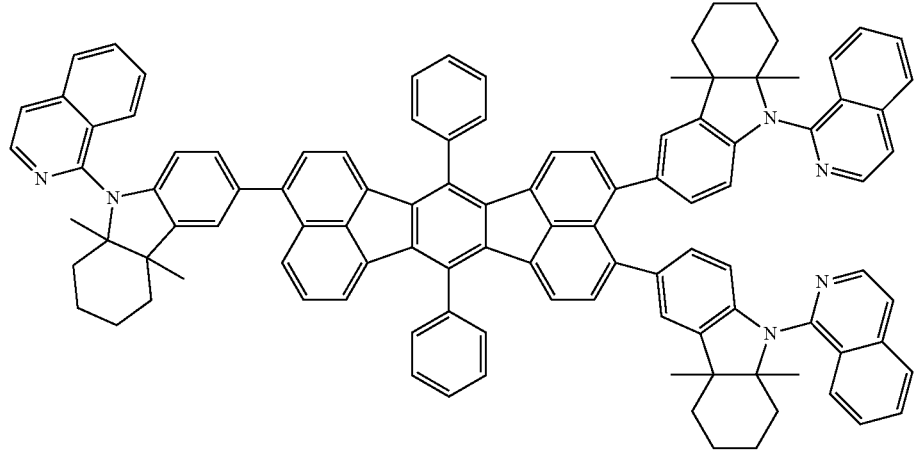
Formula 1254
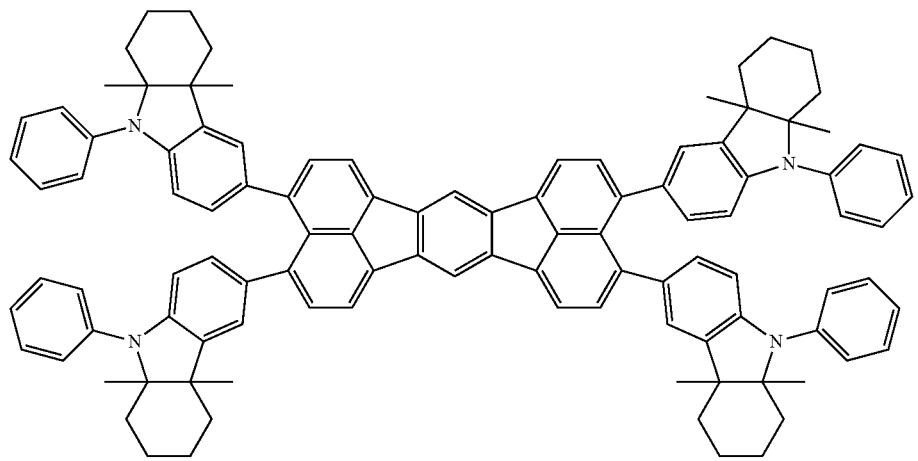
Formula 1255
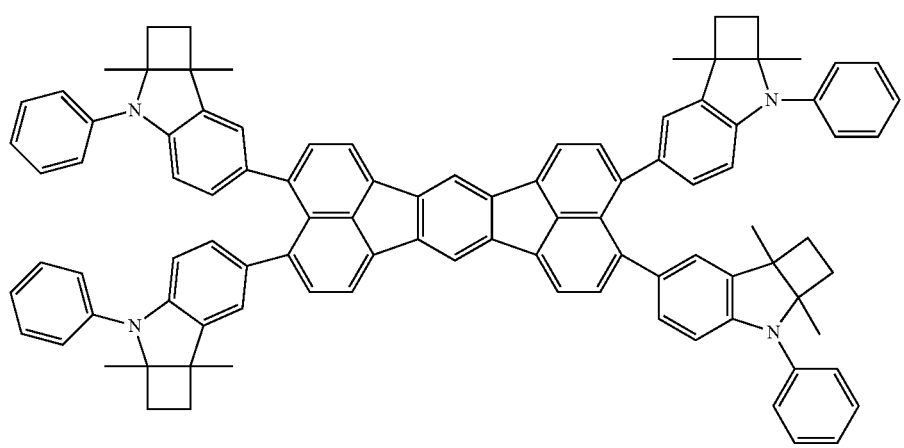

Formula 1256
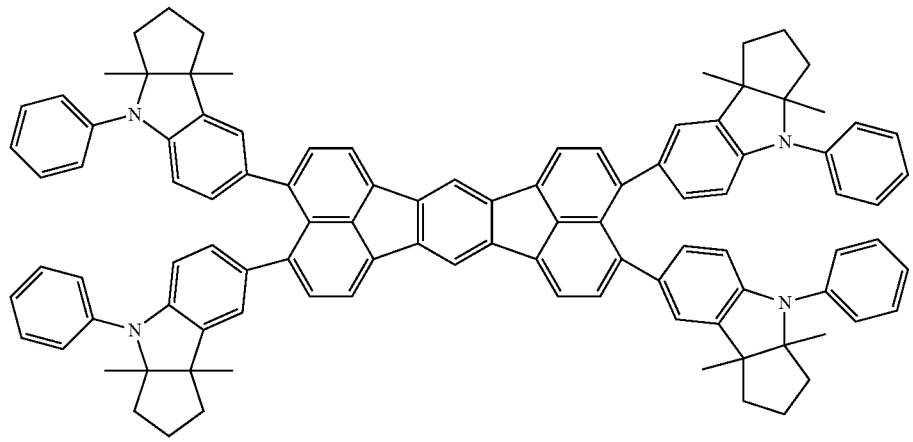
Formula 1257
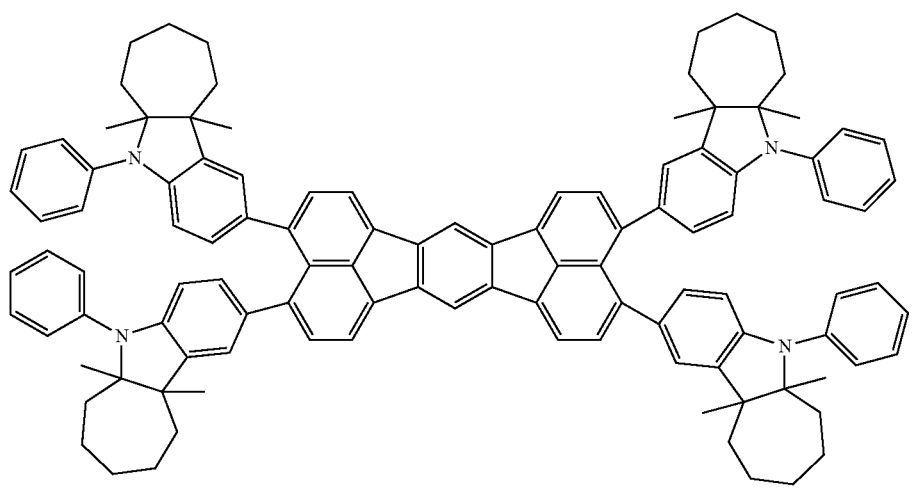
Formula 1258
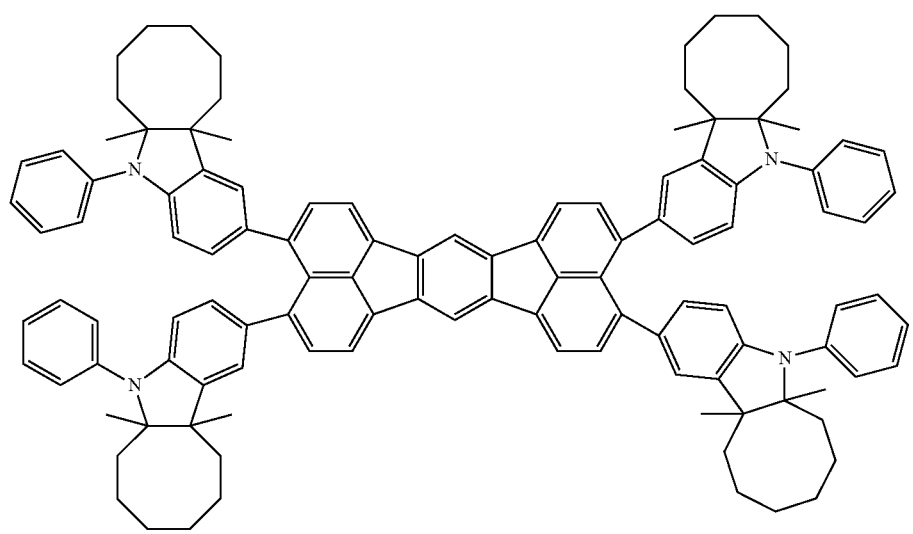

-continued
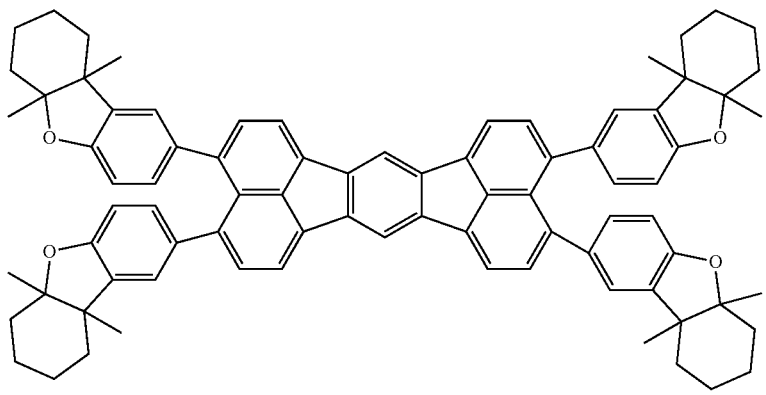
Formula 1259
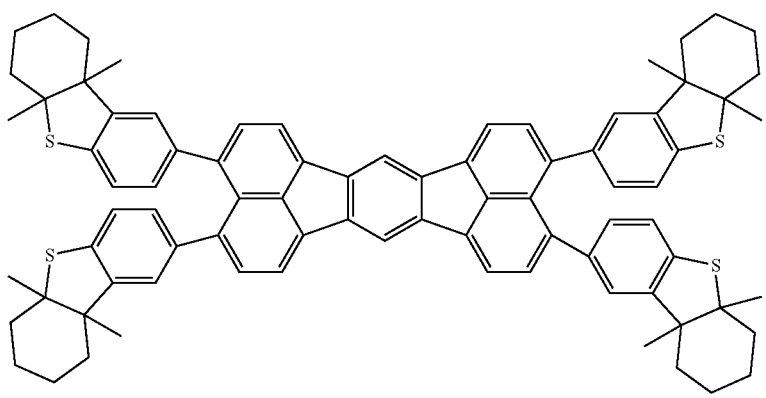
Formula 1260
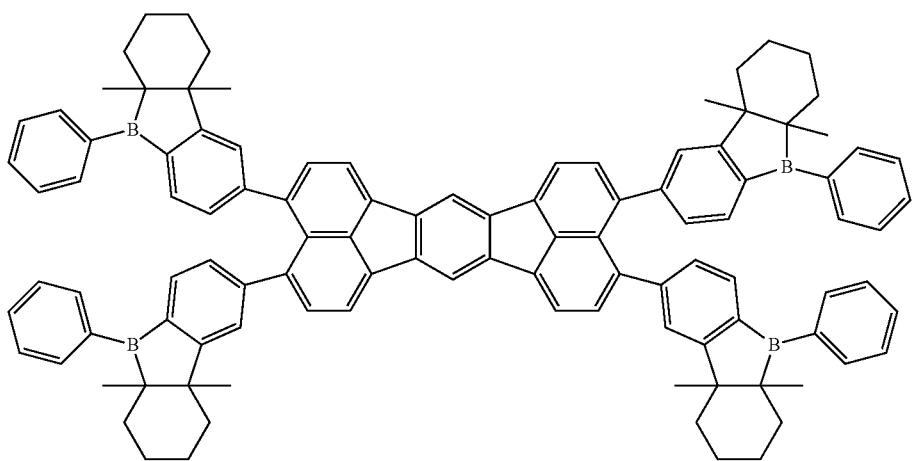
Formula 1261

-continued
Formula 1262
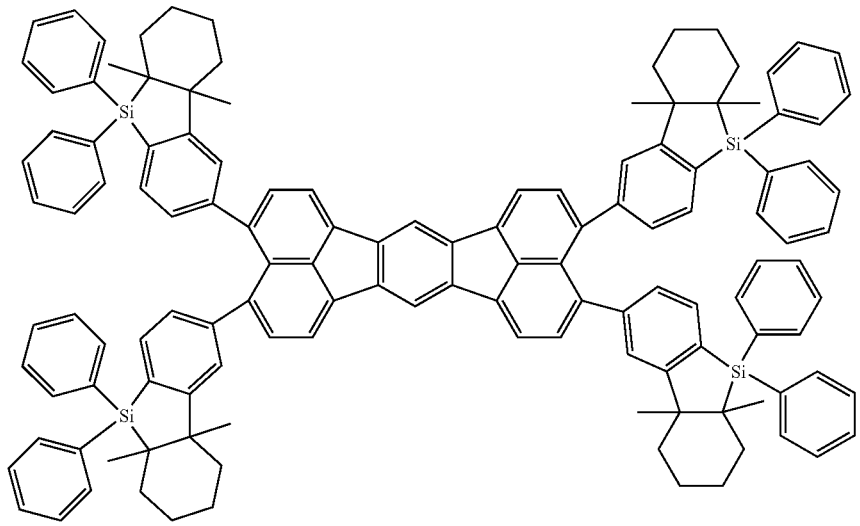
Formula 1263
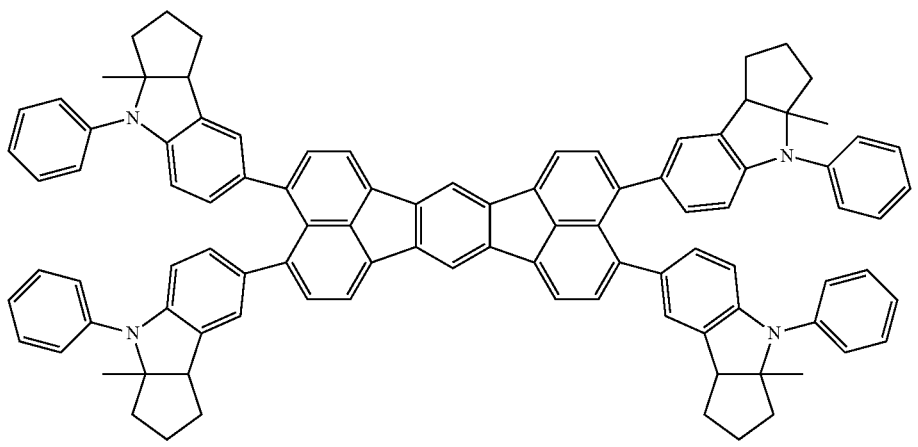
Formula 1264
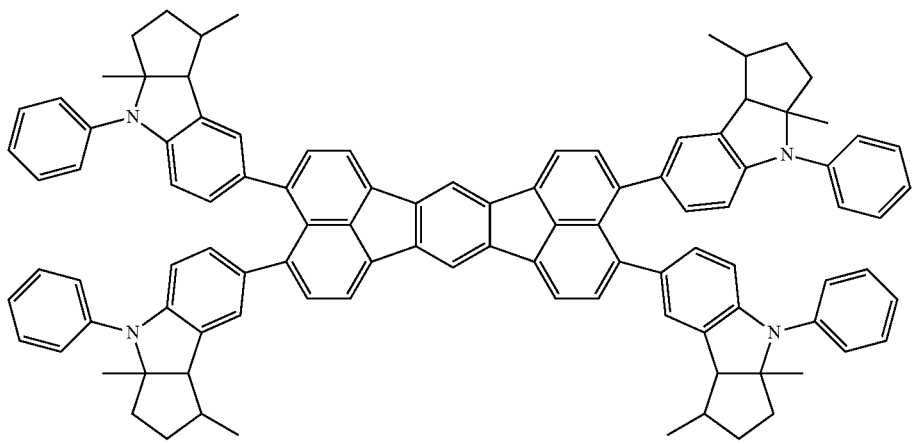

-continued
Formula 1265
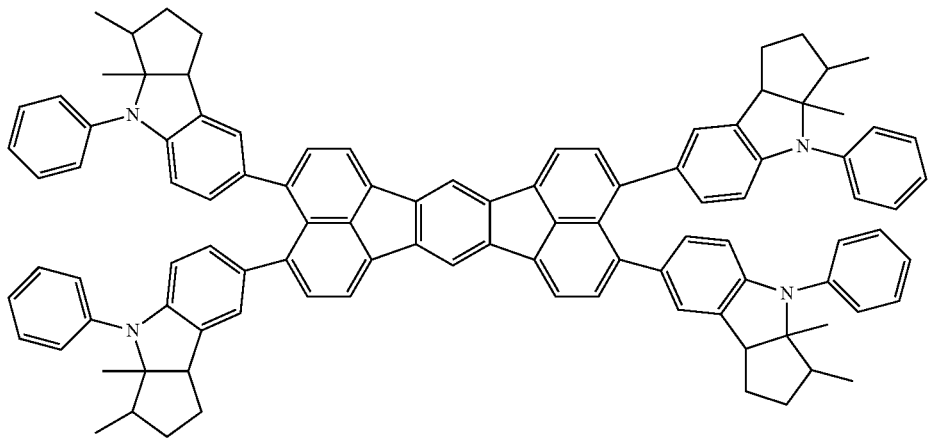
Formula 1266
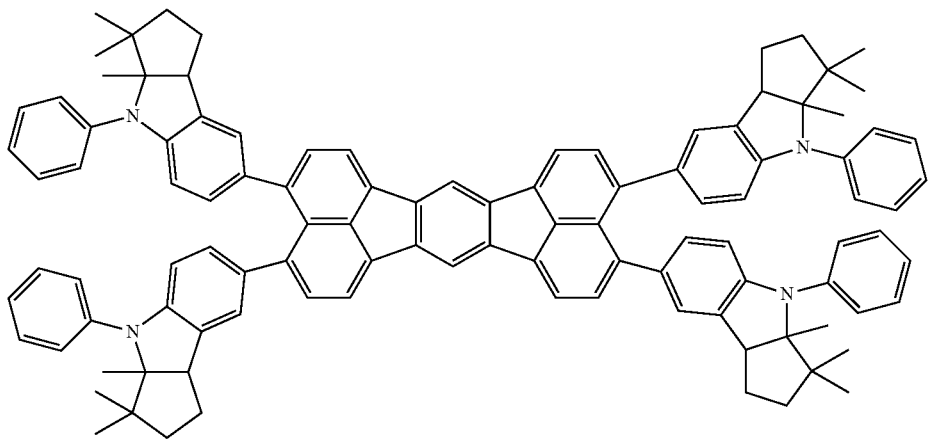
Formula 1267
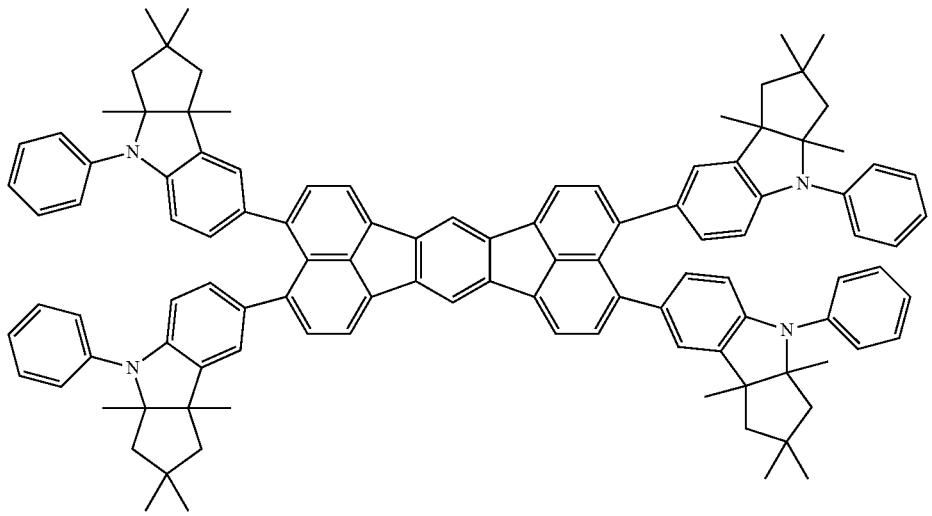

-continued
Formula 1268
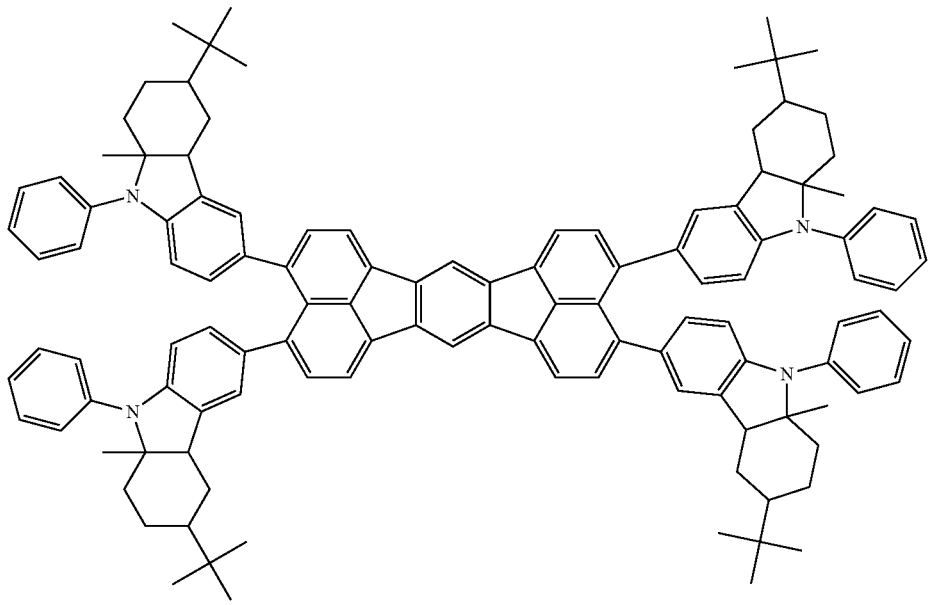
Formula 1269
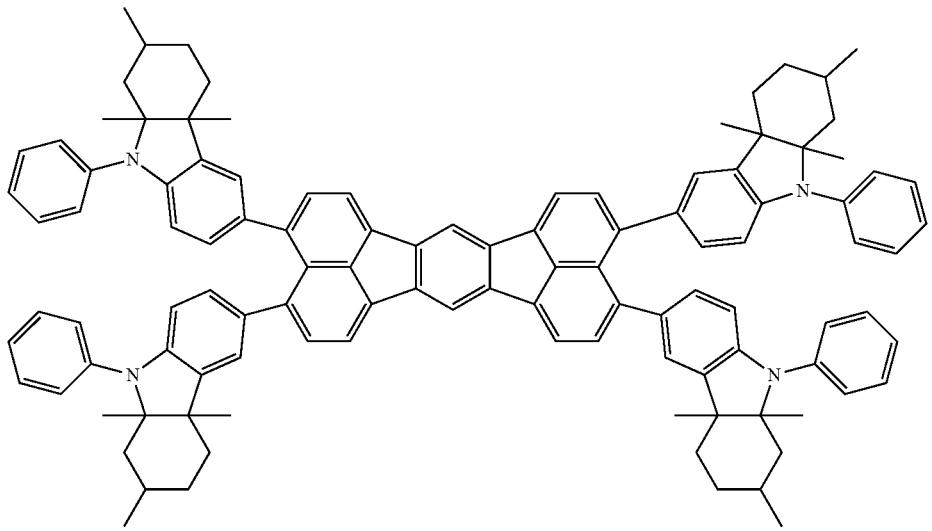
Formula 1270
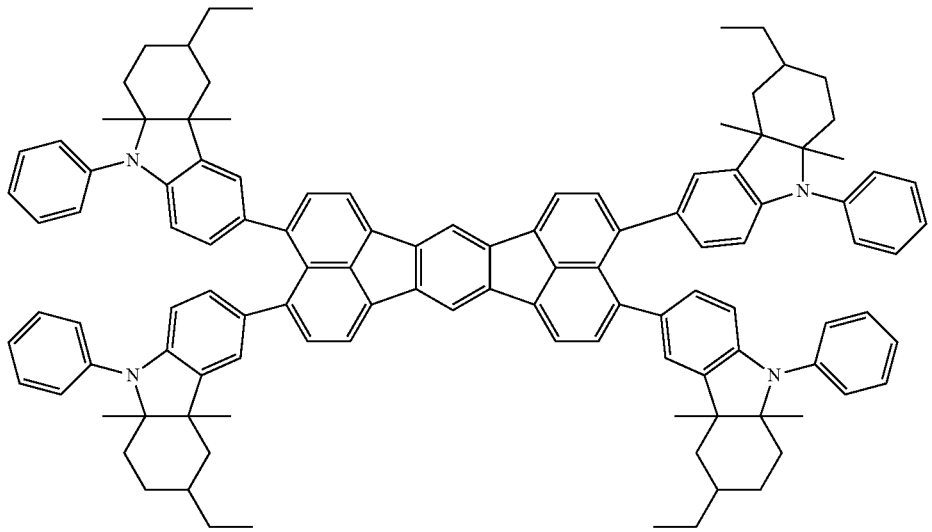

-continued
Formula 1271
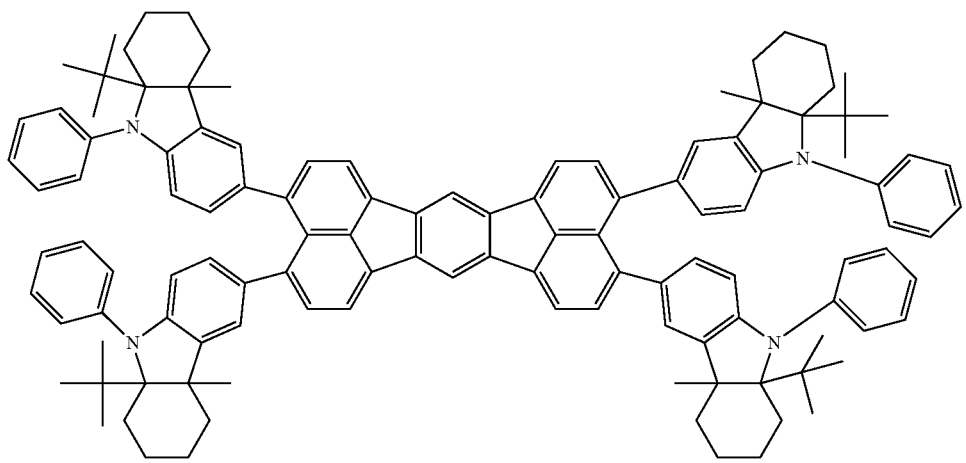
Formula 1272
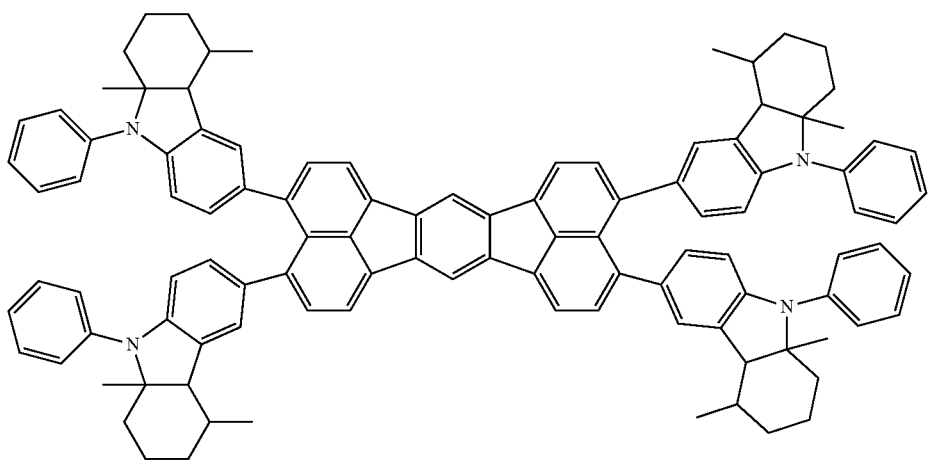
Formula 1273
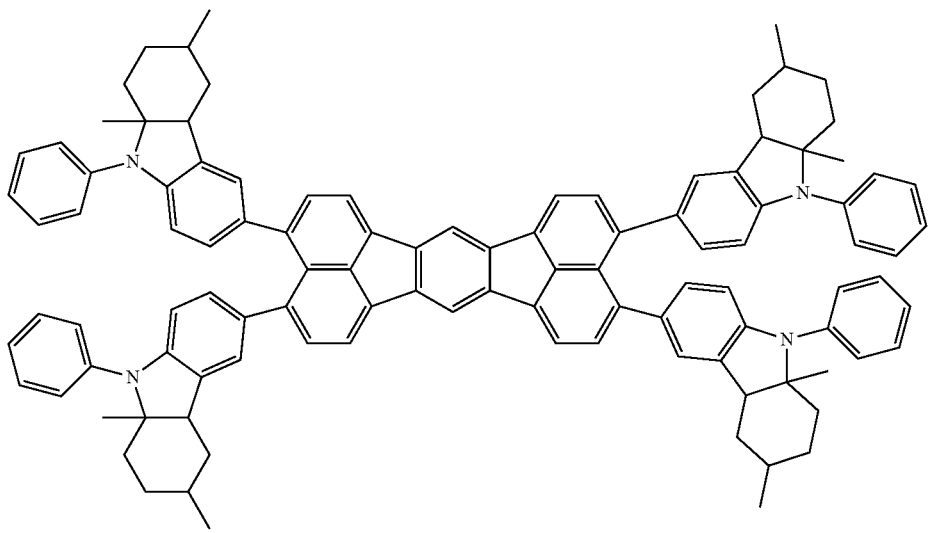

Formula 1274
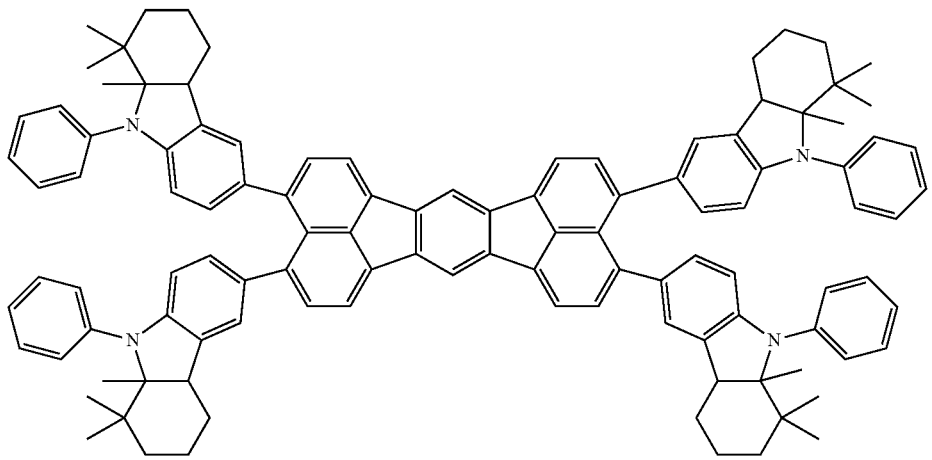
Formula 1275
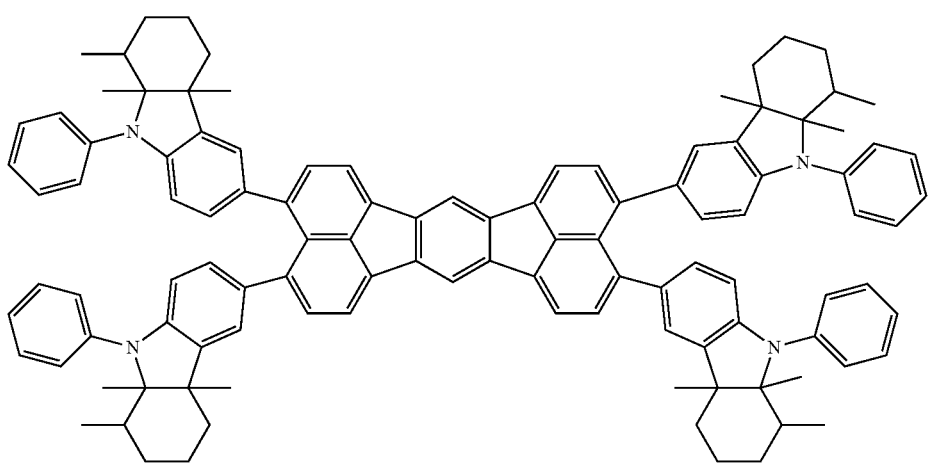
Formula 1276
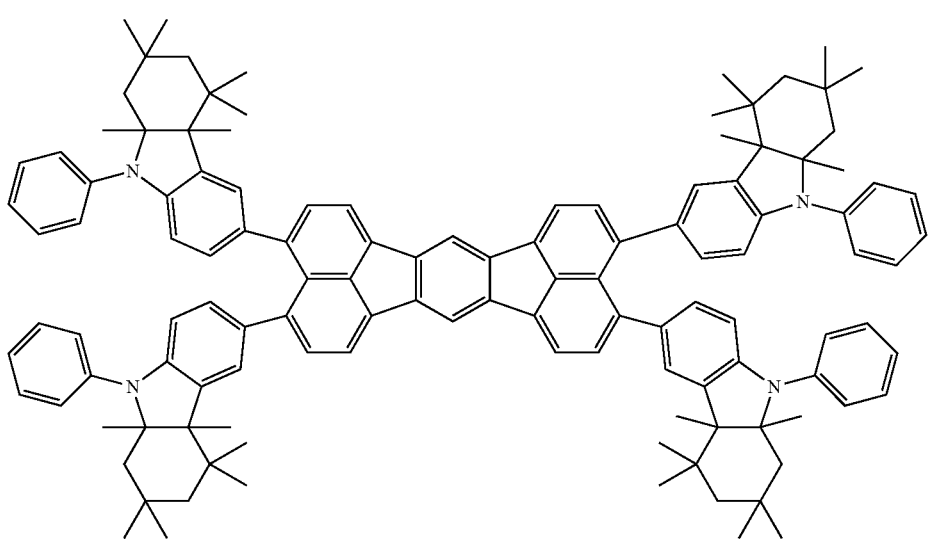

-continued
Formula 1277
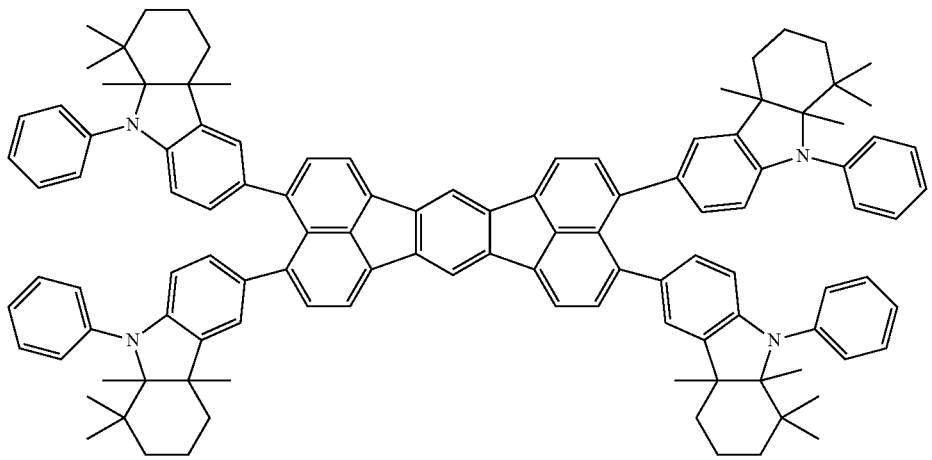
Formula 1278
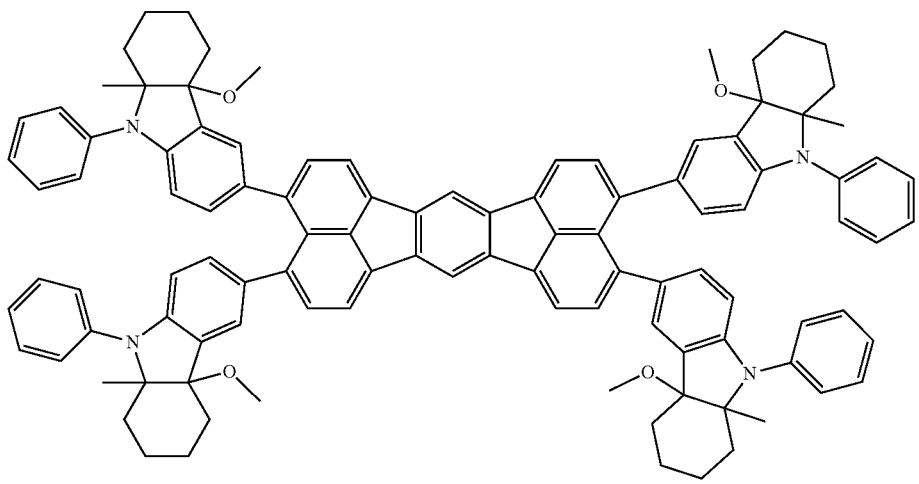
Formula 1279
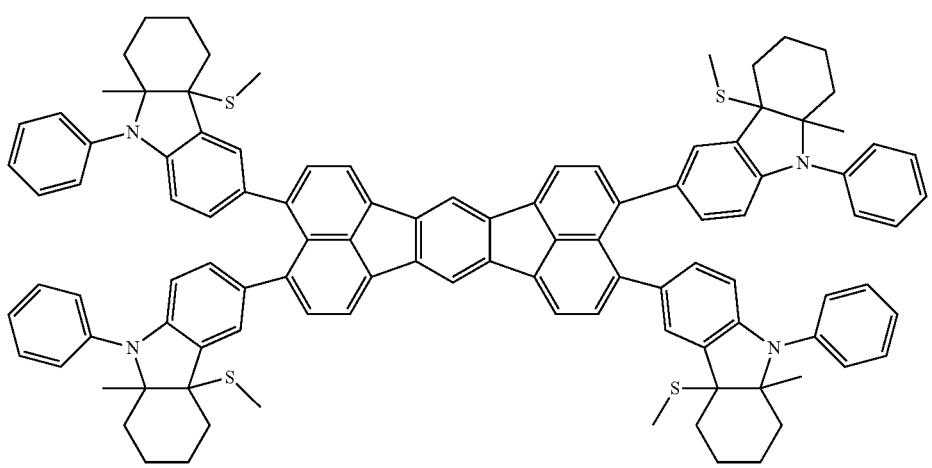

-continued
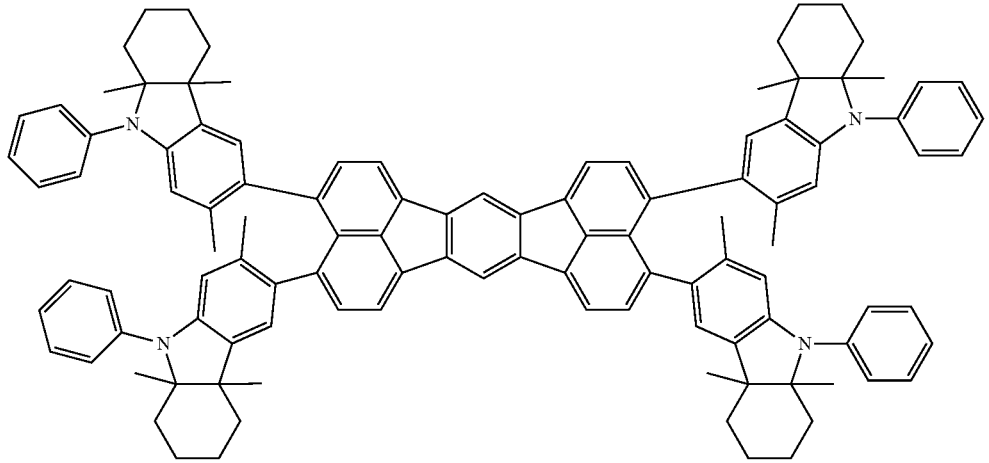
Formula 1280
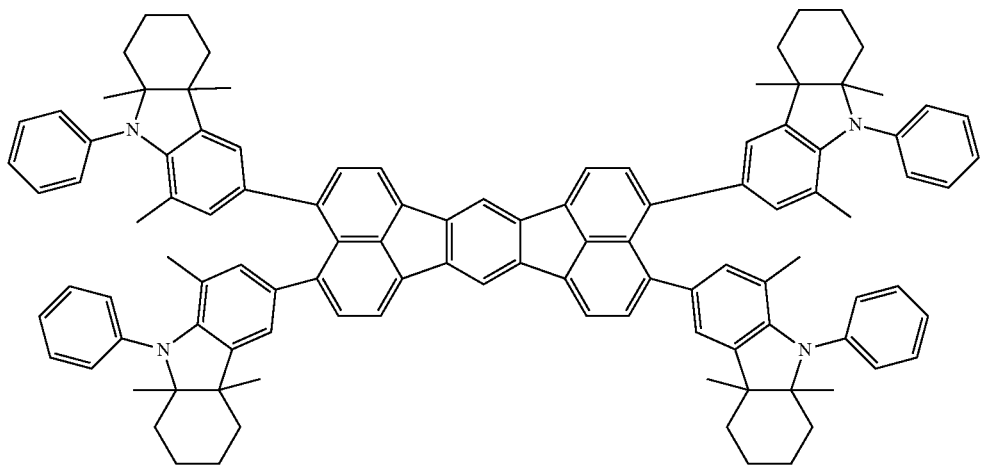
Formula 1281
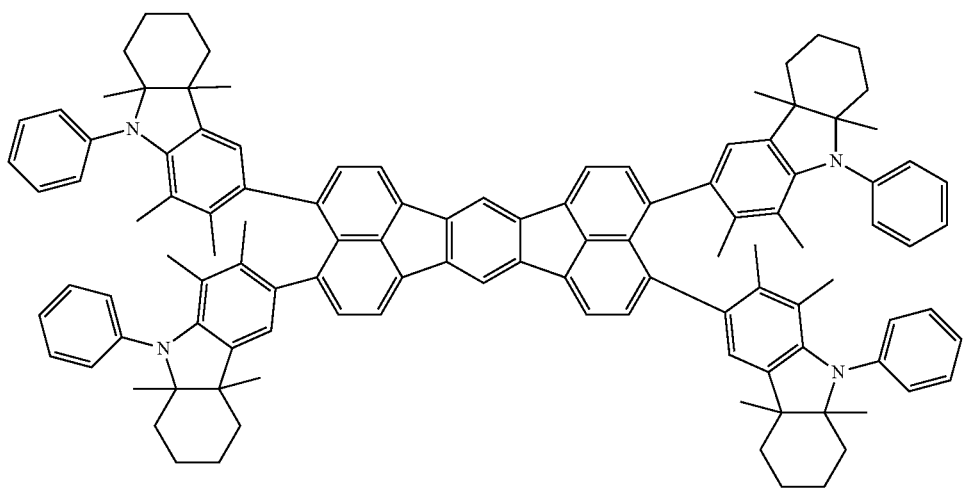
Formula 1282

-continued
Formula 1283
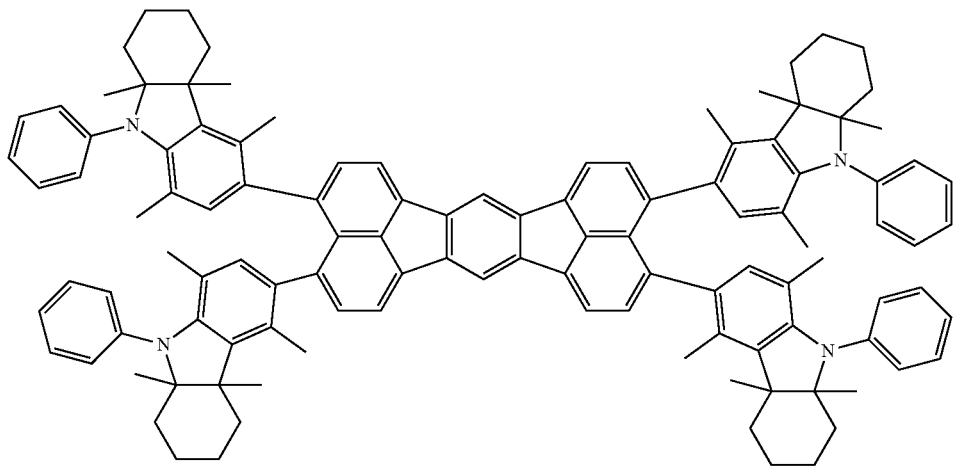
Formula 1284
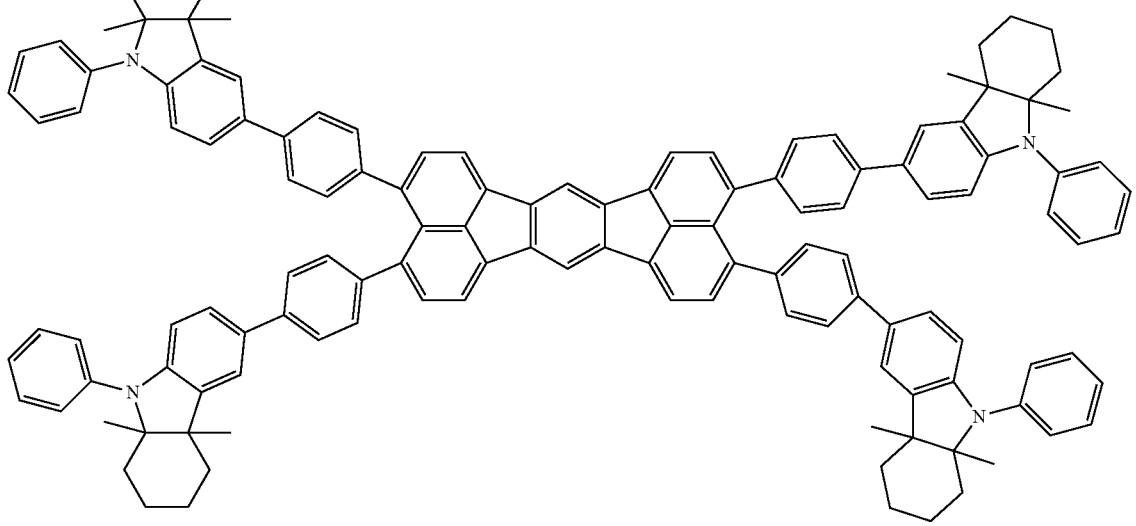
Formula 1285
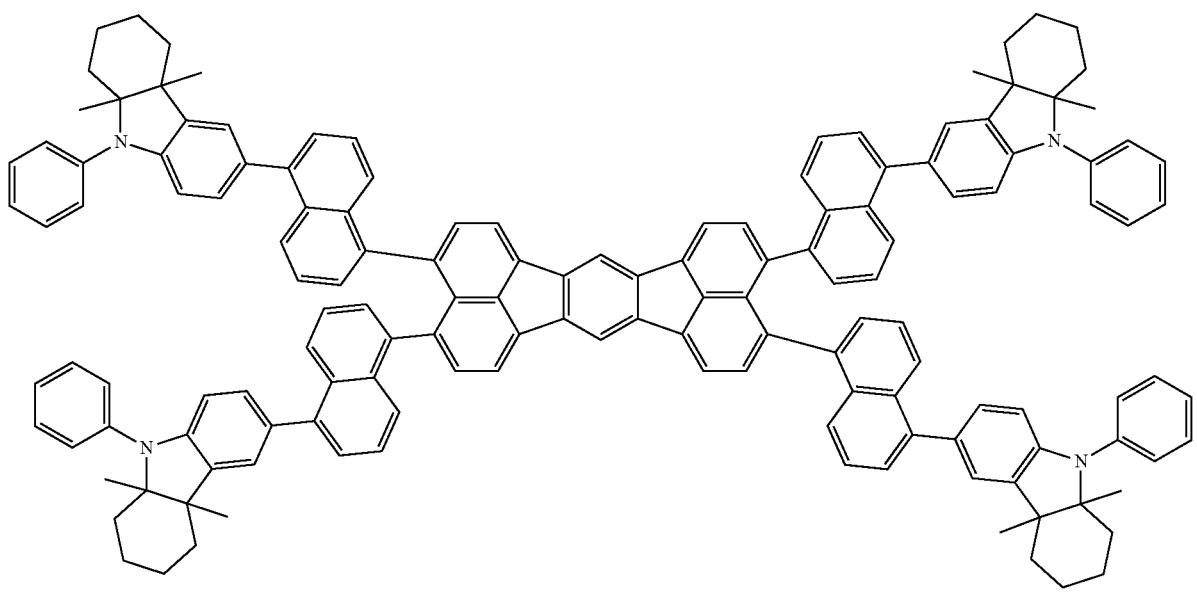

-continued
Formula 1286
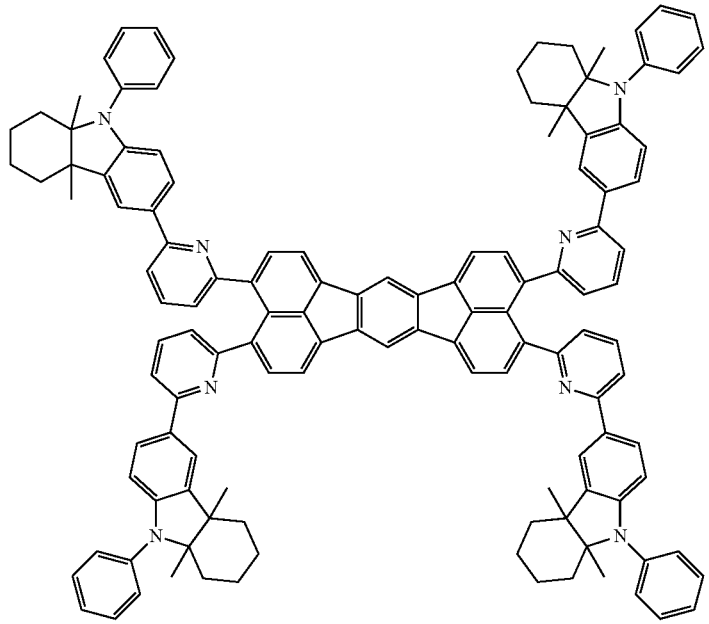
Formula 1287
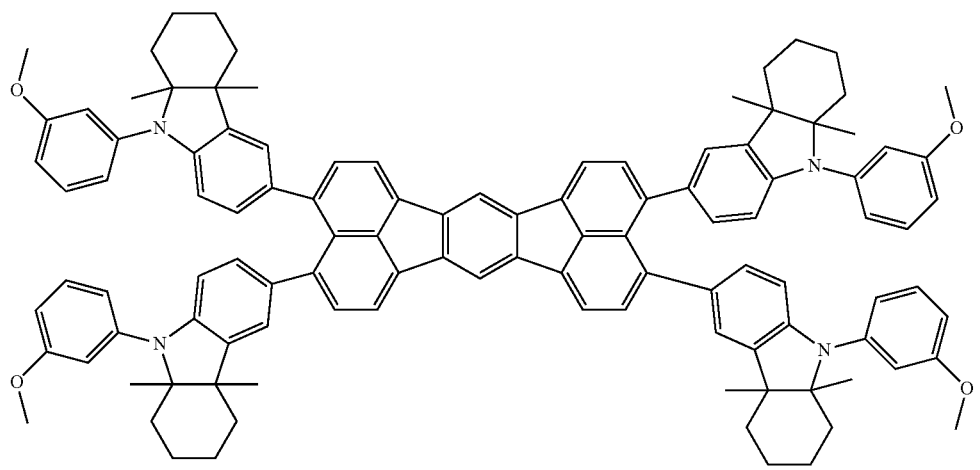
Formula 1288
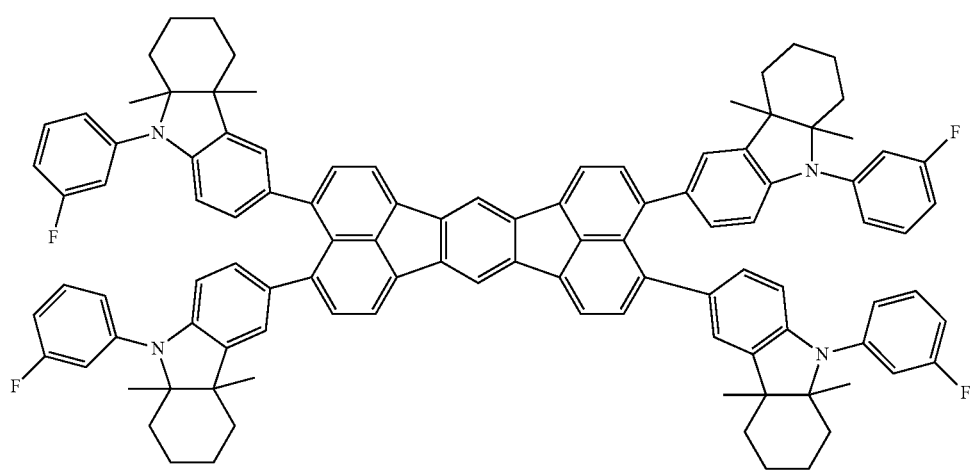

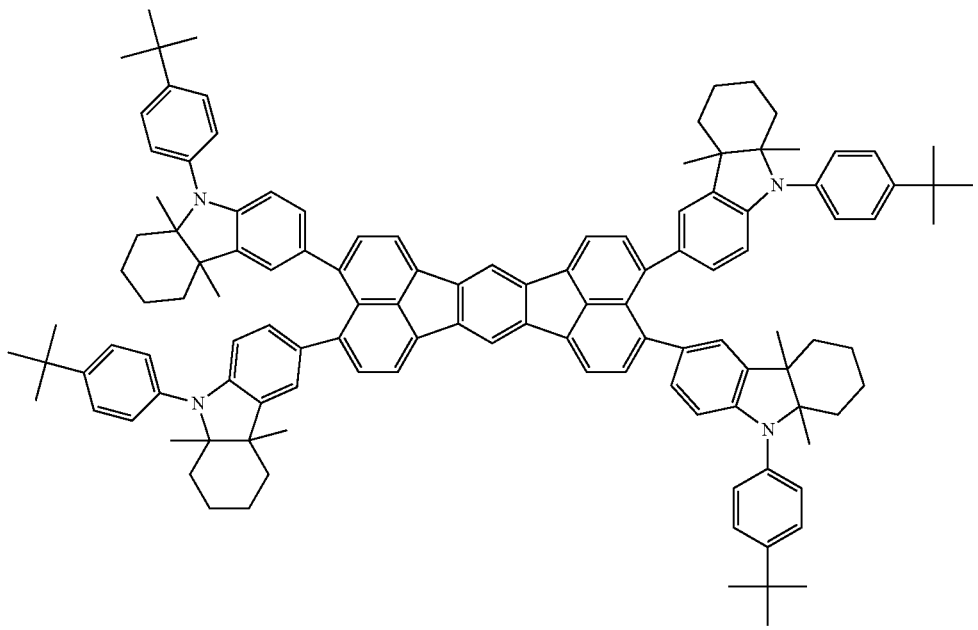
Formula 1289
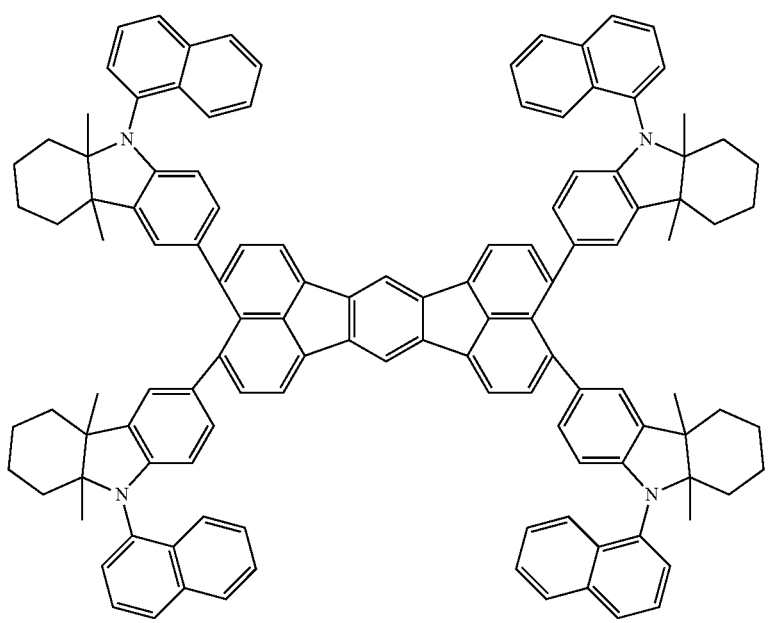
Formula 1290

Formula 1291
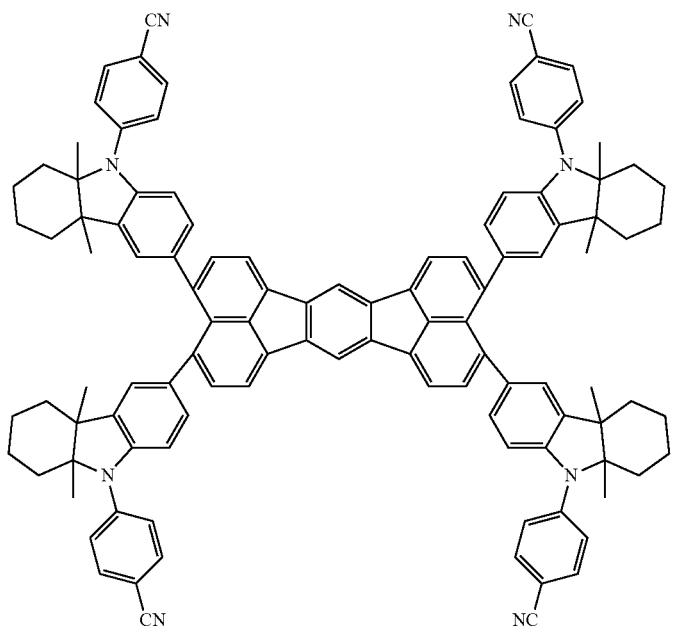
Formula 1292
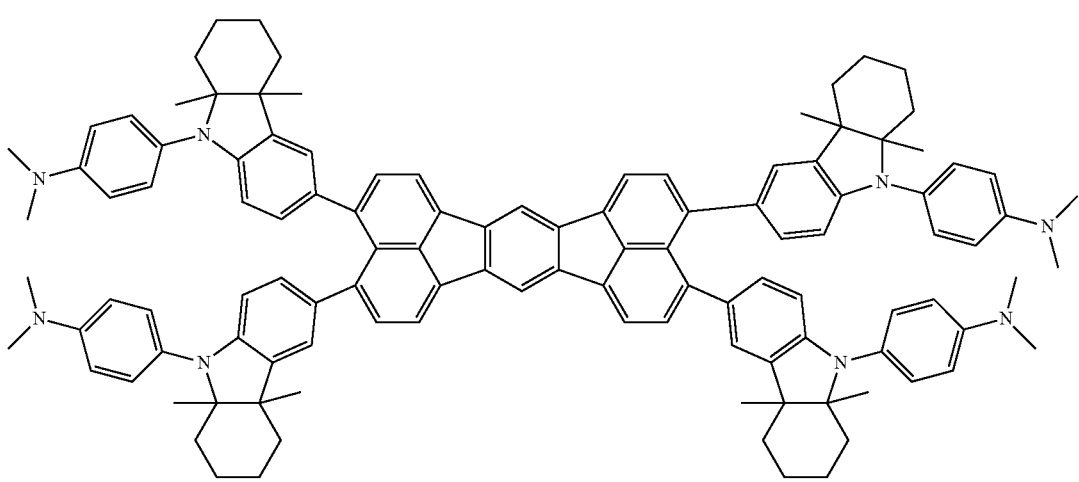
Formula 1293
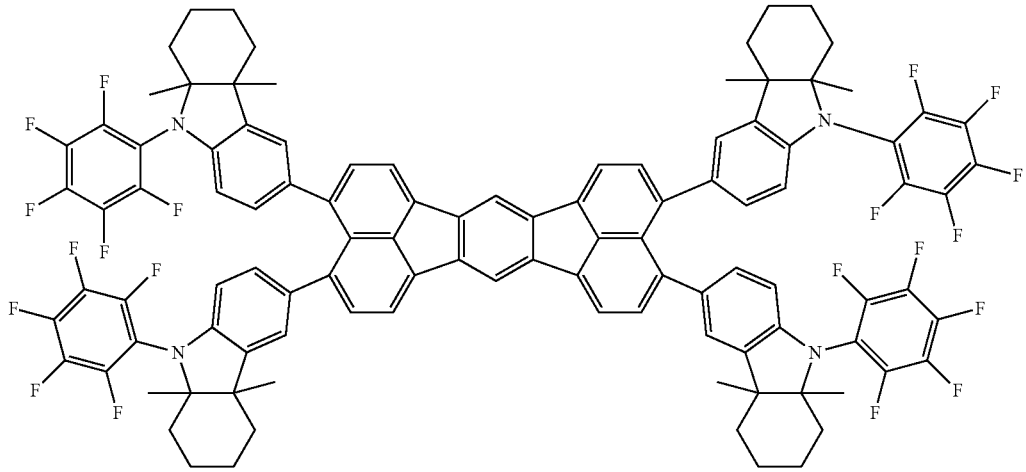

Formula 1294
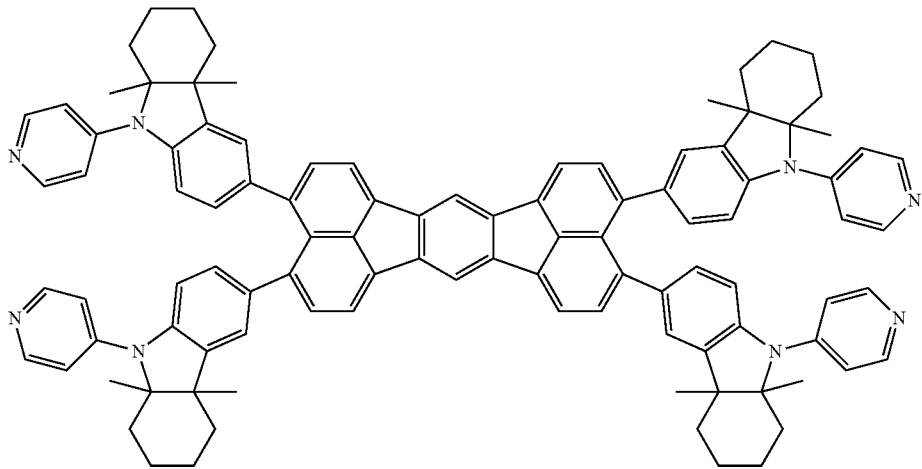
Formula 1295
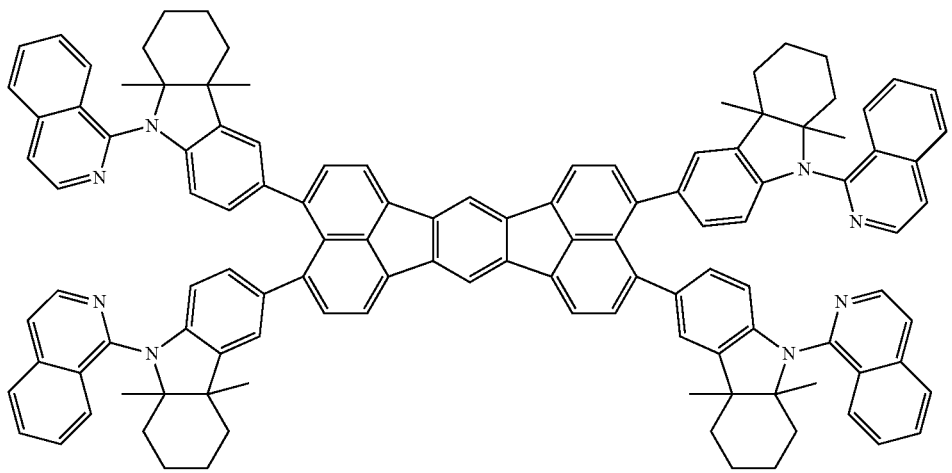
Formula 1296
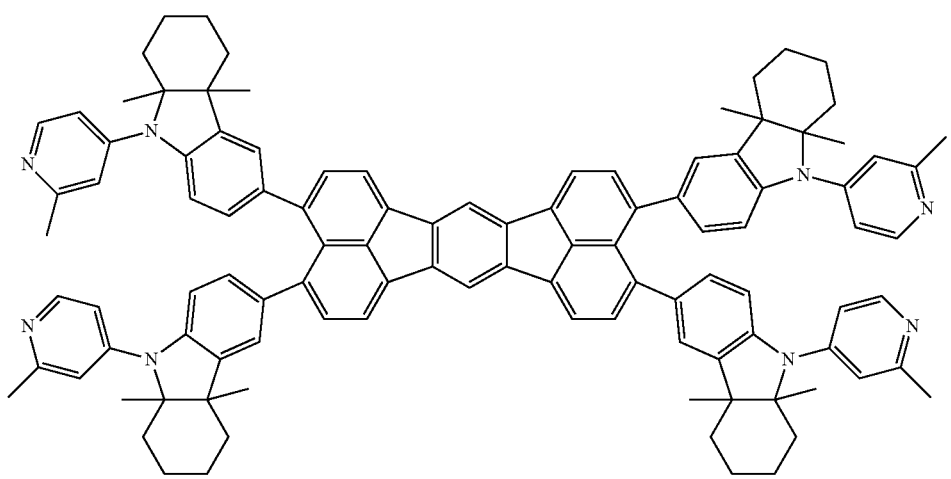

-continued
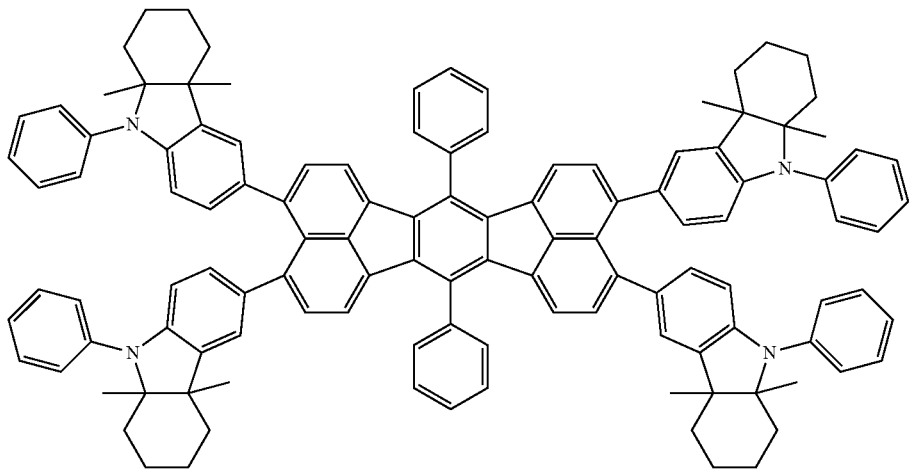
Formula 1297
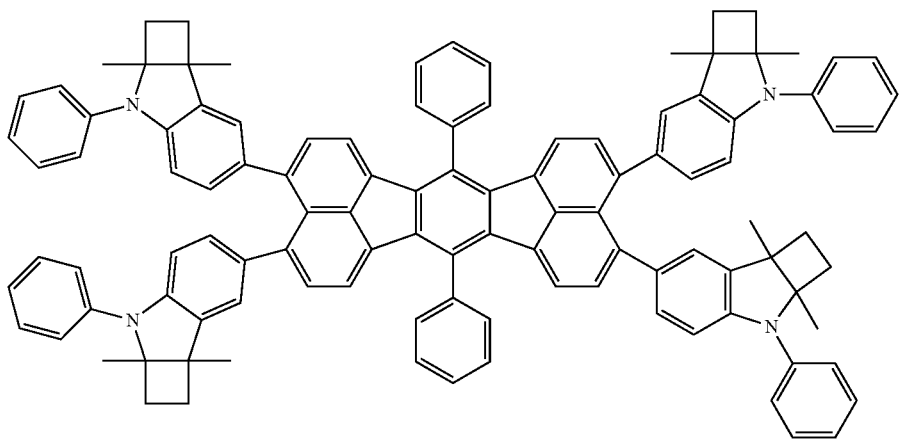
Formula 1298
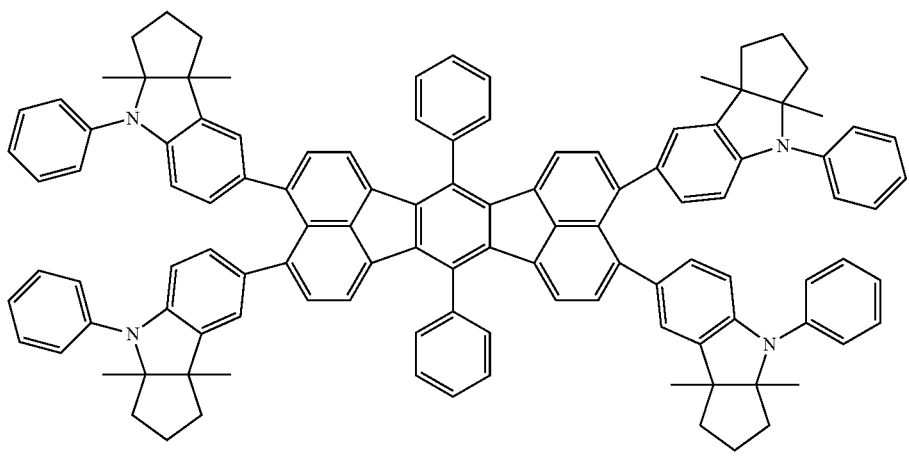
Formula 1299

-continued
Formula 1300
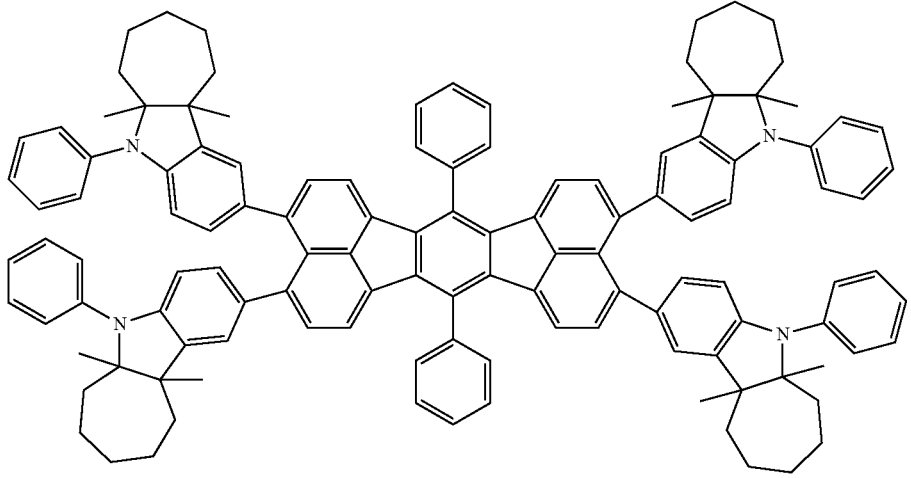
Formula 1301
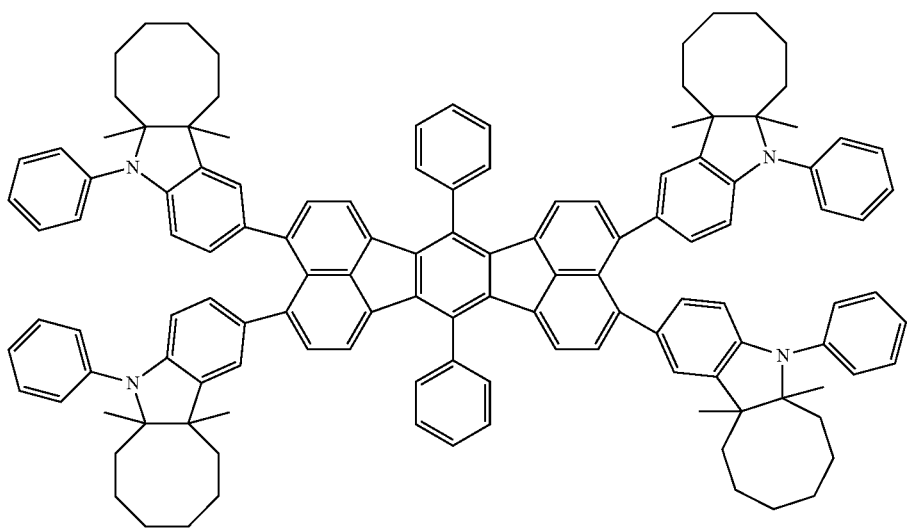
Formula 1302
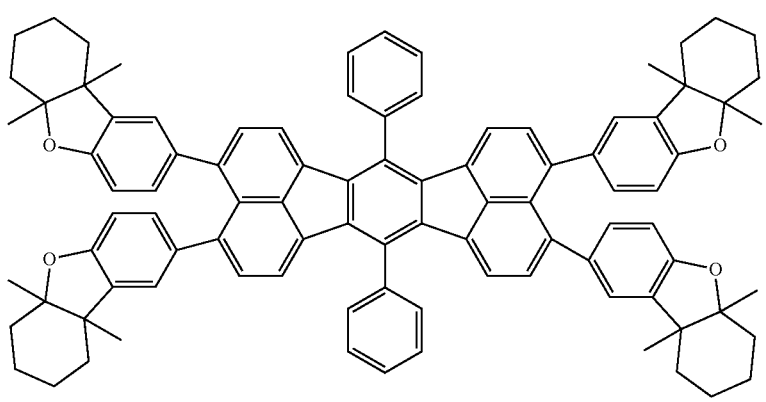

Formula 1303
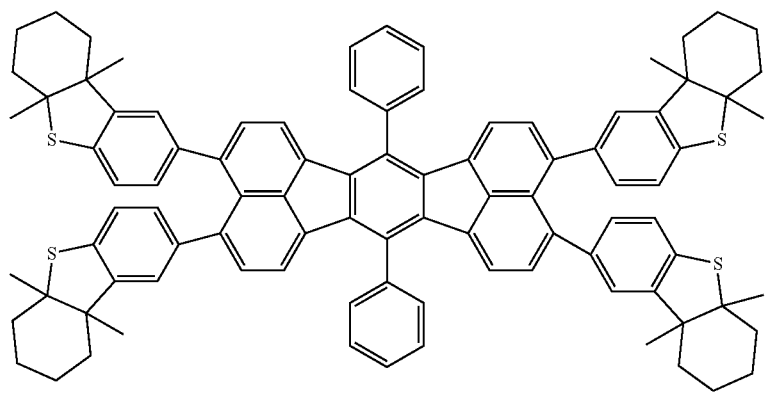
Formula 1304
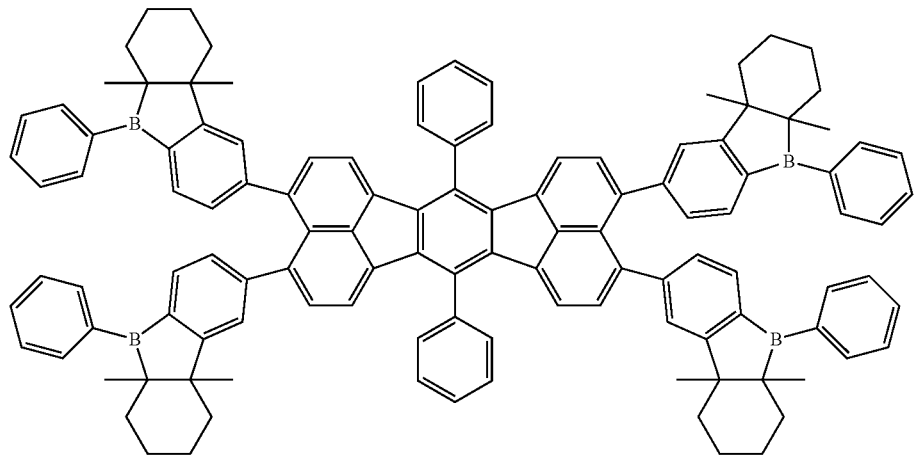
Formula 1305
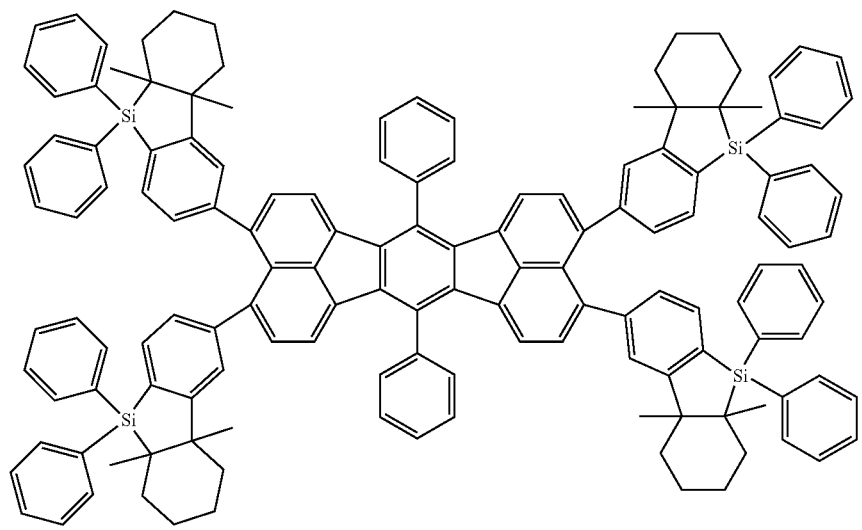

-continued
Formula 1306
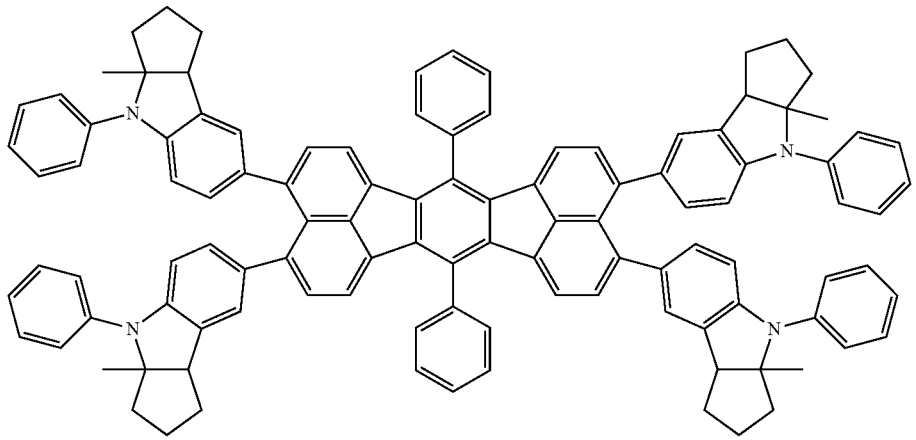
Formula 1307
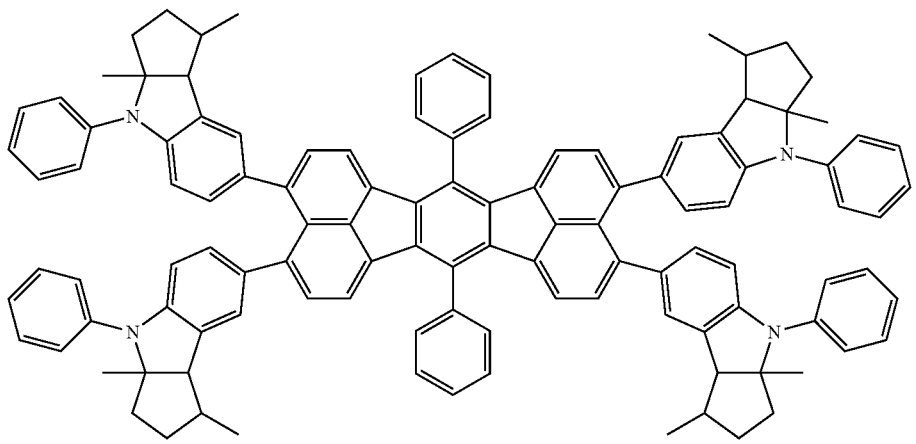
Formula 1308
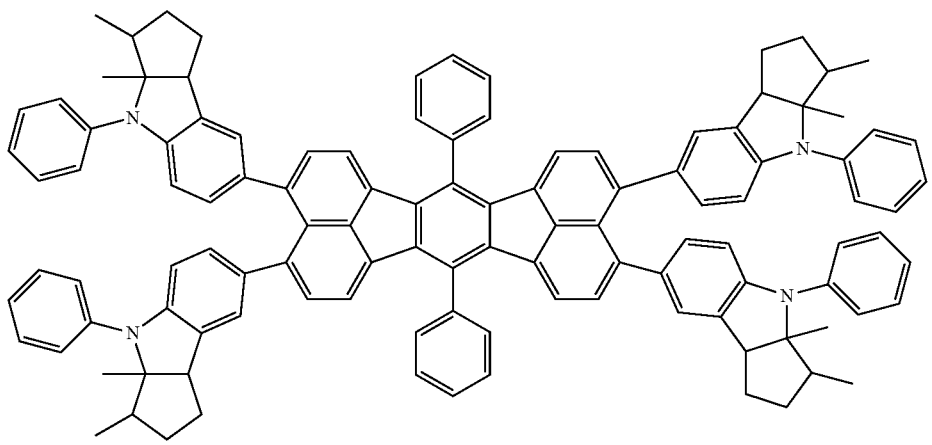

-continued
Formula 1309
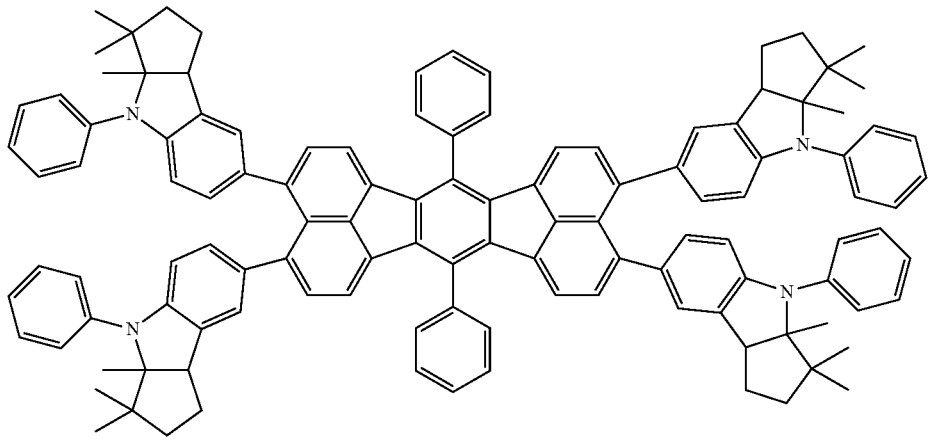
Formula 1310
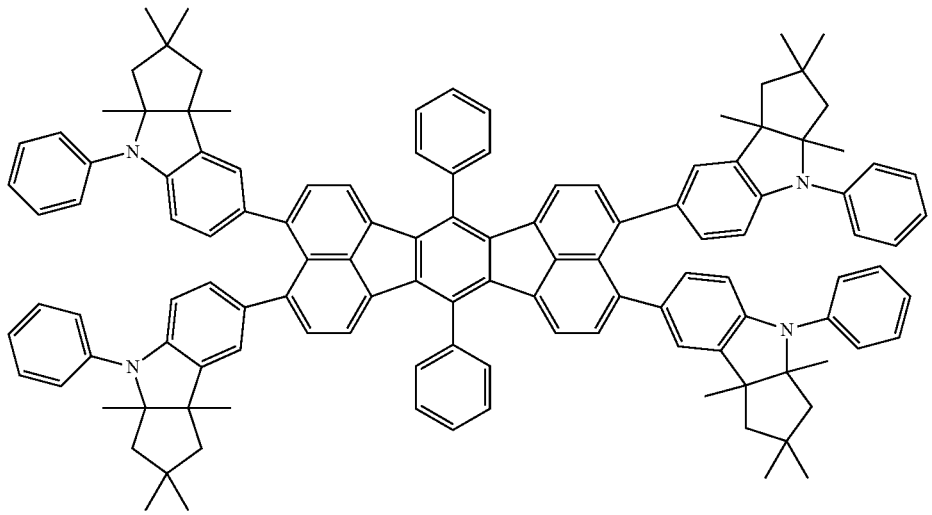
Formula 1311
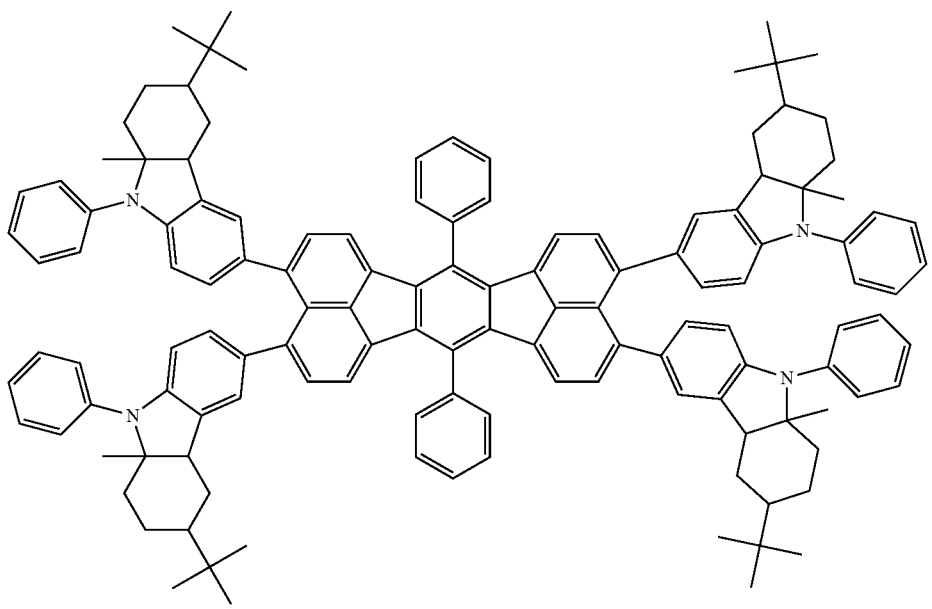

-continued
Formula 1312
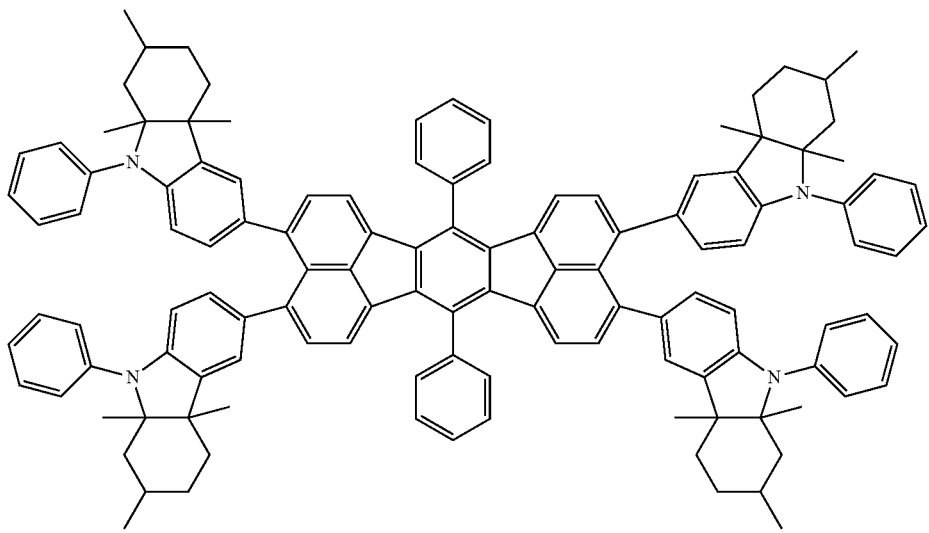
Formula 1313
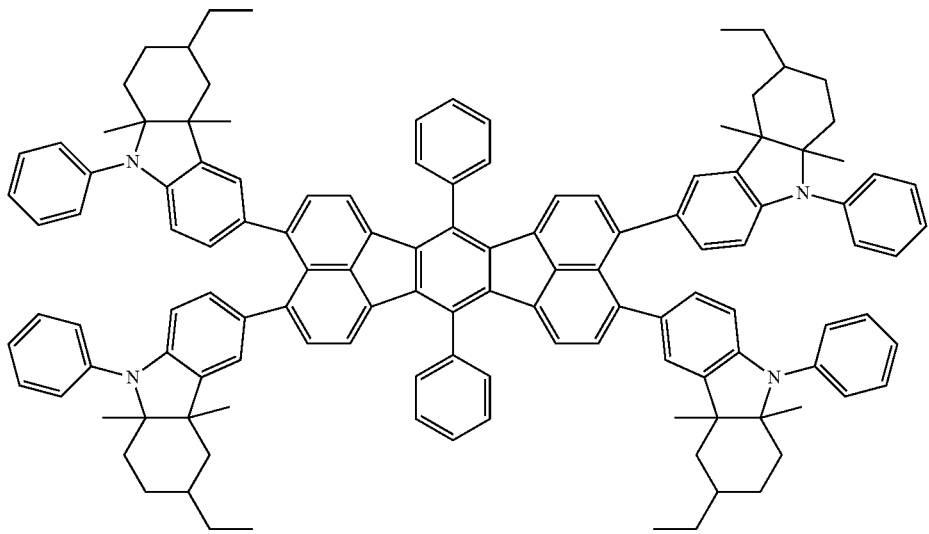
Formula 1314
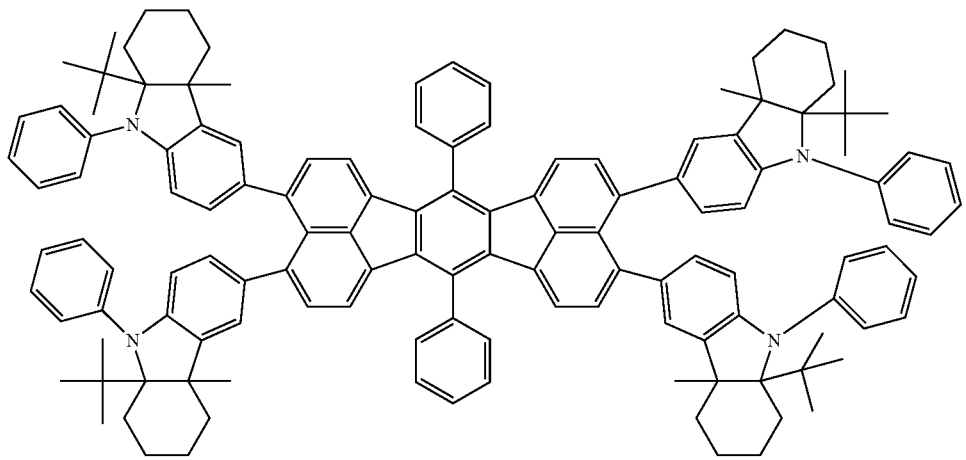

Formula 1315
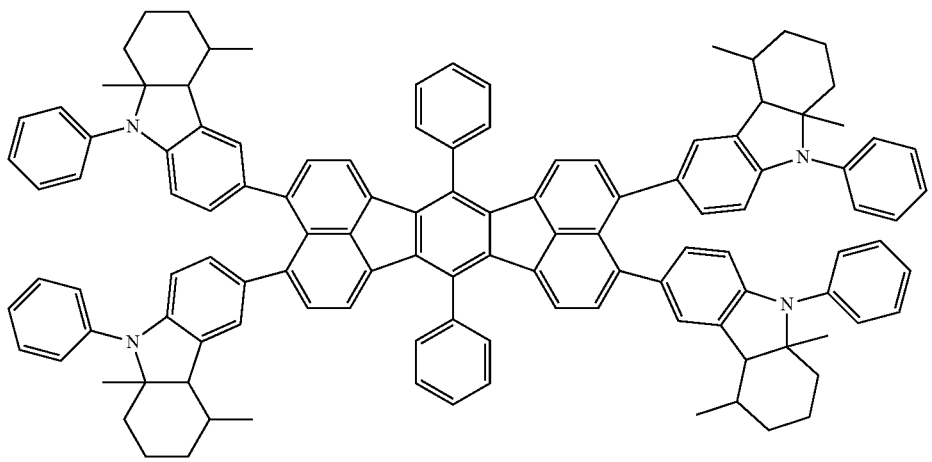
Formula 1316
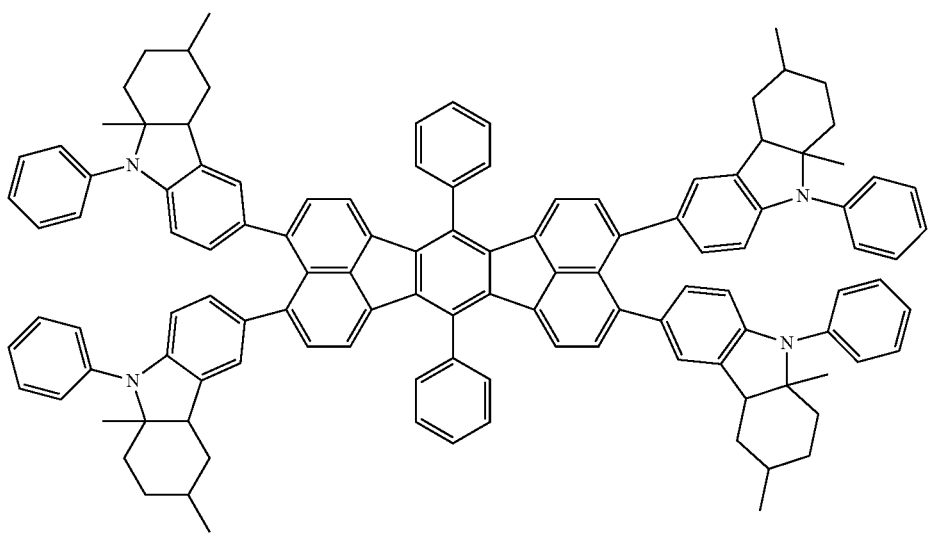
Formula 1317
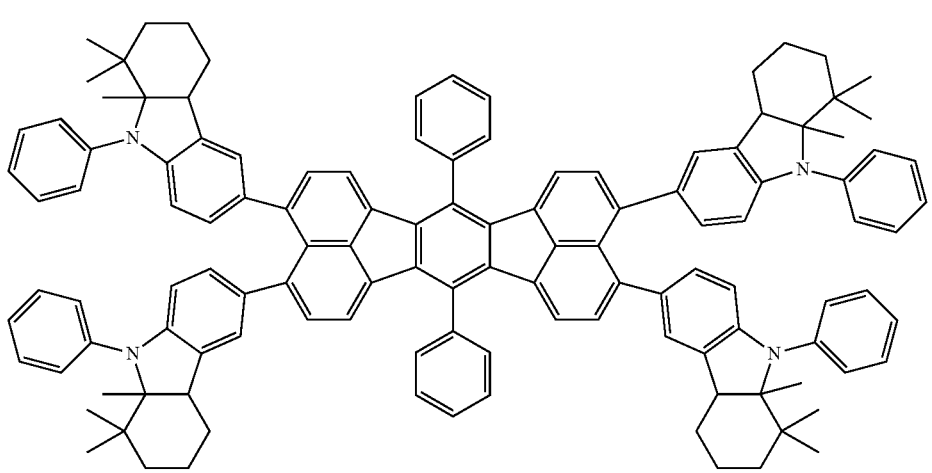

-continued
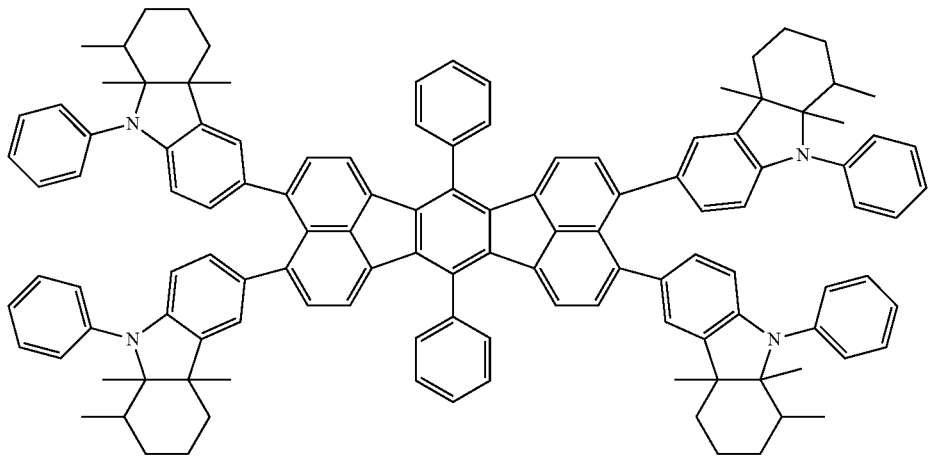
Formula 1318
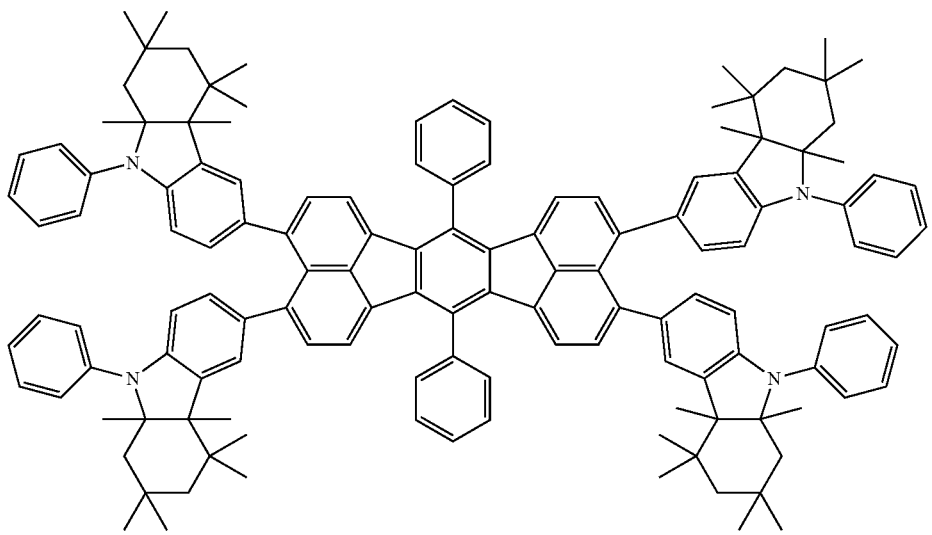
Formula 1319
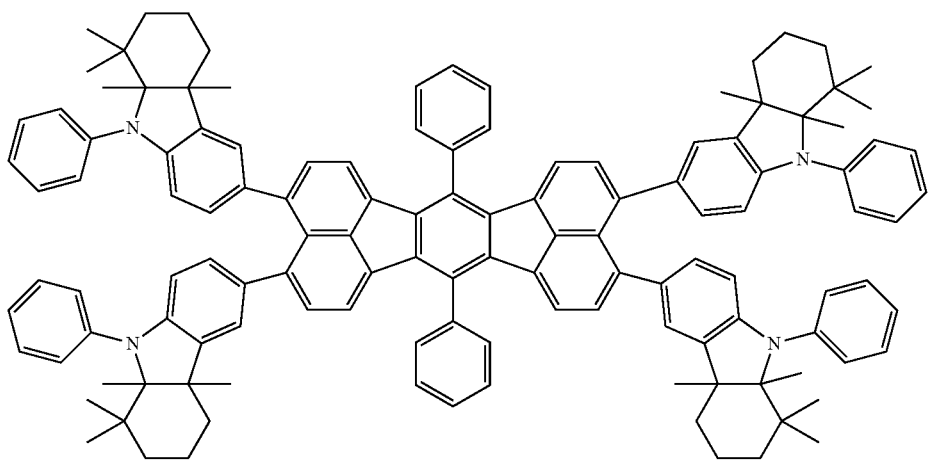
Formula 1320

-continued
Formula 1321
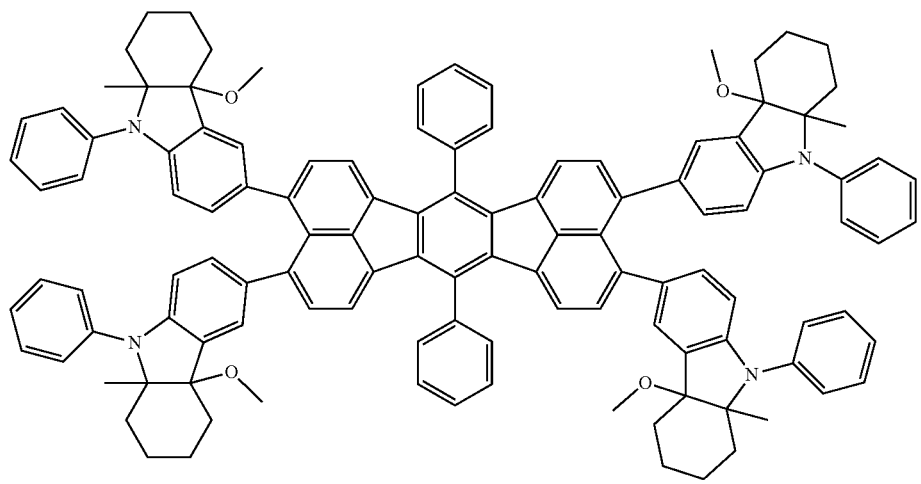
Formula 1322
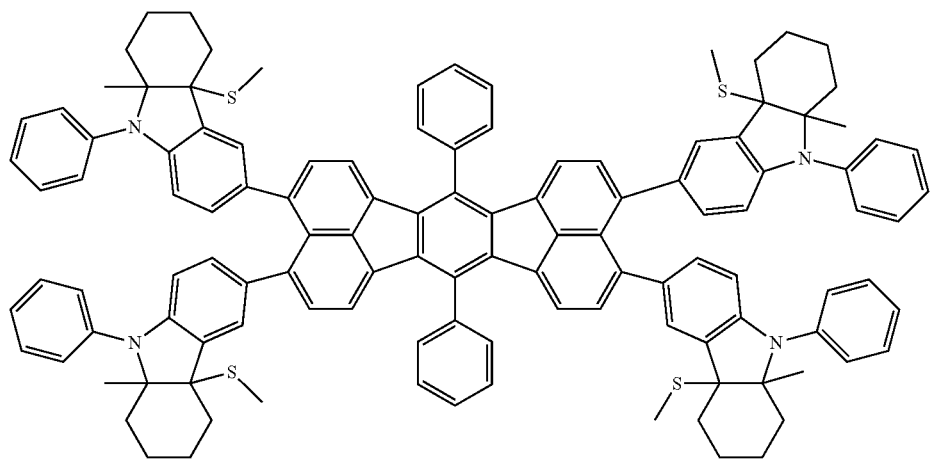
Formula 1323
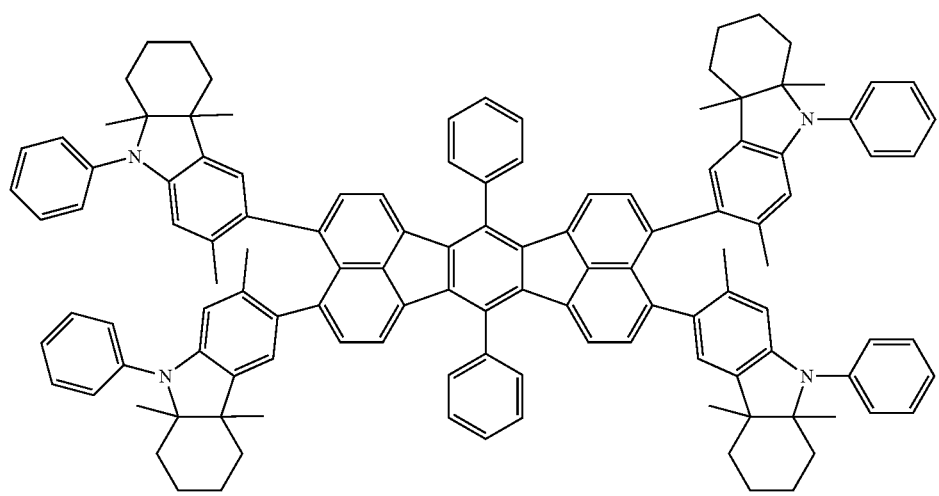

-continued
Formula 1324
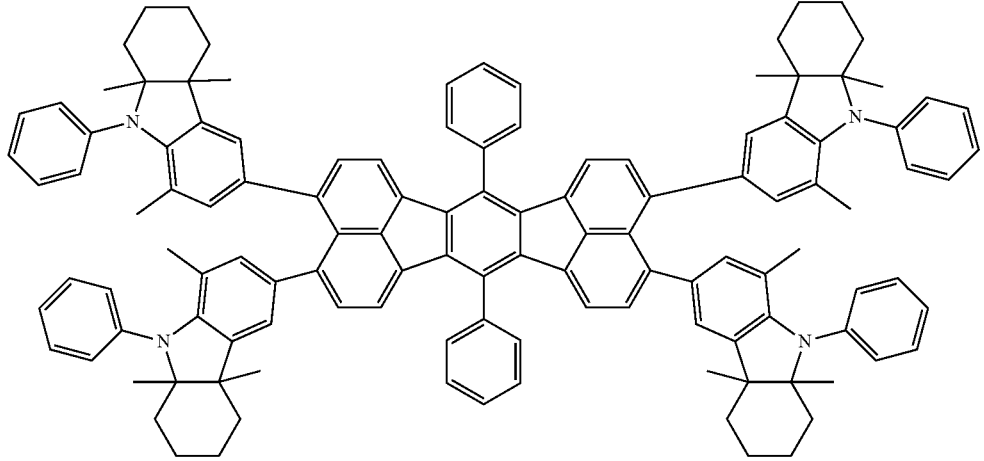
Formula 1325
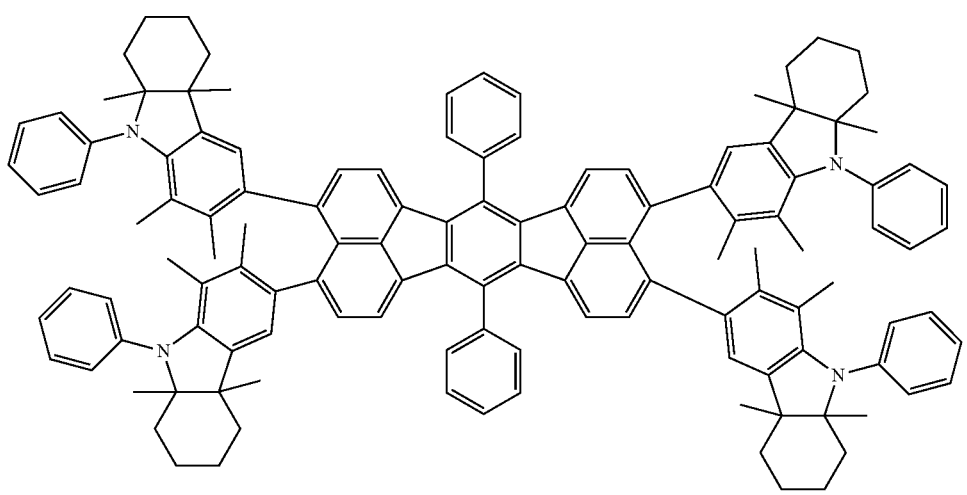
Formula 1326
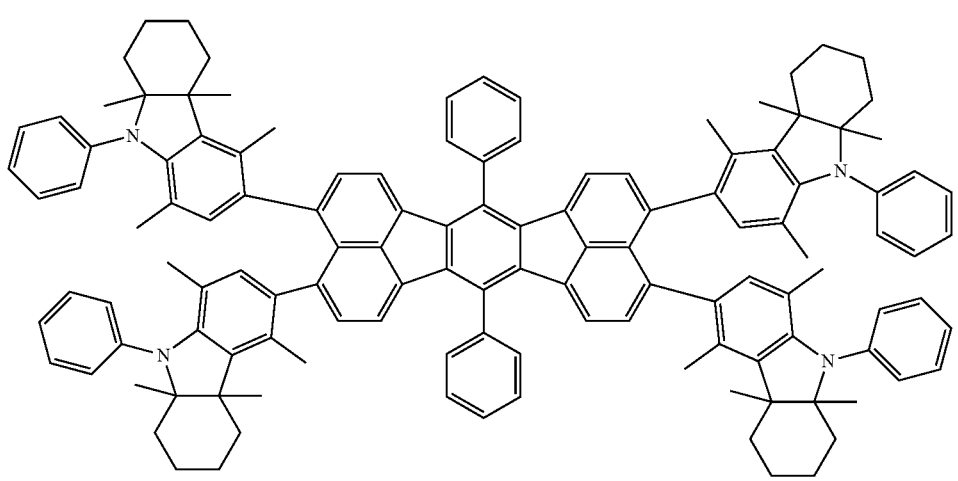

Formula 1327
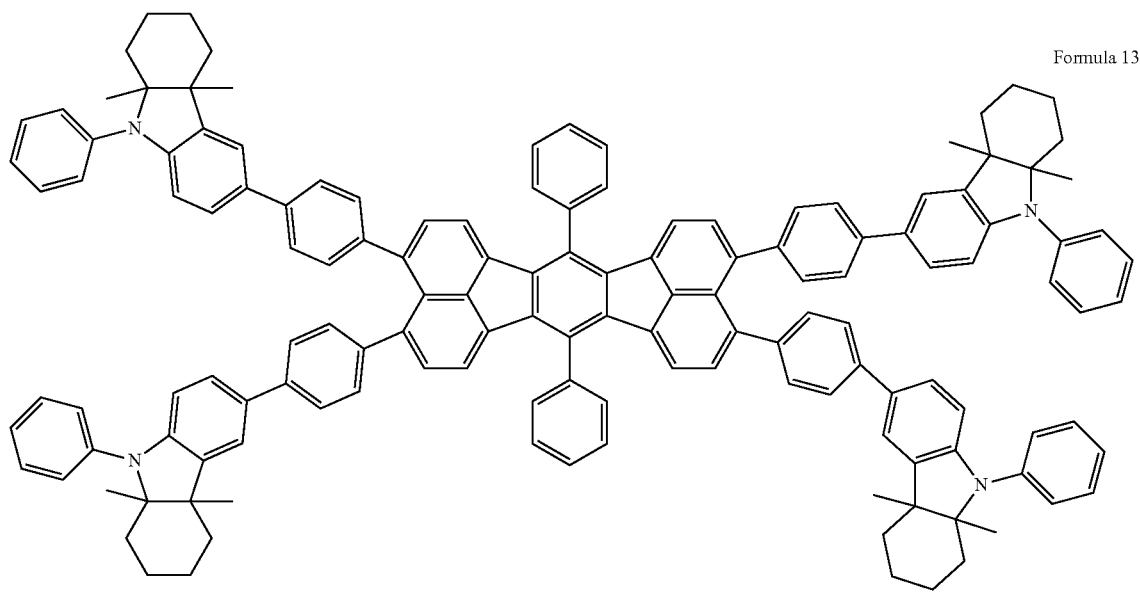
Formula 1328
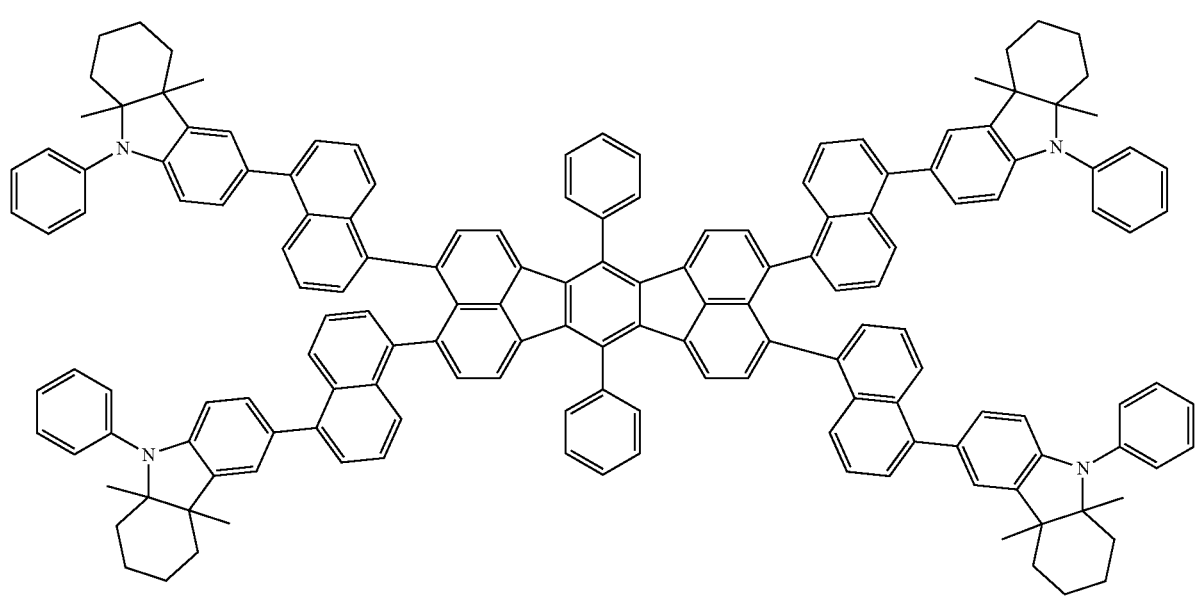

Formula 1329
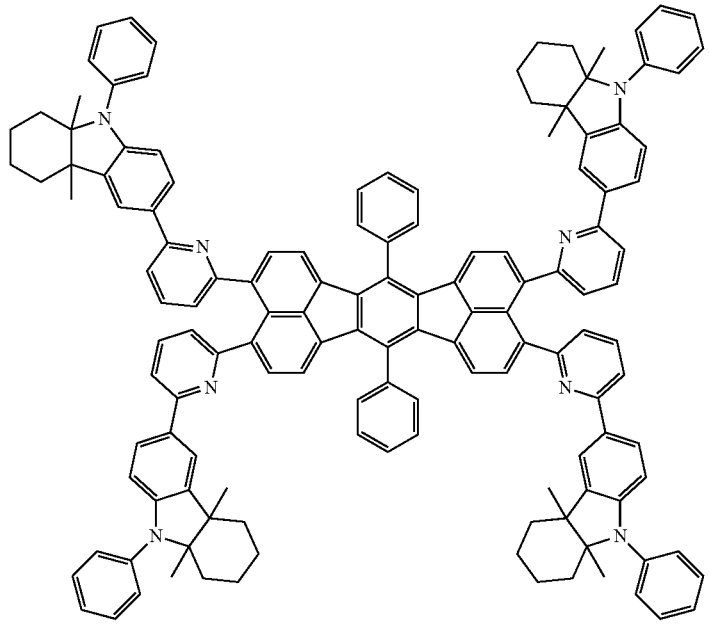
Formula 1330
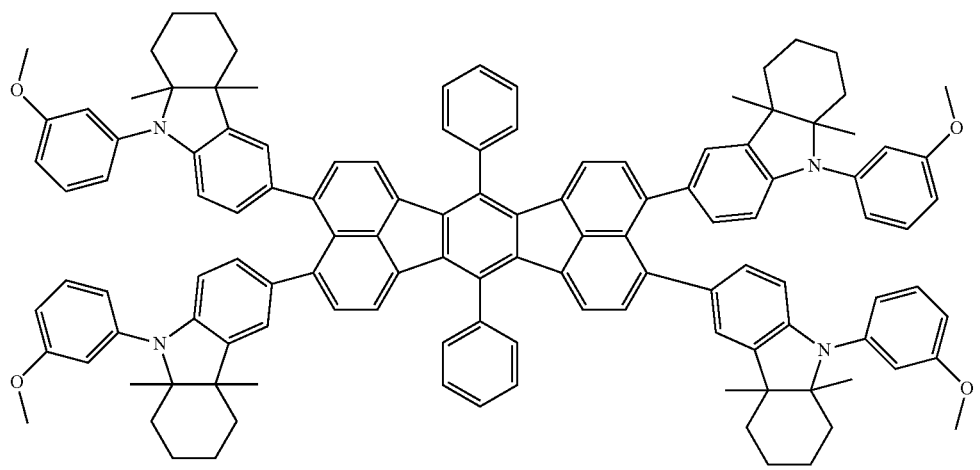
Formula 1331
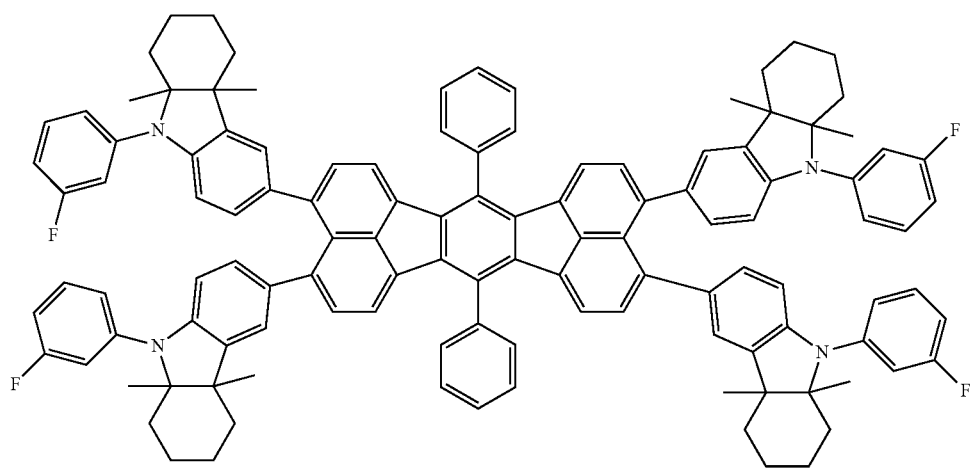

Formula 1332
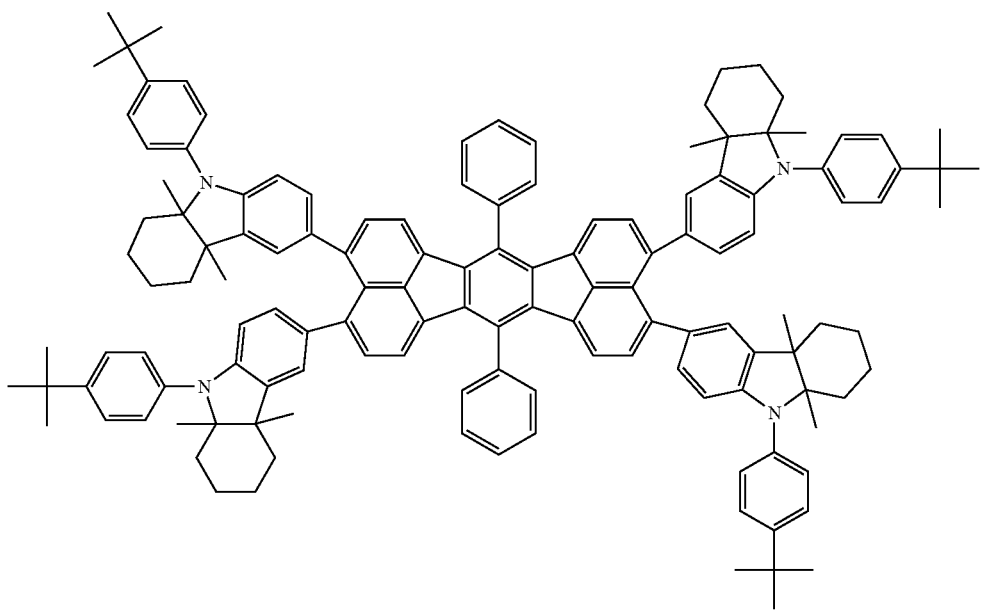
Formula 1333
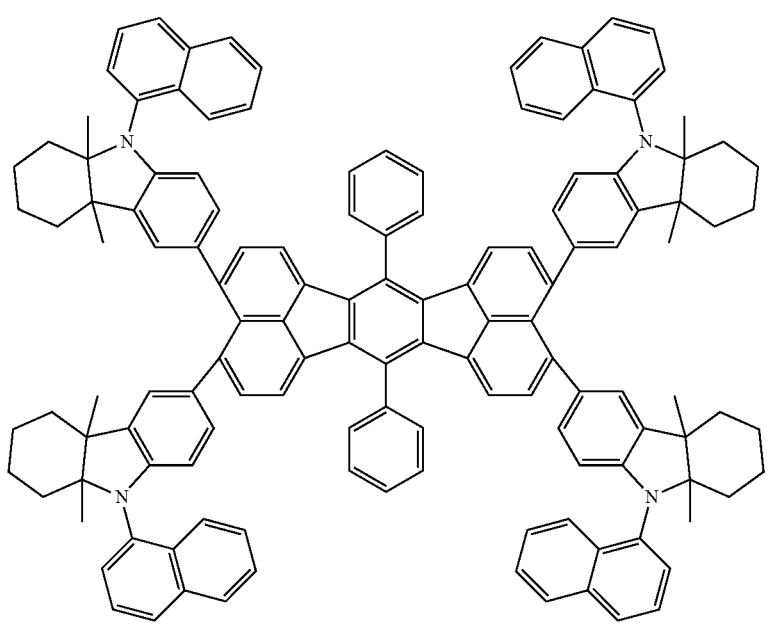

Formula 1334
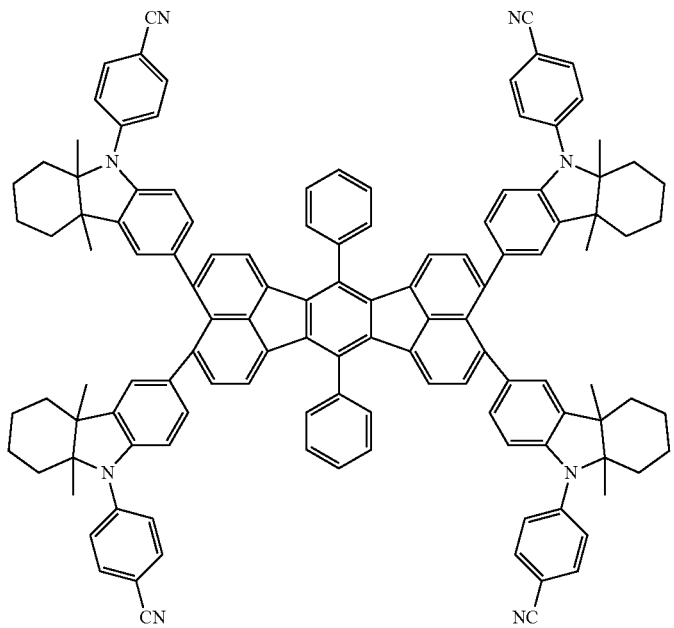
Formula 1335
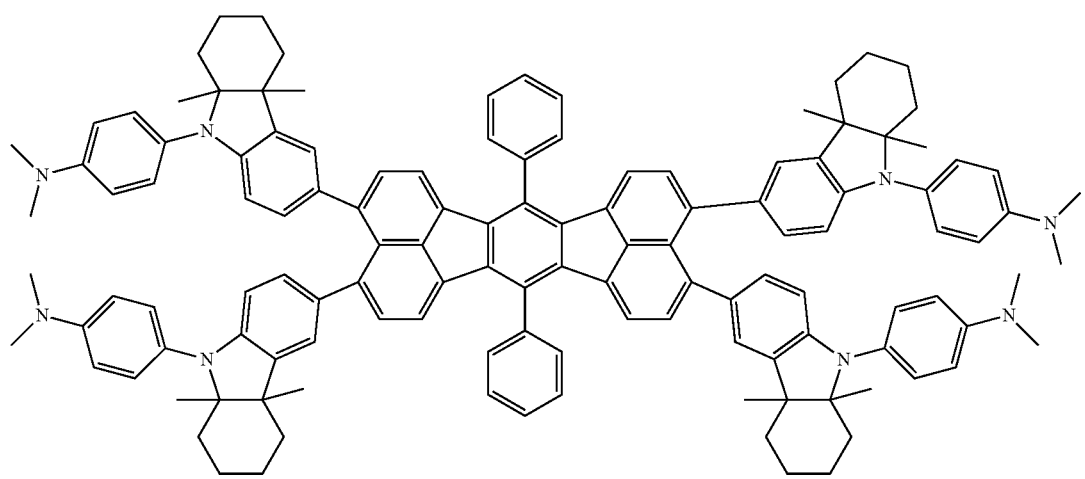
Formula 1336
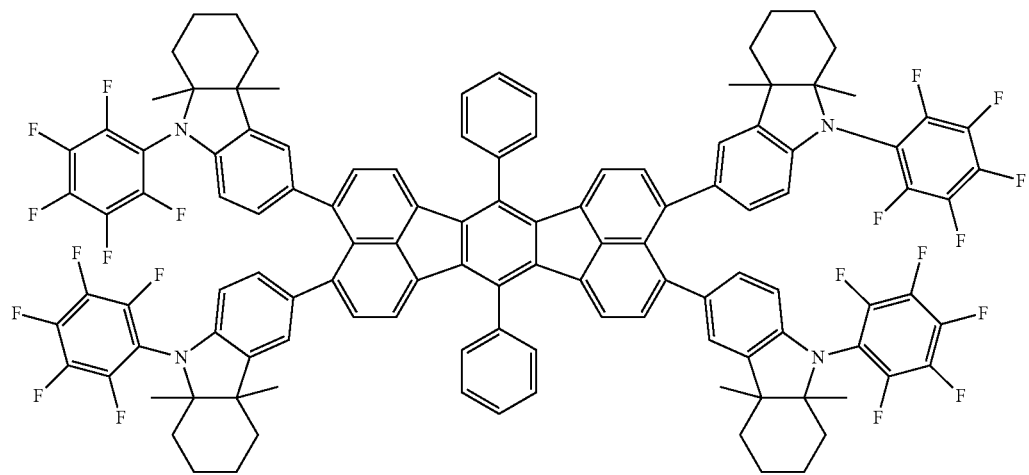

Formula 1337
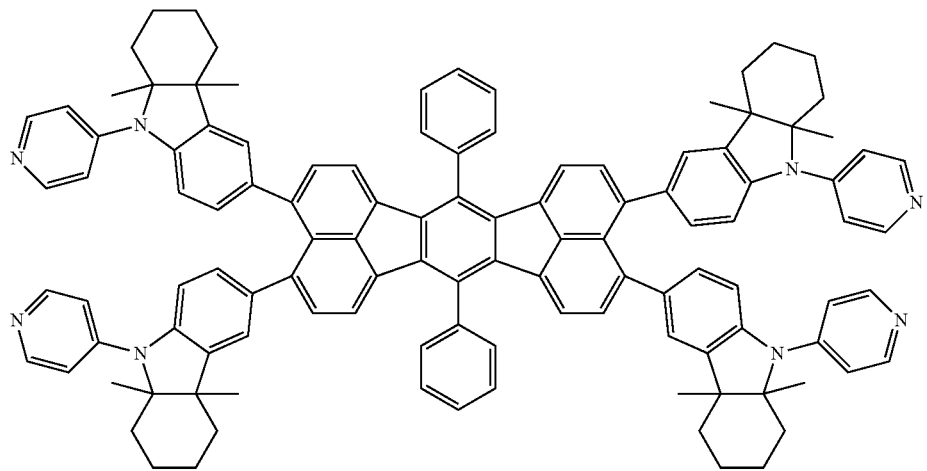
Formula 1338
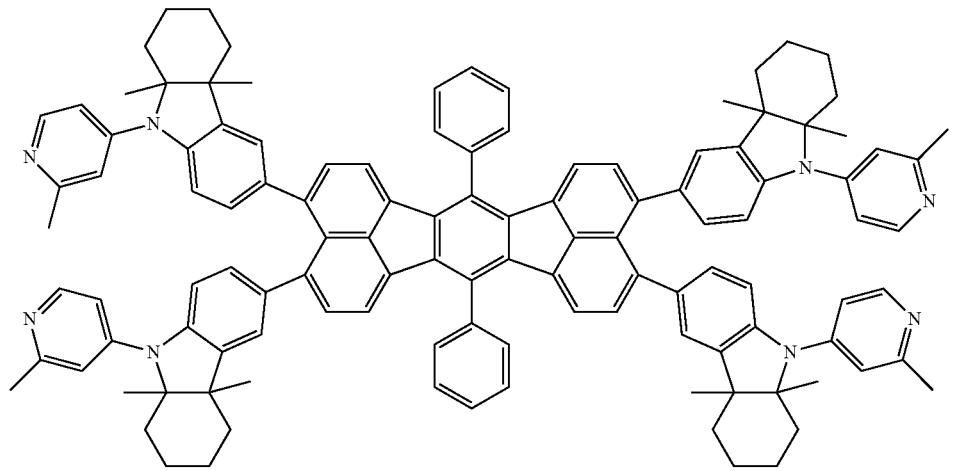
Formula 1339
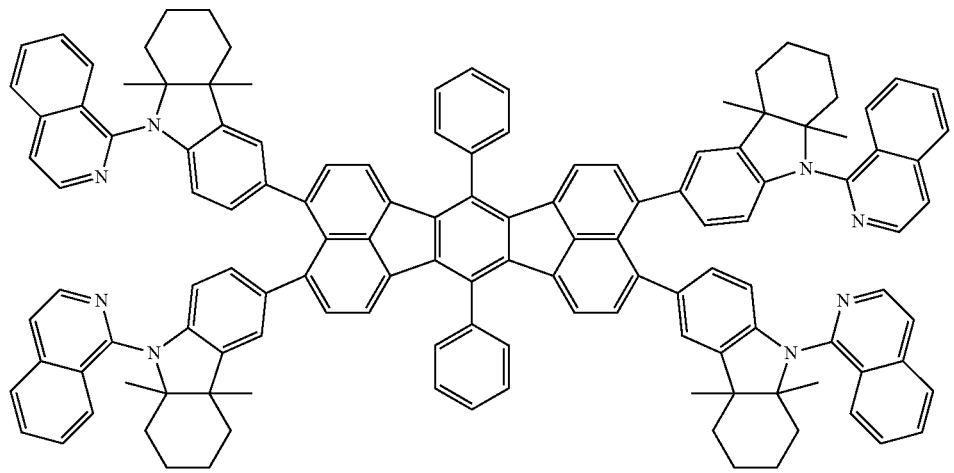

Formula 1340
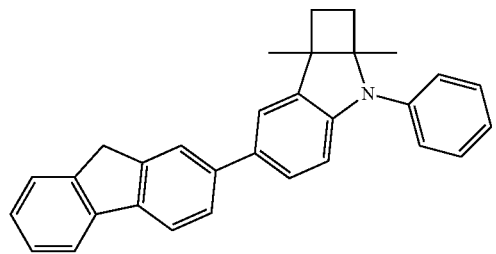
Formula 1341
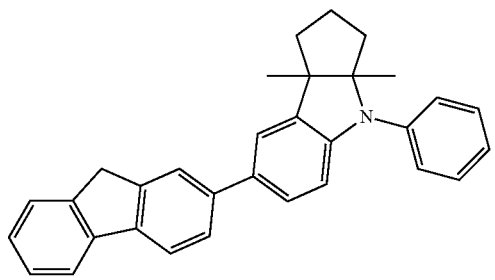
Formula 1342
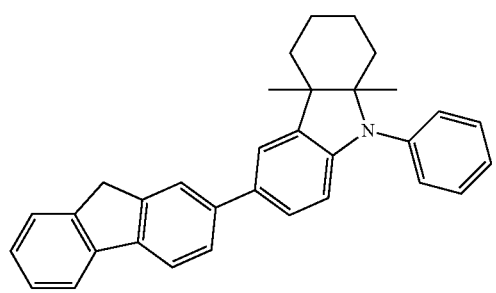
Formula 1343
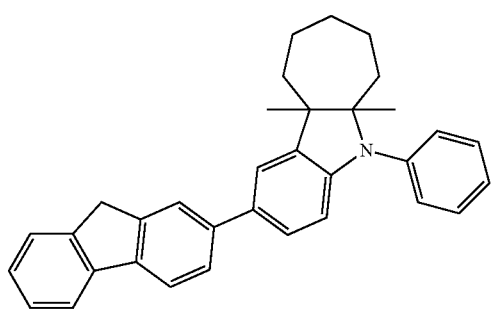
Formula 1344
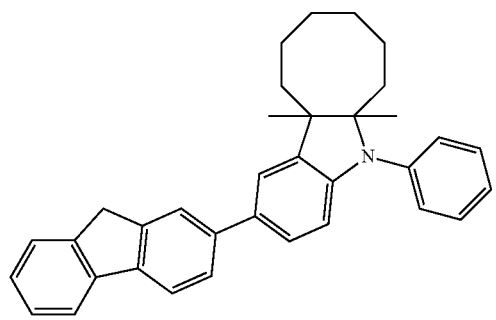
Formula 1345
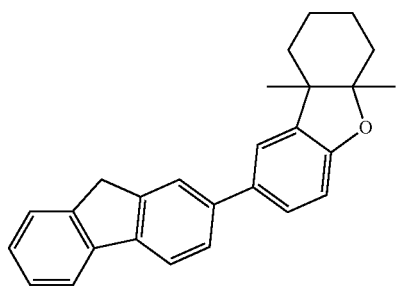
Formula 1346
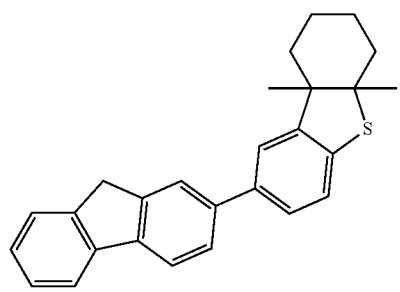
Formula 1347
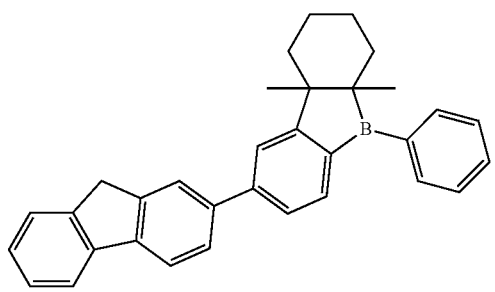
Formula 1348
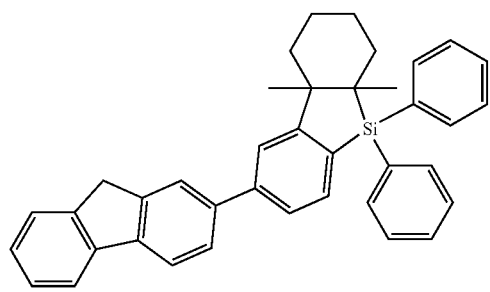
Formula 1349
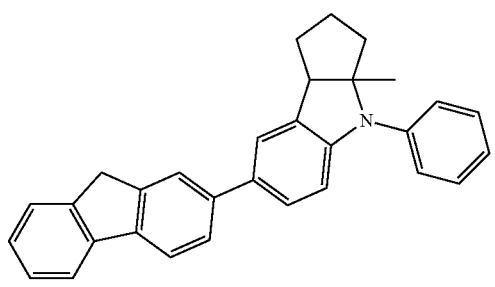

Formula 1350
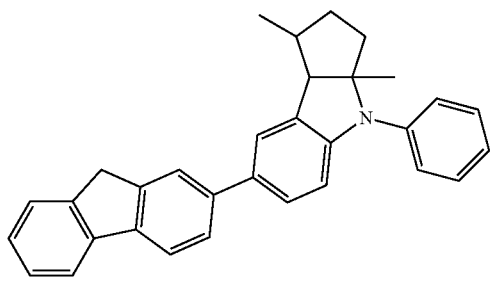
Formula 1351
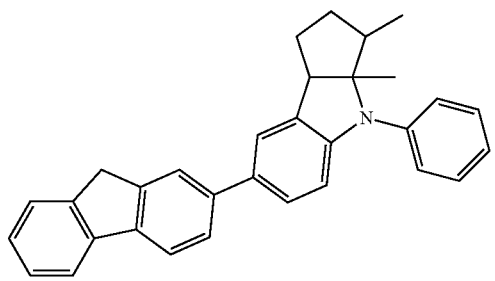
Formula 1352
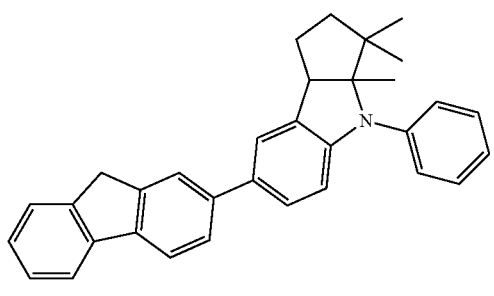
Formula 1353
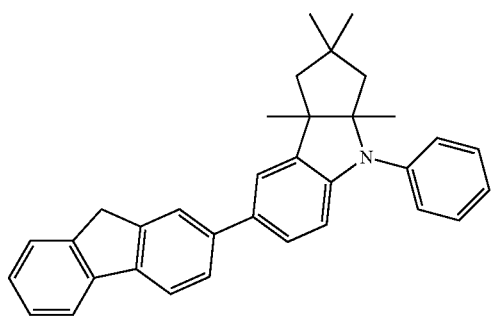
Formula 1354
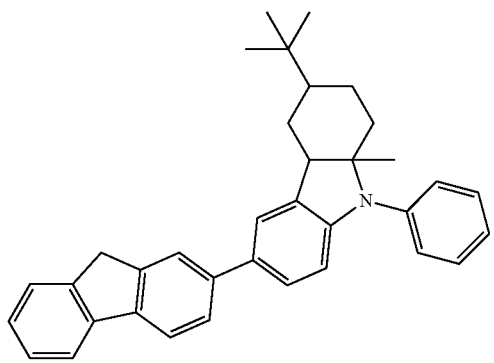
Formula 1355
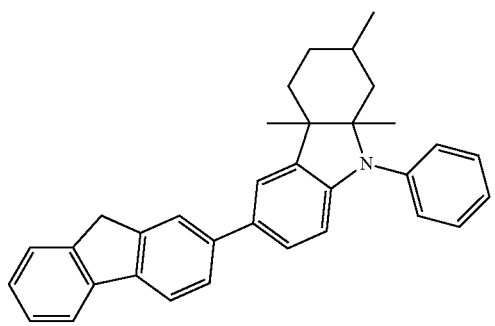
Formula 1356
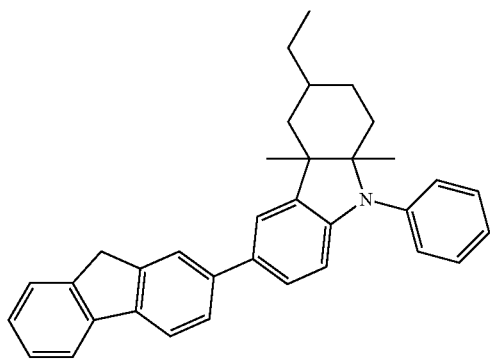
Formula 1357
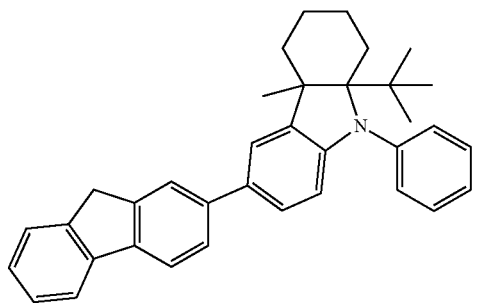

-continued
Formula 1358
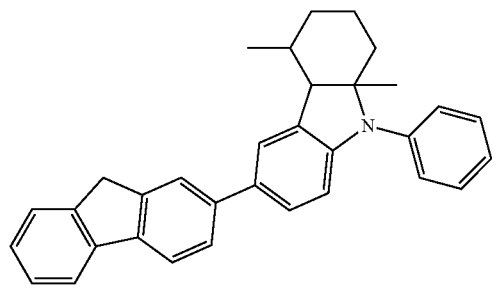
Formula 1359
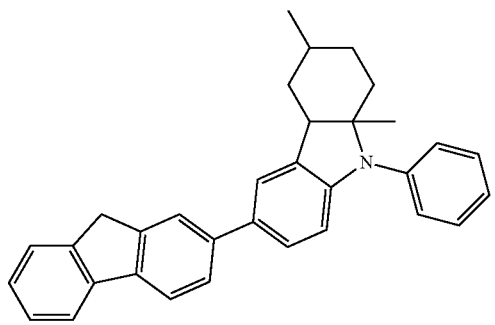
Formula 1360
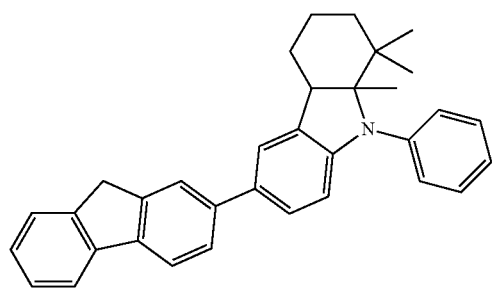
Formula 1361
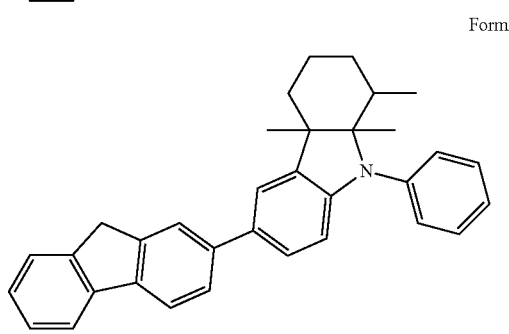
Formula 1362
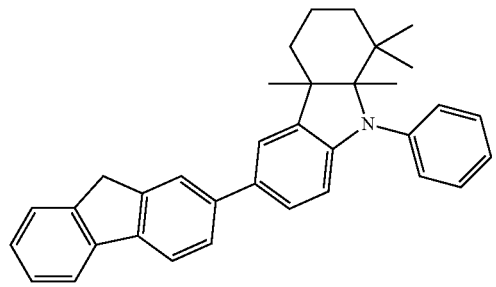
Formula 1363
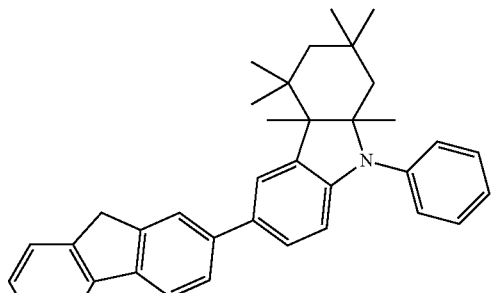
Formula 1364
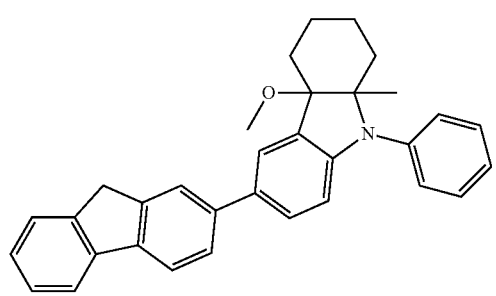
Formula 1365
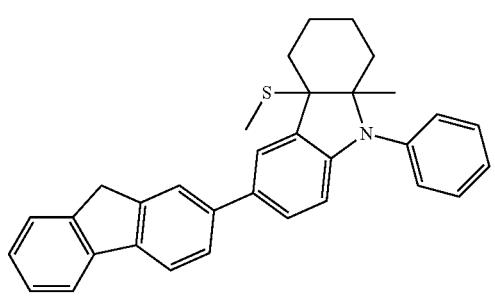
Formula 1366
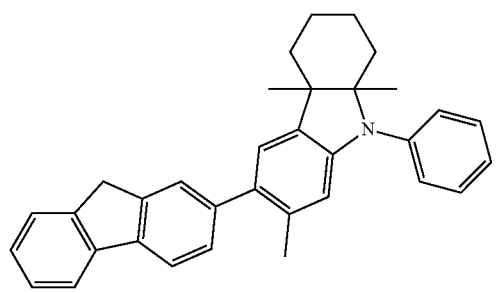
Formula 1367
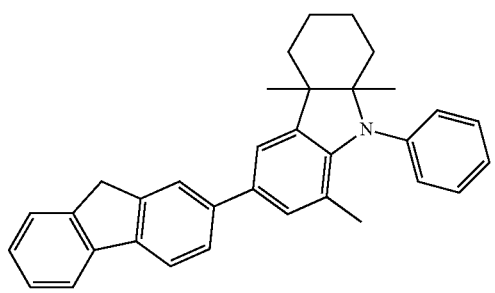

-continued
Formula 1368
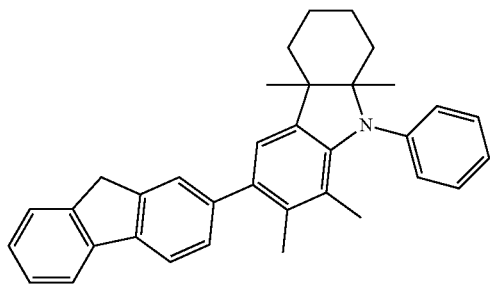
Formula 1369
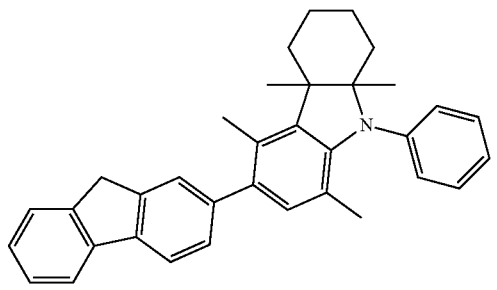
Formula 1370
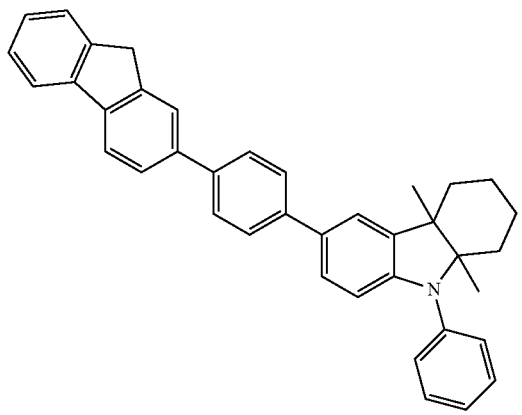
Formula 1371
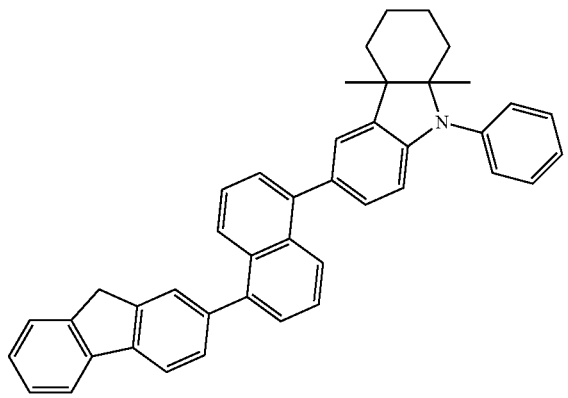
Formula 1372
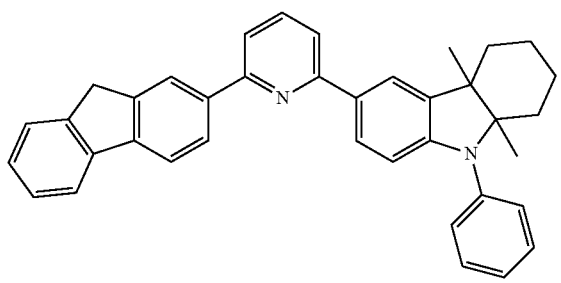
Formula 1373
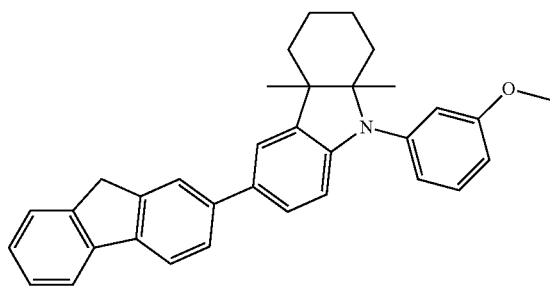
Formula 1374
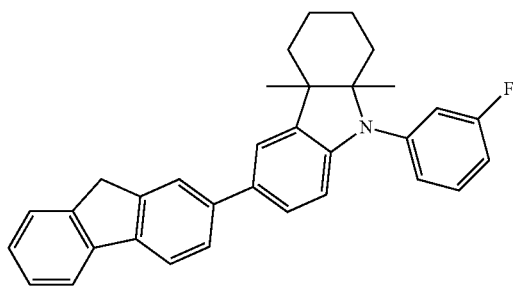
Formula 1375
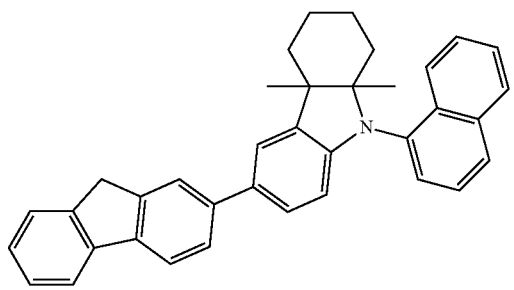

-continued
Formula 1376
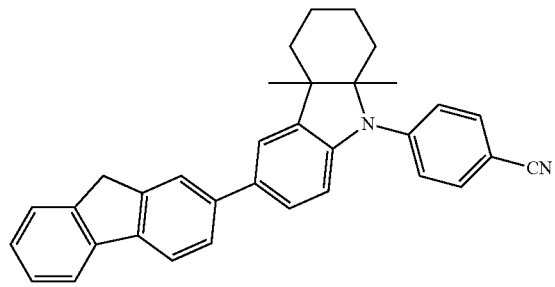
Formula 1377
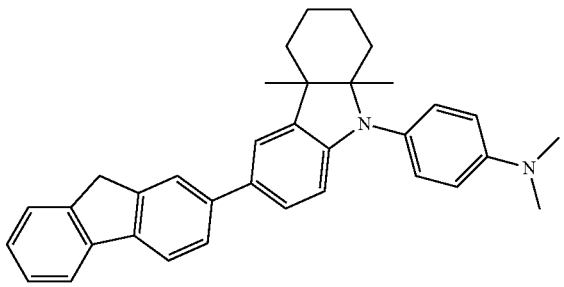
Formula 1378
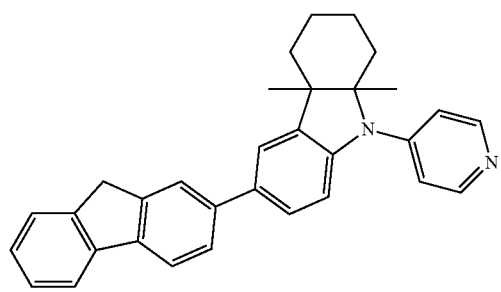
Formula 1379
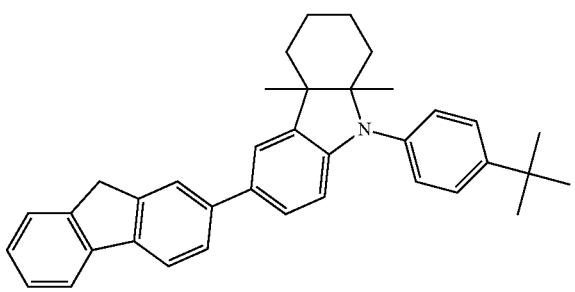
Formula 1380
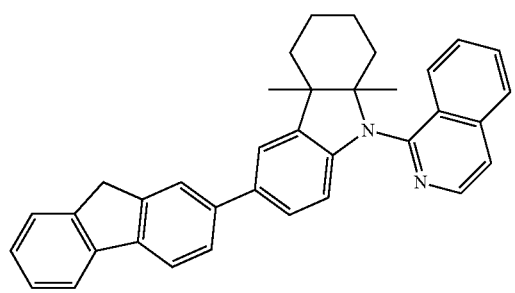
Formula 1381
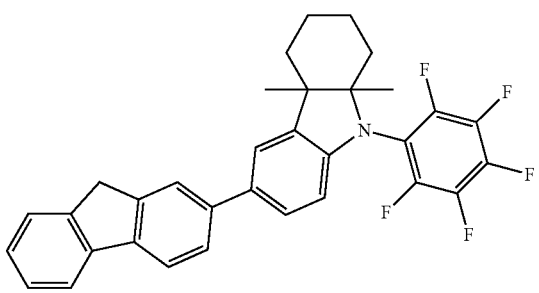
Formula 1382
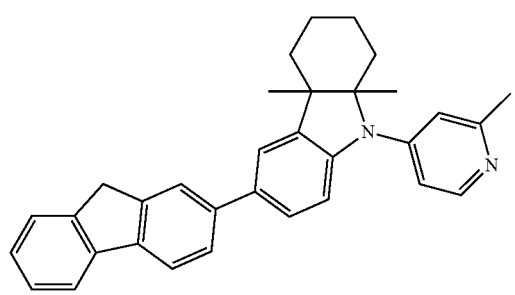
Formula 1383
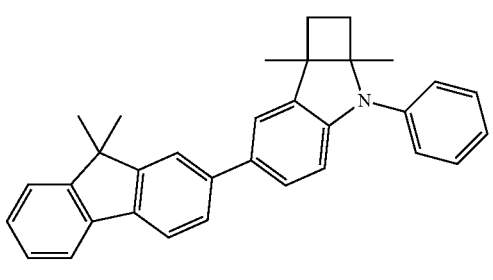
Formula 1384
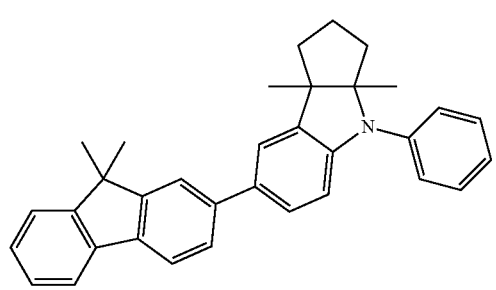
Formula 1385
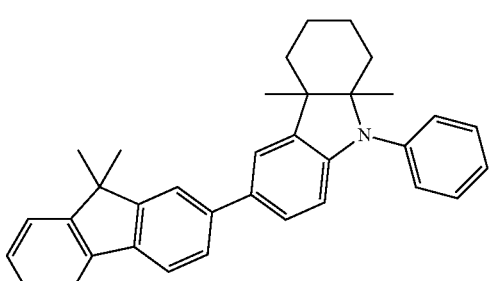

-continued
Formula 1386
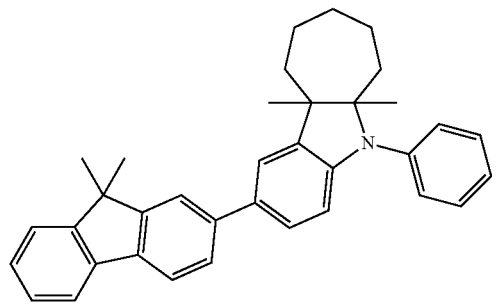
Formula 1387
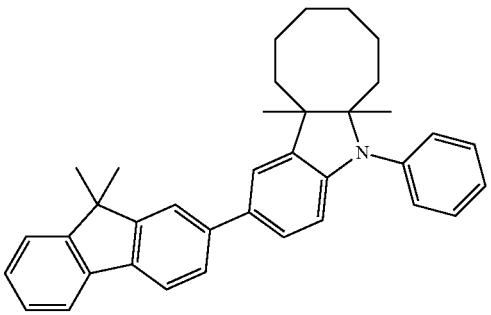
Formula 1388
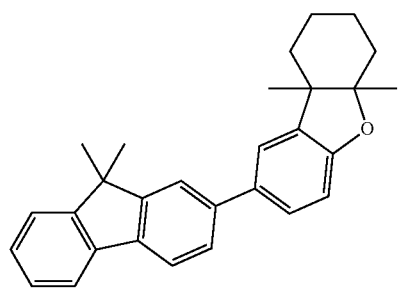
Formula 1389
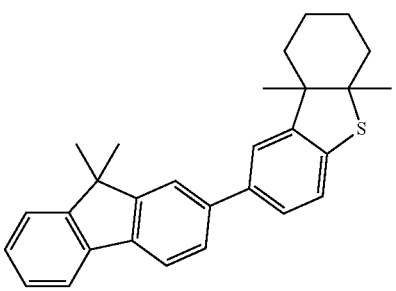
Formula 1390
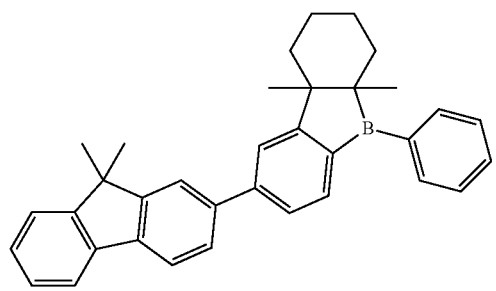
Formula 1391
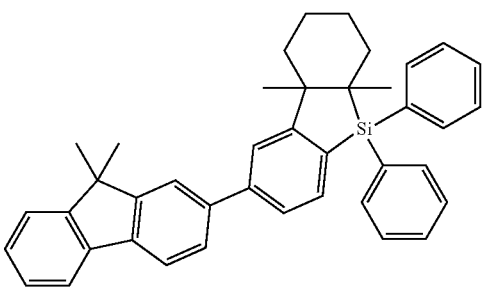
Formula 1392
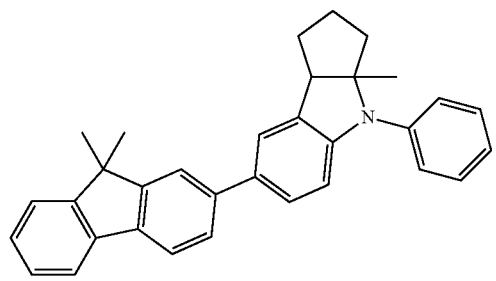
Formula 1393
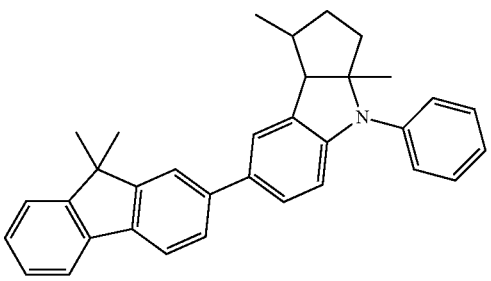
Formula 1394
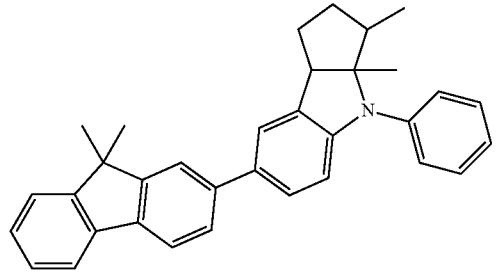
Formula 1395
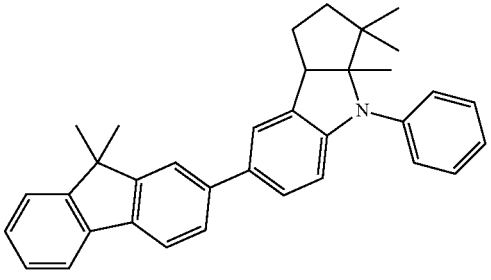

-continued
Formula 1396
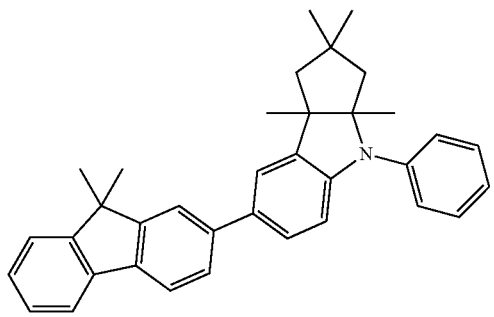
Formula 1397
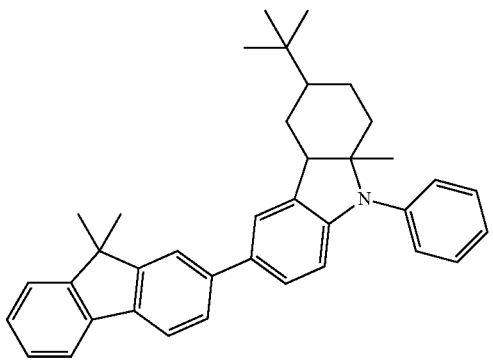
Formula 1398
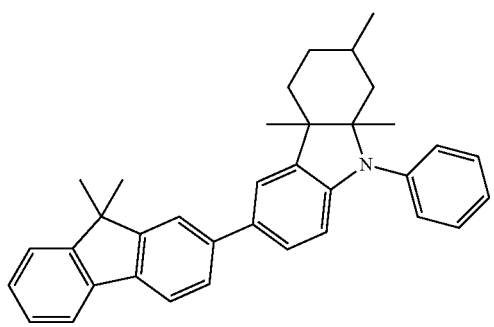
Formula 1399
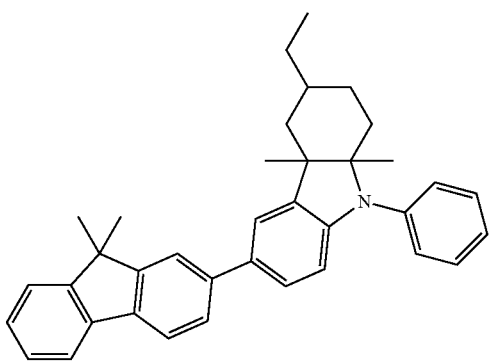
Formula 1400
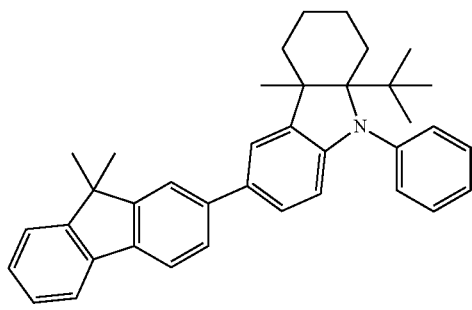
Formula 1401
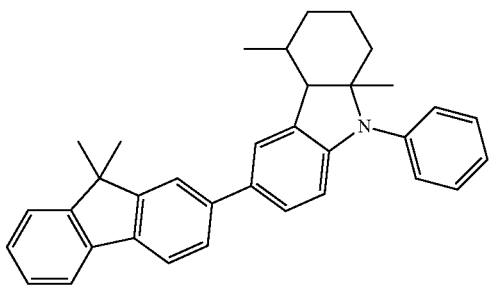
Formula 1402
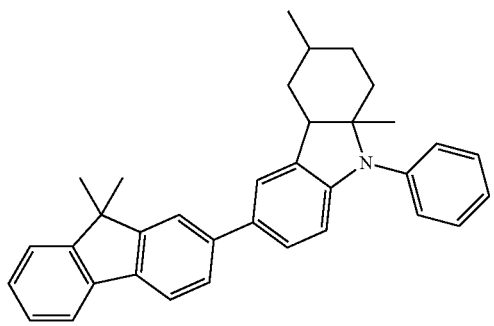
Formula 1403
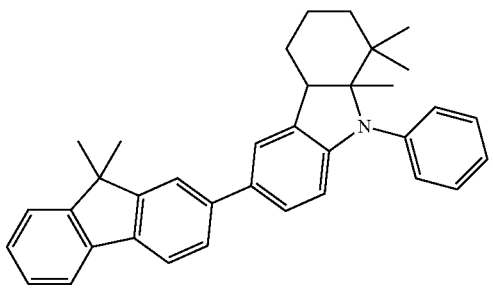

-continued
Formula 1404
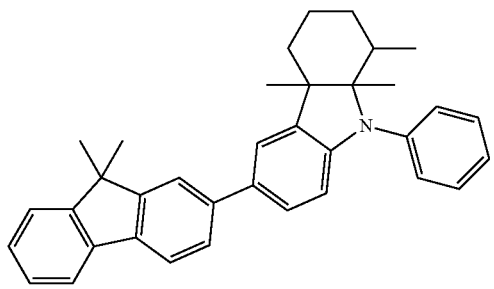
Formula 1405
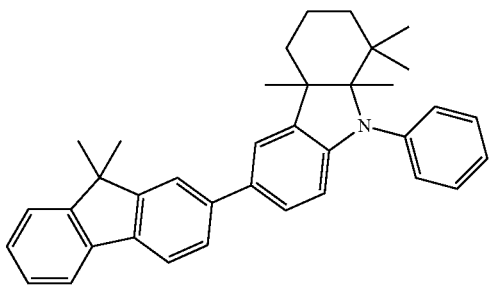
Formula 1406
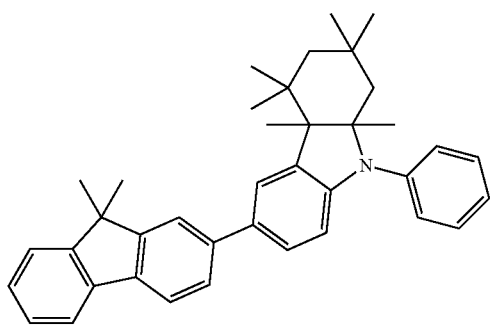
Formula 1407
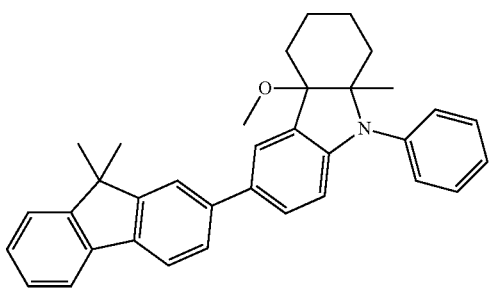
Formula 1408
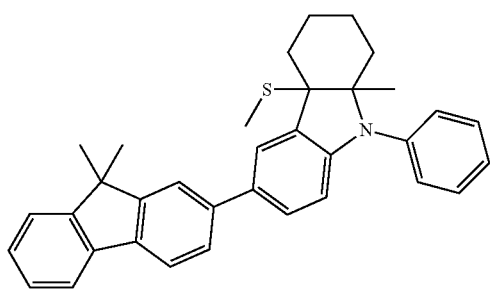
Formula 1409
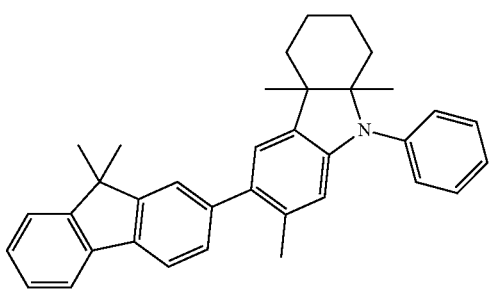
Formula 1410
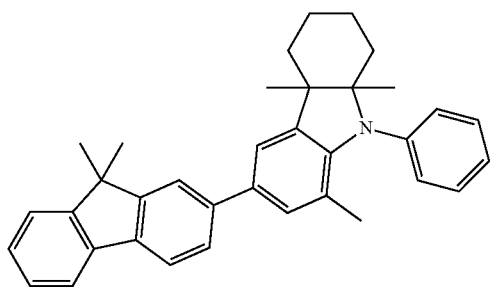
Formula 1411
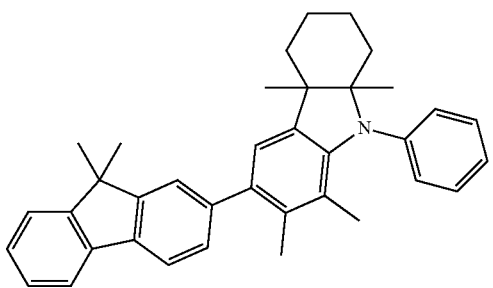

-continued
Formula 1412
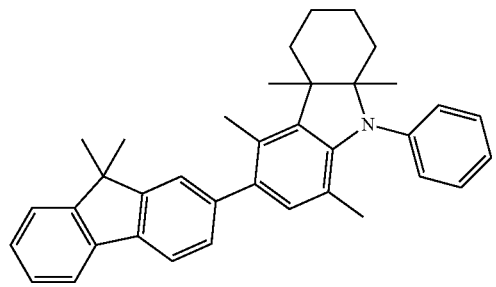
Formula 1413
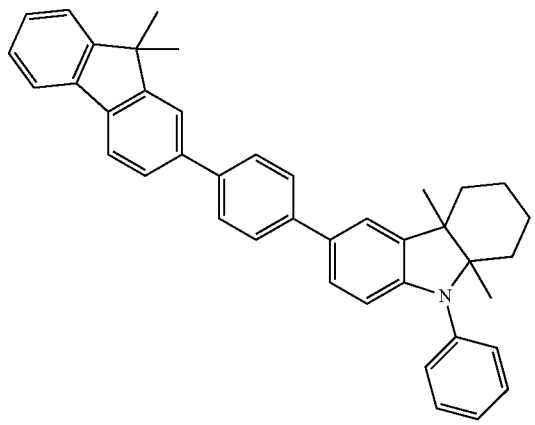
Formula 1414
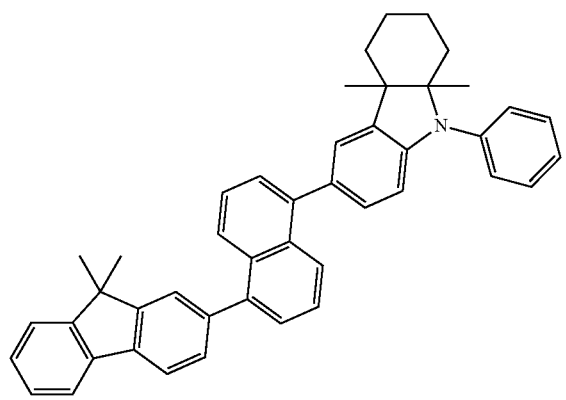
Formula 1415
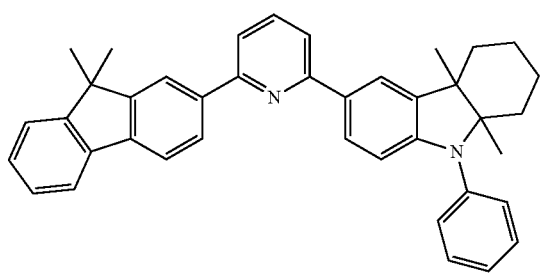
Formula 1416
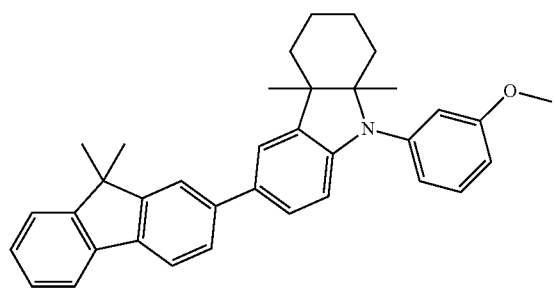
Formula 1417
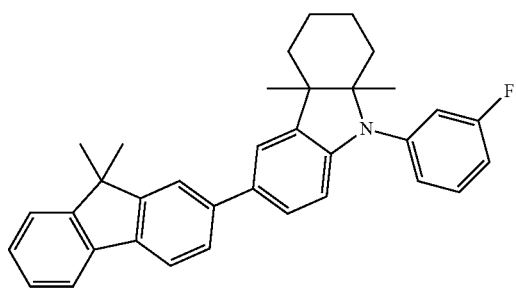
Formula 1418
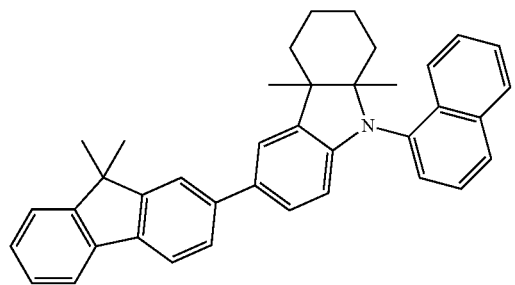
Formula 1419
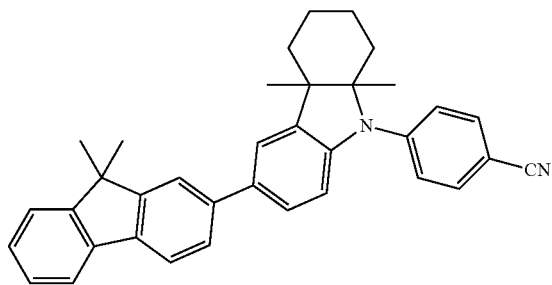

-continued
Formula 1420
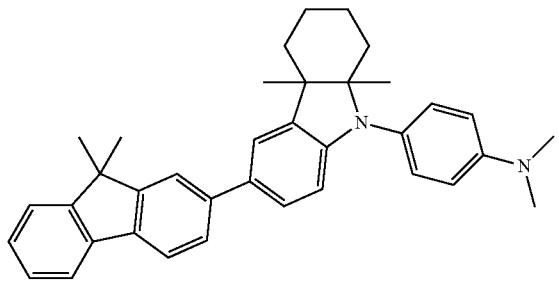
Formula 1421
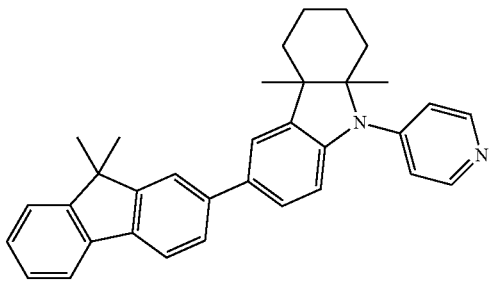
Formula 1422
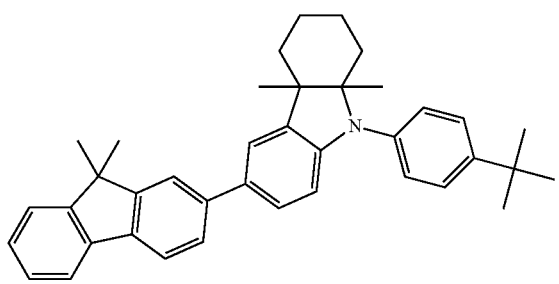
Formula 1423
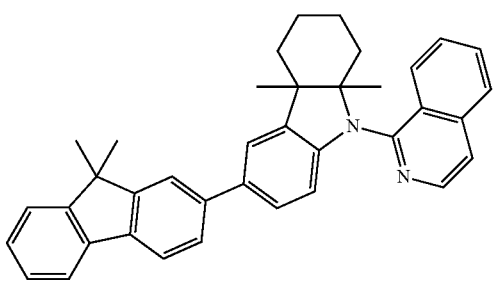
Formula 1424
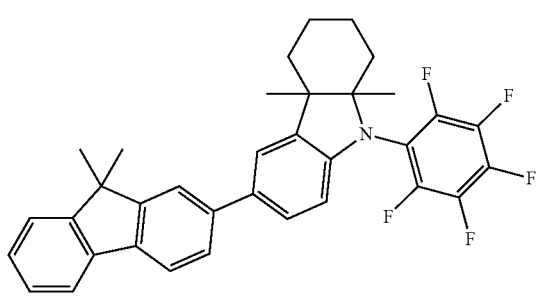
Formula 1425
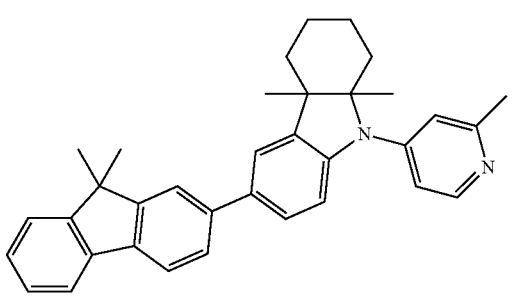
Formula 1426
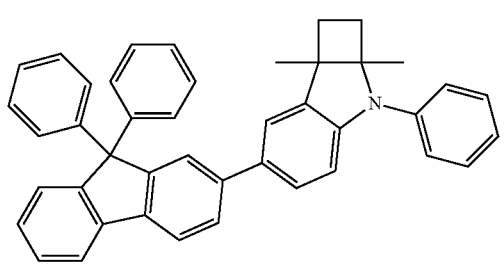
Formula 1427
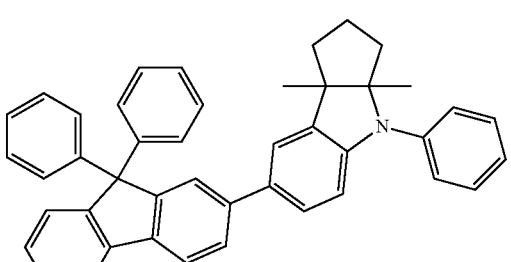
Formula 1428
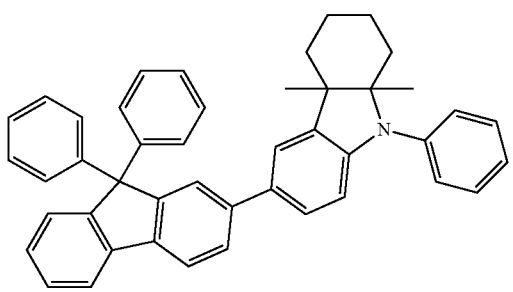
Formula 1429
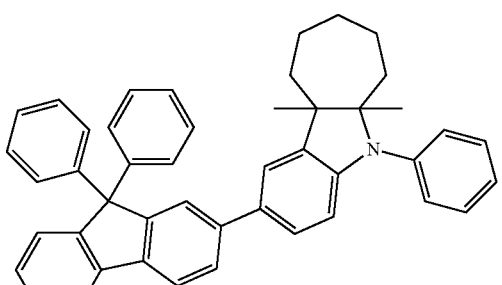

-continued
Formula 1430
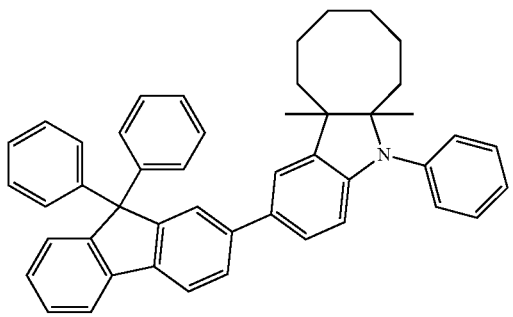
Formula 1431
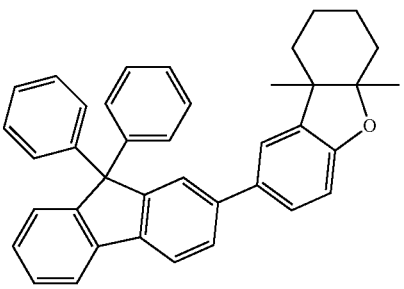
Formula 1432
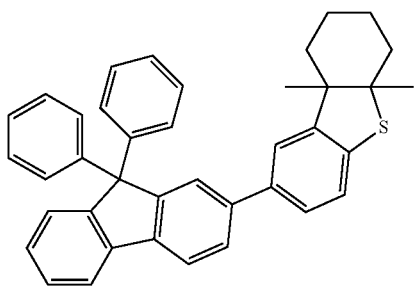
Formula 1433
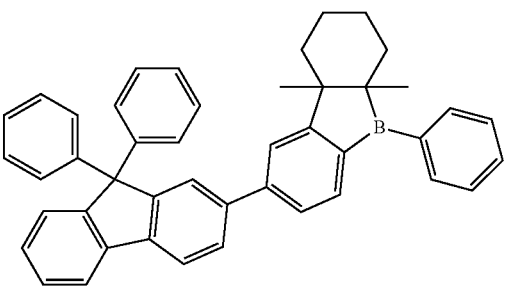
Formula 1434
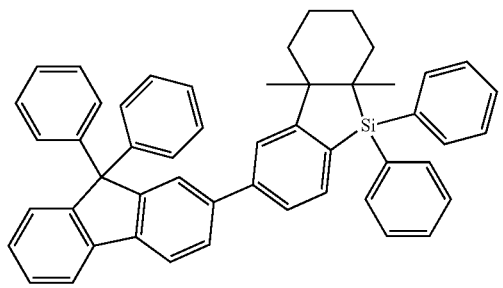
Formula 1435
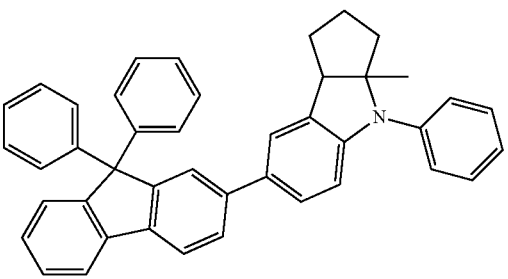
Formula 1436
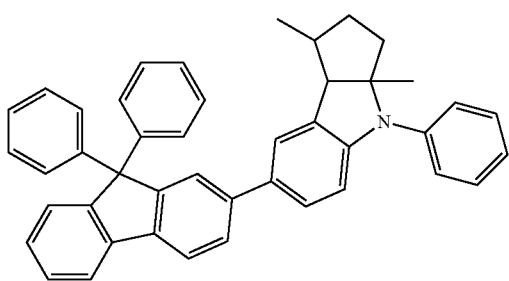
Formula 1437
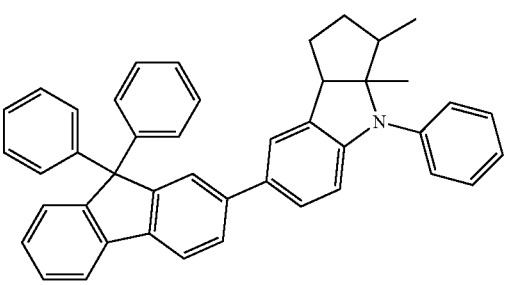
Formula 1438
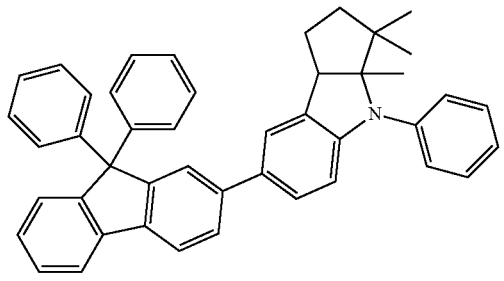
Formula 1439
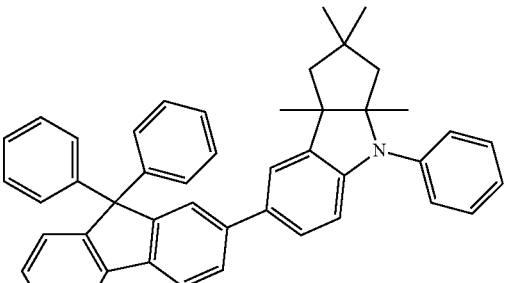

-continued
Formula 1440
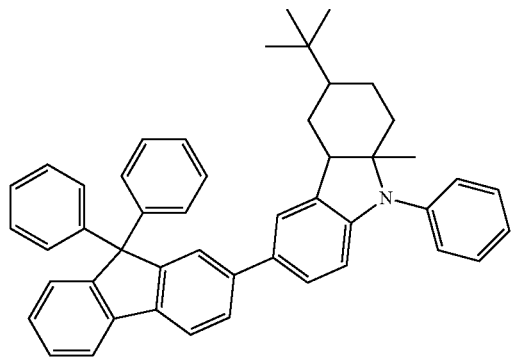
Formula 1441
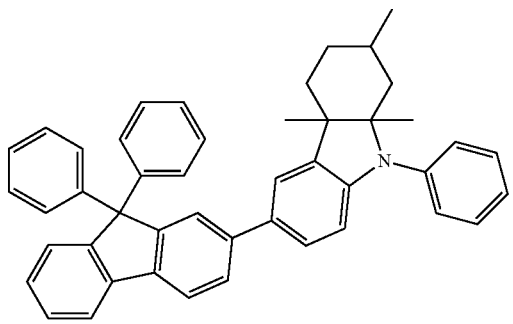
Formula 1442
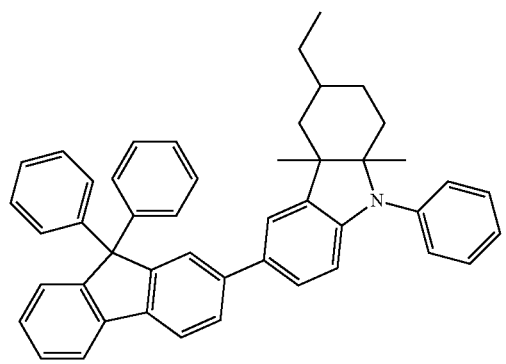
Formula 1443
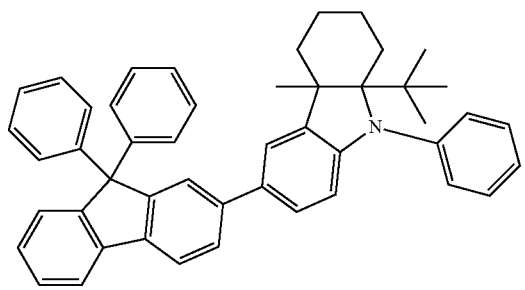
Formula 1444
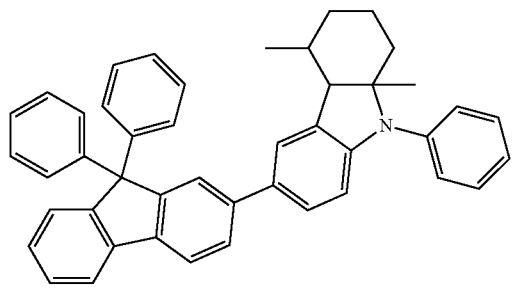
Formula 1445
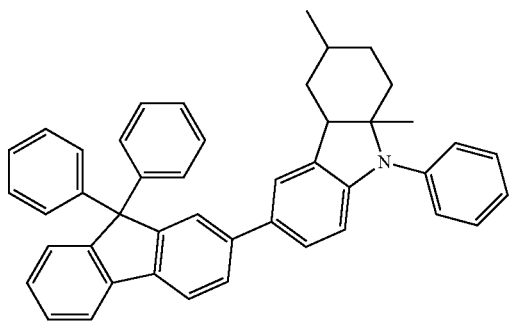
Formula 1446
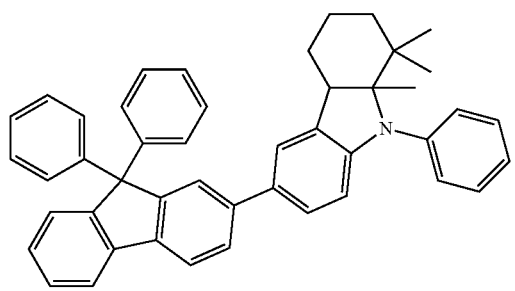
Formula 1447
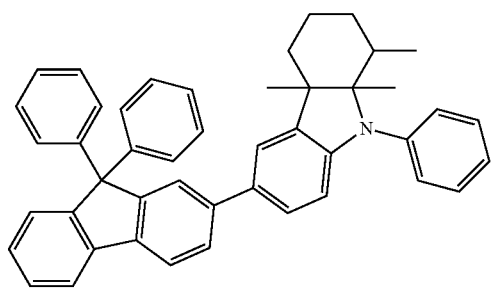

-continued
Formula 1448
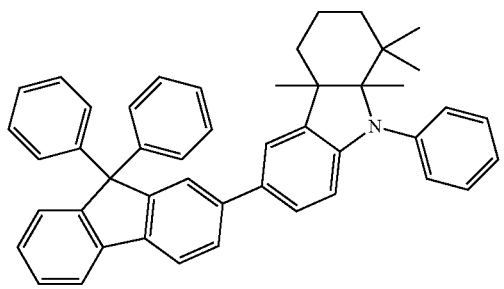
Formula 1449
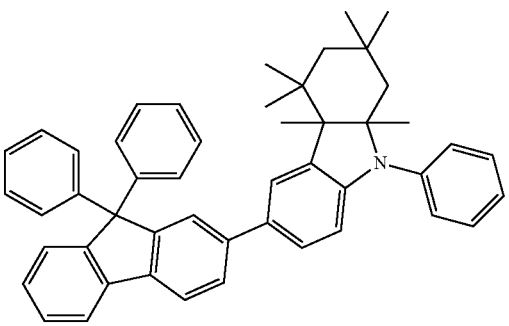
Formula 1450
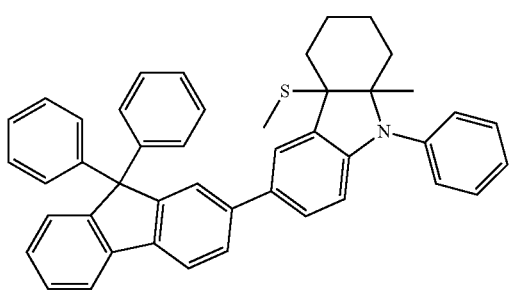
Formula 1451
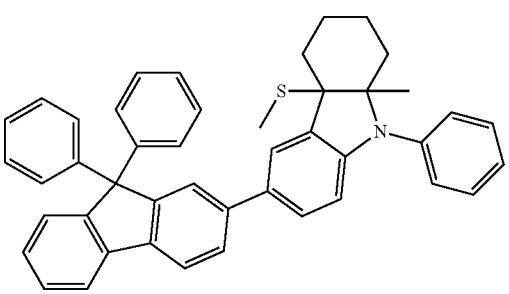
Formula 1452
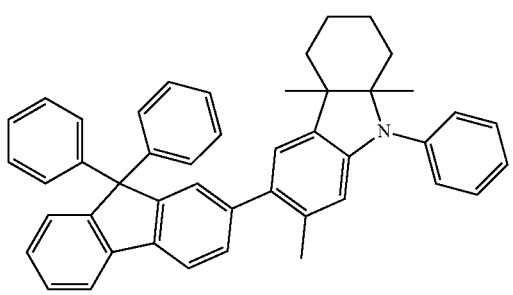
Formula 1453
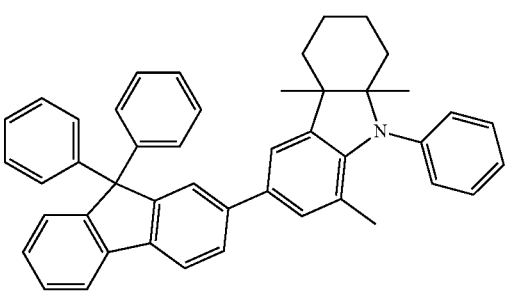
Formula 1455
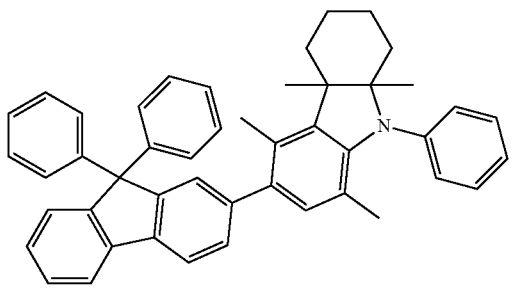
Formula 1455
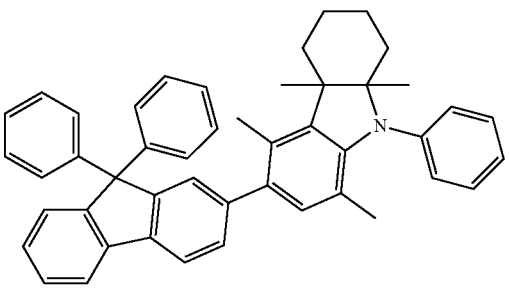

-continued
Formula 1456
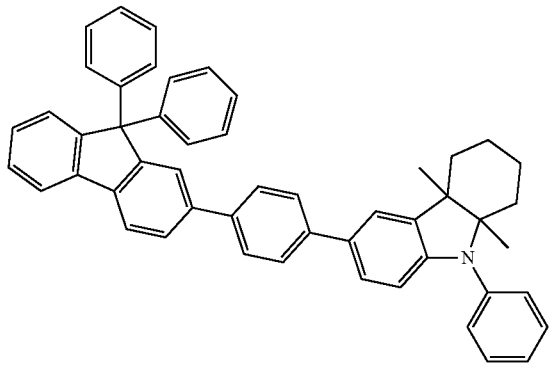
Formula 1457
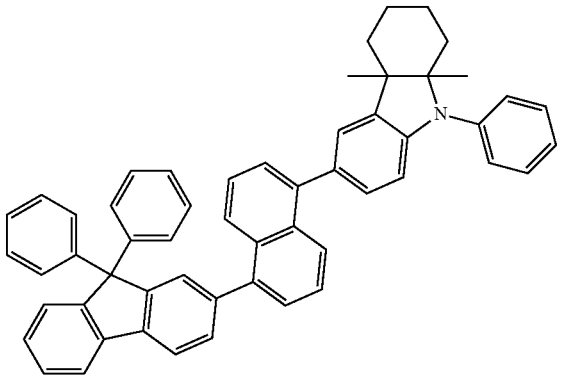
Formula 1458
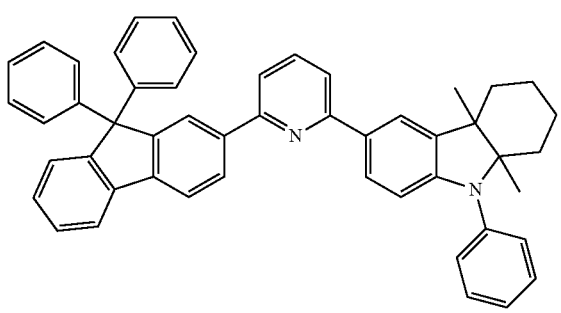
Formula 1459
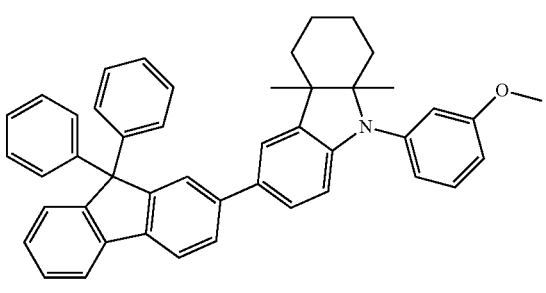
Formula 1460
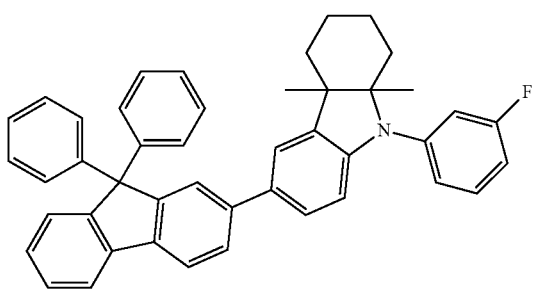
Formula 1461
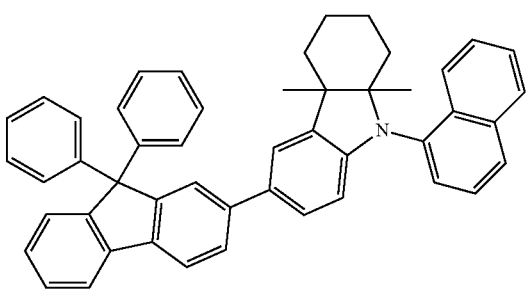
Formula 1462
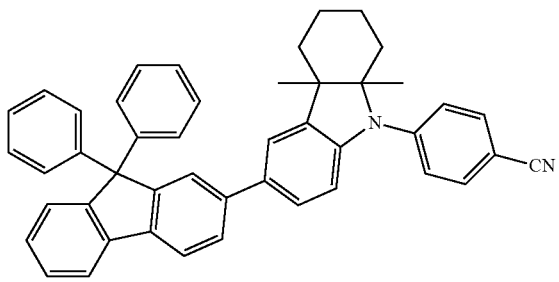
Formula 1463
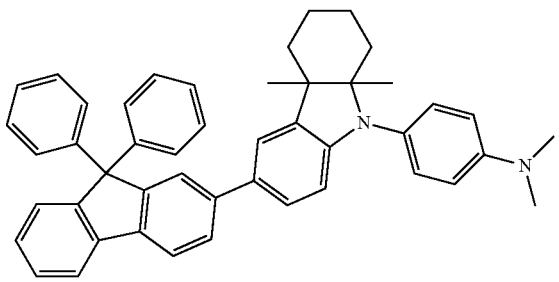
Formula 1464
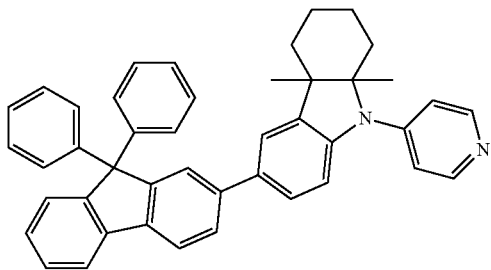
Formula 1465
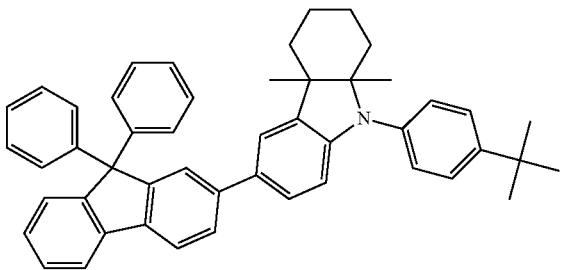

-continued
Formula 1466
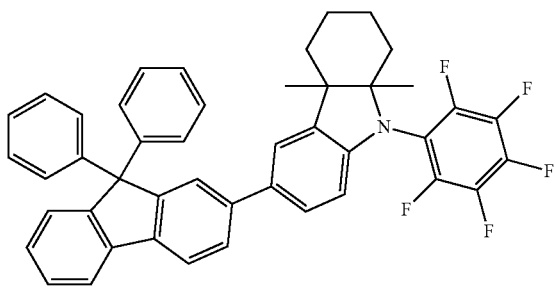
Formula 1467
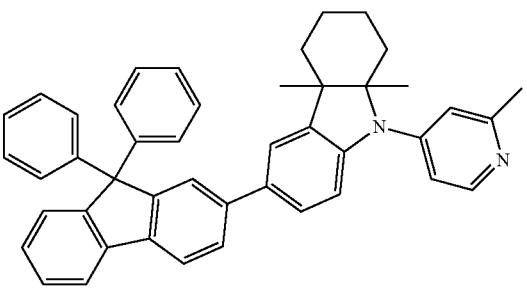
Formula 1468
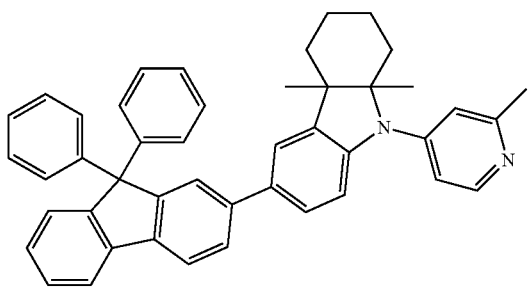
Formula 1469
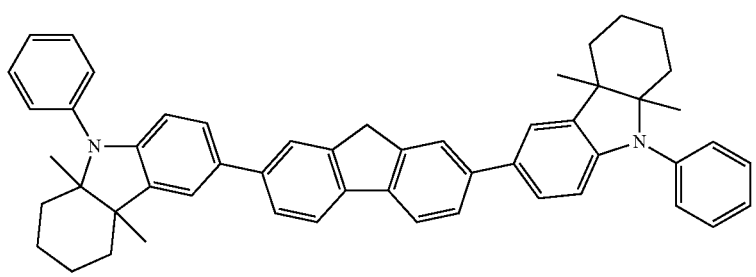
Formula 1470
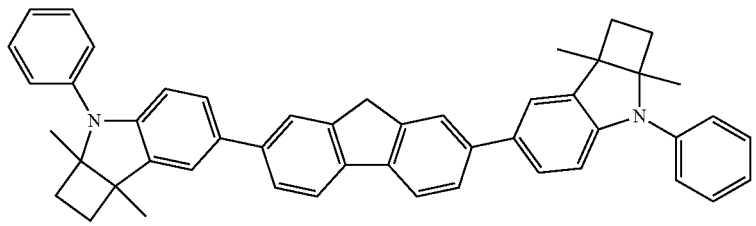
Formula 1471
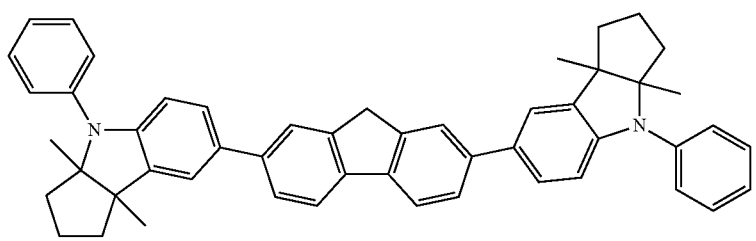
Formula 1472
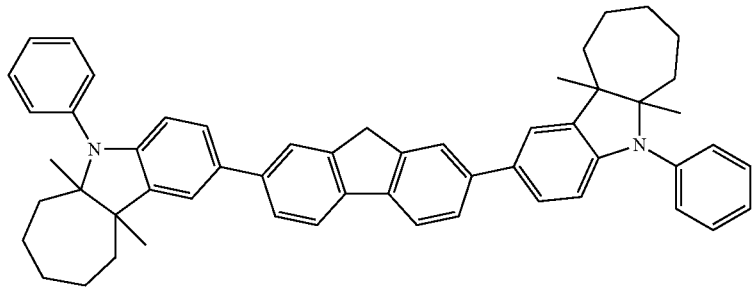

Formula 1473
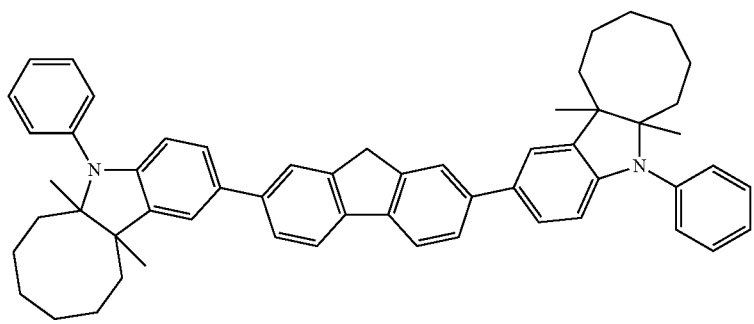
Formula 1474
Formula 1475
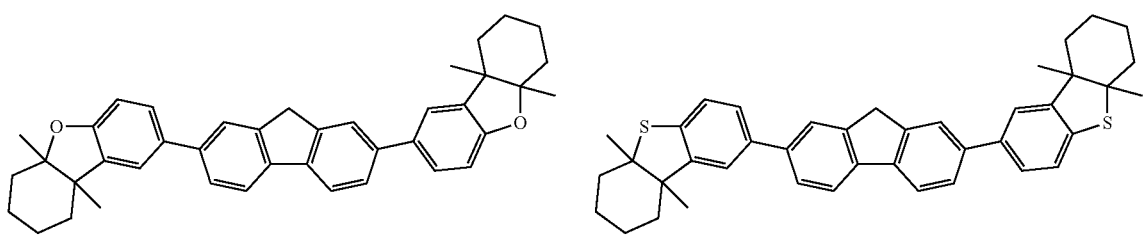
Formula 1476
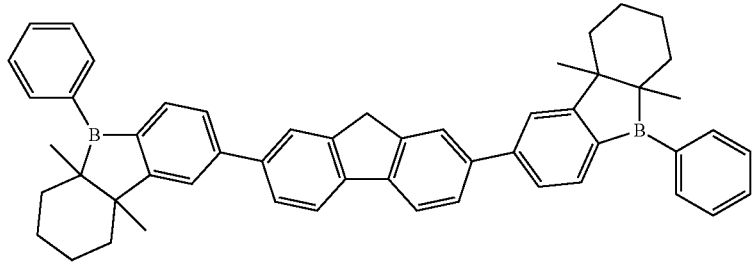
Formula 1477
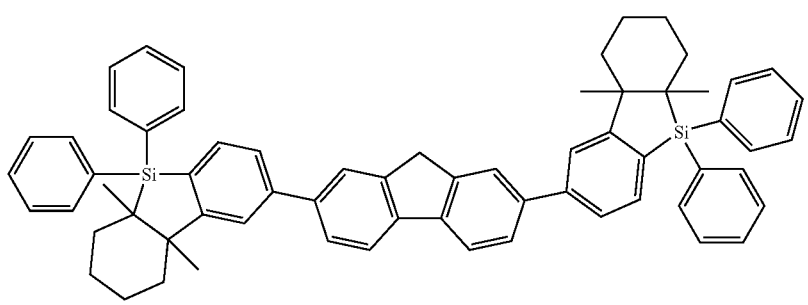
Formula 1478
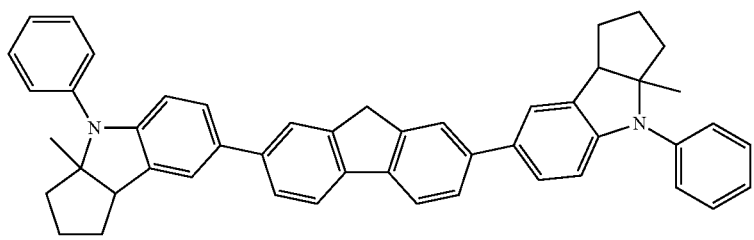

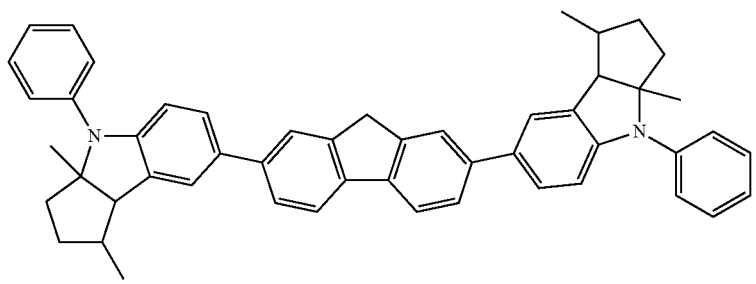
Formula 1479
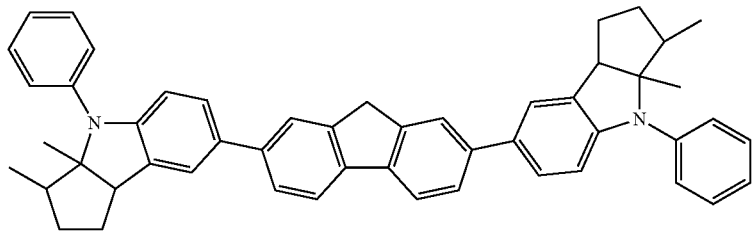
Formula 1480
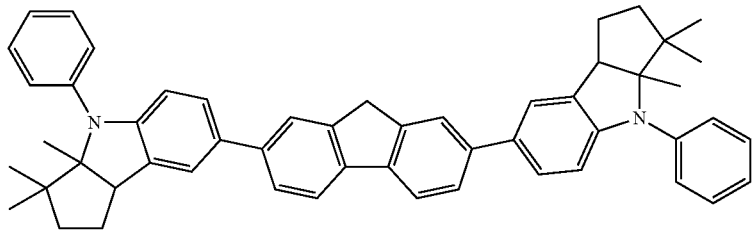
Formula 1481
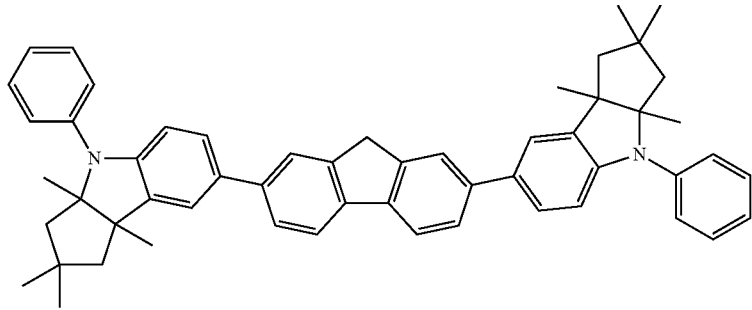
Formula 1482
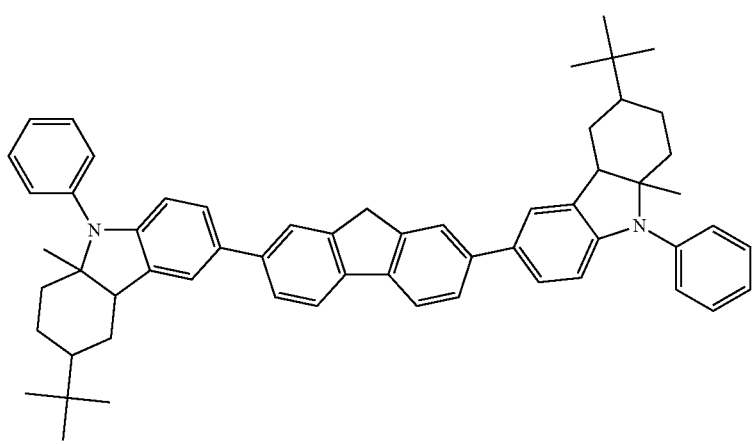
Formula 1483

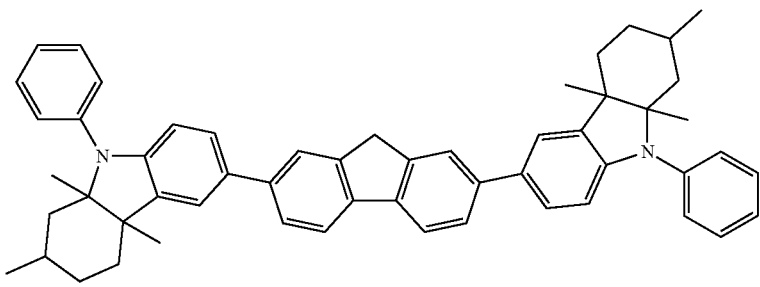
Formula 1484
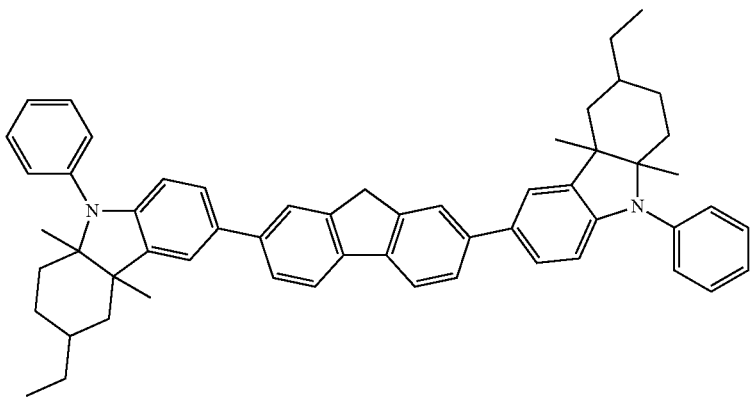
Formula 1485
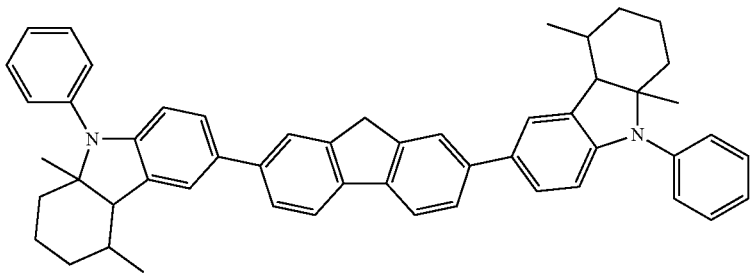
Formula 1486
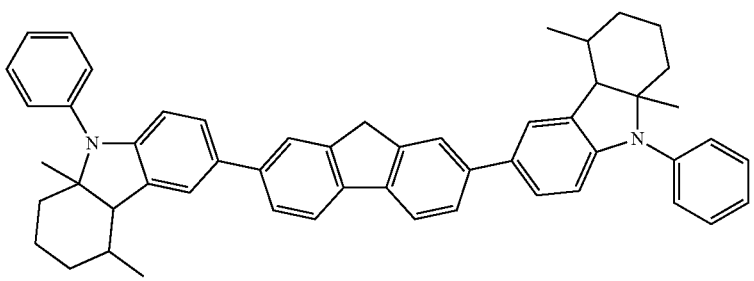
Formula 1487
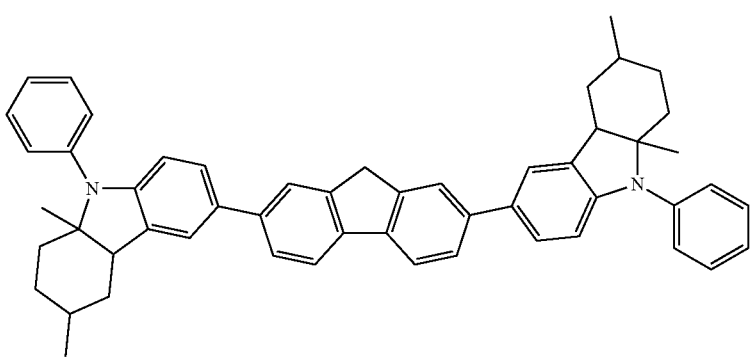
Formula 1488

-continued
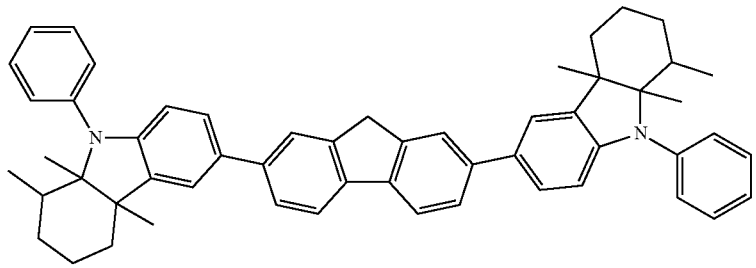
Formula 1489
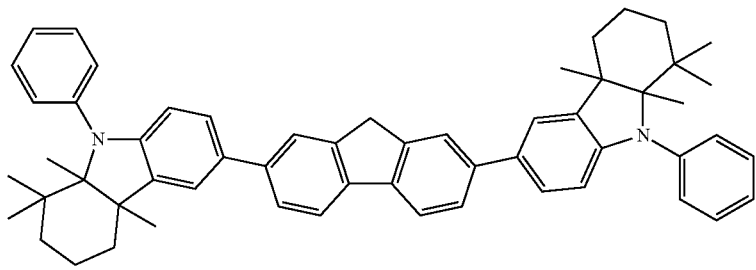
Formula 1490
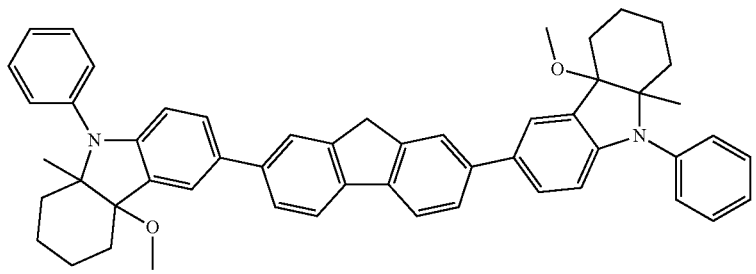
Formula 1491
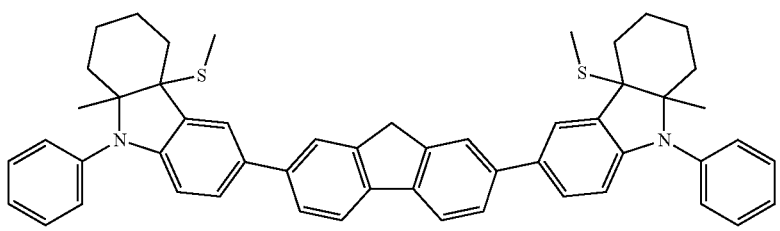
Formula 1492
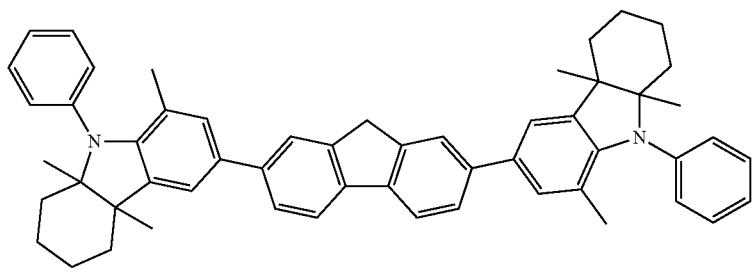
Formula 1493
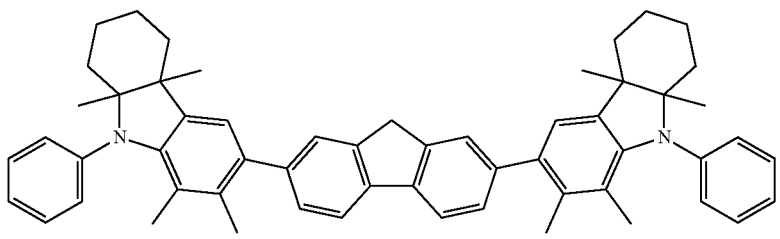
Formula 1494

-continued
Formula 1496
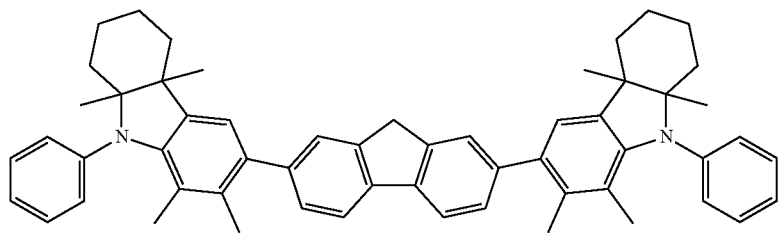
Formula 1497
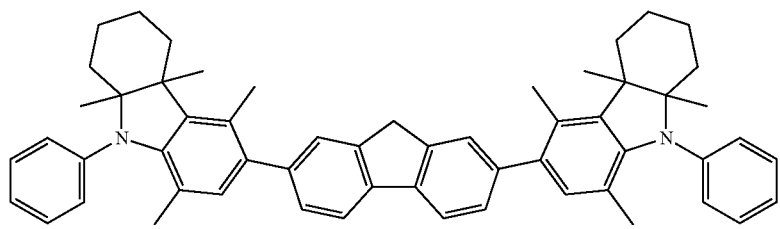
Formula 1497
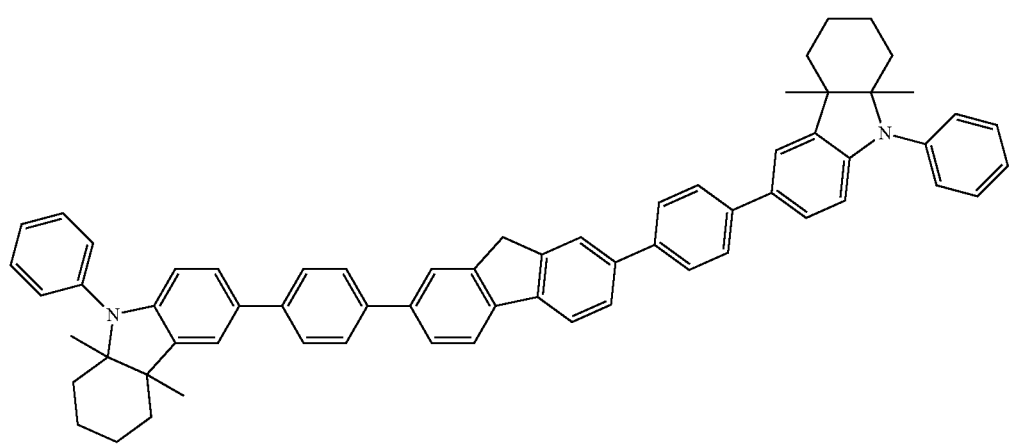
Formula 1498
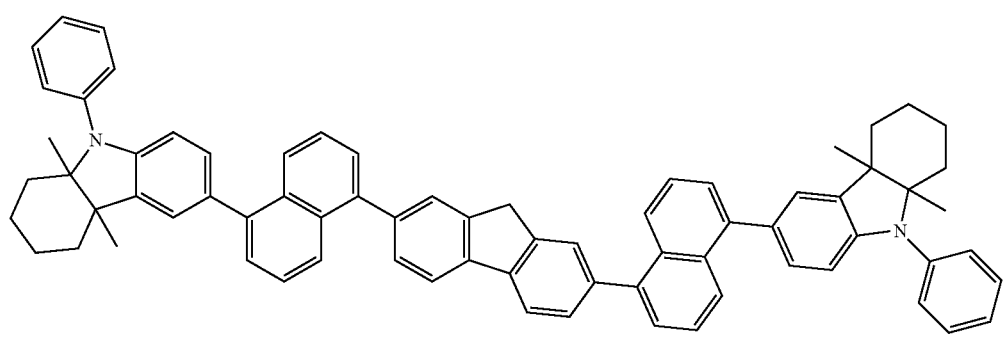
Formula 1499
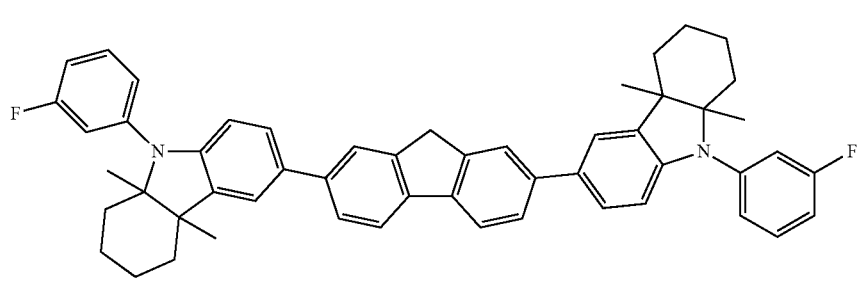

Formula 1500
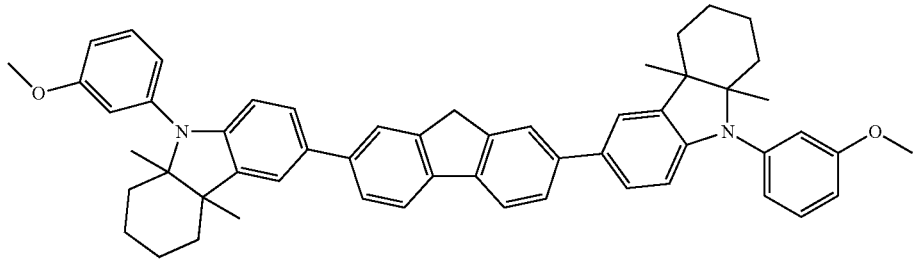
Formula 1501
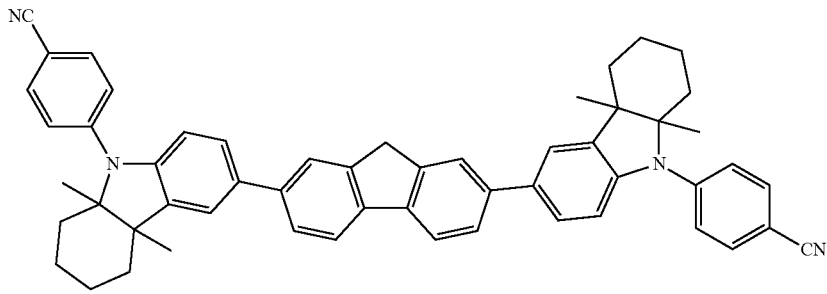
Formula 1502
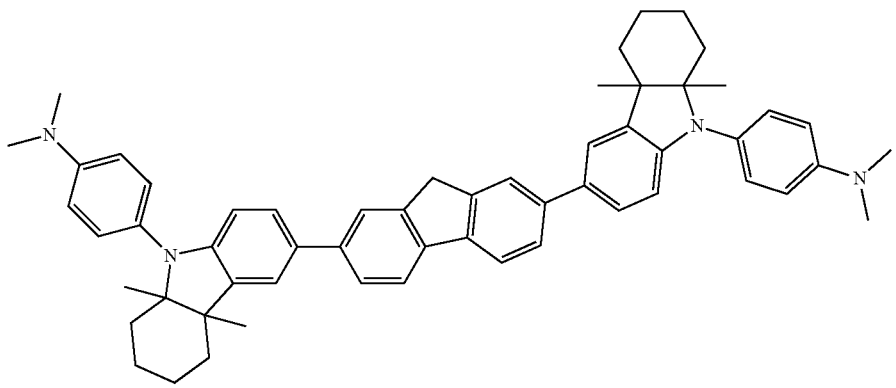
Formula 1503
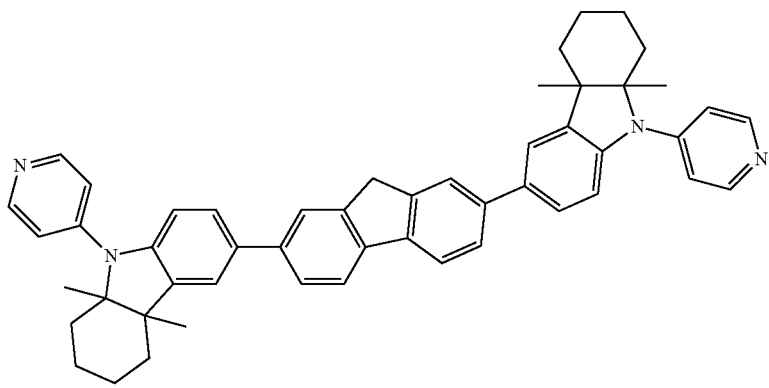
Formula 1504
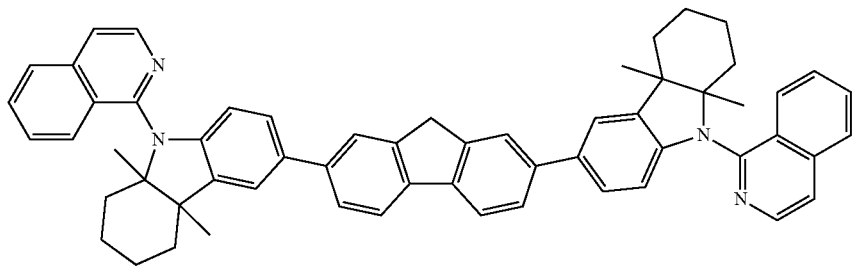

-continued
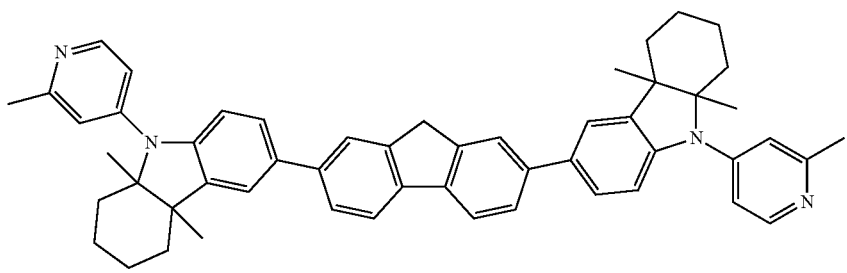
Formula 1505
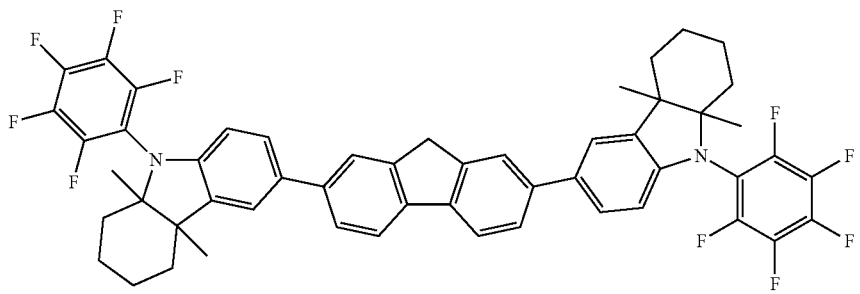
Formula 1506
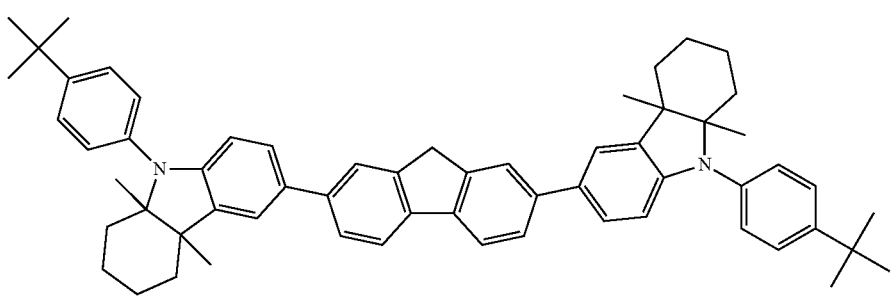
Formula 1507
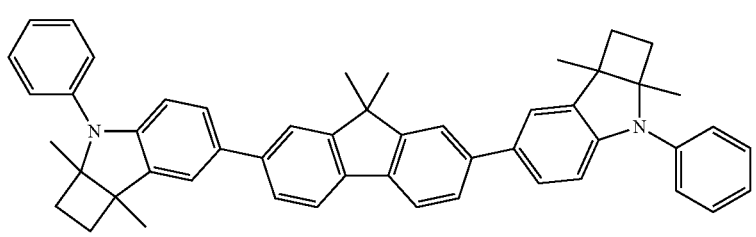
Formula 1508
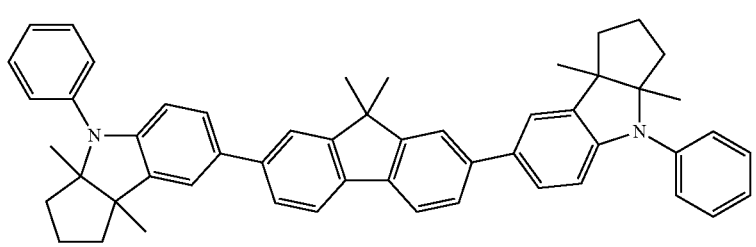
Formula 1509
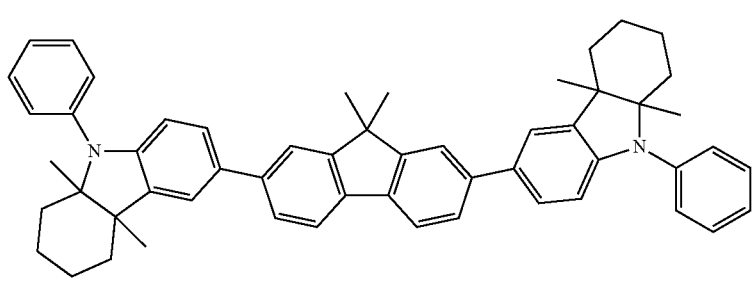
Formula 1510

Formula 1511
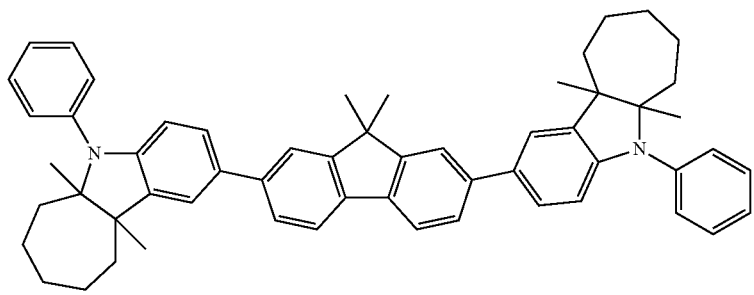
Formula 1512
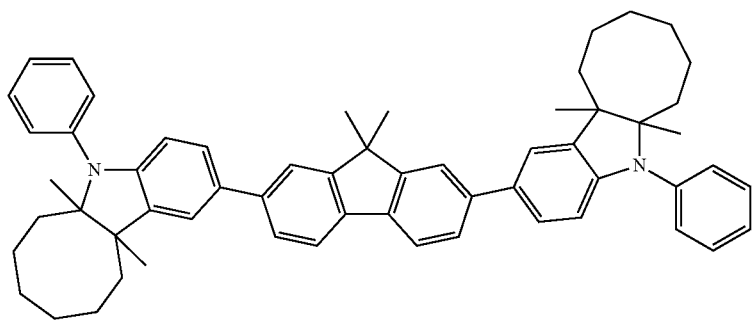
Formula 1513
Formula 1514
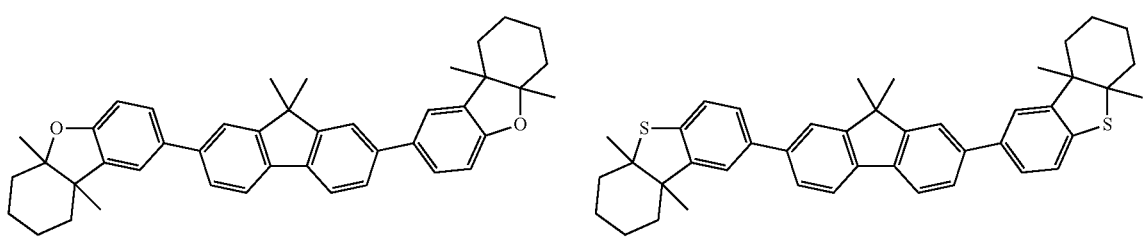
Formula 1515
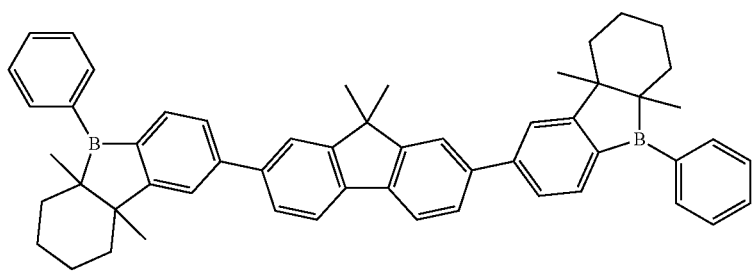
Formula 1516
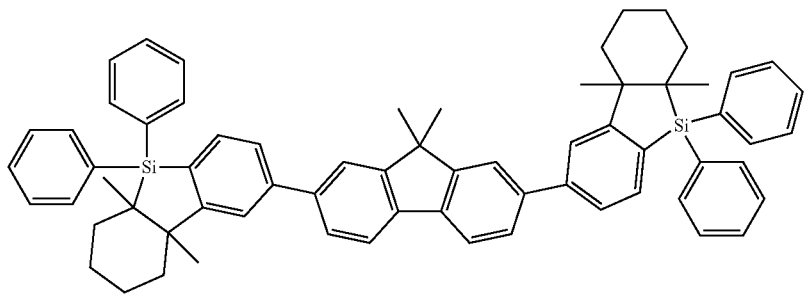

-continued
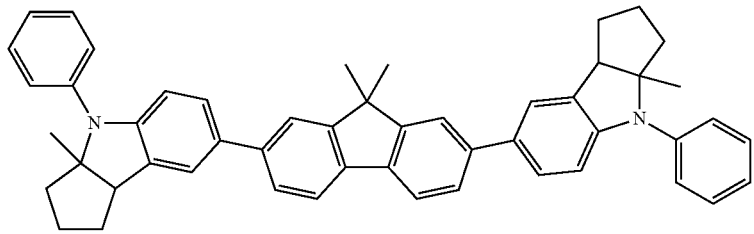
Formula 1517
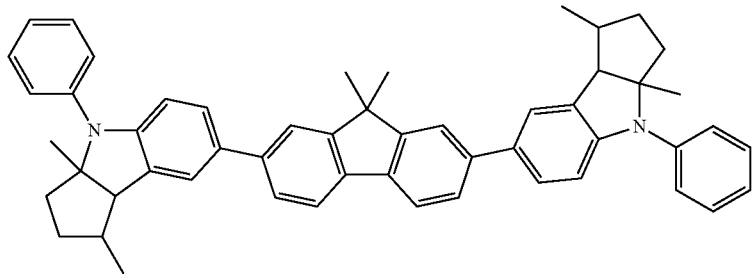
Formula 1518
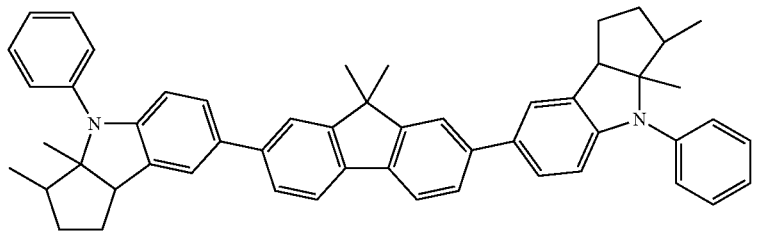
Formula 1519
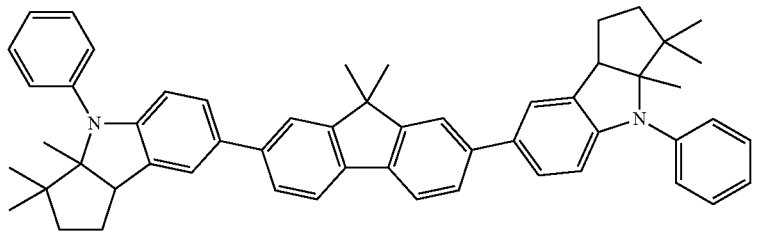
Formula 1520
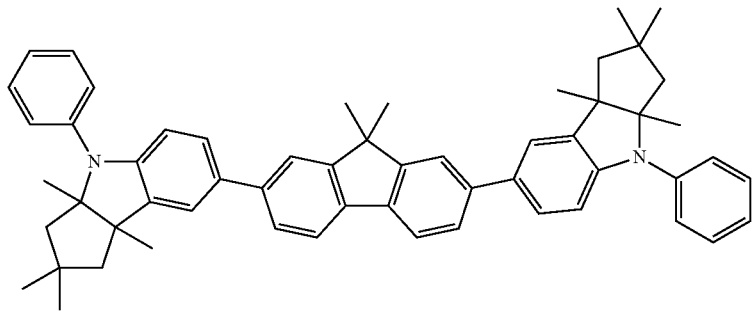
Formula 1521

-continued
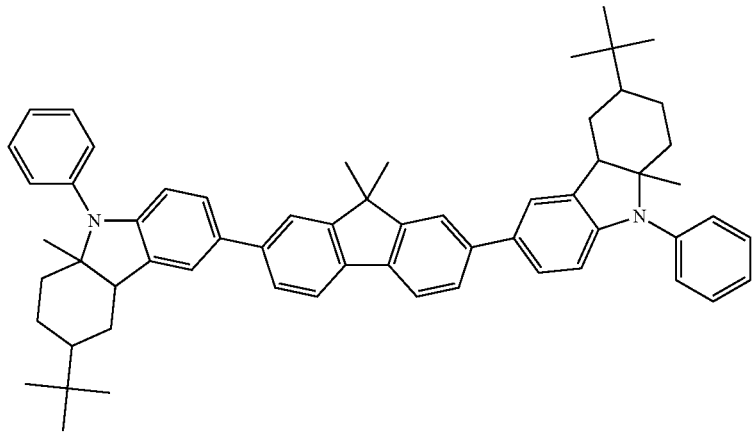
Formula 1522
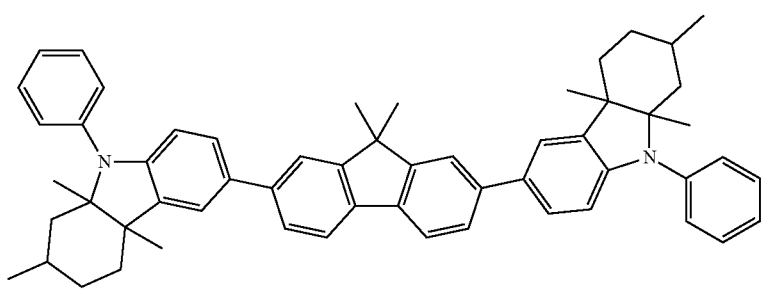
Formula 1523
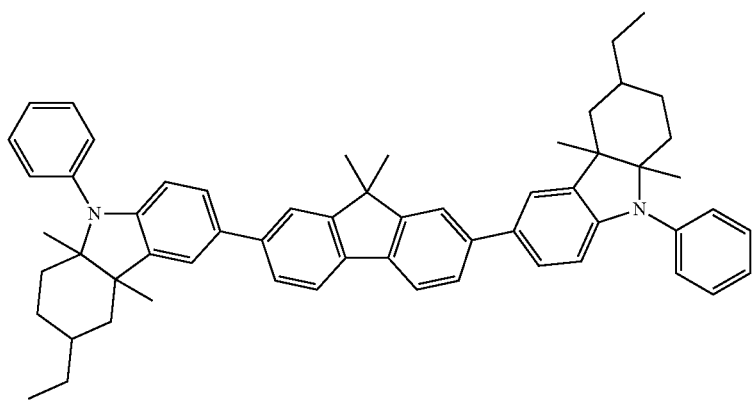
Formula 1524
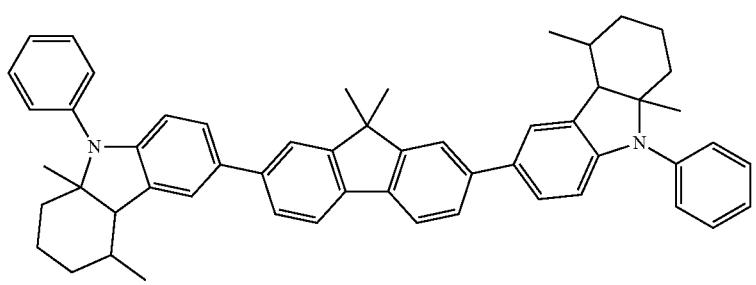
Formula 1525

-continued
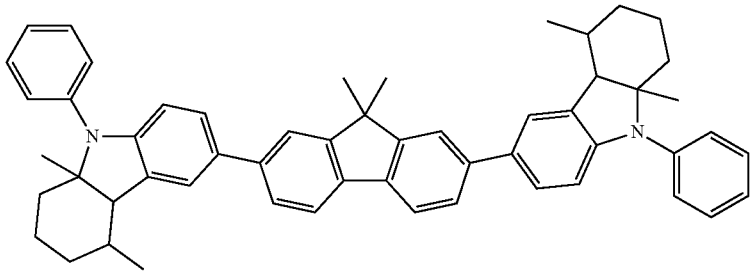
Formula 1526
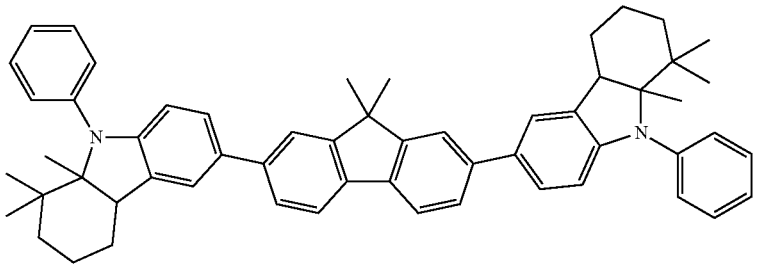
Formula 1527
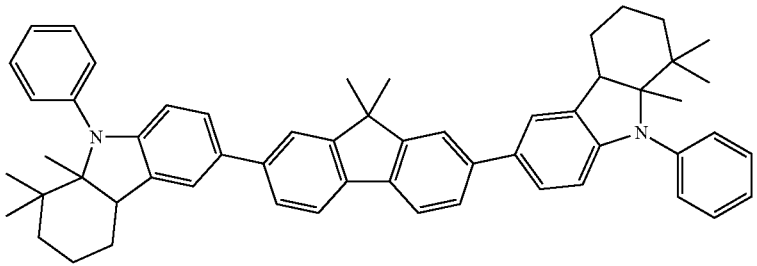
Formula 1528
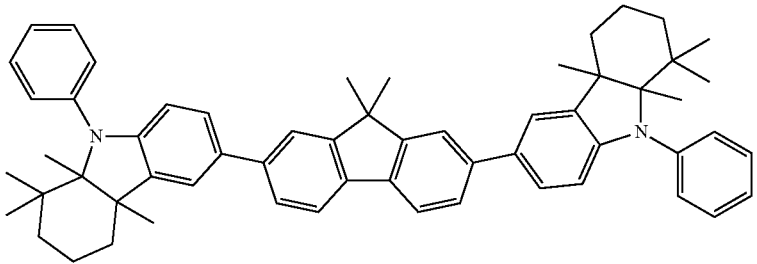
Formula 1529
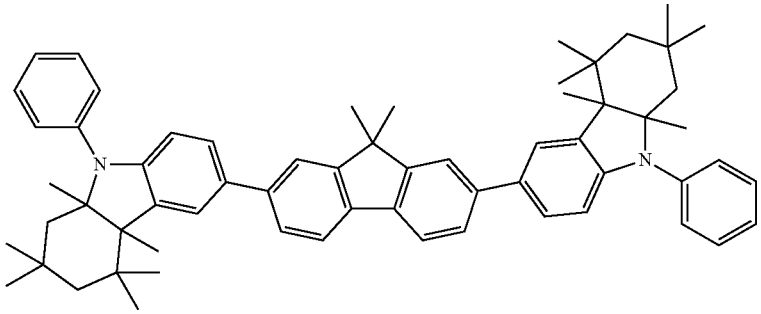
Formula 1530

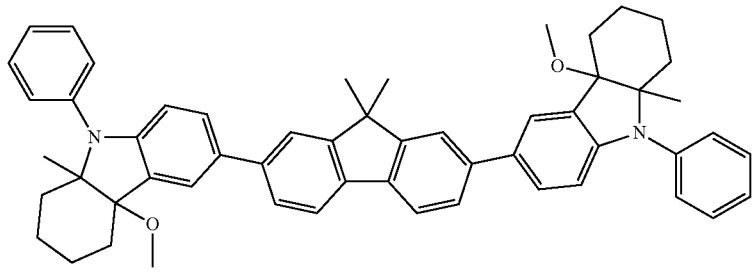
Formula 1531
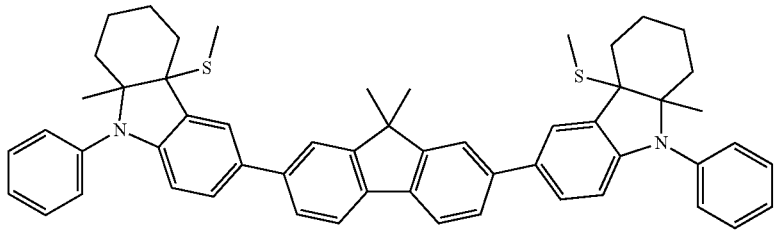
Formula 1532
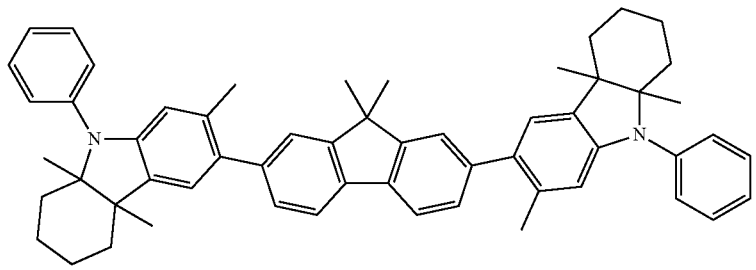
Formula 1533
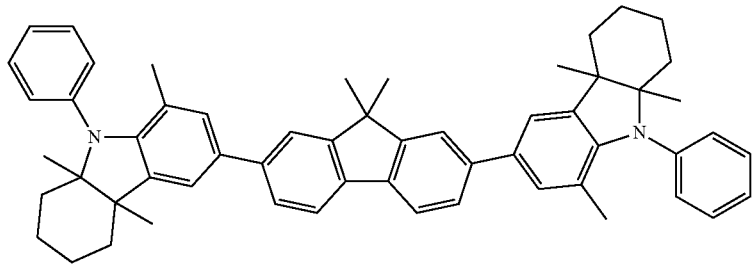
Formula 1534
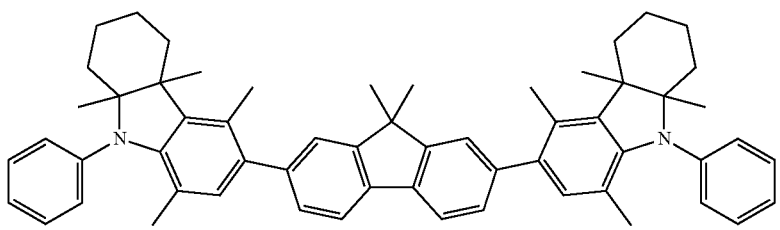
Formula 1535

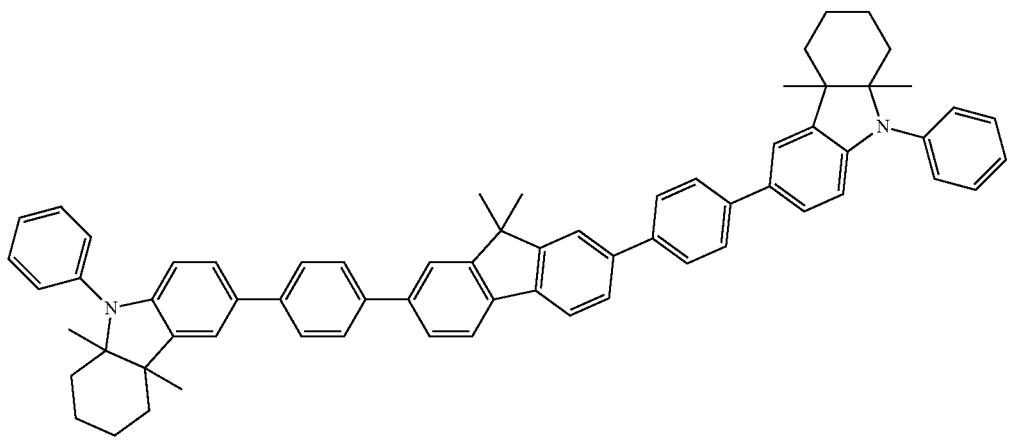
Formula 1536
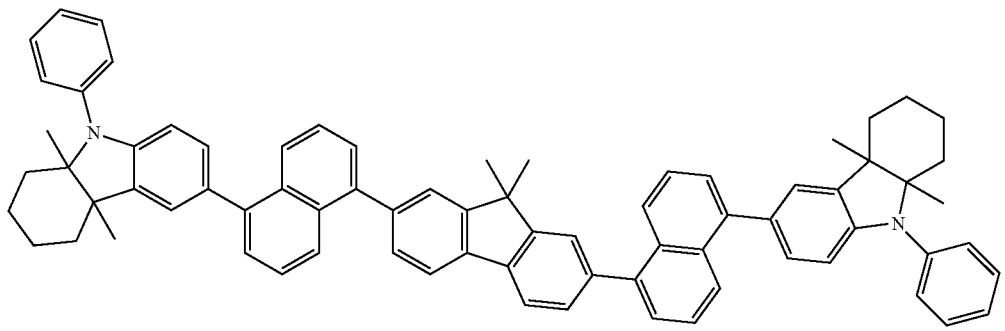
Formula 1537
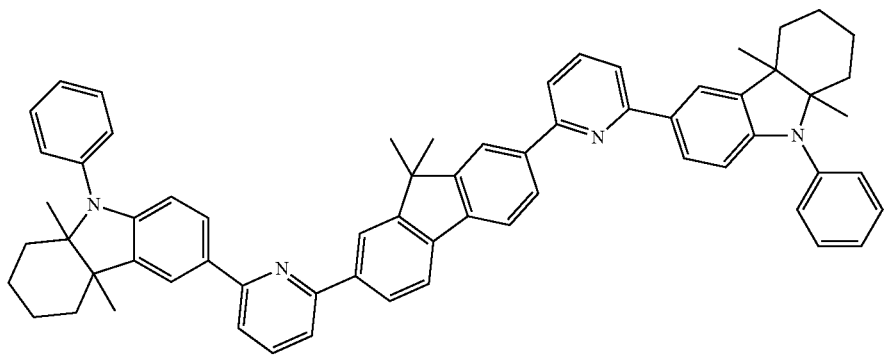
Formula 1538
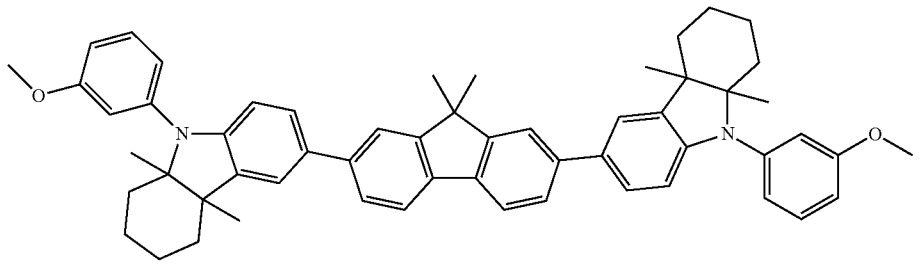
Formula 1539

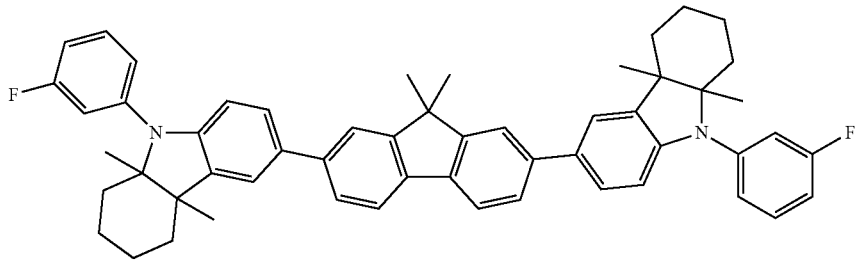
Formula 1540
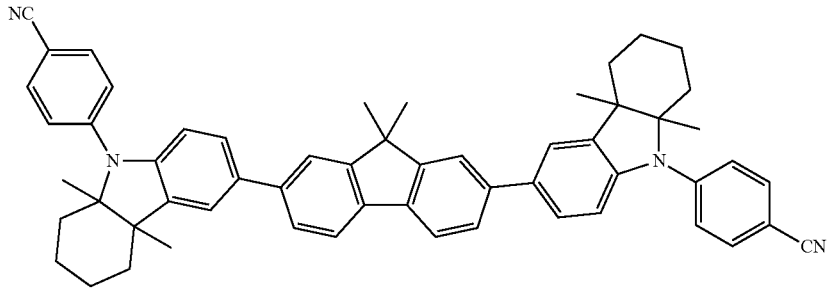
Formula 1541
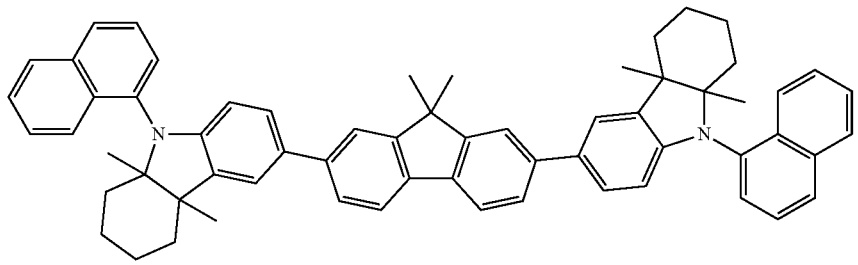
Formula 1542
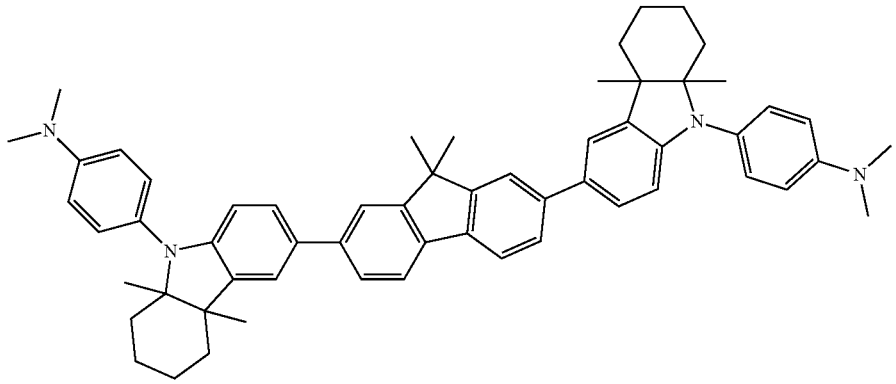
Formula 1543
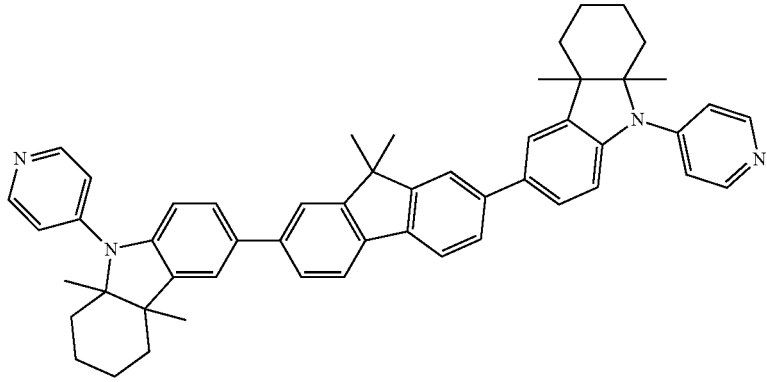
Formula 1544

-continued
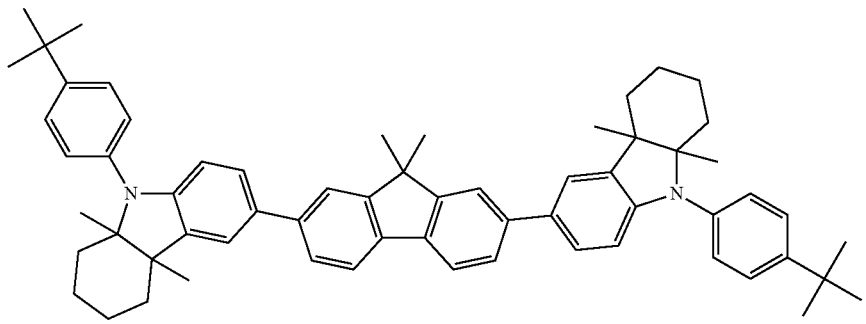
Formula 1545
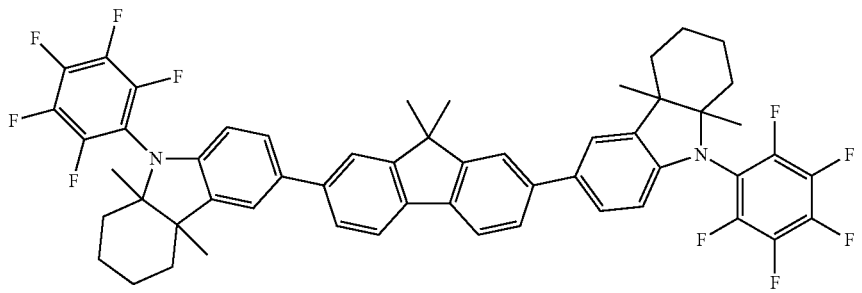
Formula 1546
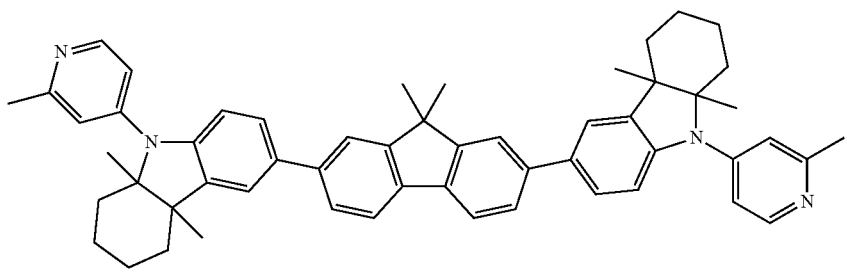
Formula 1547
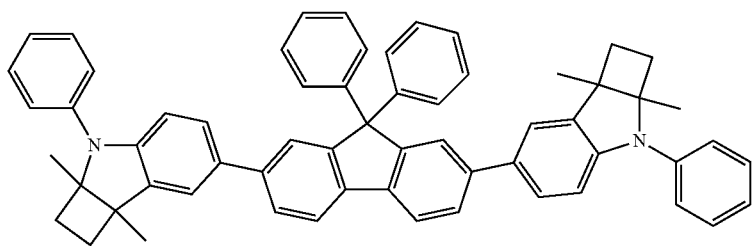
Formula 1548
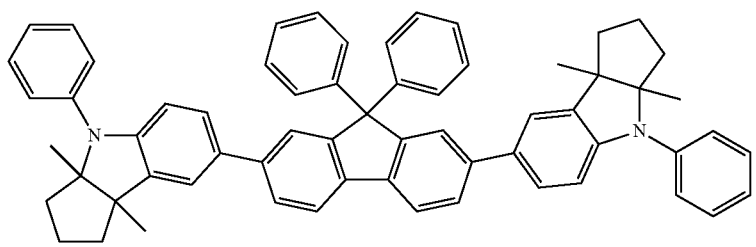
Formula 1549

Formula 1550
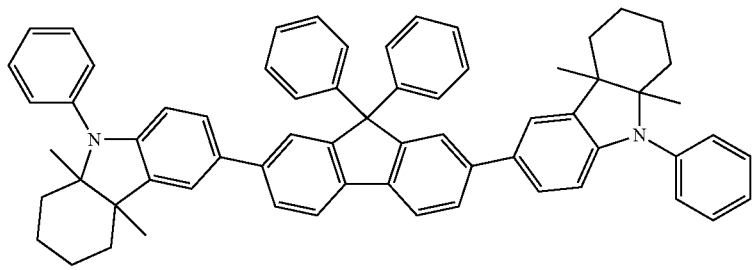
Formula 1551
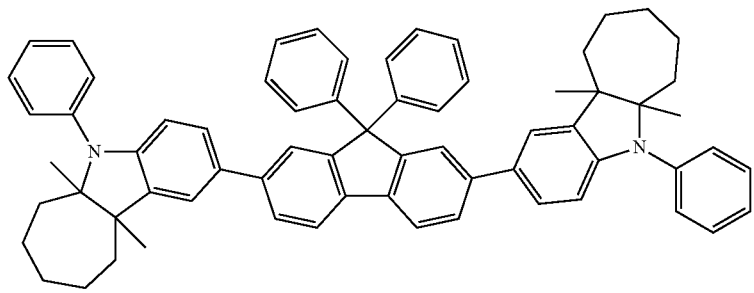
Formula 1552
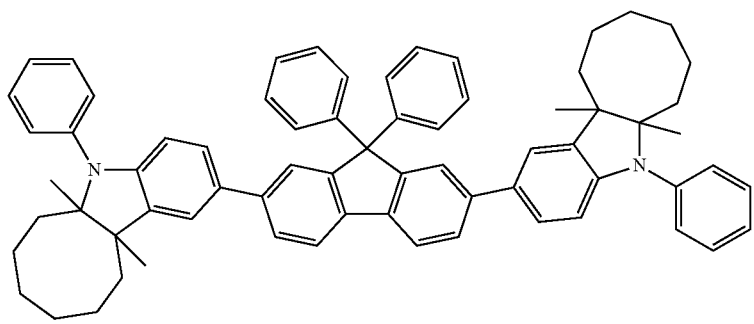
Formula 1553
Formula 1554
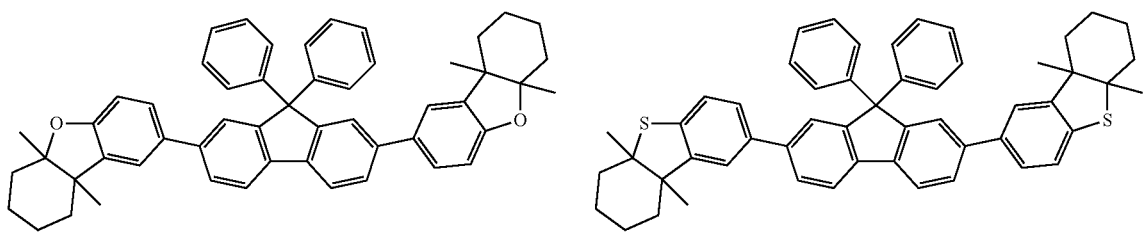
Formula 1555
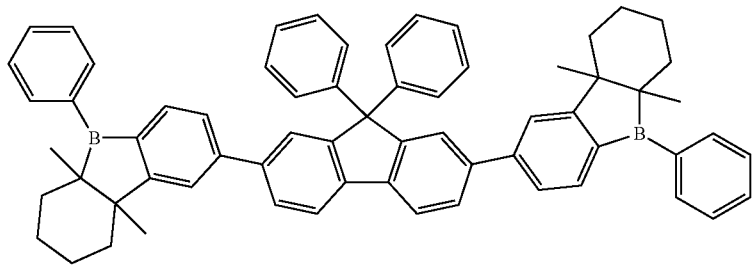

-continued
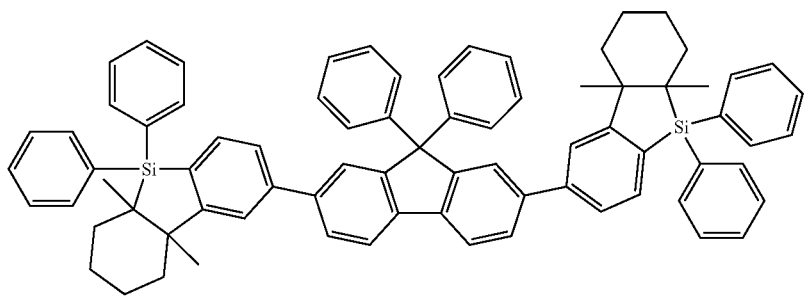
Formula 1556
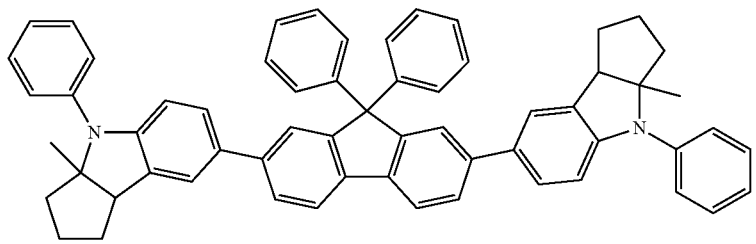
Formula 1557
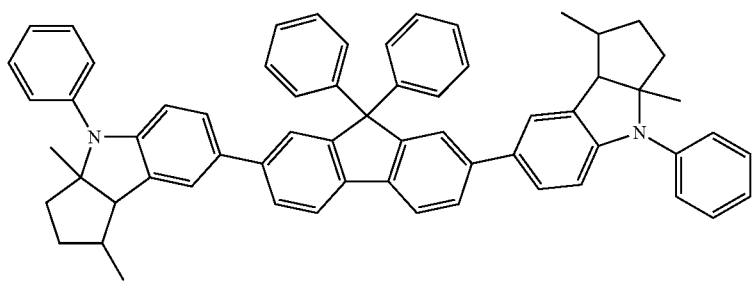
Formula 1558
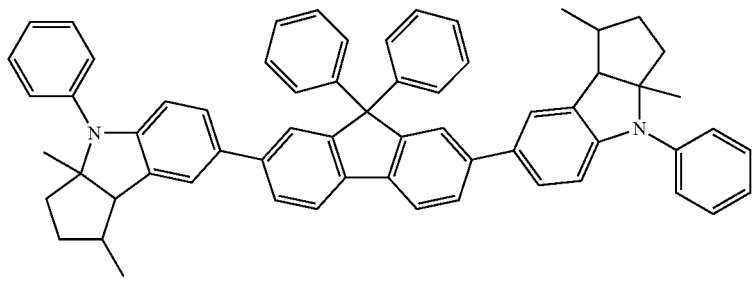
Formula 1559
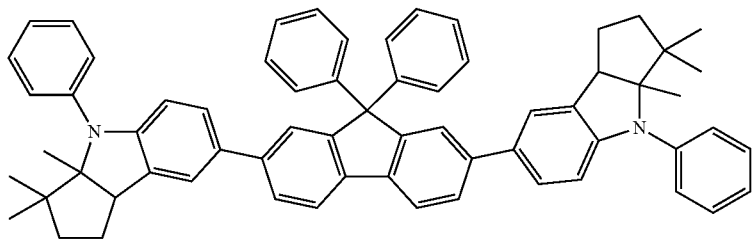
Formula 1560

-continued
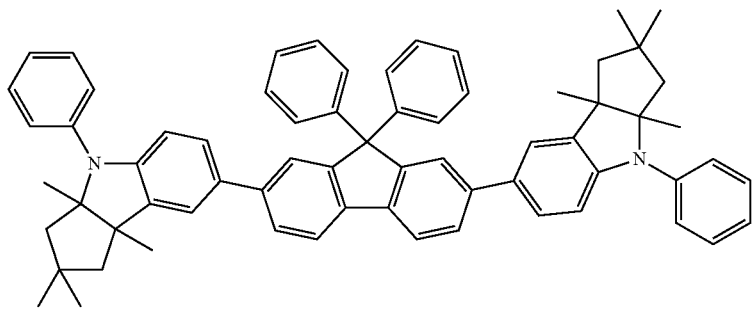
Formula 1561
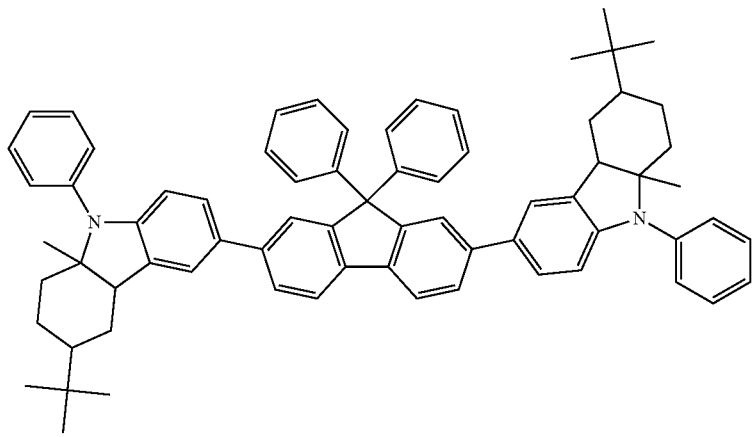
Formula 1562
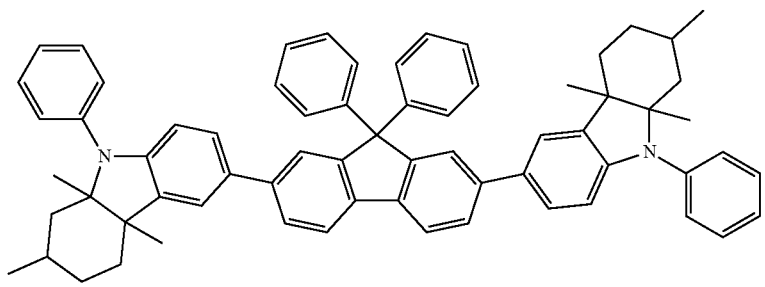
Formula 1563
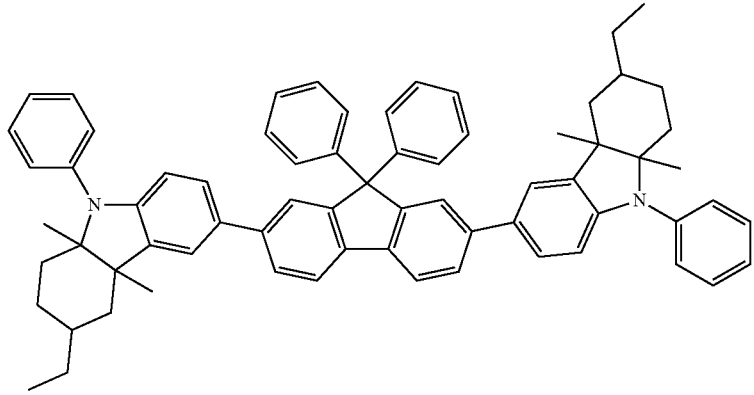
Formula 1564

-continued
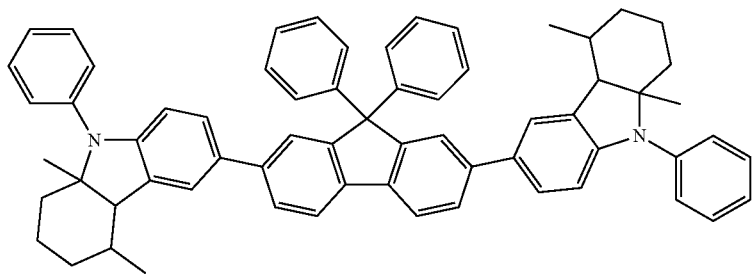
Formula 1565
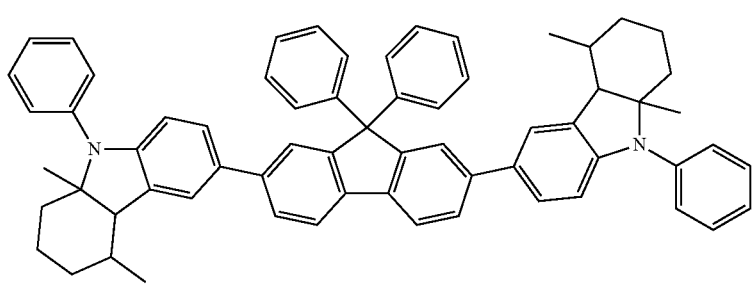
Formula 1566
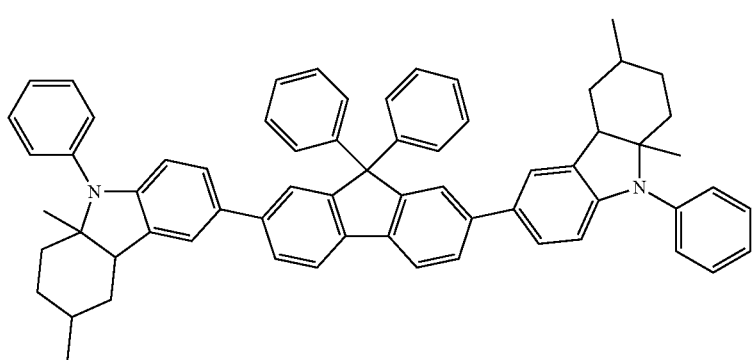
Formula 1567
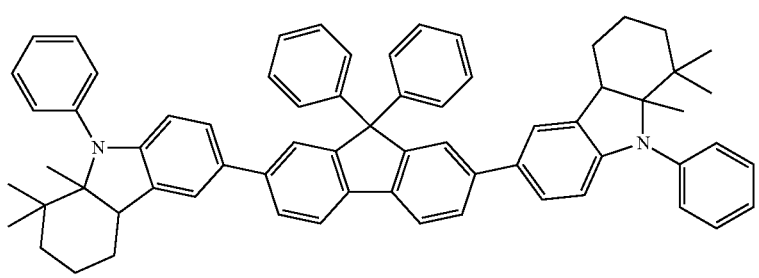
Formula 1568
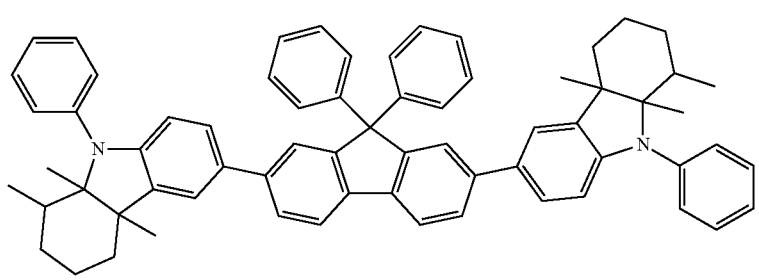
Formula 1569

-continued
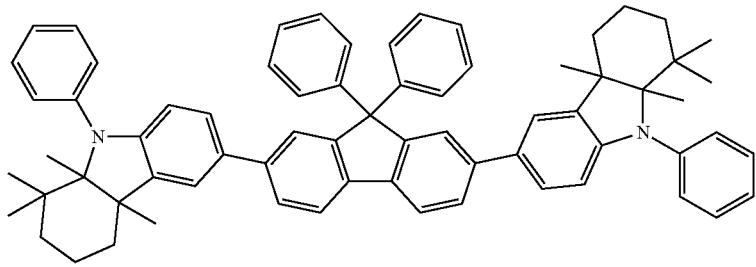
Formula 1570
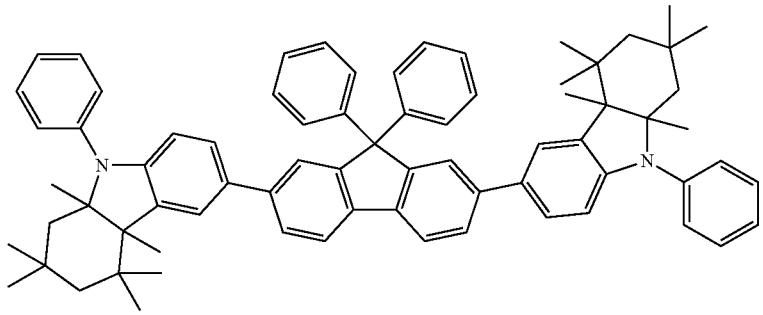
Formula 1571
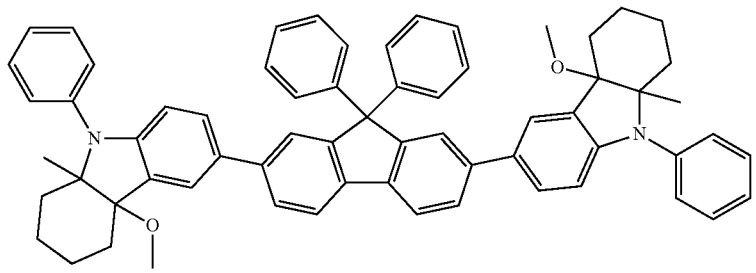
Formula 1572
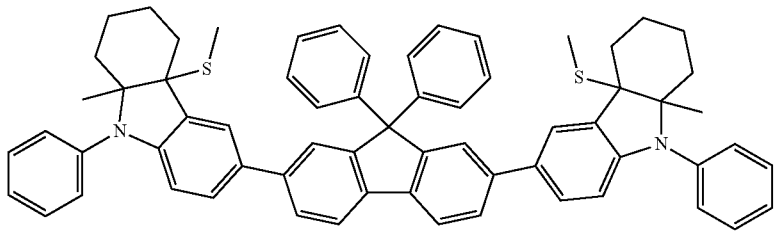
Formula 1573
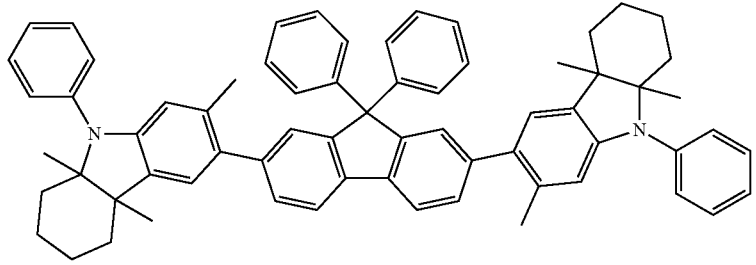
Formula 1574

-continued
Formula 1575
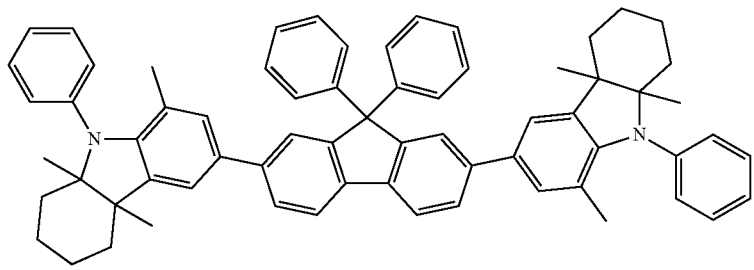
Formula 1576
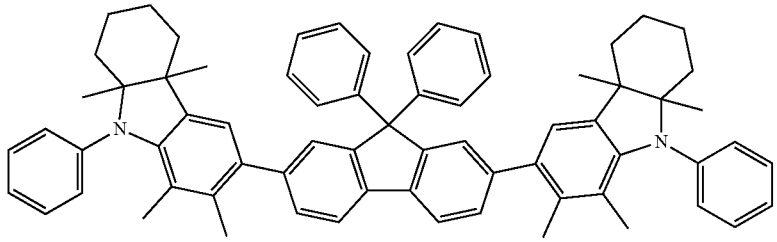
Formula 1577
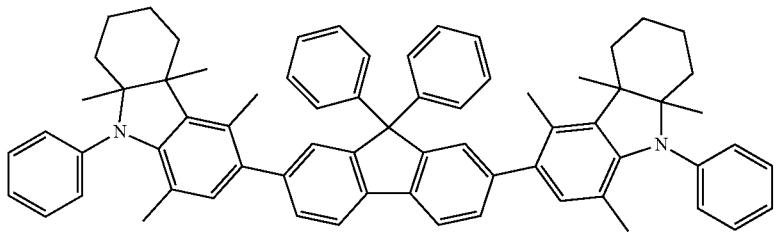
Formula 1578
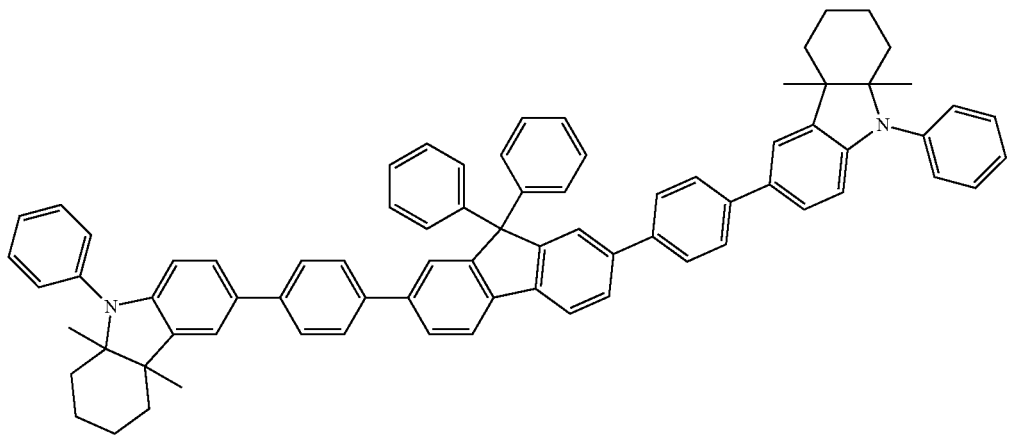
Formula 1579
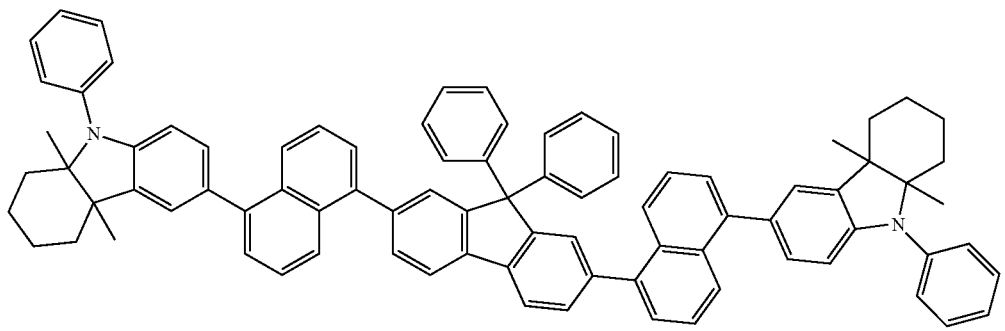

Formula 1580
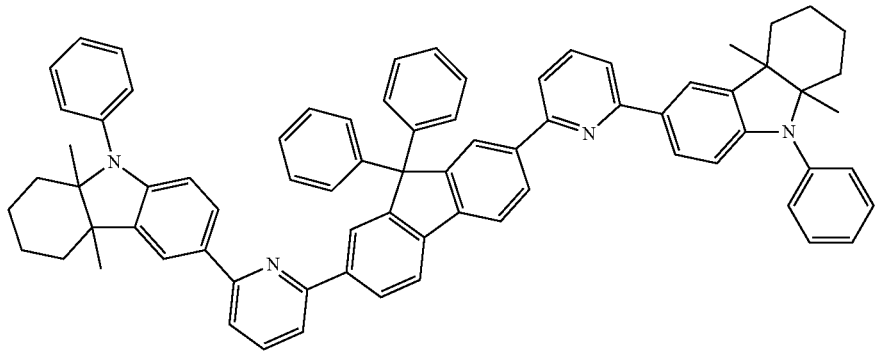
Formula 1581
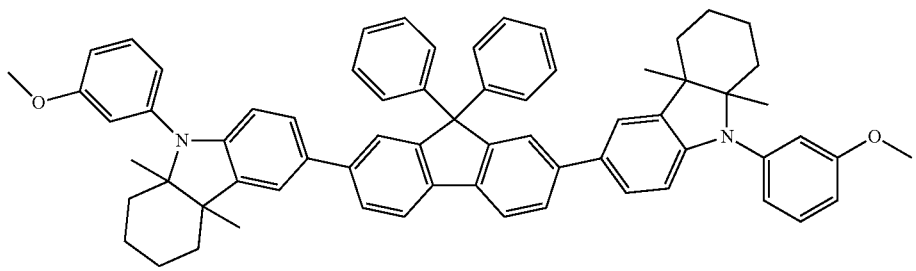
Formula 1582
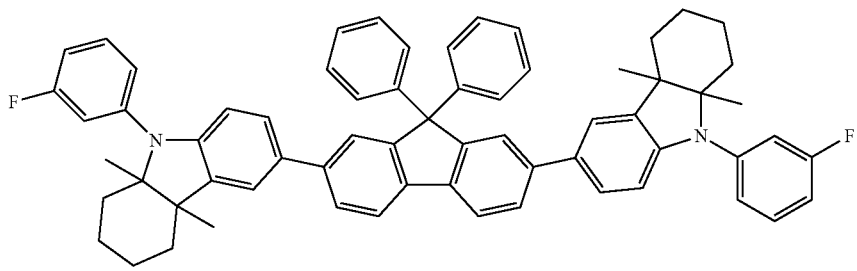
Formula 1583
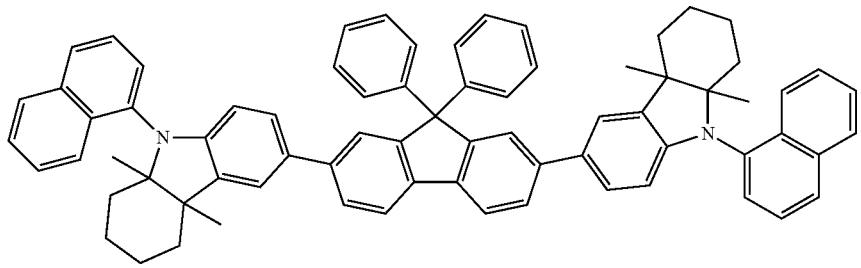
Formula 1584
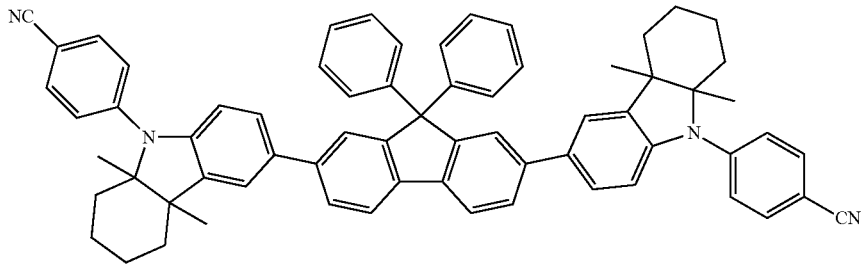

Formula 1585
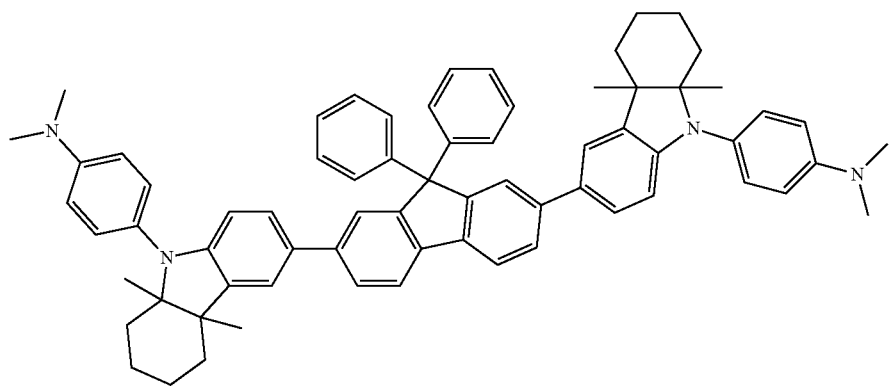
Formula 1586
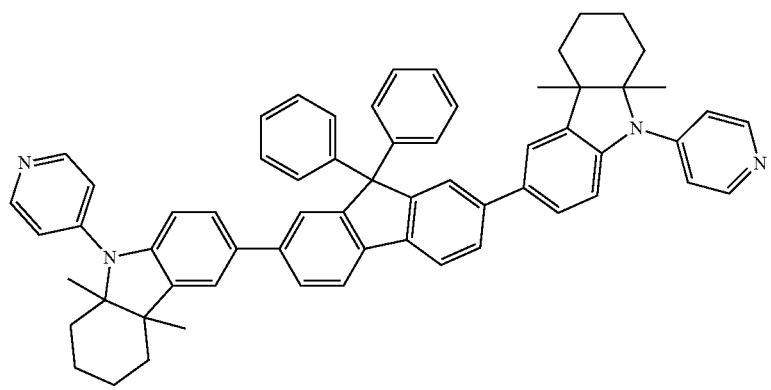
Formula 1587
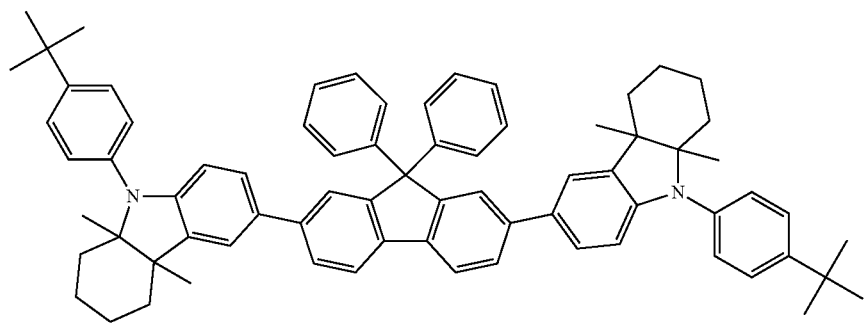
Formula 1588
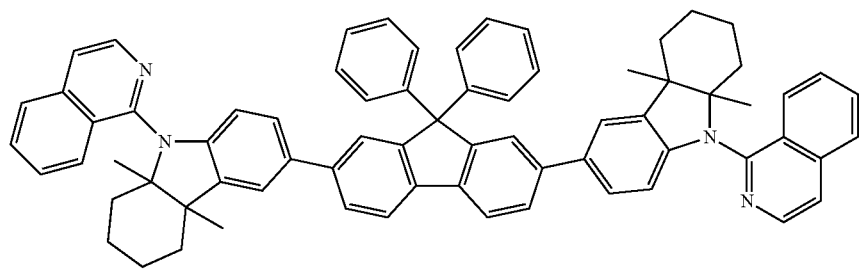

-continued
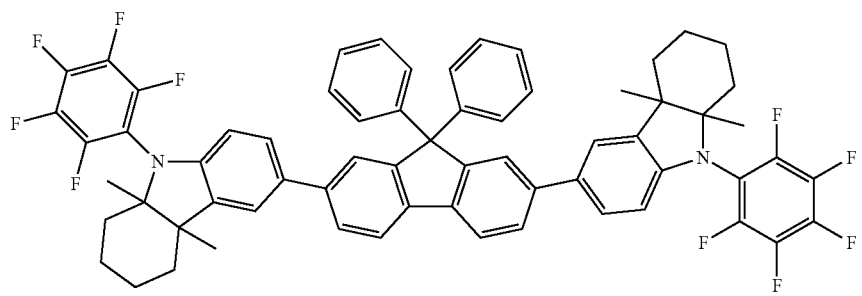
Formula 1589
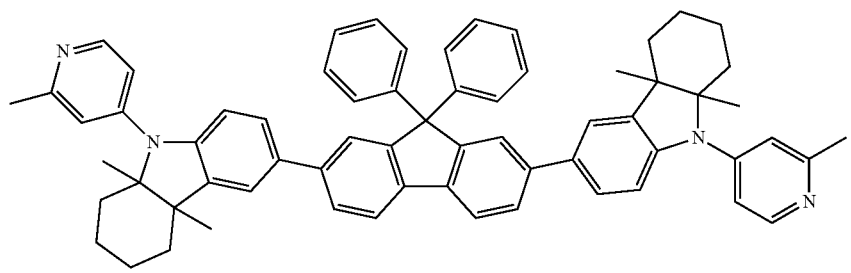
Formula 1590
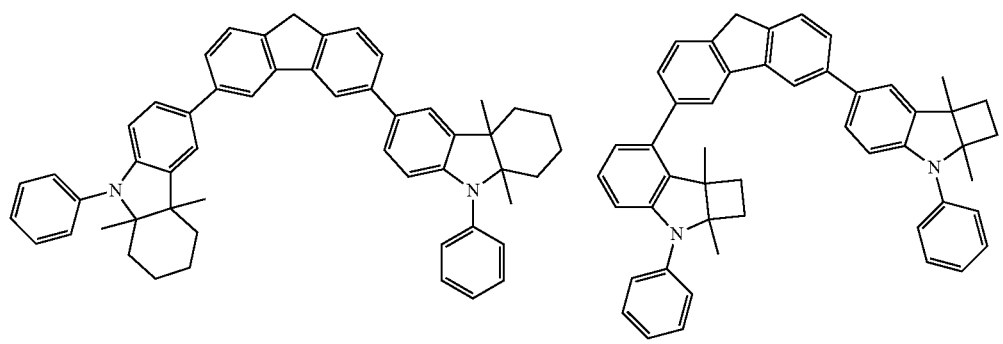
Formula 1591
Formula 1592
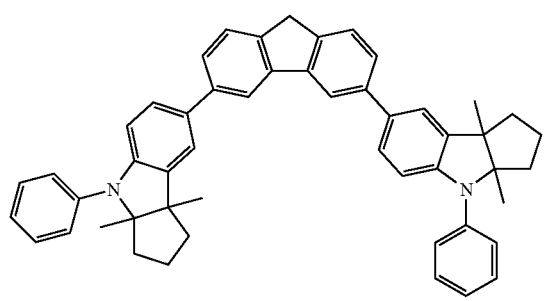
Formula 1593
Formula 1594
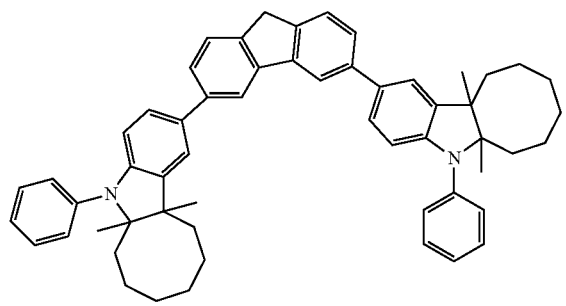
Formula 1595
Formula 1596
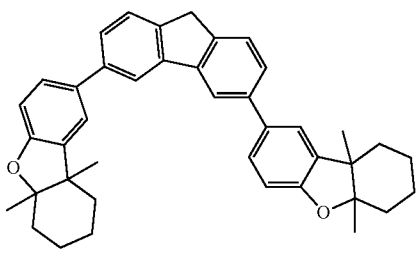

Formula 1597
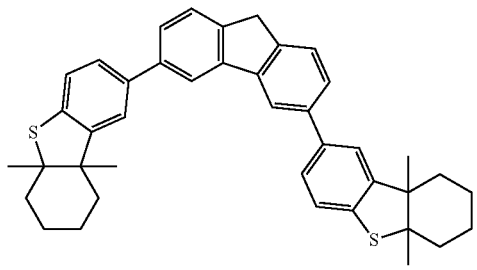
Formula 1598
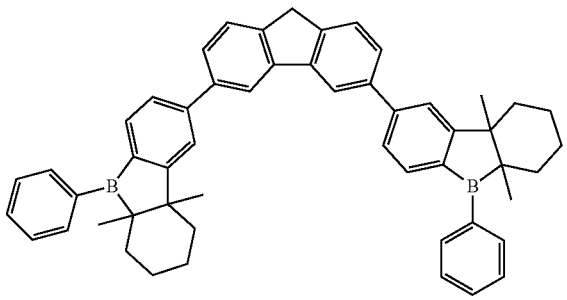
Formula 1599
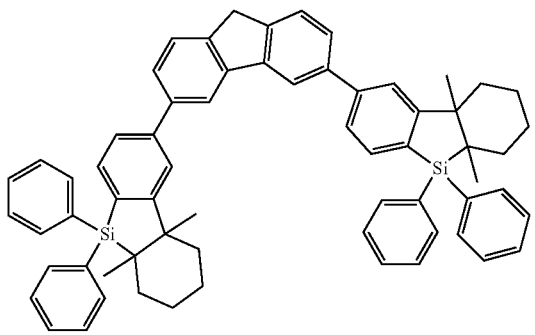
Formula 1600
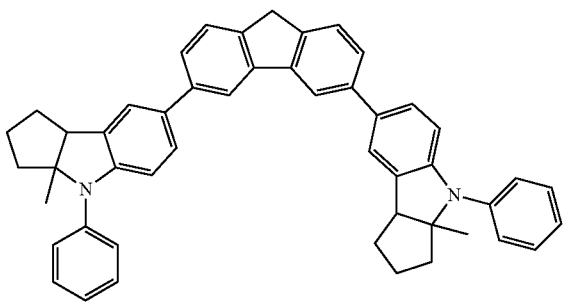
Formula 1601
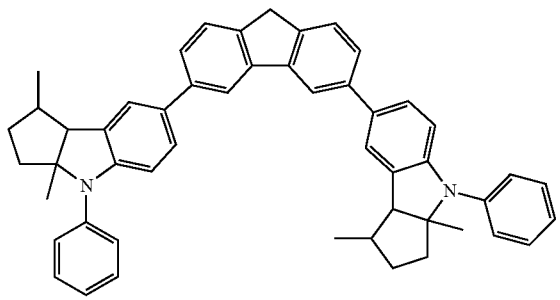
Formula 1602
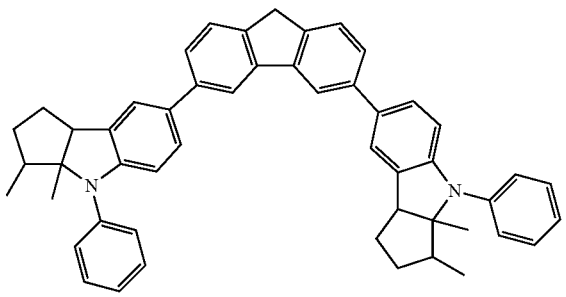
Formula 1603
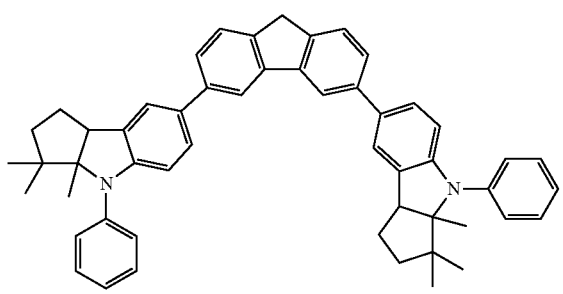
Formula 1604
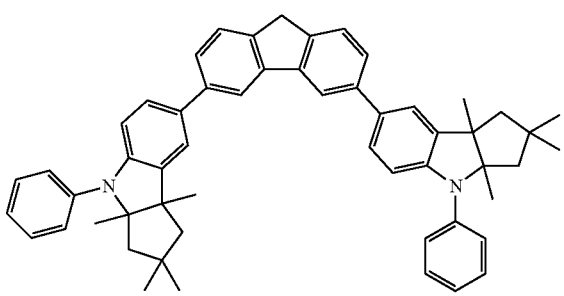
Formula 1605
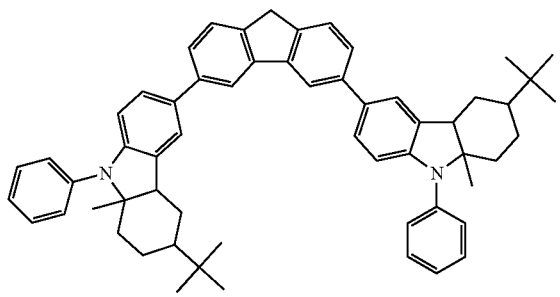
Formula 1606
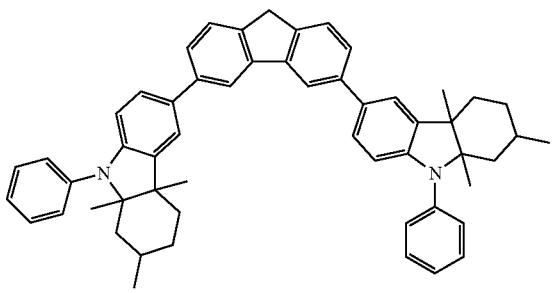

-continued
Formula 1607
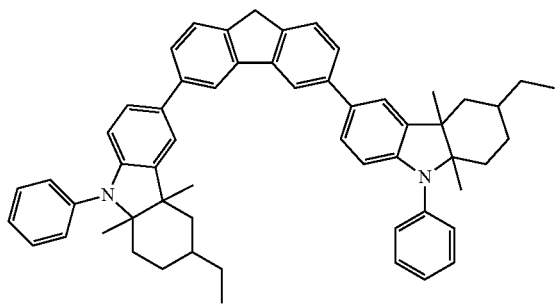
Formula 1608
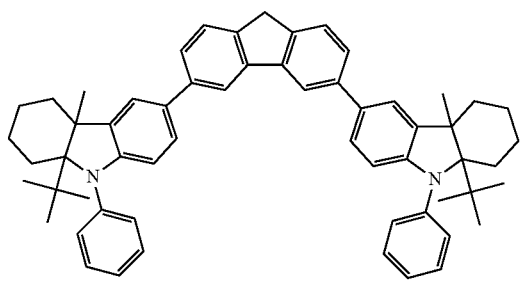
Formula 1609
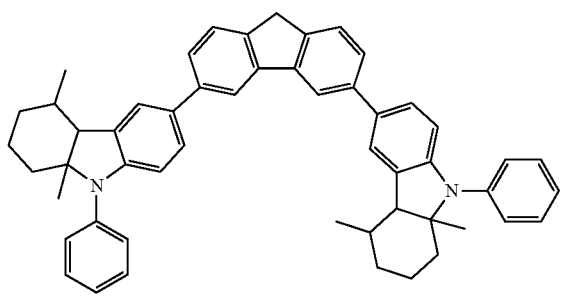
Formula 1610
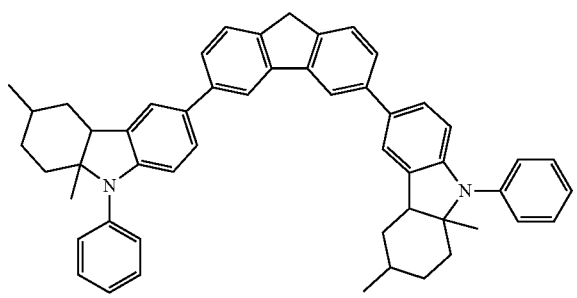
Formula 1611
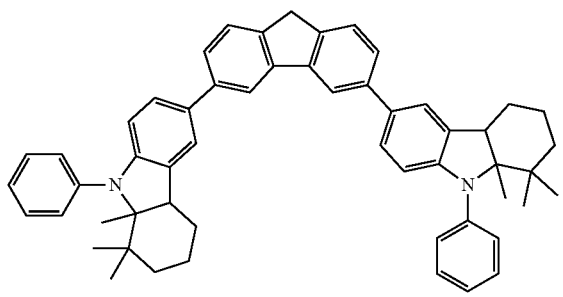
Formula 1612
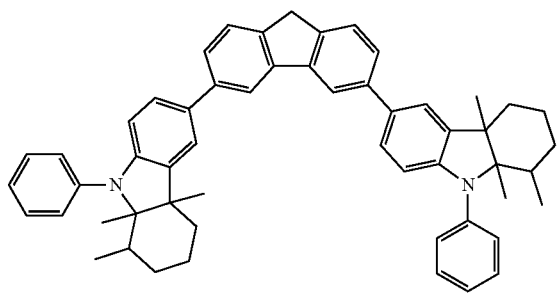
Formula 1613
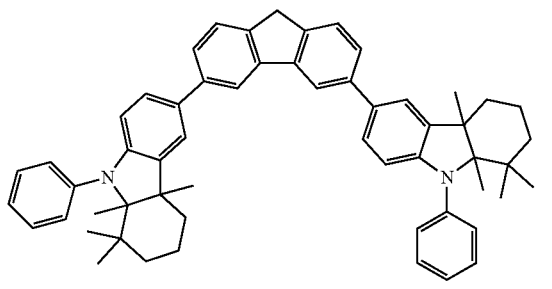
Formula 1614
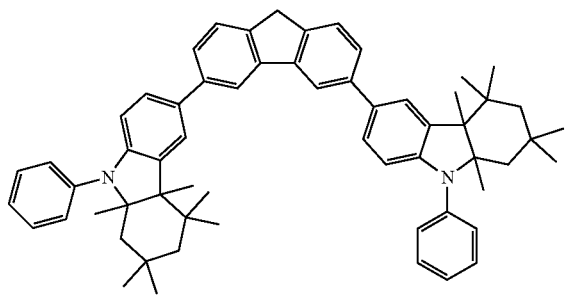
Formula 1615
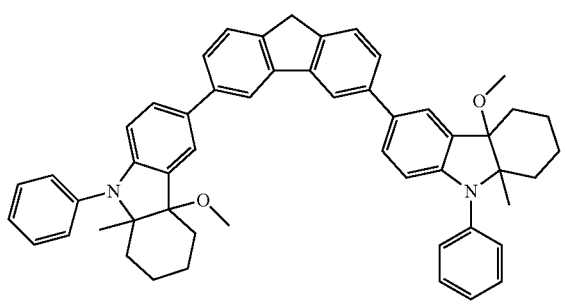
Formula 1616
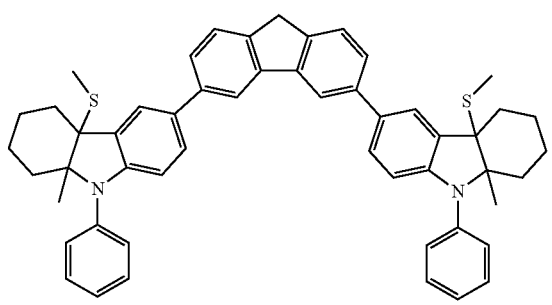

-continued
Formula 1617
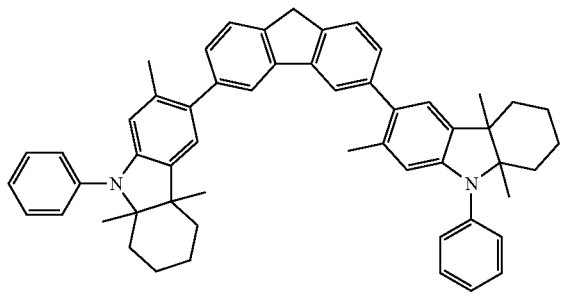
Formula 1618
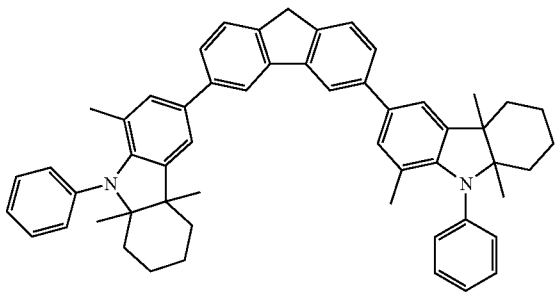
Formula 1619
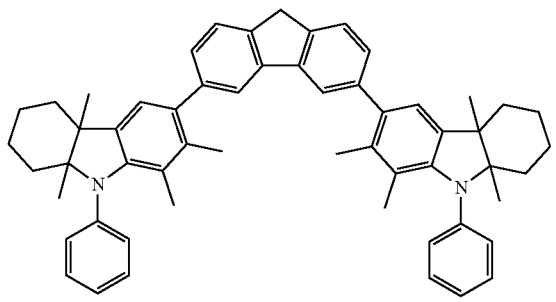
Formula 1620
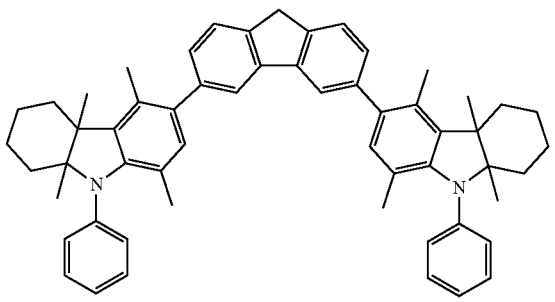
Formula 1621
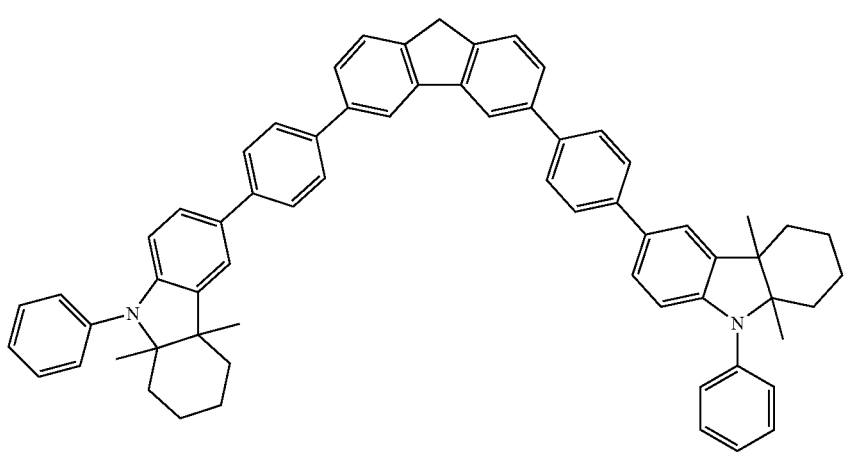
Formula 1622
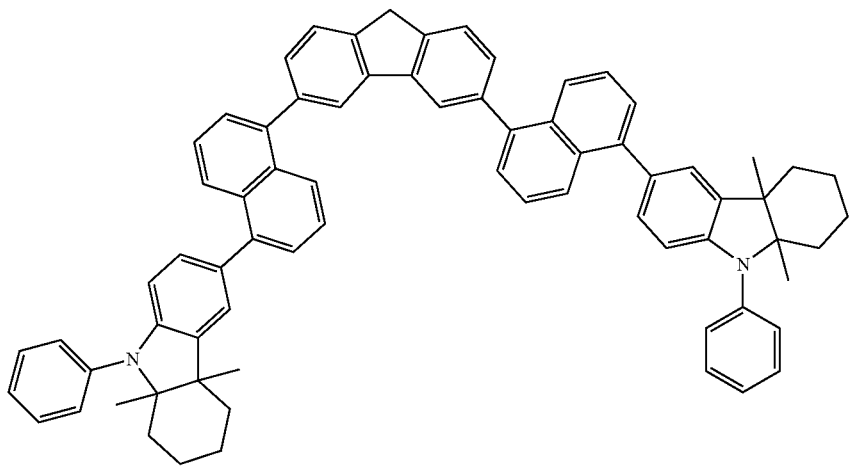

-continued
Formula 1623
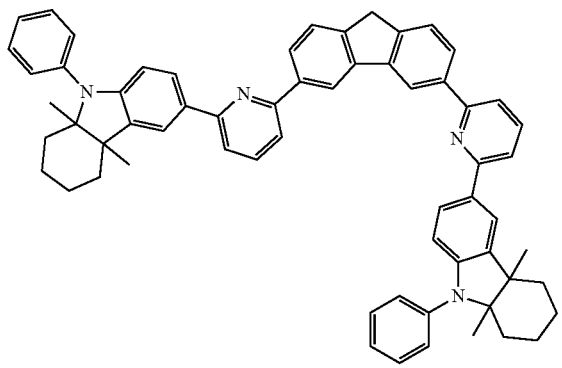
Formula 1624
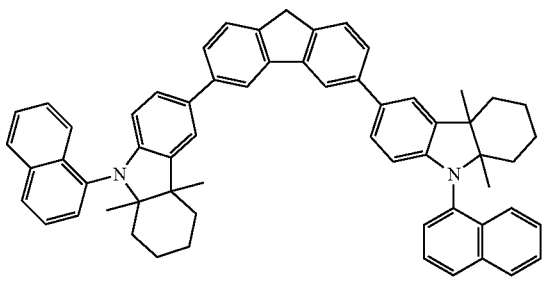
Formula 1625 Formula 1626
Formula 1627 Formula 1628
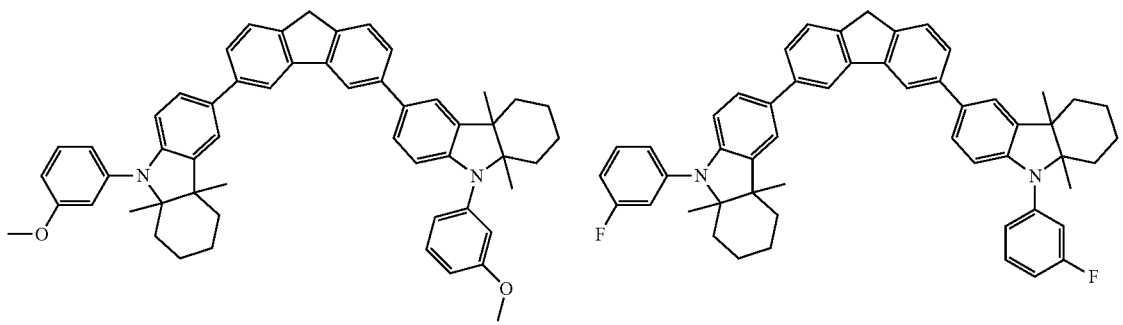
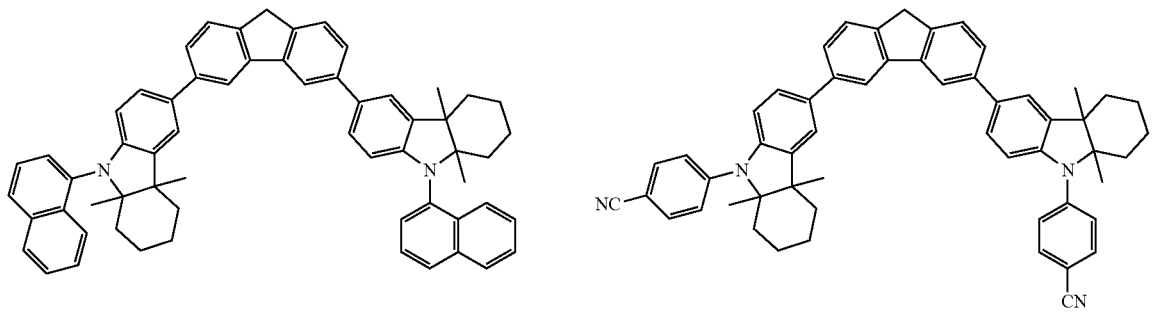
Formula 1629 Formula 1630
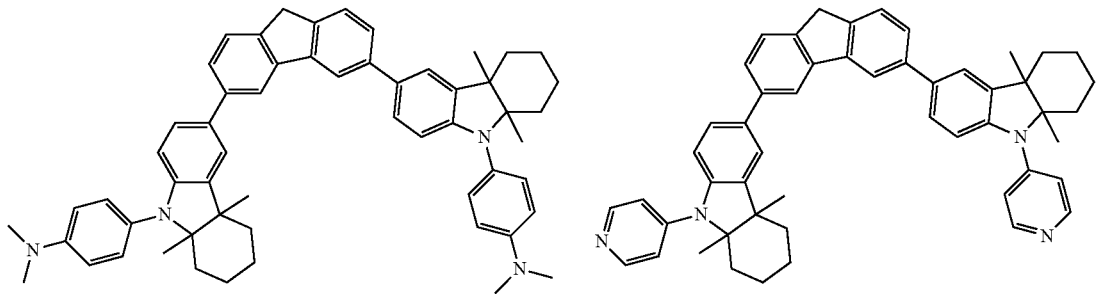

Formula 1631
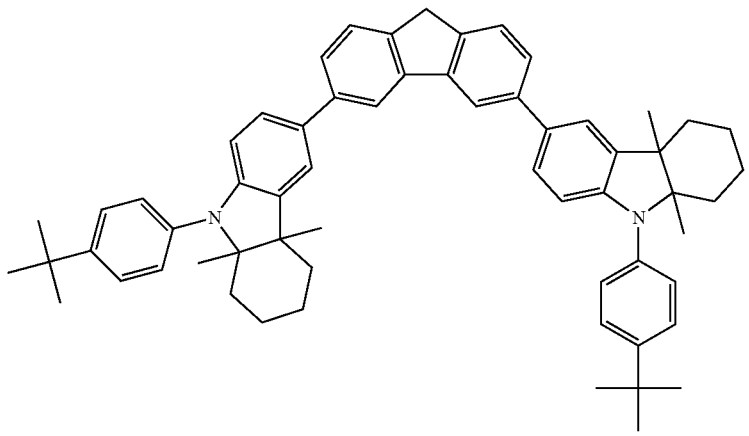
Formula 1632                    Formula 1633
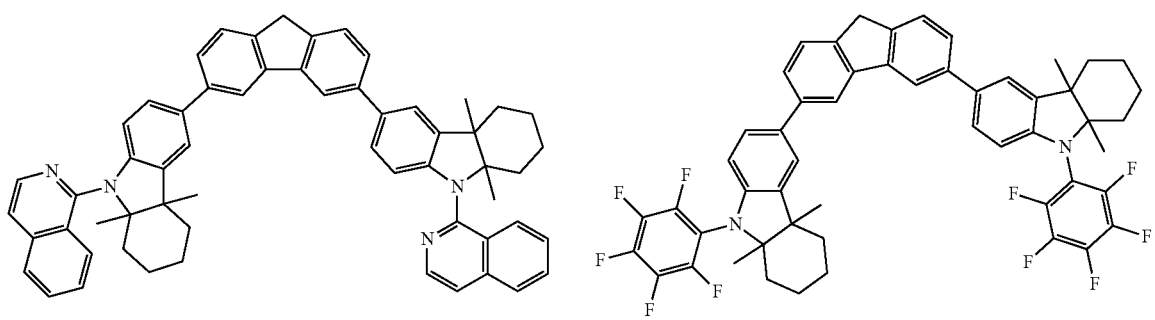
Formula 1634                    Formula 1635
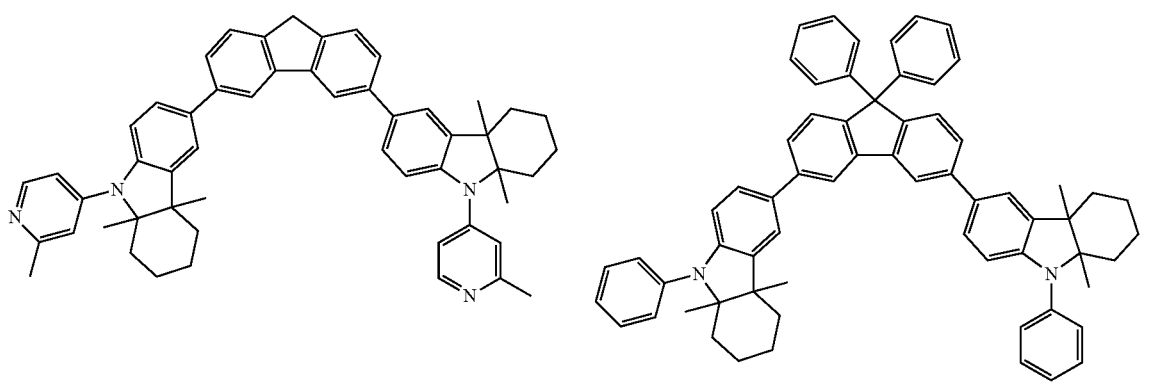
Formula 1636                    Formula 1637
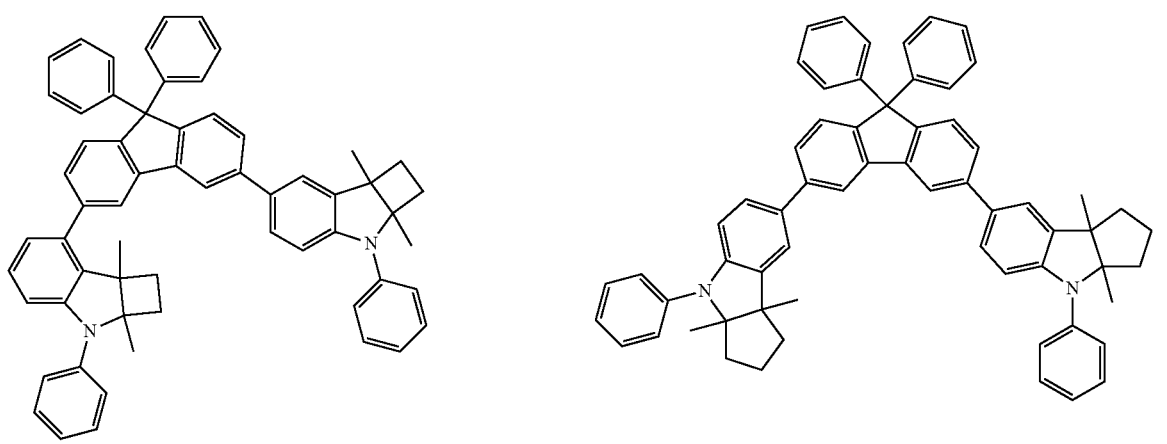

-continued
Formula 1638
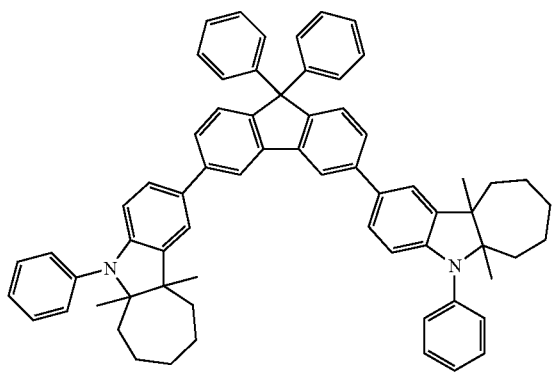
Formula 1639
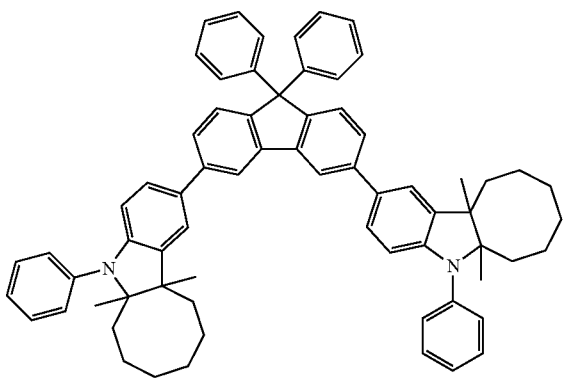
Formula 1640
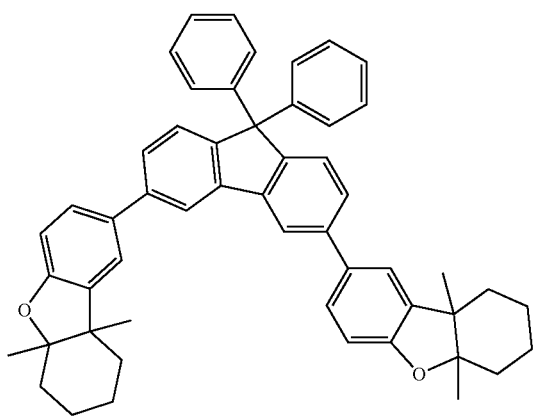
Formula 1641
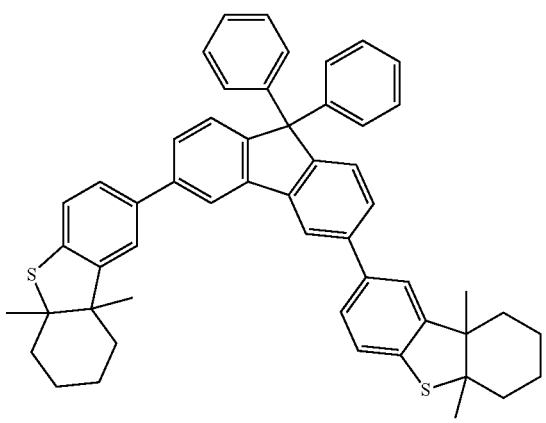
Formula 1642
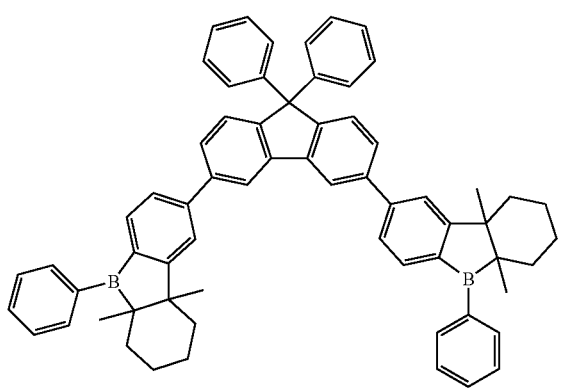
Formula 1643
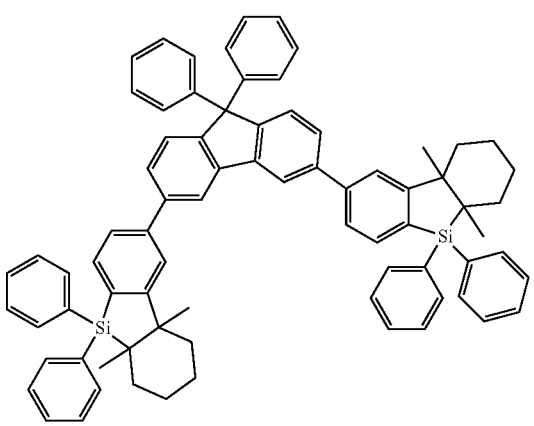

-continued
Formula 1644
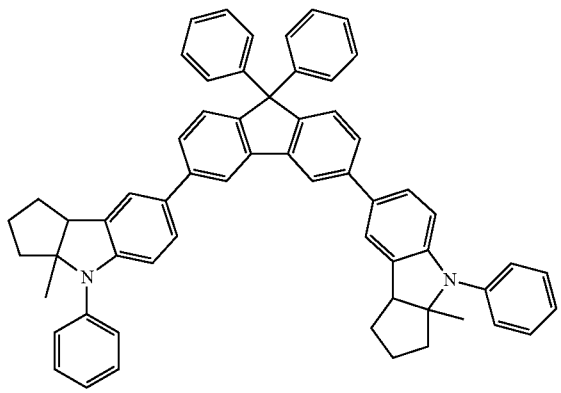
Formula 1645
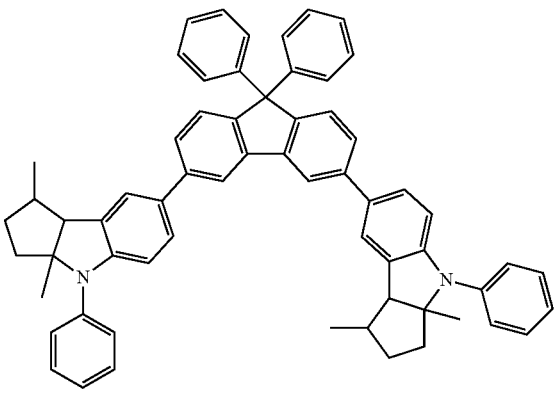
Formula 1646
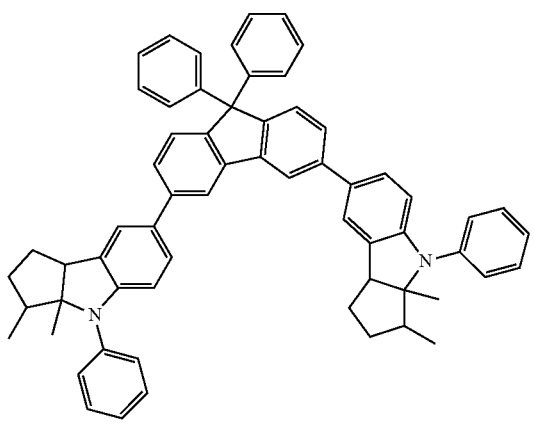
Formula 1647
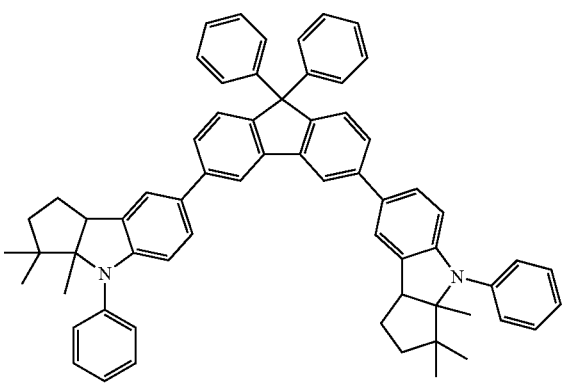
Formula 1648
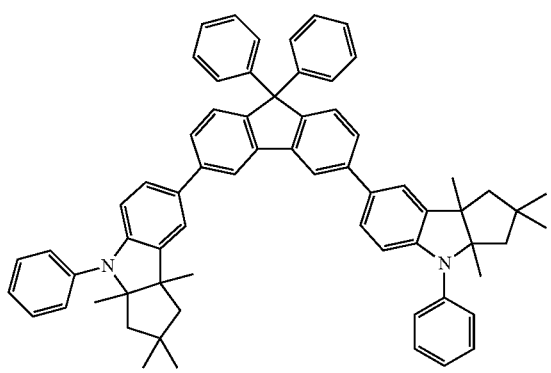
Formula 1649
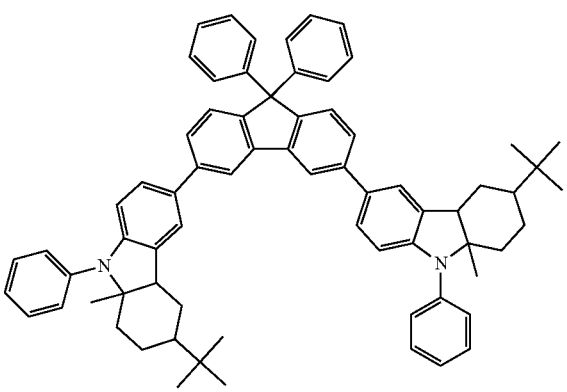
Formula 1650
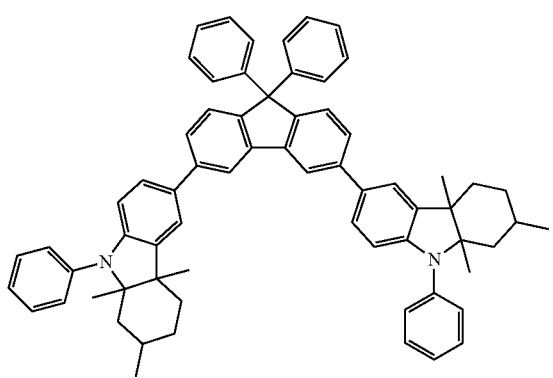
Formula 1651
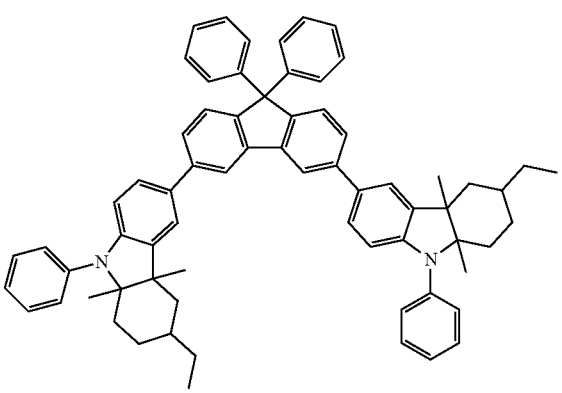

-continued
Formula 1652
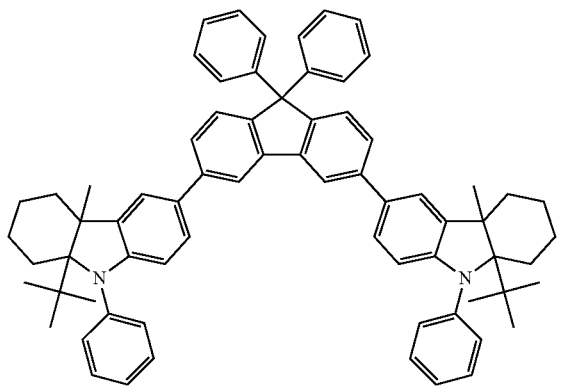
Formula 1653
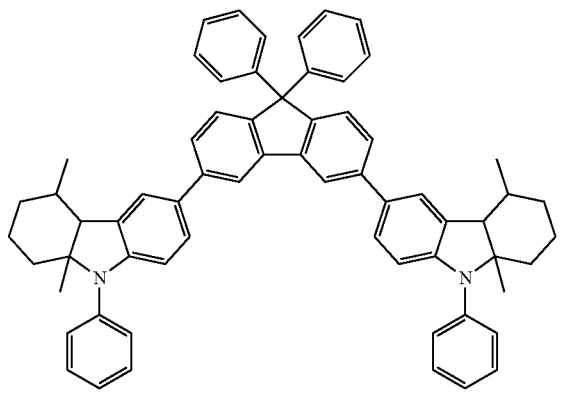
Formula 1654
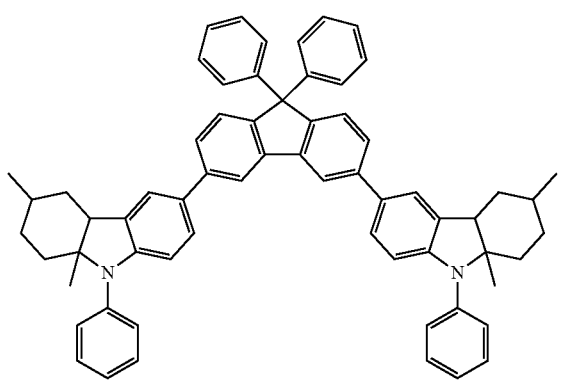
Formula 1655
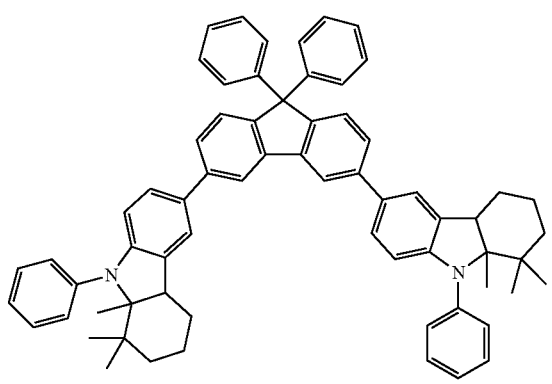
Formula 1656
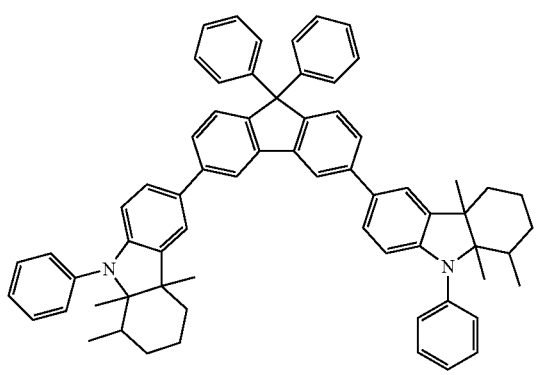
Formula 1657
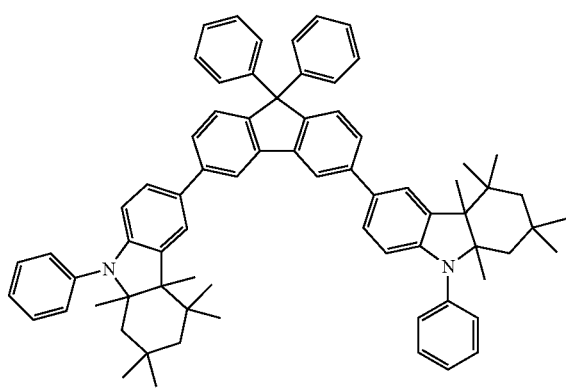
Formula 1658
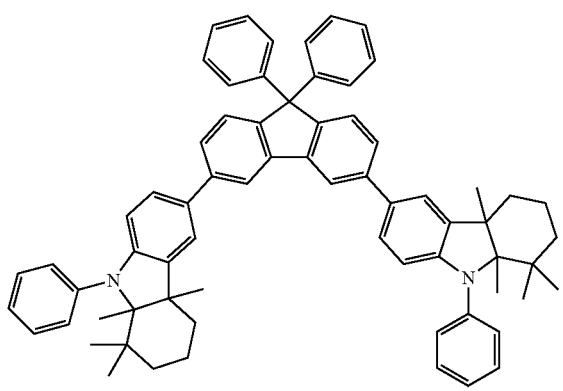
Formula 1659
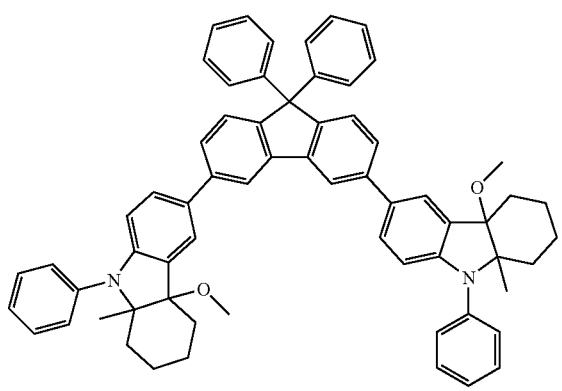

Formula 1660
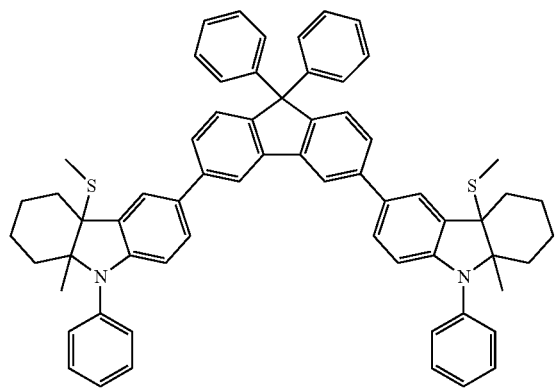
Formula 1661
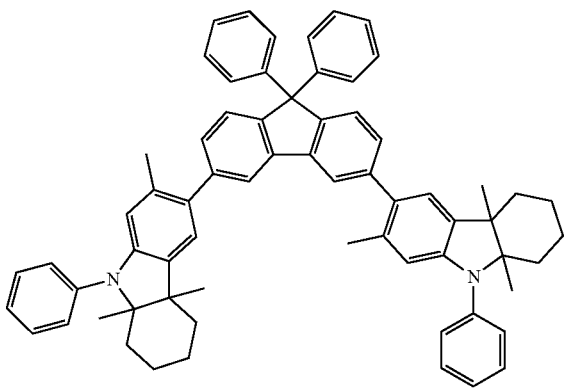
Formula 1662
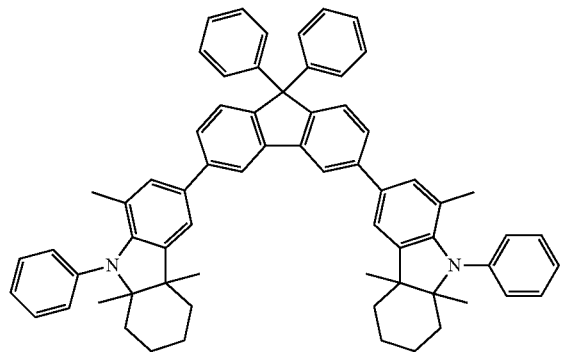
Formula 1663
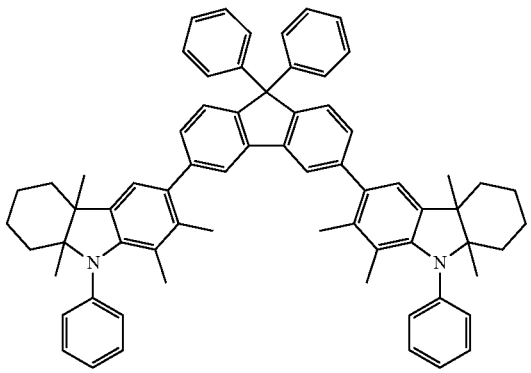
Formula 1664
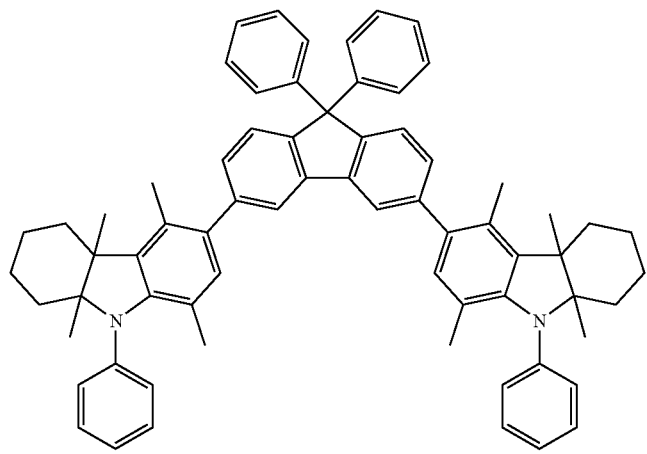

Formula 1665
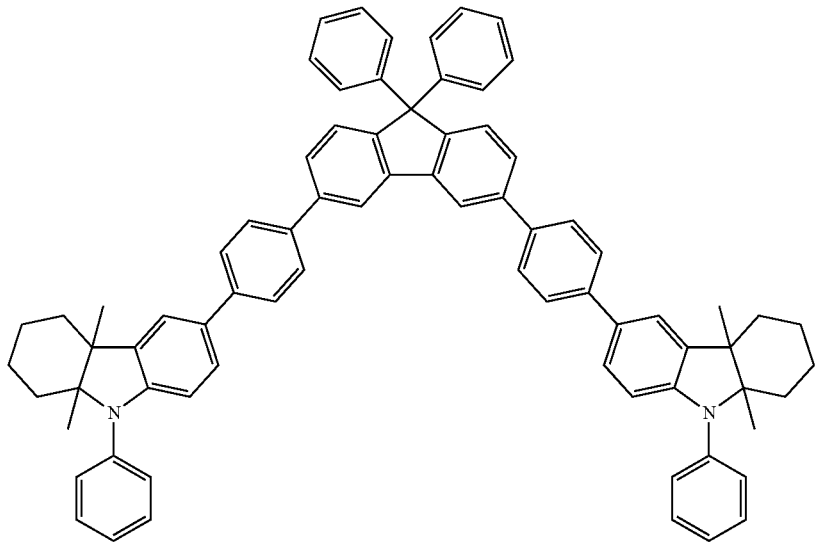
Formula 1666
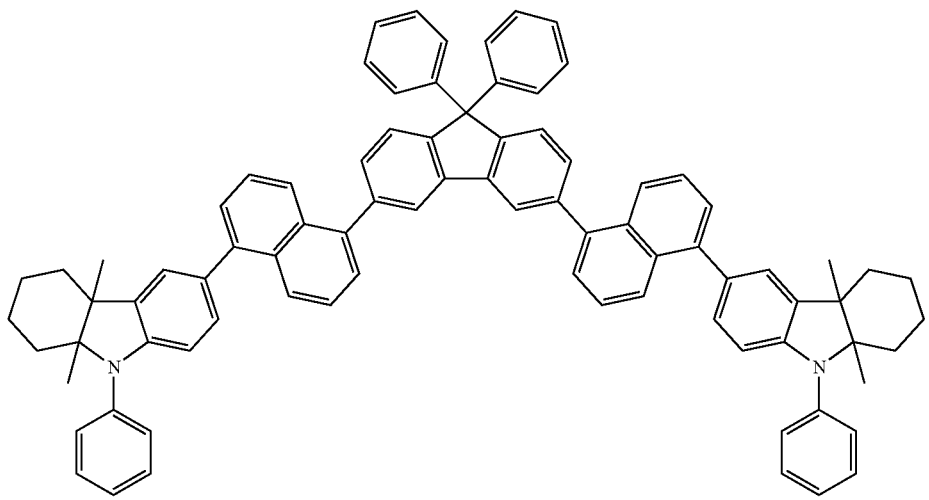
Formula 1667
Formula 1668
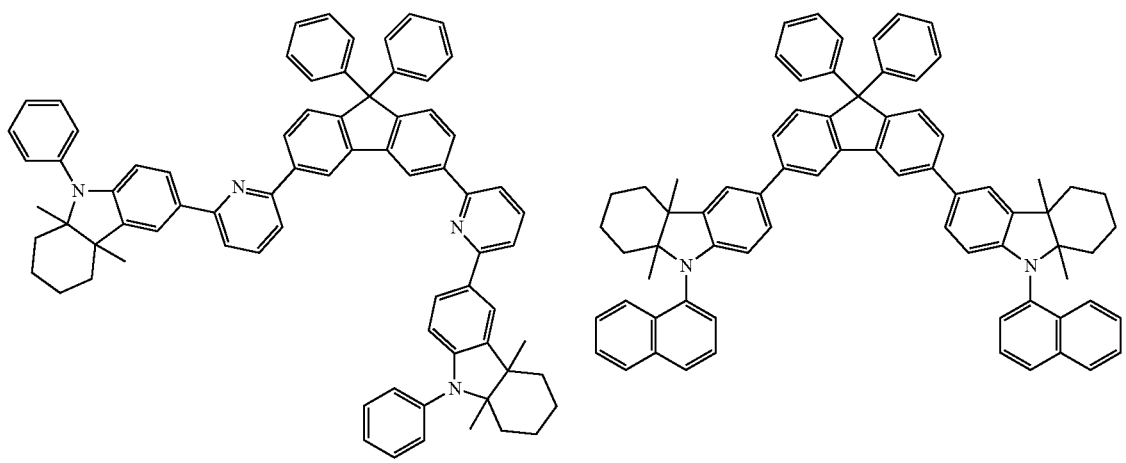

-continued
Formula 1669
Formula 1670
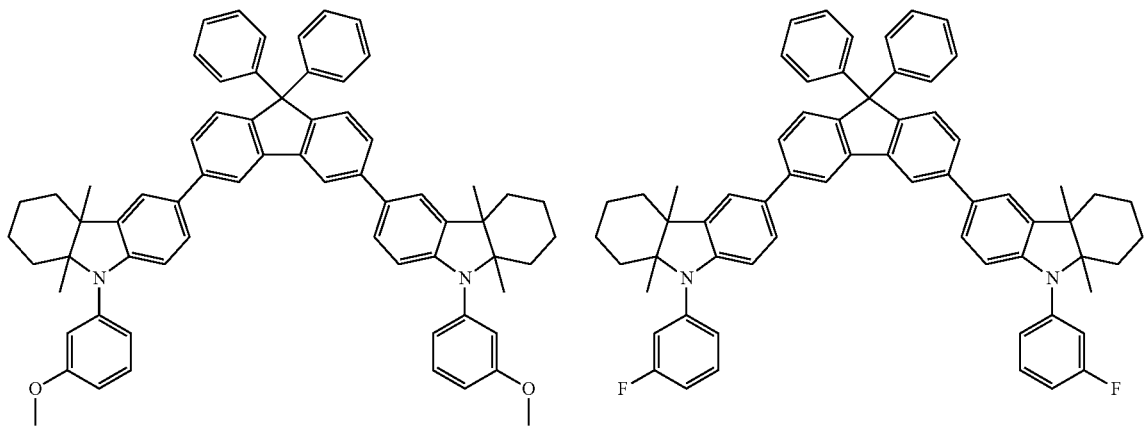
Formula 1671
Formula 1672
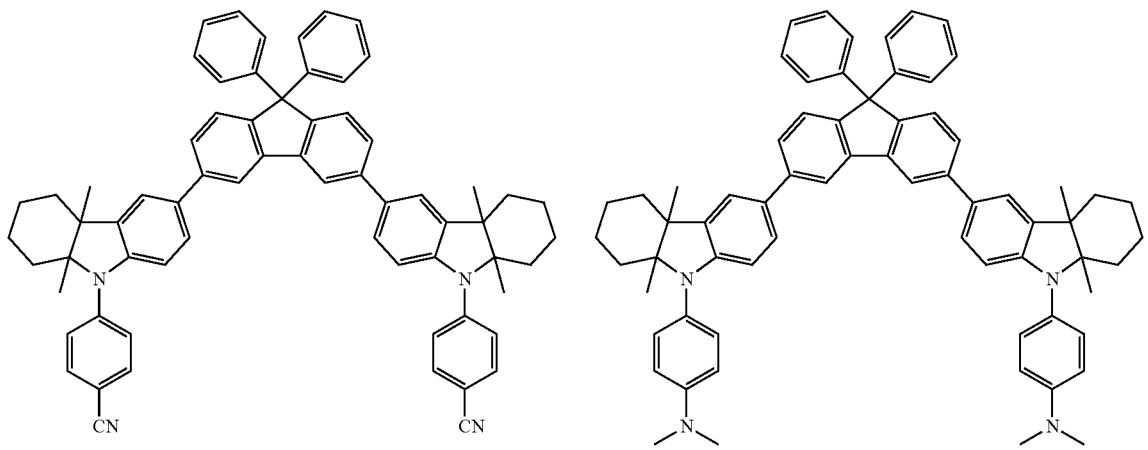
Formula 1673
Formula 1674
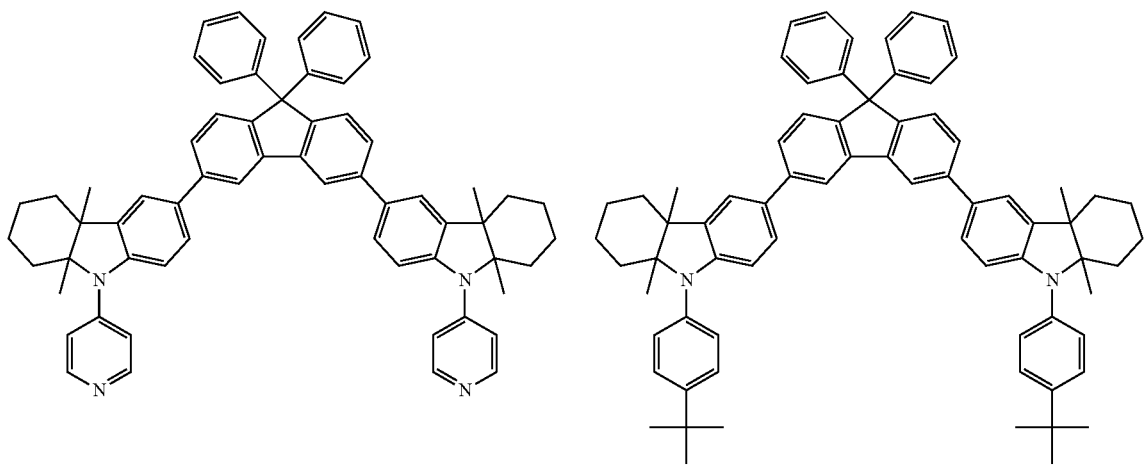

-continued
Formula 1675
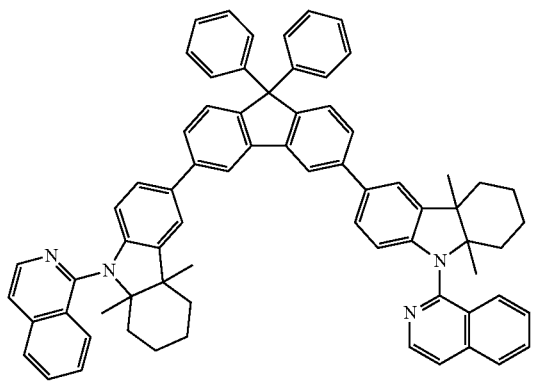
Formula 1676
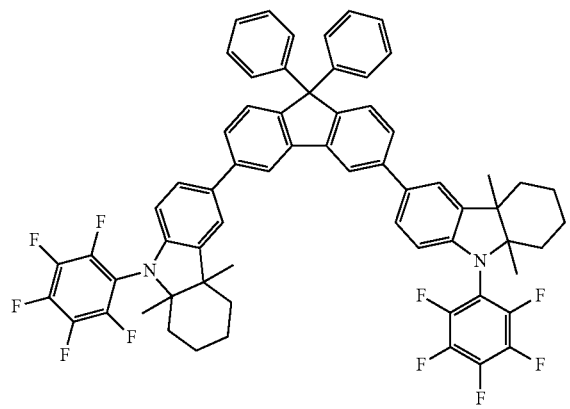
Formula 1677
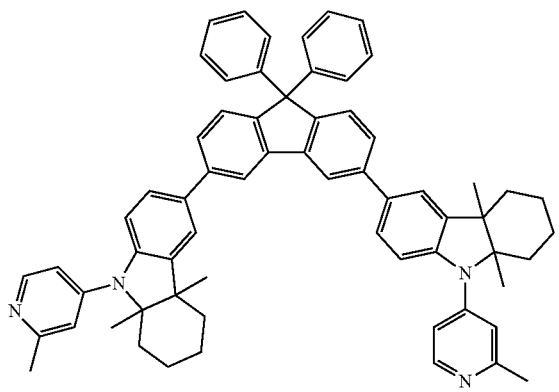
Formula 1678
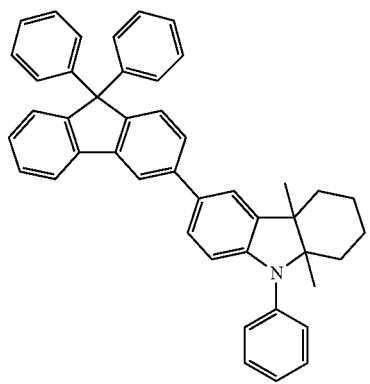
Formula 1679
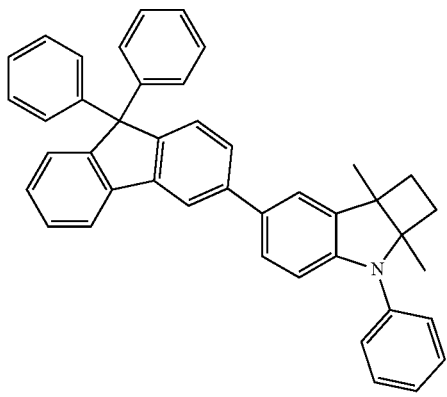
Formula 1680
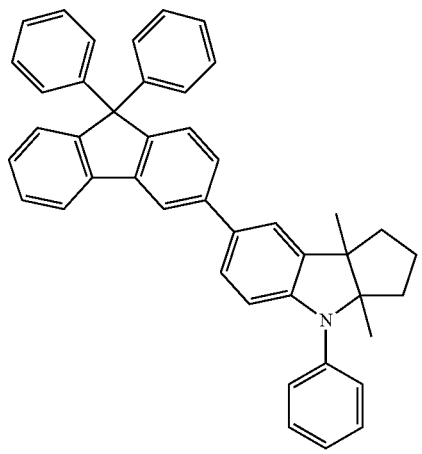

-continued
Formula 1681
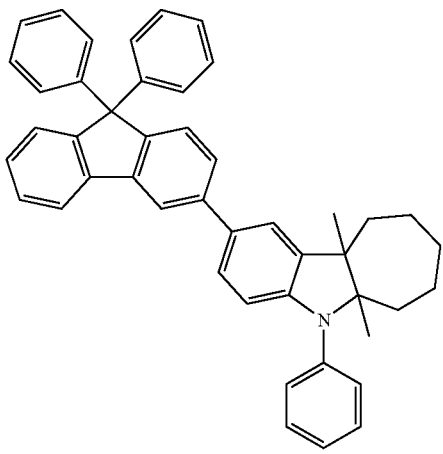
Formula 1682
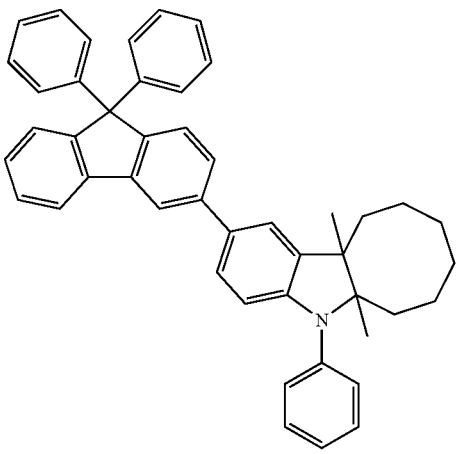
Formula 1683
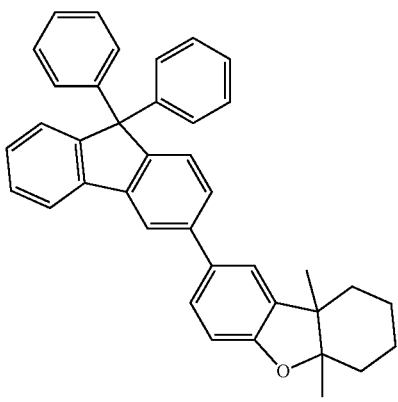
Formula 1684
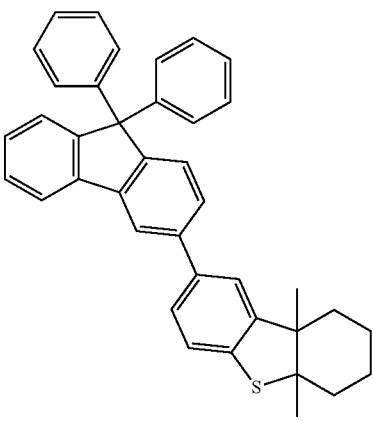
Formula 1685
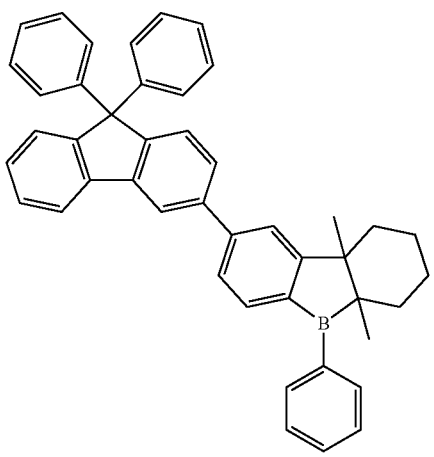
Formula 1686
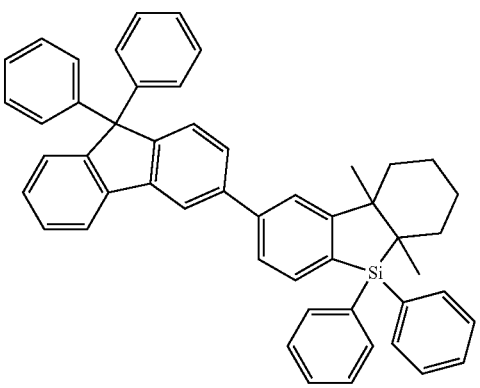

-continued
Formula 1687
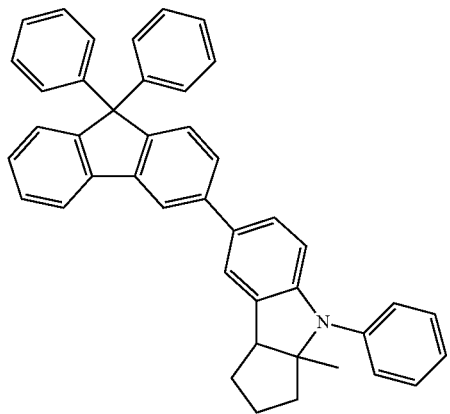
Formula 1688
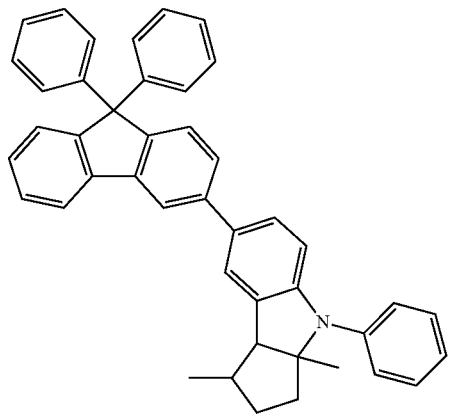
Formula 1689
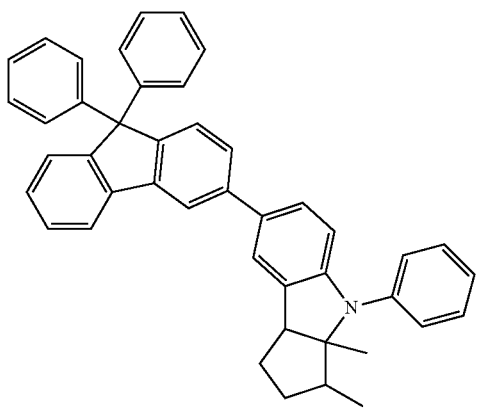
Formula 1690
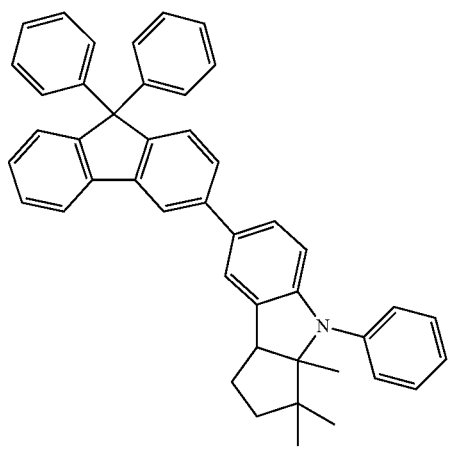
Formula 1691
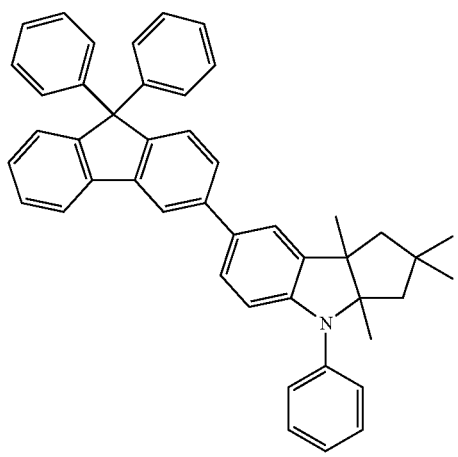
Formula 1692
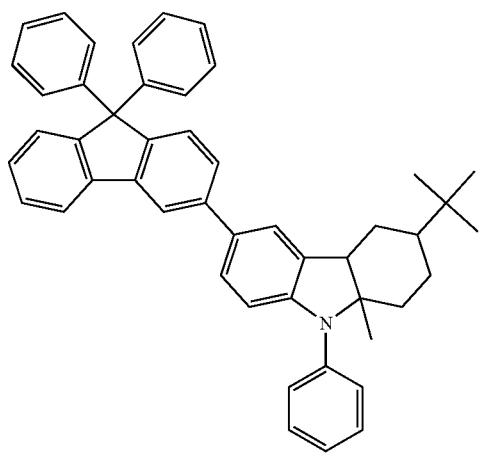

-continued
Formula 1693
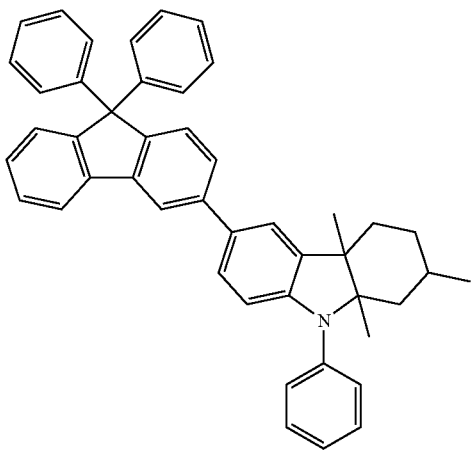
Formula 1694
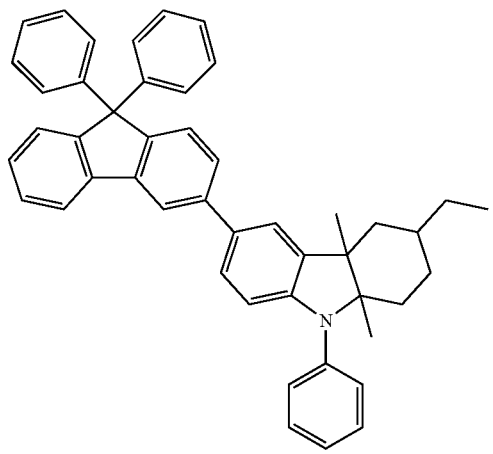
Formula 1695
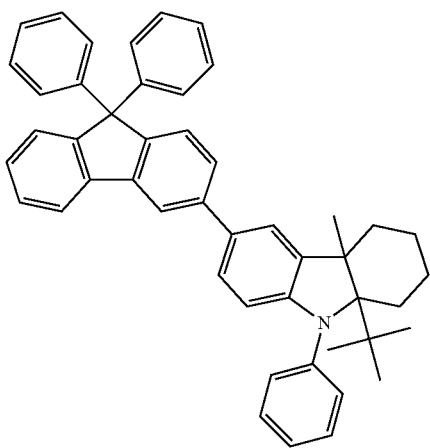
Formula 1696
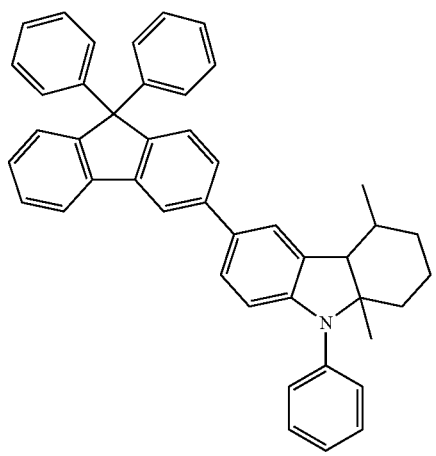
Formula 1697
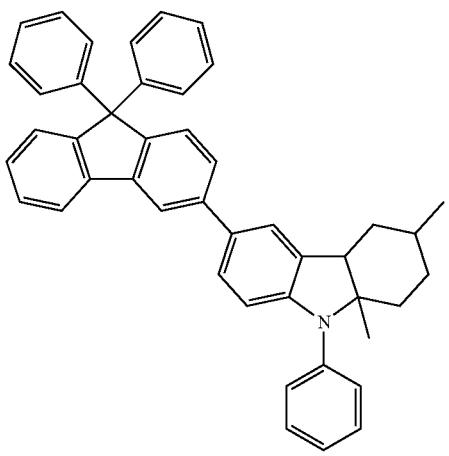
Formula 1698
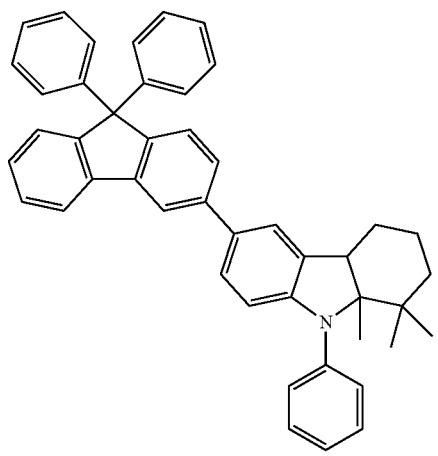

-continued
Formula 1699
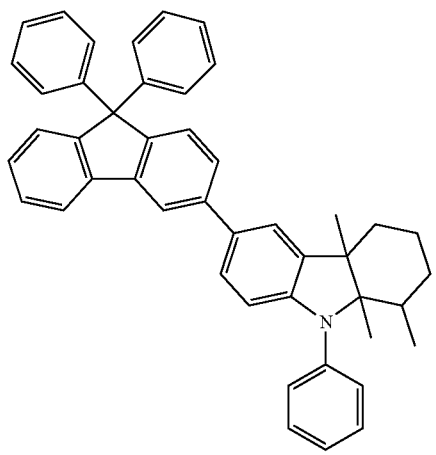
Formula 1700
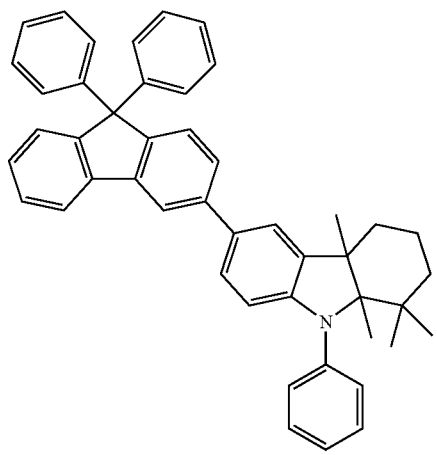
Formula 1701
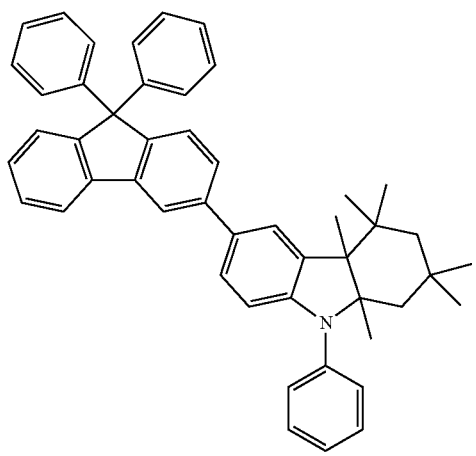
Formula 1702
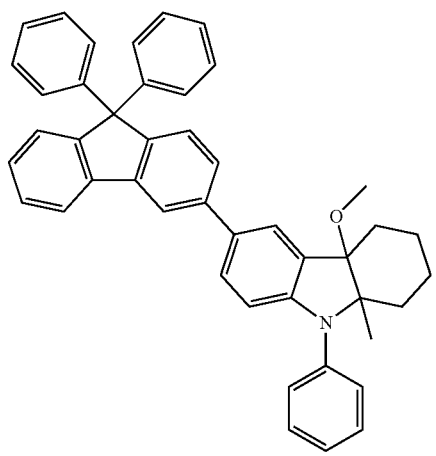
Formula 1703
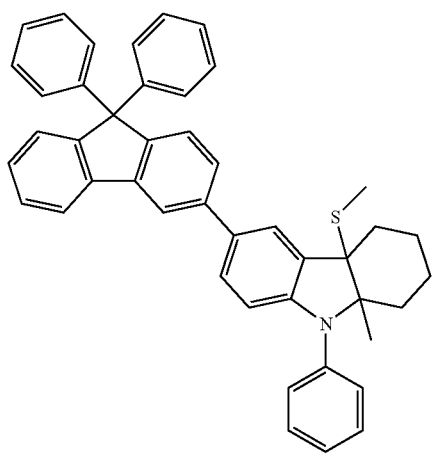
Formula 1704
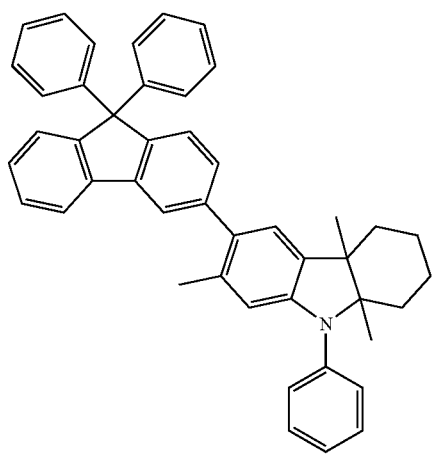

Formula 1705
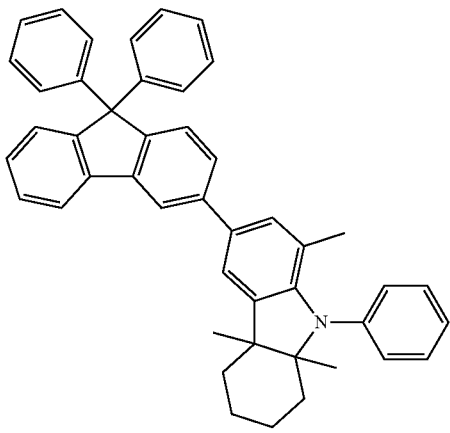
Formula 1706
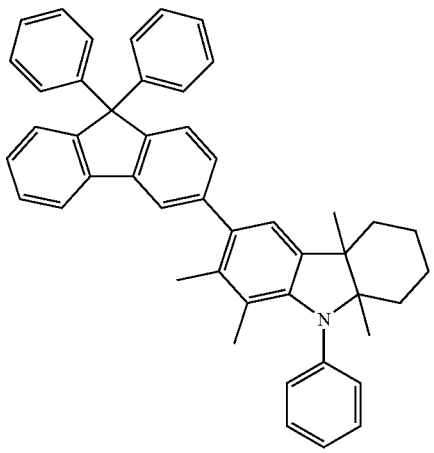
Formula 1707
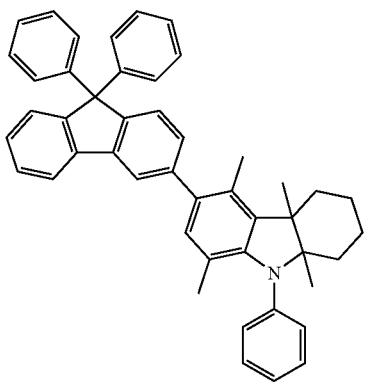
Formula 1708
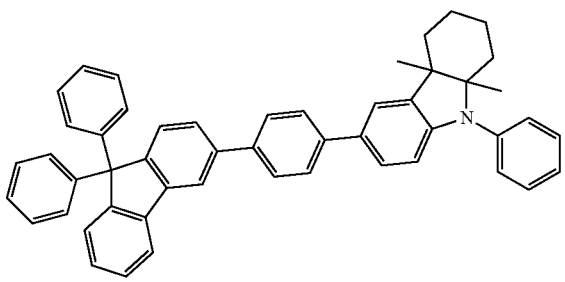
Formula 1709
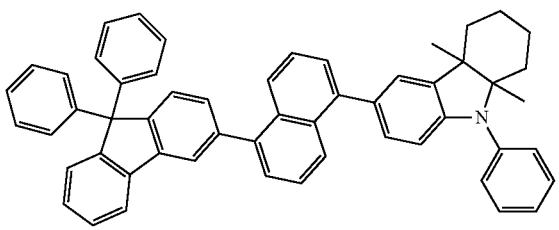
Formula 1710
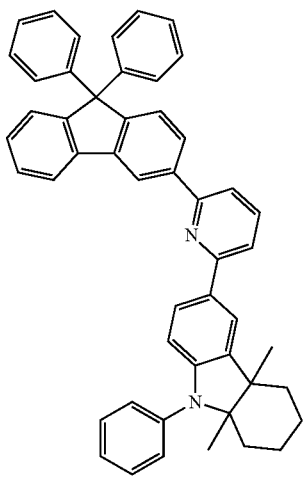

-continued
Formula 1711
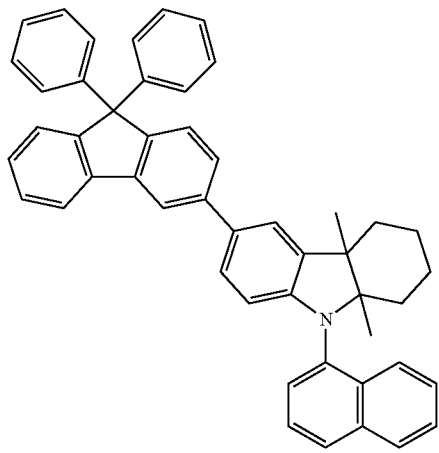
Formula 1712
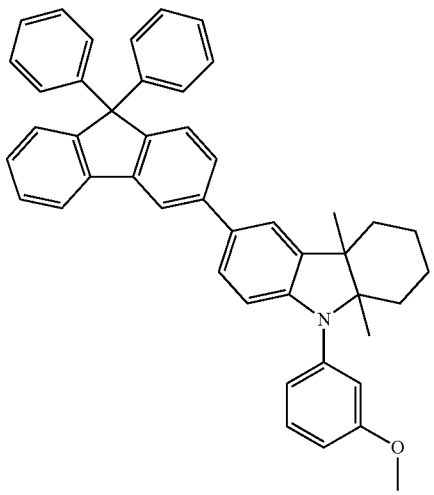
Formula 1713
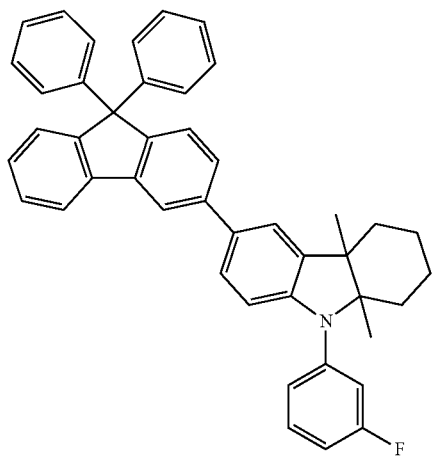
Formula 1714
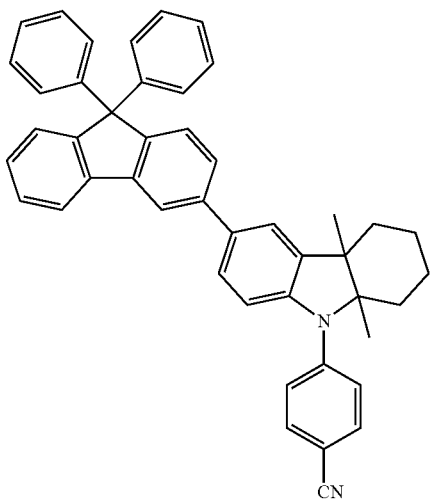
Formula 1715
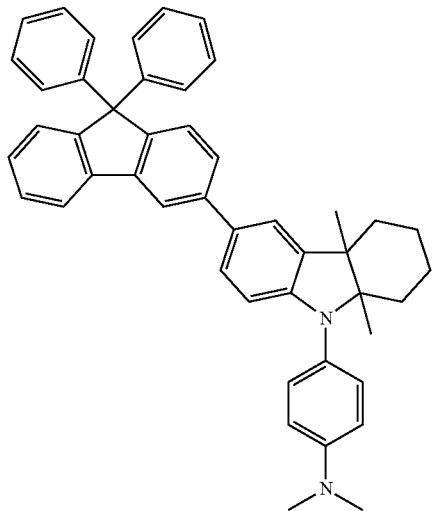
Formula 1716
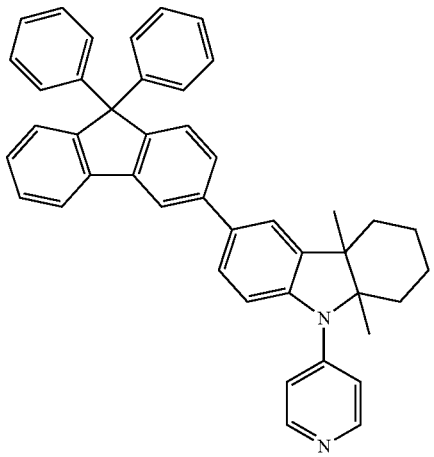

-continued
Formula 1717
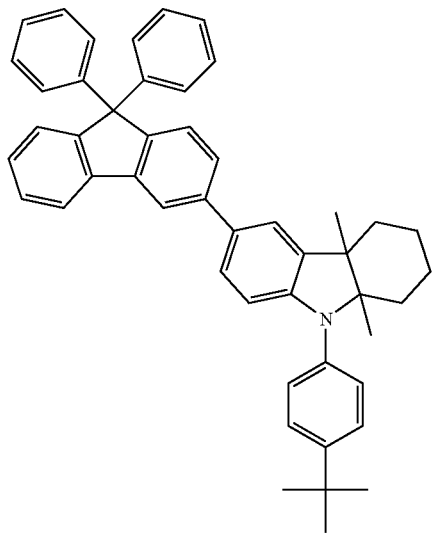
Formula 1718
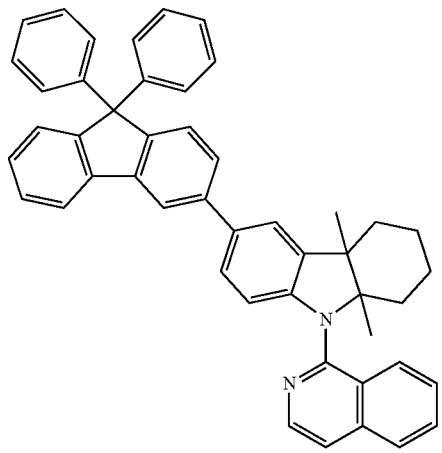
Formula 1719
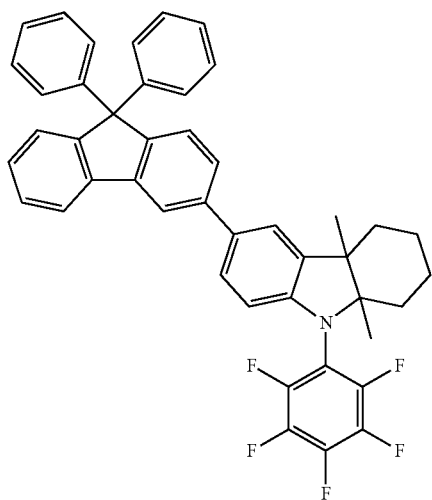
Formula 1720
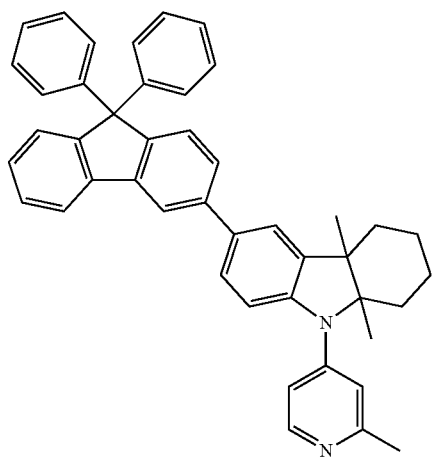
Formula 1721
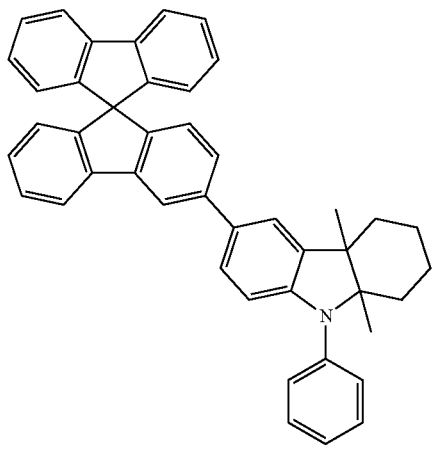
Formula 1722
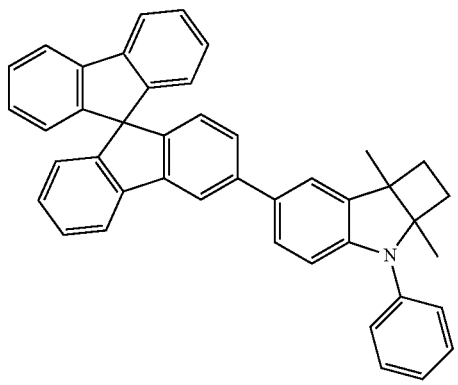

-continued
Formula 1723
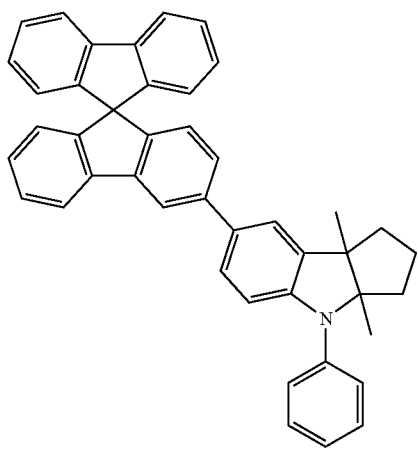
Formula 1724
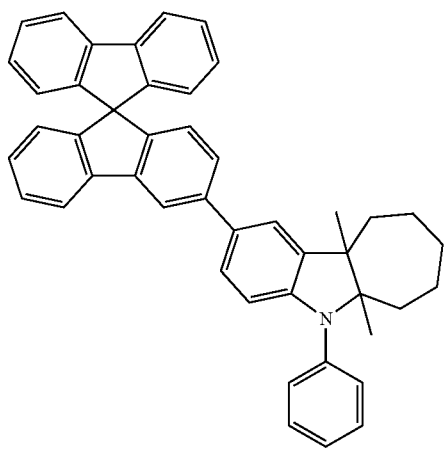
Formula 1725
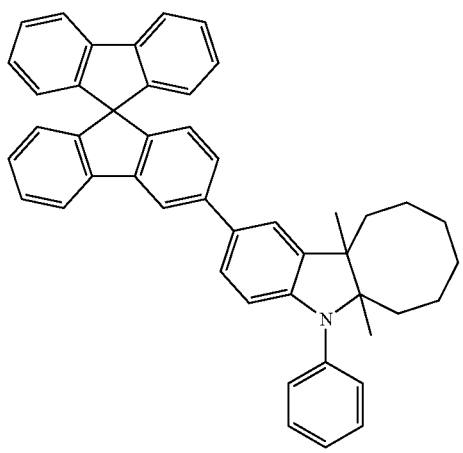
Formula 1726
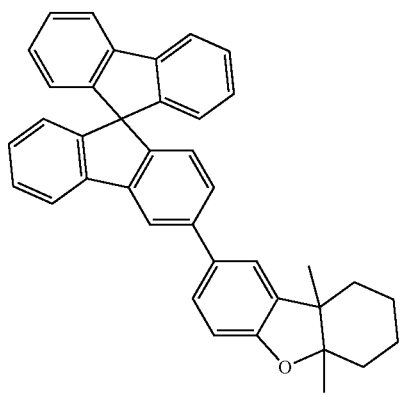
Formula 1727
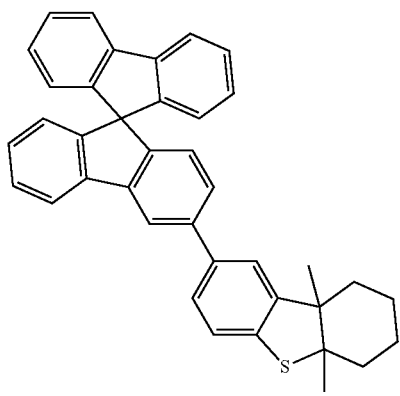
Formula 1728
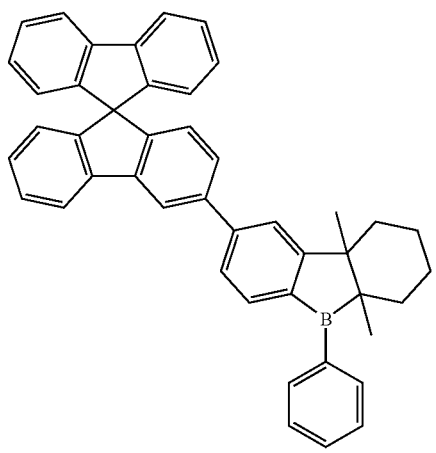

-continued
Formula 1729
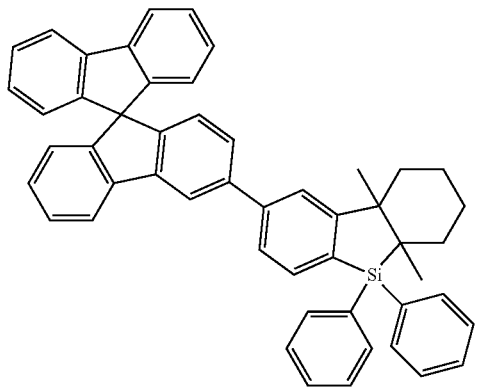
Formula 1730
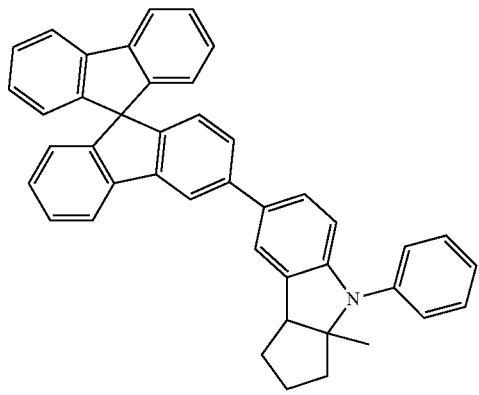
Formula 1731
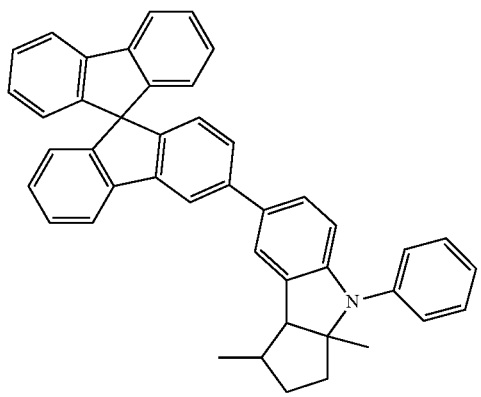
Formula 1732
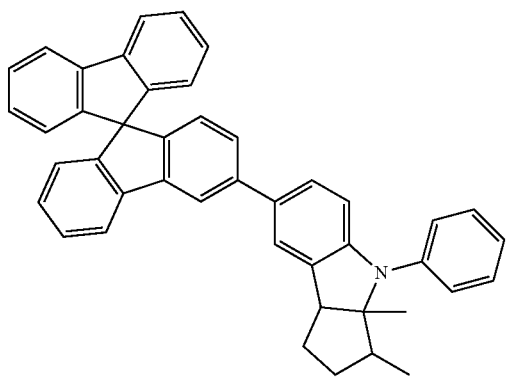
Formula 1733
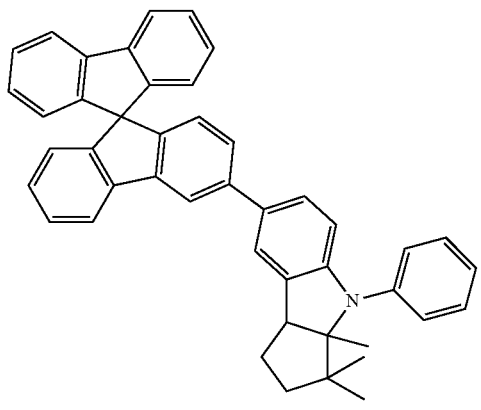
Formula 1734
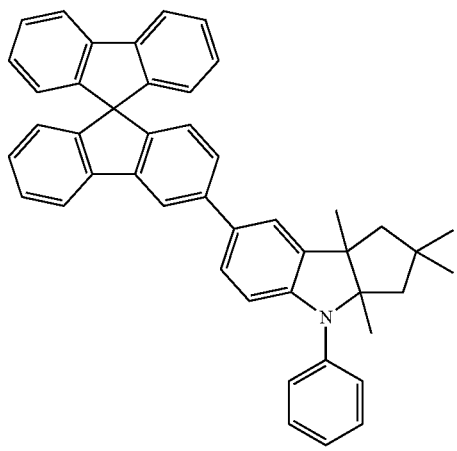

-continued
Formula 1735
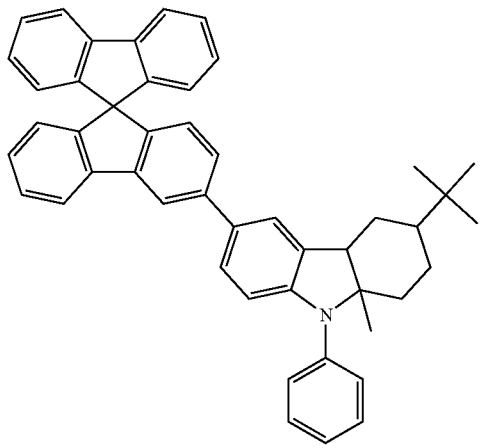
Formula 1736
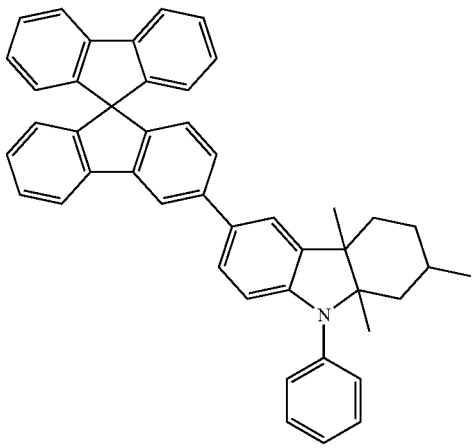
Formula 1737
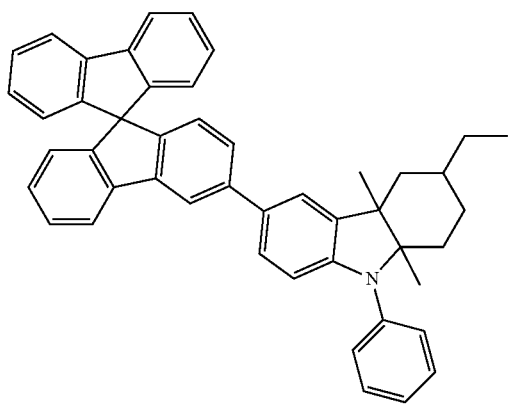
Formula 1738
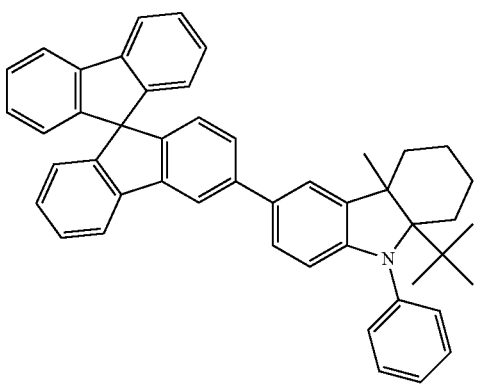
Formula 1739
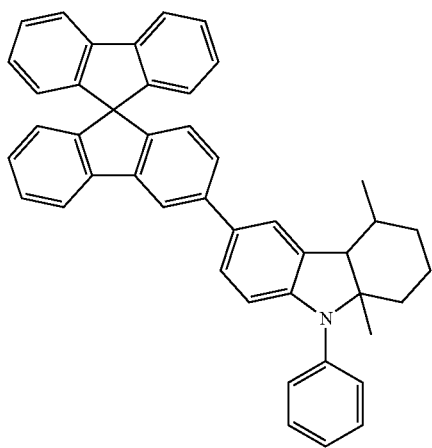
Formula 1740
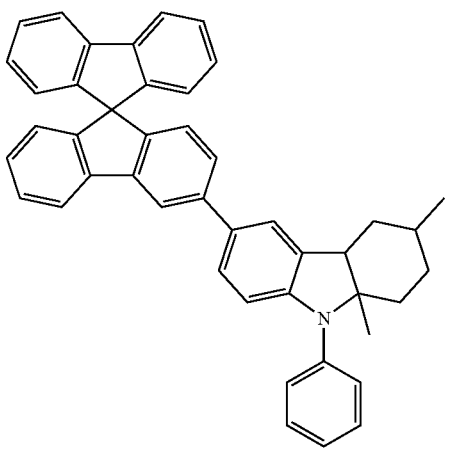

-continued
Formula 1741
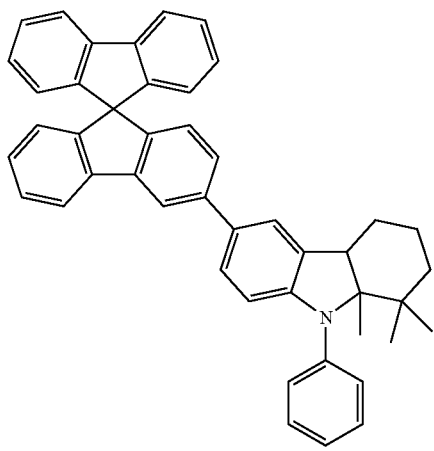
Formula 1742
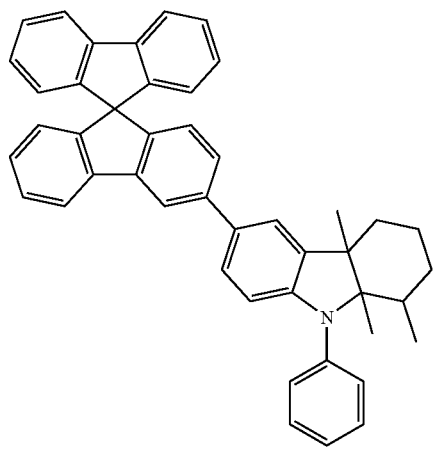
Formula 1743
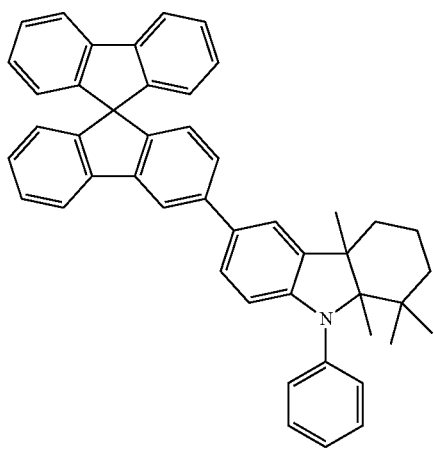
Formula 1744
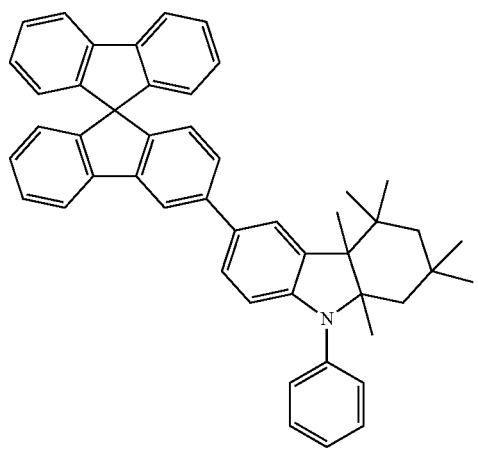
Formula 1745
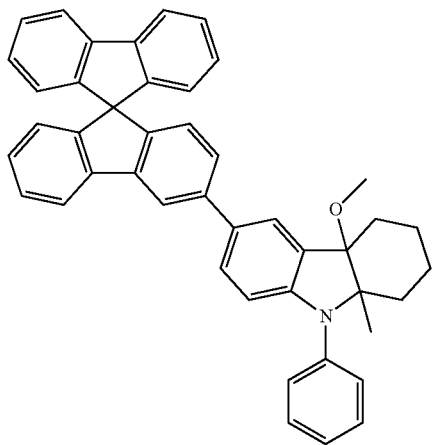
Formula 1746
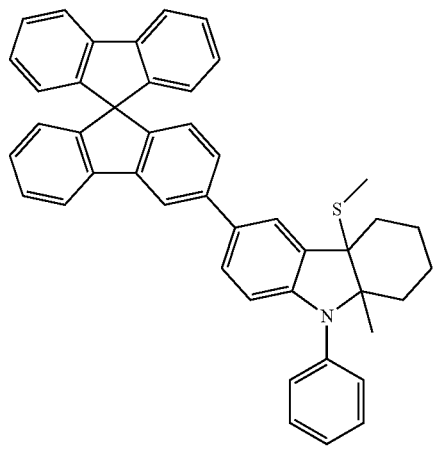

-continued
Formula 1747
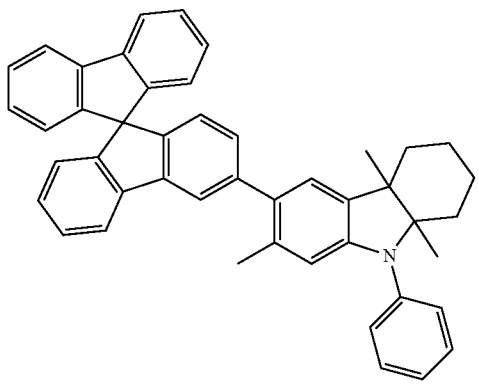
Formula 1748
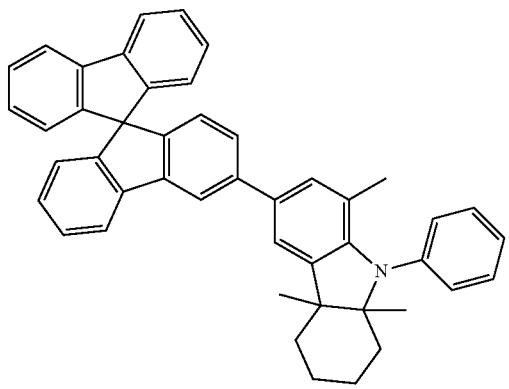
Formula 1749
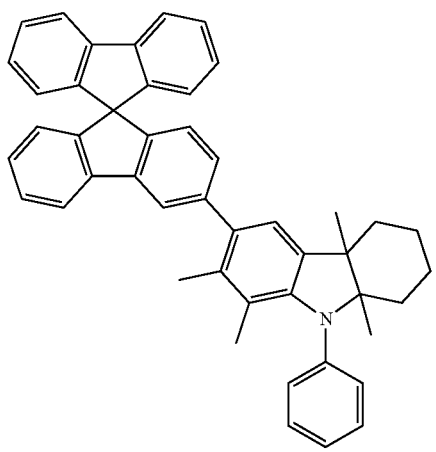
Formula 1750
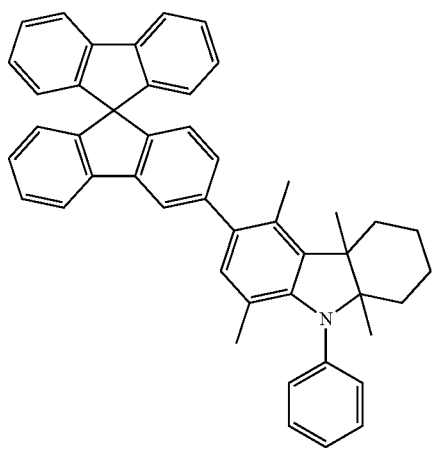
Formula 1751
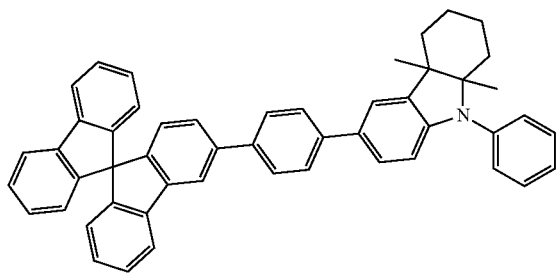
Formula 1752
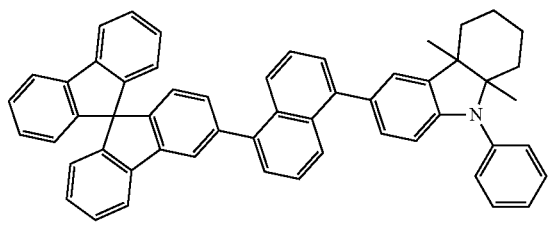

Formula 1753
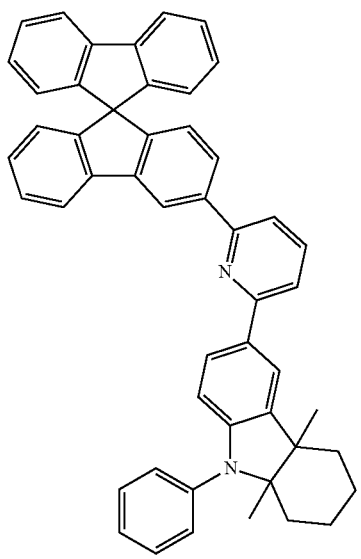
Formula 1754
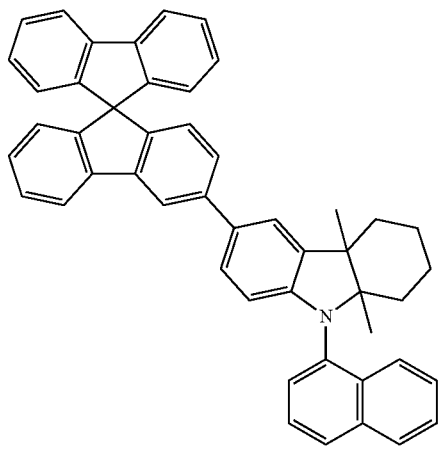
Formula 1755
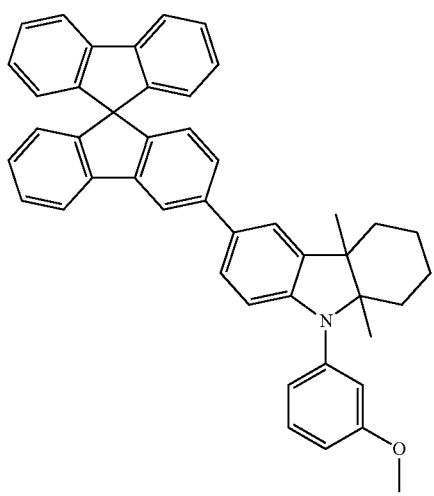
Formula 1756
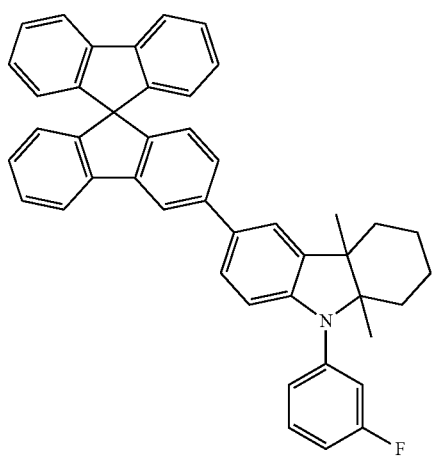
Formula 1757
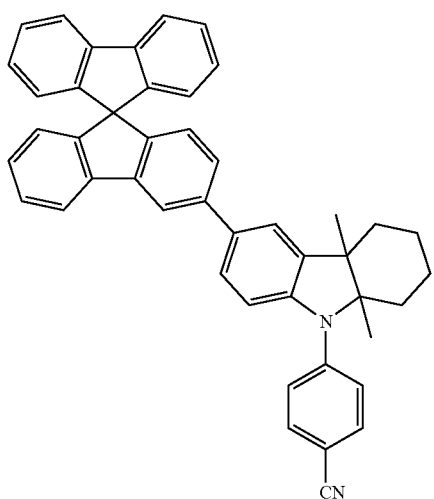
Formula 1758
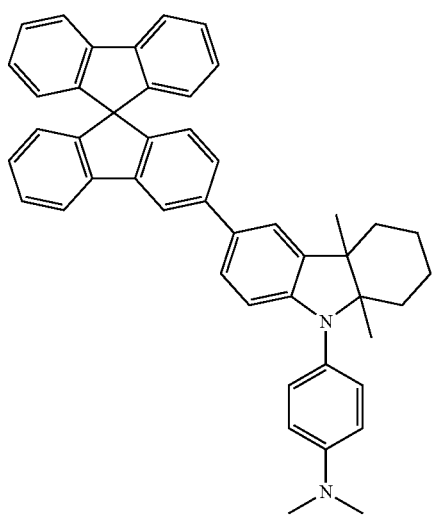

-continued
Formula 1759
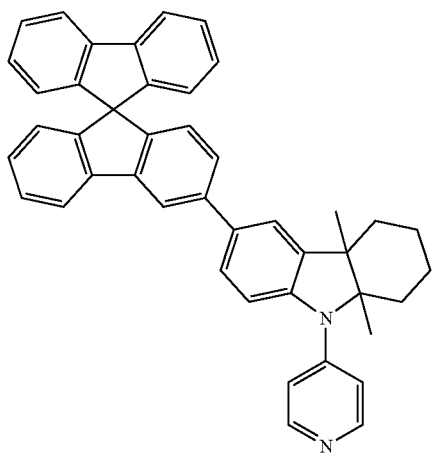
Formula 1760
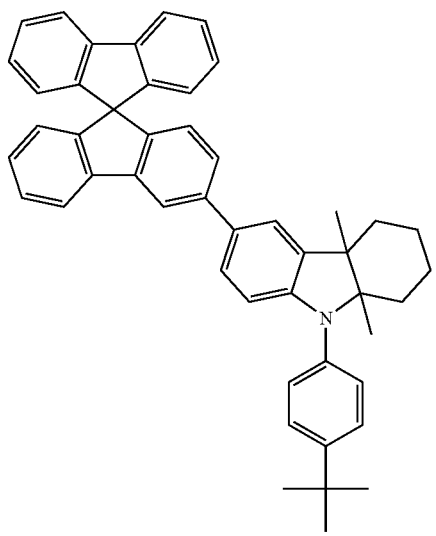
Formula 1761
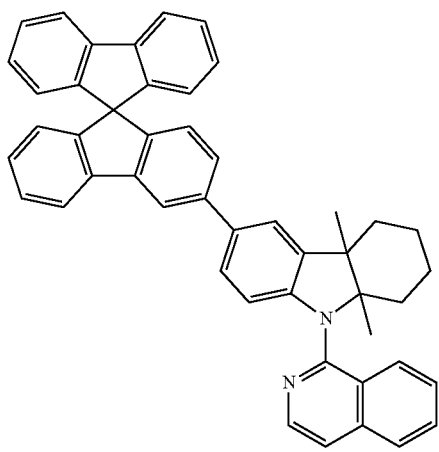
Formula 1762
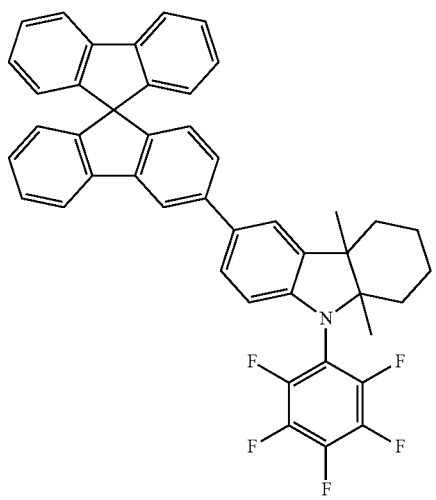
Formula 1763
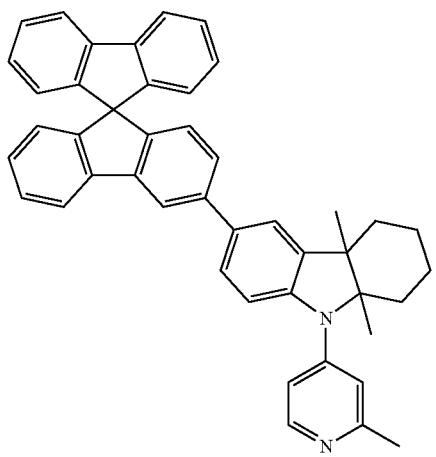
Formula 1764
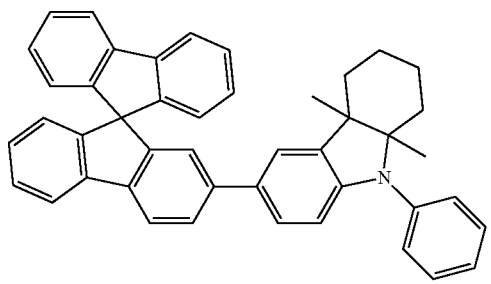

Formula 1765
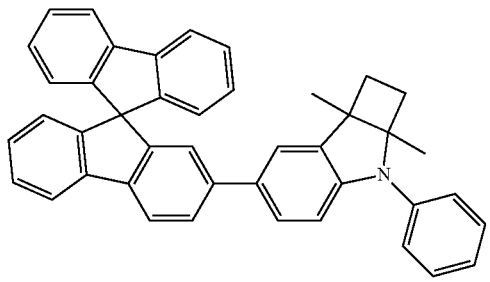
Formula 1766
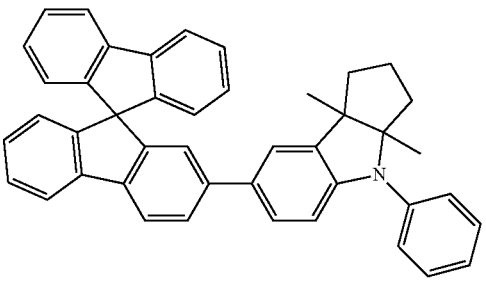
Formula 1767
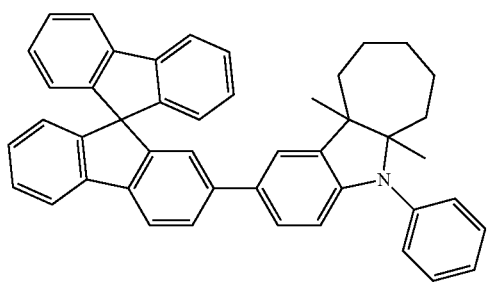
Formula 1768
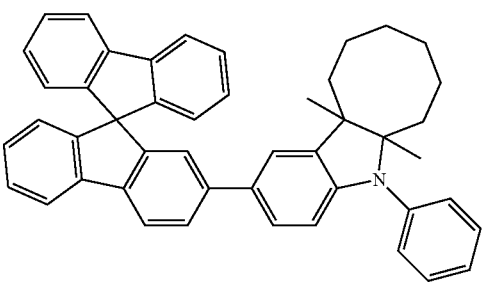
Formula 1769
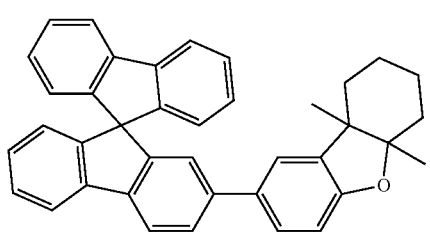
Formula 1770
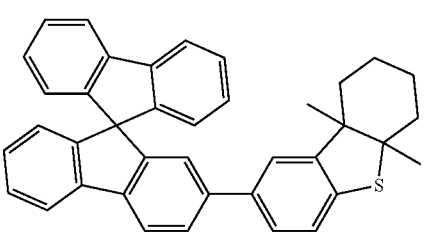
Formula 1771
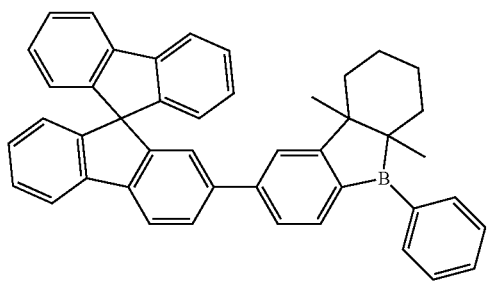
Formula 1772
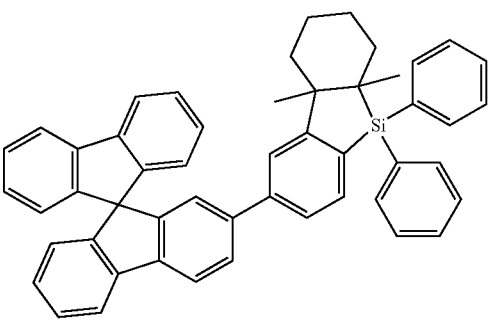
Formula 1773
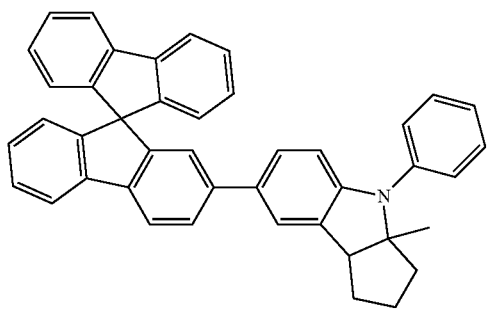
Formula 1774
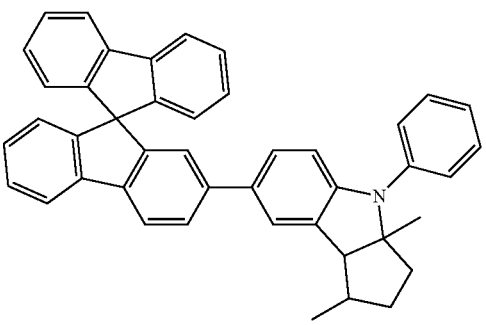

-continued
Formula 1775
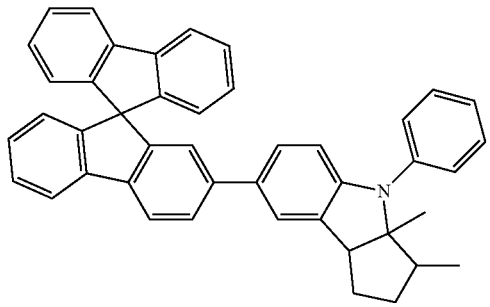
Formula 1776
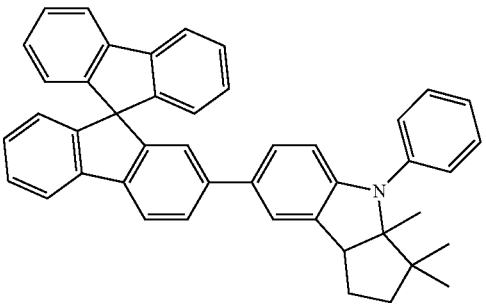
Formula 1777
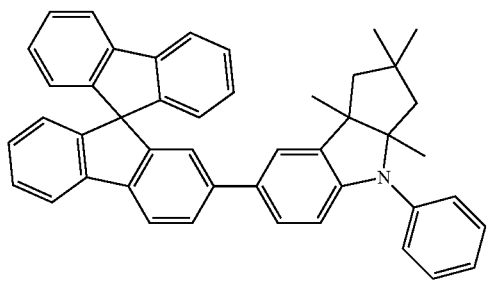
Formula 1778
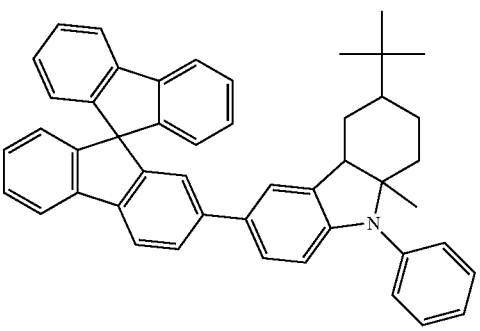
Formula 1779
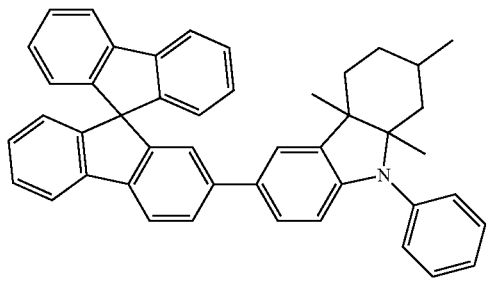
Formula 1780
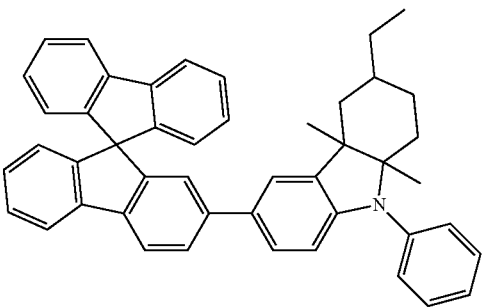
Formula 1781
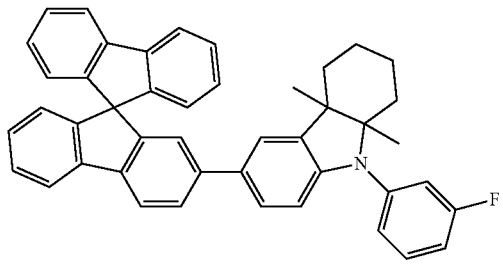
Formula 1782
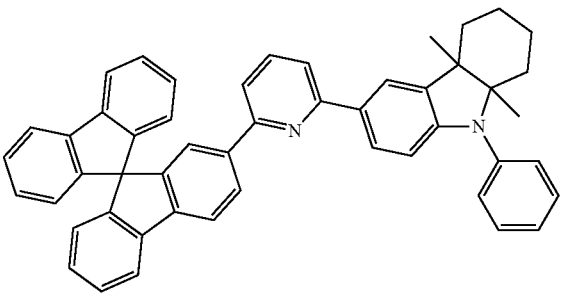
Formula 1783
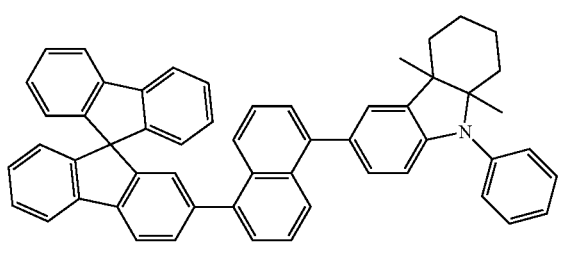
Formula 1784
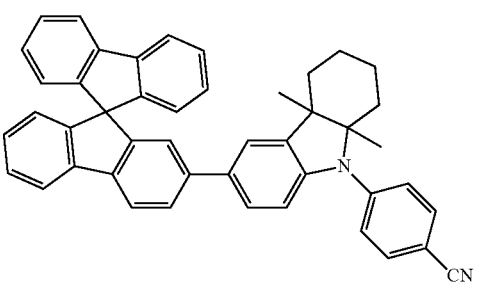

-continued
Formula 1785
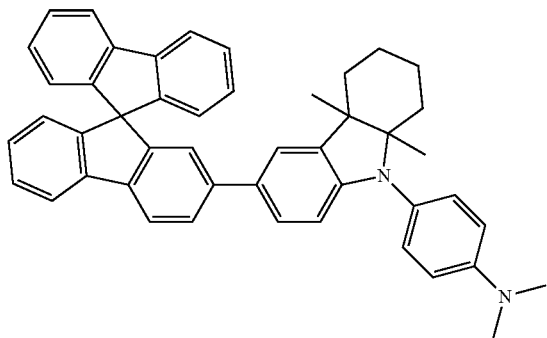
Formula 1786
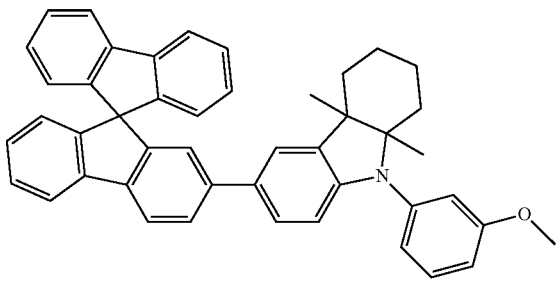
Formula 1787
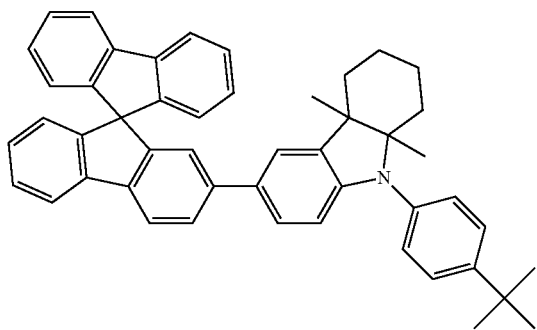
Formula 1788
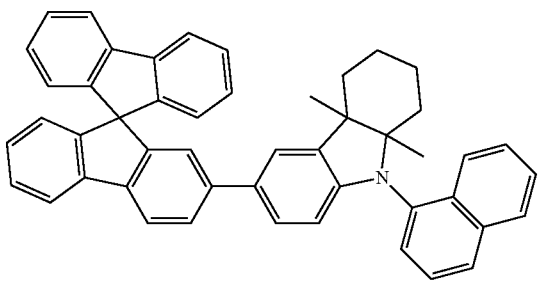
Formula 1789
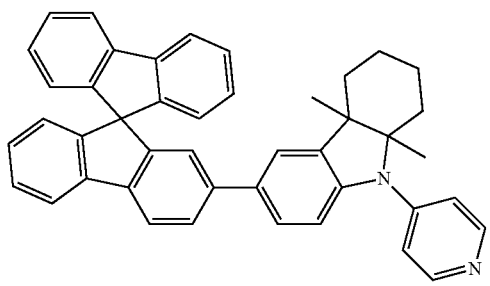
Formula 1790
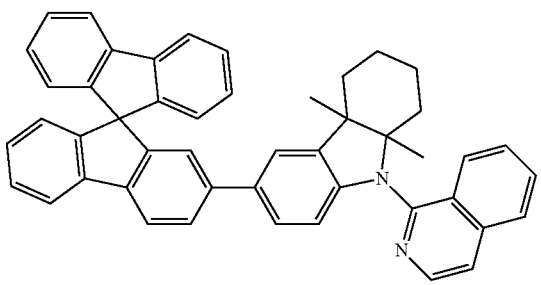
Formula 1791
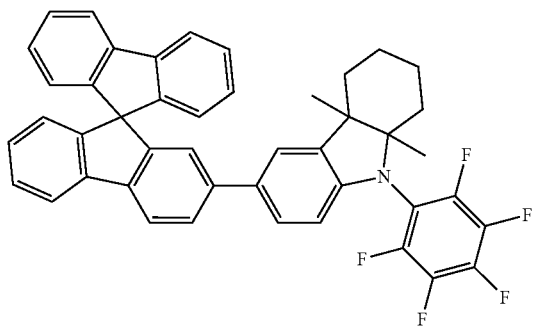
Formula 1792
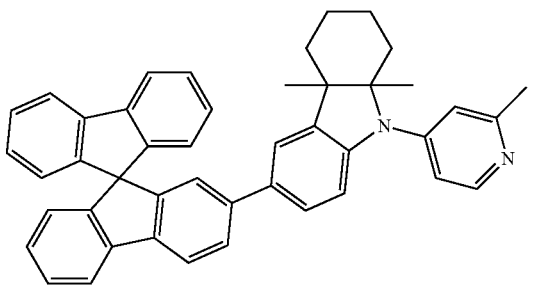

-continued
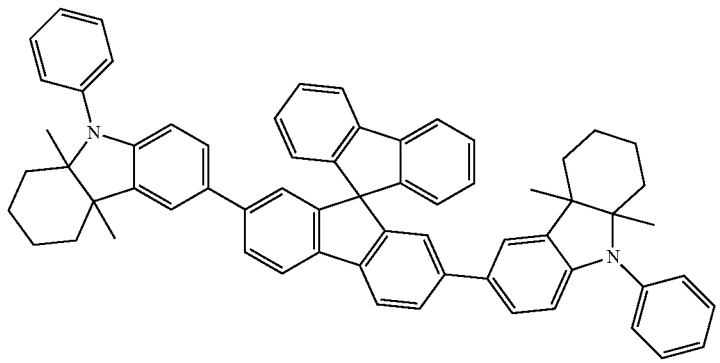
Formula 1793
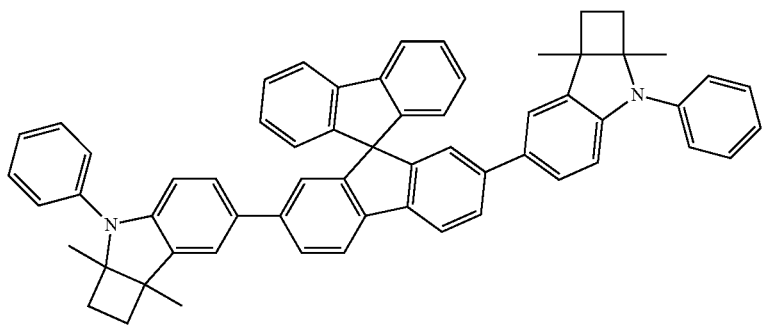
Formula 1794
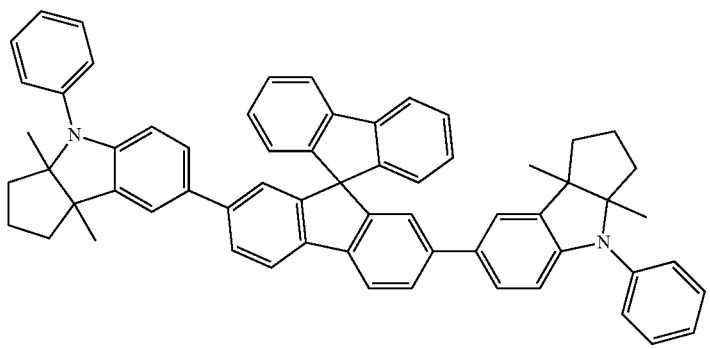
Formula 1795
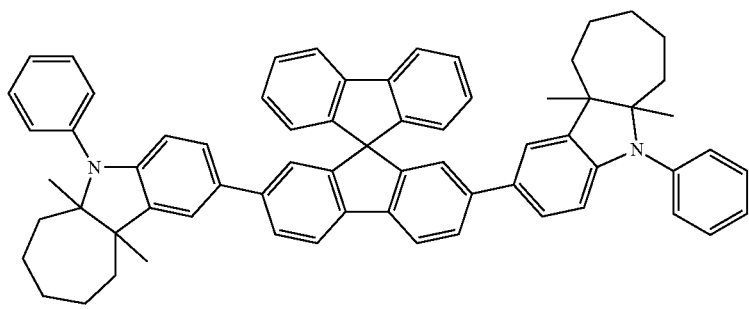
Formula 1796

-continued
Formula 1797
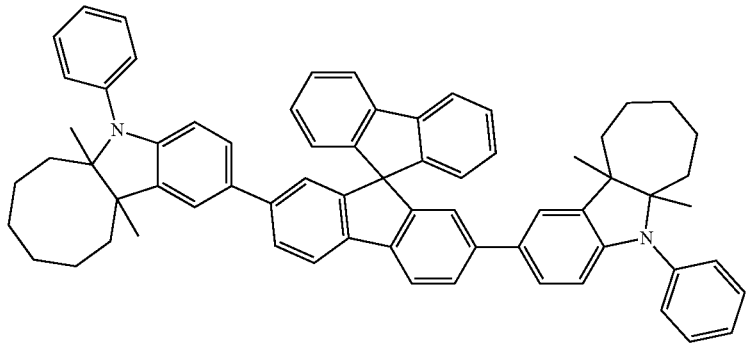
Formula 1798
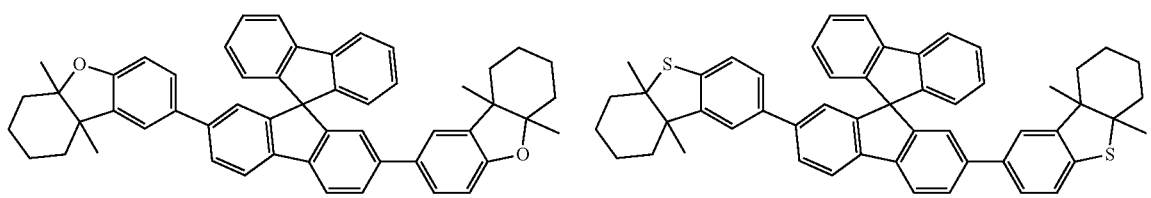
Formula 1799
Formula 1800
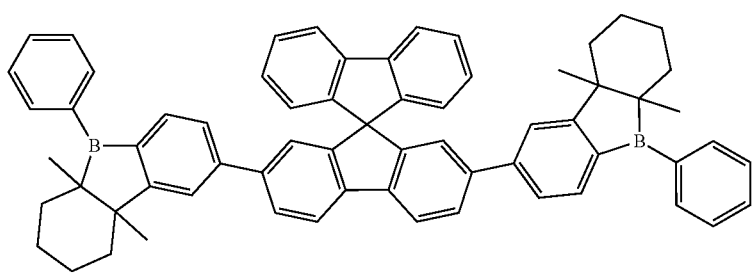
Formula 1801
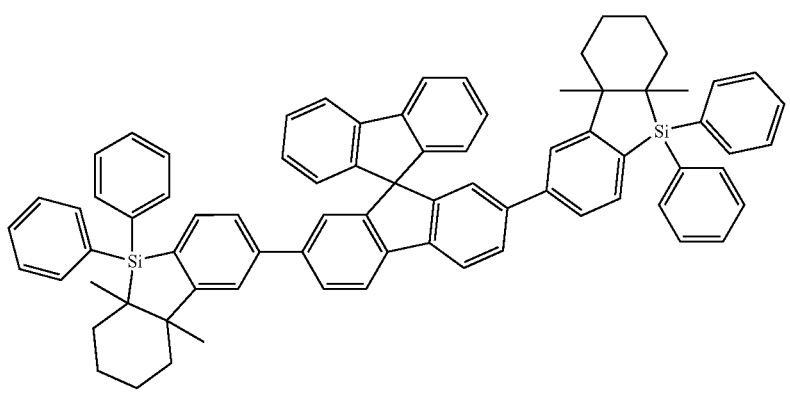
Formula 1802
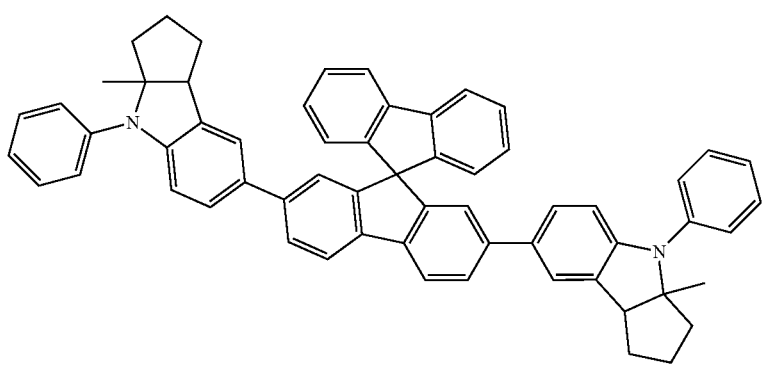

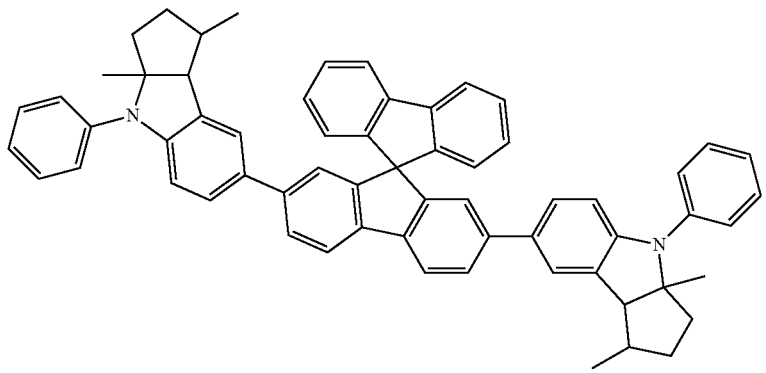
Formula 1803
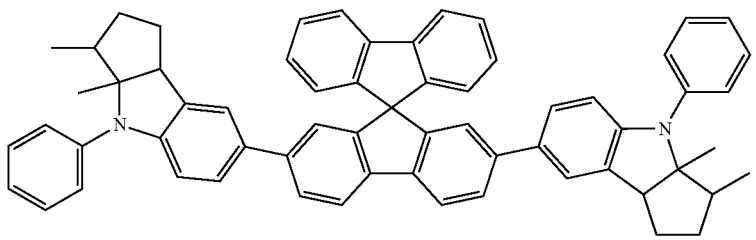
Formula 1804
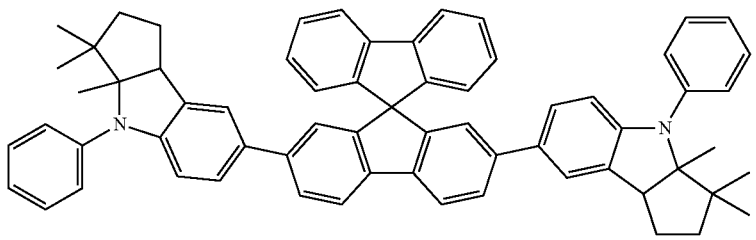
Formula 1805
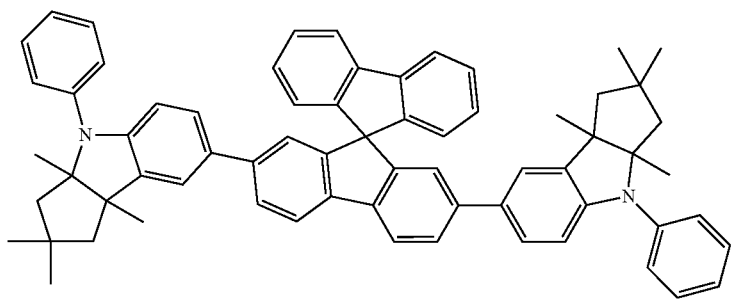
Formula 1806
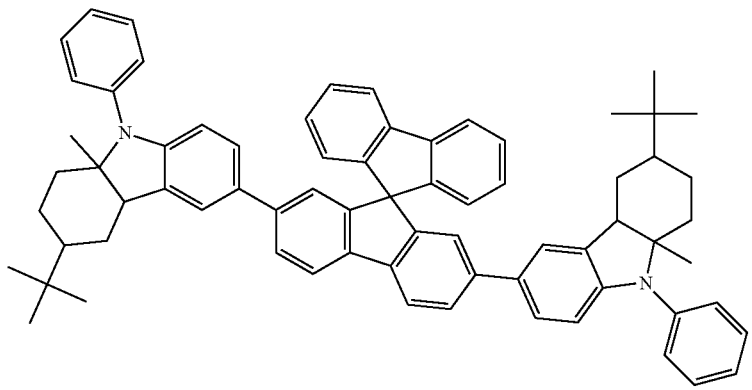
Formula 1807

-continued
Formula 1809
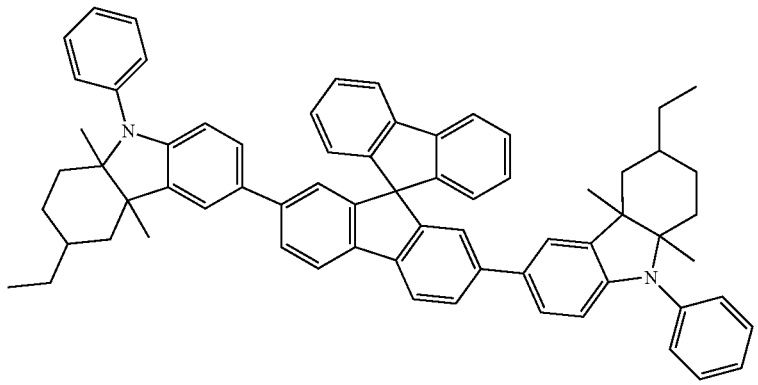
Formula 1810
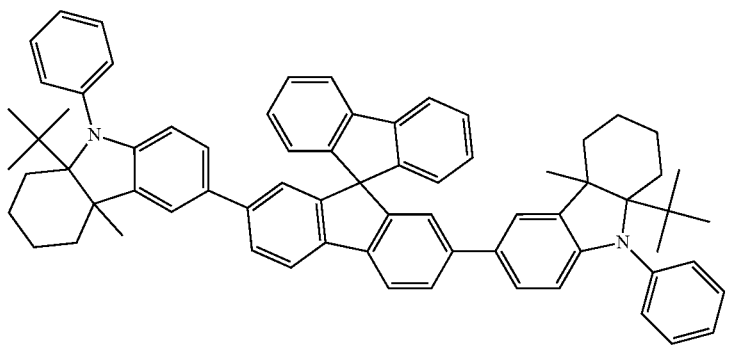
Formula 1811
Formula 1812
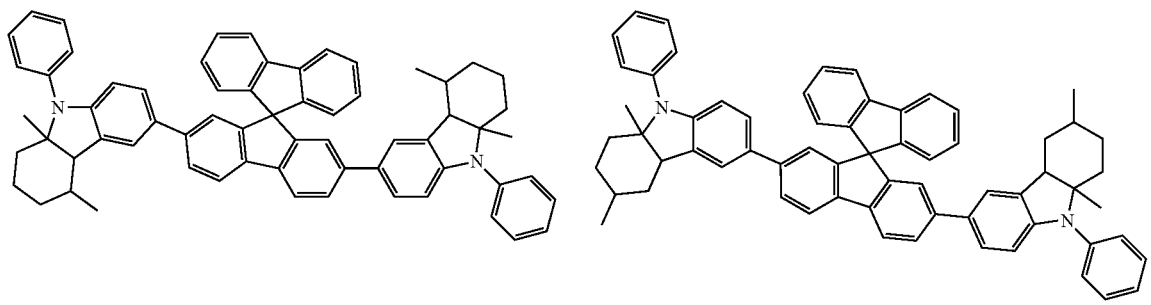
Formula 1813
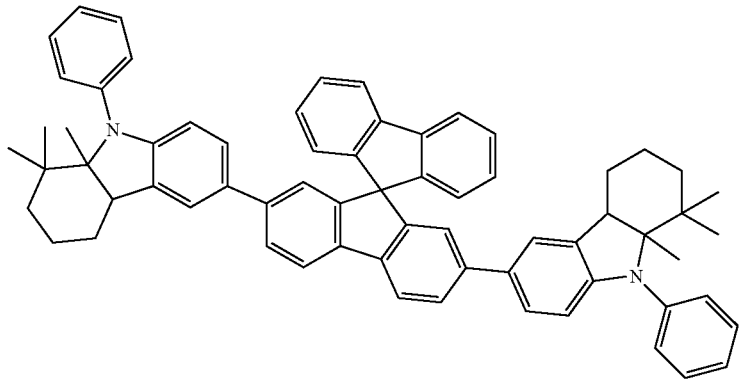

-continued
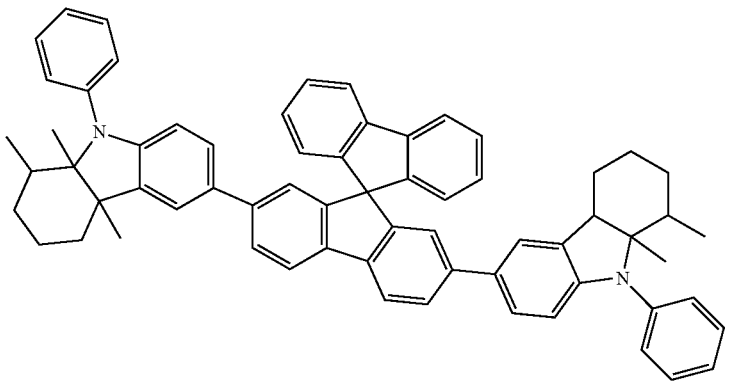
Formula 1814
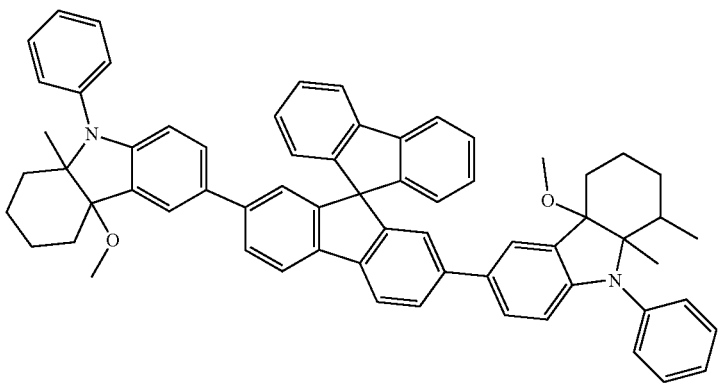
Formula 1815
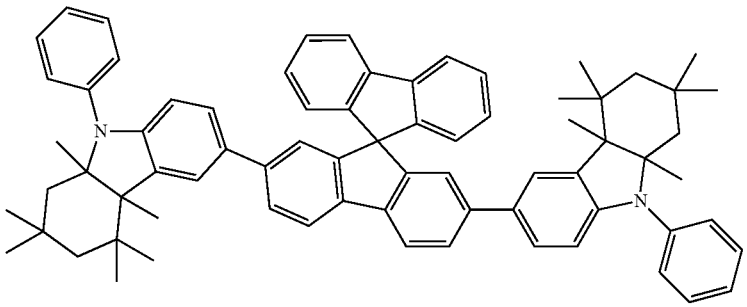
Formula 1816
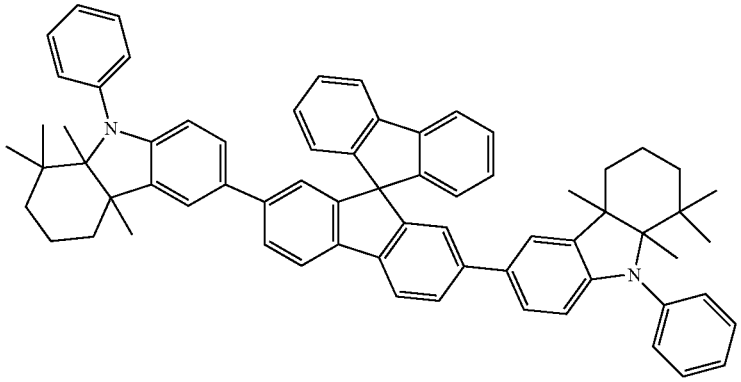
Formula 1817

-continued
Formula 1818
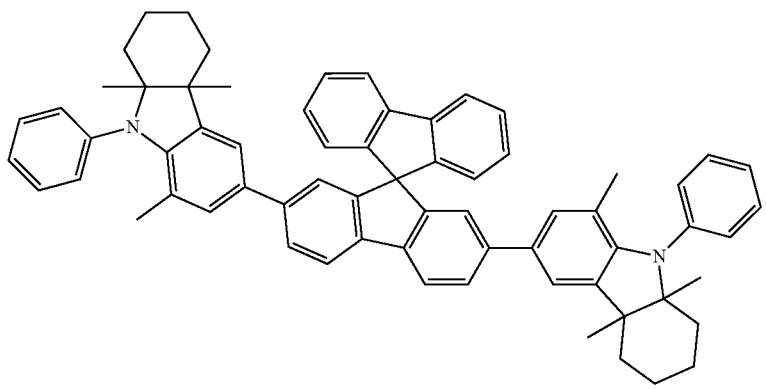
Formula 1819
Formula 1820
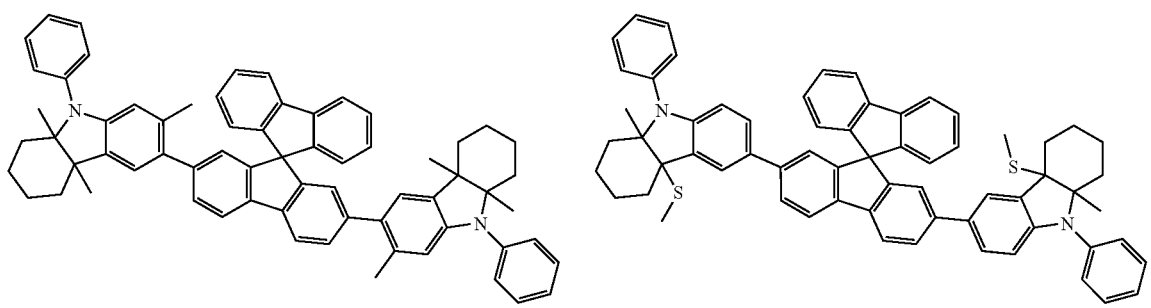
Formula 1821
Formula 1822
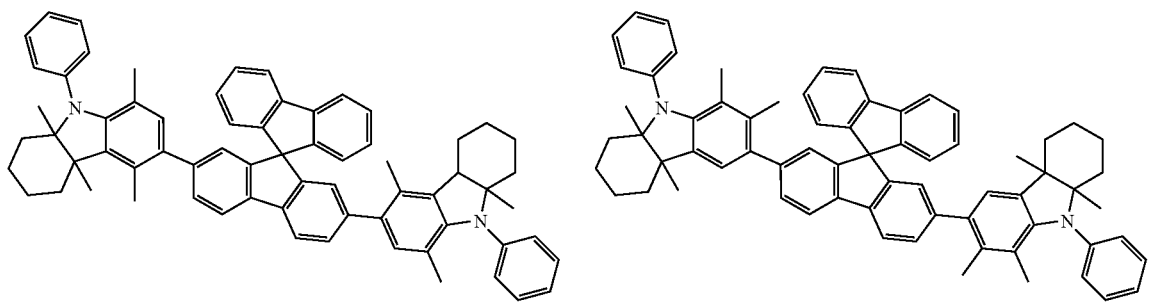
Formula 1823
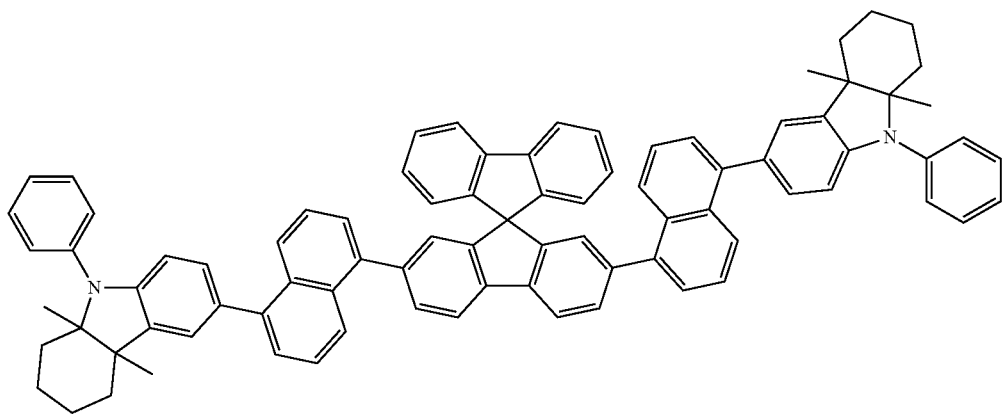

Formula 1824
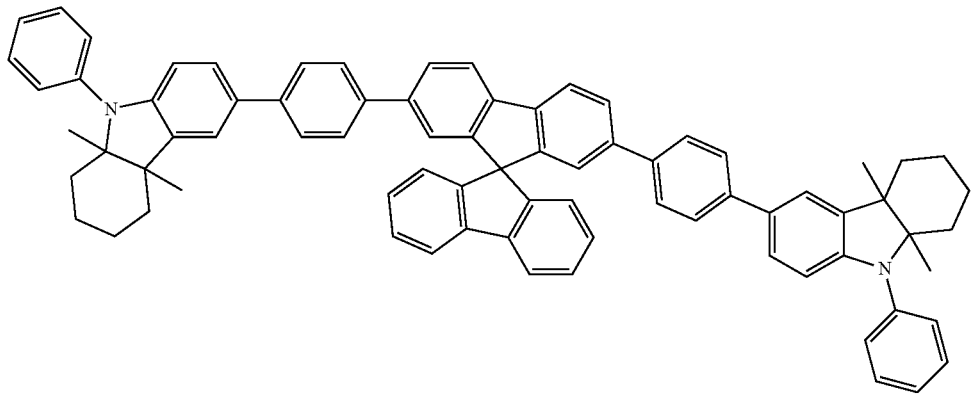
Formula 1825
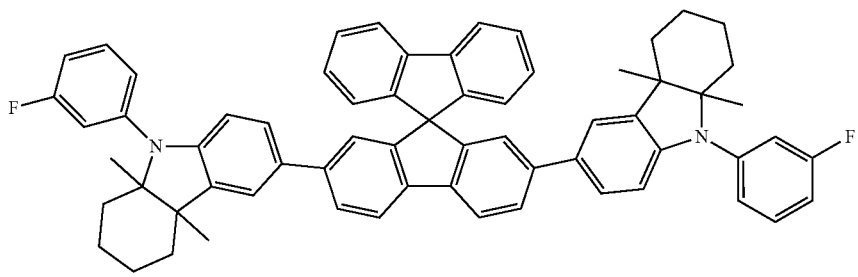
Formula 1826
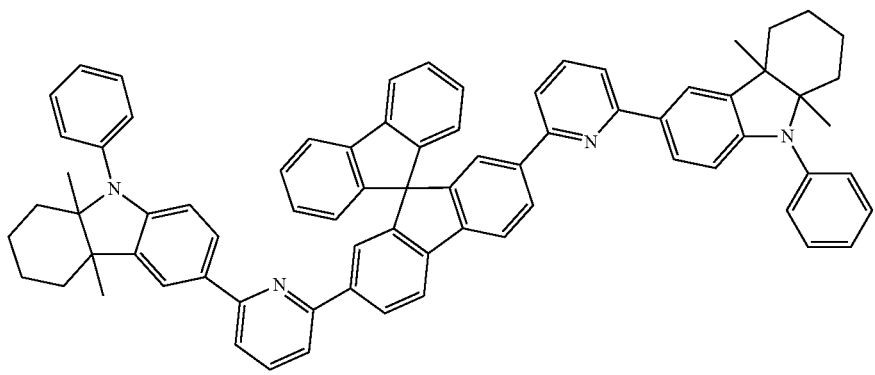
Formula 1827
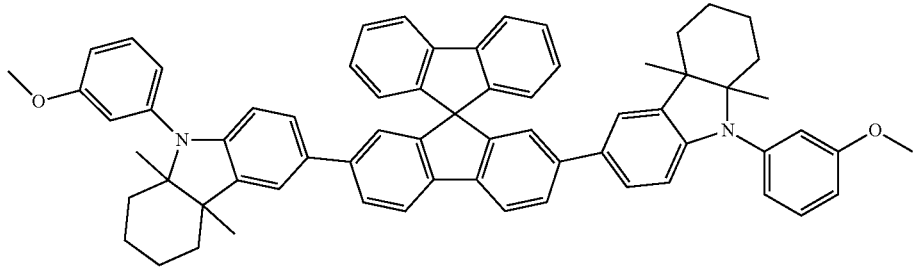
Formula 1828
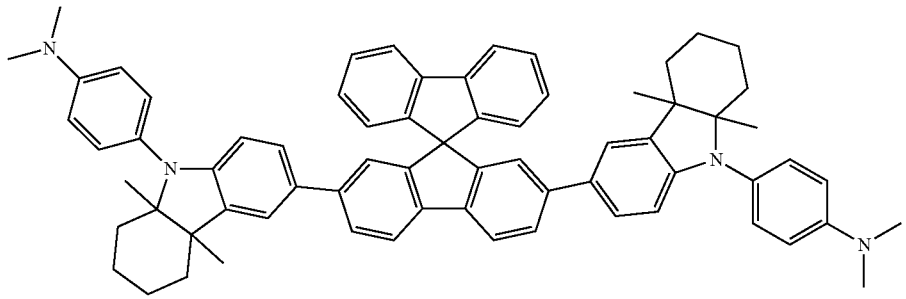

-continued
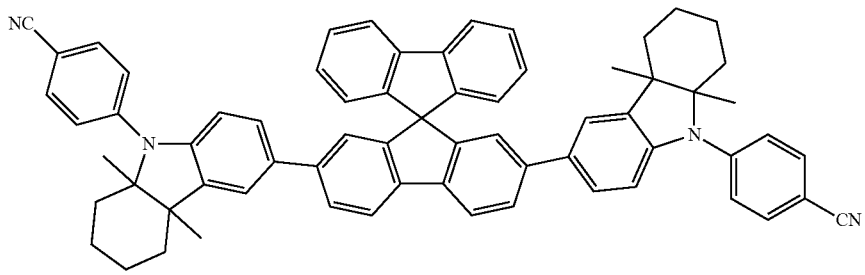
Formula 1829
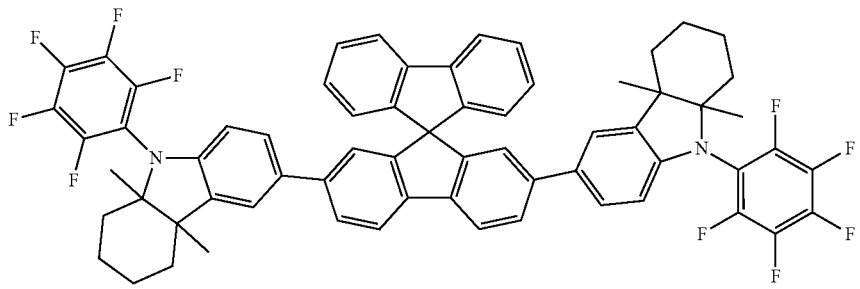
Formula 1830
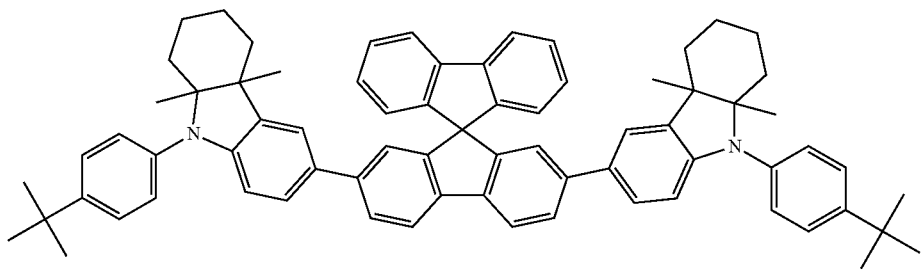
Formula 1831
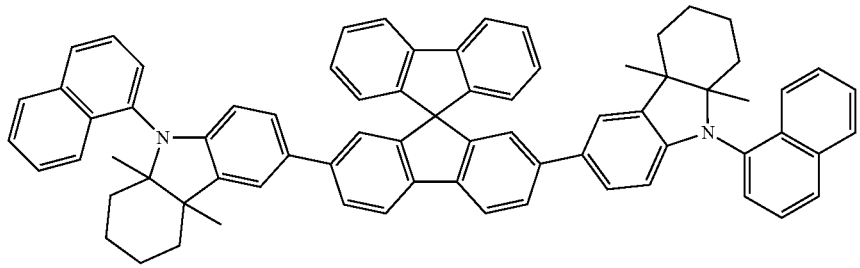
Formula 1832
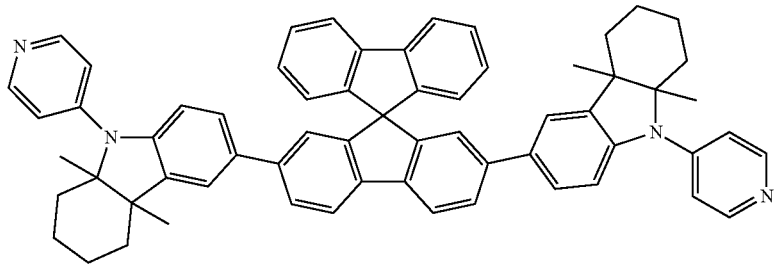
Formula 1833
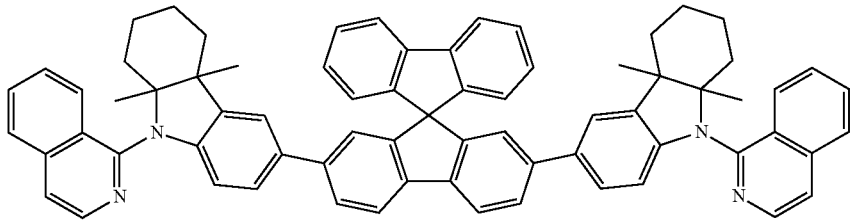
Formula 1834

Formula 1835
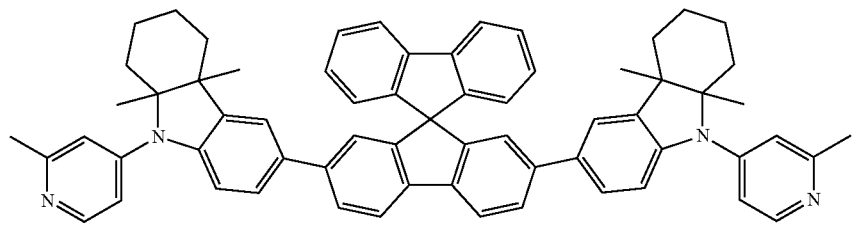
Formula 1836
Formula 1837
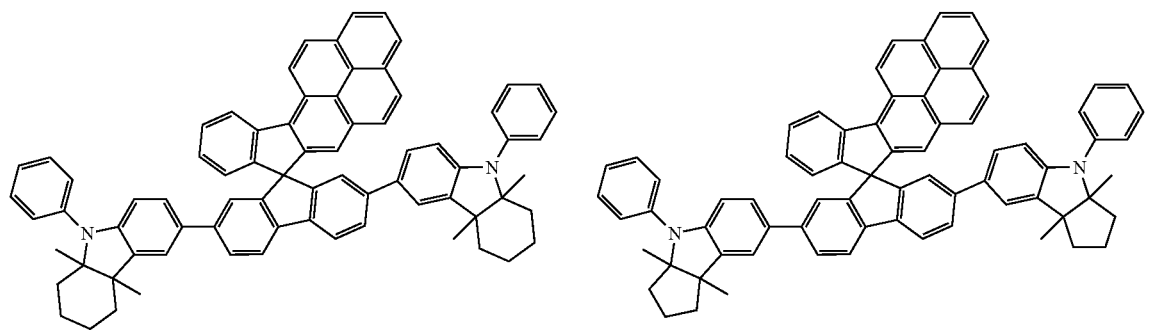
Formula 1838
Formula 1839
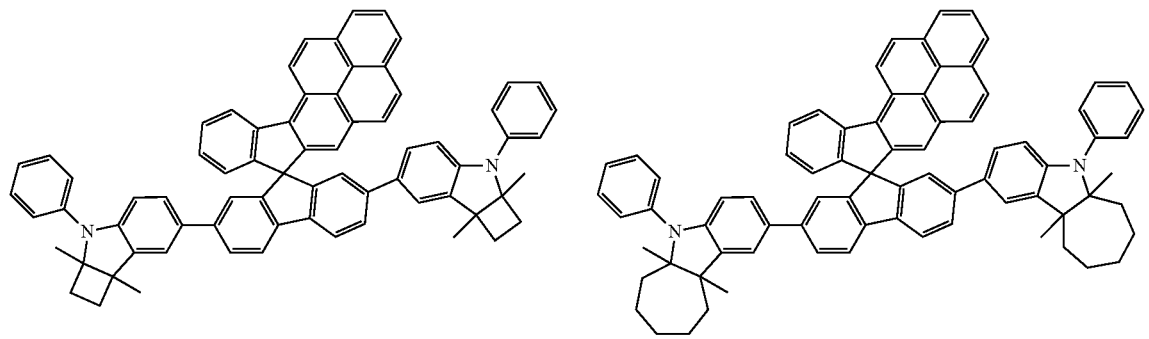
Formula 1840
Formula 1841
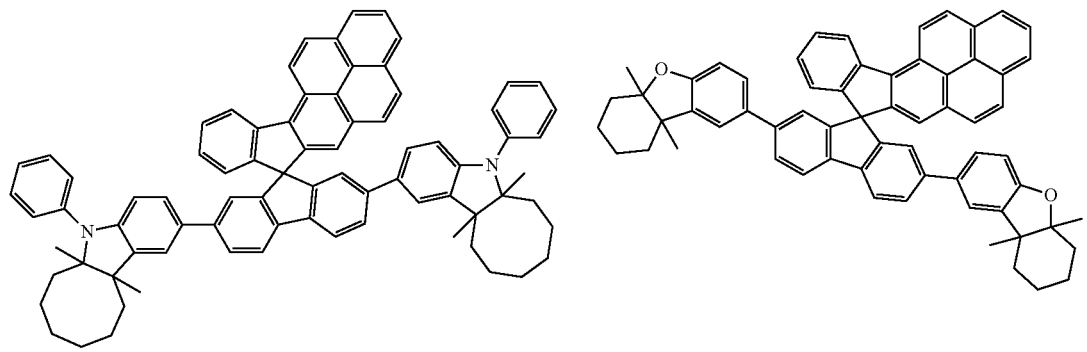

-continued
Formula 1842
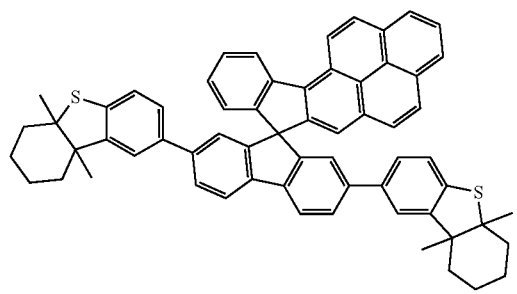
Formula 1843
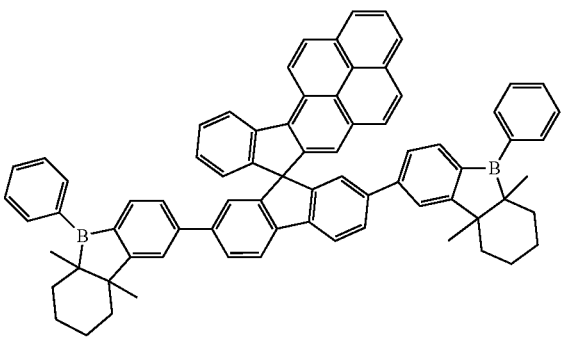
Formula 1844
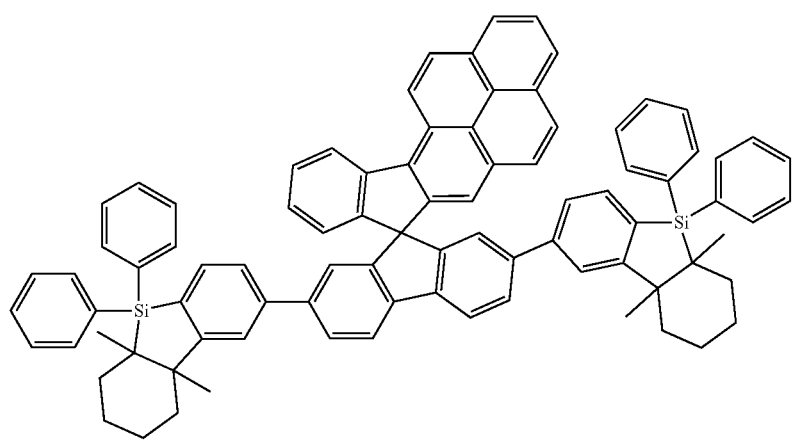
Formula 1845
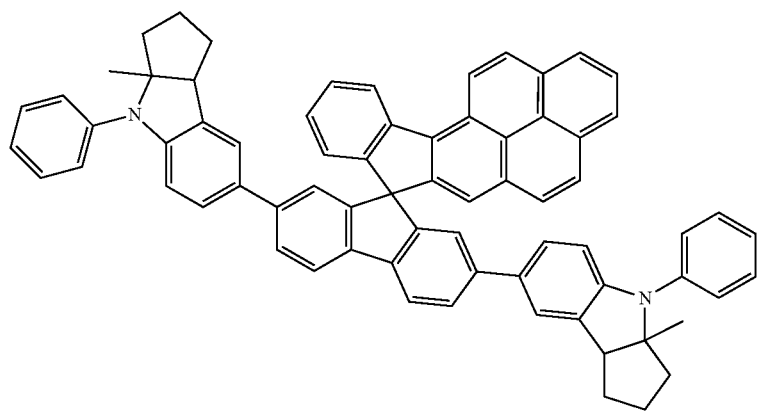
Formula 1846
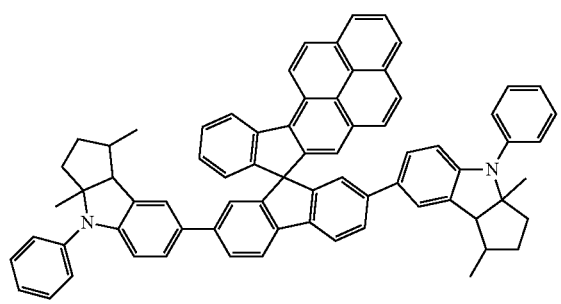
Formula 1847
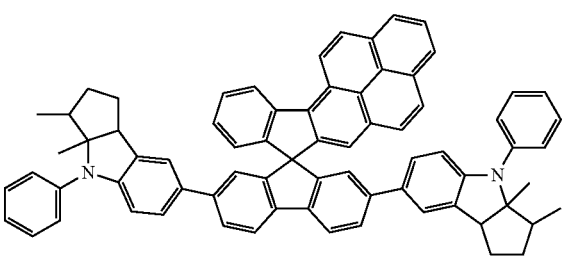

-continued
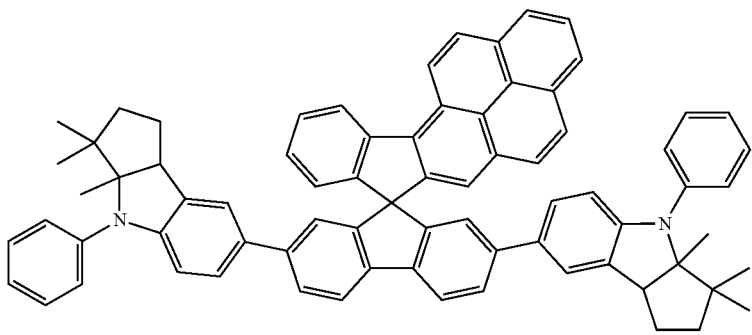
Formula 1848
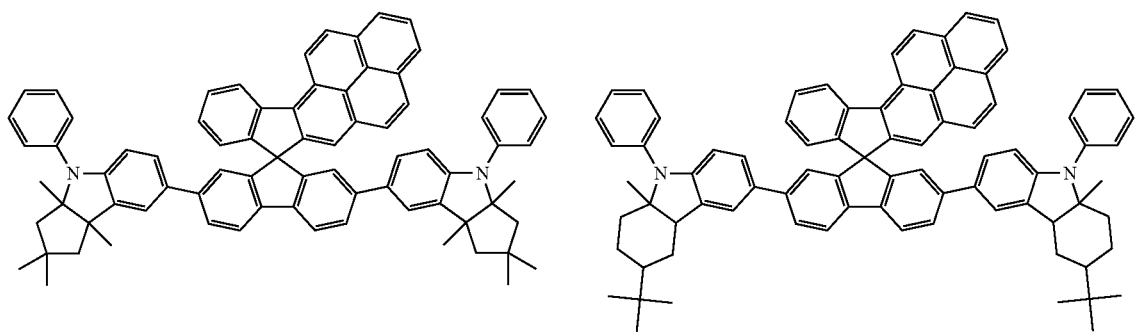
Formula 1849
Formula 1850
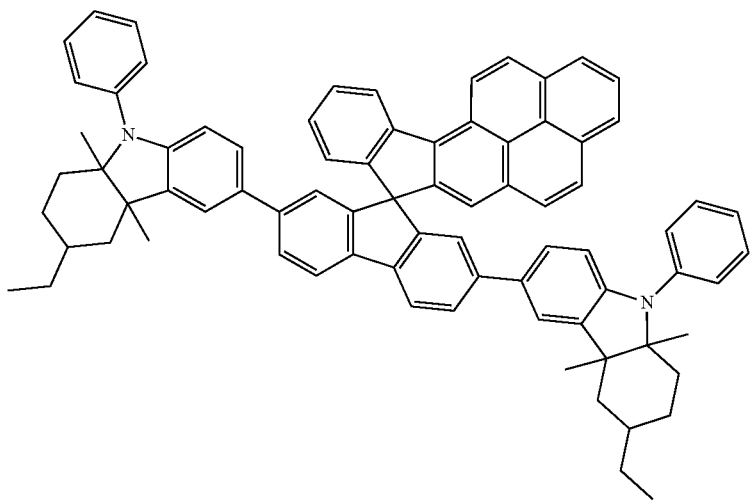
Formula 1851
Formula 1852
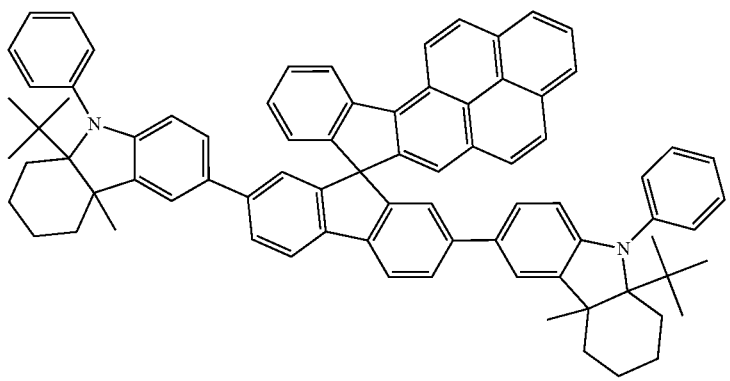

-continued
Formula 1853
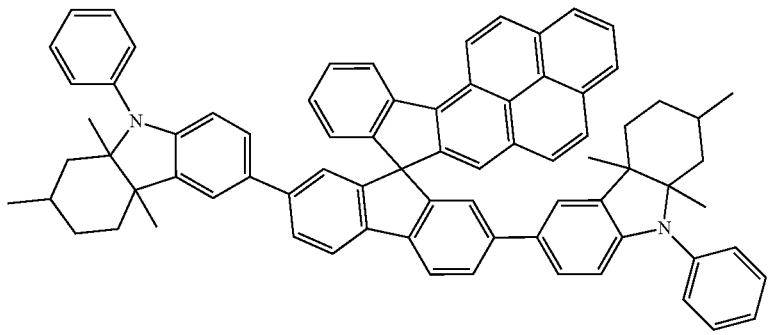
Formula 1854
Formula 1855
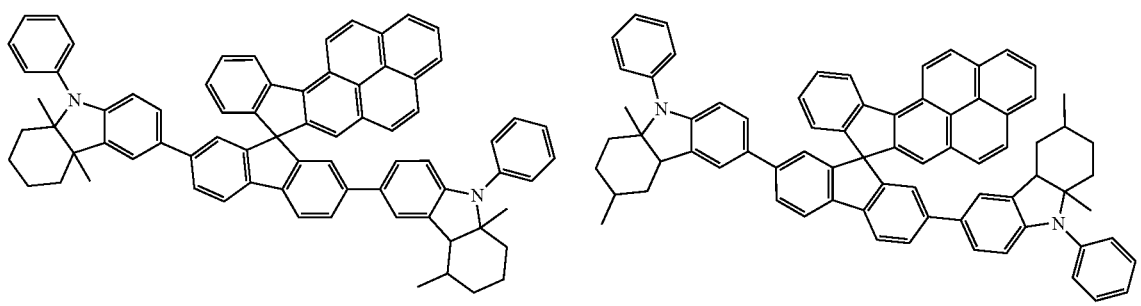
Formula 1856
Formula 1857
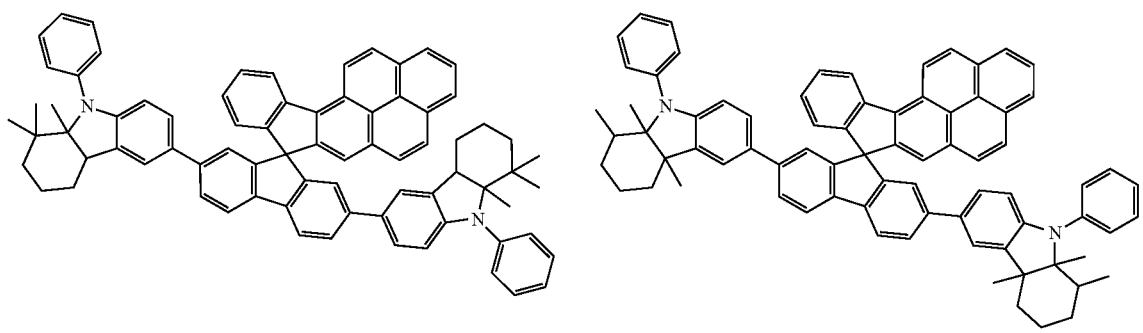
Formula 1858
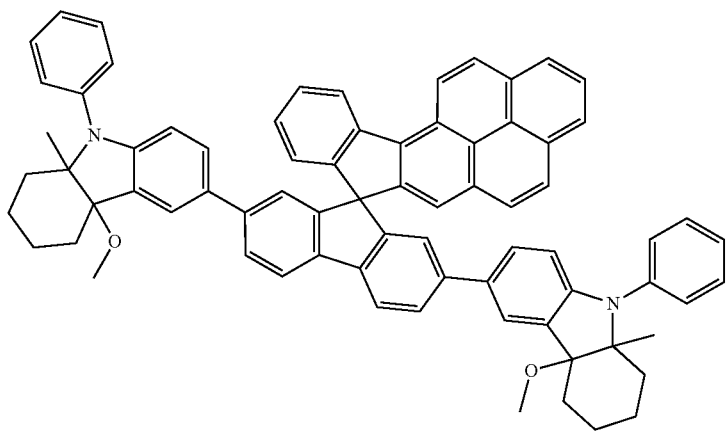

-continued
Formula 1859
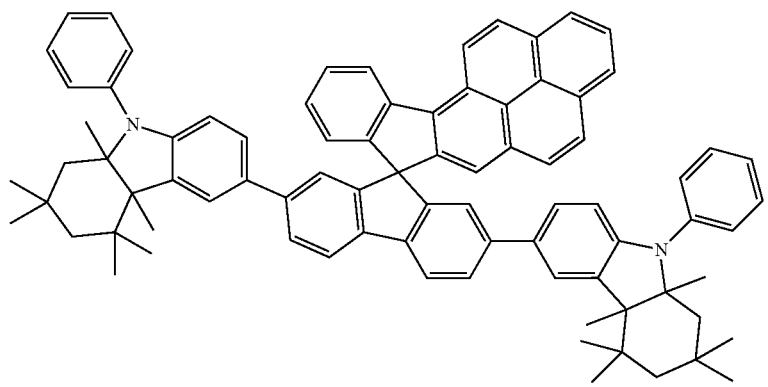
Formula 1860
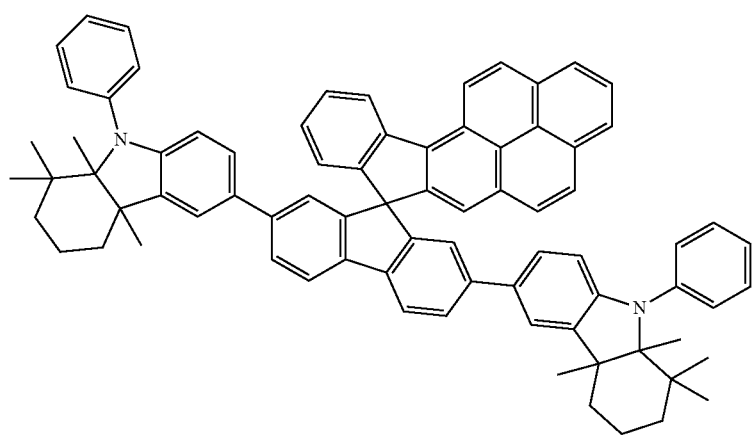
Formula 1861
Formula 1862
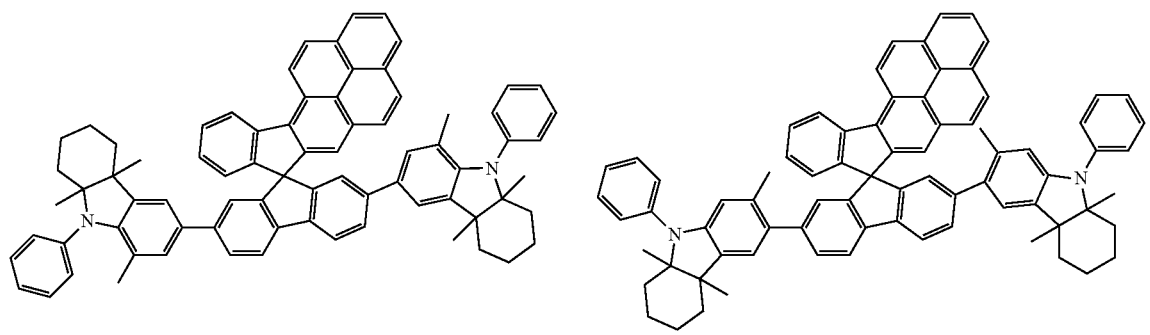
Formula 1863
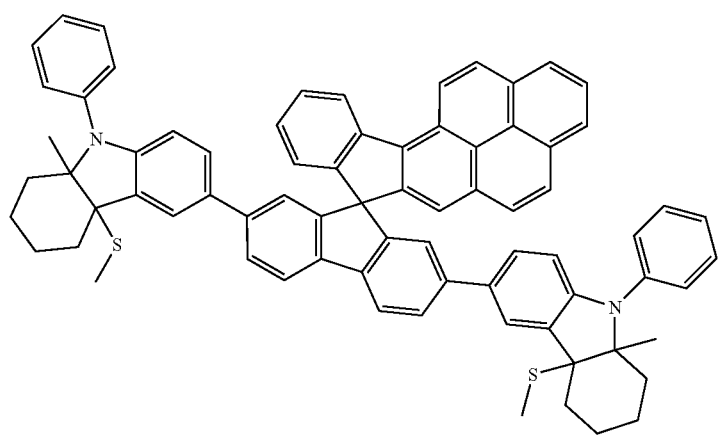

Formula 1864
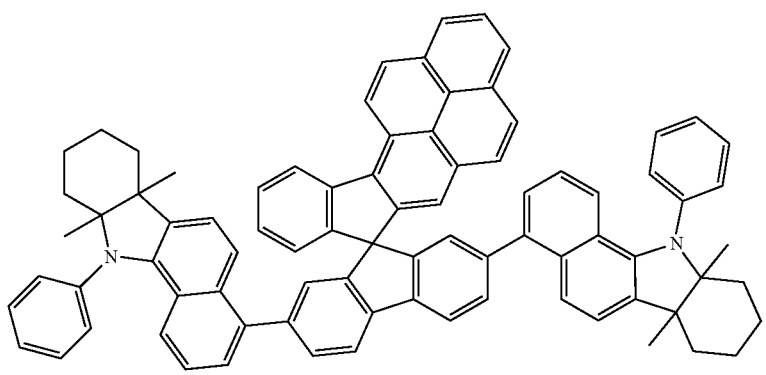
Formula 1865
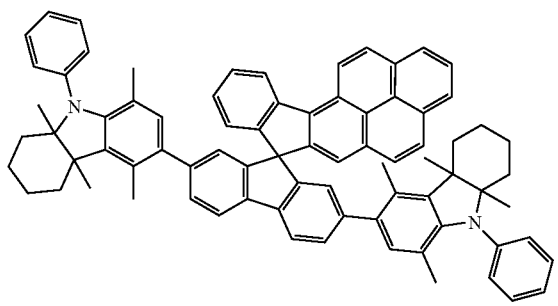
Formula 1866
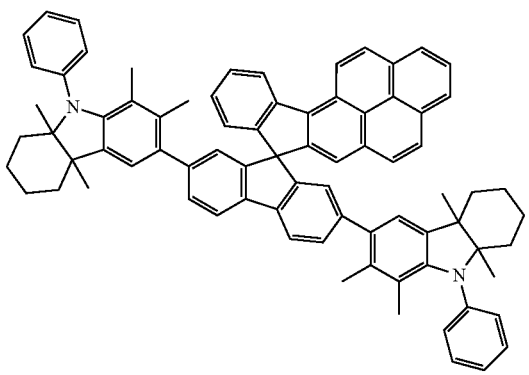
Formula 1867
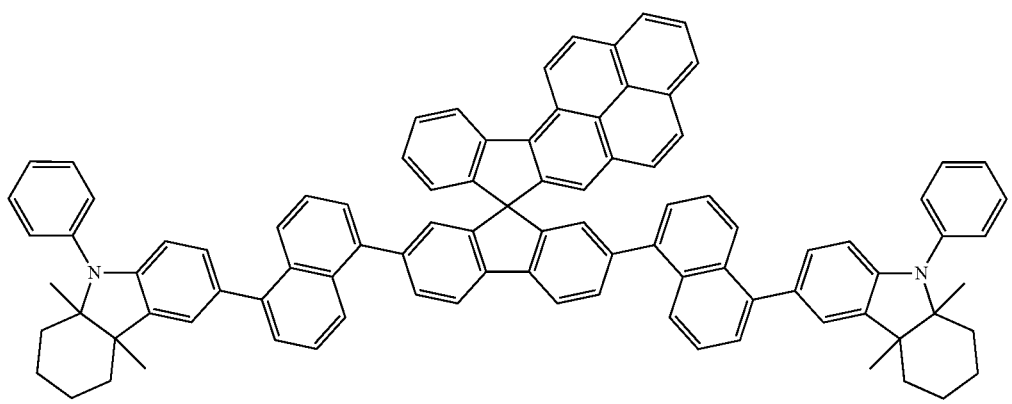
Formula 1868
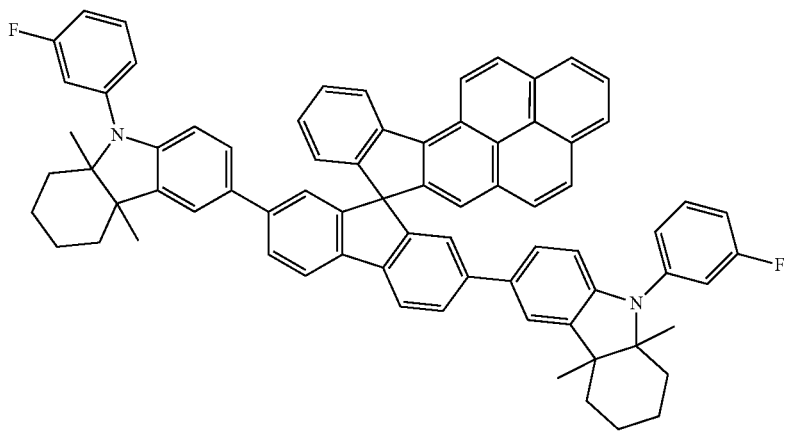

-continued
Formula 1869
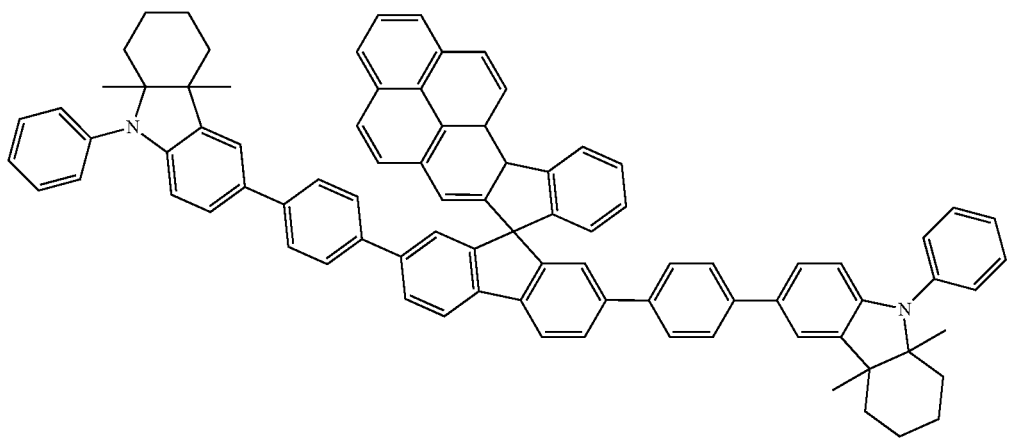
Formula 1870
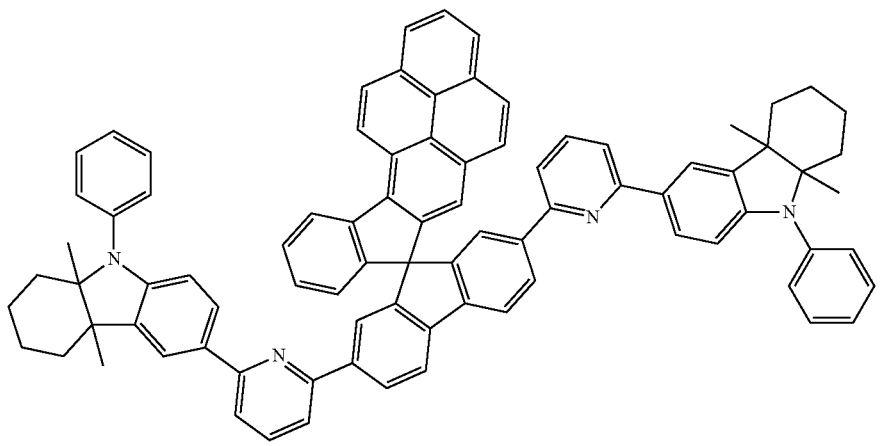
Formula 1871
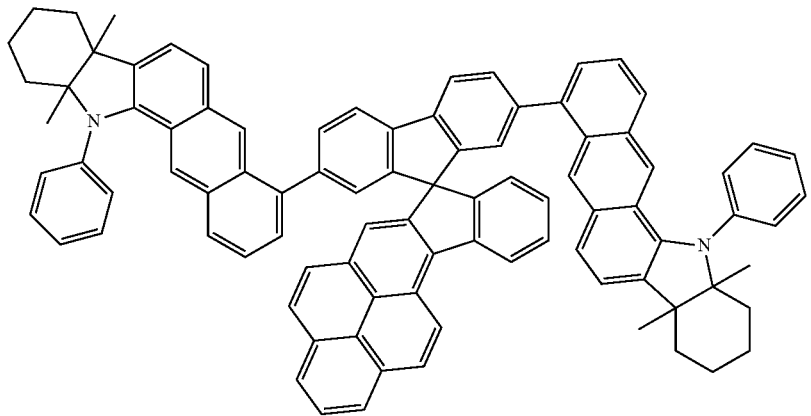

-continued
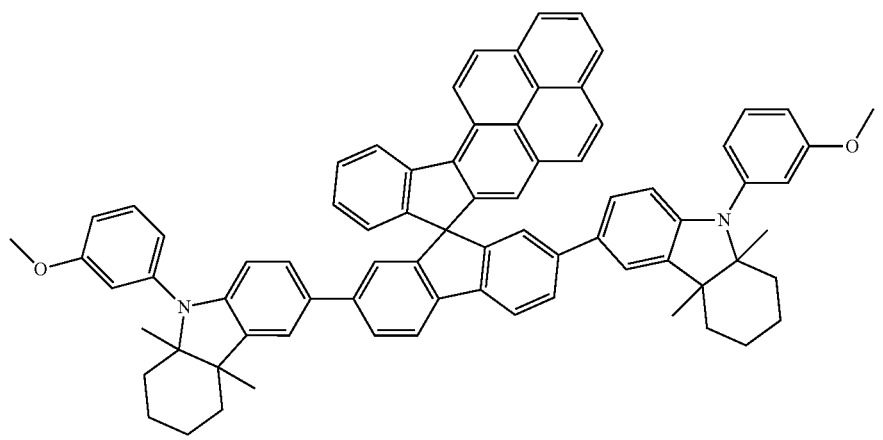
Formula 1872
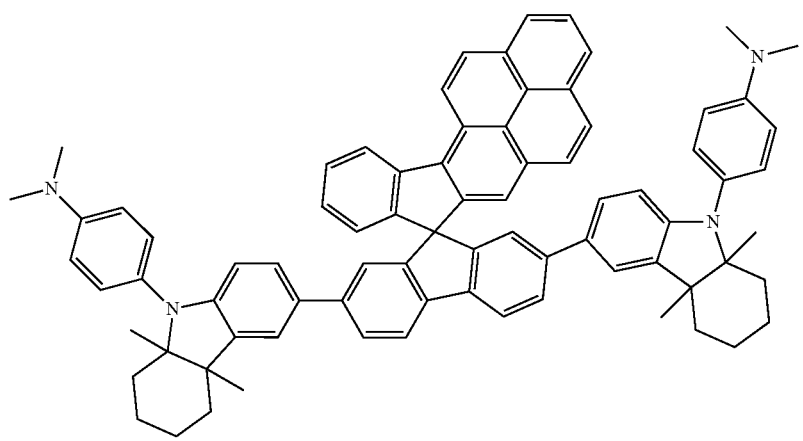
Formula 1873
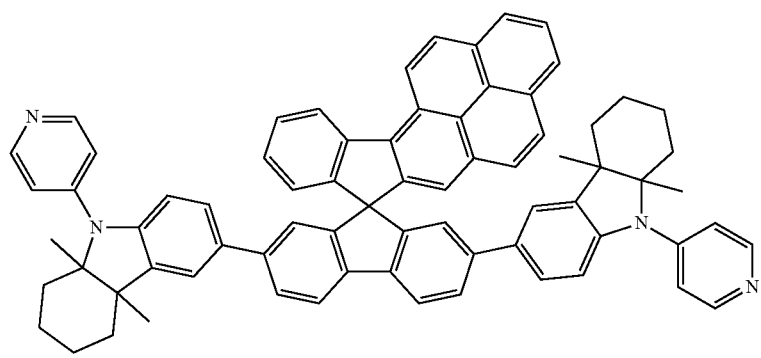
Formula 1874
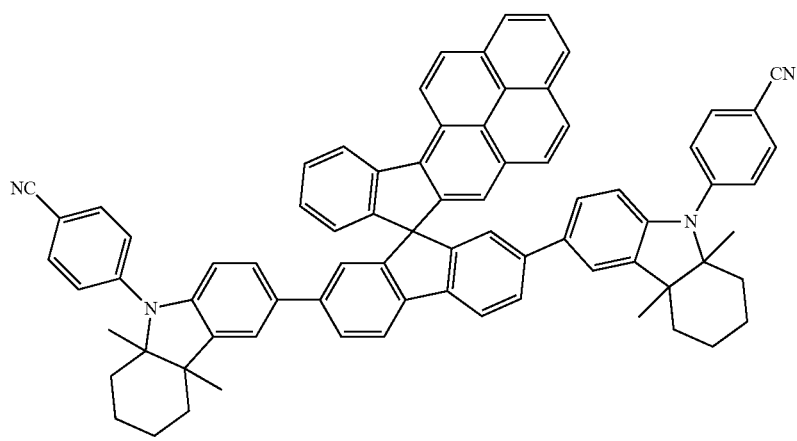
Formula 1875

Formula 1876
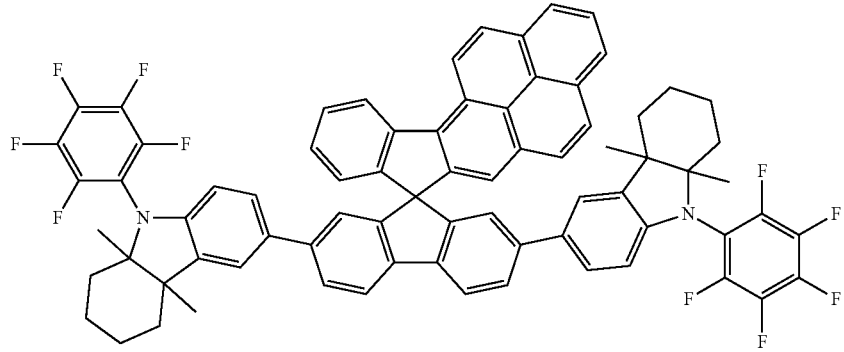
Formula 1877
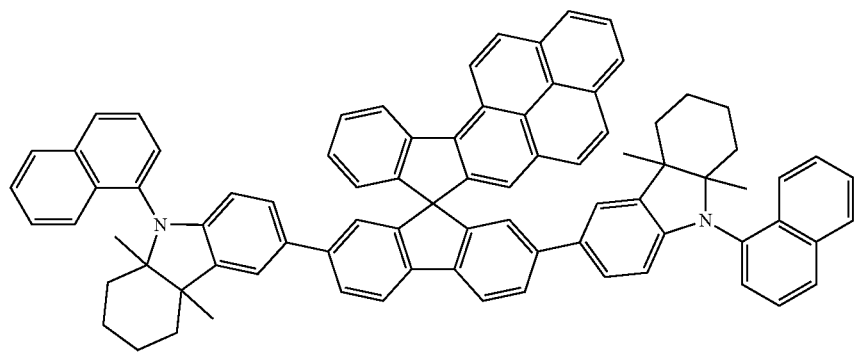
Formula 1878
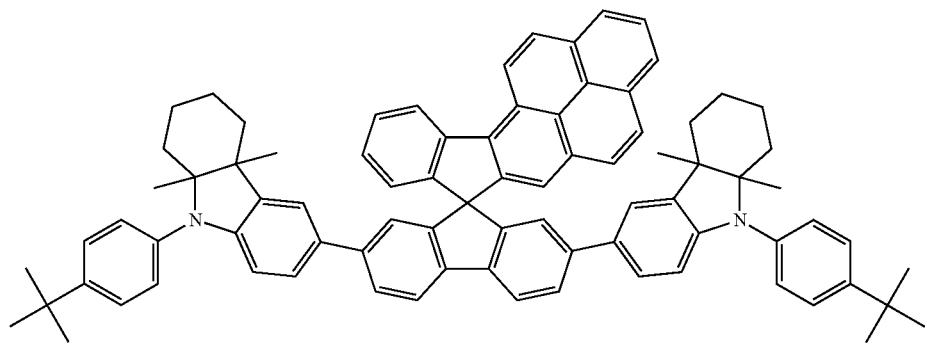
Formula 1879
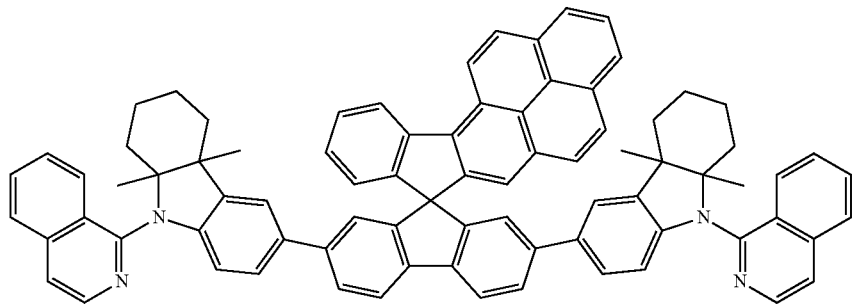

Formula 1880
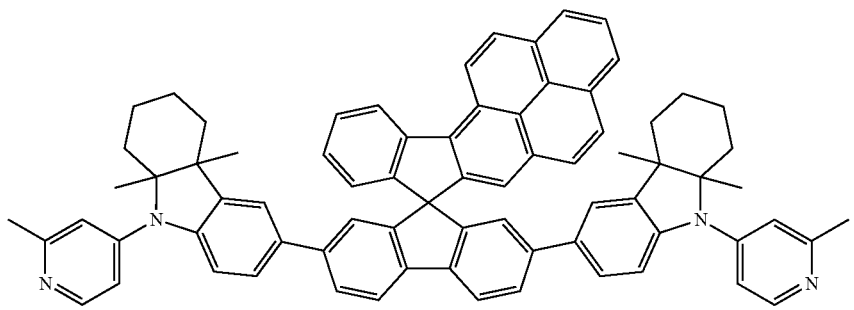
Formula 1881
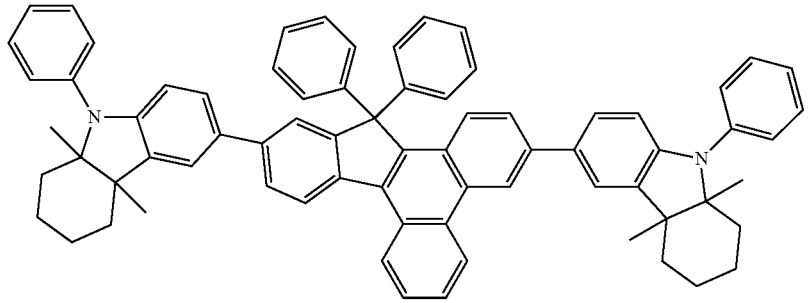
Formula 1882
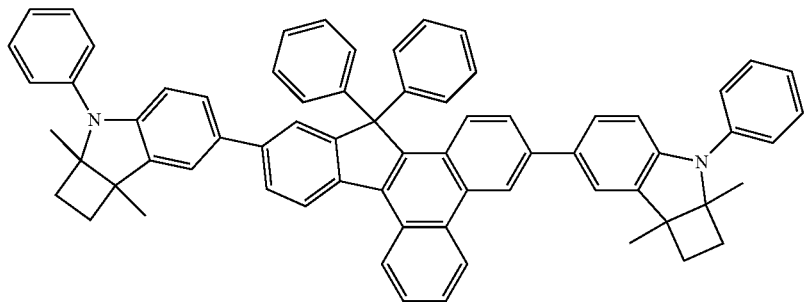
Formula 1883
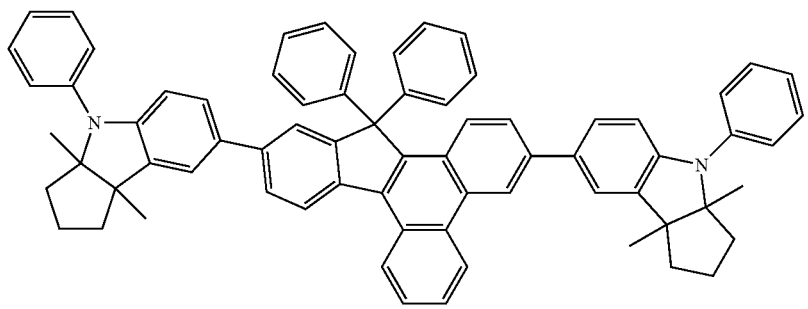
Formula 1884
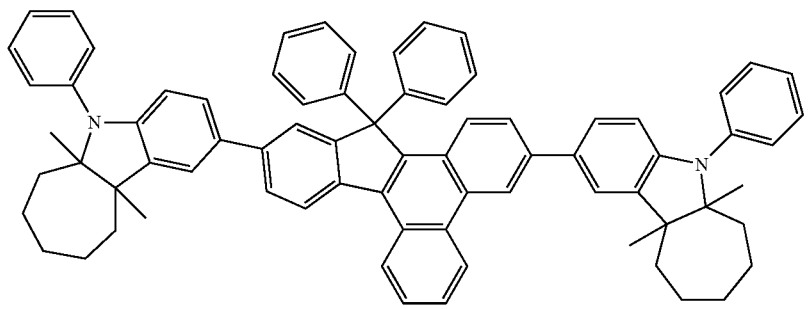

Formula 1885
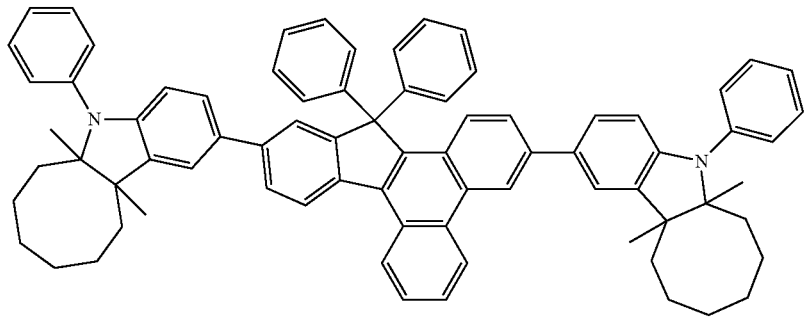
Formula 1886
Formula 1887
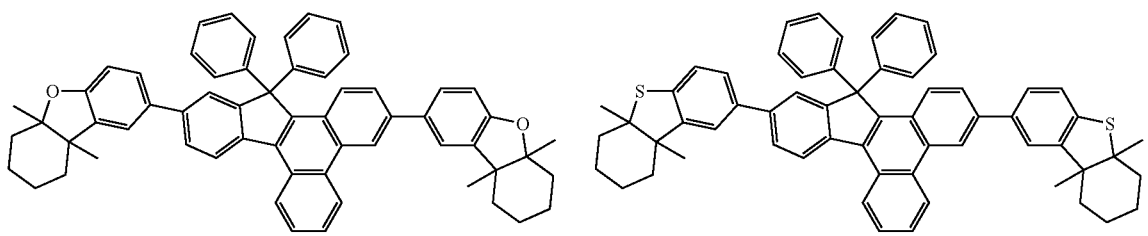
Formula 1888
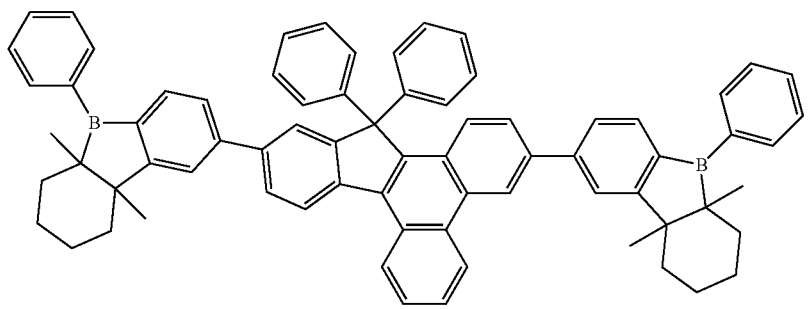
Formula 1889
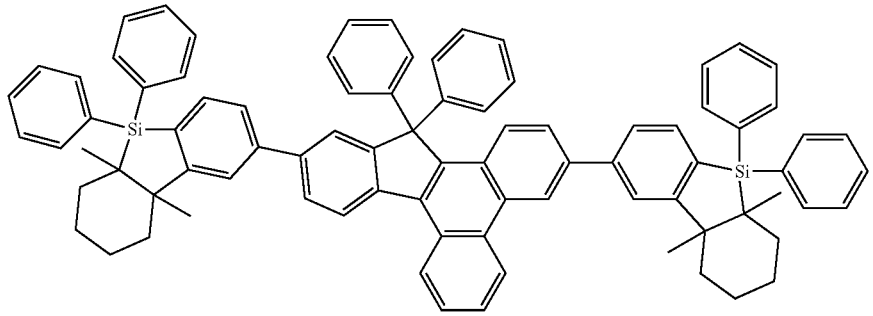
Formula 1890
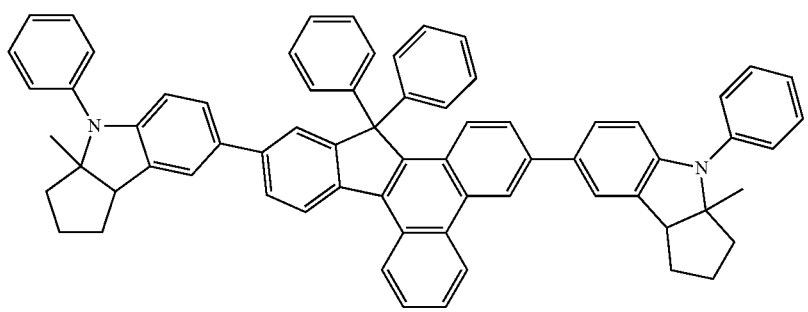

-continued
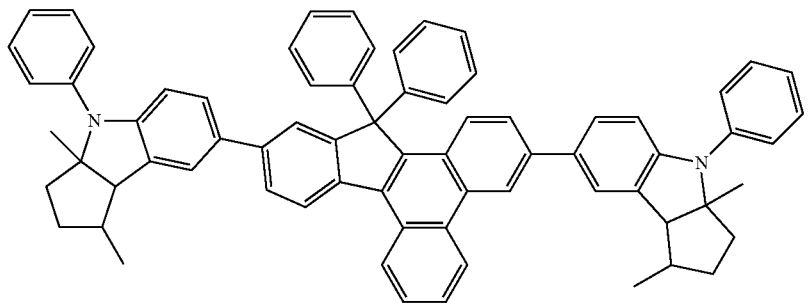
Formula 1891
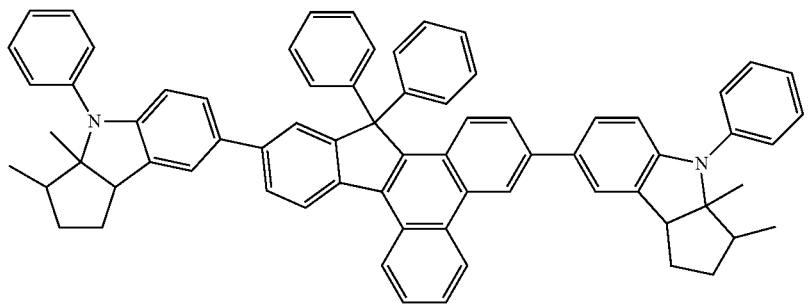
Formula 1892
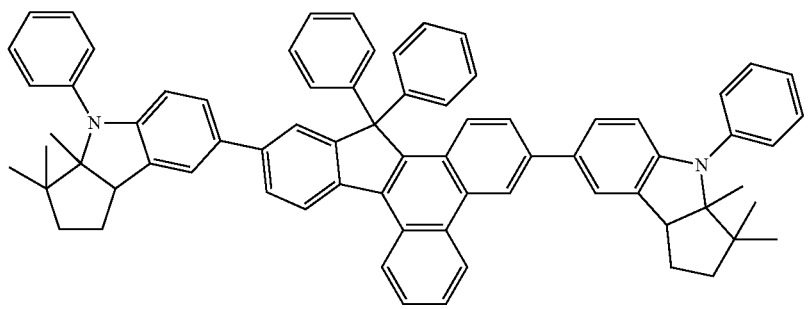
Formula 1893
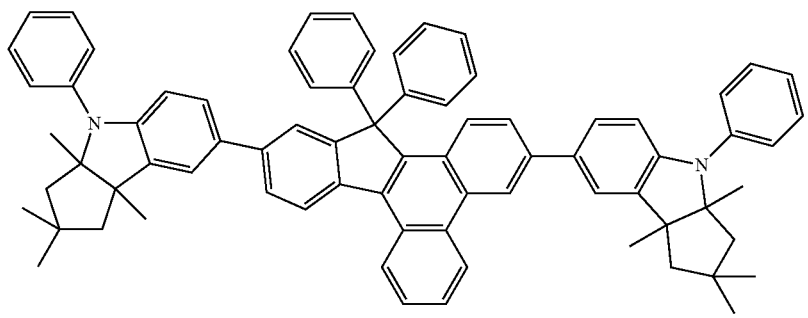
Formula 1894
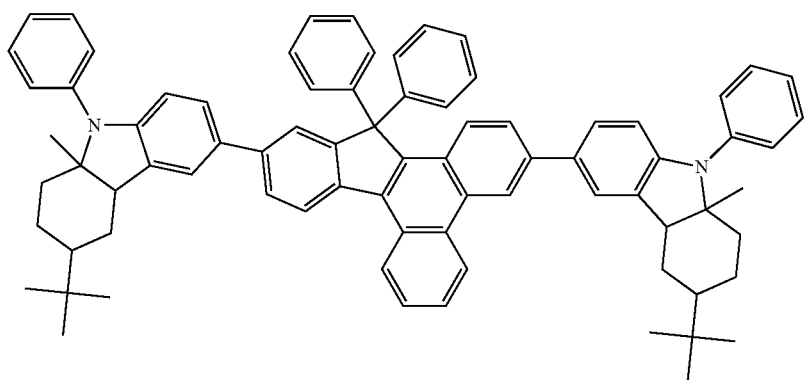
Formula 1895

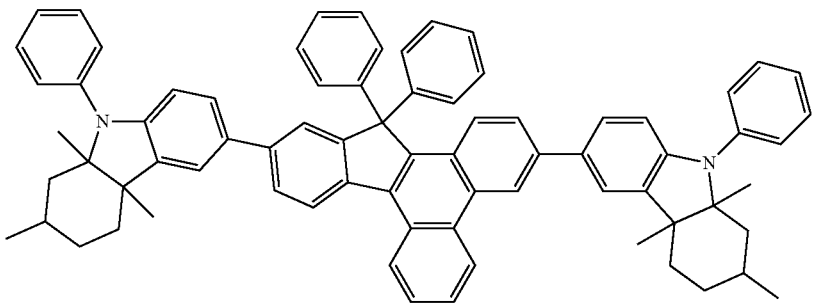
Formula 1896
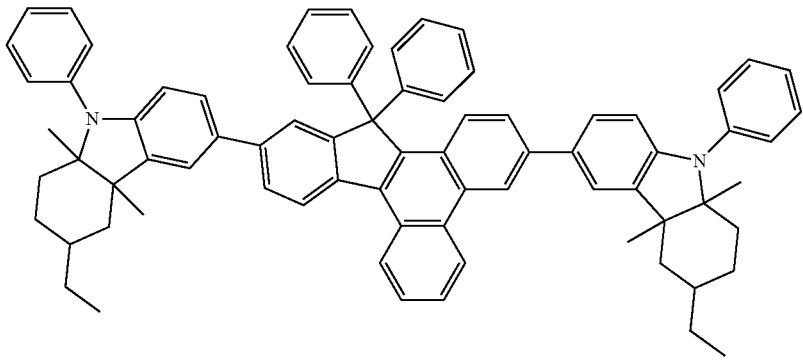
Formula 1897
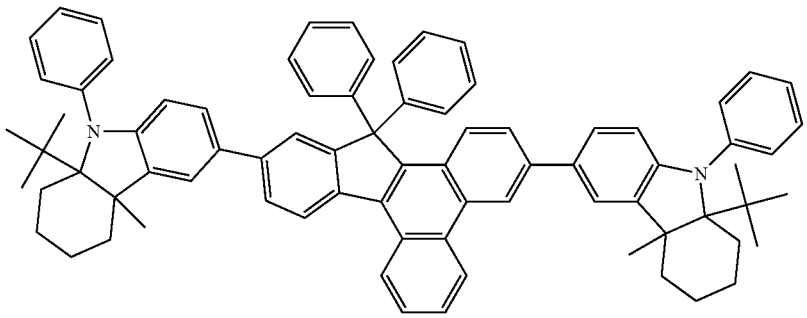
Formula 1898
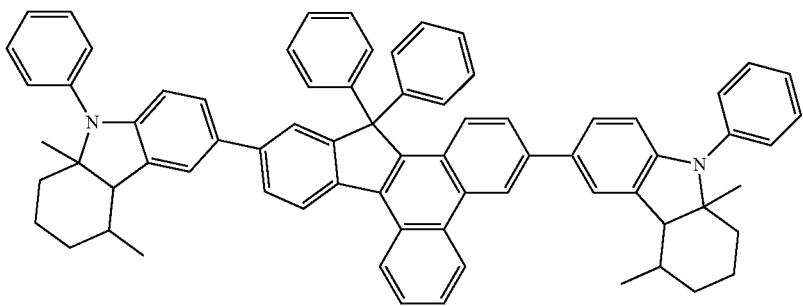
Formula 1899
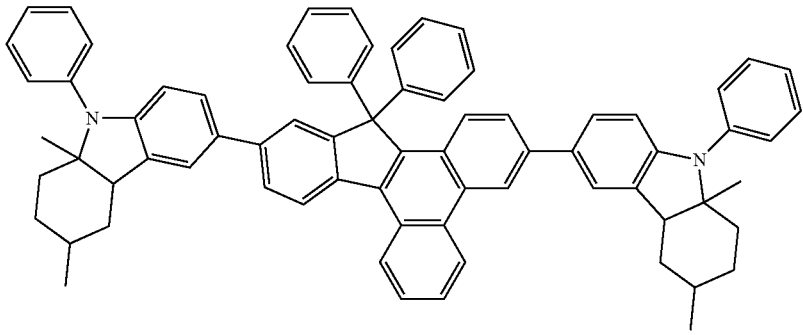
Formula 1900

-continued
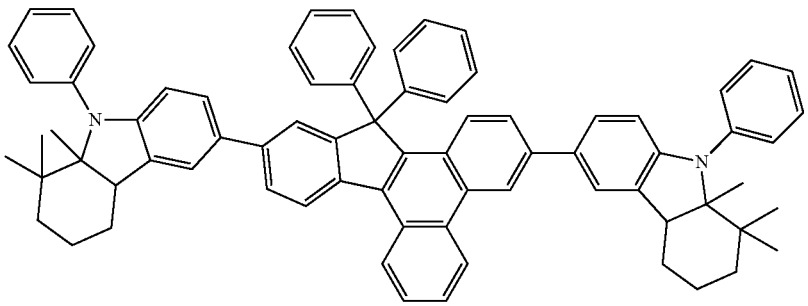
Formula 1901
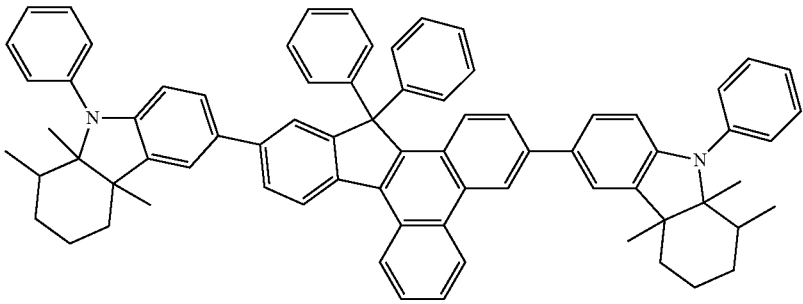
Formula 1902
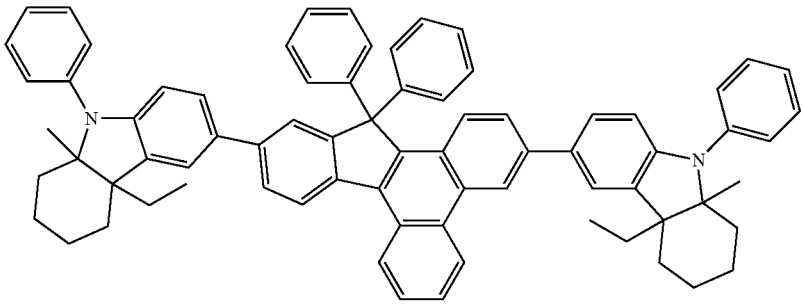
Formula 1903
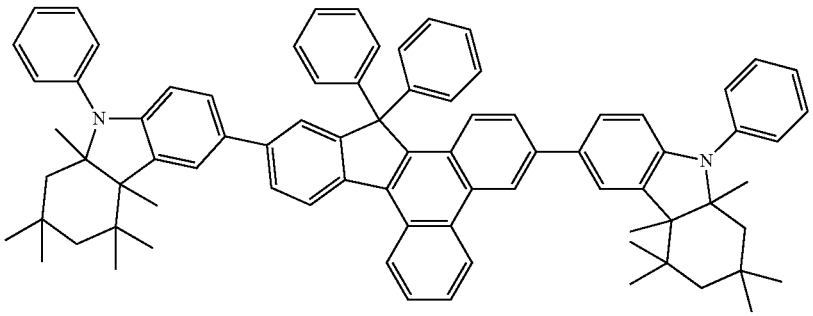
Fomula 1904
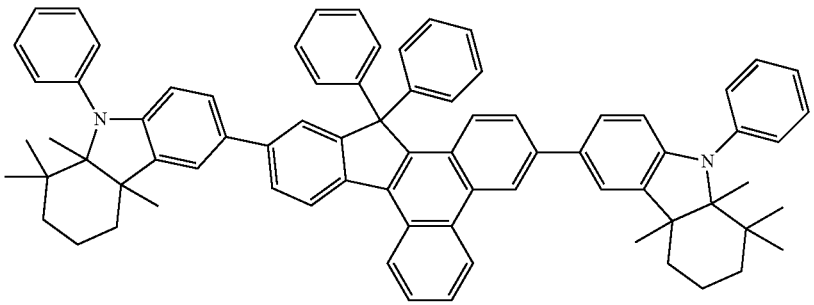
Formula 1905

-continued
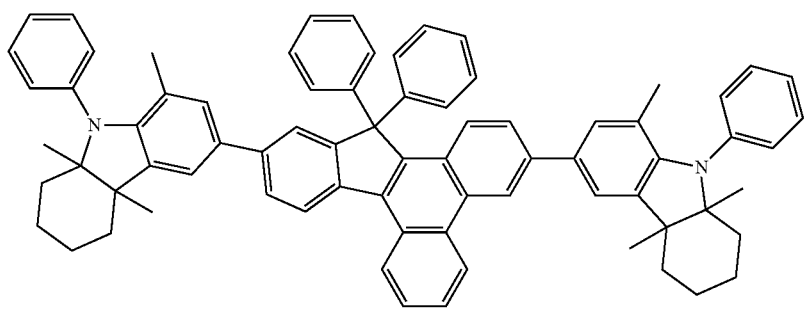
Formula 1906
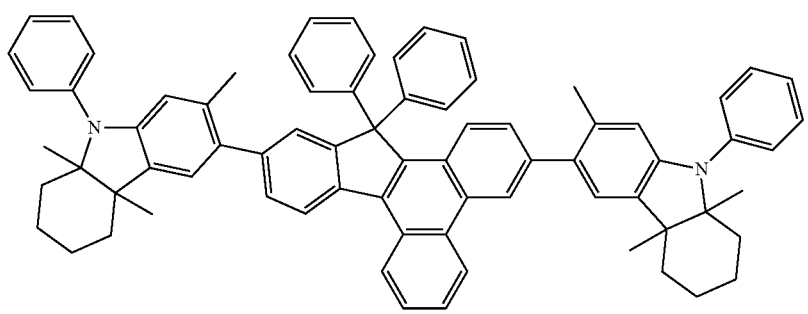
Formula 1907
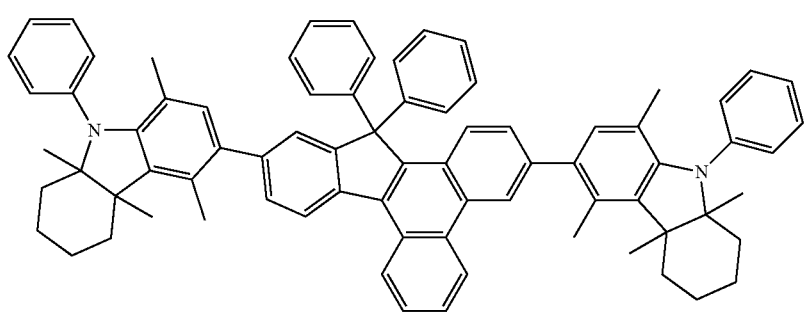
Formula 1908
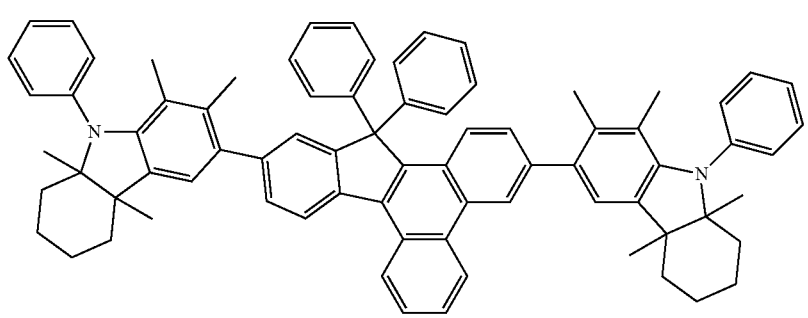
Formula 1909

Formula 1910
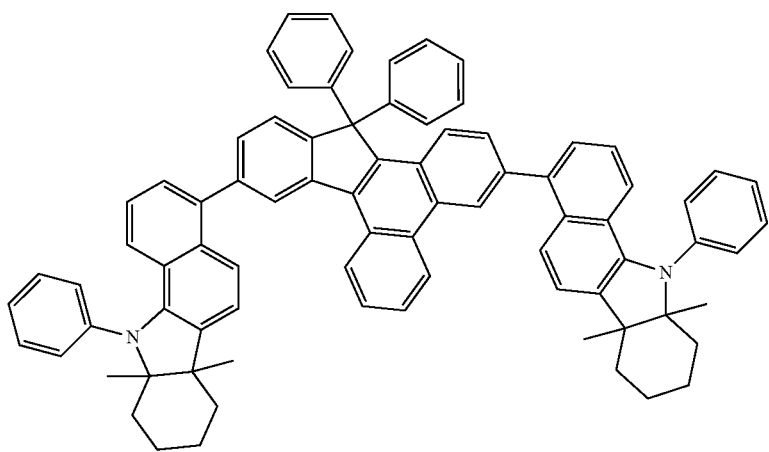
Formula 1911
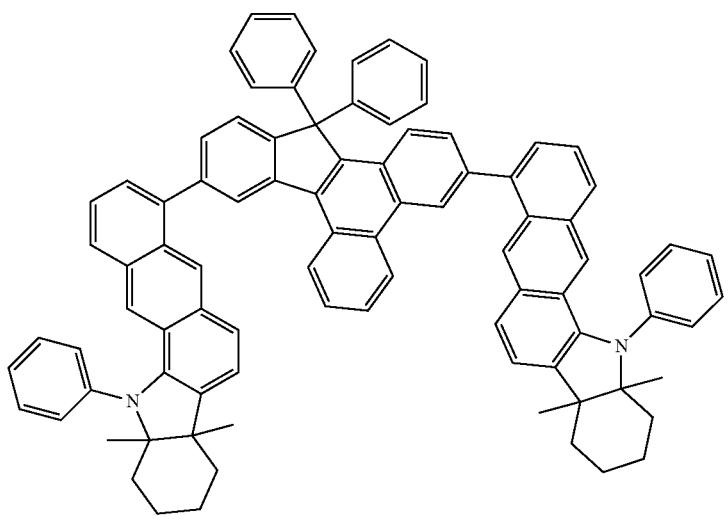
Formula 1912
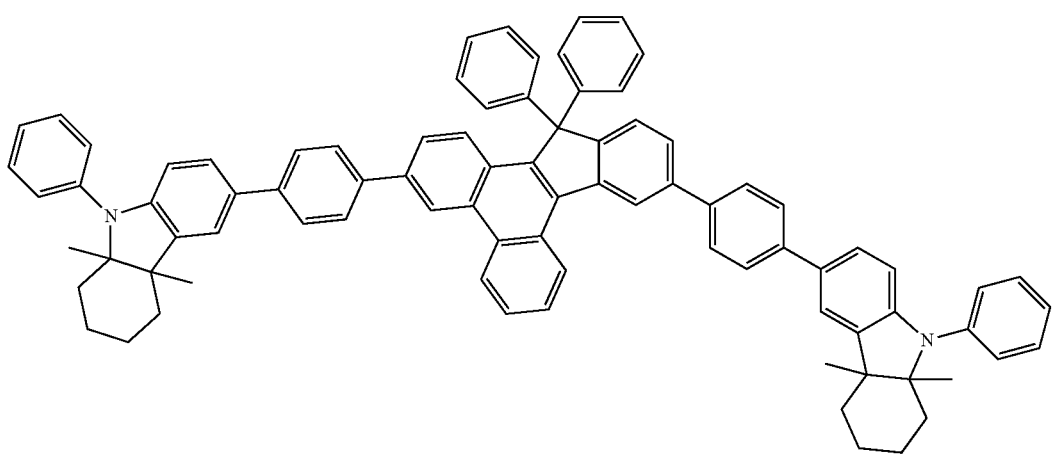

-continued
Formula 1913
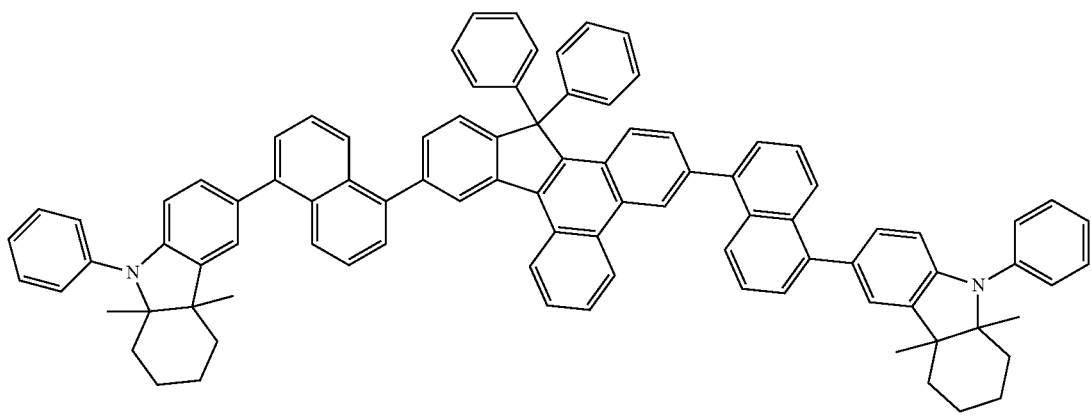
Formula 1914
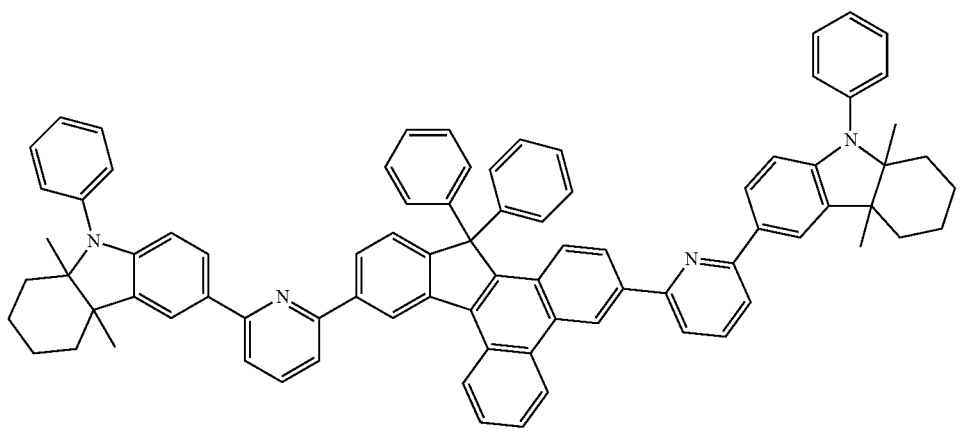
Formula 1915
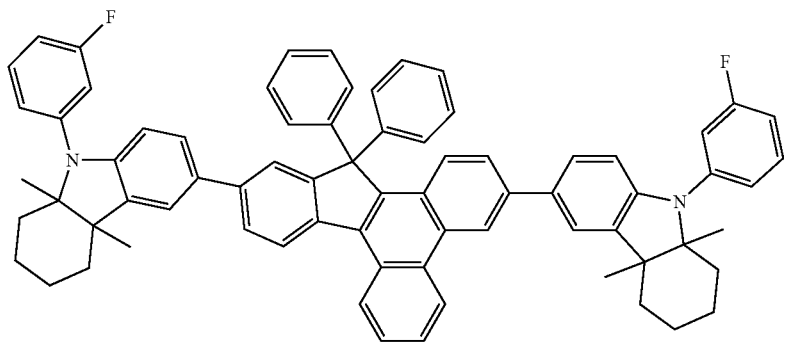
Formula 1916
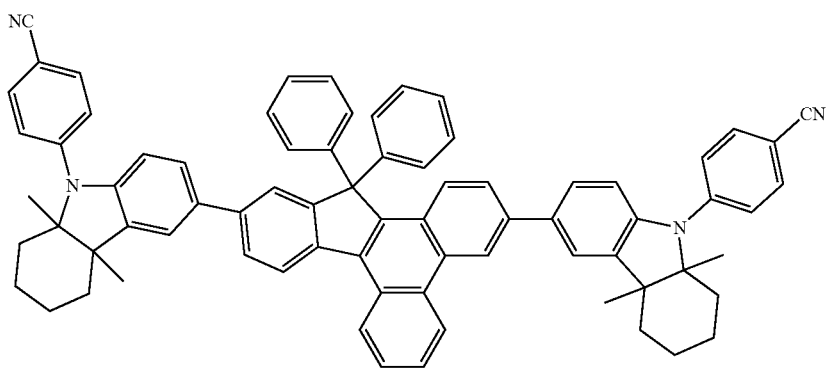

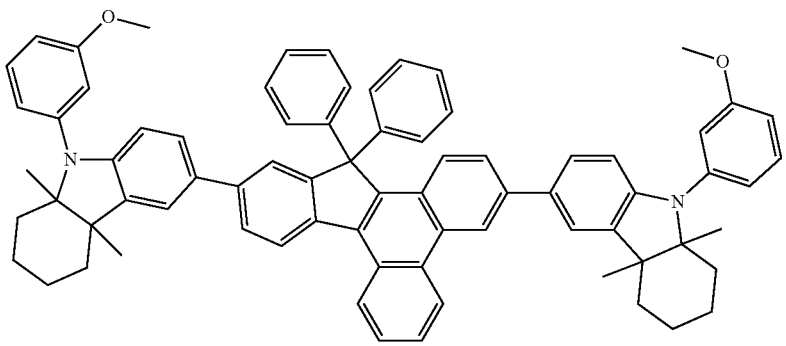
Formula 1917
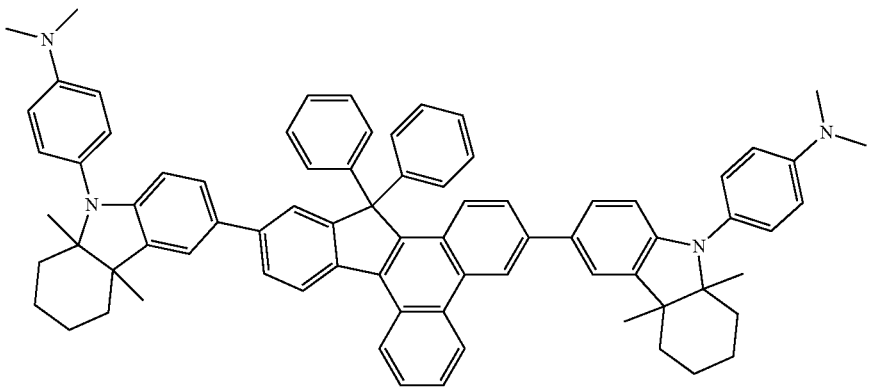
Formula 1918
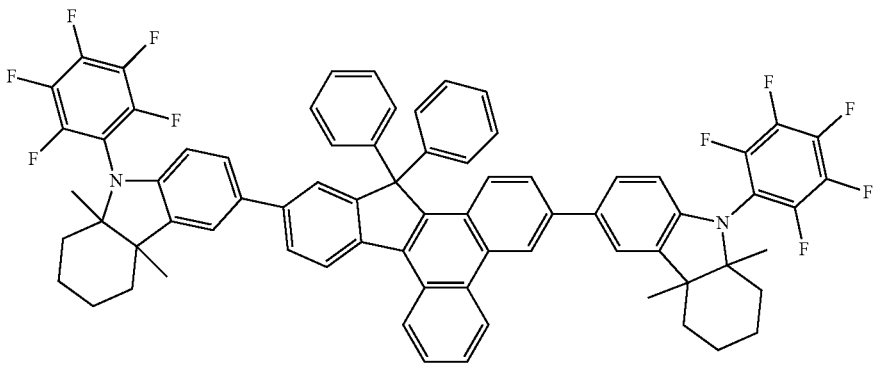
Formula 1919
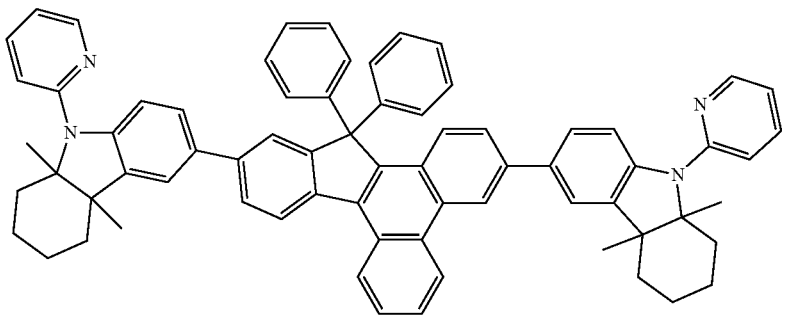
Formula 1920

-continued
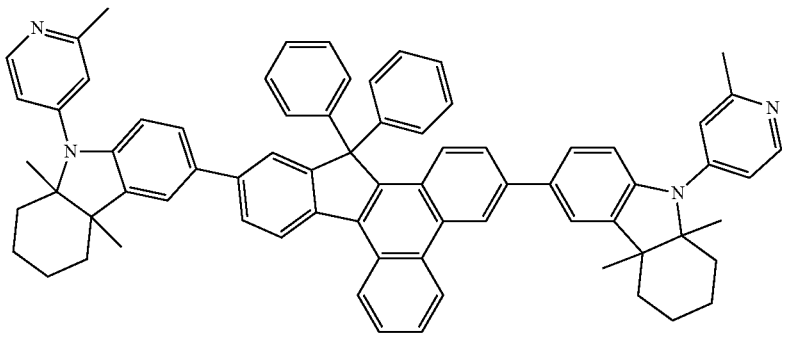
Formula 1921
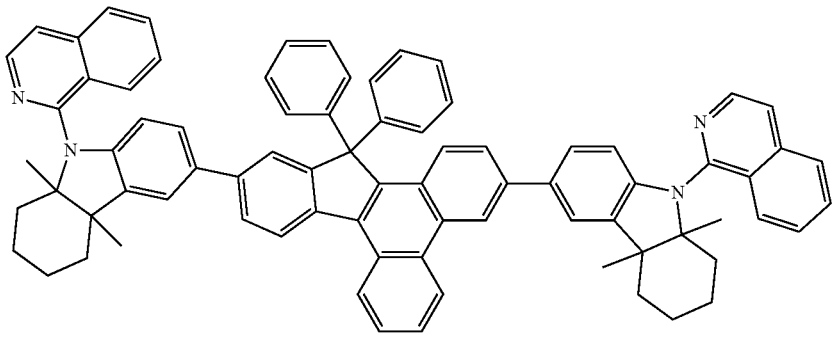
Formula 1922
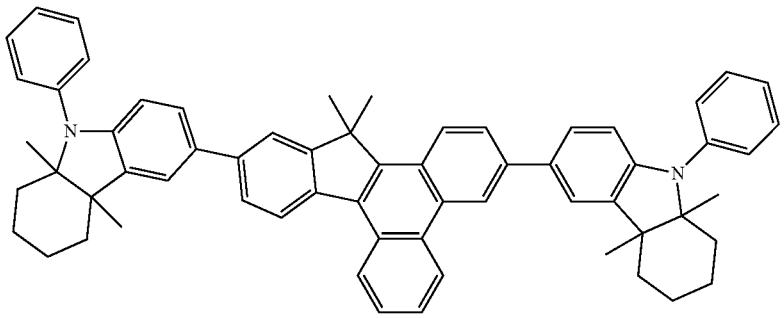
Formula 1923
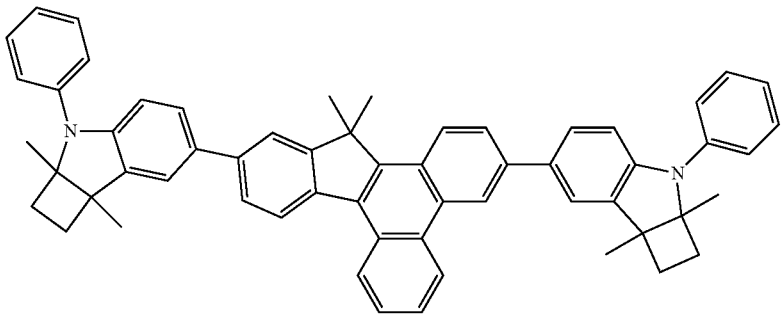
Formula 1924
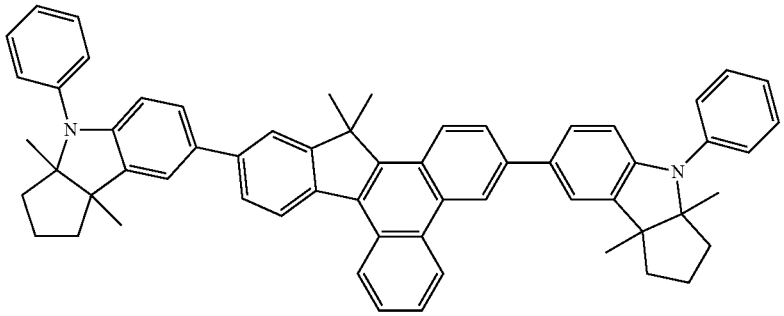
Formula 1925

Formula 1926
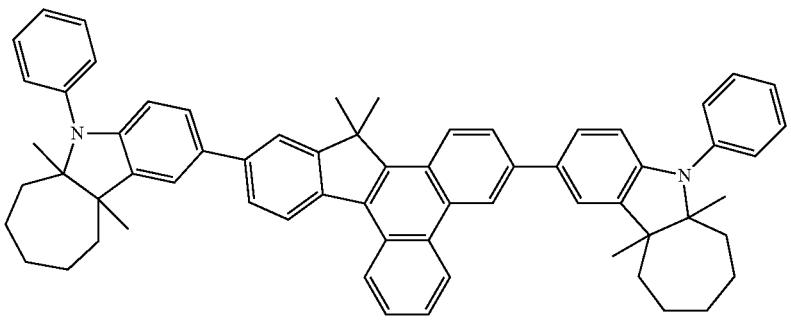
Formula 1927
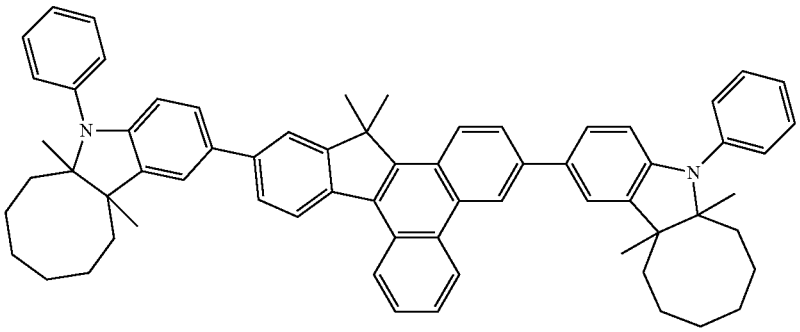
Formula 1928
Formula 1929
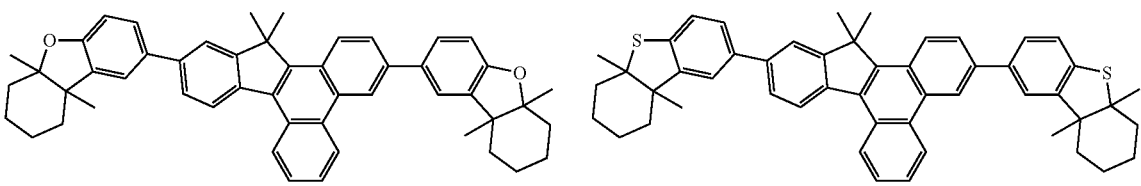
Formula 1930
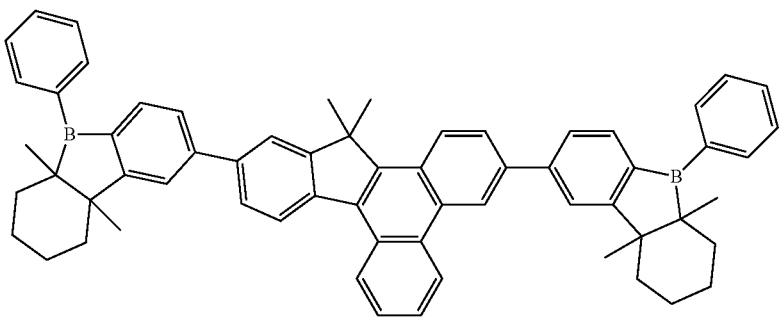
Formula 1931
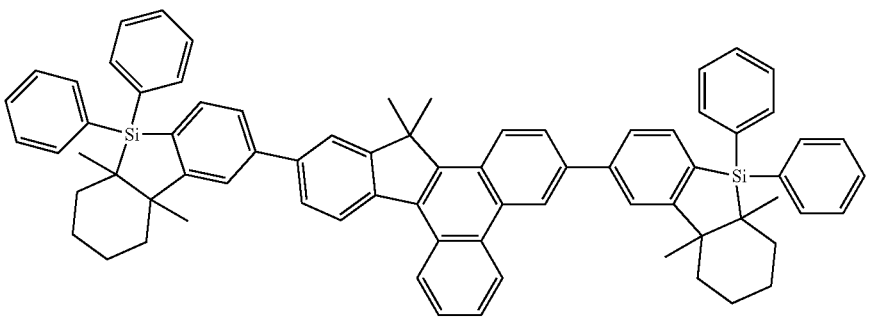

-continued
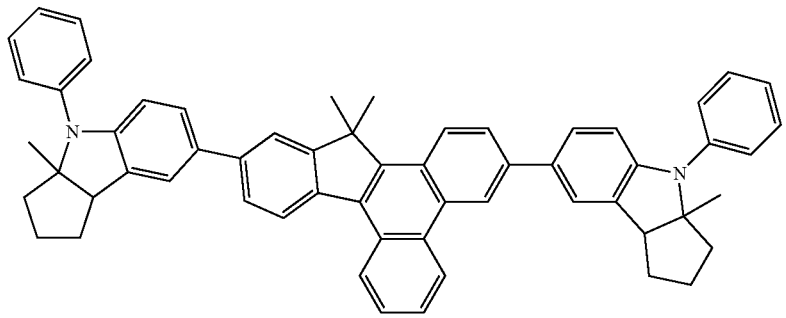
Formula 1932
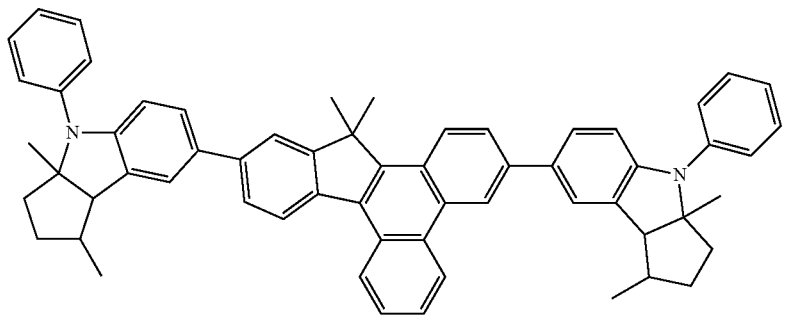
Formula 1933
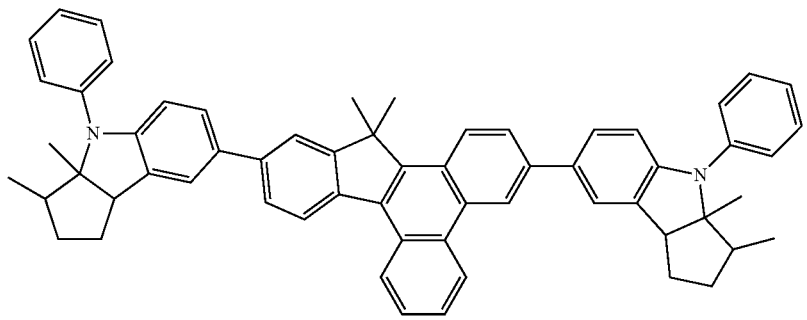
Formula 1934
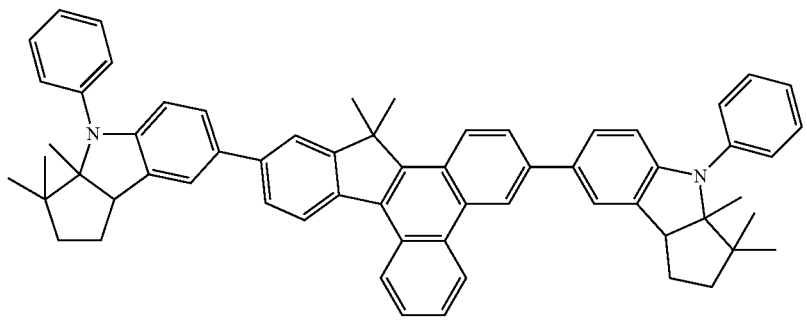
Formula 1935
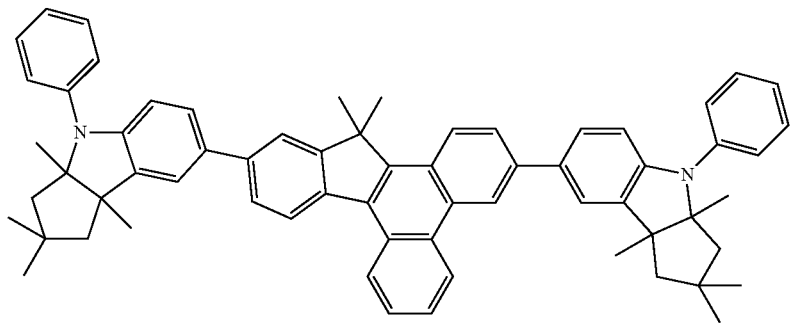
Formula 1936

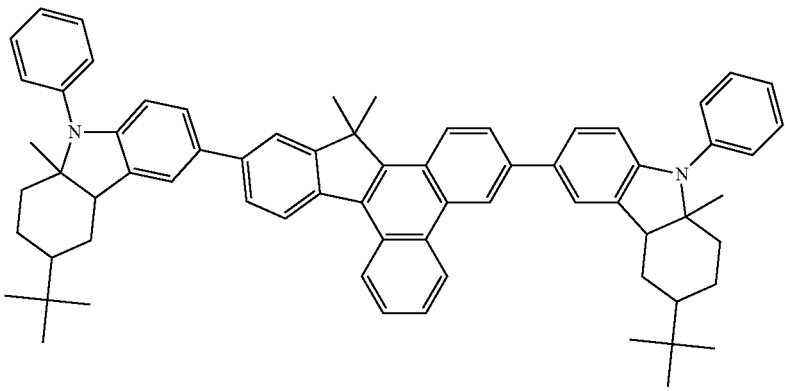
Formula 1937
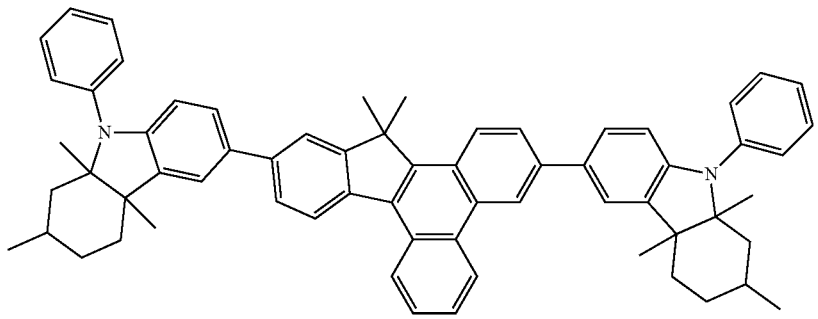
Formula 1938
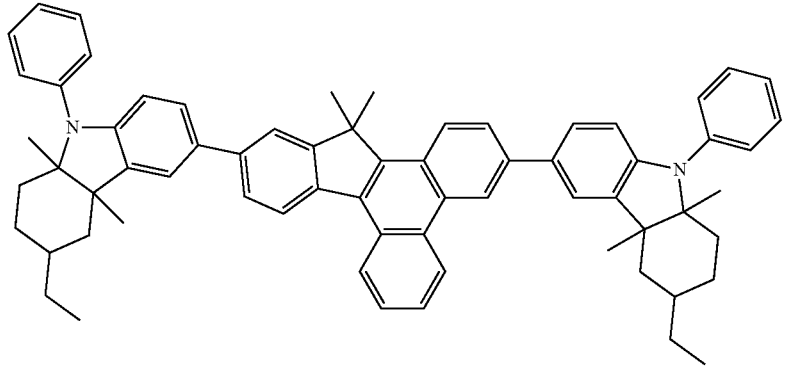
Formula 1939
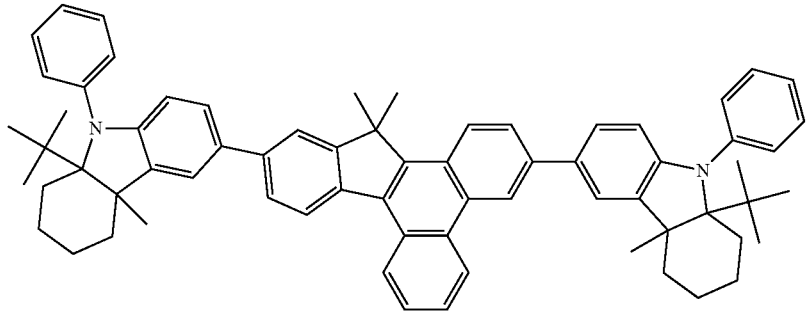
Formula 1940

Formula 1941
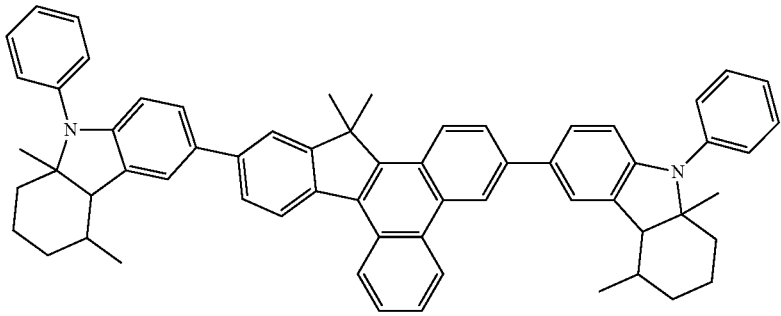
Formula 1942
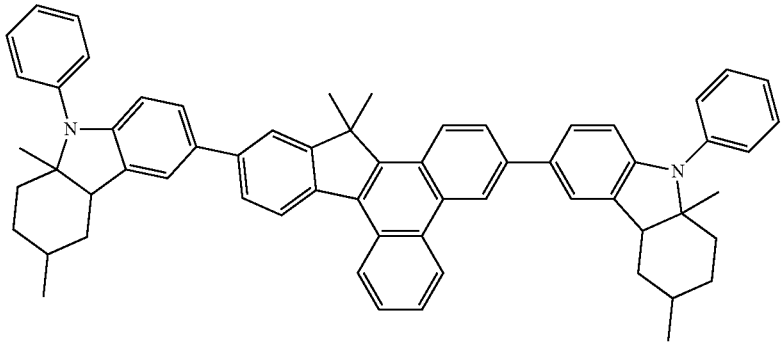
Formula 1943
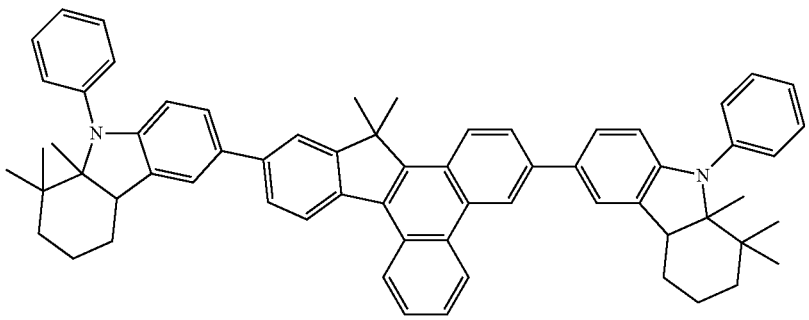
Formula 1944
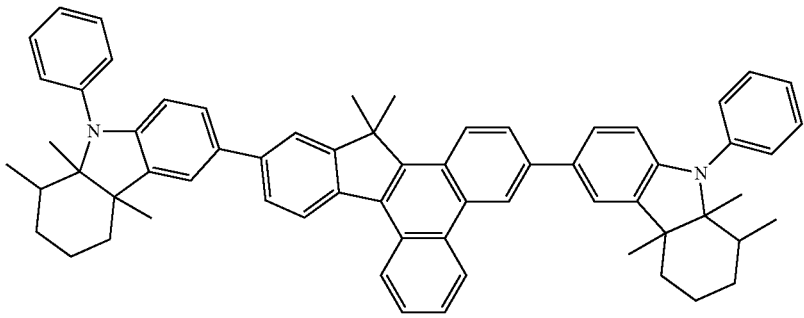
Formula 1945
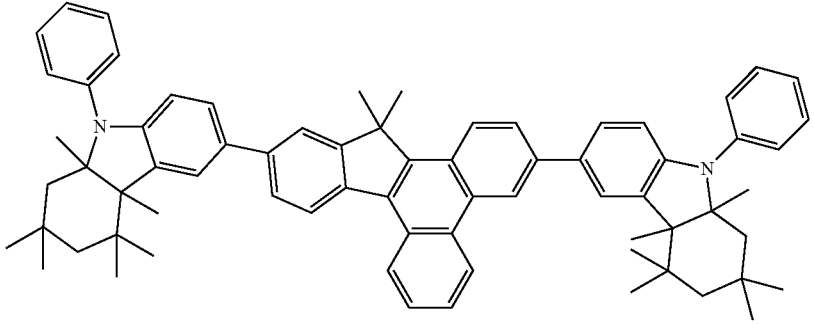

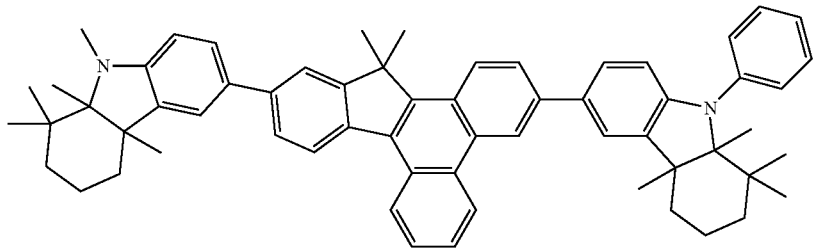
Formula 1946
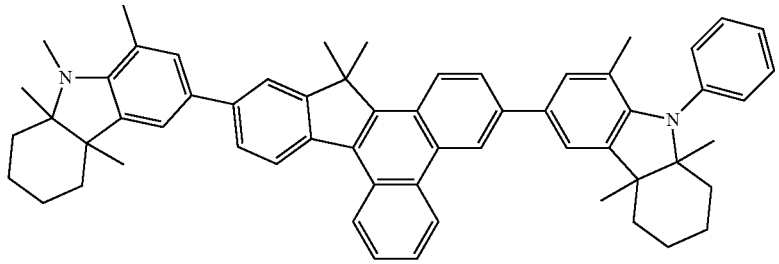
Formula 1947
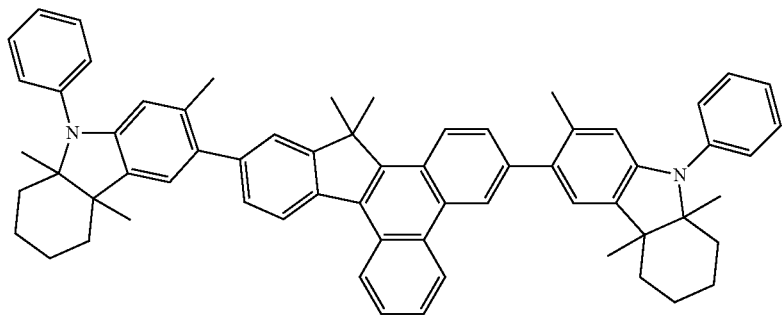
Formula 1948
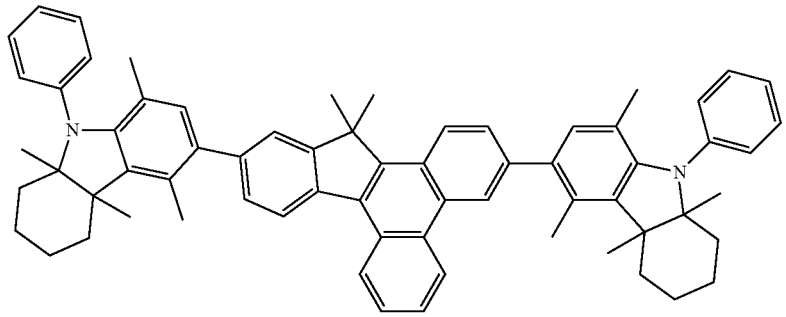
Formula 1949
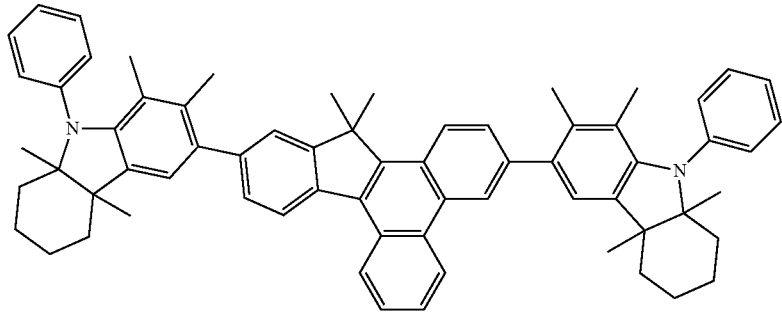
Formula 1950

Formula 1951
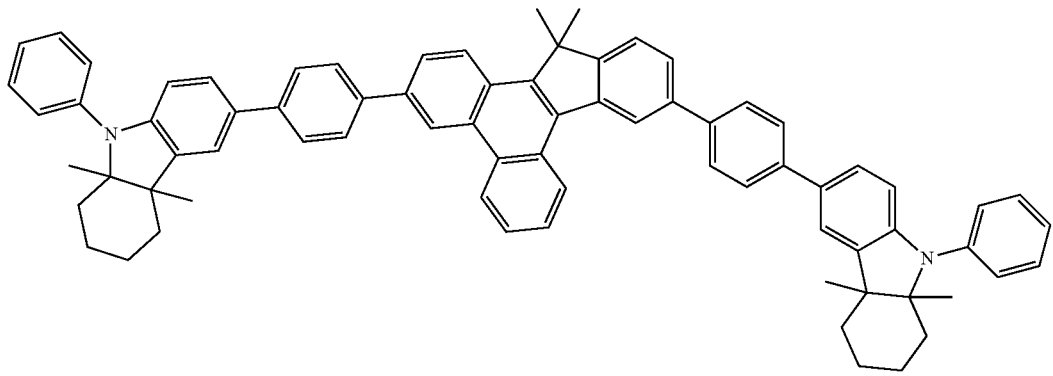
Formula 1952
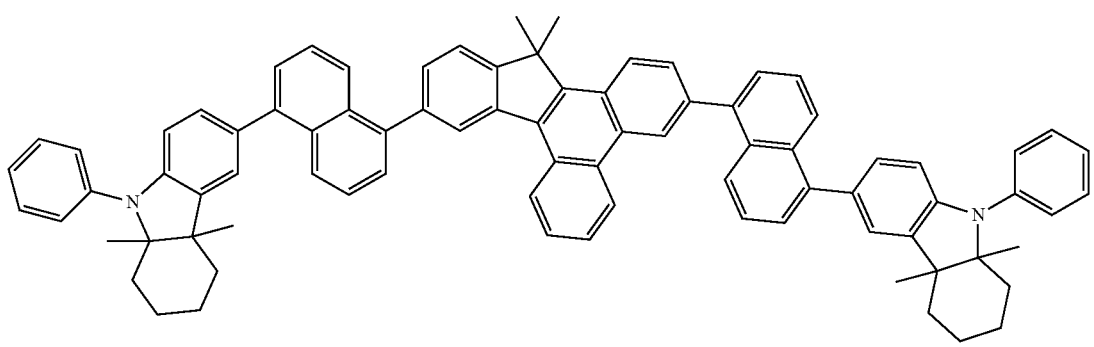
Formula 1953
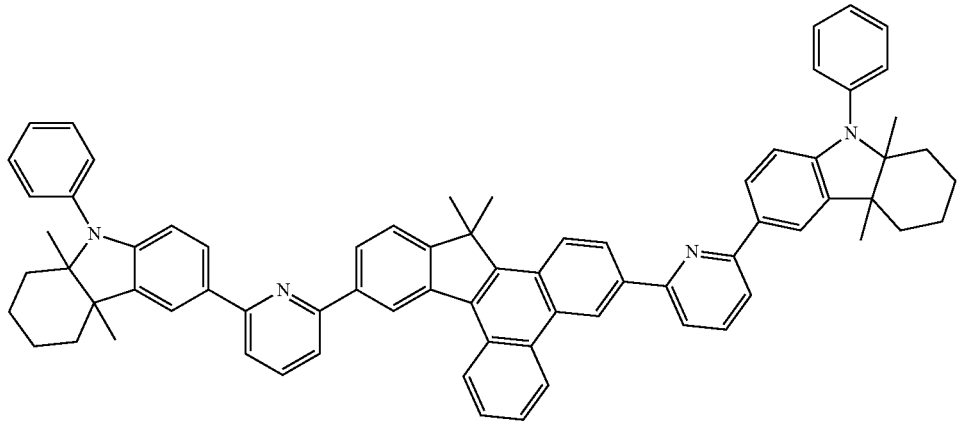
Formula 1954
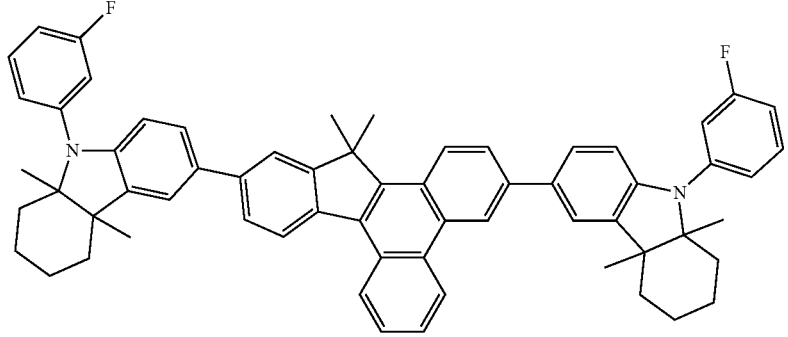

-continued
Formula 1955
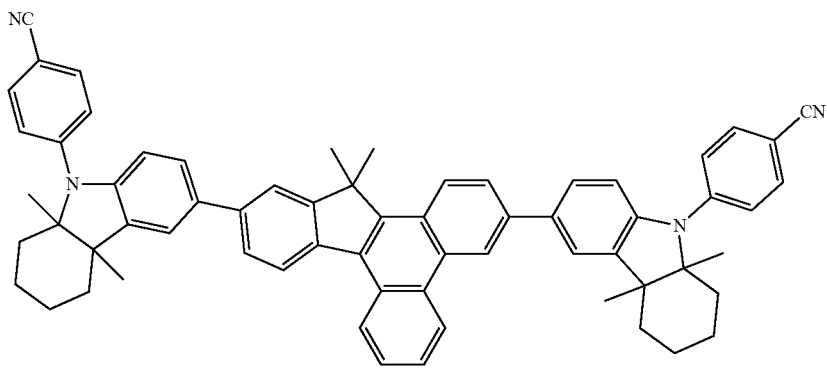
Formula 1956
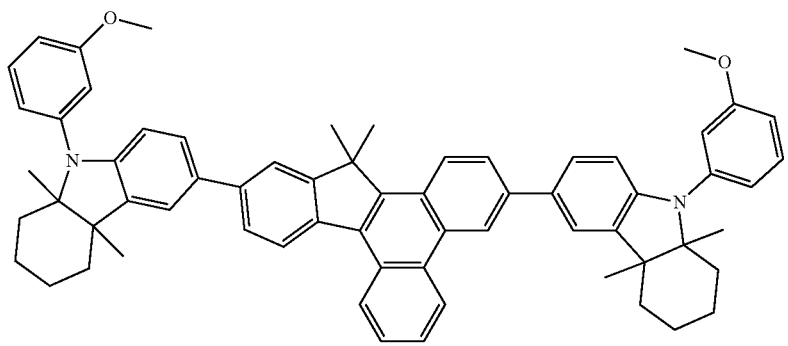
Formula 1957
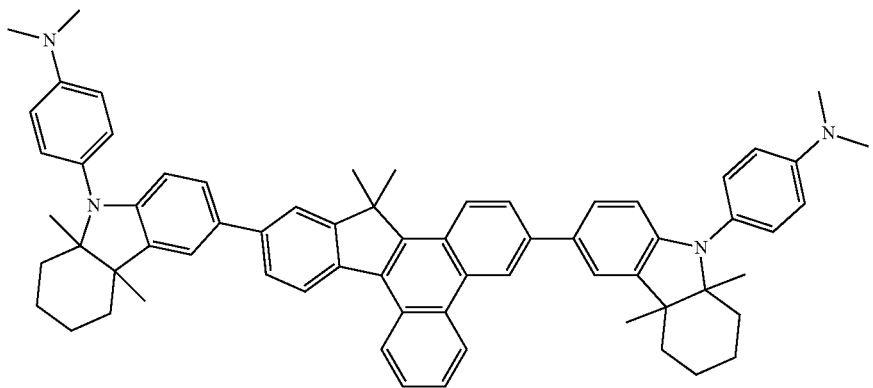
Formula 1958
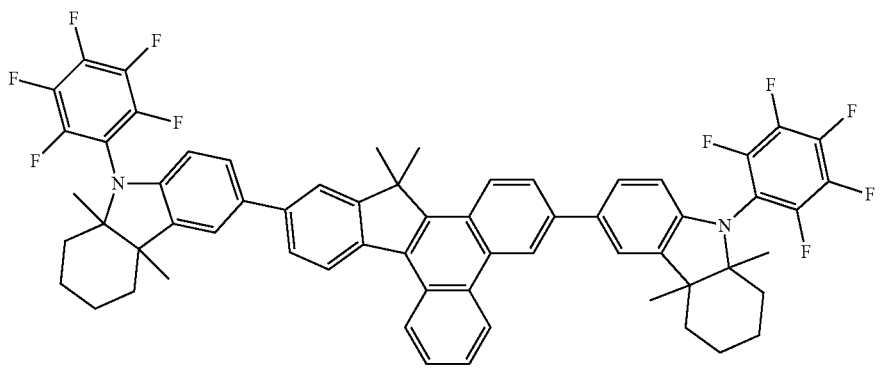

-continued
Formula 1959
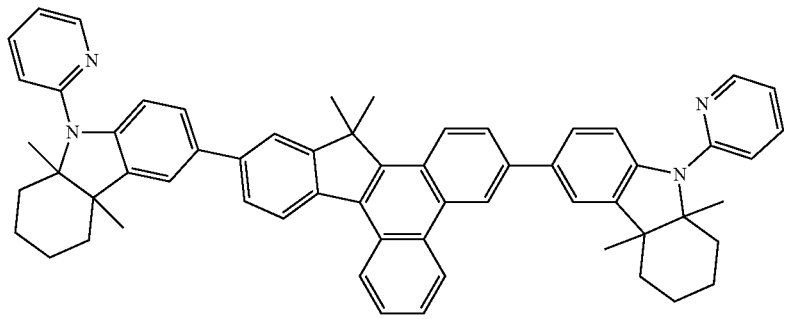
Formula 1960
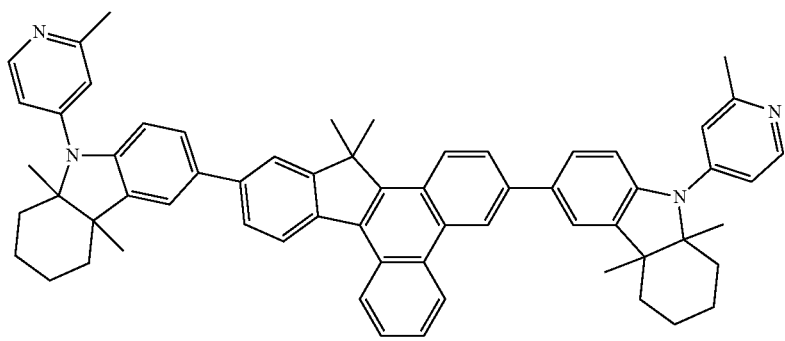
Formula 1961
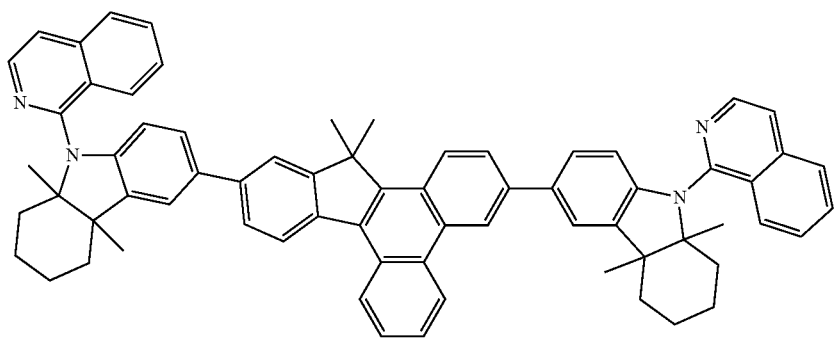
Formula 1962
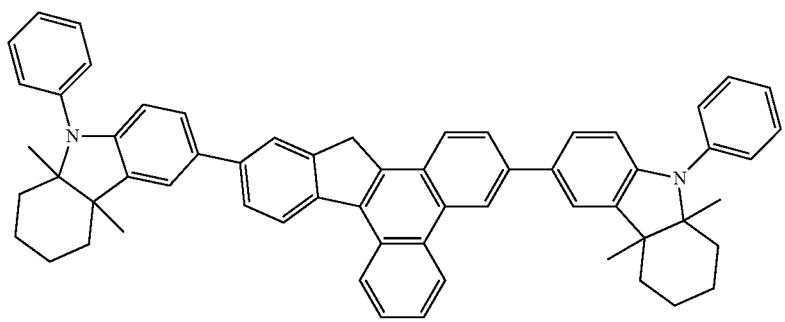
Formula 1963
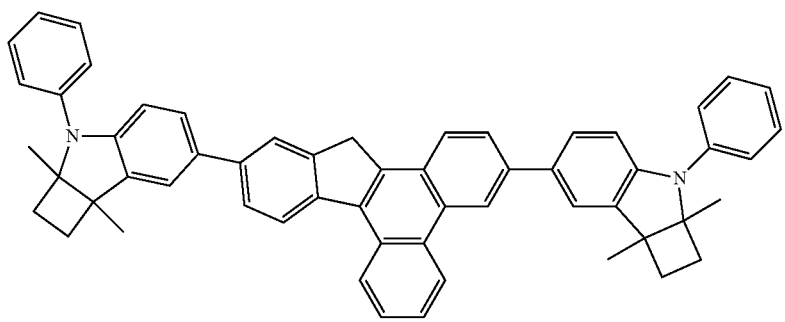

-continued
Formula 1964
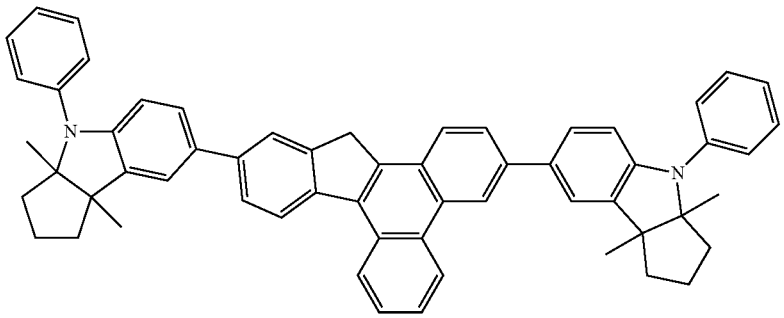
Formula 1965
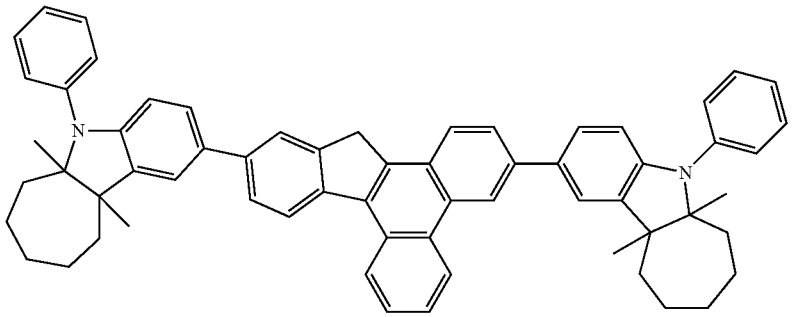
Formula 1966
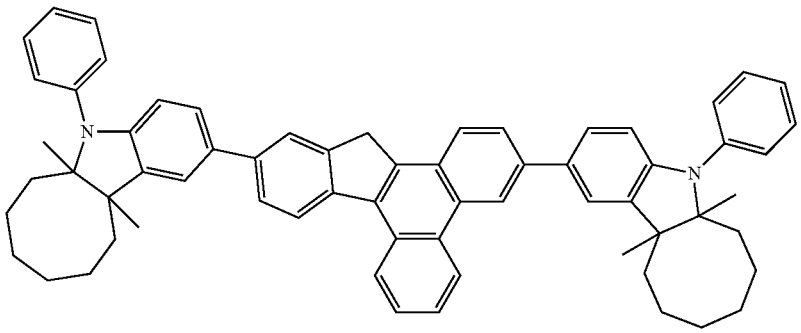
Formula 1967     Formula 1968
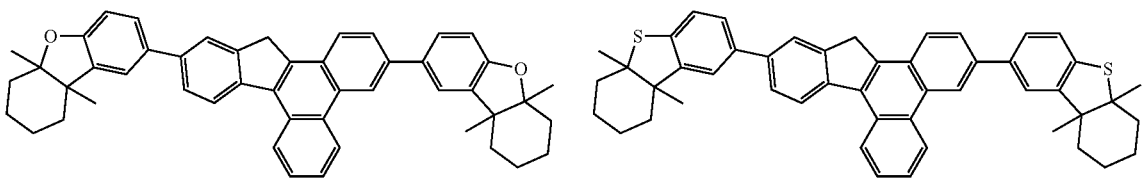
Formula 1969
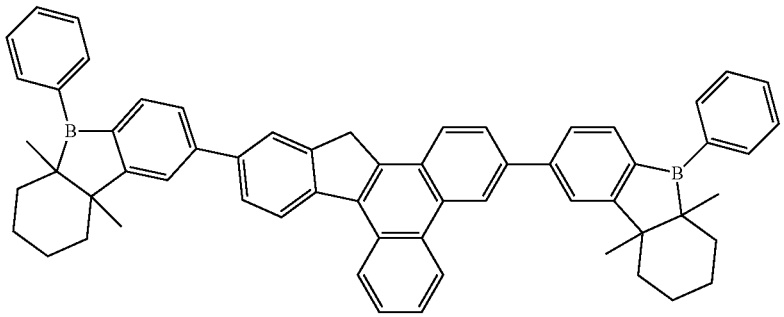

Formula 1970
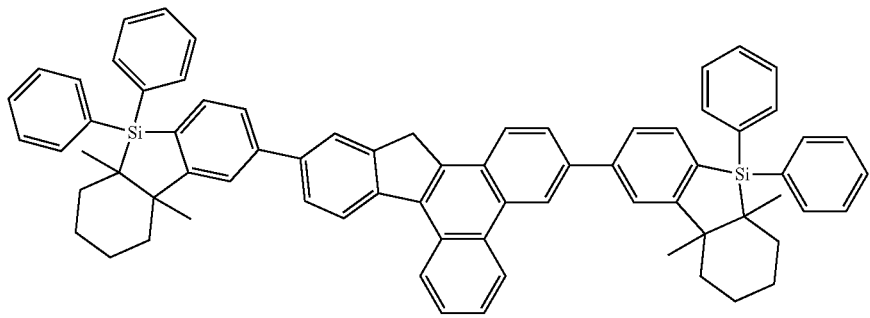
Formula 1971
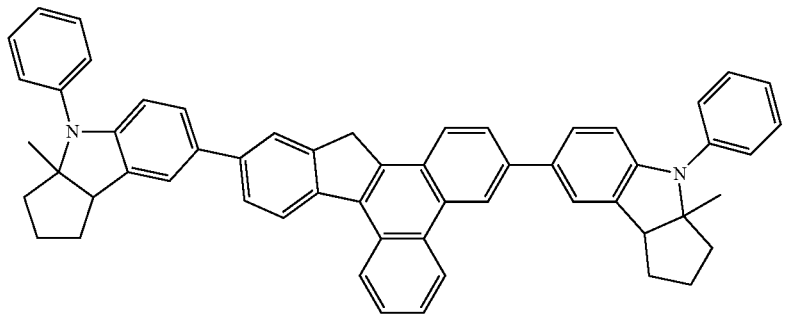
Formula 1972
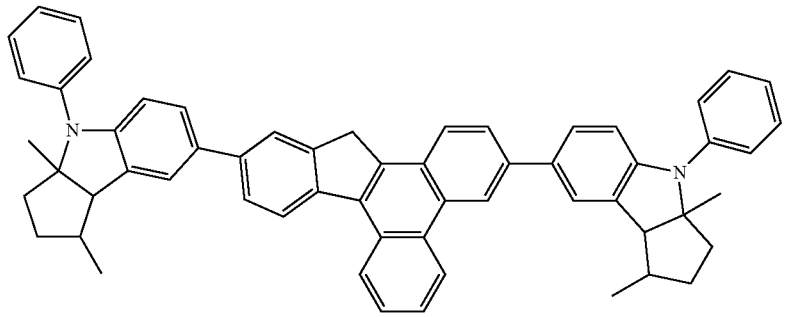
Formula 1973
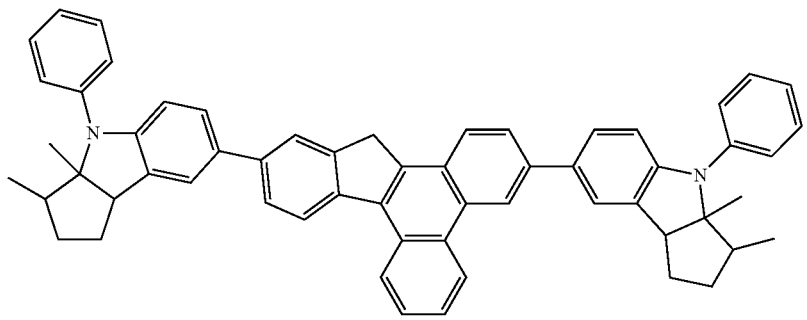
Formula 1974
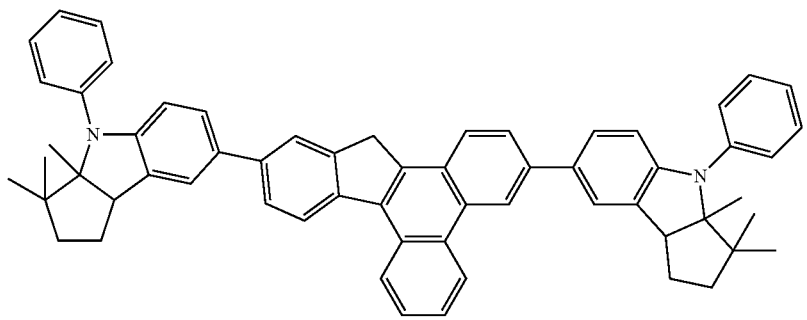

Formula 1975
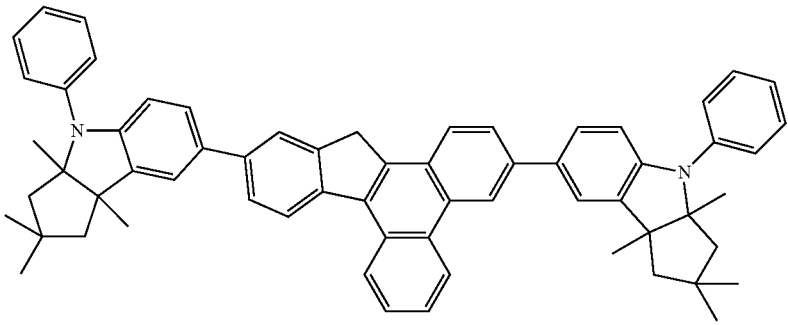
Formula 1976
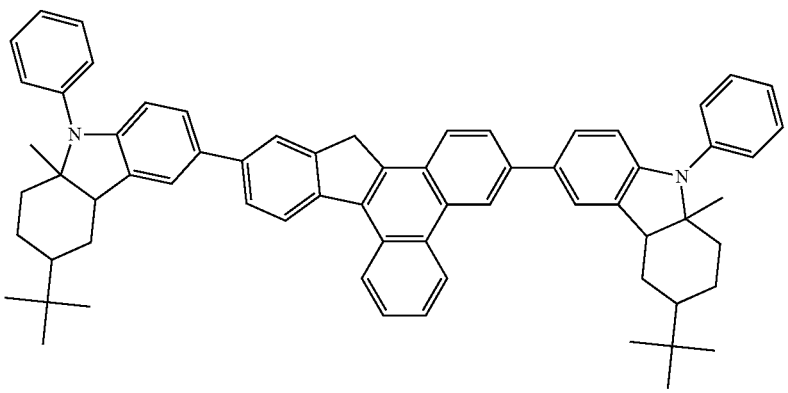
Formula 1977
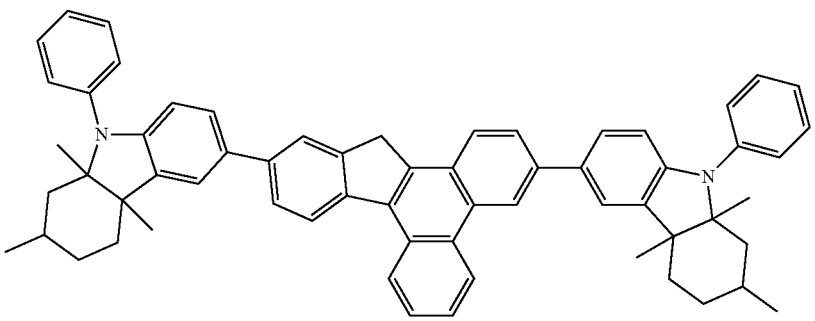
Formula 1978
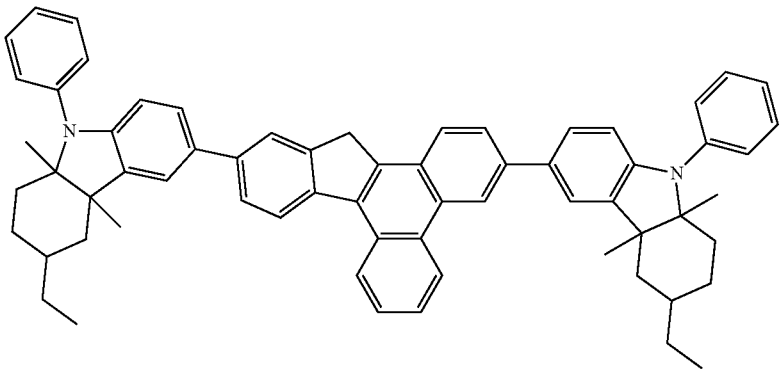

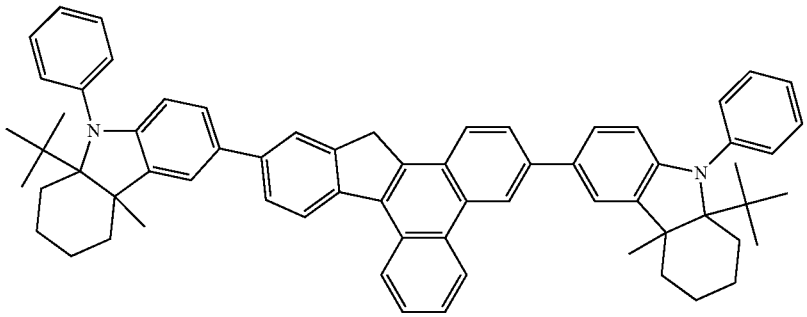
Formula 1979
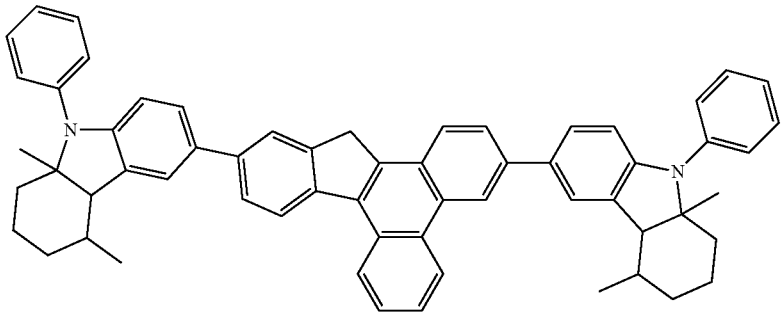
Formula 1980
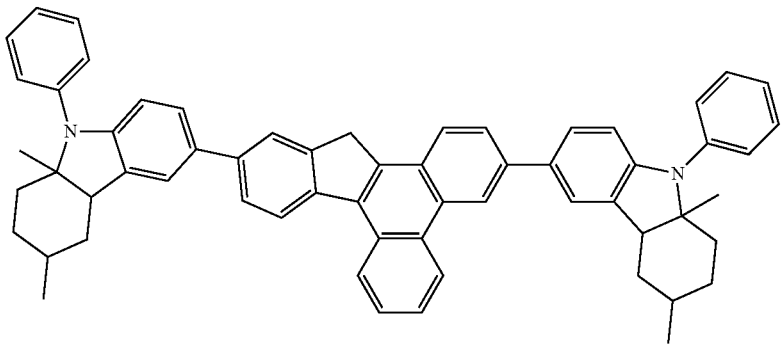
Formula 1981
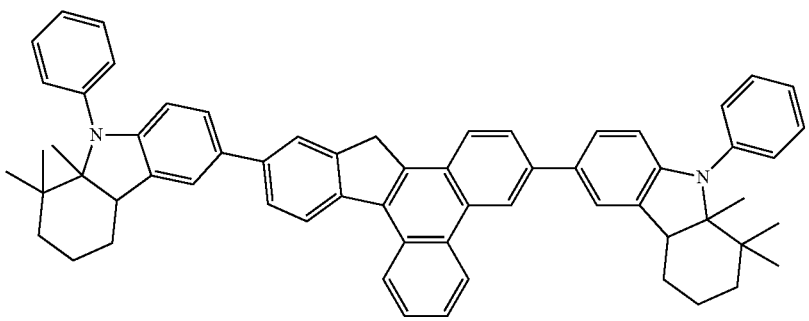
Formula 1982
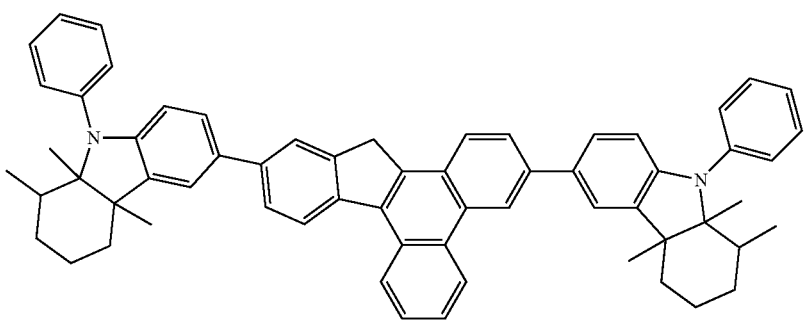
Formula 1983

Formula 1984
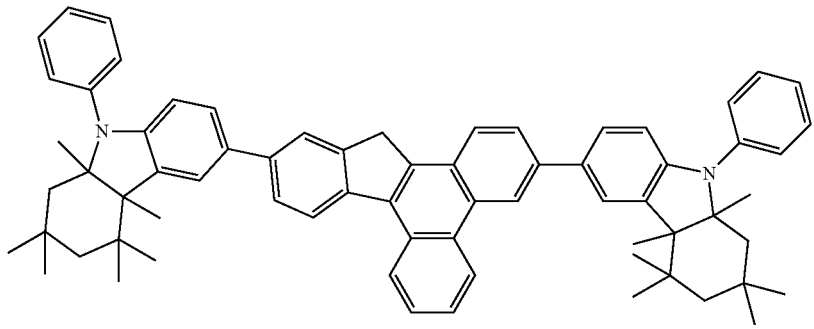
Formula 1985
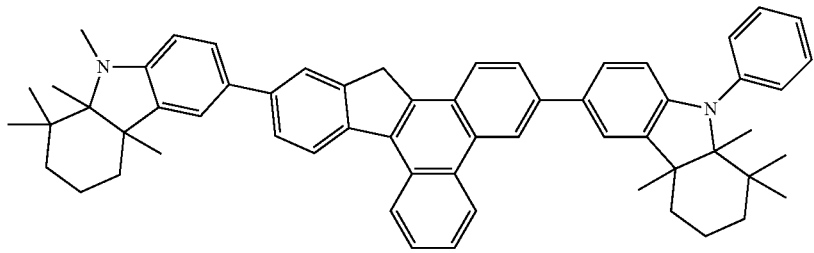
Formula 1986
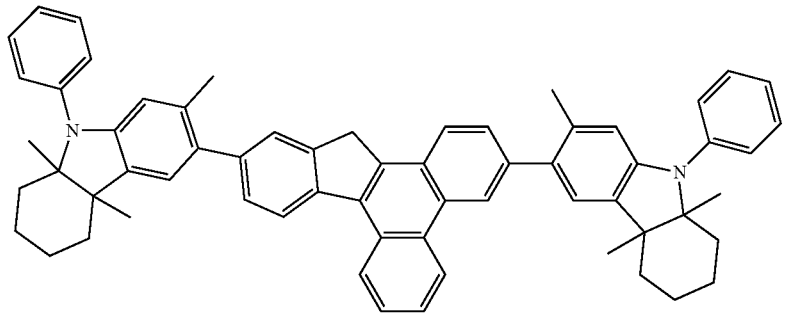
Formula 1987
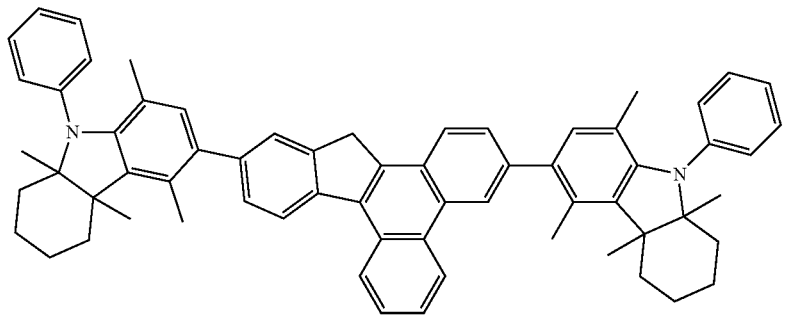
Formula 1988
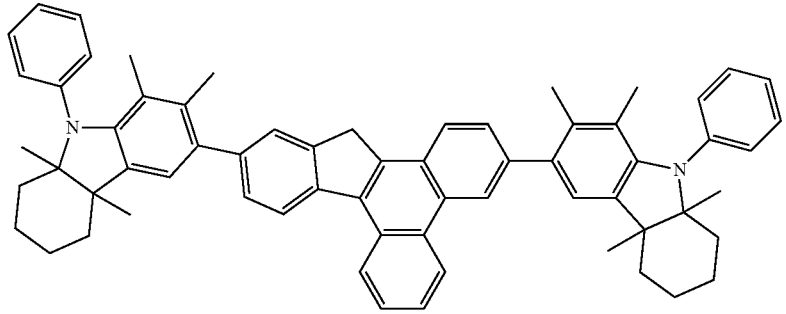

Formula 1989
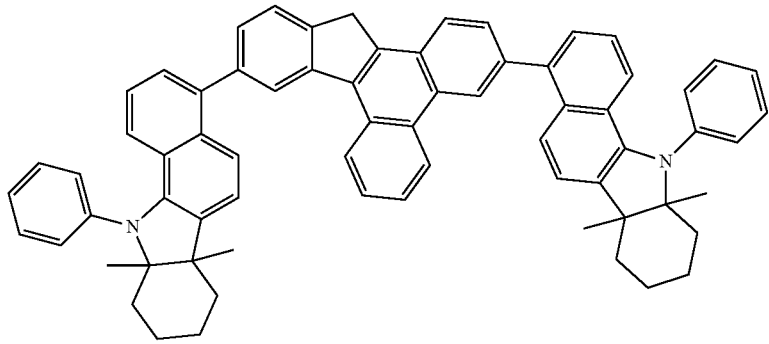
Formula 1990
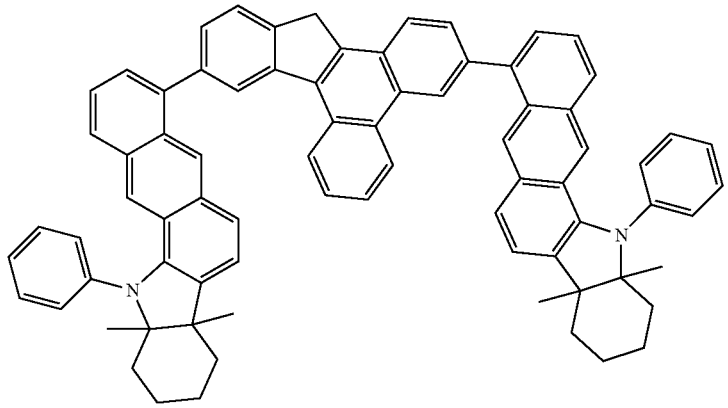
Formula 1991
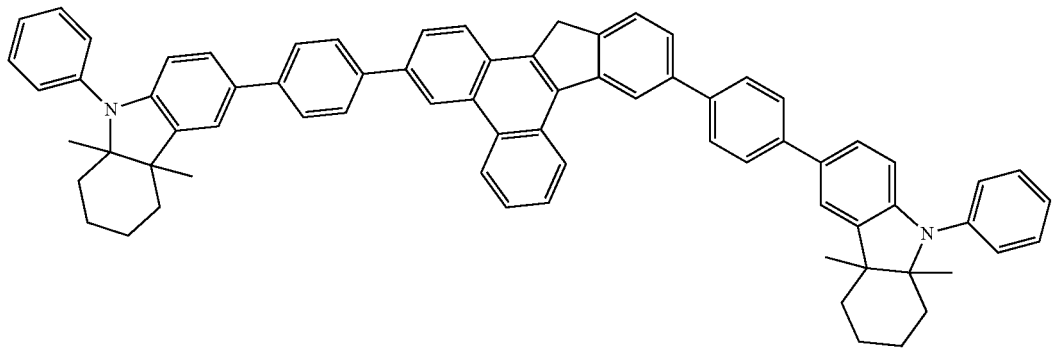
Formula 1992
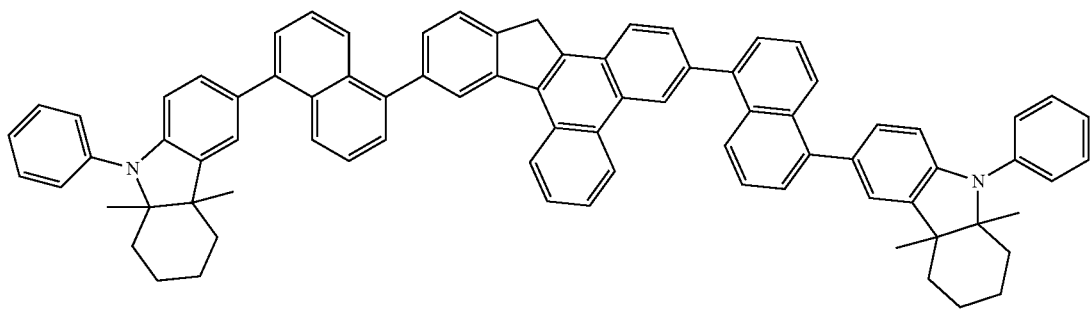

-continued
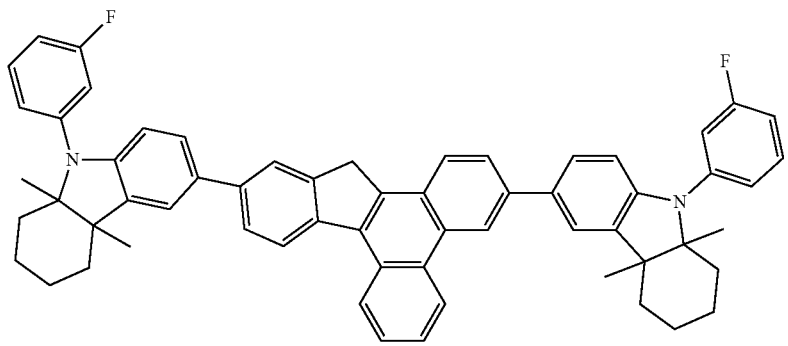
Formula 1993
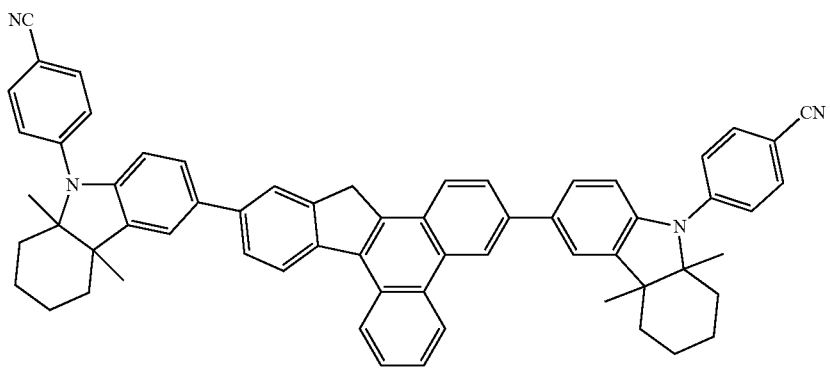
Formula 1994
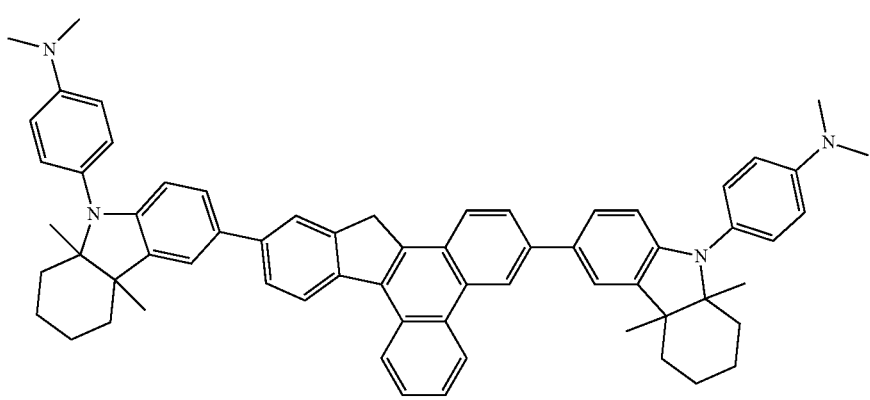
Formula 1995
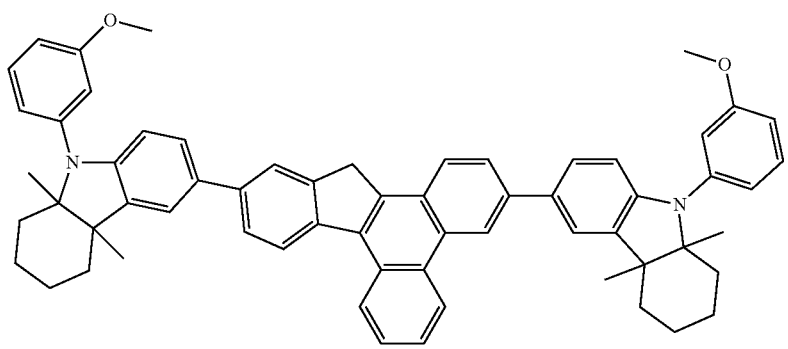
Formula 1996

-continued
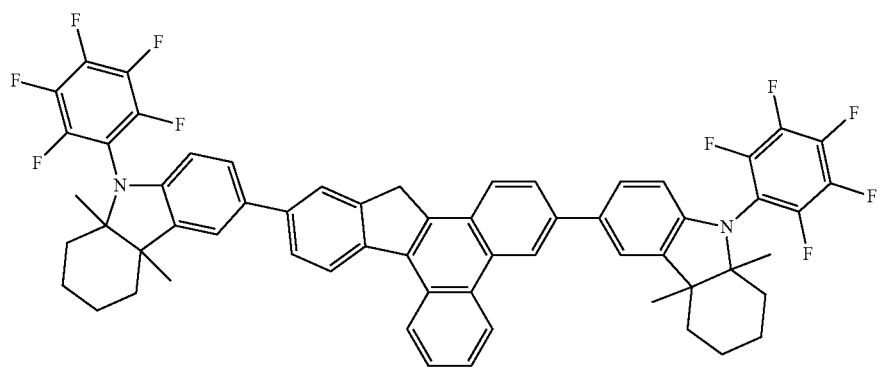
Formula 1997
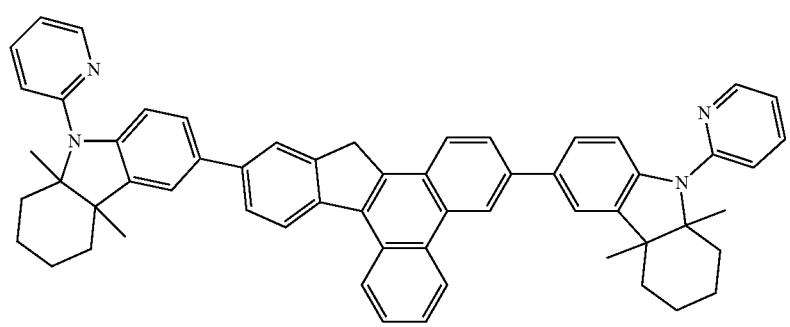
Formula 1998
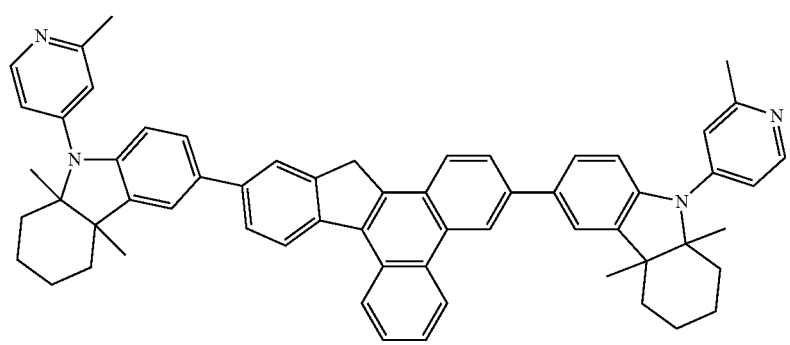
Formula 1999
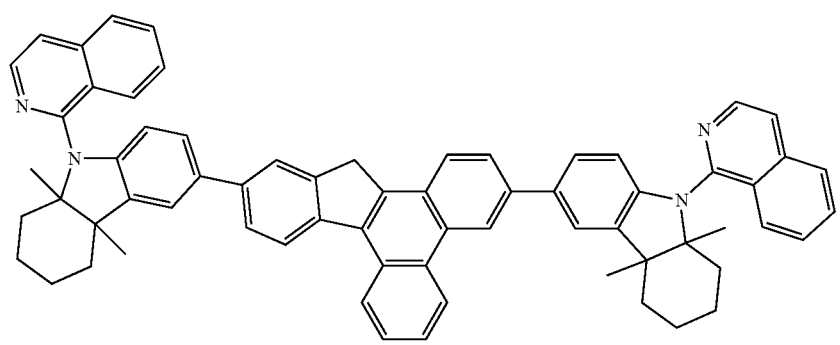
Formula 2000

The condensed-cyclic compound represented by Formula 1 includes $Ar_2$ represented by Formula 2.

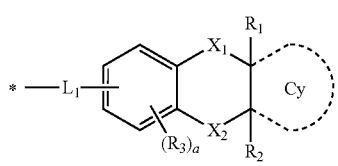

Formula 2

In Formula 2, a benzene ring and Cy are fused to each other with $X_1$ and $X_2$ therebetween. For example, when $X_1$ is $N(R_{11})$ and $X_2$ is a single bond, indoline may be formed in Formula 2 (see Formula 2(1) as below). The indoline may improve the light-emitting efficiency of the organic light emitting diode including the condensed-cyclic compound. Thus, the condensed-cyclic compound including Formula 2 may provide good light-emitting efficiency.

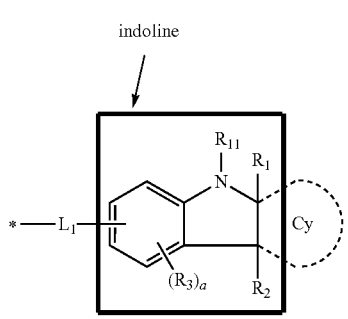

Formula 2(1)

indoline

Moreover, Cy in Formula 2 is a saturated ring. The electron donor strength of such Cy is weaker than that of an unsaturated ring (for example, benzene) where electrons are delocalized. By using the condensed-cyclic compound including Formula 2 including Cy, emission wavelengths in the deep-blue region may be obtained. The benzene ring of Formula 2 is bound to $Ar_1$ with $L_1$ in the middle. Therefore, the electron donor strength of the condensed-cyclic compound becomes weaker than before and thus an energy gap is increased. As a result, deep-blue light emission may be possible. For example, in a compound where $Ar_1$ is directly bound to $X_1$, electron donor strength is increased and thus the energy gap is decreased. As a result, light emission wavelength red-shifts and green light emission may be possible.

When an organic light-emitting diode (OLED) including the condensed-cyclic compound between a pair of electrodes (anode and cathode) is operated, the OLED may exhibit good driving voltage, efficiency, brightness and life-time characteristics due to the condensed-cyclic compound having high heat resistance to Joule's heat generated between organic layers positioned between the pair of electrodes or between one of the organic layers and one of the electrodes.

The condensed-cyclic compound of Formula 1 may be synthesized using any known organic synthesis method. The synthesis method of the condensed-cyclic compound of Formula 1 may be readily understood by those of ordinary skill in the art with reference to the provided Examples, which are described below.

The condensed-cyclic compound of Formula 1 may be used between a pair of electrodes of an OLED. For example, the condensed-cyclic compound of Formula 1 may be used in an emission layer and/or a layer between an anode and the emission layer (for example, a hole injection layer (HIL), a hole transport layer (HTL), or a functional layer having hole injection and hole transport abilities).

According to another embodiment of the present invention, there is provided an OLED including a first electrode, a second electrode facing the first electrode, and an organic layer between the first electrode and the second electrode, wherein the organic layer includes at least one of the condensed-cyclic compounds of Formula 1 described above.

As used herein, the expression "(the organic layer) may include at least one of the condensed-cyclic compounds of Formula 1" may be understood as "(the organic layer) may include one within a range of the condensed-cyclic compounds of Formula 1 or two or more of the condensed-cyclic compounds that are different from each other within the range of Formula 1".

For example, the organic layer may include only Compound 38 as the condensed-cyclic compound. Here, Compound 38 may be included in the emission layer of an OLED. In another embodiment, the organic layer may include Compound 38 and Compound 262 as the condensed-cyclic compounds. Here, Compound 38 and Compound 262 may be included in the same layer (for example, Compound 38 and Compound 262 may be included in the emission layer) or may be included in different layers (for example, Compound 38 may be included in the emission layer and Compound 262 may be included in the electron transport layer).

The organic layer may include at least one of a HIL, a HTL, a functional layer (hereinafter, referred to as "H-functional layer") having hole injection and hole transport abilities, a buffer layer, an electron blocking layer (EBL), an emission layer (EML), a hole blocking layer (HBL), an electron transport layer (ETL), an electron injection layer (EIL), and a functional layer (hereinafter, referred to as "E-functional layer") having electron transport and electron injection abilities.

The term "organic layer" used herein refers to a single layer or multiple layers positioned between the first electrode and the second electrode of an OLED.

The organic layer includes an EML including the condensed-cyclic compound of Formula 1. In some embodiments, the organic layer may include at least one of a HIL, a HTL, and a H-functional layer, and the condensed-cyclic compound of Formula 1 may be included in at least one of the HIL, the HTL, and the H-functional layer.

The condensed-cyclic compound of Formula 1 included in the EML may serve as a dopant. For example, the condensed-cyclic compound of Formula 1 may serve as a blue dopant for emitting blue light. In other embodiments, the condensed-cyclic compound of Formula 1 included in the EML may serve as a fluorescent or phosphorescent host for emitting red light, green light, or blue light.

FIG. 1 is a schematic cross-sectional view of an OLED 10 according to an embodiment of the present invention. Hereinafter, a structure and a manufacturing method of an OLED will be described in more detail with reference to FIG. 1.

The substrate 11 may be a substrate used in a conventional OLED and may be a glass substrate or a transparent plastic substrate having good mechanical strength, thermal stability, transparency, surface smoothness, ease of handling, and waterproofness.

A first electrode 13 may be formed by applying a first electrode material on the substrate 11 by deposition or sputtering. When the first electrode 13 is an anode, the first electrode material may be selected from materials having a high work function so as to facilitate hole injection. The first electrode 13 may be a reflective electrode or a transparent electrode. Examples of the first electrode material may include indium-tin oxide (ITO), indium-zinc oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode 13 may be formed as a reflective electrode.

The first electrode 13 may have a single layer or two or more layers. For example, the first electrode 13 may have a three-layered structured of ITO/Ag/ITO, but is not limited thereto.

An organic layer 15 may be formed on the first electrode 13.

The organic layer 15 may include a HIL, a HTL, a buffer layer, an EML, an ETL, and an EIT.

The HIL may be formed on the first electrode 13 using various methods such as vacuum deposition, spin coating, casting, or LB deposition.

When the HIL is formed using vacuum deposition, the deposition conditions may vary according to the compound used as the material for forming the HIL, the structure of the desired HIL, and the thermal characteristics. For example, the deposition conditions may be, but are not limited thereto, a deposition temperature of about 100 to about 500° C., a degree of vacuum of about $10^{-8}$ to about $10^{-3}$ torr, and a deposition speed of about 0.01 to about 100 Å/sec.

When the HIL is formed by spin coating, the coating conditions may vary according to the compound used as the material for forming the HIL, the structure of the desired HIL, and the thermal characteristics. For example, the coating conditions may be, but are not limited to, a coating speed of about 2,000 to about 5,000 rpm and a heat treatment temperature for removing solvent after coating of about 80 to about 200° C.

The material for forming the HIL may be any known hole injection material. Examples of hole injection materials include, but are not limited thereto, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris (3-methylphenylphenylamino) triphenylamine (m-MTDATA), N,N'-di(1-naphthyl)-N,N'-diphenylbenzidine(NPB), 4,4'4"-tris(N,N-diphenylamino) triphenylamine (TDATA), 4,4', 4"-tris{N,-(2-naphthyl)-N-phenylamino}-triphenylamine (2-TNATA), Polyaniline/Dodecylbenzenesulfonic acid (Pani/DBSA), Poly(3,4-ethylenedioxythiophene)/Poly(4-styrenesulfonate) (PEDOT/PSS), Polyaniline/Camphor sulfonicacid (Pani/CSA), or Polyaniline/Poly(4-styrenesulfonate) (PANI/PSS).

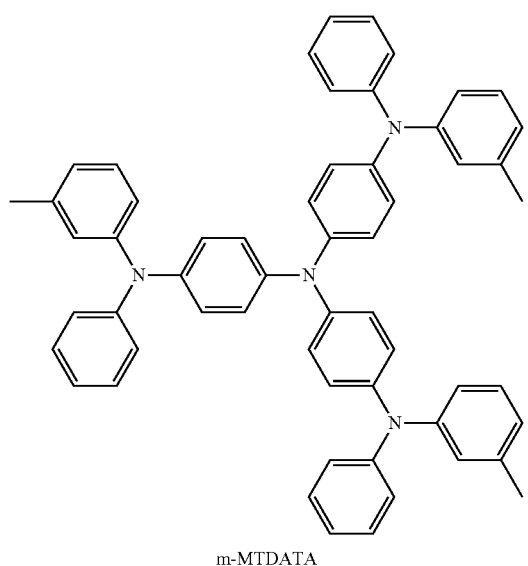

m-MTDATA

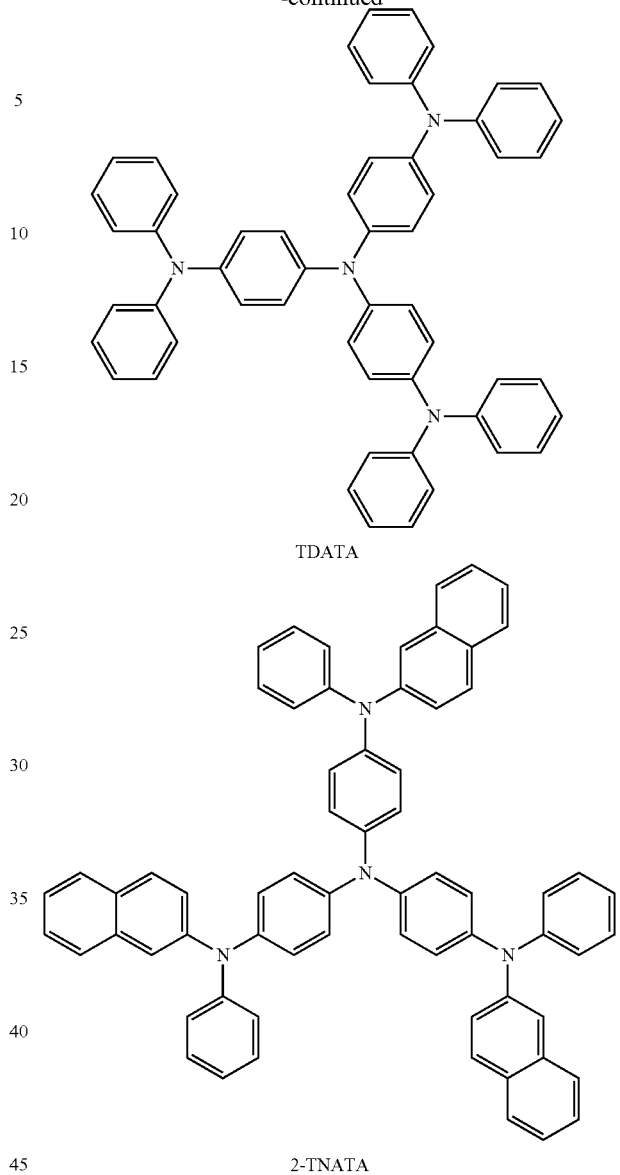

TDATA

2-TNATA

The thickness of the HIL may be in a range of about 100 Å to about 10,000 Å, for example, in a range of about 100 Å to about 1,000 Å. When the thickness of the HIL is within these ranges, satisfactory hole injection properties may be obtained without a substantial increase in driving voltage.

Next, the HTL may be formed on the HIL using various methods such as vacuum deposition, spin coating, casting, or LB deposition. When the HTL is formed by vacuum deposition or spin coating, the deposition or coating conditions may vary according to the compound used. However, in general, the conditions may be almost the same as the conditions described above for forming the HIL.

The material for forming the HTL may be any known hole transporting material. Examples of the hole transporting material include carbazole derivatives such as N-phenylcarbazole and polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), α-NPD(N,N'-Bis (naphthalene-1-yl)-N,N'-bis(phenyl)-2,2'-dimethylbenzidine) and N,N'-di(1-naphthyl)-N,N'-diphenylbenzidine (NPB), but are not limited thereto.

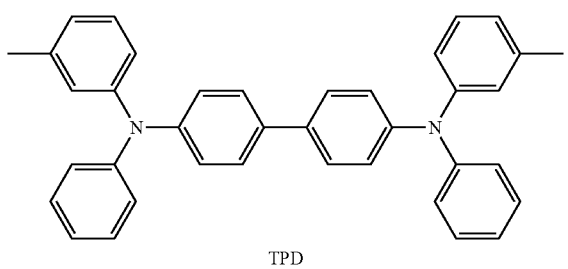

TPD

The thickness of the HTL may be in a range of about 50 Å to about 2,000 Å, for example, in a range of about 100 Å to about 1,500 Å. When the thickness of the HTL is within these ranges, satisfactory hole transport properties may be obtained without a substantial increase in driving voltage.

The H-functional layer (which is a functional layer having hole injection and hole transport abilities) may include one or more of the hole injection materials described above and the HTL materials. The thickness of the H functional layer may be in a range of about 50 Å to about 10,000 Å, for example, in a range of about 100 Å to about 1,000 Å. When the thickness of the H-functional layer is within these ranges, satisfactory hole injection and transport properties may be obtained without a substantial increase in driving voltage.

At least one of the HIL, the HTL, and the H-functional layer may further include a charge-generating material in order to improve the conductivity of the layer and the hole injection material, the hole transport material, and/or the material having hole injection and hole transport functions described above.

The charge-generating material may be, for example, a p-dopant. Examples of the p-dopant may include, but are not limited to, quinone derivatives such as tetracyanoquinodimethane (TCNQ), and 2,3,5,6-tetrafluoro-tetracyano-1,4-benzoquinodimethane (F4TCNQ); metal oxides such as a tungsten oxide and a molybdenum oxide; and cyano-containing compounds such as Compound 200 below and the like.

Compound 200

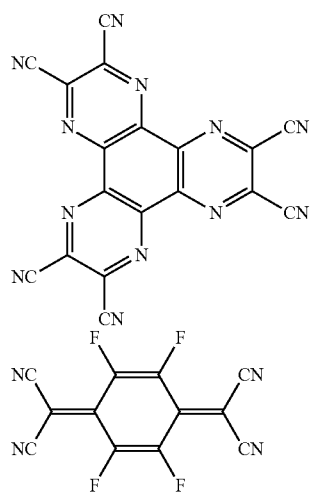

F4-CTNQ

When the HIL, the HTL, or the H-functional layer further include the charge-generating material, the charge-generating material may be homogeneously or inhomogeneously dispersed in these layers.

A buffer layer may be disposed between at least one of the HIL, the HTL, or the H-functional layer and the EML. The buffer layer may serve to improve efficiency by compensating for an optical resonance distance according to the wavelength of light emitted from the EML. The buffer layer may include the hole injection material and the hole transport material. In some embodiments, the buffer layer may include the same material included in the HIL, the HTL, or the H-functional layer formed under the buffer layer.

Subsequently, the EML may be formed on the HTL, the H-functional layer, or the buffer layer using various methods such as vacuum deposition, spin coating, casting, or LB deposition. When the EML is formed by vacuum deposition or spin coating, the deposition or coating conditions may vary according to the compound used. However, in general, the conditions may be almost the same as the conditions described above for forming the HIL.

The EML may include at least one of the condensed-cyclic compounds.

The EML may further include a host and the condensed-cyclic compound.

Examples of the host may include, but are not limited to, Alq$_3$, 4,4'-N,N'-dicabazole-biphenyl (CBP), poly(n-vinylcabazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyrylarylene (DSA), dmCBP (refer to Formula below) and Compounds 501 through 509 below.

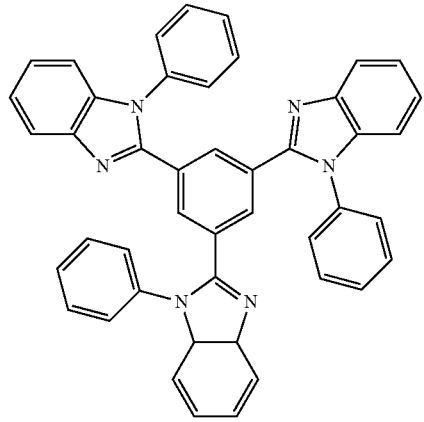

TPBI

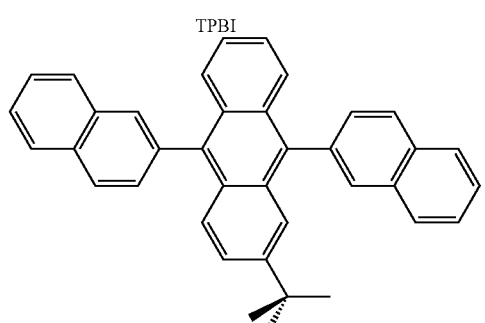

TBADN

791
-continued
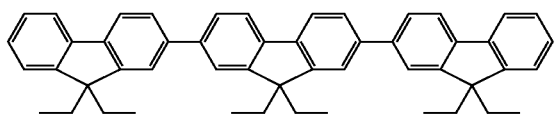
E3
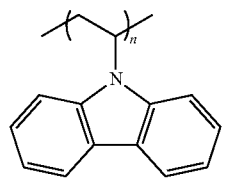
PVK
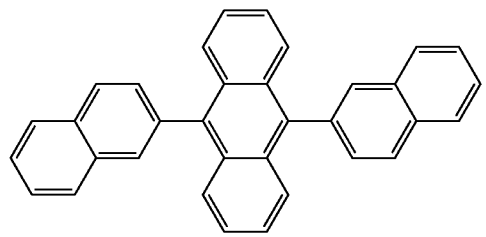
ADN
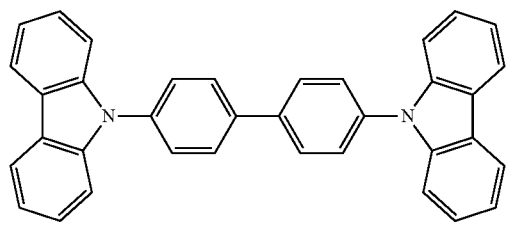
CBP
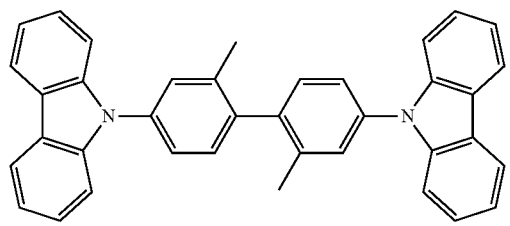
dmCBP
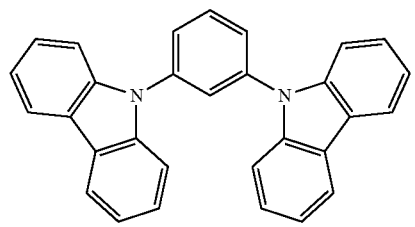
501
792
-continued
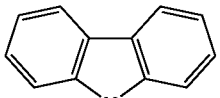
502
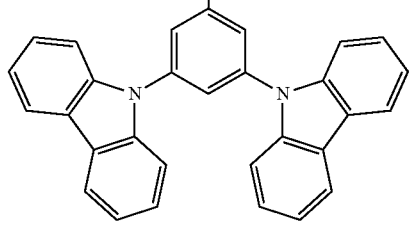
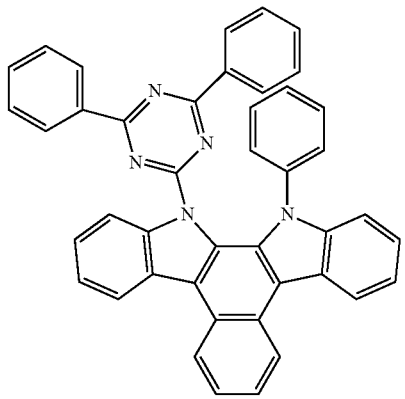
503
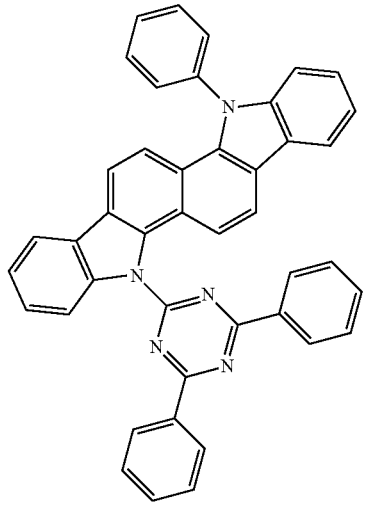
504

-continued

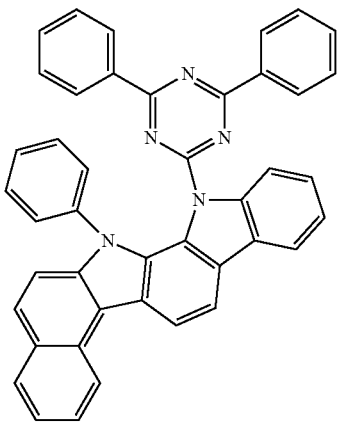
505

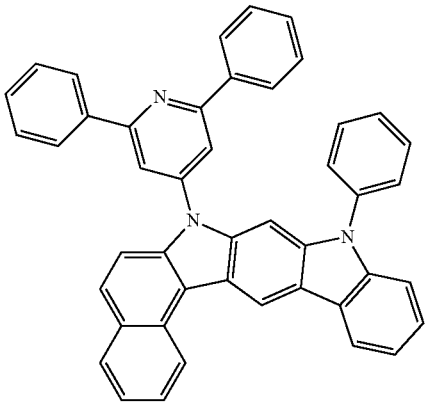
506

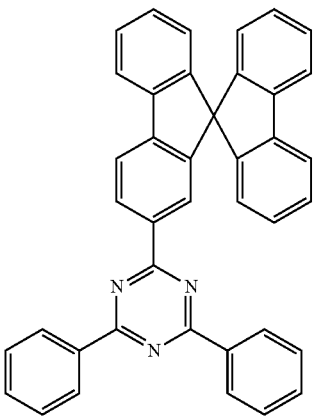
507

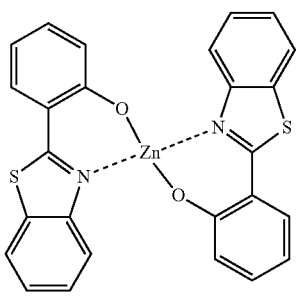
508

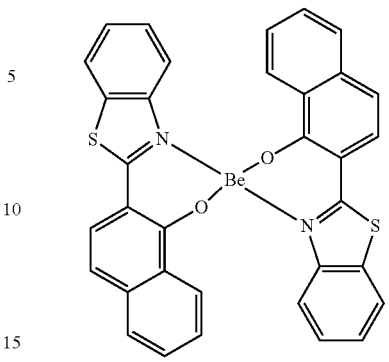
509

Alternatively, the host may be an anthracene-based compound represented by Formula 60 below:

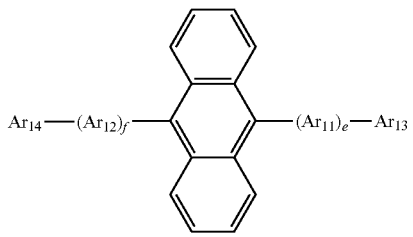

Formula 60

In Formula 60, $Ar_{11}$ and $Ar_{12}$ may each independently be a substituted or unsubstituted $C_5$-$C_{60}$ arylene group; $Ar_{13}$ and $Ar_{14}$ may each independently be a substituted or unsubstituted $C_1$-$C_{10}$ alkyl group or a substituted or unsubstituted $C_5$-$C_{60}$ aryl group; and e and f may each independently be an integer of 0 to 5.

For example, in Formula 60, $Ar_{11}$ and $Ar_{12}$ may each independently be a phenylene group; or a phenylene group that is substituted with one or more of a phenyl group, a naphthyl group, and an anthryl group, but are not limited thereto. In Formula 60, e and f may each independently be 0, 1, or 2.

In Formula 60, $Ar_{13}$ and $Ar_{14}$ may each independently be one of a $C_1$-$C_{10}$ alkyl group that is substituted with one or more of a phenyl group, a naphthyl group, or an anthryl group; a phenyl group; a naphthyl group; an anthryl group; a pyrenyl group; a phenanthrenyl group; and a phenyl group, a naphthyl group, an anthryl group, a pyrenyl group, or a phenanthrenyl group that is substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; but are not limited thereto.

For example, in Formula 60, $Ar_{11}$ and $Ar_{12}$ may each independently be a phenylene group; or a phenylene group that is substituted with one or more of a phenyl group, a naphthyl group, and an anthryl group; e and f may each independently be 0, 1, or 2; and $Ar_{13}$ and $Ar_{14}$ may each independently be one selected from a $C_1$-$C_{10}$ alkyl group that is substituted with one or more of a phenyl group, a naphthyl group, and an anthryl group; a phenyl group; a naphthyl group; an anthryl group; a pyrenyl group; and a phenanthrenyl group, but are not limited thereto.
For example, the anthracene-based compound of Formula 60 may be one of Compounds BH01 through BH39 below, but are not limited thereto:
BH01
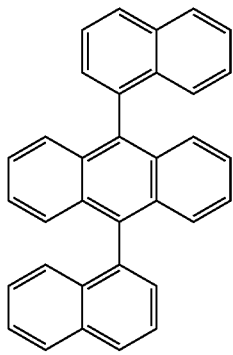
BH02
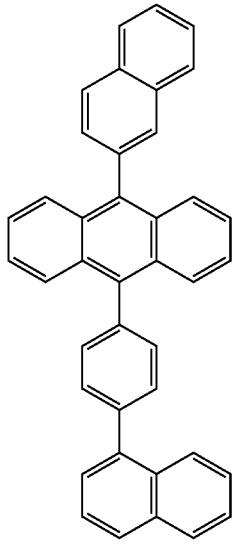
BH03
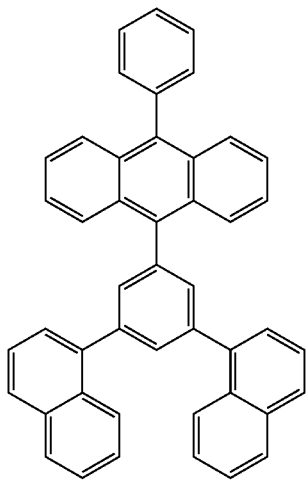
-continued
BH04
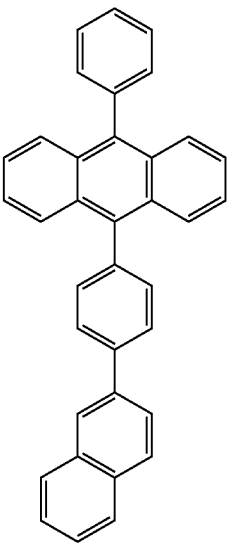
BH05
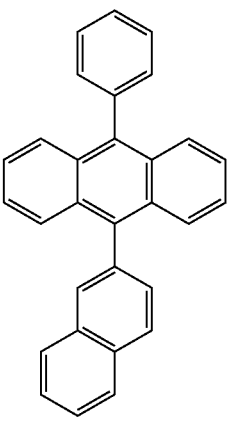
BH06
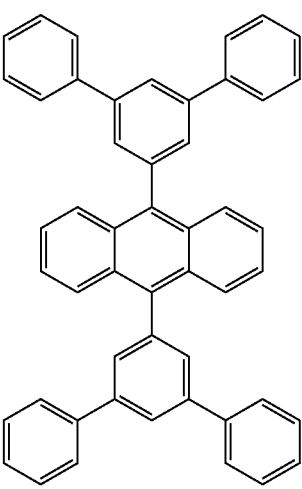

BH07
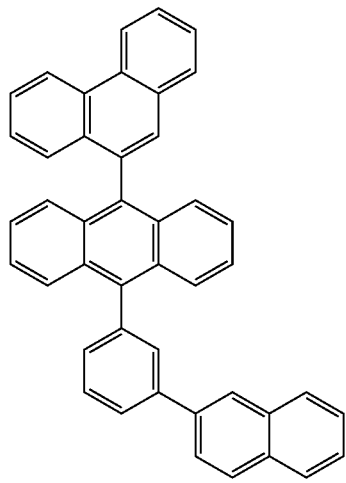
BH08
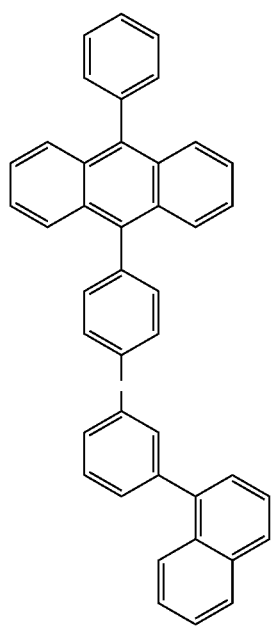
BH09
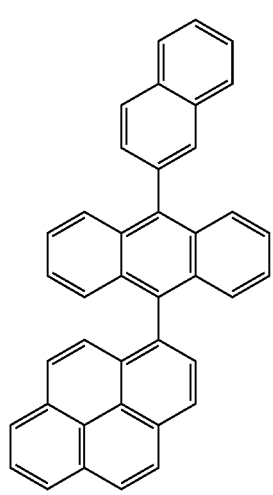
BH10
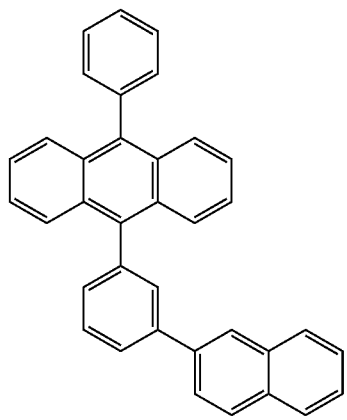
BH11
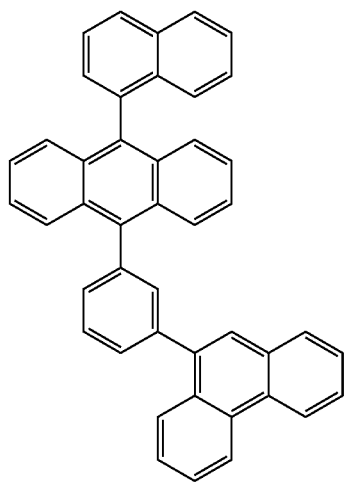
BH12
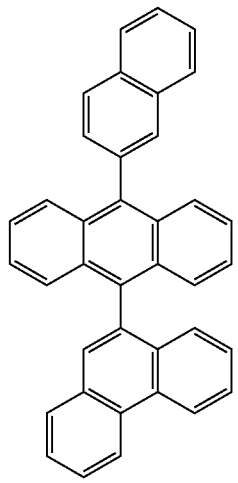

BH13
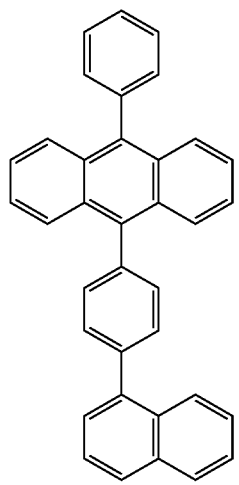
BH14
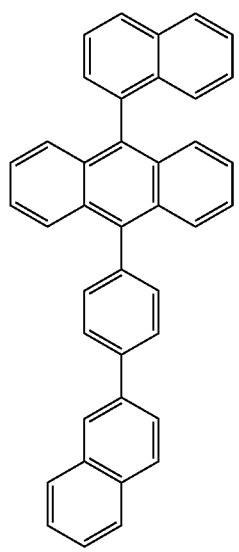
BH15
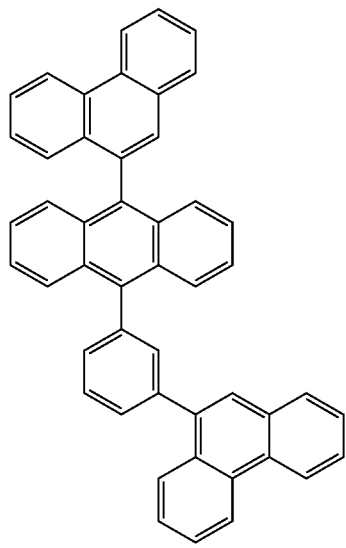
BH16
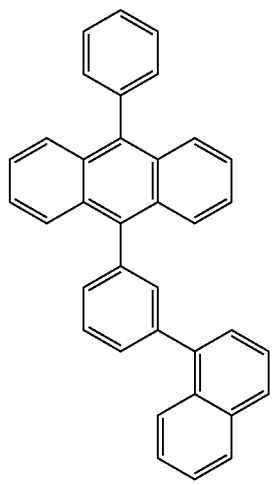
BH17
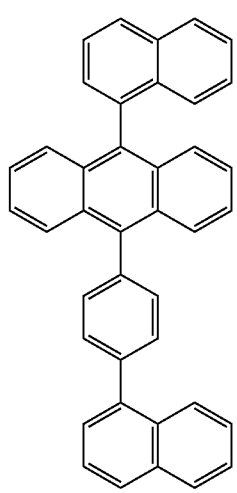
BH18
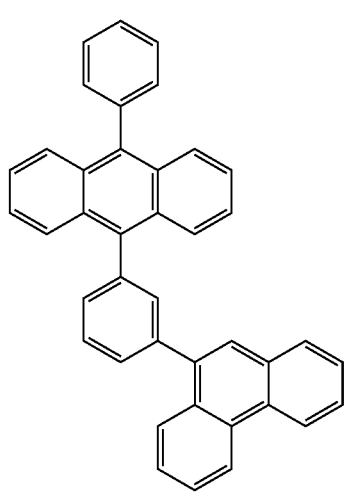

-continued
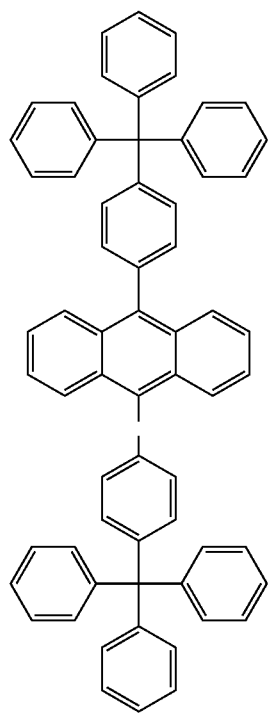
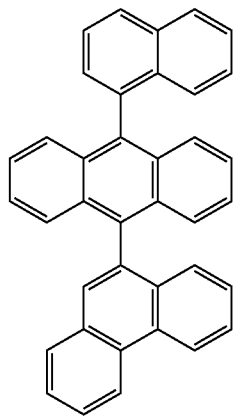
BH19
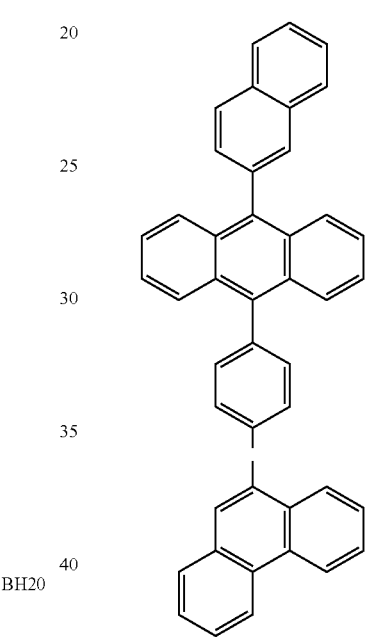
BH20
BH21
BH22
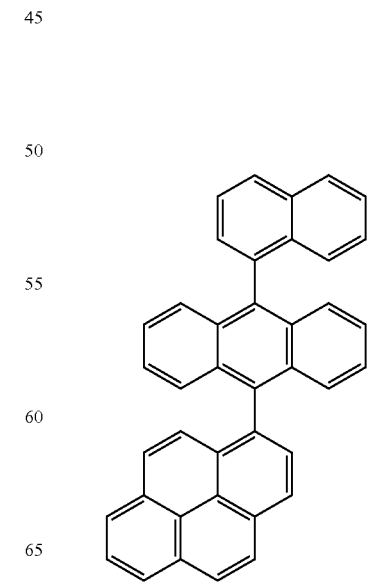
BH23

BH24
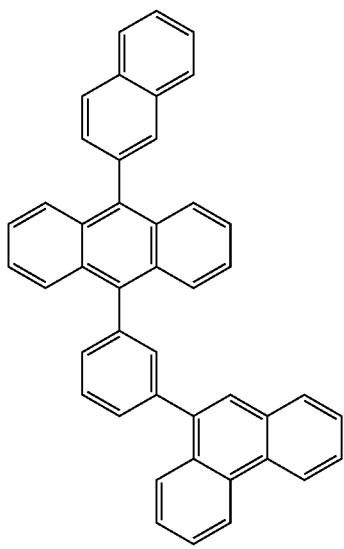
BH25
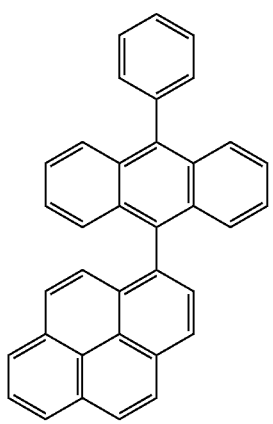
BH26
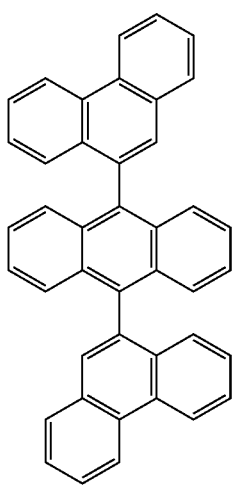
BH27
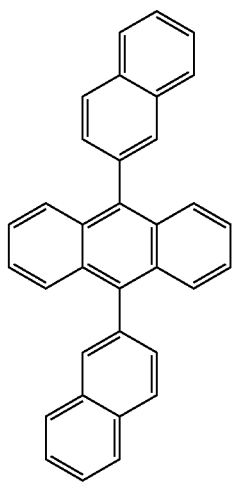
BH28
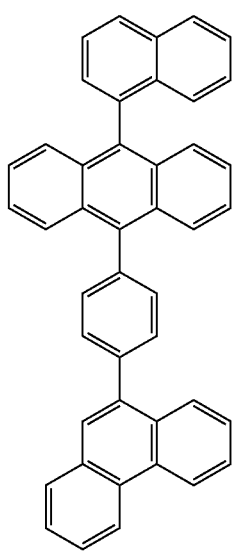
BH29
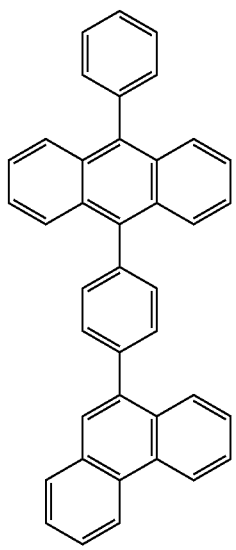

BH30
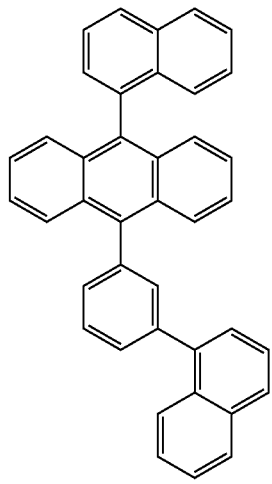
BH32
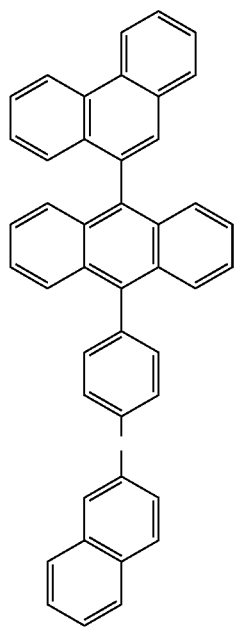
BH33
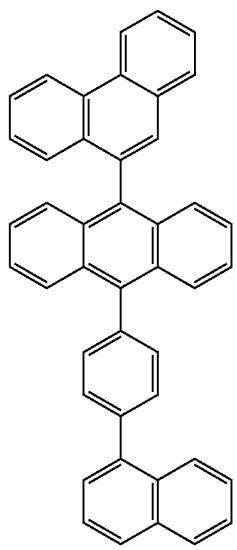
BH31
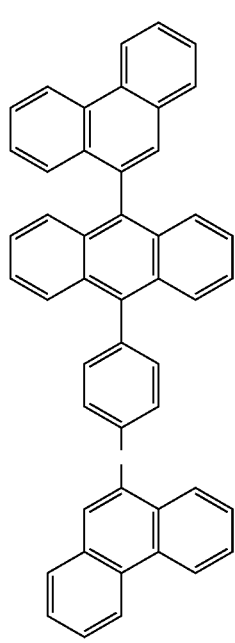
BH34
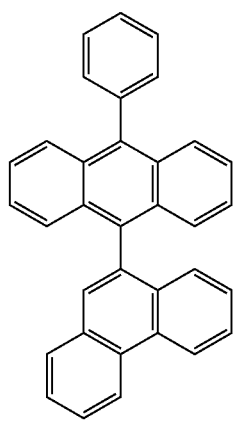

BH35

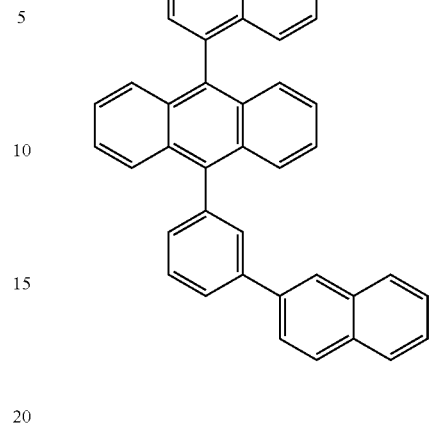

BH36

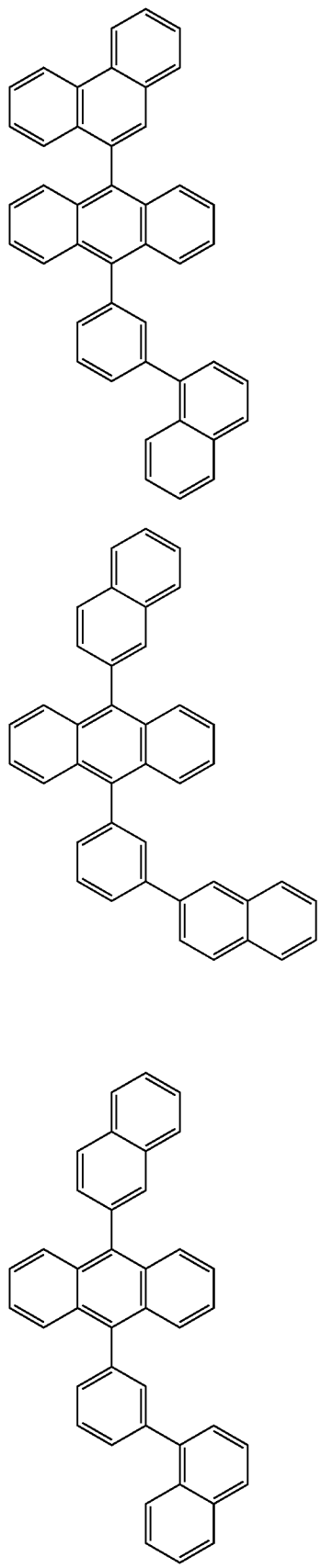

BH37

BH38

BH39

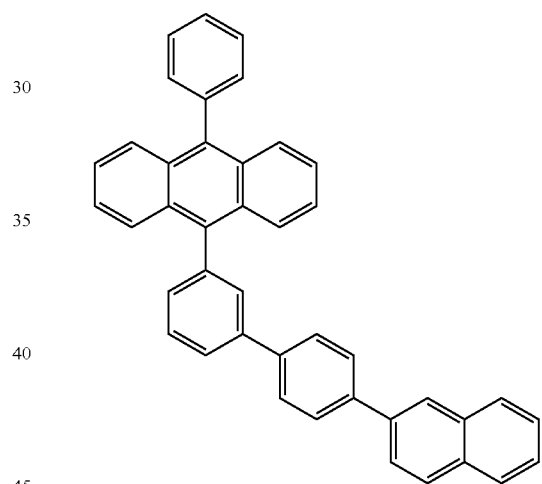

To manufacture a full-color OLED, a red EML and a green EML may be further patterned.

When the OLED is a full-color OLED, the EML may be patterned with a red EML, a green EML, or a blue EML. Here, the condensed-cyclic compound of Formula 1 described above may be included as a blue fluorescent dopant in the blue EML. At least one of the red EML, the green EML, and the blue EML may include the dopant below (ppy=phenylpyridine).

For example, the compounds below may be used as a blue dopant, but are not limited thereto:

809 810
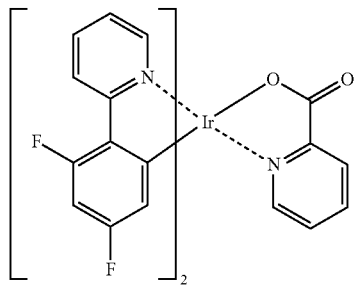
F₂Irpic
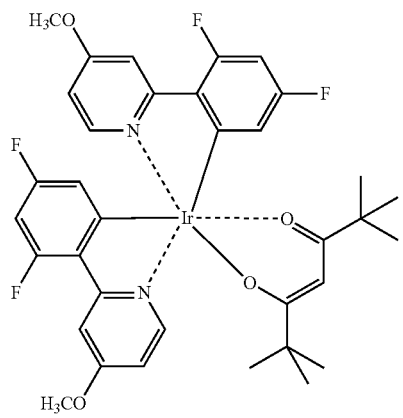
(F₂ppy)₂Ir(tmd)
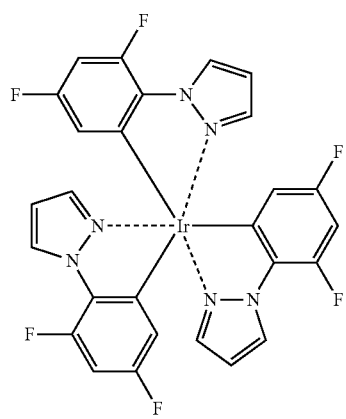
Ir(dfppz)₃
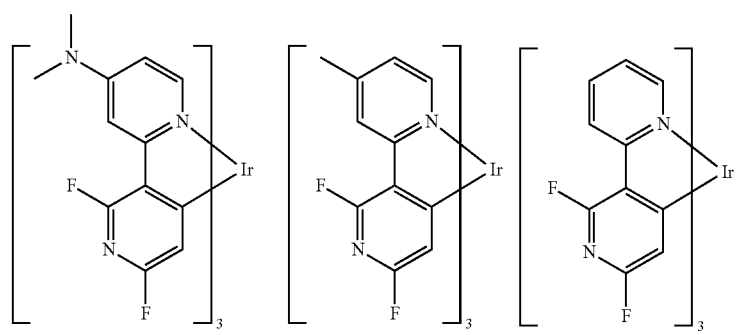
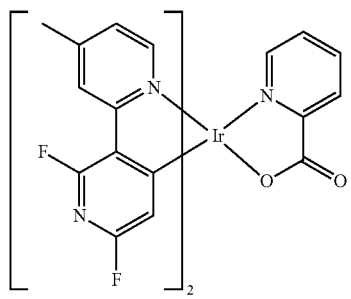 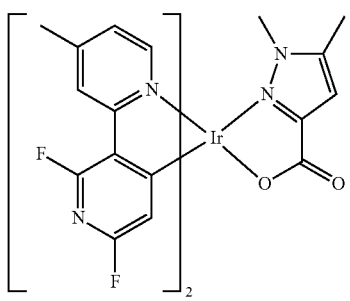 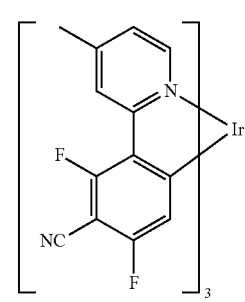
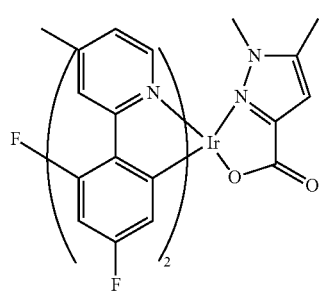 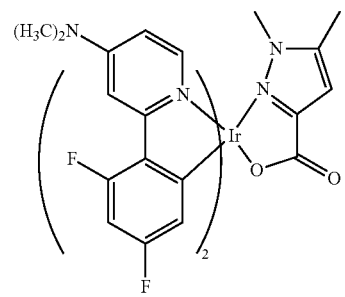 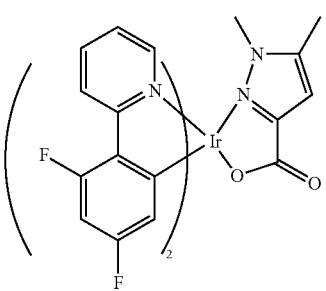

-continued
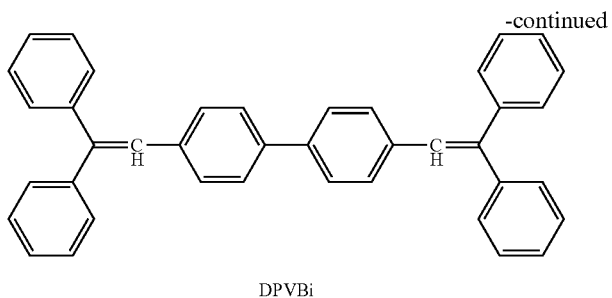
DPVBi
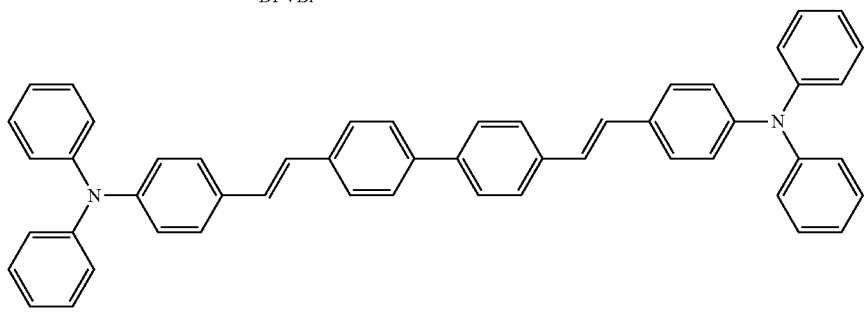
DPAVBi
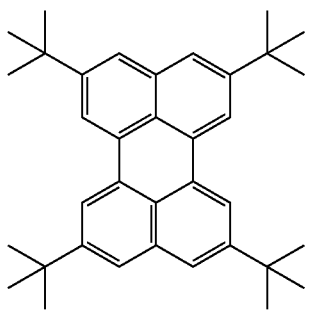
TBPe
For example, the compounds below may be used as a red dopant, but are not limited thereto:
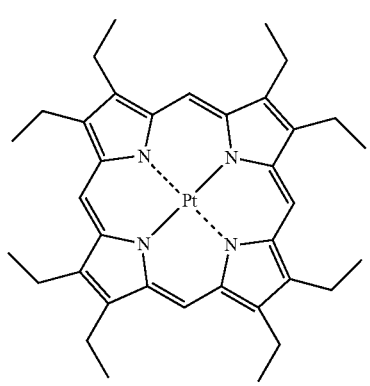
PtOEP
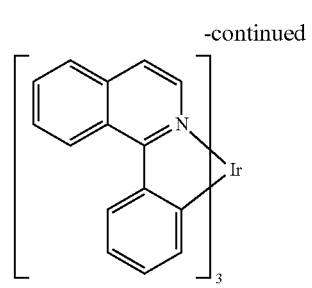
Ir(piq)₃
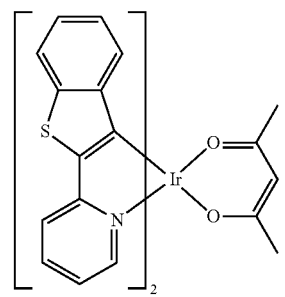
Btp₂Ir(acac)

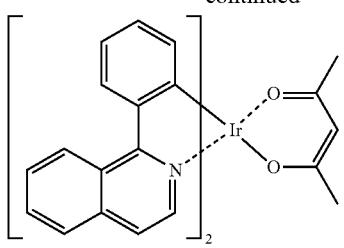
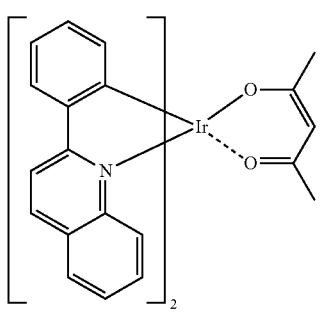
Ir(pq)₂(acac)
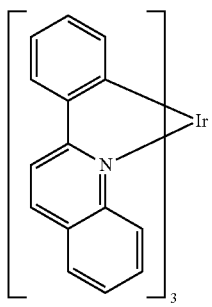
Ir(2-phq)₃
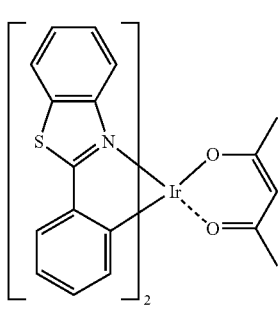
Ir(BT)₂(acac)
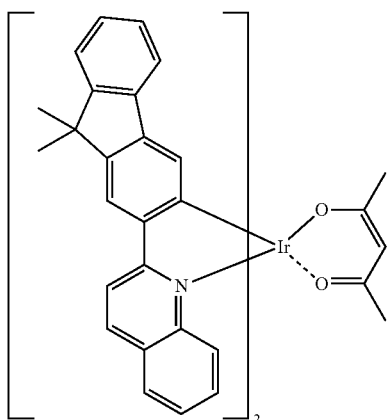
Ir(flq)₂(acac)
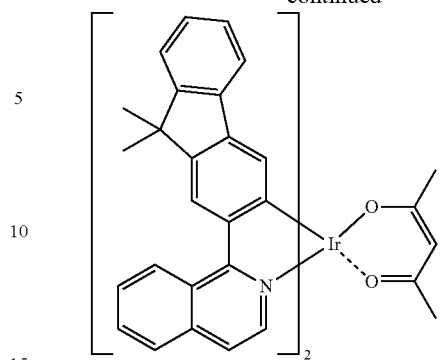
Ir(fliq)₂(acac)
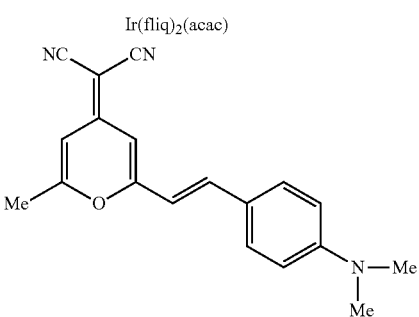
DCM
DCJTB
For example, the compounds below may be used as a green dopant, but are not limited thereto.
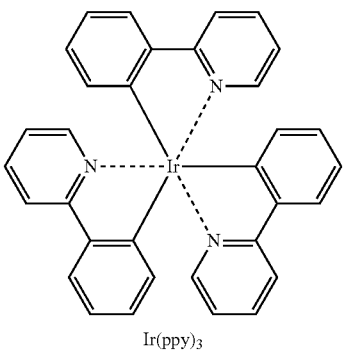
Ir(ppy)₃

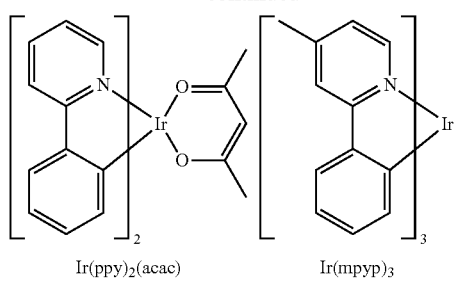
Ir(ppy)₂(acac)
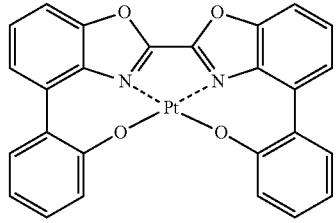
Ir(mpyp)₃
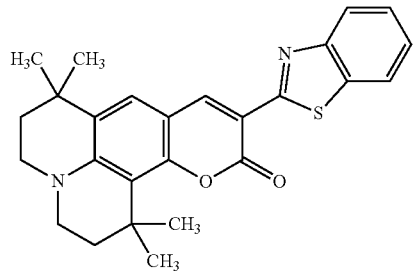
C545T
Examples of a dopant included in the EML include the Pt-complexes described below, but are not limited thereto:
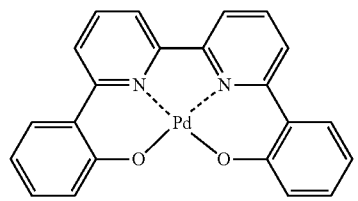
D1
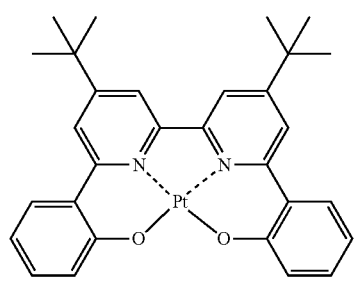
D2
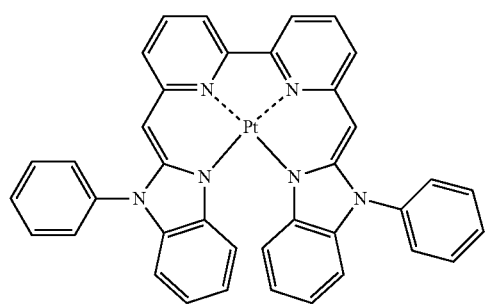
D3
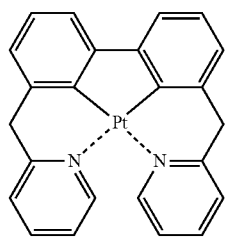
D4
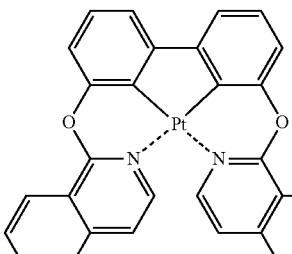
D5
D6
D7
D8
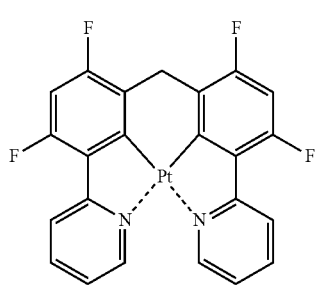
D9

817
-continued
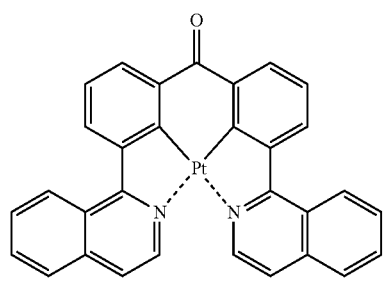
D10
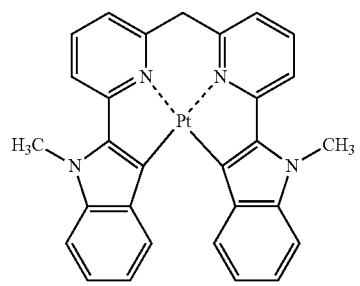
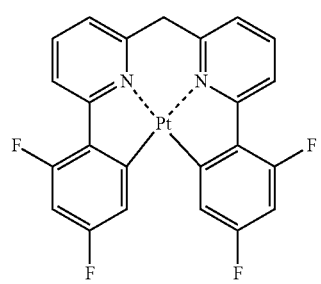
D12
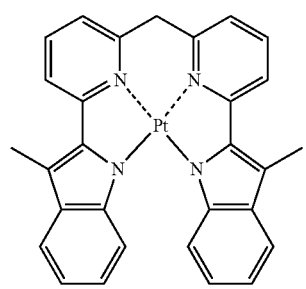
D13
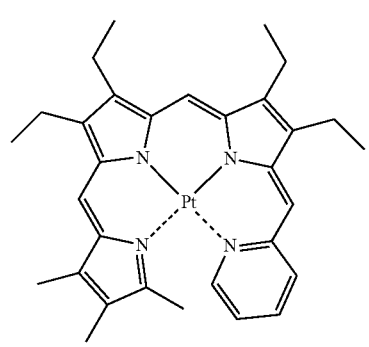
D14
818
-continued
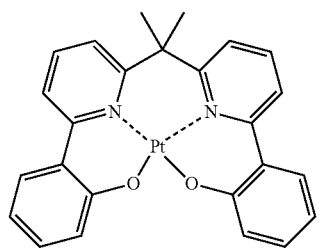
D15
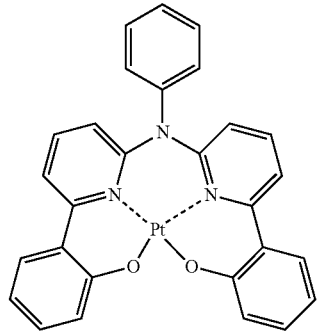
D16
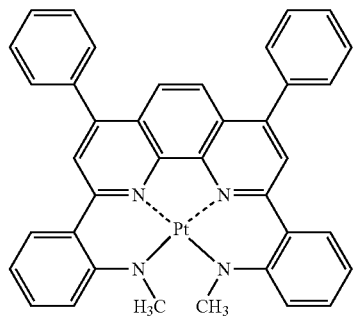
D17
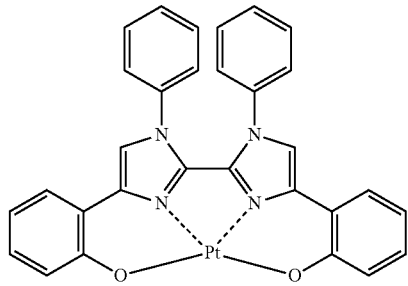
D18
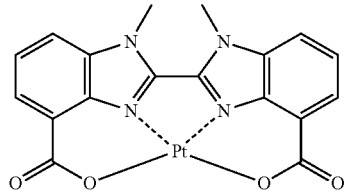
D19
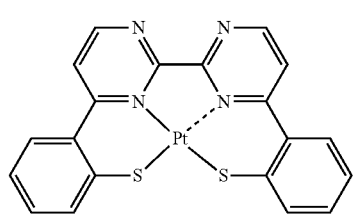
D20

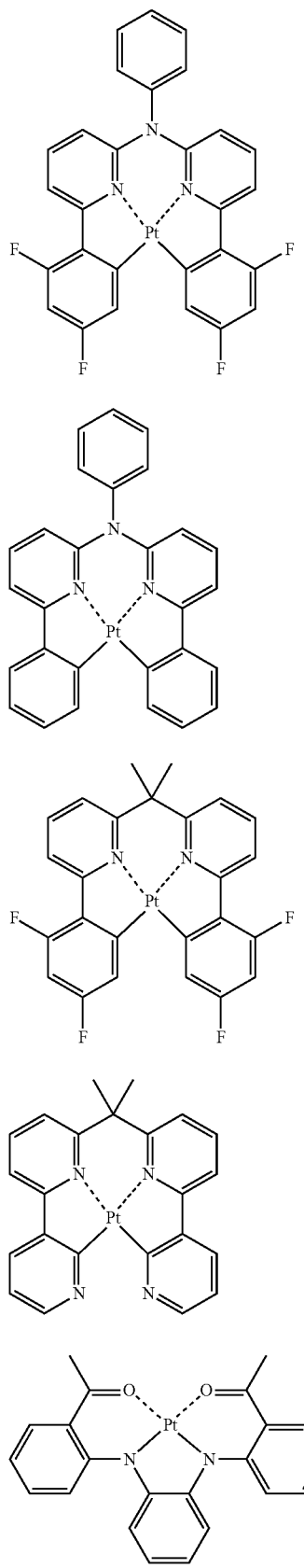

-continued
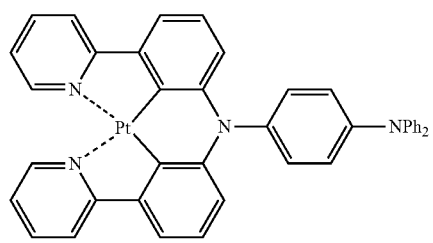
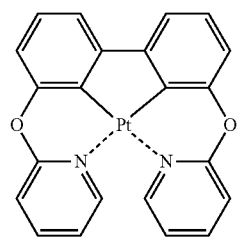
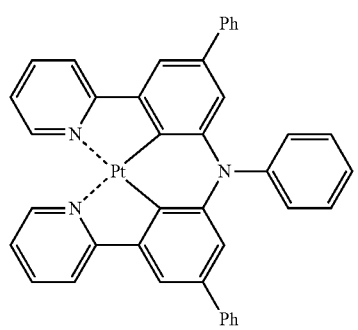
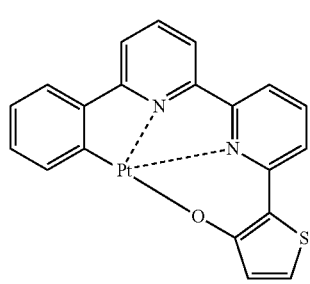
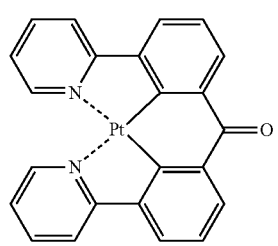
-continued
D32
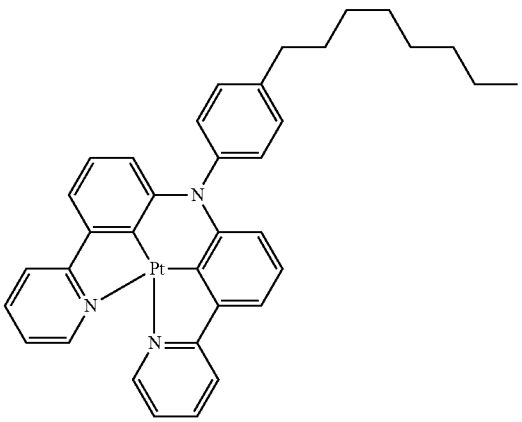
D33
D34
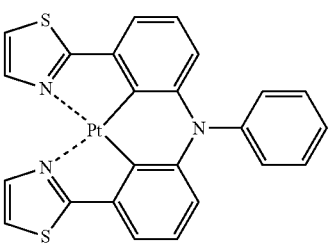
D37
D38
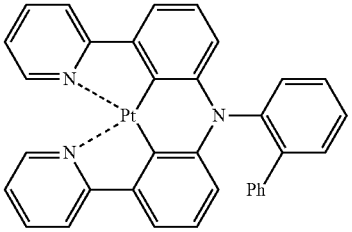
D39
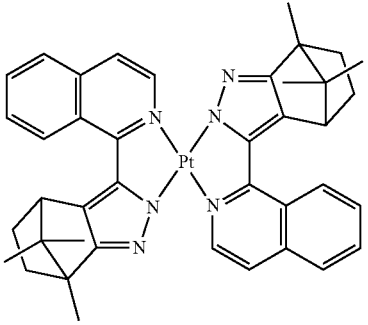
D40
D35
D36
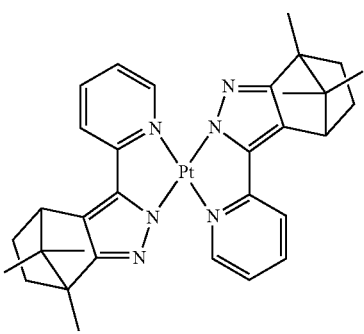
D41

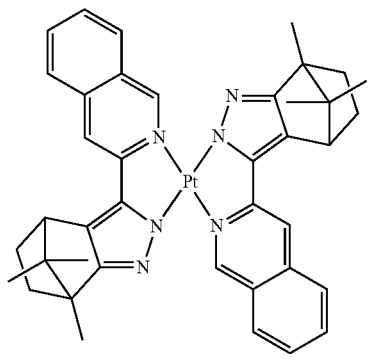
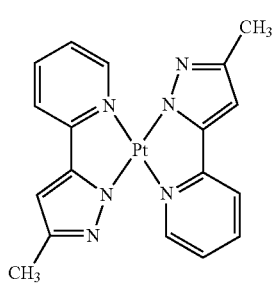
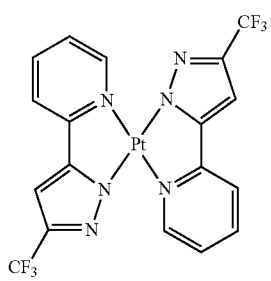
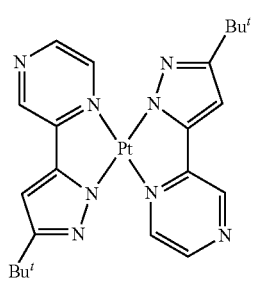
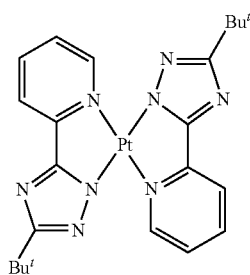
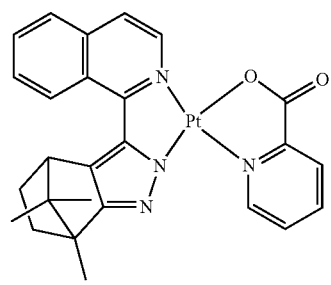
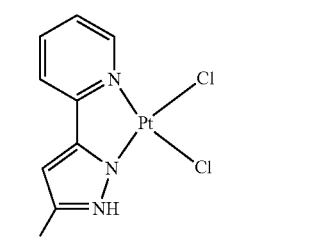
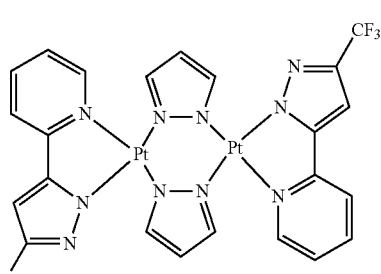
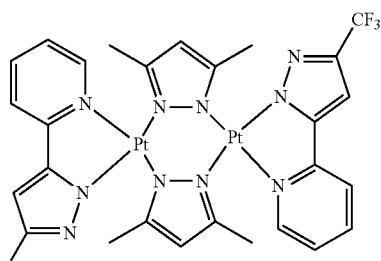
Moreover, examples of a dopant included in the EML include the Os-complexes described below, but are not limited thereto:
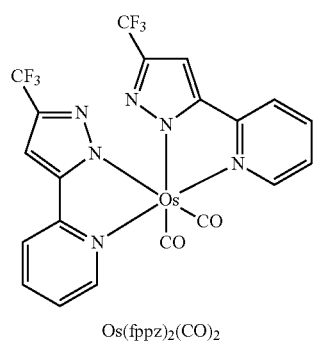
Os(fppz)₂(CO)₂

-continued

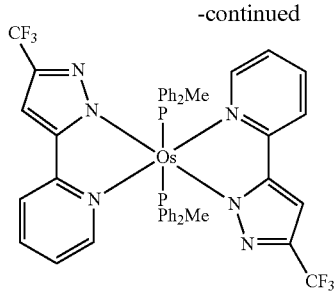

Os(fppz)₂(PPh₂Me)₂

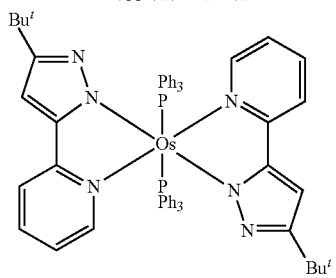

Os(bppz)₂(PPh₃)₂

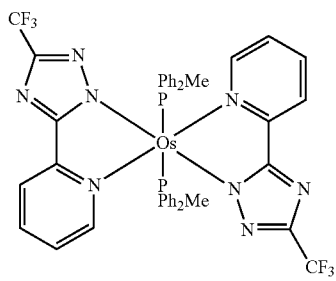

Os(fptz)₂(PPh₂Me)₂

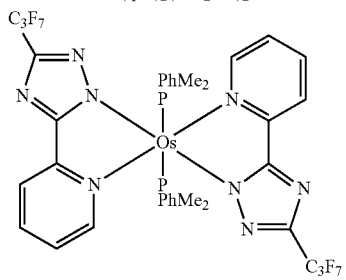

Os(hptz)₂(PPhMe₂)₂

When the EML includes a host and a dopant, the amount of the dopant in the EML may generally be in a range of about 0.01 to about 15 parts by weight based on 100 parts by weight of the host, but are not limited thereto.

The thickness of the EML may be in a range of about 100 Å to about 1,000 Å, for example, in a range of about 200 Å to about 600 Å. When the thickness of the EML is within this range, good luminescent properties may be obtained without a substantial increase in driving voltage.

Next, the ETL is formed on the EML using various methods such as vacuum deposition, spin coating, or casting. When the ETL is formed using vacuum deposition or spin coating, the deposition or coating conditions may vary according to the compound used. However, in general, the conditions may be almost the same as the conditions described above for forming the HIL. The material for forming the ETL may be used to stably transport electrons injected from the cathode and may be any known electron transporting material. Examples of the electron transporting material may include, but are not limited to, a quinoline derivative such as tris(8-quinolinolate)aluminum (Alq₃), TAZ, Balq, beryllium bis(benzoquinolin-10-olate) (Bebq₂), AND, Compound 201 below, and Compound 202 below.

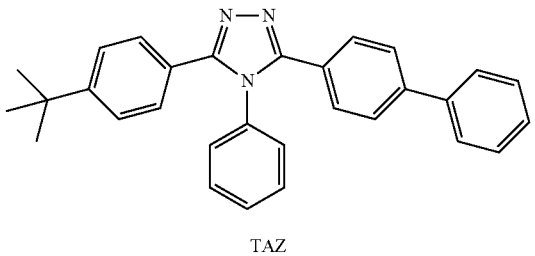

TAZ

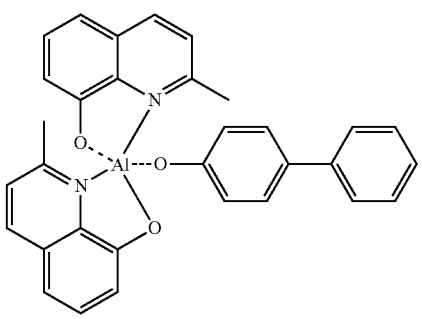

BAlq

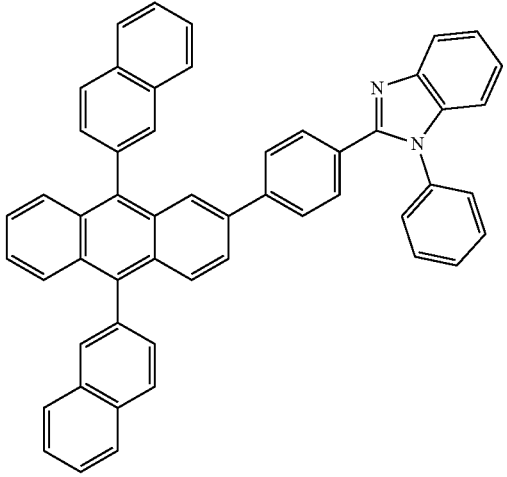

Compound 201

-continued

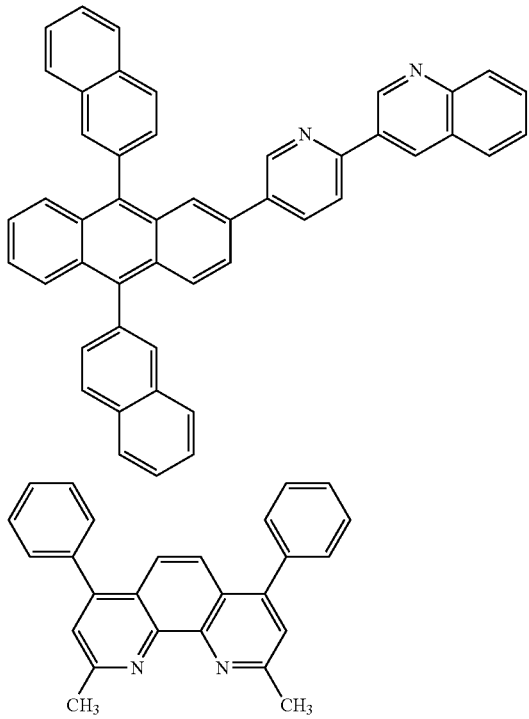

Compound 202

BCP

The thickness of the ETL may be in a range of about 100 Å to about 1,000 Å, for example, in a range of about 150 Å to about 500 Å. When the thickness of the ETL is within this range, satisfactory electron transport properties may be obtained without a substantial increase in driving voltage.

In addition, the ETL may further include a known electron transporting organic compound and a metal-containing material.

The metal-containing material may include a Li-complex. Examples of the Li-complex may include lithium quinolate (Liq) and Compound 203 below:

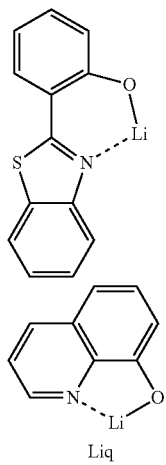

Compound 203

Liq

Also, the EIL, which facilitates electron injection from the cathode, may be deposited on the ETL, and the material for forming the EIL is not particularly limited. The material for forming the EIL may include any known material for forming an EIL, such as LiF, NaCl, CsF, $Li_2O$, or BaO. The deposition conditions of the EIL may vary according the compound used. However, in general, the conditions may be almost the same as the conditions described above for forming the HIL.

The thickness of the EIL may be in a range of about 1 Å to about 100 Å, for example, in a range of about 3 Å to about 90 Å. When the thickness of the EIL is within these ranges, satisfactory electron injection properties may be obtained without a substantial increase in driving voltage.

The second electrode 17 is formed on the organic layer 15. The second electrode 17 may be a cathode, which is an electron injection electrode. Here, a metal for forming the second electrode 17 may include a metal having a low work function, such as a metal, an alloy, an electrically conductive compound, and a mixture thereof. For example, the second electrode 17 may be formed as a thin film using lithium (Li), magnesium (Mg), aluminum (Al), aluminum-lithium (Al—Li), calcium (Ca), magnesium-indium (Mg—In), or magnesium-silver (Mg—Ag), thus being transparent. In order to obtain a top-emission type OLED, the second electrode 17 may be formed as a transparent electrode using ITO or IZO.

As described above, the OLED is described with reference to FIG. 1, but is not limited thereto.

When a phosphorescent dopant is used to form the EML, a HBL may be formed between the HTL and the EML or the H-functional layer and the EML in order to prevent diffusion of triplet excitons or holes into an ETL. The HBL may be formed using various methods such as vacuum deposition, spin coating, casting, LB deposition or the like. When the HBL is formed using vacuum deposition or spin coating, the deposition or coating conditions may vary according to the compound used. However, in general, the conditions may be almost the same as the conditions described above for forming the HIL. Any material that is commonly used to form a HBL may be used. Examples of the material for forming the HBL include an oxadiazole derivative, a triazole derivative, and a phenanthroline derivative, but are not limited thereto. For example, BCP below may be used as a HBL material.

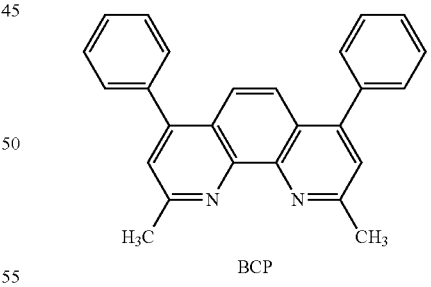

BCP

The thickness of the HBL may be in a range of about 20 Å to about 1000 Å, for example, about 30 Å to about 300 Å. When the thickness of the HBL is within these ranges, the HBL may achieve good hole blocking ability without substantially increasing driving voltage.

As used herein, specific nonlimiting examples of an unsubstituted $C_1$-$C_{60}$ alkyl group (or a $C_1$-$C_{60}$ alkyl group) include a linear or branched $C_1$-$C_{60}$ alkyl group such as a methyl, an ethyl, a propyl, an isobutyl, a sec-butyl, pentyl, an iso-amyl, or a hexyl. The substituted $C_1$-$C_{60}$ alkyl group may be the unsubstituted $C_1$-$C_{60}$ alkyl group in which one or more hydrogen atoms are substituted with deuterium, a halogen atom, a hydroxy group, a nitro group, a cyano group, an amino group, an amidino group, hydrazine, hydrazone, a carboxylic acid group or a salt thereof, a sulfonic acid group or a salt thereof, a phosphoric acid group or a salt thereof, or a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)($Q_{12}$), and —Si($Q_{13}$)($Q_{14}$)($Q_{15}$) (here, $Q_{11}$ through $Q_{15}$ are each independently selected from hydrogen, a $C_1$-$C_{60}$ alkyl group, a $C_2$-$C_{60}$ alkenyl group, a $C_2$-$C_{60}$ alkynyl group, a $C_5$-$C_{60}$ aryl group, and a $C_2$-$C_{60}$ heteroaryl group).

As used herein, the unsubstituted $C_1$-$C_{60}$ alkoxy group (or a $C_1$-$C_{60}$ alkoxy group) has the formula —OA (in this regard, A is the unsubstituted $C_1$-$C_{60}$ alkyl group as described above) and examples thereof include methoxy, ethoxy, isopropyloxy, and the like. The substituted $C_1$-$C_{60}$ alkoxy group includes the unsubstituted $C_1$-$C_{60}$ alkoxy group in which at least one or more hydrogen atoms is substituted with one or more of the substituents described above with reference to the $C_1$-$C_{60}$ alkyl group.

As used herein, the unsubstituted $C_1$-$C_{60}$ alkylthio group (or a $C_1$-$C_{60}$ alkylthio group) has the formula—SA (in this regard, A is the unsubstituted $C_1$-$C_{60}$ alkyl group as described above). The substituted $C_1$-$C_{60}$ alkylthio group is the unsubstituted $C_1$-$C_{60}$ alkylthio group in which at least one or more hydrogen atoms is substituted with one or more of the substituents described above with reference to the $C_1$-$C_{60}$ alkyl group.

As used herein, the unsubstituted $C_2$-$C_{60}$ alkenyl group is interpreted to contain one or more carbon-carbon double bonds in the center or at a terminal end of the unsubstituted $C_2$-$C_{60}$ alkyl group. Examples of the unsubstituted $C_2$-$C_{60}$ alkenyl group include ethenyl, propenyl, butenyl, and the like. The substituted $C_2$-$C_{60}$ alkenyl group is the unsubstituted $C_2$-$C_{60}$ alkenyl group in which at least one or more hydrogen atoms is substituted with one or more of the substituents described above with reference to the $C_1$-$C_{60}$ alkyl group.

As used herein, the unsubstituted $C_2$-$C_{60}$ alkynyl group is interpreted to contain one or more carbon-carbon triple bonds in the center or at a terminal end of the unsubstituted $C_2$-$C_{60}$ alkyl group defined above. Examples of the substituted $C_2$-$C_{60}$ alkynyl group include ethynyl, propynyl, and the like. The substituted $C_2$-$C_{60}$ alkynyl group is the unsubstituted $C_2$-$C_{60}$ alkynyl group in which at least one or more hydrogen atoms is substituted with one or more of the substituents described above with reference to the $C_1$-$C_{60}$ alkyl group.

As used herein, the unsubstituted $C_5$-$C_{60}$ aryl group may indicate a monovalent group having an aromatic carbocyclic system that has 5 to 60 carbon atoms and one or more aromatic rings. The unsubstituted $C_5$-$C_{60}$ arylene group may indicate a divalent group having an aromatic carbocyclic system that has 5 to 60 carbon atoms and one or more aromatic rings. If each of the unsubstituted $C_5$-$C_{60}$ aryl group and the unsubstituted $C_5$-$C_{60}$ arylene group includes two or more rings, the rings may optionally be fused to each other. The substituted $C_5$-$C_{60}$ aryl group and the substituted $C_5$-$C_{60}$ arylene group are the unsubstituted $C_5$-$C_{60}$ aryl group and the unsubstituted $C_5$-$C_{60}$ arylene group, respectively, in which at least one hydrogen atom is substituted with one or more of the substituents described above with reference to the $C_1$-$C_{60}$ alkyl group.

Examples of the substituted or unsubstituted $C_5$-$C_{60}$ aryl group include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., o-, m-, or p-fluorophenyl group, dichlorophenyl group), a dicyanophenyl group, a trifluoromethoxyphenyl group, o-, m-, or p-tolyl group, o-, m-, or p-cumenyl, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), a anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. Examples of the substituted $C_5$-$C_{60}$ aryl group may be readily recognized by reference to the examples of the unsubstituted $C_5$-$C_{60}$ aryl group described above and the substituents of the substituted $C_1$-$C_{60}$ alkyl group. Examples of the substituted or unsubstituted $C_5$-$C_{60}$ arylene group may be readily recognized by reference to the substituted or unsubstituted $C_5$-$C_{60}$ aryl group described above.

As used herein, the unsubstituted $C_2$-$C_{60}$ heteroaryl group indicates a monovalent group having at least one aromatic ring system including carbon rings and one or more hetero atoms selected from N, O, P, and S. The unsubstituted $C_2$-$C_{60}$ heteroarylene group indicates a divalent group having at least one aromatic ring system including carbon rings and one or more hetero atoms selected from N, O, P, and S. In this regard, if the $C_2$-$C_{60}$ heteroaryl group and the $C_2$-$C_{60}$ heteroarylene group each independently have two or more aromatic rings, the rings may optionally be fused to each other. The substituted $C_2$-$C_{60}$ heteroaryl group and the substituted $C_2$-$C_{60}$ heteroarylene group are the unsubstituted $C_2$-$C_{60}$ heteroaryl group and the unsubstituted $C_2$-$C_{60}$ heteroarylene group, respectively, in which one or more hydrogen atoms is substituted with one or more of the substituents described above with reference to the $C_1$-$C_{60}$ alkyl group.

Examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$ heteroarylene group may be readily recognized by reference to the examples of the unsubstituted $C_2$-$C_{60}$ heteroarylene group.

The substituted or unsubstituted $C_5$-$C_{60}$ aryloxy group has the formula —$OA_2$ where $A_2$ is the substituted or unsubstituted $C_5$-$C_{60}$ aryl group as described above. The substituted or unsubstituted $C_5$-$C_{60}$ arylthio group has the formula—$SA_3$ where $A_3$ is the substituted or unsubstituted $C_5$-$C_{60}$ aryl group described above.

Hereinafter, an OLED according to an embodiment of the present invention will now be described with reference to the following examples. However, these examples are presented for illustrative purposes only and are not intended to limit the scope of the invention.

EXAMPLE

Synthesis Example 1

Synthesis of Compound 38

Synthesis of Intermediate 1-a

Intermediate 1-a was synthesized according to Reaction Scheme 1 below:

Reaction Scheme 1

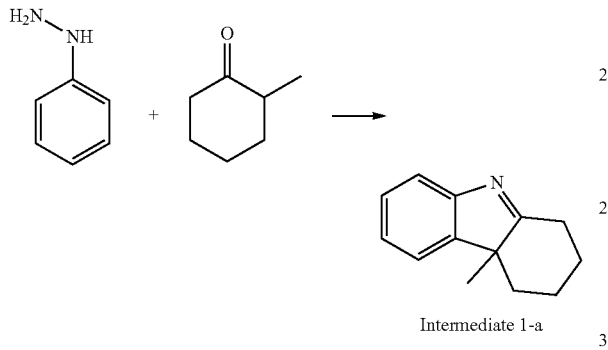

Intermediate 1-a 50 g (0.462 mol) of phenylhydrazine and 170 ml of acetic acid were put into a 500 ml round-bottom flask, and the temperature was raised to 60° C. 51.9 g (0.462 mol) of 2-methylcyclohexanone was dropped into the heated flask, and the mixture was refluxed for about 8 hours. After the reaction was completed, 100 ml of water was added to the mixture, and the resultant mixture was made alkaline with sodium hydroxide. Then, the resultant solution was extracted with water and ethyl acetate to separate an organic layer. The obtained organic layer was dried with anhydrous magnesium sulfate and concentrated under reduced pressure. Thereafter, the resulting product was purified by column chromatography using hexane and ethyl acetate as eluents. As a result, 72 g of Intermediate 1-a was obtained (yield: 84%).

Synthesis of Intermediate 1-b

Intermediate 1-b was synthesized according to Reaction Scheme 2 below:

Reaction Scheme 2

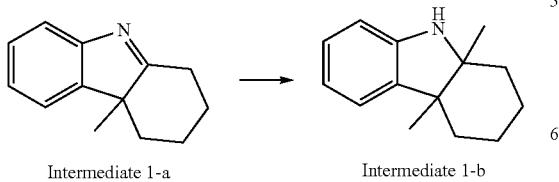

Intermediate 1-a          Intermediate 1-b 57 g (0.308 mol) of Intermediate 1-a was dissolved in 570 ml of toluene in a 2 L round-bottom flask in a nitrogen atmosphere, and the temperature was then decreased to −10° C. 300 ml (0.474 mol) of 1.6M methyl lithium was slowly dropped into the resultant mixture and the reaction was carries out at −10° C. for 3 hours. Subsequently, water was slowly added to the resultant mixture until the solution had no reactivity. The resultant solution was extracted with water and ethyl acetate to separate the organic layer. The obtained organic layer was dried with anhydrous magnesium sulfate and concentrated under reduced pressure. Thereafter, the resulting product was purified by column chromatography using hexane and ethyl acetate as eluents. As a result, 47 g of Intermediate 1-b was obtained (yield: 76%).

Synthesis of Intermediate 1-c

Intermediate 1-c was synthesized according to Reaction Scheme 3 below:

Reaction Scheme 3

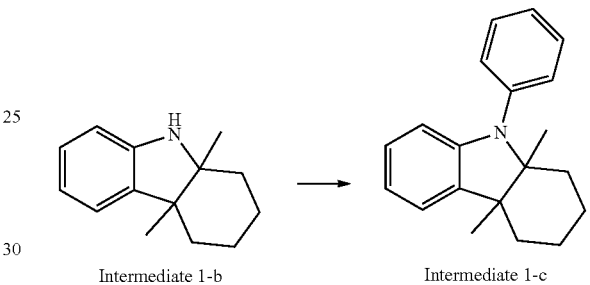

Intermediate 1-b          Intermediate 1-c 40 g (0.199 mol) of Intermediate 1-b, 48.6 g (0.238 mol) of iodobenzene, 0.89 g (0.004 mol) of tris(dibenzylideneacetone)dipalladium(0)(Pd(dba)$_3$), 2.47 g (0.004 mol) of 2,2-bis(diphenylphosphino)-1,1'-binaphthyl (BINAP), 38.19 g (0.397 mol) of sodium tertiarybutoxide, and 400 ml of toluene were added to a 1 L round-bottom flask, and the mixture was refluxed for 8 hours and filtered with celite. The filtrate was concentrated under reduced pressure. The resulting product was purified by column chromatography using hexane as the eluent. As a result, 44 g of Intermediate 1-c was obtained (yield: 79%).

Synthesis of Intermediate 1-d

Intermediate 1-d was synthesized according to Reaction Scheme 4 below:

Reactions Scheme 4

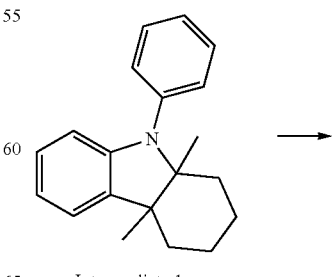

Intermediate 1-c

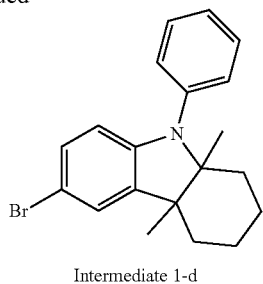

Intermediate 1-d 44 g (0.158 mol) of Intermediate 1-c and 130 ml of dimethylformamide was put into a 500 ml round-bottom flask, and the temperature was then decreased to 0° C. Subsequently, 25.2 g (0.142 mol) of N-bromosuccinimide was dissolved in 220 ml of dimethylformamide, and the solution was slowly added to the mixture. After the addition of the solution was complete, the temperature was raised to room temperature, and the resultant mixture was stirred for 2 hours. Then, the resultant solution was extracted with water and dichloromethane to separate the organic layer. The obtained organic layer was dried with anhydrous magnesium sulfate and concentrated under reduced pressure. Thereafter, the resulting product was crystallized with hexane and the crystal produced therefrom was filtered. As a result, 45 g of Intermediate 1-d was obtained (yield: 80%).

Synthesis of Intermediate 1-e

Intermediate 1-e was synthesized according to Reaction Scheme 5 below:

Reaction Scheme 5

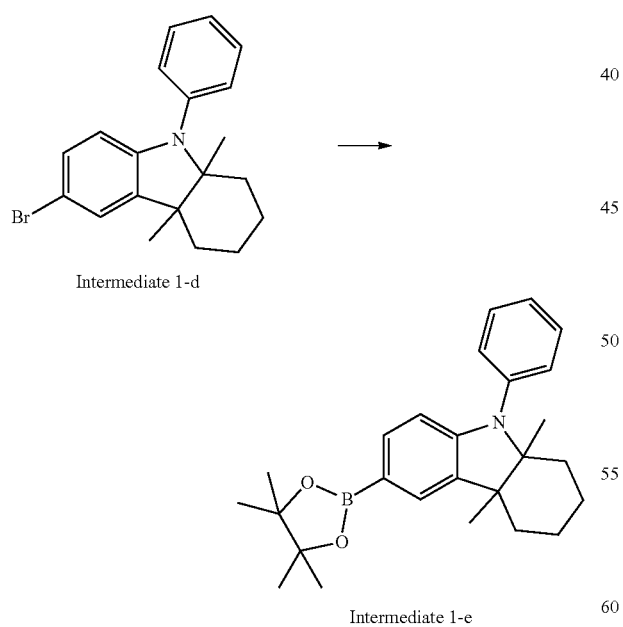

Intermediate 1-d

Intermediate 1-e 40 g (0.112 mol) of Intermediate 1-d, 34 g (0.134 mol) of bis(pinacolato)diboron, 2.73 g (0.003 mol) of palladium(II) chloride (PdCl$_2$), 32.9 g (0.335 mol) of potassium acetate, and 480 ml of toluene were put into a 1 L round-bottom flask, and the mixture was refluxed for 8 hours and filtered with celite. The filtrate was concentrated under reduced pressure. Thereafter, the resulting product was purified by column chromatography using hexane and ethyl acetate as eluents. As a result, 26 g of Intermediate 1-e was obtained (yield: 58%).

Synthesis of Intermediate 1-f

Intermediate 1-f was synthesized according to Reaction Scheme 6 below:

Reaction Scheme 6

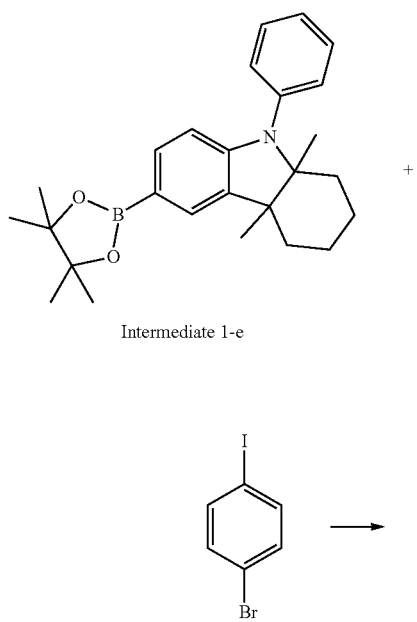

Intermediate 1-e

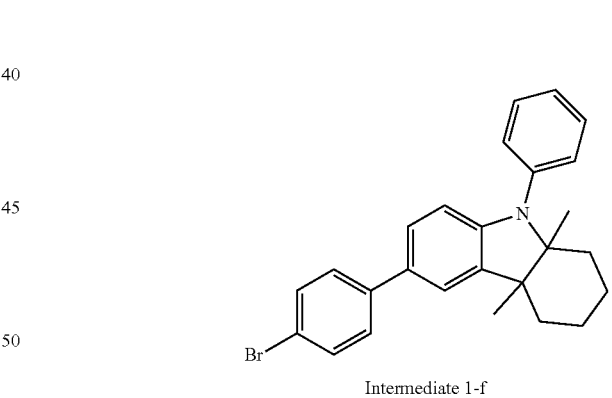

Intermediate 1-f 21 g (0.053 mol) of Intermediate 1-e, 30 g (0.053 mol) of 1-bromo-4-iodobenzene, 4.9 g (0.004 mol) of Tetrakis(triphenylphosphine)palladium(0) (Pd(pph)$_4$), 43.97 g (0.318 mol) of potassium carbonate, 150 ml of dioxane, 150 ml of toluene, and 60 ml of water were put into a 1 L round-bottom flask, and the mixture was refluxed. After the reaction was complete, the resultant solution was extracted with water and ethyl acetate to separate the organic layer. The obtained organic layer was dried with anhydrous magnesium sulfate and concentrated under reduced pressure. Thereafter the resulting product was purified by column chromatography using hexane as the eluent. As a result, 18 g of Intermediate 1-f was obtained (yield: 76%).

Synthesis of Intermediate 1-g

Intermediate 1-g was synthesized according to Reaction Scheme 7 below:

Reaction Scheme 7

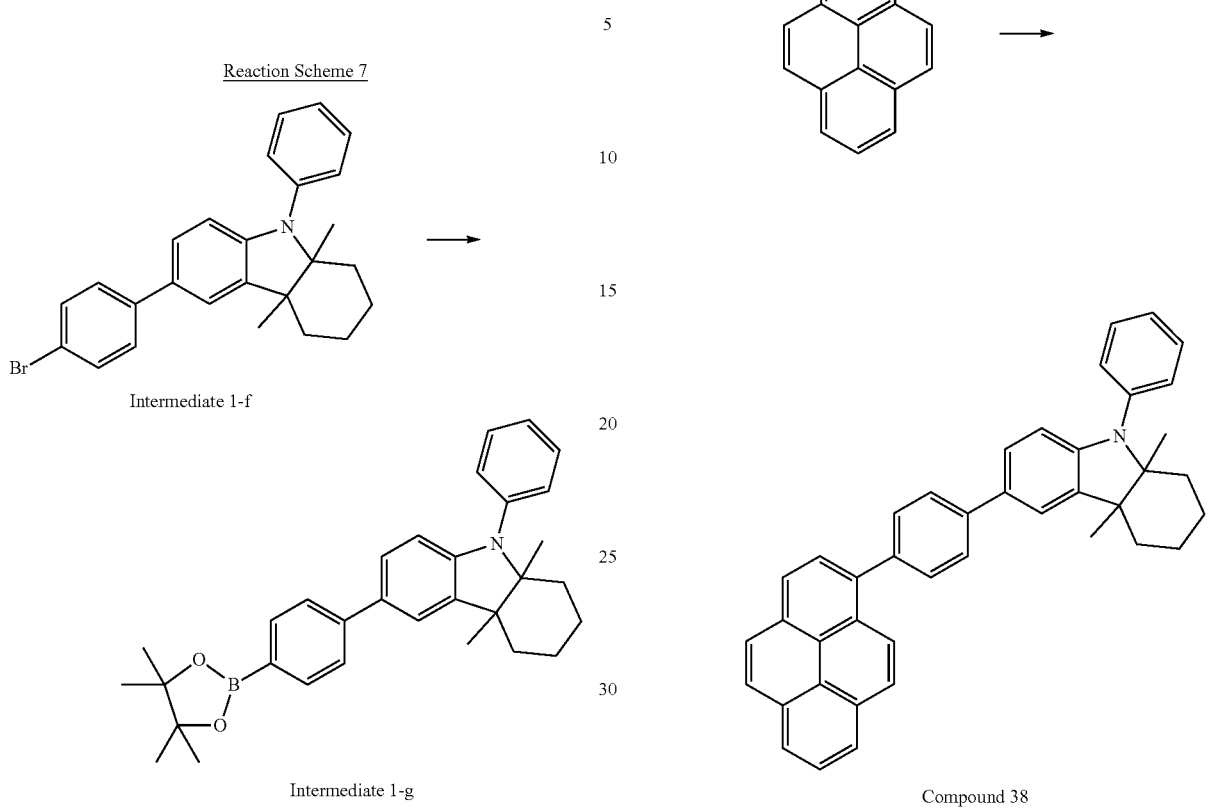

Intermediate 1-f

Intermediate 1-g 25 g (0.059 mol) of Intermediate 1-f, 18 g (0.069 mol) of bis(pinacolato)diboron, 1.4 g (0.002 mol) of PdCl$_2$, 17 g (0.174 mol) of potassium acetate, and 250 ml of toluene were put into a 500 mL round-bottom flask, and the mixture was refluxed for 8 hours. After the reaction was completed, the resultant mixture was filtered with celite, and the filtrate was concentrated under reduced pressure. Thereafter, the resulting product was purified by column chromatography using hexane and ethyl acetate as eluents. As a result, 15 g of Intermediate 1-g was obtained (yield: 54%).

Synthesis of Compound 38

Compound 38 was synthesized according to Reaction Scheme 8 below:

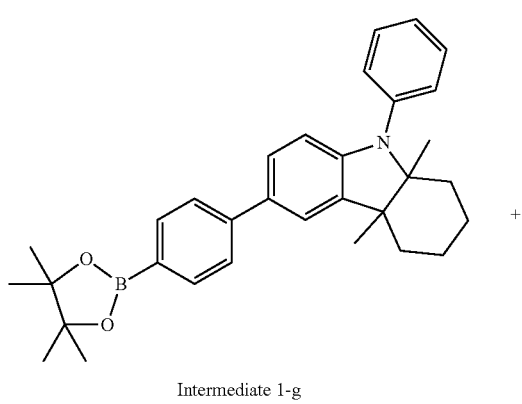

Intermediate 1-g

Compound 38

10.2 g (0.021 mol) of Intermediate 1-g, 5 g (0.018 mol) of 1-bromopyrene, 0.8 g (0.001 mol) of Pd(pph)$_4$, 7.4 g (0.053 mol) of potassium carbonate, 25 ml of dioxane, 25 ml of toluene, and 10 ml of water were put into a 250 ml round-bottom flask, and the mixture was refluxed. After the reaction was completed, water and hexane were added, and the crystals produced therefrom were filtered. The crystals were recrystallized, and 6.1 g of Compound 38 was obtained (yield 62%).

Molecular weight: 553.73

Elementary analysis: Calculated C, 91.10; H, 6.37; N, 2.53. Found C, 91.13; H, 6.39; N, 2.48

1H NMR (CDCl$_3$): δ 8.2~8.1 (m, 3H, Ar—H), δ 7.81~7.72 (m, 6H, Ar—H), δ 7.38~6.8 (m, 12H, Ar—H), δ 1.59~1.31 (m, 8H, CH$_2$—H), δ 1.31~1.15 (d, 6H, CH$_3$—H)

Synthesis Example 2

Synthesis of Compound 262

Synthesis of Intermediate 2-c

Intermediate 2-c was synthesized according to Reaction Scheme 9 below:

Reaction Scheme 9

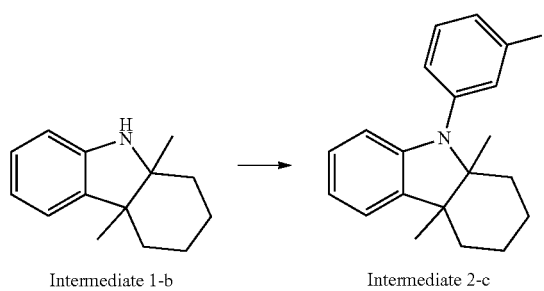

Intermediate 1-b        Intermediate 2-c 59 g of Intermediate 2-c was obtained (yield: 85.6%) in the same manner as in the Synthesis of Intermediate 1-c, except that 1-bromo-3-fluorobenzene was used instead of iodobenzene.

Synthesis of Intermediate 2-d

Intermediate 2-d was synthesized according to Reaction Scheme 10 below:

Reaction Scheme 10

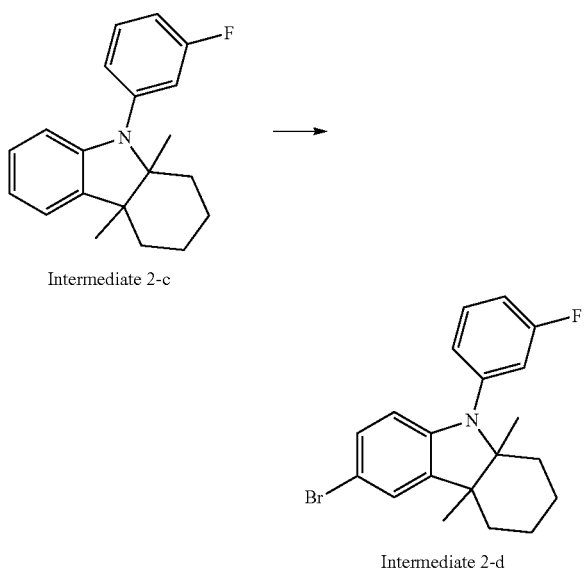

Intermediate 2-c

Intermediate 2-d 42 g of Intermediate 2-d was obtained (yield: 84.4%) in the same manner as in the Synthesis of Intermediate 1-d, except that Intermediate 2-c was used instead of Intermediate 1-c.

Synthesis of Intermediate 2-e

Intermediate 2-e was synthesized according to Reaction Scheme 11 below:

Reaction Scheme 11

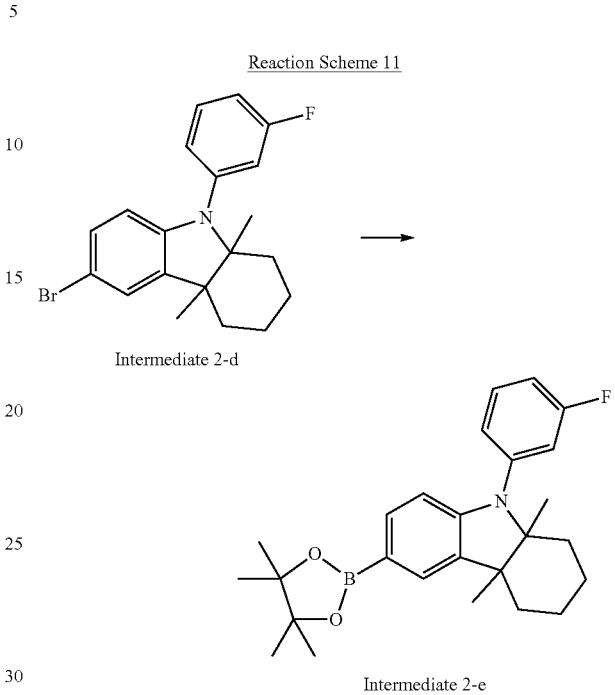

Intermediate 2-d

Intermediate 2-e 21 g of Intermediate 2-e was obtained (yield: 44.6%) in the same manner as in the Synthesis of Intermediate 1-e, except that Intermediate 2-d was used instead of Intermediate 1-d.

Synthesis of Intermediate 2-h

Intermediate 2-h was synthesized according to Reaction Scheme 12 below:

Reaction Scheme 12

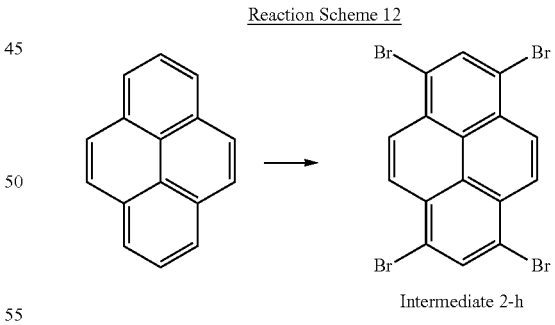

Intermediate 2-h 50 g (0.247 mol) of pyrene was dissolved in 500 ml of chloroform in a 2 L round-bottom flask, and the temperature was decreased to 0° C. Then, a solution of 158 g (0.989 mol) of bromine dissolved in 150 ml of chloroform was slowly added to the flask, the temperature was slowly raised to room temperature, and the resultant mixture was reacted for 8 hours. After the reaction was complete, 100 ml of water was added and the bromine was removed using sodium thiosulfate, and the crystals formed therefrom were filtered and recrystallized. As a result, 97.5 g of Intermediate 2-h was obtained (76%).

Synthesis of Intermediate 2-i

Intermediate 2-i was synthesized according to Reaction Scheme 13 below:

Reaction Scheme 13

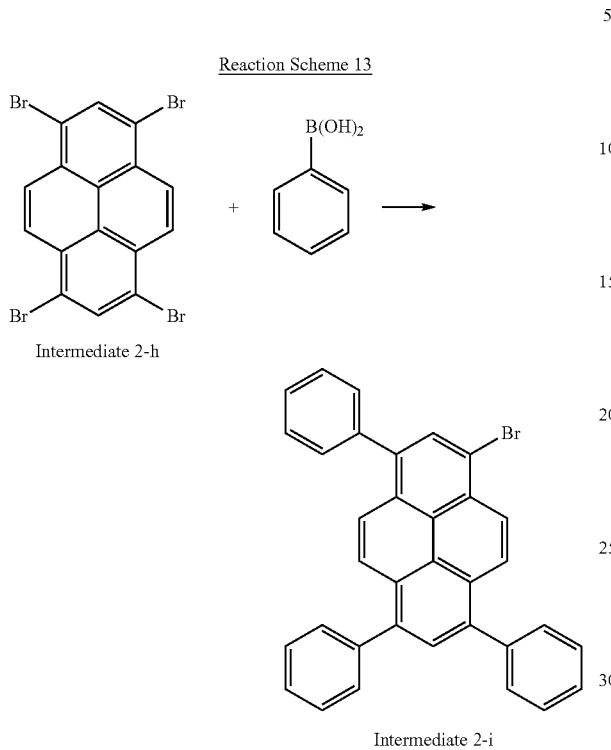

Intermediate 2-h

Intermediate 2-i 50 g (0.097 mol) of Intermediate 2-h, 35.3 g (0.290 mol) of phenylboronic acid, 4.5 g (0.004 mol) of Pd(pph)$_4$, 407.4 g (0.290 mol) of potassium carbonate, 250 ml of dioxane, 250 ml of toluene, and 100 ml of water were put into a 1 L round-bottom flask, and the mixture was refluxed. After the reaction was complete, water and hexane was added, and the crystals formed therefrom were filtered and recrystallized. As a result, 37.3 g of Intermediate 2-i was obtained (yield: 76%).

Synthesis of Compound 262

Compound 262 was synthesized according to Reaction Scheme 14 below:

Reaction Scheme 14

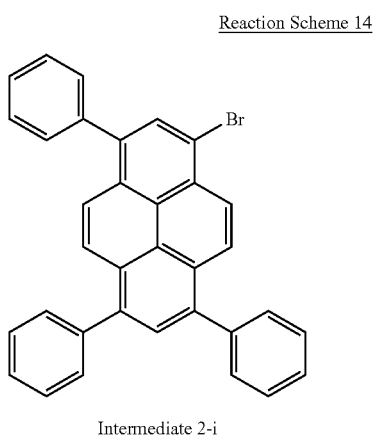

Intermediate 2-i

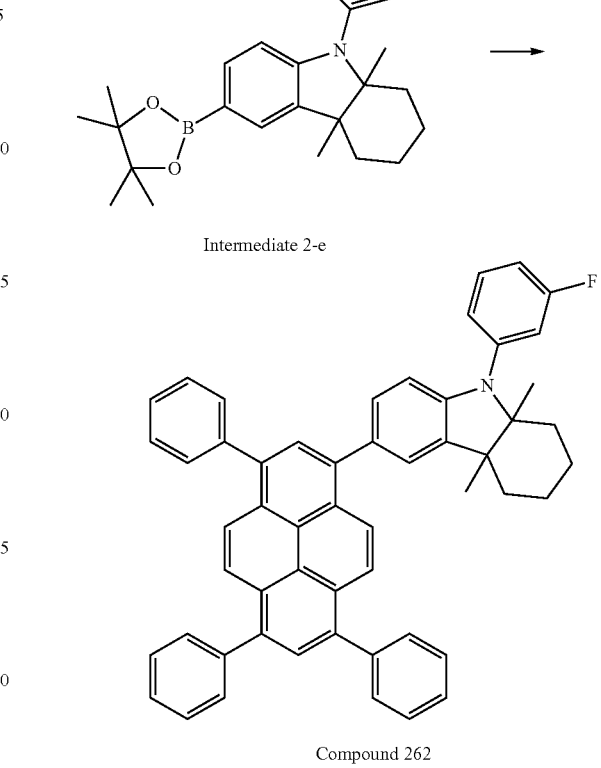

Intermediate 2-e

Compound 262

8.4 g of Compound 262 was obtained (yield: 59%) in the same manner as in the Synthesis of Compound 38, except that Intermediate 2-i was used instead of 1-bromopyrene, and Intermediate 2-e was used instead of Intermediate 1-g. Molecular weight: 723.92

Elementary analysis: Calculated C, 89.59; H, 5.85; F, 2.62; N, 1.93. Found C, 89.60; H, 5.93; F, 2.57; N, 1.90

$^1$H NMR (CDCl$_3$): δ 8.3~8.2 (d, 2H, Ar—H), δ 7.80~7.68 (m, 10H, Ar—H), δ 7.43~6.4 (m, 16H, Ar—H), δ 1.61~1.33 (m, 8H, CH$_2$—H), δ 1.31~1.15 (d, 6H, CH$_3$—H)

Synthesis Example 3

Synthesis of Compound 586

Synthesis of Intermediate 3-a

Intermediate 3-a was synthesized according to Reaction Scheme 15 below:

Reaction Scheme 15

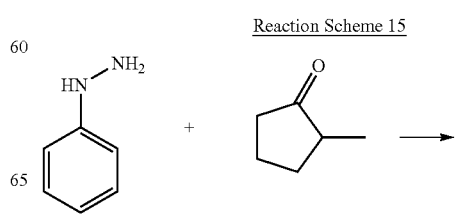

-continued

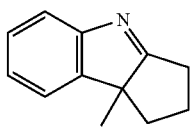

Intermediate 3-a 64.1 g of Intermediate 3-a was obtained (yield: 81.4%) in the same manner as in Synthesis of Intermediate 1-a, except that 2-methylcyclopentanone was used instead of 2-methylcyclohexanone.

Synthesis of Intermediate 3-b

Intermediate 3-b was synthesized according to Reaction Scheme 16 below:

Reaction Scheme 16

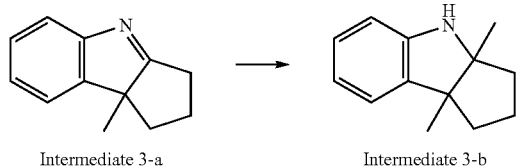

Intermediate 3-a → Intermediate 3-b 45.1 g of Intermediate 3-b was obtained (yield: 76.8%) in the same manner as in the Synthesis of Intermediate 1-b, except that Intermediate 3-a was used instead of Intermediate 1-a.

Synthesis of Intermediate 3-c

Intermediate 3-c was synthesized according to Reaction Scheme 17 below:

Reaction Scheme 17

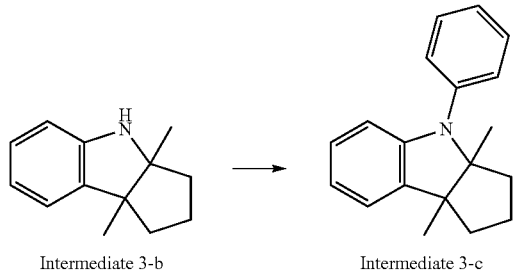

Intermediate 3-b → Intermediate 3-c 51.7 g of Intermediate 3-c was obtained (yield: 81.7%) in the same manner as in the Synthesis of Intermediate 1-c, except that Intermediate 3-b was used instead of Intermediate 1-b.

Synthesis of Intermediate 3-d

Intermediate 3-d was synthesized according to Reaction Scheme 18 below:

Reaction Scheme 18

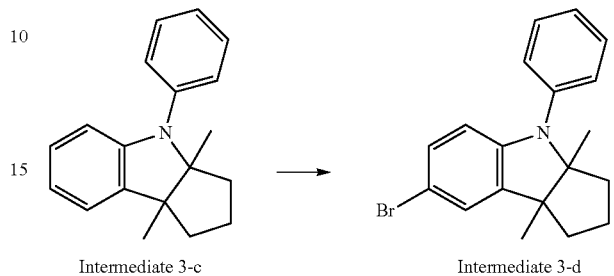

Intermediate 3-c → Intermediate 3-d 40.8 g of Intermediate 3-d was obtained (yield: 66.3%) in the same manner as in the Synthesis of Intermediate 1-d, except that Intermediate 3-c was used instead of Intermediate 1-c.

Synthesis of Intermediate 3-e

Intermediate 3-e was synthesized according to Reaction Scheme 19 below:

Reaction Scheme 19

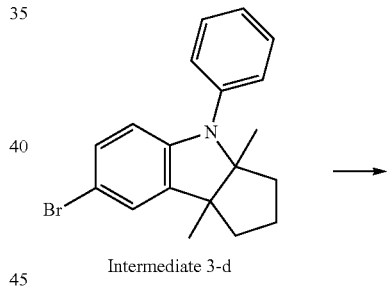

Intermediate 3-d →

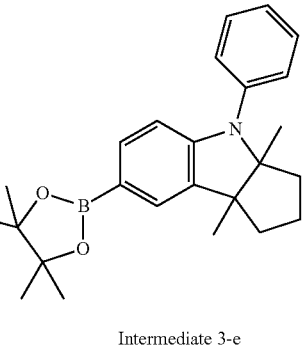

Intermediate 3-e 22.3 g of Intermediate 3-e was obtained (yield: 48.9%) in the same manner as in the Synthesis of Intermediate 1-e, except that Intermediate 3-d was used instead of Intermediate 1-d.

Synthesis of Intermediate 3-h

Intermediate 3-h was synthesized according to Reaction Scheme 20 below:

Reaction Scheme 20

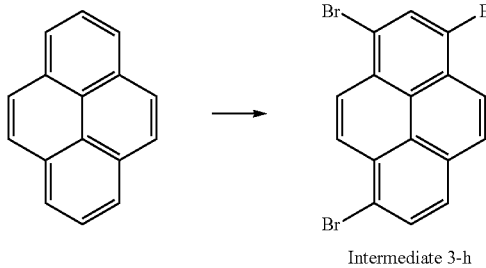

Intermediate 3-h 81.5 g of Intermediate 3-h was obtained (yield: 81.5%) in the same manner as in the Synthesis of Intermediate 2-h, except that 177 g of bromine was used instead of 158 g of bromine.

Synthesis of Compound 586

Compound 586 was synthesized according to Reaction Scheme 21 below:

Reaction Scheme 21

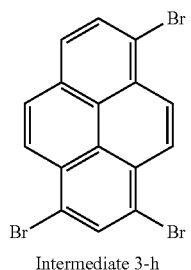

Intermediate 3-h

+

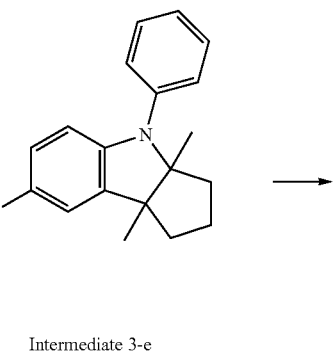

Intermediate 3-e

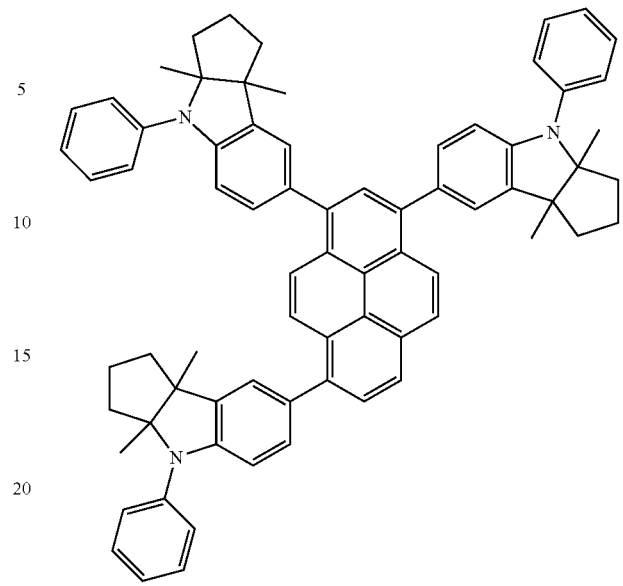

Compound 586

10.2 g of Compound 586 was obtained (yield: 45%) in the same manner as in the Synthesis of Compound 38, except that Intermediate 3-h was used instead of 1-bromopyrene and Intermediate 3-e was used instead of Intermediate 1-g. Molecular weight: 986.33

Elementary analysis: Calculated C, 88.89; H, 6.85; N, 4.26. Found C, 88.91; H, 6.90; N, 4.19

$^1$H NMR (CDCl$_3$): δ 8.3~8.1 (m, 3H, Ar—H), δ 7.85~7.77 (m, 7H, Ar—H), δ 7.32~6.75 (m, 21H, Ar—H), δ 1.81~1.43 (m, 18H, CH$_2$—H), δ 1.21~1.15 (d, 18H, CH$_3$—H)

Synthesis Example 4

Synthesis of Compound 726

Compound 726 was synthesized according to Reaction Scheme 22 below:

Reaction Scheme 22

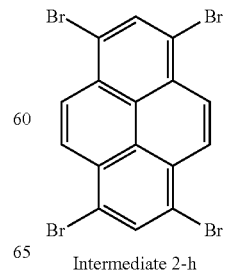

+

Intermediate 2-h

-continued

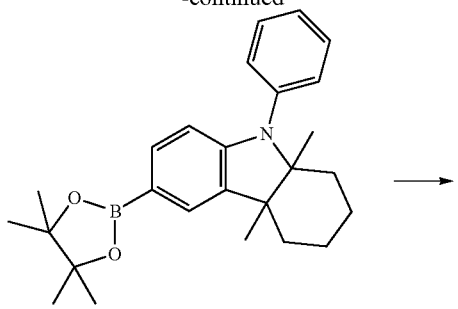

Intermediate 1-e

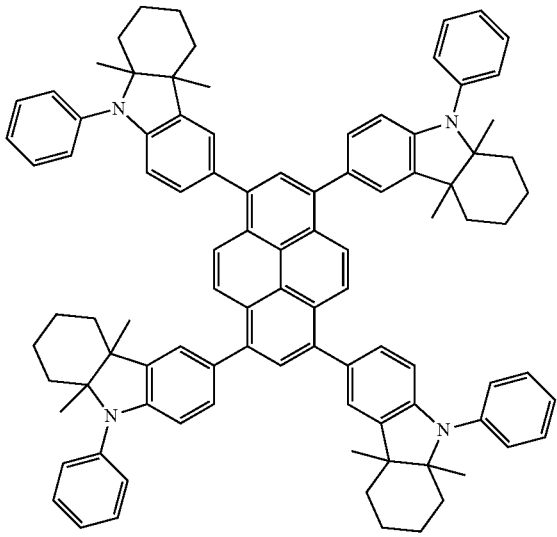

Compound 726

11.8 g of Compound 726 was obtained (yield: 46.5%) in the same manner as in the Synthesis of Compound 38, except that Intermediate 2-h was used instead of 1-bromopyrene and Intermediate 1-e was used instead of Intermediate 1-g. Molecular weight: 1303.8

Elementary analysis: Calculated C, 88.44; H, 7.27; N, 4.30. Found C, 88.43; H, 7.27; N, 4.30

1H NMR (CDCl$_3$): δ 8.22 (s, 2H, Ar—H), δ 7.82~7.76 (m, 8H, Ar—H), δ 7.45~6.7 (m, 28H, Ar—H), δ 1.59~1.31 (m, 32H, CH$_2$—H), δ 1.31~1.15 (d, 24H, CH$_3$—H)

Synthesis Example 5

Synthesis of Compound 929

Synthesis of Intermediate 5-a

Intermediate 5-a was synthesized according to Reaction Scheme 23 below:

Reaction Scheme 23

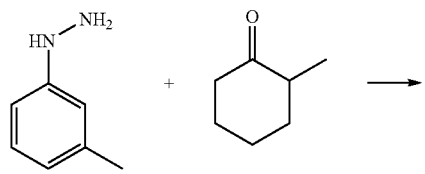

-continued

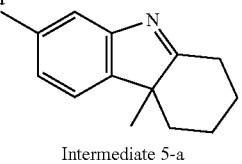

Intermediate 5-a 42 g of Intermediate 5-a was obtained (yield: 51.5%) in the same manner as in the Synthesis of Intermediate 1-a, except that 3-methylphenylhydrazine was used instead of phenylhydrazine.

Synthesis of Intermediate 5-b

Intermediate 5-b was synthesized according to Reaction Scheme 24 below:

Reaction Scheme 24

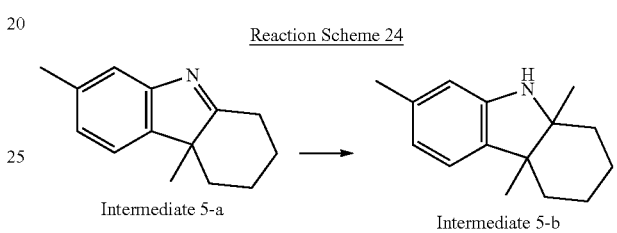

Intermediate 5-a                Intermediate 5-b 28.3 g of Intermediate 5-b was obtained (yield: 58.2%) in the same manner as in the Synthesis of Intermediate 1-b, except that Intermediate 5-a was used instead of Intermediate 1-a.

Synthesis of Intermediate 5-c

Intermediate 5-c was synthesized according to Reaction Scheme 25 below:

Reaction Scheme 25

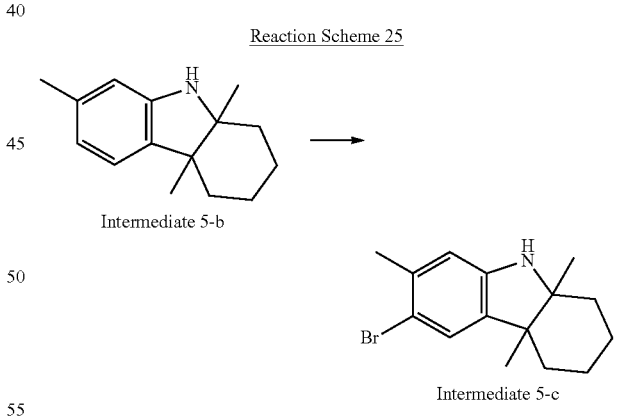

Intermediate 5-b

Intermediate 5-c 28.3 g (0.131 mol) of Intermediate 5-b and 85 ml of dimethylformamide were put into a 500 ml round-bottom flask, and the temperature was decreased to 0° C. Then, 23.4 g (0.131 mol) of N-bromosuccinimide was dissolved in 142 ml of dimethylformamide and the solution was slowly added to the mixture, and the temperature was raised to room temperature and the resultant solution was stirred for 2 hours. After the reaction was completed, the resultant solution was extracted with water and dichloromethane to separate the organic layer. The obtained organic layer was dried with anhydrous magnesium sulfate and concentrated under reduced pressure. Thereafter, the resulting product was purified by column chromatography using hexane and ethyl acetate as eluent. As a result, 29.8 g of Intermediate 5-c was obtained (yield: 77%).

Synthesis of Intermediate 5-d

Intermediate 5-d was synthesized according to Reaction Scheme 26 below:

Reaction Scheme 26

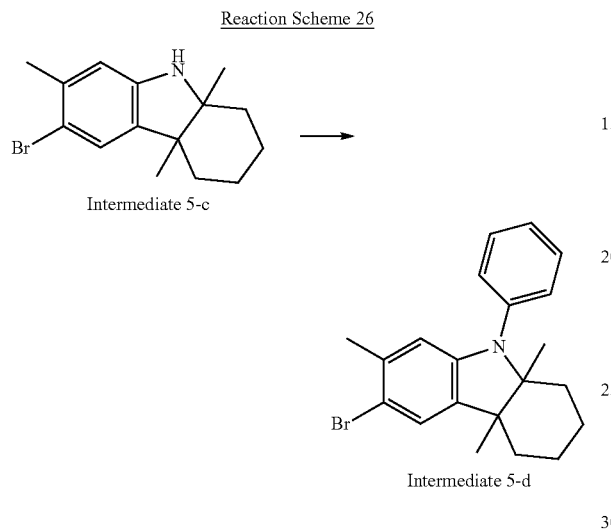

25.9 g of Intermediate 5-d was obtained (yield: 69%) in the same manner as in the Synthesis of Intermediate 1-c, except that Intermediate 5-c was used instead of Intermediate 1-b.

Synthesis of Intermediate 5-e

Intermediate 5-e was synthesized according to Reaction Scheme 27 below:

Reaction Scheme 27

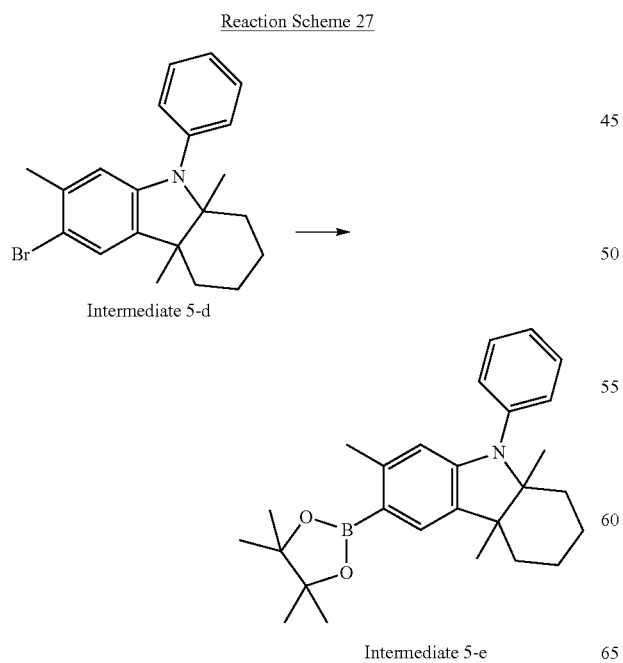

13.4 g of Intermediate 5-e was obtained (yield: 45.9%) in the same manner as in the Synthesis of Intermediate 1-e, except that Intermediate 5-d was used instead of Intermediate 1-d.

Synthesis of Compound 929

Compound 929 was synthesized according to Reaction Scheme 28 below:

Reaction Scheme 28

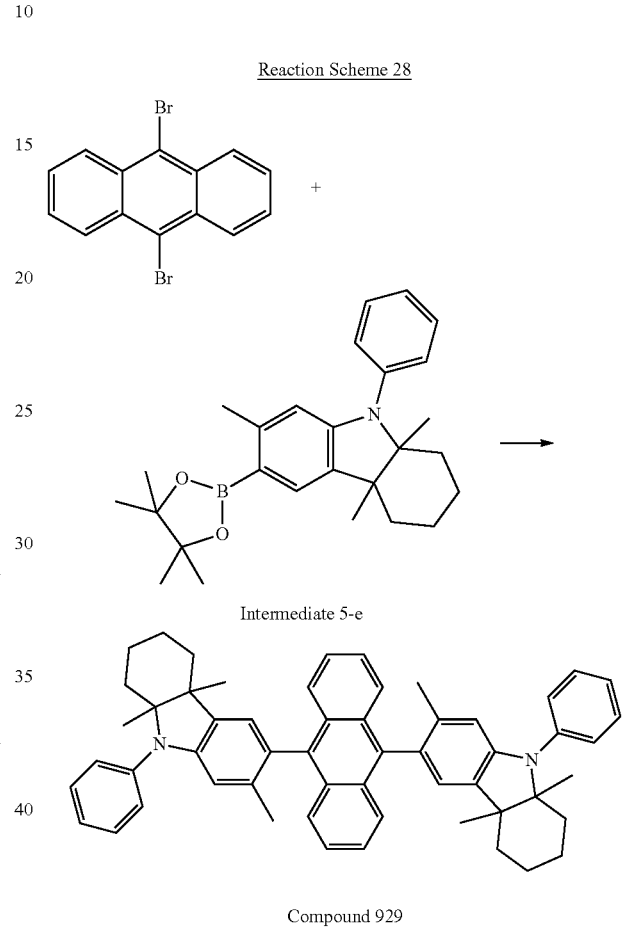

5.1 g of Compound 929 was obtained (yield: 34.5%) in the same manner as in the Synthesis of Compound 38, except that 9,10-dibromoanthracene was used instead of 1-bromopyrene and Intermediate 5-e was used instead of Intermediate 1-g. Molecular weight: 757.06

Elementary analysis: Calculated C, 88.84; H, 7.46; N, 3.70. Found C, 88.79; H, 7.65; N, 3.56

1H NMR (CDCl$_3$): δ 7.85~7.79 (m, 4H, Ar—H), δ 7.43~6.81 (m, 18H, Ar—H), δ 2.64 (s, 6H, CH$_3$—H), δ 1.61~1.33 (m, 16H, CH$_2$—H), δ 1.31~1.15 (d, 12H, CH$_3$—H)

Evaluation Example 1

Thermo Gravimetric Analysis (TGA)

The results of thermal analysis performed on each of Compounds 38, 262, 586, 726, and 929 using TGA and differential scanning calorimetry (DSC) (N$_2$ atmosphere, range of temperature: room temperature to 600° C. (10° C./min)-TGA, room temperature to 400° C. (10° C./min)-

DSC, and Pan Type: Pt Pan in disposable Al pan (TGA), disposable Al pan (DSC)) are illustrated in FIGS. 2 through 6. From the results shown in FIGS. 2 through 6, it is confirmed that Compounds 38, 262, 586, 726, and 929 have good thermal stability.

Example 1

An ITO glass substrate was patterned to have an emission area of 2 mm×2 mm and then washed. The ITO glass was placed in a vacuum chamber, CuPc(800 Å) and α-NPD(300 Å) were sequentially formed on the ITO glass at a base pressure of $1 \times 10^{-7}$ torr to form an HIL and an HTL, respectively. BH1 as a host and Compound 38 as a dopant were co-deposited on the HTL at a ratio of 97:3 to form an EML having a thickness of 250 Å. Alq3(350 Å), LiF (5 Å) and Al (500 Å) were sequentially deposited on the EML, and thereby an OLED sequentially including an ETL, an EIL, and a cathode was manufactured.

Example 2

An OLED was manufactured in the same manner as in Example 1, except that Compound 262 was used instead of Compound 38 during EML formation.

Example 3

An OLED was manufactured in the same manner as in Example 1, except that Compound 586 was used instead of Compound 38 during EML formation.

Example 4

An OLED was manufactured in the same manner as in Example 1, except that Compound 726 was used instead of Compound 38 during EML formation.

Example 5

An OLED was manufactured in the same manner as in Example 1, except that Compound 929 was used instead of Compound 38 during EML formation.

Comparative Example 1

An OLED was manufactured in the same manner as in Example 1, except that Compound A below was used instead of Compound 38 during EML formation.

Compound A

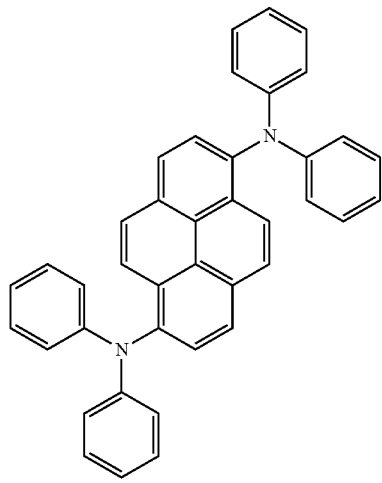

Comparative Example 2

An OLED was manufactured in the same manner as in Example 1, except that Compound B below was used instead of Compound 38 during EML formation.

Compound B

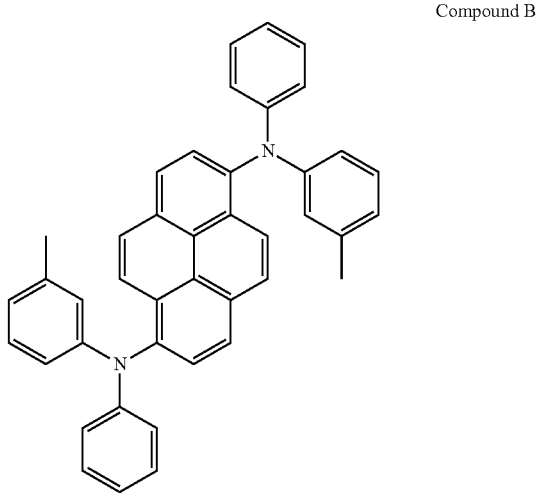 [SMILES: Cc1cccc(N(c2ccccc2)c2ccc3ccc4c(N(c5ccccc5)c5cccc(C)c5)ccc5ccc2c3c54)c1]

Comparative Example 3

An OLED was manufactured in the same manner as in Example 1, except that Compound C below was used instead of Compound 38 during EML formation.

Compound C

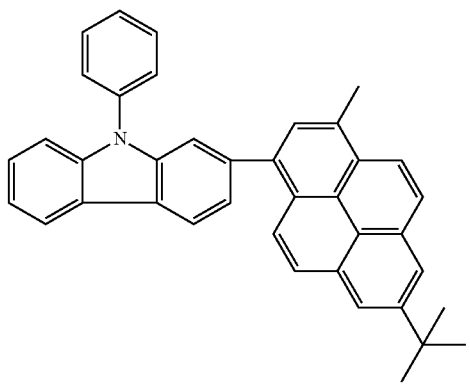

Evaluation Example 2

Figure 7:
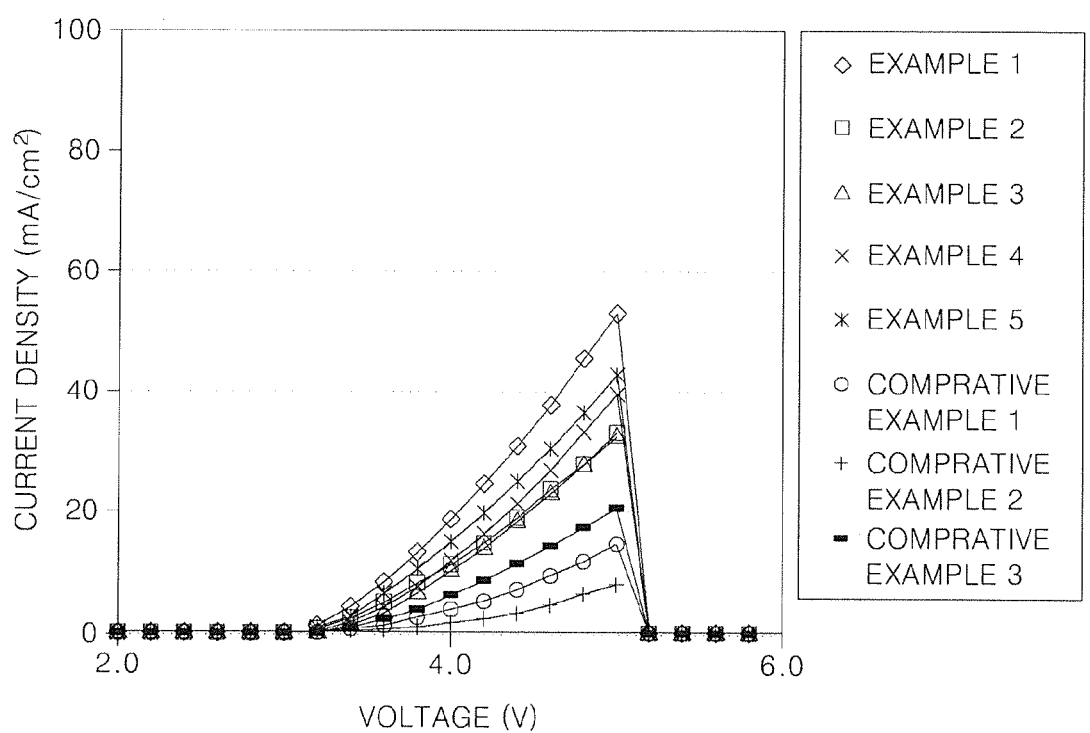
FIG. 7 is a voltage-current density graph of the OLEDs of Examples 1 through 5 and Comparative Examples 1 through 3.
Figure 8:
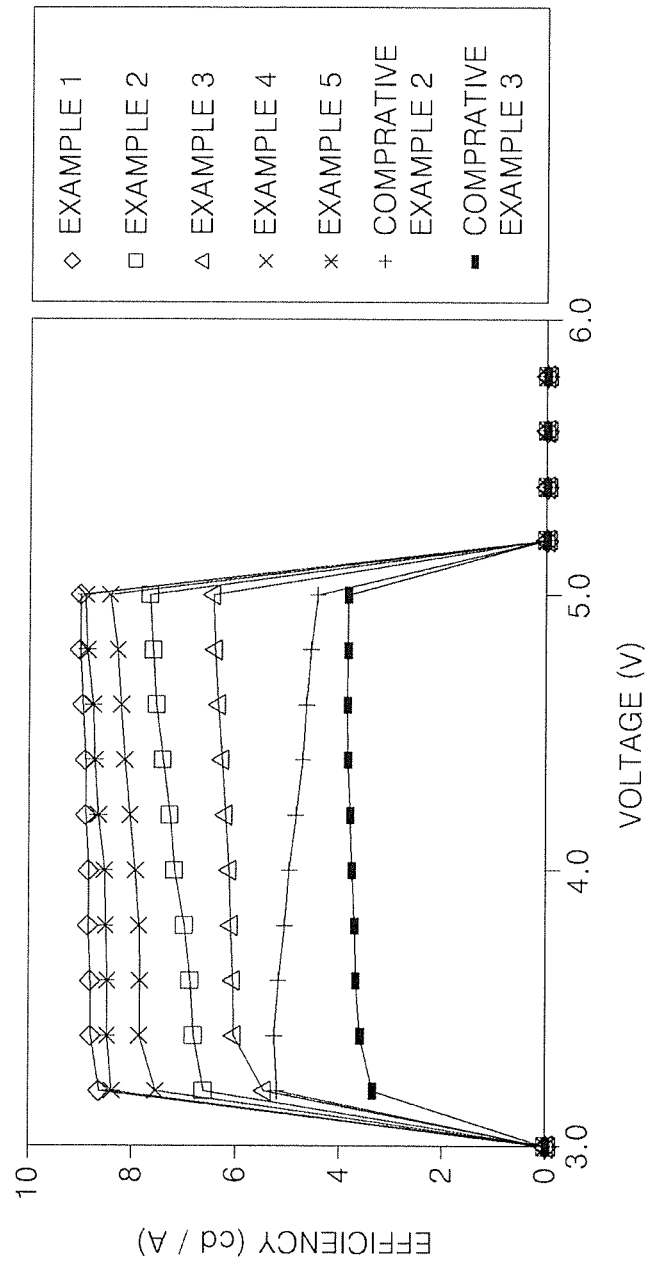
FIG. 8 is a voltage-efficiency graph of the OLEDs of Examples 1 through 5 and Comparative Examples 1 through 3.
Figure 9:
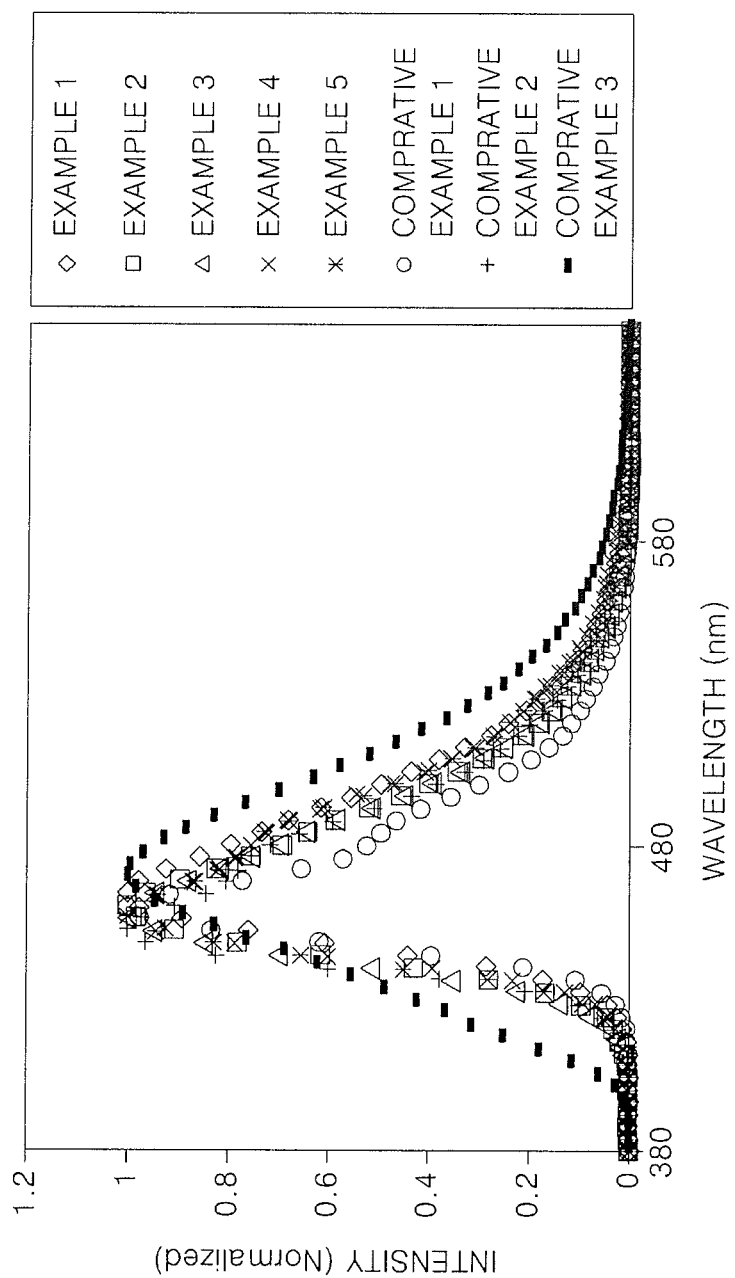
FIG. 9 is a photoluminescence (PL) spectrum of the OLEDs of Examples 1 through 5 and Comparative Examples 1 through 3.

The driving voltage, current, luminance (measured at 0.4 mA), color coordinates, and lifetime (T97) of each of the OLEDs manufactured according to Examples 1 through 5 and Comparative Examples 1 through 3 were measured using a PR650 Spectroscan Source Measurement Unit (manufactured by PhotoResearch), and the measurement results are shown in Table 1 below. A voltage-current density graph is illustrated in FIG. 7, a voltage-efficiency graph is illustrated in FIG. 8, and a photoluminescence (PL) spectrum is illustrated in FIG. 9. T97 indicates the time at which the luminance of each of the OLEDs decreased to 97% of the initial luminance and it was measured at 3,000 nit.

TABLE 1

| EML dopant | Vol. (V) | Current density (mA/cm²) | Lum. eff. (cd/A) | Lum. (cd/m²) | CIEx | CIEy | T97 (hr) |
|---|---|---|---|---|---|---|---|
| Ex. 1 Compound 38 | 3.7 | 10 | 8.8 | 883 | 0.136 | 0.123 | 308 |
| Ex. 2 Compound 262 | 4.0 | 10 | 7.1 | 713 | 0.138 | 0.110 | 250 |
| Ex. 3 Compound 586 | 4.0 | 10 | 6.2 | 618 | 0.141 | 0.125 | 150 |
| Ex. 4 Compound 726 | 3.9 | 10 | 7.9 | 793 | 0.142 | 0.118 | 500 |
| Ex. 5 Compound 929 | 3.8 | 0 | 0.5 | 851 | 0.143 | 0.114 | 150 |
| Comp. Ex. 1 Compound A | 4.3 | 0 | 0.06 | 534 | 0.133 | 0.137 | 45 |
| Comp. Ex. 1 Compound B | 5.1 | 0 | 0.59 | 504 | 0.134 | 0.144 | 35 |
| Comp. Ex. 2 Compound C | 4.3 | 0 | 0.81 | 380 | 0.151 | 0.178 | 10 |

From the results shown in Table 1, it is confirmed that the OLEDs of Examples 1 through 5 each have good driving voltage, higher luminance efficiency, higher luminance, higher color purity, and longer lifetimes, as compared to the OLEDs of Comparative Examples 1 through 3.

As described above, the OLEDs including the condensed-cyclic compound may have low driving voltages, high luminance, high efficiency, and long lifetimes.

While the present invention has been illustrated and described with reference to exemplary embodiments thereof, it will be understood by those of ordinary skill in the art that various changes to the described embodiments may be made without departing from the spirit and scope of the present invention as defined by the following claims.

What is claimed is:

1. A condensed-cyclic compound represented by Formula 1:

   Formula 1 wherein:
q is an integer of 1 to 6, and when q is 2 or greater, 2 or more of $Ar_2$ are identical to or different from each other;
$Ar_2$ is represented by Formula 2:

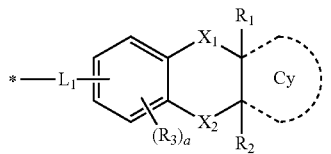   Formula 2 wherein Cy is a substituted or unsubstituted $C_3$ to $C_8$ cycloalkane;
$X_1$ is $N(R_{11})$, $B(R_{11})$, $Si(R_{11})(R_{12})$, O, or S;
$X_2$ is a single bond or $—[C(R_{15})(R_{16})]_n—$, wherein n is an integer of 1 to 3, and when n is 2 or greater, 2 or more $R_{15}$ and $R_{16}$ groups are identical to or different from each other;
$L_1$ is a single bond, a substituted or unsubstituted $C_1$-$C_{60}$ alkylene group, a substituted or unsubstituted $C_2$-$C_{60}$ alkynylene group, a substituted or unsubstituted $C_3$-$C_{60}$ cycloalkylene group, a substituted or unsubstituted $C_2$-$C_{60}$ heterocycloalkylene group, a substituted or unsubstituted $C_5$-$C_{60}$ arylene group, or a substituted or unsubstituted $C_2$-$C_{60}$ heteroarylene;

$R_1$ through $R_3$, $R_{11}$, $R_{12}$, $R_{15}$, and $R_{16}$ are each independently hydrogen, deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_1$-$C_{60}$ alkylthio group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a (substituted or unsubstituted $C_1$-$C_{60}$ alkyl) amino group, a di(substituted or unsubstituted $C_1$-$C_{60}$ alkyl) amino group, or a (substituted or unsubstituted $C_5$-$C_{60}$ aryl) amino group, a di(substituted or unsubstituted $C_5$-$C_{60}$ aryl) amino group;

a is an integer of 1 to 3, and when a is 2 or greater, 2 or more $R_3$ groups are identical to or different from each other; and

* is a binding site to $Ar_1$ of Formula 1; and $Ar_1$ is represented by any one of Formulae 3A through 3C and 3E-3G:

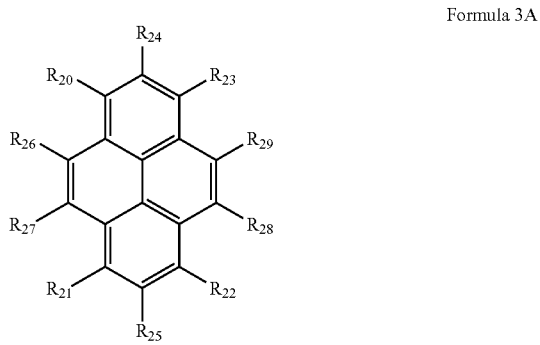

Formula 3A

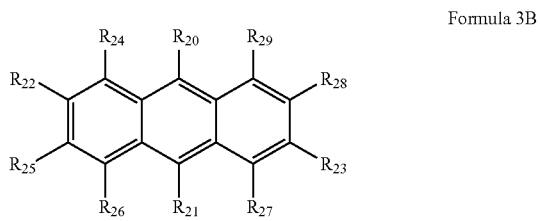

Formula 3B

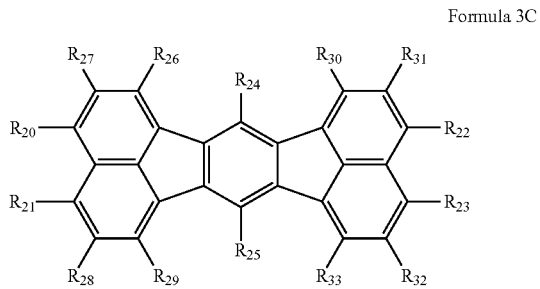

Formula 3C

-continued

Formula 3E

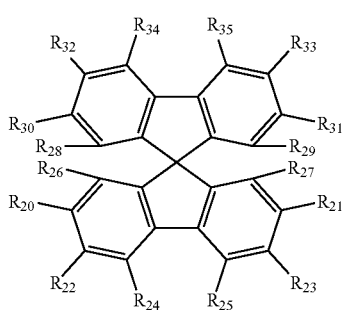

Formula 3F

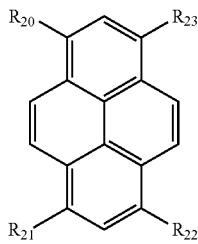

Formula 3G

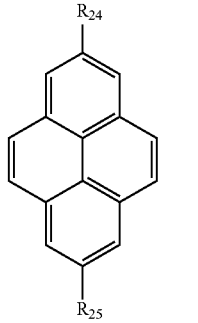

wherein $R_{20}$ through $R_{39}$ are each independently a binding site to $Ar_2$ represented by Formula 2, hydrogen, deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_1$-$C_{60}$ alkylthio group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, a substituted or unsubstituted $C_2$-$C_{60}$ heteroaryl group, a(substituted or unsubstituted $C_1$-$C_{60}$ alkyl) amino group, a di(substituted or unsubstituted $C_1$-$C_{60}$ alkyl) amino group, or a (substituted or unsubstituted $C_5$-$C_{60}$ aryl) amino group or a di(substituted or unsubstituted $C_5$-$C_{60}$ aryl) amino group, wherein one to six groups selected from $R_{20}$ through $R_{39}$ are binding sites to $Ar_2$ represented by Formula 2.

2. The condensed-cyclic compound of claim 1, wherein $Ar_1$ is represented by any one of Formulae 3A-1 through 3C-1 and 3E-1 through 3G-1:

Formula 3A-1

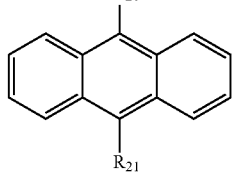

Formula 3A-2

Formula 3B-1

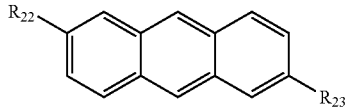

Formula 3B-2

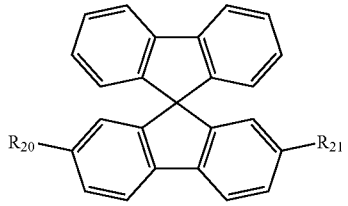

Formula 3C-1

Formula 3E-1

-continued

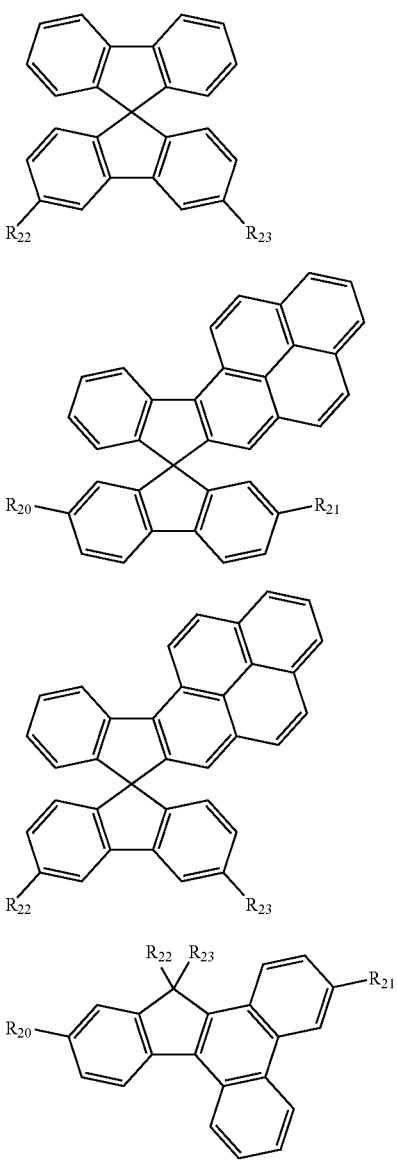

Formula 3E-2

Formula 3F-1

Formula 3F-2

Formula 3G-1 wherein R$_{20}$ through R$_{25}$ are each independently any one of a binding site to Ar$_2$ represented by Formula 2; hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a C$_1$-C$_{10}$ alkyl group; a C$_1$-C$_{10}$alkoxy group; a C$_1$-C$_{10}$ alkylthio group; a C$_1$-C$_{10}$ alkyl group, a C$_1$-C$_{10}$ alkoxy group, and C$_1$-C$_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a C$_1$-C$_{10}$ alkyl group, a C$_1$-C$_{10}$ alkoxy group, and a C$_1$-C$_{10}$ alkylthio group; an indolyl group; a benzoimidazolyl group; a carbazolyl group; an imidazolyl group; an imidazolynyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolynyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a C$_1$-C$_{10}$ alkyl group, a C$_1$-C$_{10}$ alkoxy group, a C$_1$-C$_{10}$ alkylthio group, a phenyl group, and a naphthyl group; a di(C$_1$-C$_{10}$ alkyl) amino group; and a di(C$_6$-C$_{20}$ aryl) amino group, wherein the C$_6$-C$_{20}$ aryl group is a phenyl group, a naphthyl group, a fluorenyl group, a phenanthrenyl group, an anthryl group, a pyrenyl group, or a chrysenyl group;

at least one of R$_{20}$ through R$_{23}$ of Formulae 3A-1 and 3C-1 is a binding site to Ar$_2$ represented by Formula 2;

at least one of R$_{24}$ through R$_{25}$ of Formula 3A-2 is a binding site to Ar$_2$ represented by Formula 2;

at least one of R$_{20}$ through R$_{21}$ of Formulae 3B-1, 3E-1, 3F-1, and 3G-1 is a binding site to Ar$_2$ represented by Formula 2; and at least one of R$_{22}$ through R$_{23}$ of Formulae 3B-2, 3E-2, and 3F-2 is a binding site to Ar$_2$ represented by Formula 2.

3. The condensed-cyclic compound of claim 1, wherein Ar$_1$ is represented by any one of Formulae 3A-1 through 3B-1 below:

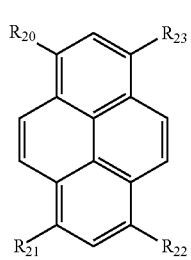

Formula 3A-1

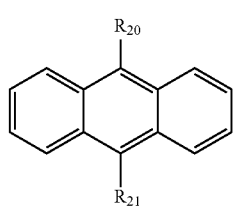

Formula 3B-1 wherein R$_{20}$ through R$_{23}$ are each independently a binding site to Ar$_2$ represented by Formula 2; hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, a $C_1$-$C_{10}$ alkoxy group, and a $C_1$-$C_{10}$ alkylthio group; a di($C_1$-$C_{10}$ alkyl) amino group; and a di($C_6$-$C_{20}$ aryl) amino group, wherein the $C_6$-$C_{20}$ aryl group is a phenyl group, a naphthyl group, a fluorenyl group, a phenanthrenyl group, an anthryl group, a pyrenyl group, or a chrysenyl group;

at least one of $R_{20}$ through $R_{23}$ of Formula 3A-1 is a binding site to $Ar_2$ represented by Formula 2; and at least one of $R_{20}$ and $R_{21}$ of Formula 3B-1 is a binding site to $Ar_2$ represented by Formula 2.

4. The condensed-cyclic compound of claim 1, wherein $X_1$ in Formula 2 is $N(R_{11})$, $B(R_{11})$, or $Si(R_{11})(R_{12})$, wherein $R_{11}$ and $R_{12}$ are each independently hydrogen, deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted phenyl group, a substituted or unsubstituted pentalenyl, a substituted or unsubstituted indenyl, a substituted or unsubstituted naphthyl group, a substituted or unsubstituted azulenyl, a substituted or unsubstituted heptalenyl, a substituted or unsubstituted indacenyl, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted quinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, or a substituted or unsubstituted oxadiazolyl group.

5. The condensed-cyclic compound of claim 1, wherein $X_1$ in Formula 2 is $N(R_{11})$, $B(R_{11})$, or $Si(R_{11})(R_{12})$, wherein $R_{11}$ and $R_{12}$ are each independently represented by any one of Formulae 4A through 4H:

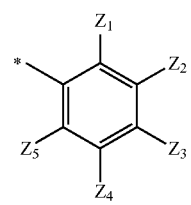

Formula 4A

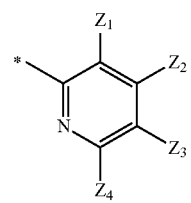

Formula 4B

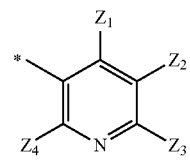

Formula 4C

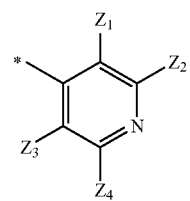

Formula 4D

Formula 4E, Formula 4F, Formula 4G, Formula 4H wherein $Z_1$ through $Z_7$ are each independently any one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolyl group; an imidazolyl group; an imidazolynyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolynyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl) amino group; and a di($C_6$-$C_{20}$ aryl) amino group, wherein the $C_6$-$C_{20}$ aryl group is a phenyl group, a naphthyl group, a fluorenyl group, a phenanthrenyl group, an anthryl group, a pyrenyl group, or a chrysenyl group.

6. The condensed-cyclic compound of claim 1, wherein $X_1$ in Formula 2 is O or S.

7. The condensed-cyclic compound of claim 1, wherein $X_2$ in Formula 2 is a single bond.

8. The condensed-cyclic compound of claim 1, wherein $L_1$ in Formula 2 is a single bond, a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted pycenylene group, a substituted or unsubstituted perylenylene group, a substituted or unsubstituted pentacenylene group, a substituted or unsubstituted hexacenylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted imidazopyridinylene group, a substituted or unsubstituted imidazopyrimidinylene group, a substituted or unsubstituted pyridinylene group, a substituted or unsubstituted pyrazinylene group, a substituted or unsubstituted pyrimidinylene group, a substituted or unsubstituted indolylene group, a substituted or unsubstituted purinyl group, a substituted or unsubstituted quinolinyl group, a substituted or unsubstituted phthalazinyl group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted carbazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group, a substituted or unsubstituted dibenzothiophenylene group, a substituted or unsubstituted dibenzofuranylene group, a substituted or unsubstituted triazinylene group, or a substituted or unsubstituted oxadiazolylene group.

9. The condensed-cyclic compound of claim 1, wherein $L_1$ in Formula 2 is a single bond or any one of Formulae 5A through 5K:

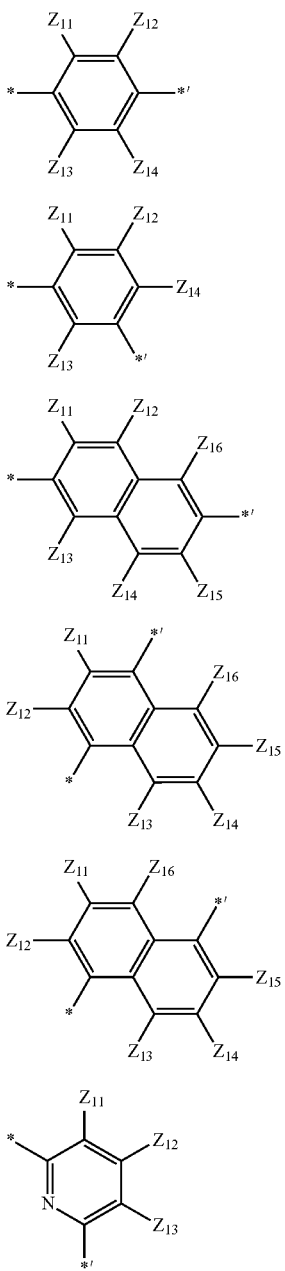

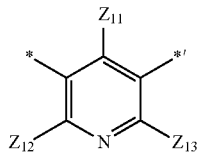

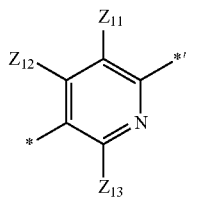

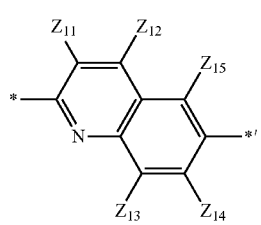

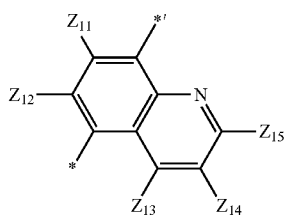

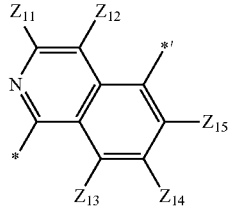

wherein $Z_{11}$ through $Z_{16}$ are each independently one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl) amino group; and a di($C_6$-$C_{20}$ aryl) amino group, wherein the $C_6$-$C_{20}$ aryl group is a phenyl group, a naphthyl group, a fluorenyl group, a phenanthrenyl group, an anthryl group, a pyrenyl group, or a chrysenyl group.

10. The condensed-cyclic compound of claim 1, wherein $Ar_2$ is represented by any one of Formulae 2A through 2K:

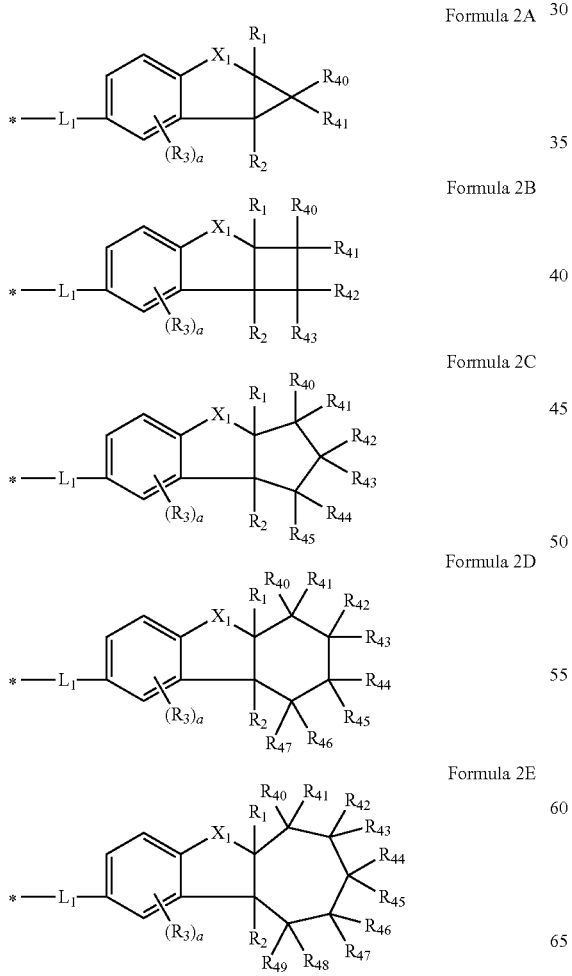

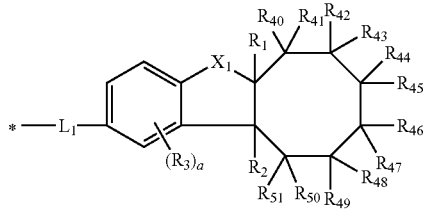

wherein $X_1$, $L_1$, $R_1$ through $R_3$, a, and * are as described in claim 1;

$R_{40}$ through $R_{51}$ are each independently one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted by one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl) amino group; and a di($C_6$-$C_{20}$ aryl) amino group, wherein the $C_6$-$C_{20}$ aryl group is a phenyl group, a naphthyl group, a fluorenyl group, a phenanthrenyl group, an anthryl group, a pyrenyl group, or a chrysenyl group.

11. The condensed-cyclic compound of claim 10, wherein $R_{40}$ through $R_{51}$ are each independently any one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; and a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof.

12. The condensed-cyclic compound of claim 10, wherein $R_1$ through $R_3$ are each independently any one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; and a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof.

13. The condensed-cyclic compound of claim 1, wherein $Ar_2$ is represented by Formula 2-1:

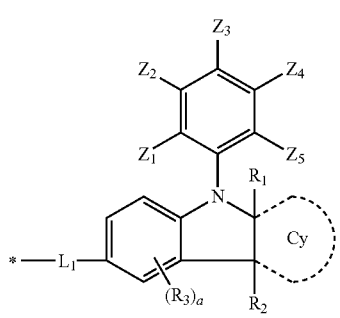

Formula 2-1 wherein $L_1$, $R_1$ through $R_3$, a, and Cy are as described in claim 1;

$Z_1$ through $Z_5$ are each independently any one of hydrogen; deuterium; a halogen atom; a hydroxyl group; a cyano group; a nitro group; an amino group; an amidino group; hydrazine; hydrazone; a carboxylic acid group or a salt thereof; a sulfonic acid group or a salt thereof; a phosphoric acid group or a salt thereof; a $C_1$-$C_{10}$ alkyl group; a $C_1$-$C_{10}$ alkoxy group; a $C_1$-$C_{10}$ alkylthio group; a $C_1$-$C_{10}$ alkyl group, a $C_1$-$C_{10}$ alkoxy group, and a $C_1$-$C_{10}$ alkylthio group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, and a phosphoric acid group or a salt thereof; a phenyl group; a naphthyl group; a fluorenyl group; a phenanthrenyl group; an anthryl group; a pyrenyl group; a chrysenyl group; a phenyl group, a naphthyl group, a fluorenyl group, a phenanthrenyl group, an anthryl group, a pyrenyl group, and a chrysenyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, and a $C_1$-$C_{10}$ alkylthio group; an indolyl group; a benzoimidazolyl group; a carbazolyl group; an imidazolyl group; an imidazolinyl group; an imidazopyridinyl group; an imidazopyrimidinyl group; a pyridinyl group; a pyrimidinyl group; a triazinyl group; a quinolinyl group; an indolyl group, a benzoimidazolyl group, a carbazolyl group, an imidazolyl group, an imidazolinyl group, an imidazopyridinyl group, an imidazopyrimidinyl group, a pyridinyl group, a pyrimidinyl group, a triazinyl group, and a quinolinyl group substituted with one or more of deuterium, a halogen atom, a hydroxyl group, a cyano group, a nitro group, an amino group, an amidino group, hydrazine, hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_1$-$C_{10}$ alkylthio group, a phenyl group, and a naphthyl group; a di($C_1$-$C_{10}$ alkyl) amino group; and a di($C_6$-$C_{20}$ aryl) amino group, wherein the $C_6$-$C_{20}$ aryl group is a phenyl group, a naphthyl group, a fluorenyl group, a phenanthrenyl group, an anthryl group, a pyrenyl group, or a chrysenyl group.

14. The condensed-cyclic compound of claim 1, wherein the condensed-cyclic compound is one of Compounds 38, 262, 586, 726, or 929:

Compound 38

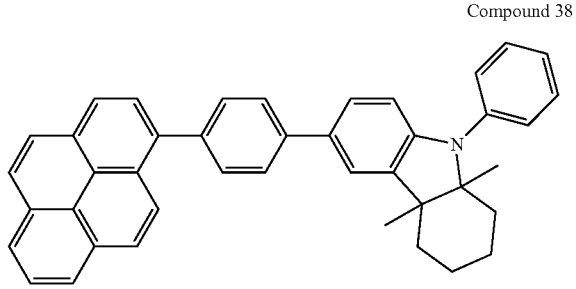

Compound 262

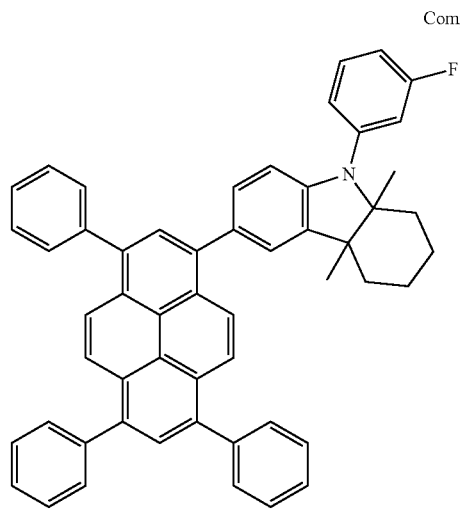

Compound 586

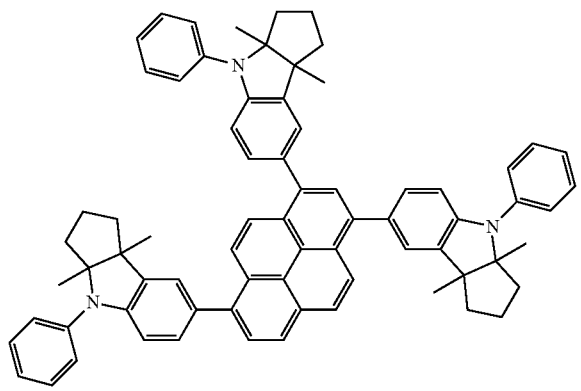

Compound 726

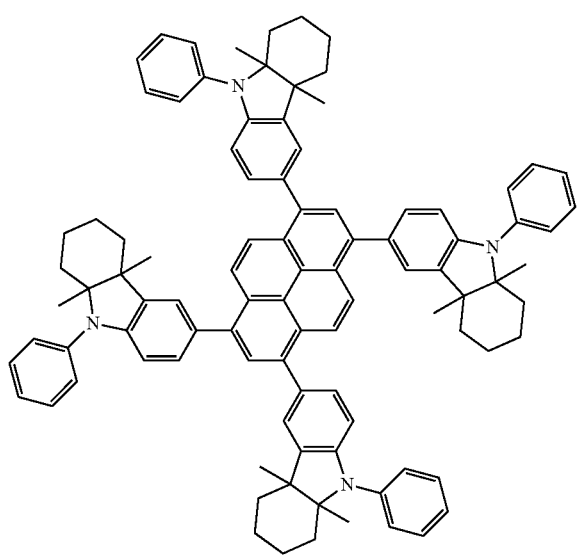

Compound 929

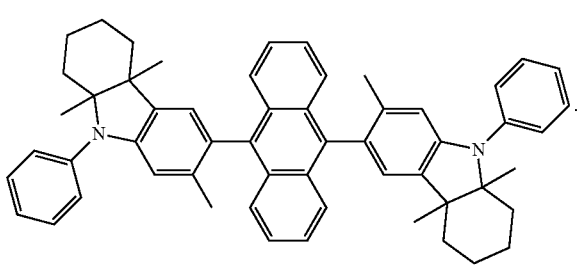

15. An organic light-emitting diode comprising:
a first electrode; a second electrode facing the first electrode; and an organic layer between the first electrode and the second electrode, wherein the organic layer comprises the condensed-cyclic compound according to claim 1.

16. The organic light-emitting diode of claim 15, wherein the organic layer comprises at least one of a hole injection layer, a hole transport layer, a functional layer having hole injection and hole transport abilities, an emission layer, an electron transport layer, and an electron injection layer.

17. The organic light-emitting diode of claim 16, wherein the organic layer comprises an emission layer comprising the condensed-cyclic compound.

18. The organic light-emitting diode of claim 17, wherein the emission layer further comprises a host and the condensed-cyclic compound in the emission layer acts as a dopant.

19. The organic light-emitting diode of claim 18, wherein the host comprises an anthracene-based compound represented by Formula 60:

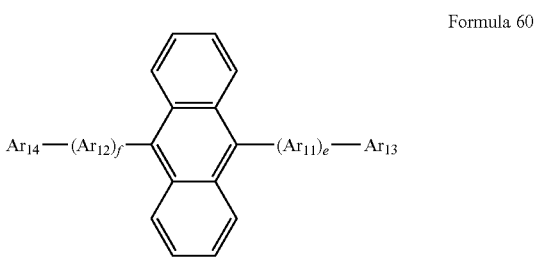

Formula 60 wherein $Ar_{11}$ and $Ar_{12}$ are each independently a substituted or unsubstituted $C_5$-$C_{60}$ arylene group;

$Ar_{13}$ and $Ar_{14}$ are each independently a substituted or unsubstituted $C_1$-$C_{10}$ alkyl group or a substituted or unsubstituted $C_5$-$C_{60}$ aryl group; and e and f are each independently an integer of 0 to 5.

* * * * *